US007670823B1

(12) United States Patent
Hartley et al.

(10) Patent No.: US 7,670,823 B1
(45) Date of Patent: Mar. 2, 2010

(54) COMPOSITIONS FOR USE IN RECOMBINATIONAL CLONING OF NUCLEIC ACIDS

(75) Inventors: James L. Hartley, Frederick, MD (US); Michael A. Brasch, Gaithersburg, MD (US); Gary F. Temple, Washington Grove, MD (US); David Cheo, Kensington, MD (US)

(73) Assignee: Life Technologies Corp., Carlsbad, CA (US)

(*) Notice: Subject to any disclaimer, the term of this patent is extended or adjusted under 35 U.S.C. 154(b) by 0 days.

(21) Appl. No.: 09/517,466

(22) Filed: Mar. 2, 2000

Related U.S. Application Data

(60) Provisional application No. 60/122,389, filed on Mar. 2, 1999, provisional application No. 60/126,049, filed on Mar. 23, 1999, provisional application No. 60/136,744, filed on May 28, 1999.

(51) Int. Cl.
*C07H 21/04* (2006.01)
*C12N 1/20* (2006.01)
*C12N 15/00* (2006.01)
*C12N 5/10* (2006.01)

(52) U.S. Cl. .................. 435/252.3; 536/23.1; 536/24.2; 435/320.1; 435/325

(58) Field of Classification Search ................ 536/23.1, 536/24.1, 24.33; 435/252.3, 320.1, 325, 435/810
See application file for complete search history.

(56) References Cited

U.S. PATENT DOCUMENTS 4,626,505 A 12/1986 Falco
4,673,640 A 6/1987 Backman ..................... 435/68
4,683,195 A 7/1987 Mullis et al.

(Continued)

FOREIGN PATENT DOCUMENTS

CA 2141412 2/1994

(Continued)

OTHER PUBLICATIONS

Zucman-Rossi, J. et al. Chromosome translocation based on illegitimate recombination in human tumors. Proceedings of the National Academy of Sciences USA 95:11786-11791 (Sep. 1998).*

(Continued)

*Primary Examiner*—Diana B Johannsen

(57) ABSTRACT

The present invention relates generally to compositions and methods for use in recombinational cloning of nucleic acid molecules. In particular, the invention relates to nucleic acid molecules encoding one or more recombination sites or portions thereof, to nucleic acid molecules comprising one or more of these recombination site nucleotide sequences and optionally comprising one or more additional physical or functional nucleotide sequences. The invention also relates to vectors comprising the nucleic acid molecules of the invention, to host cells comprising the vectors or nucleic acid molecules of the invention, to methods of producing polypeptides using the nucleic acid molecules of the invention, and to polypeptides encoded by these nucleic acid molecules or produced by the methods of the invention. The invention also relates to antibodies that bind to one or more polypeptides of the invention or epitopes thereof. The invention also relates to the use of these compositions in methods for recombinational cloning of nucleic acids, in vitro and in vivo, to provide chimeric DNA molecules that have particular characteristics and/or DNA segments.

11 Claims, 253 Drawing Sheets

U.S. PATENT DOCUMENTS 4,683,202 A 7/1987 Mullis
4,743,546 A 5/1988 Backman et al. ............ 435/108
4,808,537 A 2/1989 Stroman et al.
4,855,231 A 8/1989 Stroman et al.
4,959,217 A 9/1990 Sanders et al.
4,959,317 A 9/1990 Sauer ...................... 435/172.3
4,965,188 A 10/1990 Mullis et al.
5,093,257 A 3/1992 Gray
5,102,797 A 4/1992 Tucker et al.
5,159,062 A 10/1992 Knapp et al.
5,227,288 A 7/1993 Blattner ......................... 435/6
5,258,294 A 11/1993 Boyle et al.
5,286,632 A 2/1994 Jones ........................ 435/91.2
5,334,375 A 8/1994 Nabi et al.
5,334,575 A 8/1994 Noonan et al.
5,348,886 A 9/1994 Lee et al. ................. 435/320.1
5,354,668 A 10/1994 Auerbach .................. 435/91.1
5,378,618 A 1/1995 Sternberg et al.
5,434,066 A 7/1995 Bebee et al. ............. 435/172.3
5,451,513 A 9/1995 Maliga et al.
5,470,727 A 11/1995 Mascarenhas et al. .... 435/172.3
5,527,695 A 6/1996 Hodges et al.
5,552,314 A 9/1996 Greener
5,591,609 A 1/1997 Auerbach .................. 435/91.2
5,605,793 A 2/1997 Stemmer
5,614,389 A 3/1997 Auerbach .................. 435/91.2
5,635,381 A 6/1997 Hooykaas et al. ........ 435/172.3
5,650,308 A 7/1997 Baum ...................... 435/172.3
5,650,557 A 7/1997 Hannah et al.
5,654,182 A 8/1997 Wahl et al.
5,658,772 A 8/1997 Odell et al. .............. 435/172.3
5,677,170 A 10/1997 Devine et al. .............. 435/20.1
5,677,177 A 10/1997 Wahl et al. .................. 435/325
5,695,971 A 12/1997 Kadokami et al.
5,710,248 A 1/1998 Grose ......................... 530/327
5,723,765 A 3/1998 Oliver et al. ................ 800/208
5,728,551 A 3/1998 Devine et al.
5,733,733 A 3/1998 Auerbach ...................... 435/6
5,733,743 A 3/1998 Johnson et al. .......... 435/320.1
5,744,336 A 4/1998 Hodges et al. ........... 435/172.3
5,766,891 A 6/1998 Shuman ................... 435/91.41
5,776,449 A 7/1998 Baum et al. ................ 424/93.2
5,801,030 A 9/1998 McVey et al.
5,814,300 A 9/1998 Scott et al.
5,830,707 A 11/1998 Bushman ................... 435/69.7
5,837,242 A 11/1998 Holliger et al. .......... 424/136.1
5,837,458 A 11/1998 Minshull et al.
5,843,772 A 12/1998 Devine et al. .............. 435/69.1
5,851,808 A 12/1998 Elledge et al. ........... 435/172.3
5,858,657 A 1/1999 Winter et al. .................. 435/6
5,871,907 A 2/1999 Winter et al. .................. 435/6
5,874,259 A 2/1999 Szybalski .................. 435/91.1
5,888,732 A 3/1999 Hartley et al. .................. 435/6
5,910,438 A 6/1999 Bernard et al.
5,916,804 A 6/1999 Bushman .................... 435/325
5,919,676 A 7/1999 Graham et al. ........... 435/172.3
5,928,914 A 7/1999 Leboulch et al. ......... 435/172.3
5,929,307 A 7/1999 Hodges et al.
5,962,255 A 10/1999 Griffiths et al.
5,981,177 A 11/1999 Demirjian et al.
5,989,872 A 11/1999 Luo et al. .................. 435/91.2
5,994,136 A 11/1999 Naldini et al.
6,010,884 A 1/2000 Griffiths et al. ............ 435/69.7
6,025,192 A 2/2000 Beach et al.
6,040,138 A 3/2000 Lockhart et al.
6,040,430 A 3/2000 Stewart ...................... 530/358
6,063,627 A 5/2000 McVey et al. ............... 435/440
6,066,778 A 5/2000 Ginsburg et al.
6,080,576 A 6/2000 Zambrowicz et al.
6,110,735 A 8/2000 Chartier et al.
6,120,764 A 9/2000 Graham et al.
6,121,043 A 9/2000 Cochran et al.
6,140,086 A 10/2000 Fox et al.
6,140,087 A 10/2000 Graham et al.
6,143,557 A 11/2000 Hartley et al. ............ 435/320.1
6,156,497 A 12/2000 Kaleko
6,165,782 A 12/2000 Naldini et al.
6,171,861 B1 1/2001 Hartley et al. ............... 435/455
6,225,121 B1 5/2001 Savakis et al.
6,228,646 B1 5/2001 Hardy
6,262,341 B1 7/2001 Baszczynski et al.
6,270,969 B1 8/2001 Hartley et al.
6,271,436 B1 8/2001 Piedrahita et al.
6,277,608 B1 8/2001 Hartley et al.
6,281,000 B1 8/2001 Chartier et al.
6,303,301 B1 10/2001 Mack
6,309,822 B1 10/2001 Fodor et al.
6,333,155 B1 12/2001 Lockhart et al.
6,361,972 B1 3/2002 Harrington et al.
6,365,377 B1 4/2002 Patten et al.
6,410,266 B1 6/2002 Harrington et al.
6,410,317 B1 6/2002 Farmer
6,436,707 B1 8/2002 Zambrowicz et al.
6,544,790 B1 4/2003 Sabatini
6,576,463 B1 6/2003 Kasahara et al.
6,720,140 B1 4/2004 Hartley et al.
6,884,612 B2 * 4/2005 Maruyama et al. ....... 435/235.1
6,964,861 B1 11/2005 Gerard et al.
7,176,029 B2 2/2007 Bernard et al.
7,223,576 B2 5/2007 Hartley et al.
7,282,326 B2 10/2007 Hartley et al.
7,304,130 B2 12/2007 Hartley et al.
7,351,578 B2 4/2008 Cheo et al.
7,393,632 B2 7/2008 Cheo et al.
7,408,049 B2 8/2008 Hartley et al.
2002/0006664 A1 1/2002 Sabatini
2002/0007051 A1 1/2002 Cheo et al.
2002/0068290 A1 6/2002 Yarovinsky
2002/0094574 A1 7/2002 Hartley et al.
2002/0106797 A1 8/2002 Miles et al.
2002/0162126 A1 10/2002 Beach et al.
2002/0172997 A1 11/2002 Hartley et al.
2002/0182731 A1 12/2002 Ji et al.
2002/0192819 A1 12/2002 Hartley et al.
2003/0022179 A1 1/2003 Chesnut et al.
2003/0027289 A1 2/2003 Farmer
2003/0027337 A1 2/2003 Droge et al.
2003/0032203 A1 2/2003 Sabatini et al.
2003/0054552 A1 3/2003 Hartley et al.
2003/0054555 A1 3/2003 Farmer et al.
2003/0059900 A1 3/2003 Farmer
2003/0064515 A1 4/2003 Hartley et al.
2003/0068799 A1 4/2003 Hartley et al.
2003/0077804 A1 4/2003 Byrd et al.
2003/0100110 A1 5/2003 Hartley et al.
2003/0124555 A1 7/2003 Brasch et al.
2003/0135888 A1 7/2003 Zhu et al.
2003/0153055 A1 8/2003 Miles et al.
2003/0157662 A1 8/2003 Gerard et al.
2003/0157716 A1 8/2003 Hartley et al.
2003/0175772 A1 9/2003 Wang
2003/0175970 A1 9/2003 Hartley et al.
2003/0176644 A1 9/2003 Byrd et al.
2003/0186233 A1 10/2003 Chesnut et al.
2003/0203486 A1 10/2003 Sabatini
2003/0220249 A1 11/2003 Hackett et al.
2004/0040053 A1 2/2004 Nomura et al.
2004/0053412 A1 3/2004 Hartley et al.
2004/0063207 A1 4/2004 Hartley et al.
2004/0132133 A1 7/2004 Bennett
2004/0171156 A1 9/2004 Hartley et al.
2004/0171157 A1 9/2004 Hartley et al.
2004/0219516 A1 11/2004 Bennett et al.
2004/0219673 A1 11/2004 Hartley et al.

| | | | |
|---|---|---|---|
| 2004/0229229 A1 | 11/2004 | Cheo et al. |
| 2004/0253620 A1 | 12/2004 | Leong et al. |
| 2004/0253631 A1 | 12/2004 | Hartley et al. |
| 2004/0265863 A1 | 12/2004 | Chesnut et al. |
| 2005/0009091 A1 | 1/2005 | Hartley et al. |
| 2005/0069929 A1 | 3/2005 | Chestnut et al. |
| 2005/0095615 A1 | 5/2005 | Welch et al. |
| 2005/0176065 A1 | 8/2005 | Hanson |
| 2005/0181417 A1 | 8/2005 | Miles et al. |
| 2005/0208530 A1 | 9/2005 | Chesnut et al. |
| 2006/0008817 A1 | 1/2006 | Carrino et al. |
| 2006/0035269 A1 | 2/2006 | Hartley et al. |
| 2006/0035272 A1 | 2/2006 | Brasch et al. |
| 2006/0073593 A1 | 4/2006 | Byrd et al. |
| 2006/0204979 A1 | 9/2006 | Gray et al. |
| 2007/0128725 A1 | 6/2007 | Brasch et al. |
| 2007/0184451 A1 | 8/2007 | Byrd et al. |

FOREIGN PATENT DOCUMENTS

| | | |
|---|---|---|
| CA | 2226463 | 12/2006 |
| EP | 0 160 571 A2 | 11/1985 |
| EP | 0 220 009 | 4/1987 |
| EP | 0 300 422 | 1/1989 |
| EP | 0 427 074 | 5/1991 |
| EP | 220009 | 2/1993 |
| EP | 0 542 466 | 5/1993 |
| EP | 0542466 A2 | 5/1993 |
| EP | 1 035 208 | 9/2000 |
| EP | 0937098 | 8/2002 |
| EP | 1227147 A3 | 8/2002 |
| WO | WO 90/11375 | 10/1990 |
| WO | WO 91/02801 | 3/1991 |
| WO | WO-91/09957 | 7/1991 |
| WO | WO 91/09957 | 7/1991 |
| WO | WO 91/16427 | 10/1991 |
| WO | WO-92/15694 | 9/1992 |
| WO | WO 92/15694 | 9/1992 |
| WO | WO 92/20791 | 11/1992 |
| WO | WO 92/22650 | 12/1992 |
| WO | WO 93/15191 | 8/1993 |
| WO | WO 93/19172 | 9/1993 |
| WO | WO 94/03624 | 2/1994 |
| WO | WO-94/03624 | 2/1994 |
| WO | WO 94/09127 | 4/1994 |
| WO | WO 94/17176 | 8/1994 |
| WO | WO-94/18333 | 8/1994 |
| WO | WO 94/18333 | 8/1994 |
| WO | WO 94/20604 | 9/1994 |
| WO | WO 95/00555 | 1/1995 |
| WO | WO 96/04393 | 2/1996 |
| WO | WO 96/19497 | 6/1996 |
| WO | WO-96/23904 | 8/1996 |
| WO | WO 96/23904 A1 | 8/1996 |
| WO | WO 96/30498 | 10/1996 |
| WO | WO 96/40722 A1 | 12/1996 |
| WO | WO 96/40724 | 12/1996 |
| WO | WO-96/40724 | 12/1996 |
| WO | WO 97/06265 | 2/1997 |
| WO | WO 97/09436 | 3/1997 |
| WO | WO 97/25446 | 7/1997 |
| WO | WO 97/32481 | 9/1997 |
| WO | WO 97/47758 A1 | 12/1997 |
| WO | WO 98/10086 | 3/1998 |
| WO | WO 98/38326 A1 | 9/1998 |
| WO | WO 98/53056 | 11/1998 |
| WO | WO 99/10488 | 3/1999 |
| WO | WO 99/21977 | 5/1999 |
| WO | WO-99/21977 | 5/1999 |
| WO | WO 99/25851 | 5/1999 |
| WO | WO 99/55851 | 11/1999 |
| WO | WO 00/12687 | 3/2000 |
| WO | WO-00/29000 | 5/2000 |
| WO | WO 00/29000 | 5/2000 |
| WO | WO-00/52027 | 9/2000 |
| WO | WO 00/52027 | 9/2000 |
| WO | WO 00/52141 | 9/2000 |
| WO | WO-00/52141 | 9/2000 |
| WO | WO 00/60091 | 10/2000 |
| WO | WO-00/60091 | 10/2000 |
| WO | WO 01/05961 A1 | 1/2001 |
| WO | WO 01/07572 | 2/2001 |
| WO | WO 01/11058 A1 | 2/2001 |
| WO | WO-01/20015 | 3/2001 |
| WO | WO 01/25466 | 4/2001 |
| WO | WO-01/31039 | 5/2001 |
| WO | WO 01/31039 | 5/2001 |
| WO | WO-01/42509 | 6/2001 |
| WO | WO 01/42509 | 6/2001 |
| WO | WO 01/62892 | 8/2001 |
| WO | WO 01/68836 | 9/2001 |
| WO | WO 02/00875 | 1/2002 |
| WO | WO 02/05294 | 1/2002 |
| WO | WO 02/08391 | 1/2002 |
| WO | WO 02/16594 | 2/2002 |
| WO | WO 02/46372 | 6/2002 |
| WO | WO-02/061034 | 8/2002 |
| WO | WO 02/061034 | 8/2002 |
| WO | WO 02/062957 | 8/2002 |
| WO | WO-02062957 | 8/2002 |
| WO | WO 02/086144 | 10/2002 |
| WO | WO-02077264 | 10/2002 |
| WO | WO-02086144 | 10/2002 |
| WO | WO 02/095055 | 11/2002 |
| WO | WO-02095055 | 11/2002 |
| WO | WO-03/025161 | 3/2003 |
| WO | WO 03/025161 | 3/2003 |
| WO | WO 03/044207 | 5/2003 |
| WO | WO 03/103600 | 12/2003 |
| WO | WO 2004/009768 | 1/2004 |
| WO | WO 2004/013290 | 2/2004 |
| WO | WO-2004013290 | 2/2004 |
| WO | WO 2005/012487 A2 | 2/2005 |
| WO | WO 2005/014796 A2 | 2/2005 |

OTHER PUBLICATIONS

GenBank Accession No. Y08806, "*H. sapiens* EWS gene, 5' part and flanking region," (Zucman-Rossi, J. et al), Nov. 1996.*

Campbell, A. Comparative molecular biology of lambdoid phages. Annu. Rev. Microbiol. 48:193-222 (1994).*

Albert, H., et al., "Site-specific integration of DNA into wild-type and mutant *lox* sites placed in the plant genome," *Plant J.* 7:649-659 Oxford Bios Scientific Publishers And Blackwell Scientific Publications In Association With The Society For Experimental Biology (1995).

Bernard, P., "Positive Selection of Recombinant DNA by CcdB," *BioTechniques 21*:320-323, Eaton Publishing Company (1996).

Dale, E.C., and Ow, D.W., "Mutations in the Cre/lox recombination site enhance the stability of recombination products: Applications for gene targeting in plants," *J. Cell. Biochem. 16*(*Suppl. F*) :206, Abstract No. Y 108, Wiley-Liss, Inc. (1992).

Davies, J., and Riechmann, L., "An antibody VH domain with a *lox*-Cre site integrated into its coding region: bacterial recombination within a single polypeptide chain," *FEBS Lett. 377*:92-96, Federation of European Biochemical Societies (1995).

Hall, R.M., and Collis, C.M., "Mobile gene cassettes and integrons: capture and spread of genes by site-specific recombination," *Mol. Microbiol. 15*:593-600, Blackwell Scientific Publications (1995).

Krafte, D.S., et al., "Stable Expression and Functional Characterization of a Human Cardiac $Na^+$ Channel Gene in Mammalian Cells," *J. Mol. Cell Cardiol. 27*:823-830, Academic Press Limited (1995).

Lee, G., and Saito, I., "Role of nucleotide sequences of *loxP* spacer region in Cre-mediated recombination," *Gene 216*:55-65, Elsevier Science B.V. (Aug. 1998).

Venkatesh, T.V., and Redding, C.M., "Ribosomal Protein S1 and NusA Protein Complexed to Recombination Protein β of Phage λ," *J. Bacteriol. 175*:1844-1846, American Society for Microbiology (1993).
Zahra, D.G., et al., "Selective in-vivo recombination to increase antibody library size—an improved phage display vector system," *Gene 227*:49-54, Elsevier Science Publishers B.V. (Feb. 1999).
Dialog File 351 (Derwent World Patents Index), unverified English language abstract for WIPO/PCT Publication No. WO 98/53056 (Document No. AP4); WPI Accession No. 1999-000502/199901.
Dialog File 351 (Derwent World Patents Index), unverified English language abstract for WIPO/PCT Publication No. WO 99/25851 (Document No. AMS); WPI Accession No. 1999-347485/199929.
Akagi, K., et al., "Cre-mediated somatic site-specific recombination in mice," *Nucl. Acids Res. 25*:1781-1788, Oxford University Press (1997).
Aladjem, M.I., et al., "Positive Selection of FLP-Mediated Unequal Sister Chromatid Exchange Products in Mammalian Cells," *Mol. Cell. Biol. 17*:857-861, American Society for Microbiology (1997).
Angelastro, J.M., et al., "Identification of diverse nerve growth factor-regulated genes by serial analysis of gene expression (SAGE) profiling," *Proc. Natl. Acad. Sci. USA 97*:10424-10429, National Academy of Sciences (Sep. 2000).
Angrand, P.O., et al., "Inducible expression based on regulated recombination: a single vector strategy for stable expression in cultured cells," *Nucl. Acids Res. 26*:3263-3269, Oxford University Press (Jul. 1998).
Ayres, E.K., et al., "Precise Deletions in Large Bacterial Genomes by Vector-mediated Excision (VEX). The *trfA* Gene of Promiscuous Plasmid RK2 is Essential for Replication in Several Gram-negative Hosts," *J. Mol. Biol. 230*:174-185, Academic Press (1993).
Backman, K., et al., "Use of Synchronous Site-Specific Recombination In Vivo to Regulate Gene Expression," *Bio/Technology 2*:1045-1049, Nature Publishing Company (1984).
Bai, C., et al., "*SKP1* Connects Cell Cycle Regulators to the Ubiquitin Proteolysis Machinery through a Novel Motif, the F-Box," *Cell 86*:263-274, Cell Press (1996).
Bernard, P., et al., "The F Plasmid CcdB Protein Induces Efficient ATP-dependent DNA Cleavage by Gyrase," *J. Mol. Biol. 234*:534-541, Academic Press (1993).
Boshart, M., et al., "A Very Strong Enhancer is Located Upstream of an Immediate Early Gene of Human Cytomegalovirus," *Cell 41*:521-530, The MIT Press (1985).
Bouhassira, E.E., et al., "Transcriptional Behavior of LCR Enhancer Elements Integrated at the Same Chromosomal Locus by Recombinase-Mediated Cassette Exchange," *Blood 90*:3332-3344, The American Society of Hematology (1997).
Burioni, R., et al., "An improved phage display vector for antibody repertoire cloning by construction of combinatorial libraries," *Res. Virol. 148*:161-164, Elsevier (1997).
Capone, J.P., et al., "Introduction of UAG, UAA, and UGA Nonsense Mutations at a Specific Site in the *Escherichia coli* Chloramphenicol Acetyltransferase Gene: Use in Measurement of Amber, Ochre, and Opal Suppression in Mammalian Cells," *Mol. Cell. Biol. 6*:3059-3067, American Society for Microbiology (1986).
Chanock, R.M., et al., "Human Monoclonal Antibody Fab Fragments Cloned from Combinatorial Libraries: Potential Usefulness in Prevention and/or Treatment of Major Human Viral Diseases," *Infect. Agents Dis. 2*:118-131, Raven Press (1993).
Chong, S., et al., "Single-column purification of free recombinant proteins using a self-cleavable affinity tag derived from a protein splicing element," *Gene 192*:271-281, Elsevier Science B.V. (1997).
Choulika, A., et al., "Transfer of Single Gene-Containing Long Terminal Repeats into the Genome of Mammalian Cells by a Retroviral Vector Carrying the *cre* Gene and the *loxP* Site," *J. Virol. 70*:1792-1798, American Society for Microbiology (1996).
Chuang, C.-F., et al., "Specific and heritable genetic interference by double-stranded RNA in *Arabidopsis thaliana," Proc. Natl. Acad. Sci. USA 97*:4985-4990, National Academy of Sciences (Apr. 2000).
Cigan, A.M., et al., "Mutational Analysis of the *HIS4* Translational Initiator Region in *Saccharomyces cerevisiae," Mol. Cell. Biol. 8*:2964-2975, American Society for Microbiology (1988).
CLONTECH, "Creator™ Gene Cloning & Expression System," *CLONTECHniques 15*:7-11, CLONTECH, (Apr. 2000).
CLONTECH, "New Additions to the Creator™ Platform," *CLONTECHniques 16*:4 pages, CLONTECH, (Jan. 2001).
CLONTECH, "New Creator™ -Compatible Expression Systems," *CLONTECHniques 15*:2 pages, CLONTECH, (Oct. 2000).
CLONTECH, "Creator™ Acceptor Vector Construction Kit" *CLONTECHniques 16*:2 pages, CLONTECH, (Oct. 2001).
CLONTECH, "Creator™ SMART™ Library Construction Kit," *CLONTECHniques 16*:2 pages, CLONTECH, (Oct. 2001).
CLONTECH, "Creator™: The Universal Platform for Analysis of Gene Function," *Powerpoint Presentation*, 9 pages, CLONTECH, (Jul. 24, 2001), available at http://www.clontech.com/products/families/creator/popups/s1page1.html.
CLONTECH, "Creator™ pDNR-Dual Cloning Kit," *CLONTECHniques 16*:3 pages, CLONTECH, (Oct. 2001).
Curcio, M.J., and Garfinkel, D.J., "Single-step selection for Ty1 element retrotransposition," *Proc. Natl. Acad. Sci. USA 88*:936-940, National Academy of Sciences (1991).
Datson, N.A., et al., "MicroSAGE: a modified procedure for serial analysis of gene expression in limited amounts of tissue," *Nucl. Acids Res. 27*:1300-1307, Oxford University Press (Mar. 1999).
Davis, C.R., et al., "Analysis of the Mechanisms of Action of the *Saccharomyces cerevisiae* Dominant Lethal cdc42$^{G12V}$ and Dominant Negative cdc42$^{D118A}$ Mutations," *J. Biol. Chem. 273*:849-858, The American Society for Biochemistry and Molecular Biology, Inc. (Jan. 1998).
Deng, M.-D., and Coleman, J.R., "Ethanol Synthesis by Genetic Engineering in Cyanobacteria," *Appl. Environ. Microbiol. 65*:523-528, American Society for Microbiology (Feb. 1999).
Derbyshire, V., and Belfort, M., "Lightning strikes twice: Intron-intein coincidence," *Proc. Natl. Acad. Sci. USA 95*:1356-1357, National Academy of Sciences of the USA (Feb. 1998).
Dijkema, R., et al., "Cloning and expression of the chromosomal immune interferon gene of the rat," *EMBO J. 4*:761-767, IRL Press Limited (1985).
Esposito, D., et al., "The integrase family of tyrosine recombinases: evolution of a conserved active site domain," *Nucl. Acids Res. 25*:3605-3614, Oxford University Press (1997).
Flanagan, P.M., and Fennwald, M.A., "Analysis of Inhibitors of the Site-specific Recombination Reaction Mediated by Tn3 Resolvase," *J. Mol. Biol. 206*:295-304, Academic Press (1989).
Flores, A., et al., "A protein-protein interaction map of yeast RNA polymerase III," *Proc. Natl. Acad. Sci. USA 96*:7815-7820, National Academy of Sciences (Jul. 1999).
Francia, M.V., et al., "The IntI1 Integron Integrase Preferentially Binds Single-Stranded DNA of the *att*C Site," *J. Bacteriol. 181*:6844-6849, American Society for Microbiology (Nov. 1999).
Gateway™ Cloning Technology, Version 1, GIBCO BRL, Life Technologies Instruction Manual, [retrievable from <http://www.lifetech.com/gateway>], pp. 1-60 (Nov. 1999).
Gay, P., et al., "Positive Selection Procedure for Entrapment of Insertion Sequence Elements in Gram-Negative Bacteria," *J. Bacteriol. 164*:918-921, American Society for Microbiology (1985).
Gay, P. et al., "Cloning Structural Gene *sacB*, Which Codes for Exoenzyme Levansucrase of *Bacillus subtilis*: Expression of the Gene in *Escherichia coli," J. Bacterial. 153*:1424-1431, American Society for Microbiology (1983).
Gorman, C.M., et al., "The Rous sarcoma virus long terminal repeat is a strong promoter when introduced into a variety of eukaryotic cells by DNA-mediated transfection," *Proc. Natl. Acad. Sci. USA 79*:6777-6781, National Academy of Sciences (1982).
Grindly, N.D.F., and Kelley, W.S., "Effects of Different Alleles of the *E. coli* K12 *polA* Gene on the Replication of Non-Transferring Plasmids," *Molec. Gen. Genet. 143*:311-318, Springer Verlag (1976).
Gronostajski, R.M., and Sadowski, P.D., "The FLP Protein of the 2-micron Plasmid of Yeast. Inter- and Intramolecular Reactions," *J. Biol. Chem. 260*:12328-12335, The American Society of Biological Chemists, Inc. (1985).
Haffter, P., and Bickle, T.A., "Enhancer-independent mutants of the Cin recombinase have a relaxed topological specificity," *EMBO J. 7*:3991-3996, IRL Press Limited (1988).

Hancock, R.E.W., and Scott, M.G., "The role of antimicrobial peptides in animal defenses," *Proc. Natl. Acad. Sci. USA 97*:8856-8861, National Academy Sciences (Aug. 2000).

Hehl, R., et al., "Structural analysis of Tam3, a transposable element from *Antirrhinum majus*, reveals homologies to the Ac element from maize," *Plant Molec. Biol. 16*:369-371, Kluwer Academic Publishers (1991).

Henikoff, S., "Unidirectional digestion with exonuclease III creates targeted breakpoints for DNA sequencing," *Gene 28*:351-359, Elsevier Science Publishers (1984).

Hochuli, E., et al., "Genetic Approach to Facilitate Purification of Recombinant Proteins with a Novel Metal Chelate Adsorbent," *Bio/Technology 6*:1321-1325, Nature Publishing Company (1988).

Hoess, R.H., and Abremski, K., "Interaction of the Bacteriophage P1 Recombinase Cre with the Recombining Site *loxP*," *Proc. Natl. Acad. Sci. USA 81*:1026-1029, National Academy of Sciences (1984).

Iida, S., et al., "A site-specific, conservative recombination system carried by bacteriophage P1. Mapping of the recombinase gene *cin* and the crossover sites *cix* for the inversion of the C segment," *EMBO J.* 1:1445-1453, IRL Press Limited (1982).

Kaniga, K., et al., "A wide-host-range suicide vector for improving reverse genetics in Gram-negative bacteria: inactivation of the *blaA* Gene of *Yerainia enterocolitica*," *Gene 109*:137-141, Elsevier Science B.V. (1991).

Kealey, J.T., et al., "Production of polyketide natural product in nonpolyketide-producing prokaryotic and eukaryotic hosts," *Proc. Natl. Acad. Sci. USA 95*:505-509, National Academy of Sciences (Jan. 1998).

Kholodenko, B.N., et al., "Metabolic Design: How to Engineer a Living Cell to Desired Metabolite Concentrations and Fluxes," *Biotechnol. Bioengineer. 59*:239-247, John Wiley & Sons, Inc. (1998).

Kim, D.W., et al., "Use of the human elongation factor 1$\alpha$ promoter as a versatile and efficient expression system," *Gene 91*:217-223, Elsevier Science B. V. (1990).

Kolb, A.F., and Siddell, S.G., "Genomic targeting with an MBP-Cre fusion protein," *Gene 183*:53-60, Elsevier Science B.V. (1996).

Kouprina, N., et al., "Rescue of Targeted Regions of Mammalian Chromosomes by in Vivo Recombination in Yeast," *Genome Res. 8*:666-672, Cold Spring Harbor Laboratory Press (Jun. 1998).

Krautwald, S., and Baccarini, M., "Bacterially Expressed Murine CSF-1 Possesses Agonistic Activity in its Monomeric Form," *Biochem. Biophys. Res. Commun. 192*: 720-727, Academic Press, Inc. (1993).

Leslie, N. R., and Sherratt, D.J., "Site-specific recombination in the replication terminus region of *Escherichia coli*: functional replacement of *dif*," *EMBO J. 14*:1561-1570, Oxford University Press (1995).

Leung, L.L.K., "Application of Combinatorial Libraries and Protein Engineering to the Discovery of Novel Anti-Thrombotic Drugs," *Thromb. Haemost. 74*:373-376, F.K. Schattauer Verlagsgesellschaft mbH (1995).

Li, Z.-W., et al., "Generation of mice with a 200-kb amyloid precursor protein gene deletion by Cre recombinase-mediated site-specific recombination in embryonic stem cells," *Proc. Natl. Acad. Sci. USA 93*:6158-6162, National Academy of Sciences (1996).

Lu, F., and Churchward, G., "Conjugative transposition: Tn*916* integrase contains two independent DNA binding domains that recognize different DNA sequences," *EMBO J. 13*:1541-1548, Oxford University Press (1994).

Madison, L.L., and Huisman, G.W., "Metabolic Engineering of Poly(3-Hydroxyalkanoates): From DNA to Plastic," *Microbiol. Mol. Biol. Reviews 63*:21-53, American Society for Microbiology (Mar. 1999).

Maemura, K., et al., "Generation of a Dominant-negative Mutant of Endothelial PAS Domain Protein 1 by Deletion of a Potent C-terminal Transactivation Domain," *J. Biol. Chem. 274*:31565-31570, The American Society for Biochemistry and Molecular Biology, Inc. (Oct. 1999).

Mahillon, J., et al., "Subdivision of the *Escherichia coli* K-12 genome for sequencing: manipulation and DNA sequence of transposable elements introducing unique restriction sites," *Gene 223*:47-54, Elsevier Science B.V. (Nov. 1998).

Malynn, B.A., et al., "The *scid* Defect Affects the Final Step of the Immunoglobulin VDJ Recombinase Mechanism," *Cell 54*:453-460, Cell Press (1988).

Maniatis, T., et al., "Regulation of Inducible and Tissue-Specific Gene Expression," *Science 236*:1237-1245, American Association for the Advancement of Science (1987).

Mendiola, M.V., and de la Cruz, F., "Specificity of insertion of IS91, an insertion sequence present in $\alpha$-haemolysis plasmids of *Escherichia coli*," *Mol. Microbiol. 3*:979-984, Blackwell Scientific Publications (1989).

Mercier, J., et al., "Structural and Functional Characterization of *tnpI*, a Recombinase Locus in *Tn21* and Related $\beta$-Lactamaee Transposons," *J. Bacteriol. 172*:3745-3757, American Society for Microbiology (1990).

Metcalf, W.W., et al., "Conditionally Replicative and Conjugative Plasmids Carrying *lacZ*$\alpha$ for Cloning, Mutagenesis, and Allele Replacement in Bacteria," *Plasmid 35*:1-13, Academic Press (1996).

Mette, M.F., et al., "Transcriptional silencing and promoter methylation triggered by double-stranded RNA," *EMBO J. 19*:5194-5201, Oxford University Press (Oct. 2000).

Meyer-Leon, L., et al., "Purification of the FLP site-specific recombinase by affinity chromatography and re-examination of basic properties of the system," *Nucl. Acids Res. 15*:6469-6488, IRL Press Limited (1987).

Mizushima, S., and Nagata, S., "pEF-BOS, a powerful mammalian expression vector," *Nucl. Acids Res. 18*:5322, Oxford University Press (1990).

Nagy, A., "Cre Recombinase: The Universal Reagent for Genome Tailoring," *Genesis 26*:99-109, Wiley-Liss, Inc. (Feb. 2000).

Odell, J.T., et al., "Seed-Specific Gene Activation Mediated by the Cre/*lox* Site-Specific Recombination System," *Plant Physiol. 106*:447-458, American Society of Plant Physiologists (1994).

O'Gara, J.P., et al., "Identification and Molecular Genetic Analysis of Multiple Loci Contributing to High-Level Tellurite Resistance in *Rhodobacter sphaeroides* 2.4.1," *Appl. Environ. Microbiol. 63*:4713-4720, American Society for Microbiology (1997).

Pal, S.K., et al., "P1 Plasmid Replication. Role of Initiator Titration in Copy Number Control," *J. Mol. Biol. 192*:275-285, Academic Press (1986).

Panke, S., et al., "Engineering of Quasi-Natural *Pseudomonas putida* Strains for Toluene Metabolism through an *ortho*-Cleavage Degradation Pathway," *Appl. Environ. Microbiol. 64*:748-751, American Society for Microbiology (Feb. 1998).

Patel, P.H., and Loeb, L.A., "DNA polymerase active site is highly mutable: Evolutionary consequences," *Proc. Natl. Acad. Sci. USA 97*:5095-5100, National Academy of Sciences (May 2000).

Perler, F.B., "InBase, the New England Biolabs Intein Database," *Nucl. Acids Res. 27*:346-347, Oxford University Press (Jan. 1999).

Persson, M.A.A., "Combinatorial Libraries," *Intern. Rev. Immunol. 10*:153-163, Harwood Academic Publishers GmbH (1993).

Phillips-Jones, M.K., et al., "Context Effects on Misreading and Suppression at UAG Codons in Human Cells," *Mol. Cell. Biol. 15*:6593-6600, American Society for Microbiology (1955).

Powell, J., "Enhanced concatemer cloning-a modification to the SAGE (Serial Analysis of Gene Expression) technique," *Nucl. Acids Res. 26*:3445-3446, Oxford University Press (Jul. 1998).

Prieto, M.A., et al., "Molecular Characterization of the 4-Hydroxyphenylacetate Catabolic Pathway of *Escherichia coli* W: Engineering a Mobile Aromatic Degradative Cluster," *J. Bacteriol. 178*:111-120, American Society for Microbiology (1996).

Qin, M., et al., "Cre recombinase-mediated site-specific recombination between plant chromosomes," *Proc. Natl. Acad. Sci. USA 91*:1706-1710, National Academy of Sciences (1994).

Qin, M., et al., "Site-specific cleavage of chromosomes in vitro through Cre-*lox* recombination," *Nucl. Acids Res. 23*:1923-1927, Oxford University Press (1995).

Ross, W., and Landy, A., "Patterns of $\lambda$ Int Recognition in the Regions of Strand Exchange," *Cell 33*:261-272, the MIT Press (1983).

Sandhu, J.S., "Protein Engineering of Antibodies," *Crit. Rev. Biotechnol. 12*:437-462, CRC Press (1992).

Sato, T., et al., "The *cisA* Cistron of *Bacillus subtilis* Sporulation Gene *spoIVC* Encodes a Protein Homologous to a Site-Specific Recombinase," *J. Bacteriol. 172*:1092-1098, American Society for Microbiology (1990).

Sauer, B., et al., "Construction of Isogenic Cell Lines Expressing Human and Rat Angiotensin II $AT_1$ Receptors by Cre-Mediated Site-Specific Recombination," *Methods: A Companion to Methods in Enzymology 4*:143-149, Academic Press (1992).

Schild, D., et al., "Cloning of three human multifunction *de novo* purine biosynthetic genes by functional complementation of yeast mutations," *Proc. Natl. Acad. Sci. USA 87*:2916-2920, National Academy of Sciences (1990).

Schnepf, E., et al., "*Bacillus thuringiensis* and Its Pesticidal Crystal Proteins," *Microbial. Mol. Biol. Rev. 62*:775-806, American Society for Microbiology (Sep. 1998).

Segall, A.M., et al., "Architectural elements in nucleoprotein complexes: interchangeability of specific and non-specific DNA binding proteins," *EMBO J. 13*:4536-4548, Oxford University Press (1994).

Shim, J., et al., "Distinct and Redundant Functions of μ1 Medium Chains AP-1 Clathrin-Associated Protein Complex in the Nematode *Caenorhabditis elegans," Mol. Biol. Cell 11*:2743-2756, The American Society for Cell Biology (Aug. 2000).

Skraly, F.A., et al., "Construction and Characterization of a 1,3-Propanediol Operon," *Appl. Environ. Microbiol. 64*:98-105, American Society for Microbiology (Jan. 1998).

Spinella, D.G., et al., "Tandem arrayed ligation of expressed sequence tags (TALEST) : a new method for generating global gene expression profiles," *Nucl. Acids Res. 27(e22)*:i-viii, Oxford University Press (Sep. 1999).

Stark, W.M., et al., "Site-Specific Recombination by Tn3 Resolvase: Topological Changes in the Forward and Reverse Reactions," *Cell 58*:779-790, Cell Press (1989).

Stassi, D.L., et al., "Ethyl-substituted erythromycin derivatives produced by directed metabolic engineering," *Proc. Natl. Acad. Sci. USA 95*:7305-7309, National Academy of Sciences (Jun. 1998).

Stellwagen, A.E., and Craig, N. L., "Mobile DNA elements: controlling transposition with ATP-dependent molecular switches," *Trends Biochem. Sci. 23*:486-490, Elsevier Science Publishers (Dec. 1998).

Stenzel, T.T., et al., "The Integration Host Factor of *Escherichia coli* Binds to Bent DNA at the Origin of Replication of the Plasmid pSC101," *Cell 49*:709-717, Cell Press (1987).

Sugiura, S., et al., "Minimal Essential Origin of Plasmid pSC101 Replication: Requirement of a Region Downstream of Iterons," *J. Bacteriol. 175*:5993-6001, American Society for Microbiology (1993).

Uetsuki, T., et al., "Isolation and Characterization of the Human Chromosomal Gene for Polypeptide Chain Elongation Factor-1α," *J. Biol. Chem. 264*:5791-5798, The American Society for Biochemistry and Molecular Biology, Inc. (1989).

van den Berg, A., et al., "Serial analysis of gene expression: rapid RT-PCR analysis of unknown SAGE tags," *Nucl. Acids Res. 27(e17)*:i-iii, Oxford University Press (Sep. 1999).

Voss, S.D., et al., "The role of enhancers in the regulation of cell-type-specific transcriptional control," *Trends Biochem. Sci. 11*:287-289, Elsevier Science (1986).

Voziyanov, Y., et al., "A general model for site-specific recombination by the integrase family recombinases," *Nucl. Acids Res. 27*:930-941, Oxford University Press (Feb. 1999).

Yoon, H., et al., "*SSL1*, a suppressor of a *HIS4* 5'-UTR stem-loop mutation, is essential for translation initiation and affects UV resistance in yeast," *Genes Dev. 6*:2463-2477, Cold Spring Harbor Laboratory Press (1992).

Abremski, K., and Gottesman, S., "Purification of the Bacteriophage λ *xis* Gene Product Required for λ Excisive Recombination," *J. Biol. Chem. 257*(16):9658-9662, American Society for Biochemistry and Molecular Biology, Inc., Baltimore, MD (1982).

Abremski, K., and Hoess, R., "Bacteriophage P1 Site-specific Recombination—Purification and Properties of the Cre Recombinase Protein," *J. Biol. Chem. 259*:1509-1514, American Society for Biochemistry and Molecular Biology, Inc., Baltimore, MD (1984).

Abremski, K., et al., "Bacteriophage P1 Cre-*loxP* Site-specific Recombination: Site-specific DNA Topoisomerase Activity of the Cre Recombination Protein," *J. Biol. Chem. 261*(1)1391-396, American Society for Biochemistry and Molecular Biology, Inc., Baltimore, MD (1986).

Abremski, K., et al., "Studies on the Properties of P1 Site-Specific Recombination: Evidence for Topologically Unlinked Products Following Recombination," *Cell 32*:1301-1311, Cell Press, Cambridge, MA (1993).

Adams, D.E., et al., "Cre-*lox* Recombination in *Escherichia coli* Cells: Mechanistic Differences from the in Vitro Reaction," *J. Mol. Biol. 226*:661-673, Academic Press, Inc., New York, NY (1992).

Andrews, B.J., et al., "The FLP Recombinase of the 2μ Circle DNA of Yeast: Interaction with Its Target Sequences," *Cell 40*:795-803, Cell Press, Cambridge, MA (1985).

Andrews, B.J., et al., "Interaction of the FLP Recombinase of the *Saccharomyces cerevisiae* 2 μm Plasmid with Mutated Target Sequences," *Mol. Cell. Biol. 6*:2482-2489, American Society for Microbiology, Washington, D.C. (1986).

Anton, M., and Graham, F.L., "Site-Specific Recombination Mediated by an Adenovirus Vector Expressing the Cre Recombinase Protein: a Molecular Switch for Control of Gene Expression," *J. Virol. 69*:4600-4606, American Society for Microbiology, Washington, D.C. (1995).

Araki, H., et al., "Site-specific Recombinase, R, Encoded by Yeast Plasmid pSR1," *J. Mol. Biol. 225*:25-37, Academic Press, Inc., New York, NY (1992).

Argos, P., et al., "The integrase family of site-specific recombinases: regional similarities and global diversity," *EMBO J. 5*(2):433-440, IRL Press Limited, Oxford, England (1986).

Astumian, et al., "Site-specific recombination between cloned attP and attB sites from the *Haemophilus influenza* bacteriophage HP1 propagated in recombination deficient *Escherichia coli," J. Bacterial. 171*:1747-1750, American Society for Microbiology, Washington, D.C. (1989).

Atlung, T., et al., "A versatile method for integration of genes and gene fusions into the λ attachment site of *Escherichia coli," Gene 107*:11-17, Elsevier/North-Holland, Netherlands (1991).

Ausubel, F.M., et al., "Maps of Plasmids pBR322 and pUC19," in *Current Protocols in Molecular Biology*, John Wiley & Sons, Inc., Boston, MA, (1995), pp. 1.5.3 and 1.5.4.

Ausubel, F.M., et al., "Mutagenesis by the Polymerase Chain reaction," in: *Current Protocols in Molecular Biology*, John Wiley & Sons, Inc., Boston, MA, pp. 8.5.1-8.5.9 (1995).

Babineau, D. et al., "The FLP Protein of the 2-micron Plasmid of Yeast," *J. Biol. Chem. 260*:12313-12391, American Society for Biochemistry and Molecular Biology, Inc., Baltimore, MD (1985).

Balakrishnan, R., et al., "A gene cassette for adapting *Escherichia coli* strains as hosts for *att*-Int-mediated rearrangement and $P_L$ expression vectors," *Gene 138*:101-104, Elsevier/North-Holland, Netherlands (Jan. 1994).

Bayley, C.C., et al., "Exchange of gene activity in transgenic plants catalyzed by the Cre-*lox* site specific recombination system," *Plant Mol. Biol. 18*:353-361, Dordrecht Kluwer Academic, Boston, MA (1992).

Bethke, B., and Sauer, B., "Segmental genomic replacement by Cre-mediated recombination: genotoxic stress activation of the p53 promoter in single-copy transformants," *Nucl. Acids Res. 25*:2828-2834, Oxford University Press, Oxford, England (1997).

Bernard, P., and Couturier, M., "Cell Killing by the F plasmid Ccdb Protein Involves Poisoning of DNA-topoisomerase II Complexes," *J. Mol. Biol. 226*:735-745, Academic Press, Inc., New York, NY (1992).

Bernard, P., et al., "Positive Selection of vectors using the F plasmid *ccd*B killer gene," *Gene 148*:71-74, Elsevier Science Publishers B.V., Amsterdam, Netherlands (1994).

Betz, U.A.K., et al., "Bypass of lethality with mosaic mice generated by Cre-*loxP*-mediated recombination," *Curr. Biol. 6*:1307-1316, Current Biology Ltd., London, England (Oct. 1996).

Bhandari, P. and Gowrishankar, J., "An *Escherichia coli* host strain useful for efficient overproduction of cloned gene products with NaC1 as the inducer," *J. Bacteriol. 179*:4403-4406, American Society for Microbiology, Washington, D.C. (Jul. 1997).

Black, L.W., "In vitro packaging into phage T4 particles and specific recircularization of phage lambda DNAs," *Gene 46*:97-101, Elsevier/North-Holland, Netherlands (1986).

Bloch, C.A., et al., "Purification of *Escherichia coli* Chromosomal Segments without Cloning," *Biochem. Biophys. Res. Comm. 223*:104-111, Academic Press, Inc., New York, NY (1996).

Bochner, B. R., et al., "Positive Selection for Loss of Tetracycline Resistance," *J. Bacteriol. 143*:926-933, American Society for Microbiology, Washington, D.C. (1980).

Boyd, A. C., "Turbo cloning: a fast, efficient method for cloning PCR products and other blunt-ended DNA fragments into plasmids," *Nucl. Acids Res. 21*(4):817-821, Oxford University Press, Oxford, England (1993).

Broach, J. R., et al., "Recombination within the Yeast Plasmid 2μ Circle is Site-Specific," *Cell 29*:227-234, Cell Press, Cambridge, MA (1982).

Brunelli, J. P. and Pall, M. L., "A Series of Yeast/*Escherichia coli* λ Expression Vectors Designed for Directional Cloning of cDNAs and *cre/lox*-Mediated Plasmid Excision," *Yeast 9*:1309-1318, John Wiley, Chichester, NY (1993).

Brunelli, J.P., and Pall, M.L., "Lambda/Plasmid Vector Construction by In Vivo *cre/lox*-Mediated Recombination," *BioTechniques 16*(6):1061-1064, Eaton Publishing Company, Natick, MA (Jun. 1994).

Bubeck, P., et al., "Rapid cloning by homologous recombination in vivo," *Nucl. Acids Res. 21*:3601-3602, Oxford University Press, Oxford, England (1993).

Buchholz, F., et al., "A simple assay to determine the functionality of Cre or FLP recombination targets in genomic manipulation constructs," *Nucl. Acids Res. 24*(15):3118-3119, Oxford University Press, Oxford, England (1996).

Buchholz, F., et al., "Different thermostabilities of FLP and Cre recombinases: implications for applied site-specific recombination," *Nucl. Acids Res. 24*(21):4256-4262, Oxford University Press, Oxford, England (1996).

Bushman, W., et al., "Control of Directionality in Lambda Site Specific Recombination," *Science 230*:906-911, Association for the Advancement of Science, Washington D.C. (1985).

Campbell, A. M., "Chromosomal Insertion Sites for Phages and Plasmids," *J. Bacteriol. 174*(23):7495-7499, American Society for Microbiology, Washington, D.C. (1992).

Chapin, S.J., et al., "Differential expression of alternatively spliced forms of MAP4: a repertoire of structurally different microtubule-binding domains," *Biochem. 34*:2289-2301, American Chemical Society, Washington D.C. (1995).

Chatterjee, P.K., and Coren, J.S., "Isolating large nested deletions in bacterial and P1 artificial chromosomes by in vivo P1 packaging of products o Cre-catalyzed recombination between the endogenous and a transposed *loxP* site," *Nucl. Acids Res. 25*:2205-2212, Oxford University Press, Oxford, England (1997).

Cox, M.M., "The FLP protein of the yeast 2-μm plasmid: Expression of a eukaryotic genetic recombination system in *Escherichia coli," Proc. Natl. Acad. Sci. USA 80*:4223-4227, National Academy of Sciences of the USA, Washington, D.C. (1983).

Craig, N.L. and Nash, H.A., "The Mechanism of Phage λ Site-Specific Recombination: Site-Specific Breakage of DNA by Int Topoisomerase," *Cell 35*:795-803, Cell Press, Cambridge, MA (1983).

Dale, E.C. and Ow, D.W., "Intra- and intermolecular site-specific recombination in plant cells mediated by bacteriophage P1 recombinase," *Gene 91*:79-85, Elsevier/North-Holland, Netherlands (1990).

Dale, E.C. and Ow, D.W., "Gene transfer with subsequent removal of the selection gene from the host genome," *Proc. Natl. Acad. Sci. USA 88*:10558-10562, National Academy of Sciences of the USA, Washington, D.C. (1991).

Dang, D.T. and Perrimon, N., "Use of a Yeast Site-Specific Recombinase to Generate Embryonic Mosaics in *Drosophila," Develop. Genetics 13*:367-375, Wiley-Liss, Inc., New York, NY (1992).

Degryse, E., "In vivo intermolecular recombination in *Escherichia coli*: application to plasmid constructions," *Gene 170*:45-50, Elsevier/North-Holland, Netherlands (1996).

Devine, S. E., and Boeke, J.D., "Efficient integration of artificial transposons into plasmid targets in vitro: a useful tool for DNA mapping, sequencing and genetic analysis," *Nucl. Acids Res. 22*(18):3765-3772, Oxford University Press, Oxford, England (Sep. 1994).

Diederich, L., et al., "New Cloning Vectors for Integration into the λ Attachment Site *attB* of the *Escherichia coli* Chromosome," *Plasmid 28*:14-24, Academic Press, New York, NY (1992).

Dymecki, S. M., "A modular set of *Flp, FRT* and *lacZ* fusion vectors for manipulating genes by site-specific recombination," *Gene 171*:197-201, Elsevier/North-Holland, Netherlands (Jun. 1996).

Elledge, S. J., et al., "λYES: A multifunctional cDNA expression vector for the isolation of genes by complementation of yeast and *Escherichia coli* mutations," *Proc. Natl. Acad. Sci. USA 88*:1731-1735, National Academy of Sciences of the USA, Washington, D.C. (1991).

Feil, R., et al., "Regulation of Cre Recombinase Activity by Mutated Estrogen Receptor Ligand-Binding Domains," *Biochem. Biophys. Res. Comm. 237*:752-757, Academic Press, Inc., New York, NY (1997).

Ferguson, J., et al., "Construction and characterization of three yeast-*Escherichia coli* shuttle vectors designed for rapid subcloning of yeast genes on small DNA fragments," *Gene 16*:191-197, Elsevier/North-Holland, Netherlands (1981).

Fiering, S., et al., "An "in-out" strategy using gene targeting and FLP recombinase for the functional dissection of complex DNA regulatory elements: Analysis of the β-globin locus control region," *Proc. Natl. Acad. Sci. USA 90*:8469-8473, National Academy of Sciences of the USA, Washington, D.C. (1993).

Filutowicz, M., et al., "Purification of the *Escherichia coli* integration host factor (IHF) in one chromatographic step," *Gene 147*:149-150, Elsevier/North-Holland, Netherlands (Sep. 1994).

Francia M.V., and Lobo, J.M.G., "Gene Integration in the *Escherichia coli* Chromosome Mediated by Tn21 Integrase (Int21)," *J. Bacteriol. 178*:894-898, American Society for Microbiology, Washington, D.C. (Feb. 1996).

Fukushige, S. and Sauer, B., "Genomic targeting with a positive-selection *lox* integration vector allows highly reproducible gene expression in mammalian cells," *Proc. Natl. Acad. Sci. USA 89*:7905-7909, National Academy of Sciences of the USA, Washington, D.C. (1992).

Geoffroy, F., et al., "A new phage display system to construct multicombinatorial libraries of very large antibody repertoires," *Gene 151*:109-113, Elsevier/North-Holland, Netherlands (Dec. 1994).

Glasgow, A.C., et al., "DNA-binding Properties of the Hin Recombinase," *J. Biol. Chem. 264*:10072-10082, American Society for Biochemistry and Molecular Biology, Inc., Baltimore, MD (1989).

Golic, K. G. and Lindquist, S., "The FLP Recombinase of Yeast Catalyzes Site-Specific Recombination in the *Drosophila* Genome," *Cell 59*:499-509, Cell Press, Cambridge, MA (1989).

Gu, H., et al., "Deletion of a DNA Polymerase β Gene Segment in T Cells Using Cell Type-Specific Gene Targeting," *Science 265*:103-106, Association for the Advancement of Science, Washington D.C. (1994).

Guo, F., et al., "Asymmetric DNA bending in the Cre-*loxP* site-specific recombination synapse," *Proc. Natl. Acad. Sci. USA 96*:7143-7148, National Academy of Sciences of the USA, Washington, D.C. (1999).

Hardy, S., et al., "Construction of Adenovirus Vectors through Cre-*lox* Recombination," *J. Virol. 71*(3):1842-1849, American Society for Microbiology, Washington, D.C. (1997).

Hasan, N., and Szybalski, W., "Control of cloned gene expression by promoter inversion in vivo: construction of improved vectors with a multiple cloning site and the $p_{tac}$ promoter," *Gene 56*:145-151, Elsevier/North-Holland, Netherlands (1987).

Hasan, N., et al., "*Escherichia coli* genome targeting, I. Cre-*lox*-mediated in vitro generation of *ori* plasmids and their in vivo chromosomal integration and retrieval," *Gene 150*:51-56, Elsevier/North-Holland, Netherlands (Dec. 1994).

Hashimoto-Gotoh, T., et al., "Improved vector, pHSG664, for direct streptomycin-resistance selection: cDNA cloning with G:C-tailing procedure and subcloning of double-digested DNA fragments," *Gene 41*:125-128, Elsevier/North-Holland, Netherlands (1986).

Hoekstra, M. F., et al., "Shuttle Mutagenesis: Bacterial Transposons for Genetic Manipulations in Yeast," *Meth. Enzymol. 194*:329-342, Academic Press Inc., New York, NY (1991).
Hoess, R.H., et al., "P1 site-specific recombination: Nucleotide sequence of the recombining sites," *Proc. Natl. Acad. Sci. USA 79*:3398-3402, National Academy of Sciences of the USA, Washington, D.C. (1982).
Hoess, R.H., et al., "Mechanism of Strand Cleavage and Exchange in the Cre-*lox* Site-specific Recombination System," *J. Mol. Biol. 181*:351-362, Academic Press, Inc., New York, NY (1985).
Hoess, R., et al., "Formation of small circular DNA molecules via an in vitro site-specific recombination system," *Gene 40*:325-329, Elsevier/North-Holland, Netherlands (1985).
Hoess, R. H., et al., "The role of the *loxP* spacer region in P1 site-specific recombination," *Nucl. Acids Res. 14*(5):2287-2300, Oxford University Press, Oxford, England (1986).
Hoess, R. H., and Abremski, K., "The Cre-*lox* Recombination System," *in: Nucleic Acids and Molecular Biology*, vol. 4, ed. by Eckstein, F. and D. M. J. Lilley, Springer-Verlag, Berlin, pp. 99-109 (1990).
Hoogenboom, H.R., et al., "Multi-subunit proteins on the surface of filamentous phage: methodologies for displaying antibody (Fab) heavy and light chains," *Nucl. Acids Res. 19*:4133-4137, Oxford University Press, Oxford, England (1991).
Holt, C.L., and May, G.S., "A novel phage λ replacement Cre-*lox* vector that has automatic subcloning capabilities," *Gene 133*:95-97, Elsevier/North-Holland, Netherlands (1993).
Jaffé, A., et al., "Effects of the *ccd* Function of the F Plasmid on Bacterial Growth," *J. Bacteriol. 163*:841-849, American Society for Microbiology, Washington, D.C. (1985).
Kanaar, R., et al., "Gin-Mediated Recombination of Catenated and Knotted DNA Substrates: Implications for the Mechanism of Interaction Between *Cis*-Acting Sites," *Cell 58*:147-159, Cell Press, Cambridge, MA (1989).
Katz, L., et al., "Site-specific Recombination in *Escherichia coli* between the att sites of plasmid pSE211 from *Saccharopolyspora erythraea," Mol. Gen. Genet. 227*:155-159, Springer-Verlag, New York, NY (1991).
Kilby, N.J., et al., "Site-specific recombinases: tools for genome engineering," *Trends Genet. 9*:413-421, Elsevier Science Publishers Ltd., Cambridge, England (1993).
Kim, S., et al., "Lambda Int Protein Bridges Between Higher Complexes at Two Distant Chromosomal Loci *att*L and *att*R," *Science 256*:198-263, Association for the Advancement of Science, Washington D.C. (1992).
Kozak, M., "Comparison of Initiation of Protein Synthesis in Prokaryotes, Eucaryotes, and Organelles," *Microbiol. Rev. 47*:1-45, American Society for Microbiology, Washington, D.C. (1983).
Kozak, M., "An analysis of 5'-noncoding sequences from 699 vertebrate messenger RNAs," *Nucl. Acids res. 15*:8125-8132, Oxford University Press, Oxford, England (1987).
Kozak, M., "Structural features in eukaryotic mRNAs that modulate the initiation of translation," *J. Biol. Chem 266*:19867-19870, American Society for Biochemistry and Molecular Biology, Inc., Baltimore, MD (1991).
Kühn, R., et al., "Inducible Gene Targeting in Mice," *Science 269*:1427-1429, Association for the Advancement of Science, Washington D.C. (Sep. 1995).
Lafontaine, D., and Tollervey, D., "One-step PCR mediated strategy for the construction of conditionally expressed and epitope tagged yeast proteins," *Nucl. Acids Res. 24*:2469-2472, Oxford University Press, Oxford, England (1996).
Lakso, M., et al., "Targeted oncogene activation by site-specific recombination in transgenic mice," *Proc. Natl. Acad. Sci. USA 89*:6232-6236, National Academy of Sciences of the USA, Washington, D.C. (1992).
Lander, E.S., "The New Genomics: Global Views of Biology," *Science 274*:536-539, Association for the Advancement of Science, Washington D.C. (Oct. 1996).
Landy, A., "Dynamic, Structural, and Regulatory Aspects of λ Site-Specific Recombination," *Annu. Rev. Biochem. 58*:913-949, American Chemical Society, Washington D.C. (1989).
Landy, A., "Mechanistic and structural complexity in the site-specific recombination pathways of Int and FLP," *Curr. Op. Genet. Develop. 3*:699-707, Current Biology Ltd., London, England (1993).
Lebreton, B., et al., "Mutations That Improve the Binding of Yeast FLP Recombinase to Its Substrate," *Genetics 118*:393-400, Genetics Society of America, Baltimore, MD (1988).
Lee, E.C., et al., "Genetic Analysis of *Escherichia coli* Integration Host Factor Interactions with Its Bacteriophage λ H' Recognition Site," *J. Bacteriol. 173*:609-617, American Society for Microbiology, Washington, D.C. (1991).
Leong, J.M., et al., "Generation of single base-pair deletions, insertions, and substitutions by a site-specific recombination system," *Proc. Natl. Acad. Sci. USA 82*:6990-6994, National Academy of Sciences of the USA, Washington, D.C. (1985).
Liu, Q., et al., "The univector plasmid-fusion system, a method for rapid construction o recombinant DNA without restriction enzymes," *Curr. Biol. 8*:1300-1309, Current Biology Ltd., London, England (1998).
Lorbach, E. et al., "Site-specific Recombination in Human Cells Catalyzed by Phage λ Integrase Mutants," *J. Mol. Biol. 296*:1175-1181, Academic Press, Inc., New York, NY (Mar. 2000).
Luckow, V. A., et al., "Efficient Generation of Infectious Recombinant Baculoviruses by Site-Specific Transposon-Mediated Insertion of Foreign Genes into a Baculovirus Genome Propagated in *Escherichia coli," J. Virol. 67*(8):4566-4579, American Society for Microbiology, Washington, D.C. (1993).
Maeser, S., and Kahmann, R., "The Gin recombinase of phage Mu can catalyze site-specific recombination in plant protoplasts," *Mol. Gen. Genet. 230*:170-176, Springer-Verlag, New York, NY (1991).
Matsuzaki, H., et al., "Chromosome Engineering in *Saccharomyces cerevisiae* by Using a Site-Specific Recombination System of a Yeast Plasmid," *J. Bacteriol. 172*:610-618, American Society for Microbiology, Washington, D.C. (1990).
Mahillon, J., et al., "IS*231* and other *Bacillus thuringiensis* transposable elements: a review," *Genetica 93*:13-26, Dordrecht Kluwer Academic Publishers (Nov. 1994).
McCarthy, J.E. and Brimacombe, R., "Prokaryotic translation: the interactive pathway leading to initiation," *Trends Genet. 10*:402-407, Elsevier Science Publishers Ltd., Cambridge, England (Nov. 1994).
Medberry, S.L., et al., "Intra-chromosomal rearrangements generated by Cre-*lox* site-specific recombination," *Nucl. Acids Res. 23*:485-490, Oxford University Press, Oxford, England (1995).
Miki, T. et al., "Control of Segregation of Chromosomal DNA by Sex Factor F in *Escherichia coli.* Mutants of DNA Gyrase Subunit A Suppress *let*D (*ccdB*) Product Growth Inhibition," *J. Mol. Biol. 225*:39-52, Academic Press, Inc., New York, NY (1992).
Mizuuchi, K., and Mizuuchi, K., "Integrative Recombination of Bacteriophage λ: In Vitro Study of the Intermolecular Reaction," *Cold Spring Harb. Symp. Quant. Biol. 43*:1111-1114, Cold Spring Harbor Laboratory Press, Cold Spring Harbor, NY (1979).
Mizuuchi, M. and Mizuuchi, K., "The extent of DNA sequence required for a functional bacterial attachment site of phage lambda," *Nucl. Acids Res. 13*:1193-1208, Oxford University Press, Oxford, England (1985).
Mozo, T. and Hooykaas, P. J. J., "Design of a novel system for the construction of vectors for *Agrobacterium*-mediated plant transformation," *Mol. Gen. Genet 236*:1-7, Springer-Verlag, New York, NY (1992).
Mullins, L.J., et al., "Efficient Cre-lox linearisation of BACs: applications to physical mapping and generation of transgenic animals," *Nucl. Acids Res. 25*(12):2539-2540, Oxford University Press, Oxford, England (1997).
Nagaraja, R. and Weisberg, R. A., "Specificity Determinants in the Attachment Sites of Bacteriophages HK022 and λ," *J. Bacteriol. 172*:6540-6550, American Society for Microbiology, Washington, D.C. (1990).
Nash, H.A., "Integrative Recombination of Bacteriophage Lambda DNA In Vitro," *Proc. Natl. Acad. Sci. USA 72*:1072-1076, National Academy of Sciences of the USA, Washington, D.C. (1975).
Nash, H.A., and Robertson, C.A., "Purification and properties of the *Escherichia coli* protein factor required for lambda integrative recombination," *J. Biol. Chem. 256*:9246-9253, American Society for Biochemistry and Molecular Biology, Inc., Baltimore, MD (1981).
Nash, H. A., "Purification and Properties of the Bacteriophage Lambda Int Protein," *Meth. Enzymol. 100*:210-216, Academic Press Inc., New York, NY (1983).
Nash, H. A., et al., "Role of homology in site-specific recombination of bacteriophage λ: Evidence against joining of cohesive ends," *Proc. Natl. Acad. Sci. USA 84*:4049-4053, National Academy of Sciences of the USA, Washington, D.C. (1987).
Nash, H. and C.A. Robertson, "Heteroduplex substrates for bacteriophage lambda site-specific recombination: cleavage and strand transfer products," *EMBO J. 8*:3523-3533, IRL Press Limited, Oxford, England (1989).
Nash, H.A., "Bending and supercoiling of DNA at the attachment site of bacteriophage λ," *Trends Biochem. Sci 15*:222-227, International Union of Biochemistry and Elsevier Trends Journal, Cambridge, England (1990).
Numrych, T. E., et al., "A comparison of the effects of single-base and triple-base changes in the integrase arm-type binding sites on the site-specific recombination of bacteriophage lambda," *Nucl. Acids Res. 18*:3953-3959, Oxford University Press, Oxford, England (1990).
Numrych, T.E., et al., "Characterization of the bacteriophage lambda excisionase (Xis) protein: the C-terminus is required for Xis—integrase cooperativity but not for DNA binding," *EMBO J. 11*(10):3797-3806, IRL Press Limited, Oxford, England (1992).
Nunes-Düby, S.E., et al., "Half-*att* Site Substrates Reveal the Homology Independence and Minimal Protein Requirements for Productive Synapsis in λ Excisive Recombination," *Cell 59*:197-206, Cell Press, Cambridge, MA (1989).
Nunes-Düby, et al., "Similarities and differences among 105 members of the Int family of site-specific recombinases," *Nucl. Acids Res. 26*:391-406, Oxford University Press, Oxford, England (1998).
Oberto, J., et al., "A segment of the phage HK022 chromosome is a mosaic other lambdoid chromosomes," *Nucl. Acids Res. 22*(3):354-356, Oxford University Press, Oxford, England (Feb. 1994).
Oliner, J.D., et al., "In vivo cloning of PCR products in *E. coli," Nucl. Acids Res.* 21:5192-5197, Oxford University Press, Oxford, England (1993).
Orban, P. C. et al., "Tissue- and site-specific DNA recombination in transgenic mice," *Proc. Natl. Acad. Sci. USA 89*:6861-6865, National Academy of Sciences of the USA, Washington, D.C. (1992).
Osborne, B.I., et al., "A system for insertional mutagenesis and chromosomal rearrangement using the Ds transposon and Cre-*lox," Plant J. 7*:687-701, Oxford Bios Scientific Publishers And Blackwell Scientific Publications in Association With The Society For Experimental Biology, Oxford, England (1995).
Padgett, K. A. and Sorge, J. A., "Creating seamless junctions independent of restriction sites in PCR cloning," *Gene 168*:31-35, Elsevier/North-Holland, Netherlands (Feb. 1996).
Palazzolo, M. J., et al., "Phage lambda cDNA cloning vectors for subtractive hybridization, fusion-protein synthesis and Cre-*loxP* automatic plasmid subcloning," *Gene 88*:25-36, Elsevier/North-Holland, Netherlands (1990).
Pan, G., et al., "Ligation of Synthetic Activated DNA Substrates by Site-specific Recombinases and Topoisomerase I," *J. Biol. Chem. 268*(5):3683-3689, American Society for Biochemistry and Molecular Biology, Inc., Baltimore, (1993). MD (1993).
Parks, R.J., and Graham, F.L., "A Helper-Dependent System for Adenovirus Vector Production Helps Define a Lower Limit for Efficient DNA Packaging," *J. Virol. 71*(4):3293-3298, American Society for Microbiology, Washington, D.C. (1997).
Peakman, T. C., et al., "Highly efficient generation of recombinant baculoviruses by enzymatically mediated site-specific in vitro recombination," *Nucl. Acids Res. 20*:495-500, Oxford University Press, Oxford, England (1992).
Peredelchuk, M.Y., and Bennett, G.N., "A method for construction of *E. coli* strains with multiple DNA insertions in the chromosome," *Gene 187*:231-238, Elsevier/North-Holland, Netherlands (1997).
Pichel, J. G., et al., "Timing of SV40 oncogene activation by site-specific recombination determines subsequent tumor progression during murine lens development," *Gene 8*:3333-3342, Elsevier/North-Holland, Netherlands (1993).
Pierce, J. C., et al., "A positive selection vector for cloning high molecular weight DNA by the bacteriophage P1 system: Improved cloning efficacy," *Proc. Natl. Acad. Sci. USA 89*:2056-2060, National Academy of Sciences of the USA, Washington, D.C. (1992).
Podhajska, A. J., et al., "Control of cloned gene expression by promoter inversion in vivo: construction of the heat-pulse-activated *att-nut*L-*p-att-N* module," *Gene 40*:163-168, Elsevier/North-Holland, Netherlands (1985).
Pósfai, G., et al., "In vivo excision and amplification of large segments of the *Escherichia coli* genome," *Nucl. Acids Res. 22*(12)2392-2398, Oxford University Press, Oxford, England (Jun. 1994).
Prasad, P. V., et al., "Substrate Recognition by the 2 μm Circle Site-Specific Recombinase: Effect of Mutations within the Symmetry Elements of the Minimal Substrate," *Mol. Cell. Biol. 6*:4329-4334, American Society for Microbiology, Washington, D.C. (1986).
Qian, X., et al., "Reactions between Half- and Full-FLP Recombination Target Sites: A Model System for Analyzing Early Steps in FLP Protein-Mediated Site-Specific Recombination," *J. Biol. Chem 267*(11):7794-7805, American Society for Biochemistry and Molecular Biology, Inc., Baltimore, MD (1992).
Reed, R.R., "Transposon-Mediated Site-Specific Recombination: A Defined in Vitro System," *Cell 25*:713-719, Cell Press, Cambridge, MA (1981).
Reed, R.R. and N.D. Grindley, "Transposon-Mediated Site-Specific Recombination in Vitro: DNA Cleavage and Protein-DNA Linkage at the Recombination Site," *Cell. 25*:721-728, Cell Press, Cambridge, MA (1981).
Richet, E., et al., "The Interaction of Recombination Proteins with Supercoiled DNA: Defining the Role of Supercoiling in Lambda Integrative Recombination," *Cell 46*:1011-1021, Cell Press, Cambridge, MA (1986).
Richet, E., et al., "Synapsis of Attachment Sites during Lambda Integrative Recombination Involves Capture of a Naked DNA by a Protein-DNA Complex," *Cell 52*:9-17, Cell Press, Cambridge, MA (1988).
Sadowski, P., "Site-Specific Recombinases: Changing Partners and Doing the Twist," *J. Bacteriol. 165*(2):341-347, American Society for Microbiology, Washington, D.C. (1986).
Sadowski, P.D., "The Flp recombinase of the 2-microns plasmid of *Saccharomyces cerevisiae," Prog. Nucl. Acid Res. Mol. Biol. 51*:53-91, Academic Press, New York, NY (1995).
Sauer, B., et al., "Site-specific insertion of DNA into a pseudorabies virus vector," *Proc. Natl. Acad. Sci. USA 84*:9108-9112, National Academy of Sciences of the USA, Washington, D.C. (1987).
Sauer, B., "Functional Expression of the *cre-lox* Site-Specific Recombination System in the Yeast *Saccharomyces cerevisiae," Mol. Cell. Biol. 7*:2087-2096, American Society for Microbiology, Washington, D.C. (1987).
Sauer, B. and Henderson, N., "The cyclization of linear DNA in *Escherichia coli* by site-specific recombination," *Gene 70*:331-341, Elsevier/North-Holland, Netherlands (1988).
Sauer B. and Henderson, N., "Cre-stimulated recombination at *loxP*-containing DNA sequences placed into the mammalian genome," *Nucl. Acids Res. 17*:147-161, Oxford University Press, Oxford, England (1989).
Sauer, B., "Manipulation of Transgenes by Site-Specific Recombination: Use of Cre Recombinase," *Meth. Enzymol. 225*:890-900, Academic Press Inc., New York, NY (1993).
Sauer, B., "Site-specific recombination: developments and applications," *Curr. Op. Biotechnol. 5*:521-527, Current Biology, Ltd., London, England (Oct. 1994).
Sauer, B., "Multiplex Cre/*lox* recombination permits selective site-specific DNA targeting to both a natural and an engineered site in the yeast genome," *Nucl. Acids Res. 24*(23):4608-4613, Oxford University Press, Oxford, England (1996).
Sauer, B., "Inducible Gene Targeting in Mice Using the Cre/*lox* System," *Methods 14*:381-392, Academic Press, Inc., New York, NY (Apr. 1998).
Schindelhauer, D., and Cooke, H.J., "Efficient combination of large DNA in vitro: in gel site specific recombination (IGSSR) of PAC fragments containing α satellite DNA and the human HPRT gene locus," *Nucl. Acids Res. 25*(11):2241-2243, Oxford University Press, Oxford, England (1997).

Schlake, T., and Bode, J., "Use of Mutated FLP Recognition Target (FRT) Sites for the Exchange of Expression Cassettes at Defined Chromosomal Loci," *Biochem. 33*:12746-12751, American Chemical Society, Washington D.C. (Nov. 1994).

Segall, A. M. and Nash, H. A., "Synaptic intermediates in bacteriophage lambda site-specific recombination: integrase can align pairs of attachment sites," *EMBO J. 12*:4567-4576, IRL Press Limited, Oxford, England (1993).

Segall, A.M., and Nash, H.A., "Architectural flexibility in lambda site-specific recombination: three alternate conformations channel the *attL* site into three distinct pathways," *Genes to Cells 1*:453-463, Blackwell Science Ltd., Oxford, England (1996).

Senecoff, J.F., et al., "DNA Recognition by the FLP Recombinase of the Yeast 2 λ Plasmid—A Mutational Analysis of the FLP Binding Site," *J. Mol. Biol. 201*:405- 421, Academic Press, Inc., New York, NY (1988).

Sheffield, P. et al., "Overcoming Expression and Purification Problems of RhoGDI Using a Family of "Parallel" Expression Vectors," *Protein Expr. Purific. 15*:34-39, Academic Press, New York, NY (1999).

Shuman, S., "Recombination mediated by vaccinia virus DNA topoisomerase I in *Escherichia coli* is sequence specific," *Proc. Natl. Acad. Sci. USA 88*:10104-10108, National Academy of Sciences of the USA, Washington, D.C. (1991).

Sizemore, C., et al., "Quantitative analysis of Tn*10* Tet repressor binding to a complete set of *tet* operator mutants," *Nucl. Acids Res. 18*(10):2875-2880, Oxford University Press, Oxford, England (1990).

Smith, A. J. H., et al., "A site-directed chromosomal translocation induced in embryonic stem cells by Cre-*lox*P recombination," *Nat. Gen. 9*:376-385, Nature Publishing Co., New York, NY (Apr. 1995).

Snaith, M.R., et al., "Multiple cloning sites carrying *loxP* and *FRT* recognition sites for the Cre and Flp site-specific recombinases," *Gene 166*:173-174, Elsevier/North-Holland, Netherlands (Dec. 1995).

Spengler, S.J., et al., "The Stereostructure of Knots and Catenanes Produced by Phage λ Integrative Recombination: Implications for Mechanism and DNA Structure," *Cell 42*:325-334, Cell Press, Cambridge, MA (1985).

Sternberg, N., et al., "Site-specific Recombination and Its Role in the Life Cycle of Bacteriophage P1," *Cold Spring Harbor Symp. Quant. Biol. 45*:297-309, Cold Spring Harbor Laboratory Press, Cold Spring Harbor, NY (1981).

Sternberg, N., et al., "Bacteriophage P1 *cre* Gene and its Regulatory Region," *J. Mol. Biol. 187*:197-212, Academic Press, Inc., New York, NY (1986).

Sternberg, N., "Bacteriophage P1 cloning system for the isolation, amplification, and recovery of DNA fragments as large as 100 kilobase pairs," *Proc. Natl. Acad. Sci. USA 87*:103-107, National Academy of Sciences of the USA, Washington, D.C. (1990).

Storck, T., et al., "Rapid construction in yeast of complex targeting vectors for gene manipulation in the mouse," *Nucl. Acids Res. 24*:4594-4596, Oxford University Press, Oxford, England (1996).

Strathmann, M., et al., "Transposon-facilitated DNS sequencing," *Proc. Natl. Acad. Sci. USA 88*:1247-1250, National Academy of Sciences of the USA, Washington, D.C. (1991).

Thompson, J. F., et al., "Mutations in an Integration Host Factor-Binding Site: Effect on Lambda Site-Specific Recombination and Regulatory Implications," *J. Bacteriol. 168*:1343-1351, American Society for Microbiology, Washington, D.C. (1986).

Thompson, J.F., et al., "Helical-repeat dependence of integrative recombination of bacteriophage λ: Role of the *P1* and *H1* protein binding sites," *Proc. Natl. Acad. Sci. USA 85*:6323-6327, National Academy of Sciences of the USA, Washington, D.C. (1988).

Thorpe, H.M., and Smith, M.C.M., "In vitro site-specific integration of bacteriophage DNA catalyzed by a recombinase of the resolvase/invertase family," *Proc. Natl. Acad. Sci. USA 95*:5505-5510, National Academy of Sciences of the USA, Washington, D.C. (May 1998).

Tsurushita, N., et al., "Phage display vectors for in vivo recombination of immunoglobulin heavy and light chain genes to make large combinatorial libraries," *Gene 172*:59-63, Elsevier/North-Holland, Netherlands (1996).

Vanin, E.F., et al., "Development of High-Titer Retroviral Producer Cell Lines Using Cre-Mediated Recombination," *J. Virol. 71*:7820-7826, American Society for Microbiology, Washington, D.C. (1997).

Waterhouse, P., et al., "Combinatorial infection and in vivo recombination: a strategy for making large phage antibody repertoires," *Nucl. Acids Res. 21*(9):2265-2266, Oxford University Press, Oxford, England (1993).

Wang, G., et al., "pDUAL: A transposon-based cosmid cloning vector for generating nested deletions and DNA sequencing templates in vivo," *Proc. Natl. Acad. Sci. USA 90*:7874-7878, National Academy of Sciences of the USA, Washington, D.C. (1993).

Wasserman, S.A., et al., "The helical repeat of double-stranded DNA varies as a function of catenation and supercoiling," *Nature 334*:448-450, Macmillan Publishers Ltd., London, England (1988).

Wierzbicki, A., et al., "A Mutational Analysis of the Bacteriophage P1 Recombinase Cre," *J. Mol. Biol. 195*:785-794, Academic Press, Inc., New York, NY (1987).

Weisberg, R. A., and Landy, A., "Site-specific Recombination in Phage Lambda," in: "*Lambda II*," Hendrix, R. W. et al., eds., Cold Spring Harbor Laboratory Press, Cold Spring Harbor, N. Y., pp. 211-250 (1983).

Wild, J., et al., "A broad-host-range in vivo pop-out and amplification system for generating large quantities of 50- to 100-kb genomic fragments for direct DNA sequencing," *Gene 179*:181-188, Elsevier/North-Holland, Netherlands (1996).

Wild, J., et al., "Targeting and retrofitting pre-existing libraries of transposon insertions with *FRT* and *oriV* elements for in-vivo generation of large quantities of any genomic fragment," *Gene 223*:55-66, Elsevier/North-Holland, Netherlands (1998).

Winoto, A., et al., "Directional Control of Site-specific Recombination by Bacteriophage λ," *J. Mol. Biol. 192*:677-680, Academic Press, Inc., New York, NY (1986).

Yang, W., and Mizuuchi, K., "Site-specific recombination in plane view," *Structure 5*:1401-1406, Current Biology, London, England (1997).

Yanisch-Perron, C., et al., "Improved M13 phage cloning vectors and host strains: nucleotide sequences of the M13mp18 and pUC19 vectors," *Gene 33*:103-119, Elsevier/North-Holland, Netherlands (1985).

Yoon, Y.G., et al., "Cre/*loxP*-mediated in vivo excision of large segments from yeast genome and their amplification based on the 2 μm plasmid-derived system," *Gene 223*:67-76, Elsevier/North-Holland, Netherlands (1998).

York, D., et al., "Simple and efficient generation in vitro of nested deletions and inversions: Tn*5* intramolecular transposition," *Nucl. Acids Res. 26*:1927-1933, Oxford University Press, Oxford, England (1998).

Zhang, Y. et al., "A new logic for DNA engineering using recombination in *Escherichia coli," Nat. Genet. 20*:123-128, Nature Publishing Co., New York, NY (1998).

Zhu, et al., "Homology requirements for ligation and strand exchange by the FLP recombinase," *J. Biol. Chem. 270*:11646-11653, American Society for Biochemistry and Molecular Biology, Inc., Baltimore, MD (1995).

International Search Report for International Application No. PCT/US98/22589, mailed Oct. 26, 1998.

Gage, P.J., et al., "A Cell-Free Recombination System for Site-Specific Integration of Multigenic Shuttle Plasmids into Herpes Simplex Type 1 Genome," *J. Virol. 66*:5509-5515, American Society for Microbiology, Washington, D.C. (1992).

Götz, F., et al., "*Escherichia coli* 30S mutants lacking protein S20 are defective in translation initiation," *Biochim. Biophys. Acta 1050*:93-97, Elsevier Publishing Co., Amsterdam, Netherlands (1990).

Green, R. and Noller, H.F., "Ribosomes and Translation," *Ann. Rev. Biochem. 66*:679-716, Annual Reviews, Inc., Palo Alto, CA (1997).

Jeong, J. -H., et al., "Cloning and nucleotide sequencing of the genes, *rplU* and *rpmA*, for ribosomal proteins L21 and L27 of *Escherichia coli," J. DNA sequencing and Mapping 4*:59-67, Harwood Academic Publishers GmbH, Switzerland (1993).

Kitts, P.A. and Nash, H.A., "Bacteriophage Lambda Site-Specific Recombination Proceeds with a Defined Order of Strand Exchanges," *J. Mol. Biol. 204*:95-107, Academic Press, Inc., New York, NY (1988).
Lake, J.A., "Evolving Ribosome Structure: Domains in Archaebacteria, Eubacteria, Eocytes and Eukaryotes," *Ann. Rev. Biochem. 54*:507-530, Annual Reviews, Inc., Palo Alto, CA (1985).
Mackie, G.A., "Nucleotide Sequence of the Gene for Ribosomal Protein S20 and Its Flanking Regions," *J. Biol. Chem. 256*:8177-8182, American Society for Biochemistry and Molecular Biology, Inc., Baltimore, MD (1981).
Nomura, M. et al., "Regulation of the Synthesis of Ribosomes and Ribosomal Components," *Ann. Rev. Biochem. 53*:75-117, Annual Reviews, Inc., Palo Alto, CA (1984).
Wittman, H.G., "Components of Bacterial Ribosomes," *Ann. Rev. Biochem. 51*:155-183, Annual Reviews, Inc., Palo Alto, CA (1982).
Wittmann, H.G., "Architecture of Prokaryotic Ribosomes," *Ann. Rev. Biochem. 52*:35-65, Annual Reviews, Inc., Palo Alto, CA (1983).
Jayaram, M., "The Int family of site-specific recombinases: Some thoughts on a general reaction mechanism," *J. Genet. 67*:29-36, Indian Academy of Sciences Bangalore, Bangalore, India (1988).
Simpson, J.C., et al., "Systematic subcellular localization of novel proteins identified by large-scale cDNA sequencing," *EMBO Reports 1*:287-292, IRL Press Limited, Oxford, England (Sep. 2000).
Pending U.S. Appl. No. 09/177,387, filed Oct. 23, 1998.
Pending U.S. Appl. No. 09/233,492, filed Jan. 20, 1999.
Pending U.S. Appl. No. 09/296,280, filed Apr. 22, 1999.
Pending U.S. Appl. No. 09/296,281, filed Apr. 22, 1999.
Pending U.S. Appl. No. 09/432,085, filed Nov. 2, 1999.
Pending U.S. Appl. No. 09/438,358, filed Nov. 12, 1999.
Pending U.S. Appl. No. 09/498,074, filed Feb. 4, 2000.
Pending U.S. Appl. No. 09/518,188, filed Mar. 2, 2000.
Pending U.S. Appl. No. 09/648,790, filed Aug. 28, 2000.
Pending U.S. Appl. No. 09/695,065, filed Oct. 25, 2000.
Pending U.S. Appl. No. 09/732,914, filed Dec. 11, 2000.
Ball, C.A., and Johnson, R.C., "Efficient Excision of Phage λ from the *Escherichia coli* Chromosome Requires the Fis Protein," *J. Bacteria 173*: 4027-4031, American Society for Microbiology (1991).
Bruckner, R.C., and Cox, M.M., "The Histone-like H Protein of *Escherichia coli* is a ribosomal protein s3," *Nucl. Acids Res. 17*:3145-3161, Oxford University Press (1989).
Hartley, J.L., et al., "DNA Cloning Using in Vitro Site-Specific Recombination," *Genome Res. 10*:1788-1795, Cold Spring Harbor Laboratory Press (Nov. 2000).
Heyman, J.A., et al., "Genome-Scale Cloning and Expression of Individual Open Reading Frames Using Topoisomerase I-Mediated Ligation," *Genome Res. 9*:383-392, Cold Spring Harbor Laboratory Press (Apr. 1999).
Institut Pasteur Website, Introduction: http://www.pasteur.fr/recherche/unites/pmtg/integ/intro.html (accessed Jun. 19, 2003).
Institut Pasteur Website, Figure 1: http://www.pasteur.fr/recherche/unites/pmtg/integ/fig1.html (accessed Jun. 19, 2003).
Institut Pasteur Website, Figure 2: http://www.pasteur.fr/recherche/unites/pmtg/integ/fig2.html (accessed Jun. 19, 2003).
Institut Pasteur Website, Figure 3: http://www.pasteur.fr/recherche/unites/pmtg/integ/fig3.html (accessed Jun. 19, 2003).
Institut Pasteur Website, Main Page: http://www.pasteur.fr/recherche/unites/pmtg (accessed Jun. 19, 2003).
Invitrogen Online Catalog, "The Echo™ Cloning System: The Future of Cloning is Here," available at: http://web.archive.org/web/20010112191100/www.invitrogen.com/catalog_project/cat_echo.html (accessed Jul. 7, 2004).
Invitrogen Online Catalog, "The Echo™ Cloning System: The Future of Cloning is Here," available at: http ://invitrogen.com/content.cfm?pageid=3371&cfid=16767784&cftoken=62396683 (accessed Jul. 7, 2004).
Kuempel, P., et al., "Use of a transposon (Tn*dif*) to obtain suppressing and nonsuppressing insertions of the *dif* resolvase site of *Eschericia coli," Genes & Development 10*:1162-1171, Cold Spring Harbor Laboratory Press (1996).
Lee, M.H., et al., "Site-specific integration of mycobacteriophage L5: Integration-proficient vectors for *Mycobacterium smegmatis, Mycobacterium tuberculosis*, and bacille Calmette-Guérin," *Proc. Natl. Acad. Sci. USA 88*:3111-3115, National Academy of Sciences (1991).
Lenski, R.E., et al., "Genetic Analysis of a Plasmid-Encoded, Host Genotype-Specific Enhancement of Bacterial Fitness," *J. Bacteriol. 176*:3140-3147, American Society For Microbiology (1994).
Manning, P.A., et al., "Gene Capture in *Vibrio cholera," Trends in Microbiology 7*:93-95, Elsevier Science (Mar. 1999).
Ohara, O., and Temple, G., "Directional cDNA library construction assisted by the in vitro recombination reaction," *Nucl. Acids Research 29*:e22(1-8), Oxford University Press (Feb. 2001).
Russell, M., "A recombination-based cloning system that decreases time to protein analysis," *Am. Biotechnol. Lab. 18*:8,10, International Scientific Communications, Inc. (Jun. 2000).
Shuman, S., "Novel Approach to Molecular Cloning and Polynucleotide Synthesis Using Vaccinia DNA Topoisomerase," *J. Biol. Chem. 269*:32678-32684, American Society for Biochemistry and Molecular Biology, Inc. (1994).
Sinclair, B., "Honing Your Cloning," *The Scientist 14*:29-32, the Scientist Inc. (Aug. 21, 2000) available at: http://www.the-scientist.com/yr2000/aug/profile1_000821.html.
Stuurman, J., et al., "Single-site manipulation of tomato chromosomes in vitro and in vivo using Cre-*lox* site-specific recombination," *Plant Molecular Biology 32*:901-913, Kluwer Academic Publishers (1996).
Zechiedrich, E.L., et al., "Topoisomerase IV, not gyrase, decatenates products of site-specific recombination in *Escherichia coli," Genes Dev. 11*:2580-2592, Cold Spring Harbor Laboratory Press (1997).
Office Action for U.S. Appl. No. 09/907,719, mailed on Jul. 13, 2004.
Office Action for U.S. Appl. No. 09/432,085, mailed on Jul. 16, 2004.
Office Action for U.S. Appl. No. 10/058,291, mailed on Sep. 22, 2004.
Office Action for U.S. Appl. No. 10/058,292, mailed on Sep. 22, 2004.
Office Action for U.S. Appl. No. 09/855,797, mailed on Oct. 1, 2004.
Office Action for U.S. Appl. No. 09/695,065, mailed on Oct. 27, 2004.
Office Action for U.S. Appl. No. 10/820,133 mailed on Nov. 17, 2004.
Agah, R., et al., "Gene Recombination in Postmitotic Cells. Targeted Expression of Cre Recombinase Provokes Cardiac-restricted, Site-specific Rearrangement in Adult Ventricular Muscle In Vivo," *J. Clin. Invest. 100*:169-179, The American Society for Clinical Investigation, Inc. (1997).
Benoist, C. and Chambon, P., "In vivo sequence requirements of the SV40 early promoter region," *Nature 290*:304-310, Macmillan Journals, Ltd. (1981).
Botstein, D., et al., "Making Mutations in Vitro and Putting Them Back Into Yeast," in *From Gene to Protein: Translation into Biotechnology*, Ahmad, F., et al., eds., Academic Press, New York, NY, pp. 265-274 (1982).
Broach, J.R., "The Yeast Plasmid 2μ Circle," *Cell 28*:203-204, MIT (1982).
Cenatiempo, Y., "Prokaryotic gene expression in vitro: transcription-translation coupled systems," *Biochimie 68*:505-515, Elsevier (1986).
Christiansen, B., et al., "A Resolvase-Like Protein Is Required for the Site-Specific Integration of the Temperate Lactococcal Bacteriophage TP901-1," *J. Bacteriol. 178*:5164-5173, American Society for Microbiology (1996).
Crellin, P.K. and Rood, J.I., "The Resolvase/Invertase Domain of the Site-Specific Recombinase TnpX Is Functional and Recognizes a Target Sequence That Resembles the Junction of the Circular Form of the *Clostridium pelfringens* Transposon Tn*4451," J. Bacteriol. 179*:5148-5156, American Society for Microbiology (1997).
Ferrin, L.J. and Camerini-Otero, R.D., "Sequence-specific ligation of DNA using RecA protein," *Proc. Natl. Acad. Sci. USA 95*:2152-2157, National Academy of Sciences (Mar. 1998).
Golic, K.G. and Golic, M.M., "Engineering the *Drosophilia* Genome: Chromosome Rearrangements by Design," *Genetics 144*:1693-1711, The Genetics Society of America (1996).
Gottesman, S., "Bacterial Regulation: Global Regulatory Networks," *Ann. Rev. Genet. 18*:415-441, Annual Reviews, Inc. (1984).

Guo, F., et al., "Structure of Cre recombinase complexed with DNA in a site-specific recombination synapse," *Nature 389*:40-46, Nature Publishing Group (1997).
Hallet, B. and Sherratt, D.J., "Transposition and site-specific recombination: adapting DNA cut-and-paste mechanisms to a variety of genetic rearrangements," *FEMS Microbiol. Rev. 21*:157-178, Elsevier Science B.V. (1997).
Hamer, D.H. and Walling, M., "Regulation In Vivo of a Cloned Mammalian Gene: Cadmium Induces the Transcription of a Mouse Metallothionein Gene in SV40 Vectors," *J. Mol. Appl. Genet. 1*:273-288, Raven Press (1982).
Hanks, S.K. and Hunter, T., "The eukaryotic protein kinase superfamily: kinase (catalytic) domain structure and classification," *FASEB J. 9*:576-596, The Federation of American Societies for Experimental Biology (1995).
Huang, L-C., et al., "Convenient and Reversible Site-Specific Targeting of Exogenous DNA into a Bacterial Chromosome by Use of the FLP Recombinase: the FLIRT System," *J. Bacteriol. 179*:6076-6083, American Society for Microbiology (1997).
John, Jr., J.F. and Twitty, J.A., "Plasmids as Epidemiologic Markers in Nosocomial Gram-Negative *Bacilli*: Experience at a University and Review of the Literature," *Rev. Infect. Dis. 8*:693-704, University of Chicago (1986).
Johnston, S.A. and Hopper, J.E., "Isolation of the yeast regulatory gene *GAL4* and analysis of its dosage effects on the galactose/melibiose regulon," *Proc. Natl. Acad. Sci. USA 79*:6971-6975, National Academy of Sciences (1982).
Kendall, K.J. and Cohen, S.N., "Plasmid Transfer in *Streptomyces lividans*: Identification of a *kil-kor* System Associated with the Transfer Region of pIJ101," *J. Bacteriol. 169*:4177-4183, American Society for Microbiology (1987).
Lyznik, L.A., et al., "Activity of yeast FLP recombinase in maize and rice protoplasts," *Nucleic Acids Res. 21*:969-975, Oxford University Press (1993).
Maniatis, T., "Recombinant DNA Procedures in the Study of Eukaryotic Genes," in *Cell Biology: A Comprehensive Treatise*, vol. 3, *Gene Expression: The Production of RNA's*, Goldstein, L., and Prescott, D.M., eds., Academic Press, Inc., New York, NY, pp. 563-608 (1980).
Mayer, B.J. and Baltimore, D., "Signalling through SH2 and SH3 domains," *Trends Cell Biol. 3*:8-13, Elsevier Science (1993).
McKnight, S.L., "Functional Relationships between Transcriptional Control Signals of the Thymidine Kinase Gene of Herpes Simplex Virus," *Cell 31*:355-365, MIT (1982).
Nunes-Düby, S.E., et al., "λ Integrase cleaves DNA in cis," *EMBO J. 13*:4421-4430, Oxford University Press (1994).
Odell, J., et al., "Site-directed recombination in the genome of transgenic tobacco," *Mol. Gen. Genet. 223*:369-378, Springer-Verlag (1990).
Peterson, B.Ø. and Shuman, S., "Hisitidine 265 Is Important for Covalent Catalysis by Vaccinia Topoisomerase and Is Conserved in All Eukaryotic Type I Enzymes," *J. Biol. Chem. 272*:3891-3896, The American Society for Biochemistry and Molecular Biology, Inc. (1997).
Rausch, H. and Lehmann, M., "Structural analysis of the actinophage ΦC31 attachment site," *Nucleic Acids Res. 19*:5187-5189, IRL Press (1991).
Sadowski, I., et al., "A Noncatalytic Domain Conserved among Cytoplasmic Protein-Tyrosine Kinases Modifies the Kinase Function and Transforming Activity of Fujinami Sarcoma Virus P130$^{gag-fps}$," *Mol. Cell. Biol. 6*:4396-4408, American Society for Microbiology (1986).
Sauer, B. and Henderson, N., "Targeted Insertion of Exogenous DNA into the Eukaryotic Genome by the Cre Recombinase," *New Biol. 2*:441-449, Saunders Scientific Publications/W.B. Saunders Company (1990).
Senecoff, J.F., et al., "The FLP recombinase of the yeast 2-μm plasmid: Characterization of its recombination site," *Proc. Natl. Acad. Sci. USA 82*:7270-7274, National Academy of Sciences (1985).
Shaikh, A.C. and Sadowski, P.D., "The Cre Recombinase Cleaves the *lox* Site in *trans*," *J. Biol. Chem. 272*:5695-5702, The American Society for Biochemistry and Molecular Biology, Inc. (1997).
Shirai, M., et al., "Site-Specific Integration of the Actinophage R4 Genome into the Chromosome of *Streptomyces parvulus* upon Lysogenization," *J. Bacteriol. 173*:4237-4239, American Society for Microbiology (1991).
Shuman, S., et al., "Characterization of Vaccinia Virus DNA Topoisomerase I Expressed in *Escherichia coli*," *J. Biol. Chem. 263*:16401-16407, The American Society for Biochemistry and Molecular Biology, Inc. (1988).
Shuman, S., "Site-specific Interaction of Vaccinia Virus Topoisomerase I with Duplex DNA. Minimal DNA Substrate for Strand Cleavage in Vitro," *J. Biol. Chem. 266*:11372-11379, The American Society for Biochemistry and Molecular Biology, Inc. (1991).
Shuman, S., "Erratum: Site-specific Interaction of Vaccinia Virus Topoisomerase I with Duplex DNA. Minimal DNA Substrate for Strand Cleavage In Vitro," *J. Biol. Chem. 266*:20576-20577, The American Society for Biochemistry and Molecular Biology, Inc. (1991).
Silver, P.A., et al., "Amino terminus of the yeast *GAL4* gene product is sufficient for nuclear localization," *Proc. Natl. Acad. Sci. USA 81*:5951-5955, National Academy of Sciences (1984).
Stark, W.M., et al., "Catalysis by site-specific recombinases," *Trends Genet. 8*:432-439, Elsevier Science (1992).
Ulmanen, I., et al., "Transcription and Translation of Foreign Genes in *Bacillus subtilis* by the Aid of a Secretion Vector," *J. Bacteriol. 162*:176-182, American Society for Microbiology (1985).
van Deursen, J., et al., "Cre-mediated site-specific translocation between nonhomologous mouse chromosomes," *Proc. Natl. Acad. Sci. USA 92*:7376-7380, National Academy of Sciences (1995).
Ward, J.M., et al., "Construction and characterisation of a series of multi-copy promoter-probe plasmid vectors for *Streptomyces* using the aminoglycoside phosphotransferase gene from Tn*5* as inidicator," *Mol. Gen. Genet. 203*:468-478, Springer-Verlag (1986).
Invitrogen Life Technologies online catalog, "Directional TOPO Entry Vectors," 4 pages, accessed Sep. 27, 2002, available at: http://www.invitrogen.com/content.cfm?pageid=3799&cfid=2897960&cftoken=88086554.
Dialog File 351, Derwent World Patent Index, English Language Abstract for French Patent No. FR 2 670 502 (Document AL20) and PCT Patent No. WO 92/10577 (Document AM20), WPI Accession No. 9107201.
Office Action for U.S. Appl. No. 09/907,719 mailed on Dec. 28, 2004.
Office Action for U.S. Appl. No. 09/432,085, mailed on Dec. 28, 2004.
Baum, J.A., "Tn*5401*, a New Class II Transposable Element From *Bacillus thuringiensis*," *J. Bacteriol. 176*:2835-2845, American Society for Microbiology (1994).
Office Action for U.S. Appl. No. 10/796,868, mailed on Jan. 25, 2005.
Short, J.M. et al.,"λ ZAP: a bacteriophage λ expression vector with in vivo excision properties," *Nucleic Acids Research 16*:7583-7600, IRL Press Limited (1988).
Alonso, J.C., "Site-specific recombination in Gram-positive theta-replicating plasmids," *FEMS Microbiol. Lett. 142*:1-10, Elsevier Science B.V. (1996).
Amin, A.A., et al., "Synthesis of an Enzymatically Active FLP Recombinase In Vitro: Search for a DNA-Binding Domain," *Molec. Cell. Biol. 9*: 1987-1995, American Society for Microbiology (1989).
Aoki, K., et al., "Efficient Generation of Recombinant Adenoviral Vectors bt Cre-lox Recombination in Vitro," *Molec. Med. 5*:224-231, Springer (Apr. 1999).
Baum, J.A., "Tn*5401*, a New Class II Transposable Element from *Bacillus thuringiensis*," *J. Bacteriol. 176*:2835-2845, American Society for Microbiology (1994).
Bliska, J.B and Cozzarelli, N.R., "Use of Site-Specific Recombination as a Probe of DNA Structure and Metabolism in Vivo," *J. Molec. Biol. 194*:205-218, Academic Press Inc. (1987).
Carninci, P. and Hayashizaki, Y., "High-Efficiency Full-Length cDNA Cloning," *Meth. Enzymol. 303*:19-44, Academic Press (May 1999).
Chatterjee, P.K. and Sternberg, N.L., "Retrofitting High Molecular Weight DNA Cloned in P1: Introduction of Reporter Genes, Markers Selectable in Mammalian Cells and Generation of Nested Deletions," *Genet. Anal.: Biomolec. Eng. 13*:33-42, Elsevier Science B.V. (1996).
Gotou, N., et al., "Gateway, Cloning Technology," *Exp. Med. Sci. 18*:2716-2717, Invitrogen Corporation (Dec. 2000).
English language translation for Gotou, N., et al., "Gateway, Cloning Technology," *Exp. Med. Sci. 18*:2716-2717, Invitrogen Corporation (Dec. 2000).
Huang, L.-C., et al., "A bacterial model system for chromosomal targeting," *Nucl. Acids Res. 19*:443-448, Oxford University Press (1991).
Kanegae, Y., et al., "Efficient gene activation in mammalian cells by using recombinant adenovirus expressing site-specific Cre recombinase," *Nucl. Acids Res. 23*:3816-3821, Oxford University Press (1995).
Kijima, T., et al., "Application of the Cre Recombinase/*loxP* System Further Enhances Antitumor Effects in Cell Type-specific Gene Therapy against Carcinoembryonic Antigen-producing Cancer," *Canc. Res. 59*:4906-4911, American Association for Cancer Research, Inc. (Oct. 1999).
Lieber, A., et al., "Recombinant Adenoviruses with Large Deletions Generated by Cre-Mediated Excision Exhibit Different Biological Properties Compared with First-Generation Vectors In Vitro and In Vivo," *J. Virol. 70*:8944-8960, American Society for Microbiology (1996).
Liu, X. and Gorovsky, M.A., "Mapping the 5' and 3' Ends of *Tetrahymena thermophelia* mRNAs Using RNA Ligase Mediated Amplification of cDNA Ends (RLM-RACE)," *Nucl. Acids Res. 21*:4954-4960, Oxford University Press (1993).
NCBI Entrez, Genbank Report, Accession No. Y08806, Zucman-Rossi, J., et al., (first available Nov. 1996 and last updated Apr. 2005).
Ng, P., et al., "A High-Efficiency Cre//*loxP*-Based System for Construction of Adenoviral Vectors," *Human Gene Ther. 10*:2667-2672, Mary Ann Liebert, Inc. (Nov. 1999).
Short, J.M., et al., "λ ZAP: a bacteriophage λ expression vector with in vivo excision properties," *Nucl Acids Res. 16*:7583-7600, IRL Press Ltd. at Oxford University Press (1988).
Walhout, A.J.M., et al., "Protein Interaction Mapping in *C. elegans* Using Proteins Involved in Vulval Development," *Science 287*:116-122, American Association for the Advancement of Science (Jan. 2000).
Walhout, A.J.M., et al., "Gateway Recombinational Cloning: Application to the Cloning of Large Numbers of Open Reading Frames or ORFeomes," *Meth. Enzymol. 328*:575-592, Academic Press (Sep. 2000).
Wang, Y. et al., "Targeted DNA recombination in vivo using an adenovirus carrying the cre recombinase gene," *Proc. Natl. Acad. Sci. USA 93*:3932-3936, National Academy of Sciences (1996).
Zucman-Rossi, J., et al., "Chromosome translocation based on illegitimate recombination in human tumors," *Proc. Natl. Acad. Sci. USA 95*:11786-11791, National Academy of Sciences (Sep. 1998).
Office Action for U.S. Appl. No. 09/432,085, Hartley et al., mailed Dec. 28, 2004.
Office Action for U.S. Appl. No. 09/432,085, Hartley et al., mailed Jun. 16, 2005.
Office Action for U.S. Appl. No. 09/855,797, Hartley et al., mailed Apr. 20, 2005.
Office Action for U.S. Appl. No. 09/855,797, Hartley et al., mailed Oct. 11, 2005.
Office Action for U.S. Appl. No. 09/907,719, Hartley et al., mailed Dec. 28, 2004.
Office Action for U.S. Appl. No. 09/907,719, Hartley et al., mailed Jul. 26, 2005.
Office Action for U.S. Appl. No. 10/058,291, Hartley et al., mailed Apr. 28, 2005.
Office Action for U.S. Appl. No. 10/058,291, Hartley et al., mailed Oct. 21, 2005.
Office Action for U.S. Appl. No. 10/058,292, Hartley et al., mailed May 26, 2005.
Office Action for U.S. Appl. No. 10/058,292, Hartley et al., mailed Nov. 18, 2005.
Office Action for U.S. Appl. No. 10/151,690, Brasch et al., mailed Apr. 18, 2005.
Office Action for U.S. Appl. No. 10/162,879, Hartley et al., mailed Apr. 28, 2005.
Office Action for U.S. Appl. No. 10/162,879, Hartley et al., mailed Oct. 20, 2005.
Office Action for U.S. Appl. No. 10/796,868, Hartley et al., mailed Jan. 25, 2005.
U.S. Appl. No. 09/517,466, filed Mar. 2, 2000, Hartley, James et al.
U.S. Appl. No. 09/177,387, Office Action mailed on May 22, 2000.
U.S. Appl. No. 09/177,387, Office Action mailed on Jan. 25, 2001.
U.S. Appl. No. 09/177,387, Office Action mailed on Jul. 26, 2004.
U.S. Appl. No. 09/177,387, Office Action mailed on Jun. 24, 1999.
U.S. Appl. No. 09/177,387, Office Action mailed on Oct. 11, 2001.
U.S. Appl. No. 09/177,387, Response to Jan. 25, 2001 Office Action, filed Jul. 25, 2001.
U.S. Appl. No. 09/177,387, Response to Mar. 15, 1999 Office Action, filed Apr. 15, 1999.
U.S. Appl. No. 09/177,387, Response to Sep. 24, 1999 Office Action, filed Dec. 23, 1999.
U.S. Appl. No. 09/432,085, Notice of Allowance mailed on Jun. 28, 2007.
U.S. Appl. No. 09/432,085, Office Action mailed on Feb. 7, 2007.
U.S. Appl. No. 09/432,085, Supplemental Notice of Allowance Aug. 7, 2007.
U.S. Appl. No. 09/438,358, Application as filed Nov. 12, 1999.
U.S. Appl. No. 09/695,065, Office Action mailed Feb. 23, 2005.
U.S. Appl. No. 09/695,065, Office Action mailed Mar. 10, 2006.
U.S. Appl. No. 09/695,065, Office Action mailed Mar. 24, 2004.
U.S. Appl. No. 09/695,065, Office Action mailed Jul. 17, 2001.
U.S. Appl. No. 09/695,065, Office Action mailed Aug. 12, 2003.
U.S. Appl. No. 09/695,065, Office Action mailed Apr. 11, 2002.
U.S. Appl. No. 09/695,065, Response to May 24, 2001 Office Action, filed Jun. 21, 2001.
U.S. Appl. No. 09/695,065, Response to Aug. 12, 2003 Office Action, filed Oct. 10, 2003.
U.S. Appl. No. 09/855,797, Office Action mailed Oct. 28, 2008.
U.S. Appl. No. 09/855,797, Office Action mailed Jun. 28, 2006.
U.S. Appl. No. 09/855,797, Office Action mailed Jan. 28, 2008.
U.S. Appl. No. 09/855,797, Office Action mailed Jun. 20, 2007.
U.S. Appl. No. 09/855,797, Office Action mailed Dec. 15, 2006.
U.S. Appl. No. 09/855,797, Response to Jun. 20, 2007 Office Action, filed Oct. 31, 2007.
U.S. Appl. No. 09/855,787, Response to Dec. 15, 2006 Office Action, filed Apr. 3, 2007.
U.S. Appl. No. 09/907,719, Office Action mailed Mar. 21, 2008.
U.S. Appl. No. 09/907,719, Office Action mailed Mar. 28, 2006.
U.S. Appl. No. 09/907,719, Office Action mailed Sep. 7, 2007.
U.S. Appl. No. 09/907,719, Office Action mailed Dec. 13, 2006.
U.S. Appl. No. 09/907,719, Response to Mar. 28, 2006 Office Action, filed Sep. 28, 2006.
U.S. Appl. No. 09/907,719, Response to Sep. 7, 2007 Office Action, filed Oct. 30, 2007.
U.S. Appl. No. 10/058,291, Office Action mailed Nov. 26, 2008.
U.S. Appl. No. 10/058,291, Office Action mailed Apr. 15, 2008.
U.S. Appl. No. 10/058,291, Office Action mailed Aug. 11, 2006.
U.S. Appl. No. 10/058,292, Office Action mailed Aug. 9, 2006.
U.S. Appl. No. 10/162,879, Office Action mailed Oct. 3, 2006.
U.S. Appl. No. 10/162,879, Office Action mailed Mar. 24, 2008.
U.S. Appl. No. 10/162,879, Office Action mailed Jun. 18, 2007.
Baubonis, Wendy et al., "Genomic targeting with purified Cre recombinase", *Nucleic Acids Research*, vol. 21., No. 9, Oxford Press, 1993, 2025-2029.
Bernard, Philippe et al., "Positive-selection vectors using the F plasmid ccdB killer gene", *Gene*, vol. 148, Elsevier Science B. V., Oct. 1994, 71-74.
Csordas-Toth, Eva et al., "Nucleotide sequence of a secondary attachment site for bacteriophage lambda on the *Escherichia coli* chromosome", *Nucleic Acids Research*, vol. 7, No. 5, 1979, 1335-1341.
Edlund, Thomas et al., "Tandem Duplication Induced by an Unusual ampA1-, ampC-Transducing Lambda Phage: A Probe to Initiate Gene Amplification", *Molec. gen. Genet.*, vol. 180, Department of Microbiology, University of Umea, S-901 87, Umea, Sweden, 1980, 249-257.

Enquist, L. W. et al., "Strand exchange in site-specific recombination", *Proceedings of the National Academy of Sciences* (*PNAS*), vol. 76, No. 3, Mar. 1979, 1363-1367.
Machattie, L A. et al., "Chromosomal integration of phage [lambda] by means of a DNA insertion element", *Proceedings of the National Academy of Sciences* (*PNAS*), vol. 75, No. 3, Mar. 1978, 1490-1494.
Miller, Harvey I. et al., "Direct Role of the himA Gene Product in Phage lambda Integration", *Nature*, vol. 290, Apr. 9, 1981, 523-526.
Miller, Harvey I. et al., "int-h: an int Mutation of Phage A That Enhances Site Specific Recombination", *Cell* vol. 20, Jul. 1980, 721-729.
Mizuuchi, Michiyo et al., "Integrative recombination of bacteriophage lambda: Extent of the DNA sequence involved in attachment site function", *Proceedings of the National Academy of Sciences* (*PNAS*), vol. 77, No. 6, Jun. 1980, 3220-3224.
PCT/US00/05432, PCT ISR mailed on May 23, 2000.
PCT/US97/21880, PCT ISR mailed on Sep. 1, 1998.
Sadowski, Paul D., Site-Specific Genetic Recombination: Hops, Flips and Flops, *Faseb Journal*, vol. 7, No. 9, Jun. 1993, 760-767.
Sauer, Brian et al., Expression and Functioning in Yeast of a Bacterial Site Specific Recombination System, *Journal of Cellular Biochemistry*, Supplement 10B, Abstract #I340, Alan R. Liss, Inc., 1986, 242.
Sauer, Brian et al., "Site-specific DNA Recombination in mammalian cells by the Cre recombinase of bacteriophage P1", *Proceedings of the National Academy of Sciences* (*PNAS*), vol. 85, National Academy of Science, Jul. 1988 5166-5170.
Stratagene, Gene Characterization Kits, 1988, Catalogue, p. 39.
Temple, Gary F. et al., "Construction of a functional human suppressor tRNA gene: an approach to gene therapy for beta-thalassaemia", *Nature*, vol. 296, Macmillan Journals Ltd., Apr. 8, 1982, 537-540.
00818077.6, Office Action mailed Feb. 6, 2009.
00818077.6, Response to Feb. 6, 2009 Office Action, Filed May 20, 2009.
00914799.2, European Search Report mailed on Mar. 26, 2004.
02001134.2, European Search Report mailed Jun. 10, 2002.
02001135.9, European Search Report mailed Jun. 11, 2002.
02001135.9, European Search Report mailed Sep. 16, 2002.
U.S. Appl. No. 09/177,387, Response to May 22, 2000 Office Action, filed Aug. 22, 2000.
U.S. Appl. No. 09/432,085, Response to Feb. 7, 2007 Office Action, filed Mar. 5, 2007.
U.S. Appl. No. 09/432,085, Response to Feb. 22, 2006 Office Action, filed Jul. 24, 2006.
U.S. Appl. No. 09/695,065, Response to Mar. 24, 2004 Office Action, filed Jun. 23, 2004.
U.S. Appl. No. 09/695,065, Response to Apr. 11, 2002 Office Action, filed Apr. 11, 2003.
U.S. Appl. No. 09/695,065, Response to Jul. 17, 2001 Office Action, filed Jan. 17, 2002.
U.S. Appl. No. 09/177,387, filed Oct. 23, 1998, Hartley, James L.
U.S. Appl. No. 09/695,065, filed Oct. 25, 2000, Brasch, Michael.
U.S. Appl. No. 09/695,065, Response to Oct. 27, 2004 Office Action, filed Jan. 27, 2005.
U.S. Appl. No. 09/855,797, Final Office Action, mailed Oct. 11, 2005.
U.S. Appl. No. 09/855,797, Response to Jan. 28, 2008 Office Action, filed Jul. 28, 2008.
U.S. Appl. No. 09/855,797, Response to Jun. 28, 2006 Office Action, filed Sep. 28, 2006.
U.S. Appl. No. 09/855,797, Response to Oct. 11, 2005 Final Office Action, filed Apr. 11, 2006.
U.S. Appl. No. 09/907,719, Office Action, mailed on Jan. 29, 2004.
U.S. Appl. No. 09/907,719, Response to Dec. 13, 2006 Office Action, filed Jun. 13, 2007.
U.S. Appl. No. 09/907,719, Response to Jan. 29, 2004 Office Action, filed Apr. 29, 2004.
U.S. Appl. No. 10/058,291, Final office action mailed on Apr. 15, 2009.
U.S. Appl. No. 10/058,291, Response to Aug. 11, 2006 Office Action, filed Feb. 13, 2007.
U.S. Appl. No. 10/058,291, Response to Oct. 21, 2005 Office Action, filed Jun. 20, 2006.
U.S. Appl. No. 10/058,292, Office Action mailed May 26, 2005.
U.S. Appl. No. 10/058,292, Response to Aug. 9, 2006 Office Action, filed Feb. 9, 2007.
U.S. Appl. No. 10/058,292, Response to Nov. 18, 2005 Office Action, filed May 18, 2006.
U.S. Appl. No. 10/162,879, Response to Oct. 3, 2006 and Jun. 18, 2007 Office Actions, filed Dec. 18, 2007.
U.S. Appl. No. 10/162,879, Response to Oct. 3, 2006 Office Action, filed Apr. 2, 2007.
U.S. Appl. No. 10/162,879, Response to Oct. 20, 2005 Office Action, filed Jun. 20, 2006.
U.S. Appl. No. 11/000,371, Office Action mailed Feb. 5, 2009.
U.S. Appl. No. 11/612,445, Office Action Mailed Jun. 1, 2009.
U.S. Appl. No. 11/612,957, Office Action Mailed Jun. 1, 2009.
CN 00818077.6, Final Office Action mailed on Feb. 6, 2009.
EP 08153538.7, European Search Report mailed Jan. 16, 2009.
EP 96923288.3, European Search Report mailed Aug. 24, 1999.
EP 98955110.6, European Search report mailed on Sep. 17, 2002.
EP 98955110.6, European Search Report mailed on Jun. 11, 2002.
Hopkins, "PNas", 90 Oct. 1993 , 8759-8760.
JP 2007-175995, Response to Aug. 27, 2009 Office Action, filed Feb. 10, 2009.
Ping, Y. et al., "RNA", 1997, vol. 3, pp. 850-860.
Barnes, G., and Rine, J., "Regulated expression of endonuclease *Eco*RI in *Saccharomyces cerevisiae*: Nuclear entry and biological consequences," *Proc. Natl. Acad. Sci. USA 82*:1354-1358, National Academy of Sciences (1985).
Bauer, C.E., et al., "Extent of Sequence Homology Required for Bacteriophage Lambda Site-specific Recombination," *J. Mol. Biol. 181*:187-197, Academic Press, Inc. (1985).
Brent, R., and Ptashne, M., "A bacterial repressor protein or a yeast transcriptional terminator can block upstream activation of a yeast gene," *Nature 322*:612-615, Macmillan Journals, Ltd. (1984).
Cherepanov, P.P., and Wackernagel, W., "Gene disruption in *Escherichia coli*: $Tc^R$ and $Km^R$ cassettes with the option of Flp-catalyzed excision of the antibiotic-resistance determinant," *Gene 158*:9-14, Elsevier Science B.V. (1995).
Collis, C.M., and Hall, R.M., "Expression of Antibiotic Resistance Genes in the Integrated Cassettes of Integrons," *Antimicrobial Agents Chemother. 39*:155-162, American Society for Microbiology (1995).
Cormack, B., "Directed Mutagenesis Using the Polymerase Chain Reaction," in *Current Protocols in Molecular Biology 1*:8.5.1-8.5.10, Ausubel, F.M., et al., eds., John Wiley & Sons, Inc. (1997).
Enguist, L.W., and Weisberg, R.A., "The Red Plague Test: A Rapid Method for Identification of Excision Defective Variants of Bacteriophage Lambda," *Virology 72*:147-153, Academic Press, Inc. (1976).
Feinbaum, R., "Vectors Derived from Plasmids: Introduction to Plasmid Biology," in *Current Protocols in Molecular Biology 1*:1.5.1-1.5.17, Ausubel, F.M., et al., eds., John Wiley & Sons, Inc. (1998).
Iino, T., and Kutsukake, K., "*Trans*-acting Genes of Bacteriophages P1 and Mu Mediate Inversion of a Specific DNA Segment Involved in Flagellar Phase Variation of *Salmonella*," *Cold Spring Harb. Symp. Quant. Biol. 45*:11-16, Cold Spring Harbor Laboratory (1981).
Johnson, R.C., et al., "Isolation of the gene encoding the Hin recombinational enhancer binding protein," *Proc. Natl. Acad. Sci. USA 85*:3484-3488, National Academy of Sciences (1998).
Klippel, A., et al., "Isolation and characterization of unusual *gin* mutants," *EMBO J. 7*:3983-3989, IRL Press, Ltd. (1988).
Koch, C., et al., "*Escherichia coli* host factor for site-specific DNA inversion: Cloning and characterization of the *fis* gene," *Proc. Natl. Acad. Sci. USA 85*:4237-4241, National Academy of Sciences (1988).
Langeveld, S.A., et al., "Expression of an *Escherichia coli phr* gene in the yeast *Saccharomyces cerevisiae*," *Mol. Gen. Genet. 199*:396-400, Springer-Verlag (1985).
Miller, H.I., et al., "*int*-h: an *int* Mutation of Phage $\lambda$ That Enhances Site-Specific Recombination," *Cell 20*:721-729, MIT (1980).
Murayama, N., et al. "Evidence for Involvement of *Escherichia coli* Genes *pmbA*, *csrA* and a Previously Unrecognized Gene *tldD*, in the Control of DNA Gyrase by let*D* (*ccdB*) of Sex Factor F," *J. Mol. Biol. 256*:483-502, Academic Press, Ltd. (1996).

Okayama, H., and Berg, P., "Bacteriophage Lambda Vector for Transducing a cDNA Clone Library into Mammalian Cells," *Mol. Cell. Biol. 5*:1136-1142, American Society for Microbiology (1985).

Osuna, R., et al., "Identification of two functional regions in Fis: the N-terminus is required to promote Hin-mediated DNA inversion by not λ excision," *EMBO J. 10*:1593-1603, Oxford University Press (1991).

Sambrook, J., et al., *Molecular Cloning: A Laboratory Manual*, 2nd ed., Cold Spring Harbor Laboratory Press, New York, pp. 16.6-16.8 (1989).

Sauer, B., and Henderson, N., "Site-specific DNA recombination in mammalian cells by the Cre recombinase of bacteriophage P1," *Proc. Natl. Acad. Sci. USA 85*:5166-5170, National Academy of Sciences (1988).

Sauer, B., "Expression and Functioning in Yeast of a Bacterial Site Specific Recombination System," *J. Cell. Bio. Chem. Supp. 10*(*b*):242, Abstract No. I340, Alan R. Liss, Inc. (1986).

Stryer, L., *Biochemistry*, 2nd ed., W.H. Freeman and Co., San Francisco, CA, p. 610 (1981).

Vetter, D., et al., "Site-specific recombination of yeast 2-μm DNA in vitro," *Proc. Natl. Acad. Sci. USA 80*:7284-7288, National Academy of Sciences (1983).

Co-pending U.S. Appl. No. 09/984,239, inventors Brasch et al., filed Oct. 29, 2001 (Not Published).

Co-pending U.S. Appl. No. 10/396,696, inventors Hartley et al., filed Mar. 26, 2003 (Not Published).

Co-pending U.S. Appl. No. 10/454,793, inventors Chesnut et al., filed Jun. 5, 2003 (Not Published).

Co-pending U.S. Appl. No. 10/640,422, inventors Cheo et al., filed Aug. 14, 2003 (Not Published).

* cited by examiner

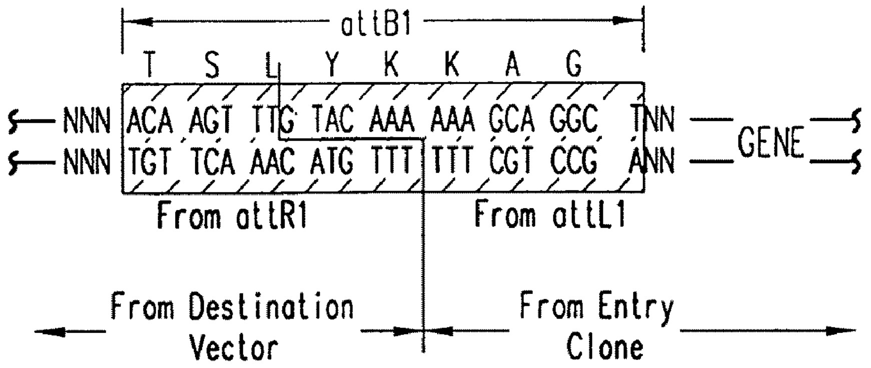
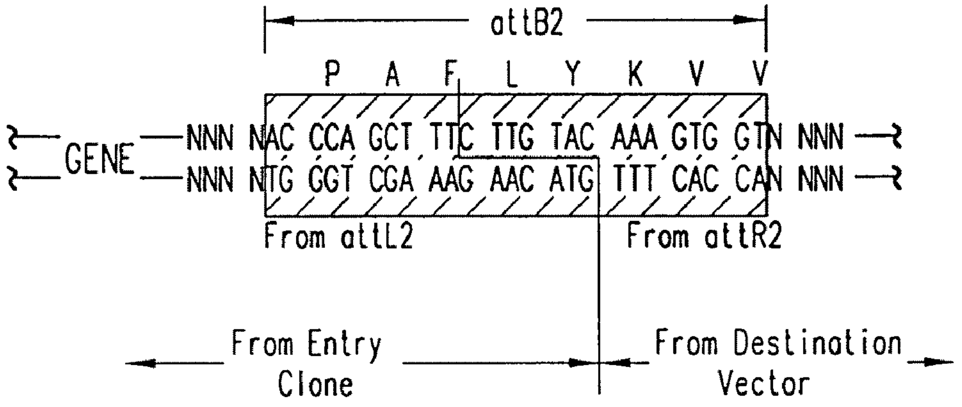
FIG.6

Recombination Site Nucleotide Sequences

<u>attB1</u>: 5'-ACAAGTTTGTACAAAAAAGCAGGCT-3'

<u>attB2</u>: 5'-ACCCAGCTTTCTTGTACAAAGTGGT-3'

<u>attP1</u>: 5'-TACAGGTCACTAATACCATCTAAGTAGTTGATTCATAGTGACTGGATATG-
TTGTGTTTTACAGTATTATGTAGTCTGTTTTTTATGCAAAATCTAATTTA-
ATATATTGATATTTATATCATTTTACGTTTCTCGTTCAGCTTTTTTGTAC-
AAAGTTGGCATTATAAAAAAGCATTGCTCATCAATTTGTTGCAACGAACA-
GGTCACTATCAGTCAAAATAAAATCATTATTTG-3'

<u>attP2</u>: 5'-CAAATAATGATTTTATTTTGACTGATAGTGACCTGTTCGTTGCAACAAAT-
TGATAAGCAATGCTTTCTTATAATGCCAACTTTGTACAAGAAAGCTGAAC-
GAGAAACGTAAAATGATATAAATATCAATATATTAAATTAGATTTTGCAT-
AAAAAACAGACTACATAATACTGTAAAACACAACATATCCAGTCACTATGA-
ATCAACTACTTAGATGGTATTAGTGACCTGTA-3'

<u>attR1</u>: 5'-ACAAGTTTGTACAAAAAAGCTGAACGAGAAACGTAAAATGATATAAA-
TATCAATATATTAAATTAGATTTTGCATAAAAAACAGACTACATAATAC-
TGTAAAACACAACATATCCAGTCACTATG-3'

<u>attR2</u>: 5'-GCAGGTCGACCATAGTGACTGGATATGTTGTGTTTTACAGTATTAT-
GTAGTCTGTTTTTTATGCAAAATCTAATTTAATATATTGATATTT-
ATATCATTTTACGTTTCTCGTTCAGCTTTCTTGTACAAAGTGGT-3'

<u>attL1</u>: 5'-CAAATAATGATTTTATTTTGACTGATAGTGACCTGTTCGTTGCAAC-
AAATTGATAAGCAATGCTTTTTTATAATGCCAACTTTGTACAAAAAA-GCAGGCT-3'

<u>attL2</u>: 5'-CAAATAATGATTTTATTTTGACTGATAGTGACCTGTTCGTTGCAACAA-
ATTGATAAGCAATGCTTTCTTATAATGCCAACTTTGTACAAGAAAGCTGGGT-3'

FIG.9 pENTR1A 2717 bp

| Base Nos. | Gene Encoded |
|---|---|
| 67..166 | attL1 |
| 321..626 | ccdB |
| 655..754 | attL2 |
| 877..1686 | KmR |
| 1791..2364 | ori |

```
   1 CTGACGGATG GCCTTTTTGC GTTTCTACAA ACTCTTCCTG TTAGTTAGTT ACTTAAGCTC
  61 GGGCCCCAAA TAATGATTTT ATTTTGACTG ATAGTGACCT GTTCGTTGCA ACAAATTGAT
 121 AAGCAATGCT TTTTTATAAT GCCAACTTTG TACAAAAAAG CAGGCTTTAA AGGAACCAAT
 181 TCAGTCGACT GGATCCGGTA CCGAATTCGC TTACTAAAAG CCAGATAACA GTATGCGTAT
 241 TTGCGCGCTG ATTTTTGCGG TATAAGAATA TATACTGATA TGTATACCCG AAGTATGTCA
 301 AAAAGAGGTG TGCTTCTAGA ATGCAGTTTA AGGTTTACAC CTATAAAAGA GAGAGCCGTT
 361 ATCGTCTGTT TGTGGATGTA CAGAGTGATA TTATTGACAC GCCCGGGCGA CGGATAGTGA
 421 TCCCCCTGGC CAGTGCACGT CTGCTGTCAG ATAAAGTCTC CCGTGAACTT TACCCGGTGG
 481 TGCATATCGG GGATGAAAGC TGGCGCATGA TGACCACCGA TATGGCCAGT GTGCCGGTCT
 541 CCGTTATCGG GGAAGAAGTG GCTGATCTCA GCCACCGCGA AAATGACATC AAAAACGCCA
 601 TTAACCTGAT GTTCTGGGGA ATATAGAATT CGCGGCCGCA CTCGAGATAT CTAGACCCAG
 661 CTTTCTTGTA CAAAGTTGGC ATTATAAGAA AGCATTGCTT ATCAATTTGT TGCAACGAAC
 721 AGGTCACTAT CAGTCAAAAT AAAATCATTA TTTGCCATCC AGCTGCAGCT CTGGCCCGTG
 781 TCTCAAAATC TCTGATGTTA CATTGCACAA GATAAAAATA TATCATCATG AACAATAAAA
 841 CTGTCTGCTT ACATAAACAG TAATACAAGG GGTGTTATGA GCCATATTCA ACGGGAAACG
 901 TCGAGGCCGC GATTAAATTC CAACATGGAT GCTGATTTAT ATGGGTATAA ATGGGCTCGC
 961 GATAATGTCG GGCAATCAGG TGCGACAATC TATCGCTTGT ATGGGAAGCC CGATGCGCCA
1021 GAGTTGTTTC TGAAACATGG CAAAGGTAGC GTTGCCAATG ATGTTACAGA TGAGATGGTC
1081 AGACTAAACT GGCTGACGGA ATTTATGCCT CTTCCGACCA TCAAGCATTT TATCCGTACT
1141 CCTGATGATG CATGGTTACT CACCACTGCG ATCCCCGGAA AAACAGCATT CCAGGTATTA
1201 GAAGAATATC CTGATTCAGG TGAAAATATT GTTGATGCGC TGGCAGTGTC CCTGCGCCGG
1261 TTGCATTCGA TTCCTGTTTG TAATTGTCCT TTTAACAGCG ATCGCGTATT TCGTCTCGCT
1321 CAGGCGCAAT CACGAATGAA TAACGGTTTG GTTGATGCGA GTGATTTTGA TGACGAGCGT
1381 AATGGCTGGC CTGTTGAACA AGTCTGGAAA GAAATGCATA AACTTTTGCC ATTCTCACCG
1441 GATTCAGTCG TCACTCATGG TGATTTCTCA CTTGATAACC TTATTTTTGA CGAGGGGAAA
1501 TTAATAGGTT GTATTGATGT TGGACGAGTC GGAATCGCAG ACCGATACCA GGATCTTGCC
1561 ATCCTATGGA ACTGCCTCGG TGAGTTTTCT CCTTCATTAC AGAAACGGCT TTTTCAAAAA
1621 TATGGTATTG ATAATCCTGA TATGAATAAA TTGCAGTTTC ATTTGATGCT CGATGAGTTT
1681 TTCTAATCAG AATTGGTTAA TTGGTTGTAA CATTATTCAG ATTGGGCCCC GTTCCACTGA
1741 GCGTCAGACC CCGTAGAAAA GATCAAAGGA TCTTCTTGAG ATCCTTTTTT TCTGCGCGTA
1801 ATCTGCTGCT TGCAAACAAA AAAACCACCG CTACCAGCGG TGGTTTGTTT GCCGGATCAA
1861 GAGCTACCAA CTCTTTTTCC GAAGGTAACT GGCTTCAGCA GAGCGCAGAT ACCAAATACT
1921 GTTCTTCTAG TGTAGCCGTA GTTAGGCCAC CACTTCAAGA ACTCTGTAGC ACCGCCTACA
1981 TACCTCGCTC TGCTAATCCT GTTACCAGTG GCTGCTGCCA GTGGCGATAA GTCGTGTCTT
2041 ACCGGGTTGG ACTCAAGACG ATAGTTACCG GATAAGGCGC AGCGGTCGGG CTGAACGGGG
2101 GGTTCGTGCA CACAGCCCAG CTTGGAGCGA ACGACCTACA CCGAACTGAG ATACCTACAG
2161 CGTGAGCTAT GAGAAAGCGC CACGCTTCCC GAAGGGAGAA AGGCGGACAG GTATCCGGTA
2221 AGCGGCAGGG TCGGAACAGG AGAGCGCACG AGGGAGCTTC CAGGGGGAAA CGCCTGGTAT
2281 CTTTATAGTC CTGTCGGGTT TCGCCACCTC TGACTTGAGC GTCGATTTTT GTGATGCTCG
2341 TCAGGGGGGC GGAGCCTATG GAAAAACGCC AGCAACGCGG CCTTTTTACG GTTCCTGGCC
2401 TTTTGCTGGC CTTTTGCTCA CATGTTCTTT CCTGCGTTAT CCCCTGATTC TGTGGATAAC
2461 CGTATTACCG CTAGCATGGA TCTCGGGGAC GTCTAACTAC TAAGCGAGAG TAGGGAACTG
2521 CCAGGCATCA AATAAAACGA AAGGCTCAGT CGGAAGACTG GGCCTTTCGT TTTATCTGTT
2581 GTTTGTCGGT GAACGCTCTC CTGAGTAGGA CAAATCCGCC GGGAGCGGAT TTGAACGTTG
2641 TGAAGCAACG GCCCGGAGGG TGGCGGGCAG GACGCCCGCC ATAAACTGCC AGGCATCAAA
2701 CTAAGCAGAA GGCCATC
```

FIG. 10B

Cloning Sites of the Entry Vector pENTR2B (reading frame B)

```
        Int    attL1              Ehel       Xmnl      Sall      BamHI
       TTG TAC AAA AAA GCA GGC TGG CGC CGG AAC CAA TTC AGT CGA CTG GAT CCG
       AAC ATG TTT TTT CGT CCG ACC GCG GCC TTG GTT AAG TCA GCT GAC CTA GGC
                                  Leu Tyr Lys Lys Ala Gly Trp Arg Arg Asn Gln Phe Ser Arg Leu Asp Pro

        KpnI EcoRI           EcoRI     NotI        XhoI EcoRV XbaI
       GTA CCG AAT TC- ccdB - - G AAT TCG CGG CCG CAC TCG AGA TAT CTA GAC CCA
       CAT GGC TTA AG            C TTA AGC GCC GGC GTG AGC TCT ATA GAT CTG GGT
       Val Pro Asn                 Asn Ser Arg Pro His Ser Arg Tyr Leu Asp Pro

         Int     attL2
        GCT TTC TTG TAC AAA G
        CGA AAG AAC ATG TTT C

        Ala Phe Leu Tyr Lys
```

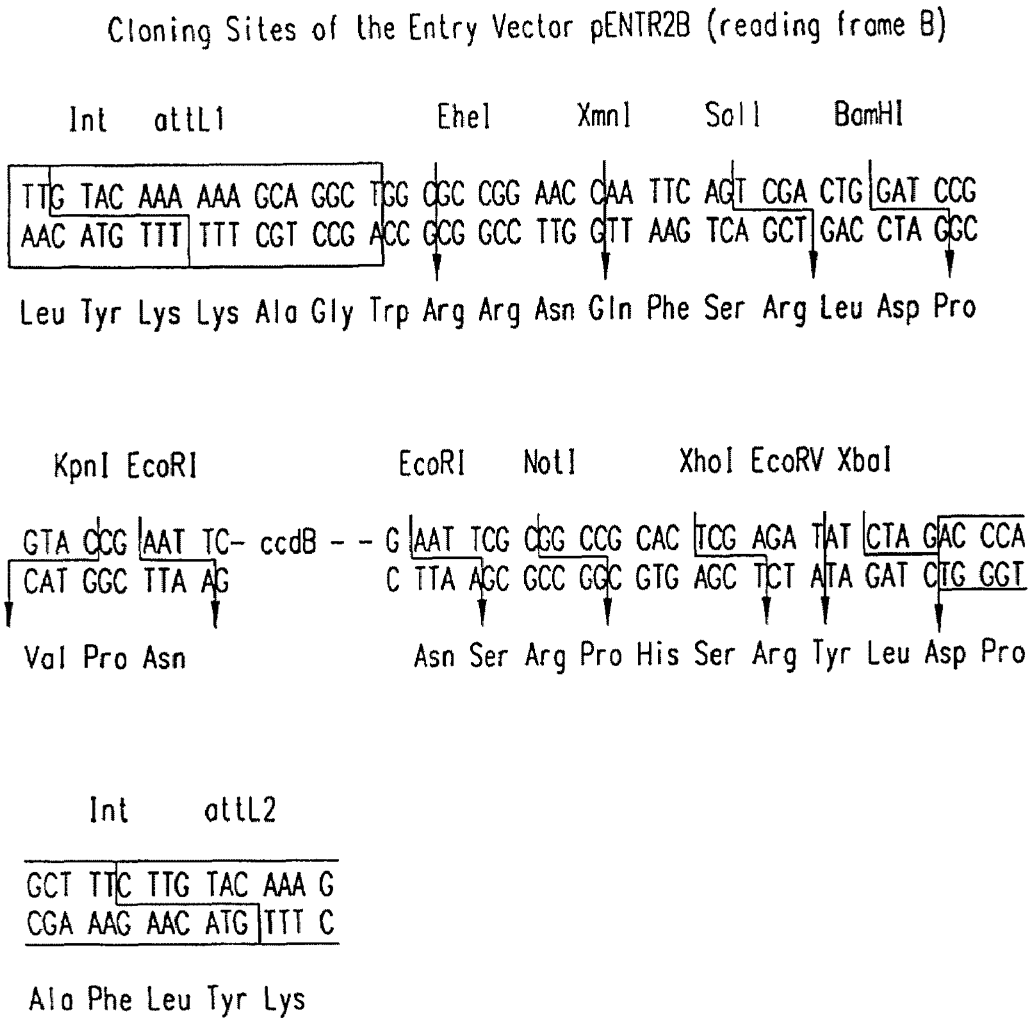

FIG.11A pENTR2B 2718 bp

| Location (Base Nos.) | Gene Encoded |
|---|---|
| 67..166 | attL1 |
| 322..627 | ccdB |
| 656..755 | attL2 |
| 878..1687 | KmR |
| 1792..2365 | ori |

```
   1 CTGACGGATG GCCTTTTTGC GTTTCTACAA ACTCTTCCTG TTAGTTAGTT ACTTAAGCTC
  61 GGGCCCCAAA TAATGATTTT ATTTTGACTG ATAGTGACCT GTTCGTTGCA ACAAATTGAT
 121 AAGCAATGCT TTTTTATAAT GCCAACTTTG TACAAAAAAG CAGGCTGGCG CCGGAACCAA
 181 TTCAGTCGAC TGGATCCGGT ACCGAATTCG CTTACTAAAA GCCAGATAAC AGTATGCGTA
 241 TTTGCGCGCT GATTTTTGCG GTATAAGAAT ATATACTGAT ATGTATACCC GAAGTATGTC
 301 AAAAAGAGGT GTGCTTCTAG AATGCAGTTT AAGGTTTACA CCTATAAAAG AGAGAGCCGT
 361 TATCGTCTGT TTGTGGATGT ACAGAGTGAT ATTATTGACA CGCCCGGGCG ACGGATGGTG
 421 ATCCCCCTGG CCAGTGCACG TCTGCTGTCA GATAAAGTCT CCCGTGAACT TTACCCGGTG
 481 GTGCATATCG GGGATGAAAG CTGGCGCATG ATGACCACCG ATATGGCCAG TGTGCCGGTC
 541 TCCGTTATCG GGGAAGAAGT GGCTGATCTC AGCCACCGCG AAAATGACAT CAAAAACGCC
 601 ATTAACCTGA TGTTCTGGGG AATATAGAAT TCGCGGCCGC ACTCGAGATA TCTAGACCCA
 661 GCTTTCTTGT ACAAAGTTGG CATTATAAGA AAGCATTGCT TATCAATTTG TTGCAACGAA
 721 CAGGTCACTA TCAGTCAAAA TAAAATCATT ATTTGCCATC CAGCTGCAGC TCTGGCCCGT
 781 GTCTCAAAAT CTCTGATGTT ACATTGCACA AGATAAAAAT ATATCATCAT GAACAATAAA
 841 ACTGTCTGCT TACATAAACA GTAATACAAG GGGTGTTATG AGCCATATTC AACGGGAAAC
 901 GTCGAGGCCG CGATTAAATT CCAACATGGA TGCTGATTTA TATGGGTATA AATGGGCTCG
 961 CGATAATGTC GGGCAATCAG GTGCGACAAT CTATCGCTTG TATGGGAAGC CCGATGCGCC
1021 AGAGTTGTTT CTGAAACATG GCAAAGGTAG CGTTGCCAAT GATGTTACAG ATGAGATGGT
1081 CAGACTAAAC TGGCTGACGG AATTTATGCC TCTTCCGACC ATCAAGCATT TTATCCGTAC
1141 TCCTGATGAT GCATGGTTAC TCACCACTGC GATCCCCGGA AAAACAGCAT TCCAGGTATT
1201 AGAAGAATAT CCTGATTCAG GTGAAAATAT TGTTGATGCG CTGGCAGTGT TCCTGCGCCG
1261 GTTGCATTCG ATTCCTGTTT GTAATTGTCC TTTTAACAGC GATCGCGTAT TTCGTCTCGC
1321 TCAGGCGCAA TCACGAATGA ATAACGGTTT GGTTGATGCG AGTGATTTTG ATGACGAGCG
1381 TAATGGCTGG CCTGTTGAAC AAGTCTGGAA AGAAATGCAT AAACTTTTGC CATTCTCACC
1441 GGATTCAGTC GTCACTCATG GTGATTTCTC ACTTGATAAC CTTATTTTTG ACGAGGGGAA
1501 ATTAATAGGT TGTATTGATG TTGGACGAGT CGGAATCGCA GACCGATACC AGGATCTTGC
1561 CATCCTATGG AACTGCCTCG GTGAGTTTTC TCCTTCATTA CAGAAACGGC TTTTTCAAAA
1621 ATATGGTATT GATAATCCTG ATATGAATAA ATTGCAGTTT CATTTGATGC TCGATGAGTT
1681 TTTCTAATCA GAATTGGTTA ATTGGTTGTA ACATTATTCA GATTGGGCCC CGTTCCACTG
1741 AGCGTCAGAC CCCGTAGAAA AGATCAAAGG ATCTTCTTGA GATCCTTTTT TTCTGCGCGT
1801 AATCTGCTGC TTGCAAACAA AAAAACCACC GCTACCAGCG GTGGTTTGTT TGCCGGATCA
1861 AGAGCTACCA ACTCTTTTTC CGAAGGTAAC TGGCTTCAGC AGAGCGCAGA TACCAAATAC
1921 TGTTCTTCTA GTGTAGCCGT AGTTAGGCCA CCACTTCAAG AACTCTGTAG CACCGCCTAC
1981 ATACCTCGCT CTGCTAATCC TGTTACCAGT GGCTGCTGCC AGTGGCGATA AGTCGTGTCT
2041 TACCGGGTTG GACTCAAGAC GATAGTTACC GGATAAGGCG CAGCGGTCGG GCTGAACGGG
2101 GGGTTCGTGC ACACAGCCCA GCTTGGAGCG AACGACCTAC ACCGAACTGA GATACCTACA
2161 GCGTGAGCTA TGAGAAAGCG CCACGCTTCC CGAAGGGAGA AAGGCGGACA GGTATCCGGT
2221 AAGCGGCAGG GTCGGAACAG GAGAGCGCAC GAGGGAGCTT CCAGGGGGAA ACGCCTGGTA
2281 TCTTTATAGT CCTGTCGGGT TTCGCCACCT CTGACTTGAG CGTCGATTTT TGTGATGCTC
2341 GTCAGGGGGG CGGAGCCTAT GGAAAAACGC CAGCAACGCG GCCTTTTTAC GGTTCCTGGC
2401 CTTTTGCTGG CCTTTTGCTC ACATGTTCTT TCCTGCGTTA TCCCCTGATT CTGTGGATAA
2461 CCGTATTACC GCTAGCATGG ATCTCGGGGA CGTCTAACTA CTAAGCGAGA GTAGGGAACT
2521 GCCAGGCATC AAATAAAACG AAAGGCTCAG TCGGAAGACT GGGCCTTTCG TTTTATCTGT
2581 TGTTTGTCGG TGAACGCTCT CCTGAGTAGG ACAAATCCGC CGGGAGCGGA TTTGAACGTT
2641 GTGAAGCAAC GGCCCGGAGG GTGGCGGGCA GGACGCCCGC CATAAACTGC CAGGCATCAA
2701 ACTAAGCAGA AGGCCATC
```

FIG. 11B

Figure 12A:
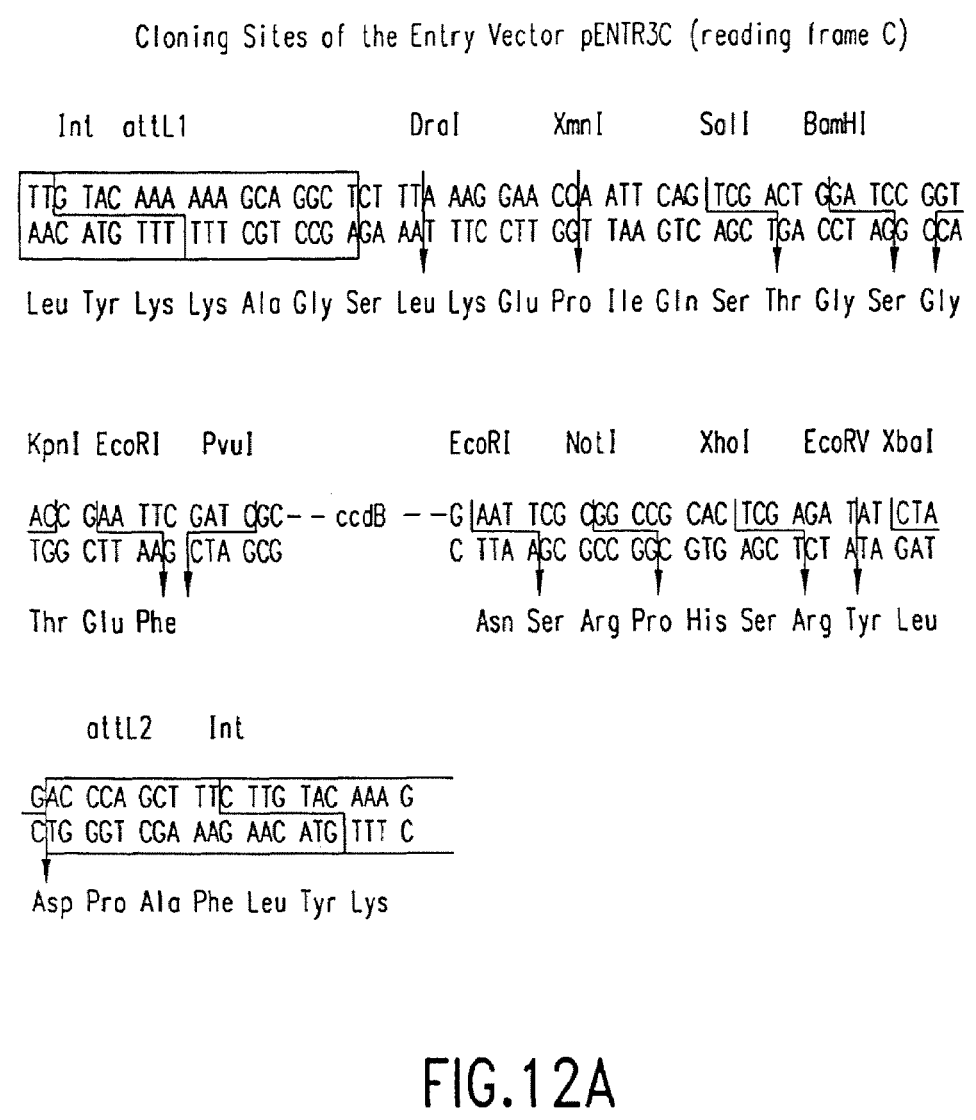

Cloning Sites of the Entry Vector pENTR3C (reading frame C)

Int attL1 DraI XmnI SalI BamHI

TTG TAC AAA AAA GCA GGC TCT TTA AAG GAA CCA ATT CAG TCG ACT GGA TCC GGT
AAC ATG TTT TTT CGT CCG AGA AAT TTC CTT GGT TAA GTC AGC TGA CCT AGG CCA

Leu Tyr Lys Lys Ala Gly Ser Leu Lys Glu Pro Ile Gln Ser Thr Gly Ser Gly

KpnI EcoRI PvuI EcoRI NotI XhoI EcoRV XbaI

ACC GAA TTC GAT CGC- - ccdB - -G AAT TCG CGG CCG CAC TCG AGA TAT CTA
TGG CTT AAG CTA GCG C TTA AGC GCC GGC GTG AGC TCT ATA GAT Thr Glu Phe Asn Ser Arg Pro His Ser Arg Tyr Leu attL2 Int

GAC CCA GCT TTC TTG TAC AAA G
CTG GGT CGA AAG AAC ATG TTT C

Asp Pro Ala Phe Leu Tyr Lys

FIG.12A pENTR3C 2723 bp

| Location (Base Nos.) | Gene Encoded |
|---|---|
| 67..166 | attL1 |
| 327..632 | ccdB |
| 661..760 | attL2 |
| 883..1692 | KmR |
| 1797..2370 | ori |

```
   1 CTGACGGATG GCCTTTTTGC GTTTCTACAA ACTCTTCCTG TTAGTTAGTT ACTTAAGCTC
  61 GGGCCCCAAA TAATGATTTT ATTTTGACTG ATAGTGACCT GTTCGTTGCA ACAAATTGAT
 121 AAGCAATGCT TTTTTATAAT GCCAACTTTG TACAAAAAAG CAGGCTCTTT AAAGGAACCA
 181 ATTCAGTCGA CTGGATCCGG TACCGAATTC GATCGCTTAC TAAAAGCCAG ATAACAGTAT
 241 GCGTATTTGC GCGCTGATTT TTGCGGTATA AGAATATATA CTGATATGTA TACCCGAAGT
 301 ATGTCAAAAA GAGGTGTGCT TCTAGAATGC AGTTTAAGGT TTACACCTAT AAAAGAGAGA
 361 GCCGTTATCG TCTGTTTGTG GATGTACAGA GTGATATTAT TGACACGCCC GGGCGACGGA
 421 TGGTGATCCC CCTGGCCAGT GCACGTCTGC TGTCAGATAA AGTCTCCCGT GAACTTTACC
 481 CGGTGGTGCA TATCGGGGAT GAAAGCTGGC GCATGATGAC CACCGATATG GCCAGTGTGC
 541 CGGTCTCCGT TATCGGGGAA GAAGTGGCTG ATCTCAGCCA CCGCGAAAAT GACATCAAAA
 601 ACGCCATTAA CCTGATGTTC TGGGGAATAT AGAATTCGCG GCCGCACTCG AGATATCTAG
 661 ACCCAGCTTT CTTGTACAAA GTTGGCATTA TAAGAAAGCA TTGCTTATCA ATTTGTTGCA
 721 ACGAACAGGT CACTATCAGT CAAAATAAAA TCATTATTTG CCATCCAGCT GCAGCTCTGG
 781 CCCGTGTCTC AAAATCTCTG ATGTTACATT GCACAAGATA AAAATATATC ATCATGAACA
 841 ATAAAACTGT CTGCTTACAT AAACAGTAAT ACAAGGGGTG TTATGAGCCA TATTCAACGG
 901 GAAACGTCGA GGCCGCGATT AAATTCCAAC ATGGATGCTG ATTTATATGG GTATAAATGG
 961 GCTCGCGATA ATGTCGGGCA ATCAGGTGCG ACAATCTATC GCTTGTATGG GAAGCCCGAT
1021 GCGCCAGAGT TGTTTCTGAA ACATGGCAAA GGTAGCGTTG CCAATGATGT TACAGATGAG
1081 ATGGTCAGAC TAAACTGGCT GACGGAATTT ATGCCTCTTC CGACCATCAA GCATTTTATC
1141 CGTACTCCTG ATGATGCATG GTTACTCACC ACTGCGATCC CCGGAAAAAC AGCATTCCAG
1201 GTATTAGAAG AATATCCTGA TTCAGGTGAA AATATTGTTG ATGCGCTGGC AGTGTTCCTG
1261 CGCCGGTTGC ATTCGATTCC TGTTTGTAAT TGTCCTTTTA ACAGCGATCG CGTATTTCGT
1321 CTCGCTCAGG CGCAATCACG AATGAATAAC GGTTTGGTTG ATGCGAGTGA TTTTGATGAC
1381 GAGCGTAATG GCTGGCCTGT TGAACAAGTC TGGAAAGAAA TGCATAAACT TTTGCCATTC
1441 TCACCGGATT CAGTCGTCAC TCATGGTGAT TTCTCACTTG ATAACCTTAT TTTTGACGAG
1501 GGGAAATTAA TAGGTTGTAT TGATGTTGGA CGAGTCGGAA TCGCAGACCG ATACCAGGAT
1561 CTTGCCATCC TATGGAACTG CCTCGGTGAG TTTTCTCCTT CATTACAGAA ACGGCTTTTT
1621 CAAAAATATG GTATTGATAA TCCTGATATG AATAAATTGC AGTTTCATTT GATGCTCGAT
1681 GAGTTTTTCT AATCAGAATT GGTTAATTGG TTGTAACATT ATTCAGATTG GGCCCCGTTC
1741 CACTGAGCGT CAGACCCCGT AGAAAAGATC AAAGGATCTT CTTGAGATCC TTTTTTTCTG
1801 CGCGTAATCT GCTGCTTGCA AACAAAAAAA CCACCGCTAC CAGCGGTGGT TTGTTTGCCG
1861 GATCAAGAGC TACCAACTCT TTTTCCGAAG GTAACTGGCT TCAGCAGAGC GCAGATACCA
1921 AATACTGTTC TTCTAGTGTA GCCGTAGTTA GGCCACCACT TCAAGAACTC TGTAGCACCG
1981 CCTACATACC TCGCTCTGCT AATCCTGTTA CCAGTGGCTG CTGCCAGTGG CGATAAGTCG
2041 TGTCTTACCG GGTTGGACTC AAGACGATAG TTACCGGATA AGGCGCAGCG GTCGGGCTGA
2101 ACGGGGGGTT CGTGCACACA GCCCAGCTTG GAGCGAACGA CCTACACCGA ACTGAGATAC
2161 CTACAGCGTG AGCTATGAGA AAGCGCCACG CTTCCCGAAG GGAGAAAGGC GGACAGGTAT
2221 CCGGTAAGCG GCAGGGTCGG AACAGGAGAG CGCACGAGGG AGCTTCCAGG GGGAAACGCC
2281 TGGTATCTTT ATAGTCCTGT CGGGTTTCGC CACCTCTGAC TTGAGCGTCG ATTTTTGTGA
2341 TGCTCGTCAG GGGGGCGGAG CCTATGGAAA AACGCCAGCA ACGCGGCCTT TTTACGGTTC
2401 CTGGCCTTTT GCTGGCCTTT TGCTCACATG TTCTTTCCTG CGTTATCCCC TGATTCTGTG
2461 GATAACCGTA TTACCGCTAG CATGGATCTC GGGGACGTCT AACTACTAAG CGAGAGTAGG
2521 GAACTGCCAG GCATCAAATA AAACGAAAGG CTCAGTCGGA AGACTGGGCC TTTCGTTTTA
2581 TCTGTTGTTT GTCGGTGAAC GCTCTCCTGA GTAGGACAAA TCCGCCGGGA GCGGATTTGA
2641 ACGTTGTGAA GCAACGGCCC GGAGGGTGGC GGGCAGGACG CCCGCCATAA ACTGCCAGGC
2701 ATCAAACTAA GCAGAAGGCC ATC
```

FIG. 12B

Cloning Sites of the Entry Vector pENTR4

```
Int    attL1                      NcoI    Kozak XmnI    SalI    BamHI
TTG TAC AAA AAA GCA GGC TCC ACC ATG GGA ACC AAT TCA GTC GAC TGG ATC CGG
AAC ATG TTT TTT CGT CCG AGG TGG TAC CCT TGG TTA AGT CAG CTG ACC TAG GCC

Leu Tyr Lys Lys Ala Gly Ser Thr Met Gly Thr Asn Ser Val Asp Trp Ile Arg

KpnI EcoRI           EcoRI      NotI           XhoI EcoRV  XbaI
TAC CGA ATT C--ccdB--G AAT TCG CGG CCG CAC TCG AGA TAT CTA GAC CCA GCT
ATG GCT TAA G          C TTA AGC GCC GGC GTG AGC TCT ATA GAT CTG GGT CGA

Tyr Arg Ile              Asn Ser Arg Pro His Ser Arg Tyr Leu Asp Pro Ala

  Int    attL2
TTC TTG TAC AAA G
AAG AAC ATG TTT C

Phe Leu Tyr Lys
```

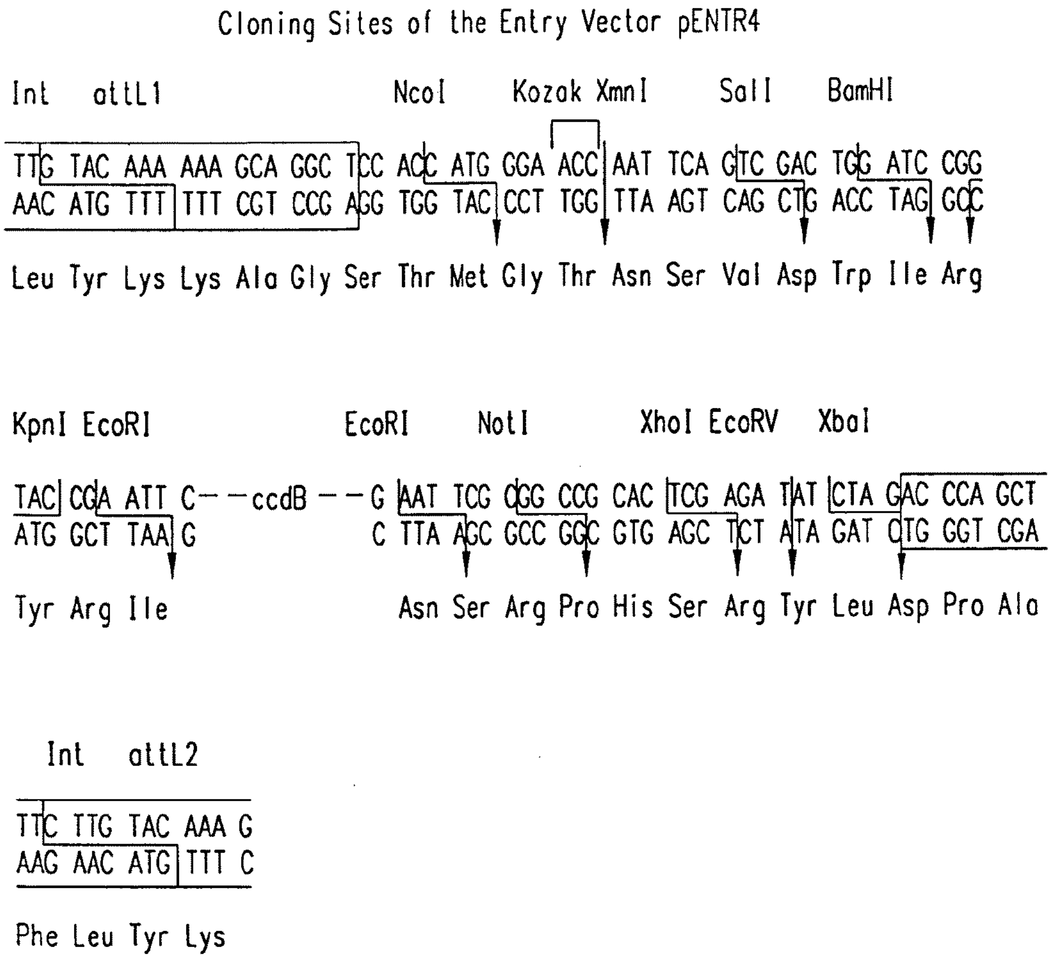

FIG.13A pENTR4 2720 bp

| Location (Base Nos.) | Gene Encoded |
|---|---|
| 67..166 | attL1 |
| 324..629 | ccdB |
| 658..757 | attL2 |
| 880..1689 | KmR |
| 1794..2367 | ori |

```
   1 CTGACGGATG GCCTTTTTGC GTTTCTACAA ACTCTTCCTG TTAGTTAGTT ACTTAAGCTC
  61 GGGCCCCAAA TAATGATTTT ATTTTGACTG ATAGTGACCT GTTCGTTGCA ACAAATTGAT
 121 AAGCAATGCT TTTTTATAAT GCCAACTTTG TACAAAAAAG CAGGCTCCAC CATGGGAACC
 181 AATTCAGTCG ACTGGATCCG GTACCGAATT CGCTTACTAA AAGCCAGATA ACAGTATGCG
 241 TATTTGCGCG CTGATTTTTG CGGTATAAGA ATATATACTG ATATGTATAC CCGAAGTATG
 301 TCAAAAAGAG GTGTGCTTCT AGAATGCAGT TTAAGGTTTA CACCTATAAA AGAGAGAGCC
 361 GTTATCGTCT GTTTGTGGAT GTACAGAGTG ATATTATTGA CACGCCCGGG CGACGGATGG
 421 TGATCCCCCT GGCCAGTGCA CGTCTGCTGT CAGATAAAGT CTCCCGTGAA CTTTACCCGG
 481 TGGTGCATAT CGGGGATGAA AGCTGGCGCA TGATGACCAC CGATATGGCC AGTGTGCCGG
 541 TCTCCGTTAT CGGGGAAGAA GTGGCTGATC TCAGCCACCG CGAAAATGAC ATCAAAAACG
 601 CCATTAACCT GATGTTCTGG GGAATATAGA ATTCGCGGCC GCACTCGAGA TATCTAGACC
 661 CAGCTTTCTT GTACAAAGTT GGCATTATAA GAAAGCATTG CTTATCAATT TGTTGCAACG
 721 AACAGGTCAC TATCAGTCAA AATAAAATCA TTATTTGCCA TCCAGCTGCA GCTCTGGCCC
 781 GTGTCTCAAA ATCTCTGATG TTACATTGCA CAAGATAAAA ATATATCATC ATGAACAATA
 841 AAACTGTCTG CTTACATAAA CAGTAATACA AGGGGTGTTA TGAGCCATAT TCAACGGGAA
 901 ACGTCGAGGC CGCGATTAAA TTCCAACATG GATGCTGATT TATATGGGTA TAAATGGGCT
 961 CGCGATAATG TCGGGCAATC AGGTGCGACA ATCTATCGCT TGTATGGGAA GCCCGATGCG
1021 CCAGAGTTGT TTCTGAAACA TGGCAAAGGT AGCGTTGCCA ATGATGTTAC AGATGAGATG
1081 GTCAGACTAA ACTGGCTGAC GGAATTTATG CCTCTTCCGA CCATCAAGCA TTTTATCCGT
1141 ACTCCTGGTG ATGCATGGTT ACTCACCACT GCGATCCCCG GAAAAACAGC ATTCCAGGTA
1201 TTAGAAGAAT ATCCTGATTC AGGTGAAAAT ATTGTTGATG CGCTGGCAGT GTTCCTGCGC
1261 CGGTTGCATT CGATTCCTGT TTGTAATTGT CCTTTTAACA GCGATCGCGT ATTTCGTCTC
1321 GCTCAGGCGC AATCACGAAT GAATAACGGT TTGGTTGATG CGAGTGATTT TGATGACGAG
1381 CGTAATGGCT GGCCTGTTGA ACAAGTCTGG AAAGAAATGC ATAAACTTTT GCCATTCTCA
1441 CCGGATTCAG TCGTCACTCA TGGTGATTTC TCACTTGATA ACCTTATTTT TGACGAGGGG
1501 AAATTAATAG GTTGTATTGA TGTTGGACGA GTCGGAATCG CAGACCGATA CCAGGATCTT
1561 GCCATCCTAT GGAACTGCCT CGGTGAGTTT TCTCCTTCAT TACAGAAACG GCTTTTTCAA
1621 AAATATGGTA TTGATAATCC TGATATGAAT AAATTGCAGT TTCATTTGAT GCTCGATGAG
1681 TTTTTCTAAT CAGAATTGGT TAATTGGTTG TAACATTATT CAGATTGGGC CCCGTTCCAC
1741 TGAGCGTCAG ACCCCGTAGA AAAGATCAAA GGATCTTCTT GAGATCCTTT TTTTCTGCGC
1801 GTAATCTGCT GCTTGCAAAC AAAAAAACCA CCGCTACCAG CGGTGGTTTG TTTGCCGGAT
1861 CAAGAGCTAC CAACTCTTTT TCCGAAGGTA ACTGGCTTCA GCAGAGCGCA GATACCAAAT
1921 ACTGTTCTTC TAGTGTAGCC GTAGTTAGGC CACCACTTCA AGAACTCTGT AGCACCGCCT
1981 ACATACCTCG CTCTGCTAAT CCTGTTACCA GTGGCTGCTG CCAGTGGCGA TAAGTCGTGT
2041 CTTACCGGGT TGGACTCAAG ACGATAGTTA CCGGATAAGG CGCAGCGGTC GGGCTGAACG
2101 GGGGGTTCGT GCACACAGCC CAGCTTGGAG CGAACGACCT ACACCGAACT GAGATACCTA
2161 CAGCGTGAGC TATGAGAAAG CGCCACGCTT CCCGAAGGGA GAAAGGCGGA CAGGTATCCG
2221 GTAAGCGGCA GGGTCGGAAC AGGAGAGCGC ACGAGGGAGC TTCCAGGGGG AAACGCCTGG
2281 TATCTTTATA GTCCTGTCGG GTTTCGCCAC CTCTGACTTG AGCGTCGATT TTTGTGATGC
2341 TCGTCAGGGG GGCGGAGCCT ATGGAAAAAC GCCAGCAACG CGGCCTTTTT ACGGTTCCTG
2401 GCCTTTTGCT GGCCTTTTGC TCACATGTTC TTTCCTGCGT TATCCCCTGA TTCTGTGGAT
2461 AACCGTATTA CCGCTAGCAT GGATCTCGGG GACGTCTAAC TACTAAGCGA GAGTAGGGAA
2521 CTGCCAGGCA TCAAATAAAA CGAAAGGCTC AGTCGGAAGA CTGGGCCTTT CGTTTTATCT
2581 GTTGTTTGTC GGTGAACGCT CTCCTGAGTA GGACAAATCC GCCGGGAGCG GATTTGAACG
2641 TTGTGAAGCA ACGGCCCGGA GGGTGGCGGG CAGGACGCCC GCCATAAACT GCCAGGCATC
2701 AAACTAAGCA GAAGGCCATC
```

FIG.13B

Cloning sites of the Entry Vector pENTR5

```
     Int        attL1              NdeI       XmnI      SalI
   ttg  tac aaa aaa gca ggc  ttt ca|t atg gga|acc aat tca g|tc
   aac  atg ttt ttt cgt ccg  aaa gta|tac cct|tgg tta agt c|ag
                              ▼          ▼         ▼         ▼
    Leu Tyr Lys Lys Ala Gly Phe His Met Gly Thr Asn Ser Val
```

```
      BamHI     KpnI    EcoRI                  EcoRI
    gac tg|g atc cgg ta|c cg|a att cgc ---Death--- ag|a att cgc
    ctg ac|c tag gcc at|g gc|t taa gcg ---(ccdB)--- tc|t taa gcg
        ▼       ▼       ▼                          ▼
    Asp Trp Ile Arg Tyr Arg Ile
```

```
     NotI    XhoI   EcoRV    Xba              Int attL2
    |ggc cgc ac|t cga gat|at|c tag|acc cag ctt tct tgt aca aag
    |ccg gcg tga gct|cta|tag|atc|tgg gtc gaa aga aca tgt ttc
         ▼      ▼        ▼    ▼                    ▼
```

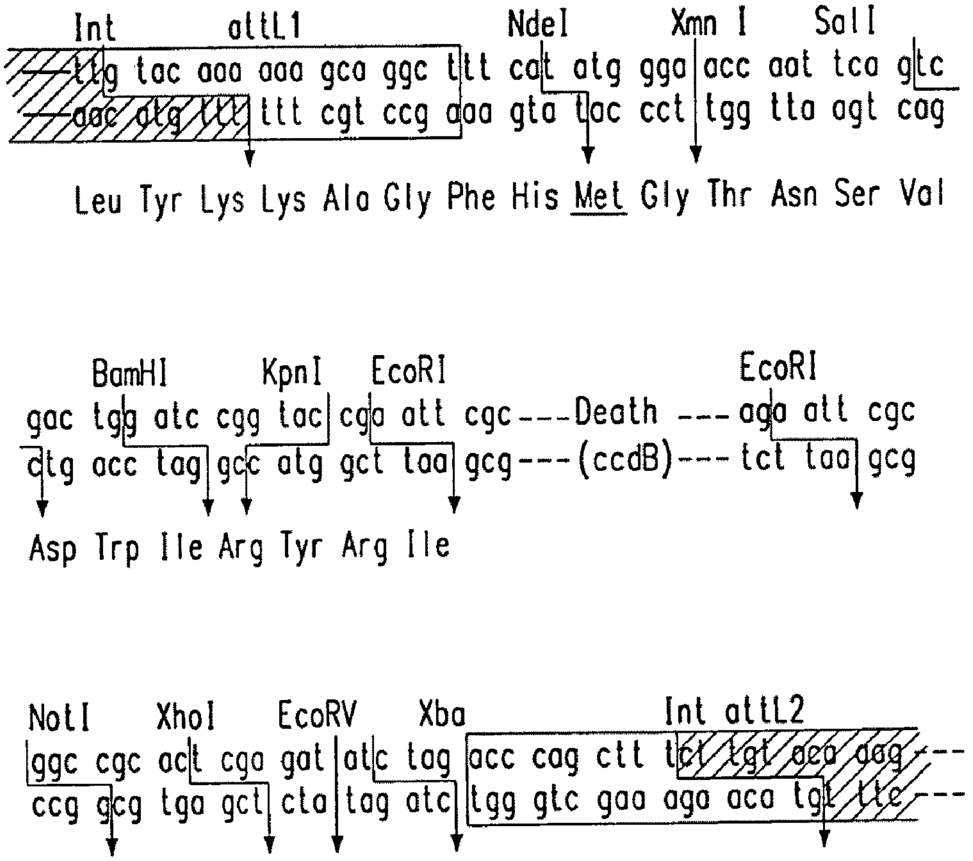

FIG.14A pENTR5 2720 bp

| Location (Base Nos.) | Gene Encoded |
|---|---|
| 67..166 | attL1 |
| 324..629 | ccdB |
| 658..757 | attL2 |
| 880..1689 | KmR |
| 1794..2367 | ori |

```
   1 CTGACGGATG GCCTTTTTGC GTTTCTACAA ACTCTTCCTG TTAGTTAGTT ACTTAAGCTC
  61 GGGCCCCAAA TAATGATTTT ATTTTGACTG ATAGTGACCT GTTCGTTGCA ACAAATTGAT
 121 AAGCAATGCT TTTTTATAAT GCCAACTTTG TACAAAAAAG CAGGCTTTCA TATGGGAACC
 181 AATTCAGTCG ACTGGATCCG GTACCGAATT CGCTTACTAA AAGCCAGATA ACAGTATGCG
 241 TATTTGCGCG CTGATTTTTG CGGTATAAGA ATATATACTG ATATGTATAC CCGAAGTATG
 301 TCAAAAAGAG GTGTGCTTCT AGAATGCAGT TTAAGGTTTA CACCTATAAA AGAGAGAGCC
 361 GTTATCGTCT GTTTGTGGAT GTACAGAGTG ATATTATTGA CACGCCCGGG CGACGGATGG
 421 TGATCCCCCT GGCCAGTGCA CGTCTGCTGT CAGATAAAGT CTCCCGTGAA CTTTACCCGG
 481 TGGTGCATAT CGGGGATGAA AGCTGGCGCA TGATGACCAC CGATATGGCC AGTGTGCCGG
 541 TCTCCGTTAT CGGGGAAGAA GTGGCTGATC TCAGCCACCG CGAAAATGAC ATCAAAAACG
 601 CCATTAACCT GATGTTCTGG GGAATATAGA ATTCGCGGCC GCACTCGAGA TATCTAGACC
 661 CAGCTTTCTT GTACAAAGTT GGCATTATAA GAAAGCATTG CTTATCAATT TGTTGCAACG
 721 AACAGGTCAC TATCAGTCAA AATAAAATCA TTATTTGCCA TCCAGCTGCA GCTCTGGCCC
 781 GTGTCTCAAA ATCTCTGATG TTACATTGCA CAAGATAAAA ATATATCATC ATGAACAATA
 841 AAACTGTCTG CTTACATAAA CAGTAATACA AGGGGTGTTA TGAGCCATAT TCAACGGGAA
 901 ACGTCGAGGC CGCGATTAAA TTCCAACATG GATGCTGATT TATATGGGTA TAAATGGGCT
 961 CGCGATAATG TCGGGCAATC AGGTGCGACA ATCTATCGCT TGTATGGGAA GCCCGATGCG
1021 CCAGAGTTGT TTCTGAAACA TGGCAAAGGT AGCGTTGCCA ATGATGTTAC AGATGAGATG
1081 GTCAGACTAA ACTGGCTGAC GGAATTTATG CCTCTTCCGA CCATCAAGCA TTTTATCCGT
1141 ACTCCTGATG ATGCATGGTT ACTCACCACT GCGATCCCCG GAAAAACAGC ATTCCAGGTA
1201 TTAGAAGAAT ATCCTGATTC AGGTGAAAAT ATTGTTGATG CGCTGGCAGT GTTCCTGCGC
1261 CGGTTGCATT CGATTCCTGT TTGTAATTGT CCTTTTAACA GCGATCGCGT ATTTCGTCTC
1321 GCTCAGGCGC AATCACGAAT GAATAACGGT TTGGTTGATG CGAGTGATTT TGATGACGAG
1381 CGTAATGGCT GGCCTGTTGA ACAAGTCTGG AAAGAAATGC ATAAACTTTT GCCATTCTCA
1441 CCGGATTCAG TCGTCACTCA TGGTGATTTC TCACTTGATA ACCTTATTTT TGACGAGGGG
1501 AAATTAATAG GTTGTATTGA TGTTGGACGA GTCGGAATCG CAGACCGATA CCAGGATCTT
1561 GCCATCCTAT GGAACTGCCT CGGTGAGTTT TCTCCTTCAT TACAGAAACG GCTTTTTCAA
1621 AAATATGGTA TTGATAATCC TGATATGAAT AAATTGCAGT TTCATTTGAT GCTCGATGAG
1681 TTTTTCTAAT CAGAATTGGT TAATTGGTTG TAACATTATT CAGATTGGGC CCCGTTCCAC
1741 TGAGCGTCAG ACCCCGTAGA AAAGATCAAA GGATCTTCTT GAGATCCTTT TTTTCTGCGC
1801 GTAATCTGCT GCTTGCAAAC AAAAAAACCA CCGCTACCAG CGGTGGTTTG TTTGCCGGAT
1861 CAAGAGCTAC CAACTCTTTT TCCGAAGGTA ACTGGCTTCA GCAGAGCGCA GATACCAAAT
1921 ACTGTTCTTC TAGTGTAGCC GTAGTTAGGC CACCACTTCA AGAACTCTGT AGCACCGCCT
1981 ACATACCTCG CTCTGCTAAT CCTGTTACCA GTGGCTGCTG CCAGTGGCGA TAAGTCGTGT
2041 CTTACCGGGT TGGACTCAAG ACGATAGTTA CCGGATAAGG CGCAGCGGTC GGGCTGAACG
2101 GGGGGTTCGT GCACACAGCC CAGCTTGGAG CGAACGACCT ACACCGAACT GAGATACCTA
2161 CAGCGTGAGC TATGAGAAAG CGCCACGCTT CCCGAAGGGA GAAAGGCGGA CAGGTATCCG
2221 GTAAGCGGCA GGGTCGGAAC AGGAGAGCGC ACGAGGGAGC TTCCAGGGGG AAACGCCTGG
2281 TATCTTTATA GTCCTGTCGG GTTTCGCCAC CTCTGACTTG AGCGTCGATT TTTGTGATGC
2341 TCGTCAGGGG GGCGGAGCCT ATGGAAAAAC GCCAGCAACG CGGCCTTTTT ACGGTTCCTG
2401 GCCTTTTGCT GGCCTTTTGC TCACATGTTC TTTCCTGCGT TATCCCCTGA TTCTGTGGAT
2461 AACCGTATTA CCGCTAGCAT GGATCTCGGG GACGTCTAAC TACTAAGCGA GAGTAGGGAA
2521 CTGCCAGGCA TCGAATAAAA CGAAAGGCTC AGTCGGAAGA CTGGGCCTTT CGTTTTATCT
2581 GTTGTTTGTC GGTGAACGCT CTCCTGAGTA GGACAAATCC GCCGGGAGCG GATTTGAACG
2641 TTGTGAAGCA ACGGCCCGGA GGGTGGCGGG CAGGACGCCC GCCATAAACT GCCAGGCATC
2701 AAACTAAGCA GAAGGCCATC
```

FIG. 14B

Cloning sites of the Entry Vector pENTR6

```
          Int        attL1                    SphI        XmnI       SalI
/////tg tac aaa aaa gca ggc tgc atg  cga acc  aat tca gtc
/////ac atg ttt ttt cgt ccg acg tac gct tgg  tta agt cag
       Leu Tyr Lys Lys Ala Gly Cys Met Arg Thr Asn Ser Val

      BamHI     KpnI EcoRI                      EcoRI
gac tgg atc cgg tac cga att cgc --- Death --- aga att cgc
ctg acc tag gcc atg gct taa gcg --- (ccdB) --- tct taa gcg
Asp Trp Ile Arg Tyr Arg Ile

Not   XhoI  EcoRV XbaI            Int       attL2
ggc cgc act cga gat atc tag  acc cag ctt tct tgt aca aag/////
ccg gcg tga gct cta tag atc  tgg gtc gaa aga aca tgt ttc/////
```

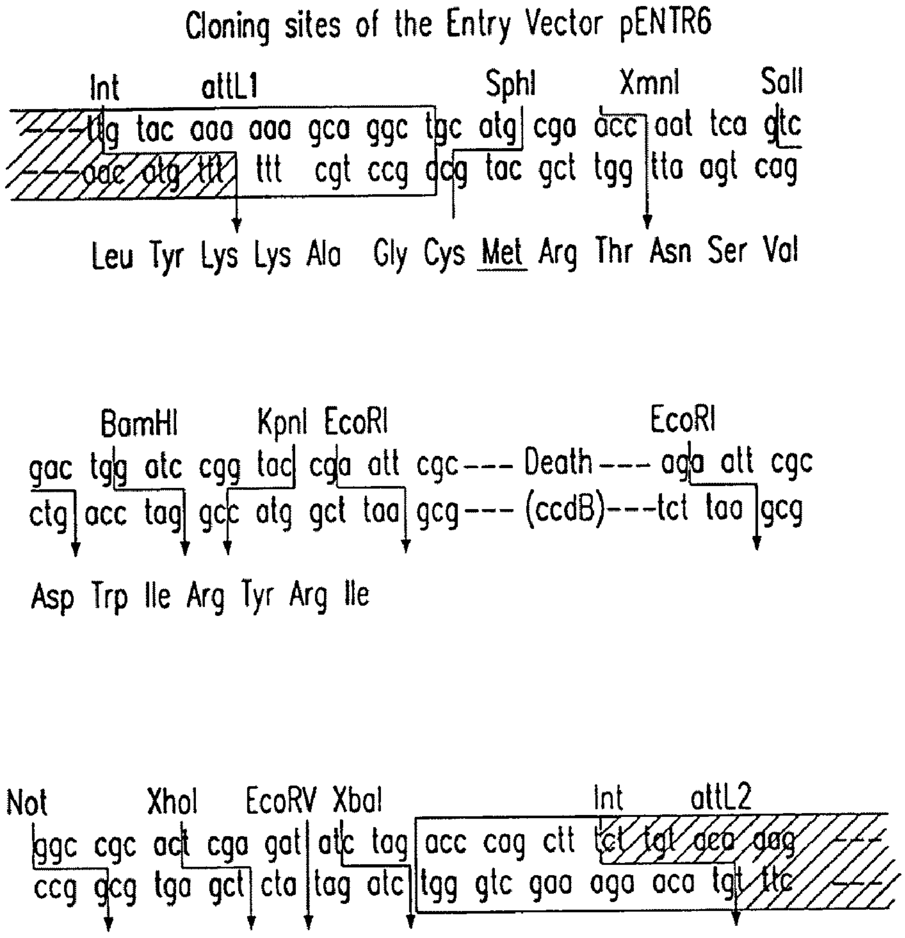

FIG.15A pENTR6 2717 bp

| Location (Base Nos.) | Gene Encoded |
|---|---|
| 67..166 | attL1 |
| 321..626 | ccdB |
| 655..754 | attL2 |
| 877..1686 | KmR |
| 1791..2364 | ori |

```
   1 CTGACGGATG GCCTTTTTGC GTTTCTACAA ACTCTTCCTG TTAGTTAGTT ACTTAAGCTC
  61 GGGCCCCAAA TAATGATTTT ATTTTGACTG ATAGTGACCT GTTCGTTGCA ACAAATTGAT
 121 AAGCAATGCT TTTTTATAAT GCCAACTTTG TACAAAAAAG CAGGCTGCAT GCGAACCAAT
 181 TCAGTCGACT GGATCCGGTA CCGAATTCGC TTACTAAAAG CCAGATAACA GTATGCGTAT
 241 TTGCGCGCTG ATTTTTGCGG TATAAGAATA TATACTGATA TGTATACCCG AAGTATGTCA
 301 AAAAGAGGTG TGCTTCTAGA ATGCAGTTTA AGGTTTACAC CTATAAAAGA GAGAGCCGTT
 361 ATCGTCTGTT TGTGGATGTA CAGAGTGATA TTATTGACAC GCCCGGGCGA CGGATGGTGA
 421 TCCCCCTGGC CAGTGCACGT CTGCTGTCAG ATAAAGTCTC CCGTGAACTT TACCCGGTGG
 481 TGCATATCGG GGATGAAAGC TGGCGCATGA TGACCACCGA TATGGCCAGT GTGCCGGTCT
 541 CCGTTATCGG GGAAGAAGTG GCTGATCTCA GCCACCGCGA AAATGACATC AAAAACGCCA
 601 TTAACCTGAT GTTCTGGGGA ATATAGAATT CGCGGCCGCA CTCGAGATAT CTAGACCCAG
 661 CTTTCTTGTA CAAAGTTGGC ATTATAAGAA AGCATTGCTT ATCAATTTGT TGCAACGAAC
 721 AGGTCACTAT CAGTCAAAAT AAAATCATTA TTTGCCATCC AGCTGCAGCT CTGGCCCGTG
 781 TCTCAAAATC TCTGATGTTA CATTGCACAA GATAAAAATA TATCATCATG AACAATAAAA
 841 CTGTCTGCTT ACATAAACAG TAATACAAGG GGTGTTATGA GCCATATTCA ACGGGAAACG
 901 TCGAGGCCGC GATTAAATTC CAACATGGAT GCTGATTTAT ATGGGTATAA ATGGGCTCGC
 961 GATAATGTCG GGCAATCAGG TGCGACAATC TATCGCTTGT ATGGGAAGCC CGATGCGCCA
1021 GAGTTGTTTC TGAAACATGG CAAAGGTAGC GTTGCCAATG ATGTTACAGA TGAGATGGTC
1081 AGACTAAACT GGCTGACGGA ATTTATGCCT CTTCCGACCA TCAAGCATTT TATCCGTACT
1141 CCTGATGATG CATGGTTACT CACCACTGCG ATCCCCGGAA AAACAGCATT CCAGGTATTA
1201 GAAGAATATC CTGATTCAGG TGAAAATATT GTTGATGCGC TGGCAGTGTT CCTGCGCCGG
1261 TTGCATTCGA TTCCTGTTTG TAATTGTCCT TTTAACAGCG ATCGCGTATT TCGTCTCGCT
1321 CAGGCGCAAT CACGAATGAA TAACGGTTTG GTTGATGCGA GTGATTTTGA TGACGAGCGT
1381 AATGGCTGGC CTGTTGAACA AGTCTGGAAA GAAATGCATA AACTTTTGCC ATTCTCACCG
1441 GATTCAGTCG TCACTCATGG TGATTTCTCA CTTGATAACC TTATTTTTGA CGAGGGGAAA
1501 TTAATAGGTT GTATTGATGT TGGACGAGTC GGAATCGCAG ACCGATACCA GGATCTTGCC
1561 ATCCTATGGA ACTGCCTCGG TGAGTTTTCT CCTTCATTAC AGAAACGGCT TTTTCAAAAA
1621 TATGGTATTG ATAATCCTGA TATGAATAAA TTGCAGTTTC ATTTGATGCT CGATGAGTTT
1681 TTCTAATCAG AATTGGTTAA TTGGTTGTAA CATTATTCAG ATTGGGCCCC GTTCCACTGA
1741 GCGTCAGACC CCGTAGAAAA GATCAAAGGA TCTTCTTGAG ATCCTTTTTT TCTGCGCGTA
1801 ATCTGCTGCT TGCAAACAAA AAAACCACCG CTACCAGCGG TGGTTTGTTT GCCGGATCAA
1861 GAGCTACCAA CTCTTTTTCC GAAGGTAACT GGCTTCAGCA GAGCGCAGAT ACCAAATACT
1921 GTTCTTCTAG TGTAGCCGTA GTTAGGCCAC CACTTCAAGA ACTCTGTAGC ACCGCCTACA
1981 TACCTCGCTC TGCTAATCCT GTTACCAGTG GCTGCTGCCA GTGGCGATAA GTCGTGTCTT
2041 ACCGGGTTGG ACTCAAGACG ATAGTTACCG GATAAGGCGC AGCGGTCGGG CTGAACGGGG
2101 GGTTCGTGCA CACAGCCCAG CTTGGAGCGA ACGACCTACA CCGAACTGAG ATACCTACAG
2161 CGTGAGCTAT GAGAAAGCGC CACGCTTCCC GAAGGGAGAA AGGCGGACAG GTATCCGGTA
2221 AGCGGCAGGG TCGGAACAGG AGAGCGCACG AGGGAGCTTC CAGGGGGAAA CGCCTGGTAT
2281 CTTTATAGTC CTGTCGGGTT TCGCCACCTC TGACTTGAGC GTCGATTTTT GTGATGCTCG
2341 TCAGGGGGGC GGAGCCTATG GAAAAACGCC AGCAACGCGG CCTTTTTACG GTTCCTGGCC
2401 TTTTGCTGGC CTTTTGCTCA CATGTTCTTT CCTGCGTTAT CCCCTGATTC TGTGGATAAC
2461 CGTATTACCG CTAGCATGGA TCTCGGGGAC GTCTAACTAC TAAGCGAGAG TAGGGAACTG
2521 CCAGGCATCA AATAAAACGA AAGGCTCAGT CGGAAGACTG GGCCTTTCGT TTTATCTGTT
2581 GTTTGTCGGT GAACGCTCTC CTGAGTAGGA CAAATCCGCC GGGAGCGGAT TTGAACGTTG
2641 TGAAGCAACG GCCCGGAGGG TGGCGGGCAG GACGCCCGCC ATAAACTGCC AGGCATCAAA
2701 CTAAGCAGAA GGCCATC
```

FIG. 15B

Cloning sites of the Entry Vector pENTR7

```
       attL1
----ttg tac aaa aaa gca ggc ttt gaa aac ctg tat ttt cag gga
----aac atg ttt ttt cgt ccg aaa ctt ttg gac ata aaa gtt cct
```

Leu Tyr Lys Lys Ala Gly Phe Glu Asn Leu Tyr Phe Gln Gly

TEV Protease

```
   XmnI        SalI       BamHI   KpnI  EcoRI
acc gtt tca tgc atc gtc gac tgg atc cgg tac cga att cgc---
tgg caa agt acg tag cag ctg acc tag gcc atg gct taa gcg---
```

Thr Val Ser Cys Ile Val Asp Trp Ile Arg Tyr Arg Ile

```
           EcoRI    NotI     XhoI  EcoRV   XbaI
-[Death]---aga att cgc ggc cgc act cga gat atc tag acc cag
-[(ccdB)]--tct taa gcg ccg gcg tga gct cta tag atc tgg gtc
```

```
  Int
      attL2
ctt tct tgt aca aag---
gaa aga aca tgt ttc---
```

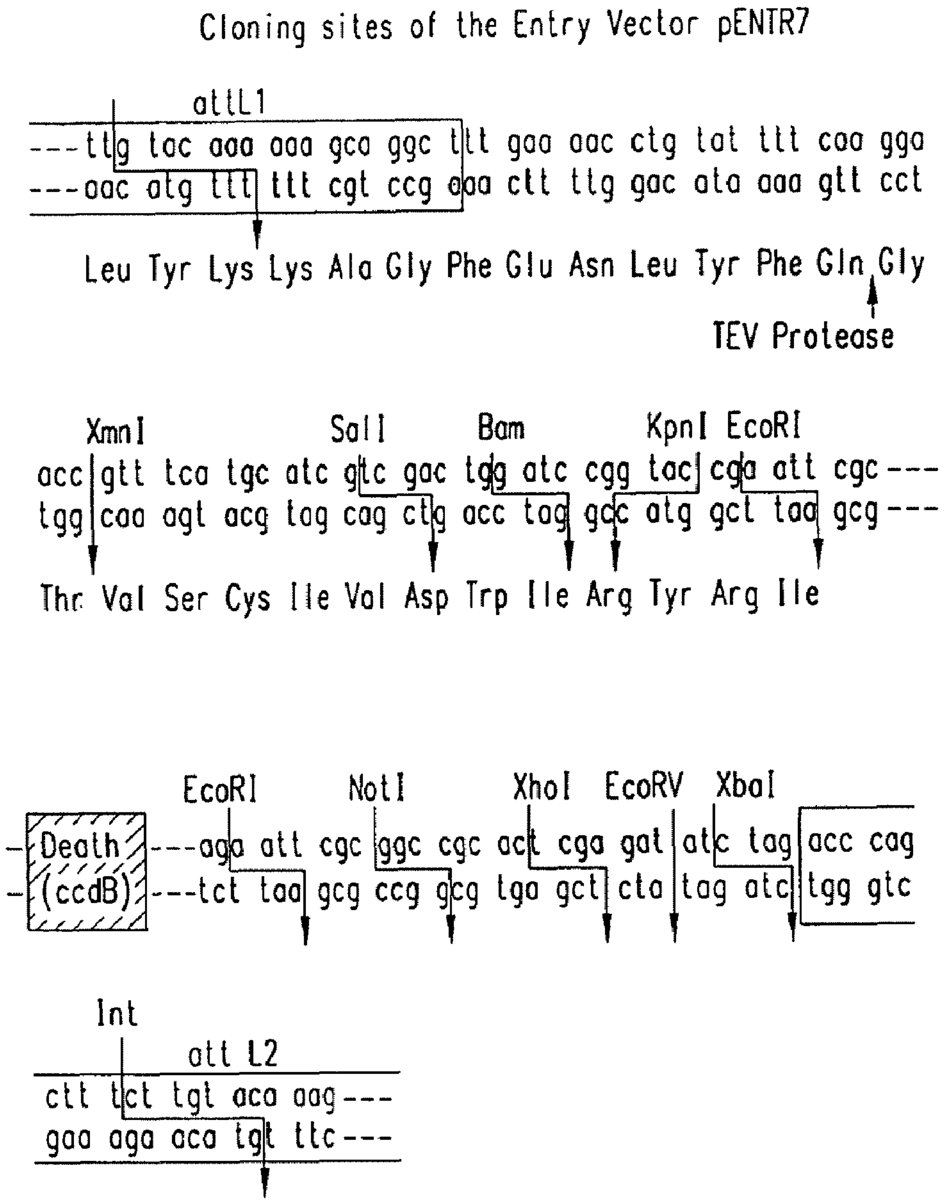

FIG.16A pENTR7 2738 bp

| Location (Base Nos.) | Gene Encoded |
|---|---|
| 67..166 | attL1 |
| 342..647 | ccdB |
| 676..775 | attL2 |
| 898..1707 | KmR |
| 1812..2385 | ori |

```
   1 CTGACGGATG GCCTTTTTGC GTTTCTACAA ACTCTTCCTG TTAGTTAGTT ACTTAAGCTC
  61 GGGCCCCAAA TAATGATTTT ATTTTGACTG ATAGTGACCT GTTCGTTGCA ACAAATTGAT
 121 AAGCAATGCT TTTTTATAAT GCCAACTTTG TACAAAAAAG CAGGCTTTGA AAACCTGTAT
 181 TTTCAAGGAA CCGTTTCATG CATCGTCGAC TGGATCCGGT ACCGAATTCG CTTACTAAAA
 241 GCCAGATAAC AGTATGCGTA TTTGCGCGCT GATTTTTGCG GTATAAGAAT ATATACTGAT
 301 ATGTATACCC GAAGTATGTC AAAAAGAGGT GTGCTTCTAG AATGCAGTTT AAGGTTTACA
 361 CCTATAAAAG AGAGAGCCGT TATCGTCTGT TTGTGGATGT ACAGAGTGAT ATTATTGACA
 421 CGCCCGGGCG ACGGATAGTG ATCCCCCTGG CCAGTGCACG TCTGCTGTCA GATAAAGTCT
 481 CCCGTGAACT TTACCCGGTG GTGCATATCG GGGATGAAAG CTGGCGCATG ATGACCACCG
 541 ATATGGCCAG TGTGCCGGTC TCCGTTATCG GGGAAGAAGT GGCTGATCTC AGCCACCGCG
 601 AAAATGACAT CAAAAACGCC ATTAACCTGA TGTTCTGGGG AATATAGAAT TCGCGGCCGC
 661 ACTCGAGATA TCTAGACCCA GCTTTCTTGT ACAAAGTTGG CATTATAAGA AAGCATTGCT
 721 TATCAATTTG TTGCAACGAA CAGGTCACTA TCAGTCAAAA TAAAATCATT ATTTGCCATC
 781 CAGCTGCAGC TCTGGCCCGT GTCTCAAAAT CTCTGATGTT ACATTGCACA AGATAAAAAT
 841 ATATCATCAT GAACAATAAA ACTGTCTGCT TACATAAACA GTAATACAAG GGGTGTTATG
 901 AGCCATATTC AACGGGAAAC GTCGAGGCCG CGATTAAATT CCAACATGGA TGCTGATTTA
 961 TATGGGTATA AATGGGCTCG CGATAATGTC GGGCAATCAG GTGCGACAAT CTATCGCTTG
1021 TATGGGAAGC CCGATGCGCC AGAGTTGTTT CTGAAACATG GCAAAGGTAG CGTTGCCAAT
1081 GATGTTACAG ATGAGATGGT CAGACTAAAC TGGCTGACGG AATTTATGCC TCTTCCGACC
1141 ATCAAGCATT TTATCCGTAC TCCTGATGAT GCATGGTTAC TCACCACTGC GATCCCCGGA
1201 AAAACAGCAT TCCAGGTATT AGAAGAATAT CCTGATTCAG GTGAAAATAT TGTTGATGCG
1261 CTGGCAGTGT TCCTGCGCCG GTTGCATTCG ATTCCTGTTT GTAATTGTCC TTTTAACAGC
1321 GATCGCGTAT TTCGTCTCGC TCAGGCGCAA TCACGAATGA ATAACGGTTT GGTTGATGCG
1381 AGTGATTTTG ATGACGAGCG TAATGGCTGG CCTGTTGAAC AAGTCTGGAA AGAAATGCAT
1441 AAACTTTTGC CATTCTCACC GGATTCAGTC GTCACTCATG GTGATTTCTC ACTTGATAAC
1501 CTTATTTTTG ACGAGGGGAA ATTAATAGGT TGTATTGATG TTGGACGAGT CGGAATCGCA
1561 GACCGATACC AGGATCTTGC CATCCTATGG AACTGCCTCG GTGAGTTTTC TCCTTCATTA
1621 CAGAAACGGC TTTTTCAAAA ATATGGTATT GATAATCCTG ATATGAATAA ATTGCAGTTT
1681 CATTTGATGC TCGATGAGTT TTTCTAATCA GAATTGGTTA ATTGGTTGTA ACATTATTCA
1741 GATTGGGCCC CGTTCCACTG AGCGTCAGAC CCCGTAGAAA AGATCAAAGG ATCTTCTTGA
1801 GATCCTTTTT TTCTGCGCGT AATCTGCTGC TTGCAAACAA AAAAACCACC GCTACCAGCG
1861 GTGGTTTGTT TGCCGGATCA AGAGCTACCA ACTCTTTTTC CGAAGGTAAC TGGCTTCAGC
1921 AGAGCGCAGA TACCAAATAC TGTTCTTCTA GTGTAGCCGT AGTTAGGCCA CCACTTCAAG
1981 AACTCTGTAG CACCGCCTAC ATACCTCGCT CTGCTAATCC TGTTACCAGT GGCTGCTGCC
2041 AGTGGCGATA AGTCGTGTCT TACCGGGTTG GACTCAAGAC GATAGTTACC GGATAAGGCG
2101 CAGCGGTCGG GCTGAACGGG GGGTTCGTGC ACACAGCCCA GCTTGGAGCG AACGACCTAC
2161 ACCGAACTGA GATACCTACA GCGTGAGCTA TGAGAAAGCG CCACGCTTCC CGAAGGGAGA
2221 AAGGCGGACA GGTATCCGGT AAGCGGCAGG GTCGGAACAG GAGAGCGCAC GAGGGAGCTT
2281 CCAGGGGGAA ACGCCTGGTA TCTTTATAGT CCTGTCGGGT TTCGCCACCT CTGACTTGAG
2341 CGTCGATTTT TGTGATGCTC GTCAGGGGGG CGGAGCCTAT GGAAAAACGC CAGCAACGCG
2401 GCCTTTTTAC GGTTCCTGGC CTTTTGCTGG CCTTTTGCTC ACATGTTCTT TCCTGCGTTA
2461 TCCCCTGATT CTGTGGATAA CCGTATTACC GCTAGCATGG ATCTCGGGGA CGTCTAACTA
2521 CTAAGCGAGA GTAGGGAACT GCCAGGCATC AAATAAAACG AAAGGCTCAG TCGGAAGACT
2581 GGGCCTTTCG TTTTATCTGT TGTTTGTCGG TGAACGCTCT CCTGAGTAGG ACAAATCCGC
2641 CGGGAGCGGA TTTGAACGTT GTGAAGCAAC GGCCCGGAGG GTGGCGGGCA GGACGCCCGC
2701 CATAAACTGC CAGGCATCAA ACTAAGCAGA AGGCCATC
```

FIG.16B

CLONING SITES OF THE ENTRY VECTOR pENTR8

```
       Int       attL1
////atg tac aaa aaa gca ggc ttt│gaa aac ctg tat ttt caa gga
////tac atg ttt ttt cgt ccg aaa│ctt ttg gac ata aaa gtt cct
      Leu Tyr Lys Lys Ala Gly Phe Glu Asn Leu Tyr Phe Gln Gly
                                                            ↑
                                                        TEV Protease
```

```
Ncol AvaII      SalI    BamHI    KpnI    EcoRI
acc atg│gac cta g│tc gac│tgg atc│cgg tac│cga att cgc ---
tgg tac│ctg│gat cag ctg│acc tag│gcc atg gct│taa│gcg ---
 ↓   ↓       ↓       ↓       ↓       ↓       ↓
Thr Met Asp Leu Val Asp Trp Ile Arg Tyr Arg Ile
```

```
              EcoRI  NotI    XhoI    EcoRV Xbal    attL
Death  ---aga att cgc│ggc cgc│act cga gat│atc tag│acc cag
       ---tct taa│gcg ccg gcg│tga gct│cta│tag atc│tgg gtc
              ↓       ↓       ↓       ↓   ↓
```

```
       Int
ctt tct tgt aca aag ////
gaa aga aca tgt ttc ////
              ↓
```

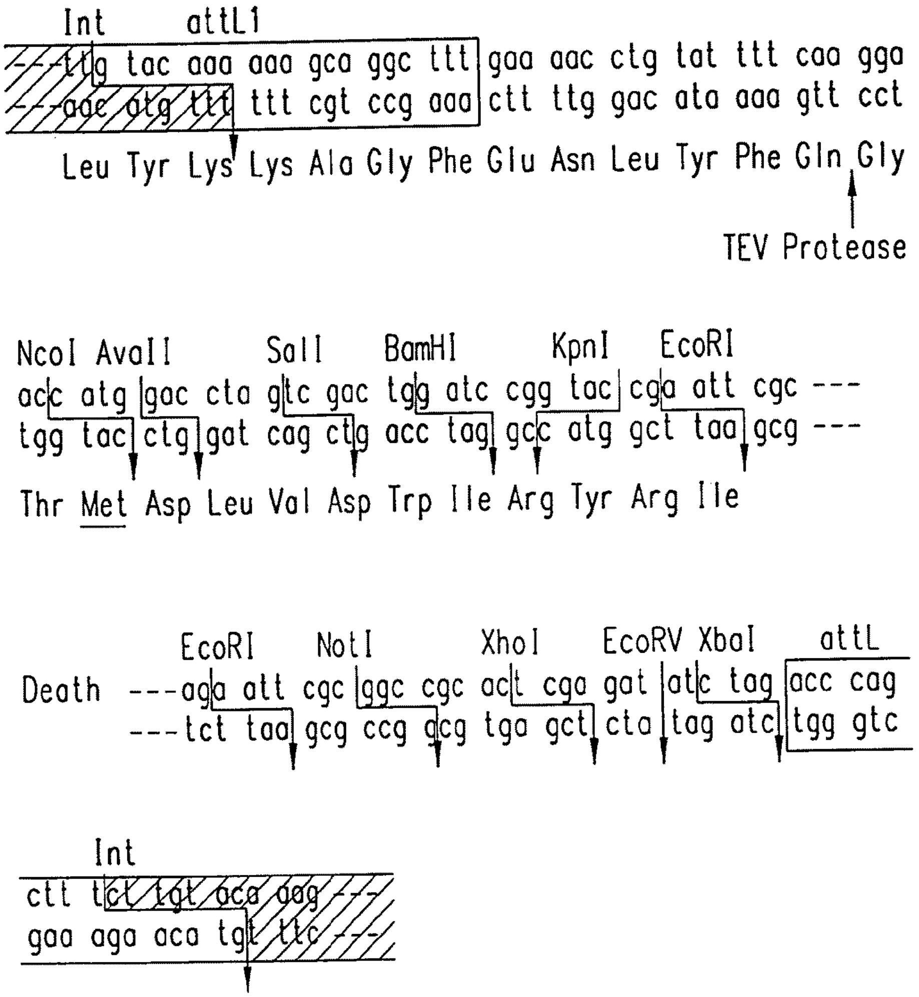

FIG.17A pENTR8 2735 bp

| Location (Base Nos.) | Gene Encoded |
|---|---|
| 67..166 | attL1 |
| 339..644 | ccdB |
| 673..772 | attL2 |
| 895..1704 | KmR |
| 1809..2382 | ori |

```
   1 CTGACGGATG GCCTTTTTGC GTTTCTACAA ACTCTTCCTG TTAGTTAGTT ACTTAAGCTC
  61 GGGCCCCAAA TAATGATTTT ATTTTGACTG ATAGTGACCT GTTCGTTGCA ACAAATTGAT
 121 AAGCAATGCT TTTTTATAAT GCCAACTTTG TACAAAAAAG CAGGCTTTGA AAACCTGTAT
 181 TTTCAAGGAA CCATGGACCT AGTCGACTGG ATCCGGTACC GAATTCGCTT ACTAAAAGCC
 241 AGATAACAGT ATGCGTATTT GCGCGCTGAT TTTTGCGGTA TAAGAATATA TACTGATATG
 301 TATACCCGAA GTATGTCAAA AAGAGGTGTG CTTCTAGAAT GCAGTTTAAG GTTTACACCT
 361 ATAAAAGAGA GAGCCGTTAT CGTCTGTTTG TGGATGTACA GAGTGATATT ATTGACACGC
 421 CCGGGCGACG GATAGTGATC CCCCTGGCCA GTGCACGTCT GCTGTCAGAT AAAGTCTCCC
 481 GTGAACTTTA CCCGGTGGTG CATATCGGGG ATGAAAGCTG GCGCATGATG ACCACCGATA
 541 TGGCCAGTGT GCCGGTCTCC GTTATCGGGG AAGAAGTGGC TGATCTCAGC CACCGCGAAA
 601 ATGACATCAA AAACGCCATT AACCTGATGT TCTGGGGAAT ATAGAATTCG CGGCCGCACT
 661 CGAGATATCT AGACCCAGCT TTCTTGTACA AAGTTGGCAT TATAAGAAAG CATTGCTTAT
 721 CAATTTGTTG CAACGAACAG GTCACTATCA GTCAAAATAA AATCATTATT TGCCATCCAG
 781 CTGCAGCTCT GGCCCGTGTC TCAAAATCTC TGATGTTACA TTGCACAAGA TAAAAATATA
 841 TCATCATGAA CAATAAAACT GTCTGCTTAC ATAAACAGTA ATACAAGGGG TGTTATGAGC
 901 CATATTCAAC GGGAAACGTC GAGGCCGCGA TTAAATTCCA ACATGGATGC TGATTTATAT
 961 GGGTATAAAT GGGCTCGCGA TAATGTCGGG CAATCAGGTG CGACAATCTA TCGCTTGTAT
1021 GGGAAGCCCG ATGCGCCAGA GTTGTTTCTG AAACATGGCA AAGGTAGCGT TGCCAATGAT
1081 GTTACAGATG AGATGGTCAG ACTAAACTGG CTGACGGAAT TTATGCCTCT TCCGACCATC
1141 AAGCATTTTA TCCGTACTCC TGATGATGCA TGGTTACTCA CCACTGCGAT CCCCGGAAAA
1201 ACAGCATTCC AGGTATTAGA AGAATATCCT GATTCAGGTG AAAATATTGT TGATGCGCTG
1261 GCAGTGTCCC TGCGCCGGTT GCATTCGATT CCTGTTTGTA ATTGTCCTTT TAACAGCGAT
1321 CGCGTATTTC GTCTCGCTCA GGCGCAATCA CGAATGAATA ACGGTTTGGT TGATGCGAGT
1381 GATTTTGATG ACGAGCGTAA TGGCTGGCCT GTTGAACAAG TCTGGAAAGA AATGCATAAA
1441 CTTTTGCCAT TCTCACCGGA TTCAGTCGTC ACTCATGGTG ATTTCTCACT TGATAACCTT
1501 ATTTTTGACG AGGGGAAATT AATAGGTTGT ATTGATGTTG GACGAGTCGG AATCGCAGAC
1561 CGATACCAGG ATCTTGCCAT CCTATGGAAC TGCCTCGGTG AGTTTTCTCC TTCATTACAG
1621 AAACGGCTTT TTCAAAAATA TGGTATTGAT AATCCTGATA TGAATAAATT GCAGTTTCAT
1681 TTGATGCTCG ATGAGTTTTT CTAATCAGAA TTGGTTAATT GGTTGTAACA TTATTCAGAT
1741 TGGGCCCCGT TCCACTGAGC GTCAGACCCC GTAGAAAAGA TCAAAGGATC TTCTTGAGAT
1801 CCTTTTTTTC TGCGCGTAAT CTGCTGCTTG CAAACAAAAA AACCACCGCT ACCAGCGGTG
1861 GTTTGTTTGC CGGATCAAGA GCTACCAACT CTTTTTCCGA AGGTAACTGG CTTCAGCAGA
1921 GCGCAGATAC CAAATACTGT TCTTCTAGTG TAGCCGTAGT TAGGCCACCA CTTCAAGAAC
1981 TCTGTAGCAC CGCCTACATA CCTCGCTCTG CTAATCCTGT TACCAGTGGC TGCTGCCAGT
2041 GGCGATAAGT CGTGTCTTAC CGGGTTGGAC TCAAGACGAT AGTTACCGGA TAAGGCGCAG
2101 CGGTCGGGCT GAACGGGGGG TTCGTGCACA CAGCCCAGCT TGGAGCGAAC GACCTACACC
2161 GAACTGAGAT ACCTACAGCG TGAGCTATGA GAAAGCGCCA CGCTTCCCGA AGGGAGAAAG
2221 GCGGACAGGT ATCCGGTAAG CGGCAGGGTC GGAACAGGAG AGCGCACGAG GGAGCTTCCA
2281 GGGGGAAACG CCTGGTATCT TTATAGTCCT GTCGGGTTTC GCCACCTCTG ACTTGAGCGT
2341 CGATTTTTGT GATGCTCGTC AGGGGGGCGG AGCCTATGGA AAAACGCCAG CAACGCGGCC
2401 TTTTTACGGT TCCTGGCCTT TTGCTGGCCT TTTGCTCACA TGTTCTTTCC TGCGTTATCC
2461 CCTGATTCTG TGGATAACCG TATTACCGCT AGCATGGATC TCGGGGACGT CTAACTACTA
2521 AGCGAGAGTA GGGAACTGCC AGGCATCAAA TAAAACGAAA GGCTCAGTCG GAAGACTGGG
2581 CCTTTCGTTT TATCTGTTGT TTGTCGGTGA ACGCTCTCCT GAGTAGGACA AATCCGCCGG
2641 GAGCGGATTT GAACGTTGTG AAGCAACGGC CCGGAGGGTG GCGGGCAGGA CGCCCGCCAT
2701 AAACTGCCAG GCATCAAACT AAGCAGAAGG CCATC
```

FIG.17B

CLONING SITES OF THE ENTRY VECTOR pENTR9

```
     Int        attL1
/////ttg tac aaa aaa gca ggc ttt|gaa aac ctg tat ttt caa gga
/////aac atg ttt ttt cgt ccg aaa|ctt ttg gac ata aaa gtt cct
```

Leu Tyr Lys Lys Ala Gly Phe Glu Asn Leu Tyr Phe Gln Gly

TEV Protease

```
Nde I   BglII  SalI   BamHI      KpnI EcoRI
cat atg aga tct gtc gac tgg atc cgg tac|cga att cgc---
gta tac tct aga cag ctg acc tag|gcc atg gct taa|gcg---
```

His Met Arg Ser Val Asp Trp Ile Arg Tyr Arg Ile

```
          EcoRI    NotI    XhoI   EcoRV Xbal    attL2
Death ---aga att cgc|ggc cgc ac|t cga gat|atc tag|acc cag
      ---tct taa|gcg ccg gcg tga gct|cta|tag atc|tgg gtc

   Int
ctt t/ct/tgt/aca/aag/////
gaa aga aca tgt/ttc/////
```

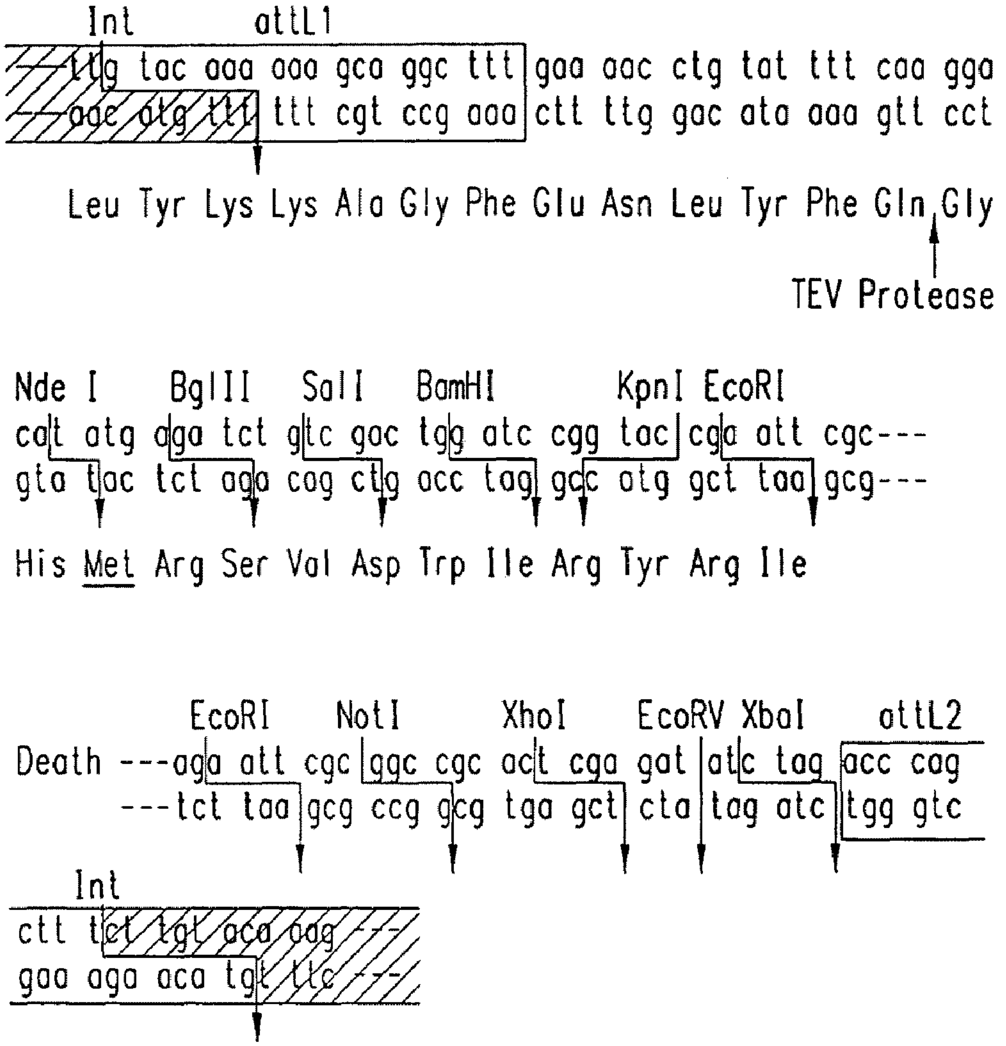

FIG.18A pENTR9 2735 bp

| Location (Base Nos.) | Gene Encoded |
|---|---|
| 67..166 | attL1 |
| 339..644 | ccdB |
| 673..772 | attL2 |
| 895..1704 | KmR |
| 1809..2382 | ori |

```
   1 CTGACGGATG GCCTTTTTGC GTTTCTACAA ACTCTTCCTG TTAGTTAGTT ACTTAAGCTC
  61 GGGCCCCAAA TAATGATTTT ATTTTGACTG ATAGTGACCT GTTCGTTGCA ACAAATTGAT
 121 AAGCAATGCT TTTTTATAAT GCCAACTTTG TACAAAAAAG CAGGCTTTGA AAACCTGTAT
 181 TTTCAAGGAC ATATGAGATC TGTCGACTGG ATCCGGTACC GAATTCGCTT ACTAAAAGCC
 241 AGATAACAGT ATGCGTATTT GCGCGCTGAT TTTTGCGGTA TAAGAATATA TACTGATATG
 301 TATACCCGAA GTATGTCAAA AAGAGGTGTG CTTCTAGAAT GCAGTTTAAG GTTTACACCT
 361 ATAAAAGAGA GAGCCGTTAT CGTCTGTTTG TGGATGTACA GAGTGATATT ATTGACACGC
 421 CCGGGCGACG GATAGTGATC CCCCTGGCCA GTGCACGTCT GCTGTCAGAT AAAGTCTCCC
 481 GTGAACTTTA CCCGGTGGTG CATATCGGGG ATGAAAGCTG GCGCATGATG ACCACCGATA
 541 TGGCCAGTGT GCCGGTCTCC GTTATCGGGG AAGAAGTGGC TGATCTCAGC CACCGCGAAA
 601 ATGACATCAA AAACGCCATT AACCTGATGT TCTGGGGAAT ATAGAATTCG CGGCCGCACT
 661 CGAGATATCT AGACCCAGCT TTCTTGTACA AAGTTGGCAT TATAAGAAAG CATTGCTTAT
 721 CAATTTGTTG CAACGAACAG GTCACTATCA GTCAAAATAA AATCATTATT TGCCATCCAG
 781 CTGCAGCTCT GGCCCGTGTC TCAAAATCTC TGATGTTACA TTGCACAAGA TAAAAATATA
 841 TCATCATGAA CAATAAAACT GTCTGCTTAC ATAAACAGTA ATACAAGGGG TGTTATGAGC
 901 CATATTCAAC GGGAAACGTC GAGGCCGCGA TTAAATTCCA ACATGGATGC TGATTTATAT
 961 GGGTATAAAT GGGCTCGCGA TAATGTCGGG CAATCAGGTG CGACAATCTA TCGCTTGTAT
1021 GGGAAGCCCG ATGCGCCAGA GTTGTTTCTG AAACATGGCA AAGGTAGCGT TGCCAATGAT
1081 GTTACAGATG AGATGGTCAG ACTAAACTGG CTGACGGAAT TTATGCCTCT TCCGACCATC
1141 AAGCATTTTA TCCGTACTCC TGATGATGCA TGGTTACTCA CCACTGCGAT CCCCGGAAAA
1201 ACAGCATTCC AGGTATTAGA AGAATATCCT GATTCAGGTG AAAATATTGT TGATGCGCTG
1261 GCAGTGTCCC TGCGCCGGTT GCATTCGATT CCTGTTTGTA ATTGTCCTTT TAACAGCGAT
1321 CGCGTATTTC GTCTCGCTCA GGCGCAATCA CGAATGAATA ACGGTTTGGT TGATGCGAGT
1381 GATTTTGATG ACGAGCGTAA TGGCTGGCCT GTTGAACAAG TCTGGAAAGA AATGCATAAA
1441 CTTTTGCCAT TCTCACCGGA TTCAGTCGTC ACTCATGGTG ATTTCTCACT TGATAACCTT
1501 ATTTTTGACG AGGGGAAATT AATAGGTTGT ATTGATGTTG GACGAGTCGG AATCGCAGAC
1561 CGATACCAGG ATCTTGCCAT CCTATGGAAC TGCCTCGGTG AGTTTTCTCC TTCATTACAG
1621 AAACGGCTTT TTCAAAAATA TGGTATTGAT AATCCTGATA TGAATAAATT GCAGTTTCAT
1681 TTGATGCTCG ATGAGTTTTT CTAATCAGAA TTGGTTAATT GGTTGTAACA TTATTCAGAT
1741 TGGGCCCCGT TCCACTGAGC GTCAGACCCC GTAGAAAAGA TCAAAGGATC TTCTTGAGAT
1801 CCTTTTTTTC TGCGCGTAAT CTGCTGCTTG CAAACAAAAA AACCACCGCT ACCAGCGGTG
1861 GTTTGTTTGC CGGATCAAGA GCTACCAACT CTTTTTCCGA AGGTAACTGG CTTCAGCAGA
1921 GCGCAGATAC CAAATACTGT TCTTCTAGTG TAGCCGTAGT TAGGCCACCA CTTCAAGAAC
1981 TCTGTAGCAC CGCCTACATA CCTCGCTCTG CTAATCCTGT TACCAGTGGC TGCTGCCAGT
2041 GGCGATAAGT CGTGTCTTAC CGGGTTGGAC TCAAGACGAT AGTTACCGGA TAAGGCGCAG
2101 CGGTCGGGCT GAACGGGGGG TTCGTGCACA CAGCCCAGCT TGGAGCGAAC GACCTACACC
2161 GAACTGAGAT ACCTACAGCG TGAGCTATGA GAAAGCGCCA CGCTTCCCGA AGGGAGAAAG
2221 GCGGACAGGT ATCCGGTAAG CGGCAGGGTC GGAACAGGAG AGCGCACGAG GGAGCTTCCA
2281 GGGGGAAACG CCTGGTATCT TTATAGTCCT GTCGGGTTTC GCCACCTCTG ACTTGAGCGT
2341 CGATTTTTGT GATGCTCGTC AGGGGGGCGG AGCCTATGGA AAAACGCCAG CAACGCGGCC
2401 TTTTTACGGT TCCTGGCCTT TTGCTGGCCT TTTGCTCACA TGTTCTTTCC TGCGTTATCC
2461 CCTGATTCTG TGGATAACCG TATTACCGCT AGCATGGATC TCGGGGACGT CTAACTACTA
2521 AGCGAGAGTA GGGAACTGCC AGGCATCAAA TAAAACGAAA GGCTCAGTCG GAAGACTGGG
2581 CCTTTCGTTT TATCTGTTGT TTGTCGGTGA ACGCTCTCCT GAGTAGGACA AATCCGCCGG
2641 GAGCGGATTT GAACGTTGTG AAGCAACGGC CCGGAGGGTG GCGGGCAGGA CGCCCGCCAT
2701 AAACTGCCAG GCATCAAACT AAGCAGAAGG CCATC
```

FIG. 18B

CLONING SITES OF THE ENTRY VECTOR pENTR10

```
    Int        attL1                      S.D.               Nde
   ///-atg tac aaa aaa gca ggc ttc gaa cta agg aaa tac tta cat
   ///-tac atg ttt ttt cgt ccg aag ctt gat tcc ttt atg aat gta
       Leu Tyr Lys Lys Ala Gly Phe Glu Leu Arg Lys Tyr Leu His

        Xmn I         Sal I    BamHI    KpnI     EcoRI
   atg gga acc aat tca gtc gac tgg atc cgg tac cga att cgc ---
   tac cct tgg tta agt cag ctg acc tag gcc atg gct taa gcg ---
       Met Gly Thr Asn Ser Val Asp Trp Ile Arg Tyr Arg Ile

             EcoRI    NotI    XhoI     EcoRV XbaI    attL2
   Death ---aga att cgc ggc cgc act cga gat atc tag acc cag
   (ccdB)---tct taa gcg ccg gcg tga gct cta tag atc tgg gtc

        Int
   ctt tct tgt aca aag ///---
   gaa aga aca tgt ttc ///---
```

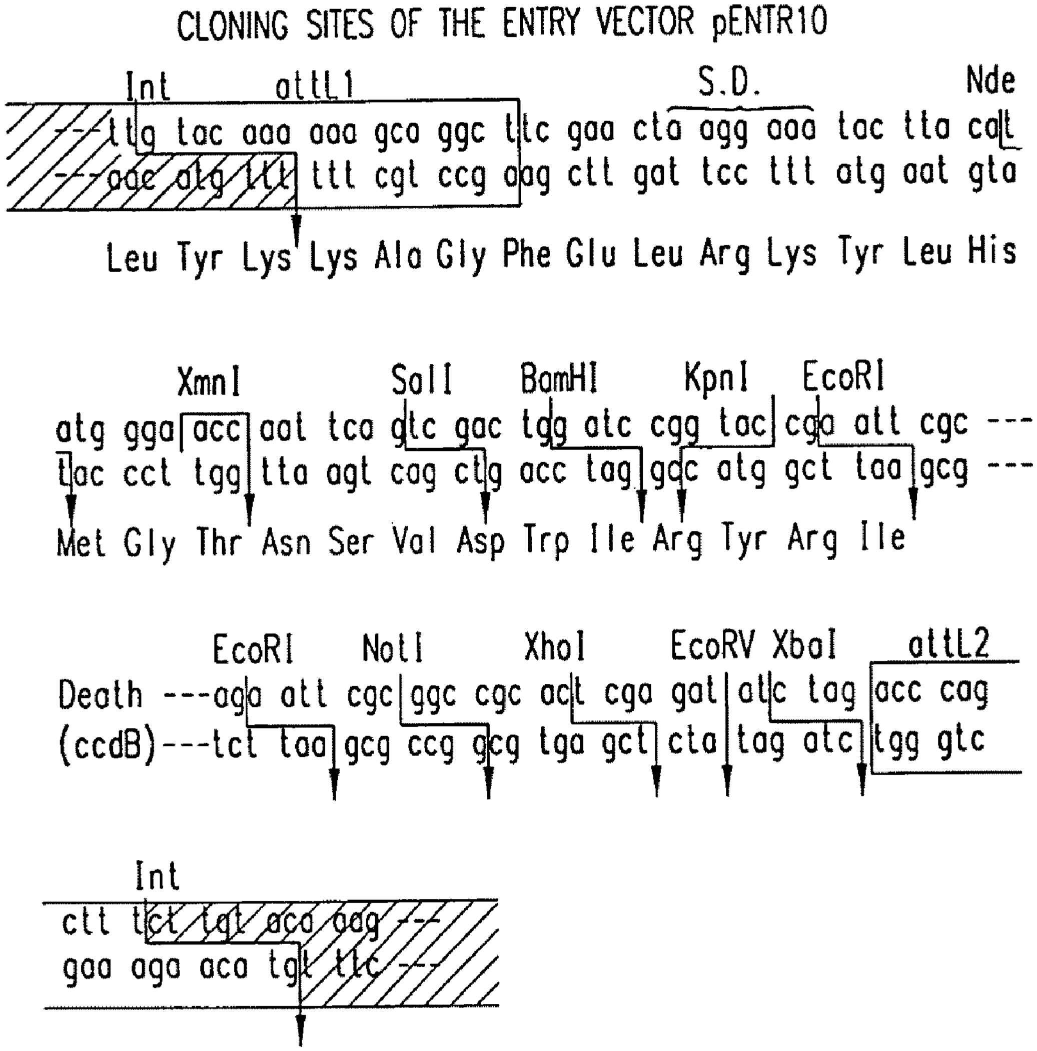

FIG.19A pENTR10 2738 bp

| Location (Base Nos.) | Gene Encoded |
|---|---|
| 67..166 | attL1 |
| 342..647 | ccdB |
| 676..775 | attL2 |
| 898..1707 | KmR |
| 1812..2385 | ori |

```
   1 CTGACGGATG GCCTTTTTGC GTTTCTACAA ACTCTTCCTG TTAGTTAGTT ACTTAAGCTC
  61 GGGCCCCAAA TAATGATTTT ATTTTGACTG ATAGTGACCT GTTCGTTGCA ACAAATTGAT
 121 AAGCAATGCT TTTTTATAAT GCCAACTTTG TACAAAAAAG CAGGCTTCGA ACTAAGGAAA
 181 TACTTACATA TGGGAACCAA TTCAGTCGAC TGGATCCGGT ACCGAATTCG CTTACTAAAA
 241 GCCAGATAAC AGTATGCGTA TTTGCGCGCT GATTTTTGCG GTATAAGAAT ATATACTGAT
 301 ATGTATACCC GAAGTATGTC AAAAAGAGGT GTGCTTCTAG AATGCAGTTT AAGGTTTACA
 361 CCTATAAAAG AGAGAGCCGT TATCGTCTGT TTGTGGATGT ACAGAGTGAT ATTATTGACA
 421 CGCCCGGGCG ACGGATGGTG ATCCCCCTGG CCAGTGCACG TCTGCTGTCA GATAAAGTCT
 481 CCCGTGAACT TTACCCGGTG GTGCATATCG GGGATGAAAG CTGGCGCATG ATGACCACCG
 541 ATATGGCCAG TGTGCCGGTC TCCGTTATCG GGGAAGAAGT GGCTGATCTC AGCCACCGCG
 601 AAAATGACAT CAAAAACGCC ATTAACCTGA TGTTCTGGGG AATATAGAAT TCGCGGCCGC
 661 ACTCGAGATA TCTAGACCCA GCTTTCTTGT ACAAAGTTGG CATTATAAGA AAGCATTGCT
 721 TATCAATTTG TTGCAACGAA CAGGTCACTA TCAGTCAAAA TAAAATCATT ATTTGCCATC
 781 CAGCTGCAGC TCTGGCCCGT GTCTCAAAAT CTCTGATGTT ACATTGCACA AGATAAAAAT
 841 ATATCATCAT GAACAATAAA ACTGTCTGCT TACATAAACA GTAATACAAG GGGTGTTATG
 901 AGCCATATTC AACGGGAAAC GTCGAGGCCG CGATTAAATT CCAACATGGA TGCTGATTTA
 961 TATGGGTATA AATGGGCTCG CGATAATGTC GGGCAATCAG GTGCGACAAT CTATCGCTTG
1021 TATGGGAAGC CCGATGCGCC AGAGTTGTTT CTGAAACATG GCAAAGGTAG CGTTGCCAAT
1081 GATGTTACAG ATGAGATGGT CAGACTAAAC TGGCTGACGG AATTTATGCC TCTTCCGACC
1141 ATCAAGCATT TTATCCGTAC TCCTGATGAT GCATGGTTAC TCACCACTGC GATCCCCGGA
1201 AAAACAGCAT TCCAGGTATT AGAAGAATAT CCTGATTCAG GTGAAAATAT TGTTGATGCG
1261 CTGGCAGTGT TCCTGCGCCG GTTGCATTCG ATTCCTGTTT GTAATTGTCC TTTTAACAGC
1321 GATCGCGTAT TTCGTCTCGC TCAGGCGCAA TCACGAATGA ATAACGGTTT GGTTGATGCG
1381 AGTGATTTTG ATGACGAGCG TAATGGCTGG CCTGTTGAAC AAGTCTGGAA AGAAATGCAT
1441 AAACTTTTGC CATTCTCACC GGATTCAGTC GTCACTCATG GTGATTTCTC ACTTGATAAC
1501 CTTATTTTTG ACGAGGGGAA ATTAATAGGT TGTATTGATG TTGGACGAGT CGGAATCGCA
1561 GACCGATACC AGGATCTTGC CATCCTATGG AACTGCCTCG GTGAGTTTTC TCCTTCATTA
1621 CAGAAACGGC TTTTTCAAAA ATATGGTATT GATAATCCTG ATATGAATAA ATTGCAGTTT
1681 CATTTGATGC TCGATGAGTT TTTCTAATCA GAATTGGTTA ATTGGTTGTA ACATTATTCA
1741 GATTGGGCCC CGTTCCACTG AGCGTCAGAC CCCGTAGAAA AGATCAAAGG ATCTTCTTGA
1801 GATCCTTTTT TTCTGCGCGT AATCTGCTGC TTGCAAACAA AAAAACCACC GCTACCAGCG
1861 GTGGTTTGTT TGCCGGATCA AGAGCTACCA ACTCTTTTTC CGAAGGTAAC TGGCTTCAGC
1921 AGAGCGCAGA TACCAAATAC TGTTCTTCTA GTGTAGCCGT AGTTAGGCCA CCACTTCAAG
1981 AACTCTGTAG CACCGCCTAC ATACCTCGCT CTGCTAATCC TGTTACCAGT GGCTGCTGCC
2041 AGTGGCGATA AGTCGTGTCT TACCGGGTTG GACTCAAGAC GATAGTTACC GGATAAGGCG
2101 CAGCGGTCGG GCTGAACGGG GGGTTCGTGC ACACAGCCCA GCTTGGAGCG AACGACCTAC
2161 ACCGAACTGA GATACCTACA GCGTGAGCTA TGAGAAAGCG CCACGCTTCC CGAAGGGAGA
2221 AAGGCGGACA GGTATCCGGT AAGCGGCAGG GTCGGAACAG GAGAGCGCAC GAGGGAGCTT
2281 CCAGGGGGAA ACGCCTGGTA TCTTTATAGT CCTGTCGGGT TTCGCCACCT CTGACTTGAG
2341 CGTCGATTTT TGTGATGCTC GTCAGGGGGG CGGAGCCTAT GGAAAAACGC CAGCAACGCG
2401 GCCTTTTTAC GGTTCCTGGC CTTTTGCTGG CCTTTTGCTC ACATGTTCTT TCCTGCGTTA
2461 TCCCCTGATT CTGTGGATAA CCGTATTACC GCTAGCATGG ATCTCGGGGA CGTCTAACTA
2521 CTAAGCGAGA GTAGGGAACT GCCAGGCATC GAATAAAACG AAAGGCTCAG TCGGAAGACT
2581 GGGCCTTTCG TTTTATCTGT TGTTTGTCGG TGAACGCTCT CCTGAGTAGG ACAAATCCGC
2641 CGGGAGCGGA TTTGAACGTT GTGAAGCAAC GGCCCGGAGG GTGGCGGGCA GGACGCCCGC
2701 CATAAACTGC CAGGCATCAA ACTAAGCAGA AGGCCATC
```

FIG. 19B

CLONING SITES OF THE ENTRY VECTOR pENTR11

```
   Int    attL1              S.D.   Kozak XmnI              S.D.
  TTG TAC AAA AAA GCA GGC TTC GAA GGA GAT AGA ACC AAT TCT CTA AGG AAA TAC
  AAC ATG TTT TTT CGT CCG AAG CTT CCT CTA TCT TGG TTA AGA GAT TCC TTT ATG
  Leu Tyr Lys Lys Ala Gly Phe Glu Gly Asp Arg Thr Asn Ser Leu Arg Lys Tyr
```

```
 Kozak NcoI   SalI    BamHI    KpnI EcoRI                EcoRI      NotI
  TTA ACC ATG GTC GAC TCG ATC CGG TAC CGA ATT C - - ccdB - - G AAT TCG CGG CCG
  AAT TGG TAC CAG CTG ACC TAG GCC ATG GCT TAA G              C TTA AGC GCC GGC
  Leu Thr Met Val Asp Trp Ile Arg Tyr Arg Ile                   Asn Ser Arg Pro
```

```
   XhoI    EcoRV XbaI           Int   attL2
  CAC TCG AGA TAT CTA GAC CCA GCT TTC TTG TAC AAA G
  GTG AGC TCT ATA GAT CTG GGT CGA AAG AAC ATG TTT C
  His Ser Arg Tyr Leu Asp Pro Ala Phe Leu Tyr Lys
```

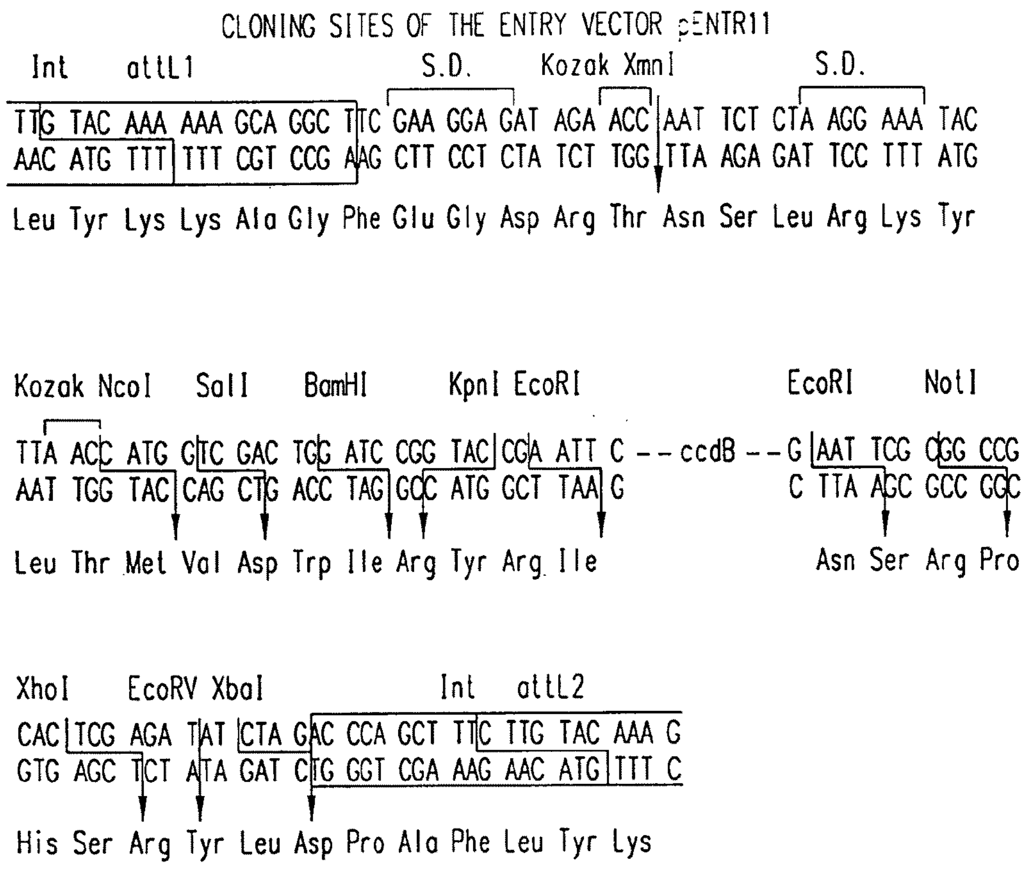

FIG.20A pENTR11 2744 bp (rotated to position 2578)

| Location (Base Nos.) | Gene Encoded |
|---|---|
| 67..166 | attL1 |
| 348..653 | ccdB |
| 683..781 | attL2 |
| 904..1713 | KmR |
| 1818..2391 | ori |

```
   1 CTGACGGATG GCCTTTTTGC GTTTCTACAA ACTCTTCCTG TTAGTTAGTT ACTTAAGCTC
  61 GGGCCCCAAA TAATGATTTT ATTTTGACTG ATAGTGACCT GTTCGTTGCA ACAAATTGAT
 121 AAGCAATGCT TTTTTATAAT GCCAACTTTG TACAAAAAAG CAGGCTTCGA AGGAGATAGA
 181 ACCAATTCTC TAAGGAAATA CTTAACCATG GTCGACTGGA TCCGGTACCG AATTCGCTTA
 241 CTAAAAGCCA GATAACAGTA TGCGTATTTG CGCGCTGATT TTTGCGGTAT AAGAATATAT
 301 ACTGATATGT ATACCCGAAG TATGTCAAAA AGAGGTGTGC TTCTAGAATG CAGTTTAAGG
 361 TTTACACCTA TAAAAGAGAG AGCCGTTATC GTCTGTTTGT GGATGTACAG AGTGATATTA
 421 TTGACACGCC CGGGCGACGG ATAGTGATCC CCCTGGCCAG TGCACGTCTG CTGTCAGATA
 481 AAGTCTCCCG TGAACTTTAC CCGGTGGTGC ATATCGGGGA TGAAAGCTGG CGCATGATGA
 541 CCACCGATAT GGCCAGTGTG CCGGTCTCCG TTATCGGGGA AGAAGTGGCT GATCTCAGCC
 601 ACCGCGAAAA TGACATCAAA AACGCCATTA ACCTGATGTT CTGGGGAATA TAGAATTCGC
 661 GGCCGCACTC GAGATATCTA GACCCAGCTT TCTTGTACAA AGTTGGCATT ATAAGAAAGC
 721 ATTGCTTATC AATTTGTTGC AACGAACAGG TCACTATCAG TCAAAATAAA ATCATTATTT
 781 GCCATCCAGC TGCAGCTCTG GCCCGTGTCT CAAAATCTCT GATGTTACAT TGCACAAGAT
 841 AAAAATATAT CATCATGAAC AATAAAACTG TCTGCTTACA TAAACAGTAA TACAAGGGGT
 901 GTTATGAGCC ATATTCAACG GGAAACGTCG AGGCCGCGAT TAAATTCCAA CATGGATGCT
 961 GATTTATATG GGTATAAATG GGCTCGCGAT AATGTCGGGC AATCAGGTGC GACAATCTAT
1021 CGCTTGTATG GGAAGCCCGA TGCGCCAGAG TTGTTTCTGA AACATGGCAA AGGTAGCGTT
1081 GCCAATGATG TTACAGATGA GATGGTCAGA CTAAACTGGC TGACGGAATT TATGCCTCTT
1141 CCGACCATCA AGCATTTTAT CCGTACTCCT GATGATGCAT GGTTACTCAC CACTGCGATC
1201 CCCGGAAAAA CAGCATTCCA GGTATTAGAA GAATATCCTG ATTCAGGTGA AAATATTGTT
1261 GATGCGCTGG CAGTGTTCCT GCGCCGGTTG CATTCGATTC CTGTTTGTAA TTGTCCTTTT
1321 AACAGCGATC GCGTATTTCG TCTCGCTCAG GCGCAATCAC GAATGAATAA CGGTTTGGTT
1381 GATGCGAGTG ATTTTGATGA CGAGCGTAAT GGCTGGCCTG TTGAACAAGT CTGGAAAGAA
1441 ATGCATAAAC TTTTGCCATT CTCACCGGAT TCAGTCGTCA CTCATGGTGA TTTCTCACTT
1501 GATAACCTTA TTTTTGACGA GGGGAAATTA ATAGGTTGTA TTGATGTTGG ACGAGTCGGA
1561 ATCGCAGACC GATACCAGGA TCTTGCCATC CTATGGAACT GCCTCGGTGA GTTTTCTCCT
1621 TCATTACAGA AACGGCTTTT TCAAAAATAT GGTATTGATA ATCCTGATAT GAATAAATTG
1681 CAGTTTCATT TGATGCTCGA TGAGTTTTTC TAATCAGAAT TGGTTAATTG GTTGTAACAT
1741 TATTCAGATT GGGCCCCGTT CCACTGAGCG TCAGACCCCG TAGAAAAGAT CAAAGGATCT
1801 TCTTGAGATC CTTTTTTTCT GCGCGTAATC TGCTGCTTGC AAACAAAAAA ACCACCGCTA
1861 CCAGCGGTGG TTTGTTTGCC GGATCAAGAG CTACCAACTC TTTTTCCGAA GGTAACTGGC
1921 TTCAGCAGAG CGCAGATACC AAATACTGTT CTTCTAGTGT AGCCGTAGTT AGGCCACCAC
1981 TTCAAGAACT CTGTAGCACC GCCTACATAC CTCGCTCTGC TAATCCTGTT ACCAGTGGCT
2041 GCTGCCAGTG GCGATAAGTC GTGTCTTACC GGGTTGGACT CAAGACGATA GTTACCGGAT
2101 AAGGCGCAGC GGTCGGGCTG AACGGGGGGT TCGTGCACAC AGCCCAGCTT GGAGCGAACG
2161 ACCTACACCG AACTGAGATA CCTACAGCGT GAGCTATGAG AAAGCGCCAC GCTTCCCGAA
2221 GGGAGAAAGG CGGACAGGTA TCCGGTAAGC GGCAGGGTCG GAACAGGAGA GCGCACGAGG
2281 GAGCTTCCAG GGGGAAACGC CTGGTATCTT TATAGTCCTG TCGGGTTTCG CCACCTCTGA
2341 CTTGAGCGTC GATTTTTGTG ATGCTCGTCA GGGGGGCGGA GCCTATGGAA AAACGCCAGC
2401 AACGCGGCCT TTTTACGGTT CCTGGCCTTT TGCTGGCCTT TTGCTCACAT GTTCTTTCCT
2461 GCGTTATCCC CTGATTCTGT GGATAACCGT ATTACCGCTA GCATGGATCT CGGGGACGTC
2521 TAACTACTAA GCGAGAGTAG GGAACTGCCA GGCATCAAAT AAAACGAAAG GCTCAGTCGG
2581 AAGACTGGGC CTTTCGTTTT ATCTGTTGTT TGTCGGTGAA CGCTCTCCTG AGTAGGACAA
2641 ATCCGCCGGG AGCGGATTTG AACGTTGTGA AGCAACGGCC CGGAGGGTGG CGGGCAGGAC
2701 GCCCGCCATA AACTGCCAGG CATCAAACTA AGCAGAAGGC CATC
```

FIG.20B

NATIVE PROTEIN EXPRESSION IN E. COLI

```
        -35      Trc PROMOTER       -10            ┌─mRNA
1   atgagctgtt gacaattaat catccggctc gtataatgtg tggaattgtg agcggataac
    tactcgacaa ctgttaatta gtaggccgag catattacac accttaacac tcgcctattg

                                              Int attR1
61  aatttcacac aggaaacaga caggtatagg atcacaagtt tgtacaaaaa agctgaacga
    ttaaagtgtg tcctttgtct gtccatatcc tagtgttcaa acatgttttt tcgacttgct
```

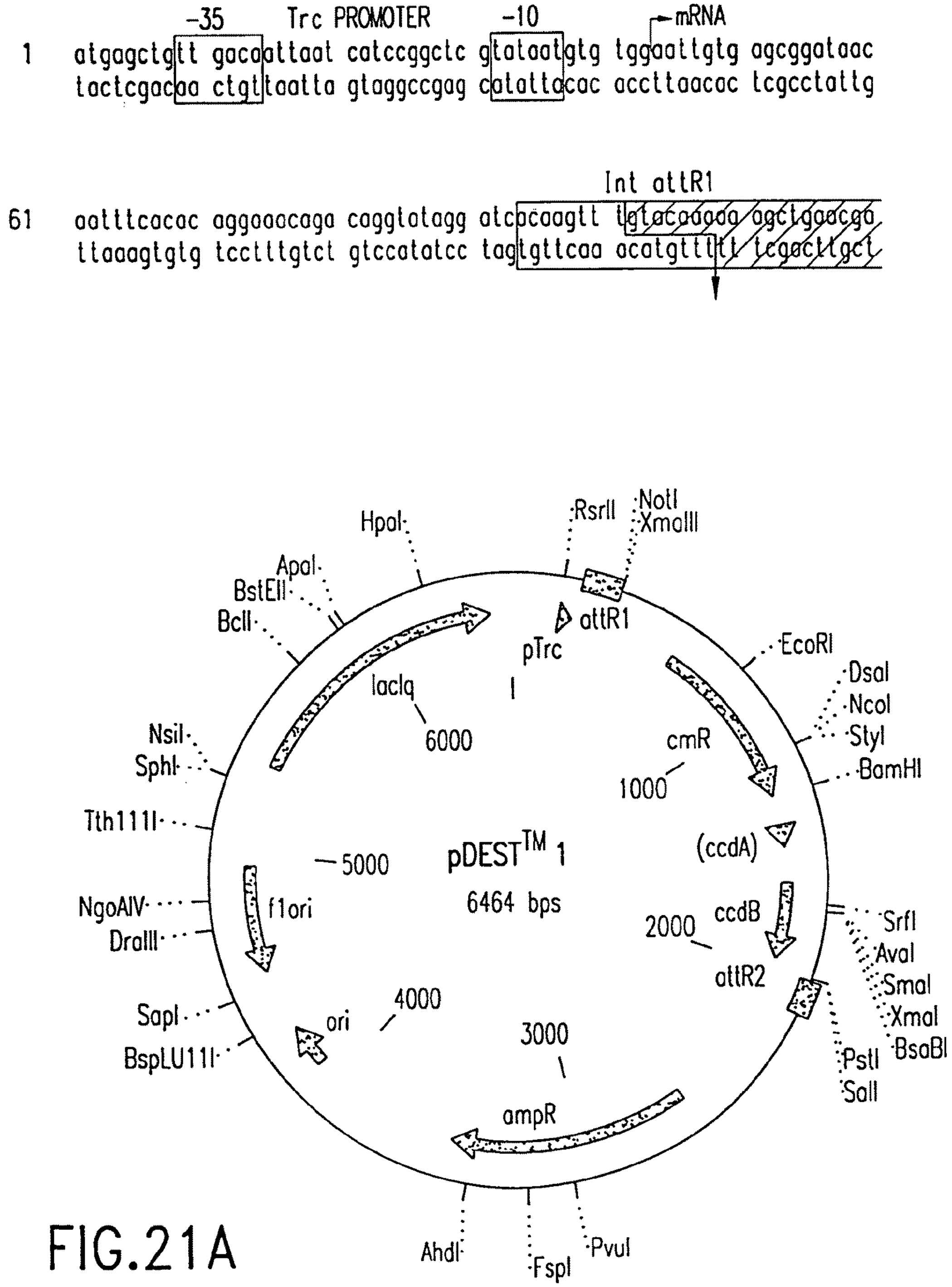

FIG.21A pDEST1 6464 bp

| Location (Base Nos.) | Gene Encoded |
|---|---|
| 216..257 | Trc promoter |
| 397..273 | attR1 |
| 647..1306 | CmR |
| 1426..1510 | inactivated ccdA |
| 1648..1953 | ccdB |
| 1994..2118 | attR2 |
| 2598..3503 | ampR |
| 4104..4264 | ori |
| 4504..4941 | flori (f1 intergenic region) |
| 5340..6420 | lacIq |

```
   1 GTTTGACAGC TTATCATCGA CTGCACGGTG CACCAATGCT TCTGGCGTCA GGCAGCCATC
  61 GGAAGCTGTG GTATGGCTGT GCAGGTCGTA AATCACTGCA TAATTCGTGT CGCTCAAGGC
 121 GCACTCCCGT TCTGGATAAT GTTTTTTGCG CCGACATCAT AACGGTTCTG GCAAATATTC
 181 TGAAATGAGC TGTTGACAAT TAATCATCCG GTCCGTATAA TCTGTGGAAT TGTGAGCGGG
 241 ATAACAATTT CATCGCGAGG TACCAAGCTA TCACAAGTTT GTACAAAAAA GCTGAACGAG
 301 AAACGTAAAA TGATATAAAT ATCAATATAT TAAATTAGAT TTTGCATAAA AAACAGACTA
 361 CATAATACTG TAAAACACAA CATATCCAGT CACTATGGCG GCCGCTAAGT TGGCAGCATC
 421 ACCCGACGCA CTTTGCGCCG AATAAATACC TGTGACGGAA GATCACTTCG CAGAATAAAT
 481 AAATCCTGGT GTCCCTGTTG ATACCGGGAA GCCCTGGGCC AACTTTTGGC GAAAATGAGA
 541 CGTTGATCGG CACGTAAGAG GTTCCAACTT TCACCATAAT GAAATAAGAT CACTACCGGG
 601 CGTATTTTTT GAGTTATCGA GATTTTCAGG AGCTAAGGAA GCTAAAATGG AGAAAAAAAT
 661 CACTGGATAT ACCACCGTTG ATATATCCCA ATGGCATCGT AAAGAACATT TTGAGGCATT
 721 TCAGTCAGTT GCTCAATGTA CCTATAACCA GACCGTTCAG CTGGATATTA CGGCCTTTTT
 781 AAAGACCGTA AAGAAAAATA AGCACAAGTT TTATCCGGCC TTTATTCACA TTCTTGCCCG
 841 CCTGATGAAT GCTCATCCGG AATTCCGTAT GGCAATGAAA GACGGTGAGC TGGTGATATG
 901 GGATAGTGTT CACCCTTGTT ACACCGTTTT CCATGAGCAA ACTGAAACGT TTTCATCGCT
 961 CTGGAGTGAA TACCACGACG ATTTCCGGCA GTTTCTACAC ATATATTCGC AAGATGTGGC
1021 GTGTTACGGT GAAAACCTGG CCTATTTCCC TAAAGGGTTT ATTGAGAATA TGTTTTTCGT
1081 CTCAGCCAAT CCCTGGGTGA GTTTCACCAG TTTTGATTTA AACGTGGCCA ATATGGACAA
1141 CTTCTTCGCC CCCGTTTTCA CCATGGGCAA ATATTATACG CAAGGCGACA AGGTGCTGAT
1201 GCCGCTGGCG ATTCAGGTTC ATCATGCCGT CTGTGATGGC TTCCATGTCG GCAGAATGCT
1261 TAATGAATTA CAACAGTACT GCGATGAGTG GCAGGGCGGG GCGTAAACGC GTGGATCCGG
1321 CTTACTAAAA GCCAGATAAC AGTATGCGTA TTTGCGCGCT GATTTTTGCG GTATAAGAAT
1381 ATATACTGAT ATGTATACCC GAAGTATGTC AAAAAGAGGT GTGCTATGAA GCAGCGTATT
1441 ACAGTGACAG TTGACAGCGA CAGCTATCAG TTGCTCAAGG CATATATGAT GTCAATATCT
1501 CCGGTCTGGT AAGCACAACC ATGCAGAATG AAGCCCGTCG TCTGCGTGCC GAACGCTGGA
1561 AAGCGGAAAA TCAGGAAGGG ATGGCTGAGG TCGCCCGGTT TATTGAAATG AACGGCTCTT
1621 TTGCTGACGA GAACAGGGAC TGGTGAAATG CAGTTTAAGG TTTACACCTA TAAAAGAGAG
1681 AGCCGTTATC GTCTGTTTGT GGATGTACAG AGTGATATTA TTGACACGCC CGGGCGACGG
```

FIG.21B

1741 ATGGTGATCC CCCTGGCCAG TGCACGTCTG CTGTCAGATA AAGTCTCCCG TGAACTTTAC
1801 CCGGTGGTGC ATATCGGGGA TGAAAGCTGG CGCATGATGA CCACCGATAT GGCCAGTGTG
1861 CCGGTCTCCG TTATCGGGGA AGAAGTGGCT GATCTCAGCC ACCGCGAAAA TGACATCAAA
1921 AACGCCATTA ACCTGATGTT CTGGGGAATA TAAATGTCAG GCTCCCTTAT ACACAGCCAG
1981 TCTGCAGGTC GACCATAGTG ACTGGATATG TTGTGTTTTA CAGTATTATG TAGTCTGTTT
2041 TTTATGCAAA ATCTAATTTA ATATATTGAT ATTTATATCA TTTTACGTTT CTCGTTCAGC
2101 TTTCTTGTAC AAAGTGGTGA TAGCTTGGCT GTTTTGGCGG ATGAGAGAAG ATTTTCAGCC
2161 TGATACAGAT TAAATCAGAA CGCAGAAGCG GTCTGATAAA ACAGAATTTG CCTGGCGGCA
2221 GTAGCGCGGT GGTCCCACCT GACCCCATGC CGAACTCAGA AGTGAAACGC CGTAGCGCCG
2281 ATGGTAGTGT GGGGTCTCCC CATGCGAGAG TAGGGAACTG CCAGGCATCA AATAAAACGA
2341 AAGGCTCAGT CGAAAGACTG GGCCTTTCGT TTTATCTGTT GTTTGTCGGT GAACGCTCTC
2401 CTGAGTAGGA CAAATCCGCC GGGAGCGGAT TTGAACGTTG CGAAGCAACG GCCCGGAGGG
2461 TGGCGGGCAG GACGCCCGCC ATAAACTGCC AGGCATCAAA TTAAGCAGAA GGCCATCCTG
2521 ACGGATGGCC TTTTTGCGTT TCTACAAACT CTTTTTGTTT ATTTTTCTAA ATACATTCAA
2581 ATATGTATCC GCTCATGAGA CAATAACCCT GATAAATGCT TCAATAATAT TGAAAAAGGA
2641 AGAGTATGAG TATTCAACAT TTCCGTGTCG CCCTTATTCC CTTTTTTGCG GCATTTTGCC
2701 TTCCTGTTTT TGCTCACCCA GAAACGCTGG TGAAAGTAAA AGATGCTGAA GATCAGTTGG
2761 GTGCACGAGT GGGTTACATC GAACTGGATC TCAACAGCGG TAAGATCCTT GAGAGTTTTC
2821 GCCCCGAAGA ACGTTTTCCA ATGATGAGCA CTTTTAAAGT TCTGCTATGT GGCGCGGTAT
2881 TATCCCGTGT TGACGCCGGG CAAGAGCAAC TCGGTCGCCG CATACACTAT TCTCAGAATG
2941 ACTTGGTTGA GTACTCACCA GTCACAGAAA AGCATCTTAC GGATGGCATG ACAGTAAGAG
3001 AATTATGCAG TGCTGCCATA ACCATGAGTG ATAACACTGC GGCCAACTTA CTTCTGACAA
3061 CGATCGGAGG ACCGAAGGAG CTAACCGCTT TTTTGCACAA CATGGGGGAT CATGTAACTC
3121 GCCTTGATCG TTGGGAACCG GAGCTGAATG AAGCCATACC AAACGACGAG CGTGACACCA
3181 CGATGCCTAC AGCAATGGCA ACAACGTTGC GCAAACTATT AACTGGCGAA CTACTTACTC
3241 TAGCTTCCCG GCAACAATTA ATAGACTGGA TGGAGGCGGA TAAAGTTGCA GGACCACTTC
3301 TGCGCTCGGC CCTTCCGGCT GGCTGGTTTA TTGCTGATAA ATCTGGAGCC GGTGAGCGTG
3361 GGTCTCGCGG TATCATTGCA GCACTGGGGC CAGATGGTAA GCCCTCCCGT ATCGTAGTTA
3421 TCTACACGAC GGGGAGTCAG GCAACTATGG ATGAACGAAA TAGACAGATC GCTGAGATAG
3481 GTGCCTCACT GATTAAGCAT TGGTAACTGT CAGACCAAGT TTACTCATAT ATACTTTAGA
3541 TTGATTTAAA ACTTCATTTT TAATTTAAAA GGATCTAGGT GAAGATCCTT TTTGATAATC
3601 TCATGACCAA AATCCCTTAA CGTGAGTTTT CGTTCCACTG AGCGTCAGAC CCCGTAGAAA
3661 AGATCAAAGG ATCTTCTTGA GATCCTTTTT TTCTGCGCGT AATCTGCTGC TTGCAAACAA
3721 AAAAACCACC GCTACCAGCG GTGGTTTGTT TGCCGGATCA AGAGCTACCA ACTCTTTTTC
3781 CGAAGGTAAC TGGCTTCAGC AGAGCGCAGA TACCAAATAC TGTCCTTCTA GTGTAGCCGT
3841 AGTTAGGCCA CCACTTCAAG AACTCTGTAG CACCGCCTAC ATACCTCGCT CTGCTAATCC
3901 TGTTACCAGT GGCTGCTGCC AGTGGCGATA AGTCGTGTCT TACCGGGTTG GACTCAAGAC
3961 GATAGTTACC GGATAAGGCG CAGCGGTCGG GCTGAACGGG GGGTTCGTGC ACACAGCCCA
4021 GCTTGGAGCG AACGACCTAC ACCGAACTGA GATACCTACA GCGTGAGCTA TGAGAAAGCG
4081 CCACGCTTCC CGAAGGGAGA AAGGCGGACA GGTATCCGGT AAGCGGCAGG GTCGGAACAG
4141 GAGAGCGCAC GAGGGAGCTT CCAGGGGGAA ACGCCTGGTA TCTTTATAGT CCTGTCGGGT

FIG.21C

4201 TTCGCCACCT CTGACTTGAG CGTCGATTTT TGTGATGCTC GTCAGGGGGG CGGAGCCTAT
4261 GGAAAAACGC CAGCAACGCG GCCTTTTTAC GGTTCCTGGC CTTTTGCTGG CCTTTTGCTC
4321 ACATGTTCTT TCCTGCGTTA TCCCCTGATT CTGTGGATAA CCGTATTACC GCCTTTGAGT
4381 GAGCTGATAC CGCTCGCCGC AGCCGAACGA CCGAGCGCAG CGAGTCAGTG AGCGAGGAAG
4441 CGGAAGAGCG CCTGATGCGG TATTTTCTCC TTACGCATCT GTGCGGTATT TCACACCGCA
4501 TAATTTTGTT AAAATTCGCG TTAAATTTTT GTTAAATCAG CTCATTTTTT AACCAATAGG
4561 CCGAAATCGG CAAAATCCCT TATAAATCAA AAGAATAGAC CGAGATAGGG TTGAGTGTTG
4621 TTCCAGTTTG GAACAAGAGT CCACTATTAA AGAACGTGGA CTCCAACGTC AAAGGGCGAA
4681 AAACCGTCTA TCAGGGCGAT GGCCCACTAC GTGAACCATC ACCCTAATCA AGTTTTTTGG
4741 GGTCGAGGTG CCGTAAAGCA CTAAATCGGA ACCCTAAAGG GAGCCCCCGA TTTAGAGCTT
4801 GACGGGGAAA GCCGGCGAAC GTGGCGAGAA AGGAAGGGAA GAAAGCGAAA GGAGCGGGCG
4861 CTAGGGCGCT GGCAAGTGTA GCGGTCACGC TGCGCGTAAC CACCACACCC GCCGCGCTTA
4921 ATGCGCCGCT ACAGGGCGCG TCCATTCGCC ATTCAGGCTG CTATGGTGCA CTCTCAGTAC
4981 AATCTGCTCT GATGCCGCAT AGTTAAGCCA GTACCAGTCA CGTAGCGATA TCGGAGTGTA
5041 TACACTCCGC TATCGCTACG TGACTGGGTC ATGGCTGCGC CCCGACACCC GCCAACACCC
5101 GCTGACGCGC CCTGACGGGC TTGTCTGCTC CCGGCATCCG CTTACAGACA AGCTGTGACC
5161 GTCTCCGGGA GCTGCATGTG TCAGAGGTTT TCACCGTCAT CACCGAAACG CGCGAGGCAG
5221 CAGATCAATT CGCGCGCGAA GGCGAAGCGG CATGCATTTA CGTTGACACC ATCGAATGGT
5281 GCAAAACCTT TCGCGGTATG GCATGATAGC GCCCGGAAGA GAGTCAATTC AGGGTGGTGA
5341 ATGTGAAACC AGTAACGTTA TACGATGTCG CAGAGTATGC CGGTGTCTCT TATCAGACCG
5401 TTTCCCGCGT GGTGAACCAG GCCAGCCACG TTTCTGCGAA AACGCGGGAA AAAGTGGAAG
5461 CGGCGATGGC GGAGCTGAAT TACATTCCCA ACCGCGTGGC ACAACAACTG GCGGGCAAAC
5521 AGTCGTTGCT GATTGGCGTT GCCACCTCCA GTCTGGCCCT GCACGCGCCG TCGCAAATTG
5581 TCGCGGCGAT TAAATCTCGC GCCGATCAAC TGGGTGCCAG CGTGGTGGTG TCGATGGTAG
5641 AACGAAGCGG CGTCGAAGCC TGTAAAGCGG CGGTGCACAA TCTTCTCGCG CAACGCGTCA
5701 GTGGGCTGAT CATTAACTAT CCGCTGGATG ACCAGGATGC CATTGCTGTG GAAGCTGCCT
5761 GCACTAATGT TCCGGCGTTA TTTCTTGATG TCTCTGACCA GACACCCATC AACAGTATTA
5821 TTTTCTCCCA TGAAGACGGT ACGCGACTGG GCGTGGAGCA TCTGGTCGCA TTGGGTCACC
5881 AGCAAATCGC GCTGTTAGCG GGCCCATTAA GTTCTGTCTC GGCGCGTCTG CGTCTGGCTG
5941 GCTGGCATAA ATATCTCACT CGCAATCAAA TTCAGCCGAT AGCGGAACGG GAAGGCGACT
6001 GGAGTGCCAT GTCCGGTTTT CAACAAACCA TGCAAATGCT GAATGAGGGC ATCGTTCCCA
6061 CTGCGATGCT GGTTGCCAAC GATCAGATGG CGCTGGGCGC AATGCGCGCC ATTACCGAGT
6121 CCGGGCTGCG CGTTGGTGCG GATATCTCGG TAGTGGGATA CGACGATACC GAAGACAGCT
6181 CATGTTATAT CCCGCCGTTA ACCACCATCA AACAGGATTT TCGCCTGCTG GGGCAAACCA
6241 GCGTGGACCG CTTGCTGCAA CTCTCTCAGG GCCAGGCGGT GAAGGGCAAT CAGCTGTTGC
6301 CCGTCTCACT GGTGAAAAGA AAAACCACCC TGGCACCCAA TACGCAAACC GCCTCTCCCC
6361 GCGCGTTGGC CGATTCATTA ATGCAGCTGG CACGACAGGT TTCCCGACTG GAAAGCGGGC
6421 AGTGAGCGCA ACGCAATTAA TGTGAGTTAG CGCGAATTGA TCTG

FIG.21D

His6 FUSIONS IN E. COLI

```
                                 -35         Trc PROMOTER       -10
970   aat att ctg aaa tga gct gtt gac aat taa tca tcc ggt ccg tat aat ctg
      tta taa gac ttt act cga caa ctg tta att agt agg cca ggc ata tta gac

         RNA                                                 Met Ser Tyr
1021  tgg aat tgt gag cgg ata aca att tca cac agg aaa cag acc atg tcg tac
      acc tta aca ctc gcc tat tgt taa agt gtg tcc ttt gtc tgg tac agc atg

      Tyr His His His His His His Gly Ile Thr Ser Int   attR1
1072  tac cat cac cat cac cat cac ggc atc aca agt ttg tac aaa aaa gct gaa
      atg gta gtg gta gtg gta gtg ccg tag tgt tca aac atg ttt ttt cga ctt
```

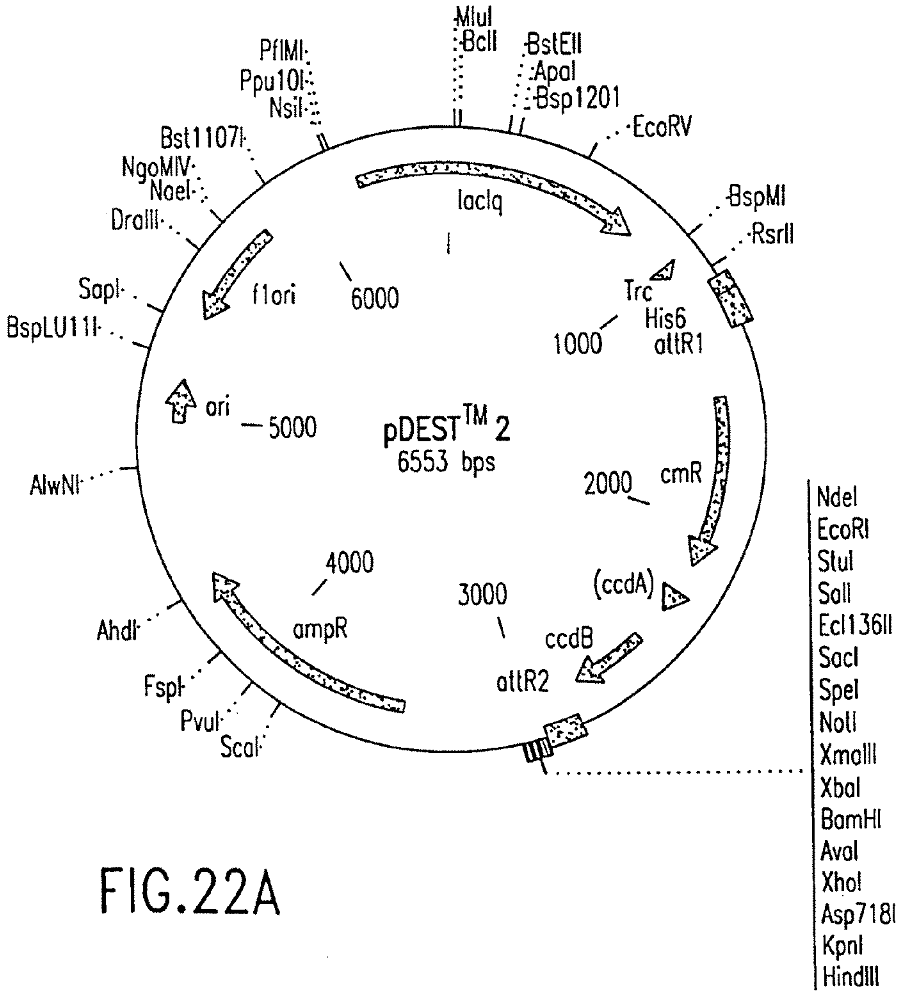

FIG.22A pDEST2 6553 bp

| Location (Base Nos.) | Gene Encoded |
|---|---|
| 912..962 | Trc |
| 1223..1009 | attR1 |
| 1473..2132 | CmR |
| 2252..2336 | inactivated ccdA |
| 2474..2779 | ccdB |
| 2820..2944 | attR2 |
| 3509..4414 | ampR |
| 5015..5175 | ori |
| 5415..5852 | flori (f1 intergenic region) |
| 6225..752 | lacIq |

```
   1 GGCGGTGCAC AATCTTCTCG CGCAACGCGT CAGTGGGCTG ATCATTAACT ATCCGCTGGA
  61 TGACCAGGAT GCCATTGCTG TGGAAGCTGC CTGCACTAAT GTTCCGGCGT TATTTCTTGA
 121 TGTCTCTGAC CAGACACCCA TCAACAGTAT TATTTTCTCC CATGAAGACG GTACGCGACT
 181 GGGCGTGGAG CATCTGGTCG CATTGGGTCA CCAGCAAATC GCGCTGTTAG CGGGCCCATT
 241 AAGTTCTGTC TCGGCGCGTC TGCGTCTGGC TGGCTGGCAT AAATATCTCA CTCGCAATCA
 301 AATTCAGCCG ATAGCGGAAC GGGAAGGCGA CTGGAGTGCC ATGTCCGGTT TTCAACAAAC
 361 CATGCAAATG CTGAATGAGG GCATCGTTCC CACTGCGATG CTGGTTGCCA ACGATCAGAT
 421 GGCGCTGGGC GCAATGCGCG CCATTACCGA GTCCGGGCTG CGCGTTGGTG CGGATATCTC
 481 GGTAGTGGGA TACGACGATA CCGAAGACAG CTCATGTTAT ATCCCGCCGT CAACCACCAT
 541 CAAACAGGAT TTTCGCCTGC TGGGGCAAAC CAGCGTGGAC CGCTTGCTGC AACTCTCTCA
 601 GGGCCAGGCG GTGAAGGGCA ATCAGCTGTT GCCCGTCTCA CTGGTGAAAA GAAAAACCAC
 661 CCTGGCACCC AATACGCAAA CCGCCTCTCC CCGCGCGTTG GCCGATTCAT TAATGCAGCT
 721 GGCACGACAG GTTTCCCGAC TGGAAAGCGG GCAGTGAGCG CAACGCAATT AATGTGAGTT
 781 AGCGCGAATT GATCTGGTTT GACAGCTTAT CATCGACTGC ACGGTGCACC AATGCTTCTG
 841 GCGTCAGGCA GCCATCGGAA GCTGTGGTAT GGCTGTGCAG GTCGTAAATC ACTGCATAAT
 901 TCGTGTCGCT CAAGGCGCAC TCCCGTTCTG GATAATGTTT TTTGCGCCGA CATCATAACG
 961 GTTCTGGCAA ATATTCTGAA ATGAGCTGTT GACAATTAAT CATCCGGTCC GTATAATCTG
1021 TGGAATTGTG AGCGGATAAC AATTTCACAC AGGAAACAGA CCATGTCGTA CTACCATCAC
1081 CATCACCATC ACGGCATCAC AAGTTTGTAC AAAAAAGCTG AACGAGAAAC GTAAAATGAT
1141 ATAAATATCA ATATATTAAA TTAGATTTTG CATAAAAAAC AGACTACATA ATACTGTAAA
1201 ACACAACATA TCCAGTCACT ATGGCGGCCG CTAAGTTGGC AGCATCACCC GACGCACTTT
1261 GCGCCGAATA AATACCTGTG ACGGAAGATC ACTTCGCAGA ATAAATAAAT CCTGGTGTCC
1321 CTGTTGATAC CGGGAAGCCC TGGGCCAACT TTTGGCGAAA ATGAGACGTT GATCGGCACG
1381 TAAGAGGTTC CAACTTTCAC CATAATGAAA TAAGATCACT ACCGGGCGTA TTTTTTGAGT
1441 TATCGAGATT TTCAGGAGCT AAGGAAGCTA AAATGGAGAA AAAAATCACT GGATATACCA
1501 CCGTTGATAT ATCCCAATGG CATCGTAAAG AACATTTTGA GGCATTTCAG TCAGTTGCTC
1561 AATGTACCTA TAACCAGACC GTTCAGCTGG ATATTACGGC CTTTTTAAAG ACCGTAAAGA
1621 AAAATAAGCA CAAGTTTTAT CCGGCCTTTA TTCACATTCT TGCCCGCCTG ATGAATGCTC
1681 ATCCGGAATT CCGTATGGCA ATGAAAGACG GTGAGCTGGT GATATGGGAT AGTGTTCACC
```

FIG.22B

1741 CTTGTTACAC CGTTTTCCAT GAGCAAACTG AAACGTTTTC ATCGCTCTGG AGTGAATACC
1801 ACGACGATTT CCGGCAGTTT CTACACATAT ATTCGCAAGA TGTGGCGTGT TACGGTGAAA
1861 ACCTGGCCTA TTTCCCTAAA GGGTTTATTG AGAATATGTT TTTCGTCTCA GCCAATCCCT
1921 GGGTGAGTTT CACCAGTTTT GATTTAAACG TGGCCAATAT GGACAACTTC TTCGCCCCCG
1981 TTTTCACCAT GGGCAAATAT TATACGCAAG GCGACAAGGT GCTGATGCCG CTGGCGATTC
2041 AGGTTCATCA TGCCGTCTGT GATGGCTTCC ATGTCGGCAG AATGCTTAAT GAATTACAAC
2101 AGTACTGCGA TGAGTGGCAG GGCGGGGCGT AAACGCGTGG ATCCGGCTTA CTAAAAGCCA
2161 GATAACAGTA TGCGTATTTG CGCGCTGATT TTTGCGGTAT AAGAATATAT ACTGATATGT
2221 ATACCCGAAG TATGTCAAAA AGAGGTGTGC TATGAAGCAG CGTATTACAG TGACAGTTGA
2281 CAGCGACAGC TATCAGTTGC TCAAGGCATA TATGATGTCA ATATCTCCGG TCTGGTAAGC
2341 ACAACCATGC AGAATGAAGC CCGTCGTCTG CGTGCCGAAC GCTGGAAAGC GGAAAATCAG
2401 GAAGGGATGG CTGAGGTCGC CCGGTTTATT GAAATGAACG GCTCTTTTGC TGACGAGAAC
2461 AGGGACTGGT GAAATGCAGT TTAAGGTTTA CACCTATAAA AGAGAGAGCC GTTATCGTCT
2521 GTTTGTGGAT GTACAGAGTG ATATTATTGA CACGCCCGGG CGACGGATGG TGATCCCCCT
2581 GGCCAGTGCA CGTCTGCTGT CAGATAAAGT CTCCCGTGAA CTTTACCCGG TGGTGCATAT
2641 CGGGGATGAA AGCTGGCGCA TGATGACCAC CGATATGGCC AGTGTGCCGG TCTCCGTTAT
2701 CGGGGAAGAA GTGGCTGATC TCAGCCACCG CGAAAATGAC ATCAAAAACG CCATTAACCT
2761 GATGTTCTGG GGAATATAAA TGTCAGGCTC CCTTATACAC AGCCAGTCTG CAGGTCGACC
2821 ATAGTGACTG GATATGTTGT GTTTTACAGT ATTATGTAGT CTGTTTTTTA TGCAAAATCT
2881 AATTTAATAT ATTGATATTT ATATCATTTT ACGTTTCTCG TTCAGCTTTC TTGTACAAAG
2941 TGGTGATGCC CATATGGGAA TTCAAAGGCC TACGTCGACG AGCTCACTAG TCGCGGCCGC
3001 TTCTAGAGGA TCCCTCGAGG CATGCGGTAC CAAGCTTGGC TGTTTTGGCG GATGAGAGAA
3061 GATTTTCAGC CTGATACAGA TTAAATCAGA ACGCAGAAGC GGTCTGATAA AACAGAATTT
3121 GCCTGGCGGC AGTAGCGCGG TGGTCCCACC TGACCCCATG CCGAACTCAG AAGTGAAACG
3181 CCGTAGCGCC GATGGTAGTG TGGGGTCTCC CCATGCGAGA GTAGGGAACT GCCAGGCATC
3241 AAATAAAACG AAAGGCTCAG TCGAAAGACT GGGCCTTTCG TTTTATCTGT TGTTTGTCGG
3301 TGAACGCTCT CCTGAGTAGG ACAAATCCGC CGGGAGCGGA TTTGAACGTT GCGAAGCAAC
3361 GGCCCGGAGG GTGGCGGGCA GGACGCCCGC CATAAACTGC CAGGCATCAA ATTAAGCAGA
3421 AGGCCATCCT GACGGATGGC CTTTTTGCGT TTCTACAAAC TCTTTTTGTT TATTTTTCTA
3481 AATACATTCA AATATGTATC CGCTCATGAG ACAATAACCC TGATAAATGC TTCAATAATA
3541 TTGAAAAAGG AAGAGTATGA GTATTCAACA TTTCCGTGTC GCCCTTATTC CCTTTTTTGC
3601 GGCATTTTGC CTTCCTGTTT TTGCTCACCC AGAAACGCTG GTGAAAGTAA AAGATGCTGA
3661 AGATCAGTTG GGTGCACGAG TGGGTTACAT CGAACTGGAT CTCAACAGCG GTAAGATCCT
3721 TGAGAGTTTT CGCCCCGAAG AACGTTTTCC AATGATGAGC ACTTTTAAAG TTCTGCTATG
3781 TGGCGCGGTA TTATCCCGTG TTGACGCCGG GCAAGAGCAA CTCGGTCGCC GCATACACTA
3841 TTCTCAGAAT GACTTGGTTG AGTACTCACC AGTCACAGAA AAGCATCTTA CGGATGGCAT
3901 GACAGTAAGA GAATTATGCA GTGCTGCCAT AACCATGAGT GATAACACTG CGGCCAACTT
3961 ACTTCTGACA ACGATCGGAG GACCGAAGGA GCTAACCGCT TTTTTGCACA ACATGGGGGA
4021 TCATGTAACT CGCCTTGATC GTTGGGAACC GGAGCTGAAT GAAGCCATAC CAAACGACGA
4081 GCGTGACACC ACGATGCCTA CAGCAATGGC AACAACGTTG CGCAAACTAT TAACTGGCGA
4141 ACTACTTACT CTAGCTTCCC GGCAACAATT AATAGACTGG ATGGAGGCGG ATAAAGTTGC

FIG.22C

4201 AGGACCACTT CTGCGCTCGG CCCTTCCGGC TGGCTGGTTT ATTGCTGATA AATCTGGAGC
4261 CGGTGAGCGT GGGTCTCGCG GTATCATTGC AGCACTGGGG CCAGATGGTA AGCCCTCCCG
4321 TATCGTAGTT ATCTACACGA CGGGGAGTCA GGCAACTATG GATGAACGAA ATAGACAGAT
4381 CGCTGAGATA GGTGCCTCAC TGATTAAGCA TTGGTAACTG TCAGACCAAG TTTACTCATA
4441 TATACTTTAG ATTGATTTAA AACTTCATTT TTAATTTAAA AGGATCTAGG TGAAGATCCT
4501 TTTTGATAAT CTCATGACCA AAATCCCTTA ACGTGAGTTT TCGTTCCACT GAGCGTCAGA
4561 CCCCGTAGAA AAGATCAAAG GATCTTCTTG AGATCCTTTT TTTCTGCGCG TAATCTGCTG
4621 CTTGCAAACA AAAAAACCAC CGCTACCAGC GGTGGTTTGT TTGCCGGATC AAGAGCTACC
4681 AACTCTTTTT CCGAAGGTAA CTGGCTTCAG CAGAGCGCAG ATACCAAATA CTGTCCTTCT
4741 AGTGTAGCCG TAGTTAGGCC ACCACTTCAA GAACTCTGTA GCACCGCCTA CATACCTCGC
4801 TCTGCTAATC CTGTTACCAG TGGCTGCTGC CAGTGGCGAT AAGTCGTGTC TTACCGGGTT
4861 GGACTCAAGA CGATAGTTAC CGGATAAGGC GCAGCGGTCG GGCTGAACGG GGGGTTCGTG
4921 CACACAGCCC AGCTTGGAGC GAACGACCTA CACCGAACTG AGATACCTAC AGCGTGAGCT
4981 ATGAGAAAGC GCCACGCTTC CCGAAGGGAG AAAGGCGGAC AGGTATCCGG TAAGCGGCAG
5041 GGTCGGAACA GGAGAGCGCA CGAGGGAGCT TCCAGGGGGA AACGCCTGGT ATCTTTATAG
5101 TCCTGTCGGG TTTCGCCACC TCTGACTTGA GCGTCGATTT TTGTGATGCT CGTCAGGGGG
5161 GCGGAGCCTA TGGAAAAACG CCAGCAACGC GGCCTTTTTA CGGTTCCTGG CCTTTTGCTG
5221 GCCTTTTGCT CACATGTTCT TTCCTGCGTT ATCCCCTGAT TCTGTGGATA ACCGTATTAC
5281 CGCCTTTGAG TGAGCTGATA CCGCTCGCCG CAGCCGAACG ACCGAGCGCA GCGAGTCAGT
5341 GAGCGAGGAA GCGGAAGAGC GCCTGATGCG GTATTTTCTC CTTACGCATC TGTGCGGTAT
5401 TTCACACCGC ATAATTTTGT TAAAATTCGC GTTAAATTTT TGTTAAATCA GCTCATTTTT
5461 TAACCAATAG GCCGAAATCG GCAAAATCCC TTATAAATCA AAAGAATAGA CCGAGATAGG
5521 GTTGAGTGTT GTTCCAGTTT GGAACAAGAG TCCACTATTA AAGAACGTGG ACTCCAACGT
5581 CAAAGGGCGA AAAACCGTCT ATCAGGGCGA TGGCCCACTA CGTGAACCAT CACCCTAATC
5641 AAGTTTTTTG GGGTCGAGGT GCCGTAAAGC ACTAAATCGG AACCCTAAAG GGAGCCCCCG
5701 ATTTAGAGCT TGACGGGGAA AGCCGGCGAA CGTGGCGAGA AAGGAAGGGA AGAAAGCGAA
5761 AGGAGCGGGC GCTAGGGCGC TGGCAAGTGT AGCGGTCACG CTGCGCGTAA CCACCACACC
5821 CGCCGCGCTT AATGCGCCGC TACAGGGCGC GTCCCATTCG CCATTCAGGC TGCTATGGTG
5881 CACTCTCAGT ACAATCTGCT CTGATGCCGC ATAGTTAAGC CAGTATACAC TCCGCTATCG
5941 CTACGTGACT GGGTCATGGC TGCGCCCCGA CACCCGCCAA CACCCGCTGA CGCGCCCTGA
6001 CGGGCTTGTC TGCTCCCGGC ATCCGCTTAC AGACAAGCTG TGACCGTCTC CGGGAGCTGC
6061 ATGTGTCAGA GGTTTTCACC GTCATCACCG AAACGCGCGA GGCAGCAGAT CAATTCGCGC
6121 GCGAAGGCGA AGCGGCATGC ATTTACGTTG ACACCATCGA ATGGTGCAAA ACCTTTCGCG
6181 GTATGGCATG ATAGCGCCCG GAAGAGAGTC AATTCAGGGT GGTGAATGTG AAACCAGTAA
6241 CGTTATACGA TGTCGCAGAG TATGCCGGTG TCTCTTATCA GACCGTTTCC CGCGTGGTGA
6301 ACCAGGCCAG CCACGTTTCT GCGAAAACGC GGGAAAAAGT GGAAGCGGCG ATGGCGGAGC
6361 TGAATTACAT TCCCAACCGC GTGGCACAAC AACTGGCGGG CAAACAGTCG TTGCTGATTG
6421 GCGTTGCCAC CTCCAGTCTG GCCCTGCACG CGCCGTCGCA AATTGTCGCG GCGATTAAAT
6481 CTCGCGCCGA TCAACTGGGT GCCAGCGTGG TGGTGTCGAT GGTAGAACGA AGCGGCGTCG
6541 AAGCCTGTAA AGC

FIG.22D

GST FUSIONS IN E. COLI

```
                                          -35          Trc PROMOTER
154 cgg ttc tgg caa ata ttc tga aat gag ctg ttg aca att aat cat cgg ctc
    gcc aag acc gtt tat aag act tta ctc gac aac tgt taa tta gta gcc gag

      -10             mRNA
205 gta taa tgt gtg gaa ttg tga gcg gat aac aat ttc aca cag gaa aca gta
    cat att aca cac ctt aac act cgc cta ttg tta aag tgt gtc ctt tgt cat

         M   S   P   I   L   GST .....
256 ttc atg tcc cct ata cta ggt tat tgg aaa att aag ggc ctt gtg caa ccc
    aag tac agg gga tat gat cca ata acc ttt taa ttc ccg gaa cac gtt ggg

...GST       R   G   S   R   R   A   S   V   G   S   P   S   T   S
919 ctg gtt ccg cgt gga tct cgt cgt gca tct gtt gga tcc cca tca aca agt
    gac caa ggc gca cct aga gca gca cgt aga caa cct agg ggt agt tgt tca
                                                                 attR1
    L   Y   K   K
970 ttg tac aaa aaa gct gaa cga gaa acg taa aat gat ata aat atc aat ata
    aac atg ttt ttt cga ctt gct ctt tgc att tta cta tat tta tag tta tat
```

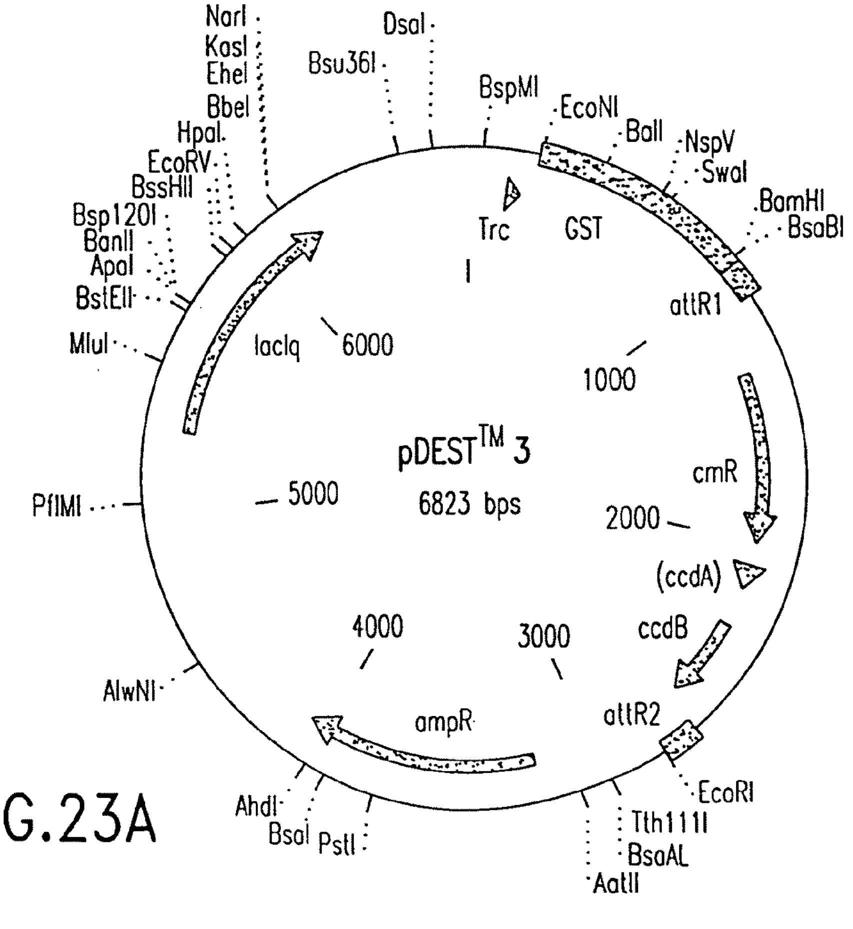

FIG.23A pDEST3 6823 bp

| Location (Base Nos.) | Gene Encoded |
|---|---|
| 150..200 | Trc |
| 1087..963 | attR1 |
| 1337..1996 | CmR |
| 2116..2200 | inactivated ccdA |
| 2338..2643 | ccdB |
| 2684..2808 | attR2 |
| 3231..4091 | ampR |
| 5295..6254 | lacIq |

```
   1 ACGTTATCGA CTGCACGGTG CACCAATGCT TCTGGCGTCA GGCAGCCATC GGAAGCTGTG
  61 GTATGGCTGT GCAGGTCGTA AATCACTGCA TAATTCGTGT CGCTCAAGGC GCACTCCCGT
 121 TCTGGATAAT GTTTTTTGCG CCGACATCAT AACGGTTCTG GCAAATATTC TGAAATGAGC
 181 TGTTGACAAT TAATCATCGG CTCGTATAAT GTGTGGAATT GTGAGCGGAT AACAATTTCA
 241 CACAGGAAAC AGTATTCATG TCCCCTATAC TAGGTTATTG GAAAATTAAG GGCCTTGTGC
 301 AACCCACTCG ACTTCTTTTG GAATATCTTG AAGAAAAATA TGAAGAGCAT TTGTATGAGC
 361 GCGATGAAGG TGATAAATGG CGAAACAAAA AGTTTGAATT GGGTTTGGAG TTTCCCAATC
 421 TTCCTTATTA TATTGATGGT GATGTTAAAT TAACACAGTC TATGGCCATC ATACGTTATA
 481 TAGCTGACAA GCACAACATG TTGGGTGGTT GTCCAAAAGA GCGTGCAGAG ATTTCAATGC
 541 TTGAAGGAGC GGTTTTGGAT ATTAGATACG GTGTTTCGAG AATTGCATAT AGTAAAGACT
 601 TTGAAACTCT CAAAGTTGAT TTTCTTAGCA AGCTACCTGA AATGCTGAAA ATGTTCGAAG
 661 ATCGTTTATG TCATAAAACA TATTTAAATG GTGATCATGT AACCCATCCT GACTTCATGT
 721 TGTATGACGC TCTTGATGTT GTTTTATACA TGGACCCAAT GTGCCTGGAT GCGTTCCCAA
 781 AATTAGTTTG TTTTAAAAAA CGTATTGAAG CTATCCCACA AATTGATAAG TACTTGAAAT
 841 CCAGCAAGTA TATAGCATGG CCTTTGCAGG GCTGGCAAGC CACGTTTGGT GGTGGCGACC
 901 ATCCTCCAAA ATCGGATCTG GTTCCGCGTG GATCTCGTCG TGCATCTGTT GGATCCCCAT
 961 CAACAAGTTT GTACAAAAAA GCTGAACGAG AAACGTAAAA TGATATAAAT ATCAATATAT
1021 TAAATTAGAT TTTGCATAAA AAACAGACTA CATAATACTG TAAAACACAA CATATCCAGT
1081 CACTATGGCG GCCGCTAAGT TGGCAGCATC ACCCGACGCA CTTTGCGCCG AATAAATACC
1141 TGTGACGGAA GATCACTTCG CAGAATAAAT AAATCCTGGT GTCCCTGTTG ATACCGGGAA
1201 GCCCTGGGCC AACTTTTGGC GAAAATGAGA CGTTGATCGG CACGTAAGAG GTTCCAACTT
1261 TCACCATAAT GAAATAAGAT CACTACCGGG CGTATTTTTT GAGTTATCGA GATTTTCAGG
1321 AGCTAAGGAA GCTAAAATGG AGAAAAAAAT CACTGGATAT ACCACCGTTG ATATATCCCA
1381 ATGGCATCGT AAAGAACATT TTGAGGCATT TCAGTCAGTT GCTCAATGTA CCTATAACCA
1441 GACCGTTCAG CTGGATATTA CGGCCTTTTT AAAGACCGTA AAGAAAAATA AGCACAAGTT
1501 TTATCCGGCC TTTATTCACA TTCTTGCCCG CCTGATGAAT GCTCATCCGG AATTCCGTAT
1561 GGCAATGAAA GACGGTGAGC TGGTGATATG GGATAGTGTT CACCCTTGTT ACACCGTTTT
1621 CCATGAGCAA ACTGAAACGT TTTCATCGCT CTGGAGTGAA TACCACGACG ATTTCCGGCA
1681 GTTTCTACAC ATATATTCGC AAGATGTGGC GTGTTACGGT GAAAACCTGG CCTATTTCCC
1741 TAAAGGGTTT ATTGAGAATA TGTTTTTCGT CTCAGCCAAT CCCTGGGTGA GTTTCACCAG
1801 TTTTGATTTA AACGTGGCCA ATATGGACAA CTTCTTCGCC CCCGTTTTCA CCATGGGCAA
```

FIG.23B

1861 ATATTATACG CAAGGCGACA AGGTGCTGAT GCCGCTGGCG ATTCAGGTTC ATCATGCCGT
1921 CTGTGATGGC TTCCATGTCG GCAGAATGCT TAATGAATTA CAACAGTACT GCGATGAGTG
1981 GCAGGGCGGG GCGTAAAGAT CTGGATCCGG CTTACTAAAA GCCAGATAAC AGTATGCGTA
2041 TTTGCGCGCT GATTTTTGCG GTATAAGAAT ATATACTGAT ATGTATACCC GAAGTATGTC
2101 AAAAAGAGGT GTGCTATGAA GCAGCGTATT ACAGTGACAG TTGACAGCGA CAGCTATCAG
2161 TTGCTCAAGG CATATATGAT GTCAATATCT CCGGTCTGGT AAGCACAACC ATGCAGAATG
2221 AAGCCCGTCG TCTGCGTGCC GAACGCTGGA AAGCGGAAAA TCAGGAAGGG ATGGCTGAGG
2281 TCGCCCGGTT TATTGAAATG AACGGCTCTT TTGCTGACGA GAACAGGGAC TGGTGAAATG
2341 CAGTTTAAGG TTTACACCTA TAAAAGAGAG AGCCGTTATC GTCTGTTTGT GGATGTACAG
2401 AGTGATATTA TTGACACGCC CGGGCGACGG ATGGTGATCC CCCTGGCCAG TGCACGTCTG
2461 CTGTCAGATA AAGTCTCCCG TGAACTTTAC CCGGTGGTGC ATATCGGGGA TGAAAGCTGG
2521 CGCATGATGA CCACCGATAT GGCCAGTGTG CCGGTCTCCG TTATCGGGGA AGAAGTGGCT
2581 GATCTCAGCC ACCGCGAAAA TGACATCAAA AACGCCATTA ACCTGATGTT CTGGGGAATA
2641 TAAATGTCAG GCTCCCTTAT ACACAGCCAG TCTGCAGGTC GACCATAGTG ACTGGATATG
2701 TTGTGTTTTA CAGTATTATG TAGTCTGTTT TTTATGCAAA ATCTAATTTA ATATATTGAT
2761 ATTTATATCA TTTTACGTTT CTCGTTCAGC TTTCTTGTAC AAAGTGGTTG ATGGGAATTC
2821 ATCGTGACTG ACTGACGATC TGCCTCGCGC GTTTCGGTGA TGACGGTGAA AACCTCTGAC
2881 ACATGCAGCT CCCGGAGACG GTCACAGCTT GTCTGTAAGC GGATGCCGGG AGCAGACAAG
2941 CCCGTCAGGG CGCGTCAGCG GGTGTTGGCG GGTGTCGGGG CGCAGCCATG ACCCAGTCAC
3001 GTAGCGATAG CGGAGTGTAT AATTCTTGAA GACGAAAGGG CCTCGTGATA CGCCTATTTT
3061 TATAGGTTAA TGTCATGATA ATAATGGTTT CTTAGACGTC AGGTGGCACT TTTCGGGGAA
3121 ATGTGCGCGG AACCCCTATT TGTTTATTTT TCTAAATACA TTCAAATATG TATCCGCTCA
3181 TGAGACAATA ACCCTGATAA ATGCTTCAAT AATATTGAAA AAGGAAGAGT ATGAGTATTC
3241 AACATTTCCG TGTCGCCCTT ATTCCCTTTT TTGCGGCATT TTGCCTTCCT GTTTTTGCTC
3301 ACCCAGAAAC GCTGGTGAAA GTAAAAGATG CTGAAGATCA GTTGGGTGCA CGAGTGGGTT
3361 ACATCGAACT GGATCTCAAC AGCGGTAAGA TCCTTGAGAG TTTTCGCCCC GAAGAACGTT
3421 TTCCAATGAT GAGCACTTTT AAAGTTCTGC TATGTGGCGC GGTATTATCC CGTGTTGACG
3481 CCGGGCAAGA GCAACTCGGT CGCCGCATAC ACTATTCTCA GAATGACTTG GTTGAGTACT
3541 CACCAGTCAC AGAAAAGCAT CTTACGGATG GCATGACAGT AAGAGAATTA TGCAGTGCTG
3601 CCATAACCAT GAGTGATAAC ACTGCGGCCA ACTTACTTCT GACAACGATC GGAGGACCGA
3661 AGGAGCTAAC CGCTTTTTTG CACAACATGG GGGATCATGT AACTCGCCTT GATCGTTGGG
3721 AACCGGAGCT GAATGAAGCC ATACCAAACG ACGAGCGTGA CACCACGATG CCTGCAGCAA
3781 TGGCAACAAC GTTGCGCAAA CTATTAACTG GCGAACTACT TACTCTAGCT TCCCGGCAAC
3841 AATTAATAGA CTGGATGGAG GCGGATAAAG TTGCAGGACC ACTTCTGCGC TCGGCCCTTC
3901 CGGCTGGCTG GTTTATTGCT GATAAATCTG GAGCCGGTGA GCGTGGGTCT CGCGGTATCA
3961 TTGCAGCACT GGGGCCAGAT GGTAAGCCCT CCCGTATCGT AGTTATCTAC ACGACGGGGA
4021 GTCAGGCAAC TATGGATGAA CGAAATAGAC AGATCGCTGA GATAGGTGCC TCACTGATTA
4081 AGCATTGGTA ACTGTCAGAC CAAGTTTACT CATATATACT TTAGATTGAT TTAAAACTTC
4141 ATTTTTAATT TAAAAGGATC TAGGTGAAGA TCCTTTTTGA TAATCTCATG ACCAAAATCC
4201 CTTAACGTGA GTTTTCGTTC CACTGAGCGT CAGACCCCGT AGAAAAGATC AAAGGATCTT
4261 CTTGAGATCC TTTTTTTCTG CGCGTAATCT GCTGCTTGCA AACAAAAAAA CCACCGCTAC

FIG.23C

4321 CAGCGGTGGT TTGTTTGCCG GATCAAGAGC TACCAACTCT TTTTCCGAAG GTAACTGGCT
4381 TCAGCAGAGC GCAGATACCA AATACTGTCC TTCTAGTGTA GCCGTAGTTA GGCCACCACT
4441 TCAAGAACTC TGTAGCACCG CCTACATACC TCGCTCTGCT AATCCTGTTA CCAGTGGCTG
4501 CTGCCAGTGG CGATAAGTCG TGTCTTACCG GGTTGGACTC AAGACGATAG TTACCGGATA
4561 AGGCGCAGCG GTCGGGCTGA ACGGGGGGTT CGTGCACACA GCCCAGCTTG GAGCGAACGA
4621 CCTACACCGA ACTGAGATAC CTACAGCGTG AGCTATGAGA AAGCGCCACG CTTCCCGAAG
4681 GGAGAAAGGC GGACAGGTAT CCGGTAAGCG GCAGGGTCGG AACAGGAGAG CGCACGAGGG
4741 AGCTTCCAGG GGGAAACGCC TGGTATCTTT ATAGTCCTGT CGGGTTTCGC CACCTCTGAC
4801 TTGAGCGTCG ATTTTTGTGA TGCTCGTCAG GGGGGCGGAG CCTATGGAAA AACGCCAGCA
4861 ACGCGGCCTT TTTACGGTTC CTGGCCTTTT GCTGGCCTTT TGCTCACATG TTCTTTCCTG
4921 CGTTATCCCC TGATTCTGTG GATAACCGTA TTACCGCCTT TGAGTGAGCT GATACCGCTC
4981 GCCGCAGCCG AACGACCGAG CGCAGCGAGT CAGTGAGCGA GGAAGCGGAA GAGCGCCTGA
5041 TGCGGTATTT TCTCCTTACG CATCTGTGCG GTATTTCACA CCGCATAAAT TCCGACACCA
5101 TCGAATGGTG CAAAACCTTT CGCGGTATGG CATGATAGCG CCCGGAAGAG AGTCAATTCA
5161 GGGTGGTGAA TGTGAAACCA GTAACGTTAT ACGATGTCGC AGAGTATGCC GGTGTCTCTT
5221 ATCAGACCGT TTCCCGCGTG GTGAACCAGG CCAGCCACGT TTCTGCGAAA ACGCGGGAAA
5281 AAGTGGAAGC GGCGATGGCG GAGCTGAATT ACATTCCCAA CCGCGTGGCA CAACAACTGG
5341 CGGGCAAACA GTCGTTGCTG ATTGGCGTTG CCACCTCCAG TCTGGCCCTG CACGCGCCGT
5401 CGCAAATTGT CGCGGCGATT AAATCTCGCG CCGATCAACT GGGTGCCAGC GTGGTGGTGT
5461 CGATGGTAGA ACGAAGCGGC GTCGAAGCCT GTAAAGCGGC GGTGCACAAT CTTCTCGCGC
5521 AACGCGTCAG TGGGCTGATC ATTAACTATC CGCTGGATGA CCAGGATGCC ATTGCTGTGG
5581 AAGCTGCCTG CACTAATGTT CCGGCGTTAT TTCTTGATGT CTCTGACCAG ACACCCATCA
5641 ACAGTATTAT TTTCTCCCAT GAAGACGGTA CGCGACTGGG CGTGGAGCAT CTGGTCGCAT
5701 TGGGTCACCA GCAAATCGCG CTGTTAGCGG GCCCATTAAG TTCTGTCTCG GCGCGTCTGC
5761 GTCTGGCTGG CTGGCATAAA TATCTCACTC GCAATCAAAT TCAGCCGATA GCGGAACGGG
5821 AAGGCGACTG GAGTGCCATG TCCGGTTTTC AACAAACCAT GCAAATGCTG AATGAGGGCA
5881 TCGTTCCCAC TGCGATGCTG GTTGCCAACG ATCAGATGGC GCTGGGCGCA ATGCGCGCCA
5941 TTACCGAGTC CGGGCTGCGC GTTGGTGCGG ATATCTCGGT AGTGGGATAC GACGATACCG
6001 AAGACAGCTC ATGTTATATC CCGCCGTTAA CCACCATCAA ACAGGATTTT CGCCTGCTGG
6061 GGCAAACCAG CGTGGACCGC TTGCTGCAAC TCTCTCAGGG CCAGGCGGTG AAGGGCAATC
6121 AGCTGTTGCC CGTCTCACTG GTGAAAAGAA AAACCACCCT GGCGCCCAAT ACGCAAACCG
6181 CCTCTCCCCG CGCGTTGGCC GATTCATTAA TGCAGCTGGC ACGACAGGTT TCCCGACTGG
6241 AAAGCGGGCA GTGAGCGCAA CGCAATTAAT GTGAGTTAGC TCACTCATTA GGCACCCCAG
6301 GCTTTACACT TTATGCTTCC GGCTCGTATG TTGTGTGGAA TTGTGAGCGG ATAACAATTT
6361 CACACAGGAA ACAGCTATGA CCATGATTAC GGATTCACTG GCCGTCGTTT TACAACGTCG
6421 TGACTGGGAA AACCCTGGCG TTACCCAACT TAATCGCCTT GCAGCACATC CCCCTTTCGC
6481 CAGCTGGCGT AATAGCGAAG AGGCCCGCAC CGATCGCCCT TCCCAACAGT TGCGCAGCCT
6541 GAATGGCGAA TGGCGCTTTG CCTGGTTTCC GGCACCAGAA GCGGTGCCGG AAAGCTGGCT
6601 GGAGTGCGAT CTTCCTGAGG CCGATACTGT CGTCGTCCCC TCAAACTGGC AGATGCACGG
6661 TTACGATGCG CCCATCTACA CCAACGTAAC CTATCCCATT ACGGTCAATC CGCCGTTTGT
6721 TCCCACGGAG AATCCGACGG GTTGTTACTC GCTCACATTT AATGTTGATG AAAGCTGGCT
6781 ACAGGAAGGC CAGACGCGAA TTATTTTTGA TGGCGTTGGA ATT

FIG.23D

His6-THIOREDOXIN FUSIONS IN E. COLI

```
                                       -35          Trc PROMOTER          -10
919  gca aat att ctg aaa tga gct g tt gac a at tac tca tcc ggt ccg  tat aat
     cgt tta taa gac ttt act cga c aa ctg t ta att agt agg cca ggc  ata tta

         ┌── mRNA                                                    Met Gly
970  ctg tgg aat tgt gag cgg ata aca att tca cac agg aaa cag acc atg ggt
     gac acc tta aca ctc gcc tat tgt taa agt gtg tcc ttt gtc tgg tac cca

            His6
         ┌─────────────────────┐
         His His His His His His  Asp Tyr Asp Ile Pro Thr Thr Gly Asn Leu Tyr
1021 cat cat cat cat cat cac gat tac gat atc cca acg acc gaa aac ctg tat
     gta gta gta gta gta gtg cta atg cta tag ggt tgc tgg ctt ttg gac ata
            TEV PROTEASE        ├── THIOREDOXIN ── (~150 AMINO ACIDS) ──

         Phe Gln Gly Ala His Met Ser Asp Lys Ile Ile His Leu Thr Asp Asp Ser
1072 ttt cag ggc gcc cat atg agc gat aaa att att cac ctg act gac gac agt
     aaa gtc ccg cgg gta tac tcg cta ttt taa taa gtg gac tga ctg ctg tca

                                                           attR1
                                               ┌────────────────────────
         Asp Asp Asp Asp Lys Val Pro Ile Thr Ser Leu Tyr Lys Lys
1429 gat gac gat gac aag gta ccc atc aca agt ttg tac aaa aaa gct gaa cga
     cta ctg cta ctg ttc cat ggg tag tgt tca aac atg ttt ttt cga ctt gct
                                                            ↑
                                                       Int CLEAVAGE
```

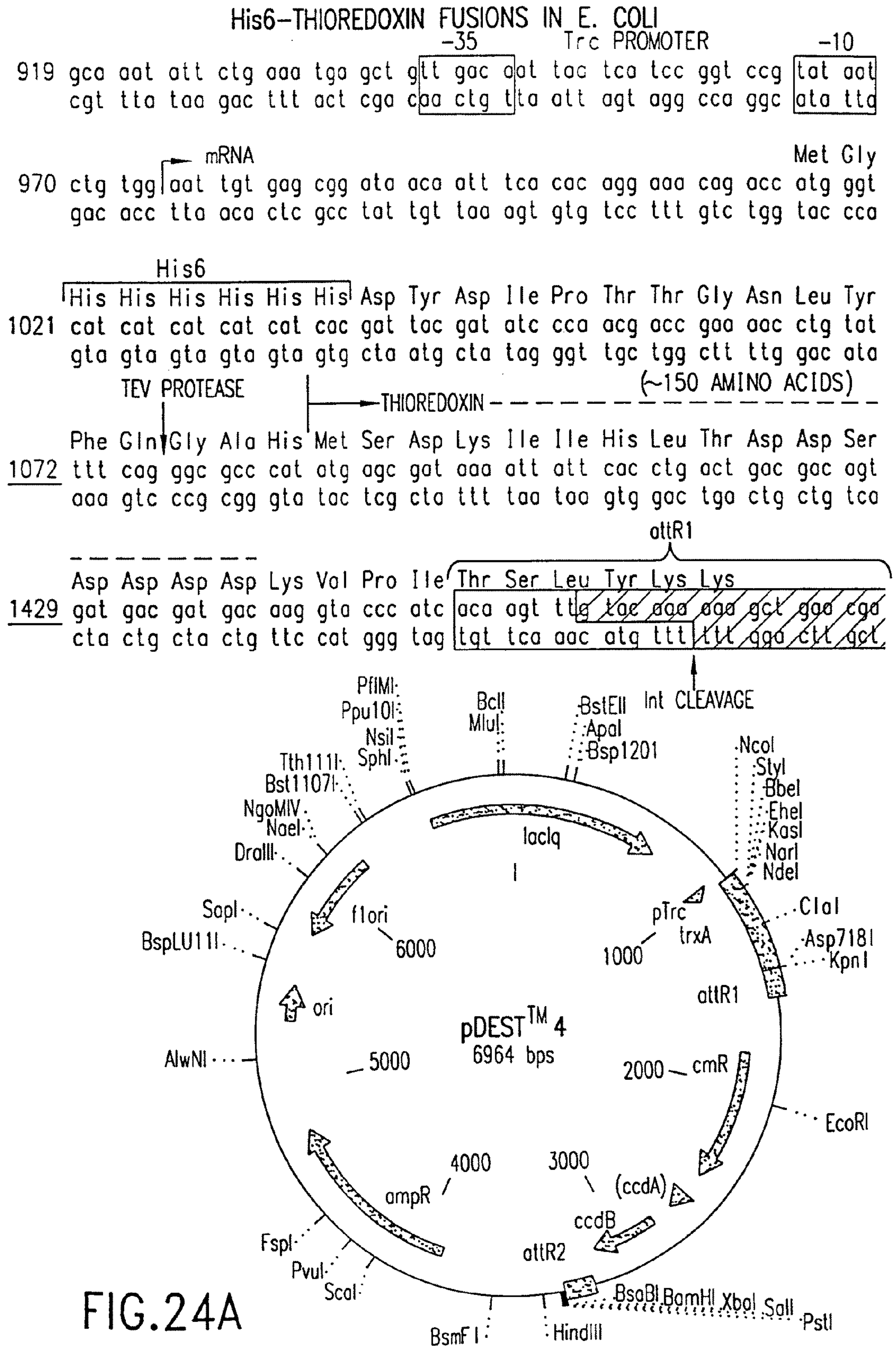

FIG. 24A pDEST4 6964 bp

| Location (Base Nos.) | Gene Encoded |
|---|---|
| 964..1003 | Trc |
| 1577..1453 | attR1 |
| 1827..2486 | CmR |
| 2606..2690 | inactivated ccdA |
| 2828..3133 | ccdB |
| 3174..3298 | attR2 |
| 3872..4777 | ampR |
| 5378..5538 | ori |
| 5778..6215 | f1ori (f1 intergenic region) |
| 6587..704 | lacIq |

```
   1 CTATCCGCTG GATGACCAGG ATGCCATTGC TGTGGAAGCT GCCTGCACTA ATGTTCCGGC
  61 GTTATTTCTT GATGTCTCTG ACCAGACACC CATCAACAGT ATTATTTTCT CCCATGAAGA
 121 CGGTACGCGA CTGGGCGTGG AGCATCTGGT CGCATTGGGT CACCAGCAAA TCGCGCTGTT
 181 AGCGGGCCCA TTAAGTTCTG TCTCGGCGCG TCTGCGTCTG GCTGGCTGGC ATAAATATCT
 241 CACTCGCAAT CAAATTCAGC CGATAGCGGA ACGGGAAGGC GACTGGAGTG CCATGTCCGG
 301 TTTTCAACAA ACCATGCAAA TGCTGAATGA GGGCATCGTT CCCACTGCGA TGCTGGTTGC
 361 CAACGATCAG ATGGCGCTGG GCGCAATGCG CGCCATTACC GAGTCCGGGC TGCGCGTTGG
 421 TGCGGATATC TCGGTAGTGG GATACGACGA TACCGAAGAC AGCTCATGTT ATATCCCGCC
 481 GTCAACCACC ATCAAACAGG ATTTTCGCCT GCTGGGGCAA ACCAGCGTGG ACCGCTTGCT
 541 GCAACTCTCT CAGGGCCAGG CGGTGAAGGG CAATCAGCTG TTGCCCGTCT CACTGGTGAA
 601 AAGAAAAACC ACCCTGGCAC CCAATACGCA AACCGCCTCT CCCCGCGCGT TGGCCGATTC
 661 ATTAATGCAG CTGGCACGAC AGGTTTCCCG ACTGGAAAGC GGGCAGTGAG CGCAACGCAA
 721 TTAATGTGAG TTAGCGCGAA TTGATCTGGT TTGACAGCTT ATCATCGACT GCACGGTGCA
 781 CCAATGCTTC TGGCGTCAGG CAGCCATCGG AAGCTGTGGT ATGGCTGTGC AGGTCGTAAA
 841 TCACTGCATA ATTCGTGTCG CTCAAGGCGC ACTCCCGTTC TGGATAATGT TTTTTGCGCC
 901 GACATCATAA CGGTTCTGGC AAATATTCTG AAATGAGCTG TTGACAATTA ATCATCCGGT
 961 CCGTATAATC TGTGGAATTG TGAGCGGATA ACAATTTCAC ACAGGAAACA GACCATGGGT
1021 CATCATCATC ATCATCACGA TTACGATATC CCAACGACCG AAAACCTGTA TTTTCAGGGC
1081 GCCCATATGA GCGATAAAAT TATTCACCTG ACTGACGACA GTTTTGACAC GGATGTACTC
1141 AAAGCGGACG GGGCGATCCT CGTCGATTTC TGGGCAGAGT GGTGCGGTCC GTGCAAAATG
1201 ATCGCCCCGA TTCTGGATGA AATCGCTGAC GAATATCAGG GCAAACTGAC CGTTGCAAAA
1261 CTGAACATCG ATCAAAACCC TGGCACTGCG CCGAAATATG GCATCCGTGG TATCCCGACT
1321 CTGCTGCTGT TCAAAAACGG TGAAGTGGCG GCAACCAAAG TGGGTGCACT GTCTAAAGGT
1381 CAGTTGAAAG AGTTCCTCGA CGCTAACCTG GCCGGTTCTG GTTCTGGTGA TGACGATGAC
1441 AAGGTACCCA TCACAAGTTT GTACAAAAAA GCTGAACGAG AAACGTAAAA TGATATAAAT
1501 ATCAATATAT TAAATTAGAT TTTGCATAAA AAACAGACTA CATAATACTG TAAAACACAA
1561 CATATCCAGT CACTATGGCG GCCGCTAAGT TGGCAGCATC ACCCGACGCA CTTTGCGCCG
1621 AATAAATACC TGTGACGGAA GATCACTTCG CAGAATAAAT AAATCCTGGT GTCCCTGTTG
1681 ATACCGGGAA GCCCTGGGCC AACTTTTGGC GAAAATGAGA CGTTGATCGG CACGTAAGAG
```

FIG.24B

1741 GTTCCAACTT TCACCATAAT GAAATAAGAT CACTACCGGG CGTATTTTTT GAGTTATCGA
1801 GATTTTCAGG AGCTAAGGAA GCTAAAATGG AGAAAAAAAT CACTGGATAT ACCACCGTTG
1861 ATATATCCCA ATGGCATCGT AAAGAACATT TTGAGGCATT TCAGTCAGTT GCTCAATGTA
1921 CCTATAACCA GACCGTTCAG CTGGATATTA CGGCCTTTTT AAAGACCGTA AAGAAAAATA
1981 AGCACAAGTT TTATCCGGCC TTTATTCACA TTCTTGCCCG CCTGATGAAT GCTCATCCGG
2041 AATTCCGTAT GGCAATGAAA GACGGTGAGC TGGTGATATG GGATAGTGTT CACCCTTGTT
2101 ACACCGTTTT CCATGAGCAA ACTGAAACGT TTTCATCGCT CTGGAGTGAA TACCACGACG
2161 ATTTCCGGCA GTTTCTACAC ATATATTCGC AAGATGTGGC GTGTTACGGT GAAAACCTGG
2221 CCTATTTCCC TAAAGGGTTT ATTGAGAATA TGTTTTTCGT CTCAGCCAAT CCCTGGGTGA
2281 GTTTCACCAG TTTTGATTTA AACGTGGCCA ATATGGACAA CTTCTTCGCC CCCGTTTTCA
2341 CCATGGGCAA ATATTATACG CAAGGCGACA AGGTGCTGAT GCCGCTGGCG ATTCAGGTTC
2401 ATCATGCCGT CTGTGATGGC TTCCATGTCG GCAGAATGCT TAATGAATTA CAACAGTACT
2461 GCGATGAGTG GCAGGGCGGG GCGTAAACGC GTGGATCCGG CTTACTAAAA GCCAGATAAC
2521 AGTATGCGTA TTTGCGCGCT GATTTTTGCG GTATAAGAAT ATATACTGAT ATGTATACCC
2581 GAAGTATGTC AAAAAGAGGT GTGCTATGAA GCAGCGTATT ACAGTGACAG TTGACAGCGA
2641 CAGCTATCAG TTGCTCAAGG CATATATGAT GTCAATATCT CCGGTCTGGT AAGCACAACC
2701 ATGCAGAATG AAGCCCGTCG TCTGCGTGCC GAACGCTGGA AAGCGGAAAA TCAGGAAGGG
2761 ATGGCTGAGG TCGCCCGGTT TATTGAAATG AACGGCTCTT TTGCTGACGA GAACAGGGAC
2821 TGGTGAAATG CAGTTTAAGG TTTACACCTA TAAAAGAGAG AGCCGTTATC GTCTGTTTGT
2881 GGATGTACAG AGTGATATTA TTGACACGCC CGGGCGACGG ATGGTGATCC CCCTGGCCAG
2941 TGCACGTCTG CTGTCAGATA AAGTCTCCCG TGAACTTTAC CCGGTGGTGC ATATCGGGGA
3001 TGAAAGCTGG CGCATGATGA CCACCGATAT GGCCAGTGTG CCGGTCTCCG TTATCGGGGA
3061 AGAAGTGGCT GATCTCAGCC ACCGCGAAAA TGACATCAAA AACGCCATTA ACCTGATGTT
3121 CTGGGGAATA TAAATGTCAG GCTCCCTTAT ACACAGCCAG TCTGCAGGTC GACCATAGTG
3181 ACTGGATATG TTGTGTTTTA CAGTATTATG TAGTCTGTTT TTTATGCAAA ATCTAATTTA
3241 ATATATTGAT ATTTATATCA TTTTACGTTT CTCGTTCAGC TTTCTTGTAC AAAGTGGTGA
3301 TGGGGATCCT CTAGAGTCGA CCTGCAGTAA TCGTACAGGG TAGTACAAAT AAAAAAGGCA
3361 CGTCAGATGA CGTGCCTTTT TTCTTGTGAG CAGTAAGCTT GGCTGTTTTG GCGGATGAGA
3421 GAAGATTTTC AGCCTGATAC AGATTAAATC AGAACGCAGA AGCGGTCTGA TAAAACAGAA
3481 TTTGCCTGGC GGCAGTAGCG CGGTGGTCCC ACCTGACCCC ATGCCGAACT CAGAAGTGAA
3541 ACGCCGTAGC GCCGATGGTA GTGTGGGGTC TCCCCATGCG AGAGTAGGGA ACTGCCAGGC
3601 ATCAAATAAA ACGAAAGGCT CAGTCGAAAG ACTGGGCCTT TCGTTTTATC TGTTGTTTGT
3661 CGGTGAACGC TCTCCTGAGT AGGACAAATC CGCCGGGAGC GGATTTGAAC GTTGCGAAGC
3721 AACGGCCCGG AGGGTGGCGG GCAGGACGCC CGCCATAAAC TGCCAGGCAT CAAATTAAGC
3781 AGAAGGCCAT CCTGACGGAT GGCCTTTTTG CGTTTCTACA AACTCTTTTT GTTTATTTTT
3841 CTAAATACAT TCAAATATGT ATCCGCTCAT GAGACAATAA CCCTGATAAA TGCTTCAATA
3901 ATATTGAAAA AGGAAGAGTA TGAGTATTCA ACATTTCCGT GTCGCCCTTA TTCCCTTTTT
3961 TGCGGCATTT TGCCTTCCTG TTTTTGCTCA CCCAGAAACG CTGGTGAAAG TAAAAGATGC
4021 TGAAGATCAG TTGGGTGCAC GAGTGGGTTA CATCGAACTG GATCTCAACA GCGGTAAGAT
4081 CCTTGAGAGT TTTCGCCCCG AAGAACGTTT TCCAATGATG AGCACTTTTA AAGTTCTGCT
4141 ATGTGGCGCG GTATTATCCC GTGTTGACGC CGGGCAAGAG CAACTCGGTC GCCGCATACA

FIG.24C

4201 CTATTCTCAG AATGACTTGG TTGAGTACTC ACCAGTCACA GAAAAGCATC TTACGGATGG
4261 CATGACAGTA AGAGAATTAT GCAGTGCTGC CATAACCATG AGTGATAACA CTGCGGCCAA
4321 CTTACTTCTG ACAACGATCG GAGGACCGAA GGAGCTAACC GCTTTTTTGC ACAACATGGG
4381 GGATCATGTA ACTCGCCTTG ATCGTTGGGA ACCGGAGCTG AATGAAGCCA TACCAAACGA
4441 CGAGCGTGAC ACCACGATGC CTACAGCAAT GGCAACAACG TTGCGCAAAC TATTAACTGG
4501 CGAACTACTT ACTCTAGCTT CCCGGCAACA ATTAATAGAC TGGATGGAGG CGGATAAAGT
4561 TGCAGGACCA CTTCTGCGCT CGGCCCTTCC GGCTGGCTGG TTTATTGCTG ATAAATCTGG
4621 AGCCGGTGAG CGTGGGTCTC GCGGTATCAT TGCAGCACTG GGGCCAGATG GTAAGCCCTC
4681 CCGTATCGTA GTTATCTACA CGACGGGGAG TCAGGCAACT ATGGATGAAC GAAATAGACA
4741 GATCGCTGAG ATAGGTGCCT CACTGATTAA GCATTGGTAA CTGTCAGACC AAGTTTACTC
4801 ATATATACTT TAGATTGATT TAAAACTTCA TTTTTAATTT AAAAGGATCT AGGTGAAGAT
4861 CCTTTTTGAT AATCTCATGA CCAAAATCCC TTAACGTGAG TTTTCGTTCC ACTGAGCGTC
4921 AGACCCCGTA GAAAAGATCA AAGGATCTTC TTGAGATCCT TTTTTTCTGC GCGTAATCTG
4981 CTGCTTGCAA ACAAAAAAAC CACCGCTACC AGCGGTGGTT TGTTTGCCGG ATCAAGAGCT
5041 ACCAACTCTT TTTCCGAAGG TAACTGGCTT CAGCAGAGCG CAGATACCAA ATACTGTCCT
5101 TCTAGTGTAG CCGTAGTTAG GCCACCACTT CAAGAACTCT GTAGCACCGC CTACATACCT
5161 CGCTCTGCTA ATCCTGTTAC CAGTGGCTGC TGCCAGTGGC GATAAGTCGT GTCTTACCGG
5221 GTTGGACTCA AGACGATAGT TACCGGATAA GGCGCAGCGG TCGGGCTGAA CGGGGGGTTC
5281 GTGCACACAG CCCAGCTTGG AGCGAACGAC CTACACCGAA CTGAGATACC TACAGCGTGA
5341 GCTATGAGAA AGCGCCACGC TTCCCGAAGG GAGAAAGGCG GACAGGTATC CGGTAAGCGG
5401 CAGGGTCGGA ACAGGAGAGC GCACGAGGGA GCTTCCAGGG GGAAACGCCT GGTATCTTTA
5461 TAGTCCTGTC GGGTTTCGCC ACCTCTGACT TGAGCGTCGA TTTTTGTGAT GCTCGTCAGG
5521 GGGGCGGAGC CTATGGAAAA ACGCCAGCAA CGCGGCCTTT TTACGGTTCC TGGCCTTTTG
5581 CTGGCCTTTT GCTCACATGT TCTTTCCTGC GTTATCCCCT GATTCTGTGG ATAACCGTAT
5641 TACCGCCTTT GAGTGAGCTG ATACCGCTCG CCGCAGCCGA ACGACCGAGC GCAGCGAGTC
5701 AGTGAGCGAG GAAGCGGAAG AGCGCCTGAT GCGGTATTTT CTCCTTACGC ATCTGTGCGG
5761 TATTTCACAC CGCATAATTT TGTTAAAATT CGCGTTAAAT TTTTGTTAAA TCAGCTCATT
5821 TTTTAACCAA TAGGCCGAAA TCGGCAAAAT CCCTTATAAA TCAAAAGAAT AGACCGAGAT
5881 AGGGTTGAGT GTTGTTCCAG TTTGGAACAA GAGTCCACTA TTAAAGAACG TGGACTCCAA
5941 CGTCAAAGGG CGAAAAACCG TCTATCAGGG CGATGGCCCA CTACGTGAAC CATCACCCTA
6001 ATCAAGTTTT TTGGGGTCGA GGTGCCGTAA AGCACTAAAT CGGAACCCTA AAGGGAGCCC
6061 CCGATTTAGA GCTTGACGGG GAAAGCCGGC GAACGTGGCG AGAAAGGAAG GGAAGAAAGC
6121 GAAAGGAGCG GGCGCTAGGG CGCTGGCAAG TGTAGCGGTC ACGCTGCGCG TAACCACCAC
6181 ACCCGCCGCG CTTAATGCGC CGCTACAGGG CGCGTCCATT CGCCATTCAG GCTGCTATGG
6241 TGCACTCTCA GTACAATCTG CTCTGATGCC GCATAGTTAA GCCAGTATAC ACTCCGCTAT
6301 CGCTACGTGA CTGGGTCATG GCTGCGCCCC GACACCCGCC AACACCCGCT GACGCGCCCT
6361 GACGGGCTTG TCTGCTCCCG GCATCCGCTT ACAGACAAGC TGTGACCGTC TCCGGGAGCT
6421 GCATGTGTCA GAGGTTTTCA CCGTCATCAC CGAAACGCGC GAGGCAGCAG ATCAATTCGC
6481 GCGCGAAGGC GAAGCGGCAT GCATTTACGT TGACACCATC GAATGGTGCA AAACCTTTCG
6541 CGGTATGGCA TGATAGCGCC CGGAAGAGAG TCAATTCAGG GTGGTGAATG TGAAACCAGT
6601 AACGTTATAC GATGTCGCAG AGTATGCCGG TGTCTCTTAT CAGACCGTTT CCCGCGTGGT
6661 GAACCAGGCC AGCCACGTTT CTGCGAAAAC GCGGGAAAAA GTGGAAGCGG CGATGGCGGA
6721 GCTGAATTAC ATTCCCAACC GCGTGGCACA ACAACTGGCG GGCAAACAGT CGTTGCTGAT
6781 TGGCGTTGCC ACCTCCAGTC TGGCCCTGCA CGCGCCGTCG CAAATTGTCG CGGCGATTAA
6841 ATCTCGCGCC GATCAACTGG GTGCCAGCGT GGTGGTGTCG ATGGTAGAAC GAAGCGGCGT
6901 CGAAGCCTGT AAAGCGGCGG TGCACAATCT TCTCGCGCAA CGCGTCAGTN GGGCTGATCA
6961 TTAA

FIG.24D pDEST5 pDEST5 5957 bp

| Location (Base Nos.) | Gene Encoded |
|---|---|
| 305..181 | attR1 |
| 555..1214 | CmR |
| 1334..1418 | inactivated ccdA |
| 1556..1861 | ccdB |
| 1902..2026 | attR2 |
| 2278..2733 | f1 (f1 intergenic region) |
| 2865..3722 | ampR |
| 5378..5538 | ori |
| 4756..5922 | lacI |

```
   1 AGGCACCCCA GGCTTTACAC TTTATGCTTC CGGCTCGTAT GTTGTGTGGA ATTGTGAGCG
  61 GATAACAATT TCACACAGGA AACAGCTATG ACCATGATTA CGCCAAGCTC TAATACGACT
 121 CACTATAGGG AAAGCTGGTA CGCCTGCAGG TACCGGTCCG GAATTCCCGG GTCGACGATC
 181 ACAAGTTTGT ACAAAAAAGC TGAACGAGAA ACGTAAAATG ATATAAATAT CAATATATTA
 241 AATTAGATTT TGCATAAAAA ACAGACTACA TAATACTGTA AAACACAACA TATCCAGTCA
 301 CTATGGCGGC CGCTAAGTTG GCAGCATCAC CCGACGCACT TTGCGCCGAA TAAATACCTG
 361 TGACGGAAGA TCACTTCGCA GAATAAATAA ATCCTGGTGT CCCTGTTGAT ACCGGGAAGC
 421 CCTGGGCCAA CTTTTGGCGA AAATGAGACG TTGATCGGCA CGTAAGAGGT TCCAACTTTC
 481 ACCATAATGA AATAAGATCA CTACCGGGCG TATTTTTTGA GTTATCGAGA TTTTCAGGAG
 541 CTAAGGAAGC TAAAATGGAG AAAAAAATCA CTGGATATAC CACCGTTGAT ATATCCCAAT
 601 GGCATCGTAA AGAACATTTT GAGGCATTTC AGTCAGTTGC TCAATGTACC TATAACCAGA
 661 CCGTTCAGCT GGATATTACG GCCTTTTTAA AGACCGTAAA GAAAAATAAG CACAAGTTTT
 721 ATCCGGCCTT TATTCACATT CTTGCCCGCC TGATGAATGC TCATCCGGAA TTCCGTATGG
 781 CAATGAAAGA CGGTGAGCTG GTGATATGGG ATAGTGTTCA CCCTTGTTAC ACCGTTTTCC
 841 ATGAGCAAAC TGAAACGTTT TCATCGCTCT GGAGTGAATA CCACGACGAT TTCCGGCAGT
 901 TTCTACACAT ATATTCGCAA GATGTGGCGT GTTACGGTGA AAACCTGGCC TATTTCCCTA
 961 AAGGGTTTAT TGAGAATATG TTTTTCGTCT CAGCCAATCC CTGGGTGAGT TTCACCAGTT
1021 TTGATTTAAA CGTGGCCAAT ATGGACAACT TCTTCGCCCC CGTTTTCACC ATGGGCAAAT
1081 ATTATACGCA AGGCGACAAG GTGCTGATGC CGCTGGCGAT TCAGGTTCAT CATGCCGTCT
1141 GTGATGGCTT CCATGTCGGC AGAATGCTTA ATGAATTACA ACAGTACTGC GATGAGTGGC
1201 AGGGCGGGGC GTAAACGCGT GGATCCGGCT TACTAAAAGC CAGATAACAG TATGCGTATT
1261 TGCGCGCTGA TTTTTGCGGT ATAAGAATAT ATACTGATAT GTATACCCGA AGTATGTCAA
1321 AAAGAGGTGT GCTATGAAGC AGCGTATTAC AGTGACAGTT GACAGCGACA GCTATCAGTT
1381 GCTCAAGGCA TATATGATGT CAATATCTCC GGTCTGGTAA GCACAACCAT GCAGAATGAA
1441 GCCCGTCGTC TGCGTGCCGA ACGCTGGAAA GCGGAAAATC AGGAAGGGAT GGCTGAGGTC
1501 GCCCGGTTTA TTGAAATGAA CGGCTCTTTT GCTGACGAGA ACAGGGACTG GTGAAATGCA
1561 GTTTAAGGTT TACACCTATA AAAGAGAGAG CCGTTATCGT CTGTTTGTGG ATGTACAGAG
1621 TGATATTATT GACACGCCCG GGCGACGGAT GGTGATCCCC CTGGCCAGTG CACGTCTGCT
1681 GTCAGATAAA GTCTCCCGTG AACTTTACCC GGTGGTGCAT ATCGGGGATG AAAGCTGGCG
1741 CATGATGACC ACCGATATGG CCAGTGTGCC GGTCTCCGTT ATCGGGGAAG AAGTGGCTGA
```

FIG.25C

1801 TCTCAGCCAC CGCGAAAATG ACATCAAAAA CGCCATTAAC CTGATGTTCT GGGGAATATA
1861 AATGTCAGGC TCCCTTATAC ACAGCCAGTC TGCAGGTCGA CCATAGTGAC TGGATATGTT
1921 GTGTTTTACA GTATTATGTA GTCTGTTTTT TATGCAAAAT CTAATTTAAT ATATTGATAT
1981 TTATATCATT TTACGTTTCT CGTTCAGCTT TCTTGTACAA AGTGGTGATC ACTAGTCGGC
2041 GGCCGCTCTA GAGGATCCAA GCTTACGTAC GCGTGCATGC GACGTCATAG CTCTTCTATA
2101 GTGTCACCTA AATTCAATTC ACTGGCCGTC GTTTTACAAC GTCGTGACTG GGAAAACCCT
2161 GGCGTTACCC AACTTAATCG CCTTGCAGCA CATCCCCCTT TCGCCAGCTG GCGTAATAGC
2221 GAAGAGGCCC GCACCGATCG CCCTTCCCAA CAGTTGCGCA GCCTGAATGG CGAATGGACG
2281 CGCCCTGTAG CGGCGCATTA AGCGCGGCGG GTGTGGTGGT TACGCGCAGC GTGACCGCTA
2341 CACTTGCCAG CGCCCTAGCG CCCGCTCCTT TCGCTTTCTT CCCTTCCTTT CTCGCCACGT
2401 TCGCCGGCTT TCCCCGTCAA GCTCTAAATC GGGGGCTCCC TTTAGGGTTC CGATTTAGTG
2461 CTTTACGGCA CCTCGACCCC AAAAAACTTG ATTAGGGTGA TGGTTCACGT AGTGGGCCAT
2521 CGCCCTGATA GACGGTTTTT CGCCCTTTGA CGTTGGAGTC CACGTTCTTT AATAGTGGAC
2581 TCTTGTTCCA AACTGGAACA ACACTCAACC CTATCTCGGT CTATTCTTTT GATTTATAAG
2641 GGATTTTGCC GATTTCGGCC TATTGGTTAA AAAATGAGCT GATTTAACAA AAATTTAACG
2701 CGAATTTTAA CAAAATATTA ACGTTTACAA TTTCAGGTGG CACTTTTCGG GGAAATGTGC
2761 GCGGAACCCC TATTTGTTTA TTTTTCTAAA TACATTCAAA TATGTATCCG CTCATGAGAC
2821 AATAACCCTG ATAAATGCTT CAATAATATT GAAAAAGGAA GAGTATGAGT ATTCAACATT
2881 TCCGTGTCGC CCTTATTCCC TTTTTTGCGG CATTTTGCCT TCCTGTTTTT GCTCACCCAG
2941 AAACGCTGGT GAAAGTAAAA GATGCTGAAG ATCAGTTGGG TGCACGAGTG GGTTACATCG
3001 AACTGGATCT CAACAGCGGT AAGATCCTTG AGAGTTTTCG CCCCGAAGAA CGTTTTCCAA
3061 TGATGAGCAC TTTTAAAGTT CTGCTATGTG GCGCGGTATT ATCCCGTATT GACGCCGGGC
3121 AAGAGCAACT CGGTCGCCGC ATACACTATT CTCAGAATGA CTTGGTTGAG TACTCACCAG
3181 TCACAGAAAA GCATCTTACG GATGGCATGA CAGTAAGAGA ATTATGCAGT GCTGCCATAA
3241 CCATGAGTGA TAACACTGCG GCCAACTTAC TTCTGACAAC GATCGGAGGA CCGAAGGAGC
3301 TAACCGCTTT TTTGCACAAC ATGGGGGATC ATGTAACTCG CCTTGATCGT TGGGAACCGG
3361 AGCTGAATGA AGCCATACCA AACGACGAGC GTGACACCAC GATGCCTGTA GCAATGGCAA
3421 CAACGTTGCG CAAACTATTA ACTGGCGAAC TACTTACTCT AGCTTCCCGG CAACAATTAA
3481 TAGACTGGAT GGAGGCGGAT AAAGTTGCAG GACCACTTCT GCGCTCGGCC CTTCCGGCTG
3541 GCTGGTTTAT TGCTGATAAA TCTGGAGCCG GTGAGCGTGG GTCTCGCGGT ATCATTGCAG
3601 CACTGGGGCC AGATGGTAAG CCCTCCCGTA TCGTAGTTAT CTACACGACG GGGAGTCAGG
3661 CAACTATGGA TGAACGAAAT AGACAGATCG CTGAGATAGG TGCCTCACTG ATTAAGCATT
3721 GGTAACTGTC AGACCAAGTT TACTCATATA TACTTTAGAT TGATTTAAAA CTTCATTTTT
3781 AATTTAAAAG GATCTAGGTG AAGATCCTTT TTGATAATCT CATGACCAAA ATCCCTTAAC
3841 GTGAGTTTTC GTTCCACTGA GCGTCAGACC CCGTAGAAAA GATCAAAGGA TCTTCTTGAG
3901 ATCCTTTTTT TCTGCGCGTA ATCTGCTGCT TGCAAACAAA AAAACCACCG CTACCAGCGG
3961 TGGTTTGTTT GCCGGATCAA GAGCTACCAA CTCTTTTTCC GAAGGTAACT GGCTTCAGCA
4021 GAGCGCAGAT ACCAAATACT GTCCTTCTAG TGTAGCCGTA GTTAGGCCAC CACTTCAAGA
4081 ACTCTGTAGC ACCGCCTACA TACCTCGCTC TGCTAATCCT GTTACCAGTG GCTGCTGCCA
4141 GTGGCGATAA GTCGTGTCTT ACCGGGTTGG ACTCAAGACG ATAGTTACCG GATAAGGCGC
4201 AGCGGTCGGG CTGAACGGGG GGTTCGTGCA CACAGCCCAG CTTGGAGCGA ACGACCTACA

FIG.25D

4261 CCGAACTGAG ATACCTACAG CGTGAGCATT GAGAAAGCGC CACGCTTCCC GAAGGGAGAA
4321 AGGCGGACAG GTATCCGGTA AGCGGCAGGG TCGGAACAGG AGAGCGCACG AGGGAGCTTC
4381 CAGGGGGAAA CGCCTGGTAT CTTTATAGTC CTGTCGGGTT TCGCCACCTC TGACTTGAGC
4441 GTCGATTTTT GTGATGCTCG TCAGGGGGGC GGAGCCTATG GAAAAACGCC AGCAACGCGG
4501 CCTTTTTACG GTTCCTGGCC TTTTGCTGGC CTTTTGCTCA CATGTTCTTT CCTGCGTTAT
4561 CCCCTGATTC TGTGGATAAC CGTATTACCG CCTTTGAGTG AGCTGATACC GCTCGCCGCA
4621 GCCGAACGAC CGAGCGCAGC GAGTCAGTGA GCGAGGAAGC GGAAGAGCGC CCAATACGCA
4681 AACCGCCTCT CCCCGCGCGT TGGCCGATTC ATTAATGCAG AGCTTGCAAT TCGCGCGCGA
4741 AGGCGAAGCG GCATTTACGT TGACACCATC GAATGGCGCA AAACCTTTCG CGGTATGGCA
4801 TGATAGCGCC CGGAAGAGAG TCAATTCAGG GTGGTGAATG TGAAACCAGT AACGTTATAC
4861 GATGTCGCAG AGTATGCCGG TGTCTCTTAT CAGACCGTTT CCCGCGTGGT GAACCAGGCC
4921 AGCCACGTTT CTGCGAAAAC GCGGGAAAAA GTGGAAGCGG CGATGGCGGA GCTGAATTAC
4981 ATTCCCAACC GCGTGGCACA ACAACTGGCG GGCAAACAGT CGTTGCTGAT TGGCGTTGCC
5041 ACCTCCAGTC TGGCCCTGCA CGCGCCGTCG CAAATTGTCG CGGCGATTAA ATCTCGCGCC
5101 GATCAACTGG GTGCCAGCGT GGTGGTGTCG ATGGTAGAAC GAAGCGGCGT CGAAGCCTGT
5161 AAAGCGGCGG TGCACAATCT TCTCGCGCAA CGGGTCAGTG GGCTGATCAT TAACTATCCG
5221 CTGGATGACC AGGATGCCAT TGCTGTGGAA GCTGCCTGCA CTAATGTTCC GGCGTTATTT
5281 CTTGATGTCT CTGACCAGAC ACCCATCAAC AGTATTATTT TCTCCCATGA AGACGGTACG
5341 CGACTGGGCG TGGAGCATCT GGTCGCATTG GGTCACCAGC AAATCGCGCT GTTAGCGGGC
5401 CCATTAAGTT CTGTCTCGGC GCGTCTGCGT CTGGCTGGCT GGCATAAATA TCTCACTCGC
5461 AATCAAATTC AGCCGATAGC GGAACGGGAA GGCGACTGGA GTGCCATGTC CGGTTTTCAA
5521 CAAACCATGC AAATGCTGAA TGAGGGCATC GTTCCCACTG CGATGCTGGT TGCCAACGAT
5581 CAGATGGCGC TGGGCGCAAT GCGCGCCATT ACCGAGTCCG GGCTGCGCGT TGGTGCGGAT
5641 ATCTCGGTAG TGGGATACGA CGATACCGAA GACAGCTCAT GTTATATCCC GCCGTCAACC
5701 ACCATCAAAC AGGATTTTCG CCTGCTGGGG CAAACCAGCG TGGACCGCTT GCTGCAACTC
5761 TCTCAGGGCC AGGCGGTGAA GGGCAATCAG CTGTTGCCCG TCTCACTGGT GAAAAGAAAA
5821 ACCACCCTGG CGCCCAATAC GCAAACCGCC TCTCCCCGCG CGTTGGCCGA TTCATTAATG
5881 CAGCTGGCAC GACAGGTTTC CCGACTGGAA AGCGGGCAGT GAGCGCAACG CAATTAATGT
5941 GAGTTAGCTC ACTCATT

FIG.25E pSPORT "−" (OPPOSITE STRAND)

"FORWARD" SEQUENCING PRIMERS 1   taa cgc cag ggt ttt ccc agt cac gac gtt gta aaa cga cgg cca gtg aat
    att gcg gtc cca aaa ggg tca gtg ctg caa cat ttt gct gcc ggt cac tta SP6 PROMOTER                                        Sph   Mlu
52  tga att tag gtg aca cta tag aag agc tat gac gtc gca tgc acg cgt acg
    act taa atc cac tgt gat atc ttc tcg ata ctg cag cgt acg tgc gca tgc Hind 3  Bam   Xba   Not    Spe         attR1    Int
103 tda gct tgg atc ctc tag agc ggc cgc cga cta gtg atc aca agt ttg tac
    att cga acc tag gag atc tcg ccg gcg gct gat cac tag tgt tca aac atg 154 ░░░░░░░░░░░░░░░░░░░░░░░░░░░░░░░░░░░░░░░░░░░░░░░░░░
    ░░░░░░░░░░░░░░░░░░░░░░░░░░░░░░░░░░░░░░░░░░░░░░░░░░
                        ↓ GENE Int attR2
1939 ░░░░░░░░░░░░░░░░░░░░░░░░░░░░░░░░░░ tct tgt aca aag tgg tga
     ░░░░░░░░░░░░░░░░░░░░░░░░░░░░░░░░░░ aga aca tgt ttc acc act Sal    Sma EcoRI          Kpn    Pst
1990 tcg tcg acc cgg gaa ttc cgg acc ggt acc tgc agg cgt acc agc ttt ccc
     agc agc tgg gcc ctt aag gcc tgg cca tgg acg tcc gca tgg tcg aaa ggg
                                                                T7 RNA 2041 tat agt gag tcg tat tag agc ttg gcg taa tca tgg tca tag ctg ttt cct
     ata tca ctc agc ata atc tcg aac cgc att agt acc agt atc gac aaa gga
           T7 PROMOTER                       α-peptide
                                                              "REVERSE"...
                                              −10      lac PROMOTER
2092 gtg tga aat tgt tat ccg ctc aca att cca cac aac ata cga gcc gga agc
     cac act tta aca ata ggc gag tgt taa ggt gtg ttg tat gct cgg cct tcg
     ──────────────────
        ... SEQUENCING PRIMERS        lac RNA −35
2143 ata aag tgt aaa gcc tgg ggt gcc taa tga gtg agc taa ctc aca tta att
     tat ttc aca ttt cgg acc cca cgg att act cac tcg att gag tgt aat taa

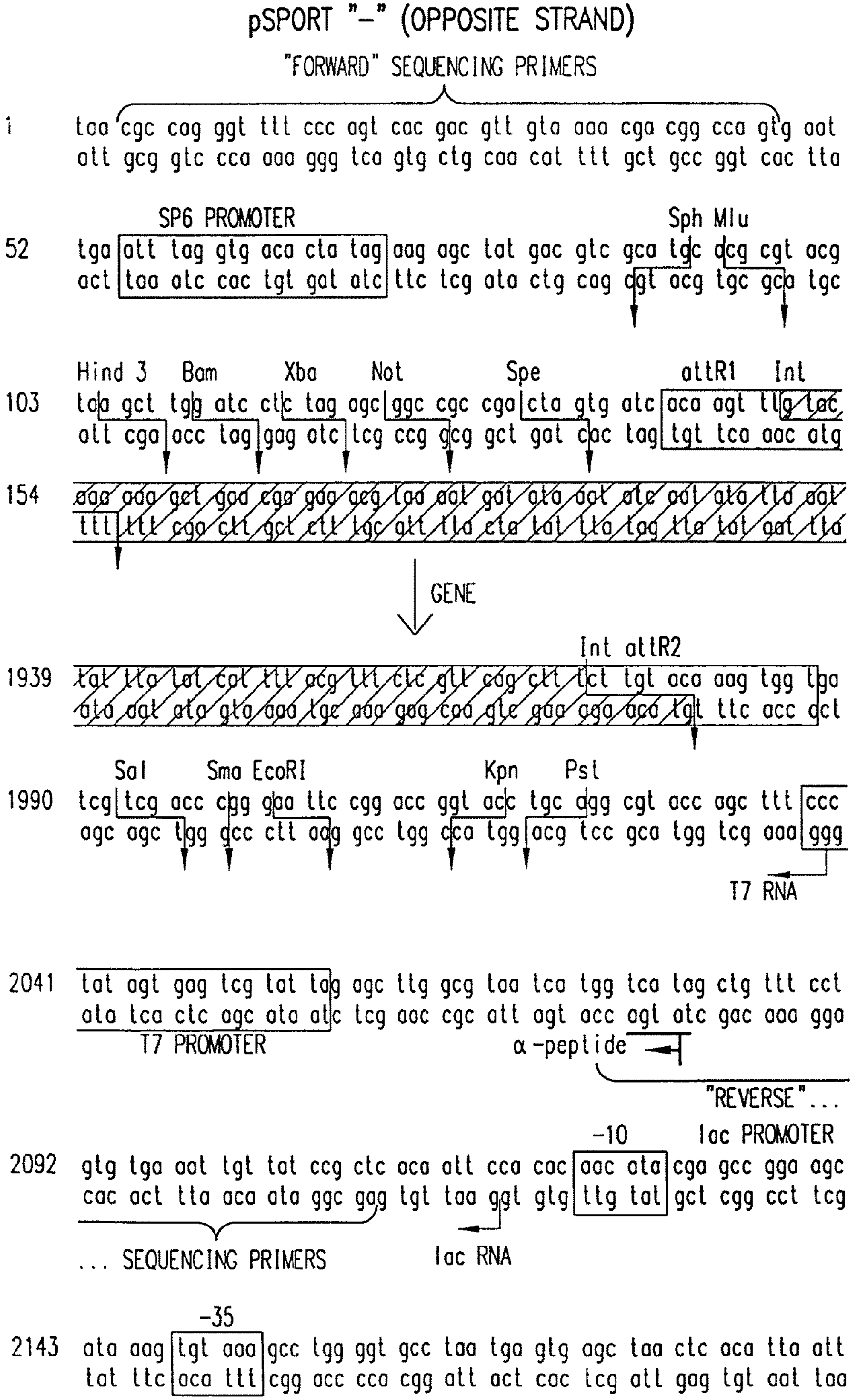

FIG.26A pDEST6 pDEST6 5957 bp

| Location (Base Nos.) | Gene Encoded |
|---|---|
| 266..142 | attR1 |
| 516..1175 | CmR |
| 1295..1379 | inactivated ccdA |
| 1517..1822 | ccdB |
| 1863..1987 | attR2 |
| 2203..3369 | lacI |
| 4403..5260 | ampR |
| 5392..5847 | f1 (f1 intergenic region) |

```
   1 TAACGCCAGG GTTTTCCCAG TCACGACGTT GTAAAACGAC GGCCAGTGAA TTGAATTTAG
  61 GTGACACTAT AGAAGAGCTA TGACGTCGCA TGCACGCGTA CGTAAGCTTG GATCCTCTAG
 121 AGCGGCCGCC GACTAGTGAT CACAAGTTTG TACAAAAAAG CTGAACGAGA AACGTAAAAT
 181 GATATAAATA TCAATATATT AAATTAGATT TTGCATAAAA AACAGACTAC ATAATACTGT
 241 AAAACACAAC ATATCCAGTC ACTATGGCGG CCGCTAAGTT GGCAGCATCA CCCGACGCAC
 301 TTTGCGCCGA ATAAATACCT GTGACGGAAG ATCACTTCGC AGAATAAATA AATCCTGGTG
 361 TCCCTGTTGA TACCGGGAAG CCCTGGGCCA ACTTTTGGCG AAAATGAGAC GTTGATCGGC
 421 ACGTAAGAGG TTCCAACTTT CACCATAATG AAATAAGATC ACTACCGGGC GTATTTTTTG
 481 AGTTATCGAG ATTTTCAGGA GCTAAGGAAG CTAAAATGGA GAAAAAAATC ACTGGATATA
 541 CCACCGTTGA TATATCCCAA TGGCATCGTA AAGAACATTT TGAGGCATTT CAGTCAGTTG
 601 CTCAATGTAC CTATAACCAG ACCGTTCAGC TGGATATTAC GGCCTTTTTA AAGACCGTAA
 661 AGAAAAATAA GCACAAGTTT TATCCGGCCT TTATTCACAT TCTTGCCCGC CTGATGAATG
 721 CTCATCCGGA ATTCCGTATG GCAATGAAAG ACGGTGAGCT GGTGATATGG GATAGTGTTC
 781 ACCCTTGTTA CACCGTTTTC CATGAGCAAA CTGAAACGTT TTCATCGCTC TGGAGTGAAT
 841 ACCACGACGA TTTCCGGCAG TTTCTACACA TATATTCGCA AGATGTGGCG TGTTACGGTG
 901 AAAACCTGGC CTATTTCCCT AAAGGGTTTA TTGAGAATAT GTTTTTCGTC TCAGCCAATC
 961 CCTGGGTGAG TTTCACCAGT TTTGATTTAA ACGTGGCCAA TATGGACAAC TTCTTCGCCC
1021 CCGTTTTCAC CATGGGCAAA TATTATACGC AAGGCGACAA GGTGCTGATG CCGCTGGCGA
1081 TTCAGGTTCA TCATGCCGTC TGTGATGGCT TCCATGTCGG CAGAATGCTT AATGAATTAC
1141 AACAGTACTG CGATGAGTGG CAGGGCGGGG CGTAAACGCG TGGATCCGGC TTACTAAAAG
1201 CCAGATAACA GTATGCGTAT TTGCGCGCTG ATTTTTGCGG TATAAGAATA TATACTGATA
1261 TGTATACCCG AAGTATGTCA AAAAGAGGTG TGCTATGAAG CAGCGTATTA CAGTGACAGT
1321 TGACAGCGAC AGCTATCAGT TGCTCAAGGC ATATATGATG TCAATATCTC CGGTCTGGTA
1381 AGCACAACCA TGCAGAATGA AGCCCGTCGT CTGCGTGCCG AACGCTGGAA AGCGGAAAAT
1441 CAGGAAGGGA TGGCTGAGGT CGCCCGGTTT ATTGAAATGA ACGGCTCTTT TGCTGACGAG
1501 AACAGGGACT GGTGAAATGC AGTTTAAGGT TTACACCTAT AAAAGAGAGA GCCGTTATCG
1561 TCTGTTTGTG GATGTACAGA GTGATATTAT TGACACGCCC GGGCGACGGA TGGTGATCCC
1621 CCTGGCCAGT GCACGTCTGC TGTCAGATAA AGTCTCCCGT GAACTTTACC CGGTGGTGCA
1681 TATCGGGGAT GAAAGCTGGC GCATGATGAC CACCGATATG GCCAGTGTGC CGGTCTCCGT
1741 TATCGGGGAA GAAGTGGCTG ATCTCAGCCA CCGCGAAAAT GACATCAAAA ACGCCATTAA
1801 CCTGATGTTC TGGGGAATAT AAATGTCAGG CTCCCTTATA CACAGCCAGT CTGCAGGTCG
```

FIG.26C

1861 ACCATAGTGA CTGGATATGT TGTGTTTTAC AGTATTATGT AGTCTGTTTT TTATGCAAAA
1921 TCTAATTTAA TATATTGATA TTTATATCAT TTTACGTTTC TCGTTCAGCT TTCTTGTACA
1981 AAGTGGTGAT CGTCGACCCG GGAATTCCGG ACCGGTACCT GCAGGCGTAC CAGCTTTCCC
2041 TATAGTGAGT CGTATTAGAG CTTGGCGTAA TCATGGTCAT AGCTGTTTCC TGTGTGAAAT
2101 TGTTATCCGC TCACAATTCC ACACAACATA CGAGCCGGAA GCATAAAGTG TAAAGCCTGG
2161 GGTGCCTAAT GAGTGAGCTA ACTCACATTA ATTGCGTTGC GCTCACTGCC CGCTTTCCAG
2221 TCGGGAAACC TGTCGTGCCA GCTGCATTAA TGAATCGGCC AACGCGCGGG GAGAGGCGGT
2281 TTGCGTATTG GGCGCCAGGG TGGTTTTTCT TTTCACCAGT GAGACGGGCA ACAGCTGATT
2341 GCCCTTCACC GCCTGGCCCT GAGAGAGTTG CAGCAAGCGG TCCACGCTGG TTTGCCCCAG
2401 CAGGCGAAAA TCCTGTTTGA TGGTGGTTGA CGGCGGGATA TAACATGAGC TGTCTTCGGT
2461 ATCGTCGTAT CCCACTACCG AGATATCCGC ACCAACGCGC AGCCCGGACT CGGTAATGGC
2521 GCGCATTGCG CCCAGCGCCA TCTGATCGTT GGCAACCAGC ATCGCAGTGG GAACGATGCC
2581 CTCATTCAGC ATTTGCATGG TTTGTTGAAA ACCGGACATG GCACTCCAGT CGCCTTCCCG
2641 TTCCGCTATC GGCTGAATTT GATTGCGAGT GAGATATTTA TGCCAGCCAG CCAGACGCAG
2701 ACGCGCCGAG ACAGAACTTA ATGGGCCCGC TAACAGCGCG ATTTGCTGGT GACCCAATGC
2761 GACCAGATGC TCCACGCCCA GTCGCGTACC GTCTTCATGG GAGAAAATAA TACTGTTGAT
2821 GGGTGTCTGG TCAGAGACAT CAAGAAATAA CGCCGGAACA TTAGTGCAGG CAGCTTCCAC
2881 AGCAATGGCA TCCTGGTCAT CCAGCGGATA GTTAATGATC AGCCCACTGA CCCGTTGCGC
2941 GAGAAGATTG TGCACCGCCG CTTTACAGGC TTCGACGCCG CTTCGTTCTA CCATCGACAC
3001 CACCACGCTG GCACCCAGTT GATCGGCGCG AGATTTAATC GCCGCGACAA TTTGCGACGG
3061 CGCGTGCAGG GCCAGACTGG AGGTGGCAAC GCCAATCAGC AACGACTGTT TGCCCGCCAG
3121 TTGTTGTGCC ACGCGGTTGG GAATGTAATT CAGCTCCGCC ATCGCCGCTT CCACTTTTTC
3181 CCGCGTTTTC GCAGAAACGT GGCTGGCCTG GTTCACCACG CGGGAAACGG TCTGATAAGA
3241 GACACCGGCA TACTCTGCGA CATCGTATAA CGTTACTGGT TTCACATTCA CCACCCTGAA
3301 TTGACTCTCT TCCGGGCGCT ATCATGCCAT ACCGCGAAAG GTTTTGCGCC ATTCGATGGT
3361 GTCAACGTAA ATGCCGCTTC GCCTTCGCGC GCGAATTGCA AGCTCTGCAT TAATGAATCG
3421 GCCAACGCGC GGGGAGAGGC GGTTTGCGTA TTGGGCGCTC TTCCGCTTCC TCGCTCACTG
3481 ACTCGCTGCG CTCGGTCGTT CGGCTGCGGC GAGCGGTATC AGCTCACTCA AAGGCGGTAA
3541 TACGGTTATC CACAGAATCA GGGGATAACG CAGGAAAGAA CATGTGAGCA AAAGGCCAGC
3601 AAAAGGCCAG GAACCGTAAA AAGGCCGCGT TGCTGGCGTT TTTCCATAGG CTCCGCCCCC
3661 CTGACGAGCA TCACAAAAAT CGACGCTCAA GTCAGAGGTG GCGAAACCCG ACAGGACTAT
3721 AAAGATACCA GGCGTTTCCC CCTGGAAGCT CCCTCGTGCG CTCTCCTGTT CCGACCCTGC
3781 CGCTTACCGG ATACCTGTCC GCCTTTCTCC CTTCGGGAAG CGTGGCGCTT TCTCAATGCT
3841 CACGCTGTAG GTATCTCAGT TCGGTGTAGG TCGTTCGCTC CAAGCTGGGC TGTGTGCACG
3901 AACCCCCCGT TCAGCCCGAC CGCTGCGCCT TATCCGGTAA CTATCGTCTT GAGTCCAACC
3961 CGGTAAGACA CGACTTATCG CCACTGGCAG CAGCCACTGG TAACAGGATT AGCAGAGCGA
4021 GGTATGTAGG CGGTGCTACA GAGTTCTTGA AGTGGTGGCC TAACTACGGC TACACTAGAA
4081 GGACAGTATT TGGTATCTGC GCTCTGCTGA AGCCAGTTAC CTTCGGAAAA AGAGTTGGTA
4141 GCTCTTGATC CGGCAAACAA ACCACCGCTG GTAGCGGTGG TTTTTTTGTT TGCAAGCAGC
4201 AGATTACGCG CAGAAAAAAA GGATCTCAAG AAGATCCTTT GATCTTTTCT ACGGGGTCTG
4261 ACGCTCAGTG GAACGAAAAC TCACGTTAAG GGATTTTGGT CATGAGATTA TCAAAAAGGA

FIG.26D

4321 TCTTCACCTA GATCCTTTTA AATTAAAAAT GAAGTTTTAA ATCAATCTAA AGTATATATG
4381 AGTAAACTTG GTCTGACAGT TACCAATGCT TAATCAGTGA GGCACCTATC TCAGCGATCT
4441 GTCTATTTCG TTCATCCATA GTTGCCTGAC TCCCCGTCGT GTAGATAACT ACGATACGGG
4501 AGGGCTTACC ATCTGGCCCC AGTGCTGCAA TGATACCGCG AGACCCACGC TCACCGGCTC
4561 CAGATTTATC AGCAATAAAC CAGCCAGCCG GAAGGGCCGA GCGCAGAAGT GGTCCTGCAA
4621 CTTTATCCGC CTCCATCCAG TCTATTAATT GTTGCCGGGA AGCTAGAGTA AGTAGTTCGC
4681 CAGTTAATAG TTTGCGCAAC GTTGTTGCCA TTGCTACAGG CATCGTGGTG TCACGCTCGT
4741 CGTTTGGTAT GGCTTCATTC AGCTCCGGTT CCCAACGATC AAGGCGAGTT ACATGATCCC
4801 CCATGTTGTG CAAAAAAGCG GTTAGCTCCT TCGGTCCTCC GATCGTTGTC AGAAGTAAGT
4861 TGGCCGCAGT GTTATCACTC ATGGTTATGG CAGCACTGCA TAATTCTCTT ACTGTCATGC
4921 CATCCGTAAG ATGCTTTTCT GTGACTGGTG AGTACTCAAC CAAGTCATTC TGAGAATAGT
4981 GTATGCGGCG ACCGAGTTGC TCTTGCCCGG CGTCAATACG GGATAATACC GCGCCACATA
5041 GCAGAACTTT AAAAGTGCTC ATCATTGGAA AACGTTCTTC GGGGCGAAAA CTCTCAAGGA
5101 TCTTACCGCT GTTGAGATCC AGTTCGATGT AACCCACTCG TGCACCCAAC TGATCTTCAG
5161 CATCTTTTAC TTTCACCAGC GTTTCTGGGT GAGCAAAAAC AGGAAGGCAA AATGCCGCAA
5221 AAAAGGGAAT AAGGGCGACA CGGAAATGTT GAATACTCAT ACTCTTCCTT TTTCAATATT
5281 ATTGAAGCAT TTATCAGGGT TATTGTCTCA TGAGCGGATA CATATTTGAA TGTATTTAGA
5341 AAAATAAACA AATAGGGGTT CCGCGCACAT TTCCCCGAAA AGTGCCACCT GAAATTGTAA
5401 ACGTTAATAT TTTGTTAAAA TTCGCGTTAA ATTTTTGTTA AATCAGCTCA TTTTTTAACC
5461 AATAGGCCGA AATCGGCAAA ATCCCTTATA AATCAAAAGA ATAGACCGAG ATAGGGTTGA
5521 GTGTTGTTCC AGTTTGGAAC AAGAGTCCAC TATTAAAGAA CGTGGACTCC AACGTCAAAG
5581 GGCGAAAAAC CGTCTATCAG GGCGATGGCC CACTACGTGA ACCATCACCC TAATCAAGTT
5641 TTTTGGGGTC GAGGTGCCGT AAAGCACTAA ATCGGAACCC TAAAGGGAGC CCCCGATTTA
5701 GAGCTTGACG GGGAAAGCCG GCGAACGTGG CGAGAAAGGA AGGGAAGAAA GCGAAAGGAG
5761 CGGGCGCTAG GGCGCTGGCA AGTGTAGCGG TCACGCTGCG CGTAACCACC ACACCCGCCG
5821 CGCTTAATGC GCCGCTACAG GGCGCGTCCA TTCGCCATTC AGGCTGCGCA ACTGTTGGGA
5881 AGGGCGATCG GTGCGGGCCT CTTCGCTATT ACGCCAGCTG GCGAAAGGGG GATGTGCTGC
5941 AAGGCGATTA AGTTGGG

FIG.26E

CMV PROMOTER FOR EUKARYOTIC EXPRESSION 970 cca ttg acg caa atg ggc ggt agg cgt gta cgg tgg gag gtc tat ata agc
ggt aac tgc gtt tac ccg cca tcc gca cat gcc acc ctc cag ata tat tcg mRNA START 1021 aga gct cgt tta gtg aac cgt cag atc gcc tgg aga cgc cat cca cgc tgt
tct cga gca aat cac ttg gca gtc tag cgg acc tct gcg gta ggt gcg aca

CMV ENHANCER/PROMOTER 1072 ttt gac ctc cat aga aga cac cgg gac cga tcc agc ctc cgg act cta gcc
aaa ctg gag gta tct tct gtg gcc ctg gct agg tcg gag gcc tga gat cgg 1123 tag gcc gcg gag cgg ata aca att tca cac agg aaa cag cta tga cca cta
atc cgg cgc ctc gcc tat tgt taa agt gtg tcc ttt gtc gat act ggt gat Pst 1174 ggc ttt tgc aaa aag cta ttt agg tga cac tat aga agg tac gcc tgc agg
ccg aaa acg ttt ttc gat aaa tcc act gtg ata tct tcc atg cgg acg tcc Kpn EcoRI Int attR1

1225 tac cgg tcc gga att ccc atc aca agt ttg tac aaa aaa gct gaa cga gaa
atg gcc agg cct taa ggg tag tgt tca aac atg ttt ttt cga ctt gct ctt

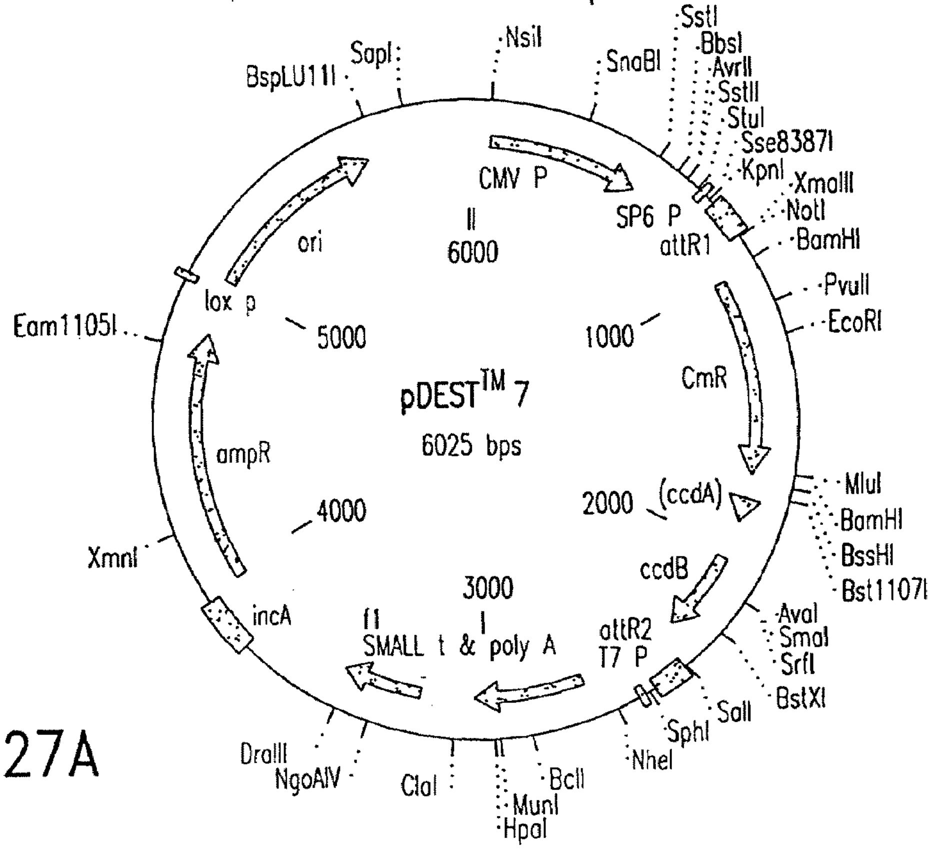

FIG.27A pDEST7 6025 bp (rotated to position 2800)

| Location (Base Nos.) | Gene Encoded |
|---|---|
| 67..589 | CMV promoter |
| 906..782 | attR1 |
| 1015..1674 | CmR |
| 1794..1878 | inactivated ccdA |
| 2016..2321 | ccdB |
| 2362..2486 | attR2 |
| 2671..3033 | small t & polyA |
| 3227..3502 | f1 |
| 3962..4822 | ampR |
| 5022..5661 | ori |

```
   1 ATTATCATGA CATTAACCTA TAAAAATAGG CGTAGTACGA GGCCCTTTCA CTCATTAGAT
  61 GCATGTCGTT ACATAACTTA CGGTAAATGG CCCGCCTGGC TGACCGCCCA ACGACCCCCG
 121 CCCATTGACG TCAATAATGA CGTATGTTCC CATAGTAACG CCAATAGGGA CTTTCCATTG
 181 ACGTCAATGG GTGGAGTATT TACGGTAAAC TGCCCACTTG GCAGTACATC AAGTGTATCA
 241 TATGCCAAGT ACGCCCCCTA TTGACGTCAA TGACGGTAAA TGGCCCGCCT GGCATTATGC
 301 CCAGTACATG ACCTTATGGG ACTTTCCTAC TTGGCAGTAC ATCTACGTAT TAGTCATCGC
 361 TATTACCATG GTGATGCGGT TTTGGCAGTA CATCAATGGG CGTGGATAGC GGTTTGACTC
 421 ACGGGGATTT CCAAGTCTCC ACCCCATTGA CGTCAATGGG AGTTTGTTTT GGCACCAAAA
 481 TCAACGGGAC TTTCCAAAAT GTCGTAACAA CTCCGCCCCA TTGACGCAAA TGGGCGGTAG
 541 GCGTGTACGG TGGGAGGTCT ATATAAGCAG AGCTCGTTTA GTGAACCGTC AGATCGCCTG
 601 GAGACGCCAT CCACGCTGTT TTGACCTCCA TAGAAGACAC CGGGACCGAT CCAGCCTCCG
 661 GACTCTAGCC TAGGCCGCGG AGCGGATAAC AATTTCACAC AGGAAACAGC TATGACCATT
 721 AGGCCTTTGC AAAAAGCTAT TTAGGTGACA CTATAGAAGG TACGCCTGCA GGTACCGGAT
 781 CACAAGTTTG TACAAAAAAG CTGAACGAGA AACGTAAAAT GATATAAATA TCAATATATT
 841 AAATTAGATT TTGCATAAAA AACAGACTAC ATAATACTGT AAAACACAAC ATATCCAGTC
 901 ACTATGGCGG CCGCATTAGG CACCCCAGGC TTTACACTTT ATGCTTCCGG CTCGTATAAT
 961 GTGTGGATTT TGAGTTAGGA TCCGTCGAGA TTTTCAGGAG CTAAGGAAGC TAAAATGGAG
1021 AAAAAAATCA CTGGATATAC CACCGTTGAT ATATCCCAAT GGCATCGTAA AGAACATTTT
1081 GAGGCATTTC AGTCAGTTGC TCAATGTACC TATAACCAGA CCGTTCAGCT GGATATTACG
1141 GCCTTTTTAA AGACCGTAAA GAAAAATAAG CACAAGTTTT ATCCGGCCTT TATTCACATT
1201 CTTGCCCGCC TGATGAATGC TCATCCGGAA TTCCGTATGG CAATGAAAGA CGGTGAGCTG
1261 GTGATATGGG ATAGTGTTCA CCCTTGTTAC ACCGTTTTCC ATGAGCAAAC TGAAACGTTT
1321 TCATCGCTCT GGAGTGAATA CCACGACGAT TTCCGGCAGT TTCTACACAT ATATTCGCAA
1381 GATGTGGCGT GTTACGGTGA AAACCTGGCC TATTTCCCTA AAGGGTTTAT TGAGAATATG
1441 TTTTTCGTCT CAGCCAATCC CTGGGTGAGT TTCACCAGTT TTGATTTAAA CGTGGCCAAT
1501 ATGGACAACT TCTTCGCCCC CGTTTTCACC ATGGGCAAAT ATTATACGCA AGGCGACAAG
1561 GTGCTGATGC CGCTGGCGAT TCAGGTTCAT CATGCCGTCT GTGATGGCTT CCATGTCGGC
1621 AGAATGCTTA ATGAATTACA ACAGTACTGC GATGAGTGGC AGGGCGGGGC GTAAACGCGT
1681 GGATCCGGCT TACTAAAAGC CAGATAACAG TATGCGTATT TGCGCGCTGA TTTTTGCGGT
```

FIG.27B

```
1741 ATAAGAATAT ATACTGATAT GTATACCCGA AGTATGTCAA AAAGAGGTGT GCTATGAAGC
1801 AGCGTATTAC AGTGACAGTT GACAGCGACA GCTATCAGTT GCTCAAGGCA TATATGATGT
1861 CAATATCTCC GGTCTGGTAA GCACAACCAT GCAGAATGAA GCCCGTCGTC TGCGTGCCGA
1921 ACGCTGGAAA GCGGAAAATC AGGAAGGGAT GGCTGAGGTC GCCCGGTTTA TTGAAATGAA
1981 CGGCTCTTTT GCTGACGAGA ACAGGGACTG GTGAAATGCA GTTTAAGGTT TACACCTATA
2041 AAAGAGAGAG CCGTTATCGT CTGTTTGTGG ATGTACAGAG TGATATTATT GACACGCCCG
2101 GGCGACGGAT GGTGATCCCC CTGGCCAGTG CACGTCTGCT GTCAGATAAA GTCTCCCGTG
2161 AACTTTACCC GGTGGTGCAT ATCGGGGATG AAAGCTGGCG CATGATGACC ACCGATATGG
2221 CCAGTGTGCC GGTCTCCGTT ATCGGGGAAG AAGTGGCTGA TCTCAGCCAC CGCGAAAATG
2281 ACATCAAAAA CGCCATTAAC CTGATGTTCT GGGGAATATA AATGTCAGGC TCCCTTATAC
2341 ACAGCCAGTC TGCAGGTCGA CCATAGTGAC TGGATATGTT GTGTTTTACA GTATTATGTA
2401 GTCTGTTTTT TATGCAAAAT CTAATTTAAT ATATTGATAT TTATATCATT TTACGTTTCT
2461 CGTTCAGCTT TCTTGTACAA AGTGGTGATC GCGTGCATGC GACGTCATAG CTCTCTCCCT
2521 ATAGTGAGTC GTATTATAAG CTAGGCACTG GCCGTCGTTT TACAACGTCG TGACTGGGAA
2581 AACTGCTAGC TTGGGATCTT TGTGAAGGAA CCTTACTTCT GTGGTGTGAC ATAATTGGAC
2641 AAACTACCTA CAGAGATTTA AAGCTCTAAG GTAAATATAA AATTTTTAAG TGTATAATGT
2701 GTTAAACTAG CTGCATATGC TTGCTGCTTG AGAGTTTTGC TTACTGAGTA TGATTTATGA
2761 AAATATTATA CACAGGAGCT AGTGATTCTA ATTGTTTGTG TATTTTAGAT TCACAGTCCC
2821 AAGGCTCATT TCAGGCCCCT CAGTCCTCAC AGTCTGTTCA TGATCATAAT CAGCCATACC
2881 ACATTTGTAG AGGTTTTACT TGCTTTAAAA AACCTCCCAC ACCTCCCCCT GAACCTGAAA
2941 CATAAAATGA ATGCAATTGT TGTTGTTAAC TTGTTTATTG CAGCTTATAA TGGTTACAAA
3001 TAAAGCAATA GCATCACAAA TTTCACAAAT AAAGCATTTT TTTCACTGCA TTCTAGTTGT
3061 GGTTTGTCCA AACTCATCAA TGTATCTTAT CATGTCTGGA TCGATCCTGC ATTAATGAAT
3121 CGGCCAACGC GCGGGGAGAG GCGGTTTGCG TATTGGCTGG CGTAATAGCG AAGAGGCCCG
3181 CACCGATCGC CCTTCCCAAC AGTTGCGCAG CCTGAATGGC GAATGGGACG CGCCCTGTAG
3241 CGGCGCATTA AGCGCGGCGG GTGTGGTGGT TACGCGCAGC GTGACCGCTA CACTTGCCAG
3301 CGCCCTAGCG CCCGCTCCTT TCGCTTTCTT CCCTTCCTTT CTCGCCACGT TCGCCGGCTT
3361 TCCCCGTCAA GCTCTAAATC GGGGGCTCCC TTTAGGGTTC CGATTTAGTG CTTTACGGCA
3421 CCTCGACCCC AAAAAACTTG ATTAGGGTGA TGGTTCACGT AGTGGGCCAT CGCCCTGATA
3481 GACGGTTTTT CGCCCTTTGA CGTTGGAGTC CACGTTCTTT AATAGTGGAC TCTTGTTCCA
3541 AACTGGAACA ACACTCAACC CTATCTCGGT CTATTCTTTT GATTTATAAG GGATTTTGCC
3601 GATTTCGGCC TATTGGTTAA AAAATGAGCT GATTTAACAA AAATTTAACG CGAATTTTAA
3661 CAAAATATTA ACGTTTACAA TTTCAGGTGG CACTTTTCGG GGAAATGTGC GCGGAACCCC
3721 TATTTGTTTA TTTTTCTAAA TACATTCAAA TATGTATCCG CTCATGCCAG GTCTTGGACT
3781 GGTGAGAACG GCTTGCTCGG CAGCTTCGAT GTGTGCTGGA GGGAGAATAA AGGTCTAAGA
3841 TGTGCGATAG AGGGAAGTCG CATTGAATTA TGTGCTGTGT AGGGATCGCT GGTATCAAAT
3901 ATGTGTGCCC ACCCCTGGCA TGAGACAATA ACCCTGATAA ATGCTTCAAT AATATTGAAA
3961 AAGGAAGAGT ATGAGTATTC AACATTTCCG TGTCGCCCTT ATTCCCTTTT TTGCGGCATT
4021 TTGCCTTCCT GTTTTTGCTC ACCCAGAAAC GCTGGTGAAA GTAAAAGATG CTGAAGATCA
4081 GTTGGGTGCA CGAGTGGGTT ACATCGAACT GGATCTCAAC AGCGGTAAGA TCCTTGAGAG
4141 TTTTCGCCCC GAAGAACGTT TTCCAATGAT GAGCACTTTT AAAGTTCTGC TATGTGGCGC
```

FIG.27C

```
4201 GGTATTATCC CGTATTGACG CCGGGCAAGA GCAACTCGGT CGCCGCATAC ACTATTCTCA
4261 GAATGACTTG GTTGAGTACT CACCAGTCAC AGAAAAGCAT CTTACGGATG GCATGACAGT
4321 AAGAGAATTA TGCAGTGCTG CCATAACCAT GAGTGATAAC ACTGCGGCCA ACTTACTTCT
4381 GACAACGATC GGAGGACCGA AGGAGCTAAC CGCTTTTTTG CACAACATGG GGGATCATGT
4441 AACTCGCCTT GATCGTTGGG AACCGGAGCT GAATGAAGCC ATACCAAACG ACGAGCGTGA
4501 CACCACGATG CCTGTAGCAA TGGCAACAAC GTTGCGCAAA CTATTAACTG GCGAACTACT
4561 TACTCTAGCT TCCCGGCAAC AATTAATAGA CTGGATGGAG GCGGATAAAG TTGCAGGACC
4621 ACTTCTGCGC TCGGCCCTTC CGGCTGGCTG GTTTATTGCT GATAAATCTG GAGCCGGTGA
4681 GCGTGGGTCT CGCGGTATCA TTGCAGCACT GGGGCCAGAT GGTAAGCCCT CCCGTATCGT
4741 AGTTATCTAC ACGACGGGGA GTCAGGCAAC TATGGATGAA CGAAATAGAC AGATCGCTGA
4801 GATAGGTGCC TCACTGATTA AGCATTGGTA ACTGTCAGAC CAAGTTTACT CATATATACT
4861 TTAGATTGAT TTAAAACTTC ATTTTTAATT TAAAAGGATC TAGGTGAAGA TCCTTTTTGA
4921 TAATCTCATG CCATAACTTC GTATAATGTA TGCTATACGA AGTTATGGCA TGACCAAAAT
4981 CCCTTAACGT GAGTTTTCGT TCCACTGAGC GTCAGACCCC GTAGAAAAGA TCAAAGGATC
5041 TTCTTGAGAT CCTTTTTTTC TGCGCGTAAT CTGCTGCTTG CAAACAAAAA AACCACCGCT
5101 ACCAGCGGTG GTTTGTTTGC CGGATCAAGA GCTACCAACT CTTTTTCCGA AGGTAACTGG
5161 CTTCAGCAGA GCGCAGATAC CAAATACTGT CCTTCTAGTG TAGCCGTAGT TAGGCCACCA
5221 CTTCAAGAAC TCTGTAGCAC CGCCTACATA CCTCGCTCTG CTAATCCTGT TACCAGTGGC
5281 TGCTGCCAGT GGCGATAAGT CGTGTCTTAC CGGGTTGGAC TCAAGACGAT AGTTACCGGA
5341 TAAGGCGCAG CGGTCGGGCT GAACGGGGGG TTCGTGCACA CAGCCCAGCT TGGAGCGAAC
5401 GACCTACACC GAACTGAGAT ACCTACAGCG TGAGCATTGA GAAAGCGCCA CGCTTCCCGA
5461 AGGGAGAAAG GCGGACAGGT ATCCGGTAAG CGGCAGGGTC GGAACAGGAG AGCGCACGAG
5521 GGAGCTTCCA GGGGGAAACG CCTGGTATCT TTATAGTCCT GTCGGGTTTC GCCACCTCTG
5581 ACTTGAGCGT CGATTTTTGT GATGCTCGTC AGGGGGGCGG AGCCTATGGA AAAACGCCAG
5641 CAACGCGGCC TTTTTACGGT TCCTGGCCTT TTGCTGGCCT TTTGCTCACA TGTTCTTTCC
5701 TGCGTTATCC CCTGATTCTG TGGATAACCG TATTACCGCC TTTGAGTGAG CTGATACCGC
5761 TCGCCGCAGC CGAACGACCG AGCGCAGCGA GTCAGTGAGC GAGGAAGCGG AAGAGCGCCC
5821 AATACGCAAA CCGCCTCTCC CCGCGCGTTG GCCGATTCAT TAATGCAGAG CTTGCAATTC
5881 GCGCGTTTTT CAATATTATT GAAGCATTTA TCAGGGTTAT TGTCTCATGA GCGGATACAT
5941 ATTTGAATGT ATTTAGAAAA ATAAACAAAT AGGGGTTCCG CGCACATTTC CCCGAAAAGT
6001 GCCACCTGAC GTCTAAGAAA CCATT
```

FIG. 27D pDEST8 Polyhedron Promoter, Baculovirus Transfer Plasmid

```
    AccI
1   cgt ata ctc cgg aat att aat aga tca tgg aga taa tta aaa tga taa cca
    gca tat gag gcc tta taa tta tct agt acc tct att aat ttt act att ggt

                             mRNA (polyhedrin)
52  tct cgc aaa taa ata agt att tta ctg ttt tcg taa cag ttt tgt aat aaa
    aga gcg ttt att tat tca taa aat gac aaa agc att gtc aaa aca tta ttt

103 aaa acc tat aaa tat tcc gga tta ttc ata ccg tcc cac cat cgg gcg cgg
    ttt tgg ata ttt ata agg cct aat aag tat ggc agg gtg gta gcc cgc gcc

    (Bam)               Int       attR1
154 atc atc aca agt ttg tac aaa aaa gct gaa cga gaa acg taa aat gat ata
    tag tag tgt tca aac atg ttt ttt cga ctt gct ctt tgc att tta cta tat
```

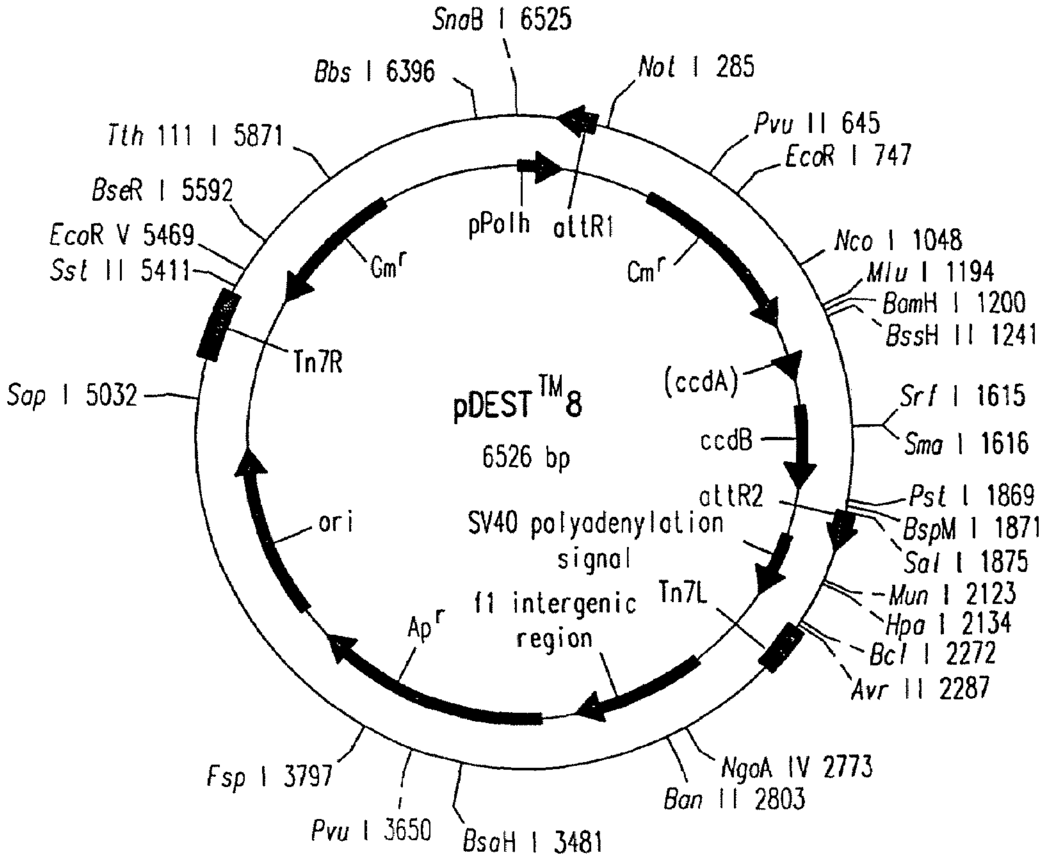

FIG.28A pDEST8 6526 bp

| Location (Base Nos.) | Gene Encoded |
|---|---|
| 23..152 | Ppolh |
| 284..160 | attR1 |
| 534..1193 | CmR |
| 1313..1397 | inactivated ccdA |
| 1535..1840 | ccdB |
| 1881..2005 | attR2 |
| 2766..3146 | f1 |
| 3240..4090 | ampR |
| 4289..4869 | ori |
| 5564..6496 | genR |

```
   1 CGTATACTCC GGAATATTAA TAGATCATGG AGATAATTAA AATGATAACC ATCTCGCAAA
  61 TAAATAAGTA TTTTACTGTT TTCGTAACAG TTTTGTAATA AAAAAACCTA TAAATATTCC
 121 GGATTATTCA TACCGTCCCA CCATCGGGCG CGGATCATCA CAAGTTTGTA CAAAAAAGCT
 181 GAACGAGAAA CGTAAAATGA TATAAATATC AATATATTAA ATTAGATTTT GCATAAAAAA
 241 CAGACTACAT AATACTGTAA AACACAACAT ATCCAGTCAC TATGGCGGCC GCTAAGTTGG
 301 CAGCATCACC CGACGCACTT TGCGCCGAAT AAATACCTGT GACGGAAGAT CACTTCGCAG
 361 AATAAATAAA TCCTGGTGTC CCTGTTGATA CCGGGAAGCC CTGGGCCAAC TTTTGGCGAA
 421 AATGAGACGT TGATCGGCAC GTAAGAGGTT CCAACTTTCA CCATAATGAA ATAAGATCAC
 481 TACCGGGCGT ATTTTTTGAG TTATCGAGAT TTTCAGGAGC TAAGGAAGCT AAAATGGAGA
 541 AAAAAATCAC TGGATATACC ACCGTTGATA TATCCCAATG GCATCGTAAA GAACATTTTG
 601 AGGCATTTCA GTCAGTTGCT CAATGTACCT ATAACCAGAC CGTTCAGCTG GATATTACGG
 661 CCTTTTTAAA GACCGTAAAG AAAAATAAGC ACAAGTTTTA TCCGGCCTTT ATTCACATTC
 721 TTGCCCGCCT GATGAATGCT CATCCGGAAT TCCGTATGGC AATGAAAGAC GGTGAGCTGG
 781 TGATATGGGA TAGTGTTCAC CCTTGTTACA CCGTTTTCCA TGAGCAAACT GAAACGTTTT
 841 CATCGCTCTG GAGTGAATAC CACGACGATT TCCGGCAGTT TCTACACATA TATTCGCAAG
 901 ATGTGGCGTG TTACGGTGAA AACCTGGCCT ATTTCCCTAA AGGGTTTATT GAGAATATGT
 961 TTTTCGTCTC AGCCAATCCC TGGGTGAGTT TCACCAGTTT TGATTTAAAC GTGGCCAATA
1021 TGGACAACTT CTTCGCCCCC GTTTTCACCA TGGGCAAATA TTATACGCAA GGCGACAAGG
1081 TGCTGATGCC GCTGGCGATT CAGGTTCATC ATGCCGTCTG TGATGGCTTC CATGTCGGCA
1141 GAATGCTTAA TGAATTACAA CAGTACTGCG ATGAGTGGCA GGGCGGGGCG TAAACGCGTG
1201 GATCCGGCTT ACTAAAAGCC AGATAACAGT ATGCGTATTT GCGCGCTGAT TTTTGCGGTA
1261 TAAGAATATA TACTGATATG TATACCCGAA GTATGTCAAA AAGAGGTGTG CTATGAAGCA
1321 GCGTATTACA GTGACAGTTG ACAGCGACAG CTATCAGTTG CTCAAGGCAT ATATGATGTC
1381 AATATCTCCG GTCTGGTAAG CACAACCATG CAGAATGAAG CCCGTCGTCT GCGTGCCGAA
1441 CGCTGGAAAG CGGAAAATCA GGAAGGGATG GCTGAGGTCG CCCGGTTTAT TGAAATGAAC
1501 GGCTCTTTTG CTGACGAGAA CAGGGACTGG TGAAATGCAG TTTAAGGTTT ACACCTATAA
1561 AAGAGAGAGC CGTTATCGTC TGTTTGTGGA TGTACAGAGT GATATTATTG ACACGCCCGG
1621 GCGACGGATG GTGATCCCCC TGGCCAGTGC ACGTCTGCTG TCAGATAAAG TCTCCCGTGA
1681 ACTTTACCCG GTGGTGCATA TCGGGGATGA AAGCTGGCGC ATGATGACCA CCGATATGGC
```

FIG.28B

```
1741 CAGTGTGCCG GTCTCCGTTA TCGGGGAAGA AGTGGCTGAT CTCAGCCACC GCGAAAATGA
1801 CATCAAAAAC GCCATTAACC TGATGTTCTG GGGAATATAA ATGTCAGGCT CCCTTATACA
1861 CAGCCAGTCT GCAGGTCGAC CATAGTGACT GGATATGTTG TGTTTTACAG TATTATGTAG
1921 TCTGTTTTTT ATGCAAAATC TAATTTAATA TATTGATATT TATATCATTT TACGTTTCTC
1981 GTTCAGCTTT CTTGTACAAA GTGGTGATAG CTTGTCGAGA AGTACTAGAG GATCATAATC
2041 AGCCATACCA CATTTGTAGA GGTTTTACTT GCTTTAAAAA ACCTCCCACA CCTCCCCCTG
2101 AACCTGAAAC ATAAAATGAA TGCAATTGTT GTTGTTAACT TGTTTATTGC AGCTTATAAT
2161 GGTTACAAAT AAAGCAATAG CATCACAAAT TTCACAAATA AAGCATTTTT TTCACTGCAT
2221 TCTAGTTGTG GTTTGTCCAA ACTCATCAAT GTATCTTATC ATGTCTGGAT CTGATCACTG
2281 CTTGAGCCTA GGAGATCCGA ACCAGATAAG TGAAATCTAG TTCCAAACTA TTTTGTCATT
2341 TTTAATTTTC GTATTAGCTT ACGACGCTAC ACCCAGTTCC CATCTATTTT GTCACTCTTC
2401 CCTAAATAAT CCTTAAAAAC TCCATTTCCA CCCCTCCCAG TTCCCAACTA TTTTGTCCGC
2461 CCACAGCGGG GCATTTTTCT TCCTGTTATG TTTTTAATCA AACATCCTGC CAACTCCATG
2521 TGACAAACCG TCATCTTCGG CTACTTTTTC TCTGTCACAG AATGAAAATT TTTCTGTCAT
2581 CTCTTCGTTA TTAATGTTTG TAATTGACTG AATATCAACG CTTATTTGCA GCCTGAATGG
2641 CGAATGGACG CGCCCTGTAG CGGCGCATTA AGCGCGGCGG GTGTGGTGGT TACGCGCAGC
2701 GTGACCGCTA CACTTGCCAG CGCCCTAGCG CCCGCTCCTT TCGCTTTCTT CCCTTCCTTT
2761 CTCGCCACGT TCGCCGGCTT TCCCCGTCAA GCTCTAAATC GGGGGCTCCC TTTAGGGTTC
2821 CGATTTAGTG CTTTACGGCA CCTCGACCCC AAAAAACTTG ATTAGGGTGA TGGTTCACGT
2881 AGTGGGCCAT CGCCCTGATA GACGGTTTTT CGCCCTTTGA CGTTGGAGTC CACGTTCTTT
2941 AATAGTGGAC TCTTGTTCCA AACTGGAACA ACACTCAACC CTATCTCGGT CTATTCTTTT
3001 GATTTATAAG GGATTTTGCC GATTTCGGCC TATTGGTTAA AAAATGAGCT GATTTAACAA
3061 AAATTTAACG CGAATTTTAA CAAAATATTA ACGTTTACAA TTTCAGGTGG CACTTTTCGG
3121 GGAAATGTGC GCGGAACCCC TATTTGTTTA TTTTTCTAAA TACATTCAAA TATGTATCCG
3181 CTCATGAGAC AATAACCCTG ATAAATGCTT CAATAATATT GAAAAAGGAA GAGTATGAGT
3241 ATTCAACATT TCCGTGTCGC CCTTATTCCC TTTTTTGCGG CATTTTGCCT TCCTGTTTTT
3301 GCTCACCCAG AAACGCTGGT GAAAGTAAAA GATGCTGAAG ATCAGTTGGG TGCACGAGTG
3361 GGTTACATCG AACTGGATCT CAACAGCGGT AAGATCCTTG AGAGTTTTCG CCCCGAAGAA
3421 CGTTTTCCAA TGATGAGCAC TTTTAAAGTT CTGCTATGTG GCGCGGTATT ATCCCGTATT
3481 GACGCCGGGC AAGAGCAACT CGGTCGCCGC ATACACTATT CTCAGAATGA CTTGGTTGAG
3541 TACTCACCAG TCACAGAAAA GCATCTTACG GATGGCATGA CAGTAAGAGA ATTATGCAGT
3601 GCTGCCATAA CCATGAGTGA TAACACTGCG GCCAACTTAC TTCTGACAAC GATCGGAGGA
3661 CCGAAGGAGC TAACCGCTTT TTTGCACAAC ATGGGGGATC ATGTAACTCG CCTTGATCGT
3721 TGGGAACCGG AGCTGAATGA AGCCATACCA AACGACGAGC GTGACACCAC GATGCCTGTA
3781 GCAATGGCAA CAACGTTGCG CAAACTATTA ACTGGCGAAC TACTTACTCT AGCTTCCCGG
3841 CAACAATTAA TAGACTGGAT GGAGGCGGAT AAAGTTGCAG GACCACTTCT GCGCTCGGCC
3901 CTTCCGGCTG GCTGGTTTAT TGCTGATAAA TCTGGAGCCG GTGAGCGTGG GTCTCGCGGT
3961 ATCATTGCAG CACTGGGGCC AGATGGTAAG CCCTCCCGTA TCGTAGTTAT CTACACGACG
4021 GGGAGTCAGG CAACTATGGA TGAACGAAAT AGACAGATCG CTGAGATAGG TGCCTCACTG
4081 ATTAAGCATT GGTAACTGTC AGACCAAGTT TACTCATATA TACTTTAGAT TGATTTAAAA
4141 CTTCATTTTT AATTTAAAAG GATCTAGGTG AAGATCCTTT TTGATAATCT CATGACCAAA
```

FIG.28C

4201 ATCCCTTAAC GTGAGTTTTC GTTCCACTGA GCGTCAGACC CCGTAGAAAA GATCAAAGGA
4261 TCTTCTTGAG ATCCTTTTTT TCTGCGCGTA ATCTGCTGCT TGCAAACAAA AAAACCACCG
4321 CTACCAGCGG TGGTTTGTTT GCCGGATCAA GAGCTACCAA CTCTTTTTCC GAAGGTAACT
4381 GGCTTCAGCA GAGCGCAGAT ACCAAATACT GTCCTTCTAG TGTAGCCGTA GTTAGGCCAC
4441 CACTTCAAGA ACTCTGTAGC ACCGCCTACA TACCTCGCTC TGCTAATCCT GTTACCAGTG
4501 GCTGCTGCCA GTGGCGATAA GTCGTGTCTT ACCGGGTTGG ACTCAAGACG ATAGTTACCG
4561 GATAAGGCGC AGCGGTCGGG CTGAACGGGG GGTTCGTGCA CACAGCCCAG CTTGGAGCGA
4621 ACGACCTACA CCGAACTGAG ATACCTACAG CGTGAGCATT GAGAAAGCGC CACGCTTCCC
4681 GAAGGGAGAA AGGCGGACAG GTATCCGGTA AGCGGCAGGG TCGGAACAGG AGAGCGCACG
4741 AGGGAGCTTC CAGGGGGAAA CGCCTGGTAT CTTTATAGTC CTGTCGGGTT TCGCCACCTC
4801 TGACTTGAGC GTCGATTTTT GTGATGCTCG TCAGGGGGGC GGAGCCTATG GAAAAACGCC
4861 AGCAACGCGG CCTTTTTACG GTTCCTGGCC TTTTGCTGGC CTTTTGCTCA CATGTTCTTT
4921 CCTGCGTTAT CCCCTGATTC TGTGGATAAC CGTATTACCG CCTTTGAGTG AGCTGATACC
4981 GCTCGCCGCA GCCGAACGAC CGAGCGCAGC GAGTCAGTGA GCGAGGAAGC GGAAGAGCGC
5041 CTGATGCGGT ATTTTCTCCT TACGCATCTG TGCGGTATTT CACACCGCAG ACCAGCCGCG
5101 TAACCTGGCA AAATCGGTTA CGGTTGAGTA ATAAATGGAT GCCCTGCGTA AGCGGGTGTG
5161 GGCGGACAAT AAAGTCTTAA ACTGAACAAA ATAGATCTAA ACTATGACAA TAAAGTCTTA
5221 AACTAGACAG AATAGTTGTA AACTGAAATC AGTCCAGTTA TGCTGTGAAA AAGCATACTG
5281 GACTTTTGTT ATGGCTAAAG CAAACTCTTC ATTTTCTGAA GTGCAAATTG CCCGTCGTAT
5341 TAAAGAGGGG CGTGGCCAAG GGCATGGTAA AGACTATATT CGCGGCGTTG TGACAATTTA
5401 CCGAACAACT CCGCGGCCGG GAAGCCGATC TCGGCTTGAA CGAATTGTTA GGTGGCGGTA
5461 CTTGGGTCGA TATCAAAGTG CATCACTTCT TCCCGTATGC CCAACTTTGT ATAGAGAGCC
5521 ACTGCGGGAT CGTCACCGTA ATCTGCTTGC ACGTAGATCA CATAAGCACC AAGCGCGTTG
5581 GCCTCATGCT TGAGGAGATT GATGAGCGCG GTGGCAATGC CCTGCCTCCG GTGCTCGCCG
5641 GAGACTGCGA GATCATAGAT ATAGATCTCA CTACGCGGCT GCTCAAACCT GGGCAGAACG
5701 TAAGCCGCGA GAGCGCCAAC AACCGCTTCT TGGTCGAAGG CAGCAAGCGC GATGAATGTC
5761 TTACTACGGA GCAAGTTCCC GAGGTAATCG GAGTCCGGCT GATGTTGGGA GTAGGTGGCT
5821 ACGTCTCCGA ACTCACGACC GAAAAGATCA AGAGCAGCCC GCATGGATTT GACTTGGTCA
5881 GGGCCGAGCC TACATGTGCG AATGATGCCC ATACTTGAGC CACCTAACTT TGTTTTAGGG
5941 CGACTGCCCT GCTGCGTAAC ATCGTTGCTG CTGCGTAACA TCGTTGCTGC TCCATAACAT
6001 CAAACATCGA CCCACGGCGT AACGCGCTTG CTGCTTGGAT GCCCGAGGCA TAGACTGTAC
6061 AAAAAAACAG TCATAACAAG CCATGAAAAC CGCCACTGCG CCGTTACCAC CGCTGCGTTC
6121 GGTCAAGGTT CTGGACCAGT TGCGTGAGCG CATACGCTAC TTGCATTACA GTTTACGAAC
6181 CGAACAGGCT TATGTCAACT GGGTTCGTGC CTTCATCCGT TTCCACGGTG TGCGTCACCC
6241 GGCAACCTTG GGCAGCAGCG AAGTCGAGGC ATTTCTGTCC TGGCTGGCGA ACGAGCGCAA
6301 GGTTTCGGTC TCCACGCATC GTCAGGCATT GGCGGCCTTG CTGTTCTTCT ACGGCAAGGT
6361 GCTGTGCACG GATCTGCCCT GGCTTCAGGA GATCGGAAGA CCTCGGCCGT CGCGGCGCTT
6421 GCCGGTGGTG CTGACCCCGG ATGAAGTGGT TCGCATCCTC GGTTTTCTGG AAGGCGAGCA
6481 TCGTTTGTTC GCCCAGGACT CTAGCTATAG TTCTAGTGGT TGGCTA

FIG.28D

SEMLIKI FOREST VIRUS VECTOR
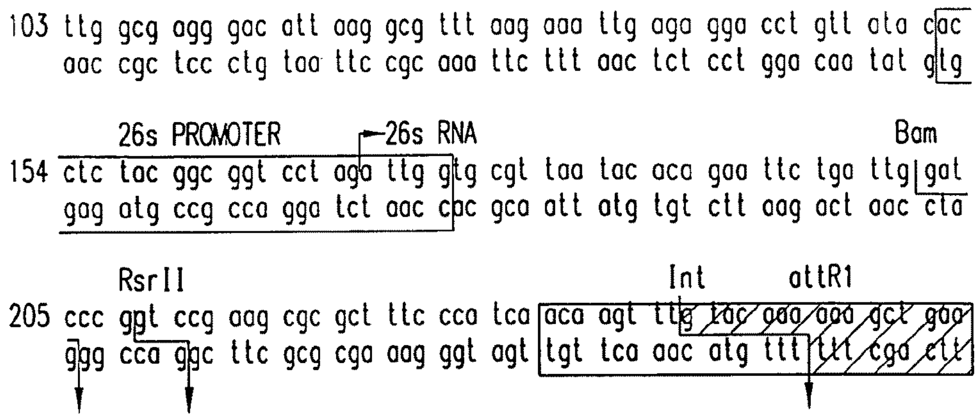
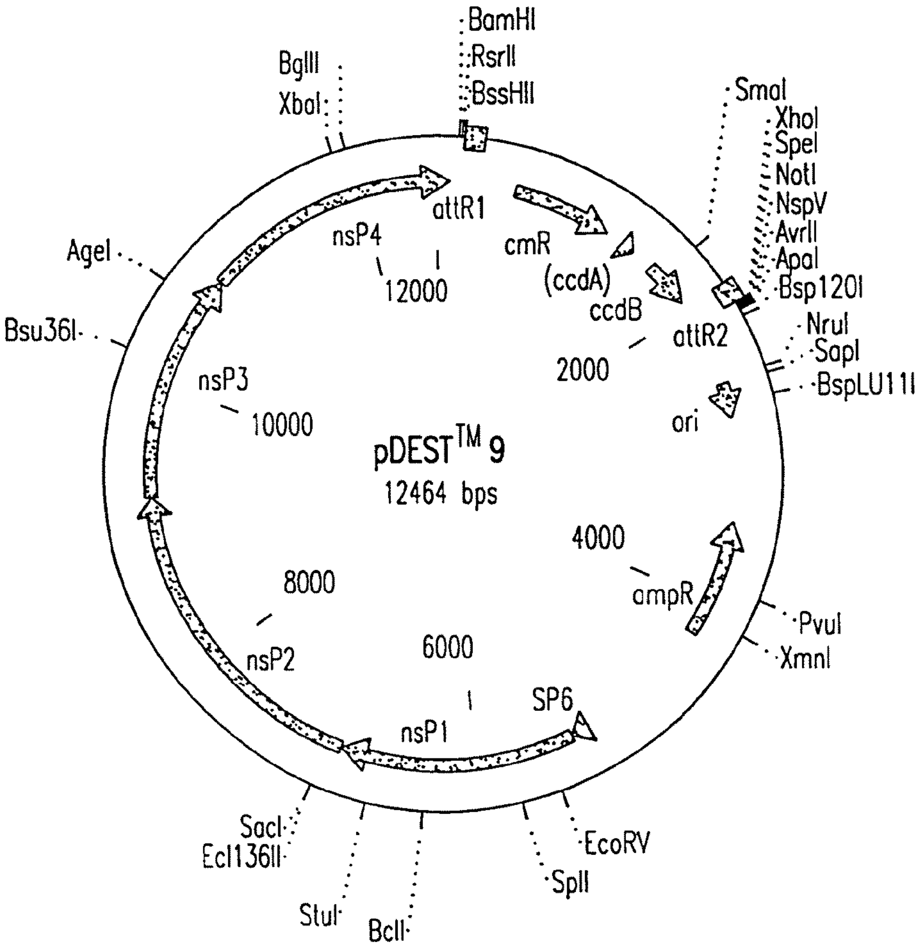
FIG.29A pDEST9 12464 bp

| Location (Base Nos.) | Gene Encoded |
|---|---|
| 355..232 | attR1 |
| 605..1264 | CmR |
| 1384..1468 | inactivated ccdA |
| 1606..1911 | ccdB |
| 1952..2078 | attR2 |
| 2532..2782 | ori |
| 3482..4282 | ampR |
| 5232..5365 | SP6 promoter |
| 5365..6965 | nsP1:non-structural protein 1 |
| 6965..9265 | nsP2:non-structural protein 2 |
| 9265..10865 | nsP3:non-structural protein 3 |
| 10865..161 | nsP4:non-structural protein 4 |

```
   1 AGCAAGTGGT TCCGGACAGG CTTGGGGGCC GAACTGGAGG TGGCACTAAC ATCTAGGTAT
  61 GAGGTAGAGG GCTGCAAAAG TATCCTCATA GCCATGGCCA CCTTGGCGAG GGACATTAAG
 121 GCGTTTAAGA AATTGAGAGG ACCTGTTATA CACCTCTACG GCGGTCCTAG ATTGGTGCGT
 181 TAATACACAG AATTCTGATT GGATCCCGGT CCGAAGCGCG CTTTCCCATC ACAAGTTTGT
 241 ACAAAAAAGC TGAACGAGAA ACGTAAAATG ATATAAATAT CAATATATTA AATTAGATTT
 301 TGCATAAAAA ACAGACTACA TAATACTGTA AAACACAACA TATCCAGTCA CTATGGCGGC
 361 CGCTAAGTTG GCAGCATCAC CCGACGCACT TTGCGCCGAA TAAATACCTG TGACGGAAGA
 421 TCACTTCGCA GAATAAATAA ATCCTGGTGT CCCTGTTGAT ACCGGGAAGC CCTGGGCCAA
 481 CTTTTGGCGA AAATGAGACG TTGATCGGCA CGTAAGAGGT TCCAACTTTC ACCATAATGA
 541 AATAAGATCA CTACCGGGCG TATTTTTTGA GTTATCGAGA TTTTCAGGAG CTAAGGAAGC
 601 TAAAATGGAG AAAAAAATCA CTGGATATAC CACCGTTGAT ATATCCCAAT GGCATCGTAA
 661 AGAACATTTT GAGGCATTTC AGTCAGTTGC TCAATGTACC TATAACCAGA CCGTTCAGCT
 721 GGATATTACG GCCTTTTTAA AGACCGTAAA GAAAAATAAG CACAAGTTTT ATCCGGCCTT
 781 TATTCACATT CTTGCCCGCC TGATGAATGC TCATCCGGAA TTCCGTATGG CAATGAAAGA
 841 CGGTGAGCTG GTGATATGGG ATAGTGTTCA CCCTTGTTAC ACCGTTTTCC ATGAGCAAAC
 901 TGAAACGTTT TCATCGCTCT GGAGTGAATA CCACGACGAT TTCCGGCAGT TTCTACACAT
 961 ATATTCGCAA GATGTGGCGT GTTACGGTGA AAACCTGGCC TATTTCCCTA AAGGGTTTAT
1021 TGAGAATATG TTTTTCGTCT CAGCCAATCC CTGGGTGAGT TTCACCAGTT TTGATTTAAA
1081 CGTGGCCAAT ATGGACAACT TCTTCGCCCC CGTTTTCACC ATGGGCAAAT ATTATACGCA
1141 AGGCGACAAG GTGCTGATGC CGCTGGCGAT TCAGGTTCAT CATGCCGTCT GTGATGGCTT
1201 CCATGTCGGC AGAATGCTTA ATGAATTACA ACAGTACTGC GATGAGTGGC AGGGCGGGGC
1261 GTAAAGATCT GGATCCGGCT TACTAAAAGC CAGATAACAG TATGCGTATT TGCGCGCTGA
1321 TTTTTGCGGT ATAAGAATAT ATACTGATAT GTATACCCGA AGTATGTCAA AAAGAGGTGT
1381 GCTATGAAGC AGCGTATTAC AGTGACAGTT GACAGCGACA GCTATCAGTT GCTCAAGGCA
1441 TATATGATGT CAATATCTCC GGTCTGGTAA GCACAACCAT GCAGAATGAA GCCCGTCGTC
1501 TGCGTGCCGA ACGCTGGAAA GCGGAAAATC AGGAAGGGAT GGCTGAGGTC GCCCGGTTTA
1561 TTGAAATGAA CGGCTCTTTT GCTGACGAGA ACAGGGACTG GTGAAATGCA GTTTAAGGTT
```

FIG.29B

```
1621 TACACCTATA AAAGAGAGAG CCGTTATCGT CTGTTTGTGG ATGTACAGAG TGATATTATT
1681 GACACGCCCG GGCGACGGAT GGTGATCCCC CTGGCCAGTG CACGTCTGCT GTCAGATAAA
1741 GTCTCCCGTG AACTTTACCC GGTGGTGCAT ATCGGGGATG AAAGCTGGCG CATGATGACC
1801 ACCGATATGG CCAGTGTGCC GGTCTCCGTT ATCGGGGAAG AAGTGGCTGA TCTCAGCCAC
1861 CGCGAAAATG ACATCAAAAA CGCCATTAAC CTGATGTTCT GGGGAATATA AATGTCAGGC
1921 TCCCTTATAC ACAGCCAGTC TGCAGGTCGA CCATAGTGAC TGGATATGTT GTGTTTTACA
1981 GTATTATGTA GTCTGTTTTT TATGCAAAAG TGCTAATTTA ATATATTGAT ATTTATATCA
2041 TTTTACGTTT CTCGTTCAGC TTTCTTGTAC AAAGTGGTGA TGGGAACTCG AGTTCACTAG
2101 TCGATCCCGC GGCCGCTTTC GAACCTAGGC AAGCATGCGG GCCCAGTGGG TAATTAATTG
2161 AATTACATCC CTACGCAAAC GTTTTACGGC CGCCGGTGGC GCCCGCGCCC GGCGGCCCGT
2221 CCTTGGCCGT TGCAGGCCAC TCCGGTGGCT CCCGTCGTCC CCGACTTCCA GGCCCAGCAG
2281 ATGCAGCAAC TCATCAGCGC CGTAAATGCG CTGACAATGA GACAGAACGC AATTGCTCCT
2341 GCTAGGAGCT TAATTCGACG AATAATTGGA TTTTTATTTT ATTTTGCAAT TGGTTTTTAA
2401 TATTTCCAAA AAAAAAAAAA AAAAAAAAAA AAAAAAAAAA AAAAAAAAAA AAAAAAAAAA
2461 AAAAAAAAAA AAAAAAACTA GAAATCGCGA TTTCTAGTCT GCATTAATGA ATCGGCCAAC
2521 GCGCGGGGAG AGGCGGTTTG CGTATTGGGC GCTCTTCCGC TTCCTCGCTC ACTGACTCGC
2581 TGCGCTCGGT CGTTCGGCTG CGGCGAGCGG TATCAGCTCA CTCAAAGGCG GTAATACGGT
2641 TATCCACAGA ATCAGGGGAT AACGCAGGAA AGAACATGTG AGCAAAAGGC CAGCAAAAGG
2701 CCAGGAACCG TAAAAAGGCC GCGTTGCTGG CGTTTTTCCA TAGGCTCCGC CCCCCTGACG
2761 AGCATCACAA AAATCGACGC TCAAGTCAGA GGTGGCGAAA CCCGACAGGA CTATAAAGAT
2821 ACCAGGCGTT TCCCCCTGGA AGCTCCCTCG TGCGCTCTCC TGTTCCGACC CTGCCGCTTA
2881 CCGGATACCT GTCCGCCTTT CTCCCTTCGG GAAGCGTGGC GCTTTCTCAA TGCTCGCGCT
2941 GTAGGTATCT CAGTTCGGTG TAGGTCGTTC GCTCCAAGCT GGGCTGTGTG CACGAACCCC
3001 CCGTTCAGCC CGACCGCTGC GCCTTATCCG GTAACTATCG TCTTGAGTCC AACCCGGTAA
3061 GACACGACTT ATCGCCACTG GCAGCAGCCA CTGGTAACAG GATTAGCAGA GCGAGGTATG
3121 TAGGCGGTGC TACAGAGTTC TTGAAGTGGT GGCCTAACTA CGGCTACACT AGAAGGACAG
3181 TATTTGGTAT CTGCGCTCTG CTGAAGCCAG TTACCTTCGG AAAAAGAGTT GGTAGCTCTT
3241 GATCCGGCAA ACAAACCACC GCTGGTAGCG GTGGTTTTTT TGTTTGCAAG CAGCAGATTA
3301 CGCGCAGAAA AAAAGGATCT CAAGAAGATC CTTTGATCTT TTCTACGGGG TCTGACGCTC
3361 AGTGGAACGA AAACTCACGT TAAGGGATTT TGGTCATGAG ATTATCAAAA AGGATCTTCA
3421 CCTAGATCCT TTTAAATTAA AAATGAAGTT TTAAATCAAT CTAAAGTATA TATGAGTAAA
3481 CTTGGTCTGA CAGTTACCAA TGCTTAATCA GTGAGGCACC TATCTCAGCG ATCTGTCTAT
3541 TTCGTTCATC CATAGTTGCC TGACTCCCCG TCGTGTAGAT AACTACGATA CGGGAGGGCT
3601 TACCATCTGG CCCCAGTGCT GCAATGATAC CGCGAGACCC ACGCTCACCG GCTCCAGATT
3661 TATCAGCAAT AAACCAGCCA GCCGGAAGGG CCGAGCGCAG AAGTGGTCCT GCAACTTTAT
3721 CCGCCTCCAT CCAGTCTATT AATTGTTGCC GGGAAGCTAG AGTAAGTAGT TCGCCAGTTA
3781 ATAGTTTGCG CAACGTTGTT GCCATTGCTA CAGGCATCGT GGTGTCACGC TCGTCGTTTG
3841 GTATGGCTTC ATTCAGCTCC GGTTCCCAAC GATCAAGGCG AGTTACATGA TCCCCCATGT
3901 TGTGCAAAAA AGCGGTTAGC TCCTTCGGTC CTCCGATCGT TGTCAGAAGT AAGTTGGCCG
3961 CAGTGTTATC ACTCATGGTT ATGGCAGCAC TGCATAATTC TCTTACTGTC ATGCCATCCG
4021 TAAGATGCTT TTCTGTGACT GGTGAGTACT CAACCAAGTC ATTCTGAGAA TAGTGTATGC
```

FIG.29C

4081 GGCGACCGAG TTGCTCTTGC CCGGCGTCAA TACGGGATAA TACCGCGCCA CATAGCAGAA
4141 CTTTAAAAGT GCTCATCATT GGAAAACGTT CTTCGGGGCG AAAACTCTCA AGGATCTTAC
4201 CGCTGTTGAG ATCCAGTTCG ATGTAACCCA CTCGTGCACC CAACTGATCT TCAGCATCTT
4261 TTACTTTCAC CAGCGTTTCT GGGTGAGCAA AAACAGGAAG GCAAAATGCC GCAAAAAAGG
4321 GAATAAGGGC GACACGGAAA TGTTGAATAC TCATACTCTT CCTTTTTCAA TATTATTGAA
4381 GCATTTATCA GGGTTATTGT CTCATGAGCG GATACATATT TGAATGTATT TAGAAAAATA
4441 AACAAATAGG GGTTCCGCGC ACATTTCCCC GAAAAGTGCC ACCTGACGTC TAAGAAACCA
4501 TTATTATCAT GACATTAACC TATAAAAATA GGCGTATCAC GAGGCCCTTT CGTCTCGCGC
4561 GTTTCGGTGA TGACGGTGAA AACCTCTGAC ACATGCAGCT CCCGGAGACG GTCACAGCTT
4621 CTGTCTAAGC GGATGCCGGG AGCAGACAAG CCCGTCAGGG CGCGTCAGCG GGTGTTGGCG
4681 GGTGTCGGGG CTGGCTTAAC TATGCGGCAT CAGAGCAGAT TGTACTGAGA GTGCACCATA
4741 TCGACGCTCT CCCTTATGCG ACTCCTGCAT TAGGAAGCAG CCCAGTACTA GGTTGAGGCC
4801 GTTGAGCACC GCCGCCGCAA GGAATGGTGC ATGCAAGGAG ATGGCGCCCA ACAGTCCCCC
4861 GGCCACGGGG CCTGCCACCA TACCCACGCC GAAACAAGCG CTCATGAGCC CGAAGTGGCG
4921 AGCCCGATCT TCCCCATCGG TGATGTCGGC GATATAGGCG CCAGCAACCG CACCTGTGGC
4981 GCCGGTGATG CCGGCCACGA TGCGTCCGGC GTAGAGGATC TGGCTAGCGA TGACCCTGCT
5041 GATTGGTTCG CTGACCATTT CCGGGGTGCG GAACGGCGTT ACCAGAAACT CAGAAGGTTC
5101 GTCCAACCAA ACCGACTCTG ACGGCAGTTT ACGAGAGAGA TGATAGGGTC TGCTTCAGTA
5161 AGCCAGATGC TACACAATTA GGCTTGTACA TATTGTCGTT AGAACGCGGC TACAATTAAT
5221 ACATAACCTT ATGTATCATA CACATACGAT TTAGGTGACA CTATAGATGG CGGATGTGTG
5281 ACATACACGA CGCCAAAAGA TTTTGTTCCA GCTCCTGCCA CCTCCGCTAC GCGAGAGATT
5341 AACCACCCAC GATGGCCGCC AAAGTGCATG TTGATATTGA GGCTGACAGC CCATTCATCA
5401 AGTCTTTGCA GAAGGCATTT CCGTCGTTCG AGGTGGAGTC ATTGCAGGTC ACACCAAATG
5461 ACCATGCAAA TGCCAGAGCA TTTTCGCACC TGGCTACCAA ATTGATCGAG CAGGAGACTG
5521 ACAAAGACAC ACTCATCTTG GATATCGGCA GTGCGCCTTC CAGGAGAATG ATGTCTACGC
5581 ACAAATACCA CTGCGTATGC CCTATGCGCA GCGCAGAAGA CCCCGAAAGG CTCGATAGCT
5641 ACGCAAAGAA ACTGGCAGCG GCCTCCGGGA AGGTGCTGGA TAGAGAGATC GCAGGAAAAA
5701 TCACCGACCT GCAGACCGTC ATGGCTACGC CAGACGCTGA ATCTCCTACC TTTTGCCTGC
5761 ATACAGACGT CACGTGTCGT ACGGCAGCCG AAGTGGCCGT ATACCAGGAC GTGTATGCTG
5821 TACATGCACC AACATCGCTG TACCATCAGG CGATGAAAGG TGTCAGAACG GCGTATTGGA
5881 TTGGGTTTGA CACCACCCCG TTTATGTTTG ACGCGCTAGC AGGCGCGTAT CCAACCTACG
5941 CCACAAACTG GGCCGACGAG CAGGTGTTAC AGGCCAGGAA CATAGGACTG TGTGCAGCAT
6001 CCTTGACTGA GGGAAGACTC GGCAAACTGT CCATTCTCCG CAAGAAGCAA TTGAAACCTT
6061 GCGACACAGT CATGTTCTCG GTAGGATCTA CATTGTACAC TGAGAGCAGA AAGCTACTGA
6121 GGAGCTGGCA CTTACCCTCC GTATTCCACC TGAAAGGTAA ACAATCCTTT ACCTGTAGGT
6181 GCGATACCAT CGTATCATGT GAAGGGTACG TAGTTAAGAA AATCACTATG TGCCCCGGCC
6241 TGTACGGTAA AACGGTAGGG TACGCCGTGA CGTATCACGC GGAGGGATTC CTAGTGTGCA
6301 AGACCACAGA CACTGTCAAA GGAGAAAGAG TCTCATTCCC TGTATGCACC TACGTCCCCT
6361 CAACCATCTG TGATCAAATG ACTGGCATAC TAGCGACCGA CGTCACACCG GAGGACGCAC
6421 AGAAGTTGTT AGTGGGATTG AATCAGAGGA TAGTTGTGAA CGGAAGAACA CAGCGAAACA
6481 CTAACACGAT GAAGAACTAT CTGCTTCCGA TTGTGGCCGT CGCATTTAGC AAGTGGGCGA

FIG.29D

```
6541 GGGAATACAA GGCAGACCTT GATGATGAAA AACCTCTGGG TGTCCGAGAG AGGTCACTTA
6601 CTTGCTGCTG CTTGTGGGCA TTTAAAACGA GGAAGATGCA CACCATGTAC AAGAAACCAG
6661 ACACCCAGAC AATAGTGAAG GTGCCTTCAG AGTTTAACTC GTTCGTCATC CCGAGCCTAT
6721 GGTCTACAGG CCTCGCAATC CCAGTCAGAT CACGCATTAA GATGCTTTTG GCCAAGAAGA
6781 CCAAGCGAGA GTTAATACCT GTTCTCGACG CGTCGTCAGC CAGGGATGCT GAACAAGAGG
6841 AGAAGGAGAG GTTGGAGGCC GAGCTGACTA GAGAAGCCTT ACCACCCCTC GTCCCCATCG
6901 CGCCGGCGGA GACGGGAGTC GTCGACGTCG ACGTTGAAGA ACTAGAGTAT CACGCAGGTG
6961 CAGGGGTCGT GGAAACACCT CGCAGCGCGT TGAAAGTCAC CGCACAGCCG AACGACGTAC
7021 TACTAGGAAA TTACGTAGTT CTGTCCCCGC AGACCGTGCT CAAGAGCTCC AAGTTGGCCC
7081 CCGTGCACCC TCTAGCAGAG CAGGTGAAAA TAATAACACA TAACGGGAGG GCCGGCGGTT
7141 ACCAGGTCGA CGGATATGAC GGCAGGGTCC TACTACCATG TGGATCGGCC ATTCCGGTCC
7201 CTGAGTTTCA GGCTTTGAGC GAGAGCGCCA CTATGGTGTA CAACGAAAGG GAGTTCGTCA
7261 ACAGGAAACT ATACCATATT GCCGTTCACG GACCCTCGCT GAACACCGAC GAGGAGAACT
7321 ACGAGAAAGT CAGAGCTGAA AGAACTGACG CCGAGTACGT GTTCGACGTA GATAAAAAAT
7381 GCTGCGTCAA GAGAGAGGAA GCGTCGGGTT TGGTGTTGGT GGGAGAGCTA ACCAACCCCC
7441 CGTTCCATGA ATTCGCCTAC GAAGGGCTGA AGATCAGGCC GTCGGCACCA TATAAGACTA
7501 CAGTAGTAGG AGTCTTTGGG GTTCCGGGAT CAGGCAAGTC TGCTATTATT AAGAGCCTCG
7561 TGACCAAACA CGATCTGGTC ACCAGCGGCA AGAAGGAGAA CTGCCAGGAA ATAGTTAACG
7621 ACGTGAAGAA GCACCGCGGG AAGGGGACAA GTAGGGAAAA CAGTGACTCC ATCCTGCTAA
7681 ACGGGTGTCG TCGTGCCGTG GACATCCTAT ATGTGGACGA GGCTTTCGCT TGCCATTCCG
7741 GTACTCTGCT GGCCCTAATT GCTCTTGTTA AACCTCGGAG CAAAGTGGTG TTATGCGGAG
7801 ACCCCAAGCA ATGCGGATTC TTCAATATGA TGCAGCTTAA GGTGAACTTC AACCACAACA
7861 TCTGCACTGA AGTATGTCAT AAAAGTATAT CCAGACGTTG CACGCGTCCA GTCACGGCCA
7921 TCGTGTCTAC GTTGCACTAC GGAGGCAAGA TGCGCACGAC CAACCCGTGC AACAAACCCA
7981 TAATCATAGA CACCACAGGA CAGACCAAGC CCAAGCCAGG AGACATCGTG TTAACATGCT
8041 TCCGAGGCTG GGCAAAGCAG CTGCAGTTGG ACTACCGTGG ACACGAAGTC ATGACAGCAG
8101 CAGCATCTCA GGGCCTCACC CGCAAAGGGG TATACGCCGT AAGGCAGAAG GTGAATGAAA
8161 ATCCCTTGTA TGCCCCTGCG TCGGAGCACG TGAATGTACT GCTGACGCGC ACTGAGGATA
8221 GGCTGGTGTG GAAAACGCTG GCCGGCGATC CCTGGATTAA GGTCCTATCA AACATTCCAC
8281 AGGGTAACTT TACGGCCACA TTGGAAGAAT GGCAAGAAGA ACACGACAAA ATAATGAAGG
8341 TGATTGAAGG ACCGGCTGCG CCTGTGGACG CGTTCCAGAA CAAAGCGAAC GTGTGTTGGG
8401 CGAAAAGCCT GGTGCCTGTC CTGGACACTG CCGGAATCAG ATTGACAGCA GAGGAGTGGA
8461 GCACCATAAT TACAGCATTT AAGGAGGACA GAGCTTACTC TCCAGTGGTG GCCTTGAATG
8521 AAATTTGCAC CAAGTACTAT GGAGTTGACC TGGACAGTGG CCTGTTTTCT GCCCCGAAGG
8581 TGTCCCTGTA TTACGAGAAC AACCACTGGG ATAACAGACC TGGTGGAAGG ATGTATGGAT
8641 TCAATGCCGC AACAGCTGCC AGGCTGGAAG CTAGACATAC CTTCCTGAAG GGGCAGTGGC
8701 ATACGGGCAA GCAGGCAGTT ATCGCAGAAA GAAAAATCCA ACCGCTTTCT GTGCTGGACA
8761 ATGTAATTCC TATCAACCGC AGGCTGCCGC ACGCCCTGGT GGCTGAGTAC AAGACGGTTA
8821 AAGGCAGTAG GGTTGAGTGG CTGGTCAATA AAGTAAGAGG GTACCACGTC CTGCTGGTGA
8881 GTGAGTACAA CCTGGCTTTG CCTCGACGCA GGGTCACTTG GTTGTCACCG CTGAATGTCA
8941 CAGGCGCCGA TAGGTGCTAC GACCTAAGTT TAGGACTGCC GGCTGACGCC GGCAGGTTCG
```

FIG.29E

```
9001 ACTTGGTCTT TGTGAACATT CACACGGAAT TCAGAATCCA CCACTACCAG CAGTGTGTCG
9061 ACCACGCCAT GAAGCTGCAG ATGCTTGGGG GAGATGCGCT ACGACTGCTA AAACCCGGCG
9121 GCATCTTGAT GAGAGCTTAC GGATACGCCG ATAAAATCAG CGAAGCCGTT GTTTCCTCCT
9181 TAAGCAGAAA GTTCTCGTCT GCAAGAGTGT TGCGCCCGGA TTGTGTCACC AGCAATACAG
9241 AAGTGTTCTT GCTGTTCTCC AACTTTGACA ACGGAAAGAG ACCCTCTACG CTACACCAGA
9301 TGAATACCAA GCTGAGTGCC GTGTATGCCG GAGAAGCCAT GCACACGGCC GGGTGTGCAC
9361 CATCCTACAG AGTTAAGAGA GCAGACATAG CCACGTGCAC AGAAGCGGCT GTGGTTAACG
9421 CAGCTAACGC CCGTGGAACT GTAGGGGATG GCGTATGCAG GGCCGTGGCG AAGAAATGGC
9481 CGTCAGCCTT TAAGGGAGCA GCAACACCAG TGGGCACAAT TAAAACAGTC ATGTGCGGCT
9541 CGTACCCCGT CATCCACGCT GTAGCGCCTA ATTTCTCTGC CACGACTGAA GCGGAAGGGG
9601 ACCGCGAATT GGCCGCTGTC TACCGGGCAG TGGCCGCCGA AGTAAACAGA CTGTCACTGA
9661 GCAGCGTAGC CATCCCGCTG CTGTCCACAG GAGTGTTCAG CGGCGGAAGA GATAGGCTGC
9721 AGCAATCCCT CAACCATCTA TTCACAGCAA TGGACGCCAC GGACGCTGAC GTGACCATCT
9781 ACTGCAGAGA CAAAAGTTGG GAGAAGAAAA TCCAGGAAGC CATTGACATG AGGACGGCTG
9841 TGGAGTTGCT CAATGATGAC GTGGAGCTGA CCACAGACTT GGTGAGAGTG CACCCGGACA
9901 GCAGCCTGGT GGGTCGTAAG GGCTACAGTA CCACTGACGG GTCGCTGTAC TCGTACTTTG
9961 AAGGTACGAA ATTCAACCAG GCTGCTATTG ATATGGCAGA GATACTGACG TTGTGGCCCA
10021 GACTGCAAGA GGCAAACGAA CAGATATGCC TATACGCGCT GGGCGAAACA ATGGACAACA
10081 TCAGATCCAA ATGTCCGGTG AACGATTCCG ATTCATCAAC ACCTCCCAGG ACAGTGCCCT
10141 GCCTGTGCCG CTACGCAATG ACAGCAGAAC GGATCGCCCG CCTTAGGTCA CACCAAGTTA
10201 AAAGCATGGT GGTTTGCTCA TCTTTTCCCC TCCCGAAATA CCATGTAGAT GGGGTGCAGA
10261 AGGTAAAGTG CGAGAAGGTT CTCCTGTTCG ACCCGACGGT ACCTTCAGTG GTTAGTCCGC
10321 GGAAGTATGC CGCATCTACG ACGGACCACT CAGATCGGTC GTTACGAGGG TTTGACTTGG
10381 ACTGGACCAC CGACTCGTCT TCCACTGCCA GCGATACCAT GTCGCTACCC AGTTTGCAGT
10441 CGTGTGACAT CGACTCGATC TACGAGCCAA TGGCTCCCAT AGTAGTGACG GCTGACGTAC
10501 ACCCTGAACC CGCAGGCATC GCGGACCTGG CGGCAGATGT GCACCCTGAA CCCGCAGACC
10561 ATGTGGACCT GGAGAACCCG ATTCCTCCAC CGCGCCCGAA GAGAGCTGCA TACCTTGCCT
10621 CCCGCGCGGC GGAGCGACCG GTGCCGGCGC CGAGAAAGCC GACGCCTGCC CCAAGGACTG
10681 CGTTTAGGAA CAAGCTGCCT TTGACGTTCG GCGACTTTGA CGAGCACGAG GTCGATGCGT
10741 TGGCCTCCGG GATTACTTTC GGAGACTTCG ACGACGTCCT GCGACTAGGC CGCGCGGGTG
10801 CATATATTTT CTCCTCGGAC ACTGGCAGCG GACATTTACA ACAAAAATCC GTTAGGCAGC
10861 ACAATCTCCA GTGCGCACAA CTGGATGCGG TCCAGGAGGA GAAAATGTAC CCGCCAAAAT
10921 TGGATACTGA GAGGGAGAAG CTGTTGCTGC TGAAAATGCA GATGCACCCA TCGGAGGCTA
10981 ATAAGAGTCG ATACCAGTCT CGCAAAGTGG AGAACATGAA AGCCACGGTG GTGGACAGGC
11041 TCACATCGGG GGCCAGATTG TACACGGGAG CGGACGTAGG CCGCATACCA ACATACGCGG
11101 TTCGGTACCC CCGCCCCGTG TACTCCCCTA CCGTGATCGA AAGATTCTCA AGCCCCGATG
11161 TAGCAATCGC AGCGTGCAAC GAATACCTAT CCAGAAATTA CCCAACAGTG GCGTCGTACC
11221 AGATAACAGA TGAATACGAC GCATACTTGG ACATGGTTGA CGGGTCGGAT AGTTGCTTGG
11281 ACAGAGCGAC ATTCTGCCCG GCGAAGCTCC GGTGCTACCC GAAACATCAT GCGTACCACC
11341 AGCCGACTGT ACGCAGTGCC GTCCCGTCAC CCTTTCAGAA CACACTACAG AACGTGCTAG
11401 CGGCTGCCAC CAAGAGAAAC TGCAACGTCA CGCAAATGCG AGAACTACCC ACCATGGACT
```

FIG.29F

11461 CGGCAGTGTT CAACGTGGAG TGCTTCAAGC GCTATGCCTG CTCCGGAGAA TATTGGGAAG
11521 AATATGCTAA ACAACCTATC CGGATAACCA CTGAGAACAT CACTACCTAT GTGACCAAAT
11581 TGAAAGGCCC GAAAGCTGCT GCCTTGTTCG CTAAGACCCA CAACTTGGTT CCGCTGCAGG
11641 AGGTTCCCAT GGACAGATTC ACGGTCGACA TGAAACGAGA TGTCAAAGTC ACTCCAGGGA
11701 CGAAACACAC AGAGGAAAGA CCCAAAGTCC AGGTAATTCA AGCAGCGGAG CCATTGGCGA
11761 CCGCTTACCT GTGCGGCATC CACAGGGAAT TAGTAAGGAG ACTAAATGCT GTGTTACGCC
11821 CTAACGTGCA CACATTGTTT GATATGTCGG CCGAAGACTT TGACGCGATC ATCGCCTCTC
11881 ACTTCCACCC AGGAGACCCG GTTCTAGAGA CGGACATTGC ATCATTCGAC AAAAGCCAGG
11941 ACGACTCCTT GGCTCTTACA GGTTTAATGA TCCTCGAAGA TCTAGGGGTG GATCAGTACC
12001 TGCTGGACTT GATCGAGGCA GCCTTTGGGG AAATATCCAG CTGTCACCTA CCAACTGGCA
12061 CGCGCTTCAA GTTCGGAGCT ATGATGAAAT CGGGCATGTT TCTGACTTTG TTTATTAACA
12121 CTGTTTTGAA CATCACCATA GCAAGCAGGG TACTGGAGCA GAGACTCACT GACTCCGCCT
12181 GTGCGGCCTT CATCGGCGAC GACAACATCG TTCACGGAGT GATCTCCGAC AAGCTGATGG
12241 CGGAGAGGTG CGCGTCGTGG GTCAACATGG AGGTGAAGAT CATTGACGCT GTCATGGGCG
12301 AAAAACCCCC ATATTTTTGT GGGGGATTCA TAGTTTTTGA CAGCGTCACA CAGACCGCCT
12361 GCCGTGTTTC AGACCCACTT AAGCGCCTGT TCAAGTTGGG TAAGCCGCTA ACAGCTGAAG
12421 ACAAGCAGGA CGAAGACAGG CGACGAGCAC TGAGTGACGA GGTT

FIG.29G pDEST10 Polyhedron Promoter with N-His6, Baculovirus Transfer Plasmid mRNA from polyhedrin promoter

```
154 aaa taa gta ttt tac tgt ttt cgt aac agt ttt gta ata aaa aaa cct ata
    ttt att cat aaa atg aca aaa gca ttg tca aaa cat tat ttt ttt gga tat

205 aat att ccg gat tat tca tac cgt ccc acc atc ggg cgc gga tct cgg tcc
    tta taa ggc cta ata agt atg gca ggg tgg tag ccc gcg cct aga gcc agg

        Met Ser Tyr Tyr His His His His His His Asp Tyr Asp Ile Pro
256 gaa acc atg tcg tac tac cat cac cat cac cat cac gat tac gat atc cca
    ctt tgg tac agc atg atg gta gtg gta gtg gta gtg cta atg cta tag ggt

                            TEV protease
    Thr Thr Glu Asn Leu Tyr Phe Gln Gly Ile Thr Ser Leu Tyr Lys Lys
307 acg acc gaa aac ctg tat ttt cag ggc atc aca agt ttg tac aaa aaa gct
    tgc tgg ctt ttg gac ata aaa gtc ccg tag tgt tca aac atg ttt ttt ctc
                                              attR1         Int
```

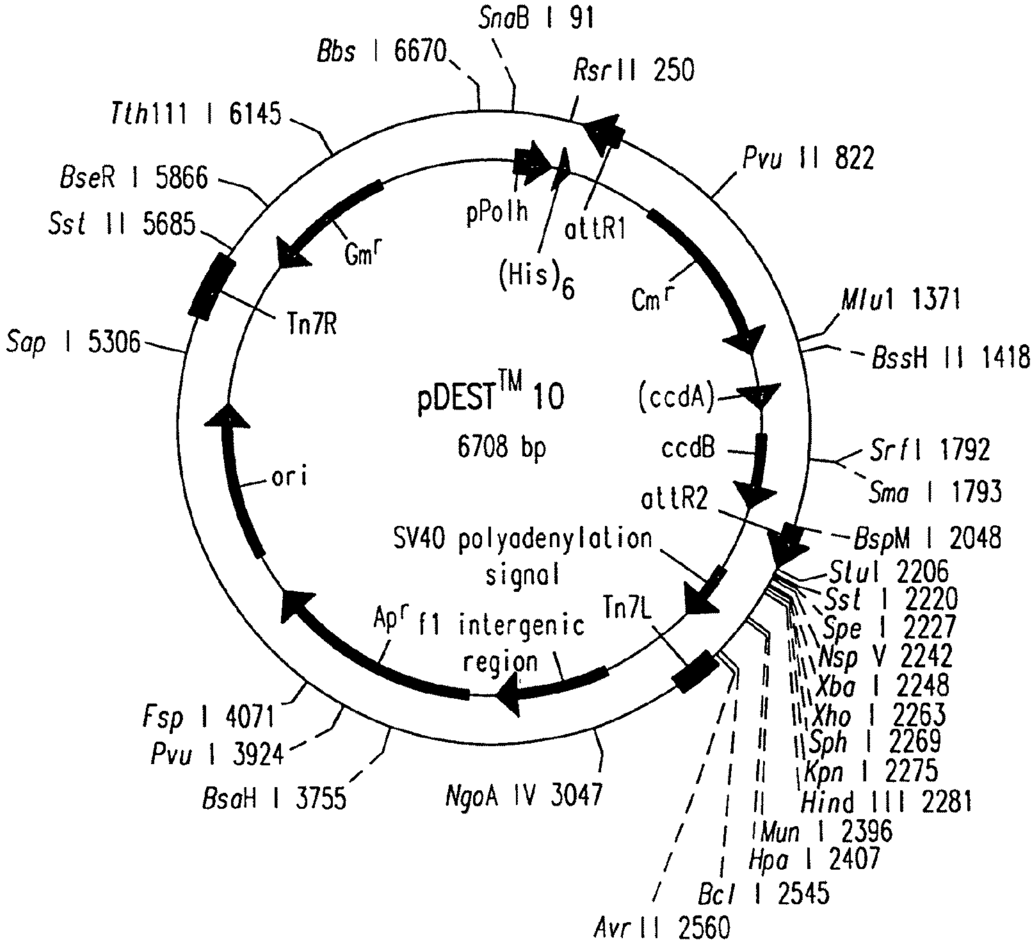

FIG.30A pDEST10 6708 bp

| Location (Base Nos.) | Gene Encoded |
|---|---|
| 23..152 | Ppolh |
| 461..337 | attR1 |
| 711..1370 | CmR |
| 1490..1574 | inactivated ccdA |
| 1712..2017 | ccdB |
| 2058..2182 | attR2 |
| 3394..4369 | ampR |
| 4510..5164 | ori |
| 5658..62 | genR |

1 CCCCGGATGA AGTGGTTCGC ATCCTCGGTT TTCTGGAAGG CGAGCATCGT TTGTTCGCCC
61 AGGACTCTAG CTATAGTTCT AGTGGTTGGC TACGTATACT CCGGAATATT AATAGATCAT
121 GGAGATAATT AAAATGATAA CCATCTCGCA AATAAATAAG TATTTTACTG TTTTCGTAAC
181 AGTTTTGTAA TAAAAAAACC TATAAATATT CCGGATTATT CATACCGTCC CACCATCGGG
241 CGCGGATCTC GGTCCGAAAC CATGTCGTAC TACCATCACC ATCACCATCA CGATTACGAT
301 ATCCCAACGA CCGAAAACCT GTATTTTCAG GGCATCACAA GTTTGTACAA AAAAGCTGAA
361 CGAGAAACGT AAAATGATAT AAATATCAAT ATATTAAATT AGATTTTGCA TAAAAAACAG
421 ACTACATAAT ACTGTAAAAC ACAACATATC CAGTCACTAT GGCGGCCGCT AAGTTGGCAG
481 CATCACCCGA CGCACTTTGC GCCGAATAAA TACCTGTGAC GGAAGATCAC TTCGCAGAAT
541 AAATAAATCC TGGTGTCCCT GTTGATACCG GGAAGCCCTG GGCCAACTTT TGGCGAAAAT
601 GAGACGTTGA TCGGCACGTA AGAGGTTCCA ACTTTCACCA TAATGAAATA AGATCACTAC
661 CGGGCGTATT TTTTGAGTTA TCGAGATTTT CAGGAGCTAA GGAAGCTAAA ATGGAGAAAA
721 AAATCACTGG ATATACCACC GTTGATATAT CCCAATGGCA TCGTAAAGAA CATTTTGAGG
781 CATTTCAGTC AGTTGCTCAA TGTACCTATA ACCAGACCGT TCAGCTGGAT ATTACGGCCT
841 TTTTAAAGAC CGTAAAGAAA AATAAGCACA AGTTTTATCC GGCCTTTATT CACATTCTTG
901 CCCGCCTGAT GAATGCTCAT CCGGAATTCC GTATGGCAAT GAAAGACGGT GAGCTGGTGA
961 TATGGGATAG TGTTCACCCT TGTTACACCG TTTTCCATGA GCAAACTGAA ACGTTTTCAT
1021 CGCTCTGGAG TGAATACCAC GACGATTTCC GGCAGTTTCT ACACATATAT TCGCAAGATG
1081 TGGCGTGTTA CGGTGAAAAC CTGGCCTATT TCCCTAAAGG GTTTATTGAG AATATGTTTT
1141 TCGTCTCAGC CAATCCCTGG GTGAGTTTCA CCAGTTTTGA TTTAAACGTG GCCAATATGG
1201 ACAACTTCTT CGCCCCCGTT TTCACCATGG GCAAATATTA TACGCAAGGC GACAAGGTGC
1261 TGATGCCGCT GGCGATTCAG GTTCATCATG CCGTCTGTGA TGGCTTCCAT GTCGGCAGAA
1321 TGCTTAATGA ATTACAACAG TACTGCGATG AGTGGCAGGG CGGGGCGTAA ACGCGTGGAT
1381 CCGGCTTACT AAAAGCCAGA TAACAGTATG CGTATTTGCG CGCTGATTTT TGCGGTATAA
1441 GAATATATAC TGATATGTAT ACCCGAAGTA TGTCAAAAAG AGGTGTGCTA TGAAGCAGCG
1501 TATTACAGTG ACAGTTGACA GCGACAGCTA TCAGTTGCTC AAGGCATATA TGATGTCAAT
1561 ATCTCCGGTC TGGTAAGCAC AACCATGCAG AATGAAGCCC GTCGTCTGCG TGCCGAACGC
1621 TGGAAAGCGG AAAATCAGGA AGGGATGGCT GAGGTCGCCC GGTTTATTGA AATGAACGGC
1681 TCTTTTGCTG ACGAGAACAG GGACTGGTGA AATGCAGTTT AAGGTTTACA CCTATAAAAG
1741 AGAGAGCCGT TATCGTCTGT TTGTGGATGT ACAGAGTGAT ATTATTGACA CGCCCGGGCG

FIG.30B

1801 ACGGATGGTG ATCCCCCTGG CCAGTGCACG TCTGCTGTCA GATAAAGTCT CCCGTGAACT
1861 TTACCCGGTG GTGCATATCG GGGATGAAAG CTGGCGCATG ATGACCACCG ATATGGCCAG
1921 TGTGCCGGTC TCCGTTATCG GGGAAGAAGT GGCTGATCTC AGCCACCGCG AAAATGACAT
1981 CAAAAACGCC ATTAACCTGA TGTTCTGGGG AATATAAATG TCAGGCTCCC TTATACACAG
2041 CCAGTCTGCA GGTCGACCAT AGTGACTGGA TATGTTGTGT TTTACAGTAT TATGTAGTCT
2101 GTTTTTTATG CAAAATCTAA TTTAATATAT TGATATTTAT ATCATTTTAC GTTTCTCGTT
2161 CAGCTTTCTT GTACAAAGTG GTGATGCCAT GGATCCGGAA TTCAAAGGCC TACGTCGACG
2221 AGCTCAACTA GTGCGGCCGC TTTCGAATCT AGAGCCTGCA GTCTCGAGGC ATGCGGTACC
2281 AAGCTTGTCG AGAAGTACTA GAGGATCATA ATCAGCCATA CCACATTTGT AGAGGTTTTA
2341 CTTGCTTTAA AAAACCTCCC ACACCTCCCC CTGAACCTGA AACATAAAAT GAATGCAATT
2401 GTTGTTGTTA ACTTGTTTAT TGCAGCTTAT AATGGTTACA AATAAAGCAA TAGCATCACA
2461 AATTTCACAA ATAAAGCATT TTTTTCACTG CATTCTAGTT GTGGTTTGTC CAAACTCATC
2521 AATGTATCTT ATCATGTCTG GATCTGATCA CTGCTTGAGC CTAGGAGATC CGAACCAGAT
2581 AAGTGAAATC TAGTTCCAAA CTATTTTGTC ATTTTTAATT TTCGTATTAG CTTACGACGC
2641 TACACCCAGT TCCCATCTAT TTTGTCACTC TTCCCTAAAT AATCCTTAAA AACTCCATTT
2701 CCACCCCTCC CAGTTCCCAA CTATTTTGTC CGCCCACAGC GGGGCATTTT TCTTCCTGTT
2761 ATGTTTTTAA TCAAACATCC TGCCAACTCC ATGTGACAAA CCGTCATCTT CGGCTACTTT
2821 TTCTCTGTCA CAGAATGAAA ATTTTTCTGT CATCTCTTCG TTATTAATGT TTGTAATTGA
2881 CTGAATATCA ACGCTTATTT GCAGCCTGAA TGGCGAATGG GACGCGCCCT GTAGCGGCGC
2941 ATTAAGCGCG GCGGGTGTGG TGGTTACGCG CAGCGTGACC GCTACACTTG CCAGCGCCCT
3001 AGCGCCCGCT CCTTTCGCTT TCTTCCCTTC CTTTCTCGCC ACGTTCGCCG GCTTTCCCCG
3061 TCAAGCTCTA AATCGGGGGC TCCCTTTAGG GTTCCGATTT AGTGCTTTAC GGCACCTCGA
3121 CCCCAAAAAA CTTGATTAGG GTGATGGTTC ACGTAGTGGG CCATCGCCCT GATAGACGGT
3181 TTTTCGCCCT TTGACGTTGG AGTCCACGTT CTTTAATAGT GGACTCTTGT TCCAAACTGG
3241 AACAACACTC AACCCTATCT CGGTCTATTC TTTTGATTTA TAAGGGATTT TGCCGATTTC
3301 GGCCTATTGG TTAAAAAATG AGCTGATTTA ACAAAAATTT AACGCGAATT TTAACAAAAT
3361 ATTAACGTTT ACAATTTCAG GTGGCACTTT TCGGGGAAAT GTGCGCGGAA CCCCTATTTG
3421 TTTATTTTTC TAAATACATT CAAATATGTA TCCGCTCATG AGACAATAAC CCTGATAAAT
3481 GCTTCAATAA TATTGAAAAA GGAAGAGTAT GAGTATTCAA CATTTCCGTG TCGCCCTTAT
3541 TCCCTTTTTT GCGGCATTTT GCCTTCCTGT TTTTGCTCAC CCAGAAACGC TGGTGAAAGT
3601 AAAAGATGCT GAAGATCAGT TGGGTGCACG AGTGGGTTAC ATCGAACTGG ATCTCAACAG
3661 CGGTAAGATC CTTGAGAGTT TTCGCCCCGA AGAACGTTTT CCAATGATGA GCACTTTTAA
3721 AGTTCTGCTA TGTGGCGCGG TATTATCCCG TATTGACGCC GGGCAAGAGC AACTCGGTCG
3781 CCGCATACAC TATTCTCAGA ATGACTTGGT TGAGTACTCA CCAGTCACAG AAAAGCATCT
3841 TACGGATGGC ATGACAGTAA GAGAATTATG CAGTGCTGCC ATAACCATGA GTGATAACAC
3901 TGCGGCCAAC TTACTTCTGA CAACGATCGG AGGACCGAAG GAGCTAACCG CTTTTTTGCA
3961 CAACATGGGG GATCATGTAA CTCGCCTTGA TCGTTGGGAA CCGGAGCTGA ATGAAGCCAT
4021 ACCAAACGAC GAGCGTGACA CCACGATGCC TGTAGCAATG GCAACAACGT TGCGCAAACT
4081 ATTAACTGGC GAACTACTTA CTCTAGCTTC CCGGCAACAA TTAATAGACT GGATGGAGGC
4141 GGATAAAGTT GCAGGACCAC TTCTGCGCTC GGCCCTTCCG GCTGGCTGGT TTATTGCTGA
4201 TAAATCTGGA GCCGGTGAGC GTGGGTCTCG CGGTATCATT GCAGCACTGG GGCCAGATGG

FIG.30C

4261 TAAGCCCTCC CGTATCGTAG TTATCTACAC GACGGGGAGT CAGGCAACTA TGGATGAACG
4321 AAATAGACAG ATCGCTGAGA TAGGTGCCTC ACTGATTAAG CATTGGTAAC TGTCAGACCA
4381 AGTTTACTCA TATATACTTT AGATTGATTT AAAACTTCAT TTTTAATTTA AAAGGATCTA
4441 GGTGAAGATC CTTTTTGATA ATCTCATGAC CAAAATCCCT TAACGTGAGT TTTCGTTCCA
4501 CTGAGCGTCA GACCCCGTAG AAAAGATCAA AGGATCTTCT TGAGATCCTT TTTTTCTGCG
4561 CGTAATCTGC TGCTTGCAAA CAAAAAAACC ACCGCTACCA GCGGTGGTTT GTTTGCCGGA
4621 TCAAGAGCTA CCAACTCTTT TTCCGAAGGT AACTGGCTTC AGCAGAGCGC AGATACCAAA
4681 TACTGTCCTT CTAGTGTAGC CGTAGTTAGG CCACCACTTC AAGAACTCTG TAGCACCGCC
4741 TACATACCTC GCTCTGCTAA TCCTGTTACC AGTGGCTGCT GCCAGTGGCG ATAAGTCGTG
4801 TCTTACCGGG TTGGACTCAA GACGATAGTT ACCGGATAAG GCGCAGCGGT CGGGCTGAAC
4861 GGGGGGTTCG TGCACACAGC CCAGCTTGGA GCGAACGACC TACACCGAAC TGAGATACCT
4921 ACAGCGTGAG CATTGAGAAA GCGCCACGCT TCCCGAAGGG AGAAAGGCGG ACAGGTATCC
4981 GGTAAGCGGC AGGGTCGGAA CAGGAGAGCG CACGAGGGAG CTTCCAGGGG GAAACGCCTG
5041 GTATCTTTAT AGTCCTGTCG GGTTTCGCCA CCTCTGACTT GAGCGTCGAT TTTTGTGATG
5101 CTCGTCAGGG GGGCGGAGCC TATGGAAAAA CGCCAGCAAC GCGGCCTTTT TACGGTTCCT
5161 GGCCTTTTGC TGGCCTTTTG CTCACATGTT CTTTCCTGCG TTATCCCCTG ATTCTGTGGA
5221 TAACCGTATT ACCGCCTTTG AGTGAGCTGA TACCGCTCGC CGCAGCCGAA CGACCGAGCG
5281 CAGCGAGTCA GTGAGCGAGG AAGCGGAAGA GCGCCTGATG CGGTATTTTC TCCTTACGCA
5341 TCTGTGCGGT ATTTCACACC GCAGACCAGC CGCGTAACCT GGCAAAATCG GTTACGGTTG
5401 AGTAATAAAT GGATGCCCTG CGTAAGCGGG TGTGGGCGGA CAATAAAGTC TTAAACTGAA
5461 CAAAATAGAT CTAAACTATG ACAATAAAGT CTTAAACTAG ACAGAATAGT TGTAAACTGA
5521 AATCAGTCCA GTTATGCTGT GAAAAAGCAT ACTGGACTTT TGTTATGGCT AAAGCAAACT
5581 CTTCATTTTC TGAAGTGCAA ATTGCCCGTC GTATTAAAGA GGGGCGTGGC CAAGGGCATG
5641 GTAAAGACTA TATTCGCGGC GTTGTGACAA TTTACCGAAC AACTCCGCGG CCGGGAAGCC
5701 GATCTCGGCT TGAACGAATT GTTAGGTGGC GGTACTTGGG TCGATATCAA AGTGCATCAC
5761 TTCTTCCCGT ATGCCCAACT TTGTATAGAG AGCCACTGCG GGATCGTCAC CGTAATCTGC
5821 TTGCACGTAG ATCACATAAG CACCAAGCGC GTTGGCCTCA TGCTTGAGGA GATTGATGAG
5881 CGCGGTGGCA ATGCCCTGCC TCCGGTGCTC GCCGGAGACT GCGAGATCAT AGATATAGAT
5941 CTCACTACGC GGCTGCTCAA ACCTGGGCAG AACGTAAGCC GCGAGAGCGC CAACAACCGC
6001 TTCTTGGTCG AAGGCAGCAA GCGCGATGAA TGTCTTACTA CGGAGCAAGT TCCCGAGGTA
6061 ATCGGAGTCC GGCTGATGTT GGGAGTAGGT GGCTACGTCT CCGAACTCAC GACCGAAAAG
6121 ATCAAGAGCA GCCCGCATGG ATTTGACTTG GTCAGGGCCG AGCCTACATG TGCGAATGAT
6181 GCCCATACTT GAGCCACCTA ACTTTGTTTT AGGGCGACTG CCCTGCTGCG TAACATCGTT
6241 GCTGCTGCGT AACATCGTTG CTGCTCCATA ACATCAAACA TCGACCCACG GCGTAACGCG
6301 CTTGCTGCTT GGATGCCCGA GGCATAGACT GTACAAAAAA ACAGTCATAA CAAGCCATGA
6361 AAACCGCCAC TGCGCCGTTA CCACCGCTGC GTTCGGTCAA GGTTCTGGAC CAGTTGCGTG
6421 AGCGCATACG CTACTTGCAT TACAGTTTAC GAACCGAACA GGCTTATGTC AACTGGGTTC
6481 GTGCCTTCAT CCGTTTCCAC GGTGTGCGTC ACCCGGCAAC CTTGGGCAGC AGCGAAGTCG
6541 AGGCATTTCT GTCCTGGCTG GCGAACGAGC GCAAGGTTTC GGTCTCCACG CATCGTCAGG
6601 CATTGGCGGC CTTGCTGTTC TTCTACGGCA AGGTGCTGTG CACGGATCTG CCCTGGCTTC
6661 AGGAGATCGG AAGACCTCGG CCGTCGCGGC GCTTGCCGGT GGTGCTGA

FIG.30D

TET-REGULATED EUKARYOTIC EXPRESSION mRNA FROM CMV PROMOTER (CONTROLLED by TETRACYCLINE)

```
358 tag tga acc gtc aga tcg cct gga gac gcc atc cac gct gtt ttg acc tcc
    atc act tgg cag tct agc gga cct ctg cgg tag gtg cga caa aac tgg agg

409 ata gaa gac acc ggg acc gat cca gcc tcc gcg gcc ccg aat tcg agc tcg
    tat ctt ctg tgg ccc tgg cta ggt cgg agg cgc cgg ggc tta agc tcg agc

                                        Sal         Cla   Hind3   EcoRV
460 gta ccc ggg gat cct cta gag tcg agg tcg acg gta tcg ata agc ttg atc
    cat ggg ccc cta gga gat ctc agc tcc agc tgc cat agc tat tcg aac tat

                  Int     attR1
511 tca aca agt ttg tac aaa aaa gct gaa cga gaa acg taa aat gat ata aat
    agt tgt tca aac atg ttt ttt cga ctt gct ctt tgc att tta cta tat tta
```

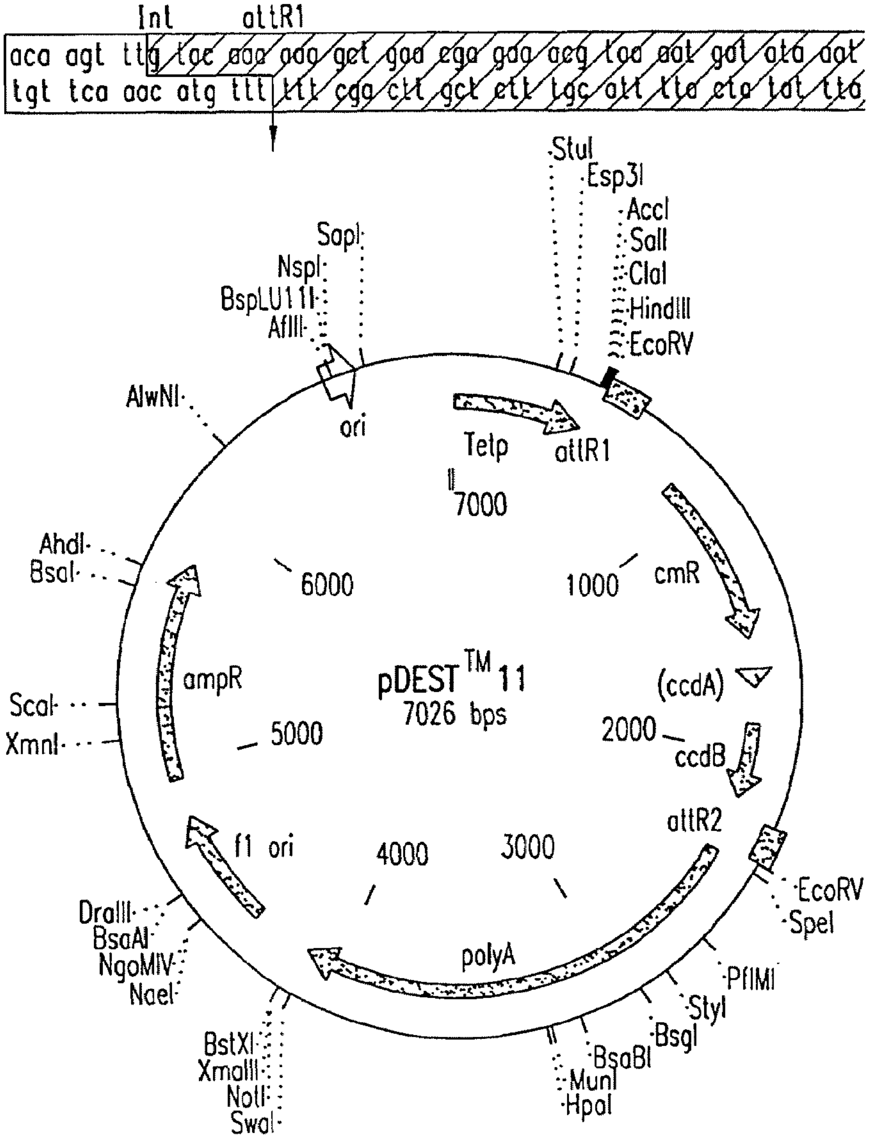

FIG.31A pDEST11 7026 bp

| Location (Base Nos.) | Gene Encoded |
|---|---|
| 4..479 | Tetp ((Tet operator)7 and min hCMV promoter) |
| 638..514 | attR1 |
| 888..1547 | CmR |
| 1667..1751 | inactivated ccdA |
| 1889..2194 | ccdB |
| 2235..2359 | attR2 |
| 2402..4132 | polyA |
| 4347..4803 | f1 ori |
| 4940..5797 | ampR |

```
   1 CGAGTTTACC ACTCCCTATC AGTGATAGAG AAAAGTGAAA GTCGAGTTTA CCACTCCCTA
  61 TCAGTGATAG AGAAAAGTGA AAGTCGAGTT TACCACTCCC TATCAGTGAT AGAGAAAAGT
 121 GAAAGTCGAG TTTACCACTC CCTATCAGTG ATAGAGAAAA GTGAAAGTCG AGTTTACCAC
 181 TCCCTATCAG TGATAGAGAA AAGTGAAAGT CGAGTTTACC ACTCCCTATC AGTGATAGAG
 241 AAAAGTGAAA GTCGAGTTTA CCACTCCCTA TCAGTGATAG AGAAAAGTGA AAGTCGAGCT
 301 CGGTACCCGG GTCGAGTAGG CGTGTACGGT GGGAGGCCTA TATAAGCAGA GCTCGTTTAG
 361 TGAACCGTCA GATCGCCTGG AGACGCCATC CACGCTGTTT TGACCTCCAT AGAAGACACC
 421 GGGACCGATC CAGCCTCCGC GGCCCCGAAT TCGAGCTCGG TACCCGGGGA TCCTCTAGAG
 481 TCGAGGTCGA CGGTATCGAT AAGCTTGATA TCAACAAGTT TGTACAAAAA AGCTGAACGA
 541 GAAACGTAAA ATGATATAAA TATCAATATA TTAAATTAGA TTTTGCATAA AAAACAGACT
 601 ACATAATACT GTAAAACACA ACATATCCAG TCACTATGGC GGCCGCTAAG TTGGCAGCAT
 661 CACCCGACGC ACTTTGCGCC GAATAAATAC CTGTGACGGA AGATCACTTC GCAGAATAAA
 721 TAAATCCTGG TGTCCCTGTT GATACCGGGA AGCCCTGGGC CAACTTTTGG CGAAAATGAG
 781 ACGTTGATCG GCACGTAAGA GGTTCCAACT TTCACCATAA TGAAATAAGA TCACTACCGG
 841 GCGTATTTTT TGAGTTATCG AGATTTTCAG GAGCTAAGGA AGCTAAAATG GAGAAAAAAA
 901 TCACTGGATA TACCACCGTT GATATATCCC AATGGCATCG TAAAGAACAT TTTGAGGCAT
 961 TTCAGTCAGT TGCTCAATGT ACCTATAACC AGACCGTTCA GCTGGATATT ACGGCCTTTT
1021 TAAAGACCGT AAAGAAAAAT AAGCACAAGT TTTATCCGGC CTTTATTCAC ATTCTTGCCC
1081 GCCTGATGAA TGCTCATCCG GAATTCCGTA TGGCAATGAA AGACGGTGAG CTGGTGATAT
1141 GGGATAGTGT TCACCCTTGT TACACCGTTT TCCATGAGCA AACTGAAACG TTTTCATCGC
1201 TCTGGAGTGA ATACCACGAC GATTTCCGGC AGTTTCTACA CATATATTCG CAAGATGTGG
1261 CGTGTTACGG TGAAAACCTG GCCTATTTCC CTAAAGGGTT TATTGAGAAT ATGTTTTTCG
1321 TCTCAGCCAA TCCCTGGGTG AGTTTCACCA GTTTTGATTT AAACGTGGCC AATATGGACA
1381 ACTTCTTCGC CCCCGTTTTC ACCATGGGCA AATATTATAC GCAAGGCGAC AAGGTGCTGA
1441 TGCCGCTGGC GATTCAGGTT CATCATGCCG TCTGTGATGG CTTCCATGTC GGCAGAATGC
1501 TTAATGAATT ACAACAGTAC TGCGATGAGT GGCAGGGCGG GGCGTAAAGA TCTGGATCCG
1561 GCTTACTAAA AGCCAGATAA CAGTATGCGT ATTTGCGCGC TGATTTTTGC GGTATAAGAA
```

FIG.31B

1621 TATATACTGA TATGTATACC CGAAGTATGT CAAAAAGAGG TGTGCTATGA AGCAGCGTAT
1681 TACAGTGACA GTTGACAGCG ACAGCTATCA GTTGCTCAAG GCATATATGA TGTCAATATC
1741 TCCGGTCTGG TAAGCACAAC CATGCAGAAT GAAGCCCGTC GTCTGCGTGC CGAACGCTGG
1801 AAAGCGGAAA ATCAGGAAGG GATGGCTGAG GTCGCCCGGT TTATTGAAAT GAACGGCTCT
1861 TTTGCTGACG AGAACAGGGA CTGGTGAAAT GCAGTTTAAG GTTTACACCT ATAAAAGAGA
1921 GAGCCGTTAT CGTCTGTTTG TGGATGTACA GAGTGATATT ATTGACACGC CCGGGCGACG
1981 GATGGTGATC CCCCTGGCCA GTGCACGTCT GCTGTCAGAT AAAGTCTCCC GTGAACTTTA
2041 CCCGGTGGTG CATATCGGGG ATGAAAGCTG GCGCATGATG ACCACCGATA TGGCCAGTGT
2101 GCCGGTCTCC GTTATCGGGG AAGAAGTGGC TGATCTCAGC CACCGCGAAA ATGACATCAA
2161 AAACGCCATT AACCTGATGT TCTGGGGAAT ATAAATGTCA GGCTCCCTTA TACACAGCCA
2221 GTCTGCAGGT CGACCATAGT GACTGGATAT GTTGTGTTTT ACAGTATTAT GTAGTCTGTT
2281 TTTTATGCAA AATCTAATTT AATATATTGA TATTTATATC ATTTTACGTT TCTCGTTCAG
2341 CTTTCTTGTA CAAAGTGGTT GATATCGAAT TCCTGCAGCC CGGGGGATCC ACTAGTTCTA
2401 GAGCACTGCG ATGAGTGGCA GGGCGGGGCG TAATTTTTTT AAGGCAGTTA TTGGTGCCCT
2461 TAAACGCCTG GTGCTACGCC TGAATAAGTG ATAATAAGCG GATGAATGGC AGAAATTCGC
2521 CGGATCTTTG TGAAGGAACC TTACTTCTGT GGTGTGACAT AATTGGACAA ACTACCTACA
2581 GAGATTTAAA GCTCTAAGGT AAATATAAAA TTTTTAAGTG TATAATGTGT TAAACTACTG
2641 ATTCTAATTG TTTGTGTATT TTAGATTCCA ACCTATGGAA CTGATGAATG GGAGCAGTGG
2701 TGGAATGCCT TTAATGAGGA AAACCTGTTT TGCTCAGAAG AAATGCCATC TAGTGATGAT
2761 GAGGCTACTG CTGACTCTCA ACATTCTACT CCTCCAAAAA AGAAGAGAAA GGTAGAAGAC
2821 CCCAAGGACT TTCCTTCAGA ATTGCTAAGT TTTTTGAGTC ATGCTGTGTT TAGTAATAGA
2881 ACTCTTGCTT GCTTTGCTAT TTACACCACA AAGGAAAAAG CTGCACTGCT ATACAAGAAA
2941 ATTATGGAAA AATATTCTGT AACCTTTATA AGTAGGCATA ACAGTTATAA TCATAACATA
3001 CTGTTTTTTC TTACTCCACA CAGGCATAGA GTGTCTGCTA TTAATAACTA TGCTCAAAAA
3061 TTGTGTACCT TTAGCTTTTT AATTTGTAAA GGGGTTAATA AGGAATATTT GATGTATAGT
3121 GCCTTGACTA GAGATCATAA TCAGCCATAC CACATTTGTA GAGGTTTTAC TTGCTTTAAA
3181 AAACCTCCCA CACCTCCCCC TGAACCTGAA ACATAAAATG AATGCAATTG TTGTTGTTAA
3241 CTTGTTTATT GCAGCTTATA ATGGTTACAA ATAAAGCAAT AGCATCACAA ATTTCACAAA
3301 TAAAGCATTT TTTTCACTGC ATTCTAGTTG TGGTTTGTCC AAACTCATCA ATGTATCTTA
3361 TCATGTCTGG ATCCCCAGGA AGCTCCTCTG TGTCCTCATA AACCCTAACC TCCTCTACTT
3421 GAGAGGACAT TCCAATCATA GGCTGCCCAT CCACCCTCTG TGTCCTCCTG TTAATTAGGT
3481 CACTTAACAA AAAGGAAATT GGGTAGGGGT TTTTCACAGA CCGCTTTCTA AGGGTAATTT
3541 TAAAATATCT GGGAAGTCCC TTCCACTGCT GTGTTCCAGA AGTGTTGGTA AACAGCCCAC
3601 AAATGTCAAC AGCAGAAACA TACAAGCTGT CAGCTTTGCA CAAGGGCCCA ACACCCTGCT
3661 CATCAAGAAG CACTGTGGTT GCTGTGTTAG TAATGTGCAA AACAGGAGGC ACATTTTCCC
3721 CACCTGTGTA GGTTCCAAAA TATCTAGTGT TTTCATTTTT ACTTGGATCA GGAACCCAGC
3781 ACTCCACTGG ATAAGCATTA TCCTTATCCA AAACAGCCTT GTGGTCAGTG TTCATCTGCT
3841 GACTGTCAAC TGTAGCATTT TTTGGGGTTA CAGTTTGAGC AGGATATTTG GTCCTGTAGT

FIG.31C

3901 TTGCTAACAC ACCCTGCAGC TCCAAAGGTT CCCCACCAAC AGCAAAAAAA TGAAAATTTG
3961 ACCCTTGAAT GGGTTTTCCA GCACCATTTT CATGAGTTTT TTGTGTCCCT GAATGCAAGT
4021 TTAACATAGC AGTTACCCCA ATAACCTCAG TTTTAACAGT AACAGCTTCC CACATCAAAA
4081 TATTTCCACA GGTTAAGTCC TCATTTAAAT TAGGCAAAGG AATTGCTCTA GAGCGGCCGC
4141 CACCGCGGTG GAGCTCCAAT TCGCCCTATA GTGAGTCGTA TTACGCGCGC TCACTGGCCG
4201 TCGTTTTACA ACGTCGTGAC TGGGAAAACC CTGGCGTTAC CCAACTTAAT CGCCTTGCAG
4261 CACATCCCCC TTTCGCCAGC TGGCGTAATA GCGAAGAGGC CCGCACCGAT CGCCCTTCCC
4321 AACAGTTGCG CAGCCTGAAT GGCGAATGGG ACGCGCCCTG TAGCGGCGCA TTAAGCGCGG
4381 CGGGTGTGGT GGTTACGCGC AGCGTGACCG CTACACTTGC CAGCGCCCTA GCGCCCGCTC
4441 CTTTCGCTTT CTTCCCTTCC TTTCTCGCCA CGTTCGCCGG CTTTCCCCGT CAAGCTCTAA
4501 ATCGGGGGCT CCCTTTAGGG TTCCGATTTA GTGCTTTACG GCACCTCGAC CCCAAAAAAC
4561 TTGATTAGGG TGATGGTTCA CGTAGTGGGC CATCGCCCTG ATAGACGGTT TTTCGCCCTT
4621 TGACGTTGGA GTCCACGTTC TTTAATAGTG GACTCTTGTT CCAAACTGGA ACAACACTCA
4681 ACCCTATCTC GGTCTATTCT TTTGATTTAT AAGGGATTTT GCCGATTTCG GCCTATTGGT
4741 TAAAAAATGA GCTGATTTAA CAAAAATTTA ACGCGAATTT TAACAAAATA TTAACGCTTA
4801 CAATTTAGGT GGCACTTTTC GGGGAAATGT GCGCGGAACC CCTATTTGTT TATTTTTCTA
4861 AATACATTCA AATATGTATC CGCTCATGAG ACAATAACCC TGATAAATGC TTCAATAATA
4921 TTGAAAAAGG AAGAGTATGA GTATTCAACA TTTCCGTGTC GCCCTTATTC CCTTTTTTGC
4981 GGCATTTTGC CTTCCTGTTT TTGCTCACCC AGAAACGCTG GTGAAAGTAA AAGATGCTGA
5041 AGATCAGTTG GGTGCACGAG TGGGTTACAT CGAACTGGAT CTCAACAGCG GTAAGATCCT
5101 TGAGAGTTTT CGCCCCGAAG AACGTTTTCC AATGATGAGC ACTTTTAAAG TTCTGCTATG
5161 TGGCGCGGTA TTATCCCGTA TTGACGCCGG GCAAGAGCAA CTCGGTCGCC GCATACACTA
5221 TTCTCAGAAT GACTTGGTTG AGTACTCACC AGTCACAGAA AAGCATCTTA CGGATGGCAT
5281 GACAGTAAGA GAATTATGCA GTGCTGCCAT AACCATGAGT GATAACACTG CGGCCAACTT
5341 ACTTCTGACA ACGATCGGAG GACCGAAGGA GCTAACCGCT TTTTTGCACA ACATGGGGGA
5401 TCATGTAACT CGCCTTGATC GTTGGGAACC GGAGCTGAAT GAAGCCATAC CAAACGACGA
5461 GCGTGACACC ACGATGCCTG TAGCAATGGC AACAACGTTG CGCAAACTAT TAACTGGCGA
5521 ACTACTTACT CTAGCTTCCC GGCAACAATT AATAGACTGG ATGGAGGCGG ATAAAGTTGC
5581 AGGACCACTT CTGCGCTCGG CCCTTCCGGC TGGCTGGTTT ATTGCTGATA AATCTGGAGC
5641 CGGTGAGCGT GGGTCTCGCG GTATCATTGC AGCACTGGGG CCAGATGGTA AGCCCTCCCG
5701 TATCGTAGTT ATCTACACGA CGGGGAGTCA GGCAACTATG GATGAACGAA ATAGACAGAT
5761 CGCTGAGATA GGTGCCTCAC TGATTAAGCA TTGGTAACTG TCAGACCAAG TTTACTCATA
5821 TATACTTTAG ATTGATTTAA AACTTCATTT TTAATTTAAA AGGATCTAGG TGAAGATCCT
5881 TTTTGATAAT CTCATGACCA AAATCCCTTA ACGTGAGTTT TCGTTCCACT GAGCGTCAGA
5941 CCCCGTAGAA AAGATCAAAG GATCTTCTTG AGATCCTTTT TTTCTGCGCG TAATCTGCTG
6001 CTTGCAAACA AAAAAACCAC CGCTACCAGC GGTGGTTTGT TTGCCGGATC AAGAGCTACC
6061 AACTCTTTTT CCGAAGGTAA CTGGCTTCAG CAGAGCGCAG ATACCAAATA CTGTCCTTCT
6121 AGTGTAGCCG TAGTTAGGCC ACCACTTCAA GAACTCTGTA GCACCGCCTA CATACCTCGC

FIG.31D

6181 TCTGCTAATC CTGTTACCAG TGGCTGCTGC CAGTGGCGAT AAGTCGTGTC TTACCGGGTT
6241 GGACTCAAGA CGATAGTTAC CGGATAAGGC GCAGCGGTCG GGCTGAACGG GGGGTTCGTG
6301 CACACAGCCC AGCTTGGAGC GAACGACCTA CACCGAACTG AGATACCTAC AGCGTGAGCT
6361 ATGAGAAAGC GCCACGCTTC CCGAAGGGAG AAAGGCGGAC AGGTATCCGG TAAGCGGCAG
6421 GGTCGGAACA GGAGAGCGCA CGAGGGAGCT TCCAGGGGGA AACGCCTGGT ATCTTTATAG
6481 TCCTGTCGGG TTTCGCCACC TCTGACTTGA GCGTCGATTT TTGTGATGCT CGTCAGGGGG
6541 GCGGAGCCTA TGGAAAAACG CCAGCAACGC GGCCTTTTTA CGGTTCCTGG CCTTTTGCTG
6601 GCCTTTTGCT CACATGTTCT TTCCTGCGTT ATCCCCTGAT TCTGTGGATA ACCGTATTAC
6661 CGCCTTTGAG TGAGCTGATA CCGCTCGCCG CAGCCGAACG ACCGAGCGCA GCGAGTCAGT
6721 GAGCGAGGAA GCGGAAGAGC GCCCAATACG CAAACCGCCT CTCCCCGCGC GTTGGCCGAT
6781 TCATTAATGC AGCTGGCACG ACAGGTTTCC CGACTGGAAA GCGGGCAGTG AGCGCAACGC
6841 AATTAATGTG AGTTAGCTCA CTCATTAGGC ACCCCAGGCT TTACACTTTA TGCTTCCGGC
6901 TCGTATGTTG TGTGGAATTG TGAGCGGATA ACAATTTCAC ACAGGAAACA GCTATGACCA
6961 TGATTACGCC AAGCGCGCAA TTAACCCTCA CTAAAGGGAA CAAAAGCTGG GTACCGGGCC
7021 CCCCCT

FIG.31E pDEST12.2 CMV Promoter for Eukaryotic Expression, SV40 Promoter/ori for G418 Resistance mRNA from CMV promoter 307 acc gtc aga tcg cct gga gac gcc atc cac gct gtt ttg acc tcc ata gaa
tgg cag tct agc gga cct ctg cgg tag gtg cga caa aac tgg agg tat ctt 358 gac acc ggg acc gat cca gcc tcc gga ctc tag cct agg ccg cgg agc gga
ctg tgg ccc tgg cta ggt cgg agg cct gag atc gga tcc ggc gcc tcg cct 409 taa caa ttt cac aca gga aac agc tat gac cat tag gcc ttt gca aaa agc
att gtt aaa gtg tgt cct ttg tcg ata ctg gta atc cgg aaa cgt ttt tcg Age EcoRI 460 tat tta ggt gac act ata gaa ggt acg cct gca ggt acc ggt ccg gaa ttc
ata aat cca ctg tga tat ctt cca tgc gga cgt cca tgg cca ggc ctt aag Int attR1

511 cca tca aca agt ttg tac aaa aaa gct gaa cga gaa acg taa aat gat ata
ggt agt tgt tca aac atg ttt ttt cga ctt gct ctt tgc att tta cta tat

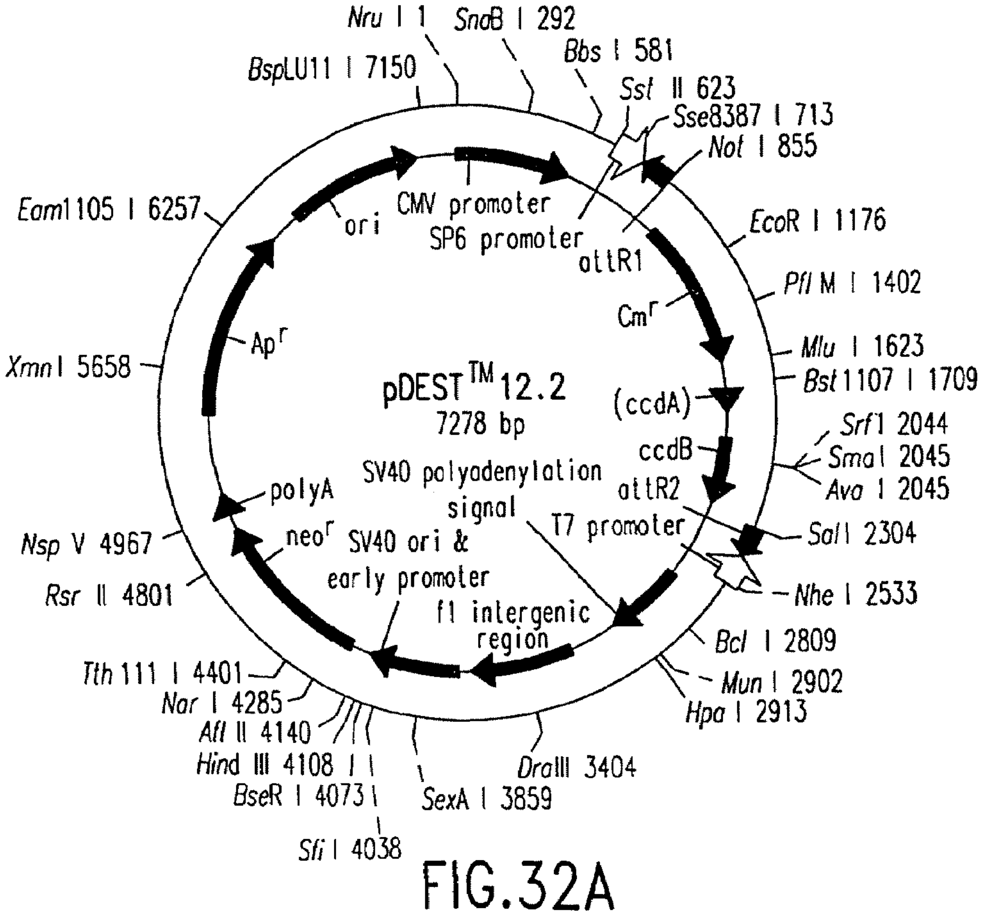

FIG.32A pDEST12.2 7278 bp (rotated to position 3900)

| Location (Base Nos.) | Gene Encoded |
|---|---|
| 86..136 | ori |
| 220..742 | CMV promoter |
| 1059..935 | attR1 |
| 1168..1827 | CmR |
| 1947..2031 | inactivated ccdA |
| 2169..2474 | ccdB |
| 2515..2639 | attR2 |
| 2824..3186 | small t & polyA |
| 3310..3378 | lac |
| 4363..5157 | neo |
| 5680..6540 | ampR |

```
   1 GGGGGGCGGA GCCTATGGAA AAACGCCAGC AACGCGGCCT TTTTACGGTT CCTGGCCTTT
  61 TGCTGGCCTT TTGCTCACAT GTTCTTTCCT GCGTTATCCC CTGATTCTGT GGATAACCGT
 121 ATTACCGCCT TTGAGTGAGC TGATACCGCT CGCCGCAGCC GAACGACCGA GCGCAGCGAG
 181 TCAGTGAGCG AGGAAGCGGA AGAGCTCGCG AATGCATGTC GTTACATAAC TTACGGTAAA
 241 TGGCCCGCCT GGCTGACCGC CCAACGACCC CCGCCCATTG ACGTCAATAA TGACGTATGT
 301 TCCCATAGTA ACGCCAATAG GGACTTTCCA TTGACGTCAA TGGGTGGAGT ATTTACGGTA
 361 AACTGCCCAC TTGGCAGTAC ATCAAGTGTA TCATATGCCA AGTACGCCCC CTATTGACGT
 421 CAATGACGGT AAATGGCCCG CCTGGCATTA TGCCCAGTAC ATGACCTTAT GGGACTTTCC
 481 TACTTGGCAG TACATCTACG TATTAGTCAT CGCTATTACC ATGGTGATGC GGTTTTGGCA
 541 GTACATCAAT GGGCGTGGAT AGCGGTTTGA CTCACGGGGA TTTCCAAGTC TCCACCCCAT
 601 TGACGTCAAT GGGAGTTTGT TTTGGCACCA AAATCAACGG GACTTTCCAA AATGTCGTAA
 661 CAACTCCGCC CCATTGACGC AAATGGGCGG TAGGCGTGTA CGGTGGGAGG TCTATATAAG
 721 CAGAGCTCGT TTAGTGAACC GTCAGATCGC CTGGAGACGC CATCCACGCT GTTTTGACCT
 781 CCATAGAAGA CACCGGGACC GATCCAGCCT CCGGACTCTA GCCTAGGCCG CGGGACGGAT
 841 AACAATTTCA CACAGGAAAC AGCTATGACC ATTAGGCCTT TGCAAAAAGC TATTTAGGTG
 901 ACACTATAGA AGGTACGCCT GCAGGTACCG GATCACAAGT TTGTACAAAA AAGCTGAACG
 961 AGAAACGTAA AATGATATAA ATATCAATAT ATTAAATTAG ATTTTGCATA AAAAACAGAC
1021 TACATAATAC TGTAAAACAC AACATATCCA GTCACTATGG CGGCCGCATT AGGCACCCCA
1081 GGCTTTACAC TTTATGCTTC CGGCTCGTAT AATGTGTGGA TTTTGAGTTA GGATCCGTCG
1141 AGATTTTCAG GAGCTAAGGA AGCTAAAATG GAGAAAAAAA TCACTGGATA TACCACCGTT
1201 GATATATCCC AATGGCATCG TAAAGAACAT TTTGAGGCAT TTCAGTCAGT TGCTCAATGT
1261 ACCTATAACC AGACCGTTCA GCTGGATATT ACGGCCTTTT TAAAGACCGT AAAGAAAAAT
1321 AAGCACAAGT TTTATCCGGC CTTTATTCAC ATTCTTGCCC GCCTGATGAA TGCTCATCCG
1381 GAATTCCGTA TGGCAATGAA AGACGGTGAG CTGGTGATAT GGGATAGTGT TCACCCTTGT
1441 TACACCGTTT TCCATGAGCA AACTGAAACG TTTTCATCGC TCTGGAGTGA ATACCACGAC
1501 GATTTCCGGC AGTTTCTACA CATATATTCG CAAGATGTGG CGTGTTACGG TGAAAACCTG
1561 GCCTATTTCC CTAAAGGGTT TATTGAGAAT ATGTTTTTCG TCTCAGCCAA TCCCTGGGTG
```

FIG.32B

1621 AGTTTCACCA GTTTTGATTT AAACGTGGCC AATATGGACA ACTTCTTCGC CCCCGTTTTC
1681 ACCATGGGCA AATATTATAC GCAAGGCGAC AAGGTGCTGA TGCCGCTGGC GATTCAGGTT
1741 CATCATGCCG TCTGTGATGG CTTCCATGTC GGCAGAATGC TTAATGAATT ACAACAGTAC
1801 TGCGATGAGT GGCAGGGCGG GGCGTAAACG CGTGGATCCG GCTTACTAAA AGCCAGATAA
1861 CAGTATGCGT ATTTGCGCGC TGATTTTTGC GGTATAAGAA TATATACTGA TATGTATACC
1921 CGAAGTATGT CAAAAAGAGG TGTGCTATGA AGCAGCGTAT TACAGTGACA GTTGACAGCG
1981 ACAGCTATCA GTTGCTCAAG GCATATATGA TGTCAATATC TCCGGTCTGG TAAGCACAAC
2041 CATGCAGAAT GAAGCCCGTC GTCTGCGTGC CGAACGCTGG AAAGCGGAAA ATCAGGAAGG
2101 GATGGCTGAG GTCGCCCGGT TTATTGAAAT GAACGGCTCT TTTGCTGACG AGAACAGGGA
2161 CTGGTGAAAT GCAGTTTAAG GTTTACACCT ATAAAAGAGA GAGCCGTTAT CGTCTGTTTG
2221 TGGATGTACA GAGTGATATT ATTGACACGC CCGGGCGACG GATGGTGATC CCCCTGGCCA
2281 GTGCACGTCT GCTGTCAGAT AAAGTCTCCC GTGAACTTTA CCCGGTGGTG CATATCGGGG
2341 ATGAAAGCTG GCGCATGATG ACCACCGATA TGGCCAGTGT GCCGGTCTCC GTTATCGGGG
2401 AAGAAGTGGC TGATCTCAGC CACCGCGAAA ATGACATCAA AAACGCCATT AACCTGATGT
2461 TCTGGGGAAT ATAAATGTCA GGCTCCCTTA TACACAGCCA GTCTGCAGGT CGACCATAGT
2521 GACTGGATAT GTTGTGTTTT ACAGTATTAT GTAGTCTGTT TTTTATGCAA AATCTAATTT
2581 AATATATTGA TATTTATATC ATTTTACGTT TCTCGTTCAG CTTTCTTGTA CAAAGTGGTG
2641 ATCGCGTGCA TGCGACGTCA TAGCTCTCTC CCTATAGTGA GTCGTATTAT AAGCTAGGCA
2701 CTGGCCGTCG TTTTACAACG TCGTGACTGG GAAAACTGCT AGCTTGGGAT CTTTGTGAAG
2761 GAACCTTACT TCTGTGGTGT GACATAATTG GACAAACTAC CTACAGAGAT TTAAAGCTCT
2821 AAGGTAAATA TAAAATTTTT AAGTGTATAA TGTGTTAAAC TAGCTGCATA TGCTTGCTGC
2881 TTGAGAGTTT TGCTTACTGA GTATGATTTA TGAAAATATT ATACACAGGA GCTAGTGATT
2941 CTAATTGTTT GTGTATTTTA GATTCACAGT CCCAAGGCTC ATTTCAGGCC CCTCAGTCCT
3001 CACAGTCTGT TCATGATCAT AATCAGCCAT ACCACATTTG TAGAGGTTTT ACTTGCTTTA
3061 AAAAACCTCC CACACCTCCC CCTGAACCTG AAACATAAAA TGAATGCAAT TGTTGTTGTT
3121 AACTTGTTTA TTGCAGCTTA TAATGGTTAC AAATAAAGCA ATAGCATCAC AAATTTCACA
3181 AATAAAGCAT TTTTTTCACT GCATTCTAGT TGTGGTTTGT CCAAACTCAT CAATGTATCT
3241 TATCATGTCT GGATCGATCC TGCATTAATG AATCGGCCAA CGCGCGGGGA GAGGCGGTTT
3301 GCGTATTGGC TGGCGTAATA GCGAAGAGGC CCGCACCGAT CGCCCTTCCC AACAGTTGCG
3361 CAGCCTGAAT GGCGAATGGG ACGCGCCCTG TAGCGGCGCA TTAAGCGCGG CGGGTGTGGT
3421 GGTTACGCGC AGCGTGACCG CTACACTTGC CAGCGCCCTA GCGCCCGCTC CTTTCGCTTT
3481 CTTCCCTTCC TTTCTCGCCA CGTTCGCCGG CTTTCCCCGT CAAGCTCTAA ATCGGGGGCT
3541 CCCTTTAGGG TTCCGATTTA GTGCTTTACG GCACCTCGAC CCCAAAAAAC TTGATTAGGG
3601 TGATGGTTCA CGTAGTGGGC CATCGCCCTG ATAGACGGTT TTTCGCCCTT TGACGTTGGA
3661 GTCCACGTTC TTTAATAGTG GACTCTTGTT CCAAACTGGA ACAACACTCA ACCCTATCTC
3721 GGTCTATTCT TTTGATTTAT AAGGGATTTT GCCGATTTCG GCCTATTGGT TAAAAAATGA
3781 GCTGATTTAA CAAATATTTA ACGCGAATTT TAACAAAATA TTAACGTTTA CAATTTCGCC
3841 TGATGCGGTA TTTTCTCCTT ACGCATCTGT GCGGTATTTC ACACCGCATA CGCGGATCTG
3901 CGCAGCACCA TGGCCTGAAA TAACCTCTGA AAGAGGAACT TGGTTAGGTA CCTTCTGAGG
3961 CGGAAAGAAC CAGCTGTGGA ATGTGTGTCA GTTAGGGTGT GGAAAGTCCC CAGGCTCCCC
4021 AGCAGGCAGA AGTATGCAAA GCATGCATCT CAATTAGTCA GCAACCAGGT GTGGAAAGTC

FIG.32C

4081 CCCAGGCTCC CCAGCAGGCA GAAGTATGCA AAGCATGCAT CTCAATTAGT CAGCAACCAT
4141 AGTCCCGCCC CTAACTCCGC CCATCCCGCC CCTAACTCCG CCCAGTTCCG CCCATTCTCC
4201 GCCCCATGGC TGACTAATTT TTTTTATTTA TGCAGAGGCC GAGGCCGCCT CGGCCTCTGA
4261 GCTATTCCAG AAGTAGTGAG GAGGCTTTTT TGGAGGCCTA GGCTTTTGCA AAAAGCTTGA
4321 TTCTTCTGAC ACAACAGTCT CGAACTTAAG GCTAGAGCCA CCATGATTGA ACAAGATGGA
4381 TTGCACGCAG GTTCTCCGGC CGCTTGGGTG GAGAGGCTAT TCGGCTATGA CTGGGCACAA
4441 CAGACAATCG GCTGCTCTGA TGCCGCCGTG TTCCGGCTGT CAGCGCAGGG GCGCCCGGTT
4501 CTTTTTGTCA AGACCGACCT GTCCGGTGCC CTGAATGAAC TGCAGGACGA GGCAGCGCGG
4561 CTATCGTGGC TGGCCACGAC GGGCGTTCCT TGCGCAGCTG TGCTCGACGT TGTCACTGAA
4621 GCGGGAAGGG ACTGGCTGCT ATTGGGCGAA GTGCCGGGGC AGGATCTCCT GTCATCTCAC
4681 CTTGCTCCTG CCGAGAAAGT ATCCATCATG GCTGATGCAA TGCGGCGGCT GCATACGCTT
4741 GATCCGGCTA CCTGCCCATT CGACCACCAA GCGAAACATC GCATCGAGCG AGCACGTACT
4801 CGGATGGAAG CCGGTCTTGT CGATCAGGAT GATCTGGACG AAGAGCATCA GGGGCTCGCG
4861 CCAGCCGAAC TGTTCGCCAG GCTCAAGGCG CGCATGCCCG ACGGCGAGGA TCTCGTCGTG
4921 ACCCATGGCG ATGCCTGCTT GCCGAATATC ATGGTGGAAA ATGGCCGCTT TTCTGGATTC
4981 ATCGACTGTG GCCGGCTGGG TGTGGCGGAC CGCTATCAGG ACATAGCGTT GGCTACCCGT
5041 GATATTGCTG AAGAGCTTGG CGGCGAATGG GCTGACCGCT TCCTCGTGCT TTACGGTATC
5101 GCCGCTCCCG ATTCGCAGCG CATCGCCTTC TATCGCCTTC TTGACGAGTT CTTCTGAGCG
5161 GGACTCTGGG GTTCGAAATG ACCGACCAAG CGACGCCCAA CCTGCCATCA CGATGGCCGC
5221 AATAAAATAT CTTTATTTTC ATTACATCTG TGTGTTGGTT TTTTGTGTGA ATCGATAGCG
5281 ATAAGGATCC GCGTATGGTG CACTCTCAGT ACAATCTGCT CTGATGCCGC ATAGTTAAGC
5341 CAGCCCCGAC ACCCGCCAAC ACCCGCTGAC GCGCCCTGAC GGGCTTGTCT GCTCCCGGCA
5401 TCCGCTTACA GACAAGCTGT GACCGTCTCC GGGAGCTGCA TGTGTCAGAG GTTTTCACCG
5461 TCATCACCGA AACGCGCGAG ACGAAAGGGC CTCGTGATAC GCCTATTTTT ATAGGTTAAT
5521 GTCATGATAA TAATGGTTTC TTAGACGTCA GGTGGCACTT TTCGGGGAAA TGTGCGCGGA
5581 ACCCCTATTT GTTTATTTTT CTAAATACAT TCAAATATGT ATCCGCTCAT GAGACAATAA
5641 CCCTGATAAA TGCTTCAATA ATATTGAAAA AGGAAGAGTA TGAGTATTCA ACATTTCCGT
5701 GTCGCCCTTA TTCCCTTTTT TGCGGCATTT TGCCTTCCTG TTTTTGCTCA CCCAGAAACG
5761 CTGGTGAAAG TAAAAGATGC TGAAGATCAG TTGGGTGCAC GAGTGGGTTA CATCGAACTG
5821 GATCTCAACA GCGGTAAGAT CCTTGAGAGT TTTCGCCCCG AAGAACGTTT TCCAATGATG
5881 AGCACTTTTA AAGTTCTGCT ATGTGGCGCG GTATTATCCC GTATTGACGC CGGGCAAGAG
5941 CAACTCGGTC GCCGCATACA CTATTCTCAG AATGACTTGG TTGAGTACTC ACCAGTCACA
6001 GAAAAGCATC TTACGGATGG CATGACAGTA AGAGAATTAT GCAGTGCTGC CATAACCATG
6061 AGTGATAACA CTGCGGCCAA CTTACTTCTG ACAACGATCG GAGGACCGAA GGAGCTAACC
6121 GCTTTTTTGC ACAACATGGG GGATCATGTA ACTCGCCTTG ATCGTTGGGA ACCGGAGCTG
6181 AATGAAGCCA TACCAAACGA CGAGCGTGAC ACCACGATGC CTGTAGCAAT GGCAACAACG
6241 TTGCGCAAAC TATTAACTGG CGAACTACTT ACTCTAGCTT CCCGGCAACA ATTAATAGAC
6301 TGGATGGAGG CGGATAAAGT TGCAGGACCA CTTCTGCGCT CGGCCCTTCC GGCTGGCTGG
6361 TTTATTGCTG ATAAATCTGG AGCCGGTGAG CGTGGGTCTC GCGGTATCAT TGCAGCACTG
6421 GGGCCAGATG GTAAGCCCTC CCGTATCGTA GTTATCTACA CGACGGGGAG TCAGGCAACT
6481 ATGGATGAAC GAAATAGACA GATCGCTGAG ATAGGTGCCT CACTGATTAA GCATTGGTAA

FIG.32D

6541 CTGTCAGACC AAGTTTACTC ATATATACTT TAGATTGATT TAAAACTTCA TTTTTAATTT
6601 AAAAGGATCT AGGTGAAGAT CCTTTTTGAT AATCTCATGA CCAAAATCCC TTAACGTGAG
6661 TTTTCGTTCC ACTGAGCGTC AGACCCCGTA GAAAAGATCA AAGGATCTTC TTGAGATCCT
6721 TTTTTTCTGC GCGTAATCTG CTGCTTGCAA ACAAAAAAAC CACCGCTACC AGCGGTGGTT
6781 TGTTTGCCGG ATCAAGAGCT ACCAACTCTT TTTCCGAAGG TAACTGGCTT CAGCAGAGCG
6841 CAGATACCAA ATACTGTCCT TCTAGTGTAG CCGTAGTTAG GCCACCACTT CAAGAACTCT
6901 GTAGCACCGC CTACATACCT CGCTCTGCTA ATCCTGTTAC CAGTGGCTGC TGCCAGTGGC
6961 GATAAGTCGT GTCTTACCGG GTTGGACTCA AGACGATAGT TACCGGATAA GGCGCAGCGG
7021 TCGGGCTGAA CGGGGGGTTC GTGCACACAG CCCAGCTTGG AGCGAACGAC CTACACCGAA
7081 CTGAGATACC TACAGCGTGA GCATTGAGAA AGCGCCACGC TTCCCGAAGG GAGAAAGGCG
7141 GACAGGTATC CGGTAAGCGG CAGGGTCGGA ACAGGAGAGC GCACGAGGGA GCTTCCAGGG
7201 GGAAACGCCT GGTATCTTTA TAGTCCTGTC GGGTTTCGCC ACCTCTGACT TGAGCGTCGA
7261 TTTTTGTGAT GCTCGTCA

FIG.32E

Native protein in E. coli:λ$P_L$ promoter

```
                                         BglII
3721 tgggcaaacc aagacagcta agatctctc acctaccaaa caatgccccc ctgcaaaaaa
     acccgtttgg ttctgtcgat ttctagagag tggatggttt gttacggggg gacgtttttt

3781 taaattcata taaaaaacat acagataacc atctgcggtg ataaattatc tctggcggtg
     atttaagtat atttttttgta tgtctattgg tagacgccac tatttaatag agaccgccac

      -35        λPL promoter    -10          ┌─► mRNA
3841 ttgacataaa taccactggc ggtgatactg agcacatcag caggacgcac tgaccaccat
     aactgtattt atggtgaccg ccactatgac tcgtgtagtc gtcctgcgtg actggtggta

                                        EcoNI
3901 gaaggtgacg ctcttaaaaa ttaagccctg aagaagggca gcattcaaag cagaaggctt
     cttccactgc gagaattttt aattcgggac ttcttcccgt cgtaagtttc gtcttccgaa

                                               Int    attR1
3961 tggggtgtgt gatacgaaac gaagcattgg gatcatcaca agtttgtaca aaaaagctga
     accccacaca ctatgctttg cttcgtaacc ctagtagtgt tcaaacatgt ttttcgact
```

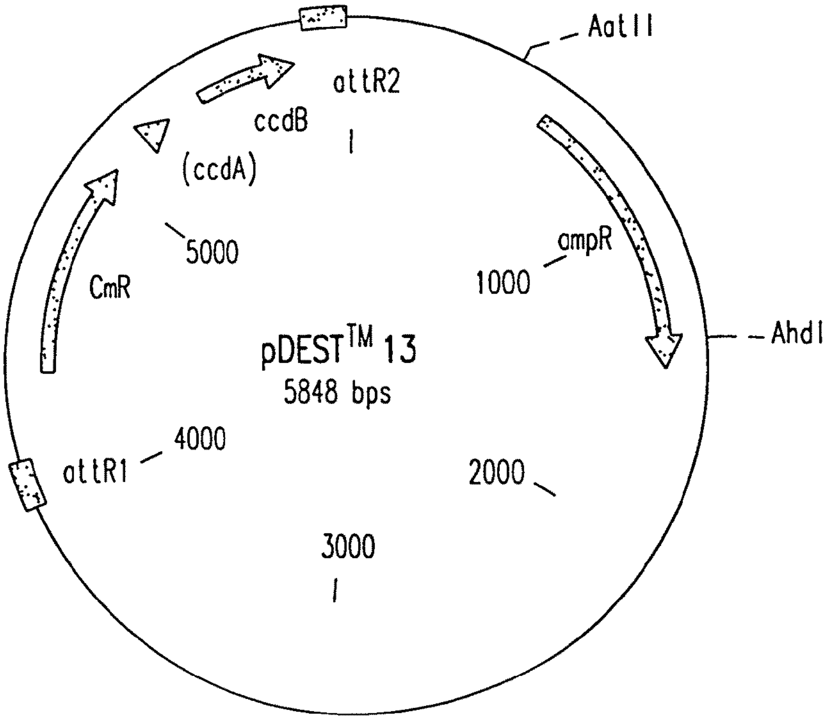

FIG.33A pDEST13 5848 bp

| Location (Base Nos.) | Gene Encoded |
|---|---|
| 599..1458 | ampR |
| 4123..3998 | attR1 |
| 4372..5031 | CmR |
| 5151..5235 | inactivated ccdA |
| 5373..5678 | ccdB |
| 5719..5843 | attR2 |

```
   1 TTCACTGGCC GTCGTTTTAC AACGTCGTGA CTGGGAAAAC CCTGGCGTTA CCCAACTTAA
  61 TCGCCTTGCA GCACATCCCC CTTTCGCCAG CTGGCGTAAT AGCGAAGAGG CCCGCACCGA
 121 TCGCCCTTCC CAACAGTTGC GCAGCCTGAA TGGCGAATGG CGCCTGATGC GGTATTTTCT
 181 CCTTACGCAT CTGTGCGGTA TTTCACACCG CATATGGTGC ACTCTCAGTA CAATCTGCTC
 241 TGATGCCGCA TAGTTAAGCC AGCCCCGACA CCCGCCAACA CCCGCTGACG CGCCCTGACG
 301 GGCTTGTCTG CTCCCGGCAT CCGCTTACAG ACAAGCTGTG ACCGTCTCCG GGAGCTGCAT
 361 GTGTCAGAGG TTTTCACCGT CATCACCGAA ACGCGCGAGA CGAAAGGGCC TCGTGATACG
 421 CCTATTTTTA TAGGTTAATG TCATGATAAT AATGGTTTCT TAGACGTCAG GTGGCACTTT
 481 TCGGGGAAAT GTGCGCGGAA CCCCTATTTG TTTATTTTTC TAAATACATT CAAATATGTA
 541 TCCGCTCATG AGACAATAAC CCTGATAAAT GCTTCAATAA TATTGAAAAA GGAAGAGTAT
 601 GAGTATTCAA CATTTCCGTG TCGCCCTTAT TCCCTTTTTT GCGGCATTTT GCCTTCCTGT
 661 TTTTGCTCAC CCAGAAACGC TGGTGAAAGT AAAAGATGCT GAAGATCAGT TGGGTGCACG
 721 AGTGGGTTAC ATCGAACTGG ATCTCAACAG CGGTAAGATC CTTGAGAGTT TTCGCCCCGA
 781 AGAACGTTTT CCAATGATGA GCACTTTTAA AGTTCTGCTA TGTGGCGCGG TATTATCCCG
 841 TATTGACGCC GGGCAAGAGC AACTCGGTCG CCGCATACAC TATTCTCAGA ATGACTTGGT
 901 TGAGTACTCA CCAGTCACAG AAAAGCATCT TACGGATGGC ATGACAGTAA GAGAATTATG
 961 CAGTGCTGCC ATAACCATGA GTGATAACAC TGCGGCCAAC TTACTTCTGA CAACGATCGG
1021 AGGACCGAAG GAGCTAACCG CTTTTTTGCA CAACATGGGG GATCATGTAA CTCGCCTTGA
1081 TCGTTGGGAA CCGGAGCTGA ATGAAGCCAT ACCAAACGAC GAGCGTGACA CCACGATGCC
1141 TGTAGCAATG GCAACAACGT TGCGCAAACT ATTAACTGGC GAACTACTTA CTCTAGCTTC
1201 CCGGCAACAA TTAATAGACT GGATGGAGGC GGATAAAGTT GCAGGACCAC TTCTGCGCTC
1261 GGCCCTTCCG GCTGGCTGGT TTATTGCTGA TAAATCTGGA GCCGGTGAGC GTGGGTCTCG
1321 CGGTATCATT GCAGCACTGG GGCCAGATGG TAAGCCCTCC CGTATCGTAG TTATCTACAC
1381 GACGGGGAGT CAGGCAACTA TGGATGAACG AAATAGACAG ATCGCTGAGA TAGGTGCCTC
1441 ACTGATTAAG CATTGGTAAC TGTCAGACCA AGTTTACTCA TATATACTTT AGATTGATTT
1501 AAAACTTCAT TTTTAATTTA AAAGGATCTA GGTGAAGATC CTTTTTGATA ATCTCATGAC
1561 CAAAATCCCT TAACGTGAGT TTTCGTTCCA CTGAGCGTCA GACCCCGTAG AAAAGATCAA
1621 AGGATCTTCT TGAGATCCTT TTTTTCTGCG CGTAATCTGC TGCTTGCAAA CAAAAAAACC
1681 ACCGCTACCA GCGGTGGTTT GTTTGCCGGA TCAAGAGCTA CCAACTCTTT TTCCGAAGGT
1741 AACTGGCTTC AGCAGAGCGC AGATACCAAA TACTGTTCTT CTAGTGTAGC CGTAGTTAGG
1801 CCACCACTTC AAGAACTCTG TAGCACCGCC TACATACCTC GCTCTGCTAA TCCTGTTACC
1861 AGTGGCTGCT GCCAGTGGCG ATAAGTCGTG TCTTACCGGG TTGGACTCAA GACGATAGTT
```

FIG.33B

1921 ACCGGATAAG GCGCAGCGGT CGGGCTGAAC GGGGGGTTCG TGCACACAGC CCAGCTTGGA
1981 GCGAACGACC TACACCGAAC TGAGATACCT ACAGCGTGAG CATTGAGAAA GCGCCACGCT
2041 TCCCGAAGGG AGAAAGGCGG ACAGGTATCC GGTAAGCGGC AGGGTCGGAA CAGGAGAGCG
2101 CACGAGGGAG CTTCCAGGGG GAAACGCCTG GTATCTTTAT AGTCCTGTCG GGTTTCGCCA
2161 CCTCTGACTT GAGCGTCGAT TTTTGTGATG CTCGTCAGGG GGGCGGAGCC TATGGAAAAA
2221 CGCCAGCAAC GCGGCCTTTT TACGGTTCCT GGCCTTTTGC TGGCCTTTTG CTCACATGTT
2281 CTTTCCTGCG TTATCCCCTG ATTCTGTGGA TAACCGTATT ACCGCCTTTG AGTGAGCTGA
2341 TACCGCTCGC CGCAGCCGAA CGACCGAGCG CAGCGAGTCA GTGAGCGAGG AAGCGGAAGA
2401 GCGCCCAATA CGCAAACCGC CTCTCCCCGC GCGTTGGCCG ATTCATTAAT GCAGCTGGCA
2461 CGACAGGTTT CCCGACTGGA AAGCGGGCAG TGAGCGCAAC GCAATTAATG TGAGTTAGCT
2521 CACTCATTAG GCACCCCAGG CTTTACACTT TATGCTTCCG GCTCGTATGT TGTGTGGAAT
2581 TGTGAGCGGA TAACAATTTC ACACAGGAAA CAGCTATGAC CATGATTACG CCAAGCTTGG
2641 CTGCAGGTGA TGATTATCAG CCAGCAGAGA TTAAGGAAAA CAGACAGGTT TATTGAGCGC
2701 TTATCTTTCC CTTTATTTTT GCTGCGGTAA GTCGCATAAA AACCATTCTT CATAATTCAA
2761 TCCATTTACT ATGTTATGTT CTGAGGGGAG TGAAAATTCC CCTAATTCGA TGAAGATTCT
2821 TGCTCAATTG TTATCAGCTA TGCGCCGACC AGAACACCTT GCCGATCAGC CAAACGTCTC
2881 TTCAGGCCAC TGACTAGCGA TAACTTTCCC CACAACGGAA CAACTCTCAT TGCATGGGAT
2941 CATTGGGTAC TGTGGGTTTA GTGGTTGTAA AAACACCTGA CCGCTATCCC TGATCAGTTT
3001 CTTGAAGGTA AACTCATCAC CCCCAAGTCT GGCTATGCAG AAATCACCTG GCTCAACAGC
3061 CTGCTCAGGG TCAACGAGAA TTAACATTCC GTCAGGAAAG CTTGGCTTGG AGCCTGTTGG
3121 TGCGGTCATG GAATTACCTT CAACCTCAAG CCAGAATGCA GAATCACTGG CTTTTTTGGT
3181 TGTGCTTACC CATCTCTCCG CATCACCTTT GGTAAAGGTT CTAAGCTTAG GTGAGAACAT
3241 CCCTGCCTGA ACATGAGAAA AAACAGGGTA CTCATACTCA CTTCTAAGTG ACGGCTGCAT
3301 ACTAACCGCT TCATACATCT CGTAGATTTC TCTGGCGATT GAAGGGCTAA ATTCTTCAAC
3361 GCTAACTTTG AGAATTTTTG CAAGCAATGC GGCGTTATAA GCATTTAATG CATTGATGCC
3421 ATTAAATAAA GCACCAACGC CTGACTGCCC CATCCCCATC TTGTCTGCGA CAGATTCCTG
3481 GGATAAGCCA AGTTCATTTT TCTTTTTTTC ATAAATTGCT TTAAGGCGAC GTGCGTCCTC
3541 AAGCTGCTCT TGTGTTAATG GTTTCTTTTT TGTGCTCATA CGTTAAATCT ATCACCGCAA
3601 GGGATAAATA TCTAACACCG TGCGTGTTGA CTATTTTACC TCTGGCGGTG ATAATGGTTG
3661 CATGTACTAA GGAGGTTGTA TGGAACAACG CATAACCCTG AAAGATTATG CAATGCGCTT
3721 TGGGCAAACC AAGACAGCTA AAGATCTCTC ACCTACCAAA CAATGCCCCC CTGCAAAAAA
3781 TAAATTCATA TAAAAAACAT ACAGATAACC ATCTGCGGTG ATAAATTATC TCTGGCGGTG
3841 TTGACATAAA TACCACTGGC GGTGATACTG AGCACATCAG CAGGACGCAC TGACCACCAT
3901 GAAGGTGACG CTCTTAAAAA TTAAGCCCTG AAGAAGGGCA GCATTCAAAG CAGAAGGCTT
3961 TGGGGTGTGT GATACGAAAC GAAGCATTGG GATCATCACA AGTTTGTACA AAAAAGCTGA
4021 ACGAGAAACG TAAAATGATA TAAATATCAA TATATTAAAT TAGATTTTGC ATAAAAAACA
4081 GACTACATAA TACTGTAAAA CACAACATAT CCAGTCACTA TGGCGGCCGC TAAGTTGGCA
4141 GCATCACCCG ACGCACTTTG CGCCGAATAA ATACCTGTGA CGGAAGATCA CTTCGCAGAA
4201 TAAATAAATC CTGGTGTCCC TGTTGATACC GGGAAGCCCT GGGCCAACTT TTGGCGAAAA
4261 TGAGACGTTG ATCGGCACGT AAGAGGTTCC AACTTTCACC ATAATGAAAT AAGATCACTA
4321 CCGGGCGTAT TTTTTGAGTT ATCGAGATTT TCAGGAGCTA AGGAAGCTAA AATGGAGAAA

FIG.33C

4381 AAAATCACTG GATATACCAC CGTTGATATA TCCCAATGGC ATCGTAAAGA ACATTTTGAG
4441 GCATTTCAGT CAGTTGCTCA ATGTACCTAT AACCAGACCG TTCAGCTGGA TATTACGGCC
4501 TTTTTAAAGA CCGTAAAGAA AAATAAGCAC AAGTTTTATC CGGCCTTTAT TCACATTCTT
4561 GCCCGCCTGA TGAATGCTCA TCCGGAATTC CGTATGGCAA TGAAAGACGG TGAGCTGGTG
4621 ATATGGGATA GTGTTCACCC TTGTTACACC GTTTTCCATG AGCAAACTGA AACGTTTTCA
4681 TCGCTCTGGA GTGAATACCA CGACGATTTC CGGCAGTTTC TACACATATA TTCGCAAGAT
4741 GTGGCGTGTT ACGGTGAAAA CCTGGCCTAT TTCCCTAAAG GGTTTATTGA GAATATGTTT
4801 TTCGTCTCAG CCAATCCCTG GGTGAGTTTC ACCAGTTTTG ATTTAAACGT GGCCAATATG
4861 GACAACTTCT TCGCCCCCGT TTTCACCATG GGCAAATATT ATACGCAAGG CGACAAGGTG
4921 CTGATGCCGC TGGCGATTCA GGTTCATCAT GCCGTCTGTG ATGGCTTCCA TGTCGGCAGA
4981 ATGCTTAATG AATTACAACA GTACTGCGAT GAGTGGCAGG GCGGGGCGTA AACGCGTGGA
5041 TCCGGCTTAC TAAAAGCCAG ATAACAGTAT GCGTATTTGC GCGCTGATTT TTGCGGTATA
5101 AGAATATATA CTGATATGTA TACCCGAAGT ATGTCAAAAA GAGGTGTGCT ATGAAGCAGC
5161 GTATTACAGT GACAGTTGAC AGCGACAGCT ATCAGTTGCT CAAGGCATAT ATGATGTCAA
5221 TATCTCCGGT CTGGTAAGCA CAACCATGCA GAATGAAGCC CGTCGTCTGC GTGCCGAACG
5281 CTGGAAAGCG GAAAATCAGG AAGGGATGGC TGAGGTCGCC CGGTTTATTG AAATGAACGG
5341 CTCTTTTGCT GACGAGAACA GGGACTGGTG AAATGCAGTT TAAGGTTTAC ACCTATAAAA
5401 GAGAGAGCCG TTATCGTCTG TTTGTGGATG TACAGAGTGA TATTATTGAC ACGCCCGGGC
5461 GACGGATGGT GATCCCCCTG GCCAGTGCAC GTCTGCTGTC AGATAAAGTC TCCCGTGAAC
5521 TTTACCCGGT GGTGCATATC GGGGATGAAA GCTGGCGCAT GATGACCACC GATATGGCCA
5581 GTGTGCCGGT CTCCGTTATC GGGGAAGAAG TGGCTGATCT CAGCCACCGC GAAAATGACA
5641 TCAAAAACGC CATTAACCTG ATGTTCTGGG GAATATAAAT GTCAGGCTCC GTTATACACA
5701 GCCAGTCTGC AGGTCGACCA TAGTGACTGG ATATGTTGTG TTTTACAGTA TTATGTAGTC
5761 TGTTTTTTAT GCAAAATCTA ATTTAATATA TTGATATTTA TATCATTTTA CGTTTCTCGT
5821 TCAGCTTTCT TGTACAAAGT GGTGATAA

FIG.33D

Native Protein Expression in E. coli, T7 Promoter

```
                                              BglII                    AseI   pT7 →
3961 tgccggccac gatgcgtccg gcgtagagga tcgagatctc gatcccgcga aattaatacg
     acggccggtg ctacgcaggc cgcatctcct agctctagag ctagggcgct ttaattatgc

                mRNA                       XbaI        Int attR1
4021 actcactata gggagaccac aacggtttcc ctctagatca caagtttgta caaaaaagct
     tgagtgatat ccctctggtg ttgccaaagg gagatctagt gttcaaacat gtttttcga
```

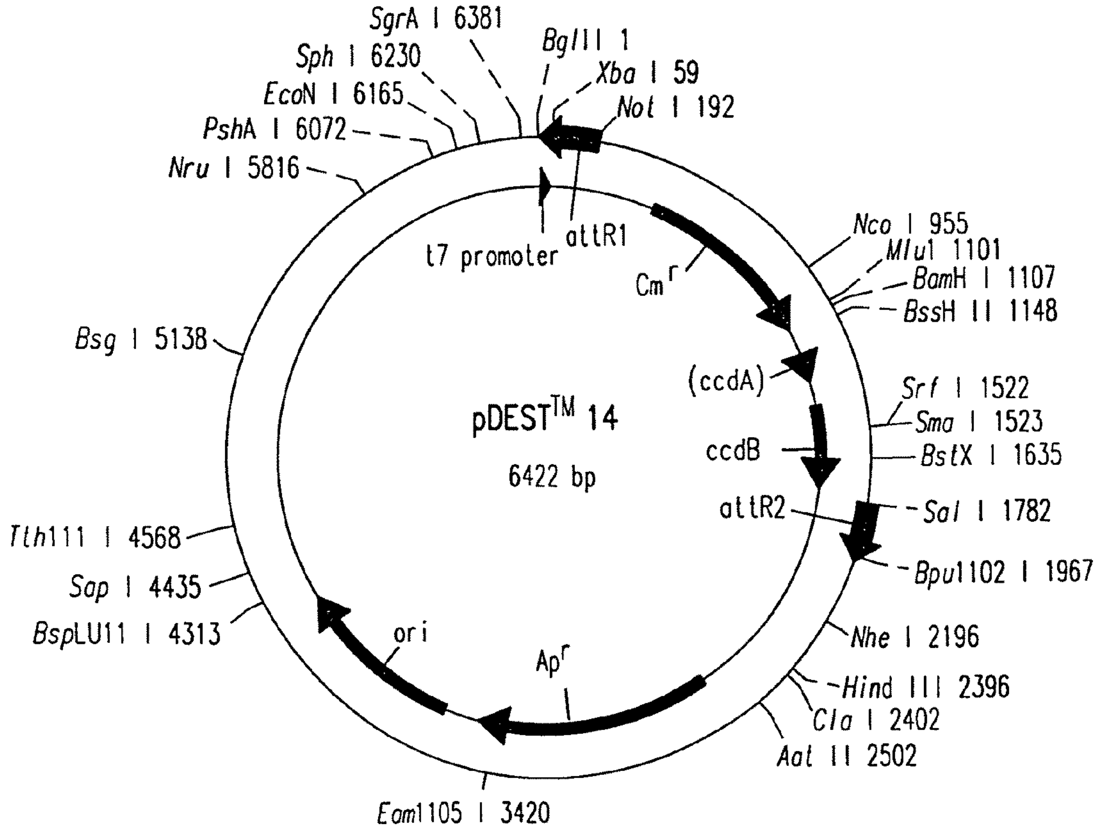

FIG.34A pDEST14 6422 bp (rotated to position 4000)

| Location (Base Nos.) | Gene Encoded |
|---|---|
| 185..61 | attR1 |
| 435..1094 | CmR |
| 1214..1298 | inactivated ccdA |
| 1436..1741 | ccdB |
| 1782..1906 | attR2 |
| 2632..3489 | ampR |

```
   1 CGATCCCGCG AAATTAATAC GACTCACTAT AGGGAGACCA CAACGGTTTC CCTCTAGATC
  61 ACAAGTTTGT ACAAAAAAGC TGAACGAGAA ACGTAAAATG ATATAAATAT CAATATATTA
 121 AATTAGATTT TGCATAAAAA ACAGACTACA TAATACTGTA AAACACAACA TATCCAGTCA
 181 CTATGGCGGC CGCTAAGTTG GCAGCATCAC CCGACGCACT TTGCGCCGAA TAAATACCTG
 241 TGACGGAAGA TCACTTCGCA GAATAAATAA ATCCTGGTGT CCCTGTTGAT ACCGGGAAGC
 301 CCTGGGCCAA CTTTTGGCGA AAATGAGACG TTGATCGGCA CGTAAGAGGT TCCAACTTTC
 361 ACCATAATGA AATAAGATCA CTACCGGGCG TATTTTTTGA GTTATCGAGA TTTTCAGGAG
 421 CTAAGGAAGC TAAAATGGAG AAAAAAATCA CTGGATATAC CACCGTTGAT ATATCCCAAT
 481 GGCATCGTAA AGAACATTTT GAGGCATTTC AGTCAGTTGC TCAATGTACC TATAACCAGA
 541 CCGTTCAGCT GGATATTACG GCCTTTTTAA AGACCGTAAA GAAAAATAAG CACAAGTTTT
 601 ATCCGGCCTT TATTCACATT CTTGCCCGCC TGATGAATGC TCATCCGGAA TTCCGTATGG
 661 CAATGAAAGA CGGTGAGCTG GTGATATGGG ATAGTGTTCA CCCTTGTTAC ACCGTTTTCC
 721 ATGAGCAAAC TGAAACGTTT TCATCGCTCT GGAGTGAATA CCACGACGAT TTCCGGCAGT
 781 TTCTACACAT ATATTCGCAA GATGTGGCGT GTTACGGTGA AAACCTGGCC TATTTCCCTA
 841 AAGGGTTTAT TGAGAATATG TTTTTCGTCT CAGCCAATCC CTGGGTGAGT TTCACCAGTT
 901 TTGATTTAAA CGTGGCCAAT ATGGACAACT TCTTCGCCCC CGTTTTCACC ATGGGCAAAT
 961 ATTATACGCA AGGCGACAAG GTGCTGATGC CGCTGGCGAT TCAGGTTCAT CATGCCGTCT
1021 GTGATGGCTT CCATGTCGGC AGAATGCTTA ATGAATTACA ACAGTACTGC GATGAGTGGC
1081 AGGGCGGGGC GTAAACGCGT GGATCCGGCT TACTAAAAGC CAGATAACAG TATGCGTATT
1141 TGCGCGCTGA TTTTTGCGGT ATAAGAATAT ATACTGATAT GTATACCCGA AGTATGTCAA
1201 AAAGAGGTGT GCTATGAAGC AGCGTATTAC AGTGACAGTT GACAGCGACA GCTATCAGTT
1261 GCTCAAGGCA TATATGATGT CAATATCTCC GGTCTGGTAA GCACAACCAT GCAGAATGAA
1321 GCCCGTCGTC TGCGTGCCGA ACGCTGGAAA GCGGAAAATC AGGAAGGGAT GGCTGAGGTC
1381 GCCCGGTTTA TTGAAATGAA CGGCTCTTTT GCTGACGAGA ACAGGGACTG GTGAAATGCA
1441 GTTTAAGGTT TACACCTATA AAAGAGAGAG CCGTTATCGT CTGTTTGTGG ATGTACAGAG
1501 TGATATTATT GACACGCCCG GGCGACGGAT GGTGATCCCC CTGGCCAGTG CACGTCTGCT
1561 GTCAGATAAA GTCTCCCGTG AACTTTACCC GGTGGTGCAT ATCGGGGATG AAAGCTGGCG
1621 CATGATGACC ACCGATATGG CCAGTGTGCC GGTCTCCGTT ATCGGGGAAG AAGTGGCTGA
1681 TCTCAGCCAC CGCGAAAATG ACATCAAAAA CGCCATTAAC CTGATGTTCT GGGGAATATA
1741 AATGTCAGGC TCCCTTATAC ACAGCCAGTC TGCAGGTCGA CCATAGTGAC TGGATATGTT
1801 GTGTTTTACA GTATTATGTA GTCTGTTTTT TATGCAAAAT CTAATTTAAT ATATTGATAT
1861 TTATATCATT TTACGTTTCT CGTTCAGCTT TCTTGTACAA AGTGGTGATG ATCCGGCTGC
1921 TAACAAAGCC CGAAAGGAAG CTGAGTTGGC TGCTGCCACC GCTGAGCAAT AACTAGCATA
```

FIG.34B

```
1981 ACCCCTTGGG GCCTCTAAAC GGGTCTTGAG GGGTTTTTTG CTGAAAGGAG GAACTATATC
2041 CGGATATCCA CAGGACGGGT GTGGTCGCCA TGATCGCGTA GTCGATAGTG GCTCCAAGTA
2101 GCGAAGCGAG CAGGACTGGG CGGCGGCCAA AGCGGTCGGA CAGTGCTCCG AGAACGGGTG
2161 CGCATAGAAA TTGCATCAAC GCATATAGCG CTAGCAGCAC GCCATAGTGA CTGGCGATGC
2221 TGTCGGAATG GACGATATCC CGCAAGAGGC CCGGCAGTAC CGGCATAACC AAGCCTATGC
2281 CTACAGCATC CAGGGTGACG GTGCCGAGGA TGACGATGAG CGCATTGTTA GATTTCATAC
2341 ACGGTGCCTG ACTGCGTTAG CAATTTAACT GTGATAAACT ACCGCATTAA AGCTTATCGA
2401 TGATAAGCTG TCAAACATGA GAATTCTTGA AGACGAAAGG GCCTCGTGAT ACGCCTATTT
2461 TTATAGGTTA ATGTCATGAT AATAATGGTT TCTTAGACGT CAGGTGGCAC TTTTCGGGGA
2521 AATGTGCGCG GAACCCCTAT TTGTTTATTT TTCTAAATAC ATTCAAATAT GTATCCGCTC
2581 ATGAGACAAT AACCCTGATA AATGCTTCAA TAATATTGAA AAAGGAAGAG TATGAGTATT
2641 CAACATTTCC GTGTCGCCCT TATTCCCTTT TTTGCGGCAT TTTGCCTTCC TGTTTTTGCT
2701 CACCCAGAAA CGCTGGTGAA AGTAAAAGAT GCTGAAGATC AGTTGGGTGC ACGAGTGGGT
2761 TACATCGAAC TGGATCTCAA CAGCGGTAAG ATCCTTGAGA GTTTTCGCCC CGAAGAACGT
2821 TTTCCAATGA TGAGCACTTT TAAAGTTCTG CTATGTGGCG CGGTATTATC CCGTGTTGAC
2881 GCCGGGCAAG AGCAACTCGG TCGCCGCATA CACTATTCTC AGAATGACTT GGTTGAGTAC
2941 TCACCAGTCA CAGAAAAGCA TCTTACGGAT GGCATGACAG TAAGAGAATT ATGCAGTGCT
3001 GCCATAACCA TGAGTGATAA CACTGCGGCC AACTTACTTC TGACAACGAT CGGAGGACCG
3061 AAGGAGCTAA CCGCTTTTTT GCACAACATG GGGGATCATG TAACTCGCCT TGATCGTTGG
3121 GAACCGGAGC TGAATGAAGC CATACCAAAC GACGAGCGTG ACACCACGAT GCCTGCAGCA
3181 ATGGCAACAA CGTTGCGCAA ACTATTAACT GGCGAACTAC TTACTCTAGC TTCCCGGCAA
3241 CAATTAATAG ACTGGATGGA GGCGGATAAA GTTGCAGGAC CACTTCTGCG CTCGGCCCTT
3301 CCGGCTGGCT GGTTTATTGC TGATAAATCT GGAGCCGGTG AGCGTGGGTC TCGCGGTATC
3361 ATTGCAGCAC TGGGGCCAGA TGGTAAGCCC TCCCGTATCG TAGTTATCTA CACGACGGGG
3421 AGTCAGGCAA CTATGGATGA ACGAAATAGA CAGATCGCTG AGATAGGTGC CTCACTGATT
3481 AAGCATTGGT AACTGTCAGA CCAAGTTTAC TCATATATAC TTTAGATTGA TTTAAAACTT
3541 CATTTTTAAT TTAAAAGGAT CTAGGTGAAG ATCCTTTTTG ATAATCTCAT GACCAAAATC
3601 CCTTAACGTG AGTTTTCGTT CCACTGAGCG TCAGACCCCG TAGAAAAGAT CAAAGGATCT
3661 TCTTGAGATC CTTTTTTTCT GCGCGTAATC TGCTGCTTGC AAACAAAAAA ACCACCGCTA
3721 CCAGCGGTGG TTTGTTTGCC GGATCAAGAG CTACCAACTC TTTTTCCGAA GGTAACTGGC
3781 TTCAGCAGAG CGCAGATACC AAATACTGTC CTTCTAGTGT AGCCGTAGTT AGGCCACCAC
3841 TTCAAGAACT CTGTAGCACC GCCTACATAC CTCGCTCTGC TAATCCTGTT ACCAGTGGCT
3901 GCTGCCAGTG GCGATAAGTC GTGTCTTACC GGGTTGGACT CAAGACGATA GTTACCGGAT
3961 AAGGCGCAGC GGTCGGGCTG AACGGGGGGT TCGTGCACAC AGCCCAGCTT GGAGCGAACG
4021 ACCTACACCG AACTGAGATA CCTACAGCGT GAGCTATGAG AAAGCGCCAC GCTTCCCGAA
4081 GGGAGAAAGG CGGACAGGTA TCCGGTAAGC GGCAGGGTCG GAACAGGAGA GCGCACGAGG
4141 GAGCTTCCAG GGGGAAACGC CTGGTATCTT TATAGTCCTG TCGGGTTTCG CCACCTCTGA
4201 CTTGAGCGTC GATTTTTGTG ATGCTCGTCA GGGGGGCGGA GCCTATGGAA AAACGCCAGC
4261 AACGCGGCCT TTTTACGGTT CCTGGCCTTT TGCTGGCCTT TTGCTCACAT GTTCTTTCCT
4321 GCGTTATCCC CTGATTCTGT GGATAACCGT ATTACCGCCT TTGAGTGAGC TGATACCGCT
4381 CGCCGCAGCC GAACGACCGA GCGCAGCGAG TCAGTGAGCG AGGAAGCGGA AGAGCGCCTG
```

FIG.34C

4441 ATGCGGTATT TTCTCCTTAC GCATCTGTGC GGTATTTCAC ACCGCATATA TGGTGCACTC
4501 TCAGTACAAT CTGCTCTGAT GCCGCATAGT TAAGCCAGTA TACACTCCGC TATCGCTACG
4561 TGACTGGGTC ATGGCTGCGC CCCGACACCC GCCAACACCC GCTGACGCGC CCTGACGGGC
4621 TTGTCTGCTC CCGGCATCCG CTTACAGACA AGCTGTGACC GTCTCCGGGA GCTGCATGTG
4681 TCAGAGGTTT TCACCGTCAT CACCGAAACG CGCGAGGCAG CTGCGGTAAA GCTCATCAGC
4741 GTGGTCGTGA AGCGATTCAC AGATGTCTGC CTGTTCATCC GCGTCCAGCT CGTTGAGTTT
4801 CTCCAGAAGC GTTAATGTCT GGCTTCTGAT AAAGCGGGCC ATGTTAAGGG CGGTTTTTTC
4861 CTGTTTGGTC ACTGATGCCT CCGTGTAAGG GGGATTTCTG TTCATGGGGG TAATGATACC
4921 GATGAAACGA GAGAGGATGC TCACGATACG GGTTACTGAT GATGAACATG CCCGGTTACT
4981 GGAACGTTGT GAGGGTAAAC AACTGGCGGT ATGGATGCGG CGGGACCAGA GAAAAATCAC
5041 TCAGGGTCAA TGCCAGCGCT TCGTTAATAC AGATGTAGGT GTTCCACAGG GTAGCCAGCA
5101 GCATCCTGCG ATGCAGATCC GGAACATAAT GGTGCAGGGC GCTGACTTCC GCGTTTCCAG
5161 ACTTTACGAA ACACGGAAAC CGAAGACCAT TCATGTTGTT GCTCAGGTCG CAGACGTTTT
5221 GCAGCAGCAG TCGCTTCACG TTCGCTCGCG TATCGGTGAT TCATTCTGCT AACCAGTAAG
5281 GCAACCCCGC CAGCCTAGCC GGGTCCTCAA CGACAGGAGC ACGATCATGC GCACCCGTGG
5341 CCAGGACCCA ACGCTGCCCG AGATGCGCCG CGTGCGGCTG CTGGAGATGG CGGACGCGAT
5401 GGATATGTTC TGCCAAGGGT TGGTTTGCGC ATTCACAGTT CTCCGCAAGA ATTGATTGGC
5461 TCCAATTCTT GGAGTGGTGA ATCCGTTAGC GAGGTGCCGC CGGCTTCCAT TCAGGTCGAG
5521 GTGGCCCGGC TCCATGCACC GCGACGCAAC GCGGGGAGGC AGACAAGGTA TAGGGCGGCG
5581 CCTACAATCC ATGCCAACCC GTTCCATGTG CTCGCCGAGG CGGCATAAAT CGCCGTGACG
5641 ATCAGCGGTC CAGTGATCGA AGTTAGGCTG GTAAGAGCCG CGAGCGATCC TTGAAGCTGT
5701 CCCTGATGGT CGTCATCTAC CTGCCTGGAC AGCATGGCCT GCAACGCGGG CATCCCGATG
5761 CCGCCGGAAG CGAGAAGAAT CATAATGGGG AAGGCCATCC AGCCTCGCGT CGCGAACGCC
5821 AGCAAGACGT AGCCCAGCGC GTCGGCCGCC ATGCCGGCGA TAATGGCCTG CTTCTCGCCG
5881 AAACGTTTGG TGGCGGGACC AGTGACGAAG GCTTGAGCGA GGGCGTGCAA GATTCCGAAT
5941 ACCGCAAGCG ACAGGCCGAT CATCGTCGCG CTCCAGCGAA AGCGGTCCTC GCCGAAAATG
6001 ACCCAGAGCG CTGCCGGCAC CTGTCCTACG AGTTGCATGA TAAAGAAGAC AGTCATAAGT
6061 GCGGCGACGA TAGTCATGCC CCGCGCCCAC CGGAAGGAGC TGACTGGGTT GAAGGCTCTC
6121 AAGGGCATCG GTCGATCGAC GCTCTCCCTT ATGCGACTCC TGCATTAGGA AGCAGCCCAG
6181 TAGTAGGTTG AGGCCGTTGA GCACCGCCGC CGCAAGGAAT GGTGCATGCA AGGAGATGGC
6241 GCCCAACAGT CCCCCGGCCA CGGGGCCTGC CACCATACCC ACGCCGAAAC AAGCGCTCAT
6301 GAGCCCGAAG TGGCGAGCCC GATCTTCCCC ATCGGTGATG TCGGCGATAT AGGCGCCAGC
6361 AACCGCACCT GTGGCGCCGG TGATGCCGGC CACGATGCGT CCGGCGTAGA GGATCGAGAT
6421 CT

FIG.34D pDest15 Glutathione-S-transferase Fusion in E. Coli, T7 Promoter

```
                                   T7 Promoter                 mRNA
1   aat cga gat ctc gat ccc gcg aaa ttaata cga ctc act ata ggg aga cca
    tta gct cta gag cta ggg cgc ttt aat tat gct gag tga tat ccc tct ggt

                   XbaI
52  caa cgg ttt ccc tct aga aat aat ttt gtt taa ctt taa gaa gga gat ata
    gtt gcc aaa ggg aga tct tta tta aaa caa att gaa att ctt cct cta tat

NdeI  M   S   P   I   L - - -
103 cat atg tcc cct ata cta ggt tat tgg aaa att aag ggc ctt gtg caa ccc
    gta tac agg gga tat gat cca ata acc ttt taa ttc ccg gaa cac gtt ggg
             Start Translation GST

154 act cga ctt ctt ttg gaa tat ctt gaa gaa aaa tat gaa gag cat ttg tat
    tga gct gaa gaa aac ctt ata gaa ctt ctt ttt ata ctt ctc gta aac ata

715 cag ggc tgg caa gcc acg ttt ggt ggt ggc gac cat cct cca aaa tcg gat
    gtc ccg acc gtt cgg tgc aaa cca cca ccg ctg gta gga ggt ttt agc cta

                      - - -   S   N   Q   T   S   L   Y   K   K   A
766 ctg gtt ccg cgt cca tgg tcg aat caa aca agt ttg tac aaa aaa gct gaa
    gac caa ggc gca ggt acc agc tta gtt tgt tca aac atg ttt ttt cga ctt

                                   attR1        Int
817 cga gaa acg taa aat gat ata aat atc aat ata tta aat tag att ttg cat
    gct ctt tgc att tta cta tat tta tag tta tat aat tta atc taa aac gta
```

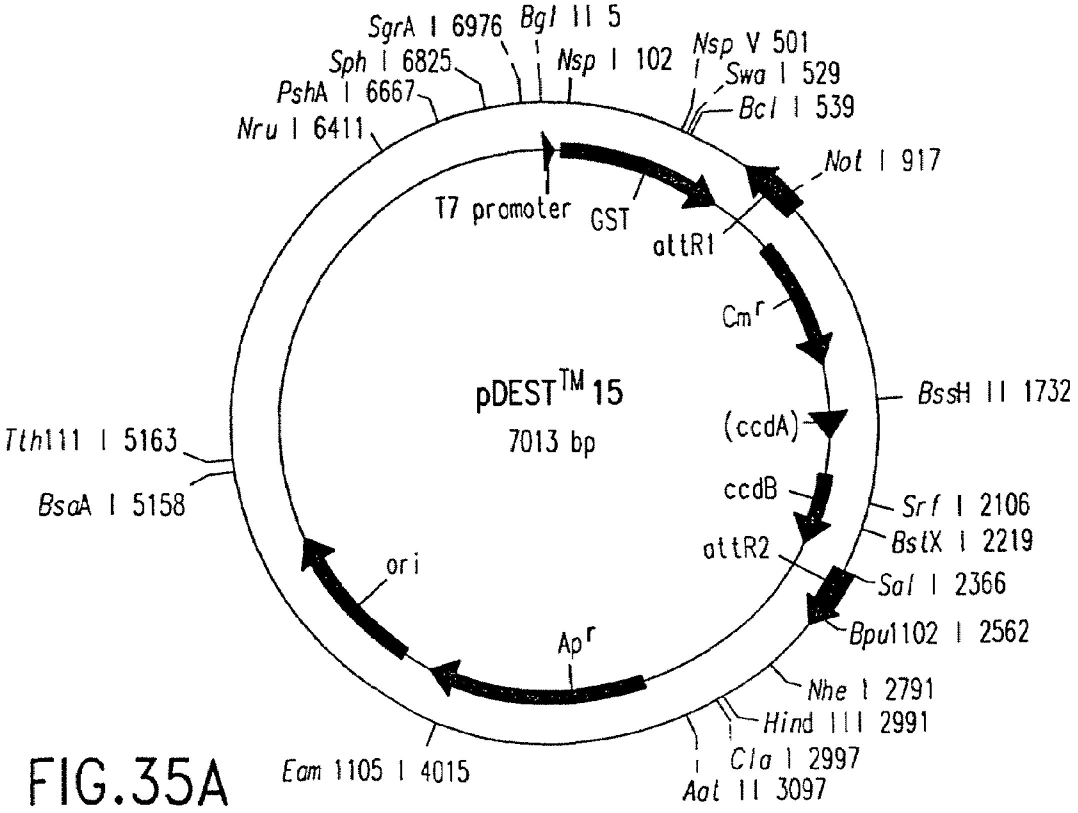

FIG.35A pDEST15 7013 bp

| Location (Base Nos.) | Gene Encoded |
|---|---|
| 108..776 | GST |
| 916..792 | attR1 |
| 1025..1537 | CmR |
| 1804..1888 | inactivated ccdA |
| 2026..2331 | ccdB |
| 2372..2496 | attR2 |
| 3233..4093 | ampR |

```
   1 ATCGAGATCT CGATCCCGCG AAATTAATAC GACTCACTAT AGGGAGACCA CAACGGTTTC
  61 CCTCTAGAAA TAATTTTGTT TAACTTTAAG AAGGAGATAT ACATATGTCC CCTATACTAG
 121 GTTATTGGAA AATTAAGGGC CTTGTGCAAC CCACTCGACT TCTTTTGGAA TATCTTGAAG
 181 AAAAATATGA AGAGCATTTG TATGAGCGCG ATGAAGGTGA TAAATGGCGA AACAAAAAGT
 241 TTGAATTGGG TTTGGAGTTT CCCAATCTTC CTTATTATAT TGATGGTGAT GTTAAATTAA
 301 CACAGTCTAT GGCCATCATA CGTTATATAG CTGACAAGCA CAACATGTTG GGTGGTTGTC
 361 CAAAAGAGCG TGCAGAGATT TCAATGCTTG AAGGAGCGGT TTTGGATATT AGATACGGTG
 421 TTTCGAGAAT TGCATATAGT AAAGACTTTG AAACTCTCAA AGTTGATTTT CTTAGCAAGC
 481 TACCTGAAAT GCTGAAAATG TTCGAAGATC GTTTATGTCA TAAAACATAT TTAAATGGTG
 541 ATCATGTAAC CCATCCTGAC TTCATGTTGT ATGACGCTCT TGATGTTGTT TTATACATGG
 601 ACCCAATGTG CCTGGATGCG TTCCCAAAAT TAGTTTGTTT TAAAAAACGT ATTGAAGCTA
 661 TCCCACAAAT TGATAAGTAC TTGAAATCCA GCAAGTATAT AGCATGGCCT TTGCAGGGCT
 721 GGCAAGCCAC GTTTGGTGGT GGCGACCATC CTCCAAAATC GGATCTGGTT CCGCGTCCAT
 781 GGTCGAATCA AACAAGTTTG TACAAAAAAG CTGAACGAGA AACGTAAAAT GATATAAATA
 841 TCAATATATT AAATTAGATT TTGCATAAAA AACAGACTAC ATAATACTGT AAAACACAAC
 901 ATATCCAGTC ACTATGGCGG CCGCATTAGG CACCCCAGGC TTTACACTTT ATGCTTCCGG
 961 CTCGTATAAT GTGTGGATTT TGAGTTAGGA TCCGTCGAGA TTTTCAGGAG CTAAGGAAGC
1021 TAAAATGGAG AAAAAAATCA CTGGATATAC CACCGTTGAT ATATCCCAAT GGCATCGTAA
1081 AGAACATTTT GAGGCATTTC AGTCAGTTGC TCAATGTACC TATAACCAGA CCGTTCAGCT
1141 GGATATTACG GCCTTTTTAA AGACCGTAAA GAAAAATAAG CACAAGTTTT ATCCGGCCTT
1201 TATTCACATT CTTGCCCGCC TGATGAATGC TCATCCGGAA TTCCGTATGG CAATGAAAGA
1261 CGGTGAGCTG GTGATATGGG ATAGTGTTCA CCCTTGTTAC ACCGTTTTCC ATGAGCAAAC
1321 TGAAACGTTT TCATCGCTCT GGAGTGAATA CCACGACGAT TTCCGGCAGT TTCTACACAT
1381 ATATTCGCAA GATGTGGCGT GTTACGGTGA AAACCTGGCC TATTTCCCTA AAGGGTTTAT
1441 TGAGAATATG TTTTTCGTCT CAGCCAATCC CTGGGTGAGT TTCACCAGTT TTGATTTAAA
1501 CGTGGCCAAT ATGGACAACT TCTTCGCCCC CGTTTTCACC ATGGGCAAAT ATTATACGCA
1561 AGGCGACAAG GTGCTGATGC CGCTGGCGAT TCAGGTTCAT CATGCCGTCT GTGATGGCTT
1621 CCATGTCGGC AGAATGCTTA ATGAATTACA ACAGTACTGC GATGAGTGGC AGGGCGGGGC
1681 GTAATCTAGA GGATCCGGCT TACTAAAAGC CAGATAACAG TATGCGTATT TGCGCGCTGA
1741 TTTTTGCGGT ATAAGAATAT ATACTGATAT GTATACCCGA AGTATGTCAA AAAGAGGTGT
1801 GCTATGAAGC AGCGTATTAC AGTGACAGTT GACAGCGACA GCTATCAGTT GCTCAAGGCA
```

FIG.35B

1861 TATATGATGT CAATATCTCC GGTCTGGTAA GCACAACCAT GCAGAATGAA GCCCGTCGTC
1921 TGCGTGCCGA ACGCTGGAAA GCGGAAAATC AGGAAGGGAT GGCTGAGGTC GCCCGGTTTA
1981 TTGAAATGAA CGGCTCTTTT GCTGACGAGA ACAGGGACTG GTGAAATGCA GTTTAAGGTT
2041 TACACCTATA AAAGAGAGAG CCGTTATCGT CTGTTTGTGG ATGTACAGAG TGATATTATT
2101 GACACGCCCG GGCGACGGAT GGTGATCCCC CTGGCCAGTG CACGTCTGCT GTCAGATAAA
2161 GTCTCCCGTG AACTTTACCC GGTGGTGCAT ATCGGGGATG AAAGCTGGCG CATGATGACC
2221 ACCGATATGG CCAGTGTGCC GGTCTCCGTT ATCGGGGAAG AAGTGGCTGA TCTCAGCCAC
2281 CGCGAAAATG ACATCAAAAA CGCCATTAAC CTGATGTTCT GGGGAATATA AATGTCAGGC
2341 TCCCTTATAC ACAGCCAGTC TGCAGGTCGA CCATAGTGAC TGGATATGTT GTGTTTTACA
2401 GTATTATGTA GTCTGTTTTT TATGCAAAAT CTAATTTAAT ATATTGATAT TTATATCATT
2461 TTACGTTTCT CGTTCAGCTT TCTTGTACAA AGTGGTTTGA TTCGACCCGG GATCCGGCTG
2521 CTAACAAAGC CCGAAAGGAA GCTGAGTTGG CTGCTGCCAC CGCTGAGCAA TAACTAGCAT
2581 AACCCCTTGG GGCCTCTAAA CGGGTCTTGA GGGGTTTTTT GCTGAAAGGA GGAACTATAT
2641 CCGGATATCC ACAGGACGGG TGTGGTCGCC ATGATCGCGT AGTCGATAGT GGCTCCAAGT
2701 AGCGAAGCGA GCAGGACTGG GCGGCGGCCA AAGCGGTCGG ACAGTGCTCC GAGAACGGGT
2761 GCGCATAGAA ATTGCATCAA CGCATATAGC GCTAGCAGCA CGCCATAGTG ACTGGCGATG
2821 CTGTCGGAAT GGACGATATC CCGCAAGAGG CCCGGCAGTA CCGGCATAAC CAAGCCTATG
2881 CCTACAGCAT CCAGGGTGAC GGTGCCGAGG ATGACGATGA GCGCATTGTT AGATTTCATA
2941 CACGGTGCCT GACTGCGTTA GCAATTTAAC TGTGATAAAC TACCGCATTA AAGCTTATCG
3001 ATGATAAGCT GTCAAACATG AGAATTCTTG AAGACGAAAG GGCCTCGTGA TACGCCTATT
3061 TTTATAGGTT AATGTCATGA TAATAATGGT TTCTTAGACG TCAGGTGGCA CTTTTCGGGG
3121 AAATGTGCGC GGAACCCCTA TTTGTTTATT TTTCTAAATA CATTCAAATA TGTATCCGCT
3181 CATGAGACAA TAACCCTGAT AAATGCTTCA ATAATATTGA AAAAGGAAGA GTATGAGTAT
3241 TCAACATTTC CGTGTCGCCC TTATTCCCTT TTTTGCGGCA TTTTGCCTTC CTGTTTTTGC
3301 TCACCCAGAA ACGCTGGTGA AAGTAAAAGA TGCTGAAGAT CAGTTGGGTG CACGAGTGGG
3361 TTACATCGAA CTGGATCTCA ACAGCGGTAA GATCCTTGAG AGTTTTCGCC CCGAAGAACG
3421 TTTTCCAATG ATGAGCACTT TTAAAGTTCT GCTATGTGGC GCGGTATTAT CCCGTGTTGA
3481 CGCCGGGCAA GAGCAACTCG GTCGCCGCAT ACACTATTCT CAGAATGACT TGGTTGAGTA
3541 CTCACCAGTC ACAGAAAAGC ATCTTACGGA TGGCATGACA GTAAGAGAAT TATGCAGTGC
3601 TGCCATAACC ATGAGTGATA ACACTGCGGC CAACTTACTT CTGACAACGA TCGGAGGACC
3661 GAAGGAGCTA ACCGCTTTTT TGCACAACAT GGGGGATCAT GTAACTCGCC TTGATCGTTG
3721 GGAACCGGAG CTGAATGAAG CCATACCAAA CGACGAGCGT GACACCACGA TGCCTGCAGC
3781 AATGGCAACA ACGTTGCGCA AACTATTAAC TGGCGAACTA CTTACTCTAG CTTCCCGGCA
3841 ACAATTAATA GACTGGATGG AGGCGGATAA AGTTGCAGGA CCACTTCTGC GCTCGGCCCT
3901 TCCGGCTGGC TGGTTTATTG CTGATAAATC TGGAGCCGGT GAGCGTGGGT CTCGCGGTAT
3961 CATTGCAGCA CTGGGGCCAG ATGGTAAGCC CTCCCGTATC GTAGTTATCT ACACGACGGG
4021 GAGTCAGGCA ACTATGGATG AACGAAATAG ACAGATCGCT GAGATAGGTG CCTCACTGAT
4081 TAAGCATTGG TAACTGTCAG ACCAAGTTTA CTCATATATA CTTTAGATTG ATTTAAAACT
4141 TCATTTTTAA TTTAAAAGGA TCTAGGTGAA GATCCTTTTT GATAATCTCA TGACCAAAAT
4201 CCCTTAACGT GAGTTTTCGT TCCACTGAGC GTCAGACCCC GTAGAAAAGA TCAAAGGATC
4261 TTCTTGAGAT CCTTTTTTTC TGCGCGTAAT CTGCTGCTTG CAAACAAAAA AACCACCGCT

FIG.35C

4321 ACCAGCGGTG GTTTGTTTGC CGGATCAAGA GCTACCAACT CTTTTTCCGA AGGTAACTGG
4381 CTTCAGCAGA GCGCAGATAC CAAATACTGT CCTTCTAGTG TAGCCGTAGT TAGGCCACCA
4441 CTTCAAGAAC TCTGTAGCAC CGCCTACATA CCTCGCTCTG CTAATCCTGT TACCAGTGGC
4501 TGCTGCCAGT GGCGATAAGT CGTGTCTTAC CGGGTTGGAC TCAAGACGAT AGTTACCGGA
4561 TAAGGCGCAG CGGTCGGGCT GAACGGGGGG TTCGTGCACA CAGCCCAGCT TGGAGCGAAC
4621 GACCTACACC GAACTGAGAT ACCTACAGCG TGAGCTATGA GAAAGCGCCA CGCTTCCCGA
4681 AGGGAGAAAG GCGGACAGGT ATCCGGTAAG CGGCAGGGTC GGAACAGGAG AGCGCACGAG
4741 GGAGCTTCCA GGGGGAAACG CCTGGTATCT TTATAGTCCT GTCGGGTTTC GCCACCTCTG
4801 ACTTGAGCGT CGATTTTTGT GATGCTCGTC AGGGGGGCGG AGCCTATGGA AAAACGCCAG
4861 CAACGCGGCC TTTTTACGGT TCCTGGCCTT TTGCTGGCCT TTTGCTCACA TGTTCTTTCC
4921 TGCGTTATCC CCTGATTCTG TGGATAACCG TATTACCGCC TTTGAGTGAG CTGATACCGC
4981 TCGCCGCAGC CGAACGACCG AGCGCAGCGA GTCAGTGAGC GAGGAAGCGG AAGAGCGCCT
5041 GATGCGGTAT TTTCTCCTTA CGCATCTGTG CGGTATTTCA CACCGCATAT ATGGTGCACT
5101 CTCAGTACAA TCTGCTCTGA TGCCGCATAG TTAAGCCAGT ATACACTCCG CTATCGCTAC
5161 GTGACTGGGT CATGGCTGCG CCCCGACACC CGCCAACACC CGCTGACGCG CCCTGACGGG
5221 CTTGTCTGCT CCCGGCATCC GCTTACAGAC AAGCTGTGAC CGTCTCCGGG AGCTGCATGT
5281 GTCAGAGGTT TTCACCGTCA TCACCGAAAC GCGCGAGGCA GCTGCGGTAA AGCTCATCAG
5341 CGTGGTCGTG AAGCGATTCA CAGATGTCTG CCTGTTCATC CGCGTCCAGC TCGTTGAGTT
5401 TCTCCAGAAG CGTTAATGTC TGGCTTCTGA TAAAGCGGGC CATGTTAAGG GCGGTTTTTT
5461 CCTGTTTGGT CACTGATGCC TCCGTGTAAG GGGGATTTCT GTTCATGGGG GTAATGATAC
5521 CGATGAAACG AGAGAGGATG CTCACGATAC GGGTTACTGA TGATGAACAT GCCCGGTTAC
5581 TGGAACGTTG TGAGGGTAAA CAACTGGCGG TATGGATGCG GCGGGACCAG AGAAAAATCA
5641 CTCAGGGTCA ATGCCAGCGC TTCGTTAATA CAGATGTAGG TGTTCCACAG GGTAGCCAGC
5701 AGCATCCTGC GATGCAGATC CGGAACATAA TGGTGCAGGG CGCTGACTTC CGCGTTTCCA
5761 GACTTTACGA AACACGGAAA CCGAAGACCA TTCATGTTGT TGCTCAGGTC GCAGACGTTT
5821 TGCAGCAGCA GTCGCTTCAC GTTCGCTCGC GTATCGGTGA TTCATTCTGC TAACCAGTAA
5881 GGCAACCCCG CCAGCCTAGC CGGGTCCTCA ACGACAGGAG CACGATCATG CGCACCCGTG
5941 GCCAGGACCC AACGCTGCCC GAGATGCGCC GCGTGCGGCT GCTGGAGATG GCGGACGCGA
6001 TGGATATGTT CTGCCAAGGG TTGGTTTGCG CATTCACAGT TCTCCGCAAG AATTGATTGG
6061 CTCCAATTCT TGGAGTGGTG AATCCGTTAG CGAGGTGCCG CCGGCTTCCA TTCAGGTCGA
6121 GGTGGCCCGG CTCCATGCAC CGCGACGCAA CGCGGGGAGG CAGACAAGGT ATAGGGCGGC
6181 GCCTACAATC CATGCCAACC CGTTCCATGT GCTCGCCGAG GCGGCATAAA TCGCCGTGAC
6241 GATCAGCGGT CCAGTGATCG AAGTTAGGCT GGTAAGAGCC GCGAGCGATC CTTGAAGCTG
6301 TCCCTGATGG TCGTCATCTA CCTGCCTGGA CAGCATGGCC TGCAACGCGG GCATCCCGAT
6361 GCCGCCGGAA GCGAGAAGAA TCATAATGGG GAAGGCCATC CAGCCTCGCG TCGCGAACGC
6421 CAGCAAGACG TAGCCCAGCG CGTCGGCCGC CATGCCGGCG ATAATGGCCT GCTTCTCGCC
6481 GAAACGTTTG GTGGCGGGAC CAGTGACGAA GGCTTGAGCG AGGGCGTGCA AGATTCCGAA
6541 TACCGCAAGC GACAGGCCGA TCATCGTCGC GCTCCAGCGA AAGCGGTCCT CGCCGAAAAT
6601 GACCCAGAGC GCTGCCGGCA CCTGTCCTAC GAGTTGCATG ATAAAGAAGA CAGTCATAAG
6661 TGCGGCGACG ATAGTCATGC CCCGCGCCCA CCGGAAGGAG CTGACTGGGT TGAAGGCTCT
6721 CAAGGGCATC GGTCGATCGA CGCTCTCCCT TATGCGACTC CTGCATTAGG AAGCAGCCCA
6781 GTAGTAGGTT GAGGCCGTTG AGCACCGCCG CCGCAAGGAA TGGTGCATGC AAGGAGATGG
6841 CGCCCAACAG TCCCCCGGCC ACGGGGCCTG CCACCATACC CACGCCGAAA CAAGCGCTCA
6901 TGAGCCCGAA GTGGCGAGCC CGATCTTCCC CATCGGTGAT GTCGGCGATA TAGGCGCCAG
6961 CAACCGCACC TGTGGCGCCG GTGATGCCGG CCACGATGCG TCCGGCGTAG AGG

FIG.35D pDEST16 6675 bp

| Location (Base Nos.) | Gene Encoded |
|---|---|
| 104..457 | trxA |
| 585..461 | attR1 |
| 694..1353 | CmR |
| 1473..1557 | inactivated ccdA |
| 1695..2000 | ccdB |
| 2041..2165 | attR2 |

```
   1 AGATCTCGAT CCCGCGAAAT TAATACGACT CACTATAGGG AGACCACAAC GGTTTCCCTC
  61 TAGAAATAAT TTTGTTTAAC TTTAAGAAGG AGATATACAT ATGAGCGATA AAATTATTCA
 121 CCTGACTGAC GACAGTTTTG ACACGGATGT ACTCAAAGCG GACGGGGCGA TCCTCGTCGA
 181 TTTCTGGGCA GAGTGGTGCG GTCCGTGCAA AATGATCGCC CCGATTCTGG ATGAAATCGC
 241 TGACGAATAT CAGGGCAAAC TGACCGTTGC AAAACTGAAC ATCGATCAAA ACCCTGGCAC
 301 TGCGCCGAAA TATGGCATCC GTGGTATCCC GACTCTGCTG CTGTTCAAAA ACGGTGAAGT
 361 GGCGGCAACC AAAGTGGGTG CACTGTCTAA AGGTCAGTTG AAAGAGTTCC TCGACGCTAA
 421 CCTGGCCGGT TCTGGTTCTG GTGATGACGA TGACAAGATC ACAAGTTTGT ACAAAAAAGC
 481 TGAACGAGAA ACGTAAAATG ATATAAATAT CAATATATTA AATTAGATTT TGCATAAAAA
 541 ACAGACTACA TAATACTGTA AAACACAACA TATCCAGTCA CTATGGCGGC CGCATTAGGC
 601 ACCCCAGGCT TTACACTTTA TGCTTCCGGC TCGTATAATG TGTGGATTTT GAGTTAGGAT
 661 CCGGCGAGAT TTTCAGGAGC TAAGGAAGCT AAAATGGAGA AAAAAATCAC TGGATATACC
 721 ACCGTTGATA TATCCCAATG GCATCGTAAA GAACATTTTG AGGCATTTCA GTCAGTTGCT
 781 CAATGTACCT ATAACCAGAC CGTTCAGCTG GATATTACGG CCTTTTTAAA GACCGTAAAG
 841 AAAAATAAGC ACAAGTTTTA TCCGGCCTTT ATTCACATTC TTGCCCGCCT GATGAATGCT
 901 CATCCGGAAT TCCGTATGGC AATGAAAGAC GGTGAGCTGG TGATATGGGA TAGTGTTCAC
 961 CCTTGTTACA CCGTTTTCCA TGAGCAAACT GAAACGTTTT CATCGCTCTG GAGTGAATAC
1021 CACGACGATT TCCGGCAGTT TCTACACATA TATTCGCAAG ATGTGGCGTG TTACGGTGAA
1081 AACCTGGCCT ATTTCCCTAA AGGGTTTATT GAGAATATGT TTTTCGTCTC AGCCAATCCC
1141 TGGGTGAGTT TCACCAGTTT TGATTTAAAC GTGGCCAATA TGGACAACTT CTTCGCCCCC
1201 GTTTTCACCA TGGGCAAATA TTATACGCAA GGCGACAAGG TGCTGATGCC GCTGGCGATT
1261 CAGGTTCATC ATGCCGTCTG TGATGGCTTC CATGTCGGCA GAATGCTTAA TGAATTACAA
1321 CAGTACTGCG ATGAGTGGCA GGGCGGGGCG TAAACGCGTG GATCCGGCTT ACTAAAAGCC
1381 AGATAACAGT ATGCGTATTT GCGCGCTGAT TTTTGCGGTA TAAGAATATA TACTGATATG
1441 TATACCCGAA GTATGTCAAA AAGAGGTGTG CTATGAAGCA GCGTATTACA GTGACAGTTG
1501 ACAGCGACAG CTATCAGTTG CTCAAGGCAT ATATGATGTC AATATCTCCG GTCTGGTAAG
1561 CACAACCATG CAGAATGAAG CCCGTCGTCT GCGTGCCGAA CGCTGGAAAG CGGAAAATCA
1621 GGAAGGGATG GCTGAGGTCG CCCGGTTTAT TGAAATGAAC GGCTCTTTTG CTGACGAGAA
1681 CAGGGACTGG TGAAATGCAG TTTAAGGTTT ACACCTATAA AAGAGAGAGC CGTTATCGTC
1741 TGTTTGTGGA TGTACAGAGT GATATTATTG ACACGCCCGG GCGACGGATG GTGATCCCCC
1801 TGGCCAGTGC ACGTCTGCTG TCAGATAAAG TCTCCCGTGA ACTTTACCCG GTGGTGCATA
1861 TCGGGGATGA AAGCTGGCGC ATGATGACCA CCGATATGGC CAGTGTGCCG GTCTCCGTTA
1921 TCGGGGAAGA AGTGGCTGAT CTCAGCCACC GCGAAAATGA CATCAAAAAC GCCATTAACC
```

FIG.36B

```
1981 TGATGTTCTG GGGAATATAA ATGTCAGGCT CCCTTATACA CAGCCAGTCT GCAGGTCGAC
2041 CATAGTGACT GGATATGTTG TGTTTTACAG TATTATGTAG TCTGTTTTTT ATGCAAAATC
2101 TAATTTAATA TATTGATATT TATATCATTT TACGTTTCTC GTTCAGCTTT CTTGTACAAA
2161 GTGGTGATGA TCCGGCTGCT AACAAAGCCC GAAAGGAAGC TGAGTTGGCT GCTGCCACCG
2221 CTGAGCAATA ACTAGCATAA CCCCTTGGGG CCTCTAAACG GGTCTTGAGG GGTTTTTTGC
2281 TGAAAGGAGG AACTATATCC GGATATCCAC AGGACGGGTG TGGTCGCCAT GATCGCGTAG
2341 TCGATAGTGG CTCCAAGTAG CGAAGCGAGC AGGACTGGGC GGCGGCCAAA GCGGTCGGAC
2401 AGTGCTCCGA GAACGGGTGC GCATAGAAAT TGCATCAACG CATATAGCGC TAGCAGCACG
2461 CCATAGTGAC TGGCGATGCT GTCGGAATGG ACGATATCCC GCAAGAGGCC CGGCAGTACC
2521 GGCATAACCA AGCCTATGCC TACAGCATCC AGGGTGACGG TGCCGAGGAT GACGATGAGC
2581 GCATTGTTAG ATTTCATACA CGGTGCCTGA CTGCGTTAGC AATTTAACTG TGATAAACTA
2641 CCGCATTAAA GCTTATCGAT GATAAGCTGT CAAACATGAG AATTCTTGAA GACGAAAGGG
2701 CCTCGTGATA CGCCTATTTT TATAGGTTAA TGTCATGATA ATAATGGTTT CTTAGACGTC
2761 AGGTGGCACT TTTCGGGGAA ATGTGCGCGG AACCCCTATT TGTTTATTTT TCTAAATACA
2821 TTCAAATATG TATCCGCTCA TGAGACAATA ACCCTGATAA ATGCTTCAAT AATATTGAAA
2881 AAGGAAGAGT ATGAGTATTC AACATTTCCG TGTCGCCCTT ATTCCCTTTT TTGCGGCATT
2941 TTGCCTTCCT GTTTTTGCTC ACCCAGAAAC GCTGGTGAAA GTAAAAGATG CTGAAGATCA
3001 GTTGGGTGCA CGAGTGGGTT ACATCGAACT GGATCTCAAC AGCGGTAAGA TCCTTGAGAG
3061 TTTTCGCCCC GAAGAACGTT TTCCAATGAT GAGCACTTTT AAAGTTCTGC TATGTGGCGC
3121 GGTATTATCC CGTGTTGACG CCGGGCAAGA GCAACTCGGT CGCCGCATAC ACTATTCTCA
3181 GAATGACTTG GTTGAGTACT CACCAGTCAC AGAAAAGCAT CTTACGGATG GCATGACAGT
3241 AAGAGAATTA TGCAGTGCTG CCATAACCAT GAGTGATAAC ACTGCGGCCA ACTTACTTCT
3301 GACAACGATC GGAGGACCGA AGGAGCTAAC CGCTTTTTTG CACAACATGG GGGATCATGT
3361 AACTCGCCTT GATCGTTGGG AACCGGAGCT GAATGAAGCC ATACCAAACG ACGAGCGTGA
3421 CACCACGATG CCTGCAGCAA TGGCAACAAC GTTGCGCAAA CTATTAACTG GCGAACTACT
3481 TACTCTAGCT TCCCGGCAAC AATTAATAGA CTGGATGGAG GCGGATAAAG TTGCAGGACC
3541 ACTTCTGCGC TCGGCCCTTC CGGCTGGCTG GTTTATTGCT GATAAATCTG GAGCCGGTGA
3601 GCGTGGGTCT CGCGGTATCA TTGCAGCACT GGGGCCAGAT GGTAAGCCCT CCCGTATCGT
3661 AGTTATCTAC ACGACGGGGA GTCAGGCAAC TATGGATGAA CGAAATAGAC AGATCGCTGA
3721 GATAGGTGCC TCACTGATTA AGCATTGGTA ACTGTCAGAC CAAGTTTACT CATATATACT
3781 TTAGATTGAT TTAAAACTTC ATTTTTAATT TAAAAGGATC TAGGTGAAGA TCCTTTTTGA
3841 TAATCTCATG ACCAAAATCC CTTAACGTGA GTTTTCGTTC CACTGAGCGT CAGACCCCGT
3901 AGAAAAGATC AAAGGATCTT CTTGAGATCC TTTTTTTCTG CGCGTAATCT GCTGCTTGCA
3961 AACAAAAAAA CCACCGCTAC CAGCGGTGGT TTGTTTGCCG GATCAAGAGC TACCAACTCT
4021 TTTTCCGAAG GTAACTGGCT TCAGCAGAGC GCAGATACCA AATACTGTCC TTCTAGTGTA
4081 GCCGTAGTTA GGCCACCACT TCAAGAACTC TGTAGCACCG CCTACATACC TCGCTCTGCT
4141 AATCCTGTTA CCAGTGGCTG CTGCCAGTGG CGATAAGTCG TGTCTTACCG GGTTGGACTC
4201 AAGACGATAG TTACCGGATA AGGCGCAGCG GTCGGGCTGA ACGGGGGGTT CGTGCACACA
4261 GCCCAGCTTG GAGCGAACGA CCTACACCGA ACTGAGATAC CTACAGCGTG AGCTATGAGA
4321 AAGCGCCACG CTTCCCGAAG GGAGAAAGGC GGACAGGTAT CCGGTAAGCG GCAGGGTCGG
4381 AACAGGAGAG CGCACGAGGG AGCTTCCAGG GGGAAACGCC TGGTATCTTT ATAGTCCTGT
```

FIG.36C

4441 CGGGTTTCGC CACCTCTGAC TTGAGCGTCG ATTTTTGTGA TGCTCGTCAG GGGGGCGGAG
4501 CCTATGGAAA AACGCCAGCA ACGCGGCCTT TTTACGGTTC CTGGCCTTTT GCTGGCCTTT
4561 TGCTCACATG TTCTTTCCTG CGTTATCCCC TGATTCTGTG GATAACCGTA TTACCGCCTT
4621 TGAGTGAGCT GATACCGCTC GCCGCAGCCG AACGACCGAG CGCAGCGAGT CAGTGAGCGA
4681 GGAAGCGGAA GAGCGCCTGA TGCGGTATTT TCTCCTTACG CATCTGTGCG GTATTTCACA
4741 CCGCATATAT GGTGCACTCT CAGTACAATC TGCTCTGATG CCGCATAGTT AAGCCAGTAT
4801 ACACTCCGCT ATCGCTACGT GACTGGGTCA TGGCTGCGCC CCGACACCCG CCAACACCCG
4861 CTGACGCGCC CTGACGGGCT TGTCTGCTCC CGGCATCCGC TTACAGACAA GCTGTGACCG
4921 TCTCCGGGAG CTGCATGTGT CAGAGGTTTT CACCGTCATC ACCGAAACGC GCGAGGCAGC
4981 TGCGGTAAAG CTCATCAGCG TGGTCGTGAA GCGATTCACA GATGTCTGCC TGTTCATCCG
5041 CGTCCAGCTC GTTGAGTTTC TCCAGAAGCG TTAATGTCTG GCTTCTGATA AAGCGGGCCA
5101 TGTTAAGGGC GGTTTTTTCC TGTTTGGTCA CTGATGCCTC CGTGTAAGGG GGATTTCTGT
5161 TCATGGGGGT AATGATACCG ATGAAACGAG AGAGGATGCT CACGATACGG GTTACTGATG
5221 ATGAACATGC CCGGTTACTG GAACGTTGTG AGGGTAAACA ACTGGCGGTA TGGATGCGGC
5281 GGGACCAGAG AAAAATCACT CAGGGTCAAT GCCAGCGCTT CGTTAATACA GATGTAGGTG
5341 TTCCACAGGG TAGCCAGCAG CATCCTGCGA TGCAGATCCG GAACATAATG GTGCAGGGCG
5401 CTGACTTCCG CGTTTCCAGA CTTTACGAAA CACGGAAACC GAAGACCATT CATGTTGTTG
5461 CTCAGGTCGC AGACGTTTTG CAGCAGCAGT CGCTTCACGT TCGCTCGCGT ATCGGTGATT
5521 CATTCTGCTA ACCAGTAAGG CAACCCCGCC AGCCTAGCCG GGTCCTCAAC GACAGGAGCA
5581 CGATCATGCG CACCCGTGGC CAGGACCCAA CGCTGCCCGA GATGCGCCGC GTGCGGCTGC
5641 TGGAGATGGC GGACGCGATG GATATGTTCT GCCAAGGGTT GGTTTGCGCA TTCACAGTTC
5701 TCCGCAAGAA TTGATTGGCT CCAATTCTTG GAGTGGTGAA TCCGTTAGCG AGGTGCCGCC
5761 GGCTTCCATT CAGGTCGAGG TGGCCCGGCT CCATGCACCG CGACGCAACG CGGGGAGGCA
5821 GACAAGGTAT AGGGCGGCGC CTACAATCCA TGCCAACCCG TTCCATGTGC TCGCCGAGGC
5881 GGCATAAATC GCCGTGACGA TCAGCGGTCC AGTGATCGAA GTTAGGCTGG TAAGAGCCGC
5941 GAGCGATCCT TGAAGCTGTC CCTGATGGTC GTCATCTACC TGCCTGGACA GCATGGCCTG
6001 CAACGCGGGC ATCCCGATGC CGCCGGAAGC GAGAAGAATC ATAATGGGGA AGGCCATCCA
6061 GCCTCGCGTC GCGAACGCCA GCAAGACGTA GCCCAGCGCG TCGGCCGCCA TGCCGGCGAT
6121 AATGGCCTGC TTCTCGCCGA AACGTTTGGT GGCGGGACCA GTGACGAAGG CTTGAGCGAG
6181 GGCGTGCAAG ATTCCGAATA CCGCAAGCGA CAGGCCGATC ATCGTCGCGC TCCAGCGAAA
6241 GCGGTCCTCG CCGAAAATGA CCCAGAGCGC TGCCGGCACC TGTCCTACGA GTTGCATGAT
6301 AAAGAAGACA GTCATAAGTG CGGCGACGAT AGTCATGCCC CGCGCCCACC GGAAGGAGCT
6361 GACTGGGTTG AAGGCTCTCA AGGGCATCGG TCGATCGACG CTCTCCCTTA TGCGACTCCT
6421 GCATTAGGAA GCAGCCCAGT AGTAGGTTGA GGCCGTTGAG CACCGCCGCC GCAAGGAATG
6481 GTGCATGCAA GGAGATGGCG CCCAACAGTC CCCCGGCCAC GGGGCCTGCC ACCATACCCA
6541 CGCCGAAACA AGCGCTCATG AGCCCGAAGT GGCGAGCCCG ATCTTCCCCA TCGGTGATGT
6601 CGGCGATATA GGCGCCAGCA ACCGCACCTG TGGCGCCGGT GATGCCGGCC ACGATGCGTC
6661 CGGCGTAGAG GATCG

FIG.36D

His6 Fusion in E. coli T7 Promoter

T7 Promoter mRNA

```
1 gat ccc gcg aaa tta ata cga ctc act ata ggg aga cca caa cgg ttt ccc
  cta ggg cgc ttt aat tat gct gag tga tat ccc tct ggt gtt gcc aaa ggg
```

Start Translation M S Y

```
52 tct aga aat aat ttt gtt taa ctt taa gaa gga gat ata cat atg tcg tac
   aga tct tta tta aaa caa att gaa att ctt cct cta tat gta tac agc atg
```

```
    Y   H   H   H   H   H   H   L   E   S   T   S   L   Y   K   K   A
103 tac cat cac cat cac cat cac ctc gaa tca aca agt ttg tac aaa aaa gct
    atg gta gtg gta gtg gta gtg gag ctt agt tgt tca aac atg ttt ttt cga
```

attR1 Int

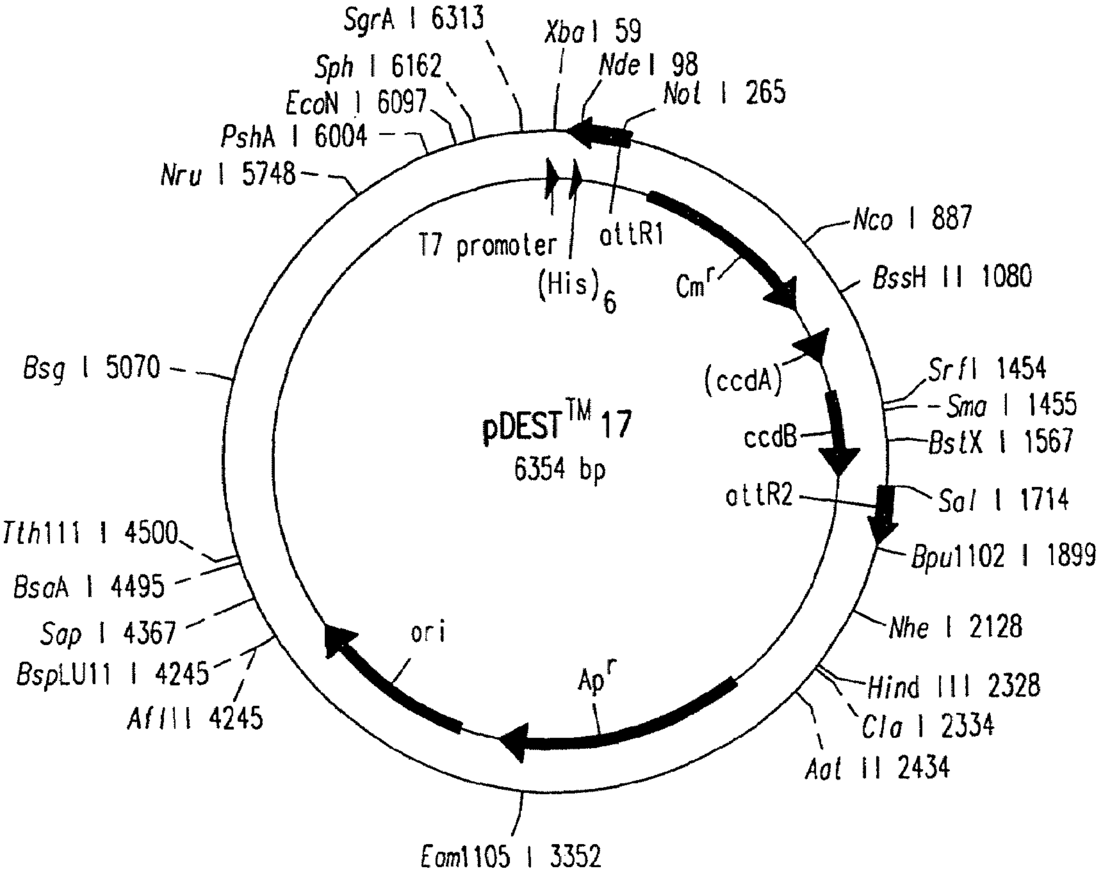

FIG.37A pDEST17 6354 bp

| Location (Base Nos.) | Gene Encoded |
|---|---|
| 258..134 | attR1 |
| 367..1026 | CmR |
| 1146..1230 | inactivated ccdA |
| 1368..1673 | ccdB |
| 1714..1838 | attR2 |
| 2564..3421 | ampR |

```
   1 CGATCCCGCG AAATTAATAC GACTCACTAT AGGGAGACCA CAACGGTTTC CCTCTAGAAA
  61 TAATTTTGTT TAACTTTAAG AAGGAGATAT ACATATGTCG TACTACCATC ACCATCACCA
 121 TCACCTCGAA TCAACAAGTT TGTACAAAAA AGCTGAACGA GAAACGTAAA ATGATATAAA
 181 TATCAATATA TTAAATTAGA TTTTGCATAA AAAACAGACT ACATAATACT GTAAAACACA
 241 ACATATCCAG TCACTATGGC GGCCGCATTA GGCACCCCAG GCTTTACACT TTATGCTTCC
 301 GGCTCGTATA ATGTGTGGAT TTTGAGTTAG GATCCGTCGA GATTTTCAGG AGCTAAGGAA
 361 GCTAAAATGG AGAAAAAAAT CACTGGATAT ACCACCGTTG ATATATCCCA ATGGCATCGT
 421 AAAGAACATT TTGAGGCATT TCAGTCAGTT GCTCAATGTA CCTATAACCA GACCGTTCAG
 481 CTGGATATTA CGGCCTTTTT AAAGACCGTA AAGAAAAATA AGCACAAGTT TTATCCGGCC
 541 TTTATTCACA TTCTTGCCCG CCTGATGAAT GCTCATCCGG AATTCCGTAT GGCAATGAAA
 601 GACGGTGAGC TGGTGATATG GGATAGTGTT CACCCTTGTT ACACCGTTTT CCATGAGCAA
 661 ACTGAAACGT TTTCATCGCT CTGGAGTGAA TACCACGACG ATTTCCGGCA GTTTCTACAC
 721 ATATATTCGC AAGATGTGGC GTGTTACGGT GAAAACCTGG CCTATTTCCC TAAAGGGTTT
 781 ATTGAGAATA TGTTTTTCGT CTCAGCCAAT CCCTGGGTGA GTTTCACCAG TTTTGATTTA
 841 AACGTGGCCA ATATGGACAA CTTCTTCGCC CCCGTTTTCA CCATGGGCAA ATATTATACG
 901 CAAGGCGACA AGGTGCTGAT GCCGCTGGCG ATTCAGGTTC ATCATGCCGT CTGTGATGGC
 961 TTCCATGTCG GCAGAATGCT TAATGAATTA CAACAGTACT GCGATGAGTG GCAGGGCGGG
1021 GCGTAAAGAT CTGGATCCGG CTTACTAAAA GCCAGATAAC AGTATGCGTA TTTGCGCGCT
1081 GATTTTTGCG GTATAAGAAT ATATACTGAT ATGTATACCC GAAGTATGTC AAAAAGAGGT
1141 GTGCTATGAA GCAGCGTATT ACAGTGACAG TTGACAGCGA CAGCTATCAG TTGCTCAAGG
1201 CATATATGAT GTCAATATCT CCGGTCTGGT AAGCACAACC ATGCAGAATG AAGCCCGTCG
1261 TCTGCGTGCC GAACGCTGGA AAGCGGAAAA TCAGGAAGGG ATGGCTGAGG TCGCCCGGTT
1321 TATTGAAATG AACGGCTCTT TTGCTGACGA GAACAGGGAC TGGTGAAATG CAGTTTAAGG
1381 TTTACACCTA TAAAAGAGAG AGCCGTTATC GTCTGTTTGT GGATGTACAG AGTGATATTA
1441 TTGACACGCC CGGGCGACGG ATGGTGATCC CCCTGGCCAG TGCACGTCTG CTGTCAGATA
1501 AAGTCTCCCG TGAACTTTAC CCGGTGGTGC ATATCGGGGA TGAAAGCTGG CGCATGATGA
1561 CCACCGATAT GGCCAGTGTG CCGGTCTCCG TTATCGGGGA AGAAGTGGCT GATCTCAGCC
1621 ACCGCGAAAA TGACATCAAA AACGCCATTA ACCTGATGTT CTGGGGAATA TAAATGTCAG
1681 GCTCCCTTAT ACACAGCCAG TCTGCAGGTC GACCATAGTG ACTGGATATG TTGTGTTTTA
```

FIG.37B

1741 CAGTATTATG TAGTCTGTTT TTTATGCAAA ATCTAATTTA ATATATTGAT ATTTATATCA
1801 TTTTACGTTT CTCGTTCAGC TTTCTTGTAC AAAGTGGTTG ATTCGAGGCT GCTAACAAAG
1861 CCCGAAAGGA AGCTGAGTTG GCTGCTGCCA CCGCTGAGCA ATAACTAGCA TAACCCCTTG
1921 GGGCCTCTAA ACGGGTCTTG AGGGGTTTTT TGCTGAAAGG AGGAACTATA TCCGGATATC
1981 CACAGGACGG GTGTGGTCGC CATGATCGCG TAGTCGATAG TGGCTCCAAG TAGCGAAGCG
2041 AGCAGGACTG GGCGGCGGCC AAAGCGGTCG GACAGTGCTC CGAGAACGGG TGCGCATAGA
2101 AATTGCATCA ACGCATATAG CGCTAGCAGC ACGCCATAGT GACTGGCGAT GCTGTCGGAA
2161 TGGACGATAT CCCGCAAGAG GCCCGGCAGT ACCGGCATAA CCAAGCCTAT GCCTACAGCA
2221 TCCAGGGTGA CGGTGCCGAG GATGACGATG AGCGCATTGT TAGATTTCAT ACACGGTGCC
2281 TGACTGCGTT AGCAATTTAA CTGTGATAAA CTACCGCATT AAAGCTTATC GATGATAAGC
2341 TGTCAAACAT GAGAATTCTT GAAGACGAAA GGGCCTCGTG ATACGCCTAT TTTTATAGGT
2401 TAATGTCATG ATAATAATGG TTTCTTAGAC GTCAGGTGGC ACTTTTCGGG GAAATGTGCG
2461 CGGAACCCCT ATTTGTTTAT TTTTCTAAAT ACATTCAAAT ATGTATCCGC TCATGAGACA
2521 ATAACCCTGA TAAATGCTTC AATAATATTG AAAAAGGAAG AGTATGAGTA TTCAACATTT
2581 CCGTGTCGCC CTTATTCCCT TTTTTGCGGC ATTTTGCCTT CCTGTTTTTG CTCACCCAGA
2641 AACGCTGGTG AAAGTAAAAG ATGCTGAAGA TCAGTTGGGT GCACGAGTGG GTTACATCGA
2701 ACTGGATCTC AACAGCGGTA AGATCCTTGA GAGTTTTCGC CCCGAAGAAC GTTTTCCAAT
2761 GATGAGCACT TTTAAAGTTC TGCTATGTGG CGCGGTATTA TCCCGTGTTG ACGCCGGGCA
2821 AGAGCAACTC GGTCGCCGCA TACACTATTC TCAGAATGAC TTGGTTGAGT ACTCACCAGT
2881 CACAGAAAAG CATCTTACGG ATGGCATGAC AGTAAGAGAA TTATGCAGTG CTGCCATAAC
2941 CATGAGTGAT AACACTGCGG CCAACTTACT TCTGACAACG ATCGGAGGAC CGAAGGAGCT
3001 AACCGCTTTT TTGCACAACA TGGGGGATCA TGTAACTCGC CTTGATCGTT GGGAACCGGA
3061 GCTGAATGAA GCCATACCAA ACGACGAGCG TGACACCACG ATGCCTGCAG CAATGGCAAC
3121 AACGTTGCGC AAACTATTAA CTGGCGAACT ACTTACTCTA GCTTCCCGGC AACAATTAAT
3181 AGACTGGATG GAGGCGGATA AAGTTGCAGG ACCACTTCTG CGCTCGGCCC TTCCGGCTGG
3241 CTGGTTTATT GCTGATAAAT CTGGAGCCGG TGAGCGTGGG TCTCGCGGTA TCATTGCAGC
3301 ACTGGGGCCA GATGGTAAGC CCTCCCGTAT CGTAGTTATC TACACGACGG GGAGTCAGGC
3361 AACTATGGAT GAACGAAATA GACAGATCGC TGAGATAGGT GCCTCACTGA TTAAGCATTG
3421 GTAACTGTCA GACCAAGTTT ACTCATATAT ACTTTAGATT GATTTAAAAC TTCATTTTTA
3481 ATTTAAAAGG ATCTAGGTGA AGATCCTTTT TGATAATCTC ATGACCAAAA TCCCTTAACG
3541 TGAGTTTTCG TTCCACTGAG CGTCAGACCC CGTAGAAAAG ATCAAAGGAT CTTCTTGAGA
3601 TCCTTTTTTT CTGCGCGTAA TCTGCTGCTT GCAAACAAAA AAACCACCGC TACCAGCGGT
3661 GGTTTGTTTG CCGGATCAAG AGCTACCAAC TCTTTTTCCG AAGGTAACTG GCTTCAGCAG
3721 AGCGCAGATA CCAAATACTG TCCTTCTAGT GTAGCCGTAG TTAGGCCACC ACTTCAAGAA
3781 CTCTGTAGCA CCGCCTACAT ACCTCGCTCT GCTAATCCTG TTACCAGTGG CTGCTGCCAG
3841 TGGCGATAAG TCGTGTCTTA CCGGGTTGGA CTCAAGACGA TAGTTACCGG ATAAGGCGCA
3901 GCGGTCGGGC TGAACGGGGG GTTCGTGCAC ACAGCCCAGC TTGGAGCGAA CGACCTACAC
3961 CGAACTGAGA TACCTACAGC GTGAGCTATG AGAAAGCGCC ACGCTTCCCG AAGGGAGAAA
4021 GGCGGACAGG TATCCGGTAA GCGGCAGGGT CGGAACAGGA GAGCGCACGA GGGAGCTTCC

FIG.37C

4081 AGGGGGAAAC GCCTGGTATC TTTATAGTCC TGTCGGGTTT CGCCACCTCT GACTTGAGCG
4141 TCGATTTTTG TGATGCTCGT CAGGGGGGCG GAGCCTATGG AAAAACGCCA GCAACGCGGC
4201 CTTTTTACGG TTCCTGGCCT TTTGCTGGCC TTTTGCTCAC ATGTTCTTTC CTGCGTTATC
4261 CCCTGATTCT GTGGATAACC GTATTACCGC CTTTGAGTGA GCTGATACCG CTCGCCGCAG
4321 CCGAACGACC GAGCGCAGCG AGTCAGTGAG CGAGGAAGCG GAAGAGCGCC TGATGCGGTA
4381 TTTTCTCCTT ACGCATCTGT GCGGTATTTC ACACCGCATA TATGGTGCAC TCTCAGTACA
4441 ATCTGCTCTG ATGCCGCATA GTTAAGCCAG TATACACTCC GCTATCGCTA CGTGACTGGG
4501 TCATGGCTGC GCCCCGACAC CCGCCAACAC CCGCTGACGC GCCCTGACGG GCTTGTCTGC
4561 TCCCGGCATC CGCTTACAGA CAAGCTGTGA CCGTCTCCGG GAGCTGCATG TGTCAGAGGT
4621 TTTCACCGTC ATCACCGAAA CGCGCGAGGC AGCTGCGGTA AAGCTCATCA GCGTGGTCGT
4681 GAAGCGATTC ACAGATGTCT GCCTGTTCAT CCGCGTCCAG CTCGTTGAGT TTCTCCAGAA
4741 GCGTTAATGT CTGGCTTCTG ATAAAGCGGG CCATGTTAAG GGCGGTTTTT TCCTGTTTGG
4801 TCACTGATGC CTCCGTGTAA GGGGGATTTC TGTTCATGGG GGTAATGATA CCGATGAAAC
4861 GAGAGAGGAT GCTCACGATA CGGGTTACTG ATGATGAACA TGCCCGGTTA CTGGAACGTT
4921 GTGAGGGTAA ACAACTGGCG GTATGGATGC GGCGGGACCA GAGAAAAATC ACTCAGGGTC
4981 AATGCCAGCG CTTCGTTAAT ACAGATGTAG GTGTTCCACA GGGTAGCCAG CAGCATCCTG
5041 CGATGCAGAT CCGGAACATA ATGGTGCAGG GCGCTGACTT CCGCGTTTCC AGACTTTACG
5101 AAACACGGAA ACCGAAGACC ATTCATGTTG TTGCTCAGGT CGCAGACGTT TTGCAGCAGC
5161 AGTCGCTTCA CGTTCGCTCG CGTATCGGTG ATTCATTCTG CTAACCAGTA AGGCAACCCC
5221 GCCAGCCTAG CCGGGTCCTC AACGACAGGA GCACGATCAT GCGCACCCGT GGCCAGGACC
5281 CAACGCTGCC CGAGATGCGC CGCGTGCGGC TGCTGGAGAT GGCGGACGCG ATGGATATGT
5341 TCTGCCAAGG GTTGGTTTGC GCATTCACAG TTCTCCGCAA GAATTGATTG GCTCCAATTC
5401 TTGGAGTGGT GAATCCGTTA GCGAGGTGCC GCCGGCTTCC ATTCAGGTCG AGGTGGCCCG
5461 GCTCCATGCA CCGCGACGCA ACGCGGGGAG GCAGACAAGG TATAGGGCGG CGCCTACAAT
5521 CCATGCCAAC CCGTTCCATG TGCTCGCCGA GGCGGCATAA ATCGCCGTGA CGATCAGCGG
5581 TCCAGTGATC GAAGTTAGGC TGGTAAGAGC CGCGAGCGAT CCTTGAAGCT GTCCCTGATG
5641 GTCGTCATCT ACCTGCCTGG ACAGCATGGC CTGCAACGCG GGCATCCCGA TGCCGCCGGA
5701 AGCGAGAAGA ATCATAATGG GGAAGGCCAT CCAGCCTCGC GTCGCGAACG CCAGCAAGAC
5761 GTAGCCCAGC GCGTCGGCCG CCATGCCGGC GATAATGGCC TGCTTCTCGC CGAAACGTTT
5821 GGTGGCGGGA CCAGTGACGA AGGCTTGAGC GAGGGCGTGC AAGATTCCGA ATACCGCAAG
5881 CGACAGGCCG ATCATCGTCG CGCTCCAGCG AAAGCGGTCC TCGCCGAAAA TGACCCAGAG
5941 CGCTGCCGGC ACCTGTCCTA CGAGTTGCAT GATAAAGAAG ACAGTCATAA GTGCGGCGAC
6001 GATAGTCATG CCCCGCGCCC ACCGGAAGGA GCTGACTGGG TTGAAGGCTC TCAAGGGCAT
6061 CGGTCGATCG ACGCTCTCCC TTATGCGACT CCTGCATTAG GAAGCAGCCC AGTAGTAGGT
6121 TGAGGCCGTT GAGCACCGCC GCCGCAAGGA ATGGTGCATG CAAGGAGATG GCGCCCAACA
6181 GTCCCCCGGC CACGGGGCCT GCCACCATAC CCACGCCGAA ACAAGCGCTC ATGAGCCCGA
6241 AGTGGCGAGC CCGATCTTCC CCATCGGTGA TGTCGGCGAT ATAGGCGCCA GCAACCGCAC
6301 CTGTGGCGCC GGTGATGCCG GCCACGATGC GTCCGGCGTA GAGGATCGAG ATCT

FIG.37D

FastBac Transfer Vector with p10 Baculovirus Promoter 1 gaagacctcg gccgtcgcgg cgcttgccgg tggtgctgac cccggatgaa gtggttcgca
cttctggagc cggcagcgcc gcgaacggcc accacgactg gggcctactt caccaagcgt 61 tcctcggttt tctggaaggc gagcatcgtt tgttcgccca ggactctagc tatagttcta
aggagccaaa agaccttccg ctcgtagcaa acaagcgggt cctgagatcg atatcaagat 121 gtggttggct acgtatcgag caagaaaata aaacgccaaa cgcgttggag tcttgtgtgc
caccaaccga tgcatagctc gttcttttat tttgcggttt gcgcaacctc agaacacacg p10 Promoter 181 tattttaca aagattcaga aatacgcatc acttacaaca aggggggacta tgaaattatg
ataaaaatgt ttctaagtct ttatgcgtag tgaatgttgt tccccctgat actttaatac 241 cattttgagg atgccgggac ctttaattca acccaacaca atatattata gttaaataag mRNA
gtaaaactcc tacggccctg gaaattaagt tgggttgtgt tatataatat caatttattc 301 aattatttat caaatcattt gtatattaat taaaatacta tactgtaaat tacattttat
ttaataaata gtttagtaaa catataatta attttatgat atgacattta atgtaaaata 361 ttacaatgag gatcatcaca agtttgtaca aaaaagctga acgagaaacg taaaatgata
aatgttactc ctagtagtgt tcaaacatgt tttttcgact tgctctttgc attttactat ....Int attR1

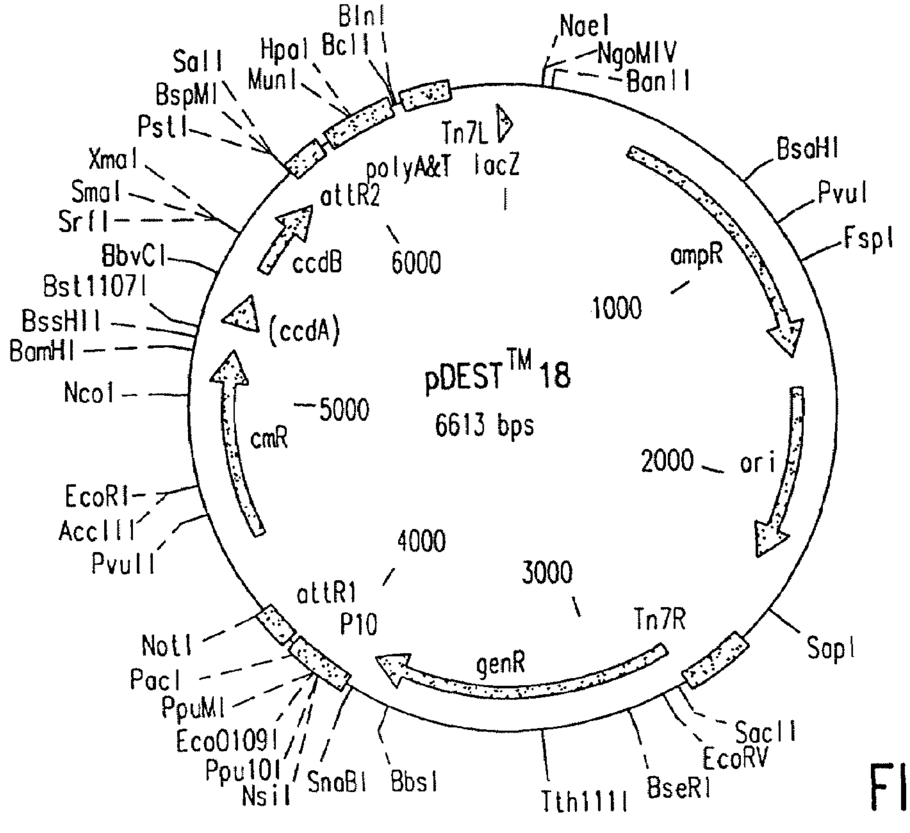

FIG.38A pDEST18 6613 bp

| Location (Base Nos.) | Gene Encoded |
|---|---|
| 474..1449 | ampR |
| 1590..2244 | ori |
| 2738..3850 | genR |
| 4251..4127 | attR1 |
| 4501..5160 | CmR |
| 5280..5364 | inactivated ccdA |
| 5502..5807 | ccdB |
| 5848..5972 | attR2 |
| 6595..25 | lacZ |

```
   1 GACGCGCCCT GTAGCGGCGC ATTAAGCGCG GCGGGTGTGG TGGTTACGCG CAGCGTGACC
  61 GCTACACTTG CCAGCGCCCT AGCGCCCGCT CCTTTCGCTT TCTTCCCTTC CTTTCTCGCC
 121 ACGTTCGCCG GCTTTCCCCG TCAAGCTCTA AATCGGGGGC TCCCTTTAGG GTTCCGATTT
 181 AGTGCTTTAC GGCACCTCGA CCCCAAAAAA CTTGATTAGG GTGATGGTTC ACGTAGTGGG
 241 CCATCGCCCT GATAGACGGT TTTTCGCCCT TTGACGTTGG AGTCCACGTT CTTTAATAGT
 301 GGACTCTTGT TCCAAACTGG AACAACACTC AACCCTATCT CGGTCTATTC TTTTGATTTA
 361 TAAGGGATTT TGCCGATTTC GGCCTATTGG TTAAAAAATG AGCTGATTTA ACAAAAATTT
 421 AACGCGAATT TTAACAAAAT ATTAACGTTT ACAATTTCAG GTGGCACTTT TCGGGGAAAT
 481 GTGCGCGGAA CCCCTATTTG TTTATTTTTC TAAATACATT CAAATATGTA TCCGCTCATG
 541 AGACAATAAC CCTGATAAAT GCTTCAATAA TATTGAAAAA GGAAGAGTAT GAGTATTCAA
 601 CATTTCCGTG TCGCCCTTAT TCCCTTTTTT GCGGCATTTT GCCTTCCTGT TTTTGCTCAC
 661 CCAGAAACGC TGGTGAAAGT AAAAGATGCT GAAGATCAGT TGGGTGCACG AGTGGGTTAC
 721 ATCGAACTGG ATCTCAACAG CGGTAAGATC CTTGAGAGTT TTCGCCCCGA AGAACGTTTT
 781 CCAATGATGA GCACTTTTAA AGTTCTGCTA TGTGGCGCGG TATTATCCCG TATTGACGCC
 841 GGGCAAGAGC AACTCGGTCG CCGCATACAC TATTCTCAGA ATGACTTGGT TGAGTACTCA
 901 CCAGTCACAG AAAAGCATCT TACGGATGGC ATGACAGTAA GAGAATTATG CAGTGCTGCC
 961 ATAACCATGA GTGATAACAC TGCGGCCAAC TTACTTCTGA CAACGATCGG AGGACCGAAG
1021 GAGCTAACCG CTTTTTTGCA CAACATGGGG GATCATGTAA CTCGCCTTGA TCGTTGGGAA
1081 CCGGAGCTGA ATGAAGCCAT ACCAAACGAC GAGCGTGACA CCACGATGCC TGTAGCAATG
1141 GCAACAACGT TGCGCAAACT ATTAACTGGC GAACTACTTA CTCTAGCTTC CCGGCAACAA
1201 TTAATAGACT GGATGGAGGC GGATAAAGTT GCAGGACCAC TTCTGCGCTC GGCCCTTCCG
1261 GCTGGCTGGT TTATTGCTGA TAAATCTGGA GCCGGTGAGC GTGGGTCTCG CGGTATCATT
1321 GCAGCACTGG GGCCAGATGG TAAGCCCTCC CGTATCGTAG TTATCTACAC GACGGGGAGT
1381 CAGGCAACTA TGGATGAACG AAATAGACAG ATCGCTGAGA TAGGTGCCTC ACTGATTAAG
1441 CATTGGTAAC TGTCAGACCA AGTTTACTCA TATATACTTT AGATTGATTT AAAACTTCAT
1501 TTTTAATTTA AAAGGATCTA GGTGAAGATC CTTTTTGATA ATCTCATGAC CAAAATCCCT
1561 TAACGTGAGT TTTCGTTCCA CTGAGCGTCA GACCCCGTAG AAAAGATCAA AGGATCTTCT
1621 TGAGATCCTT TTTTTCTGCG CGTAATCTGC TGCTTGCAAA CAAAAAAACC ACCGCTACCA
1681 GCGGTGGTTT GTTTGCCGGA TCAAGAGCTA CCAACTCTTT TTCCGAAGGT AACTGGCTTC
1741 AGCAGAGCGC AGATACCAAA TACTGTCCTT CTAGTGTAGC CGTAGTTAGG CCACCACTTC
```

FIG.38B

1801 AAGAACTCTG TAGCACCGCC TACATACCTC GCTCTGCTAA TCCTGTTACC AGTGGCTGCT
1861 GCCAGTGGCG ATAAGTCGTG TCTTACCGGG TTGGACTCAA GACGATAGTT ACCGGATAAG
1921 GCGCAGCGGT CGGGCTGAAC GGGGGGTTCG TGCACACAGC CCAGCTTGGA GCGAACGACC
1981 TACACCGAAC TGAGATACCT ACAGCGTGAG CATTGAGAAA GCGCCACGCT TCCCGAAGGG
2041 AGAAAGGCGG ACAGGTATCC GGTAAGCGGC AGGGTCGGAA CAGGAGAGCG CACGAGGGAG
2101 CTTCCAGGGG GAAACGCCTG GTATCTTTAT AGTCCTGTCG GGTTTCGCCA CCTCTGACTT
2161 GAGCGTCGAT TTTTGTGATG CTCGTCAGGG GGGCGGAGCC TATGGAAAAA CGCCAGCAAC
2221 GCGGCCTTTT TACGGTTCCT GGCCTTTTGC TGGCCTTTTG CTCACATGTT CTTTCCTGCG
2281 TTATCCCCTG ATTCTGTGGA TAACCGTATT ACCGCCTTTG AGTGAGCTGA TACCGCTCGC
2341 CGCAGCCGAA CGACCGAGCG CAGCGAGTCA GTGAGCGAGG AAGCGGAAGA GCGCCTGATG
2401 CGGTATTTTC TCCTTACGCA TCTGTGCGGT ATTTCACACC GCAGACCAGC CGCGTAACCT
2461 GGCAAAATCG GTTACGGTTG AGTAATAAAT GGATGCCCTG CGTAAGCGGG TGTGGGCGGA
2521 CAATAAAGTC TTAAACTGAA CAAAATAGAT CTAAACTATG ACAATAAAGT CTTAAACTAG
2581 ACAGAATAGT TGTAAACTGA AATCAGTCCA GTTATGCTGT GAAAAAGCAT ACTGGACTTT
2641 TGTTATGGCT AAAGCAAACT CTTCATTTTC TGAAGTGCAA ATTGCCCGTC GTATTAAAGA
2701 GGGGCGTGGC CAAGGGCATG GTAAAGACTA TATTCGCGGC GTTGTGACAA TTTACCGAAC
2761 AACTCCGCGG CCGGGAAGCC GATCTCGGCT TGAACGAATT GTTAGGTGGC GGTACTTGGG
2821 TCGATATCAA AGTGCATCAC TTCTTCCCGT ATGCCCAACT TTGTATAGAG AGCCACTGCG
2881 GGATCGTCAC CGTAATCTGC TTGCACGTAG ATCACATAAG CACCAAGCGC GTTGGCCTCA
2941 TGCTTGAGGA GATTGATGAG CGCGGTGGCA ATGCCCTGCC TCCGGTGCTC GCCGGAGACT
3001 GCGAGATCAT AGATATAGAT CTCACTACGC GGCTGCTCAA ACCTGGGCAG AACGTAAGCC
3061 GCGAGAGCGC CAACAACCGC TTCTTGGTCG AAGGCAGCAA GCGCGATGAA TGTCTTACTA
3121 CGGAGCAAGT TCCCGAGGTA ATCGGAGTCC GGCTGATGTT GGGAGTAGGT GGCTACGTCT
3181 CCGAACTCAC GACCGAAAAG ATCAAGAGCA GCCCGCATGG ATTTGACTTG GTCAGGGCCG
3241 AGCCTACATG TGCGAATGAT GCCCATACTT GAGCCACCTA ACTTTGTTTT AGGGCGACTG
3301 CCCTGCTGCG TAACATCGTT GCTGCTGCGT AACATCGTTG CTGCTCCATA ACATCAAACA
3361 TCGACCCACG GCGTAACGCG CTTGCTGCTT GGATGCCCGA GGCATAGACT GTACAAAAAA
3421 ACAGTCATAA CAAGCCATGA AAACCGCCAC TGCGCCGTTA CCACCGCTGC GTTCGGTCAA
3481 GGTTCTGGAC CAGTTGCGTG AGCGCATACG CTACTTGCAT TACAGTTTAC GAACCGAACA
3541 GGCTTATGTC AACTGGGTTC GTGCCTTCAT CCGTTTCCAC GGTGTGCGTC ACCCGGCAAC
3601 CTTGGGCAGC AGCGAAGTCG AGGCATTTCT GTCCTGGCTG GCGAACGAGC GCAAGGTTTC
3661 GGTCTCCACG CATCGTCAGG CATTGGCGGC CTTGCTGTTC TTCTACGGCA AGGTGCTGTG
3721 CACGGATCTG CCCTGGCTTC AGGAGATCGG AAGACCTCGG CCGTCGCGGC GCTTGCCGGT
3781 GGTGCTGACC CCGGATGAAG TGGTTCGCAT CCTCGGTTTT CTGGAAGGCG AGCATCGTTT
3841 GTTCGCCCAG GACTCTAGCT ATAGTTCTAG TGGTTGGCTA CGTATCGAGC AAGAAAATAA
3901 AACGCCAAAC GCGTTGGAGT CTTGTGTGCT ATTTTTACAA AGATTCAGAA ATACGCATCA
3961 CTTACAACAA GGGGGACTAT GAAATTATGC ATTTTGAGGA TGCCGGGACC TTTAATTCAA
4021 CCCAACACAA TATATTATAG TTAAATAAGA ATTATTTATC AAATCATTTG TATATTAATT
4081 AAAATACTAT ACTGTAAATT ACATTTTATT TACAATGAGG ATCATCACAA GTTTGTACAA
4141 AAAAGCTGAA CGAGAAACGT AAAATGATAT AAATATCAAT ATATTAAATT AGATTTTGCA
4201 TAAAAAACAG ACTACATAAT ACTGTAAAAC ACAACATATC CAGTCACTAT GGCGGCCGCT
4261 AAGTTGGCAG CATCACCCGA CGCACTTTGC GCCGAATAAA TACCTGTGAC GGAAGATCAC
4321 TTCGCAGAAT AAATAAATCC TGGTGTCCCT GTTGATACCG GGAAGCCCTG GGCCAACTTT

FIG.38C

```
4381 TGGCGAAAAT GAGACGTTGA TCGGCACGTA AGAGGTTCCA ACTTTCACCA TAATGAAATA
4441 AGATCACTAC CGGGCGTATT TTTTGAGTTA TCGAGATTTT CAGGAGCTAA GGAAGCTAAA
4501 ATGGAGAAAA AAATCACTGG ATATACCACC GTTGATATAT CCCAATGGCA TCGTAAAGAA
4561 CATTTTGAGG CATTTCAGTC AGTTGCTCAA TGTACCTATA ACCAGACCGT TCAGCTGGAT
4621 ATTACGGCCT TTTTAAAGAC CGTAAAGAAA AATAAGCACA AGTTTTATCC GGCCTTTATT
4681 CACATTCTTG CCCGCCTGAT GAATGCTCAT CCGGAATTCC GTATGGCAAT GAAAGACGGT
4741 GAGCTGGTGA TATGGGATAG TGTTCACCCT TGTTACACCG TTTTCCATGA GCAAACTGAA
4801 ACGTTTTCAT CGCTCTGGAG TGAATACCAC GACGATTTCC GGCAGTTTCT ACACATATAT
4861 TCGCAAGATG TGGCGTGTTA CGGTGAAAAC CTGGCCTATT TCCCTAAAGG GTTTATTGAG
4921 AATATGTTTT TCGTCTCAGC CAATCCCTGG GTGAGTTTCA CCAGTTTTGA TTTAAACGTG
4981 GCCAATATGG ACAACTTCTT CGCCCCCGTT TTCACCATGG GCAAATATTA TACGCAAGGC
5041 GACAAGGTGC TGATGCCGCT GGCGATTCAG GTTCATCATG CCGTCTGTGA TGGCTTCCAT
5101 GTCGGCAGAA TGCTTAATGA ATTACAACAG TACTGCGATG AGTGGCAGGG CGGGGCGTAA
5161 ACGCGTGGAT CCGGCTTACT AAAAGCCAGA TAACAGTATG CGTATTTGCG CGCTGATTTT
5221 TGCGGTATAA GAATATATAC TGATATGTAT ACCCGAAGTA TGTCAAAAAG AGGTGTGCTA
5281 TGAAGCAGCG TATTACAGTG ACAGTTGACA GCGACAGCTA TCAGTTGCTC AAGGCATATA
5341 TGATGTCAAT ATCTCCGGTC TGGTAAGCAC AACCATGCAG AATGAAGCCC GTCGTCTGCG
5401 TGCCGAACGC TGGAAAGCGG AAAATCAGGA AGGGATGGCT GAGGTCGCCC GGTTTATTGA
5461 AATGAACGGC TCTTTTGCTG ACGAGAACAG GGACTGGTGA AATGCAGTTT AAGGTTTACA
5521 CCTATAAAAG AGAGAGCCGT TATCGTCTGT TTGTGGATGT ACAGAGTGAT ATTATTGACA
5581 CGCCCGGGCG ACGGATGGTG ATCCCCCTGG CCAGTGCACG TCTGCTGTCA GATAAAGTCT
5641 CCCGTGAACT TTACCCGGTG GTGCATATCG GGGATGAAAG CTGGCGCATG ATGACCACCG
5701 ATATGGCCAG TGTGCCGGTC TCCGTTATCG GGGAAGAAGT GGCTGATCTC AGCCACCGCG
5761 AAAATGACAT CAAAAACGCC ATTAACCTGA TGTTCTGGGG AATATAAATG TCAGGCTCCC
5821 TTATACACAG CCAGTCTGCA GGTCGACCAT AGTGACTGGA TATGTTGTGT TTTACAGTAT
5881 TATGTAGTCT GTTTTTTATG CAAAATCTAA TTTAATATAT TGATATTTAT ATCATTTTAC
5941 GTTTCTCGTT CAGCTTTCTT GTACAAAGTG GTGATAGCTT GTCGAGAAGT ACTAGAGGAT
6001 CATAATCAGC CATACCACAT TTGTAGAGGT TTTACTTGCT TTAAAAAACC TCCCACACCT
6061 CCCCCTGAAC CTGAAACATA AAATGAATGC AATTGTTGTT GTTAACTTGT TTATTGCAGC
6121 TTATAATGGT TACAAATAAA GCAATAGCAT CACAAATTTC ACAAATAAAG CATTTTTTTC
6181 ACTGCATTCT AGTTGTGGTT TGTCCAAACT CATCAATGTA TCTTATCATG TCTGGATCTG
6241 ATCACTGCTT GAGCCTAGGA GATCCGAACC AGATAAGTGA AATCTAGTTC CAAACTATTT
6301 TGTCATTTTT AATTTTCGTA TTAGCTTACG ACGCTACACC CAGTTCCCAT CTATTTTGTC
6361 ACTCTTCCCT AAATAATCCT TAAAAACTCC ATTTCCACCC CTCCCAGTTC CCAACTATTT
6421 TGTCCGCCCA CAGCGGGGCA TTTTTCTTCC TGTTATGTTT TTAATCAAAC ATCCTGCCAA
6481 CTCCATGTGA CAAACCGTCA TCTTCGGCTA CTTTTTCTCT GTCACAGAAT GAAAATTTTT
6541 CTGTCATCTC TTCGTTATTA ATGTTTGTAA TTGACTGAAT ATCAACGCTT ATTTGCAGCC
6601 TGAATGGCGA ATG
```

FIG.38D

FastBac Transfer Vector with 39K Baculovirus Promoter

```
  1 ggtgacgccg tcatctttcc attgtaacgt aaatggcaac ttgtagatga acgcgctgtc
    ccactgcggc agtagaaagg taacattgca tttaccgttg aacatctact tgcgcgacag

 61 aaaaaaccgg ccagtttctt ccacaaactc gcgcacggct gtctcgtaaa cttttgcgtc
    ttttttggcc ggtcaaagaa ggtgtttgag cgcgtgccga cagagcattt gaaaacgcag
                                                  39K Promoter
121 gcaacaatcg cgatgacctc gtggtatgga aatttttttct aaaaaagtgt cgttcatgtc
    cgttgttagc gctactggag caccatacct ttaaaaaaga ttttttcaca gcaagtacag

181 ggcggcggcg ttcgcgctcc ggtacgcgcg acgggcacac agcaggacag ccttgtccgg
    ccgccgccgc aagcgcgagg ccatgcgcgc tgcccgtgtg tcgtcctgtc ggaacaggcc
                                                                          attR1
241 ctcgattatc ataaacaatc ctgcaggcat gcaagctgga tcatcacaag tttgtacaaa
    gagctaatag tatttgttag gacgtccgta cgttcgacct agtagtgttc aaacatgttt
                                                                          Int
```

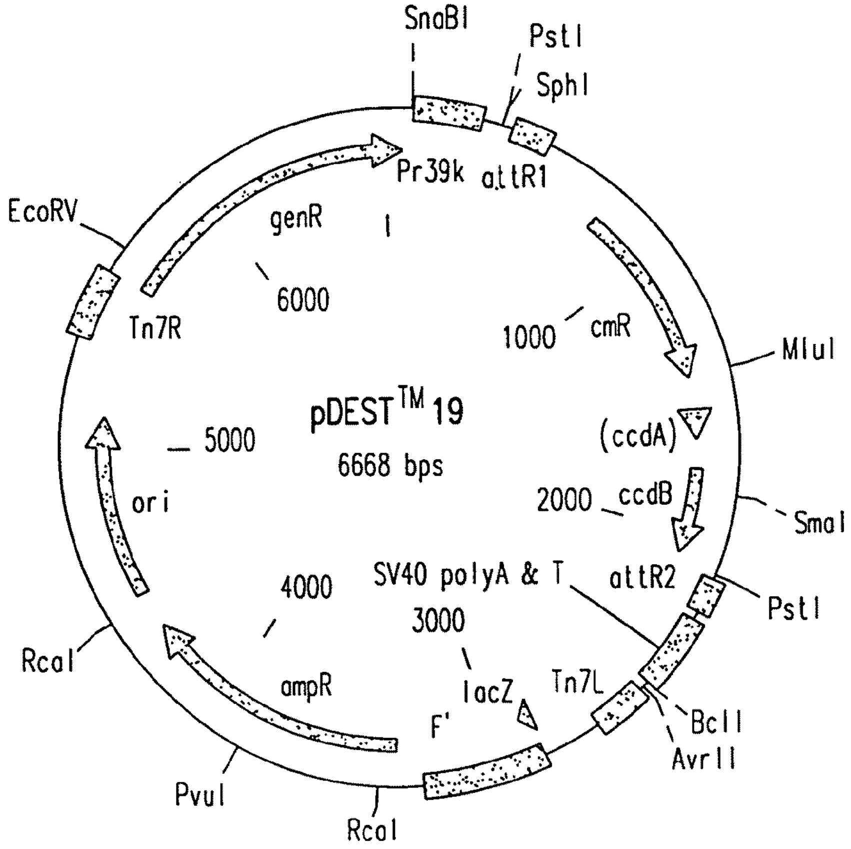

FIG.39A pDEST19 6668 bp (rotated to position 1000)

| Location (Base Nos.) | Gene Encoded |
|---|---|
| 515..391 | attR1 |
| 765..1424 | CmR |
| 1544..1628 | inactivated ccdA |
| 1766..2071 | ccdB |
| 2112..2236 | attR2 |
| 2852..2895 | lacZ |
| 3344..4319 | ampR |
| 4460..5114 | ori |
| 5608..52 | genR |

```
   1 AGTGGTTCGC ATCCTCGGTT TTCTGGAAGG CGAGCATCGT TTGTTCGCCC AGGACTCTAG
  61 CTATAGTTCT AGTGGTTGGC TACGTATATC AAATACTTGT AGGTGACGCC GTCATCTTTC
 121 CATTGTAACG TAAATGGCAA CTTGTAGATG AACGCGCTGT CAAAAAACCG GCCAGTTTCT
 181 TCCACAAACT CGCGCACGGC TGTCTCGTAA ACTTTTGCGT CGCAACAATC GCGATGACCT
 241 CGTGGTATGG AAATTTTTTC TAAAAAAGTG TCGTTCATGT CGGCGGCGGG CGCGTTCGCG
 301 CTCCGGTACG CGCGACGGGC ACACAGCAGG ACAGCCTTGT CCGGCTCGAT TATCATAAAC
 361 AATCCTGCAG GCATGCAAGC TCGGATCATC ACAAGTTTGT ACAAAAAAGC TGAACGAGAA
 421 ACGTAAAATG ATATAAATAT CAATATATTA AATTAGATTT TGCATAAAAA ACAGACTACA
 481 TAATACTGTA AAACACAACA TATCCAGTCA CTATGGCGGC CGCTAAGTTG GCAGCATCAC
 541 CCGACGCACT TTGCGCCGAA TAAATACCTG TGACGGAAGA TCACTTCGCA GAATAAATAA
 601 ATCCTGGTGT CCCTGTTGAT ACCGGGAAGC CCTGGGCCAA CTTTTGGCGA AAATGAGACG
 661 TTGATCGGCA CGTAAGAGGT TCCAACTTTC ACCATAATGA AATAAGATCA CTACCGGGCG
 721 TATTTTTTGA GTTATCGAGA TTTTCAGGAG CTAAGGAAGC TAAAATGGAG AAAAAAATCA
 781 CTGGATATAC CACCGTTGAT ATATCCCAAT GGCATCGTAA AGAACATTTT GAGGCATTTC
 841 AGTCAGTTGC TCAATGTACC TATAACCAGA CCGTTCAGCT GGATATTACG GCCTTTTTAA
 901 AGACCGTAAA GAAAAATAAG CACAAGTTTT ATCCGGCCTT TATTCACATT CTTGCCCGCC
 961 TGATGAATGC TCATCCGGAA TTCCGTATGG CAATGAAAGA CGGTGAGCTG GTGATATGGG
1021 ATAGTGTTCA CCCTTGTTAC ACCGTTTTCC ATGAGCAAAC TGAAACGTTT TCATCGCTCT
1081 GGAGTGAATA CCACGACGAT TTCCGGCAGT TTCTACACAT ATATTCGCAA GATGTGGCGT
1141 GTTACGGTGA AAACCTGGCC TATTTCCCTA AAGGGTTTAT TGAGAATATG TTTTTCGTCT
1201 CAGCCAATCC CTGGGTGAGT TTCACCAGTT TTGATTTAAA CGTGGCCAAT ATGGACAACT
1261 TCTTCGCCCC CGTTTTCACC ATGGGCAAAT ATTATACGCA AGGCGACAAG GTGCTGATGC
1321 CGCTGGCGAT TCAGGTTCAT CATGCCGTCT GTGATGGCTT CCATGTCGGC AGAATGCTTA
1381 ATGAATTACA ACAGTACTGC GATGAGTGGC AGGGCGGGGC GTAAACGCGT GGATCCGGCT
1441 TACTAAAAGC CAGATAACAG TATGCGTATT TGCGCGCTGA TTTTTGCGGT ATAAGAATAT
1501 ATACTGATAT GTATACCCGA AGTATGTCAA AAAGAGGTGT GCTATGAAGC AGCGTATTAC
1561 AGTGACAGTT GACAGCGACA GCTATCAGTT GCTCAAGGCA TATATGATGT CAATATCTCC
1621 GGTCTGGTAA GCACAACCAT GCAGAATGAA GCCCGTCGTC TGCGTGCCGA ACGCTGGAAA
1681 GCGGAAAATC AGGAAGGGAT GGCTGAGGTC GCCCGGTTTA TTGAAATGAA CGGCTCTTTT
1741 GCTGACGAGA ACAGGGACTG GTGAAATGCA GTTTAAGGTT TACACCTATA AAAGAGAGAG
1801 CCGTTATCGT CTGTTTGTGG ATGTACAGAG TGATATTATT GACACGCCCG GGCGACGGAT
1861 GGTGATCCCC CTGGCCAGTG CACGTCTGCT GTCAGATAAA GTCTCCCGTG AACTTTACCC
```

FIG.39B

1921 GGTGGTGCAT ATCGGGGATG AAAGCTGGCG CATGATGACC ACCGATATGG CCAGTGTGCC
1981 GGTCTCCGTT ATCGGGGAAG AAGTGGCTGA TCTCAGCCAC CGCGAAAATG ACATCAAAAA
2041 CGCCATTAAC CTGATGTTCT GGGGAATATA AATGTCAGGC TCCCTTATAC ACAGCCAGTC
2101 TGCAGGTCGA CCATAGTGAC TGGATATGTT GTGTTTTACA GTATTATGTA GTCTGTTTTT
2161 TATGCAAAAT CTAATTTAAT ATATTGATAT TTATATCATT TTACGTTTCT CGTTCAGCTT
2221 TCTTGTACAA AGTGGTGATC GAGAAGTACT AGAGGATCAT AATCAGCCAT ACCACATTTG
2281 TAGAGGTTTT ACTTGCTTTA AAAAACCTCC CACACCTCCC CCTGAACCTG AAACATAAAA
2341 TGAATGCAAT TGTTGTTGTT AACTTGTTTA TTGCAGCTTA TAATGGTTAC AAATAAAGCA
2401 ATAGCATCAC AAATTTCACA AATAAAGCAT TTTTTTCACT GCATTCTAGT TGTGGTTTGT
2461 CCAAACTCAT CAATGTATCT TATCATGTCT GGATCTGATC ACTGCTTGAG CCTAGGAGAT
2521 CCGAACCAGA TAAGTGAAAT CTAGTTCCAA ACTATTTTGT CATTTTTAAT TTTCGTATTA
2581 GCTTACGACG CTACACCCAG TTCCCATCTA TTTTGTCACT CTTCCCTAAA TAATCCTTAA
2641 AAACTCCATT TCCACCCCTC CCAGTTCCCA ACTATTTTGT CCGCCCACAG CGGGGCATTT
2701 TTCTTCCTGT TATGTTTTTA ATCAAACATC CTGCCAACTC CATGTGACAA ACCGTCATCT
2761 TCGGCTACTT TTTCTCTGTC ACAGAATGAA AATTTTTCTG TCATCTCTTC GTTATTAATG
2821 TTTGTAATTG ACTGAATATC AACGCTTATT TGCAGCCTGA ATGGCGAATG GACGCGCCCT
2881 GTAGCGGCGC ATTAAGCGCG GCGGGTGTGG TGGTTACGCG CAGCGTGACC GCTACACTTG
2941 CCAGCGCCCT AGCGCCCGCT CCTTTCGCTT TCTTCCCTTC CTTTCTCGCC ACGTTCGCCG
3001 GCTTTCCCCG TCAAGCTCTA AATCGGGGGC TCCCTTTAGG GTTCCGATTT AGTGCTTTAC
3061 GGCACCTCGA CCCCAAAAAA CTTGATTAGG GTGATGGTTC ACGTAGTGGG CCATCGCCCT
3121 GATAGACGGT TTTTCGCCCT TTGACGTTGG AGTCCACGTT CTTTAATAGT GGACTCTTGT
3181 TCCAAACTGG AACAACACTC AACCCTATCT CGGTCTATTC TTTTGATTTA TAAGGGATTT
3241 TGCCGATTTC GGCCTATTGG TTAAAAAATG AGCTGATTTA ACAAAAATTT AACGCGAATT
3301 TTAACAAAAT ATTAACGTTT ACAATTTCAG GTGGCACTTT TCGGGGAAAT GTGCGCGGAA
3361 CCCCTATTTG TTTATTTTTC TAAATACATT CAAATATGTA TCCGCTCATG AGACAATAAC
3421 CCTGATAAAT GCTTCAATAA TATTGAAAAA GGAAGAGTAT GAGTATTCAA CATTTCCGTG
3481 TCGCCCTTAT TCCCTTTTTT GCGGCATTTT GCCTTCCTGT TTTTGCTCAC CCAGAAACGC
3541 TGGTGAAAGT AAAAGATGCT GAAGATCAGT TGGGTGCACG AGTGGGTTAC ATCGAACTGG
3601 ATCTCAACAG CGGTAAGATC CTTGAGAGTT TTCGCCCCGA AGAACGTTTT CCAATGATGA
3661 GCACTTTTAA AGTTCTGCTA TGTGGCGCGG TATTATCCCG TATTGACGCC GGGCAAGAGC
3721 AACTCGGTCG CCGCATACAC TATTCTCAGA ATGACTTGGT TGAGTACTCA CCAGTCACAG
3781 AAAAGCATCT TACGGATGGC ATGACAGTAA GAGAATTATG CAGTGCTGCC ATAACCATGA
3841 GTGATAACAC TGCGGCCAAC TTACTTCTGA CAACGATCGG AGGACCGAAG GAGCTAACCG
3901 CTTTTTTGCA CAACATGGGG GATCATGTAA CTCGCCTTGA TCGTTGGGAA CCGGAGCTGA
3961 ATGAAGCCAT ACCAAACGAC GAGCGTGACA CCACGATGCC TGTAGCAATG GCAACAACGT
4021 TGCGCAAACT ATTAACTGGC GAACTACTTA CTCTAGCTTC CCGGCAACAA TTAATAGACT
4081 GGATGGAGGC GGATAAAGTT GCAGGACCAC TTCTGCGCTC GGCCCTTCCG GCTGGCTGGT
4141 TTATTGCTGA TAAATCTGGA GCCGGTGAGC GTGGGTCTCG CGGTATCATT GCAGCACTGG
4201 GGCCAGATGG TAAGCCCTCC CGTATCGTAG TTATCTACAC GACGGGGAGT CAGGCAACTA
4261 TGGATGAACG AAATAGACAG ATCGCTGAGA TAGGTGCCTC ACTGATTAAG CATTGGTAAC
4321 TGTCAGACCA AGTTTACTCA TATATACTTT AGATTGATTT AAAACTTCAT TTTTAATTTA
4381 AAAGGATCTA GGTGAAGATC CTTTTTGATA ATCTCATGAC CAAAATCCCT TAACGTGAGT
4441 TTTCGTTCCA CTGAGCGTCA GACCCCGTAG AAAAGATCAA AGGATCTTCT TGAGATCCTT

FIG.39C

4501 TTTTTCTGCG CGTAATCTGC TGCTTGCAAA CAAAAAAACC ACCGCTACCA GCGGTGGTTT
4561 GTTTGCCGGA TCAAGAGCTA CCAACTCTTT TTCCGAAGGT AACTGGCTTC AGCAGAGCGC
4621 AGATACCAAA TACTGTCCTT CTAGTGTAGC CGTAGTTAGG CCACCACTTC AAGAACTCTG
4681 TAGCACCGCC TACATACCTC GCTCTGCTAA TCCTGTTACC AGTGGCTGCT GCCAGTGGCG
4741 ATAAGTCGTG TCTTACCGGG TTGGACTCAA GACGATAGTT ACCGGATAAG GCGCAGCGGT
4801 CGGGCTGAAC GGGGGGTTCG TGCACACAGC CCAGCTTGGA GCGAACGACC TACACCGAAC
4861 TGAGATACCT ACAGCGTGAG CATTGAGAAA GCGCCACGCT TCCCGAAGGG AGAAAGGCGG
4921 ACAGGTATCC GGTAAGCGGC AGGGTCGGAA CAGGAGAGCG CACGAGGGAG CTTCCAGGGG
4981 GAAACGCCTG GTATCTTTAT AGTCCTGTCG GGTTTCGCCA CCTCTGACTT GAGCGTCGAT
5041 TTTTGTGATG CTCGTCAGGG GGGCGGAGCC TATGGAAAAA CGCCAGCAAC GCGGCCTTTT
5101 TACGGTTCCT GGCCTTTTGC TGGCCTTTTG CTCACATGTT CTTTCCTGCG TTATCCCCTG
5161 ATTCTGTGGA TAACCGTATT ACCGCCTTTG AGTGAGCTGA TACCGCTCGC CGCAGCCGAA
5221 CGACCGAGCG CAGCGAGTCA GTGAGCGAGG AAGCGGAAGA GCGCCTGATG CGGTATTTTC
5281 TCCTTACGCA TCTGTGCGGT ATTTCACACC GCAGACCAGC CGCGTAACCT GGCAAAATCG
5341 GTTACGGTTG AGTAATAAAT GGATGCCCTG CGTAAGCGGG TGTGGGCGGA CAATAAAGTC
5401 TTAAACTGAA CAAAATAGAT CTAAACTATG ACAATAAAGT CTTAAACTAG ACAGAATAGT
5461 TGTAAACTGA AATCAGTCCA GTTATGCTGT GAAAAAGCAT ACTGGACTTT TGTTATGGCT
5521 AAAGCAAACT CTTCATTTTC TGAAGTGCAA ATTGCCCGTC GTATTAAAGA GGGGCGTGGC
5581 CAAGGGCATG GTAAAGACTA TATTCGCGGC GTTGTGACAA TTTACCGAAC AACTCCGCGG
5641 CCGGGAAGCC GATCTCGGCT TGAACGAATT GTTAGGTGGC GGTACTTGGG TCGATATCAA
5701 AGTGCATCAC TTCTTCCCGT ATGCCCAACT TTGTATAGAG AGCCACTGCG GGATCGTCAC
5761 CGTAATCTGC TTGCACGTAG ATCACATAAG CACCAAGCGC GTTGGCCTCA TGCTTGAGGA
5821 GATTGATGAG CGCGGTGGCA ATGCCCTGCC TCCGGTGCTC GCCGGAGACT GCGAGATCAT
5881 AGATATAGAT CTCACTACGC GGCTGCTCAA ACCTGGGCAG AACGTAAGCC GCGAGAGCGC
5941 CAACAACCGC TTCTTGGTCG AAGGCAGCAA GCGCGATGAA TGTCTTACTA CGGAGCAAGT
6001 TCCCGAGGTA ATCGGAGTCC GGCTGATGTT GGGAGTAGGT GGCTACGTCT CCGAACTCAC
6061 GACCGAAAAG ATCAAGAGCA GCCCGCATGG ATTTGACTTG GTCAGGGCCG AGCCTACATG
6121 TGCGAATGAT GCCCATACTT GAGCCACCTA ACTTTGTTTT AGGGCGACTG CCCTGCTGCG
6181 TAACATCGTT GCTGCTGCGT AACATCGTTG CTGCTCCATA ACATCAAACA TCGACCCACG
6241 GCGTAACGCG CTTGCTGCTT GGATGCCCGA GGCATAGACT GTACAAAAAA ACAGTCATAA
6301 CAAGCCATGA AAACCGCCAC TGCGCCGTTA CCACCGCTGC GTTCGGTCAA GGTTCTGGAC
6361 CAGTTGCGTG AGCGCATACG CTACTTGCAT TACAGTTTAC GAACCGAACA GGCTTATGTC
6421 AACTGGGTTC GTGCCTTCAT CCGTTTCCAC GGTGTGCGTC ACCCGGCAAC CTTGGGCAGC
6481 AGCGAAGTCG AGGCATTTCT GTCCTGGCTG GCGAACGAGC GCAAGGTTTC GGTCTCCACG
6541 CATCGTCAGG CATTGGCGGC CTTGCTGTTC TTCTACGGCA AGGTGCTGTG CACGGATCTG
6601 CCCTGGCTTC AGGAGATCGG AAGACCTCGG CCGTCGCGGC GCTTGCCGGT GGTGCTGACC
6661 CCGGATGA

FIG.39D

GLUTATHIONE-S-TRANSFERASE FUSION WITH POLYHEDRON PROMOTER FOR BACULOVIRUS EXPRESSION polh PROMOTER 430 ggc tac gta tac tcc gga ata tta ata gat cat gga gat aat taa aat gat
ccg atg cat atg agg cct tat aat tat cta gta cct cta tta att tta cta mRNA 481 aac cat ctc gca aat aaa tag gta ttt tac tgt ttt cgt aac agt ttt gta
ttg gta gag cgt tta ttt atc cat aaa atg aca aaa gca ttg tca aaa cat 532 ata aaa aaa cct ata aat att ccg gat tat tca tac cgt ccc acc atc ggg
tat ttt ttt gga tat tta taa ggc cta ata agt atg gca ggg tgg tag ccc

START TRANSLN. M A P I - - - - GST - -

583 cgc gga tcc atg gcc cct ata cta ggt tat tgg aaa att aag ggc ctt gtg
gcg cct agg tac cgg gga tat gat cca ata acc ttt taa ttc ccg gaa cac

S D L V P R H N Q T S L Y K K A 1246 tcg gat ctg gtt ccg cgt cat aat cag aca agt ttg tac aaa aaa gct gaa
agc cta gac caa ggc gca gta tta gtc tgt tca aac atg ttt ttt cga ctt Int 1297 cga gaa acg taa aat gat ata aat atc aat ata tta aat tag at
gct ctt tgc att tta cta tat tta tag tta tat aat tta atc ta

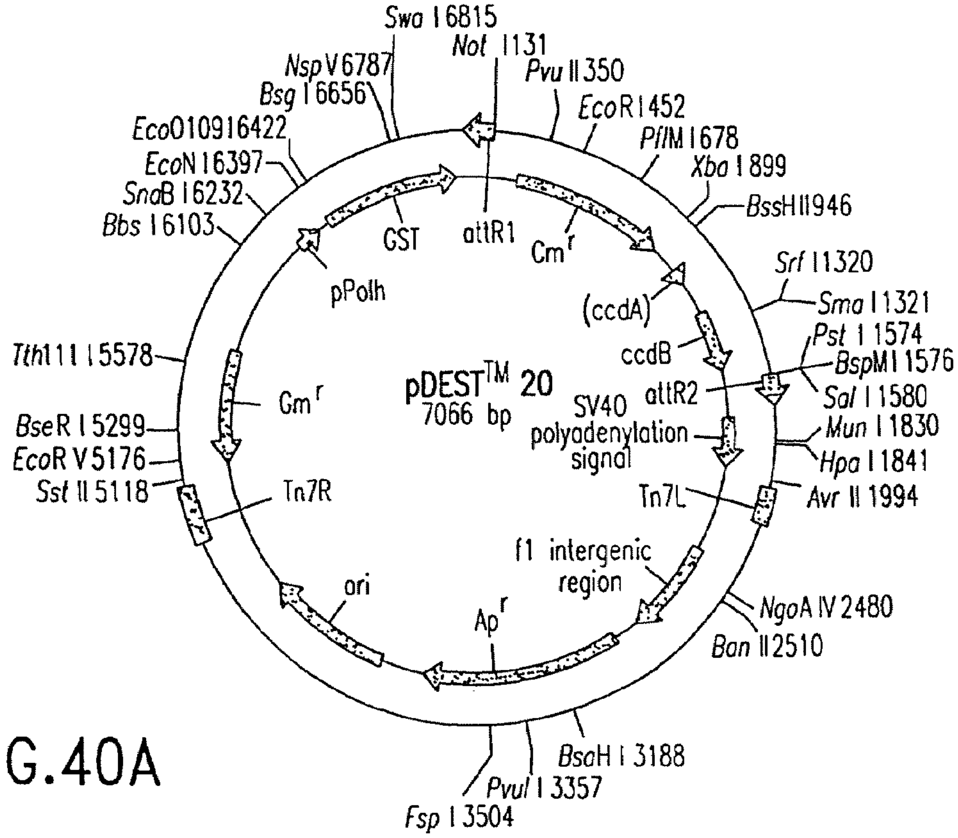

FIG.40A pDEST20 7066 bp (rotated to position 5800)

| Location (Base Nos.) | Gene Encoded |
|---|---|
| 592..1263 | GST |
| 1397..1273 | attR1 |
| 1506..2165 | CmR |
| 2285..2369 | inactivated ccdA |
| 2507..2812 | ccdB |
| 2853..2977 | attR2 |
| 4214..5064 | ampR |
| 5263..5843 | ori |

```
   1 CCACTGCGCC GTTACCACCG CTGCGTTCGG TCAAGGTTCT GGACCAGTTG CGTGAGCGCA
  61 TACGCTACTT GCATTACAGT TTACGAACCG AACAGGCTTA TGTCAACTGG GTTCGTGCCT
 121 TCATCCGTTT CCACGGTGTG CGTCACCCGG CAACCTTGGG CAGCAGCGAA GTCGAGGCAT
 181 TTCTGTCCTG GCTGGCGAAC GAGCGCAAGG TTTCGGTCTC CACGCATCGT CAGGCATTGG
 241 CGGCCTTGCT GTTCTTCTAC GGCAAGGTGC TGTGCACGGA TCTGCCCTGG CTTCAGGAGA
 301 TCGGAAGACC TCGGCCGTCG CGGCGCTTGC CGGTGGTGCT GACCCCGGAT GAAGTGGTTC
 361 GCATCCTCGG TTTTCTGGAA GGCGAGCATC GTTTGTTCGC CCAGGACTCT AGCTATAGTT
 421 CTAGTGGTTG GCTACGTATA CTCCGGAATA TTAATAGATC ATGGAGATAA TTAAAATGAT
 481 AACCATCTCG CAAATAAATA AGTATTTTAC TGTTTTCGTA ACAGTTTTGT AATAAAAAAA
 541 CCTATAAATA TTCCGGATTA TTCATACCGT CCCACCATCG GGCGCGGATC CATGGCCCCT
 601 ATACTAGGTT ATTGGAAAAT TAAGGGCCTT GTGCAACCCA CTCGACTTCT TTTGGAATAT
 661 CTTGAAGAAA AATATGAAGA GCATTTGTAT GAGCGCGATG AAGGTGATAA ATGGCGAAAC
 721 AAAAAGTTTG AATTGGGTTT GGAGTTTCCC AATCTTCCTT ATTATATTGA TGGTGATGTT
 781 AAATTAACAC AGTCTATGGC CATCATACGT TATATAGCTG ACAAGCACAA CATGTTGGGT
 841 GGTTGTCCAA AAGAGCGTGC AGAGATTTCA ATGCTTGAAG GAGCGGTTTT GGATATTAGA
 901 TACGGTGTTT CGAGAATTGC ATATAGTAAA GACTTTGAAA CTCTCAAAGT TGATTTTCTT
 961 AGCAAGCTAC CTGAAATGCT GAAAATGTTC GAAGATCGTT TATGTCATAA AACATATTTA
1021 AATGGTGATC ATGTAACCCA TCCTGACTTC ATGTTGTATG ACGCTCTTGA TGTTGTTTTA
1081 TACATGGACC CAATGTGCCT GGATGCGTTC CCAAAATTAG TTTGTTTTAA AAAACGTATT
1141 GAAGCTATCC CACAAATTGA TAAGTACTTG AAATCCAGCA AGTATATAGC ATGGCCTTTG
1201 CAGGGCTGGC AAGCCACGTT TGGTGGTGGC GACCATCCTC CAAAATCGGA TCTGGTTCCG
1261 CGTCATAATC AAACAAGTTT GTACAAAAAA GCTGAACGAG AAACGTAAAA TGATATAAAT
1321 ATCAATATAT TAAATTAGAT TTTGCATAAA AAACAGACTA CATAATACTG TAAAACACAA
1381 CATATCCAGT CACTATGGCG GCCGCATTAG GCACCCCAGG CTTTACACTT TATGCTTCCG
1441 GCTCGTATGT TGTGTGGATT TTGAGTTAGG ATCCGGCGAG ATTTTCAGGA GCTAAGGAAG
1501 CTAAAATGGA GAAAAAAATC ACTGGATATA CCACCGTTGA TATATCCCAA TGGCATCGTA
1561 AAGAACATTT TGAGGCATTT CAGTCAGTTG CTCAATGTAC CTATAACCAG ACCGTTCAGC
1621 TGGATATTAC GGCCTTTTTA AAGACCGTAA AGAAAAATAA GCACAAGTTT TATCCGGCCT
1681 TTATTCACAT TCTTGCCCGC CTGATGAATG CTCATCCGGA ATTCCGTATG GCAATGAAAG
1741 ACGGTGAGCT GGTGATATGG GATAGTGTTC ACCCTTGTTA CACCGTTTTC CATGAGCAAA
1801 CTGAAACGTT TTCATCGCTC TGGAGTGAAT ACCACGACGA TTTCCGGCAG TTTCTACACA
1861 TATATTCGCA AGATGTGGCG TGTTACGGTG AAAACCTGGC CTATTTCCCT AAAGGGTTTA
1921 TTGAGAATAT GTTTTTCGTC TCAGCCAATC CCTGGGTGAG TTTCACCAGT TTTGATTTAA
```

FIG.40B

1981 ACGTGGCCAA TATGGACAAC TTCTTCGCCC CCGTTTTCAC CATGGGCAAA TATTATACGC
2041 AAGGCGACAA GGTGCTGATG CCGCTGGCGA TTCAGGTTCA TCATGCCGTC TGTGATGGCT
2101 TCCATGTCGG CAGAATGCTT AATGAATTAC AACAGTACTG CGATGAGTGG CAGGGCGGGG
2161 CGTAATCTAG AGGATCCGGC TTACTAAAAG CCAGATAACA GTATGCGTAT TTGCGCGCTG
2221 ATTTTTGCGG TATAAGAATA TATACTGATA TGTATACCCG AAGTATGTCA AAAAGAGGTG
2281 TGCTATGAAG CAGCGTATTA CAGTGACAGT TGACAGCGAC AGCTATCAGT TGCTCAAGGC
2341 ATATATGATG TCAATATCTC CGGTCTGGTA AGCACAACCA TGCAGAATGA AGCCCGTCGT
2401 CTGCGTGCCG AACGCTGGAA AGCGGAAAAT CAGGAAGGGA TGGCTGAGGT CGCCCGGTTT
2461 ATTGAAATGA ACGGCTCTTT TGCTGACGAG AACAGGGACT GGTGAAATGC AGTTTAAGGT
2521 TTACACCTAT AAAAGAGAGA GCCGTTATCG TCTGTTTGTG GATGTACAGA GTGATATTAT
2581 TGACACGCCC GGGCGACGGA TGGTGATCCC CCTGGCCAGT GCACGTCTGC TGTCAGATAA
2641 AGTCTCCCGT GAACTTTACC CGGTGGTGCA TATCGGGGAT GAAAGCTGGC GCATGATGAC
2701 CACCGATATG GCCAGTGTGC CGGTCTCCGT TATCGGGGAA GAAGTGGCTG ATCTCAGCCA
2761 CCGCGAAAAT GACATCAAAA ACGCCATTAA CCTGATGTTC TGGGGAATAT AAATGTCAGG
2821 CTCCCTTATA CACAGCCAGT CTGCAGGTCG ACCATAGTGA CTGGATATGT TGTGTTTTAC
2881 AGTATTATGT AGTCTGTTTT TTATGCAAAA TCTAATTTAA TATATTGATA TTTATATCAT
2941 TTTACGTTTC TCGTTCAGCT TTCTTGTACA AAGTGGTTTG ATAGCTTGTC GAGAAGTACT
3001 AGAGGATCAT AATCAGCCAT ACCACATTTG TAGAGGTTTT ACTTGCTTTA AAAAACCTCC
3061 CACACCTCCC CCTGAACCTG AAACATAAAA TGAATGCAAT TGTTGTTGTT AACTTGTTTA
3121 TTGCAGCTTA TAATGGTTAC AAATAAAGCA ATAGCATCAC AAATTTCACA AATAAAGCAT
3181 TTTTTTCACT GCATTCTAGT TGTGGTTTGT CCAAACTCAT CAATGTATCT TATCATGTCT
3241 GGATCTGATC ACTGCTTGAG CCTAGGAGAT CCGAACCAGA TAAGTGAAAT CTAGTTCCAA
3301 ACTATTTTGT CATTTTTAAT TTTCGTATTA GCTTACGACG CTACACCCAG TTCCCATCTA
3361 TTTTGTCACT CTTCCCTAAA TAATCCTTAA AAACTCCATT TCCACCCCTC CCAGTTCCCA
3421 ACTATTTTGT CCGCCCACAG CGGGGCATTT TTCTTCCTGT TATGTTTTTA ATCAAACATC
3481 CTGCCAACTC CATGTGACAA ACCGTCATCT TCGGCTACTT TTTCTCTGTC ACAGAATGAA
3541 AATTTTTCTG TCATCTCTTC GTTATTAATG TTTGTAATTG ACTGAATATC AACGCTTATT
3601 TGCAGCCTGA ATGGCGAATG GACGCGCCCT GTAGCGGCGC ATTAAGCGCG GCGGGTGTGG
3661 TGGTTACGCG CAGCGTGACC GCTACACTTG CCAGCGCCCT AGCGCCCGCT CCTTTCGCTT
3721 TCTTCCCTTC CTTTCTCGCC ACGTTCGCCG GCTTTCCCCG TCAAGCTCTA AATCGGGGGC
3781 TCCCTTTAGG GTTCCGATTT AGTGCTTTAC GGCACCTCGA CCCCAAAAAA CTTGATTAGG
3841 GTGATGGTTC ACGTAGTGGG CCATCGCCCT GATAGACGGT TTTTCGCCCT TTGACGTTGG
3901 AGTCCACGTT CTTTAATAGT GGACTCTTGT TCCAAACTGG AACAACACTC AACCCTATCT
3961 CGGTCTATTC TTTTGATTTA TAAGGGATTT TGCCGATTTC GGCCTATTGG TTAAAAAATG
4021 AGCTGATTTA ACAAAAATTT AACGCGAATT TTAACAAAAT ATTAACGTTT ACAATTTCAG
4081 GTGGCACTTT TCGGGGAAAT GTGCGCGGAA CCCCTATTTG TTTATTTTTC TAAATACATT
4141 CAAATATGTA TCCGCTCATG AGACAATAAC CCTGATAAAT GCTTCAATAA TATTGAAAAA
4201 GGAAGAGTAT GAGTATTCAA CATTTCCGTG TCGCCCTTAT TCCCTTTTTT GCGGCATTTT
4261 GCCTTCCTGT TTTTGCTCAC CCAGAAACGC TGGTGAAAGT AAAAGATGCT GAAGATCAGT
4321 TGGGTGCACG AGTGGGTTAC ATCGAACTGG ATCTCAACAG CGGTAAGATC CTTGAGAGTT
4381 TTCGCCCCGA AGAACGTTTT CCAATGATGA GCACTTTTAA AGTTCTGCTA TGTGGCGCGG
4441 TATTATCCCG TATTGACGCC GGGCAAGAGC AACTCGGTCG CCGCATACAC TATTCTCAGA
4501 ATGACTTGGT TGAGTACTCA CCAGTCACAG AAAAGCATCT TACGGATGGC ATGACAGTAA

FIG.40C

4561 GAGAATTATG CAGTGCTGCC ATAACCATGA GTGATAACAC TGCGGCCAAC TTACTTCTGA
4621 CAACGATCGG AGGACCGAAG GAGCTAACCG CTTTTTTGCA CAACATGGGG GATCATGTAA
4681 CTCGCCTTGA TCGTTGGGAA CCGGAGCTGA ATGAAGCCAT ACCAAACGAC GAGCGTGACA
4741 CCACGATGCC TGTAGCAATG GCAACAACGT TGCGCAAACT ATTAACTGGC GAACTACTTA
4801 CTCTAGCTTC CCGGCAACAA TTAATAGACT GGATGGAGGC GGATAAAGTT GCAGGACCAC
4861 TTCTGCGCTC GGCCCTTCCG GCTGGCTGGT TTATTGCTGA TAAATCTGGA GCCGGTGAGC
4921 GTGGGTCTCG CGGTATCATT GCAGCACTGG GGCCAGATGG TAAGCCCTCC CGTATCGTAG
4981 TTATCTACAC GACGGGGAGT CAGGCAACTA TGGATGAACG AAATAGACAG ATCGCTGAGA
5041 TAGGTGCCTC ACTGATTAAG CATTGGTAAC TGTCAGACCA AGTTTACTCA TATATACTTT
5101 AGATTGATTT AAAACTTCAT TTTTAATTTA AAAGGATCTA GGTGAAGATC CTTTTTGATA
5161 ATCTCATGAC CAAAATCCCT TAACGTGAGT TTTCGTTCCA CTGAGCGTCA GACCCCGTAG
5221 AAAAGATCAA AGGATCTTCT TGAGATCCTT TTTTTCTGCG CGTAATCTGC TGCTTGCAAA
5281 CAAAAAAACC ACCGCTACCA GCGGTGGTTT GTTTGCCGGA TCAAGAGCTA CCAACTCTTT
5341 TTCCGAAGGT AACTGGCTTC AGCAGAGCGC AGATACCAAA TACTGTCCTT CTAGTGTAGC
5401 CGTAGTTAGG CCACCACTTC AAGAACTCTG TAGCACCGCC TACATACCTC GCTCTGCTAA
5461 TCCTGTTACC AGTGGCTGCT GCCAGTGGCG ATAAGTCGTG TCTTACCGGG TTGGACTCAA
5521 GACGATAGTT ACCGGATAAG GCGCAGCGGT CGGGCTGAAC GGGGGGTTCG TGCACACAGC
5581 CCAGCTTGGA GCGAACGACC TACACCGAAC TGAGATACCT ACAGCGTGAG CATTGAGAAA
5641 GCGCCACGCT TCCCGAAGGG AGAAAGGCGG ACAGGTATCC GGTAAGCGGC AGGGTCGGAA
5701 CAGGAGAGCG CACGAGGGAG CTTCCAGGGG GAAACGCCTG GTATCTTTAT AGTCCTGTCG
5761 GGTTTCGCCA CCTCTGACTT GAGCGTCGAT TTTTGTGATG CTCGTCAGGG GGGCGGAGCC
5821 TATGGAAAAA CGCCAGCAAC GCGGCCTTTT TACGGTTCCT GGCCTTTTGC TGGCCTTTTG
5881 CTCACATGTT CTTTCCTGCG TTATCCCCTG ATTCTGTGGA TAACCGTATT ACCGCCTTTG
5941 AGTGAGCTGA TACCGCTCGC CGCAGCCGAA CGACCGAGCG CAGCGAGTCA GTGAGCGAGG
6001 AAGCGGAAGA GCGCCTGATG CGGTATTTTC TCCTTACGCA TCTGTGCGGT ATTTCACACC
6061 GCAGACCAGC CGCGTAACCT GGCAAAATCG GTTACGGTTG AGTAATAAAT GGATGCCCTG
6121 CGTAAGCGGG TGTGGGCGGA CAATAAAGTC TTAAACTGAA CAAAATAGAT CTAAACTATG
6181 ACAATAAAGT CTTAAACTAG ACAGAATAGT TGTAAACTGA AATCAGTCCA GTTATGCTGT
6241 GAAAAAGCAT ACTGGACTTT TGTTATGGCT AAAGCAAACT CTTCATTTTC TGAAGTGCAA
6301 ATTGCCCGTC GTATTAAAGA GGGGCGTGGC CAAGGGCATG GTAAAGACTA TATTCGCGGC
6361 GTTGTGACAA TTTACCGAAC AACTCCGCGG CCGGGAAGCC GATCTCGGCT TGAACGAATT
6421 GTTAGGTGGC GGTACTTGGG TCGATATCAA AGTGCATCAC TTCTTCCCGT ATGCCCAACT
6481 TTGTATAGAG AGCCACTGCG GGATCGTCAC CGTAATCTGC TTGCACGTAG ATCACATAAG
6541 CACCAAGCGC GTTGGCCTCA TGCTTGAGGA GATTGATGAG CGCGGTGGCA ATGCCCTGCC
6601 TCCGGTGCTC GCCGGAGACT GCGAGATCAT AGATATAGAT CTCACTACGC GGCTGCTCAA
6661 ACCTGGGCAG AACGTAAGCC GCGAGAGCGC CAACAACCGC TTCTTGGTCG AAGGCAGCAA
6721 GCGCGATGAA TGTCTTACTA CGGAGCAAGT TCCCGAGGTA ATCGGAGTCC GGCTGATGTT
6781 GGGAGTAGGT GGCTACGTCT CCGAACTCAC GACCGAAAAG ATCAAGAGCA GCCCGCATGG
6841 ATTTGACTTG GTCAGGGCCG AGCCTACATG TGCGAATGAT GCCCATACTT GAGCCACCTA
6901 ACTTTGTTTT AGGGCGACTG CCCTGCTGCG TAACATCGTT GCTGCTGCGT AACATCGTTG
6961 CTGCTCCATA ACATCAAACA TCGACCCACG GCGTAACGCG CTTGCTGCTT GGATGCCCGA
7021 GGCATAGACT GTACAAAAAA ACAGTCATAA CAAGCCATGA AAACCG

FIG.40D

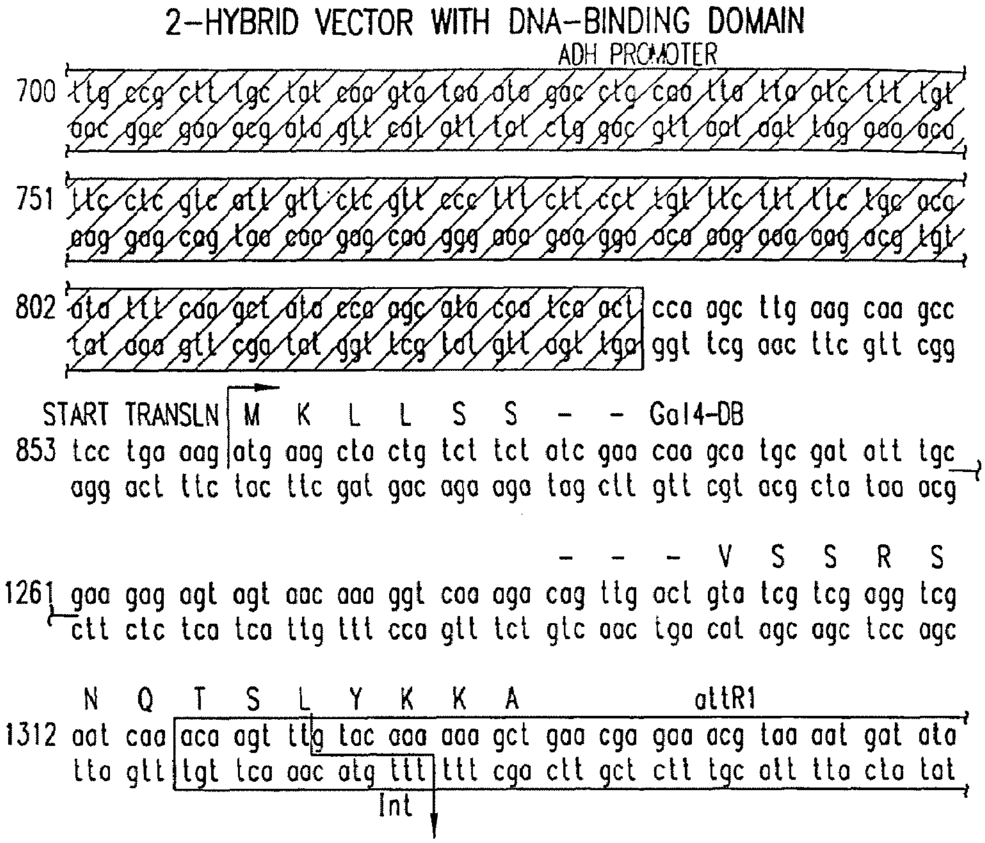
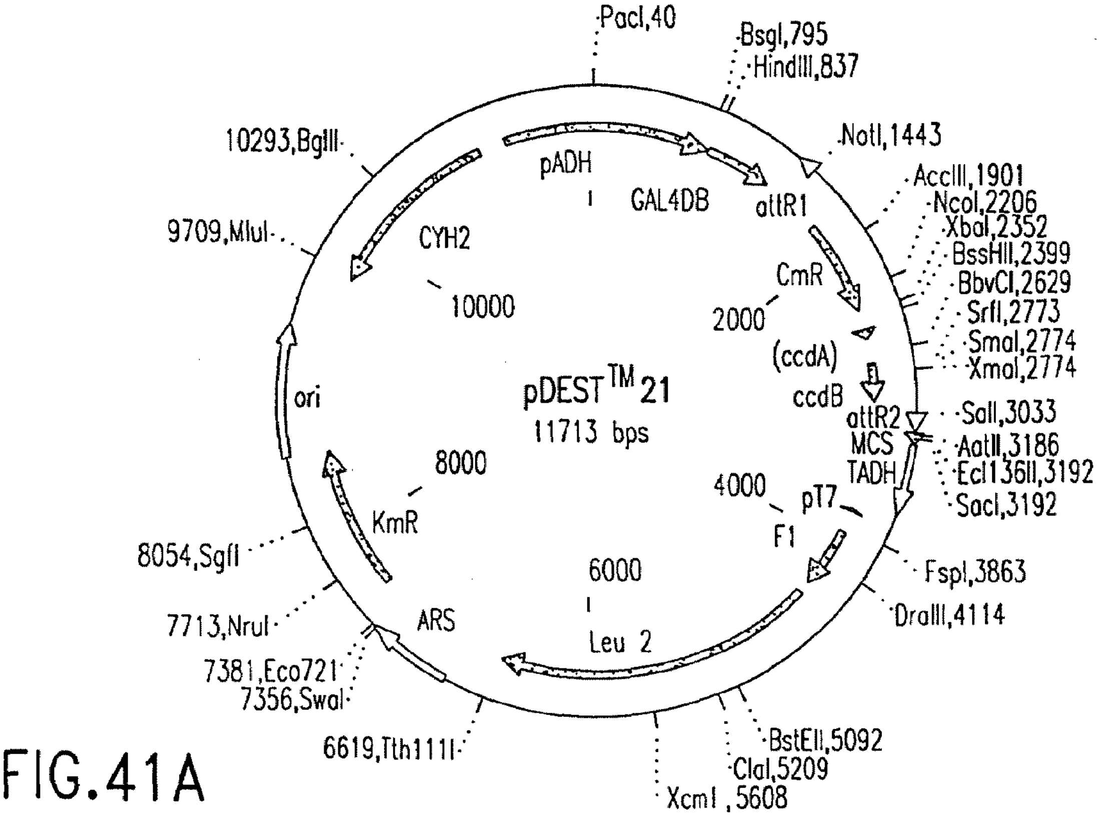
FIG.41A pDEST21 11713 bp (rotated to position 11000)

| Location (Base Nos.) | Gene Encoded |
|---|---|
| 857..1322 | GAL4DB |
| 1456..1332 | attR1 |
| 1706..2365 | CmR |
| 2485..2569 | inactivated ccdA |
| 2707..3012 | ccdB |
| 3053..3177 | attR2 |
| 3716..3735 | pT7 (T7 promoter) |
| 3899..4354 | f1 (f1 intergenic region) |
| 4414..6642 | Leu2 |
| 7541..8515 | kanR |
| 9668..10958 | CYH2 |
| 11118..848 | pADH (ADH promoter) |

```
   1 TTTATTATGT TACAATATGG AAGGGAACTT TACACTTCTC CTATGCACAT ATATTAATTA
  61 AAGTCCAATG CTAGTAGAGA AGGGGGGTAA CACCCCTCCG CGCTCTTTTC CGATTTTTTT
 121 CTAAACCGTG GAATATTTCG GATATCCTTT TGTTGTTTCC GGGTGTACAA TATGGACTTC
 181 CTCTTTTCTG GCAACCAAAC CCATACATCG GGATTCCTAT AATACCTTCG TTGGTCTCCC
 241 TAACATGTAG GTGGCGGAGG GGAGATATAC AATAGAACAG ATACCAGACA AGACATAATG
 301 GGCTAAACAA GACTACACCA ATTACACTGC CTCATTGATG GTGGTACATA ACGAACTAAT
 361 ACTGTAGCCC TAGACTTGAT AGCCATCATC ATATCGAAGT TTCACTACCC TTTTTCCATT
 421 TGCCATCTAT TGAAGTAATA ATAGGCGCAT GCAACTTCTT TTCTTTTTTT TTCTTTTCTC
 481 TCTCCCCCGT TGTTGTCTCA CCATATCCGC AATGACAAAA AAAATGATGG AAGACACTAA
 541 AGGAAAAAAT TAACGACAAA GACAGCACCA ACAGATGTCG TTGTTCCAGA GCTGATGAGG
 601 GGTATCTTCG AACACACGAA ACTTTTTCCT TCCTTCATTC ACGCACACTA CTCTCTAATG
 661 AGCAACGGTA TACGGCCTTC CTTCCAGTTA CTTGAATTTG AAATAAAAAA AGTTTGCCGC
 721 TTTGCTATCA AGTATAAATA GACCTGCAAT TATTAATCTT TTGTTTCCTC GTCATTGTTC
 781 TCGTTCCCTT TCTTCCTTGT TTCTTTTTCT GCACAATATT TCAAGCTATA CCAAGCATAC
 841 AATCAACTCC AAGCTTGAAG CAAGCCTCCT GAAAGATGAA GCTACTGTCT TCTATCGAAC
 901 AAGCATGCGA TATTTGCCGA CTTAAAAAGC TCAAGTGCTC CAAAGAAAAA CCGAAGTGCG
 961 CCAAGTGTCT GAAGAACAAC TGGGAGTGTC GCTACTCTCC CAAAACCAAA AGGTCTCCGC
1021 TGACTAGGGC ACATCTGACA GAAGTGGAAT CAAGGCTAGA AAGACTGGAA CAGCTATTTC
1081 TACTGATTTT TCCTCGAGAA GACCTTGACA TGATTTTGAA AATGGATTCT TTACAGGATA
1141 TAAAAGCATT GTTAACAGGA TTATTTGTAC AAGATAATGT GAATAAAGAT GCCGTCACAG
1201 ATAGATTGGC TTCAGTGGAG ACTGATATGC CTCTAACATT GAGACAGCAT AGAATAAGTG
1261 CGACATCATC ATCGGAAGAG AGTAGTAACA AAGGTCAAAG ACAGTTGACT GTATCGTCGA
1321 GGTCGAATCA AACAAGTTTG TACAAAAAAG CTGAACGAGA AACGTAAAAT GATATAAATA
1381 TCAATATATT AAATTAGATT TTGCATAAAA AACAGACTAC ATAATACTGT AAAACACAAC
1441 ATATCCAGTC ACTATGGCGG CCGCTAAGTT GGCAGCATCA CCCGACGCAC TTTGCGCCGA
1501 ATAAATACCT GTGACGGAAG ATCACTTCGC AGAATAAATA AATCCTGGTG TCCCTGTTGA
1561 TACCGGGAAG CCCTGGGCCA ACTTTTGGCG AAAATGAGAC GTTGATCGGC ACGTAAGAGG
1621 TTCCAACTTT CACCATAATG AAATAAGATC ACTACCGGGC GTATTTTTTG AGTTATCGAG
1681 ATTTTCAGGA GCTAAGGAAG CTAAAATGGA GAAAAAAATC ACTGGATATA CCACCGTTGA
```

FIG.41B

```
1741 TATATCCCAA TGGCATCGTA AAGAACATTT TGAGGCATTT CAGTCAGTTG CTCAATGTAC
1801 CTATAACCAG ACCGTTCAGC TGGATATTAC GGCCTTTTTA AAGACCGTAA AGAAAAATAA
1861 GCACAAGTTT TATCCGGCCT TTATTCACAT TCTTGCCCGC CTGATGAATG CTCATCCGGA
1921 ATTCCGTATG GCAATGAAAG ACGGTGAGCT GGTGATATGG GATAGTGTTC ACCCTTGTTA
1981 CACCGTTTTC CATGAGCAAA CTGAAACGTT TTCATCGCTC TGGAGTGAAT ACCACGACGA
2041 TTTCCGGCAG TTTCTACACA TATATTCGCA AGATGTGGCG TGTTACGGTG AAAACCTGGC
2101 CTATTTCCCT AAAGGGTTTA TTGAGAATAT GTTTTTCGTC TCAGCCAATC CCTGGGTGAG
2161 TTTCACCAGT TTTGATTTAA ACGTGGCCAA TATGGACAAC TTCTTCGCCC CCGTTTTCAC
2221 CATGGGCAAA TATTATACGC AAGGCGACAA GGTGCTGATG CCGCTGGCGA TTCAGGTTCA
2281 TCATGCCGTC TGTGATGGCT TCCATGTCGG CAGAATGCTT AATGAATTAC AACAGTACTG
2341 CGATGAGTGG CAGGGCGGGG CGTAATCTAG AGGATCCGGC TTACTAAAAG CCAGATAACA
2401 GTATGCGTAT TTGCGCGCTG ATTTTTGCGG TATAAGAATA TATACTGATA TGTATACCCG
2461 AAGTATGTCA AAAAGAGGTG TGCTATGAAG CAGCGTATTA CAGTGACAGT TGACAGCGAC
2521 AGCTATCAGT TGCTCAAGGC ATATATGATG TCAATATCTC CGGTCTGGTA AGCACAACCA
2581 TGCAGAATGA AGCCCGTCGT CTGCGTGCCG AACGCTGGAA AGCGGAAAAT CAGGAAGGGA
2641 TGGCTGAGGT CGCCCGGTTT ATTGAAATGA ACGGCTCTTT TGCTGACGAG AACAGGGACT
2701 GGTGAAATGC AGTTTAAGGT TTACACCTAT AAAAGAGAGA GCCGTTATCG TCTGTTTGTG
2761 GATGTACAGA GTGATATTAT TGACACGCCC GGGCGACGGA TGGTGATCCC CCTGGCCAGT
2821 GCACGTCTGC TGTCAGATAA AGTCTCCCGT GAACTTTACC CGGTGGTGCA TATCGGGGAT
2881 GAAAGCTGGC GCATGATGAC CACCGATATG GCCAGTGTGC CGGTCTCCGT TATCGGGGAA
2941 GAAGTGGCTG ATCTCAGCCA CCGCGAAAAT GACATCAAAA ACGCCATTAA CCTGATGTTC
3001 TGGGGAATAT AAATGTCAGG CTCCCTTATA CACAGCCAGT CTGCAGGTCG ACCATAGTGA
3061 CTGGATATGT TGTGTTTTAC AGTATTATGT AGTCTGTTTT TTATGCAAAA TCTAATTTAA
3121 TATATTGATA TTTATATCAT TTTACGTTTC TCGTTCAGCT TTCTTGTACA AAGTGGTTTG
3181 ATGGCCGCTA AGTAAGTAAG ACGTCGAGCT CTAAGTAAGT AACGGCCGCC ACCGCGGTGG
3241 AGCTTTGGAC TTCTTCGCCA GAGGTTTGGT CAAGTCTCCA ATCAAGGTTG TCGGCTTGTC
3301 TACCTTGCCA GAAATTTACG AAAAGATGGA AAAGGGTCAA ATCGTTGGTA GATACGTTGT
3361 TGACACTTCT AAATAAGCGA ATTTCTTATG ATTTATGATT TTTATTATTA AATAAGTTAT
3421 AAAAAAAATA AGTGTATACA AATTTTAAAG TGACTCTTAG GTTTTAAAAC GAAAATTCTT
3481 ATTCTTGAGT AACTCTTTCC TGTAGGTCAG GTTGCTTTCT CAGGTATAGC ATGAGGTCGC
3541 TCTTATTGAC CACACCTCTA CCGGCATGCC GAGCAAATGC CTGCAAATCG CTCCCCATTT
3601 CACCCAATTG TAGATATGCT AACTCCAGCA ATGAGTTGAT GAATCTCGGT GTGTATTTTA
3661 TGTCCTCAGA GGACAATACC TGTTGTAATC GTTCTTCCAC ACGGATCCCA ATTCGCCCTA
3721 TAGTGAGTCG TATTACAATT CACTGGCCGT CGTTTTACAA CGTCGTGACT GGGAAAACCC
3781 TGGCGTTACC CAACTTAATC GCCTTGCAGC ACATCCCCCT TTCGCCAGCT GGCGTAATAG
3841 CGAAGAGGCC CGCACCGATC GCCCTTCCCA ACAGTTGCGC AGCCTGAATG GCGAATGGAC
3901 GCGCCCTGTA GCGGCGCATT AAGCGCGGCG GGTGTGGTGG TTACGCGCAG CGTGACCGCT
3961 ACACTTGCCA GCGCCCTAGC GCCCGCTCCT TTCGCTTTCT TCCCTTCCTT TCTCGCCACG
4021 TTCGCCGGCT TTCCCCGTCA AGCTCTAAAT CGGGGGCTCC CTTTAGGGTT CCGATTTAGT
4081 GCTTTACGGC ACCTCGACCC CAAAAAACTT GATTAGGGTG ATGGTTCACG TAGTGGGCCA
4141 TCGCCCTGAT AGACGGTTTT TCGCCCTTTG ACGTTGGAGT CCACGTTCTT TAATAGTGGA
4201 CTCTTGTTCC AAACTGGAAC AACACTCAAC CCTATCTCGG TCTATTCTTT TGATTTATAA
4261 GGGATTTTGC CGATTTCGGC CTATTGGTTA AAAAATGAGC TGATTTAACA AAAATTTAAC
```

FIG.41C

4321 GCGAATTTTA ACAAAATATT AACGTTTACA ATTTCCTGAT GCGGTATTTT CTCCTTACGC
4381 ATCTGTGCGG TATTTCACAC CGCATATCGA CCGGTCGAGG AGAACTTCTA GTATATCCAC
4441 ATACCTAATA TTATTGCCTT ATTAAAAATG GAATCGGAAC AATTACATCA AAATCCACAT
4501 TCTCTTCAAA ATCAATTGTC CTGTACTTCC TTGTTCATGT GTGTTCAAAA ACGTTATATT
4561 TATAGGATAA TTATACTCTA TTTCTCAACA AGTAATTGGT TGTTTGGCCG AGCGGTCTAA
4621 GGCGCCTGAT TCAAGAAATA TCTTGACCGC AGTTAACTGT GGGAATACTC AGGTATCGTA
4681 AGATGCAAGA GTTCGAATCT CTTAGCAACC ATTATTTTTT TCCTCAACAT AACGAGAACA
4741 CACAGGGGCG CTATCGCACA GAATCAAATT CGATGACTGG AAATTTTTTG TTAATTTCAG
4801 AGGTCGCCTG ACGCATATAC CTTTTTCAAC TGAAAAATTG GGAGAAAAAG GAAAGGTGAG
4861 AGGCCGGAAC CGGCTTTTCA TATAGAATAG AGAAGCGTTC ATGACTAAAT GCTTGCATCA
4921 CAATACTTGA AGTTGACAAT ATTATTTAAG GACCTATTGT TTTTTCCAAT AGGTGGTTAG
4981 CAATCGTCTT ACTTTCTAAC TTTTCTTACC TTTTACATTT CAGCAATATA TATATATATT
5041 TCAAGGATAT ACCATTCTAA TGTCTGCCCC TATGTCTGCC CCTAAGAAGA TCGTCGTTTT
5101 GCCAGGTGAC CACGTTGGTC AAGAAATCAC AGCCGAAGCC ATTAAGGTTC TTAAAGCTAT
5161 TTCTGATGTT CGTTCCAATG TCAAGTTCGA TTTCGAAAAT CATTTAATTG GTGGTGCTGC
5221 TATCGATGCT ACAGGTGTCC CACTTCCAGA TGAGGCGCTG GAAGCCTCCA AGAAGGTTGA
5281 TGCCGTTTTG TTAGGTGCTG TGGGTGGTCC TAAATGGGGT ACCGGTAGTG TTAGACCTGA
5341 ACAAGGTTTA CTAAAAATCC GTAAAGAACT TCAATTGTAC GCCAACTTAA GACCATGTAA
5401 CTTTGCATCC GACTCTCTTT TAGACTTATC TCCAATCAAG CCACAATTTG CTAAAGGTAC
5461 TGACTTCGTT GTTGTCAGAG AATTAGTGGG AGGTATTTAC TTTGGTAAGA GAAAGGAAGA
5521 CGATGGTGAT GGTGTCGCTT GGGATAGTGA ACAATACACC GTTCCAGAAG TGCAAAGAAT
5581 CACAAGAATG GCCGCTTTCA TGGCCCTACA ACATGAGCCA CCATTGCCTA TTTGGTCCTT
5641 GGATAAAGCT AATGTTTTGG CCTCTTCAAG ATTATGGAGA AAAACTGTGG AGGAAACCAT
5701 CAAGAACGAA TTCCCTACAT TGAAGGTTCA ACATCAATTG ATTGATTCTG CCGCCATGAT
5761 CCTAGTTAAG AACCCAACCC ACCTAAATGG TATTATAATC ACCAGCAACA TGTTTGGTGA
5821 TATCATCTCC GATGAAGCCT CCGTTATCCC AGGTTCCTTG GGTTTGTTGC CATCTGCGTC
5881 CTTGGCCTCT TTGCCAGACA AGAACACCGC ATTTGGTTTG TACGAACCAT GCCACGGTTC
5941 TGCTCCAGAT TTGCCAAAGA ATAAGGTTGA CCCTATCGCC ACTATCTTGT CTGCTGCAAT
6001 GATGTTGAAA TTGTCATTGA ACTTGCCTGA AGAAGGTAAG GCCATTGAAG ATGCAGTTAA
6061 AAAGGTTTTG GATGCAGGTA TCAGAACTGG TGATTTAGGT GGTTCCAACA GTACCACCGA
6121 AGTCGGTGAT GCTGTCGCCG AAGAAGTTAA GAAAATCCTT GCTTAAAAAG ATTCTCTTTT
6181 TTTATGATAT TTGTACATAA ACTTTATAAA TGAAATTCAT AATAGAAACG ACACGAAATT
6241 ACAAAATGGA ATATGTTCAT AGGGTAGACG AAACTATATA CGCAATCTAC ATACATTTAT
6301 CAAGAAGGAG AAAAAGGAGG ATAGTAAAGG AATACAGGTA AGCAAATTGA TACTAATGGC
6361 TCAACGTGAT AAGGAAAAAG AATTGCACTT TAACATTAAT ATTGACAAGG AGGAGGGCAC
6421 CACACAAAAA GTTAGGTGTA ACAGAAAATC ATGAAACTAC GATTCCTAAT TTGATATTGG
6481 AGGATTTTCT CTAAAAAAAA AAAAATACAA CAAATAAAAA ACACTCAATG ACCTGACCAT
6541 TTGATGGAGT TTAAGTCAAT ACCTTCTTGA ACCATTTCCC ATAATGGTGA AAGTTCCCTC
6601 AAGAATTTTA CTCTGTCAGA AACGGCCTTA CGACGTAGTC GATATGGTGC ACTCTCAGTA
6661 CAATCTGCTC TGATGCCGCA TAGTTAAGCC AGCCCCGACA CCCGCCAACA CCCGCTGACG
6721 CGCCCTGACG GGCTTGTCTG CTCCCGGCAT CCGCTTACAG ACAAGCTGTG ACCGTCTCCG
6781 GGAGCTGCAT GTGTCAGAGG TTTTCACCGT CATCACCGAA ACGCGCGAGA CGAAAGGGCC
6841 TCGTGATACG CCTATTTTTA TAGGTTAATG TCATGATAAT AATGGTTTCT TAGGACGGAT

FIG.41D

```
6901 CGCTTGCCTG TAACTTACAC GCGCCTCGTA TCTTTTAATG ATGGAATAAT TTGGGAATTT
6961 ACTCTGTGTT TATTTATTTT TATGTTTTGT ATTTGGATTT TAGAAAGTAA ATAAAGAAGG
7021 TAGAAGAGTT ACGGAATGAA GAAAAAAAAA TAAACAAAGG TTTAAAAAAT TTCAACAAAA
7081 AGCGTACTTT ACATATATAT TTATTAGACA AGAAAAGCAG ATTAAATAGA TATACATTCG
7141 ATTAACGATA AGTAAAATGT AAAATCACAG GATTTTCGTG TGTGGTCTTC TACACAGACA
7201 AGATGAAACA ATTCGGCATT AATACCTGAG AGCAGGAAGA GCAAGATAAA AGGTAGTATT
7261 TGTTGGCGAT CCCCCTAGAG TCTTTTACAT CTTCGGAAAA CAAAAACTAT TTTTTCTTTA
7321 ATTTCTTTTT TTACTTTCTA TTTTTAATTT ATATATTTAT ATTAAAAAAT TTAAATTATA
7381 ATTATTTTTA TAGCACGTGA TGAAAAGGAC CCAGGTGGCA CTTTTCGGGG AAATGTGCGC
7441 GGAACCCCTA TTTGTTTATT TTTCTAAATA CATTCAAATA TGTATCCGCT CATGAGACAA
7501 TAACCCTGAT AAATGCTTCA ATAATCTGCA GCTCTGGCCC GTGTCTCAAA ATCTCTGATG
7561 TTACATTGCA CAAGATAAAA ATATATCATC ATGAACAATA AAACTGTCTG CTTACATAAA
7621 CAGTAATACA AGGGGTGTTA TGAGCCATAT TCAACGGGAA ACGTCTTGCT GGAGGCCGCG
7681 ATTAAATTCC AACATGGATG CTGATTTATA TGGGTATAAA TGGGCTCGCG ATAATGTCGG
7741 GCAATCAGGT GCGACAATCT TTCGATTGTA TGGGAAGCCC GATGCGCCAG AGTTGTTTCT
7801 GAAACATGGC AAAGGTAGCG TTGCCAATGA TGTTACAGAT GAGATGGTCA GACTAAACTG
7861 GCTGACGGAA TTTATGCCTC TTCCGACCAT CAAGCATTTT ATCCGTACTC CTGATGATGC
7921 ATGGTTACTC ACCACTGCGA TCCGCGGGAA AACAGCATTC CAGGTATTAG AAGAATATCC
7981 TGATTCAGGT GAAAATATTG TTGATGCGCT GGCAGTGTTC CTGCGCCGGT TGCATTCGAT
8041 TCCTGTTTGT AATTGTCCTT TTAACAGCGA TCGCGTATTT CGTCTCGCTC AGGCGCAATC
8101 ACGAATGAAT AACGGTTTGG TTGATGCGAG TGATTTTGAT GACGAGCGTA ATGGCTGGCC
8161 TGTTGAACAA GTCTGGAAAG AAATGCATAC GCTTTTGCCA TTCTCACCGG ATTCAGTCGT
8221 CACTCATGGT GATTTCTCAC TTGATAACCT TATTTTTGAC GAGGGGAAAT TAATAGGTTG
8281 TATTGATGTT GGACGAGTCG GAATCGCAGA CCGATACCAG GATCTTGCCA TCCTATGGAA
8341 CTGCCTCGGT GAGTTTTCTC CTTCATTACA GAAACGGCTT TTTCAAAAAT ATGGTATTGA
8401 TAATCCTGAT ATGAATAAAT TGCAGTTTCA TTTGATGCTC GATGAGTTTT TCTAATCAGA
8461 ATTGGTTAAT TGGTTGTAAC ACTGGCAGAG CATTACGCTG ACTTGACGGG ACGGCGCATG
8521 ACCAAAATCC CTTAACGTGA GTTTTCGTTC CACTGAGCGT CAGACCCCGT AGAAAAGATC
8581 AAAGGATCTT CTTGAGATCC TTTTTTTCTG CGCGTAATCT GCTGCTTGCA AACAAAAAAA
8641 CCACCGCTAC CAGCGGTGGT TTGTTTGCCG GATCAAGAGC TACCAACTCT TTTTCCGAAG
8701 GTAACTGGCT TCAGCAGAGC GCAGATACCA AATACTGTCC TTCTAGTGTA GCCGTAGTTA
8761 GGCCACCACT TCAAGAACTC TGTAGCACCG CCTACATACC TCGCTCTGCT AATCCTGTTA
8821 CCAGTGGCTG CTGCCAGTGG CGATAAGTCG TGTCTTACCG GGTTGGACTC AAGACGATAG
8881 TTACCGGATA AGGCGCAGCG GTCGGGCTGA ACGGGGGGTT CGTGCACACA GCCCAGCTTG
8941 GAGCGAACGA CCTACACCGA ACTGAGATAC CTACAGCGTG AGCATTGAGA AAGCGCCACG
9001 CTTCCCGAAG GGAGAAAGGC GGACAGGTAT CCGGTAAGCG GCAGGGTCGG AACAGGAGAG
9061 CGCACGAGGG AGCTTCCAGG GGGGAACGCC TGGTATCTTT ATAGTCCTGT CGGGTTTCGC
9121 CACCTCTGAC TTGAGCGTCG ATTTTTGTGA TGCTCGTCAG GGGGGCCGAG CCTATGGAAA
9181 AACGCCAGCA ACGCGGCCTT TTTACGGTTC CTGGCCTTTT GCTGGCCTTT TGCTCACATG
9241 TTCTTTCCTG CGTTATCCCC TGATTCTGTG GATAACCGTA TTACCGCCTT TGAGTGAGCT
9301 GATACCGCTC GCCGCAGCCG AACGACCGAG CGCAGCGAGT CAGTGAGCGA GGAAGCGGAA
9361 GAGCGCCCAA TACGCAAACC GCCTCTCCCC GCGCGTTGGC CGATTCATTA ATGCAGCTGG
9421 CACGACAGGT TTCCCGACTG GAAAGCGGGC AGTGAGCGCA ACGCAATTAA TGTGAGTTAC
```

FIG. 41E

```
9481 CTCACTCATT AGGCACCCCA GGCTTTACAC TTTATGCTTC CGGCTCCTAT GTTGTGTGGA
9541 ATTGTGAGCG GATAACAATT TCACACAGGA AACAGCTATG ACCATGATTA CGCCAAGCTC
9601 GGAATTAACC CTCACTAAAG GGAACAAAAG CTGGTACCGA TCCCGAGCTT TGCAAATTAA
9661 AGCCTTCGAG CGTCCCAAAA CCTTCTCAAG CAAGGTTTTC AGTATAATGT TACATGCGTA
9721 CACGCGTCTG TACAGAAAAA AAAGAAAAAT TTGAAATATA AATAACGTTC TTAATACTAA
9781 CATAACTATA AAAAAATAAA TAGGGACCTA GACTTCAGGT TGTCTAACTC CTTCCTTTTC
9841 GGTTAGAGCG GATGTGGGGG GAGGGCGTGA ATGTAAGCGT GACATAACTA ATTACATGAT
9901 ATCGACAAAG GAAAAGGGGC CTGTTTACTC ACAGGCTTTT TTCAAGTAGG TAATTAAGTC
9961 GTTTCTGTCT TTTTCCTTCT TCAACCCACC AAAGGCCATC TTGGTACTTT TTTTTTTTTT
10021 TTTTTTTTTT TTTTTTTTTT TTTTTTTTTT TTTTTTTTTT TTTTTTTTTT TTTTTTTTTT
10081 TTTTTTTTTT TTTTTTTTTT TCATAGAAAT AATACAGAAG TAGATGTTGA ATTAGATTAA
10141 ACTGAAGATA TATAATTTAT TGGAAAATAC ATAGAGCTTT TTGTTGATGC GCTTAAGCGA
10201 TCAATTCAAC AACACCACCA GCAGCTCTGA TTTTTTCTTC AGCCAACTTG GAGACGAATC
10261 TAGCTTTGAC GATAACTGGA ACATTTGGAA TTCTACCCTT ACCCAAGATC TTACCGTAAC
10321 CGGCTGCCAA AGTGTCAATA ACTGGAGCAG TTTCCTTAGA AGCAGATTTC AAGTATTGGT
10381 CTCTCTTGTC TTCTGGGATC AATGTCCACA ATTTGTCCAA GTTCAAGACT GGCTTCCAGA
10441 AATGAGCTTG TTGCTTGTGG AAGTATCTCA TACCAACCTT ACCGAAATAA CCTGGATGGT
10501 ATTTATCCAT GTTAATTCTG TGGTGATGTT GACCACCGGC CATACCTCTA CCACCGGGGT
10561 GCTTTCTGTG CTTACCGATA CGACCTTTAC CGGCTGAGAC GTGACCTCTG TGCTTTCTAG
10621 TCTTAGTGAA TCTGGAAGGC ATTCTTGATT AGTTGGATGA TTGTTCTGGG ATTTAATGCA
10681 AAAATCACTT AAGAAGGAAA ATCAACGGAG AAAGCAAACG CCATCTTAAA TATACGGGAT
10741 ACAGATGAAA GGGTTTGAAC CTATCTGGAA AATAGCATTA AACAAGCGAA AAACTGCGAG
10801 GAAAATTGTT TGCGTCTCTG CGGGCTATTC ACGCGCCAGA GGAAAATAGG AAAAATAACA
10861 GGGCATTAGA AAAATAATTT TGATTTTGGT AATGTGTGGG TCCTGGTGTA CAGATGTTAC
10921 ATTGGTTACA GTACTCTTGT TTTTGCTGTG TTTTTCGATG AATCTCCAAA ATGGTTGTTA
10981 GCACATGGAA GAGTCACCGA TGCTAAGTTA TCTCTATGTA AGCTACGTGG CGTGACTTTT
11041 GATGAAGCCG CACAAGAGAT ACAGGATTGG CAACTGCAAA TAGAATCTGG GGATCCCCCC
11101 TCGAGATCCG GGATCGAAGA AATGATGGTA AATGAAATAG GAAATCAAGG AGCATGAAGG
11161 CAAAAGACAA ATATAAGGGT CGAACGAAAA ATAAAGTGAA AAGTGTTGAT ATGATGTATT
11221 TGGCTTTGCG GCGCCGAAAA AACGAGTTTA CGCAATTGCA CAATCATGCT GACTCTGTGG
11281 CGGACCCGCG CTCTTGCCGG CCCGGCGATA ACGCTGGGCG TGAGGCTGTG CCCGGCGGAG
11341 TTTTTTGCGC CTGCATTTTC CAAGGTTTAC CCTGCGCTAA GGGGCGAGAT TGGAGAAGCA
11401 ATAAGAATGC CGGTTGGGGT TGCGATGATG ACGACCACGA CAACTGGTGT CATTATTTAA
11461 GTTGCCGAAA GAACCTGAGT GCATTTGCAA CATGAGTATA CTAGAAGAAT GAGCCAAGAC
11521 TTGCGAGACG CGAGTTTGCC GGTGGTGCGA ACAATAGAGC GACCATGACC TTGAAGGTGA
11581 GACGCGCATA ACCGCTAGAG TACTTTGAAG AGGAAACAGC AATAGGGTTG CTACCAGTAT
11641 AAATAGACAG GTACATACAA CACTGGAAAT GGTTGTCTGT TTGAGTACGC TTTCAATTCA
11701 TTTGGGTGTG CAC
```

FIG.41F

2-HYBRID VECTOR WITH ACTIVATION DOMAIN 657 acg cac act act ctc taa tga gca acg gta tac ggc ctt cct tcc agt tac
tgc gtg tga tga gag att act cgt tgc cat atg ccg gaa gga agg tca atg 708 ttg aat ttg aaa taa aaa aag ttt gcc gct ttg cta tca agt ata aat aga
aac tta aac ttt att ttt ttc aaa cgg cga aac gat agt tca tat tta tct 759 cct gca att att aat ctt ttg ttt cct cgt cat tgt tct cgt tcc ctt tct
gga cgt taa taa tta gaa aac aaa gga gca gta aca aga gca agg gaa aga

ADH PROMOTER 810 tcc ttg ttt ctt ttt ctg cac aat att tca agc tat acc aag cat aca atc
agg aac aaa gaa aaa gac gtg tta taa agt tcg ata tgg ttc gta tgt tag M P K K Gal4-AD 861 aac tcc aag ctt atg ccc aag aag aag cgg aag gtc tcg agc ggc gcc aat
ttg agg ttc gaa tac ggg ttc ttc ttc gcc ttc cag agc tcg ccg cgg tta

START TRANSLATION

D G G S N Q T S 1218 gaa gat acc cca cca aac cca aaa aaa gag ggt ggg tcg aat caa aca agt
ctt cta tgg ggt ggt ttg ggt ttt ttt ctc cca ccc agc tta gtt tgt tca L Y K K A attR1

1269 ttg tac aaa aaa gct gaa cga gaa acg taa a
aac atg ttt ttt cga ctt gct ctt tgc att t Int

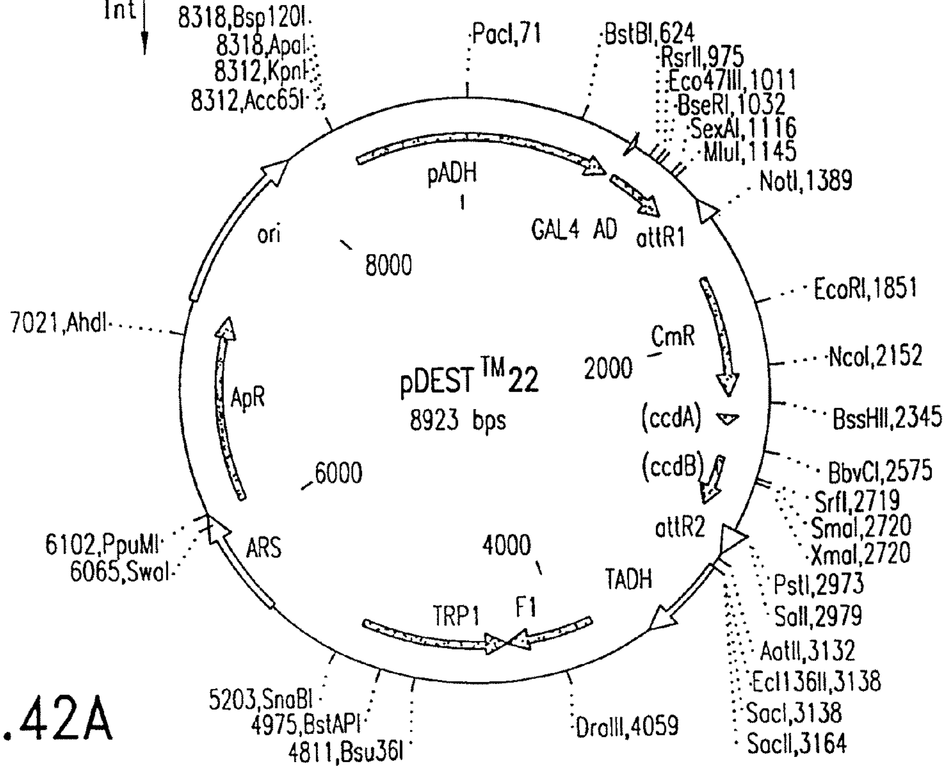

FIG.42A pDEST22 8923 bp

| Location (Base Nos.) | Gene Encoded |
|---|---|
| 904..1248 | GAL4 AD |
| 1388..1264 | attR1 |
| 1638..2297 | CmR |
| 2417..2501 | inactivated ccdA |
| 2639..2944 | ccdB |
| 2985..3109 | attR2 |
| 3831..4318 | f1 (f1 intergenic region) |
| 4334..5176 | TRP1 |
| 6110..7194 | ampR |
| 8344..866 | pADH (yeast ADH promoter) |

```
   1 TTCATTTGGG TGTGCACTTT ATTATGTTAC AATATGGAAG GGAACTTTAC ACTTCTCCTA
  61 TGCACATATA TTAATTAAAG TCCAATGCTA GTAGAGAAGG GGGGTAACAC CCCTCCGCGC
 121 TCTTTTCCGA TTTTTTTCTA AACCGTGGAA TATTTCGGAT ATCCTTTTGT TGTTTCCGGG
 181 TGTACAATAT GGACTTCCTC TTTTCTGGCA ACCAAACCCA TACATCGGGA TTCCTATAAT
 241 ACCTTCGTTG GTCTCCCTAA CATGTAGGTG GCGGAGGGGA GATATACAAT AGAACAGATA
 301 CCAGACAAGA CATAATGGGC TAAACAAGAC TACACCAATT ACACTGCCTC ATTGATGGTG
 361 GTACATAACG AACTAATACT GTAGCCCTAG ACTTGATAGC CATCATCATA TCGAAGTTTC
 421 ACTACCCTTT TTCCATTTGC CATCTATTGA AGTAATAATA GGCGCATGCA ACTTCTTTTC
 481 TTTTTTTTTC TTTTCTCTCT CCCCCGTTGT TGTCTCACCA TATCCGCAAT GACAAAAAAA
 541 ATGATGGAAG ACACTAAAGG AAAAAATTAA CGACAAAGAC AGCACCAACA GATGTCGTTG
 601 TTCCAGAGCT GATGAGGGGT ATCTTCGAAC ACACGAAACT TTTTCCTTCC TTCATTCACG
 661 CACACTACTC TCTAATGAGC AACGGTATAC GGCCTTCCTT CCAGTTACTT GAATTTGAAA
 721 TAAAAAAAGT TTGCCGCTTT GCTATCAAGT ATAAATAGAC CTGCAATTAT TAATCTTTTG
 781 TTTCCTCGTC ATTGTTCTCG TTCCCTTTCT TCCTTGTTTC TTTTTCTGCA CAATATTTCA
 841 AGCTATACCA AGCATACAAT CAACTCCAAG CTTATGCCCA AGAAGAAGCG GAAGGTCTCG
 901 AGCGGCGCCA ATTTTAATCA AAGTGGGAAT ATTGCTGATA GCTCATTGTC CTTCACTTTC
 961 ACTAACAGTA GCAACGGTCC GAACCTCATA ACAACTCAAA CAAATTCTCA AGCGCTTTCA
1021 CAACCAATTG CCTCCTCTAA CGTTCATGAT AACTTCATGA ATAATGAAAT CACGGCTAGT
1081 AAAATTGATG ATGGTAATAA TTCAAAACCA CTGTCACCTG GTTGGACGGA CCAAACTGCG
1141 TATAACGCGT TTGGAATCAC TACAGGGATG TTTAATACCA CTACAATGGA TGATGTATAT
1201 AACTATCTAT TCGATGATGA AGATACCCCA CCAAACCCAA AAAAAGAGGG TGGGTCGAAT
1261 CAAACAAGTT TGTACAAAAA AGCTGAACGA GAAACGTAAA ATGATATAAA TATCAATATA
1321 TTAAATTAGA TTTTGCATAA AAAACAGACT ACATAATACT GTAAAACACA ACATATCCAG
1381 TCACTATGGC GGCCGCTAAG TTGGCAGCAT CACCCGACGC ACTTTGCGCC GAATAAATAC
1441 CTGTGACGGA AGATCACTTC GCAGAATAAA TAAATCCTGG TGTCCCTGTT GATACCGGGA
1501 AGCCCTGGGC CAACTTTTGG CGAAAATGAG ACGTTGATCG GCACGTAAGA GGTTCCAACT
1561 TTCACCATAA TGAAATAAGA TCACTACCGG GCGTATTTTT TGAGTTATCG AGATTTTCAG
1621 GAGCTAAGGA AGCTAAAATG GAGAAAAAAA TCACTGGATA TACCACCGTT GATATATCCC
1681 AATGGCATCG TAAAGAACAT TTTGAGGCAT TTCAGTCAGT TGCTCAATGT ACCTATAACC
1741 AGACCGTTCA GCTGGATATT ACGGCCTTTT TAAAGACCGT AAAGAAAAAT AAGCACAAGT
1801 TTTATCCGGC CTTTATTCAC ATTCTTGCCC GCCTGATGAA TGCTCATCCG GAATTCCGTA
```

FIG.42B

```
1861 TGGCAATGAA AGACGGTGAG CTGGTGATAT GGGATAGTGT TCACCCTTGT TACACCGTTT
1921 TCCATGAGCA AACTGAAACG TTTTCATCGC TCTGGAGTGA ATACCACGAC GATTTCCGGC
1981 AGTTTCTACA CATATATTCG CAAGATGTGG CGTGTTACGG TGAAAACCTG GCCTATTTCC
2041 CTAAAGGGTT TATTGAGAAT ATGTTTTTCG TCTCAGCCAA TCCCTGGGTG AGTTTCACCA
2101 GTTTTGATTT AAACGTGGCC AATATGGACA ACTTCTTCGC CCCCGTTTTC ACCATGGGCA
2161 AATATTATAC GCAAGGCGAC AAGGTGCTGA TGCCGCTGGC GATTCAGGTT CATCATGCCG
2221 TCTGTGATGG CTTCCATGTC GGCAGAATGC TTAATGAATT ACAACAGTAC TGCGATGAGT
2281 GGCAGGGCGG GGCGTAATCT AGAGGATCCG GCTTACTAAA AGCCAGATAA CAGTATGCGT
2341 ATTTGCGCGC TGATTTTTGC GGTATAAGAA TATATACTGA TATGTATACC CGAAGTATGT
2401 CAAAAAGAGG TGTGCTATGA AGCAGCGTAT TACAGTGACA GTTGACAGCG ACAGCTATCA
2461 GTTGCTCAAG GCATATATGA TGTCAATATC TCCGGTCTGG TAAGCACAAC CATGCAGAAT
2521 GAAGCCCGTC GTCTGCGTGC CGAACGCTGG AAAGCGGAAA ATCAGGAAGG GATGGCTGAG
2581 GTCGCCCGGT TTATTGAAAT GAACGGCTCT TTTGCTGACG AGAACAGGGA CTGGTGAAAT
2641 GCAGTTTAAG GTTTACACCT ATAAAAGAGA GAGCCGTTAT CGTCTGTTTG TGGATGTACA
2701 GAGTGATATT ATTGACACGC CCGGGCGACG GATGGTGATC CCCCTGGCCA GTGCACGTCT
2761 GCTGTCAGAT AAAGTCTCCC GTGAACTTTA CCCGGTGGTG CATATCGGGG ATGAAAGCTG
2821 GCGCATGATG ACCACCGATA TGGCCAGTGT GCCGGTCTCC GTTATCGGGG AAGAAGTGGC
2881 TGATCTCAGC CACCGCGAAA ATGACATCAA AAACGCCATT AACCTGATGT TCTGGGGAAT
2941 ATAAATGTCA GGCTCCCTTA TACACAGCCA GTCTGCAGGT CGACCATAGT GACTGGATAT
3001 GTTGTGTTTT ACAGTATTAT GTAGTCTGTT TTTTATGCAA AATCTAATTT AATATATTGA
3061 TATTTATATC ATTTTACGTT TCTCGTTCAG CTTTCTTGTA CAAAGTGGTT TGATGGCCGC
3121 TAAGTAAGTA AGACGTCGAG CTCTAAGTAA GTAACGGCCG CCACCGCGGT GGAGCTTTGG
3181 ACTTCTTCGC CAGAGGTTTG GTCAAGTCTC CAATCAAGGT TGTCGGCTTG TCTACCTTGC
3241 CAGAAATTTA CGAAAAGATG GAAAAGGGTC AAATCGTTGG TAGATACGTT GTTGACACTT
3301 CTAAATAAGC GAATTTCTTA TGATTTATGA TTTTTATTAT TAAATAAGTT ATAAAAAAAA
3361 TAAGTGTATA CAAATTTTAA AGTGACTCTT AGGTTTTAAA ACGAAAATTC TTATTCTTGA
3421 GTAACTCTTT CCTGTAGGTC AGGTTGCTTT CTCAGGTATA GCATGAGGTC GCTCTTATTG
3481 ACCACACCTC TACCGGCATG CCGAGCAAAT GCCTGCAAAT CGCTCCCCAT TTCACCCAAT
3541 TGTAGATATG CTAACTCCAG CAATGAGTTG ATGAATCTCG GTGTGTATTT TATGTCCTCA
3601 GAGGACAATA CCTGTTGTAA TCGTTCTTCC ACACGGATCC CAATTCGCCC TATAGTGAGT
3661 CGTATTACAA TTCACTGGCC GTCGTTTTAC AACGTCGTGA CTGGGAAAAC CCTGGCGTTA
3721 CCCAACTTAA TCGCCTTGCA GCACATCCCC CTTTCGCCAG CTGGCGTAAT AGCGAAGAGG
3781 CCCGCACCGA TCGCCCTTCC CAACAGTTGC GCAGCCTGAA TGGCGAATGG ACGCGCCCTG
3841 TAGCGGCGCA TTAAGCGCGG CGGGTGTGGT GGTTACGCGC AGCGTGACCG CTACACTTGC
3901 CAGCGCCCTA GCGCCCGCTC CTTTCGCTTT CTTCCCTTCC TTTCTCGCCA CGTTCGCCGG
3961 CTTTCCCCGT CAAGCTCTAA ATCGGGGGCT CCCTTTAGGG TTCCGATTTA GTGCTTTACG
4021 GCACCTCGAC CCCAAAAAAC TTGATTAGGG TGATGGTTCA CGTAGTGGGC CATCGCCCTG
4081 ATAGACGGTT TTTCGCCCTT TGACGTTGGA GTCCACGTTC TTTAATAGTG GACTCTTGTT
4141 CCAAACTGGA ACAACACTCA ACCCTATCTC GGTCTATTCT TTTGATTTAT AAGGGATTTT
4201 GCCGATTTCG GCCTATTGGT TAAAAAATGA GCTGATTTAA CAAAAATTTA ACGCGAATTT
4261 TAACAAAATA TTAACGTTTA CAATTTCCTG ATGCGGTATT TTCTCCTTAC GCATCTGTGC
4321 GGTATTTCAC ACCGCAGGCA AGTGCACAAA CAATACTTAA ATAAATACTA CTCAGTAATA
4381 ACCTATTTCT TAGCATTTTT GACGAAATTT GCTATTTTGT TAGAGTCTTT TACACCATTT
```

FIG.42C

4441 GTCTCCACAC CTCCGCTTAC ATCAACACCA ATAACGCCAT TTAATCTAAG CGCATCACCA
4501 ACATTTTCTG GCGTCAGTCC ACCAGCTAAC ATAAAATGTA AGCTTTCGGG GCTCTCTTGC
4561 CTTCCAACCC AGTCAGAAAT CGAGTTCCAA TCCAAAAGTT CACCTGTCCC ACCTGCTTCT
4621 GAATCAAACA AGGGAATAAA CGAATGAGGT TTCTGTGAAG CTGCACTGAG TAGTATGTTG
4681 CAGTCTTTTG GAAATACGAG TCTTTTAATA ACTGGCAAAC CGAGGAACTC TTGGTATTCT
4741 TGCCACGACT CATCTCCATG CAGTTGGACG ATATCAATGC CGTAATCATT GACCAGAGCC
4801 AAAACATCCT CCTTAGGTTG ATTACGAAAC ACGCCAACCA AGTATTTCGG AGTGCCTGAA
4861 CTATTTTTAT ATGCTTTTAC AAGACTTGAA ATTTTCCTTG CAATAACCGG GTCAATTGTT
4921 CTCTTTCTAT TGGGCACACA TATAATACCC AGCAAGTCAG CATCGGAATC TAGAGCACAT
4981 TCTGCGGCCT CTGTGCTCTG CAAGCCGCAA ACTTTCACCA ATGGACCAGA ACTACCTGTG
5041 AAATTAATAA CAGACATACT CCAAGCTGCC TTTGTGTGCT TAATCACGTA TACTCACGTG
5101 CTCAATAGTC ACCAATGCCC TCCCTCTTGG CCCTCTCCTT TTCTTTTTTC GACCGAATTA
5161 ATTCTTAATC GGCAAAAAAA GAAAAGCTCC GGATCAAGAT TGTACGTAAG GTGACAAGCT
5221 ATTTTTCAAT AAAGAATATC TTCCACTACT GCCATCTGGC GTCATAACTG CAAAGTACAC
5281 ATATATTACG ATGCTGTCTA TTAAATGCTT CCTATATTAT ATATATAGTA ATGTCGTTTA
5341 TGGTGCACTC TCAGTACAAT CTGCTCTGAT GCCGCATAGT TAAGCCAGCC CCGACACCCG
5401 CCAACACCCG CTGACGCGCC CTGACGGGCT TGTCTGCTCC CGGCATCCGC TTACAGACAA
5461 GCTGTGACCG TCTCCGGGAG CTGCATGTGT CAGAGGTTTT CACCGTCATC ACCGAAACGC
5521 GCGAGACGAA AGGGCCTCGT GATACGCCTA TTTTTATAGG TTAATGTCAT GATAATAATG
5581 GTTTCTTAGG ACGGATCGCT TGCCTGTAAC TTACACGCGC CTCGTATCTT TTAATGATGG
5641 AATAATTTGG GAATTTACTC TGTGTTTATT TATTTTTATG TTTTGTATTT GGATTTTAGA
5701 AAGTAAATAA AGAAGGTAGA AGAGTTACGG AATGAAGAAA AAAAAATAAA CAAAGGTTTA
5761 AAAAATTTCA ACAAAAAGCG TACTTTACAT ATATATTTAT TAGACAAGAA AAGCAGATTA
5821 AATAGATATA CATTCGATTA ACGATAAGTA AAATGTAAAA TCACAGGATT TTCGTGTGTG
5881 GTCTTCTACA CAGACAAGAT GAAACAATTC GGCATTAATA CCTGAGAGCA GGAAGAGCAA
5941 GATAAAAGGT AGTATTTGTT GGCGATCCCC CTAGAGTCTT TTACATCTTC GGAAAACAAA
6001 AACTATTTTT TCTTTAATTT CTTTTTTTAC TTTCTATTTT TAATTTATAT ATTTATATTA
6061 AAAAATTTAA ATTATAATTA TTTTTATAGC ACGTGATGAA AAGGACCCAG GTGGCACTTT
6121 TCGGGGAAAT GTGCGCGGAA CCCCTATTTG TTTATTTTTC TAAATACATT CAAATATGTA
6181 TCCGCTCATG AGACAATAAC CCTGATAAAT GCTTCAATAA TATTGAAAAA GGAAGAGTAT
6241 GAGTATTCAA CATTTCCGTG TCGCCCTTAT TCCCTTTTTT GCGGCATTTT GCCTTCCTGT
6301 TTTTGCTCAC CCAGAAACGC TGGTGAAAGT AAAAGATGCT GAAGATCAGT TGGGTGCACG
6361 AGTGGGTTAC ATCGAACTGG ATCTCAACAG CGGTAAGATC CTTGAGAGTT TTCGCCCCGA
6421 AGAACGTTTT CCAATGATGA GCACTTTTAA AGTTCTGCTA TGTGGCGCGG TATTATCCCG
6481 TATTGACGCC GGGCAAGAGC AACTCGGTCG CCGCATACAC TATTCTCAGA ATGACTTGGT
6541 TGAGTACTCA CCAGTCACAG AAAAGCATCT TACGGATGGC ATGACAGTAA GAGAATTATG
6601 CAGTGCTGCC ATAACCATGA GTGATAACAC TGCGGCCAAC TTACTTCTGA CAACGATCGG
6661 AGGACCGAAG GAGCTAACCG CTTTTTTTCA CAACATGGGG GATCATGTAA CTCGCCTTGA
6721 TCGTTGGGAA CCGGAGCTGA ATGAAGCCAT ACCAAACGAC GAGCGTGACA CCACGATGCC
6781 TGTAGCAATG GCAACAACGT TGCGCAAACT ATTAACTGGC GAACTACTTA CTCTAGCTTC
6841 CCGGCAACAA TTAATAGACT GGATGGAGGC GGATAAAGTT GCAGGACCAC TTCTGCGCTC
6901 GGCCCTTCCG GCTGGCTGGT TTATTGCTGA TAAATCTGGA GCCGGTGAGC GTGGGTCTCG
6961 CGGTATCATT GCAGCACTGG GGCCAGATGG TAAGCCCTCC CGTATCGTAG TTATCTACAC

FIG.42D

```
7021 GACGGGCAGT CAGGCAACTA TGGATGAACG AAATAGACAG ATCGCTGAGA TAGGTGCCTC
7081 ACTGATTAAG CATTGGTAAC TGTCAGACCA AGTTTACTCA TATATACTTT AGATTGATTT
7141 AAAACTTCAT TTTTAATTTA AAAGGATCTA GGTGAAGATC CTTTTTGATA ATCTCATGAC
7201 CAAAATCCCT TAACGTGAGT TTTCGTTCCA CTGAGCGTCA GACCCCGTAG AAAAGATCAA
7261 AGGATCTTCT TGAGATCCTT TTTTTCTGCG CGTAATCTGC TGCTTGCAAA CAAAAAAACC
7321 ACCGCTACCA GCGGTGGTTT GTTTGCCGGA TCAAGAGCTA CCAACTCTTT TTCCGAAGGT
7381 AACTGGCTTC AGCAGAGCGC AGATACCAAA TACTGTCCTT CTAGTGTAGC CGTAGTTAGG
7441 CCACCACTTC AAGAACTCTG TAGCACCGCC TACATACCTC GCTCTGCTAA TCCTGTTACC
7501 AGTGGCTGCT GCCAGTGGCG ATAAGTCGTG TCTTACCGGG TTGGACTCAA GACGATAGTT
7561 ACCGGATAAG GCGCAGCGGT CGGGCTGAAC GGGGGGTTCG TGCACACAGC CCAGCTTGGA
7621 GCGAACGACC TACACCGAAC TGAGATACCT ACAGCGTGAG CATTGAGAAA GCGCCACGCT
7681 TCCCGAAGGG AGAAAGGCGG ACAGGTATCC GGTAAGCGGC AGGGTCGGAA CAGGAGAGCG
7741 CACGAGGGAG CTTCCAGGGG GGAACGCCTG GTATCTTTAT AGTCCTGTCG GGTTTCGCCA
7801 CCTCTGACTT GAGCGTCGAT TTTTGTGATG CTCGTCAGGG GGGCCGAGCC TATGGAAAAA
7861 CGCCAGCAAC GCGGCCTTTT TACGGTTCCT GGCCTTTTGC TGGCCTTTTG CTCACATGTT
7921 CTTTCCTGCG TTATCCCCTG ATTCTGTGGA TAACCGTATT ACCGCCTTTG AGTGAGCTGA
7981 TACCGCTCGC CGCAGCCGAA CGACCGAGCG CAGCGAGTCA GTGAGCGAGG AAGCGGAAGA
8041 GCGCCCAATA CGCAAACCGC CTCTCCCCGC GCGTTGGCCG ATTCATTAAT GCAGCTGGCA
8101 CGACAGGTTT CCCGACTGGA AAGCGGGCAG TGAGCGCAAC GCAATTAATG TGAGTTACCT
8161 CACTCATTAG GCACCCCAGG CTTTACACTT TATGCTTCCG GCTCCTATGT TGTGTGGAAT
8221 TGTGAGCGGA TAACAATTTC ACACAGGAAA CAGCTATGAC CATGATTACG CCAAGCTCGG
8281 AATTAACCCT CACTAAAGGG AACAAAAGCT GGGTACCGGG CCCCCCCTCG AGATCCGGGA
8341 TCGAAGAAAT GATGGTAAAT GAAATAGGAA ATCAAGGAGC ATGAAGGCAA AAGACAAATA
8401 TAAGGGTCGA ACGAAAAATA AAGTGAAAAG TGTTGATATG ATGTATTTGG CTTTGCGGCG
8461 CCGAAAAAAC GAGTTTACGC AATTGCACAA TCATGCTGAC TCTGTGGCGG ACCCGCGCTC
8521 TTGCCGGCCC GGCGATAACG CTGGGCGTGA GGCTGTGCCC GGCGGAGTTT TTTGCGCCTG
8581 CATTTTCCAA GGTTTACCCT GCGCTAAGGG GCGAGATTGG AGAAGCAATA AGAATGCCGG
8641 TTGGGGTTGC GATGATGACG ACCACGACAA CTGGTGTCAT TATTTAAGTT GCCGAAAGAA
8701 CCTGAGTGCA TTTGCAACAT GAGTATACTA GAAGAATGAG CCAAGACTTG CGAGACGCGA
8761 GTTTGCCGGT GGTGCGAACA ATAGAGCGAC CATGACCTTG AAGGTGAGAC GCGCATAACC
8821 GCTAGAGTAC TTTGAAGAGG AAACAGCAAT AGGGTTGCTA CCAGTATAAA TAGACAGGTA
8881 CATACAACAC TGGAAATGGT TGTCTGTTTG AGTACGCTTT CAA
```

FIG.42E pDEST23
His6 CARBOXY-FUSION VECTOR, T7 PROMOTER

```
                     T7 PROMOTER            ——> mRNA
205  atc ccg cga aat taa tac gac tca cta tag gga gac cac aac ggt ttc cct
     tag ggc gct tta att atg ctg agt gat atc cct ctg gtg ttg cca aag gga

                       Int                      attR1
256  cta gat cac aag ttt gta caa aaa agc tga acg aga aac gta aaa tga tat
     gat cta gtg ttc aaa cat gtt ttt tcg act tgc tct ttg cat ttt act ata

     |———————— CmR ———————— ccdB ————————|

1888 ttt tta tgc aaa atc taa ttt aat ata ttg ata ttt ata tca ttt tac gtt
     aaa aat acg ttt tag att aaa tta tat aac tat aaa tat agt aaa atg caa

     attR2          A   F   L   Y   K   V   V   I   M   S   Y   Y   H   H
1939 tct cgt tca gct ttc ttg tac aaa gtg gtg att atg tcg tac tac cat cac
     aga gca agt cga aag aac atg ttt cac cac taa tac agc atg atg gta gtg
                                                                  His6

     H   H   H   H   L   D   E   Q   TERM
1990 cat cac cat cac ctc gat gag caa taa cta gca taa ccc ctt ggg gcc tct
     gta gtg gta gtg gag cta ctc gtt att gat cgt att ggg gaa ccc cgg aga
```

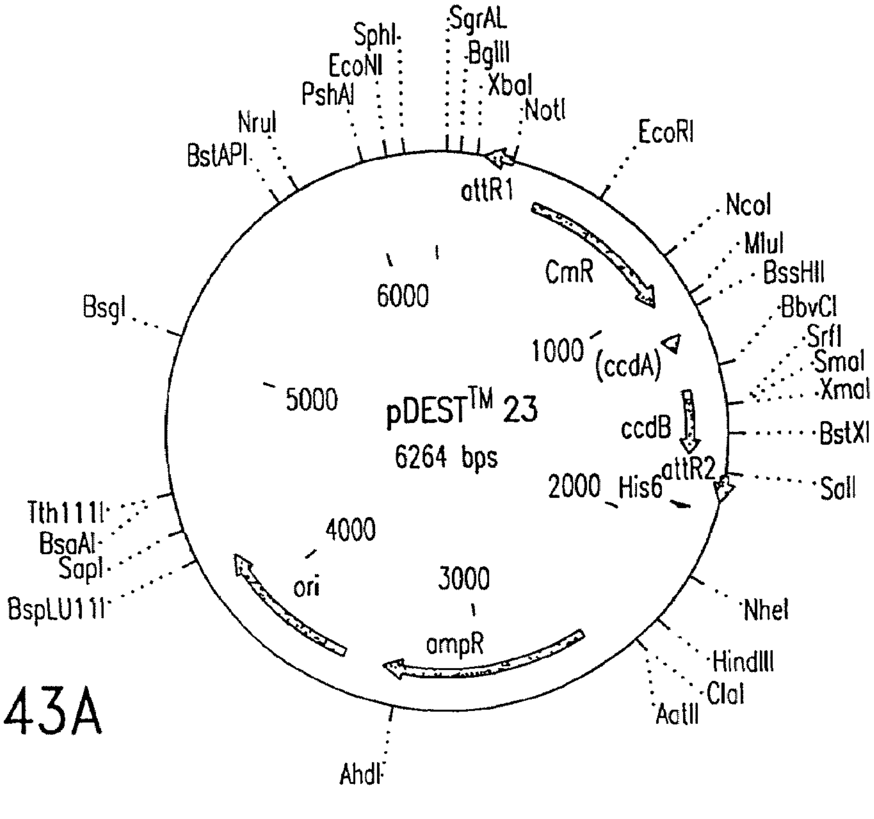

FIG.43A pDEST23 6264 bp

| Location (Base Nos.) | Gene Encoded |
|---|---|
| 285..161 | attR1 |
| 394..1053 | CmR |
| 1173..1257 | inactivated ccdA |
| 1395..1700 | ccdB |
| 1741..1865 | attR2 |
| 1883..1911 | his6 |
| 2574..3434 | ampR |
| 3583..4222 | ori |

1 TCTTCCCCAT CGGTGATGTC GGCGATATAG GCGCCAGCAA CCGCACCTGT GGCGCCGGTG
61 ATGCCGGCCA CGATGCGTCC GGCGTAGAGG ATCGAGATCT CGATCCCGCG AAATTAATAC
121 GACTCACTAT AGGGAGACCA CAACGGTTTC CCTCTAGATC ACAAGTTTGT ACAAAAAAGC
181 TGAACGAGAA ACGTAAAATG ATATAAATAT CAATATATTA AATTAGATTT TGCATAAAAA
241 ACAGACTACA TAATACTGTA AAACACAACA TATCCAGTCA CTATGGCGGC CGCATTAGGC
301 ACCCCAGGCT TTACACTTTA TGCTTCCGGC TCGTATAATG TGTGGATTTT GAGTTAGGAT
361 CCGGCGAGAT TTTCAGGAGC TAAGGAAGCT AAAATGGAGA AAAAAATCAC TGGATATACC
421 ACCGTTGATA TATCCCAATG GCATCGTAAA GAACATTTTG AGGCATTTCA GTCAGTTGCT
481 CAATGTACCT ATAACCAGAC CGTTCAGCTG GATATTACGG CCTTTTTAAA GACCGTAAAG
541 AAAAATAAGC ACAAGTTTTA TCCGGCCTTT ATTCACATTC TTGCCCGCCT GATGAATGCT
601 CATCCGGAAT TCCGTATGGC AATGAAAGAC GGTGAGCTGG TGATATGGGA TAGTGTTCAC
661 CCTTGTTACA CCGTTTTCCA TGAGCAAACT GAAACGTTTT CATCGCTCTG GAGTGAATAC
721 CACGACGATT TCCGGCAGTT TCTACACATA TATTCGCAAG ATGTGGCGTG TTACGGTGAA
781 AACCTGGCCT ATTTCCCTAA AGGGTTTATT GAGAATATGT TTTTCGTCTC AGCCAATCCC
841 TGGGTGAGTT TCACCAGTTT TGATTTAAAC GTGGCCAATA TGGACAACTT CTTCGCCCCC
901 GTTTTCACCA TGGGCAAATA TTATACGCAA GGCGACAAGG TGCTGATGCC GCTGGCGATT
961 CAGGTTCATC ATGCCGTCTG TGATGGCTTC CATGTCGGCA GAATGCTTAA TGAATTACAA
1021 CAGTACTGCG ATGAGTGGCA GGGCGGGGCG TAAACGCGTG GATCCGGCTT ACTAAAAGCC
1081 AGATAACAGT ATGCGTATTT GCGCGCTGAT TTTTGCGGTA TAAGAATATA TACTGATATG
1141 TATACCCGAA GTATGTCAAA AAGAGGTGTG CTATGAAGCA GCGTATTACA GTGACAGTTG
1201 ACAGCGACAG CTATCAGTTG CTCAAGGCAT ATATGATGTC AATATCTCCG GTCTGGTAAG
1261 CACAACCATG CAGAATGAAG CCCGTCGTCT GCGTGCCGAA CGCTGGAAAG CGGAAAATCA
1321 GGAAGGGATG GCTGAGGTCG CCCGGTTTAT TGAAATGAAC GGCTCTTTTG CTGACGAGAA
1381 CAGGGACTGG TGAAATGCAG TTTAAGGTTT ACACCTATAA AAGAGAGAGC CGTTATCGTC
1441 TGTTTGTGGA TGTACAGAGT GATATTATTG ACACGCCCGG GCGACGGATG GTGATCCCCC
1501 TGGCCAGTGC ACGTCTGCTG TCAGATAAAG TCTCCCGTGA ACTTTACCCG GTGGTGCATA
1561 TCGGGGATGA AAGCTGGCGC ATGATGACCA CCGATATGGC CAGTGTGCCG GTCTCCGTTA
1621 TCGGGGAAGA AGTGGCTGAT CTCAGCCACC GCGAAAATGA CATCAAAAAC GCCATTAACC
1681 TGATGTTCTG GGGAATATAA ATGTCAGGCT CCCTTATACA CAGCCAGTCT GCAGGTCGAC

FIG.43B

1741 CATAGTGACT GGATATGTTG TGTTTTACAG TATTATGTAG TCTGTTTTTT ATGCAAAATC
1801 TAATTTAATA TATTGATATT TATATCATTT TACGTTTCTC GTTCAGCTTT CTTGTACAAA
1861 GTGGTGATTA TGTCGTACTA CCATCACCAT CACCATCACC TCGATGAGCA ATAACTAGCA
1921 TAACCCCTTG GGGCCTCTAA ACGGGTCTTG AGGGGTTTTT TGCTGAAAGG AGGAACTATA
1981 TCCGGATATC CACAGGACGG GTGTGGTCGC CATGATCGCG TAGTCGATAG TGGCTCCAAG
2041 TAGCGAAGCG AGCAGGACTG GGCGGCGGCC AAAGCGGTCG GACAGTGCTC CGAGAACGGG
2101 TGCGCATAGA AATTGCATCA ACGCATATAG CGCTAGCAGC ACGCCATAGT GACTGGCGAT
2161 GCTGTCGGAA TGGACGATAT CCCGCAAGAG GCCCGGCAGT ACCGGCATAA CCAAGCCTAT
2221 GCCTACAGCA TCCAGGGTGA CGGTGCCGAG GATGACGATG AGCGCATTGT TAGATTTCAT
2281 ACACGGTGCC TGACTGCGTT AGCAATTTAA CTGTGATAAA CTACCGCATT AAAGCTTATC
2341 GATGATAAGC TGTCAAACAT GAGAATTCTT GAAGACGAAA GGGCCTCGTG ATACGCCTAT
2401 TTTTATAGGT TAATGTCATG ATAATAATGG TTTCTTAGAC GTCAGGTGGC ACTTTTCGGG
2461 GAAATGTGCG CGGAACCCCT ATTTGTTTAT TTTTCTAAAT ACATTCAAAT ATGTATCCGC
2521 TCATGAGACA ATAACCCTGA TAAATGCTTC AATAATATTG AAAAAGGAAG AGTATGAGTA
2581 TTCAACATTT CCGTGTCGCC CTTATTCCCT TTTTTGCGGC ATTTTGCCTT CCTGTTTTTG
2641 CTCACCCAGA AACGCTGGTG AAAGTAAAAG ATGCTGAAGA TCAGTTGGGT GCACGAGTGG
2701 GTTACATCGA ACTGGATCTC AACAGCGGTA AGATCCTTGA GAGTTTTCGC CCCGAAGAAC
2761 GTTTTCCAAT GATGAGCACT TTTAAAGTTC TGCTATGTGG CGCGGTATTA TCCCGTGTTG
2821 ACGCCGGGCA AGAGCAACTC GGTCGCCGCA TACACTATTC TCAGAATGAC TTGGTTGAGT
2881 ACTCACCAGT CACAGAAAAG CATCTTACGG ATGGCATGAC AGTAAGAGAA TTATGCAGTG
2941 CTGCCATAAC CATGAGTGAT AACACTGCGG CCAACTTACT TCTGACAACG ATCGGAGGAC
3001 CGAAGGAGCT AACCGCTTTT TTGCACAACA TGGGGGATCA TGTAACTCGC CTTGATCGTT
3061 GGGAACCGGA GCTGAATGAA GCCATACCAA ACGACGAGCG TGACACCACG ATGCCTGCAG
3121 CAATGGCAAC AACGTTGCGC AAACTATTAA CTGGCGAACT ACTTACTCTA GCTTCCCGGC
3181 AACAATTAAT AGACTGGATG GAGGCGGATA AAGTTGCAGG ACCACTTCTG CGCTCGGCCC
3241 TTCCGGCTGG CTGGTTTATT GCTGATAAAT CTGGAGCCGG TGAGCGTGGG TCTCGCGGTA
3301 TCATTGCAGC ACTGGGGCCA GATGGTAAGC CCTCCCGTAT CGTAGTTATC TACACGACGG
3361 GGAGTCAGGC AACTATGGAT GAACGAAATA GACAGATCGC TGAGATAGGT GCCTCACTGA
3421 TTAAGCATTG GTAACTGTCA GACCAAGTTT ACTCATATAT ACTTTAGATT GATTTAAAAC
3481 TTCATTTTTA ATTTAAAAGG ATCTAGGTGA AGATCCTTTT TGATAATCTC ATGACCAAAA
3541 TCCCTTAACG TGAGTTTTCG TTCCACTGAG CGTCAGACCC CGTAGAAAAG ATCAAAGGAT
3601 CTTCTTGAGA TCCTTTTTTT CTGCGCGTAA TCTGCTGCTT GCAAACAAAA AAACCACCGC
3661 TACCAGCGGT GGTTTGTTTG CCGGATCAAG AGCTACCAAC TCTTTTTCCG AAGGTAACTG
3721 GCTTCAGCAG AGCGCAGATA CCAAATACTG TCCTTCTAGT GTAGCCGTAG TTAGGCCACC
3781 ACTTCAAGAA CTCTGTAGCA CCGCCTACAT ACCTCGCTCT GCTAATCCTG TTACCAGTGG
3841 CTGCTGCCAG TGGCGATAAG TCGTGTCTTA CCGGGTTGGA CTCAAGACGA TAGTTACCGG
3901 ATAAGGCGCA GCGGTCGGGC TGAACGGGGG GTTCGTGCAC ACAGCCCAGC TTGGAGCGAA
3961 CGACCTACAC CGAACTGAGA TACCTACAGC GTGAGCTATG AGAAAGCGCC ACGCTTCCCG
4021 AAGGGAGAAA GGCGGACAGG TATCCGGTAA GCGGCAGGGT CGGAACAGGA GAGCGCACGA

FIG.43C

4081 GGGAGCTTCC AGGGGGAAAC GCCTGGTATC TTTATAGTCC TGTCGGGTTT CGCCACCTCT
4141 GACTTGAGCG TCGATTTTTG TGATGCTCGT CAGGGGGGCG GAGCCTATGG AAAAACGCCA
4201 GCAACGCGGC CTTTTTACGG TTCCTGGCCT TTTGCTGGCC TTTTGCTCAC ATGTTCTTTC
4261 CTGCGTTATC CCCTGATTCT GTGGATAACC GTATTACCGC CTTTGAGTGA GCTGATACCG
4321 CTCGCCGCAG CCGAACGACC GAGCGCAGCG AGTCAGTGAG CGAGGAAGCG GAAGAGCGCC
4381 TGATGCGGTA TTTTCTCCTT ACGCATCTGT GCGGTATTTC ACACCGCATA TATGGTGCAC
4441 TCTCAGTACA ATCTGCTCTG ATGCCGCATA GTTAAGCCAG TATACACTCC GCTATCGCTA
4501 CGTGACTGGG TCATGGCTGC GCCCCGACAC CCGCCAACAC CCGCTGACGC GCCCTGACGG
4561 GCTTGTCTGC TCCCGGCATC CGCTTACAGA CAAGCTGTGA CCGTCTCCGG GAGCTGCATG
4621 TGTCAGAGGT TTTCACCGTC ATCACCGAAA CGCGCGAGGC AGCTGCGGTA AAGCTCATCA
4681 GCGTGGTCGT GAAGCGATTC ACAGATGTCT GCCTGTTCAT CCGCGTCCAG CTCGTTGAGT
4741 TTCTCCAGAA GCGTTAATGT CTGGCTTCTG ATAAAGCGGG CCATGTTAAG GGCGGTTTTT
4801 TCCTGTTTGG TCACTGATGC CTCCGTGTAA GGGGGATTTC TGTTCATGGG GGTAATGATA
4861 CCGATGAAAC GAGAGAGGAT GCTCACGATA CGGGTTACTG ATGATGAACA TGCCCGGTTA
4921 CTGGAACGTT GTGAGGGTAA ACAACTGGCG GTATGGATGC GGCGGGACCA GAGAAAAATC
4981 ACTCAGGGTC AATGCCAGCG CTTCGTTAAT ACAGATGTAG GTGTTCCACA GGGTAGCCAG
5041 CAGCATCCTG CGATGCAGAT CCGGAACATA ATGGTGCAGG GCGCTGACTT CCGCGTTTCC
5101 AGACTTTACG AAACACGGAA ACCGAAGACC ATTCATGTTG TTGCTCAGGT CGCAGACGTT
5161 TTGCAGCAGC AGTCGCTTCA CGTTCGCTCG CGTATCGGTG ATTCATTCTG CTAACCAGTA
5221 AGGCAACCCC GCCAGCCTAG CCGGGTCCTC AACGACAGGA GCACGATCAT GCGCACCCGT
5281 GGCCAGGACC CAACGCTGCC CGAGATGCGC CGCGTGCGGC TGCTGGAGAT GGCGGACGCG
5341 ATGGATATGT TCTGCCAAGG GTTGGTTTGC GCATTCACAG TTCTCCGCAA GAATTGATTG
5401 GCTCCAATTC TTGGAGTGGT GAATCCGTTA GCGAGGTGCC GCCGGCTTCC ATTCAGGTCG
5461 AGGTGGCCCG GCTCCATGCA CCGCGACGCA ACGCGGGGAG GCAGACAAGG TATAGGGCGG
5521 CGCCTACAAT CCATGCCAAC CCGTTCCATG TGCTCGCCGA GGCGGCATAA ATCGCCGTGA
5581 CGATCAGCGG TCCAGTGATC GAAGTTAGGC TGGTAAGAGC CGCGAGCGAT CCTTGAAGCT
5641 GTCCCTGATG GTCGTCATCT ACCTGCCTGG ACAGCATGGC CTGCAACGCG GGCATCCCGA
5701 TGCCGCCGGA AGCGAGAAGA ATCATAATGG GGAAGGCCAT CCAGCCTCGC GTCGCGAACG
5761 CCAGCAAGAC GTAGCCCAGC GCGTCGGCCG CCATGCCGGC GATAATGGCC TGCTTCTCGC
5821 CGAAACGTTT GGTGGCGGGA CCAGTGACGA AGGCTTGAGC GAGGGCGTGC AAGATTCCGA
5881 ATACCGCAAG CGACAGGCCG ATCATCGTCG CGCTCCAGCG AAAGCGGTCC TCGCCGAAAA
5941 TGACCCAGAG CGCTGCCGGC ACCTGTCCTA CGAGTTGCAT GATAAAGAAG ACAGTCATAA
6001 GTGCGGCGAC GATAGTCATG CCCCGCGCCC ACCGGAAGGA GCTGACTGGG TTGAAGGCTC
6061 TCAAGGGCAT CGGTCGATCG ACGCTCTCCC TTATGCGACT CCTGCATTAG GAAGCAGCCC
6121 AGTAGTAGGT TGAGGCCGTT GAGCACCGCC GCCGCAAGGA ATGGTGCATG CAAGGAGATG
6181 GCGCCCAACA GTCCCCCGGC CACGGGGCCT GCCACCATAC CCACGCCGAA ACAAGCGCTC
6241 ATGAGCCCGA AGTGGCGAGC CCGA

FIG.43D pDEST24

GST CARBOXY-FUSION VECTOR, T7 PROMOTER

```
                                    T7 PROMOTER              mRNA
1    atc gag atc tcg atc ccg cga aat taa tac gac tca cta tag gga gac cac
     tag ctc tag agc tag ggc gct tta att atg ctg agt gat atc cct ctg gtg

                                        Int                 attR1
52   aac ggt ttc cct cta gat cac aag ttt gta caa aaa agc tga acg aga aac
     ttg cca aag gga gat cta gtg ttc aaa cat gtt ttt tcg act tgc tct ttg
              CmR ccdB

        attR2                       A   F   L   Y   K   V   V   I   M   S
1735 tca ttt tac gtt tct cgt tca gct ttc ttg tac aaa gtg gtg att atg tcc
     agt aaa atg caa aga gca agt cga aag aac atg ttt cac cac taa tac agg

     P   I   L      GST PROTEIN            (~223 aa)
1786 cct ata cta ggt tat tgg aaa att aag ggc ctt gtg caa ccc act cga ctt
     gga tat gat cca ata acc ttt taa ttc ccg gaa cac gtt ggg tga gct gaa
```

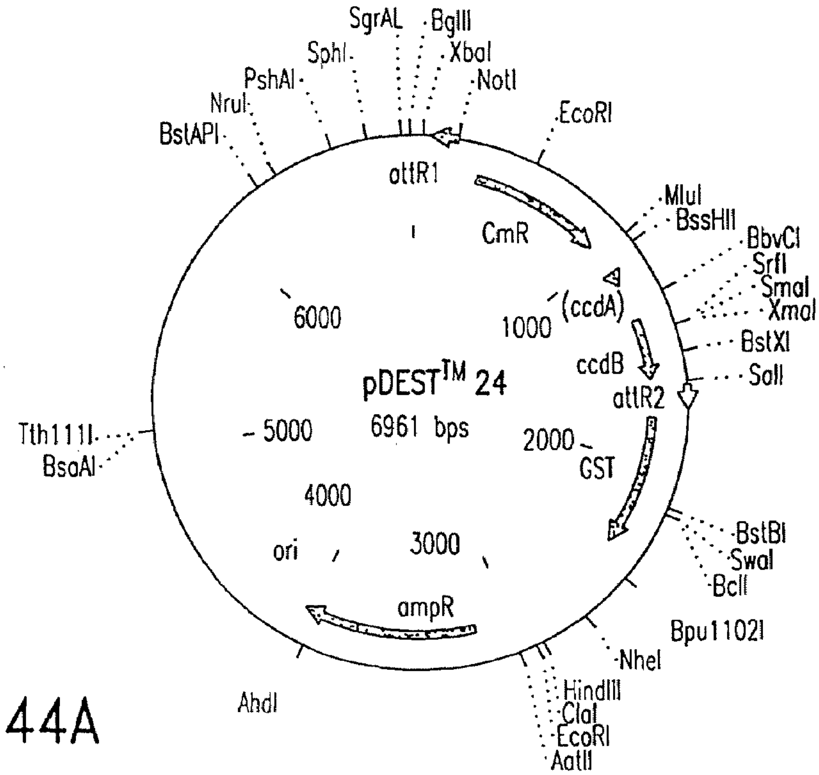

FIG.44A pDEST24 6961 bp

| Location (Base Nos.) | Gene Encoded |
|---|---|
| 195..71 | attR1 |
| 304..963 | CmR |
| 1083..1167 | inactivated ccdA |
| 1305..1610 | ccdB |
| 1651..1775 | attR2 |
| 1783..2451 | GST |
| 3181..4041 | ampR |
| 4190..4829 | ori |

```
   1 ATCGAGATCT CGATCCCGCG AAATTAATAC GACTCACTAT AGGGAGACCA CAACGGTTTC
  61 CCTCTAGATC ACAAGTTTGT ACAAAAAAGC TGAACGAGAA ACGTAAAATG ATATAAATAT
 121 CAATATATTA AATTAGATTT TGCATAAAAA ACAGACTACA TAATACTGTA AAACACAACA
 181 TATCCAGTCA CTATGGCGGC CGCATTAGGC ACCCCAGGCT TTACACTTTA TGCTTCCGGC
 241 TCGTATAATG TGTGGATTTT GAGTTAGGAT CCGGCGAGAT TTTCAGGAGC TAAGGAAGCT
 301 AAAATGGAGA AAAAAATCAC TGGATATACC ACCGTTGATA TATCCCAATG GCATCGTAAA
 361 GAACATTTTG AGGCATTTCA GTCAGTTGCT CAATGTACCT ATAACCAGAC CGTTCAGCTG
 421 GATATTACGG CCTTTTTAAA GACCGTAAAG AAAAATAAGC ACAAGTTTTA TCCGGCCTTT
 481 ATTCACATTC TTGCCCGCCT GATGAATGCT CATCCGGAAT TCCGTATGGC AATGAAAGAC
 541 GGTGAGCTGG TGATATGGGA TAGTGTTCAC CCTTGTTACA CCGTTTTCCA TGAGCAAACT
 601 GAAACGTTTT CATCGCTCTG GAGTGAATAC CACGACGATT TCCGGCAGTT TCTACACATA
 661 TATTCGCAAG ATGTGGCGTG TTACGGTGAA AACCTGGCCT ATTTCCCTAA AGGGTTTATT
 721 GAGAATATGT TTTTCGTCTC AGCCAATCCC TGGGTGAGTT TCACCAGTTT TGATTTAAAC
 781 GTGGCCAATA TGGACAACTT CTTCGCCCCC GTTTTCACCA TGGGCAAATA TTATACGCAA
 841 GGCGACAAGG TGCTGATGCC GCTGGCGATT CAGGTTCATC ATGCCGTCTG TGATGGCTTC
 901 CATGTCGGCA GAATGCTTAA TGAATTACAA CAGTACTGCG ATGAGTGGCA GGGCGGGGCG
 961 TAAACGCGTG GATCCGGCTT ACTAAAAGCC AGATAACAGT ATGCGTATTT GCGCGCTGAT
1021 TTTTGCGGTA TAAGAATATA TACTGATATG TATACCCGAA GTATGTCAAA AAGAGGTGTG
1081 CTATGAAGCA GCGTATTACA GTGACAGTTG ACAGCGACAG CTATCAGTTG CTCAAGGCAT
1141 ATATGATGTC AATATCTCCG GTCTGGTAAG CACAACCATG CAGAATGAAG CCCGTCGTCT
1201 GCGTGCCGAA CGCTGGAAAG CGGAAAATCA GGAAGGGATG GCTGAGGTCG CCCGGTTTAT
1261 TGAAATGAAC GGCTCTTTTG CTGACGAGAA CAGGGACTGG TGAAATGCAG TTTAAGGTTT
1321 ACACCTATAA AAGAGAGAGC CGTTATCGTC TGTTTGTGGA TGTACAGAGT GATATTATTG
1381 ACACGCCCGG GCGACGGATG GTGATCCCCC TGGCCAGTGC ACGTCTGCTG TCAGATAAAG
1441 TCTCCCGTGA ACTTTACCCG GTGGTGCATA TCGGGGATGA AAGCTGGCGC ATGATGACCA
1501 CCGATATGGC CAGTGTGCCG GTCTCCGTTA TCGGGGAAGA AGTGGCTGAT CTCAGCCACC
1561 GCGAAAATGA CATCAAAAAC GCCATTAACC TGATGTTCTG GGGAATATAA ATGTCAGGCT
1621 CCCTTATACA CAGCCAGTCT GCAGGTCGAC CATAGTGACT GGATATGTTG TGTTTTACAG
1681 TATTATGTAG TCTGTTTTTT ATGCAAAATC TAATTTAATA TATTGATATT TATATCATTT
1741 TACGTTTCTC GTTCAGCTTT CTTGTACAAA GTGGTGATTA TGTCCCCTAT ACTAGGTTAT
1801 TGGAAAATTA AGGGCCTTGT GCAACCCACT CGACTTCTTT TGGAATATCT TGAAGAAAAA
1861 TATGAAGAGC ATTTGTATGA GCGCGATGAA GGTGATAAAT GGCGAAACAA AAAGTTTGAA
1921 TTGGGTTTGG AGTTTCCCAA TCTTCCTTAT TATATTGATG GTGATGTTAA ATTAACACAG
```

FIG.44B

```
1981 TCTATGGCCA TCATACGTTA TATAGCTGAC AAGCACAACA TGTTGGGTGG TTGTCCAAAA
2041 GAGCGTGCAG AGATTTCAAT GCTTGAAGGA GCGGTTTTGG ATATTAGATA CGGTGTTTCG
2101 AGAATTGCAT ATAGTAAAGA CTTTGAAACT CTCAAAGTTG ATTTTCTTAG CAAGCTACCT
2161 GAAATGCTGA AAATGTTCGA AGATCGTTTA TGTCATAAAA CATATTTAAA TGGTGATCAT
2221 GTAACCCATC CTGACTTCAT GTTGTATGAC GCTCTTGATG TTGTTTTATA CATGGACCCA
2281 ATGTGCCTGG ATGCGTTCCC AAAATTAGTT TGTTTTAAAA AACGTATTGA AGCTATCCCA
2341 CAAATTGATA AGTACTTGAA ATCCAGCAAG TATATAGCAT GGCCTTTGCA GGGCTGGCAA
2401 GCCACGTTTG GTGGTGGCGA CCATCCTCCA AAATCGGATC TGGTTCCGCG TCCATGGGGA
2461 TCCGGCTGCT AACAAAGCCC GAAAGGAAGC TGAGTTGGCT GCTGCCACCG CTGAGCAATA
2521 ACTAGCATAA CCCCTTGGGG CCTCTAAACG GGTCTTGAGG GGTTTTTTGC TGAAAGGAGG
2581 AACTATATCC GGATATCCAC AGGACGGGTG TGGTCGCCAT GATCGCGTAG TCGATAGTGG
2641 CTCCAAGTAG CGAAGCGAGC AGGACTGGGC GGCGGCCAAA GCGGTCGGAC AGTGCTCCGA
2701 GAACGGGTGC GCATAGAAAT TGCATCAACG CATATAGCGC TAGCAGCACG CCATAGTGAC
2761 TGGCGATGCT GTCGGAATGG ACGATATCCC GCAAGAGGCC CGGCAGTACC GGCATAACCA
2821 AGCCTATGCC TACAGCATCC AGGGTGACGG TGCCGAGGAT GACGATGAGC GCATTGTTAG
2881 ATTTCATACA CGGTGCCTGA CTGCGTTAGC AATTTAACTG TGATAAACTA CCGCATTAAA
2941 GCTTATCGAT GATAAGCTGT CAAACATGAG AATTCTTGAA GACGAAAGGG CCTCGTGATA
3001 CGCCTATTTT TATAGGTTAA TGTCATGATA ATAATGGTTT CTTAGACGTC AGGTGGCACT
3061 TTTCGGGGAA ATGTGCGCGG AACCCCTATT TGTTTATTTT TCTAAATACA TTCAAATATG
3121 TATCCGCTCA TGAGACAATA ACCCTGATAA ATGCTTCAAT AATATTGAAA AAGGAAGAGT
3181 ATGAGTATTC AACATTTCCG TGTCGCCCTT ATTCCCTTTT TTGCGGCATT TTGCCTTCCT
3241 GTTTTTGCTC ACCCAGAAAC GCTGGTGAAA GTAAAAGATG CTGAAGATCA GTTGGGTGCA
3301 CGAGTGGGTT ACATCGAACT GGATCTCAAC AGCGGTAAGA TCCTTGAGAG TTTTCGCCCC
3361 GAAGAACGTT TTCCAATGAT GAGCACTTTT AAAGTTCTGC TATGTGGCGC GGTATTATCC
3421 CGTGTTGACG CCGGGCAAGA GCAACTCGGT CGCCGCATAC ACTATTCTCA GAATGACTTG
3481 GTTGAGTACT CACCAGTCAC AGAAAAGCAT CTTACGGATG GCATGACAGT AAGAGAATTA
3541 TGCAGTGCTG CCATAACCAT GAGTGATAAC ACTGCGGCCA ACTTACTTCT GACAACGATC
3601 GGAGGACCGA AGGAGCTAAC CGCTTTTTTG CACAACATGG GGGATCATGT AACTCGCCTT
3661 GATCGTTGGG AACCGGAGCT GAATGAAGCC ATACCAAACG ACGAGCGTGA CACCACGATG
3721 CCTGCAGCAA TGGCAACAAC GTTGCGCAAA CTATTAACTG GCGAACTACT TACTCTAGCT
3781 TCCCGGCAAC AATTAATAGA CTGGATGGAG GCGGATAAAG TTGCAGGACC ACTTCTGCGC
3841 TCGGCCCTTC CGGCTGGCTG GTTTATTGCT GATAAATCTG GAGCCGGTGA GCGTGGGTCT
3901 CGCGGTATCA TTGCAGCACT GGGGCCAGAT GGTAAGCCCT CCCGTATCGT AGTTATCTAC
3961 ACGACGGGGA GTCAGGCAAC TATGGATGAA CGAAATAGAC AGATCGCTGA GATAGGTGCC
4021 TCACTGATTA AGCATTGGTA ACTGTCAGAC CAAGTTTACT CATATATACT TTAGATTGAT
4081 TTAAAACTTC ATTTTTAATT TAAAAGGATC TAGGTGAAGA TCCTTTTTGA TAATCTCATG
4141 ACCAAAATCC CTTAACGTGA GTTTTCGTTC CACTGAGCGT CAGACCCCGT AGAAAAGATC
4201 AAAGGATCTT CTTGAGATCC TTTTTTTCTG CGCGTAATCT GCTGCTTGCA AACAAAAAAA
4261 CCACCGCTAC CAGCGGTGGT TTGTTTGCCG GATCAAGAGC TACCAACTCT TTTTCCGAAG
4321 GTAACTGGCT TCAGCAGAGC GCAGATACCA AATACTGTCC TTCTAGTGTA GCCGTAGTTA
4381 GGCCACCACT TCAAGAACTC TGTAGCACCG CCTACATACC TCGCTCTGCT AATCCTGTTA
4441 CCAGTGGCTG CTGCCAGTGG CGATAAGTCG TGTCTTACCG GGTTGGACTC AAGACGATAG
4501 TTACCGGATA AGGCGCAGCG GTCGGGCTGA ACGGGGGGTT CGTGCACACA GCCCAGCTTG
4561 GAGCGAACGA CCTACACCGA ACTGAGATAC CTACAGCGTG AGCTATGAGA AAGCGCCACG
4621 CTTCCCGAAG GGAGAAAGGC GGACAGGTAT CCGGTAAGCG GCAGGGTCGG AACAGGAGAG
4681 CGCACGAGGG AGCTTCCAGG GGGAAACGCC TGGTATCTTT ATAGTCCTGT CGGGTTTCGC
```

FIG.44C

4741 CACCTCTGAC TTGAGCGTCG ATTTTTGTGA TGCTCGTCAG GGGGGCGGAG CCTATGGAAA
4801 AACGCCAGCA ACGCGGCCTT TTTACGGTTC CTGGCCTTTT GCTGGCCTTT TGCTCACATG
4861 TTCTTTCCTG CGTTATCCCC TGATTCTGTG GATAACCGTA TTACCGCCTT TGAGTGAGCT
4921 GATACCGCTC GCCGCAGCCG AACGACCGAG CGCAGCGAGT CAGTGAGCGA GGAAGCGGAA
4981 GAGCGCCTGA TGCGGTATTT TCTCCTTACG CATCTGTGCG GTATTTCACA CCGCATATAT
5041 GGTGCACTCT CAGTACAATC TGCTCTGATG CCGCATAGTT AAGCCAGTAT ACACTCCGCT
5101 ATCGCTACGT GACTGGGTCA TGGCTGCGCC CCGACACCCG CCAACACCCG CTGACGCGCC
5161 CTGACGGGCT TGTCTGCTCC CGGCATCCGC TTACAGACAA GCTGTGACCG TCTCCGGGAG
5221 CTGCATGTGT CAGAGGTTTT CACCGTCATC ACCGAAACGC GCGAGGCAGC TGCGGTAAAG
5281 CTCATCAGCG TGGTCGTGAA GCGATTCACA GATGTCTGCC TGTTCATCCG CGTCCAGCTC
5341 GTTGAGTTTC TCCAGAAGCG TTAATGTCTG GCTTCTGATA AAGCGGGCCA TGTTAAGGGC
5401 GGTTTTTTCC TGTTTGGTCA CTGATGCCTC CGTGTAAGGG GGATTTCTGT TCATGGGGGT
5461 AATGATACCG ATGAAACGAG AGAGGATGCT CACGATACGG GTTACTGATG ATGAACATGC
5521 CCGGTTACTG GAACGTTGTG AGGGTAAACA ACTGGCGGTA TGGATGCGGC GGGACCAGAG
5581 AAAAATCACT CAGGGTCAAT GCCAGCGCTT CGTTAATACA GATGTAGGTG TTCCACAGGG
5641 TAGCCAGCAG CATCCTGCGA TGCAGATCCG GAACATAATG GTGCAGGGCG CTGACTTCCG
5701 CGTTTCCAGA CTTTACGAAA CACGGAAACC GAAGACCATT CATGTTGTTG CTCAGGTCGC
5761 AGACGTTTTG CAGCAGCAGT CGCTTCACGT TCGCTCGCGT ATCGGTGATT CATTCTGCTA
5821 ACCAGTAAGG CAACCCCGCC AGCCTAGCCG GGTCCTCAAC GACAGGAGCA CGATCATGCG
5881 CACCCGTGGC CAGGACCCAA CGCTGCCCGA GATGCGCCGC GTGCGGCTGC TGGAGATGGC
5941 GGACGCGATG GATATGTTCT GCCAAGGGTT GGTTTGCGCA TTCACAGTTC TCCGCAAGAA
6001 TTGATTGGCT CCAATTCTTG GAGTGGTGAA TCCGTTAGCG AGGTGCCGCC GGCTTCCATT
6061 CAGGTCGAGG TGGCCCGGCT CCATGCACCG CGACGCAACG CGGGGAGGCA GACAAGGTAT
6121 AGGGCGGCGC CTACAATCCA TGCCAACCCG TTCCATGTGC TCGCCGAGGC GGCATAAATC
6181 GCCGTGACGA TCAGCGGTCC AGTGATCGAA GTTAGGCTGG TAAGAGCCGC GAGCGATCCT
6241 TGAAGCTGTC CCTGATGGTC GTCATCTACC TGCCTGGACA GCATGGCCTG CAACGCGGGC
6301 ATCCCGATGC CGCCGGAAGC GAGAAGAATC ATAATGGGGA AGGCCATCCA GCCTCGCGTC
6361 GCGAACGCCA GCAAGACGTA GCCCAGCGCG TCGGCCGCCA TGCCGGCGAT AATGGCCTGC
6421 TTCTCGCCGA AACGTTTGGT GGCGGGACCA GTGACGAAGG CTTGAGCGAG GGCGTGCAAG
6481 ATTCCGAATA CCGCAAGCGA CAGGCCGATC ATCGTCGCGC TCCAGCGAAA GCGGTCCTCG
6541 CCGAAAATGA CCCAGAGCGC TGCCGGCACC TGTCCTACGA GTTGCATGAT AAAGAAGACA
6601 GTCATAAGTG CGGCGACGAT AGTCATGCCC CGCGCCCACC GGAAGGAGCT GACTGGGTTG
6661 AAGGCTCTCA AGGGCATCGG TCGATCGACG CTCTCCCTTA TGCGACTCCT GCATTAGGAA
6721 GCAGCCCAGT AGTAGGTTGA GGCCGTTGAG CACCGCCGCC GCAAGGAATG GTGCATGCAA
6781 GGAGATGGCG CCCAACAGTC CCCCGGCCAC GGGGCCTGCC ACCATACCCA CGCCGAAACA
6841 AGCGCTCATG AGCCCGAAGT GGCGAGCCCG ATCTTCCCCA TCGGTGATGT CGGCGATATA
6901 GGCGCCAGCA ACCGCACCTG TGGCGCCGGT GATGCCGGCC ACGATGCGTC CGGCGTAGAG
6961 G

FIG.44D pDEST25
THIOREDOXIN CARBOXY-FUSION VECTOR, T7 PROMOTER

```
                                     T7 PROMOTER            mRNA
 1 nag atc tcg atc ccg cga aat taa tac gac tca cta tag gga gac cac aac
   ntc tag agc tag ggc gct tta att atg ctg agt gat atc cct ctg gtg ttg

                                   Int                attR1
52 ggt ttc cct cta gat cac aag ttt gta caa aaa agc tga acg aga aac gta
   cca aag gga gat cta gcg ttc aaa cat gtt ttt tcg act tgc tct ttg cat

          CmR ———— ccdB ————

                                   Int
      attR2             — A  F  L  Y  K  V  V  I  M  S  D
1735 ttt tac gtt tct cgt tca gct ttc ttg tac aaa gtg gtg att atg agc gat
     aaa atg caa aga gca agt cga aag aac atg ttt cac cac taa tac tcg cta

      K  I  I  ———— Trx PROTEIN  (~130 aa.) ———→
1786 aaa att att cac ctg act gac gac agt ttt gac acg gat gta ctc aaa gcg
     ttt taa taa gtg gac tga ctg ctg tca aaa ctg tgc cta cat gag ttt cgc
```

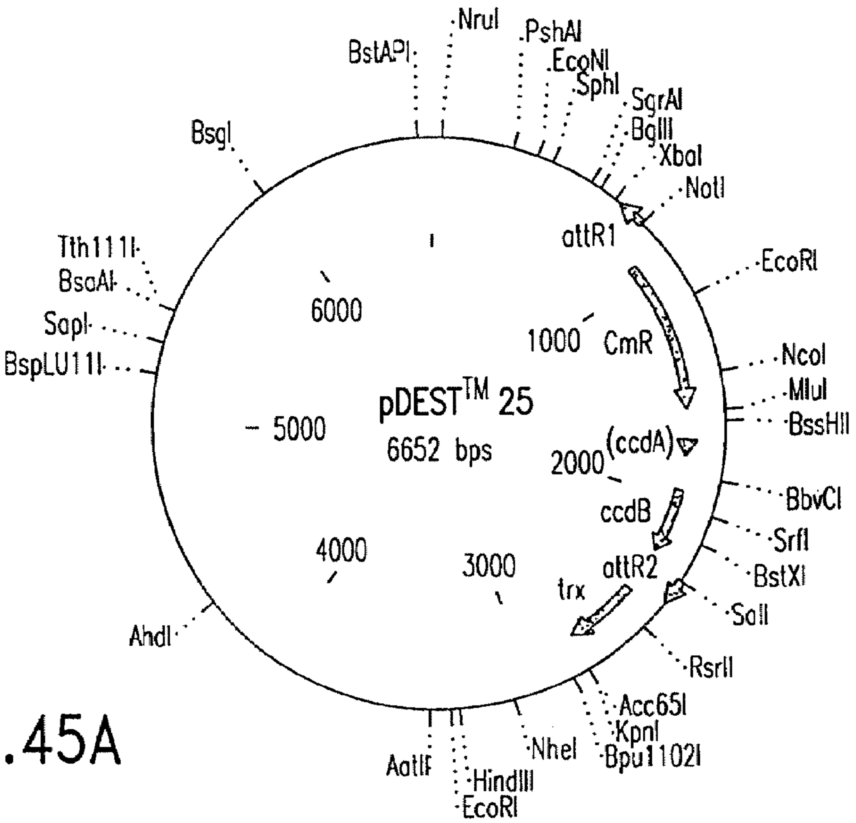

FIG.45A pDEST25 6652 bp

| Location (Base Nos.) | Gene Encoded |
|---|---|
| 844..720 | attR1 |
| 953..1612 | CmR |
| 1732..1816 | inactivated ccdA |
| 1954..2259 | ccdB |
| 2300..2424 | attR2 |
| 2432..2794 | trx |

```
   1 CCGGAAGCGA GAAGAATCAT AATGGGGAAG GCCATCCAGC CTCGCGTCGC GAACGCCAGC
  61 AAGACGTAGC CCAGCGCGTC GGCCGCCATG CCGGCGATAA TGGCCTGCTT CTCGCCGAAA
 121 CGTTTGGTGG CGGGACCAGT GACGAAGGCT TGAGCGAGGG CGTGCAAGAT TCCGAATACC
 181 GCAAGCGACA GGCCGATCAT CGTCGCGCTC CAGCGAAAGC GGTCCTCGCC GAAAATGACC
 241 CAGAGCGCTG CCGGCACCTG TCCTACGAGT TGCATGATAA AGAAGACAGT CATAAGTGCG
 301 GCGACGATAG TCATGCCCCG CGCCCACCGG AAGGAGCTGA CTGGGTTGAA GGCTCTCAAG
 361 GGCATCGGTC GATCGACGCT CTCCCTTATG CGACTCCTGC ATTAGGAAGC AGCCCAGTAG
 421 TAGGTTGAGG CCGTTGAGCA CCGCCGCCGC AAGGAATGGT GCATGCAAGG AGATGGCGCC
 481 CAACAGTCCC CCGGCCACGG GGCCTGCCAC CATACCCACG CCGAAACAAG CGCTCATGAG
 541 CCCGAAGTGG CGAGCCCGAT CTTCCCCATC GGTGATGTCG GCGATATAGG CGCCAGCAAC
 601 CGCACCTGTG GCGCCGGTGA TGCCGGCCAC GATGCGTCCG GCGTAGAGGA TCGAGATCTC
 661 GATCCCGCGA AATTAATACG ACTCACTATA GGGAGACCAC AACGGTTTCC CTCTAGATCA
 721 CAAGTTTGTA CAAAAAAGCT GAACGAGAAA CGTAAAATGA TATAAATATC AATATATTAA
 781 ATTAGATTTT GCATAAAAAA CAGACTACAT AATACTGTAA AACACAACAT ATCCAGTCAC
 841 TATGGCGGCC GCATTAGGCA CCCCAGGCTT TACACTTTAT GCTTCCGGCT CGTATAATGT
 901 GTGGATTTTG AGTTAGGATC CGGCGAGATT TTCAGGAGCT AAGGAAGCTA AAATGGAGAA
 961 AAAAATCACT GGATATACCA CCGTTGATAT ATCCCAATGG CATCGTAAAG AACATTTTGA
1021 GGCATTTCAG TCAGTTGCTC AATGTACCTA TAACCAGACC GTTCAGCTGG ATATTACGGC
1081 CTTTTTAAAG ACCGTAAAGA AAAATAAGCA CAAGTTTTAT CCGGCCTTTA TTCACATTCT
1141 TGCCCGCCTG ATGAATGCTC ATCCGGAATT CCGTATGGCA ATGAAAGACG GTGAGCTGGT
1201 GATATGGGAT AGTGTTCACC CTTGTTACAC CGTTTTCCAT GAGCAAACTG AAACGTTTTC
1261 ATCGCTCTGG AGTGAATACC ACGACGATTT CCGGCAGTTT CTACACATAT ATTCGCAAGA
1321 TGTGGCGTGT TACGGTGAAA ACCTGGCCTA TTTCCCTAAA GGGTTTATTG AGAATATGTT
1381 TTTCGTCTCA GCCAATCCCT GGGTGAGTTT CACCAGTTTT GATTTAAACG TGGCCAATAT
1441 GGACAACTTC TTCGCCCCCG TTTTCACCAT GGGCAAATAT TATACGCAAG GCGACAAGGT
1501 GCTGATGCCG CTGGCGATTC AGGTTCATCA TGCCGTCTGT GATGGCTTCC ATGTCGGCAG
1561 AATGCTTAAT GAATTACAAC AGTACTGCGA TGAGTGGCAG GGCGGGGCGT AAACGCGTGG
1621 ATCCGGCTTA CTAAAAGCCA GATAACAGTA TGCGTATTTG CGCGCTGATT TTTGCGGTAT
1681 AAGAATATAT ACTGATATGT ATACCCGAAG TATGTCAAAA AGAGGTGTGC TATGAAGCAG
1741 CGTATTACAG TGACAGTTGA CAGCGACAGC TATCAGTTGC TCAAGGCATA TATGATGTCA
1801 ATATCTCCGG TCTGGTAAGC ACAACCATGC AGAATGAAGC CCGTCGTCTG CGTGCCGAAC
1861 GCTGGAAAGC GGAAAATCAG GAAGGGATGG CTGAGGTCGC CCGGTTTATT GAAATGAACG
1921 GCTCTTTTGC TGACGAGAAC AGGGACTGGT GAAATGCAGT TTAAGGTTTA CACCTATAAA
1981 AGAGAGAGCC GTTATCGTCT GTTTGTGGAT GTACAGAGTG ATATTATTGA CACGCCCGGG
2041 CGACGGATGG TGATCCCCCT GGCCAGTGCA CGTCTGCTGT CAGATAAAGT CTCCCGTGAA
```

FIG.45B

```
2101 CTTTACCCGG TGGTGCATAT CGGGGATGAA AGCTGGCGCA TGATGACCAC CGATATGGCC
2161 AGTGTGCCGG TCTCCGTTAT CGGGGAAGAA GTGGCTGATC TCAGCCACCG CGAAAATGAC
2221 ATCAAAAACG CCATTAACCT GATGTTCTGG GGAATATAAA TGTCAGGCTC CCTTATACAC
2281 AGCCAGTCTG CAGGTCGACC ATAGTGACTG GATATGTTGT GTTTTACAGT ATTATGTAGT
2341 CTGTTTTTTA TGCAAAATCT AATTTAATAT ATTGATATTT ATATCATTTT ACGTTTCTCG
2401 TTCAGCTTTC TTGTACAAAG TGGTGATTAT GAGCGATAAA ATTATTCACC TGACTGACGA
2461 CAGTTTTGAC ACGGATGTAC TCAAAGCGGA CGGGGCGATC CTCGTCGATT TCTGGGCAGA
2521 GTGGTGCGGT CCGTGCAAAA TGATCGCCCC GATTCTGGAT GAAATCGCTG ACGAATATCA
2581 GGGCAAACTG ACCGTTGCAA AACTGAACAT CGATCAAAAC CCTGGCACTG CGCCGAAATA
2641 TGGCATCCGT GGTATCCCGA CTCTGCTGCT GTTCAAAAAC GGTGAAGTGG CGGCAACCAA
2701 AGTGGGTGCA CTGTCTAAAG GTCAGTTGAA AGAGTTCCTC GACGCTAACC TGGCCGGTTC
2761 TGGTTCTGGT GATGACGATG ACAAGGTACC CGGGGATCGA TCCGGCTGCT AACAAAGCCC
2821 GAAAGGAAGC TGAGTTGGCT GCTGCCACCG CTGAGCAATA ACTAGCATAA CCCCTTGGGG
2881 CCTCTAAACG GGTCTTGAGG GGTTTTTTGC TGAAAGGAGG AACTATATCC GGATATCCAC
2941 AGGACGGGTG TGGTCGCCAT GATCGCGTAG TCGATAGTGG CTCCAAGTAG CGAAGCGAGC
3001 AGGACTGGGC GGCGGCCAAA GCGGTCGGAC AGTGCTCCGA GAACGGGTGC GCATAGAAAT
3061 TGCATCAACG CATATAGCGC TAGCAGCACG CCATAGTGAC TGGCGATGCT GTCGGAATGG
3121 ACGATATCCC GCAAGAGGCC CGGCAGTACC GGCATAACCA AGCCTATGCC TACAGCATCC
3181 AGGGTGACGG TGCCGAGGAT GACGATGAGC GCATTGTTAG ATTTCATACA CGGTGCCTGA
3241 CTGCGTTAGC AATTTAACTG TGATAAACTA CCGCATTAAA GCTTATCGAT GATAAGCTGT
3301 CAAACATGAG AATTCTTGAA GACGAAAGGG CCTCGTGATA CGCCTATTTT TATAGGTTAA
3361 TGTCATGATA ATAATGGTTT CTTAGACGTC AGGTGGCACT TTTCGGGGAA ATGTGCGCGG
3421 AACCCCTATT TGTTTATTTT TCTAAATACA TTCAAATATG TATCCGCTCA TGAGACAATA
3481 ACCCTGATAA ATGCTTCAAT AATATTGAAA AAGGAAGAGT ATGAGTATTC AACATTTCCG
3541 TGTCGCCCTT ATTCCCTTTT TTGCGGCATT TTGCCTTCCT GTTTTTGCTC ACCCAGAAAC
3601 GCTGGTGAAA GTAAAAGATG CTGAAGATCA GTTGGGTGCA CGAGTGGGTT ACATCGAACT
3661 GGATCTCAAC AGCGGTAAGA TCCTTGAGAG TTTTCGCCCC GAAGAACGTT TTCCAATGAT
3721 GAGCACTTTT AAAGTTCTGC TATGTGGCGC GGTATTATCC CGTGTTGACG CCGGGCAAGA
3781 GCAACTCGGT CGCCGCATAC ACTATTCTCA GAATGACTTG GTTGAGTACT CACCAGTCAC
3841 AGAAAAGCAT CTTACGGATG GCATGACAGT AAGAGAATTA TGCAGTGCTG CCATAACCAT
3901 GAGTGATAAC ACTGCGGCCA ACTTACTTCT GACAACGATC GGAGGACCGA AGGAGCTAAC
3961 CGCTTTTTTG CACAACATGG GGGATCATGT AACTCGCCTT GATCGTTGGG AACCGGAGCT
4021 GAATGAAGCC ATACCAAACG ACGAGCGTGA CACCACGATG CCTGCAGCAA TGGCAACAAC
4081 GTTGCGCAAA CTATTAACTG GCGAACTACT TACTCTAGCT TCCCGGCAAC AATTAATAGA
4141 CTGGATGGAG GCGGATAAAG TTGCAGGACC ACTTCTGCGC TCGGCCCTTC CGGCTGGCTG
4201 GTTTATTGCT GATAAATCTG GAGCCGGTGA GCGTGGGTCT CGCGGTATCA TTGCAGCACT
4261 GGGGCCAGAT GGTAAGCCCT CCCGTATCGT AGTTATCTAC ACGACGGGGA GTCAGGCAAC
4321 TATGGATGAA CGAAATAGAC AGATCGCTGA GATAGGTGCC TCACTGATTA AGCATTGGTA
4381 ACTGTCAGAC CAAGTTTACT CATATATACT TTAGATTGAT TTAAAACTTC ATTTTTAATT
4441 TAAAAGGATC TAGGTGAAGA TCCTTTTTGA TAATCTCATG ACCAAAATCC CTTAACGTGA
4501 GTTTTCGTTC CACTGAGCGT CAGACCCCGT AGAAAAGATC AAAGGATCTT CTTGAGATCC
4561 TTTTTTTCTG CGCGTAATCT GCTGCTTGCA AACAAAAAAA CCACCGCTAC CAGCGGTGGT
4621 TTGTTTGCCG GATCAAGAGC TACCAACTCT TTTTCCGAAG GTAACTGGCT TCAGCAGAGC
4681 GCAGATACCA AATACTGTCC TTCTAGTGTA GCCGTAGTTA GGCCACCACT TCAAGAACTC
4741 TGTAGCACCG CCTACATACC TCGCTCTGCT AATCCTGTTA CCAGTGGCTG CTGCCAGTGG
4801 CGATAAGTCG TGTCTTACCG GGTTGGACTC AAGACGATAG TTACCGGATA AGGCGCAGCG
```

FIG.45C

4861 GTCGGGCTGA ACGGGGGGTT CGTGCACACA GCCCAGCTTG GAGCGAACGA CCTACACCGA
4921 ACTGAGATAC CTACAGCGTG AGCTATGAGA AAGCGCCACG CTTCCCGAAG GGAGAAAGGC
4981 GGACAGGTAT CCGGTAAGCG GCAGGGTCGG AACAGGAGAG CGCACGAGGG AGCTTCCAGG
5041 GGGAAACGCC TGGTATCTTT ATAGTCCTGT CGGGTTTCGC CACCTCTGAC TTGAGCGTCG
5101 ATTTTTGTGA TGCTCGTCAG GGGGGCGGAG CCTATGGAAA AACGCCAGCA ACGCGGCCTT
5161 TTTACGGTTC CTGGCCTTTT GCTGGCCTTT TGCTCACATG TTCTTTCCTG CGTTATCCCC
5221 TGATTCTGTG GATAACCGTA TTACCGCCTT TGAGTGAGCT GATACCGCTC GCCGCAGCCG
5281 AACGACCGAG CGCAGCGAGT CAGTGAGCGA GGAAGCGGAA GAGCGCCTGA TGCGGTATTT
5341 TCTCCTTACG CATCTGTGCG GTATTTCACA CCGCATATAT GGTGCACTCT CAGTACAATC
5401 TGCTCTGATG CCGCATAGTT AAGCCAGTAT ACACTCCGCT ATCGCTACGT GACTGGGTCA
5461 TGGCTGCGCC CCGACACCCG CCAACACCCG CTGACGCGCC CTGACGGGCT TGTCTGCTCC
5521 CGGCATCCGC TTACAGACAA GCTGTGACCG TCTCCGGGAG CTGCATGTGT CAGAGGTTTT
5581 CACCGTCATC ACCGAAACGC GCGAGGCAGC TGCGGTAAAG CTCATCAGCG TGGTCGTGAA
5641 GCGATTCACA GATGTCTGCC TGTTCATCCG CGTCCAGCTC GTTGAGTTTC TCCAGAAGCG
5701 TTAATGTCTG GCTTCTGATA AAGCGGGCCA TGTTAAGGGC GGTTTTTTCC TGTTTGGTCA
5761 CTGATGCCTC CGTGTAAGGG GGATTTCTGT TCATGGGGGT AATGATACCG ATGAAACGAG
5821 AGAGGATGCT CACGATACGG GTTACTGATG ATGAACATGC CCGGTTACTG GAACGTTGTG
5881 AGGGTAAACA ACTGGCGGTA TGGATGCGGC GGGACCAGAG AAAAATCACT CAGGGTCAAT
5941 GCCAGCGCTT CGTTAATACA GATGTAGGTG TTCCACAGGG TAGCCAGCAG CATCCTGCGA
6001 TGCAGATCCG GAACATAATG GTGCAGGGCG CTGACTTCCG CGTTTCCAGA CTTTACGAAA
6061 CACGGAAACC GAAGACCATT CATGTTGTTG CTCAGGTCGC AGACGTTTTG CAGCAGCAGT
6121 CGCTTCACGT TCGCTCGCGT ATCGGTGATT CATTCTGCTA ACCAGTAAGG CAACCCCGCC
6181 AGCCTAGCCG GGTCCTCAAC GACAGGAGCA CGATCATGCG CACCCGTGGC CAGGACCCAA
6241 CGCTGCCCGA GATGCGCCGC GTGCGGCTGC TGGAGATGGC GGACGCGATG GATATGTTCT
6301 GCCAAGGGTT GGTTTGCGCA TTCACAGTTC TCCGCAAGAA TTGATTGGCT CCAATTCTTG
6361 GAGTGGTGAA TCCGTTAGCG AGGTGCCGCC GGCTTCCATT CAGGTCGAGG TGGCCCGGCT
6421 CCATGCACCG CGACGCAACG CGGGGAGGCA GACAAGGTAT AGGGCGGCGC CTACAATCCA
6481 TGCCAACCCG TTCCATGTGC TCGCCGAGGC GGCATAAATC GCCGTGACGA TCAGCGGTCC
6541 AGTGATCGAA GTTAGGCTGG TAAGAGCCGC GAGCGATCCT TGAAGCTGTC CCTGATGGTC
6601 GTCATCTACC TGCCTGGACA GCATGGCCTG CAACGCGGGC ATCCCGATGC CG

FIG.45D pDEST26 His6 AMINO FUSION IN pCMV Sport-neo VECTOR 600 ttg acg tca atg gga gtt tgt ttt ggc acc aaa atc aac ggg act ttc caa
aac tgc agt tac cct caa aca aaa ccg tgg ttt tag ttg ccc tga aag gtt 651 aat gtc gta aca act ccg ccc cat tga cgc aaa tgg gcg gta ggc gtg tac
tta cag cat tgt tga ggc ggg gta act gcg ttt acc cgc cat ccg cac atg CMV promoter → mRNA start
702 ggt ggg agg tct ata taa gca gag ctc gtt tag tga acc gtc aga tcg cct
cca ccc tcc aga tat att cgt ctc gag caa atc act tgg cag tct agc gga 753 gga gac gcc atc cac gct gtt ttg acc tcc ata gaa gac acc ggg acc gat
cct ctg cgg tag gtg cga caa aac tgg agg tat ctt ctg tgg ccc tgg cta Start Translation M A Y Y H H
804 cca gcc tcc gga ctc tag cct agg ccg cgg acc atg gcg tac tac cat cac
ggt cgg agg cct gag atc gga tcc ggc gcc tgg tac cgc atg atg gta gtg H H H H S R S T S L Y K K A attR1
855 cat cac cat cac tct aga tca aca agt ttg tac aaa aaa gct gaa cga gaa
gta gtg gta gtg aga tct agt tgt tca aac atg ttt ttt cga ctt gct ctt
Int

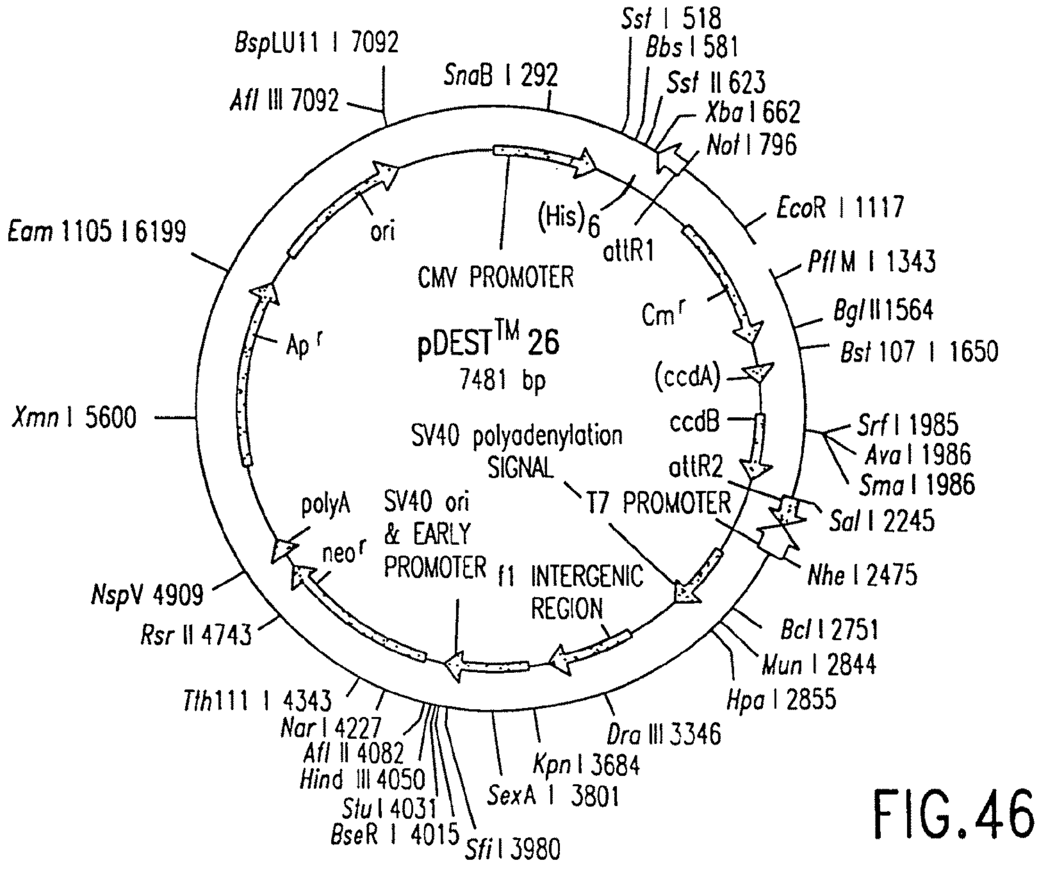

FIG.46A pDEST26 7481 bp

| Location (Base Nos.) | Gene Encoded |
|---|---|
| 492..509 | his6 |
| 619..519 | attR1 |
| 752..1411 | CmR |
| 1531..1615 | inactivated ccdA |
| 1753..2058 | ccdB |
| 2099..2223 | attR2 |
| 2409..2771 | SV40 polyA |
| 2966..3421 | f1 intergenic region |
| 3485..3903 | SV40 promoter |
| 3948..4742 | neo |
| 4806..4854 | polyA |
| 5265..6125 | Apr |
| 6274..6913 | ori |
| 7344..385 | CMV promoter |

```
   1 GTAAACTGCC CACTTGGCAG TACATCAAGT GTATCATATG CCAAGTACGC CCCCTATTGA
  61 CGTCAATGAC GGTAAATGGC CCGCCTGGCA TTATGCCCAG TACATGACCT TATGGGACTT
 121 TCCTACTTGG CAGTACATCT ACGTATTAGT CATCGCTATT ACCATGGTGA TGCGGTTTTG
 181 GCAGTACATC AATGGGCGTG GATAGCGGTT TGACTCACGG GGATTTCCAA GTCTCCACCC
 241 CATTGACGTC AATGGGAGTT TGTTTTGGCA CCAAAATCAA CGGGACTTTC CAAAATGTCG
 301 TAACAACTCC GCCCCATTGA CGCAAATGGG CGGTAGGCGT GTACGGTGGG AGGTCTATAT
 361 AAGCAGAGCT CGTTTAGTGA ACCGTCAGAT CGCCTGGAGA CGCCATCCAC GCTGTTTTGA
 421 CCTCCATAGA AGACACCGGG ACCGATCCAG CCTCCGGACT CTAGCCTAGG CCGCGGACCA
 481 TGGCGTACTA CCATCACCAT CACCATCACT CTAGATCAAC AAGTTTGTAC AAAAAAGCTG
 541 AACGAGAAAC GTAAAATGAT ATAAATATCA ATATATTAAA TTAGATTTTG CATAAAAAAC
 601 AGACTACATA ATACTGTAAA ACACAACATA TCCAGTCACT ATGGCGGCCG CATTAGGCAC
 661 CCCAGGCTTT ACACTTTATG CTTCCGGCTC GTATAATGTG TGGATTTTGA GTTAGGATCC
 721 GGCGAGATTT TCAGGAGCTA AGGAAGCTAA AATGGAGAAA AAAATCACTG GATATACCAC
 781 CGTTGATATA TCCCAATGGC ATCGTAAAGA ACATTTTGAG GCATTTCAGT CAGTTGCTCA
 841 ATGTACCTAT AACCAGACCG TTCAGCTGGA TATTACGGCC TTTTTAAAGA CCGTAAAGAA
 901 AAATAAGCAC AAGTTTTATC CGGCCTTTAT TCACATTCTT GCCCGCCTGA TGAATGCTCA
 961 TCCGGAATTC CGTATGGCAA TGAAAGACGG TGAGCTGGTG ATATGGGATA GTGTTCACCC
1021 TTGTTACACC GTTTTCCATG AGCAAACTGA AACGTTTTCA TCGCTCTGGA GTGAATACCA
1081 CGACGATTTC CGGCAGTTTC TACACATATA TTCGCAAGAT GTGGCGTGTT ACGGTGAAAA
1141 CCTGGCCTAT TTCCCTAAAG GGTTTATTGA GAATATGTTT TTCGTCTCAG CCAATCCCTG
1201 GGTGAGTTTC ACCAGTTTTG ATTTAAACGT GGCCAATATG GACAACTTCT TCGCCCCCGT
1261 TTTCACCATG GGCAAATATT ATACGCAAGG CGACAAGGTG CTGATGCCGC TGGCGATTCA
1321 GGTTCATCAT GCCGTCTGTG ATGGCTTCCA TGTCGGCAGA ATGCTTAATG AATTACAACA
1381 GTACTGCGAT GAGTGGCAGG GCGGGGCGTA AAGATCTGGA TCCGGCTTAC TAAAAGCCAG
1441 ATAACAGTAT GCGTATTTGC GCGCTGATTT TTGCGGTATA AGAATATATA CTGATATGTA
1501 TACCCGAAGT ATGTCAAAAA GAGGTGTGCT ATGAAGCAGC GTATTACAGT GACAGTTGAC
1561 AGCGACAGCT ATCAGTTGCT CAAGGCATAT ATGATGTCAA TATCTCCGGT CTGGTAAGCA
```

FIG.46B

```
1621 CAACCATGCA GAATGAAGCC CGTCGTCTGC GTGCCGAACG CTGGAAAGCG GAAAATCAGG
1681 AAGGGATGGC TGAGGTCGCC CGGTTTATTG AAATGAACGG CTCTTTTGCT GACGAGAACA
1741 GGGACTGGTG AAATGCAGTT TAAGGTTTAC ACCTATAAAA GAGAGAGCCG TTATCGTCTG
1801 TTTGTGGATG TACAGAGTGA TATTATTGAC ACGCCCGGGC GACGGATGGT GATCCCCCTG
1861 GCCAGTGCAC GTCTGCTGTC AGATAAAGTC TCCCGTGAAC TTTACCCGGT GGTGCATATC
1921 GGGGATGAAA GCTGGCGCAT GATGACCACC GATATGGCCA GTGTGCCGGT CTCCGTTATC
1981 GGGGAAGAAG TGGCTGATCT CAGCCACCGC GAAAATGACA TCAAAAACGC CATTAACCTG
2041 ATGTTCTGGG GAATATAAAT GTCAGGCTCC CTTATACACA GCCAGTCTGC AGGTCGACCA
2101 TAGTGACTGG ATATGTTGTG TTTTACAGTA TTATGTAGTC TGTTTTTTAT GCAAAATCTA
2161 ATTTAATATA TTGATATTTA TATCATTTTA CGTTTCTCGT TCAGCTTTCT TGTACAAAGT
2221 GGTTGATCGC GTGCATGCGA CGTCATAGCT CTCTCCCTAT AGTGAGTCGT ATTATAAGCT
2281 AGGCACTGGC CGTCGTTTTA CAACGTCGTG ACTGGGAAAA CTGCTAGCTT GGGATCTTTG
2341 TGAAGGAACC TTACTTCTGT GGTGTGACAT AATTGGACAA ACTACCTACA GAGATTTAAA
2401 GCTCTAAGGT AAATATAAAA TTTTTAAGTG TATAATGTGT TAAACTAGCT GCATATGCTT
2461 GCTGCTTGAG AGTTTTGCTT ACTGAGTATG ATTTATGAAA ATATTATACA CAGGAGCTAG
2521 TGATTCTAAT TGTTTGTGTA TTTTAGATTC ACAGTCCCAA GGCTCATTTC AGGCCCCTCA
2581 GTCCTCACAG TCTGTTCATG ATCATAATCA GCCATACCAC ATTTGTAGAG GTTTTACTTG
2641 CTTTAAAAAA CCTCCCACAC CTCCCCCTGA ACCTGAAACA TAAAATGAAT GCAATTGTTG
2701 TTGTTAACTT GTTTATTGCA GCTTATAATG GTTACAAATA AAGCAATAGC ATCACAAATT
2761 TCACAAATAA AGCATTTTTT TCACTGCATT CTAGTTGTGG TTTGTCCAAA CTCATCAATG
2821 TATCTTATCA TGTCTGGATC GATCCTGCAT TAATGAATCG GCCAACGCGC GGGGAGAGGC
2881 GGTTTGCGTA TTGGCTGGCG TAATAGCGAA GAGGCCCGCA CCGATCGCCC TTCCCAACAG
2941 TTGCGCAGCC TGAATGGCGA ATGGGACGCG CCCTGTAGCG GCGCATTAAG CGCGGCGGGT
3001 GTGGTGGTTA CGCGCAGCGT GACCGCTACA CTTGCCAGCG CCCTAGCGCC CGCTCCTTTC
3061 GCTTTCTTCC CTTCCTTTCT CGCCACGTTC GCCGGCTTTC CCCGTCAAGC TCTAAATCGG
3121 GGGCTCCCTT TAGGGTTCCG ATTTAGTGCT TTACGGCACC TCGACCCCAA AAAACTTGAT
3181 TAGGGTGATG GTTCACGTAG TGGGCCATCG CCCTGATAGA CGGTTTTTCG CCCTTTGACG
3241 TTGGAGTCCA CGTTCTTTAA TAGTGGACTC TTGTTCCAAA CTGGAACAAC ACTCAACCCT
3301 ATCTCGGTCT ATTCTTTTGA TTTATAAGGG ATTTTGCCGA TTTCGGCCTA TTGGTTAAAA
3361 AATGAGCTGA TTTAACAAAT ATTTAACGCG AATTTTAACA AAATATTAAC GTTTACAATT
3421 TCGCCTGATG CGGTATTTTC TCCTTACGCA TCTGTGCGGT ATTTCACACC GCATACGCGG
3481 ATCTGCGCAG CACCATGGCC TGAAATAACC TCTGAAAGAG GAACTTGGTT AGGTACCTTC
3541 TGAGGCGGAA AGAACCAGCT GTGGAATGTG TGTCAGTTAG GGTGTGGAAA GTCCCCAGGC
3601 TCCCCAGCAG GCAGAAGTAT GCAAAGCATG CATCTCAATT AGTCAGCAAC CAGGTGTGGA
3661 AAGTCCCCAG GCTCCCCAGC AGGCAGAAGT ATGCAAAGCA TGCATCTCAA TTAGTCAGCA
3721 ACCATAGTCC CGCCCCTAAC TCCGCCCATC CCGCCCCTAA CTCCGCCCAG TTCCGCCCAT
3781 TCTCCGCCCC ATGGCTGACT AATTTTTTTT ATTTATGCAG AGGCCGAGGC CGCCTCGGCC
3841 TCTGAGCTAT TCCAGAAGTA GTGAGGAGGC TTTTTTGGAG GCCTAGGCTT TTGCAAAAAG
3901 CTTGATTCTT CTGACACAAC AGTCTCGAAC TTAAGGCTAG AGCCACCATG ATTGAACAAG
3961 ATGGATTGCA CGCAGGTTCT CCGGCCGCTT GGGTGGAGAG GCTATTCGGC TATGACTGGG
4021 CACAACAGAC AATCGGCTGC TCTGATGCCG CCGTGTTCCG GCTGTCAGCG CAGGGGCGCC
4081 CGGTTCTTTT TGTCAAGACC GACCTGTCCG GTGCCCTGAA TGAACTGCAG GACGAGGCAG
4141 CGCGGCTATC GTGGCTGGCC ACGACGGGCG TTCCTTGCGC AGCTGTGCTC GACGTTGTCA
4201 CTGAAGCGGG AAGGGACTGG CTGCTATTGG GCGAAGTGCC GGGGCAGGAT CTCCTGTCAT
4261 CTCACCTTGC TCCTGCCGAG AAAGTATCCA TCATGGCTGA TGCAATGCGG CGGCTGCATA
4321 CGCTTGATCC GGCTACCTGC CCATTCGACC ACCAAGCGAA ACATCGCATC GAGCGAGCAC
```

FIG.46C

```
4381 GTACTCGGAT GGAAGCCGGT CTTGTCGATC AGGATGATCT GGACGAAGAG CATCAGGGGC
4441 TCGCGCCAGC CGAACTGTTC GCCAGGCTCA AGGCGCGCAT GCCCGACGGC GAGGATCTCG
4501 TCGTGACCCA TGGCGATGCC TGCTTGCCGA ATATCATGGT GGAAAATGGC CGCTTTTCTG
4561 GATTCATCGA CTGTGGCCGG CTGGGTGTGG CGGACCGCTA TCAGGACATA GCGTTGGCTA
4621 CCCGTGATAT TGCTGAAGAG CTTGGCGGCG AATGGGCTGA CCGCTTCCTC GTGCTTTACG
4681 GTATCGCCGC TCCCGATTCG CAGCGCATCG CCTTCTATCG CCTTCTTGAC GAGTTCTTCT
4741 GAGCGGGACT CTGGGGTTCG AAATGACCGA CCAAGCGACG CCCAACCTGC CATCACGATG
4801 GCCGCAATAA AATATCTTTA TTTTCATTAC ATCTGTGTGT TGGTTTTTTG TGTGAATCGA
4861 TAGCGATAAG GATCCGCGTA TGGTGCACTC TCAGTACAAT CTGCTCTGAT GCCGCATAGT
4921 TAAGCCAGCC CCGACACCCG CCAACACCCG CTGACGCGCC CTGACGGGCT TGTCTGCTCC
4981 CGGCATCCGC TTACAGACAA GCTGTGACCG TCTCCGGGAG CTGCATGTGT CAGAGGTTTT
5041 CACCGTCATC ACCGAAACGC GCGAGACGAA AGGGCCTCGT GATACGCCTA TTTTTATAGG
5101 TTAATGTCAT GATAATAATG GTTTCTTAGA CGTCAGGTGG CACTTTTCGG GGAAATGTGC
5161 GCGGAACCCC TATTTGTTTA TTTTTCTAAA TACATTCAAA TATGTATCCG CTCATGAGAC
5221 AATAACCCTG ATAAATGCTT CAATAATATT GAAAAAGGAA GAGTATGAGT ATTCAACATT
5281 TCCGTGTCGC CCTTATTCCC TTTTTTGCGG CATTTTGCCT TCCTGTTTTT GCTCACCCAG
5341 AAACGCTGGT GAAAGTAAAA GATGCTGAAG ATCAGTTGGG TGCACGAGTG GGTTACATCG
5401 AACTGGATCT CAACAGCGGT AAGATCCTTG AGAGTTTTCG CCCCGAAGAA CGTTTTCCAA
5461 TGATGAGCAC TTTTAAAGTT CTGCTATGTG GCGCGGTATT ATCCCGTATT GACGCCGGGC
5521 AAGAGCAACT CGGTCGCCGC ATACACTATT CTCAGAATGA CTTGGTTGAG TACTCACCAG
5581 TCACAGAAAA GCATCTTACG GATGGCATGA CAGTAAGAGA ATTATGCAGT GCTGCCATAA
5641 CCATGAGTGA TAACACTGCG GCCAACTTAC TTCTGACAAC GATCGGAGGA CCGAAGGAGC
5701 TAACCGCTTT TTTGCACAAC ATGGGGGATC ATGTAACTCG CCTTGATCGT TGGGAACCGG
5761 AGCTGAATGA AGCCATACCA AACGACGAGC GTGACACCAC GATGCCTGTA GCAATGGCAA
5821 CAACGTTGCG CAAACTATTA ACTGGCGAAC TACTTACTCT AGCTTCCCGG CAACAATTAA
5881 TAGACTGGAT GGAGGCGGAT AAAGTTGCAG GACCACTTCT GCGCTCGGCC CTTCCGGCTG
5941 GCTGGTTTAT TGCTGATAAA TCTGGAGCCG GTGAGCGTGG GTCTCGCGGT ATCATTGCAG
6001 CACTGGGGCC AGATGGTAAG CCCTCCCGTA TCGTAGTTAT CTACACGACG GGGAGTCAGG
6061 CAACTATGGA TGAACGAAAT AGACAGATCG CTGAGATAGG TGCCTCACTG ATTAAGCATT
6121 GGTAACTGTC AGACCAAGTT TACTCATATA TACTTTAGAT TGATTTAAAA CTTCATTTTT
6181 AATTTAAAAG GATCTAGGTG AAGATCCTTT TTGATAATCT CATGACCAAA ATCCCTTAAC
6241 GTGAGTTTTC GTTCCACTGA GCGTCAGACC CCGTAGAAAA GATCAAAGGA TCTTCTTGAG
6301 ATCCTTTTTT TCTGCGCGTA ATCTGCTGCT TGCAAACAAA AAAACCACCG CTACCAGCGG
6361 TGGTTTGTTT GCCGGATCAA GAGCTACCAA CTCTTTTTCC GAAGGTAACT GGCTTCAGCA
6421 GAGCGCAGAT ACCAAATACT GTCCTTCTAG TGTAGCCGTA GTTAGGCCAC CACTTCAAGA
6481 ACTCTGTAGC ACCGCCTACA TACCTCGCTC TGCTAATCCT GTTACCAGTG GCTGCTGCCA
6541 GTGGCGATAA GTCGTGTCTT ACCGGGTTGG ACTCAAGACG ATAGTTACCG GATAAGGCGC
6601 AGCGGTCGGG CTGAACGGGG GGTTCGTGCA CACAGCCCAG CTTGGAGCGA ACGACCTACA
6661 CCGAACTGAG ATACCTACAG CGTGAGCATT GAGAAAGCGC CACGCTTCCC GAAGGGAGAA
6721 AGGCGGACAG GTATCCGGTA AGCGGCAGGG TCGGAACAGG AGAGCGCACG AGGGAGCTTC
6781 CAGGGGGAAA CGCCTGGTAT CTTTATAGTC CTGTCGGGTT TCGCCACCTC TGACTTGAGC
6841 GTCGATTTTT GTGATGCTCG TCAGGGGGGC GGAGCCTATG GAAAAACGCC AGCAACGCGG
6901 CCTTTTTACG GTTCCTGGCC TTTTGCTGGC CTTTTGCTCA CATGTTCTTT CCTGCGTTAT
6961 CCCCTGATTC TGTGGATAAC CGTATTACCG CCTTTGAGTG AGCTGATACC GCTCGCCGCA
7021 GCCGAACGAC CGAGCGCAGC GAGTCAGTGA GCGAGGAAGC GGAAGAGCGC CCAATACGCA
7081 AACCGCCTCT CCCCGCGCGT TGGCCGATTC ATTAATGCAG AGCTTGCAAT TCGCGCGTTT
7141 TTCAATATTA TTGAAGCATT TATCAGGGTT ATTGTCTCAT GAGCGGATAC ATATTTGAAT
7201 GTATTTAGAA AAATAAACAA ATAGGGGTTC CGCGCACATT TCCCCGAAAA GTGCCACCTG
7261 ACGTCTAAGA AACCATTATT ATCATGACAT TAACCTATAA AAATAGGCGT AGTACGAGGC
7321 CCTTTCACTC ATTAGATGCA TGTCGTTACA TAACTTACGG TAAATGGCCC GCCTGGCTGA
7381 CCGCCCAACG ACCCCCGCCC ATTGACGTCA ATAATGACGT ATGTTCCCAT AGTAACGCCA
7441 ATAGGGACTT TCCATTGACG TCAATGGGTG GAGTATTTAC G
```

FIG.46D pDEST27 GST AMINO FUSION IN pCMV Sport-neo VECTOR
CMV promoter                                      mRNA start 600 nac ggt ggg agg tct ata taa gca gag ctc gtt tag tga acc gtc aga tcg
    ntg cca ccc tcc aga tat att cgt ctc gag caa atc act tgg cag tct agc 651 cct gga gac gcc atc cac gct gtt ttg acc tcc ata gaa gac acc ggg acc
    gga cct ctg cgg tag gtg cga caa aac tgg agg tat ctt ctg tgg ccc tgg M   A   P   I   L
702 gat cca gcc tcc gga ctc tag cct agg ccg cgg acc atg gcc cct ata cta
    cta ggt cgg agg cct gag atc gga tcc ggc gcc tgg tac cgg gga tat gat
                                                Start Translation GST 753 ggt tat tgg aaa att aag ggc ctt gtg caa ccc act cga ctt ctt ttg gaa
    cca ata acc ttt taa ttc ccg gaa cac gtt ggg tga gct gaa gaa aac ctt
                                    - GST Protein -
804 tat ctt gaa gaa aaa tat gaa gag cat ttg tat gag cgc gat gaa ggt gat
    ata gaa ctt ctt ttt ata ctt ctc gta aac ata ctc gcg cta ctt cca cta V   P   R   S   R
1365 ttt ggt ggt ggc gac cat cct cca aaa tcg gat ctg gtt ccg cgt tct aga
     aaa cca cca ccg ctg gta gga ggt ttt agc cta gac caa ggc gca aga tct S   T   S   L   Y   K   K   A
1416 tca aca agt ttg tac aaa aaa gct gaa cga gaa acg
     agt tgt tca aac atg ttt ttt cga ctt gct ctt tgc
         Int                 attR1

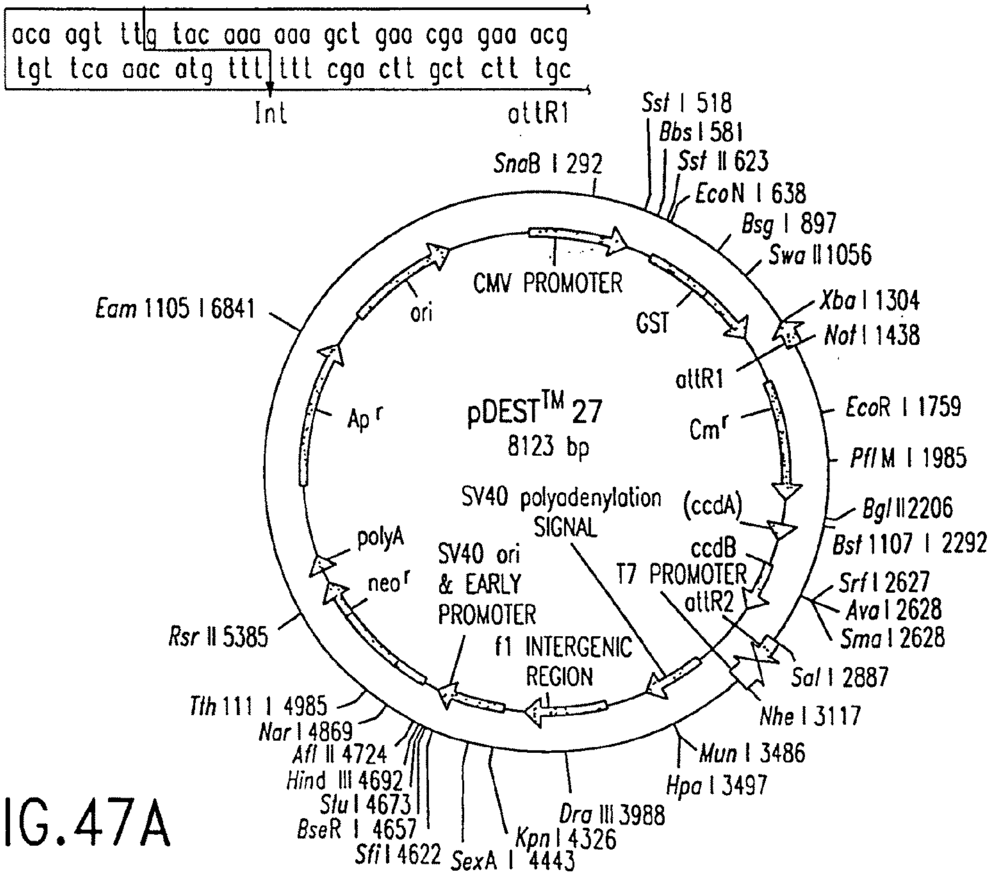

FIG.47A pDEST27 8123 bp (rotated to position 7800)

| Location (Base Nos.) | Gene Encoded |
|---|---|
| 130..793 | GST |
| 803..927 | attR1 |
| 1036..1695 | CmR |
| 1815..1899 | inactivated ccdA |
| 2037..2342 | ccdB |
| 2383..2507 | attR2 |
| 2693..3055 | SV40 polyA |
| 3250..3705 | f1 intergenic region |
| 3769..4187 | SV40 promoter |
| 4232..5026 | neo |
| 5090..5138 | polyA |
| 5549..6409 | Apr |
| 6558..7197 | ori |
| 7628..27 | CMV promoter |

```
   1 ATAAGCAGAG CTCGTTTAGT GAACCGTCAG ATCGCCTGGA GACGCCATCC ACGCTGTTTT
  61 GACCTCCATA GAAGACACCG GGACCGATCC AGCCTCCGGA CTCTAGCCTA GGCCGCGGAC
 121 CATGGCCCCT ATACTAGGTT ATTGGAAAAT TAAGGGCCTT GTGCAACCCA CTCGACTTCT
 181 TTTGGAATAT CTTGAAGAAA AATATGAAGA GCATTTGTAT GAGCGCGATG AAGGTGATAA
 241 ATGGCGAAAC AAAAAGTTTG AATTGGGTTT GGAGTTTCCC AATCTTCCTT ATTATATTGA
 301 TGGTGATGTT AAATTAACAC AGTCTATGGC CATCATACGT TATATAGCTG ACAAGCACAA
 361 CATGTTGGGT GGTTGTCCAA AAGAGCGTGC AGAGATTTCA ATGCTTGAAG GAGCGGTTTT
 421 GGATATTAGA TACGGTGTTT CGAGAATTGC ATATAGTAAA GACTTTGAAA CTCTCAAAGT
 481 TGATTTTCTT AGCAAGCTAC CTGAAATGCT GAAAATGTTC GAAGATCGTT TATGTCATAA
 541 AACATATTTA AATGGTGATC ATGTAACCCA TCCTGACTTC ATGTTGTATG ACGCTCTTGA
 601 TGTTGTTTTA TACATGGACC CAATGTGCCT GGATGCGTTC CCAAAATTAG TTTGTTTTAA
 661 AAAACGTATT GAAGCTATCC CACAAATTGA TAAGTACTTG AAATCCAGCA AGTATATAGC
 721 ATGGCCTTTG CAGGGCTGGC AAGCCACGTT TGGTGGTGGC GACCATCCTC CAAAATCGGA
 781 TCTGGTTCCG CGTTCTAGAT CAACAAGTTT GTACAAAAAA GCTGAACGAG AAACGTAAAA
 841 TGATATAAAT ATCAATATAT TAAATTAGAT TTTGCATAAA AAACAGACTA CATAATACTG
 901 TAAAACACAA CATATCCAGT CACTATGGCG GCCGCATTAG GCACCCCAGG CTTTACACTT
 961 TATGCTTCCG GCTCGTATAA TGTGTGGATT TTGAGTTAGG ATCCGGCGAG ATTTTCAGGA
1021 GCTAAGGAAG CTAAAATGGA GAAAAAAATC ACTGGATATA CCACCGTTGA TATATCCCAA
1081 TGGCATCGTA AAGAACATTT TGAGGCATTT CAGTCAGTTG CTCAATGTAC CTATAACCAG
1141 ACCGTTCAGC TGGATATTAC GGCCTTTTTA AAGACCGTAA AGAAAAATAA GCACAAGTTT
1201 TATCCGGCCT TTATTCACAT TCTTGCCCGC CTGATGAATG CTCATCCGGA ATTCCGTATG
```

FIG.47B

1261 GCAATGAAAG ACGGTGAGCT GGTGATATGG GATAGTGTTC ACCCTTGTTA CACCGTTTTC
1321 CATGAGCAAA CTGAAACGTT TTCATCGCTC TGGAGTGAAT ACCACGACGA TTTCCGGCAG
1381 TTTCTACACA TATATTCGCA AGATGTGGCG TGTTACGGTG AAAACCTGGC CTATTTCCCT
1441 AAAGGGTTTA TTGAGAATAT GTTTTTCGTC TCAGCCAATC CCTGGGTGAG TTTCACCAGT
1501 TTTGATTTAA ACGTGGCCAA TATGGACAAC TTCTTCGCCC CCGTTTTCAC CATGGGCAAA
1561 TATTATACGC AAGGCGACAA GGTGCTGATG CCGCTGGCGA TTCAGGTTCA TCATGCCGTC
1621 TGTGATGGCT TCCATGTCGG CAGAATGCTT AATGAATTAC AACAGTACTG CGATGAGTGG
1681 CAGGGCGGGG CGTAAAGATC TGGATCCGGC TTACTAAAAG CCAGATAACA GTATGCGTAT
1741 TTGCGCGCTG ATTTTTGCGG TATAAGAATA TATACTGATA TGTATACCCG AAGTATGTCA
1801 AAAAGAGGTG TGCTATGAAG CAGCGTATTA CAGTGACAGT TGACAGCGAC AGCTATCAGT
1861 TGCTCAAGGC ATATATGATG TCAATATCTC CGGTCTGGTA AGCACAACCA TGCAGAATGA
1921 AGCCCGTCGT CTGCGTGCCG AACGCTGGAA AGCGGAAAAT CAGGAAGGGA TGGCTGAGGT
1981 CGCCCGGTTT ATTGAAATGA ACGGCTCTTT TGCTGACGAG AACAGGGACT GGTGAAATGC
2041 AGTTTAAGGT TTACACCTAT AAAAGAGAGA GCCGTTATCG TCTGTTTGTG GATGTACAGA
2101 GTGATATTAT TGACACGCCC GGGCGACGGA TGGTGATCCC CCTGGCCAGT GCACGTCTGC
2161 TGTCAGATAA AGTCTCCCGT GAACTTTACC CGGTGGTGCA TATCGGGGAT GAAAGCTGGC
2221 GCATGATGAC CACCGATATG GCCAGTGTGC CGGTCTCCGT TATCGGGGAA GAAGTGGCTG
2281 ATCTCAGCCA CCGCGAAAAT GACATCAAAA ACGCCATTAA CCTGATGTTC TGGGGAATAT
2341 AAATGTCAGG CTCCCTTATA CACAGCCAGT CTGCAGGTCG ACCATAGTGA CTGGATATGT
2401 TGTGTTTTAC AGTATTATGT AGTCTGTTTT TTATGCAAAA TCTAATTTAA TATATTGATA
2461 TTTATATCAT TTTACGTTTC TCGTTCAGCT TTCTTGTACA AAGTGGTTGA TCGCGTGCAT
2521 GCGACGTCAT AGCTCTCTCC CTATAGTGAG TCGTATTATA AGCTAGGCAC TGGCCGTCGT
2581 TTTACAACGT CGTGACTGGG AAAACTGCTA GCTTGGGATC TTTGTGAAGG AACCTTACTT
2641 CTGTGGTGTG ACATAATTGG ACAAACTACC TACAGAGATT TAAAGCTCTA AGGTAAATAT
2701 AAAATTTTTA AGTGTATAAT GTGTTAAACT AGCTGCATAT GCTTGCTGCT TGAGAGTTTT
2761 GCTTACTGAG TATGATTTAT GAAAATATTA TACACAGGAG CTAGTGATTC TAATTGTTTG
2821 TGTATTTTAG ATTCACAGTC CCAAGGCTCA TTTCAGGCCC CTCAGTCCTC ACAGTCTGTT
2881 CATGATCATA ATCAGCCATA CCACATTTGT AGAGGTTTTA CTTGCTTTAA AAAACCTCCC
2941 ACACCTCCCC CTGAACCTGA AACATAAAAT GAATGCAATT GTTGTTGTTA ACTTGTTTAT
3001 TGCAGCTTAT AATGGTTACA AATAAAGCAA TAGCATCACA AATTTCACAA ATAAAGCATT
3061 TTTTTCACTG CATTCTAGTT GTGGTTTGTC CAAACTCATC AATGTATCTT ATCATGTCTG
3121 GATCGATCCT GCATTAATGA ATCGGCCAAC GCGCGGGGAG AGGCGGTTTG CGTATTGGCT
3181 GGCGTAATAG CGAAGAGGCC CGCACCGATC GCCCTTCCCA ACAGTTGCGC AGCCTGAATG
3241 GCGAATGGGA CGCGCCCTGT AGCGGCGCAT TAAGCGCGGC GGGTGTGGTG GTTACGCGCA
3301 GCGTGACCGC TACACTTGCC AGCGCCCTAG CGCCCGCTCC TTTCGCTTTC TTCCCTTCCT
3361 TTCTCGCCAC GTTCGCCGGC TTTCCCCGTC AAGCTCTAAA TCGGGGGCTC CCTTTAGGGT
3421 TCCGATTTAG TGCTTTACGG CACCTCGACC CCAAAAAACT TGATTAGGGT GATGGTTCAC
3481 GTAGTGGGCC ATCGCCCTGA TAGACGGTTT TTCGCCCTTT GACGTTGGAG TCCACGTTCT
3541 TTAATAGTGG ACTCTTGTTC CAAACTGGAA CAACACTCAA CCCTATCTCG GTCTATTCTT
3601 TTGATTTATA AGGGATTTTG CCGATTTCGG CCTATTGGTT AAAAAATGAG CTGATTTAAC

FIG.47C

3661 AAATATTTAA CGCGAATTTT AACAAAATAT TAACGTTTAC AATTTCGCCT GATGCGGTAT
3721 TTTCTCCTTA CGCATCTGTG CGGTATTTCA CACCGCATAC GCGGATCTGC GCAGCACCAT
3781 GGCCTGAAAT AACCTCTGAA AGAGGAACTT GGTTAGGTAC CTTCTGAGGC GGAAAGAACC
3841 AGCTGTGGAA TGTGTGTCAG TTAGGGTGTG GAAAGTCCCC AGGCTCCCCA GCAGGCAGAA
3901 GTATGCAAAG CATGCATCTC AATTAGTCAG CAACCAGGTG TGGAAAGTCC CCAGGCTCCC
3961 CAGCAGGCAG AAGTATGCAA AGCATGCATC TCAATTAGTC AGCAACCATA GTCCCGCCCC
4021 TAACTCCGCC CATCCCGCCC CTAACTCCGC CCAGTTCCGC CCATTCTCCG CCCCATGGCT
4081 GACTAATTTT TTTTATTTAT GCAGAGGCCG AGGCCGCCTC GGCCTCTGAG CTATTCCAGA
4141 AGTAGTGAGG AGGCTTTTTT GGAGGCCTAG GCTTTTGCAA AAAGCTTGAT TCTTCTGACA
4201 CAACAGTCTC GAACTTAAGG CTAGAGCCAC CATGATTGAA CAAGATGGAT TGCACGCAGG
4261 TTCTCCGGCC GCTTGGGTGG AGAGGCTATT CGGCTATGAC TGGGCACAAC AGACAATCGG
4321 CTGCTCTGAT GCCGCCGTGT TCCGGCTGTC AGCGCAGGGG CGCCCGGTTC TTTTTGTCAA
4381 GACCGACCTG TCCGGTGCCC TGAATGAACT GCAGGACGAG GCAGCGCGGC TATCGTGGCT
4441 GGCCACGACG GGCGTTCCTT GCGCAGCTGT GCTCGACGTT GTCACTGAAG CGGGAAGGGA
4501 CTGGCTGCTA TTGGGCGAAG TGCCGGGGCA GGATCTCCTG TCATCTCACC TTGCTCCTGC
4561 CGAGAAAGTA TCCATCATGG CTGATGCAAT GCGGCGGCTG CATACGCTTG ATCCGGCTAC
4621 CTGCCCATTC GACCACCAAG CGAAACATCG CATCGAGCGA GCACGTACTC GGATGGAAGC
4681 CGGTCTTGTC GATCAGGATG ATCTGGACGA AGAGCATCAG GGGCTCGCGC CAGCCGAACT
4741 GTTCGCCAGG CTCAAGGCGC GCATGCCCGA CGGCGAGGAT CTCGTCGTGA CCCATGGCGA
4801 TGCCTGCTTG CCGAATATCA TGGTGGAAAA TGGCCGCTTT TCTGGATTCA TCGACTGTGG
4861 CCGGCTGGGT GTGGCGGACC GCTATCAGGA CATAGCGTTG GCTACCCGTG ATATTGCTGA
4921 AGAGCTTGGC GGCGAATGGG CTGACCGCTT CCTCGTGCTT TACGGTATCG CCGCTCCCGA
4981 TTCGCAGCGC ATCGCCTTCT ATCGCCTTCT TGACGAGTTC TTCTGAGCGG GACTCTGGGG
5041 TTCGAAATGA CCGACCAAGC GACGCCCAAC CTGCCATCAC GATGGCCGCA ATAAAATATC
5101 TTTATTTTCA TTACATCTGT GTGTTGGTTT TTTGTGTGAA TCGATAGCGA TAAGGATCCG
5161 CGTATGGTGC ACTCTCAGTA CAATCTGCTC TGATGCCGCA TAGTTAAGCC AGCCCCGACA
5221 CCCGCCAACA CCCGCTGACG CGCCCTGACG GGCTTGTCTG CTCCCGGCAT CCGCTTACAG
5281 ACAAGCTGTG ACCGTCTCCG GGAGCTGCAT GTGTCAGAGG TTTTCACCGT CATCACCGAA
5341 ACGCGCGAGA CGAAAGGGCC TCGTGATACG CCTATTTTTA TAGGTTAATG TCATGATAAT
5401 AATGGTTTCT TAGACGTCAG GTGGCACTTT TCGGGGAAAT GTGCGCGGAA CCCCTATTTG
5461 TTTATTTTTC TAAATACATT CAAATATGTA TCCGCTCATG AGACAATAAC CCTGATAAAT
5521 GCTTCAATAA TATTGAAAAA GGAAGAGTAT GAGTATTCAA CATTTCCGTG TCGCCCTTAT
5581 TCCCTTTTTT GCGGCATTTT GCCTTCCTGT TTTTGCTCAC CCAGAAACGC TGGTGAAAGT
5641 AAAAGATGCT GAAGATCAGT TGGGTGCACG AGTGGGTTAC ATCGAACTGG ATCTCAACAG
5701 CGGTAAGATC CTTGAGAGTT TTCGCCCCGA AGAACGTTTT CCAATGATGA GCACTTTTAA
5761 AGTTCTGCTA TGTGGCGCGG TATTATCCCG TATTGACGCC GGGCAAGAGC AACTCGGTCG
5821 CCGCATACAC TATTCTCAGA ATGACTTGGT TGAGTACTCA CCAGTCACAG AAAAGCATCT
5881 TACGGATGGC ATGACAGTAA GAGAATTATG CAGTGCTGCC ATAACCATGA GTGATAACAC
5941 TGCGGCCAAC TTACTTCTGA CAACGATCGG AGGACCGAAG GAGCTAACCG CTTTTTTGCA
6001 CAACATGGGG GATCATGTAA CTCGCCTTGA TCGTTGGGAA CCGGAGCTGA ATGAAGCCAT

FIG.47D

6061 ACCAAACGAC GAGCGTGACA CCACGATGCC TGTAGCAATG GCAACAACGT TGCGCAAACT
6121 ATTAACTGGC GAACTACTTA CTCTAGCTTC CCGGCAACAA TTAATAGACT GGATGGAGGC
6181 GGATAAAGTT GCAGGACCAC TTCTGCGCTC GGCCCTTCCG GCTGGCTGGT TTATTGCTGA
6241 TAAATCTGGA GCCGGTGAGC GTGGGTCTCG CGGTATCATT GCAGCACTGG GGCCAGATGG
6301 TAAGCCCTCC CGTATCGTAG TTATCTACAC GACGGGGAGT CAGGCAACTA TGGATGAACG
6361 AAATAGACAG ATCGCTGAGA TAGGTGCCTC ACTGATTAAG CATTGGTAAC TGTCAGACCA
6421 AGTTTACTCA TATATACTTT AGATTGATTT AAAACTTCAT TTTTAATTTA AAAGGATCTA
6481 GGTGAAGATC CTTTTTGATA ATCTCATGAC CAAAATCCCT TAACGTGAGT TTTCGTTCCA
6541 CTGAGCGTCA GACCCCGTAG AAAAGATCAA AGGATCTTCT TGAGATCCTT TTTTTCTGCG
6601 CGTAATCTGC TGCTTGCAAA CAAAAAAACC ACCGCTACCA GCGGTGGTTT GTTTGCCGGA
6661 TCAAGAGCTA CCAACTCTTT TTCCGAAGGT AACTGGCTTC AGCAGAGCGC AGATACCAAA
6721 TACTGTCCTT CTAGTGTAGC CGTAGTTAGG CCACCACTTC AAGAACTCTG TAGCACCGCC
6781 TACATACCTC GCTCTGCTAA TCCTGTTACC AGTGGCTGCT GCCAGTGGCG ATAAGTCGTG
6841 TCTTACCGGG TTGGACTCAA GACGATAGTT ACCGGATAAG GCGCAGCGGT CGGGCTGAAC
6901 GGGGGGTTCG TGCACACAGC CCAGCTTGGA GCGAACGACC TACACCGAAC TGAGATACCT
6961 ACAGCGTGAG CATTGAGAAA GCGCCACGCT TCCCGAAGGG AGAAAGGCGG ACAGGTATCC
7021 GGTAAGCGGC AGGGTCGGAA CAGGAGAGCG CACGAGGGAG CTTCCAGGGG GAAACGCCTG
7081 GTATCTTTAT AGTCCTGTCG GGTTTCGCCA CCTCTGACTT GAGCGTCGAT TTTTGTGATG
7141 CTCGTCAGGG GGGCGGAGCC TATGGAAAAA CGCCAGCAAC GCGGCCTTTT TACGGTTCCT
7201 GGCCTTTTGC TGGCCTTTTG CTCACATGTT CTTTCCTGCG TTATCCCCTG ATTCTGTGGA
7261 TAACCGTATT ACCGCCTTTG AGTGAGCTGA TACCGCTCGC CGCAGCCGAA CGACCGAGCG
7321 CAGCGAGTCA GTGAGCGAGG AAGCGGAAGA GCGCCCAATA CGCAAACCGC CTCTCCCCGC
7381 GCGTTGGCCG ATTCATTAAT GCAGAGCTTG CAATTCGCGC GTTTTTCAAT ATTATTGAAG
7441 CATTTATCAG GGTTATTGTC TCATGAGCGG ATACATATTT GAATGTATTT AGAAAAATAA
7501 ACAAATAGGG GTTCCGCGCA CATTTCCCCG AAAAGTGCCA CCTGACGTCT AAGAAACCAT
7561 TATTATCATG ACATTAACCT ATAAAAATAG GCGTAGTACG AGGCCCTTTC ACTCATTAGA
7621 TGCATGTCGT TACATAACTT ACGGTAAATG GCCCGCCTGG CTGACCGCCC AACGACCCCC
7681 GCCCATTGAC GTCAATAATG ACGTATGTTC CCATAGTAAC GCCAATAGGG ACTTTCCATT
7741 GACGTCAATG GGTGGAGTAT TTACGGTAAA CTGCCCACTT GGCAGTACAT CAAGTGTATC
7801 ATATGCCAAG TACGCCCCCT ATTGACGTCA ATGACGGTAA ATGGCCCGCC TGGCATTATG
7861 CCCAGTACAT GACCTTATGG GACTTTCCTA CTTGGCAGTA CATCTACGTA TTAGTCATCG
7921 CTATTACCAT GGTGATGCGG TTTTGGCAGT ACATCAATGG GCGTGGATAG CGGTTTGACT
7981 CACGGGGATT TCCAAGTCTC CACCCCATTG ACGTCAATGG GAGTTTGTTT TGGCACCAAA
8041 ATCAACGGGA CTTTCCAAAA TGTCGTAACA ACTCCGCCCC ATTGACGCAA ATGGGCGGTA
8101 GGCGTGTACG GTGGGAGGTC TAT

FIG.47E pEXP501: pCMV·SPORT 6 HOST FOR attB LIBRARIES pEXP501(cont'd)
FEATURES OF THE attB CLONING VECTOR, pEXP501.
BASES WITHIN HATCHED AREA ARE REPLACED BY cDNA IN SOME LTI cDNA LIBRARIES.

86B
　　　　　　　　　　　　　　　　　　　　⎡—CMV mRNA
—aga gct cgt tta gtg aac cg|t cag atc gcc tgg aga cgc cat cca
—tct cga gca aat cac ttg gca gtc tag cgg acc tct gcg gta ggt cgc tgt ttt gac ctc cat aga aga cac cgg gac cga tcc agc ctc
gcg aca aaa ctg gag gta tct tct gtg gcc ctg gct agg tcg gag Sst I　　LTI rev PRIMER
cgg act cta gcc tag gcc gcg|gag cgg ata aca att tca cac agg
gcc tga gat cgg atc cgg|cgc ctc gcc tat tgt taa agt gtg tcc ABI rev PRIMER　　　　Stu　　SP6 PROMOTER　　　⎡—SP6
aaa cag cta tga cca tta gg|c cta ttt agg tga cac tat aga|aca
ttt gtc gat act ggt aat cc|g gat aaa tcc act gtg ata tct|tgt Int　　attB1　　　　　　　　Age Kpn RsrII　EcoRI　　Sma
agt tt|g tac aaa aaa gca ggc t|gg ta|c|cgg tcc gg|a att ccc|ggg
tca aa|c atg ttt|ttt cgt ccg a|cc atg gcc|agg cct taa|ggg ccc EcoRV Sal　　　　Spe　　　　　　　Not　　　　Xba
at|a/tcg|/tcg/acg/agc/tca/cta/gtc/g|gc|ggc cgc t|ct aga gta tcc
ta|t/agc/agc/tgc/tcg/agt/gat/cag/c|cg ccg gcg aga t|ct cat agg Xho I　　Apa I Hind III Mlu　　attB2　　　Int
ctc gag ggg cc|c aag ctt a|cg cgt|acc cag ctt t|ct tgt aca aag
gag ctc ccc ggg ttc gaa tgc gca|tgg gtc gaa aga aca tgt ttc tgg t|cc cta tag tga gtc gta tta taa gct agg cac tgg ccg tcg
acc a|gg gat atc act cag cat aat|att cga tcc gtg acc ggc agc
T7　　　T7 PROMOTER　　　　　　　　　　　　　ABI fwd Nhe　　　　　　　　　　　　　1272
ttt tac aac gtc gtg act ggg aaa act g|ct agc ttg gga tct ttg—
aaa atg ttg cag cac tga ccc ttt tga cga t|cg aac cct aga aac—

LTI fwd

FIG.48B pEXP501 4396 bp

```
   1 CCATTCGCCA TTCAGGCTGC GCAACTGTTG GGAAGGGCGA TCGGTGCGGG CCTCTTCGCT
  61 ATTACGCCAG CCAATACGCA AACCGCCTCT CCCCGCGCGT TGGCCGATTC ATTAATGCAG
 121 GATCGATCCA GACATGATAA GATACATTGA TGAGTTTGGA CAAACCACAA CTAGAATGCA
 181 GTGAAAAAAA TGCTTTATTT GTGAAATTTG TGATGCTATT GCTTTATTTG TAACCATTAT
 241 AAGCTGCAAT AAACAAGTTA ACAACAACAA TTGCATTCAT TTTATGTTTC AGGTTCAGGG
 301 GGAGGTGTGG GAGGTTTTTT AAAGCAAGTA AAACCTCTAC AAATGTGGTA TGGCTGATTA
 361 TGATCATGAA CAGACTGTGA GGACTGAGGG GCCTGAAATG AGCCTTGGGA CTGTGAATCT
 421 AAAATACACA AACAATTAGA ATCACTAGCT CCTGTGTATA ATATTTTCAT AAATCATACT
 481 CAGTAAGCAA AACTCTCAAG CAGCAAGCAT ATGCAGCTAG TTTAACACAT TATACACTTA
 541 AAAATTTTAT ATTTACCTTA GAGCTTTAAA TCTCTGTAGG TAGTTTGTCC AATTATGTCA
 601 CACCACAGAA GTAAGGTTCC TTCACAAAGA TCCCAAGCTA GCAGTTTTCC CAGTCACGAC
 661 GTTGTAAAAC GACGGCCAGT GCCTAGCTTA TAATACGACT CACTATAGGG ACCACTTTGT
 721 ACAAGAAAGC TGGGTACGCG TAAGCTTGGG CCCCTCGAGG GATCCTCTAG AGCGGCCGCC
 781 GACTAGTGAG CTCGTCGACG ATATCCCGGG AATTCCGGAC CGGTACCAGC CTGCTTTTTT
 841 GTACAAACTT GTTCTATAGT GTCACCTAAA TAGGCCTAAT GGTCATAGCT GTTTCCTGTG
 901 TGAAATTGTT ATCCGCTCCG CGGCCTAGGC TAGAGTCCGG AGGCTGGATC GGTCCCGGTG
 961 TCTTCTATGG AGGTCAAAAC AGCGTGGATG GCGTCTCCAG GCGATCTGAC GGTTCACTAA
1021 ACGAGCTCTG CTTATATAGA CCTCCCACCG TACACGCCTA CCGCCCATTT GCGTCAATGG
1081 GGCGGAGTTG TTACGACATT TTGGAAAGTC CCGTTGATTT TGGTGCCAAA ACAAACTCCC
1141 ATTGACGTCA ATGGGGTGGA GACTTGGAAA TCCCCGTGAG TCAAACCGCT ATCCACGCCC
1201 ATTGATGTAC TGCCAAAACC GCATCACCAT GGTAATAGCG ATGACTAATA CGTAGATGTA
1261 CTGCCAAGTA GGAAAGTCCC ATAAGGTCAT GTACTGGGCA TAATGCCAGG CGGGCCATTT
1321 ACCGTCATTG ACGTCAATAG GGGGCGTACT TGGCATATGA TACACTTGAT GTACTGCCAA
1381 GTGGGCAGTT TACCGTAAAT ACTCCACCCA TTGACGTCAA TGGAAAGTCC CTATTGGCGT
1441 TACTATGGGA ACATACGTCA TTATTGACGT CAATGGGCGG GGGTCGTTGG GCGGTCAGCC
1501 AGGCGGGCCA TTTACCGTAA GTTATGTAAC GACATGCATC TAATGAGTGA AAGGGCCTCG
1561 TACTACGCCT ATTTTTATAG GTTAATGTCA TGATAATAAT GGTTTCTTAG ACGTCAGGTG
1621 GCACTTTTCG GGGAAATGTG CGCGGAACCC CTATTTGTTT ATTTTTCTAA ATACATTCAA
1681 ATATGTATCC GCTCATGAGA CAATAACCCT GATAAATGCT TCAATAATAT TGAAAAACGC
1741 GCGAATTGCA AGCTCTGCAT TAATGAATCG GCCAACGCGC GGGGAGAGGC GGTTTGCGTA
1801 TTGGGCGCTC TTCCGCTTCC TCGCTCACTG ACTCGCTGCG CTCGGTCGTT CGGCTGCGGC
1861 GAGCGGTATC AGCTCACTCA AAGGCGGTAA TACGGTTATC CACAGAATCA GGGGATAACG
1921 CAGGAAAGAA CATGTGAGCA AAAGGCCAGC AAAAGGCCAG GAACCGTAAA AAGGCCGCGT
1981 TGCTGGCGTT TTTCCATAGG CTCCGCCCCC CTGACGAGCA TCACAAAAAT CGACGCTCAA
2041 GTCAGAGGTG GCGAAACCCG ACAGGACTAT AAAGATACCA GGCGTTTCCC CCTGGAAGCT
2101 CCCTCGTGCG CTCTCCTGTT CCGACCCTGC CGCTTACCGG ATACCTGTCC GCCTTTCTCC
2161 CTTCGGGAAG CGTGGCGCTT TCTCAATGCT CACGCTGTAG GTATCTCAGT TCGGTGTAGG
```

FIG.48C

2221 TCGTTCGCTC CAAGCTGGGC TGTGTGCACG AACCCCCCGT TCAGCCCGAC CGCTGCGCCT
2281 TATCCGGTAA CTATCGTCTT GAGTCCAACC CGGTAAGACA CGACTTATCG CCACTGGCAG
2341 CAGCCACTGG TAACAGGATT AGCAGAGCGA GGTATGTAGG CGGTGCTACA GAGTTCTTGA
2401 AGTGGTGGCC TAACTACGGC TACACTAGAA GGACAGTATT TGGTATCTGC GCTCTGCTGA
2461 AGCCAGTTAC CTTCGGAAAA AGAGTTGGTA GCTCTTGATC CGGCAAACAA ACCACCGCTG
2521 GTAGCGGTGG TTTTTTTGTT TGCAAGCAGC AGATTACGCG CAGAAAAAAA GGATCTCAAG
2581 AAGATCCTTT GATCTTTTCT ACGGGGTCTG ACGCTCAGTG GAACGAAAAC TCACGTTAAG
2641 GGATTTTGGT CATGCCATAA CTTCGTATAG CATACATTAT ACGAAGTTAT GGCATGAGAT
2701 TATCAAAAAG GATCTTCACC TAGATCCTTT TAAATTAAAA ATGAAGTTTT AAATCAATCT
2761 AAAGTATATA TGAGTAAACT TGGTCTGACA GTTACCAATG CTTAATCAGT GAGGCACCTA
2821 TCTCAGCGAT CTGTCTATTT CGTTCATCCA TAGTTGCCTG ACTCCCCGTC GTGTAGATAA
2881 CTACGATACG GGAGGGCTTA CCATCTGGCC CCAGTGCTGC AATGATACCG CGAGACCCAC
2941 GCTCACCGGC TCCAGATTTA TCAGCAATAA ACCAGCCAGC CGGAAGGGCC GAGCGCAGAA
3001 GTGGTCCTGC AACTTTATCC GCCTCCATCC AGTCTATTAA TTGTTGCCGG GAAGCTAGAG
3061 TAAGTAGTTC GCCAGTTAAT AGTTTGCGCA ACGTTGTTGC CATTGCTACA GGCATCGTGG
3121 TGTCACGCTC GTCGTTTGGT ATGGCTTCAT TCAGCTCCGG TTCCCAACGA TCAAGGCGAG
3181 TTACATGATC CCCCATGTTG TGCAAAAAAG CGGTTAGCTC CTTCGGTCCT CCGATCGTTG
3241 TCAGAAGTAA GTTGGCCGCA GTGTTATCAC TCATGGTTAT GGCAGCACTG CATAATTCTC
3301 TTACTGTCAT GCCATCCGTA AGATGCTTTT CTGTGACTGG TGAGTACTCA ACCAAGTCAT
3361 TCTGAGAATA GTGTATGCGG CGACCGAGTT GCTCTTGCCC GGCGTCAATA CGGGATAATA
3421 CCGCGCCACA TAGCAGAACT TTAAAAGTGC TCATCATTGG AAAACGTTCT TCGGGGCGAA
3481 AACTCTCAAG GATCTTACCG CTGTTGAGAT CCAGTTCGAT GTAACCCACT CGTGCACCCA
3541 ACTGATCTTC AGCATCTTTT ACTTTCACCA GCGTTTCTGG GTGAGCAAAA ACAGGAAGGC
3601 AAAATGCCGC AAAAAAGGGA ATAAGGGCGA CACGGAAATG TTGAATACTC ATACTCTTCC
3661 TTTTTCAATA TTATTGAAGC ATTTATCAGG GTTATTGTCT CATGCCAGGG GTGGGCACAC
3721 ATATTTGATA CCAGCGATCC CTACACAGCA CATAATTCAA TGCGACTTCC CTCTATCGCA
3781 CATCTTAGAC CTTTATTCTC CCTCCAGCAC ACATCGAAGC TGCCGAGCAA GCCGTTCTCA
3841 CCAGTCCAAG ACCTGGCATG AGCGGATACA TATTTGAATG TATTTAGAAA AATAAACAAA
3901 TAGGGGTTCC GCGCACATTT CCCCGAAAAG TGCCACCTGA AATTGTAAAC GTTAATATTT
3961 TGTTAAAATT CGCGTTAAAT TTTTGTTAAA TCAGCTCATT TTTTAACCAA TAGGCCGAAA
4021 TCGGCAAAAT CCCTTATAAA TCAAAAGAAT AGACCGAGAT AGGGTTGAGT GTTGTTCCAG
4081 TTTGGAACAA GAGTCCACTA TTAAAGAACG TGGACTCCAA CGTCAAAGGG CGAAAAACCG
4141 TCTATCAGGG CGATGGCCCA CTACGTGAAC CATCACCCTA ATCAAGTTTT TTGGGGTCGA
4201 GGTGCCGTAA AGCACTAAAT CGGAACCCTA AAGGGAGCCC CCGATTTAGA GCTTGACGGG
4261 GAAAGCCGGC GAACGTGGCG AGAAAGGAAG GGAAGAAAGC GAAAGGAGCG GGCGCTAGGG
4321 CGCTGGCAAG TGTAGCGGTC ACGCTGCGCG TAACCACCAC ACCCGCCGCG CTTAATGCGC
4381 CGCTACAGGG CGCGTC

FIG.48D pDONR201 (kanR)

pDONR201 4470 bp (rotated to position 3516)

| Location (Base Nos.) | Gene Encoded |
|---|---|
| 260..29 | attP1 |
| 656..961 | ccdB |
| 1099..1184 | ccdA |
| 1303..1962 | CmR |
| 2210..2442 | attP2 |
| 2565..3374 | Kmr |
| 3495..4134 | ori |

```
   1 GTTAACGCTA GCATGGATCT CGGGCCCCAA ATAATGATTT TATTTTGACT GATAGTGACC
  61 TGTTCGTTGC AACAAATTGA TGAGCAATGC TTTTTTATAA TGCCAACTTT GTACAAAAAA
 121 GCTGAACGAG AAACGTAAAA TGATATAAAT ATCAATATAT TAAATTAGAT TTTGCATAAA
 181 AAACAGACTA CATAATACTG TAAAACACAA CATATCCAGT CACTATGAAT CAACTACTTA
 241 GATGGTATTA GTGACCTGTA GTCGACCGAC AGCCTTCCAA ATGTTCTTCG GGTGATGCTG
 301 CCAACTTAGT CGACCGACAG CCTTCCAAAT GTTCTTCTCA AACGGAATCG TCGTATCCAG
 361 CCTACTCGCT ATTGTCCTCA ATGCCGTATT AAATCATAAA AAGAAATAAG AAAAAGAGGT
 421 GCGAGCCTCT TTTTTGTGTG ACAAAATAAA AACATCTACC TATTCATATA CGCTAGTGTC
 481 ATAGTCCTGA AAATCATCTG CATCAAGAAC AATTTCACAA CTCTTATACT TTTCTCTTAC
 541 AAGTCGTTCG GCTTCATCTG GATTTTCAGC CTCTATACTT ACTAAACGTG ATAAAGTTTC
 601 TGTAATTTCT ACTGTATCGA CCTGCAGACT GGCTGTGTAT AAGGGAGCCT GACATTTATA
 661 TTCCCCAGAA CATCAGGTTA ATGGCGTTTT TGATGTCATT TTCGCGGTGG CTGAGATCAG
 721 CCACTTCTTC CCCGATAACG GAGACCGGCA CACTGGCCAT ATCGGTGGTC ATCATGCGCC
 781 AGCTTTCATC CCCGATATGC ACCACCGGGT AAAGTTCACG GGAGACTTTA TCTGACAGCA
 841 GACGTGCACT GGCCAGGGGG ATCACCATCC GTCGCCCGGG CGTGTCAATA ATATCACTCT
 901 GTACATCCAC AAACAGACGA TAACGGCTCT CTCTTTTATA GGTGTAAACC TTAAACTGCA
 961 TTTCACCAGT CCCTGTTCTC GTCAGCAAAA GAGCCGTTCA TTTCAATAAA CCGGGCGACC
1021 TCAGCCATCC CTTCCTGATT TTCCGCTTTC CAGCGTTCGG CACGCAGACG ACGGGCTTCA
1081 TTCTGCATGG TTGTGCTTAC CAGACCGGAG ATATTGACAT CATATATGCC TTGAGCAACT
1141 GATAGCTGTC GCTGTCAACT GTCACTGTAA TACGCTGCTT CATAGCACAC CTCTTTTTGA
1201 CATACTTCGG GTATACATAT CAGTATATAT TCTTATACCG CAAAAATCAG CGCGCAAATA
1261 CGCATACTGT TATCTGGCTT TTAGTAAGCC GGATCCACGC GATTACGCCC CGCCCTGCCA
1321 CTCATCGCAG TACTGTTGTA ATTCATTAAG CATTCTGCCG ACATGGAAGC CATCACAGAC
1381 GGCATGATGA ACCTGAATCG CCAGCGGCAT CAGCACCTTG TCGCCTTGCG TATAATATTT
1441 GCCCATGGTG AAAACGGGGG CGAAGAAGTT GTCCATATTG GCCACGTTTA AATCAAAACT
1501 GGTGAAACTC ACCCAGGGAT TGGCTGAGAC GAAAAACATA TTCTCAATAA ACCCTTTAGG
1561 GAAATAGGCC AGGTTTTCAC CGTAACACGC CACATCTTGC GAATATATGT GTAGAAACTG
1621 CCGGAAATCG TCGTGGTATT CACTCCAGAG CGATGAAAAC GTTTCAGTTT GCTCATGGAA
1681 AACGGTGTAA CAAGGGTGAA CACTATCCCA TATCACCAGC TCACCGTCTT TCATTGCCAT
1741 ACGGAATTCC GGATGAGCAT TCATCAGGCG GGCAAGAATG TGAATAAAGG CCGGATAAAA
1801 CTTGTGCTTA TTTTTCTTTA CGGTCTTTAA AAAGGCCGTA ATATCCAGCT GAACGGTCTG
1861 GTTATAGGTA CATTGAGCAA CTGACTGAAA TGCCTCAAAA TGTTCTTTAC GATGCCATTG
1921 GGATATATCA ACGGTGGTAT ATCCAGTGAT TTTTTTCTCC ATTTTAGCTT CCTTAGCTCC
```

FIG.49B

1981 TGAAAATCTC GATAACTCAA AAAATACGCC CGGTAGTGAT CTTATTTCAT TATGGTGAAA
2041 GTTGGAACCT CTTACGTGCC GATCAACGTC TCATTTTCGC CAAAAGTTGG CCCAGGGCTT
2101 CCCGGTATCA ACAGGGACAC CAGGATTTAT TTATTCTGCG AAGTGATCTT CCGTCACAGG
2161 TATTTATTCG GCGCAAAGTG CGTCGGGTGA TGCTGCCAAC TTAGTCGACT ACAGGTCACT
2221 AATACCATCT AAGTAGTTGA TTCATAGTGA CTGGATATGT TGTGTTTTAC AGTATTATGT
2281 AGTCTGTTTT TTATGCAAAA TCTAATTTAA TATATTGATA TTTATATCAT TTTACGTTTC
2341 TCGTTCAGCT TTCTTGTACA AAGTTGGCAT TATAAGAAAG CATTGCTTAT CAATTTGTTG
2401 CAACGAACAG GTCACTATCA GTCAAAATAA AATCATTATT TGCCATCCAG CTGCAGCTCT
2461 GGCCCGTGTC TCAAAATCTC TGATGTTACA TTGCACAAGA TAAAAATATA TCATCATGAA
2521 CAATAAAACT GTCTGCTTAC ATAAACAGTA ATACAAGGGG TGTTATGAGC CATATTCAAC
2581 GGGAAACGTC GAGGCCGCGA TTAAATTCCA ACATGGATGC TGATTTATAT GGGTATAAAT
2641 GGGCTCGCGA TAATGTCGGG CAATCAGGTG CGACAATCTA TCGCTTGTAT GGGAAGCCCG
2701 ATGCGCCAGA GTTGTTTCTG AAACATGGCA AAGGTAGCGT TGCCAATGAT GTTACAGATG
2761 AGATGGTCAG ACTAAACTGG CTGACGGAAT TTATGCCTCT TCCGACCATC AAGCATTTTA
2821 TCCGTACTCC TGATGATGCA TGGTTACTCA CCACTGCGAT CCCCGGAAAA ACAGCATTCC
2881 AGGTATTAGA AGAATATCCT GATTCAGGTG AAAATATTGT TGATGCGCTG GCAGTGTTCC
2941 TGCGCCGGTT GCATTCGATT CCTGTTTGTA ATTGTCCTTT TAACAGCGAT CGCGTATTTC
3001 GTCTCGCTCA GGCGCAATCA CGAATGAATA ACGGTTTGGT TGATGCGAGT GATTTTGATG
3061 ACGAGCGTAA TGGCTGGCCT GTTGAACAAG TCTGGAAAGA AATGCATAAA CTTTTGCCAT
3121 TCTCACCGGA TTCAGTCGTC ACTCATGGTG ATTTCTCACT TGATAACCTT ATTTTTGACG
3181 AGGGGAAATT AATAGGTTGT ATTGATGTTG GACGAGTCGG AATCGCAGAC CGATACCAGG
3241 ATCTTGCCAT CCTATGGAAC TGCCTCGGTG AGTTTTCTCC TTCATTACAG AAACGGCTTT
3301 TTCAAAAATA TGGTATTGAT AATCCTGATA TGAATAAATT GCAGTTTCAT TTGATGCTCG
3361 ATGAGTTTTT CTAATCAGAA TTGGTTAATT GGTTGTAACA CTGGCAGAGC ATTACGCTGA
3421 CTTGACGGGA CGGCGCAAGC TCATGACCAA AATCCCTTAA CGTGAGTTTT CGTTCCACTG
3481 AGCGTCAGAC CCCGTAGAAA AGATCAAAGG ATCTTCTTGA GATCCTTTTT TTCTGCGCGT
3541 AATCTGCTGC TTGCAAACAA AAAAACCACC GCTACCAGCG GTGGTTTGTT TGCCGGATCA
3601 AGAGCTACCA ACTCTTTTTC CGAAGGTAAC TGGCTTCAGC AGAGCGCAGA TACCAAATAC
3661 TGTCCTTCTA GTGTAGCCGT AGTTAGGCCA CCACTTCAAG AACTCTGTAG CACCGCCTAC
3721 ATACCTCGCT CTGCTAATCC TGTTACCAGT GGCTGCTGCC AGTGGCGATA AGTCGTGTCT
3781 TACCGGGTTG GACTCAAGAC GATAGTTACC GGATAAGGCG CAGCGGTCGG GCTGAACGGG
3841 GGGTTCGTGC ACACAGCCCA GCTTGGAGCG AACGACCTAC ACCGAACTGA GATACCTACA
3901 GCGTGAGCTA TGAGAAAGCG CCACGCTTCC CGAAGGGAGA AAGGCGGACA GGTATCCGGT
3961 AAGCGGCAGG GTCGGAACAG GAGAGCGCAC GAGGGAGCTT CCAGGGGGAA ACGCCTGGTA
4021 TCTTTATAGT CCTGTCGGGT TTCGCCACCT CTGACTTGAG CGTCGATTTT TGTGATGCTC
4081 GTCAGGGGGG CGGAGCCTAT GGAAAAACGC CAGCAACGCG GCCTTTTTAC GGTTCCTGGC
4141 CTTTTGCTGG CCTTTTGCTC ACATGTTCTT TCCTGCGTTA TCCCCTGATT CTGTGGATAA
4201 CCGTATTACC GCTAGCCAGG AAGAGTTTGT AGAAACGCAA AAAGGCCATC CGTCAGGATG
4261 GCCTTCTGCT TAGTTTGATG CCTGGCAGTT TATGGCGGGC GTCCTGCCCG CCACCCTCCG
4321 GGCCGTTGCT TCACAACGTT CAAATCCGCT CCCGGCGGAT TTGTCCTACT CAGGAGAGCG
4381 TTCACCGACA AACAACAGAT AAAACGAAAG GCCCAGTCTT CCGACTGAGC CTTTCGTTTT
4441 ATTTGATGCC TGGCAGTTCC CTACTCTCGC

FIG.49C pDONR202 4204 bp

| Location (Base Nos.) | Gene Encoded |
|---|---|
| 369..127 | attP1 |
| 486..1059 | ori |
| 1228..2107 | KmR |
| 2381..2140 | attP2 |
| 2629..3288 | CmR |
| 3408..3492 | inactivated ccdA |
| 3630..3935 | ccdB |

```
   1 CGGCATTGAG GACAATAGCG AGTAGGCTGG ATACGACGAT TCCGTTTGAG AAGAACATTT
  61 GGAAGGCTGT CGGTCGACTA AGTTGGCAGC ATCACCCGAA GAACATTTGG AAGGCTGTCG
 121 GTCGACTACA GGTCACTAAT ACCATCTAAG TAGTTGATTC ATAGTGACTG GATATGTTGT
 181 GTTTTACAGT ATTATGTAGT CTGTTTTTTA TGCAAAATCT AATTTAATAT ATTGATATTT
 241 ATATCATTTT ACGTTTCTCG TTCAGCTTTT TTGTACAAAG TTGGCATTAT AAAAAAGCAT
 301 TGCTCATCAA TTTGTTGCAA CGAACAGGTC ACTATCAGTC AAAATAAAAT CATTATTTGG
 361 GGCCCGAGAT CCATGCTAGC GGTAATACGG TTATCCACAG AATCAGGGGA TAACGCAGGA
 421 AAGAACATGT GAGCAAAAGG CCAGCAAAAG GCCAGGAACC GTAAAAAGGC CGCGTTGCTG
 481 GCGTTTTTCC ATAGGCTCCG CCCCCCTGAC GAGCATCACA AAAATCGACG CTCAAGTCAG
 541 AGGTGGCGAA ACCCGACAGG ACTATAAAGA TACCAGGCGT TTCCCCCTGG AAGCTCCCTC
 601 GTGCGCTCTC CTGTTCCGAC CCTGCCGCTT ACCGGATACC TGTCCGCCTT TCTCCCTTCG
 661 GGAAGCGTGG CGCTTTCTCA TAGCTCACGC TGTAGGTATC TCAGTTCGGT GTAGGTCGTT
 721 CGCTCCAAGC TGGGCTGTGT GCACGAACCC CCCGTTCAGC CCGACCGCTG CGCCTTATCC
 781 GGTAACTATC GTCTTGAGTC CAACCCGGTA AGACACGACT TATCGCCACT GGCAGCAGCC
 841 ACTGGTAACA GGATTAGCAG AGCGAGGTAT GTAGGCGGTG CTACAGAGTT CTTGAAGTGG
 901 TGGCCTAACT ACGGCTACAC TAGAAGGACA GTATTTGGTA TCTGCGCTCT GCTGAAGCCA
 961 GTTACCTTCG GAAAAAGAGT TGGTAGCTCT TGATCCGGCA AACAAACCAC CGCTGGTAGC
1021 GGTGGTTTTT TTGTTTGCAA GCAGCAGATT ACGCGCAGAA AAAAAGGATC TCAAGAAGAT
1081 CCTTTGATCT TTTCTACGGG GTCTGACGCT CAGTGGAACG AAAACTCACG TTAAGGGATT
1141 TTGGTCATGA GCTTGCGCCG TCCCGTCAAG TCAGCGTAAT GCTCTGCCAG TGTTACAACC
1201 AATTAACCAA TTCTGATTAG AAAAACTCAT CGAGCATCAA ATGAAACTGC AATTTATTCA
1261 TATCAGGATT ATCAATACCA TATTTTTGAA AAAGCCGTTT CTGTAATGAA GGAGAAAACT
1321 CACCGAGGCA GTTCCATAGG ATGGCAAGAT CCTGGTATCG GTCTGCGATT CCGACTCGTC
1381 CAACATCAAT ACAACCTATT AATTTCCCCT CGTCAAAAAT AAGGTTATCA AGTGAGAAAT
1441 CACCATGAGT GACGACTGAA TCCGGTGAGA ATGGCAAAAG TTTATGCATT TCTTTCCAGA
1501 CTTGTTCAAC AGGCCAGCCA TTACGCTCGT CATCAAAATC ACTCGCATCA ACCAAACCGT
1561 TATTCATTCG TGATTGCGCC TGAGCGAGAC GAAATACGCG ATCGCTGTTA AAAGGACAAT
1621 TACAAACAGG AATCGAATGC AACCGGCGCA GGAACACTGC CAGCGCATCA ACAATATTTT
1681 CACCTGAATC AGGATATTCT TCTAATACCT GGAATGCTGT TTTTCCGGGG ATCGCAGTGG
```

FIG.50B

1741 TGAGTAACCA TGCATCATCA GGAGTACGGA TAAAATGCTT GATGGTCGGA AGAGGCATAA
1801 ATTCCGTCAG CCAGTTTAGT CTGACCATCT CATCTGTAAC ATCATTGGCA ACGCTACCTT
1861 TGCCATGTTT CAGAAACAAC TCTGGCGCAT CGGGCTTCCC ATACAAGCGA TAGATTGTCG
1921 CACCTGATTG CCCGACATTA TCGCGAGCCC ATTTATACCC ATATAAATCA GCATCCATGT
1981 TGGAATTTAA TCGCGGCCTC GACGTTTCCC GTTGAATATG GCTCATAACA CCCCTTGTAT
2041 TACTGTTTAT GTAAGCAGAC AGTTTTATTG TTCATGATGA TATATTTTTA TCTTGTGCAA
2101 TGTAACATCA GAGATTTTGA GACACGGGCC AGAGCTGCAG CTGGATGGCA AATAATGATT
2161 TTATTTTGAC TGATAGTGAC CTGTTCGTTG CAACAAATTG ATAAGCAATG CTTTCTTATA
2221 ATGCCAACTT TGTACAAGAA AGCTGAACGA GAAACGTAAA ATGATATAAA TATCAATATA
2281 TTAAATTAGA TTTTGCATAA AAAACAGACT ACATAATACT GTAAAACACA ACATATCCAG
2341 TCACTATGAA TCAACTACTT AGATGGTATT AGTGACCTGT AGTCGACTAA GTTGGCAGCA
2401 TCACCCGACG CACTTTGCGC CGAATAAATA CCTGTGACGG AAGATCACTT CGCAGAATAA
2461 ATAAATCCTG GTGTCCCTGT TGATACCGGG AAGCCCTGGG CCAACTTTTG GCGAAAATGA
2521 GACGTTGATC GGCACGTAAG AGGTTCCAAC TTTCACCATA ATGAAATAAG ATCACTACCG
2581 GGCGTATTTT TTGAGTTATC GAGATTTTCA GGAGCTAAGG AAGCTAAAAT GGAGAAAAAA
2641 ATCACTGGAT ATACCACCGT TGATATATCC CAATGGCATC GTAAAGAACA TTTTGAGGCA
2701 TTTCAGTCAG TTGCTCAATG TACCTATAAC CAGACCGTTC AGCTGGATAT TACGGCCTTT
2761 TTAAAGACCG TAAAGAAAAA TAAGCACAAG TTTTATCCGG CCTTTATTCA CATTCTTGCC
2821 CGCCTGATGA ATGCTCATCC GGAATTCCGT ATGGCAATGA AAGACGGTGA GCTGGTGATA
2881 TGGGATAGTG TTCACCCTTG TTACACCGTT TTCCATGAGC AAACTGAAAC GTTTTCATCG
2941 CTCTGGAGTG AATACCACGA CGATTTCCGG CAGTTTCTAC ACATATATTC GCAAGATGTG
3001 GCGTGTTACG GTGAAAACCT GGCCTATTTC CCTAAAGGGT TTATTGAGAA TATGTTTTTC
3061 GTCTCAGCCA ATCCCTGGGT GAGTTTCACC AGTTTTGATT TAAACGTGGC CAATATGGAC
3121 AACTTCTTCG CCCCCGTTTT CACCATGGGC AAATATTATA CGCAAGGCGA CAAGGTGCTG
3181 ATGCCGCTGG CGATTCAGGT TCATCATGCC GTCTGTGATG GCTTCCATGT CGGCAGAATG
3241 CTTAATGAAT TACAACAGTA CTGCGATGAG TGGCAGGGCG GGGCGTAATC GCGTGGATCC
3301 GGCTTACTAA AAGCCAGATA ACAGTATGCG TATTTGCGCG CTGATTTTTG CGGTATAAGA
3361 ATATATACTG ATATGTATAC CCGAAGTATG TCAAAAAGAG GTGTGCTATG AAGCAGCGTA
3421 TTACAGTGAC AGTTGACAGC GACAGCTATC AGTTGCTCAA GGCATATATG ATGTCAATAT
3481 CTCCGGTCTG GTAAGCACAA CCATGCAGAA TGAAGCCCGT CGTCTGCGTG CCGAACGCTG
3541 GAAAGCGGAA AATCAGGAAG GGATGGCTGA GGTCGCCCGG TTTATTGAAA TGAACGGCTC
3601 TTTTGCTGAC GAGAACAGGG ACTGGTGAAA TGCAGTTTAA GGTTTACACC TATAAAAGAG
3661 AGAGCCGTTA TCGTCTGTTT GTGGATGTAC AGAGTGATAT TATTGACACG CCCGGGCGAC
3721 GGATGGTGAT CCCCCTGGCC AGTGCACGTC TGCTGTCAGA TAAAGTCTCC CGTGAACTTT
3781 ACCCGGTGGT GCATATCGGG GATGAAAGCT GGCGCATGAT GACCACCGAT ATGGCCAGTG
3841 TGCCGGTCTC CGTTATCGGG GAAGAAGTGG CTGATCTCAG CCACCGCGAA AATGACATCA
3901 AAAACGCCAT TAACCTGATG TTCTGGGGAA TATAAATGTC AGGCTCCCTT ATACACAGCC
3961 AGTCTGCAGG TCGATACAGT AGAAATTACA GAAACTTTAT CACGTTTAGT AAGTATAGAG
4021 GCTGAAAATC CAGATGAAGC CGAACGACTT GTAAGAGAAA AGTATAAGAG TTGTGAAATT
4081 GTTCTTGATG CAGATGATTT TCAGGACTAT GACACTAGCG TATATGAATA GGTAGATGTT
4141 TTTATTTTGT CACACAAAAA AGAGGCTCGC ACCTCTTTTT CTTATTTCTT TTTATGATTT
4201 AATA

FIG.50C pDONR203 4208 bp

| Location (Base Nos.) | Gene Encoded |
|---|---|
| 47..131 | inactivated ccdA |
| 251..910 | CmR |
| 1158..1398 | attP2 |
| 1509..2082 | ori |
| 2251..3130 | KmR |
| 3464..3174 | attP1 |
| 3812..4117 | ccdB |

```
   1 GCGTTCGGCA CGCAGACGAC GGGCTTCATT CTGCATGGTT GTGCTTACCA GACCGGAGAT
  61 ATTGACATCA TATATGCCTT GAGCAACTGA TAGCTGTCGC TGTCAACTGT CACTGTAATA
 121 CGCTGCTTCA TAGCACACCT CTTTTTGACA TACTTCGGGT ATACATATCA GTATATATTC
 181 TTATACCGCA AAAATCAGCG CGCAAATACG CATACTGTTA TCTGGCTTTT AGTAAGCCGG
 241 ATCCACGCGT TTACGCCCCG CCCTGCCACT CATCGCAGTA CTGTTGTAAT TCATTAAGCA
 301 TTCTGCCGAC ATGGAAGCCA TCACAGACGG CATGATGAAC CTGAATCGCC AGCGGCATCA
 361 GCACCTTGTC GCCTTGCGTA TAATATTTGC CCATGGTGAA AACGGGGGCG AAGAAGTTGT
 421 CCATATTGGC CACGTTTAAA TCAAAACTGG TGAAACTCAC CCAGGGATTG GCTGAGACGA
 481 AAAACATATT CTCAATAAAC CCTTTAGGGA AATAGGCCAG GTTTTCACCG TAACACGCCA
 541 CATCTTGCGA ATATATGTGT AGAAACTGCC GGAAATCGTC GTGGTATTCA CTCCAGAGCG
 601 ATGAAAACGT TTCAGTTTGC TCATGGAAAA CGGTGTAACA AGGGTGAACA CTATCCCATA
 661 TCACCAGCTC ACCGTCTTTC ATTGCCATAC GGAATTCCGG ATGAGCATTC ATCAGGCGGG
 721 CAAGAATGTG AATAAAGGCC GGATAAAACT TGTGCTTATT TTTCTTTACG GTCTTTAAAA
 781 AGGCCGTAAT ATCCAGCTGA ACGGTCTGGT TATAGGTACA TTGAGCAACT GACTGAAATG
 841 CCTCAAAATG TTCTTTACGA TGCCATTGGG ATATATCAAC GGTGGTATAT CCAGTGATTT
 901 TTTTCTCCAT TTTAGCTTCC TTAGCTCCTG AAAATCTCGA TAACTCAAAA AATACGCCCG
 961 GTAGTGATCT TATTTCATTA TGGTGAAAGT TGGAACCTCT TACGTGCCGA TCAACGTCTC
1021 ATTTTCGCCA AAAGTTGGCC CAGGGCTTCC CGGTATCAAC AGGGACACCA GGATTTATTT
1081 ATTCTGCGAA GTGATCTTCC GTCACAGGTA TTTATTCGGC GCAAAGTGCG TCGGGTGATG
1141 CTGCCAACTT AGTCGACTAC AGGTCACTAA TACCATCTAA GTAGTTGATT CATAGTGACT
1201 GGATATGTTG TGTTTTACAG TATTATGTAG TCTGTTTTTT ATGCAAAATC TAATTTAATA
1261 TATTGATATT TATATCATTT TACGTTTCTC GTTCAGCTTT CTTGTACAAA GTTGGCATTA
1321 TAAGAAAGCA TTGCTTATCA ATTTGTTGCA ACGAACAGGT CACTATCAGT CAAAATAAAA
1381 TCATTATTTG CCATCCAGCT AGCGGTAATA CGGTTATCCA CAGAATCAGG GGATAACGCA
1441 GGAAAGAACA TGTGAGCAAA AGGCCAGCAA AAGGCCAGGA ACCGTAAAAA GGCCGCGTTG
1501 CTGGCGTTTT TCCATAGGCT CCGCCCCCCT GACGAGCATC ACAAAAATCG ACGCTCAAGT
1561 CAGAGGTGGC GAAACCCGAC AGGACTATAA AGATACCAGG CGTTTCCCCC TGGAAGCTCC
1621 CTCGTGCGCT CTCCTGTTCC GACCCTGCCG CTTACCGGAT ACCTGTCCGC CTTTCTCCCT
1681 TCGGGAAGCG TGGCGCTTTC TCATAGCTCA CGCTGTAGGT ATCTCAGTTC GGTGTAGGTC
1741 GTTCGCTCCA AGCTGGGCTG TGTGCACGAA CCCCCCGTTC AGCCCGACCG CTGCGCCTTA
1801 TCCGGTAACT ATCGTCTTGA GTCCAACCCG GTAAGACACG ACTTATCGCC ACTGGCAGCA
1861 GCCACTGGTA ACAGGATTAG CAGAGCGAGG TATGTAGGCG GTGCTACAGA GTTCTTGAAG
1921 TGGTGGCCTA ACTACGGCTA CACTAGAAGA ACAGTATTTG GTATCTGCGC TCTGCTGAAG
```

FIG.51B

```
1981 CCAGTTACCT TCGGAAAAAG AGTTGGTAGC TCTTGATCCG GCAAACAAAC CACCGCTGGT
2041 AGCGGTGGTT TTTTTGTTTG CAAGCAGCAG ATTACGCGCA GAAAAAAAGG ATCTCAAGAA
2101 GATCCTTTGA TCTTTTCTAC GGGGTCTGAC GCTCAGTGGA ACGAAAACTC ACGTTAAGGG
2161 ATTTTGGTCA TGAGCTTGCG CCGTCCCGTC AAGTCAGCGT AATGCTCTGC CAGTGTTACA
2221 ACCAATTAAC CAATTCTGAT TAGAAAAACT CATCGAGCAT CAAATGAAAC TGCAATTTAT
2281 TCATATCAGG ATTATCAATA CCATATTTTT GAAAAAGCCG TTTCTGTAAT GAAGGAGAAA
2341 ACTCACCGAG GCAGTTCCAT AGGATGGCAA GATCCTGGTA TCGGTCTGCG ATTCCGACTC
2401 GTCCAACATC AATACAACCT ATTAATTTCC CCTCGTCAAA AATAAGGTTA TCAAGTGAGA
2461 AATCACCATG AGTGACGACT GAATCCGGTG AGAATGGCAA AAGTTTATGC ATTTCTTTCC
2521 AGACTTGTTC AACAGGCCAG CCATTACGCT CGTCATCAAA ATCACTCGCA TCAACCAAAC
2581 CGTTATTCAT TCGTGATTGC GCCTGAGCGA GACGAAATAC GCGATCGCTG TTAAAAGGAC
2641 AATTACAAAC AGGAATCGAA TGCAACCGGC GCAGGAACAC TGCCAGCGCA TCAACAATAT
2701 TTTCACCTGA ATCAGGATAT TCTTCTAATA CCTGGAATGC TGTTTTTCCG GGGATCGCAG
2761 TGGTGAGTAA CCATGCATCA TCAGGAGTAC GGATAAAATG CTTGATGGTC GGAAGAGGCA
2821 TAAATTCCGT CAGCCAGTTT AGTCTGACCA TCTCATCTGT AACATCATTG GCAACGCTAC
2881 CTTTGCCATG TTTCAGAAAC AACTCTGGCG CATCGGGCTT CCCATACAAG CGATAGATTG
2941 TCGCACCTGA TTGCCCGACA TTATCGCGAG CCCATTTATA CCCATATAAA TCAGCATCCA
3001 TGTTGGAATT TAATCGCGGC CTCGACGTTT CCCGTTGAAT ATGGCTCATA ACACCCCTTG
3061 TATTACTGTT TATGTAAGCA GACAGTTTTA TTGTTCATGA TGATATATTT TTATCTTGTG
3121 CAATGTAACA TCAGAGATTT TGAGACACGG GCCAGAGCTG CAGCTAGCAT GGATCTCGGG
3181 CCCCAAATAA TGATTTTATT TTGACTGATA GTGACCTGTT CGTTGCAACA AATTGATGAG
3241 CAATGCTTTT TTATAATGCC AACTTTGTAC AAAAAAGCTG AACGAGAAAC GTAAAATGAT
3301 ATAAATATCA ATATATTAAA TTAGATTTTG CATAAAAAAC AGACTACATA ATACTGTAAA
3361 ACACAACATA TCCAGTCACT ATGAATCAAC TACTTAGATG GTATTAGTGA CCTGTAGTCG
3421 ACCGACAGCC TTCCAAATGT TCTTCGGGTG ATGCTGCCAA CTTAGTCGAC CGACAGCCTT
3481 CCAAATGTTC TTCTCAAACG GAATCGTCGT ATCCAGCCTA CTCGCTATTG TCCTCAATGC
3541 CGTATTAAAT CATAAAAAGA AATAAGAAAA AGAGGTGCGA GCCTCTTTTT TGTGTGACAA
3601 AATAAAAACA TCTACCTATT CATATACGCT AGTGTCATAG TCCTGAAAAT CATCTGCATC
3661 AAGAACAATT TCACAACTCT TATACTTTTC TCTTACAAGT CGTTCGGCTT CATCTGGATT
3721 TTCAGCCTCT ATACTTACTA AACGTGATAA AGTTTCTGTA ATTTCTACTG TATCGACCTG
3781 CAGACTGGCT GTGTATAAGG GAGCCTGACA TTTATATTCC CCAGAACATC AGGTTAATGG
3841 CGTTTTTGAT GTCATTTTCG CGGTGGCTGA GATCAGCCAC TTCTTCCCCG ATAACGGAGA
3901 CCGGCACACT GGCCATATCG GTGGTCATCA TGCGCCAGCT TTCATCCCCG ATATGCACCA
3961 CCGGGTAAAG TTCACGGGAG ACTTTATCTG ACAGCAGACG TGCACTGGCC AGGGGGATCA
4021 CCATCCGTCG CCCGGGCGTG TCAATAATAT CACTCTGTAC ATCCACAAAC AGACGATAAC
4081 GGCTCTCTCT TTTATAGGTG TAAACCTTAA ACTGCATTTC ACCAGTCCCT GTTCTCGTCA
4141 GCAAAAGAGC CGTTCATTTC AATAAACCGG GCGACCTCAG CCATCCCTTC CTGATTTTCC
4201 GCTTTCCA
```

FIG.51C pDONR204 4165 bp

```
   1 CGGCATTGAG GACAATAGCG AGTAGGCTGG ATACGACGAT TCCGTTTGAG AAGAACATTT
  61 GGAAGGCTGT CGGTCGACTA CAGGTCACTA ATACCATCTA AGTAGTTGAA TCATAGTGAC
 121 TGGATATGTT GTGTTTTACA GTATTATGTA GTCTGTTTTT TATGCAAAAT CTAATTTAAT
 181 ATATTGATAT TTATATCATT TTACGTTTCT CGTTCAGCTT TTTTGTACAA AGTTGGCATT
 241 ATAAAAAAGC ATTGCTTATC AATTTGTTGC AACGAACAGG TCACTATCAG TCAAAATAAA
 301 ATCATTATTT GGGGCCCGAG ATCCATGCTA GCTGCAGTGC GCAGGGCCCG TGTCTCAAAA
 361 TCTCTGATGT TACATTGCAC AAGATAAAAA TATATCATCA TGAACAATAA AACTGTCTGC
 421 TTACATAAAC AGTAATACAA GGGGTGTTAT GAGCCATATT CAACGGGAAA CGTCTTGCTG
 481 GAGGCCGCGA TTAAATTCCA ACATGGATGC TGATTTATAT GGGTATAAAT GGGCTCGCGA
 541 TAATGTCGGG CAATCAGGTG CGACAATCTT TCGATTGTAT GGGAAGCCCG ATGCGCCAGA
 601 GTTGTTTCTG AAACATGGCA AAGGTAGCGT TGCCAATGAT GTTACAGATG AGATGGTCAG
 661 ACTAAACTGG CTGACGGAAT TTATGCCTCT TCCGACCATC AAGCATTTTA TCCGTACTCC
 721 TGATGATGCA TGGTTACTCA CCACTGCGAT CCGCGGGAAA ACAGCATTCC AGGTATTAGA
 781 AGAATATCCT GATTCAGGTG AAAATATTGT TGATGCGCTG GCAGTGTTCC TGCGCCGGTT
 841 GCATTCGATT CCTGTTTGTA ATTGTCCTTT TAACAGCGAT CGCGTATTTC GTCTCGCTCA
 901 GGCGCAATCA CGAATGAATA ACGGTTTGGT TGATGCGAGT GATTTTGATG ACGAGCGTAA
 961 TGGCTGGCCT GTTGAACAAG TCTGGAAAGA AATGCATACG CTTTTGCCAT TCTCACCGGA
1021 TTCAGTCGTC ACTCATGGTG ATTTCTCACT TGATAACCTT ATTTTTGACG AGGGGAAATT
1081 AATAGGTTGT ATTGATGTTG GACGAGTCGG AATCGCAGAC CGATACCAGG ATCTTGCCAT
1141 CCTATGGAAC TGCCTCGGTG AGTTTTCTCC TTCATTACAG AAACGGCTTT TTCAAAAATA
1201 TGGTATTGAT AATCCTGATA TGAATAAATT GCAGTTTCAT TTGATGCTCG ATGAGTTTTT
1261 CTAATCAGAA TTGGTTAATT GGTTGTAACA CTGGCAGAGC ATTACGCTGA CTTGACGGGA
1321 CGGCGNCATG ACCAAAATCC CTTAACGTGA GTTTTCGTTC CACTGAGCGT CAGACCCCGT
1381 AGAAAAGATC AAAGGATCTT CTTGAGATCC TTTTTTTCTG CGCGTAATCT GCTGCTTGCA
1441 AACAAAAAAA CCACCGCTAC CAGCGGTGGT TTGTTTGCCG GATCAAGAGC TACCAACTCT
1501 TTTTCCGAAG GTAACTGGCT TCAGCAGAGC GCAGATACCA AATACTGTCC TTCTAGTGTA
1561 GCCGTAGTTA GGCCACCACT TCAAGAACTC TGTAGCACCG CCTACATACC TCGCTCTGCT
1621 AATCCTGTTA CCAGTGGCTG CTGCCAGTGG CGATAAGTCG TGTCTTACCG GGTTGGACTC
1681 AAGACGATAG TTACCGGATA AGGCGCAGCG GTCGGGCTGA ACGGGGGGTT CGTGCACACA
1741 GCCCAGCTTG GAGCGAACGA CCTACACCGA ACTGAGATAC CTACAGCGTG AGCTATGAGA
1801 AAGCGCCACG CTTCCCGAAG GGAGAAAGGC GGACAGGTAT CCGGTAAGCG GCAGGGTCGG
1861 AACAGGAGAG CGCACGAGGG AGCTTCCAGG GGGAAACGCC TGGTATCTTT ATAGTCCTGT
1921 CGGGTTTCGC CACCTCTGAC TTGAGCGTCG ATTTTTGTGA TGCTCGTCAG GGGGGCGGAG
1981 CCTATGGAAA AACGCCAGCA ACGCGGCCTT TTTACGGTTC CTGGCCTTTT GCTGGCCTTT
2041 TGCTCACATG TTCTTTCCTG CGTTATCCCC TGATTCTGTG GATAACCGTA TTACCGCTAG
2101 CTGGATCGGC AAATAATGAT TTTATTTTGA CTGATAGTGA CCTGTTCGTT GCAACAAATT
2161 GATAAGCAAT GCTTTTTTAT AATGCCAACT TTGTACAAGA AAGCTGAACG AGAAACGTAA
```

FIG.52B

2221 AATGATATAA ATATCAATAT ATTAAATTAG ATTTTGCATA AAAAACAGAC TACATAATAC
2281 TGTAAAACAC AACATATCCA GTCACTATGA TTCAACTACT TAGATGGTAT TAGTGACCTG
2341 TAGTCGACTA AGTTGGCAGC ATCACCCGAC GCACTTTGCG CCGAATAAAT ACCTGTGACG
2401 GAAGATCACT TCGCAGAATA AATAAATCCT GGTGTCCCTG TTGATACCGG GAAGCCCTGG
2461 GCCAACTTTT GGCGAAAATG AGACGTTGAT CGGCACATTT CACAACTCTT ATACTTTTCT
2521 CTTACAAGTC GTTCGGCTTC ATCTGGATTT TCAGCCTCTA TACTTACTAA ACGTGATAAA
2581 GTTTCTGTAA TTTCTACTGT ATCGACCTGC AGACTGGCTG TGTATAACGG AGCCTGACAT
2641 TTATATTCCC CAGAACATCA GGTTAATGGC GTTTTTGATG TCATTTTCGC GGTGGCTGAG
2701 ATCAGCCACT TCTTCCCCGA TAACGGAGAC CGGCACACTG GCCATATCGG TGGTCATCAT
2761 GCGCCAGCTT TCATCCCCGA TATGCACCAC CGGGTAAAGT TCACGGGAGA CTTTATCTGA
2821 CAGCAGACGT GCACTGGCCA GGGGGATCAC CATCCGTCGC CCGGGCGTGT CAATAATATC
2881 ACTCTGTACA TCCACAAACA GACGATAACG GCTCTCTCTT TTATAGGTGT AAACCTTAAA
2941 CTGCATTTCA CCAGTCCCTG TTCTCGTCAG CAAAAGAGCC GTTCATTTCA ATAAACCGGG
3001 CGACCTCAGC CATCCCTTCC TGATTTTCCG CTTTCCAGCG TTCGGCACGC AGACGACGGG
3061 CTTCATTCTG CATGGTTGTG CTTACCAGAC CGGAGATATT GACATCATAT ATGCCTTGAG
3121 CAACTGATAG CTGTCGCTGT CAACTGTCAC TGTAATACGC TGCTTCATAG CACACCTCTT
3181 TTTGACATAC TTCGGGTATA CATATCAGTA TATATTCTTA TACCGCAAAA ATCAGCGCGC
3241 AAATACGCAT ACTGTTATCT GGCTTTTAGT AAGCCGGATC CACGCGTTTA CGCCCCGCCC
3301 TGCCACTCAT CGCAGTACTG TTGTAATTCA TTAAGCATTC TGCCGACATG GAAGCCATCA
3361 CAGACGGCAT GATGAACCTG AATCGCCAGC GGCATCAGCA CCTTGTCGCC TTGCGTATAA
3421 TATTTGCCCA TGGTGAAAAC GGGGGCGAAG AAGTTGTCCA TATTGGCCAC GTTTAAATCA
3481 AAACTGGTGA AACTCACCCA GGGATTGGCT GAGACGAAAA ACATATTCTC AATAAACCCT
3541 TTAGGGAAAT AGGCCAGGTT TTCACCGTAA CACGCCACAT CTTGCGAATA TATGTGTAGA
3601 AACTGCCGGA AATCGTCGTG GTATTCACTC CAGAGCGATG AAAACGTTTC AGTTTGCTCA
3661 TGGAAAACGG TGTAACAAGG GTGAACACTA TCCCATATCA CCAGCTCACC GTCTTTCATT
3721 GCCATACGGA ATTCCGGATG AGCATTCATC AGGCGGGCAA GAATGTGAAT AAAGGCCGGA
3781 TAAAACTTGT GCTTATTTTT CTTTACGGTC TTTAAAAAGG CCGTAATATC CAGCTGAACG
3841 GTCTGGTTAT AGGTACATTG AGCAACTGAC TGAAATGCCT CAAAATGTTC TTTACGATGC
3901 CATTGGGATA TATCAACGGT GGTATATCCA GTGATTTTTT TCTCCATTTT AGCTTCCTTA
3961 GCTCCTGAAA ATCTCGATAA CTCAAAAAAT ACGCCCGGTA GTGATCTTAT TTCATTATGG
4021 TGAAAGTTGG AACCTCTTAC TGTTCTTGAT GCAGATGATT TTCAGGACTA TGACACTAGC
4081 ATATATGAAT AGGTAGATGT TTTTATTTTG TCACACAAAA AAGAGGCTCG CACCTCTTTT
4141 TCTTATTTCT TTTTATGATT TAATA

FIG.52C pDONR205(tetR)

pDONR205 4939 bp

GGCATCAGCACCTTGTCGCCTTGCGTATAATATTTGCCCATGGTGAAAACGGGGGCGAAG
AAGTTGTCCATATTGGCCACGTTTAAATCAAAACTGGTGAAACTCACCCAGGGATTGGCT
GAGACGAAAAACATATTCTCAATAAACCCTTTAGGGAAATAGGCCAGGTTTTCACCGTAA
CACGCCACATCTTGCGAATATATGTGTAGAAACTGCCGGAAATCGTCGTGGTATTCACTC
CAGAGCGATGAAAACGTTTCAGTTTGCTCATGGAAAACGGTGTAACAAGGGTGAACACTA
TCCCATATCACCAGCTCACCGTCTTTCATTGCCATACGGAATTCCGGATGAGCATTCATC
AGGCGGGCAAGAATGTGAATAAAGGCCGGATAAAACTTGTGCTTATTTTTCTTTACGGTC
TTTAAAAAGGCCGTAATATCCAGCTGAACGGTCTGGTTATAGGTACATTGAGCAACTGAC
TGAAATGCCTCAAAATGTTCTTTACGATGCCATTGGGATATATCAACGGTGGTATATCCA
GTGATTTTTTTCTCCATTTTAGCTTCCTTAGCTCCTGAAAATCTCGATAACTCAAAAAAT
ACGCCCGGTAGTGATCTTATTTCATTATGGTGAAAGTTGGAACCTCTTACGTGCCGATCA
ACGTCTCATTTTCGCCAAAAGTTGGCCCAGGGCTTCCCGGTATCAACAGGGACACCAGGA
TTTATTTATTCTGCGAAGTGATCTTCCGTCACAGGTATTTATTCGGCGCAAAGTGCGTCG
GGTGATGCTGCCAACTTAGTCGACTACAGGTCACTAATACCATCTAAGTAGTTGATTCAT
AGTGACTGGATATGTTGTGTTTTACAGTATTATGTAGTCTGTTTTTTATGCAAAATCTAA
TTTAATATATTGATATTTATATCATTTTACGTTTCTCGTTCAGCTTTCTTGTACAAAGTT
GGCATTATAAGAAAGCATTGCTTATCAATTTGTTGCAACGAACAGGTCACTATCAGTCAA
AATAAAATCATTATTTGCCATCCAGCTGCAGCTCTGGCCCGTGTCTCAAAATCTCTGATG
TTACATTGCACAAGATAAAAATATATCATCATGAATTCTCATGTTTGACAGCTTATCATC
GATAAGCTTTAATGCGGTAGTTTATCACAGTTAAATTGCTAACGCAGTCAGGCACCGTGT
ATGAAATCTAACAATGCGCTCATCGTCATCCTCGGCACCGTCACCCTGGATGCTGTAGGC
ATAGGCTTGGTTATGCCGGTACTGCCGGGCCTCTTGCGGGATATCGTCCATTCCGACAGC
ATCGCCAGTCACTATGGCGTGCTGCTAGCGCTATATGCGTTGATGCAATTTCTATGCGCA
CCCGTTCTCGGAGCACTGTCCGACCGCTTTGGCCGCCGCCCAGTCCTGCTCGCTTCGCTA
CTTGGAGCCACTATCGACTACGCGATCATGGCGACCACACCCGTCCTGTGGATCCTCTAC
GCCGGACGCATCGTGGCCGGCATCACCGGCGCCACAGGTGCGGTTGCTGGCGCCTATATC
GCCGACATCACCGATGGGGAAGATCGGGCTCGCCACTTCGGGCTCATGAGCGCTTGTTTC
GGCGTGGGTATGGTGGCAGGCCCCGTGGCCGGGGGACTGTTGGGCGCCATCTCCTTGCAT
GCACCATTCCTTGCGGCGGCGGTGCTCAACGGCCTCAACCTACTACTGGGCTGCTTCCTA
ATGCAGGAGTCGCATAAGGGAGAGCGTCGACCGATGCCCTTGAGAGCCTTCAACCCAGTC
AGCTCCTTCCGGTGGGCGCGGGGCATGACTATCGTCGCCGCACTTATGACTGTCTTCTTT
ATCATGCAACTCGTAGGACAGGTGCCGGCAGCGCTCTGGGTCATTTTCGGCGAGGACCGC
TTTCGCTGGAGCGCGACGATGATCGGCCTGTCGCTTGCGGTATTCGGAATCTTGCACGCC
CTCGCTCAAGCCTTCGTCACTGGTCCCGCCACCAAACGTTTCGGCGAGAAGCAGGCCATT
ATCGCCGGCATGGCGGCCGACGCGCTGGGCTACGTCTTGCTGGCGTTCGCGACGCGAGGC
TGGATGGCCTTCCCCATTATGATTCTTCTCGCTTCCGGCGGCATCGGGATGCCCGCGTTG
CAGGCCATGCTGTCCAGGCAGGTAGATGACGACCATCAGGGACAGCTTCAAGGATCGCTC
GCGGCTCTTACCAGCCTAACTTCGATCATTGGACCGCTGATCGTCACGGCGATTTATGCC
GCCTCGGCGAGCACATGGAACGGGTTGGCATGGATTGTAGGCGCCGCCCTATACCTTGTC
TGCCTCCCCGCGTTGCGTCGCGGTGCATGGAGCCGGGCCACCTCGACCTGAATGGAAGCC
GGCGGCACCTCGCTAACGGATTCACCACTCCAAGAATTGGAGCCAATCAATTCTTGCGGA
GAACTGTGAATGCGCAAACCAACCCTTGGCAGAACATATCCATCGCATGACCAAAATCCC

FIG.53B

TTAACGTGAGTTTTCGTTCCACTGAGCGTCAGACCCCGTAGAAAAGATCAAAGGATCTTC
TTGAGATCCTTTTTTTCTGCGCGTAATCTGCTGCTTGCAAACAAAAAAACCACCGCTACC
AGCGGTGGTTTGTTTGCCGGATCAAGAGCTACCAACTCTTTTTCCGAAGGTAACTGGCTT
CAGCAGAGCGCAGATACCAAATACTGTCCTTCTAGTGTAGCCGTAGTTAGGCCACCACTT
CAAGAACTCTGTAGCACCGCCTACATACCTCGCTCTGCTAATCCTGTTACCAGTGGCTGC
TGCCAGTGGCGATAAGTCGTGTCTTACCGGGTTGGACTCAAGACGATAGTTACCGGATAA
GGCGCAGCGGTCGGGCTGAACGGGGGGTTCGTGCACACAGCCCAGCTTGGAGCGAACGAC
CTACACCGAACTGAGATACCTACAGCGTGAGCTATGAGAAAGCGCCACGCTTCCCGAAGG
GAGAAAGGCGGACAGGTATCCGGTAAGCGGCAGGGTCGGAACAGGAGAGCGCACGAGGGA
GCTTCCAGGGGGAAACGCCTGGTATCTTTATAGTCCTGTCGGGTTTCGCCACCTCTGACT
TGAGCGTCGATTTTTGTGATGCTCGTCAGGGGGGCGGAGCCTATGGAAAAACGCCAGCAA
CGCGGCCTTTTTACGGTTCCTGGCCTTTTGCTGGCCTTTTGCTCACATGTTCTTTCCTGC
GTTATCCCCTGATTCTGTGGATAACCGTATTACCGCTAGCCAGGAAGAGTTTGTAGAAAC
GCAAAAAGGCCATCCGTCAGGATGGCCTTCTGCTTAGTTTGATGCCTGGCAGTTTATGGC
GGGCGTCCTGCCCGCCACCCTCCGGGCCGTTGCTTCACAACGTTCAAATCCGCTCCCGGC
GGATTTGTCCTACTCAGGAGAGCGTTCACCGACAAACAACAGATAAAACGAAAGGCCCAG
TCTTCCGACTGAGCCTTTCGTTTTATTTGATGCCTGGCAGTTCCCTACTCTCGCGTTAAC
GCTAGCATGGATCTCGGGCCCCAAATAATGATTTTATTTTGACTGATAGTGACCTGTTCG
TTGCAACAAATTGATGAGCAATGCTTTTTTATAATGCCAACTTTGTACAAAAAAGCTGAA
CGAGAAACGTAAAATGATATAAATATCAATATATTAAATTAGATTTTGCATAAAAAACAG
ACTACATAATACTGTAAAACACAACATATCCAGTCACTATGAATCAACTACTTAGATGGT
ATTAGTGACCTGTAGTCGACCGACAGCCTTCCAAATGTTCTTCGGGTGATGCTGCCAACT
TAGTCGACCGACAGCCTTCCAAATGTTCTTCTCAAACGGAATCGTCGTATCCAGCCTACT
CGCTATTGTCCTCAATGCCGTATTAAATCATAAAAAGAAATAAGAAAAAGAGGTGCGAGC
CTCTTTTTTGTGTGACAAAATAAAAACATCTACCTATTCATATACGCTAGTGTCATAGTC
CTGAAAATCATCTGCATCAAGAACAATTTCACAACTCTTATACTTTTCTCTTACAAGTCG
TTCGGCTTCATCTGGATTTTCAGCCTCTATACTTACTAAACGTGATAAAGTTTCTGTAAT
TTCTACTGTATCGACCTGCAGACTGGCTGTGTATAAGGGAGCCTGACATTTATATTCCCC
AGAACATCAGGTTAATGGCGTTTTTGATGTCATTTTCGCGGTGGCTGAGATCAGCCACTT
CTTCCCCGATAACGGAGACCGGCACACTGGCCATATCGGTGGTCATCATGCGCCAGCTTT
CATCCCCGATATGCACCACCGGGTAAAGTTCACGGGAGACTTTATCTGACAGCAGACGTG
CACTGGCCAGGGGGATCACCATCCGTCGCCCGGGCGTGTCAATAATATCACTCTGTACAT
CCACAAACAGACGATAACGGCTCTCTCTTTTATAGGTGTAAACCTTAAACTGCATTTCAC
CAGTCCCTGTTCTCGTCAGCAAAAGAGCCGTTCATTTCAATAAACCGGGCGACCTCAGCC
ATCCCTTCCTGATTTTCCGCTTTCCAGCGTTCGGCACGCAGACGACGGGCTTCATTCTGC
ATGGTTGTGCTTACCAGACCGGAGATATTGACATCATATATGCCTTGAGCAACTGATAGC
TGTCGCTGTCAACTGTCACTGTAATACGCTGCTTCATAGCACACCTCTTTTTGACATACT
TCGGGTATACATATCAGTATATATTCTTATACCGCAAAAATCAGCGCGCAAATACGCATA
CTGTTATCTGGCTTTTAGTAAGCCGGATCCACGCGATTACGCCCCGCCCTGCCACTCATC
GCAGTACTGTTGTAATTCATTAAGCATTCTGCCGACATGGAAGCCATCACAGACGGCATG
ATGAACCTGAATCGCCAGC

FIG.53C pDONR206 (genR)

pDONR206 4415 bp

CGGCATTGAGGACAATAGCGAGTAGGCTGGATACGACGATTCCGTTTGAGAAGAACATTT
GGAAGGCTGTCGGTCGACTACAGGTCACTAATACCATCTAAGTAGTTGAATCATAGTGAC
TGGATATGTTGTGTTTTACAGTATTATGTAGTCTGTTTTTTATGCAAAATCTAATTTAAT
ATATTGATATTTATATCATTTTACGTTTCTCGTTCAGCTTTTTTGTACAAAGTTGGCATT
ATAAAAAAGCATTGCTTATCAATTTGTTGCAACGAACAGGTCACTATCAGTCAAAATAAA
ATCATTATTTGGGGCCCGAGATCCATGCTAGCGGTAATACGGTTATCCACAGAATCAGGG
GATAACGCAGGAAAGAACATGTGAGCAAAAGGCCAGCAAAAGGCCAGGAACCGTAAAAAG
GCCGCGTTGCTGGCGTTTTTCCATAGGCTCCGCCCCCCTGACGAGCATCACAAAAATCGA
CGCTCAAGTCAGAGGTGGCGAAACCCGACAGGACTATAAAGATACCAGGCGTTTCCCCCT
GGAAGCTCCCTCGTGCGCTCTCCTGTTCCGACCCTGCCGCTTACCGGATACCTGTCCGCC
TTTCTCCCTTCGGGAAGCGTGGCGCTTTCTCATAGCTCACGCTGTAGGTATCTCAGTTCG
GTGTAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCGCCA
CTGGCAGCAGCCACTGGTAACAGGATTAGCAGAGCGAGGTATGTAGGCGGTGCTACAGAG
TTCTTGAAGTGGTGGCCTAACTACGGCTACACTAGAAGGACAGTATTTGGTATCTGCGCT
CTGCTGAAGCCAGTTACCTTCGGAAAAAGAGTTGGTAGCTCTTGATCCGGCAAACAAACC
ACCGCTGGTAGCGGTGGTTTTTTTGTTTGCAAGCAGCAGATTACGCGCAGAAAAAAAGGA
TCTCAAGAAGATCCTTTGATCTTTTCTACGGGGTCTGACGCTCAGTGGAACGAAAACTCA
CGTTAAGGGATTTTGGTCATGNCGCCGTCCCGTCAAGTCAGCGTAATGCTCTGCCAGTGT
TACAACCAATTAACCAATTCTGATTAGAAAAACTCATCGAGCATCAAATGAAACTGCAAT
TTATTCATATCAGGATTATCAATACCATATTTTTGAAAAAGCCGTTTCTGTAATGAAGGA
GAAAACTCACCGAGGCAGTTCCATAGGATGGCAAGATCCTGGTATCGGTCTGCGATTCCG
ACTCGTCCAACATCAATACAACCTATTAGCCGAGGTCTTCCGATCTCCTGAAGCCAGGGC
AGATCCGTGCACAGCACCTTGCCGTAGAAGAACAGCAAGGCCGCCAATGCCTGACGATGC
GTGGAGACCGAAACCTTGCGCTCGTTCGCCAGCCAGGACAGAAATGCCTCGACTTCGCTG
CTGCCCAAGGTTGCCGGGTGACGCACACCGTGGAAACGGATGAAGGCACGAACCCAGTTG
ACATAAGCCTGTTCGGTTCGTAAACTGTAATGCAAGTAGCGTATGCGCTCACGCAACTGG
TCCAGAACCTTGACCGAACGCAGCGGTGGTAACGGCGCAGTGGCGGTTTTCATGGCTTGT
TATGACTGTTTTTTTGTACAGTCTATGCCTCGGGCATCCAAGCAGCAAGCGCGTTACGCC
GTGGGTCGATGTTTGATGTTATGGAGCAGCAACGATGTTACGCAGCAGCAACGATGTTAC
GCAGCAGGGCAGTCGCCCTAAAACAAAGTTAGGTGGCTCAAGTATGGGCATCATTCGCAC
ATGTAGGCTCGGCCCTGACCAAGTCAAATCCATGCGGGCTGCTCTTGATCTTTTCGGTCG
TGAGTTCGGAGACGTAGCCACCTACTCCCAACATCAGCCGGACTCCGATTACCTCGGGAA
CTTGCTCCGTAGTAAGACATTCATCGCGCTTGCTGCCTTCGACCAAGAAGCGGTTGTTGG
CGCTCTCGCGGCTTACGTTCTGCCCAGGTTTGAGCAGCCGCGTAGTGAGATCTATATCTA
TGATCTCGCAGTCTCCGGCGAGCACCGGAGGCAGGGCATTGCCACCGCGCTCATCAATCT
CCTCAAGCATGAGGCCAACGCGCTTGGTGCTTATGTGATCTACGTGCAAGCAGATTACGG
TGACGATCCCGCAGTGGCTCTCTATACAAAGTTGGGCATACGGGAAGAAGTGATGCACTT
TGATATCGACCCAAGTACCGCCACCTAACAATTCGTTCAAGCCGAGATCGGCTTCCCGGC
CTAATTTCCCCTCGTCAAAAATAAGGTTATCAAGTGAGAAATCACCATGAGTGACGACTG
AATCCGGTGAGAATGGCAAAAGCGTATGCATTTCTTTCCAGACTTGTTCAACAGGCCAGC
CATTACGCTCGTCATCAAAATCACTCGCATCAACCAAACCGTTATTCATTCGTGATTGCG

FIG.54B

CCTGAGCGAGACGAAATACGCGATCGCTGTTAAAAGGACAATTACAAACAGGAATCGAAT
GCAACCGGCGCAGGAACACTGCCAGCGCATCAACAATATTTTCACCTGAATCAGGATATT
CTTCTAATACCTGGAATGCTGTTTTCCCGCGGATCGCAGTGGTGAGTAACCATGCATCAT
CAGGAGTACGGATAAAATGCTTGATGGTCGGAAGAGGCATAAATTCCGTCAGCCAGTTTA
GTCTGACCATCTCATCTGTAACATCATTGGCAACGCTACCTTTGCCATGTTTCAGAAACA
ACTCTGGCGCATCGGGCTTCCCATACAATCGAAAGATTGTCGCACCTGATTGCCCGACAT
TATCGCGAGCCCATTTATACCCATATAAATCAGCATCCATGTTGGAATTTAATCGCGGCC
TCCAGCAAGACGTTTCCCGTTGAATATGGCTCATAACACCCCTTGTATTACTGTTTATGT
AAGCAGACAGTTTTATTGTTCATGATGATATATTTTTATCTTGTGCAATGTAACATCAGA
GATTTTGAGACACGGGCCCNGCGCACTGCAGCTGGATCGGCAAATAATGATTTTATTTTG
ACTGATAGTGACCTGTTCGTTGCAACAAATTGATAAGCAATGCTTTTTTATAATGCCAAC
TTTGTACAAGAAAGCTGAACGAGAAACGTAAAATGATATAAATATCAATATATTAAATTA
GATTTTGCATAAAAAACAGACTACATAATACTGTAAAACACAACATATCCAGTCACTATG
ATTCAACTACTTAGATGGTATTAGTGACCTGTAGTCGACTAAGTTGGCAGCATCACCCGA
CGCACTTTGCGCCGAATAAATACCTGTGACGGAAGATCACTTCGCAGAATAAATAAATCC
TGGTGTCCCTGTTGATACCGGGAAGCCCTGGGCCAACTTTTGGCGAAAATGAGACGTTGA
TCGGCACGTAAGAGGTTCCAACTTTCACCATAATGAAATAAGATCACTACCGGGCGTATT
TTTTGAGTTATCGAGATTTTCAGGAGCTAAGGAAGCTAAAATGGAGAAAAAAATCACTGG
ATATACCACCGTTGATATATCCCAATGGCATCGTAAAGAACATTTTGAGGCATTTCAGTC
AGTTGCTCAATGTACCTATAACCAGACCGTTCAGCTGGATATTACGGCCTTTTTAAAGAC
CGTAAAGAAAAATAAGCACAAGTTTTATCCGGCCTTTATTCACATTCTTGCCCGCCTGAT
GAATGCTCATCCGGAATTCCGTATGGCAATGAAAGACGGTGAGCTGGTGATATGGGATAG
TGTTCACCCTTGTTACACCGTTTTCCATGAGCAAACTGAAACGTTTTCATCGCTCTGGAG
TGAATACCACGACGATTTCCGGCAGTTTCTACACATATATTCGCAAGATGTGGCGTGTTA
CGGTGAAAACCTGGCCTATTTCCCTAAAGGGTTTATTGAGAATATGTTTTTCGTCTCAGC
CAATCCCTGGGTGAGTTTCACCAGTTTTGATTTAAACGTGGCCAATATGGACAACTTCTT
CGCCCCCGTTTTCACCATGGGCAAATATTATACGCAAGGCGACAAGGTGCTGATGCCGCT
GGCGATTCAGGTTCATCATGCCGTCTGTGATGGCTTCCATGTCGGCAGAATGCTTAATGA
ATTACAACAGTACTGCGATGAGTGGCAGGGCGGGGCGTAAACGCGTGGATCCGGCTTACT
AAAAGCCAGATAACAGTATGCGTATTTGCGCGCTGATTTTTGCGGTATAAGAATATATAC
TGATATGTATACCCGAAGTATGTCAAAAAGAGGTGTGCTATGAAGCAGCGTATTACAGTG
ACAGTTGACAGCGACAGCTATCAGTTGCTCAAGGCATATATGATGTCAATATCTCCGGTC
TGGTAAGCACAACCATGCAGAATGAAGCCCGTCGTCTGCGTGCCGAACGCTGGAAAGCGG
AAAATCAGGAAGGGATGGCTGAGGTCGCCCGGTTTATTGAAATGAACGGCTCTTTTGCTG
ACGAGAACAGGGACTGGTGAAATGCAGTTTAAGGTTTACACCTATAAAAGAGAGAGCCGT
TATCGTCTGTTTGTGGATGTACAGAGTGATATTATTGACACGCCCGGGCGACGGATGGTG
ATCCCCCTGGCCAGTGCACGTCTGCTGTCAGATAAAGTCTCCCGTGAACTTTACCCGGTG
GTGCATATCGGGGATGAAAGCTGGCGCATGATGACCACCGATATGGCCAGTGTGCCGGTC
TCCGTTATCGGGGAAGAAGTGGCTGATCTCAGCCACCGCGAAAATGACATCAAAAACGCC
ATTAACCTGATGTTCTGGGGAATATAAATGTCAGGCTCCGTTATACACAGCCAGTCTGCA
GGTCGATACAGTAGAAATTACAGAAACTTTATCACGTTTAGTAAGTATAGAGGCTGAAAA
TCCAGATGAAGCCGAACGACTTGTAAGAGAAAAGTATAAGAGTTGTGAAATTGTTCTTGA
TGCAGATGATTTTCAGGACTATGACACTAGCATATATGAATAGGTAGATGTTTTTATTTT
GTCACACAAAAAAGAGGCTCGCACCTCTTTTTCTTATTTCTTTTTATGATTTAATA

FIG.54C

An Entry (pENTR7) Clone of CAT Subcloned into pDEST2

Start translation

```
                                                 Met Ser Tyr Tyr His His His
1021 cgg ata aca att tca cac agg aaa cag acc atg tcg tac tac cat cac cat
     gcc tat tgt taa agt gtg tcc ttt gtc tgg tac agc atg atg gta gtg gta
```

His 6 attB1

```
     His His His Gly Ile Thr Ser Leu Tyr Lys Lys Ala Gly Phe Glu Asn Leu
1072 cac cat cac ggc atc aca agt ttg tac aaa aaa gca ggc ttt gaa aac ctg
     gtg gta gtg ccg tag tgt tca aac atg ttt ttt cgt ccg aaa ctt ttg gac
```

From pDEST2 → ← From PENTR7

TEV protease Start CAT

```
     Tyr Phe Gln Gly Thr Met Gly Lys Lys Ile Thr Gly Tyr Thr Thr Val Asp
1123 tat ttt caa gga acc atg gag aaa aaa atc act gga tat acc acc gtt gat
     ata aaa gtt cct tgg tac ctc ttt ttt tag tga cct ata tgg tgg caa cta
```

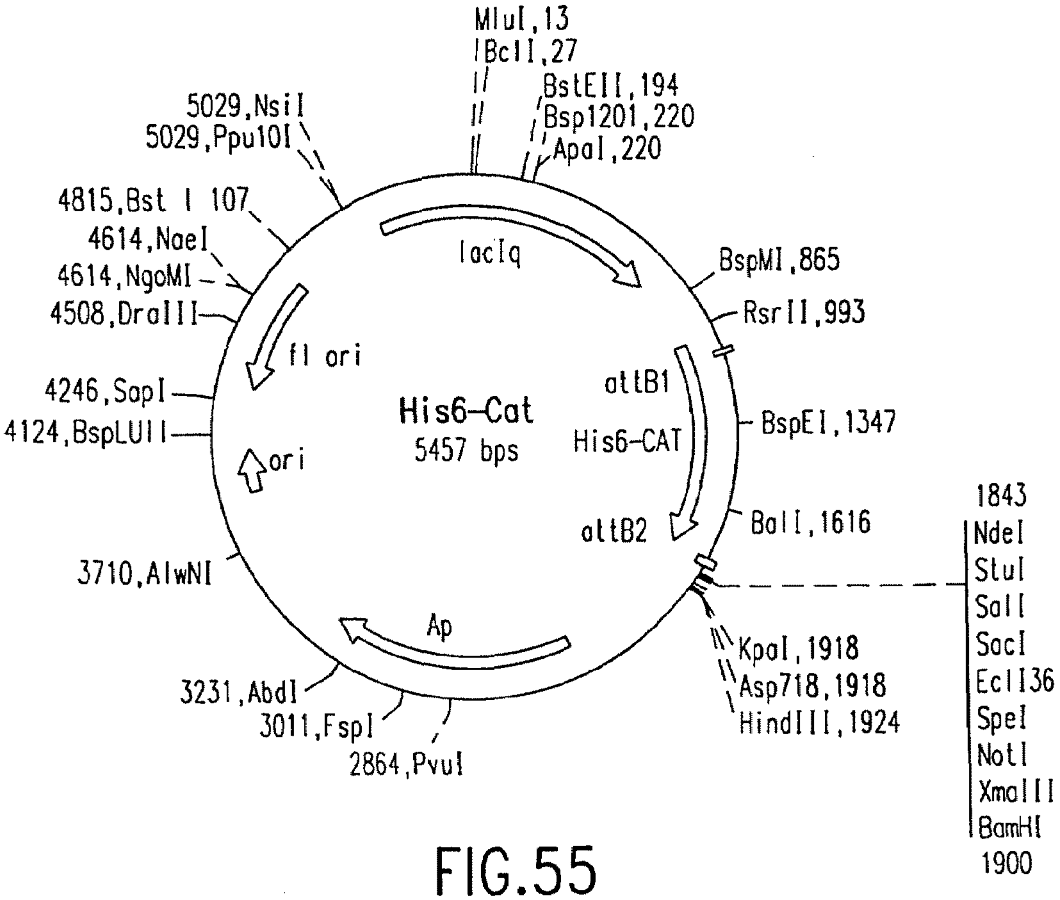

FIG.55

PRIMERS FOR AMPLIFYING $Tet^R$ AND $Amp^R$ FOR CLONING BY RECOMBINATION
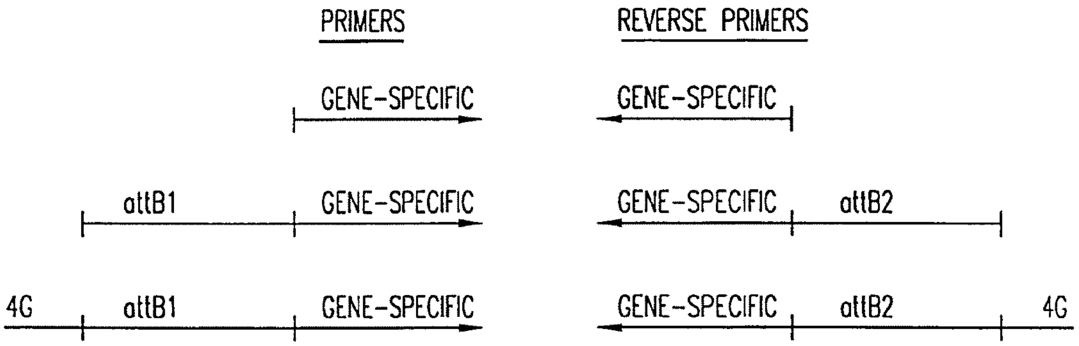
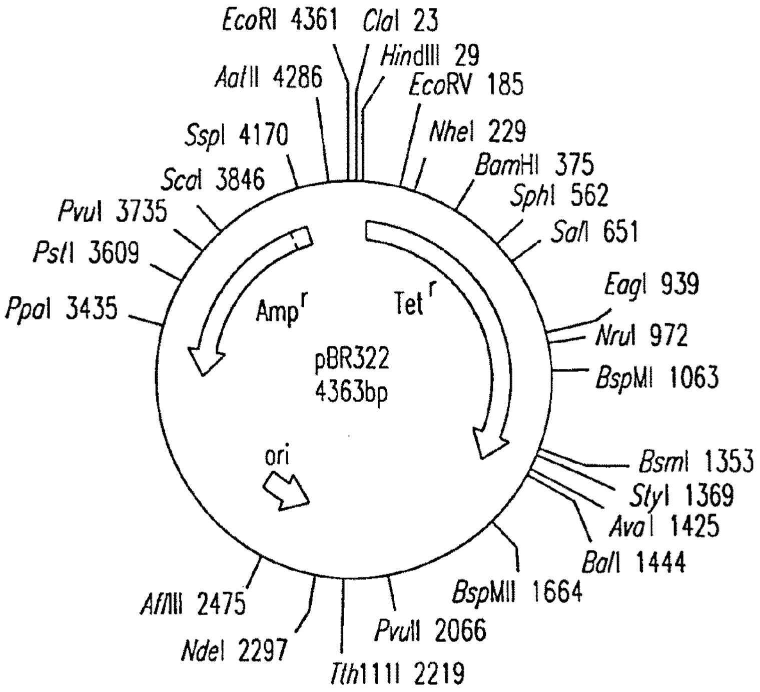
FIG. 65

RESULTS OF CLONING
tet AND amp PCR PRODUCTS
BY RECOMBINATION

| PCR PRODUCT USED IN GCS REACTIONS | NO. COLONIES OBTAINED (100 ul PLATED) | FORM OF DNA ANALYZED | COLONIES OBTAINED OF PREDICTED SIZE |
|---|---|---|---|
| tet | 6, 10 | SC | 0 OF 8 |
| attB-tet | 9, 6 | SC | 1 OF 8 |
| attB+4G-tet | 824, 1064 | SC<br>AvaI+Bam | 7 OF 7<br>7 OF 7 |
| amp | 7, 13 | SC | 0 OF 8 |
| attB-amp | 18, 22 | SC | 3 OF 8 |
| attB+4G-amp | 3020, 3540 | SC<br>PstI | 8 OF 8<br>8 OF 8 |
| attB Plasmid (Pos. Control) | 320, 394 | | |

FIG. 66

6.9 kb PCR DNA Titration in a BxP Reaction 10.1 kb PCR DNA Titration in a BXP Reaction

| CLONING OF PCR PRODUCTS OF DIFFERENT SIZES WITH THE GATEWAY™ PCR CLONING SYSTEM | | | | |
|---|---|---|---|---|
| SIZE | fmols PCR DNA | ng PCR DNA | Cols/ml TRANSFORMATION ($pUC=10^8$ CFU/ml) | CORRECT CLONES/TOTAL EXAMINED ** |
| 0.26 kb* | 15<br>37.5 | 3<br>7.5 | 1223<br>2815 | 10/10 (a) |
| 1.0 kb | 15<br>37.5 | 10<br>25 | 507<br>1447 | 49/50 (b) |
| 1.4 kb | 15<br>37.5 | 14<br>35 | 271<br>683 | 48/50 (c) |
| 3.4 kb | 15<br>37.5 | 34<br>85 | 478<br>976 | 9/10 (a) |
| 4.6 kb | 15<br>37.5 | 46<br>115 | 190<br>195 | 10/10 (a) |
| 6.9 kb | 15<br>37.5 | 69<br>173 | 30 (235)**<br>54 (463)** | 47/50 (b) |

* THE 0.26 kb PCR PRODUCT WAS USED UNPURIFIED; ALL THE OTHERS WERE PURIFIED BY PRECIPITATION WITH PEG/$MgCl_2$ AS DESCRIBED IN THE TEXT OF EXAMPLE 9, TO REMOVE PRIMER DIMERS POTENTIALLY PRESENT. STANDARD INCUBATIONS WERE FOR 60 MIN.

** OVERNIGHT INCUBATION (a) DNA MINIPREPS
(b) ampR/kanR
(c) tetR/kanR

FIG.77

Reading frame A:

EcoRV
1/2 site  attR1
ATC ACA AGT TTG TAC AAA AAA
TAG TGT TCA AAC ATG TTT TTT  —[Cm^r]— attR2
T TTC TTG TAC AAA GTG GTG AT
A AAG AAC ATG TTT CAC CAC TA

EcoRV
1/2 site

Reading frame B:

attR1
A TCA ACA AGT TTG TAC AAA AAA
T AGT TGT TCA AAC ATG TTT TTT  —[Cm^r]— attR2
T TTC TTG TAC AAA GTG GTT GAT
A AAG AAC ATG TTT CAC CAA CTA

Reading frame C: (Alternative A)

attR1
AT CAA ACA AGT TTG TAC AAA AAA
TA GTT TGT TCA AAC ATG TTT TTT  —[Cm^r]— attR2
T TTC TTG TAC AAA GTG GTT CGA T
A AAG AAC ATG TTT CAC CAA GCT A

Reading frame C: (Alternative B)

attR1
AT CAA ACA AGT TTG TAC AAA AAA
TA GTT TGT TCA AAC ATG TTT TTT  —[CmR−ccdB]— attR2
T TTC TTG TAC AAA GTG GTT TGA T
A AAG AAC ATG TTT CAC CAA ACT A

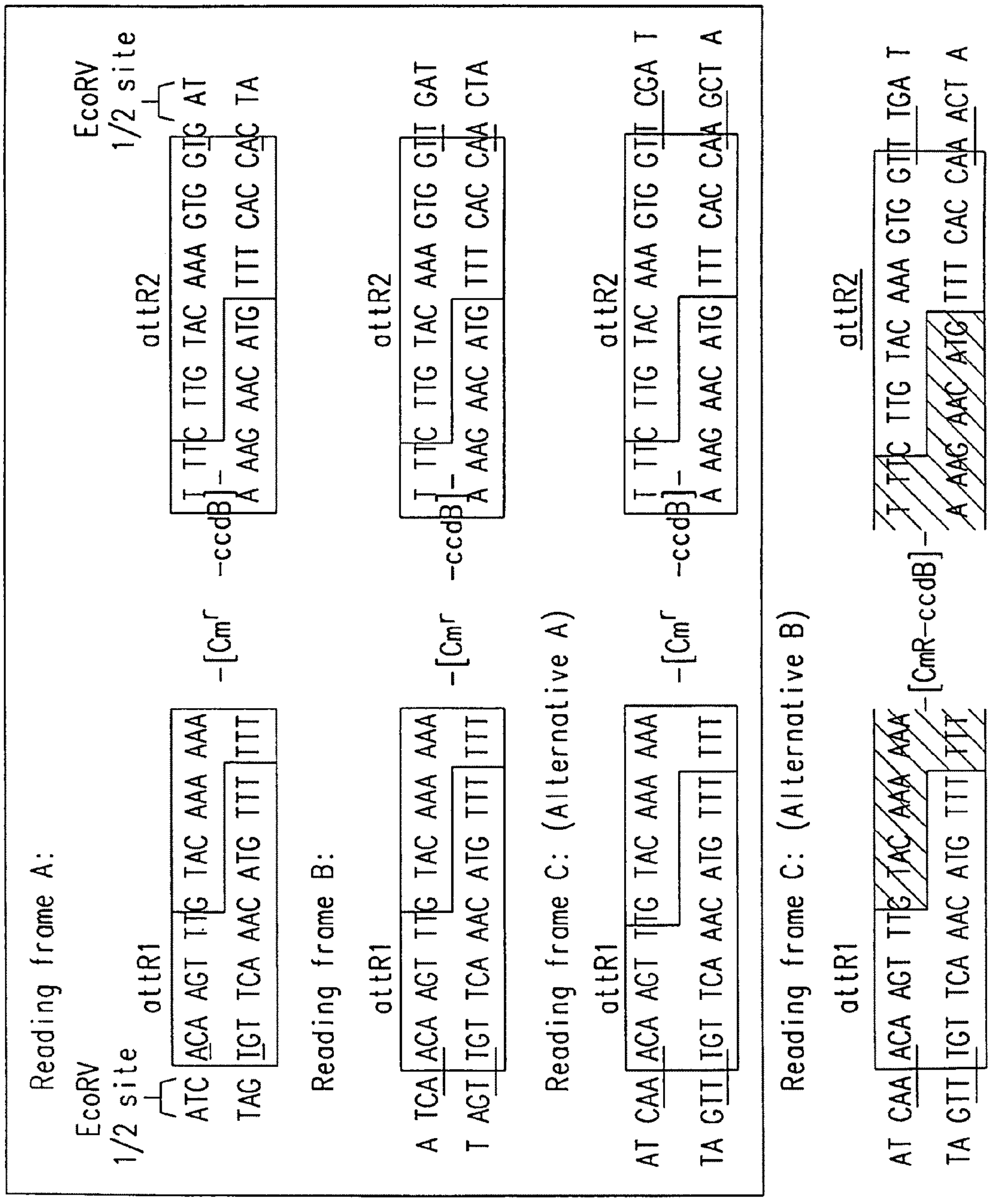

FIG.78

Fusion protein codon    Reading frame A cassette

---nnn nnn atc aca agt ttg tac aaa aaa gct---

---nnn nnn tag tgt tca aac atg ttt ttt cga--- attR1

\* Reading frame B cassette

---nnn nnn nna tca aca agt ttg tac aaa aaa gct---

---nnn nnn nnt agt tgt tca aac atg ttt ttt cga---

*cannot be TG or TA

Reading frame C cassette

---nnn nnn nat caa aca agt ttg tac aaa aaa gct---

---nnn nnn nta gtt tgt tca aac atg ttt ttt cga--- rfA CASSETTE (1711 bps)

rfB CASSETTE (1713 bps)

prfC Parent III 4554 bp

| Location (Base Nos.) | Gene Encoded |
|---|---|
| 410..286 | attR1 |
| 660..1319 | CmR |
| 1439..1523 | inactivated ccdA |
| 1661..1966 | ccdB |
| 2007..2131 | attR2 |
| 2753..3613 | amp |

```
   1 GCGCCCAATA CGCAAACCGC CTCTCCCCGC GCGTTGGCCG ATTCATTAAT GCAGCTGGCA
  61 CGACAGGTTT CCCGACTGGA AAGCGGGCAG TGAGCGCAAC GCAATTAATG TGAGTTAGCT
 121 CACTCATTAG GCACCCCAGG CTTTACACTT TATGCTTCCG GCTCGTATGT TGTGTGGAAT
 181 TGTGAGCGGA TAACAATTTC ACACAGGAAA CAGCTATGAC CATGATTACG CCAAGCTTGC
 241 ATGCCTGCAG GTCGACTCTA GAGGATCCCC GGGTACCGAT ATCAAACAAG TTTGTACAAA
 301 AAAGCTGAAC GAGAAACGTA AAATGATATA AATATCAATA TATTAAATTA GATTTTGCAT
 361 AAAAAACAGA CTACATAATA CTGTAAAACA CAACATATCC AGTCACTATG GCGGCCGCTA
 421 AGTTGGCAGC ATCACCCGAC GCACTTTGCG CCGAATAAAT ACCTGTGACG GAAGATCACT
 481 TCGCAGAATA AATAAATCCT GGTGTCCCTG TTGATACCGG GAAGCCCTGG GCCAACTTTT
 541 GGCGAAAATG AGACGTTGAT CGGCACGTAA GAGGTTCCAA CTTTCACCAT AATGAAATAA
 601 GATCACTACC GGGCGTATTT TTTGAGTTAT CGAGATTTTC AGGAGCTAAG GAAGCTAAAA
 661 TGGAGAAAAA AATCACTGGA TATACCACCG TTGATATATC CCAATGGCAT CGTAAAGAAC
 721 ATTTTGAGGC ATTTCAGTCA GTTGCTCAAT GTACCTATAA CCAGACCGTT CAGCTGGATA
 781 TTACGGCCTT TTTAAAGACC GTAAAGAAAA ATAAGCACAA GTTTTATCCG GCCTTTATTC
 841 ACATTCTTGC CCGCCTGATG AATGCTCATC CGGAATTCCG TATGGCAATG AAAGACGGTG
 901 AGCTGGTGAT ATGGGATAGT GTTCACCCTT GTTACACCGT TTTCCATGAG CAAACTGAAA
 961 CGTTTTCATC GCTCTGGAGT GAATACCACG ACGATTTCCG GCAGTTTCTA CACATATATT
1021 CGCAAGATGT GGCGTGTTAC GGTGAAAACC TGGCCTATTT CCCTAAAGGG TTTATTGAGA
1081 ATATGTTTTT CGTCTCAGCC AATCCCTGGG TGAGTTTCAC CAGTTTTGAT TTAAACGTGG
1141 CCAATATGGA CAACTTCTTC GCCCCCGTTT TCACCATGGG CAAATATTAT ACGCAAGGCG
1201 ACAAGGTGCT GATGCCGCTG GCGATTCAGG TTCATCATGC CGTCTGTGAT GGCTTCCATG
1261 TCGGCAGAAT GCTTAATGAA TTACAACAGT ACTGCGATGA GTGGCAGGGC GGGGCGTAAT
1321 CTAGAGGATC CGGCTTACTA AAAGCCAGAT AACAGTATGC GTATTTGCGC GCTGATTTTT
1381 GCGGTATAAG AATATATACT GATATGTATA CCCGAAGTAT GTCAAAAAGA GGTGTGCTAT
1441 GAAGCAGCGT ATTACAGTGA CAGTTGACAG CGACAGCTAT CAGTTGCTCA AGGCATATAT
1501 GATGTCAATA TCTCCGGTCT GGTAAGCACA ACCATGCAGA ATGAAGCCCG TCGTCTGCGT
1561 GCCGAACGCT GGAAAGCGGA AAATCAGGAA GGGATGGCTG AGGTCGCCCG GTTTATTGAA
1621 ATGAACGGCT CTTTTGCTGA CGAGAACAGG GACTGGTGAA ATGCAGTTTA AGGTTTACAC
1681 CTATAAAAGA GAGAGCCGTT ATCGTCTGTT TGTGGATGTA CAGAGTGATA TTATTGACAC
1741 GCCCGGGCGA CGGATGGTGA TCCCCCTGGC CAGTGCACGT CTGCTGTCAG ATAAAGTCTC
1801 CCGTGAACTT TACCCGGTGG TGCATATCGG GGATGAAAGC TGGCGCATGA TGACCACCGA
1861 TATGGCCAGT GTGCCGGTCT CCGTTATCGG GGAAGAAGTG GCTGATCTCA GCCACCGCGA
1921 AAATGACATC AAAAACGCCA TTAACCTGAT GTTCTGGGGA ATATAAATGT CAGGCTCCGT
1981 TATACACAGC CAGTCTGCAG GTCGACCATA GTGACTGGAT ATGTTGTGTT TTACAGTATT
2041 ATGTAGTCTG TTTTTTATGC AAAATCTAAT TTAATATATT GATATTTATA TCATTTTACG
```

FIG.83B

2101 TTTCTCGTTC AGCTTTCTTG TACAAAGTGG TTCGATATCG GTACCGAGCT CGAATTCACT
2161 GGCCGTCGTT TTACAACGTC GTGACTGGGA AAACCCTGGC GTTACCCAAC TTAATCGCCT
2221 TGCAGCACAT CCCCCTTTCG CCAGCTGGCG TAATAGCGAA GAGGCCCGCA CCGATCGCCC
2281 TTCCCAACAG TTGCGCAGCC TGAATGGCGA ATGGCGCCTG ATGCGGTATT TTCTCCTTAC
2341 GCATCTGTGC GGTATTTCAC ACCGCATATG GTGCACTCTC AGTACAATCT GCTCTGATGC
2401 CGCATAGTTA AGCCAGCCCC GACACCCGCC AACACCCGCT GACGCGCCCT GACGGGCTTG
2461 TCTGCTCCCG GCATCCGCTT ACAGACAAGC TGTGACCGTC TCCGGGAGCT GCATGTGTCA
2521 GAGGTTTTCA CCGTCATCAC CGAAACGCGC GAGACGAAAG GGCCTCGTGA TACGCCTATT
2581 TTTATAGGTT AATGTCATGA TAATAATGGT TTCTTAGACG TCAGGTGGCA CTTTTCGGGG
2641 AAATGTGCGC GGAACCCCTA TTTGTTTATT TTTCTAAATA CATTCAAATA TGTATCCGCT
2701 CATGAGACAA TAACCCTGAT AAATGCTTCA ATAATATTGA AAAAGGAAGA GTATGAGTAT
2761 TCAACATTTC CGTGTCGCCC TTATTCCCTT TTTTGCGGCA TTTTGCCTTC CTGTTTTTGC
2821 TCACCCAGAA ACGCTGGTGA AAGTAAAAGA TGCTGAAGAT CAGTTGGGTG CACGAGTGGG
2881 TTACATCGAA CTGGATCTCA ACAGCGGTAA GATCCTTGAG AGTTTTCGCC CCGAAGAACG
2941 TTTTCCAATG ATGAGCACTT TTAAAGTTCT GCTATGTGGC GCGGTATTAT CCCGTATTGA
3001 CGCCGGGCAA GAGCAACTCG GTCGCCGCAT ACACTATTCT CAGAATGACT TGGTTGAGTA
3061 CTCACCAGTC ACAGAAAAGC ATCTTACGGA TGGCATGACA GTAAGAGAAT TATGCAGTGC
3121 TGCCATAACC ATGAGTGATA ACACTGCGGC CAACTTACTT CTGACAACGA TCGGAGGACC
3181 GAAGGAGCTA ACCGCTTTTT TGCACAACAT GGGGGATCAT GTAACTCGCC TTGATCGTTG
3241 GGAACCGGAG CTGAATGAAG CCATACCAAA CGACGAGCGT GACACCACGA TGCCTGTAGC
3301 AATGGCAACA ACGTTGCGCA AACTATTAAC TGGCGAACTA CTTACTCTAG CTTCCCGGCA
3361 ACAATTAATA GACTGGATGG AGGCGGATAA AGTTGCAGGA CCACTTCTGC GCTCGGCCCT
3421 TCCGGCTGGC TGGTTTATTG CTGATAAATC TGGAGCCGGT GAGCGTGGGT CTCGCGGTAT
3481 CATTGCAGCA CTGGGGCCAG ATGGTAAGCC CTCCCGTATC GTAGTTATCT ACACGACGGG
3541 GAGTCAGGCA ACTATGGATG AACGAAATAG ACAGATCGCT GAGATAGGTG CCTCACTGAT
3601 TAAGCATTGG TAACTGTCAG ACCAAGTTTA CTCATATATA CTTTAGATTG ATTTAAAACT
3661 TCATTTTTAA TTTAAAAGGA TCTAGGTGAA GATCCTTTTT GATAATCTCA TGACCAAAAT
3721 CCCTTAACGT GAGTTTTCGT TCCACTGAGC GTCAGACCCC GTAGAAAAGA TCAAAGGATC
3781 TTCTTGAGAT CCTTTTTTTC TGCGCGTAAT CTGCTGCTTG CAAACAAAAA AACCACCGCT
3841 ACCAGCGGTG GTTTGTTTGC CGGATCAAGA GCTACCAACT CTTTTTCCGA AGGTAACTGG
3901 CTTCAGCAGA GCGCAGATAC CAAATACTGT CCTTCTAGTG TAGCCGTAGT TAGGCCACCA
3961 CTTCAAGAAC TCTGTAGCAC CGCCTACATA CCTCGCTCTG CTAATCCTGT TACCAGTGGC
4021 TGCTGCCAGT GGCGATAAGT CGTGTCTTAC CGGGTTGGAC TCAAGACGAT AGTTACCGGA
4081 TAAGGCGCAG CGGTCGGGCT GAACGGGGGG TTCGTGCACA CAGCCCAGCT TGGAGCGAAC
4141 GACCTACACC GAACTGAGAT ACCTACAGCG TGAGCTATGA GAAAGCGCCA CGCTTCCCGA
4201 AGGGAGAAAG GCGGACAGGT ATCCGGTAAG CGGCAGGGTC GGAACAGGAG AGCGCACGAG
4261 GGAGCTTCCA GGGGGAAACG CCTGGTATCT TTATAGTCCT GTCGGGTTTC GCCACCTCTG
4321 ACTTGAGCGT CGATTTTTGT GATGCTCGTC AGGGGGGCGG AGCCTATGGA AAAACGCCAG
4381 CAACGCGGCC TTTTTACGGT TCCTGGCCTT TTGCTGGCCT TTTGCTCACA TGTTCTTTCC
4441 TGCGTTATCC CCTGATTCTG TGGATAACCG TATTACCGCC TTTGAGTGAG CTGATACCGC
4501 TCGCCGCAGC CGAACGACCG AGCGCAGCGA GTCAGTGAGC GAGGAAGCGG AAGA

FIG.83C pDEST28 7141 bp

ATGCATGTCGTTACATAACTTACGGTAAATGGCCCGCCTGGCTGACCGCCCAACGACCCC
CGCCCATTGACGTCAATAATGACGTATGTTCCCATAGTAACGCCAATAGGGACTTTCCAT
TGACGTCAATGGGTGGAGTATTTACGGTAAACTGCCCACTTGGCAGTACATCAAGTGTAT
CATATGCCAAGTACGCCCCCTATTGACGTCAATGACGGTAAATGGCCCGCCTGGCATTAT
GCCCAGTACATGACCTTATGGGACTTTCCTACTTGGCAGTACATCTACGTATTAGTCATC
GCTATTACCATGGTGATGCGGTTTTGGCAGTACATCAATGGGCGTGGATAGCGGTTTGAC
TCACGGGGATTTCCAAGTCTCCACCCCATTGACGTCAATGGGAGTTTGTTTTGGCACCAA
AATCAACGGGACTTTCCAAAATGTCGTAACAACTCCGCCCCATTGACGCAAATGGGCGGT
AGGCGTGTACGGTGGGAGGTCTATATAAGCAGAGCTCTCCCTATCAGTGATAGAGATCTC
CCTATCAGTGATAGAGATCGTCGACGAGCTCGTTTAGTGAACCGTCAGATCGCCTGGAGA
CGCCATCCACGCTGTTTTGACCTCCATAGAAGACACCGGGACCGATCCAGCCTCCGGACT
CTAGAGGATCCCTACCGGTGATATCCTCGAGCCCATCAACAAGTTTGTACAAAAAAGCTG
AACGAGAAACGTAAAATGATATAAATATCAATATATTAAATTAGATTTTGCATAAAAAAC
AGACTACATAATACTGTAAAACACAACATATCCAGTCACTATGGCGGCCGCATTAGGCAC
CCCAGGCTTTACACTTTATGCTTCCGGCTCGTATAATGTGTGGATTTTGAGTTAGGATCC
GGCGAGATTTTCAGGAGCTAAGGAAGCTAAAATGGAGAAAAAAATCACTGGATATACCAC
CGTTGATATATCCCAATGGCATCGTAAAGAACATTTTGAGGCATTTCAGTCAGTTGCTCA
ATGTACCTATAACCAGACCGTTCAGCTGGATATTACGGCCTTTTTAAAGACCGTAAAGAA
AAATAAGCACAAGTTTTATCCGGCCTTTATTCACATTCTTGCCCGCCTGATGAATGCTCA
TCCGGAATTCCGTATGGCAATGAAAGACGGTGAGCTGGTGATATGGGATAGTGTTCACCC
TTGTTACACCGTTTTCCATGAGCAAACTGAAACGTTTTCATCGCTCTGGAGTGAATACCA
CGACGATTTCCGGCAGTTTCTACACATATATTCGCAAGATGTGGCGTGTTACGGTGAAAA
CCTGGCCTATTTCCCTAAAGGGTTTATTGAGAATATGTTTTTCGTCTCAGCCAATCCCTG
GGTGAGTTTCACCAGTTTTGATTTAAACGTGGCCAATATGGACAACTTCTTCGCCCCCGT
TTTCACCATGGGCAAATATTATACGCAAGGCGACAAGGTGCTGATGCCGCTGGCGATTCA
GGTTCATCATGCCGTCTGTGATGGCTTCCATGTCGGCAGAATGCTTAATGAATTACAACA
GTACTGCGATGAGTGGCAGGGCGGGGCGTAAAGATCTGGATCCGGCTTACTAAAAGCCAG
ATAACAGTATGCGTATTTGCGCGCTGATTTTTGCGGTATAAGAATATATACTGATATGTA
TACCCGAAGTATGTCAAAAAGAGGTGTGCTATGAAGCAGCGTATTACAGTGACAGTTGAC
AGCGACAGCTATCAGTTGCTCAAGGCATATATGATGTCAATATCTCCGGTCTGGTAAGCA
CAACCATGCAGAATGAAGCCCGTCGTCTGCGTGCCGAACGCTGGAAAGCGGAAAATCAGG
AAGGGATGGCTGAGGTCGCCCGGTTTATTGAAATGAACGGCTCTTTTGCTGACGAGAACA
GGGACTGGTGAAATGCAGTTTAAGGTTTACACCTATAAAAGAGAGAGCCGTTATCGTCTG
TTTGTGGATGTACAGAGTGATATTATTGACACGCCCGGGCGACGGATGGTGATCCCCCTG
GCCAGTGCACGTCTGCTGTCAGATAAAGTCTCCCGTGAACTTTACCCGGTGGTGCATATC
GGGGATGAAAGCTGGCGCATGATGACCACCGATATGGCCAGTGTGCCGGTCTCCGTTATC
GGGGAAGAAGTGGCTGATCTCAGCCACCGCGAAAATGACATCAAAAACGCCATTAACCTG
ATGTTCTGGGGAATATAAATGTCAGGCTCCCTTATACACAGCCAGTCTGCAGGTCGACCA

FIG.90B

TAGTGACTGGATATGTTGTGTTTTACAGTATTATGTAGTCTGTTTTTTATGCAAAATCTA
ATTTAATATATTGATATTTATATCATTTTACGTTTCTCGTTCAGCTTTCTTGTACAAAGT
GGTTGATGGGCGGCCGCTCTAGAGGGCCCAAGCTTACGCGTGCATGCGACGTCATAGCTC
TCTCCCTATAGTGAGTCGTATTATAAGCTAGGCACTGGCCGTCGTTTTACAACGTCGTGA
CTGGGAAAACTGCTAGCTTGGGATCTTTGTGAAGGAACCTTACTTCTGTGGTGTGACATA
ATTGGACAAACTACCTACAGAGATTTAAAGCTCTAAGGTAAATATAAAATTTTTAAGTGT
ATAATGTGTTAAACTAGCTGCATATGCTTGCTGCTTGAGAGTTTTGCTTACTGAGTATGA
TTTATGAAAATATTATACACAGGAGCTAGTGATTCTAATTGTTTGTGTATTTTAGATTCA
CAGTCCCAAGGCTCATTTCAGGCCCCTCAGTCCTCACAGTCTGTTCATGATCATAATCAG
CCATACCACATTTGTAGAGGTTTTACTTGCTTTAAAAAACCTCCCACACCTCCCCCTGAA
CCTGAAACATAAAATGAATGCAATTGTTGTTGTTAACTTGTTTATTGCAGCTTATAATGG
TTACAAATAAAGCAATAGCATCACAAATTTCACAAATAAAGCATTTTTTTCACTGCATTC
TAGTTGTGGTTTGTCCAAACTCATCAATGTATCTTATCATGTCTGGATCGATCCTGCATT
AATGAATCGGCCAACGCGCGGGGAGAGGCGGTTTGCGTATTGGCTGGCGTAATAGCGAAG
AGGCCCGCACCGATCGCCCTTCCCAACAGTTGCGCAGCCTGAATGGCGAATGGGACGCGC
CCTGTAGCGGCGCATTAAGCGCGGCGGGTGTGGTGGTTACGCGCAGCGTGACCGCTACAC
TTGCCAGCGCCCTAGCGCCCGCTCCTTTCGCTTTCTTCCCTTCCTTTCTCGCCACGTTCG
CCGGCTTTCCCCGTCAAGCTCTAAATCGGGGGCTCCCTTTAGGGTTCCGATTTAGTGCTT
TACGGCACCTCGACCCCAAAAAACTTGATTAGGGTGATGGTTCACGTAGTGGGCCATCGC
CCTGATAGACGGTTTTTCGCCCTTTGACGTTGGAGTCCACGTTCTTTAATAGTGGACTCT
TGTTCCAAACTGGAACAACACTCAACCCTATCTCGGTCTATTCTTTTGATTTATAAGGGA
TTTTGCCGATTTCGGCCTATTGGTTAAAAAATGAGCTGATTTAACAAATATTTAACGCGA
ATTTTAACAAAATATTAACGTTTACAATTTCGCCTGATGCGGTATTTTCTCCTTACGCAT
CTGTGCGGTATTTCACACCGCATACGCGGATCTGCGCAGCACCATGGCCTGAAATAACCT
CTGAAAGAGGAACTTGGTTAGGTACCTTCTGAGGCGGAAAGAACCAGCTGTGGAATGTGT
GTCAGTTAGGGTGTGGAAAGTCCCCAGGCTCCCCAGCAGGCAGAAGTATGCAAAGCATGC
ATCTCAATTAGTCAGCAACCAGGTGTGGAAAGTCCCCAGGCTCCCCAGCAGGCAGAAGTA
TGCAAAGCATGCATCTCAATTAGTCAGCAACCATAGTCCCGCCCCTAACTCCGCCCATCC
CGCCCCTAACTCCGCCCAGTTCCGCCCATTCTCCGCCCCATGGCTGACTAATTTTTTTTA
TTTATGCAGAGGCCGAGGCCGCCTCGGCCTCTGAGCTATTCCAGAAGTAGTGAGGAGGCT
TTTTTGGAGGCCTAGGCTTTTGCAAAAAGCTTGATTCTTCTGACACAACAGTCTCGAACT
TAAGACCATGGCCAAGCCTTTGTCTCAAGAAGAATCCACCCTCATTGAAAGAGCAACGGC
TACAATCAACAGCATCCCCATCTCTGAAGACTACAGCGTCGCCAGCGCAGCTCTCTCTAG
CGACGGCCGCATCTTCACTGGTGTCAATGTATATCATTTTACTGGGGGACCTTGTGCAGA
ACTCGTGGTGCTGGGCACTGCTGCTGCTGCGGCAGCTGGCAACCTGACTTGTATCGTCGC
GATCGGAAATGAGAACAGGGGCATCTTGAGCCCCTGCGGACGGTGCCGACAGGTGCTTCT
CGATCTGCATCCTGGGATCAAAGCCATAGTGAAGGACAGTGATGGACAGCCGACGGCAGT
TGGGATTCGTGAATTGCTGCCCTCTGGTTATGTGTGGGAGGGCTAAGCACTTCGTGGCCG
AGTTCGAAATGACCGACCAAGCGACGCCCAACCTGCCATCACGATGGCCGCAATAAAATA
TCTTTATTTTCATTACATCTGTGTGTTGGTTTTTTGTGTGAATCGATAGCGATAAGGATC
CGCGTATGGTGCACTCTCAGTACAATCTGCTCTGATGCCGCATAGTTAAGCCAGCCCCGA

FIG.90C

CACCCGCCAACACCCGCTGACGCGCCCTGACGGGCTTGTCTGCTCCCGGCATCCGCTTAC
AGACAAGCTGTGACCGTCTCCGGGAGCTGCATGTGTCAGAGGTTTTCACCGTCATCACCG
AAACGCGCGAGACGAAAGGGCCTCGTGATACGCCTATTTTTATAGGTTAATGTCATGATA
ATAATGGTTTCTTAGACGTCAGGTGGCACTTTTCGGGGAAATGTGCGCGGAACCCCTATT
TGTTTATTTTTCTAAATACATTCAAATATGTATCCGCTCATGAGACAATAACCCTGATAA
ATGCTTCAATAATATTGAAAAAGGAAGAGTATGAGTATTCAACATTTCCGTGTCGCCCTT
ATTCCCTTTTTTGCGGCATTTTGCCTTCCTGTTTTTGCTCACCCAGAAACGCTGGTGAAA
GTAAAAGATGCTGAAGATCAGTTGGGTGCACGAGTGGGTTACATCGAACTGGATCTCAAC
AGCGGTAAGATCCTTGAGAGTTTTCGCCCCGAAGAACGTTTTCCAATGATGAGCACTTTT
AAAGTTCTGCTATGTGGCGCGGTATTATCCCGTATTGACGCCGGGCAAGAGCAACTCGGT
CGCCGCATACACTATTCTCAGAATGACTTGGTTGAGTACTCACCAGTCACAGAAAAGCAT
CTTACGGATGGCATGACAGTAAGAGAATTATGCAGTGCTGCCATAACCATGAGTGATAAC
ACTGCGGCCAACTTACTTCTGACAACGATCGGAGGACCGAAGGAGCTAACCGCTTTTTTG
CACAACATGGGGGATCATGTAACTCGCCTTGATCGTTGGGAACCGGAGCTGAATGAAGCC
ATACCAAACGACGAGCGTGACACCACGATGCCTGTAGCAATGGCAACAACGTTGCGCAAA
CTATTAACTGGCGAACTACTTACTCTAGCTTCCCGGCAACAATTAATAGACTGGATGGAG
GCGGATAAAGTTGCAGGACCACTTCTGCGCTCGGCCCTTCCGGCTGGCTGGTTTATTGCT
GATAAATCTGGAGCCGGTGAGCGTGGGTCTCGCGGTATCATTGCAGCACTGGGGCCAGAT
GGTAAGCCCTCCCGTATCGTAGTTATCTACACGACGGGGAGTCAGGCAACTATGGATGAA
CGAAATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGATC
TAGGTGAAGATCCTTTTTGATAATCTCATGACCAAAATCCCTTAACGTGAGTTTTCGTTC
CACTGAGCGTCAGACCCCGTAGAAAAGATCAAAGGATCTTCTTGAGATCCTTTTTTTCTG
CGCGTAATCTGCTGCTTGCAAACAAAAAAACCACCGCTACCAGCGGTGGTTTGTTTGCCG
GATCAAGAGCTACCAACTCTTTTTCCGAAGGTAACTGGCTTCAGCAGAGCGCAGATACCA
AATACTGTCCTTCTAGTGTAGCCGTAGTTAGGCCACCACTTCAAGAACTCTGTAGCACCG
CCTACATACCTCGCTCTGCTAATCCTGTTACCAGTGGCTGCTGCCAGTGGCGATAAGTCG
TGTCTTACCGGGTTGGACTCAAGACGATAGTTACCGGATAAGGCGCAGCGGTCGGGCTGA
ACGGGGGGTTCGTGCACACAGCCCAGCTTGGAGCGAACGACCTACACCGAACTGAGATAC
CTACAGCGTGAGCATTGAGAAAGCGCCACGCTTCCCGAAGGGAGAAAGGCGGACAGGTAT
CCGGTAAGCGGCAGGGTCGGAACAGGAGAGCGCACGAGGGAGCTTCCAGGGGGAAACGCC
TGGTATCTTTATAGTCCTGTCGGGTTTCGCCACCTCTGACTTGAGCGTCGATTTTTGTGA
TGCTCGTCAGGGGGGCGGAGCCTATGGAAAAACGCCAGCAACGCGGCCTTTTTACGGTTC
CTGGCCTTTTGCTGGCCTTTTGCTCACATGTTCTTTCCTGCGTTATCCCCTGATTCTGTG
GATAACCGTATTACCGCCTTTGAGTGAGCTGATACCGCTCGCCGCAGCCGAACGACCGAG
CGCAGCGAGTCAGTGAGCGAGGAAGCGGAAGAGCGCCCAATACGCAAACCGCCTCTCCCC
GCGCGTTGGCCGATTCATTAATGCAGAGCTTGCAATTCGCGCGTTTTTCAATATTATTGA
AGCATTTATCAGGGTTATTGTCTCATGAGCGGATACATATTTGAATGTATTTAGAAAAAT
AAACAAATAGGGGTTCCGCGCACATTTCCCCGAAAAGTGCCACCTGACGTCTAAGAAACC
ATTATTATCATGACATTAACCTATAAAAATAGGCGTAGTACGAGGCCCTTTCACTCATTA
G

FIG.90D pDEST29 7156 bp

ATGCATGTCGTTACATAACTTACGGTAAATGGCCCGCCTGGCTGACCGCCCAACGACCCC
CGCCCATTGACGTCAATAATGACGTATGTTCCCATAGTAACGCCAATAGGGACTTTCCAT
TGACGTCAATGGGTGGAGTATTTACGGTAAACTGCCCACTTGGCAGTACATCAAGTGTAT
CATATGCCAAGTACGCCCCCTATTGACGTCAATGACGGTAAATGGCCCGCCTGGCATTAT
GCCCAGTACATGACCTTATGGGACTTTCCTACTTGGCAGTACATCTACGTATTAGTCATC
GCTATTACCATGGTGATGCGGTTTTGGCAGTACATCAATGGGCGTGGATAGCGGTTTGAC
TCACGGGGATTTCCAAGTCTCCACCCCATTGACGTCAATGGGAGTTTGTTTTGGCACCAA
AATCAACGGGACTTTCCAAAATGTCGTAACAACTCCGCCCCATTGACGCAAATGGGCGGT
AGGCGTGTACGGTGGGAGGTCTATATAAGCAGAGCTCTCCCTATCAGTGATAGAGATCTC
CCTATCAGTGATAGAGATCGTCGACGAGCTCGTTTAGTGAACCGTCAGATCGCCTGGAGA
CGCCATCCACGCTGTTTTGACCTCCATAGAAGACACCGGGACCGATCCAGCCTCCGGACC
ATGGCGTACTACCATCACCATCACCATCACACCGGTGATATCCTCGAGCCCATCACAAGT
TTGTACAAAAAAGCTGAACGAGAAACGTAAAATGATATAAATATCAATATATTAAATTAG
ATTTTGCATAAAAAACAGACTACATAATACTGTAAAACACAACATATCCAGTCACTATGG
CGGCCGCATTAGGCACCCCAGGCTTTACACTTTATGCTTCCGGCTCGTATAATGTGTGGA
TTTTGAGTTAGGATCCGGCGAGATTTTCAGGAGCTAAGGAAGCTAAAATGGAGAAAAAAA
TCACTGGATATACCACCGTTGATATATCCCAATGGCATCGTAAAGAACATTTTGAGGCAT
TTCAGTCAGTTGCTCAATGTACCTATAACCAGACCGTTCAGCTGGATATTACGGCCTTTT
TAAAGACCGTAAAGAAAAATAAGCACAAGTTTTATCCGGCCTTTATTCACATTCTTGCCC
GCCTGATGAATGCTCATCCGGAATTCCGTATGGCAATGAAAGACGGTGAGCTGGTGATAT
GGGATAGTGTTCACCCTTGTTACACCGTTTTCCATGAGCAAACTGAAACGTTTTCATCGC
TCTGGAGTGAATACCACGACGATTTCCGGCAGTTTCTACACATATATTCGCAAGATGTGG
CGTGTTACGGTGAAAACCTGGCCTATTTCCCTAAAGGGTTTATTGAGAATATGTTTTTCG
TCTCAGCCAATCCCTGGGTGAGTTTCACCAGTTTTGATTTAAACGTGGCCAATATGGACA
ACTTCTTCGCCCCCGTTTTCACCATGGGCAAATATTATACGCAAGGCGACAAGGTGCTGA
TGCCGCTGGCGATTCAGGTTCATCATGCCGTCTGTGATGGCTTCCATGTCGGCAGAATGC
TTAATGAATTACAACAGTACTGCGATGAGTGGCAGGGCGGGGCGTAAACGCGTGGATCCG
GCTTACTAAAAGCCAGATAACAGTATGCGTATTTGCGCGCTGATTTTTGCGGTATAAGAA
TATATACTGATATGTATACCCGAAGTATGTCAAAAAGAGGTGTGCTATGAAGCAGCGTAT
TACAGTGACAGTTGACAGCGACAGCTATCAGTTGCTCAAGGCATATATGATGTCAATATC
TCCGGTCTGGTAAGCACAACCATGCAGAATGAAGCCCGTCGTCTGCGTGCCGAACGCTGG
AAAGCGGAAAATCAGGAAGGGATGGCTGAGGTCGCCCGGTTTATTGAAATGAACGGCTCT
TTTGCTGACGAGAACAGGGACTGGTGAAATGCAGTTTAAGGTTTACACCTATAAAAGAGA
GAGCCGTTATCGTCTGTTTGTGGATGTACAGAGTGATATTATTGACACGCCCGGGCGACG
GATGGTGATCCCCCTGGCCAGTGCACGTCTGCTGTCAGATAAAGTCTCCCGTGAACTTTA
CCCGGTGGTGCATATCGGGGATGAAAGCTGGCGCATGATGACCACCGATATGGCCAGTGT
GCCGGTCTCCGTTATCGGGGAAGAAGTGGCTGATCTCAGCCACCGCGAAAATGACATCAA
AAACGCCATTAACCTGATGTTCTGGGGAATATAAATGTCAGGCTCCGTTATACACAGCCA

FIG.91B

```
GTCTGCAGGTCGACCATAGTGACTGGATATGTTGTGTTTTACAGTATTATGTAGTCTGTT
TTTTATGCAAAATCTAATTTAATATATTGATATTTATATCATTTTACGTTTCTCGTTCAG
CTTTCTTGTACAAAGTGGTGATGGGCGGCCGCTCTAGAGGGCCCAAGCTTACGCGTGCAT
GCGACGTCATAGCTCTCTCCCTATAGTGAGTCGTATTATAAGCTAGGCACTGGCCGTCGT
TTTACAACGTCGTGACTGGGAAAACTGCTAGCTTGGGATCTTTGTGAAGGAACCTTACTT
CTGTGGTGTGACATAATTGGACAAACTACCTACAGAGATTTAAAGCTCTAAGGTAAATAT
AAAATTTTTAAGTGTATAATGTGTTAAACTAGCTGCATATGCTTGCTGCTTGAGAGTTTT
GCTTACTGAGTATGATTTATGAAAATATTATACACAGGAGCTAGTGATTCTAATTGTTTG
TGTATTTTAGATTCACAGTCCCAAGGCTCATTTCAGGCCCCTCAGTCCTCACAGTCTGTT
CATGATCATAATCAGCCATACCACATTTGTAGAGGTTTTACTTGCTTTAAAAAACCTCCC
ACACCTCCCCCTGAACCTGAAACATAAAATGAATGCAATTGTTGTTGTTAACTTGTTTAT
TGCAGCTTATAATGGTTACAAATAAAGCAATAGCATCACAAATTTCACAAATAAAGCATT
TTTTTCACTGCATTCTAGTTGTGGTTTGTCCAAACTCATCAATGTATCTTATCATGTCTG
GATCGATCCTGCATTAATGAATCGGCCAACGCGCGGGGAGAGGCGGTTTGCGTATTGGCT
GGCGTAATAGCGAAGAGGCCCGCACCGATCGCCCTTCCCAACAGTTGCGCAGCCTGAATG
GCGAATGGGACGCGCCCTGTAGCGGCGCATTAAGCGCGGCGGGTGTGGTGGTTACGCGCA
GCGTGACCGCTACACTTGCCAGCGCCCTAGCGCCCGCTCCTTTCGCTTTCTTCCCTTCCT
TTCTCGCCACGTTCGCCGGCTTTCCCCGTCAAGCTCTAAATCGGGGGCTCCCTTTAGGGT
TCCGATTTAGTGCTTTACGGCACCTCGACCCCAAAAAACTTGATTAGGGTGATGGTTCAC
GTAGTGGGCCATCGCCCTGATAGACGGTTTTTCGCCCTTTGACGTTGGAGTCCACGTTCT
TTAATAGTGGACTCTTGTTCCAAACTGGAACAACACTCAACCCTATCTCGGTCTATTCTT
TTGATTTATAAGGGATTTTGCCGATTTCGGCCTATTGGTTAAAAAATGAGCTGATTTAAC
AAATATTTAACGCGAATTTTAACAAAATATTAACGTTTACAATTTCGCCTGATGCGGTAT
TTTCTCCTTACGCATCTGTGCGGTATTTCACACCGCATACGCGGATCTGCGCAGCACCAT
GGCCTGAAATAACCTCTGAAAGAGGAACTTGGTTAGGTACCTTCTGAGGCGGAAAGAACC
AGCTGTGGAATGTGTGTCAGTTAGGGTGTGGAAAGTCCCCAGGCTCCCCAGCAGGCAGAA
GTATGCAAAGCATGCATCTCAATTAGTCAGCAACCAGGTGTGGAAAGTCCCCAGGCTCCC
CAGCAGGCAGAAGTATGCAAAGCATGCATCTCAATTAGTCAGCAACCATAGTCCCGCCCC
TAACTCCGCCCATCCCGCCCCTAACTCCGCCCAGTTCCGCCCATTCTCCGCCCCATGGCT
GACTAATTTTTTTTATTTATGCAGAGGCCGAGGCCGCCTCGGCCTCTGAGCTATTCCAGA
AGTAGTGAGGAGGCTTTTTTGGAGGCCTAGGCTTTTGCAAAAAGCTTGATTCTTCTGACA
CAACAGTCTCGAACTTAAGACCATGGCCAAGCCTTTGTCTCAAGAAGAATCCACCCTCAT
TGAAAGAGCAACGGCTACAATCAACAGCATCCCCATCTCTGAAGACTACAGCGTCGCCAG
CGCAGCTCTCTCTAGCGACGGCCGCATCTTCACTGGTGTCAATGTATATCATTTTACTGG
GGGACCTTGTGCAGAACTCGTGGTGCTGGGCACTGCTGCTGCTGCGGCAGCTGGCAACCT
GACTTGTATCGTCGCGATCGGAAATGAGAACAGGGGCATCTTGAGCCCCTGCGGACGGTG
CCGACAGGTGCTTCTCGATCTGCATCCTGGGATCAAAGCCATAGTGAAGGACAGTGATGG
ACAGCCGACGGCAGTTGGGATTCGTGAATTGCTGCCCTCTGGTTATGTGTGGGAGGGCTA
AGCACTTCGTGGCCGAGTTCGAAATGACCGACCAAGCGACGCCCAACCTGCCATCACGAT
GGCCGCAATAAAATATCTTTATTTTCATTACATCTGTGTGTTGGTTTTTTGTGTGAATCG
ATAGCGATAAGGATCCGCGTATGGTGCACTCTCAGTACAATCTGCTCTGATGCCGCATAG
```

FIG.91C

TTAAGCCAGCCCCGACACCCGCCAACACCCGCTGACGCGCCCTGACGGGCTTGTCTGCTC
CCGGCATCCGCTTACAGACAAGCTGTGACCGTCTCCGGGAGCTGCATGTGTCAGAGGTTT
TCACCGTCATCACCGAAACGCGCGAGACGAAAGGGCCTCGTGATACGCCTATTTTTATAG
GTTAATGTCATGATAATAATGGTTTCTTAGACGTCAGGTGGCACTTTTCGGGGAAATGTG
CGCGGAACCCCTATTTGTTTATTTTTCTAAATACATTCAAATATGTATCCGCTCATGAGA
CAATAACCCTGATAAATGCTTCAATAATATTGAAAAAGGAAGAGTATGAGTATTCAACAT
TTCCGTGTCGCCCTTATTCCCTTTTTTGCGGCATTTTGCCTTCCTGTTTTTGCTCACCCA
GAAACGCTGGTGAAAGTAAAAGATGCTGAAGATCAGTTGGGTGCACGAGTGGGTTACATC
GAACTGGATCTCAACAGCGGTAAGATCCTTGAGAGTTTTCGCCCCGAAGAACGTTTTCCA
ATGATGAGCACTTTTAAAGTTCTGCTATGTGGCGCGGTATTATCCCGTATTGACGCCGGG
CAAGAGCAACTCGGTCGCCGCATACACTATTCTCAGAATGACTTGGTTGAGTACTCACCA
GTCACAGAAAAGCATCTTACGGATGGCATGACAGTAAGAGAATTATGCAGTGCTGCCATA
ACCATGAGTGATAACACTGCGGCCAACTTACTTCTGACAACGATCGGAGGACCGAAGGAG
CTAACCGCTTTTTTGCACAACATGGGGGATCATGTAACTCGCCTTGATCGTTGGGAACCG
GAGCTGAATGAAGCCATACCAAACGACGAGCGTGACACCACGATGCCTGTAGCAATGGCA
ACAACGTTGCGCAAACTATTAACTGGCGAACTACTTACTCTAGCTTCCCGGCAACAATTA
ATAGACTGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCATTGCA
GCACTGGGGCCAGATGGTAAGCCCTCCCGTATCGTAGTTATCTACACGACGGGGAGTCAG
GCAACTATGGATGAACGAAATAGACAGATCGCTGAGATAGGTGCCTCACTGATTAAGCAT
TGGTAACTGTCAGACCAAGTTTACTCATATATACTTTAGATTGATTTAAAACTTCATTTT
TAATTTAAAAGGATCTAGGTGAAGATCCTTTTTGATAATCTCATGACCAAAATCCCTTAA
CGTGAGTTTTCGTTCCACTGAGCGTCAGACCCCGTAGAAAAGATCAAAGGATCTTCTTGA
GATCCTTTTTTTCTGCGCGTAATCTGCTGCTTGCAAACAAAAAAACCACCGCTACCAGCG
GTGGTTTGTTTGCCGGATCAAGAGCTACCAACTCTTTTTCCGAAGGTAACTGGCTTCAGC
AGAGCGCAGATACCAAATACTGTCCTTCTAGTGTAGCCGTAGTTAGGCCACCACTTCAAG
AACTCTGTAGCACCGCCTACATACCTCGCTCTGCTAATCCTGTTACCAGTGGCTGCTGCC
AGTGGCGATAAGTCGTGTCTTACCGGGTTGGACTCAAGACGATAGTTACCGGATAAGGCG
CAGCGGTCGGGCTGAACGGGGGGTTCGTGCACACAGCCCAGCTTGGAGCGAACGACCTAC
ACCGAACTGAGATACCTACAGCGTGAGCATTGAGAAAGCGCCACGCTTCCCGAAGGGAGA
AAGGCGGACAGGTATCCGGTAAGCGGCAGGGTCGGAACAGGAGAGCGCACGAGGGAGCTT
CCAGGGGGAAACGCCTGGTATCTTTATAGTCCTGTCGGGTTTCGCCACCTCTGACTTGAG
CGTCGATTTTTGTGATGCTCGTCAGGGGGGCGGAGCCTATGGAAAAACGCCAGCAACGCG
GCCTTTTTACGGTTCCTGGCCTTTTGCTGGCCTTTTGCTCACATGTTCTTTCCTGCGTTA
TCCCCTGATTCTGTGGATAACCGTATTACCGCCTTTGAGTGAGCTGATACCGCTCGCCGC
AGCCGAACGACCGAGCGCAGCGAGTCAGTGAGCGAGGAAGCGGAAGAGCGCCCAATACGC
AAACCGCCTCTCCCCGCGCGTTGGCCGATTCATTAATGCAGAGCTTGCAATTCGCGCGTT
TTTCAATATTATTGAAGCATTTATCAGGGTTATTGTCTCATGAGCGGATACATATTTGAA
TGTATTTAGAAAAATAAACAAATAGGGGTTCCGCGCACATTTCCCCGAAAAGTGCCACCT
GACGTCTAAGAAACCATTATTATCATGACATTAACCTATAAAAATAGGCGTAGTACGAGG
CCCTTTCACTCATTAG

FIG.91D pDEST30 7544 bp

ATGCATGTCGTTACATAACTTACGGTAAATGGCCCGCCTGGCTGACCGCCCAACGACCCC
CGCCCATTGACGTCAATAATGACGTATGTTCCCATAGTAACGCCAATAGGGACTTTCCAT
TGACGTCAATGGGTGGAGTATTTACGGTAAACTGCCCACTTGGCAGTACATCAAGTGTAT
CATATGCCAAGTACGCCCCCTATTGACGTCAATGACGGTAAATGGCCCGCCTGGCATTAT
GCCCAGTACATGACCTTATGGGACTTTCCTACTTGGCAGTACATCTACGTATTAGTCATC
GCTATTACCATGGTGATGCGGTTTTGGCAGTACATCAATGGGCGTGGATAGCGGTTTGAC
TCACGGGGATTTCCAAGTCTCCACCCCATTGACGTCAATGGGAGTTTGTTTTGGCACCAA
AATCAACGGGACTTTCCAAAATGTCGTAACAACTCCGCCCCATTGACGCAAATGGGCGGT
AGGCGTGTACGGTGGGAGGTCTATATAAGCAGAGCTCTCCCTATCAGTGATAGAGATCTC
CCTATCAGTGATAGAGATCGTCGACGAGCTCGTTTAGTGAACCGTCAGATCGCCTGGAGA
CGCCATCCACGCTGTTTTGACCTCCATAGAAGACACCGGGACCGATCCAGCCTCCGGACT
CTAGAGGATCCCTACCGGTGATATCCTCGAGCCCATCAACAAGTTTGTACAAAAAAGCTG
AACGAGAAACGTAAAATGATATAAATATCAATATATTAAATTAGATTTTGCATAAAAAAC
AGACTACATAATACTGTAAAACACAACATATCCAGTCACTATGGCGGCCGCATTAGGCAC
CCCAGGCTTTACACTTTATGCTTCCGGCTCGTATAATGTGTGGATTTTGAGTTAGGATCC
GGCGAGATTTTCAGGAGCTAAGGAAGCTAAAATGGAGAAAAAAATCACTGGATATACCAC
CGTTGATATATCCCAATGGCATCGTAAAGAACATTTTGAGGCATTTCAGTCAGTTGCTCA
ATGTACCTATAACCAGACCGTTCAGCTGGATATTACGGCCTTTTTAAAGACCGTAAAGAA
AAATAAGCACAAGTTTTATCCGGCCTTTATTCACATTCTTGCCCGCCTGATGAATGCTCA
TCCGGAATTCCGTATGGCAATGAAAGACGGTGAGCTGGTGATATGGGATAGTGTTCACCC
TTGTTACACCGTTTTCCATGAGCAAACTGAAACGTTTTCATCGCTCTGGAGTGAATACCA
CGACGATTTCCGGCAGTTTCTACACATATATTCGCAAGATGTGGCGTGTTACGGTGAAAA
CCTGGCCTATTTCCCTAAAGGGTTTATTGAGAATATGTTTTTCGTCTCAGCCAATCCCTG
GGTGAGTTTCACCAGTTTTGATTTAAACGTGGCCAATATGGACAACTTCTTCGCCCCCGT
TTTCACCATGGGCAAATATTATACGCAAGGCGACAAGGTGCTGATGCCGCTGGCGATTCA
GGTTCATCATGCCGTCTGTGATGGCTTCCATGTCGGCAGAATGCTTAATGAATTACAACA
GTACTGCGATGAGTGGCAGGGCGGGGCGTAAAGATCTGGATCCGGCTTACTAAAAGCCAG
ATAACAGTATGCGTATTTGCGCGCTGATTTTTGCGGTATAAGAATATATACTGATATGTA
TACCCGAAGTATGTCAAAAAGAGGTGTGCTATGAAGCAGCGTATTACAGTGACAGTTGAC
AGCGACAGCTATCAGTTGCTCAAGGCATATATGATGTCAATATCTCCGGTCTGGTAAGCA
CAACCATGCAGAATGAAGCCCGTCGTCTGCGTGCCGAACGCTGGAAAGCGGAAAATCAGG
AAGGGATGGCTGAGGTCGCCCGGTTTATTGAAATGAACGGCTCTTTTGCTGACGAGAACA
GGGACTGGTGAAATGCAGTTTAAGGTTTACACCTATAAAAGAGAGAGCCGTTATCGTCTG
TTTGTGGATGTACAGAGTGATATTATTGACACGCCCGGGCGACGGATGGTGATCCCCCTG
GCCAGTGCACGTCTGCTGTCAGATAAAGTCTCCCGTGAACTTTACCCGGTGGTGCATATC
GGGGATGAAAGCTGGCGCATGATGACCACCGATATGGCCAGTGTGCCGGTCTCCGTTATC
GGGGAAGAAGTGGCTGATCTCAGCCACCGCGAAAATGACATCAAAAACGCCATTAACCTG
ATGTTCTGGGGAATATAAATGTCAGGCTCCCTTATACACAGCCAGTCTGCAGGTCGACCA
TAGTGACTGGATATGTTGTGTTTTACAGTATTATGTAGTCTGTTTTTTATGCAAAATCTA
ATTTAATATATTGATATTTATATCATTTTACGTTTCTCGTTCAGCTTTCTTGTACAAAGT
GGTTGATGGGCGGCCGCTCTAGAGGGCCCAAGCTTACGCGTGCATGCGACGTCATAGCTC
TCTCCCTATAGTGAGTCGTATTATAAGCTAGGCACTGGCCGTCGTTTTACAACGTCGTGA
CTGGGAAAACTGCTAGCTTGGGATCTTTGTGAAGGAACCTTACTTCTGTGGTGTGACATA

FIG.92B

ATTGGACAAACTACCTACAGAGATTTAAAGCTCTAAGGTAAATATAAAATTTTTAAGTGT
ATAATGTGTTAAACTAGCTGCATATGCTTGCTGCTTGAGAGTTTTGCTTACTGAGTATGA
TTTATGAAAATATTATACACAGGAGCTAGTGATTCTAATTGTTTGTGTATTTTAGATTCA
CAGTCCCAAGGCTCATTTCAGGCCCCTCAGTCCTCACAGTCTGTTCATGATCATAATCAG
CCATACCACATTTGTAGAGGTTTTACTTGCTTTAAAAAACCTCCCACACCTCCCCCTGAA
CCTGAAACATAAAATGAATGCAATTGTTGTTGTTAACTTGTTTATTGCAGCTTATAATGG
TTACAAATAAAGCAATAGCATCACAAATTTCACAAATAAAGCATTTTTTTCACTGCATTC
TAGTTGTGGTTTGTCCAAACTCATCAATGTATCTTATCATGTCTGGATCGATCCTGCATT
AATGAATCGGCCAACGCGCGGGGAGAGGCGGTTTGCGTATTGGCTGGCGTAATAGCGAAG
AGGCCCGCACCGATCGCCCTTCCCAACAGTTGCGCAGCCTGAATGGCGAATGGGACGCGC
CCTGTAGCGGCGCATTAAGCGCGGCGGGTGTGGTGGTTACGCGCAGCGTGACCGCTACAC
TTGCCAGCGCCCTAGCGCCCGCTCCTTTCGCTTTCTTCCCTTCCTTTCTCGCCACGTTCG
CCGGCTTTCCCCGTCAAGCTCTAAATCGGGGGCTCCCTTTAGGGTTCCGATTTAGTGCTT
TACGGCACCTCGACCCCAAAAAACTTGATTAGGGTGATGGTTCACGTAGTGGGCCATCGC
CCTGATAGACGGTTTTTCGCCCTTTGACGTTGGAGTCCACGTTCTTTAATAGTGGACTCT
TGTTCCAAACTGGAACAACACTCAACCCTATCTCGGTCTATTCTTTTGATTTATAAGGGA
TTTTGCCGATTTCGGCCTATTGGTTAAAAAATGAGCTGATTTAACAAATATTTAACGCGA
ATTTTAACAAAATATTAACGTTTACAATTTCGCCTGATGCGGTATTTTCTCCTTACGCAT
CTGTGCGGTATTTCACACCGCATACGCGGATCTGCGCAGCACCATGGCCTGAAATAACCT
CTGAAAGAGGAACTTGGTTAGGTACCTTCTGAGGCGGAAAGAACCAGCTGTGGAATGTGT
GTCAGTTAGGGTGTGGAAAGTCCCCAGGCTCCCCAGCAGGCAGAAGTATGCAAAGCATGC
ATCTCAATTAGTCAGCAACCAGGTGTGGAAAGTCCCCAGGCTCCCCAGCAGGCAGAAGTA
TGCAAAGCATGCATCTCAATTAGTCAGCAACCATAGTCCCGCCCCTAACTCCGCCCATCC
CGCCCCTAACTCCGCCCAGTTCCGCCCATTCTCCGCCCCATGGCTGACTAATTTTTTTTA
TTTATGCAGAGGCCGAGGCCGCCTCGGCCTCTGAGCTATTCCAGAAGTAGTGAGGAGGCT
TTTTTGGAGGCCTAGGCTTTTGCAAAAAGCTTGATTCTTCTGACACAACAGTCTCGAACT
TAAGGCTAGAGCCACCATGATTGAACAAGATGGATTGCACGCAGGTTCTCCGGCCGCTTG
GGTGGAGAGGCTATTCGGCTATGACTGGGCACAACAGACAATCGGCTGCTCTGATGCCGC
CGTGTTCCGGCTGTCAGCGCAGGGGCGCCCGGTTCTTTTTGTCAAGACCGACCTGTCCGG
TGCCCTGAATGAACTGCAGGACGAGGCAGCGCGGCTATCGTGGCTGGCCACGACGGGCGT
TCCTTGCGCAGCTGTGCTCGACGTTGTCACTGAAGCGGGAAGGGACTGGCTGCTATTGGG
CGAAGTGCCGGGGCAGGATCTCCTGTCATCTCACCTTGCTCCTGCCGAGAAAGTATCCAT
CATGGCTGATGCAATGCGGCGGCTGCATACGCTTGATCCGGCTACCTGCCCATTCGACCA
CCAAGCGAAACATCGCATCGAGCGAGCACGTACTCGGATGGAAGCCGGTCTTGTCGATCA
GGATGATCTGGACGAAGAGCATCAGGGGCTCGCGCCAGCCGAACTGTTCGCCAGGCTCAA
GGCGCGCATGCCCGACGGCGAGGATCTCGTCGTGACCCATGGCGATGCCTGCTTGCCGAA
TATCATGGTGGAAAATGGCCGCTTTTCTGGATTCATCGACTGTGGCCGGCTGGGTGTGGC
GGACCGCTATCAGGACATAGCGTTGGCTACCCGTGATATTGCTGAAGAGCTTGGCGGCGA
ATGGGCTGACCGCTTCCTCGTGCTTTACGGTATCGCCGCTCCCGATTCGCAGCGCATCGC
CTTCTATCGCCTTCTTGACGAGTTCTTCTGAGCGGGACTCTGGGGTTCGAAATGACCGAC
CAAGCGACGCCCAACCTGCCATCACGATGGCCGCAATAAAATATCTTTATTTTCATTACA
TCTGTGTGTTGGTTTTTTGTGTGAATCGATAGCGATAAGGATCCGCGTATGGTGCACTCT
CAGTACAATCTGCTCTGATGCCGCATAGTTAAGCCAGCCCCGACACCCGCCAACACCCGC
TGACGCGCCCTGACGGGCTTGTCTGCTCCCGGCATCCGCTTACAGACAAGCTGTGACCGT
CTCCGGGAGCTGCATGTGTCAGAGGTTTTCACCGTCATCACCGAAACGCGCGAGACGAAA
GGGCCTCGTGATACGCCTATTTTTATAGGTTAATGTCATGATAATAATGGTTTCTTAGAC

FIG.92C

GTCAGGTGGCACTTTTCGGGGAAATGTGCGCGGAACCCCTATTTGTTTATTTTTCTAAAT
ACATTCAAATATGTATCCGCTCATGAGACAATAACCCTGATAAATGCTTCAATAATATTG
AAAAAGGAAGAGTATGAGTATTCAACATTTCCGTGTCGCCCTTATTCCCTTTTTTGCGGC
ATTTTGCCTTCCTGTTTTTGCTCACCCAGAAACGCTGGTGAAAGTAAAAGATGCTGAAGA
TCAGTTGGGTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGCTATGTGG
CGCGGTATTATCCCGTATTGACGCCGGGCAAGAGCAACTCGGTCGCCGCATACACTATTC
TCAGAATGACTTGGTTGAGTACTCACCAGTCACAGAAAAGCATCTTACGGATGGCATGAC
AGTAAGAGAATTATGCAGTGCTGCCATAACCATGAGTGATAACACTGCGGCCAACTTACT
TCTGACAACGATCGGAGGACCGAAGGAGCTAACCGCTTTTTTGCACAACATGGGGGATCA
TGTAACTCGCCTTGATCGTTGGGAACCGGAGCTGAATGAAGCCATACCAAACGACGAGCG
TGACACCACGATGCCTGTAGCAATGGCAACAACGTTGCGCAAACTATTAACTGGCGAACT
ACTTACTCTAGCTTCCCGGCAACAATTAATAGACTGGATGGAGGCGGATAAAGTTGCAGG
ACCACTTCTGCGCTCGGCCCTTCCGGCTGGCTGGTTTATTGCTGATAAATCTGGAGCCGG
TGAGCGTGGGTCTCGCGGTATCATTGCAGCACTGGGGCCAGATGGTAAGCCCTCCCGTAT
CGTAGTTATCTACACGACGGGGAGTCAGGCAACTATGGATGAACGAAATAGACAGATCGC
TGAGATAGGTGCCTCACTGATTAAGCATTGGTAACTGTCAGACCAAGTTTACTCATATAT
ACTTTAGATTGATTTAAAACTTCATTTTTAATTTAAAAGGATCTAGGTGAAGATCCTTTT
TGATAATCTCATGACCAAAATCCCTTAACGTGAGTTTTCGTTCCACTGAGCGTCAGACCC
CGTAGAAAAGATCAAAGGATCTTCTTGAGATCCTTTTTTTCTGCGCGTAATCTGCTGCTT
GCAAACAAAAAAACCACCGCTACCAGCGGTGGTTTGTTTGCCGGATCAAGAGCTACCAAC
TCTTTTTCCGAAGGTAACTGGCTTCAGCAGAGCGCAGATACCAAATACTGTCCTTCTAGT
GTAGCCGTAGTTAGGCCACCACTTCAAGAACTCTGTAGCACCGCCTACATACCTCGCTCT
GCTAATCCTGTTACCAGTGGCTGCTGCCAGTGGCGATAAGTCGTGTCTTACCGGGTTGGA
CTCAAGACGATAGTTACCGGATAAGGCGCAGCGGTCGGGCTGAACGGGGGGTTCGTGCAC
ACAGCCCAGCTTGGAGCGAACGACCTACACCGAACTGAGATACCTACAGCGTGAGCATTG
AGAAAGCGCCACGCTTCCCGAAGGGAGAAAGGCGGACAGGTATCCGGTAAGCGGCAGGGT
CGGAACAGGAGAGCGCACGAGGGAGCTTCCAGGGGGAAACGCCTGGTATCTTTATAGTCC
TGTCGGGTTTCGCCACCTCTGACTTGAGCGTCGATTTTTGTGATGCTCGTCAGGGGGGCG
GAGCCTATGGAAAAACGCCAGCAACGCGGCCTTTTTACGGTTCCTGGCCTTTTGCTGGCC
TTTTGCTCACATGTTCTTTCCTGCGTTATCCCCTGATTCTGTGGATAACCGTATTACCGC
CTTTGAGTGAGCTGATACCGCTCGCCGCAGCCGAACGACCGAGCGCAGCGAGTCAGTGAG
CGAGGAAGCGGAAGAGCGCCCAATACGCAAACCGCCTCTCCCCGCGCGTTGGCCGATTCA
TTAATGCAGAGCTTGCAATTCGCGCGTTTTTCAATATTATTGAAGCATTTATCAGGGTTA
TTGTCTCATGAGCGGATACATATTTGAATGTATTTAGAAAAATAAACAAATAGGGGTTCC
GCGCACATTTCCCCGAAAAGTGCCACCTGACGTCTAAGAAACCATTATTATCATGACATT
AACCTATAAAAATAGGCGTAGTACGAGGCCCTTTCACTCATTAG

FIG.92D pDEST31 7559 bp

ATGCATGTCGTTACATAACTTACGGTAAATGGCCCGCCTGGCTGACCGCCCAACGACCCC
CGCCCATTGACGTCAATAATGACGTATGTTCCCATAGTAACGCCAATAGGGACTTTCCAT
TGACGTCAATGGGTGGAGTATTTACGGTAAACTGCCCACTTGGCAGTACATCAAGTGTAT
CATATGCCAAGTACGCCCCCTATTGACGTCAATGACGGTAAATGGCCCGCCTGGCATTAT
GCCCAGTACATGACCTTATGGGACTTTCCTACTTGGCAGTACATCTACGTATTAGTCATC
GCTATTACCATGGTGATGCGGTTTTGGCAGTACATCAATGGGCGTGGATAGCGGTTTGAC
TCACGGGGATTTCCAAGTCTCCACCCCATTGACGTCAATGGGAGTTTGTTTTGGCACCAA
AATCAACGGGACTTTCCAAAATGTCGTAACAACTCCGCCCCATTGACGCAAATGGGCGGT
AGGCGTGTACGGTGGGAGGTCTATATAAGCAGAGCTCTCCCTATCAGTGATAGAGATCTC
CCTATCAGTGATAGAGATCGTCGACGAGCTCGTTTAGTGAACCGTCAGATCGCCTGGAGA
CGCCATCCACGCTGTTTTGACCTCCATAGAAGACACCGGGACCGATCCAGCCTCCGGACC
ATGGCGTACTACCATCACCATCACCATCACACCGGTGATATCCTCGAGCCCATCACAAGT
TTGTACAAAAAAGCTGAACGAGAAACGTAAAATGATATAAATATCAATATATTAAATTAG
ATTTTGCATAAAAAACAGACTACATAATACTGTAAAACACAACATATCCAGTCACTATGG
CGGCCGCATTAGGCACCCCAGGCTTTACACTTTATGCTTCCGGCTCGTATAATGTGTGGA
TTTTGAGTTAGGATCCGGCGAGATTTTCAGGAGCTAAGGAAGCTAAAATGGAGAAAAAAA
TCACTGGATATACCACCGTTGATATATCCCAATGGCATCGTAAAGAACATTTTGAGGCAT
TTCAGTCAGTTGCTCAATGTACCTATAACCAGACCGTTCAGCTGGATATTACGGCCTTTT
TAAAGACCGTAAAGAAAAATAAGCACAAGTTTTATCCGGCCTTTATTCACATTCTTGCCC
GCCTGATGAATGCTCATCCGGAATTCCGTATGGCAATGAAAGACGGTGAGCTGGTGATAT
GGGATAGTGTTCACCCTTGTTACACCGTTTTCCATGAGCAAACTGAAACGTTTTCATCGC
TCTGGAGTGAATACCACGACGATTTCCGGCAGTTTCTACACATATATTCGCAAGATGTGG
CGTGTTACGGTGAAAACCTGGCCTATTTCCCTAAAGGGTTTATTGAGAATATGTTTTTCG
TCTCAGCCAATCCCTGGGTGAGTTTCACCAGTTTTGATTTAAACGTGGCCAATATGGACA
ACTTCTTCGCCCCCGTTTTCACCATGGGCAAATATTATACGCAAGGCGACAAGGTGCTGA
TGCCGCTGGCGATTCAGGTTCATCATGCCGTCTGTGATGGCTTCCATGTCGGCAGAATGC
TTAATGAATTACAACAGTACTGCGATGAGTGGCAGGGCGGGGCGTAAACGCGTGGATCCG
GCTTACTAAAAGCCAGATAACAGTATGCGTATTTGCGCGCTGATTTTTGCGGTATAAGAA
TATATACTGATATGTATACCCGAAGTATGTCAAAAAGAGGTGTGCTATGAAGCAGCGTAT
TACAGTGACAGTTGACAGCGACAGCTATCAGTTGCTCAAGGCATATATGATGTCAATATC
TCCGGTCTGGTAAGCACAACCATGCAGAATGAAGCCCGTCGTCTGCGTGCCGAACGCTGG
AAAGCGGAAAATCAGGAAGGGATGGCTGAGGTCGCCCGGTTTATTGAAATGAACGGCTCT
TTTGCTGACGAGAACAGGGACTGGTGAAATGCAGTTTAAGGTTTACACCTATAAAAGAGA
GAGCCGTTATCGTCTGTTTGTGGATGTACAGAGTGATATTATTGACACGCCCGGGCGACG
GATGGTGATCCCCCTGGCCAGTGCACGTCTGCTGTCAGATAAAGTCTCCCGTGAACTTTA
CCCGGTGGTGCATATCGGGGATGAAAGCTGGCGCATGATGACCACCGATATGGCCAGTGT
GCCGGTCTCCGTTATCGGGGAAGAAGTGGCTGATCTCAGCCACCGCGAAAATGACATCAA
AAACGCCATTAACCTGATGTTCTGGGGAATATAAATGTCAGGCTCCGTTATACACAGCCA
GTCTGCAGGTCGACCATAGTGACTGGATATGTTGTGTTTTACAGTATTATGTAGTCTGTT
TTTTATGCAAAATCTAATTTAATATATTGATATTTATATCATTTTACGTTTCTCGTTCAG
CTTTCTTGTACAAAGTGGTGATGGGCGGCCGCTCTAGAGGGCCCAAGCTTACGCGTGCAT
GCGACGTCATAGCTCTCTCCCTATAGTGAGTCGTATTATAAGCTAGGCACTGGCCGTCGT
TTTACAACGTCGTGACTGGGAAAACTGCTAGCTTGGGATCTTTGTGAAGGAACCTTACTT

FIG.93B

CTGTGGTGTGACATAATTGGACAAACTACCTACAGAGATTTAAAGCTCTAAGGTAAATAT
AAAATTTTTAAGTGTATAATGTGTTAAACTAGCTGCATATGCTTGCTGCTTGAGAGTTTT
GCTTACTGAGTATGATTTATGAAAATATTATACACAGGAGCTAGTGATTCTAATTGTTTG
TGTATTTTAGATTCACAGTCCCAAGGCTCATTTCAGGCCCCTCAGTCCTCACAGTCTGTT
CATGATCATAATCAGCCATACCACATTTGTAGAGGTTTTACTTGCTTTAAAAAACCTCCC
ACACCTCCCCCTGAACCTGAAACATAAAATGAATGCAATTGTTGTTGTTAACTTGTTTAT
TGCAGCTTATAATGGTTACAAATAAAGCAATAGCATCACAAATTTCACAAATAAAGCATT
TTTTTCACTGCATTCTAGTTGTGGTTTGTCCAAACTCATCAATGTATCTTATCATGTCTG
GATCGATCCTGCATTAATGAATCGGCCAACGCGCGGGGAGAGGCGGTTTGCGTATTGGCT
GGCGTAATAGCGAAGAGGCCCGCACCGATCGCCCTTCCCAACAGTTGCGCAGCCTGAATG
GCGAATGGGACGCGCCCTGTAGCGGCGCATTAAGCGCGGCGGGTGTGGTGGTTACGCGCA
GCGTGACCGCTACACTTGCCAGCGCCCTAGCGCCCGCTCCTTTCGCTTTCTTCCCTTCCT
TTCTCGCCACGTTCGCCGGCTTTCCCCGTCAAGCTCTAAATCGGGGGCTCCCTTTAGGGT
TCCGATTTAGTGCTTTACGGCACCTCGACCCCAAAAAACTTGATTAGGGTGATGGTTCAC
GTAGTGGGCCATCGCCCTGATAGACGGTTTTTCGCCCTTTGACGTTGGAGTCCACGTTCT
TTAATAGTGGACTCTTGTTCCAAACTGGAACAACACTCAACCCTATCTCGGTCTATTCTT
TTGATTTATAAGGGATTTTGCCGATTTCGGCCTATTGGTTAAAAAATGAGCTGATTTAAC
AAATATTTAACGCGAATTTTAACAAAATATTAACGTTTACAATTTCGCCTGATGCGGTAT
TTTCTCCTTACGCATCTGTGCGGTATTTCACACCGCATACGCGGATCTGCGCAGCACCAT
GGCCTGAAATAACCTCTGAAAGAGGAACTTGGTTAGGTACCTTCTGAGGCGGAAAGAACC
AGCTGTGGAATGTGTGTCAGTTAGGGTGTGGAAAGTCCCCAGGCTCCCCAGCAGGCAGAA
GTATGCAAAGCATGCATCTCAATTAGTCAGCAACCAGGTGTGGAAAGTCCCCAGGCTCCC
CAGCAGGCAGAAGTATGCAAAGCATGCATCTCAATTAGTCAGCAACCATAGTCCCGCCCC
TAACTCCGCCCATCCCGCCCCTAACTCCGCCCAGTTCCGCCCATTCTCCGCCCCATGGCT
GACTAATTTTTTTTATTTATGCAGAGGCCGAGGCCGCCTCGGCCTCTGAGCTATTCCAGA
AGTAGTGAGGAGGCTTTTTTGGAGGCCTAGGCTTTTGCAAAAAGCTTGATTCTTCTGACA
CAACAGTCTCGAACTTAAGGCTAGAGCCACCATGATTGAACAAGATGGATTGCACGCAGG
TTCTCCGGCCGCTTGGGTGGAGAGGCTATTCGGCTATGACTGGGCACAACAGACAATCGG
CTGCTCTGATGCCGCCGTGTTCCGGCTGTCAGCGCAGGGGCGCCCGGTTCTTTTTGTCAA
GACCGACCTGTCCGGTGCCCTGAATGAACTGCAGGACGAGGCAGCGCGGCTATCGTGGCT
GGCCACGACGGGCGTTCCTTGCGCAGCTGTGCTCGACGTTGTCACTGAAGCGGGAAGGGA
CTGGCTGCTATTGGGCGAAGTGCCGGGGCAGGATCTCCTGTCATCTCACCTTGCTCCTGC
CGAGAAAGTATCCATCATGGCTGATGCAATGCGGCGGCTGCATACGCTTGATCCGGCTAC
CTGCCCATTCGACCACCAAGCGAAACATCGCATCGAGCGAGCACGTACTCGGATGGAAGC
CGGTCTTGTCGATCAGGATGATCTGGACGAAGAGCATCAGGGGCTCGCGCCAGCCGAACT
GTTCGCCAGGCTCAAGGCGCGCATGCCCGACGGCGAGGATCTCGTCGTGACCCATGGCGA
TGCCTGCTTGCCGAATATCATGGTGGAAAATGGCCGCTTTTCTGGATTCATCGACTGTGG
CCGGCTGGGTGTGGCGGACCGCTATCAGGACATAGCGTTGGCTACCCGTGATATTGCTGA
AGAGCTTGGCGGCGAATGGGCTGACCGCTTCCTCGTGCTTTACGGTATCGCCGCTCCCGA
TTCGCAGCGCATCGCCTTCTATCGCCTTCTTGACGAGTTCTTCTGAGCGGGACTCTGGGG
TTCGAAATGACCGACCAAGCGACGCCCAACCTGCCATCACGATGGCCGCAATAAAATATC
TTTATTTTCATTACATCTGTGTGTTGGTTTTTTGTGTGAATCGATAGCGATAAGGATCCG
CGTATGGTGCACTCTCAGTACAATCTGCTCTGATGCCGCATAGTTAAGCCAGCCCCGACA
CCCGCCAACACCCGCTGACGCGCCCTGACGGGCTTGTCTGCTCCCGGCATCCGCTTACAG
ACAAGCTGTGACCGTCTCCGGGAGCTGCATGTGTCAGAGGTTTTCACCGTCATCACCGAA
ACGCGCGAGACGAAAGGGCCTCGTGATACGCCTATTTTTATAGGTTAATGTCATGATAAT

FIG.93C

AATGGTTTCTTAGACGTCAGGTGGCACTTTTCGGGGAAATGTGCGCGGAACCCCTATTTG
TTTATTTTTCTAAATACATTCAAATATGTATCCGCTCATGAGACAATAACCCTGATAAAT
GCTTCAATAATATTGAAAAAGGAAGAGTATGAGTATTCAACATTTCCGTGTCGCCCTTAT
TCCCTTTTTTGCGGCATTTTGCCTTCCTGTTTTTGCTCACCCAGAAACGCTGGTGAAAGT
AAAAGATGCTGAAGATCAGTTGGGTGCACGAGTGGGTTACATCGAACTGGATCTCAACAG
CGGTAAGATCCTTGAGAGTTTTCGCCCCGAAGAACGTTTTCCAATGATGAGCACTTTTAA
AGTTCTGCTATGTGGCGCGGTATTATCCCGTATTGACGCCGGGCAAGAGCAACTCGGTCG
CCGCATACACTATTCTCAGAATGACTTGGTTGAGTACTCACCAGTCACAGAAAAGCATCT
TACGGATGGCATGACAGTAAGAGAATTATGCAGTGCTGCCATAACCATGAGTGATAACAC
TGCGGCCAACTTACTTCTGACAACGATCGGAGGACCGAAGGAGCTAACCGCTTTTTTGCA
CAACATGGGGGATCATGTAACTCGCCTTGATCGTTGGGAACCGGAGCTGAATGAAGCCAT
ACCAAACGACGAGCGTGACACCACGATGCCTGTAGCAATGGCAACAACGTTGCGCAAACT
ATTAACTGGCGAACTACTTACTCTAGCTTCCCGGCAACAATTAATAGACTGGATGGAGGC
GGATAAAGTTGCAGGACCACTTCTGCGCTCGGCCCTTCCGGCTGGCTGGTTTATTGCTGA
TAAATCTGGAGCCGGTGAGCGTGGGTCTCGCGGTATCATTGCAGCACTGGGGCCAGATGG
TAAGCCCTCCCGTATCGTAGTTATCTACACGACGGGGAGTCAGGCAACTATGGATGAACG
AAATAGACAGATCGCTGAGATAGGTGCCTCACTGATTAAGCATTGGTAACTGTCAGACCA
AGTTTACTCATATATACTTTAGATTGATTTAAAACTTCATTTTTAATTTAAAAGGATCTA
GGTGAAGATCCTTTTTGATAATCTCATGACCAAAATCCCTTAACGTGAGTTTTCGTTCCA
CTGAGCGTCAGACCCCGTAGAAAAGATCAAAGGATCTTCTTGAGATCCTTTTTTTCTGCG
CGTAATCTGCTGCTTGCAAACAAAAAAACCACCGCTACCAGCGGTGGTTTGTTTGCCGGA
TCAAGAGCTACCAACTCTTTTTCCGAAGGTAACTGGCTTCAGCAGAGCGCAGATACCAAA
TACTGTCCTTCTAGTGTAGCCGTAGTTAGGCCACCACTTCAAGAACTCTGTAGCACCGCC
TACATACCTCGCTCTGCTAATCCTGTTACCAGTGGCTGCTGCCAGTGGCGATAAGTCGTG
TCTTACCGGGTTGGACTCAAGACGATAGTTACCGGATAAGGCGCAGCGGTCGGGCTGAAC
GGGGGGTTCGTGCACACAGCCCAGCTTGGAGCGAACGACCTACACCGAACTGAGATACCT
ACAGCGTGAGCATTGAGAAAGCGCCACGCTTCCCGAAGGGAGAAAGGCGGACAGGTATCC
GGTAAGCGGCAGGGTCGGAACAGGAGAGCGCACGAGGGAGCTTCCAGGGGGAAACGCCTG
GTATCTTTATAGTCCTGTCGGGTTTCGCCACCTCTGACTTGAGCGTCGATTTTTGTGATG
CTCGTCAGGGGGGCGGAGCCTATGGAAAAACGCCAGCAACGCGGCCTTTTTACGGTTCCT
GGCCTTTTGCTGGCCTTTTGCTCACATGTTCTTTCCTGCGTTATCCCCTGATTCTGTGGA
TAACCGTATTACCGCCTTTGAGTGAGCTGATACCGCTCGCCGCAGCCGAACGACCGAGCG
CAGCGAGTCAGTGAGCGAGGAAGCGGAAGAGCGCCCAATACGCAAACCGCCTCTCCCCGC
GCGTTGGCCGATTCATTAATGCAGAGCTTGCAATTCGCGCGTTTTTCAATATTATTGAAG
CATTTATCAGGGTTATTGTCTCATGAGCGGATACATATTTGAATGTATTTAGAAAAATAA
ACAAATAGGGGTTCCGCGCACATTTCCCCGAAAAGTGCCACCTGACGTCTAAGAAACCAT
TATTATCATGACATTAACCTATAAAAATAGGCGTAGTACGAGGCCCTTTCACTCATTAG

FIG.93D pDEST32 12288 bp

GACGAAAGGGCCTCGTGATACGCCTATTTTTATAGGTTAATGTCATGATAATAATGGTTT
CTTAGGACGGATCGCTTGCCTGTAACTTACACGCGCCTCGTATCTTTTAATGATGGAATA
ATTTGGGAATTTACTCTGTGTTTATTTATTTTTATGTTTTGTATTTGGATTTTAGAAAGT
AAATAAAGAAGGTAGAAGAGTTACGGAATGAAGAAAAAAAAATAAACAAAGGTTTAAAAA
ATTTCAACAAAAAGCGTACTTTACATATATATTTATTAGACAAGAAAAGCAGATTAAATA
GATATACATTCGATTAACGATAAGTAAAATGTAAAATCACAGGATTTTCGTGTGTGGTCT
TCTACACAGACAAGATGAAACAATTCGGCATTAATACCTGAGAGCAGGAAGAGCAAGATA
AAAGGTAGTATTTGTTGGCGATCCCCCTAGAGTCTTTTACATCTTCGGAAAACAAAAACT
ATTTTTTCTTTAATTTCTTTTTTTACTTTCTATTTTTAATTTATATATTTATATTAAAAA
ATTTAAATTATAATTATTTTTATAGCACGTGATGAAAAGGACCCAGGTGGCACTTTTCGG
GGAAATGTGCGCGGAACCCCTATTTGTTTATTTTTCTAAATACATTCAAATATGTATCCG
CTCATGAGACAATAACCCTGATAAATGCTTCAATAATCTGCAGTGCGCAGGGCCCGTGTC
TCAAAATCTCTGATGTTACATTGCACAAGATAAAAATATATCATCATGAACAATAAAACT
GTCTGCTTACATAAACAGTAATACAAGGGGTGTTATGAGCCATATTCAACGGGAAACGTC
TTGCTGGAGGCCGCGATTAAATTCCAACATGGATGCTGATTTATATGGGTATAAATGGGC
TCGGTAGCCAACCACTAGAACTATAGCTAGAGTCCTGGGCGAACAAACGATGCTCGCCTT
CCAGAAAACCGAGGATGCGAACCACTTCATCCGGGGTCAGCACCACCGGCAAGCGCCGCG
ACGGCCGAGGTCTTCCGATCTCCTGAAGCCAGGGCAGATCCGTGCACAGCACCTTGCCGT
AGAAGAACAGCAAGGCCGCCAATGCCTGACGATGCGTGGAGACCGAAACCTTGCGCTCGT
TCGCCAGCCAGGACAGAAATGCCTCGACTTCGCTGCTGCCCAAGGTTGCCGGGTGACGCA
CACCGTGGAAACGGATGAAGGCACGAACCCAGTTGACATAAGCCTGTTCGGTTCGTAAAC
TGTAATGCAAGTAGCGTATGCGCTCACGCAACTGGTCCAGAACCTTGACCGAACGCAGCG
GTGGTAACGGCGCAGTGGCGGTTTTCATGGCTTGTTATGACTGTTTTTTTGTACAGTCTA
TGCCTCGGGCATCCAAGCAGCAAGCGCGTTACGCCGTGGGTCGATGTTTGATGTTATGGA
GCAGCAACGATGTTACGCAGCAGCAACGATGTTACGCAGCAGGGCAGTCGCCCTAAAACA
AAGTTAGGTGGCTCAAGTATGGGCATCATTCGCACATGTAGGCTCGGCCCTGACCAAGTC
AAATCCATGCGGGCTGCTCTTGATCTTTTCGGTCGTGAGTTCGGAGACGTAGCCACCTAC
TCCCAACATCAGCCGGACTCCGATTACCTCGGGAACTTGCTCCGTAGTAAGACATTCATC
GCGCTTGCTGCCTTCGACCAAGAAGCGGTTGTTGGCGCTCTCGCGGCTTACGTTCTGCCC
AGGTTTGAGCAGCCGCGTAGTGAGATCTATATCTATGATCTCGCAGTCTCCGGCGAGCAC
CGGAGGCAGGGCATTGCCACCGCGCTCATCAATCTCCTCAAGCATGAGGCCAACGCGCTT
GGTGCTTATGTGATCTACGTGCAAGCAGATTACGGTGACGATCCCGCAGTGGCTCTCTAT
ACAAAGTTGGGCATACGGGAAGAAGTGATGCACTTTGATATCGACCCAAGTACCGCCACC
TAACAATTCGTTCAAGCCGAGATCGGCTTCCCGGCCTAATAGGTTGTATTGATGTTGGAC
GAGTCGGAATCGCAGACCGATACCAGGATCTTGCCATCCTATGGAACTGCCTCGGTGAGT
TTTCTCCTTCATTACAGAAACGGCTTTTTCAAAAATATGGTATTGATAATCCTGATATGA
ATAAATTGCAGTTTCATTTGATGCTCGATGAGTTTTTCTAATCAGAATTGGTTAATTGGT
TGTAACACTGGCAGAGCATTACGCTGACTTGACGGGACGGCGNCATGACCAAAATCCCTT
AACGTGAGTTTTCGTTCCACTGAGCGTCAGACCCCGTAGAAAAGATCAAAGGATCTTCTT
GAGATCCTTTTTTTCTGCGCGTAATCTGCTGCTTGCAAACAAAAAAACCACCGCTACCAG

FIG.94B

CGGTGGTTTGTTTGCCGGATCAAGAGCTACCAACTCTTTTTCCGAAGGTAACTGGCTTCA
GCAGAGCGCAGATACCAAATACTGTCCTTCTAGTGTAGCCGTAGTTAGGCCACCACTTCA
AGAACTCTGTAGCACCGCCTACATACCTCGCTCTGCTAATCCTGTTACCAGTGGCTGCTG
CCAGTGGCGATAAGTCGTGTCTTACCGGGTTGGACTCAAGACGATAGTTACCGGATAAGG
CGCAGCGGTCGGGCTGAACGGGGGGTTCGTGCACACAGCCCAGCTTGGAGCGAACGACCT
ACACCGAACTGAGATACCTACAGCGTGAGCATTGAGAAAGCGCCACGCTTCCCGAAGGGA
GAAAGGCGGACAGGTATCCGGTAAGCGGCAGGGTCGGAACAGGAGAGCGCACGAGGGAGC
TTCCAGGGGGGAACGCCTGGTATCTTTATAGTCCTGTCGGGTTTCGCCACCTCTGACTTG
AGCGTCGATTTTTGTGATGCTCGTCAGGGGGGCCGAGCCTATGGAAAAACGCCAGCAACG
CGGCCTTTTTACGGTTCCTGGCCTTTTGCTGGCCTTTTGCTCACATGTTCTTTCCTGCGT
TATCCCCTGATTCTGTGGATAACCGTATTACCGCCTTTGAGTGAGCTGATACCGCTCGCC
GCAGCCGAACGACCGAGCGCAGCGAGTCAGTGAGCGAGGAAGCGGAAGAGCGCCCAATAC
GCAAACCGCCTCTCCCCGCGCGTTGGCCGATTCATTAATGCAGCTGGCACGACAGGTTTC
CCGACTGGAAAGCGGGCAGTGAGCGCAACGCAATTAATGTGAGTTACCTCACTCATTAGG
CACCCCAGGCTTTACACTTTATGCTTCCGGCTCCTATGTTGTGTGGAATTGTGAGCGGAT
AACAATTTCACACAGGAAACAGCTATGACCATGATTACGCCAAGCTCGGAATTAACCCTC
ACTAAAGGGAACAAAAGCTGGTACCGATCCCGAGCTTTGCAAATTAAAGCCTTCGAGCGT
CCCAAAACCTTCTCAAGCAAGGTTTTCAGTATAATGTTACATGCGTACACGCGTCTGTAC
AGAAAAAAAAGAAAAATTTGAAATATAAATAACGTTCTTAATACTAACATAACTATAAAA
AAATAAATAGGGACCTAGACTTCAGGTTGTCTAACTCCTTCCTTTTCGGTTAGAGCGGAT
GTGGGGGGAGGGCGTGAATGTAAGCGTGACATAACTAATTACATGATATCGACAAAGGAA
AAGGGGCCTGTTTACTCACAGGCTTTTTTCAAGTAGGTAATTAAGTCGTTTCTGTCTTTT
TCCTTCTTCAACCCACCAAAGGCCATCTTGGTACTTTTTTTTTTTTTTTTTTTTTTTTTT
TTTTTTTTTTTTTTTTTTTTTTTTTTTTTTTTTTTTTTTTTTTTTTTTTTTTTTTTTTTT
TTTTTTTTCATAGAAATAATACAGAAGTAGATGTTGAATTAGATTAAACTGAAGATATAT
AATTTATTGGAAAATACATAGAGCTTTTTGTTGATGCGCTTAAGCGATCAATTCAACAAC
ACCACCAGCAGCTCTGATTTTTTCTTCAGCCAACTTGGAGACGAATCTAGCTTTGACGAT
AACTGGAACATTTGGAATTCTACCCTTACCCAAGATCTTACCGTAACCGGCTGCCAAAGT
GTCAATAACTGGAGCAGTTTCCTTAGAAGCAGATTTCAAGTATTGGTCTCTCTTGTCTTC
TGGGATCAATGTCCACAATTTGTCCAAGTTCAAGACTGGCTTCCAGAAATGAGCTTGTTG
CTTGTGGAAGTATCTCATACCAACCTTACCGAAATAACCTGGATGGTATTTATCCATGTT
AATTCTGTGGTGATGTTGACCACCGGCCATACCTCTACCACCGGGGTGCTTTCTGTGCTT
ACCGATACGACCTTTACCGGCTGAGACGTGACCTCTGTGCTTTCTAGTCTTAGTGAATCT
GGAAGGCATTCTTGATTAGTTGGATGATTGTTCTGGGATTTAATGCAAAAATCACTTAAG
AAGGAAAATCAACGGAGAAAGCAAACGCCATCTTAAATATACGGGATACAGATGAAAGGG
TTTGAACCTATCTGGAAAATAGCATTAAACAAGCGAAAAACTGCGAGGAAAATTGTTTGC
GTCTCTGCGGGCTATTCACGCGCCAGAGGAAAATAGGAAAAATAACAGGGCATTAGAAAA
ATAATTTTGATTTTGGTAATGTGTGGGTCCTGGTGTACAGATGTTACATTGGTTACAGTA
CTCTTGTTTTTGCTGTGTTTTTCGATGAATCTCCAAAATGGTTGTTAGCACATGGAAGAG
TCACCGATGCTAAGTTATCTCTATGTAAGCTACGTGGCGTGACTTTTGATGAAGCCGCAC
AAGAGATACAGGATTGGCAACTGCAAATAGAATCTGGGGATCCCCCCTCGAGATCCGGGA
TCGAAGAAATGATGGTAAATGAAATAGGAAATCAAGGAGCATGAAGGCAAAAGACAAATA
TAAGGGTCGAACGAAAAATAAAGTGAAAAGTGTTGATATGATGTATTTGGCTTTGCGGCG

FIG.94C

```
CCGAAAAAACGAGTTTACGCAATTGCACAATCATGCTGACTCTGTGGCGGACCCGCGCTC
TTGCCGGCCCGGCGATAACGCTGGGCGTGAGGCTGTGCCCGGCGGAGTTTTTTGCGCCTG
CATTTTCCAAGGTTTACCCTGCGCTAAGGGGCGAGATTGGAGAAGCAATAAGAATGCCGG
TTGGGGTTGCGATGATGACGACCACGACAACTGGTGTCATTATTTAAGTTGCCGAAAGAA
CCTGAGTGCATTTGCAACATGAGTATACTAGAAGAATGAGCCAAGACTTGCGAGACGCGA
GTTTGCCGGTGGTGCGAACAATAGAGCGACCATGACCTTGAAGGTGAGACGCGCATAACC
GCTAGAGTACTTTGAAGAGGAAACAGCAATAGGGTTGCTACCAGTATAAATAGACAGGTA
CATACAACACTGGAAATGGTTGTCTGTTTGAGTACGCTTTCAATTCATTTGGGTGTGCAC
TTTATTATGTTACAATATGGAAGGGAACTTTACACTTCTCCTATGCACATATATTAATTA
AAGTCCAATGCTAGTAGAGAAGGGGGGTAACACCCCTCCGCGCTCTTTTCCGATTTTTTT
CTAAACCGTGGAATATTTCGGATATCCTTTTGTTGTTTCCGGGTGTACAATATGGACTTC
CTCTTTTCTGGCAACCAAACCCATACATCGGGATTCCTATAATACCTTCGTTGGTCTCCC
TAACATGTAGGTGGCGGAGGGGAGATATACAATAGAACAGATACCAGACAAGACATAATG
GGCTAAACAAGACTACACCAATTACACTGCCTCATTGATGGTGGTACATAACGAACTAAT
ACTGTAGCCCTAGACTTGATAGCCATCATCATATCGAAGTTTCACTACCCTTTTTCCATT
TGCCATCTATTGAAGTAATAATAGGCGCATGCAACTTCTTTTCTTTTTTTTCTTTTCTC
TCTCCCCCGTTGTTGTCTCACCATATCCGCAATGACAAAAAAAATGATGGAAGACACTAA
AGGAAAAAATTAACGACAAAGACAGCACCAACAGATGTCGTTGTTCCAGAGCTGATGAGG
GGTATCTTCGAACACACGAAACTTTTTCCTTCCTTCATTCACGCACACTACTCTCTAATG
AGCAACGGTATACGGCCTTCCTTCCAGTTACTTGAATTTGAAATAAAAAAAGTTTGCCGC
TTTGCTATCAAGTATAAATAGACCTGCAATTATTAATCTTTTGTTTCCTCGTCATTGTTC
TCGTTCCCTTTCTTCCTTGTTTCTTTTTCTGCACAATATTTCAAGCTATACCAAGCATAC
AATCAACTCCAAGCTTGAAGCAAGCCTCCTGAAAGATGAAGCTACTGTCTTCTATCGAAC
AAGCATGCGATATTTGCCGACTTAAAAAGCTCAAGTGCTCCAAAGAAAAACCGAAGTGCG
CCAAGTGTCTGAAGAACAACTGGGAGTGTCGCTACTCTCCCAAAACCAAAAGGTCTCCGC
TGACTAGGGCACATCTGACAGAAGTGGAATCAAGGCTAGAAAGACTGGAACAGCTATTTC
TACTGATTTTTCCTCGAGAAGACCTTGACATGATTTTGAAAATGGATTCTTTACAGGATA
TAAAAGCATTGTTAACAGGATTATTTGTACAAGATAATGTGAATAAAGATGCCGTCACAG
ATAGATTGGCTTCAGTGGAGACTGATATGCCTCTAACATTGAGACAGCATAGAATAAGTG
CGACATCATCATCGGAAGAGAGTAGTAACAAAGGTCAAAGACAGTTGACTGTATCGTCGA
GGTCGAATCAAACAAGTTTGTACAAAAAAGCTGAACGAGAAACGTAAAATGATATAAATA
TCAATATATTAAATTAGATTTTGCATAAAAAACAGACTACATAATACTGTAAAACACAAC
ATATCCAGTCACTATGGCGGCCGCTAAGTTGGCAGCATCACCCGACGCACTTTGCGCCGA
ATAAATACCTGTGACGGAAGATCACTTCGCAGAATAAATAAATCCTGGTGTCCCTGTTGA
TACCGGGAAGCCCTGGGCCAACTTTTGGCGAAAATGAGACGTTGATCGGCACGTAAGAGG
TTCCAACTTTCACCATAATGAAATAAGATCACTACCGGGCGTATTTTTTGAGTTATCGAG
ATTTTCAGGAGCTAAGGAAGCTAAAATGGAGAAAAAAATCACTGGATATACCACCGTTGA
TATATCCCAATGGCATCGTAAAGAACATTTTGAGGCATTTCAGTCAGTTGCTCAATGTAC
CTATAACCAGACCGTTCAGCTGGATATTACGGCCTTTTTAAAGACCGTAAAGAAAAATAA
GCACAAGTTTTATCCGGCCTTTATTCACATTCTTGCCCGCCTGATGAATGCTCATCCGGA
ATTCCGTATGGCAATGAAAGACGGTGAGCTGGTGATATGGGATAGTGTTCACCCTTGTTA
CACCGTTTTCCATGAGCAAACTGAAACGTTTTCATCGCTCTGGAGTGAATACCACGACGA
TTTCCGGCAGTTTCTACACATATATTCGCAAGATGTGGCGTGTTACGGTGAAAACCTGGC
```

FIG.94D

CTATTTCCCTAAAGGGTTTATTGAGAATATGTTTTTCGTCTCAGCCAATCCCTGGGTGAG
TTTCACCAGTTTTGATTTAAACGTGGCCAATATGGACAACTTCTTCGCCCCCGTTTTCAC
CATGGGCAAATATTATACGCAAGGCGACAAGGTGCTGATGCCGCTGGCGATTCAGGTTCA
TCATGCCGTCTGTGATGGCTTCCATGTCGGCAGAATGCTTAATGAATTACAACAGTACTG
CGATGAGTGGCAGGGCGGGGCGTAATCTAGAGGATCCGGCTTACTAAAAGCCAGATAACA
GTATGCGTATTTGCGCGCTGATTTTTGCGGTATAAGAATATATACTGATATGTATACCCG
AAGTATGTCAAAAAGAGGTGTGCTATGAAGCAGCGTATTACAGTGACAGTTGACAGCGAC
AGCTATCAGTTGCTCAAGGCATATATGATGTCAATATCTCCGGTCTGGTAAGCACAACCA
TGCAGAATGAAGCCCGTCGTCTGCGTGCCGAACGCTGGAAAGCGGAAAATCAGGAAGGGA
TGGCTGAGGTCGCCCGGTTTATTGAAATGAACGGCTCTTTTGCTGACGAGAACAGGGACT
GGTGAAATGCAGTTTAAGGTTTACACCTATAAAAGAGAGAGCCGTTATCGTCTGTTTGTG
GATGTACAGAGTGATATTATTGACACGCCCGGGCGACGGATGGTGATCCCCCTGGCCAGT
GCACGTCTGCTGTCAGATAAAGTCTCCCGTGAACTTTACCCGGTGGTGCATATCGGGGAT
GAAAGCTGGCGCATGATGACCACCGATATGGCCAGTGTGCCGGTCTCCGTTATCGGGGAA
GAAGTGGCTGATCTCAGCCACCGCGAAAATGACATCAAAAACGCCATTAACCTGATGTTC
TGGGGAATATAAATGTCAGGCTCCCTTATACACAGCCAGTCTGCAGGTCGACCATAGTGA
CTGGATATGTTGTGTTTTACAGTATTATGTAGTCTGTTTTTTATGCAAAATCTAATTTAA
TATATTGATATTTATATCATTTTACGTTTCTCGTTCAGCTTTCTTGTACAAAGTGGTTTG
ATGGCCGCTAAGTAAGTAAGACGTCGAGCTCTAAGTAAGTAACGGCCGCCACCGCGGTGG
AGCTTTGGACTTCTTCGCCAGAGGTTTGGTCAAGTCTCCAATCAAGGTTGTCGGCTTGTC
TACCTTGCCAGAAATTTACGAAAAGATGGAAAAGGGTCAAATCGTTGGTAGATACGTTGT
TGACACTTCTAAATAAGCGAATTTCTTATGATTTATGATTTTTATTATTAAATAAGTTAT
AAAAAAAATAAGTGTATACAAATTTTAAAGTGACTCTTAGGTTTTAAAACGAAAATTCTT
GTTCTTGAGTAACTCTTTCCTGTAGGTCAGGTTGCTTTCTCAGGTATAGCATGAGGTCGC
TCTTATTGACCACACCTCTACCGGCATGCCGAGCAAATGCCTGCAAATCGCTCCCCATTT
CACCCAATTGTAGATATGCTAACTCCAGCAATGAGTTGATGAATCTCGGTGTGTATTTTA
TGTCCTCAGAGGACAATACCTGTTGTAATCGTTCTTCCACACGGATCCCAATTCGCCCTA
TAGTGAGTCGTATTACAATTCACTGGCCGTCGTTTTACAACGTCGTGACTGGGAAAACCC
TGGCGTTACCCAACTTAATCGCCTTGCAGCACATCCCCCTTTCGCCAGCTGGCGTAATAG
CGAAGAGGCCCGCACCGATCGCCCTTCCCAACAGTTGCGCAGCCTGAATGGCGAATGGAC
GCGCCCTGTAGCGGCGCATTAAGCGCGGCGGGTGTGGTGGTTACGCGCAGCGTGACCGCT
ACACTTGCCAGCGCCCTAGCGCCCGCTCCTTTCGCTTTCTTCCCTTCCTTTCTCGCCACG
TTCGCCGGCTTTCCCCGTCAAGCTCTAAATCGGGGGCTCCCTTTAGGGTTCCGATTTAGT
GCTTTACGGCACCTCGACCCCAAAAAACTTGATTAGGGTGATGGTTCACGTAGTGGGCCA
TCGCCCTGATAGACGGTTTTTCGCCCTTTGACGTTGGAGTCCACGTTCTTTAATAGTGGA
CTCTTGTTCCAAACTGGAACAACACTCAACCCTATCTCGGTCTATTCTTTTGATTTATAA
GGGATTTTGCCGATTTCGGCCTATTGGTTAAAAAATGAGCTGATTTAACAAAAATTTAAC
GCGAATTTTAACAAAATATTAACGTTTACAATTTCCTGATGCGGTATTTTCTCCTTACGC
ATCTGTGCGGTATTTCACACCGCATATCGACCGGTCGAGGAGAACTTCTAGTATATCCAC
ATACCTAATATTATTGCCTTATTAAAAATGGAATCGGAACAATTACATCAAAATCCACAT
TCTCTTCAAAATCAATTGTCCTGTACTTCCTTGTTCATGTGTGTTCAAAAACGTTATATT
TATAGGATAATTATACTCTATTTCTCAACAAGTAATTGGTTGTTTGGCCGAGCGGTCTAA
GGCGCCTGATTCAAGAAATATCTTGACCGCAGTTAACTGTGGGAATACTCAGGTATCGTA

FIG.94E

AGATGCAAGAGTTCGAATCTCTTAGCAACCATTATTTTTTTCCTCAACATAACGAGAACA
CACAGGGGCGCTATCGCACAGAATCAAATTCGATGACTGGAAATTTTTTGTTAATTTCAG
AGGTCGCCTGACGCATATACCTTTTTCAACTGAAAAATTGGGAGAAAAAGGAAAGGTGAG
AGGCCGGAACCGGCTTTTCATATAGAATAGAGAAGCGTTCATGACTAAATGCTTGCATCA
CAATACTTGAAGTTGACAATATTATTTAAGGACCTATTGTTTTTTCCAATAGGTGGTTAG
CAATCGTCTTACTTTCTAACTTTTCTTACCTTTTACATTTCAGCAATATATATATATATT
TCAAGGATATACCATTCTAATGTCTGCCCCTATGTCTGCCCCTAAGAAGATCGTCGTTTT
GCCAGGTGACCACGTTGGTCAAGAAATCACAGCCGAAGCCATTAAGGTTCTTAAAGCTAT
TTCTGATGTTCGTTCCAATGTCAAGTTCGATTTCGAAAATCATTTAATTGGTGGTGCTGC
TATCGATGCTACAGGTGTCCCACTTCCAGATGAGGCGCTGGAAGCCTCCAAGAAGGTTGA
TGCCGTTTTGTTAGGTGCTGTGGGTGGTCCTAAATGGGGTACCGGTAGTGTTAGACCTGA
ACAAGGTTTACTAAAAATCCGTAAAGAACTTCAATTGTACGCCAACTTAAGACCATGTAA
CTTTGCATCCGACTCTCTTTTAGACTTATCTCCAATCAAGCCACAATTTGCTAAAGGTAC
TGACTTCGTTGTTGTCAGAGAATTAGTGGGAGGTATTTACTTTGGTAAGAGAAAGGAAGA
CGATGGTGATGGTGTCGCTTGGGATAGTGAACAATACACCGTTCCAGAAGTGCAAAGAAT
CACAAGAATGGCCGCTTTCATGGCCCTACAACATGAGCCACCATTGCCTATTTGGTCCTT
GGATAAAGCTAATGTTTTGGCCTCTTCAAGATTATGGAGAAAAACTGTGGAGGAAACCAT
CAAGAACGAATTCCCTACATTGAAGGTTCAACATCAATTGATTGATTCTGCCGCCATGAT
CCTAGTTAAGAACCCAACCCACCTAAATGGTATTATAATCACCAGCAACATGTTTGGTGA
TATCATCTCCGATGAAGCCTCCGTTATCCCAGGTTCCTTGGGTTTGTTGCCATCTGCGTC
CTTGGCCTCTTTGCCAGACAAGAACACCGCATTTGGTTTGTACGAACCATGCCACGGTTC
TGCTCCAGATTTGCCAAAGAATAAGGTTGACCCTATCGCCACTATCTTGTCTGCTGCAAT
GATGTTGAAATTGTCATTGAACTTGCCTGAAGAAGGTAAGGCCATTGAAGATGCAGTTAA
AAAGGTTTTGGATGCAGGTATCAGAACTGGTGATTTAGGTGGTTCCAACAGTACCACCGA
AGTCGGTGATGCTGTCGCCGAAGAAGTTAAGAAAATCCTTGCTTAAAAAGATTCTCTTTT
TTTATGATATTTGTACATAAACTTTATAAATGAAATTCATAATAGAAACGACACGAAATT
ACAAAATGGAATATGTTCATAGGGTAGACGAAACTATATACGCAATCTACATACATTTAT
CAAGAAGGAGAAAAAGGAGGATAGTAAAGGAATACAGGTAAGCAAATTGATACTAATGGC
TCAACGTGATAAGGAAAAAGAATTGCACTTTAACATTAATATTGACAAGGAGGAGGGCAC
CACACAAAAAGTTAGGTGTAACAGAAAATCATGAAACTACGATTCCTAATTTGATATTGG
AGGATTTTCTCTAAAAAAAAAAAAATACAACAAATAAAAAACACTCAATGACCTGACCAT
TTGATGGAGTTTAAGTCAATACCTTCTTGAACCATTTCCCATAATGGTGAAAGTTCCCTC
AAGAATTTTACTCTGTCAGAAACGGCCTTACGACGTAGTCGATATGGTGCACTCTCAGTA
CAATCTGCTCTGATGCCGCATAGTTAAGCCAGCCCCGACACCCGCCAACACCCGCTGACG
CGCCCTGACGGGCTTGTCTGCTCCCGGCATCCGCTTACAGACAAGCTGTGACCGTCTCCG
GGAGCTGCATGTGTCAGAGGTTTTCACCGTCATCACCGAAACGCGCGA

FIG.94F pDEST33 8815 bp

GCCTTACGCATCTGTGCGGTATTTCACACCGCAGGCAAGTGCACAAACAATACTTAAATA
AATACTACTCAGTAATAACCTATTTCTTAGCATTTTTGACGAAATTTGCTATTTTGTTAG
AGTCTTTTACACCATTTGTCTCCACACCTCCGCTTACATCAACACCAATAACGCCATTTA
ATCTAAGCGCATCACCAACATTTTCTGGCGTCAGTCCACCAGCTAACATAAAATGTAAGC
TTTCGGGGCTCTCTTGCCTTCCAACCCAGTCAGAAATCGAGTTCCAATCCAAAAGTTCAC
CTGTCCCACCTGCTTCTGAATCAAACAAGGGAATAAACGAATGAGGTTTCTGTGAAGCTG
CACTGAGTAGTATGTTGCAGTCTTTTGGAAATACGAGTCTTTTAATAACTGGCAAACCGA
GGAACTCTTGGTATTCTTGCCACGACTCATCTCCATGCAGTTGGACGATATCAATGCCGT
AATCATTGACCAGAGCCAAAACATCCTCCTTAGGTTGATTACGAAACACGCCAACCAAGT
ATTTCGGAGTGCCTGAACTATTTTTATATGCTTTTACAAGACTTGAAATTTTCCTTGCAA
TAACCGGGTCAATTGTTCTCTTTCTATTGGGCACACATATAATACCCAGCAAGTCAGCAT
CGGAATCTAGAGCACATTCTGCGGCCTCTGTGCTCTGCAAGCCGCAAACTTTCACCAATG
GACCAGAACTACCTGTGAAATTAATAACAGACATACTCCAAGCTGCCTTTGTGTGCTTAA
TCACGTATACTCACGTGCTCAATAGTCACCAATGCCCTCCCTCTTGGCCCTCTCCTTTTC
TTTTTTCGACCGAATTAATTCTTAATCGGCAAAAAAAGAAAAGCTCCGGATCAAGATTGT
ACGTAAGGTGACAAGCTATTTTTCAATAAAGAATATCTTCCACTACTGCCATCTGGCGTC
ATAACTGCAAAGTACACATATATTACGATGCTGTCTATTAAATGCTTCCTATATTATATA
TATAGTAATGTCGTTTATGGTGCACTCTCAGTACAATCTGCTCTGATGCCGCATAGTTAA
GCCAGCCCCGACACCCGCCAACACCCGCTGACGCGCCCTGACGGGCTTGTCTGCTCCCGG
CATCCGCTTACAGACAAGCTGTGACCGTCTCCGGGAGCTGCATGTGTCAGAGGTTTTCAC
CGTCATCACCGAAACGCGCGAGACGAAAGGGCCTCGTGATACGCCTATTTTTATAGGTTA
ATGTCATGATAATAATGGTTTCTTAGGACGGATCGCTTGCCTGTAACTTACACGCGCCTC
GTATCTTTTAATGATGGAATAATTTGGGAATTTACTCTGTGTTTATTTATTTTTATGTTT
TGTATTTGGATTTTAGAAAGTAAATAAAGAAGGTAGAAGAGTTACGGAATGAAGAAAAAA
AAATAAACAAAGGTTTAAAAAATTTCAACAAAAAGCGTACTTTACATATATATTTATTAG
ACAAGAAAAGCAGATTAAATAGATATACATTCGATTAACGATAAGTAAAATGTAAAATCA
CAGGATTTTCGTGTGTGGTCTTCTACACAGACAAGATGAAACAATTCGGCATTAATACCT
GAGAGCAGGAAGAGCAAGATAAAAGGTAGTATTTGTTGGCGATCCCCCTAGAGTCTTTTA
CATCTTCGGAAAACAAAAACTATTTTTTCTTTAATTTCTTTTTTTACTTTCTATTTTTAA
TTTATATATTTATATTAAAAAATTTAAATTATAATTATTTTTATAGCACGTGATGAAAAG
GACCCAGGTGGCACTTTTCGGGGAAATGTGCGCGGAACCCCTATTTGTTTATTTTTCTAA
ATACATTCAAATATGTATCCGCTCATGAGACAATAACCCTGATAAATGCTTCAATAATAT
TGAAAAAGGAAGAGTATGAGTATTCAACATTTCCGTGTCGCCCTTATTCCCTTTTTTGCG
GCATTTTGCCTTCCTGTTTTTGCTCACCCAGAAACGCTGGTGAAAGTAAAAGATGCTGAA
GATCAGTTGGGTGCACGAGTGGGTTACATCGAACTGGATCTCAACAGCGGTAAGATCCTT
GAGAGTTTTCGCCCCGAAGAACGTTTTCCAATGATGAGCACTTTTAAAGTTCTGCTATGT
GGCGCGGTATTATCCCGTATTGACGCCGGGCAAGAGCAACTCGGTCGCCGCATACACTAT
TCTCAGAATGACTTGGTTGAGTACTCACCAGTCACAGAAAAGCATCTTACGGATGGCATG

FIG.95B

```
ACAGTAAGAGAATTATGCAGTGCTGCCATAACCATGAGTGATAACACTGCGGCCAACTTA
CTTCTGACAACGATCGGAGGACCGAAGGAGCTAACCGCTTTTTTTCACAACATGGGGGAT
CATGTAACTCGCCTTGATCGTTGGGAACCGGAGCTGAATGAAGCCATACCAAACGACGAG
CGTGACACCACGATGCCTGTAGCAATGGCAACAACGTTGCGCAAACTATTAACTGGCGAA
CTACTTACTCTAGCTTCCCGGCAACAATTAATAGACTGGATGGAGGCGGATAAAGTTGCA
GGACCACTTCTGCGCTCGGCCCTTCCGGCTGGCTGGTTTATTGCTGATAAATCTGGAGCC
GGTGAGCGTGGGTCTCGCGGTATCATTGCAGCACTGGGGCCAGATGGTAAGCCCTCCCGT
ATCGTAGTTATCTACACGACGGGCAGTCAGGCAACTATGGATGAACGAAATAGACAGATC
GCTGAGATAGGTGCCTCACTGATTAAGCATTGGTAACTGTCAGACCAAGTTTACTCATAT
ATACTTTAGATTGATTTAAAACTTCATTTTTAATTTAAAAGGATCTAGGTGAAGATCCTT
TTTGATAATCTCATGACCAAAATCCCTTAACGTGAGTTTTCGTTCCACTGAGCGTCAGAC
CCCGTAGAAAAGATCAAAGGATCTTCTTGAGATCCTTTTTTTCTGCGCGTAATCTGCTGC
TTGCAAACAAAAAAACCACCGCTACCAGCGGTGGTTTGTTTGCCGGATCAAGAGCTACCA
ACTCTTTTTCCGAAGGTAACTGGCTTCAGCAGAGCGCAGATACCAAATACTGTCCTTCTA
GTGTAGCCGTAGTTAGGCCACCACTTCAAGAACTCTGTAGCACCGCCTACATACCTCGCT
CTGCTAATCCTGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGGGGGTTCGTGC
ACACAGCCCAGCTTGGAGCGAACGACCTACACCGAACTGAGATACCTACAGCGTGAGCAT
TGAGAAAGCGCCACGCTTCCCGAAGGGAGAAAGGCGGACAGGTATCCGGTAAGCGGCAGG
GTCGGAACAGGAGAGCGCACGAGGGAGCTTCCAGGGGGGAACGCCTGGTATCTTTATAGT
CCTGTCGGGTTTCGCCACCTCTGACTTGAGCGTCGATTTTTGTGATGCTCGTCAGGGGGG
CCGAGCCTATGGAAAAACGCCAGCAACGCGGCCTTTTTACGGTTCCTGGCCTTTTGCTGG
CCTTTTGCTCACATGTTCTTTCCTGCGTTATCCCCTGATTCTGTGGATAACCGTATTACC
GCCTTTGAGTGAGCTGATACCGCTCGCCGCAGCCGAACGACCGAGCGCAGCGAGTCAGTG
AGCGAGGAAGCGGAAGAGCGCCCAATACGCAAACCGCCTCTCCCCGCGCGTTGGCCGATT
CATTAATGCAGCTGGCACGACAGGTTTCCCGACTGGAAAGCGGGCAGTGAGCGCAACGCA
ATTAATGTGAGTTACCTCACTCATTAGGCACCCCAGGCTTTACACTTTATGCTTCCGGCT
CCTATGTTGTGTGGAATTGTGAGCGGATAACAATTTCACACAGGAAACAGCTATGACCAT
GATTACGCCAAGCTCGGAATTAACCCTCACTAAAGGGAACAAAAGCTGGGTACCGGGCCC
CCCCTCGAGATCCGGGATCGAAGAAATGATGGTAAATGAAATAGGAAATCAAGGAGCATG
AAGGCAAAAGACAAATATAAGGGTCGAACGAAAAATAAAGTGAAAAGTGTTGATATGATG
TATTTGGCTTTGCGGCGCCGAAAAAACGAGTTTACGCAATTGCACAATCATGCTGACTCT
GTGGCGGACCCGCGCTCTTGCCGGCCCGGCGATAACGCTGGGCGTGAGGCTGTGCCCGGC
GGAGTTTTTTGCGCCTGCATTTTCCAAGGTTTACCCTGCGCTAAGGGGCGAGATTGGAGA
AGCAATAAGAATGCCGGTTGGGGTTGCGATGATGACGACCACGACAACTGGTGTCATTAT
TTAAGTTGCCGAAAGAACCTGAGTGCATTTGCAACATGAGTATACTAGAAGAATGAGCCA
AGACTTGCGAGACGCGAGTTTGCCGGTGGTGCGAACAATAGAGCGACCATGACCTTGAAG
GTGAGACGCGCATAACCGCTAGAGTACTTTGAAGAGGAAACAGCAATAGGGTTGCTACCA
GTATAAATAGACAGGTACATACAACACTGGAAATGGTTGTCTGTTTGAGTACGCTTTCAA
TTCATTTGGGTGTGCACTTTATTATGTTACAATATGGAAGGGAACTTTACACTTCTCCTA
TGCACATATATTAATTAAAGTCCAATGCTAGTAGAGAAGGGGGGGTAACACCCCTCCGCGC
```

FIG.95C

TCTTTTCCGATTTTTTTCTAAACCGTGGAATATTTCGGATATCCTTTTGTTGTTTCCGGG
TGTACAATATGGACTTCCTCTTTTCTGGCAACCAAACCCATACATCGGGATTCCTATAAT
ACCTTCGTTGGTCTCCCTAACATGTAGGTGGCGGAGGGGAGATATACAATAGAACAGATA
CCAGACAAGACATAATGGGCTAAACAAGACTACACCAATTACACTGCCTCATTGATGGTG
GTACATAACGAACTAATACTGTAGCCCTAGACTTGATAGCCATCATCATATCGAAGTTTC
ACTACCCTTTTTCCATTTGCCATCTATTGAAGTAATAATAGGCGCATGCAACTTCTTTTC
TTTTTTTTTCTTTTCTCTCTCCCCCGTTGTTGTCTCACCATATCCGCAATGACAAAAAAA
ATGATGGAAGACACTAAAGGAAAAAATTAACGACAAAGACAGCACCAACAGATGTCGTTG
TTCCAGAGCTGATGAGGGGTATCTTCGAACACACGAAACTTTTTCCTTCCTTCATTCACG
CACACTACTCTCTAATGAGCAACGGTATACGGCCTTCCTTCCAGTTACTTGAATTTGAAA
TAAAAAAAGTTTGCCGCTTTGCTATCAAGTATAAATAGACCTGCAATTATTAATCTTTTG
TTTCCTCGTCATTGTTCTCGTTCCCTTTCTTCCTTGTTTCTTTTTCTGCACAATATTTCA
AGCTATACCAAGCATACAATCAACTCCAAGCTTATGCCCAAGAAGAAGCGGAAGGTCTCG
AGCGGCGCCAATTTTAATCAAAGTGGGAATATTGCTGATAGCTCATTGTCCTTCACTTTC
ACTAACAGTAGCAACGGTCCGAACCTCATAACAACTCAAACAAATTCTCAAGCGCTTTCA
CAACCAATTGCCTCCTCTAACGTTCATGATAACTTCATGAATAATGAAATCACGGCTAGT
AAAATTGATGATGGTAATAATTCAAAACCACTGTCACCTGGTTGGACGGACCAAACTGCG
TATAACGCGTTTGGAATCACTACAGGGATGTTTAATACCACTACAATGGATGATGTATAT
AACTATCTATTCGATGATGAAGATACCCCACCAAACCCAAAAAAAGAGGGTGGGTCGAAT
CAAACAAGTTTGTACAAAAAAGCTGAACGAGAAACGTAAAATGATATAAATATCAATATA
TTAAATTAGATTTTGCATAAAAAACAGACTACATAATACTGTAAAACACAACATATCCAG
TCACTATGGCGGCCGCTAAGTTGGCAGCATCACCCGACGCACTTTGCGCCGAATAAATAC
CTGTGACGGAAGATCACTTCGCAGAATAAATAAATCCTGGTGTCCCTGTTGATACCGGGA
AGCCCTGGGCCAACTTTTGGCGAAAATGAGACGTTGATCGGCACGTAAGAGGTTCCAACT
TTCACCATAATGAAATAAGATCACTACCGGGCGTATTTTTTGAGTTATCGAGATTTTCAG
GAGCTAAGGAAGCTAAAATGGAGAAAAAAATCACTGGATATACCACCGTTGATATATCCC
AATGGCATCGTAAAGAACATTTTGAGGCATTTCAGTCAGTTGCTCAATGTACCTATAACC
AGACCGTTCAGCTGGATATTACGGCCTTTTTAAAGACCGTAAAGAAAAATAAGCACAAGT
TTTATCCGGCCTTTATTCACATTCTTGCCCGCCTGATGAATGCTCATCCGGAATTCCGTA
TGGCAATGAAAGACGGTGAGCTGGTGATATGGGATAGTGTTCACCCTTGTTACACCGTTT
TCCATGAGCAAACTGAAACGTTTTCATCGCTCTGGAGTGAATACCACGACGATTTCCGGC
AGTTTCTACACATATATTCGCAAGATGTGGCGTGTTACGGTGAAAACCTGGCCTATTTCC
CTAAAGGGTTTATTGAGAATATGTTTTTCGTCTCAGCCAATCCCTGGGTGAGTTTCACCA
GTTTTGATTTAAACGTGGCCAATATGGACAACTTCTTCGCCCCCGTTTTCACCATGGGCA
AATATTATACGCAAGGCGACAAGGTGCTGATGCCGCTGGCGATTCAGGTTCATCATGCCG
TCTGTGATGGCTTCCATGTCGGCAGAATGCTTAATGAATTACAACAGTACTGCGATGAGT
GGCAGGGCGGGGCGTAATCTAGAGGATCCGGCTTACTAAAAGCCAGATAACAGTATGCGT
ATTTGCGCGCTGATTTTTGCGGTATAAGAATATATACTGATATGTATACCCGAAGTATGT
CAAAAAGAGGTGTGCTATGAAGCAGCGTATTACAGTGACAGTTGACAGCGACAGCTATCA
GTTGCTCAAGGCATATATGATGTCAATATCTCCGGTCTGGTAAGCACAACCATGCAGAAT
GAAGCCCGTCGTCTGCGTGCCGAACGCTGGAAAGCGGAAAATCAGGAAGGGATGGCTGAG

FIG.95D

GTCGCCCGGTTTATTGAAATGAACGGCTCTTTTGCTGACGAGAACAGGGACTGGTGAAAT
GCAGTTTAAGGTTTACACCTATAAAAGAGAGAGCCGTTATCGTCTGTTTGTGGATGTACA
GAGTGATATTATTGACACGCCCGGGCGACGGATGGTGATCCCCCTGGCCAGTGCACGTCT
GCTGTCAGATAAAGTCTCCCGTGAACTTTACCCGGTGGTGCATATCGGGGATGAAAGCTG
GCGCATGATGACCACCGATATGGCCAGTGTGCCGGTCTCCGTTATCGGGGAAGAAGTGGC
TGATCTCAGCCACCGCGAAAATGACATCAAAAACGCCATTAACCTGATGTTCTGGGGAAT
ATAAATGTCAGGCTCCGTTATACACAGCCAGTCTGCAGGTCGACCATAGTGACTGGATAT
GTTGTGTTTTACAGTATTATGTAGTCTGTTTTTTATGCAAAATCTAATTTAATATATTGA
TATTTATATCATTTTACGTTTCTCGTTCAGCTTTCTTGTACAAAGTGGTTTGATGGCCGC
TAAGTAAGTAAGACGTCGAGCTCCCTATAGTGAGTCGTATTACACTGGCCGTCGTTTTAC
AACGTCGTGACTGGGAAAACACCGGTGAGCTCTAAGTAAGTAACGGCCGCCACCGCGGTG
GAGCTTTGGACTTCTTCGCCAGAGGTTTGGTCAAGTCTCCAATCAAGGTTGTCGGCTTGT
CTACCTTGCCAGAAATTTACGAAAAGATGGAAAAGGGTCAAATCGTTGGTAGATACGTTG
TTGACACTTCTAAATAAGCGAATTTCTTATGATTTATGATTTTTATTATTAAATAAGTTA
TAAAAAAAATAAGTGTATACAAATTTTAAAGTGACTCTTAGGTTTTAAAACGAAAATTCT
TGTTCTTGAGTAACTCTTTCCTGTAGGTCAGGTTGCTTTCTCAGGTATAGCATGAGGTCG
CTCTTATTGACCACACCTCTACCGGCATGCCGAGCAAATGCCTGCAAATCGCTCCCCATT
TCACCCAATTGTAGATATGCTAACTCCAGCAATGAGTTGATGAATCTCGGTGTGTATTTT
ATGTCCTCAGAGGACAATACCTGTTGTAATCGTTCTTCCACACGGATCCGCATCAGGCGA
AATTGTAAACGTTAATATTTTGTTAAAATTCGCGTTAAATATTTGTTAAATCAGCTCATT
TTTTAACCAATAGGCCGAAATCGGCAAAATCCCTTATAAATCAAAAGAATAGACCGAGAT
AGGGTTGAGTGTTGTTCCAGTTTGGAACAAGAGTCCACTATTAAAGAACGTGGACTCCAA
CGTCAAAGGGCGAAAAACCGTCTATCAGGGCGATGGCCCACTACGTGAACCATCACCCTA
ATCAAGTTTTTTGGGGTCGAGGTGCCGTAAAGCACTAAATCGGAACCCTAAAGGGAGCCC
CCGATTTAGAGCTTGACGGGGAAAGCCGGCGAACGTGGCGAGAAAGGAAGGGAAGAAAGC
GAAAGGAGCGGGCGCTAGGGCGCTGGCAAGTGTAGCGGTCACGCTGCGCGTAACCACCAC
ACCCGCCGCGCTTAATGCGCCGCTACAGGGCGCGTCCCATTCGCCATTCACTGCA

FIG.95E pDEST34 7114 bp

| Location (Base Nos.) | Gene Encoded |
|---|---|
| 195..71 | attR1 |
| 304..963 | CmR |
| 1305..1610 | ccdB |
| 1651..1775 | attR2 |
| 1780..2472 | GST |
| 2675..2720 | T7stop |
| 3334..4194 | ampR |
| 4343..4982 | ori |

ATCGAGATCTCGATCCCGCGAAATTAATACGACTCACTATAGGGAGACCACAACGGTTTC
CCTCTAGATCACAAGTTTGTACAAAAAAGCTGAACGAGAAACGTAAAATGATATAAATAT
CAATATATTAAATTAGATTTTGCATAAAAAACAGACTACATAATACTGTAAAACACAACA
TATCCAGTCACTATGGCGGCCGCATTAGGCACCCCAGGCTTTACACTTTATGCTTCCGGC
TCGTATAATGTGTGGATTTTGAGTTAGGATCCGGCGAGATTTTCAGGAGCTAAGGAAGCT
AAAATGGAGAAAAAAATCACTGGATATACCACCGTTGATATATCCCAATGGCATCGTAAA
GAACATTTTGAGGCATTTCAGTCAGTTGCTCAATGTACCTATAACCAGACCGTTCAGCTG
GATATTACGGCCTTTTTAAAGACCGTAAAGAAAAATAAGCACAAGTTTTATCCGGCCTTT
ATTCACATTCTTGCCCGCCTGATGAATGCTCATCCGGAATTCCGTATGGCAATGAAAGAC
GGTGAGCTGGTGATATGGGATAGTGTTCACCCTTGTTACACCGTTTTCCATGAGCAAACT
GAAACGTTTTCATCGCTCTGGAGTGAATACCACGACGATTTCCGGCAGTTTCTACACATA
TATTCGCAAGATGTGGCGTGTTACGGTGAAAACCTGGCCTATTTCCCTAAAGGGTTTATT
GAGAATATGTTTTTCGTCTCAGCCAATCCCTGGGTGAGTTTCACCAGTTTTGATTTAAAC
GTGGCCAATATGGACAACTTCTTCGCCCCCGTTTTCACCATGGGCAAATATTATACGCAA
GGCGACAAGGTGCTGATGCCGCTGGCGATTCAGGTTCATCATGCCGTCTGTGATGGCTTC
CATGTCGGCAGAATGCTTAATGAATTACAACAGTACTGCGATGAGTGGCAGGGCGGGGCG
TAAACGCGTGGATCCGGCTTACTAAAAGCCAGATAACAGTATGCGTATTTGCGCGCTGAT
TTTTGCGGTATAAGAATATATACTGATATGTATACCCGAAGTATGTCAAAAAGAGGTGTG
CTATGAAGCAGCGTATTACAGTGACAGTTGACAGCGACAGCTATCAGTTGCTCAAGGCAT
ATATGATGTCAATATCTCCGGTCTGGTAAGCACAACCATGCAGAATGAAGCCCGTCGTCT
GCGTGCCGAACGCTGGAAAGCGGAAAATCAGGAAGGGATGGCTGAGGTCGCCCGGTTTAT
TGAAATGAACGGCTCTTTTGCTGACGAGAACAGGGACTGGTGAAATGCAGTTTAAGGTTT
ACACCTATAAAAGAGAGAGCCGTTATCGTCTGTTTGTGGATGTACAGAGTGATATTATTG
ACACGCCCGGGCGACGGATGGTGATCCCCCTGGCCAGTGCACGTCTGCTGTCAGATAAAG
TCTCCCGTGAACTTTACCCGGTGGTGCATATCGGGGATGAAAGCTGGCGCATGATGACCA
CCGATATGGCCAGTGTGCCGGTCTCCGTTATCGGGGAAGAAGTGGCTGATCTCAGCCACC
GCGAAAATGACATCAAAAACGCCATTAACCTGATGTTCTGGGGAATATAAATGTCAGGCT
CCCTTATACACAGCCAGTCTGCAGGTCGACCATAGTGACTGGATATGTTGTGTTTTACAG
TATTATGTAGTCTGTTTTTTATGCAAAATCTAATTTAATATATTGATATTTATATCATTT
TACGTTTCTCGTTCAGCTTTCTTGTACAAAGTGGTGATTATGTCCCCTATACTAGGTTAT
TGGAAAATTAAGGGCCTTGTGCAACCCACTCGACTTCTTTTGGAATATCTTGAAGAAAAA
TATGAAGAGCATTTGTATGAGCGCGATGAAGGTGATAAATGGCGAAACAAAAAGTTTGAA

FIG.96B

TTGGGTTTGGAGTTTCCCAATCTTCCTTATTATATTGATGGTGATGTTAAATTAACACAG
TCTATGGCCATCATACGTTATATAGCTGACAAGCACAACATGTTGGGTGGTTGTCCAAAA
GAGCGTGCAGAGATTTCAATGCTTGAAGGAGCGGTTTTGGATATTAGATACGGTGTTTCG
AGAATTGCATATAGTAAAGACTTTGAAACTCTCAAAGTTGATTTTCTTAGCAAGCTACCT
GAAATGCTGAAAATGTTCGAAGATCGTTTATGTCATAAAACATATTTAAATGGTGATCAT
GTAACCCATCCTGACTTCATGTTGTATGACGCTCTTGATGTTGTTTTATACATGGACCCA
ATGTGCCTGGATGCGTTCCCAAAATTAGTTTGTTTTAAAAAACGTATTGAAGCTATCCCA
CAAATTGATAAGTACTTGAAATCCAGCAAGTATATAGCATGGCCTTTGCAGGGCTGGCAA
GCCACGTTTGGTGGTGGCGACCATCCTCCAAAATCGGATCTGGTTCCGCGTCCATGGGGA
TCCGGCTGCTAACAAAGCCCGAAAGGAAGCTGAGTTGGCTGCTGCCACCGCTGAGCGCTT
CCCGATAAGGGAGCAGGCCAGTAAAAGCATTACCCGTGGTGGGGTTCCCGAGCGGCCAAA
GGGAGCAGACTCTAAATCTGCCGTCATCGACTTCGAAGGTTCGAATCCTTCCCCCACCAC
CATCACTTTCAAAAGTGAATTCGCTGAGCAATAACTAGCATAACCCCTTGGGGCCTCTAA
ACGGGTCTTGAGGGGTTTTTTGCTGAAAGGAGGAACTATATCCGGATATCCACAGGACGG
GTGTGGTCGCCATGATCGCGTAGTCGATAGTGGCTCCAAGTAGCGAAGCGAGCAGGACTG
GGCGGCGGCCAAAGCGGTCGGACAGTGCTCCGAGAACGGGTGCGCATAGAAATTGCATCA
ACGCATATAGCGCTAGCAGCACGCCATAGTGACTGGCGATGCTGTCGGAATGGACGATAT
CCCGCAAGAGGCCCGGCAGTACCGGCATAACCAAGCCTATGCCTACAGCATCCAGGGTGA
CGGTGCCGAGGATGACGATGAGCGCATTGTTAGATTTCATACACGGTGCCTGACTGCGTT
AGCAATTTAACTGTGATAAACTACCGCATTAAAGCTTATCGATGATAAGCTGTCAAACAT
GAGAATTCTTGAAGACGAAAGGGCCTCGTGATACGCCTATTTTTATAGGTTAATGTCATG
ATAATAATGGTTTCTTAGACGTCAGGTGGCACTTTTCGGGGAAATGTGCGCGGAACCCCT
ATTTGTTTATTTTTCTAAATACATTCAAATATGTATCCGCTCATGAGACAATAACCCTGA
TAAATGCTTCAATAATATTGAAAAAGGAAGAGTATGAGTATTCAACATTTCCGTGTCGCC
CTTATTCCCTTTTTTGCGGCATTTTGCCTTCCTGTTTTTGCTCACCCAGAAACGCTGGTG
AAAGTAAAAGATGCTGAAGATCAGTTGGGTGCACGAGTGGGTTACATCGAACTGGATCTC
AACAGCGGTAAGATCCTTGAGAGTTTTCGCCCCGAAGAACGTTTTCCAATGATGAGCACT
TTTAAAGTTCTGCTATGTGGCGCGGTATTATCCCGTGTTGACGCCGGGCAAGAGCAACTC
GGTCGCCGCATACACTATTCTCAGAATGACTTGGTTGAGTACTCACCAGTCACAGAAAAG
CATCTTACGGATGGCATGACAGTAAGAGAATTATGCAGTGCTGCCATAACCATGAGTGAT
AACACTGCGGCCAACTTACTTCTGACAACGATCGGAGGACCGAAGGAGCTAACCGCTTTT
TTGCACAACATGGGGGATCATGTAACTCGCCTTGATCGTTGGGAACCGGAGCTGAATGAA
GCCATACCAAACGACGAGCGTGACACCACGATGCCTGCAGCAATGGCAACAACGTTGCGC
AAACTATTAACTGGCGAACTACTTACTCTAGCTTCCCGGCAACAATTAATAGACTGGATG
GAGGCGGATAAAGTTGCAGGACCACTTCTGCGCTCGGCCCTTCCGGCTGGCTGGTTTATT
GCTGATAAATCTGGAGCCGGTGAGCGTGGGTCTCGCGGTATCATTGCAGCACTGGGGCCA
GATGGTAAGCCCTCCCGTATCGTAGTTATCTACACGACGGGGAGTCAGGCAACTATGGAT
GAACGAAATAGACAGATCGCTGAGATAGGTGCCTCACTGATTAAGCATTGGTAACTGTCA
GACCAAGTTTACTCATATATACTTTAGATTGATTTAAAACTTCATTTTTAATTTAAAAGG
ATCTAGGTGAAGATCCTTTTTGATAATCTCATGACCAAAATCCCTTAACGTGAGTTTTCG
TTCCACTGAGCGTCAGACCCCGTAGAAAAGATCAAAGGATCTTCTTGAGATCCTTTTTTT
CTGCGCGTAATCTGCTGCTTGCAAACAAAAAAACCACCGCTACCAGCGGTGGTTTGTTTG
CCGGATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTAGCA
CCGCCTACATACCTCGCTCTGCTAATCCTGTTACCAGTGGCTGCTGCCAGTGGCGATAAG
TCGTGTCTTACCGGGTTGGACTCAAGACGATAGTTACCGGATAAGGCGCAGCGGTCGGGC

FIG.96C

TGAACGGGGGGTTCGTGCACACAGCCCAGCTTGGAGCGAACGACCTACACCGAACTGAGA
TACCTACAGCGTGAGCTATGAGAAAGCGCCACGCTTCCCGAAGGGAGAAAGGCGGACAGG
TATCCGGTAAGCGGCAGGGTCGGAACAGGAGAGCGCACGAGGGAGCTTCCAGGGGGAAAC
GCCTGGTATCTTTATAGTCCTGTCGGGTTTCGCCACCTCTGACTTGAGCGTCGATTTTTG
TGATGCTCGTCAGGGGGGCGGAGCCTATGGAAAAACGCCAGCAACGCGGCCTTTTTACGG
TTCCTGGCCTTTTGCTGGCCTTTTGCTCACATGTTCTTTCCTGCGTTATCCCCTGATTCT
GTGGATAACCGTATTACCGCCTTTGAGTGAGCTGATACCGCTCGCCGCAGCCGAACGACC
GAGCGCAGCGAGTCAGTGAGCGAGGAAGCGGAAGAGCGCCTGATGCGGTATTTTCTCCTT
ACGCATCTGTGCGGTATTTCACACCGCATATATGGTGCACTCTCAGTACAATCTGCTCTG
ATGCCGCATAGTTAAGCCAGTATACACTCCGCTATCGCTACGTGACTGGGTCATGGCTGC
GCCCCGACACCCGCCAACACCCGCTGACGCGCCCTGACGGGCTTGTCTGCTCCCGGCATC
CGCTTACAGACAAGCTGTGACCGTCTCCGGGAGCTGCATGTGTCAGAGGTTTTCACCGTC
ATCACCGAAACGCGCGAGGCAGCTGCGGTAAAGCTCATCAGCGTGGTCGTGAAGCGATTC
ACAGATGTCTGCCTGTTCATCCGCGTCCAGCTCGTTGAGTTTCTCCAGAAGCGTTAATGT
CTGGCTTCTGATAAAGCGGGCCATGTTAAGGGCGGTTTTTTCCTGTTTGGTCACTGATGC
CTCCGTGTAAGGGGGATTTCTGTTCATGGGGGTAATGATACCGATGAAACGAGAGAGGAT
GCTCACGATACGGGTTACTGATGATGAACATGCCCGGTTACTGGAACGTTGTGAGGGTAA
ACAACTGGCGGTATGGATGCGGCGGGACCAGAGAAAAATCACTCAGGGTCAATGCCAGCG
CTTCGTTAATACAGATGTAGGTGTTCCACAGGGTAGCCAGCAGCATCCTGCGATGCAGAT
CCGGAACATAATGGTGCAGGGCGCTGACTTCCGCGTTTCCAGACTTTACGAAACACGGAA
ACCGAAGACCATTCATGTTGTTGCTCAGGTCGCAGACGTTTTGCAGCAGCAGTCGCTTCA
CGTTCGCTCGCGTATCGGTGATTCATTCTGCTAACCAGTAAGGCAACCCCGCCAGCCTAG
CCGGGTCCTCAACGACAGGAGCACGATCATGCGCACCCGTGGCCAGGACCCAACGCTGCC
CGAGATGCGCCGCGTGCGGCTGCTGGAGATGGCGGACGCGATGGATATGTTCTGCCAAGG
GTTGGTTTGCGCATTCACAGTTCTCCGCAAGAATTGATTGGCTCCAATTCTTGGAGTGGT
GAATCCGTTAGCGAGGTGCCGCCGGCTTCCATTCAGGTCGAGGTGGCCCGGCTCCATGCA
CCGCGACGCAACGCGGGGAGGCAGACAAGGTATAGGGCGGCGCCTACAATCCATGCCAAC
CCGTTCCATGTGCTCGCCGAGGCGGCATAAATCGCCGTGACGATCAGCGGTCCAGTGATC
GAAGTTAGGCTGGTAAGAGCCGCGAGCGATCCTTGAAGCTGTCCCTGATGGTCGTCATCT
ACCTGCCTGGACAGCATGGCCTGCAACGCGGGCATCCCGATGCCGCCGGAAGCGAGAAGA
ATCATAATGGGGAAGGCCATCCAGCCTCGCGTCGCGAACGCCAGCAAGACGTAGCCCAGC
GCGTCGGCCGCCATGCCGGCGATAATGGCCTGCTTCTCGCCGAAACGTTTGGTGGCGGGA
CCAGTGACGAAGGCTTGAGCGAGGGCGTGCAAGATTCCGAATACCGCAAGCGACAGGCCG
ATCATCGTCGCGCTCCAGCGAAAGCGGTCCTCGCCGAAAATGACCCAGAGCGCTGCCGGC
ACCTGTCCTACGAGTTGCATGATAAAGAAGACAGTCATAAGTGCGGCGACGATAGTCATG
CCCCGCGCCCACCGGAAGGAGCTGACTGGGTTGAAGGCTCTCAAGGGCATCGGTCGATCG
ACGCTCTCCCTTATGCGACTCCTGCATTAGGAAGCAGCCCAGTAGTAGGTTGAGGCCGTT
GAGCACCGCCGCCGCAAGGAATGGTGCATGCAAGGAGATGGCGCCCAACAGTCCCCCGGC
CACGGGGCCTGCCACCATACCCACGCCGAAACAAGCGCTCATGAGCCCGAAGTGGCGAGC
CCGATCTTCCCCATCGGTGATGTCGGCGATATAGGCGCCAGCAACCGCACCTGTGGCGCC
GGTGATGCCGGCCACGATGCGTCCGGCGTAGAGG

FIG.96D pDONR207 5584 bp

GCGAGAGTAGGGAACTGCCAGGCATCAAATAAAACGAAAGGCTCAGTCGGAAGACTGGGC
CTTTCGTTTTATCTGTTGTTTGTCGGTGAACGCTCTCCTGAGTAGGACAAATCCGCCGGG
AGCGGATTTGAACGTTGTGAAGCAACGGCCCGGAGGGTGGCGGGCAGGACGCCCGCCATA
AACTGCCAGGCATCAAACTAAGCAGAAGGCCATCCTGACGGATGGCCTTTTTGCGTTTCT
ACAAACTCTTCCTGGCTAGCGGTAATACGGTTATCCACAGAATCAGGGGATAACGCAGGA
AAGAACATGTGAGCAAAAGGCCAGCAAAAGGCCAGGAACCGTAAAAAGGCCGCGTTGCTG
GCGTTTTTCCATAGGCTCCGCCCCCCTGACGAGCATCACAAAAATCGACGCTCAAGTCAG
AGGTGGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTATCC
GGTAACTATCGTCTTGAGTCCAACCCGGTAAGACACGACTTATCGCCACTGGCAGCAGCC
ACTGGTAACAGGATTAGCAGAGCGAGGTATGTAGGCGGTGCTACAGAGTTCTTGAAGTGG
TGGCCTAACTACGGCTACACTAGAAGGACAGTATTTGGTATCTGCGCTCTGCTGAAGCCA
GTTACCTTCGGAAAAAGAGTTGGTAGCTCTTGATCCGGCAAACAAACCACCGCTGGTAGC
GGTGGTTTTTTTGTTTGCAAGCAGCAGATTACGCGCAGAAAAAAAGGATCTCAAGAAGAT
CCTTTGATCTTTTCTACGGGGTCTGACGCTCAGTGGAACGAAAACTCACGTTAAGGGATT
TTGGTCATGAGCTTGCGCCGTCCCGTCAAGTCAGCGTAATGCTCTGCCAGTGTTACAACC
AATTAACCAATTCTGATTAGAAAAACTCATCGAGCATCAAATGAAACTGCAATTTATTCA
TATCAGGATTATCAATACCATATTTTTGAAAAAGCCGTTTCTGTAATGAAGGAGAAAACT
CACCGAGGCAGTTCCATAGGATGGCAAGATCCTGGTATCGGTCTGCGATTCCGACTCGTC
CAACATCAATACAACCTATTAGTAGCCAACCACTAGAACTATAGCTAGAGTCCTGGGCGA
ACAAACGATGCTCGCCTTCCAGAAAACCGAGGATGCGAACCACTTCATCCGGGGTCAGCA
CCACCGGCAAGCGCCGCGACGGCCGAGGTCTTCCGATCTCCTGAAGCCAGGGCAGATCCG
TGCACAGCACCTTGCCGTAGAAGAACAGCAAGGCCGCCAATGCCTGACGATGCGTGGAGA
CCGAAACCTTGCGCTCGTTCGCCAGCCAGGACAGAAATGCCTCGACTTCGCTGCTGCCCA
AGGTTGCCGGGTGACGCACACCGTGGAAACGGATGAAGGCACGAACCCAGTTGACATAAG
CCTGTTCGGTTCGTAAACTGTAATGCAAGTAGCGTATGCGCTCACGCAACTGGTCCAGAA
CCTTGACCGAACGCAGCGGTGGTAACGGCGCAGTGGCGGTTTTCATGGCTTGTTATGACT
GTTTTTTTGTACAGTCTATGCCTCGGGCATCCAAGCAGCAAGCGCGTTACGCCGTGGGTC
GATGTTTGATGTTATGGAGCAGCAACGATGTTACGCAGCAGCAACGATGTTACGCAGCAG
GGCAGTCGCCCTAAAACAAAGTTAGGTGGCTCAAGTATGGGCATCATTCGCACATGTAGG
CTCGGCCCTGACCAAGTCAAATCCATGCGGGCTGCTCTTGATCTTTTCGGTCGTGAGTTC
GGAGACGTAGCCACCTACTCCCAACATCAGCCGGACTCCGATTACCTCGGGAACTTGCTC
CGTAGTAAGACATTCATCGCGCTTGCTGCCTTCGACCAAGAAGCGGTTGTTGGCGCTCTC
GCGGCTTACGTTCTGCCCAGGTTTGAGCAGCCGCGTAGTGAGATCTATATCTATGATCTC
GCAGTCTCCGGCGAGCACCGGAGGCAGGGCATTGCCACCGCGCTCATCAATCTCCTCAAG
CATGAGGCCAACGCGCTTGGTGCTTATGTGATCTACGTGCAAGCAGATTACGGTGACGAT
CCCGCAGTGGCTCTCTATACAAAGTTGGGCATACGGGAAGAAGTGATGCACTTTGATATC
GACCCAAGTACCGCCACCTAACAATTCGTTCAAGCCGAGATCGGCTTCCCGGCCTAATTT
CCCCTCGTCAAAAATAAGGTTATCAAGTGAGAAATCACCATGAGTGACGACTGAATCCGG
TGAGAATGGCAAAAGTTTATGCATTTCTTTCCAGACTTGTTCAACAGGCCAGCCATTACG
CTCGTCATCAAAATCACTCGCATCAACCAAACCGTTATTCATTCGTGATTGCGCCTGAGC
GAGACGAAATACGCGATCGCTGTTAAAAGGACAATTACAAACAGGAATCGAATGCAACCG
GCGCAGGAACACTGCCAGCGCATCAACAATATTTTCACCTGAATCAGGATATTCTTCTAA
TACCTGGAATGCTGTTTTTCCGGGGATCGCAGTGGTGAGTAACCATGCATCATCAGGAGT
ACGGATAAAATGCTTGATGGTCGGAAGAGGCATAAATTCCGTCAGCCAGTTTAGTCTGAC
CATCTCATCTGTAACATCATTGGCAACGCTACCTTTGCCATGTTTCAGAAACAACTCTGG

FIG.97B

CGCATCGGGCTTCCCATACAAGCGATAGATTGTCGCACCTGATTGCCCGACATTATCGCG
AGCCCATTTATACCCATATAAATCAGCATCCATGTTGGAATTTAATCGCGGCCTCGACGT
TTCCCGTTGAATATGGCTCATAACACCCCCTGTATTACTGTTTATGTAAGCAGACAGTTT
TATTGTTCATGATGATATATTTTTATCTTGTGCAATGTAACATCAGAGATTTTGAGACAC
GGGCCAGAGCTGCAGCTGGATGGCAAATAATGATTTTATTTTGACTGATAGTGACCTGTT
CGTTGCAACAAATTGATAAGCAATGCTTTCTTATAATGCCAACTTTGTACAAGAAAGCTG
AACGAGAAACGTAAAATGATATAAATATCAATATATTAAATTAGATTTTGCATAAAAAAC
AGACTACATAATACTGTAAAACACAACATATCCAGTCACTATGAATCAACTACTTAGATG
GTATTAGTGACCTGTAGTCGACTAAGTTGGCAGCATCACCCGACGCACTTTGCGCCGAAT
AAATACCTGTGACGGAAGATCACTTCGCAGAATAAATAAATCCTGGTGTCCCTGTTGATA
CCGGGAAGCCCTGGGCCAACTTTTGGCGAAAATGAGACGTTGATCGGCACGTAAGAGGTTC
CAACTTTCACCATAATGAAATAAGATCACTACCGGGCGTATTTTTTGAGTTATCGAGATT
TTCAGGAGCTAAGGAAGCTAAAATGGAGAAAAAAATCACTGGATATACCACCGTTGATAT
ATCCCAATGGCATCGTAAAGAACATTTTGAGGCATTTCAGTCAGTTGCTCAATGTACCTA
TAACCAGACCGTTCAGCTGGATATTACGGCCTTTTTAAAGACCGTAAAGAAAAATAAGCA
CAAGTTTTATCCGGCCTTTATTCACATTCTTGCCCGCCTGATGAATGCTCATCCGGAATT
CCGTATGGCAATGAAAGACGGTGAGCTGGTGATATGGGATAGTGTTCACCCTTGTTACAC
CGTTTTCCATGAGCAAACTGAAACGTTTTCATCGCTCTGGAGTGAATACCACGACGATTT
CCGGCAGTTTCTACACATATATTCGCAAGATGTGGCGTGTTACGGTGAAAACCTGGCCTA
TTTCCCTAAAGGGTTTATTGAGAATATGTTTTTCGTCTCAGCCAATCCCTGGGTGAGTTT
CACCAGTTTTGATTTAAACGTGGCCAATATGGACAACTTCTTCGCCCCCGTTTTCACCAT
GGGCAAATATTATACGCAAGGCGACAAGGTGCTGATGCCGCTGGCGATTCAGGTTCATCA
TGCCGTCTGTGATGGCTTCCATGTCGGCAGAATGCTTAATGAATTACAACAGTACTGCGA
TGAGTGGCAGGGCGGGGCGTAATCGCGTGGATCCGGCTTACTAAAAGCCAGATAACAGTA
TGCGTATTTGCGCGCTGATTTTTGCGGTATAAGAATATATACTGATATGTATACCCGAAG
TATGTCAAAAAGAGGTGTGCTATGAAGCAGCGTATTACAGTGACAGTTGACAGCGACAGC
TATCAGTTGCTCAAGGCATATATGATGTCAATATCTCCGGTCTGGTAAGCACAACCATGC
AGAATGAAGCCCGTCGTCTGCGTGCCGAACGCTGGAAAGCGGAAAATCAGGAAGGGATGG
CTGAGGTCGCCCGGTTTATTGAAATGAACGGCTCTTTTGCTGACGAGAACAGGGACTGGT
GAAATGCAGTTTAAGGTTTACACCTATAAAAGAGAGAGCCGTTATCGTCTGTTTGTGGAT
GTACAGAGTGATATTATTGACACGCCCGGGCGACGGATGGTGATCCCCCTGGCCAGTGCA
CGTCTGCTGTCAGATAAAGTCTCCCGTGAACTTTACCCGGTGGTGCATATCGGGGATGAA
AGCTGGCGCATGATGACCACCGATATGGCCAGTGTGCCGGTCTCCGTTATCGGGGAAGAA
GTGGCTGATCTCAGCCACCGCGAAAATGACATCAAAAACGCCATTAACCTGATGTTCTGG
GGAATATAAATGTCAGGCTCCCTTATACACAGCCAGTCTGCAGGTCGATACAGTAGAAAT
TACAGAAACTTTATCACGTTTAGTAAGTATAGAGGCTGAAAATCCAGATGAAGCCGAACG
ACTTGTAAGAGAAAAGTATAAGAGTTGTGAAATTGTTCTTGATGCAGATGATTTTCAGGA
CTATGACACTAGCGTATATGAATAGGTAGATGTTTTTATTTTGTCACACAAAAAAGAGGC
TCGCACCTCTTTTTCTTATTTCTTTTTATGATTTAATACGGCATTGAGGACAATAGCGAG
TAGGCTGGATACGACGATTCCGTTTGAGAAGAACATTTGGAAGGCTGTCGGTCGACTAAG
TTGGCAGCATCACCCGAAGAACATTTGGAAGGCTGTCGGTCGACTACAGGTCACTAATAC
CATCTAAGTAGTTGATTCATAGTGACTGGATATGTTGTGTTTTACAGTATTATGTAGTCT
GTTTTTTATGCAAAATCTAATTTAATATATTGATATTTATATCATTTTACGTTTCTCGTT
CAGCTTTTTTGTACAAAGTTGGCATTATAAAAAAGCATTGCTCATCAATTTGTTGCAACG
AACAGGTCACTATCAGTCAAAATAAAATCATTATTTGGGGCCCGAGATCCATGCTAGCGT
TAAC

FIG.97C pMAB85 pMAB85 7038 bp

GCCTTACGCATCTGTGCGGTATTTCACACCGCAGGCAAGTGCACAAACAATACTTAAATA
AATACTACTCAGTAATAACCTATTTCTTAGCATTTTTGACGAAATTTGCTATTTTGTTAG
AGTCTTTTACACCATTTGTCTCCACACCTCCGCTTACATCAACACCAATAACGCCATTTA
ATCTAAGCGCATCACCAACATTTTCTGGCGTCAGTCCACCAGCTAACATAAAATGTAAGC
TTTCGGGGCTCTCTTGCCTTCCAACCCAGTCAGAAATCGAGTTCCAATCCAAAAGTTCAC
CTGTCCCACCTGCTTCTGAATCAAACAAGGGAATAAACGAATGAGGTTTCTGTGAAGCTG
CACTGAGTAGTATGTTGCAGTCTTTTGGAAATACGAGTCTTTTAATAACTGGCAAACCGA
GGAACTCTTGGTATTCTTGCCACGACTCATCTCCATGCAGTTGGACGATATCAATGCCGT
AATCATTGACCAGAGCCAAAACATCCTCCTTAGGTTGATTACGAAACACGCCAACCAAGT
ATTTCGGAGTGCCTGAACTATTTTTATATGCTTTTACAAGACTTGAAATTTTCCTTGCAA
TAACCGGGTCAATTGTTCTCTTTCTATTGGGCACACATATAATACCCAGCAAGTCAGCAT
CGGAATCTAGAGCACATTCTGCGGCCTCTGTGCTCTGCAAGCCGCAAACTTTCACCAATG
GACCAGAACTACCTGTGAAATTAATAACAGACATACTCCAAGCTGCCTTTGTGTGCTTAA
TCACGTATACTCACGTGCTCAATAGTCACCAATGCCCTCCCTCTTGGCCCTCTCCTTTTC
TTTTTTCGACCGAATTAATTCTTAATCGGCAAAAAAAGAAAAGCTCCGGATCAAGATTGT
ACGTAAGGTGACAAGCTATTTTTCAATAAAGAATATCTTCCACTACTGCCATCTGGCGTC
ATAACTGCAAAGTACACATATATTACGATGCTGTCTATTAAATGCTTCCTATATTATATA
TATAGTAATGTCGTTTATGGTGCACTCTCAGTACAATCTGCTCTGATGCCGCATAGTTAA
GCCAGCCCCGACACCCGCCAACACCCGCTGACGCGCCCTGACGGGCTTGTCTGCTCCCGG
CATCCGCTTACAGACAAGCTGTGACCGTCTCCGGGAGCTGCATGTGTCAGAGGTTTTCAC
CGTCATCACCGAAACGCGCGAGACGAAAGGGCCTCGTGATACGCCTATTTTTATAGGTTA
ATGTCATGATAATAATGGTTTCTTAGGACGGATCGCTTGCCTGTAACTTACACGCGCCTC
GTATCTTTTAATGATGGAATAATTTGGGAATTTACTCTGTGTTTATTTATTTTTATGTTT
TGTATTTGGATTTTAGAAAGTAAATAAAGAAGGTAGAAGAGTTACGGAATGAAGAAAAAA
AAATAAACAAAGGTTTAAAAAATTTCAACAAAAAGCGTACTTTACATATATATTTATTAG
ACAAGAAAAGCAGATTAAATAGATATACATTCGATTAACGATAAGTAAAATGTAAAATCA
CAGGATTTTCGTGTGTGGTCTTCTACACAGACAAGATGAAACAATTCGGCATTAATACCT
GAGAGCAGGAAGAGCAAGATAAAAGGTAGTATTTGTTGGCGATCCCCCTAGAGTCTTTTA
CATCTTCGGAAAACAAAAACTATTTTTTCTTTAATTTCTTTTTTTACTTTCTATTTTTAA
TTTATATATTTATATTAAAAAATTTAAATTATAATTATTTTTATAGCACGTGATGAAAAG
GACCCAGGTGGCACTTTTCGGGGAAATGTGCGCGGAACCCCTATTTGTTTATTTTTCTAA
ATACATTCAAATATGTATCCGCTCATGAGACAATAACCCTGATAAATGCTTCAATAATAT
TGAAAAAGGAAGAGTATGAGTATTCAACATTTCCGTGTCGCCCTTATTCCCTTTTTTGCG
GCATTTTGCCTTCCTGTTTTTGCTCACCCAGAAACGCTGGTGAAAGTAAAAGATGCTGAA
GATCAGTTGGGTGCACGAGTGGGTTACATCGAACTGGATCTCAACAGCGGTAAGATCCTT
GAGAGTTTTCGCCCCGAAGAACGTTTTCCAATGATGAGCACTTTTAAAGTTCTGCTATGT
GGCGCGGTATTATCCCGTATTGACGCCGGGCAAGAGCAACTCGGTCGCCGCATACACTAT
TCTCAGAATGACTTGGTTGAGTACTCACCAGTCACAGAAAAGCATCTTACGGATGGCATG

FIG.98B

```
ACAGTAAGAGAATTATGCAGTGCTGCCATAACCATGAGTGATAACACTGCGGCCAACTTA
CTTCTGACAACGATCGGAGGACCGAAGGAGCTAACCGCTTTTTTTCACAACATGGGGGAT
CATGTAACTCGCCTTGATCGTTGGGAACCGGAGCTGAATGAAGCCATACCAAACGACGAG
CGTGACACCACGATGCCTGTAGCAATGGCAACAACGTTGCGCAAACTATTAACTGGCGAA
CTACTTACTCTAGCTTCCCGGCAACAATTAATAGACTGGATGGAGGCGGATAAAGTTGCA
GGACCACTTCTGCGCTCGGCCCTTCCGGCTGGCTGGTTTATTGCTGATAAATCTGGAGCC
GGTGAGCGTGGGTCTCGCGGTATCATTGCAGCACTGGGGCCAGATGGTAAGCCCTCCCGT
ATCGTAGTTATCTACACGACGGGCAGTCAGGCAACTATGGATGAACGAAATAGACAGATC
GCTGAGATAGGTGCCTCACTGATTAAGCATTGGTAACTGTCAGACCAAGTTTACTCATAT
ATACTTTAGATTGATTTAAAACTTCATTTTTAATTTAAAAGGATCTAGGTGAAGATCCTT
TTTGATAATCTCATGACCAAAATCCCTTAACGTGAGTTTTCGTTCCACTGAGCGTCAGAC
CCCGTAGAAAAGATCAAAGGATCTTCTTGAGATCCTTTTTTTCTGCGCGTAATCTGCTGC
TTGCAAACAAAAAAACCACCGCTACCAGCGGTGGTTTGTTTGCCGGATCAAGAGCTACCA
ACTCTTTTTCCGAAGGTAACTGGCTTCAGCAGAGCGCAGATACCAAATACTGTCCTTCTA
GTGTAGCCGTAGTTAGGCCACCACTTCAAGAACTCTGTAGCACCGCCTACATACCTCGCT
CTGCTAATCCTGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGGGGGTTCGTGC
ACACAGCCCAGCTTGGAGCGAACGACCTACACCGAACTGAGATACCTACAGCGTGAGCAT
TGAGAAAGCGCCACGCTTCCCGAAGGGAGAAAGGCGGACAGGTATCCGGTAAGCGGCAGG
GTCGGAACAGGAGAGCGCACGAGGGAGCTTCCAGGGGGGAACGCCTGGTATCTTTATAGT
CCTGTCGGGTTTCGCCACCTCTGACTTGAGCGTCGATTTTTGTGATGCTCGTCAGGGGGG
CCGAGCCTATGGAAAAACGCCAGCAACGCGGCCTTTTTACGGTTCCTGGCCTTTTGCTGG
CCTTTTGCTCACATGTTCTTTCCTGCGTTATCCCCTGATTCTGTGGATAACCGTATTACC
GCCTTTGAGTGAGCTGATACCGCTCGCCGCAGCCGAACGACCGAGCGCAGCGAGTCAGTG
AGCGAGGAAGCGGAAGAGCGCCCAATACGCAAACCGCCTCTCCCCGCGCGTTGGCCGATT
CATTAATGCAGCTGGCACGACAGGTTTCCCGACTGGAAAGCGGGCAGTGAGCGCAACGCA
ATTAATGTGAGTTACCTCACTCATTAGGCACCCCAGGCTTTACACTTTATGCTTCCGGCT
CCTATGTTGTGTGGAATTGTGAGCGGATAACAATTTCACACAGGAAACAGCTATGACCAT
GATTACGCCAAGCTCGGAATTAACCCTCACTAAAGGGAACAAAAGCTGGGTACCGGGCCC
CCCCTCGAGATCCGGGATCGAAGAAATGATGGTAAATGAAATAGGAAATCAAGGAGCATG
AAGGCAAAAGACAAATATAAGGGTCGAACGAAAAATAAAGTGAAAAGTGTTGATATGATG
TATTTGGCTTTGCGGCGCCGAAAAAACGAGTTTACGCAATTGCACAATCATGCTGACTCT
GTGGCGGACCCGCGCTCTTGCCGGCCCGGCGATAACGCTGGGCGTGAGGCTGTGCCCGGC
GGAGTTTTTTGCGCCTGCATTTTCCAAGGTTTACCCTGCGCTAAGGGGCGAGATTGGAGA
AGCAATAAGAATGCCGGTTGGGGTTGCGATGATGACGACCACGACAACTGGTGTCATTAT
TTAAGTTGCCGAAAGAACCTGAGTGCATTTGCAACATGAGTATACTAGAAGAATGAGCCA
AGACTTGCGAGACGCGAGTTTGCCGGTGGTGCGAACAATAGAGCGACCATGACCTTGAAG
GTGAGACGCGCATAACCGCTAGAGTACTTTGAAGAGGAAACAGCAATAGGGTTGCTACCA
GTATAAATAGACAGGTACATACAACACTGGAAATGGTTGTCTGTTTGAGTACGCTTTCAA
TTCATTTGGGTGTGCACTTTATTATGTTACAATATGGAAGGGAACTTTACACTTCTCCTA
TGCACATATATTAATTAAAGTCCAATGCTAGTAGAGAAGGGGGGTAACACCCCTCCGCGC
```

FIG.98C

TCTTTTCCGATTTTTTTCTAAACCGTGGAATATTTCGGATATCCTTTTGTTGTTTCCGGG
TGTACAATATGGACTTCCTCTTTTCTGGCAACCAAACCCATACATCGGGATTCCTATAAT
ACCTTCGTTGGTCTCCCTAACATGTAGGTGGCGGAGGGGAGATATACAATAGAACAGATA
CCAGACAAGACATAATGGGCTAAACAAGACTACACCAATTACACTGCCTCATTGATGGTG
GTACATAACGAACTAATACTGTAGCCCTAGACTTGATAGCCATCATCATATCGAAGTTTC
ACTACCCTTTTTCCATTTGCCATCTATTGAAGTAATAATAGGCGCATGCAACTTCTTTTC
TTTTTTTTTCTTTTCTCTCTCCCCCGTTGTTGTCTCACCATATCCGCAATGACAAAAAAA
ATGATGGAAGACACTAAAGGAAAAAATTAACGACAAAGACAGCACCAACAGATGTCGTTG
TTCCAGAGCTGATGAGGGGTATCTTCGAACACACGAAACTTTTTCCTTCCTTCATTCACG
CACACTACTCTCTAATGAGCAACGGTATACGGCCTTCCTTCCAGTTACTTGAATTTGAAA
TAAAAAAAGTTTGCCGCTTTGCTATCAAGTATAAATAGACCTGCAATTATTAATCTTTTG
TTTCCTCGTCATTGTTCTCGTTCCCTTTCTTCCTTGTTTCTTTTTCTGCACAATATTTCA
AGCTATACCAAGCATACAATCAACTCCAAGCTTATGCCCAAGAAGAAGCGGAAGGTCTCG
AGCGGCGCCAATTTTAATCAAAGTGGGAATATTGCTGATAGCTCATTGTCCTTCACTTTC
ACTAACAGTAGCAACGGTCCGAACCTCATAACAACTCAAACAAATTCTCAAGCGCTTTCA
CAACCAATTGCCTCCTCTAACGTTCATGATAACTTCATGAATAATGAAATCACGGCTAGT
AAAATTGATGATGGTAATAATTCAAAACCACTGTCACCTGGTTGGACGGACCAAACTGCG
TATAACGCGTTTGGAATCACTACAGGGATGTTTAATACCACTACAATGGATGATGTATAT
AACTATCTATTCGATGATGAAGATACCCCACCAAACCCAAAAAAAGAGGGTGGGTCGATC
ACAAGTTTGTACAAAAAAGCAGGCTTGTCGACCCCGGGAATTCAGATCTACTAGTGCGGC
CGCACGCGTACCCAGCTTTCTTGTACAAAGTGGTGACGTCGAGCTCCCTATAGTGAGTCG
TATTACACTGGCCGTCGTTTTACAACGTCGTGACTGGGAAAACACCGGTGAGCTCTAAGT
AAGTAACGGCCGCCACCGCGGTGGAGCTTTGGACTTCTTCGCCAGAGGTTTGGTCAAGTC
TCCAATCAAGGTTGTCGGCTTGTCTACCTTGCCAGAAATTTACGAAAAGATGGAAAAGGG
TCAAATCGTTGGTAGATACGTTGTTGACACTTCTAAATAAGCGAATTTCTTATGATTTAT
GATTTTTATTATTAAATAAGTTATAAAAAAAATAAGTGTATACAAATTTTAAAGTGACTC
TTAGGTTTTAAAACGAAAATTCTTGTTCTTGAGTAACTCTTTCCTGTAGGTCAGGTTGCT
TTCTCAGGTATAGCATGAGGTCGCTCTTATTGACCACACCTCTACCGGCATGCCGAGCAA
ATGCCTGCAAATCGCTCCCCATTTCACCCAATTGTAGATATGCTAACTCCAGCAATGAGT
TGATGAATCTCGGTGTGTATTTTATGTCCTCAGAGGACAATACCTGTTGTAATCGTTCTT
CCACACGGATCCGCATCAGGCGAAATTGTAAACGTTAATATTTTGTTAAAATTCGCGTTA
AATATTTGTTAAATCAGCTCATTTTTTAACCAATAGGCCGAAATCGGCAAAATCCCTTAT
AAATCAAAAGAATAGACCGAGATAGGGTTGAGTGTTGTTCCAGTTTGGAACAAGAGTCCA
CTATTAAAGAACGTGGACTCCAACGTCAAAGGGCGAAAAACCGTCTATCAGGGCGATGGC
CCACTACGTGAACCATCACCCTAATCAAGTTTTTTGGGGTCGAGGTGCCGTAAAGCACTA
AATCGGAACCCTAAAGGGAGCCCCCGATTTAGAGCTTGACGGGGAAAGCCGGCGAACGTG
GCGAGAAAGGAAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACAGGGCGCGTCC
CATTCGCCATTCACTGCA

FIG.98D pMAB86 7146 bp

```
GACGAAAGGGCCTCGTGATACGCCTATTTTTATAGGTTAATGTCATGATAATAATGGTTT
CTTAGGACGGATCGCTTGCCTGTAACTTACACGCGCCTCGTATCTTTTAATGATGGAATA
ATTTGGGAATTTACTCTGTGTTTATTTATTTTTATGTTTTGTATTTGGATTTTAGAAAGT
AAATAAAGAAGGTAGAAGAGTTACGGAATGAAGAAAAAAAAATAAACAAAGGTTTAAAAA
ATTTCAACAAAAAGCGTACTTTACATATATATTTATTAGACAAGAAAAGCAGATTAAATA
GATATACATTCGATTAACGATAAGTAAAATGTAAAATCACAGGATTTTCGTGTGTGGTCT
TCTACACAGACAAGATGAAACAATTCGGCATTAATACCTGAGAGCAGGAAGAGCAAGATA
AAAGGTAGTATTTGTTGGCGATCCCCCTAGAGTCTTTTACATCTTCGGAAAACAAAAACT
ATTTTTTCTTTAATTTCTTTTTTTACTTTCTATTTTTAATTTATATATTTATATTAAAAA
ATTTAAATTATAATTATTTTTATAGCACGTGATGAAAAGGACCCAGGTGGCACTTTTCGG
GGAAATGTGCGCGGAACCCCTATTTGTTTATTTTTCTAAATACATTCAAATATGTATCCG
CTCATGAGACAATAACCCTGATAAATGCTTCAATAATATTGAAAAAGGAAGAGTATGAGT
ATTCAACATTTCCGTGTCGCCCTTATTCCCTTTTTTGCGGCATTTTGCCTTCCTGTTTTT
GCTCACCCAGAAACGCTGGTGAAAGTAAAAGATGCTGAAGATCAGTTGGGTGCACGAGTG
GGTTACATCGAACTGGATCTCAACAGCGGTAAGATCCTTGAGAGTTTTCGCCCCGAAGAA
CGTTTTCCAATGATGAGCACTTTTAAAGTTCTGCTATGTGGCGCGGTATTATCCCGTATT
GACGCCGGGCAAGAGCAACTCGGTCGCCGCATACACTATTCTCAGAATGACTTGGTTGAG
TACTCACCAGTCACAGAAAAGCATCTTACGGATGGCATGACAGTAAGAGAATTATGCAGT
GCTGCCATAACCATGAGTGATAACACTGCGGCCAACTTACTTCTGACAACGATCGGAGGA
CCGAAGGAGCTAACCGCTTTTTTTCACAACATGGGGGATCATGTAACTCGCCTTGATCGT
TGGGAACCGGAGCTGAATGAAGCCATACCAAACGACGAGCGTGACACCACGATGCCTGTA
GCAATGGCAACAACGTTGCGCAAACTATTAACTGGCGAACTACTTACTCTAGCTTCCCGG
CAACAATTAATAGACTGGATGGAGGCGGATAAAGTTGCAGGACCACTTCTGCGCTCGGCC
CTTCCGGCTGGCTGGTTTATTGCTGATAAATCTGGAGCCGGTGAGCGTGGGTCTCGCGGT
ATCATTGCAGCACTGGGGCCAGATGGTAAGCCCTCCCGTATCGTAGTTATCTACACGACG
GGCAGTCAGGCAACTATGGATGAACGAAATAGACAGATCGCTGAGATAGGTGCCTCACTG
ATTAAGCATTGGTAACTGTCAGACCAAGTTTACTCATATATACTTTAGATTGATTTAAAA
CTTCATTTTTAATTTAAAAGGATCTAGGTGAAGATCCTTTTTGATAATCTCATGACCAAA
ATCCCTTAACGTGAGTTTTCGTTCCACTGAGCGTCAGACCCCGTAGAAAAGATCAAAGGA
TCTTCTTGAGATCCTTTTTTTCTGCGCGTAATCTGCTGCTTGCAAACAAAAAAACCACCG
CTACCAGCGGTGGTTTGTTTGCCGGATCAAGAGCTACCAACTCTTTTTCCGAAGGTAACT
GGCTTCAGCAGAGCGCAGATACCAAATACTGTCCTTCTAGTGTAGCCGTAGTTAGGCCAC
CACTTCAAGAACTCTGTAGCACCGCCTACATACCTCGCTCTGCTAATCCTGTTACCAGTG
GCTGCTGCCAGTGGCGATAAGTCGTGTCTTACCGGGTTGGACTCAAGACGATAGTTACCG
GATAAGGCGCAGCGGTCGGGCTGAACGGGGGGTTCGTGCACACAGCCCAGCTTGGAGCGA
ACGACCTACACCGAACTGAGATACCTACAGCGTGAGCATTGAGAAAGCGCCACGCTTCCC
GAAGGGAGAAAGGCGGACAGGTATCCGGTAAGCGGCAGGGTCGGAACAGGAGAGCGCACG
AGGGAGCTTCCAGGGGGGAACGCCTGGTATCTTTATAGTCCTGTCGGGTTTCGCCACCTC
```

FIG.99B

```
TGACTTGAGCGTCGATTTTTGTGATGCTCGTCAGGGGGGCCGAGCCTATGGAAAAACGCC
AGCAACGCGGCCTTTTTACGGTTCCTGGCCTTTTGCTGGCCTTTTGCTCACATGTTCTTT
CCTGCGTTATCCCCTGATTCTGTGGATAACCGTATTACCGCCTTTGAGTGAGCTGATACC
GCTCGCCGCAGCCGAACGACCGAGCGCAGCGAGTCAGTGAGCGAGGAAGCGGAAGAGCGC
CCAATACGCAAACCGCCTCTCCCCGCGCGTTGGCCGATTCATTAATGCAGCTGGCACGAC
AGGTTTCCCGACTGGAAAGCGGGCAGTGAGCGCAACGCAATTAATGTGAGTTACCTCACT
CATTAGGCACCCCAGGCTTTACACTTTATGCTTCCGGCTCCTATGTTGTGTGGAATTGTG
AGCGGATAACAATTTCACACAGGAAACAGCTATGACCATGATTACGCCAAGCTCGGAATT
AACCCTCACTAAAGGGAACAAAAGCTGGGTACCGGGCCCCCCCTCGAGATCCGGGATCGA
AGAAATGATGGTAAATGAAATAGGAAATCAAGGAGCATGAAGGCAAAAGACAAATATAAG
GGTCGAACGAAAAATAAAGTGAAAAGTGTTGATATGATGTATTTGGCTTTGCGGCGCCGA
AAAAACGAGTTTACGCAATTGCACAATCATGCTGACTCTGTGGCGGACCCGCGCTCTTGC
CGGCCCGGCGATAACGCTGGGCGTGAGGCTGTGCCCGGCGGAGTTTTTTGCGCCTGCATT
TTCCAAGGTTTACCCTGCGCTAAGGGGCGAGATTGGAGAAGCAATAAGAATGCCGGTTGG
GGTTGCGATGATGACGACCACGACAACTGGTGTCATTATTTAAGTTGCCGAAAGAACCTG
AGTGCATTTGCAACATGAGTATACTAGAAGAATGAGCCAAGACTTGCGAGACGCGAGTTT
GCCGGTGGTGCGAACAATAGAGCGACCATGACCTTGAAGGTGAGACGCGCATAACCGCTA
GAGTACTTTGAAGAGGAAACAGCAATAGGGTTGCTACCAGTATAAATAGACAGGTACATA
CAACACTGGAAATGGTTGTCTGTTTGAGTACGCTTTCAATTCATTTGGGTGTGCACTTTA
TTATGTTACAATATGGAAGGGAACTTTACACTTCTCCTATGCACATATATTAATTAAAGT
CCAATGCTAGTAGAGAAGGGGGGTAACACCCCTCCGCGCTCTTTTCCGATTTTTTTCTAA
ACCGTGGAATATTTCGGATATCCTTTTGTTGTTTCCGGGTGTACAATATGGACTTCCTCT
TTTCTGGCAACCAAACCCATACATCGGGATTCCTATAATACCTTCGTTGGTCTCCCTAAC
ATGTAGGTGGCGGAGGGGAGATATACAATAGAACAGATACCAGACAAGACATAATGGGCT
AAACAAGACTACACCAATTACACTGCCTCATTGATGGTGGTACATAACGAACTAATACTG
TAGCCCTAGACTTGATAGCCATCATCATATCGAAGTTTCACTACCCTTTTTCCATTTGCC
ATCTATTGAAGTAATAATAGGCGCATGCAACTTCTTTTCTTTTTTTTTCTTTTCTCTCTC
CCCCGTTGTTGTCTCACCATATCCGCAATGACAAAAAAAATGATGGAAGACACTAAAGGA
AAAAATTAACGACAAAGACAGCACCAACAGATGTCGTTGTTCCAGAGCTGATGAGGGGTA
TCTTCGAACACACGAAACTTTTTCCTTCCTTCATTCACGCACACTACTCTCTAATGAGCA
ACGGTATACGGCCTTCCTTCCAGTTACTTGAATTTGAAATAAAAAAAGTTTGCCGCTTTG
CTATCAAGTATAAATAGACCTGCAATTATTAATCTTTTGTTTCCTCGTCATTGTTCTCGT
TCCCTTTCTTCCTTGTTTCTTTTTCTGCACAATATTTCAAGCTATACCAAGCATACAATC
AACTCCAAGCTTATGCCCAAGAAGAAGCGGAAGGTCTCGAGCGGCGCCAATTTTAATCAA
AGTGGGAATATTGCTGATAGCTCATTGTCCTTCACTTTCACTAACAGTAGCAACGGTCCG
AACCTCATAACAACTCAAACAAATTCTCAAGCGCTTTCACAACCAATTGCCTCCTCTAAC
GTTCATGATAACTTCATGAATAATGAAATCACGGCTAGTAAAATTGATGATGGTAATAAT
TCAAAACCACTGTCACCTGGTTGGACGGACCAAACTGCGTATAACGCGTTTGGAATCACT
ACAGGGATGTTTAATACCACTACAATGGATGATGTATATAACTATCTATTCGATGATGAA
GATACCCCACCAAACCCAAAAAAGAGGGTGGGTCGATCACAAGTTTGTACAAAAAAGCA
GGCTTGTCGACCCCGGGAATTCAGATCTACTAGTGCGGCCGCACGCGTACCCAGCTTTCT
```

FIG.99C

TGTACAAAGTGGTGACGTCGAGCTCTAAGTAAGTAACGGCCGCCACCGCGGTGGAGCTTT
GGACTTCTTCGCCAGAGGTTTGGTCAAGTCTCCAATCAAGGTTGTCGGCTTGTCTACCTT
GCCAGAAATTTACGAAAAGATGGAAAAGGGTCAAATCGTTGGTAGATACGTTGTTGACAC
TTCTAAATAAGCGAATTTCTTATGATTTATGATTTTTATTATTAAATAAGTTATAAAAAA
AATAAGTGTATACAAATTTTAAAGTGACTCTTAGGTTTTAAAACGAAAATTCTTGTTCTT
GAGTAACTCTTTCCTGTAGGTCAGGTTGCTTTCTCAGGTATAGCATGAGGTCGCTCTTAT
TGACCACACCTCTACCGGCATGCCGAGCAAATGCCTGCAAATCGCTCCCCATTTCACCCA
ATTGTAGATATGCTAACTCCAGCAATGAGTTGATGAATCTCGGTGTGTATTTTATGTCCT
CAGAGGACAATACCTGTTGTAATCGTTCTTCCACACGGATCCCAATTCGCCCTATAGTGA
GTCGTATTACAATTCACTGGCCGTCGTTTTACAACGTCGTGACTGGGAAAACCCTGGCGT
TACCCAACTTAATCGCCTTGCAGCACATCCCCCTTTCGCCAGCTGGCGTAATAGCGAAGA
GGCCCGCACCGATCGCCCTTCCCAACAGTTGCGCAGCCTGAATGGCGAATGGACGCGCCC
TGTAGCGGCGCATTAAGCGCGGCGGGTGTGGTGGTTACGCGCAGCGTGACCGCTACACTT
GCCAGCGCCCTAGCGCCCGCTCCTTTCGCTTTCTTCCCTTCCTTTCTCGCCACGTTCGCC
GGCTTTCCCCGTCAAGCTCTAAATCGGGGGCTCCCTTTAGGGTTCCGATTTAGTGCTTTA
CGGCACCTCGACCCCAAAAAACTTGATTAGGGTGATGGTTCACGTAGTGGGCCATCGCCC
TGATAGACGGTTTTTCGCCCTTTGACGTTGGAGTCCACGTTCTTTAATAGTGGACTCTTG
TTCCAAACTGGAACAACACTCAACCCTATCTCGGTCTATTCTTTTGATTTATAAGGGATT
TTGCCGATTTCGGCCTATTGGTTAAAAAATGAGCTGATTTAACAAAAATTTAACGCGAAT
TTTAACAAAATATTAACGTTTACAATTTCCTGATGCGGTATTTTCTCCTTACGCATCTGT
GCGGTATTTCACACCGCAGGCAAGTGCACAAACAATACTTAAATAAATACTACTCAGTAA
TAACCTATTTCTTAGCATTTTTGACGAAATTTGCTATTTTGTTAGAGTCTTTTACACCAT
TTGTCTCCACACCTCCGCTTACATCAACACCAATAACGCCATTTAATCTAAGCGCATCAC
CAACATTTTCTGGCGTCAGTCCACCAGCTAACATAAAATGTAAGCTTTCGGGGCTCTCTT
GCCTTCCAACCCAGTCAGAAATCGAGTTCCAATCCAAAAGTTCACCTGTCCCACCTGCTT
CTGAATCAAACAAGGGAATAAACGAATGAGGTTTCTGTGAAGCTGCACTGAGTAGTATGT
TGCAGTCTTTTGGAAATACGAGTCTTTTAATAACTGGCAAACCGAGGAACTCTTGGTATT
CTTGCCACGACTCATCTCCATGCAGTTGGACGATATCAATGCCGTAATCATTGACCAGAG
CCAAAACATCCTCCTTAGGTTGATTACGAAACACGCCAACCAAGTATTTCGGAGTGCCTG
AACTATTTTTATATGCTTTTACAAGACTTGAAATTTTCCTTGCAATAACCGGGTCAATTG
TTCTCTTTCTATTGGGCACACATATAATACCCAGCAAGTCAGCATCGGAATCTAGAGCAC
ATTCTGCGGCCTCTGTGCTCTGCAAGCCGCAAACTTTCACCAATGGACCAGAACTACCTG
TGAAATTAATAACAGACATACTCCAAGCTGCCTTTGTGTGCTTAATCACGTATACTCACG
TGCTCAATAGTCACCAATGCCCTCCCTCTTGGCCCTCTCCTTTTCTTTTTTCGACCGAAT
TAATTCTTAATCGGCAAAAAAAGAAAAGCTCCGGATCAAGATTGTACGTAAGGTGACAAG
CTATTTTTCAATAAAGAATATCTTCCACTACTGCCATCTGGCGTCATAACTGCAAAGTAC
ACATATATTACGATGCTGTCTATTAAATGCTTCCTATATTATATATATAGTAATGTCGTT
TATGGTGCACTCTCAGTACAATCTGCTCTGATGCCGCATAGTTAAGCCAGCCCCGACACC
CGCCAACACCCGCTGACGCGCCCTGACGGGCTTGTCTGCTCCCGGCATCCGCTTACAGAC
AAGCTGTGACCGTCTCCGGGAGCTGCATGTGTCAGAGGTTTTCACCGTCATCACCGAAAC
GCGCGA

FIG.99D

COMPOSITIONS FOR USE IN RECOMBINATIONAL CLONING OF NUCLEIC ACIDS

CROSS REFERENCE TO RELATED APPLICATIONS

The present application claims the benefit of the filing dates of U.S. Provisional Application Nos. 60/122,389, filed Mar. 2, 1999, 60/126,049, filed Mar. 23, 1999, and 60/136,744, filed May 28, 1999. The present application is also related to U.S. application Ser. No. 08/486,139, filed Jun. 7, 1995 (now abandoned), 08/663,002, filed Jun. 7, 1996 (now U.S. Pat. No. 5,888,732), 09/005,476, filed Jan. 12, 1998 (now U.S. Pat. No. 6,171,861), 09/177,387, filed Oct. 23, 1998 (now abandoned), 09/233,492, filed Jan. 20, 1999 (now U.S. Pat. No. 6,270,969), 09/233,493, filed Jan. 20, 1999 (now U.S. Pat. No. 6,143,557), 09/296,280, filed Apr. 22, 1999 (now U.S. Pat. No. 6,277,608), 09/296,281, filed Apr. 22, 1999 (now abandoned), 09/432,085, filed Nov. 2, 1999 (now U.S. Pat. No. 7,304,130), and 09/438,358, filed Nov. 12, 1999 (now U.S. Pat. No. 6,964,861). The disclosures of all of the applications cross-referenced above are incorporated by reference herein in their entireties.

BACKGROUND OF THE INVENTION

1. Field of the Invention

The present invention relates generally to recombinant DNA technology. More particularly, the present invention relates to compositions and methods for use in recombinational cloning of nucleic acid molecules. The invention relates specifically to nucleic acid molecules encoding one or more recombination sites or one or more partial recombination sites, particularly attB, attP, attL, and attR, and fragments, mutants, variants and derivatives thereof. The invention also relates to such nucleic acid molecules wherein the one or more recombination site nucleotide sequences is operably linked to the one or more additional physical or functional nucleotide sequences. The invention also relates to vectors comprising the nucleic acid molecules of the invention, to host cells comprising the vectors or nucleic acid molecules of the invention, to methods of producing polypeptides and RNAs encoded by the nucleic acid molecules of the invention, and to polypeptides encoded by these nucleic acid molecules or produced by the methods of the invention, which may be fusion proteins. The invention also relates to antibodies that bind to one or more polypeptides of the invention or epitopes thereof, which may be monoclonal or polyclonal antibodies. The invention also relates to the use of these nucleic acid molecules, vectors, polypeptides and antibodies in methods for recombinational cloning of nucleic acids, in vitro and in vivo, to provide chimeric DNA molecules that have particular characteristics and/or DNA segments. More particularly, the antibodies of the invention may be used to identify and/or purify proteins or fusion proteins encoded by the nucleic acid molecules or vectors of the invention, or to identify and/or purify the nucleic acid molecules of the invention.

2. Related Art

Site-specific recombinases. Site-specific recombinases are proteins that are present in many organisms (e.g. viruses and bacteria) and have been characterized to have both endonuclease and ligase properties. These recombinases (along with associated proteins in some cases) recognize specific sequences of bases in DNA and exchange the DNA segments flanking those segments. The recombinases and associated proteins are collectively referred to as "recombination proteins" (see, e.g., Landy, A., *Current Opinion in Biotechnology* 3:699-707 (1993)).

Numerous recombination systems from various organisms have been described. See, e.g., Hoess et al., *Nucleic Acids Research* 14(6):2287 (1986); Abremski et al., *J. Biol. Chem.* 261(1):391 (1986); Campbell, *J. Bacteriol.* 174(23):7495 (1992); Qian et al., *J. Biol. Chem.* 267(11):7794 (1992); Araki et al., *J. Mol. Biol.* 225(1):25 (1992); Maeser and Kahnmann *Mol. Gen. Genet.* 230:170-176) (1991); Esposito et al., *Nucl. Acids Res.* 25(18):3605 (1997).

Many of these belong to the integrase family of recombinases (Argos et al. *EMBO J.* 5:433-440 (1986); Voziyanov et al., *Nucl. Acids Res.* 27:930 (1999)). Perhaps the best studied of these are the Integrase/att system from bacteriophage λ (Landy, A. *Current Opinions in Genetics and Devel.* 3:699-707 (1993)), the Cre/loxP system from bacteriophage P1 (Hoess and Abremski (1990) In *Nucleic Acids and Molecular Biology*, vol. 4. Eds.: Eckstein and Lilley, Berlin-Heidelberg: Springer-Verlag; pp. 90-109), and the FLP/FRT system from the *Saccharomyces cerevisiae* 2μ circle plasmid (Broach et al. *Cell* 29:227-234 (1982)).

Backman (U.S. Pat. No. 4,673,640) discloses the in vivo use of λ recombinase to recombine a protein producing DNA segment by enzymatic site-specific recombination using wild-type recombination sites attB and attP.

Hasan and Szybalski (Gene 56:145-151 (1987)) discloses the use of λ Int recombinase in vivo for intramolecular recombination between wild type attP and attB sites which flank a promoter. Because the orientations of these sites are inverted relative to each other, this causes an irreversible flipping of the promoter region relative to the gene of interest.

Palazzolo et al. *Gene* 88:25-36 (1990), discloses phage lambda vectors having bacteriophage λ arms that contain restriction sites positioned outside a cloned DNA sequence and between wild-type loxP sites. Infection of *E. coli* cells that express the Cre recombinase with these phage vectors results in recombination between the loxP sites and the in vivo excision of the plasmid replicon, including the cloned cDNA.

Pósfai et al. (*Nucl. Acids Res.* 22:2392-2398 (1994)) discloses a method for inserting into genomic DNA partial expression vectors having a selectable marker, flanked by two wild-type FRT recognition sequences. FLP site-specific recombinase as present in the cells is used to integrate the vectors into the genome at predetermined sites. Under conditions where the replicon is functional, this cloned genomic DNA can be amplified.

Bebee et al. (U.S. Pat. No. 5,434,066) discloses the use of site-specific recombinases such as Cre for DNA containing two loxP sites for in vivo recombination between the sites.

Boyd (*Nucl. Acids Res.* 21:817-821 (1993)) discloses a method to facilitate the cloning of blunt-ended DNA using conditions that encourage intermolecular ligation to a dephosphorylated vector that contains a wild-type loxP site acted upon by a Cre site-specific recombinase present in *E. coli* host cells.

Waterhouse et al. (WO 93/19172 and *Nucleic Acids Res.* 21 (9):2265 (1993)) disclose an in vivo method where light and heavy chains of a particular antibody were cloned in different phage vectors between loxP and loxP 511 sites and used to transfect new *E. coli* cells. Cre, acting in the host cells on the two parental molecules (one plasmid, one phage), produced four products in equilibrium: two different cointegrates (produced by recombination at either loxP or loxP 511 sites), and two daughter molecules, one of which was the desired product.

Schlake & Bode (*Biochemistry* 33:12746-12751 (1994)) discloses an in vivo method to exchange expression cassettes at defined chromosomal locations, each flanked by a wild type and a spacer-mutated FRT recombination site. A double-reciprocal crossover was mediated in cultured mammalian cells by using this FLP/FRT system for site-specific recombination.

Hartley et al. (U.S. Pat. No. 5,888,732) disclose compositions and methods for recombinational exchange of nucleic acid segments and molecules, including for use in recombinational cloning of a variety of nucleic acid molecules in vitro and in vivo, using a combination of wildtype and mutated recombination sites and recombination proteins.

Transposases. The family of enzymes, the transposases, has also been used to transfer genetic information between replicons. Transposons are structurally variable, being described as simple or compound, but typically encode the recombinase gene flanked by DNA sequences organized in inverted orientations. Integration of transposons can be random or highly specific. Representatives such as Tn7, which are highly site-specific, have been applied to the in vivo movement of DNA segments between replicons (Lucklow et al., *J. Virol.* 67:4566-4579 (1993)).

Devine and Boeke *Nucl. Acids Res.* 22:3765-3772 (1994), discloses the construction of artificial transposons for the insertion of DNA segments, in vitro, into recipient DNA molecules. The system makes use of the integrase of yeast TY1 virus-like particles. The DNA segment of interest is cloned, using standard methods, between the ends of the transposon-like element TY1. In the presence of the TY1 integrase, the resulting element integrates randomly into a second target DNA molecule.

Recombination Sites. Also key to the integration/recombination reactions mediated by the above-noted recombination proteins and/or transposases are recognition sequences, often termed "recombination sites," on the DNA molecules participating in the integration/recombination reactions. These recombination sites are discrete sections or segments of DNA on the participating nucleic acid molecules that are recognized and bound by the recombination proteins during the initial stages of integration or recombination. For example, the recombination site for Cre recombinase is loxP which is a 34 base pair sequence comprised of two 13 base pair inverted repeats (serving as the recombinase binding sites) flanking an 8 base pair core sequence. See FIG. 1 of Sauer, B., *Curr. Opin. Biotech.* 5:521-527 (1994). Other examples of recognition sequences include the attB, attP, attL, and attR sequences which are recognized by the recombination protein λ Int. attB is an approximately 25 base pair sequence containing two 9 base pair core-type Int binding sites and a 7 base pair overlap region, while attP is an approximately 240 base pair sequence containing core-type Int binding sites and arm-type Int binding sites as well as sites for auxiliary proteins integration host factor (IHF), FIS and excisionase (Xis). See Landy, *Curr. Opin. Biotech.* 3:699-707 (1993); see also U.S. Pat. No. 5,888,732, which is incorporated by reference herein.

DNA cloning. The cloning of DNA segments currently occurs as a daily routine in many research labs and as a prerequisite step in many genetic analyses. The purpose of these clonings is various, however, two general purposes can be considered: (1) the initial cloning of DNA from large DNA or RNA segments (chromosomes, YACs, PCR fragments, mRNA, etc.), done in a relative handful of known vectors such as pUC, pGem, pBlueScript, and (2) the subcloning of these DNA segments into specialized vectors for functional analysis. A great deal of time and effort is expended both in the transfer of DNA segments from the initial cloning vectors to the more specialized vectors. This transfer is called subcloning.

The basic methods for cloning have been known for many years and have changed little during that time. A typical cloning protocol is as follows:

(1) digest the DNA of interest with one or two restriction enzymes;

(2) gel purify the DNA segment of interest when known;

(3) prepare the vector by cutting with appropriate restriction enzymes, treating with alkaline phosphatase, gel purify etc., as appropriate;

(4) ligate the DNA segment to the vector, with appropriate controls to eliminate background of uncut and self-ligated vector;

(5) introduce the resulting vector into an *E. coli* host cell;

(6) pick selected colonies and grow small cultures overnight;

(7) make DNA minipreps; and (8) analyze the isolated plasmid on agarose gels (often after diagnostic restriction enzyme digestions) or by PCR.

The specialized vectors used for subcloning DNA segments are functionally diverse. These include but are not limited to: vectors for expressing nucleic acid molecules in various organisms; for regulating nucleic acid molecule expression; for providing tags to aid in protein purification or to allow tracking of proteins in cells, for modifying the cloned DNA segment (e.g., generating deletions); for the synthesis of probes (e.g., riboprobes); for the preparation of templates for DNA sequencing; for the identification of protein coding regions; for the fusion of various protein-coding regions; to provide large amounts of the DNA of interest, etc. It is common that a particular investigation will involve subcloning the DNA segment of interest into several different specialized vectors.

As known in the art, simple subclonings can be done in one day (e.g., the DNA segment is not large and the restriction sites are compatible with those of the subcloning vector). However, many other subclonings can take several weeks, especially those involving unknown sequences, long fragments, toxic genes, unsuitable placement of restriction sites, high backgrounds, impure enzymes, etc. Subcloning DNA fragments is thus often viewed as a chore to be done as few times as possible.

Several methods for facilitating the cloning of DNA segments have been described, e.g., as in the following references.

Ferguson, J., et al. *Gene* 16:191 (1981), discloses a family of vectors for subcloning fragments of yeast DNA. The vectors encode kanamycin resistance. Clones of longer yeast DNA segments can be partially digested and ligated into the subcloning vectors. If the original cloning vector conveys resistance to ampicillin, no purification is necessary prior to transformation, since the selection will be for kanamycin.

Hashimoto-Gotoh, T., et al. *Gene* 41:125 (1986), discloses a subcloning vector with unique cloning sites within a streptomycin sensitivity gene; in a streptomycin-resistant host, only plasmids with inserts or deletions in the dominant sensitivity gene will survive streptomycin selection.

Accordingly, traditional subcloning methods, using restriction enzymes and ligase, are time consuming and relatively unreliable. Considerable labor is expended, and if two or more days later the desired subclone can not be found among the candidate plasmids, the entire process must then be repeated with alternative conditions attempted. Although site specific recombinases have been used to recombine DNA in vivo, the successful use of such enzymes in vitro was expected to suffer from several problems. For example, the site specificities and efficiencies were expected to differ in vitro; topologically linked products were expected; and the topology of the DNA substrates and recombination proteins was expected to differ significantly in vitro (see, e.g., Adams et al, *J. Mol. Biol.* 226:661-73 (1992)). Reactions that could go on for many hours in vivo were expected to occur in significantly less time in vitro before the enzymes became inactive. In addition, the stabilities of the recombination enzymes after incubation for extended periods of time in in vitro reactions was unknown, as were the effects of the topologies (i.e., linear, coiled, supercoiled, etc.) of the nucleic acid molecules involved in the reaction. Multiple DNA recombination products were expected in the biological host used, resulting in unsatisfactory reliability, specificity or efficiency of subcloning. Thus, in vitro recombination reactions were not expected to be sufficiently efficient to yield the desired levels of product.

Accordingly, there is a long felt need to provide an alternative subcloning system that provides advantages over the known use of restriction enzymes and ligases.

SUMMARY OF THE INVENTION

The present invention relates to nucleic acid molecules encoding one or more recombination sites or one or more partial recombination sites, particularly attB, attP, attL, and attR, and fragments, mutants, variants and derivatives thereof. The invention also relates to such nucleic acid molecules comprising one or more of the recombination site nucleotide sequences or portions thereof and one or more additional physical or functional nucleotide sequences, such as those encoding one or more multiple cloning sites, one or more transcription termination sites, one or more transcriptional regulatory sequences (e.g., one or more promoters, enhancers, or repressors), one or more translational signal sequences, one or more nucleotide sequences encoding a fusion partner protein or peptide (e.g., GST, $His_6$ or thioredoxin), one or more selection markers or modules, one or more nucleotide sequences encoding localization signals such as nuclear localization signals or secretion signals, one or more origins of replication, one or more protease cleavage sites, one or more desired proteins or peptides encoded by a gene or a portion of a gene, and one or more 5' or 3' polynucleotide tails (particularly a poly-G tail). The invention also relates to such nucleic acid molecules wherein the one or more recombination site nucleotide sequences is operably linked to the one or more additional physical or functional nucleotide sequences.

The invention also relates to primer nucleic acid molecules comprising the recombination site nucleotide sequences of the invention (or portions thereof), and to such primer nucleic acid molecules linked to one or more target-specific (e.g., one or more gene-specific) primer-nucleic acid sequences. Such primers may also comprise sequences complementary or homologous to DNA or RNA sequences to be amplified, e.g., by PCR, RT-PCR, etc. Such primers may also comprise sequences or portions of sequences useful in the expression of protein genes (ribosome binding sites, localization signals, protease cleavage sites, repressor binding sites, promoters, transcription stops, stop codons, etc.). Said primers may also comprise sequences or portions of sequences useful in the manipulation of DNA molecules (restriction sites, transposition sites, sequencing primers, etc.). The primers of the invention may be used in nucleic acid synthesis and preferably are used for amplification (e.g., PCR) of nucleic acid molecules. When the primers of the invention include target- or gene-specific sequences (any sequence contained within the target to be synthesized or amplified including translation signals, gene sequences, stop codons, transcriptional signals (e.g., promoters) and the like), amplification or synthesis of target sequences or genes may be accomplished. Thus, the invention relates to synthesis of a nucleic acid molecules comprising mixing one or more primers of the invention with a nucleic acid template, and incubating said mixture under conditions sufficient to make a first nucleic acid molecule complementary to all or a portion of said template. Thus, the invention relates specifically to a method of synthesizing a nucleic acid molecule comprising:

(a) mixing a nucleic acid template with a polypeptide having polymerase activity and one or more primers comprising one or more recombination sites or portions thereof; and (b) incubating said mixture under conditions sufficient to synthesize a first nucleic acid molecule complementary to all or a portion of said template and which preferably comprises one or more recombination sites or portions thereof.

Such method of the invention may further comprise incubating said first synthesized nucleic acid molecule under conditions sufficient to synthesize a second nucleic acid molecule complementary to all or a portion of said first nucleic acid molecule. Such synthesis may provide for a first nucleic acid molecule having a recombination site or portion thereof at one or both of its termini.

In a preferred aspect, for the synthesis of the nucleic acid molecules, at least two primers are used wherein each primer comprises a homologous sequence at its terminus and/or within internal sequences of each primer (which may have a homology length of about 2 to about 500 bases, preferably about 3 to about 100 bases, about 4 to about 50 bases, about 5 to about 25 bases and most preferably about 6 to about 18 base overlap). In a preferred aspect, the first such primer comprises at least one target-specific sequence and at least one recombination site or portion thereof while the second primer comprises at least one recombination site or portion thereof. Preferably, the homologous regions between the first and second primers comprise at least a portion of the recombination site. In another aspect, the homologous regions between the first and second primers may comprise one or more additional sequences, e.g., expression signals, translational start motifs, or other sequences adding functionality to the desired nucleic acid sequence upon amplification. In practice, two pairs of primers prime synthesis or amplification of a nucleic acid molecule. In a preferred aspect, all or at least a portion of the synthesized or amplified nucleic acid molecule will be homologous to all or a portion of the template and further comprises a recombination site or a portion thereof at least one terminus and preferably both termini of the synthesized or amplified molecule. Such synthesized or amplified nucleic acid molecule may be double stranded or single stranded and may be used in the recombinational cloning methods of the invention. The homologous primers of the invention provide a substantial advantage in that one set of the primers may be standardized for any synthesis or amplification reaction. That is, the primers providing the recombination site sequences (without the target specific sequences) can be pre-made and readily available for use. This in practice allows the use of shorter custom made primers that contain the target specific sequence needed to synthesize or amplify the desired nucleic acid molecule. Thus, this provides reduced time and cost in preparing target specific primers (e.g., shorter primers containing the target specific sequences can be prepared and used in synthesis reactions). The standardized primers, on the other hand, may be produced in mass to reduce cost and can be readily provided (e.g., in kits or as a product) to facilitate synthesis of the desired nucleic acid molecules.

Thus, in one preferred aspect, the invention relates to a method of synthesizing or amplifying one or more nucleic acid molecules comprising:

(a) mixing one or more nucleic acid templates with at least one polypeptide having polymerase or reverse transcriptase activity and at least a first primer comprising a template specific sequence (complementary to or capable of hybridizing to said templates) and at least a second primer comprising all or a portion of a recombination site wherein said at least a portion of said second primer is homologous to or complementary to at least a portion of said first primer; and (b) incubating said mixture under conditions sufficient to synthesize or amplify one or more nucleic acid molecules complementary to all or a portion of said templates and comprising one or more recombination sites or portions thereof at one and preferably both termini of said molecules.

More specifically, the invention relates to a method of synthesizing or amplifying one or more nucleic acid molecules comprising:

(a) mixing one or more nucleic acid templates with at least one polypeptide having polymerase or reverse transcriptase activity and at least a first primer comprising a template specific sequence (complementary to or capable of hybridizing to said templates) and at least a portion of a recombination site, and at least a second primer comprising all or a portion of a recombination site wherein said at least a portion of said recombination site on said second primer is complementary to or homologous to at least a portion of said recombination site on said first primer; and (b) incubating said mixture under conditions sufficient to synthesize or amplify one or more nucleic acid molecules complementary to all or a portion of said templates and comprising one or more recombination sites or portions thereof at one and preferably both termini of said molecules.

In a more preferred aspect, the invention relates to a method of amplifying or synthesizing one or more nucleic acid molecules comprising:

(a) mixing one or more nucleic acid templates with at least one polypeptide having polymerase or reverse transcriptase activity and one or more first primers comprising at least a portion of a recombination site and a template specific sequence (complementary to or capable of hybridizing to said template);

(b) incubating said mixture under conditions sufficient to synthesize or amplify one or more first nucleic acid molecules complementary to all or a portion of said templates wherein said molecules comprise at least a portion of a recombination site at one and preferably both termini of said molecules;

(c) mixing said molecules with one or more second primers comprising one or more recombination sites, wherein said recombination sites of said second primers are homologous to or complementary to at least a portion of said recombination sites on said first nucleic acid molecules; and (d) incubating said mixture under conditions sufficient to synthesize or amplify one or more second nucleic acid molecules complementary to all or a portion of said first nucleic acid molecules and which comprise one or more recombination sites at one and preferably both termini of said molecules.

The invention also relates to vectors comprising the nucleic acid molecules of the invention, to host cells comprising the vectors or nucleic acid molecules of the invention, to methods of producing polypeptides encoded by the nucleic acid molecules of the invention, and to polypeptides encoded by these nucleic acid molecules or produced by the methods of the invention, which may be fusion proteins. The invention also relates to antibodies that bind to one or more polypeptides of the invention or epitopes thereof, which may be monoclonal or polyclonal antibodies. The invention also relates to the use of these nucleic acid molecules, primers, vectors, polypeptides and antibodies in methods for recombinational cloning of nucleic acids, in vitro and in vivo, to provide chimeric DNA molecules that have particular characteristics and/or DNA segments.

The antibodies of the invention may have particular use to identify and/or purify peptides or proteins (including fusion proteins produced by the invention), and to identify and/or purify the nucleic acid molecules of the invention or portions thereof.

The methods for in vitro or in vivo recombinational cloning of nucleic acid molecule generally relate to recombination between at least a first nucleic acid molecule having at least one recombination site and a second nucleic acid molecule having at least one recombination site to provide a chimeric nucleic acid molecule. In one aspect, the methods relate to recombination between and first vector having at least one recombination site and a second vector having at least one recombination site to provide a chimeric vector. In another aspect, a nucleic acid molecule having at least one recombination site is combined with a vector having at least one recombination site to provide a chimeric vector. In a most preferred aspect, the nucleic acid molecules or vectors used in recombination comprise two or more recombination sites. In a more specific embodiment of the invention, the recombination methods relate to a Destination Reaction (also referred to herein as an "LR reaction") in which recombination occurs between an Entry clone and a Destination Vector. Such a reaction transfers the nucleic acid molecule of interest from the Entry Clone into the Destination Vector to create an Expression Clone. The methods of the invention also specifically relate to an Entry or Gateward reaction (also referred to herein as a "BP reaction") in which an Expression Clone is recombined with a Donor vector to produce an Entry clone. In other aspects, the invention relates to methods to prepare Entry clones by combining an Entry vector with at least one nucleic acid molecule (e.g., gene or portion of a gene). The invention also relates to conversion of a desired vector into a Destination Vector by including one or more (preferably at least two) recombination sites in the vector of interest. In a more preferred aspect, a nucleic acid molecule (e.g., a cassette) having at least two recombination sites flanking a selectable marker (e.g., a toxic gene or a genetic element preventing the survival of a host cell containing that gene or element, and/or preventing replication, partition or heritability of a nucleic acid molecule (e.g., a vector or plasmid) comprising that gene or element) is added to the vector to make a Destination Vector of the invention.

Preferred vectors for use in the invention include prokaryotic vectors, eukaryotic vectors, or vectors which may shuttle between various prokaryotic and/or eukaryotic systems (e.g. shuttle vectors). Preferred prokaryotic vectors for use in the invention include but are not limited to vectors which may propagate and/or replicate in gram negative and/or gram positive bacteria, including bacteria of the genera *Escherichia, Salmonella, Proteus, Clostridium, Klebsiella, Bacillus, Streptomyces*, and *Pseudomonas* and preferably in the species *E. coli*. Eukaryotic vectors for use in the invention include vectors which propagate and/or replicate and yeast cells, plant cells, mammalian cells, (particularly human and mouse), fungal cells, insect cells, nematode cells, fish cells and the like. Particular vectors of interest include but are not limited to cloning vectors, sequencing vectors, expression vectors, fusion vectors, two-hybrid vectors, gene therapy vectors, phage display vectors, gene-targeting vectors, PACs, BACs, YACs, MACs, and reverse two-hybrid vectors. Such vectors may be used in prokaryotic and/or eukaryotic systems depending on the particular vector.

In another aspect, the invention relates to kits which may be used in carrying out the methods of the invention, and more specifically relates to cloning or subcloning kits and kits for carrying out the LR Reaction (e.g., making an Expression Clone), for carrying out the BP Reaction (e.g., making an Entry Clone), and for making Entry Clone and Destination Vector molecules of the invention. Such kits may comprise a carrier or receptacle being compartmentalized to receive and hold therein any number of containers. Such containers may contain any number of components for carrying out the methods of the invention or combinations of such components. In particular, a kit of the invention may comprise one or more components (or combinations thereof) selected from the group consisting of one or more recombination proteins or auxiliary factors or combinations thereof, one or more compositions comprising one or more recombination proteins or auxiliary factors or combinations thereof (for example, GATEWAY™ LR Clonase™ Enzyme Mix or GATEWAY™ BP Clonase™ Enzyme Mix), one or more reaction buffers, one or more nucleotides, one or more primers of the invention, one or more restriction enzymes, one or more ligases, one or more polypeptides having polymerase activity (e.g., one or more reverse transcriptases or DNA polymerases), one or more proteinases (e.g., proteinase K or other proteinases), one or more Destination Vector molecules, one or more Entry Clone molecules, one or more host cells (e.g. competent cells, such as *E. coli* cells, yeast cells, animal cells (including mammalian cells, insect cells, nematode cells, avian cells, fish cells, etc.), plant cells, and most particularly *E. coli* DB3.1 host cells, such as *E. coli* LIBRARY EFFICIENCY® DB3.1™ Competent Cells), instructions for using the kits of the invention (e.g., to carry out the methods of the invention), and the like. In related aspects, the kits of the invention may comprise one or more nucleic acid molecules encoding one or more recombination sites or portions thereof, particularly one or more nucleic acid molecules comprising a nucleotide sequence encoding the one or more recombination sites or portions thereof of the invention. Preferably, such nucleic acid molecules comprise at least two recombination sites which flank a selectable marker (e.g., a toxic gene and/or antibiotic resistance gene). In a preferred aspect, such nucleic acid molecules are in the form of a cassette (e.g., a linear nucleic acid molecule comprising one or more and preferably two or more recombination sites or portions thereof).

Kits for inserting or adding recombination sites to nucleic acid molecules of interest may comprise one or more nucleases (preferably restriction endonucleases), one or more ligases, one or more topoisomerases, one or more polymerases, and one or more nucleic acid molecules or adapters comprising one or more recombination sites. Kits for integrating recombination sites into one or more nucleic acid molecules of interest may comprise one or more components (or combinations thereof) selected from the group consisting of one or more integration sequences comprising one or more recombination sites. Such integration sequences may comprise one or more transposons, integrating viruses, homologous recombination sequences, RNA molecules, one or more host cells and the like.

Kits for making the Entry Clone molecules of the invention may comprise any or a number of components and the composition of such kits may vary depending on the specific method involved. Such methods may involve inserting the nucleic acid molecules of interest into an Entry or Donor Vector by the recombinational cloning methods of the invention, or using conventional molecular biology techniques (e.g., restriction enzyme digestion and ligation). In a preferred aspect, the Entry Clone is made using nucleic acid amplification or synthesis products. Kits for synthesizing Entry Clone molecules from amplification or synthesis products may comprise one or more components (or combinations thereof) selected from the group consisting of one or more Donor Vectors (e.g., one or more attP vectors including, but not limited to, pDONR201 (FIG. 49), pDONR202 (FIG. 50), pDONR203 (FIG. 51), pDONR204 (FIG. 52), pDONR205 (FIG. 53), pDONR206 (FIG. 53), and the like), one or more polypeptides having polymerase activity (preferably DNA polymerases and most preferably thermostable DNA polymerases), one or more proteinases, one or more reaction buffers, one or more nucleotides, one or more primers comprising one or more recombination sites or portions thereof, and instructions for making one or more Entry Clones.

Kits for making the Destination vectors of the invention may comprise any number of components and the compositions of such kits may vary depending on the specific method involved. Such methods may include the recombination methods of the invention or conventional molecular biology techniques (e.g., restriction endonuclease digestion and ligation). In a preferred aspect, the Destination vector is made by inserting a nucleic acid molecule comprising at least one recombination site (or portion thereof) of the invention (preferably a nucleic acid molecule comprising at least two recombination sites or portions thereof flanking a selectable marker) into a desired vector to convert the desired vector into a Destination vector of the invention. Such kits may comprise at least one component (or combinations thereof) selected from the group consisting of one or more restriction endonucleases, one or more ligases, one or more polymerases, one or more nucleotides, reaction buffers, one or more nucleic acid molecules comprising at least one recombination site or portion thereof (preferably at least one nucleic acid molecule comprising at least two recombination sites flanking at least one selectable marker, such as a cassette comprising at least one selectable marker such as antibiotic resistance genes and/or toxic genes), and instructions for making such Destination vectors.

The invention also relates to kits for using the antibodies of the invention in identification and/or isolation of peptides and proteins (which may be fusion proteins) produced by the nucleic acid molecules of the invention, and for identification and/or isolation of the nucleic acid molecules of the invention or portions thereof. Such kits may comprise one or more components (or combination thereof) selected from the group consisting of one or more antibodies of the invention, one or more detectable labels, one or more solid supports and the like.

Other preferred embodiments of the present invention will be apparent to one of ordinary skill in light of what is known in the art, in light of the following drawings and description of the invention, and in light of the claims.

BRIEF DESCRIPTION OF THE DRAWINGS

FIG. 6 shows the sequences of the attB1 (SEQ ID NO:1) and attB2 (SEQ ID NO:2) sites flanking a gene of interest after subcloning into a Destination Vector to create an Expression Clone.

FIG. 7 is a schematic depiction of four ways to make Entry Clones using the compositions and methods of the invention: 1. using restriction enzymes and ligase; 2. starting with a cDNA library prepared in an attL Entry Vector; 3. using an Expression Clone from a library prepared in an attB Expression Vector via the BxP reaction; and 4. recombinational cloning of PCR fragments with terminal attB sites, via the BxP reaction. Approaches 3 and 4 rely on recombination with a Donor vector (here, an attP vector such as pDONR201 (see FIGS. 49A-C), pDONR202 (see FIGS. 50A-C), pDONR203 (see FIGS. 51A-C), pDONR204 (see FIGS. 52A-C), pDONR205 (see FIGS. 53A-C), or pDONR206 (see FIGS. 54A-C), for example) that provides an Entry Clone carrying a selection marker such as $kan^r$, $gen^r$, $tet^r$, or the like.

FIG. 9 is a listing of the nucleotide sequences of the recombination sites designated herein as attB1, attB2, attP1, attP2, attL1, attL2, attR1 and attR2 (SEQ ID NOs:1-8, respectively). Sequences are written conventionally, from 5' to 3'.

FIG. 11 is a schematic depiction of the cloning sites (FIG. 11A) (SEQ ID NO:188, SEQ ID NO:189, SEQ ID NO:190, and SEQ ID NO:191) and the nucleotide sequence (FIG. 11B) (SEQ ID NO:119) of the Entry Vector pENTR2B.

FIG. 12 is a schematic depiction of the cloning sites (FIG. 12A) (SEQ ID NO:192, SEQ ID NO:193, SEQ ID NO:194, and SEQ ID NO:195) and the nucleotide sequence (FIG. 12B) (SEQ ID NO:120) of the Entry Vector pENTR3c.

FIG. 13 is a schematic depiction of the cloning sites (FIG. 13A) (SEQ ID NO:196, SEQ ID NO:197, SEQ ID NO:198, and SEQ ID NO:199) and the nucleotide sequence (FIG. 13B) (SEQ ID NO:121) of the Entry Vector pENTR4.

FIG. 14 is a schematic depiction of the cloning sites (FIG. 14A) (SEQ ID NO:200, SEQ ID NO:201, and SEQ ID NO:202) and the nucleotide sequence (FIG. 14B) (SEQ ID NO:122) of the Entry Vector pENTR5.

FIG. 15 is a schematic depiction of the cloning sites (FIG. 15A) (SEQ ID NO:203, SEQ ID NO:204, and SEQ ID NO:205) and the nucleotide sequence (FIG. 15B) (SEQ ID NO:123) of the Entry Vector pENTR6.

FIG. 16 is a schematic depiction of the cloning sites (FIG. 16A) (SEQ ID NO:206, SEQ ID NO:207, and SEQ ID NO:208) and the nucleotide sequence (FIG. 16B) (SEQ ID NO:124) of the Entry Vector pENTR7.

FIG. 17 is a schematic depiction of the cloning sites (FIG. 17A) (SEQ ID NO:209, SEQ ID NO:210, and SEQ ID NO:211) and the nucleotide sequence (FIG. 17B) (SEQ ID NO:125) of the Entry Vector pENTR8.

FIG. 18 is a schematic depiction of the cloning sites (FIG. 18A) (SEQ ID NO:212, SEQ ID NO:213, and SEQ ID NO:214) and the nucleotide sequence (FIG. 18B) (SEQ ID NO:126) of the Entry Vector pENTR9.

FIG. 19 is a schematic depiction of the cloning sites (FIG. 19A) (SEQ ID NO:215, SEQ ID NO:216, and SEQ ID NO:217) and the nucleotide sequence (FIG. 19B) (SEQ ID NO:127) of the Entry Vector pENTR10.

FIG. 20 is a schematic depiction of the cloning sites (FIG. 20A) (SEQ ID NO:218, SEQ ID NO:219, and SEQ ID NO:220) and the nucleotide sequence (FIG. 20B) (SEQ ID NO:128) of the Entry Vector pENTR11.

FIG. 21 is a schematic depiction of the physical map and the Trc expression cassette (FIG. 21A) (SEQ ID NO:222) showing the promoter sequences at -35 and at -10 from the initiation codon, and the nucleotide sequence (FIGS. 21B-D) (SEQ ID NO:129), of Destination Vector pDEST1. This vector may also be referred to as pTrc-DEST1.

FIG. 22 is a schematic depiction of the physical map and the His6 expression cassette (FIG. 22A) (SEQ ID NO:223 and SEQ ID NO:224) showing the promoter sequences at -35 and at -10 from the initiation codon, and the nucleotide sequence (FIGS. 22B-D) (SEQ ID NO:130), of Destination Vector pDEST2. This vector may also be referred to as pHis6-DEST2.

FIG. 23 is a schematic depiction of the physical map and the GST expression cassette (FIG. 23A) (SEQ ID NO:225, SEQ ID NO:226, SEQ ID NO:227, and SEQ ID NO:228) showing the promoter sequences at −35 and at −10 from the initiation codon, and the nucleotide sequence (FIGS. 23B-D) (SEQ ID NO:131), of Destination Vector pDEST3. This vector may also be referred to as pGST-DEST3.

FIG. 24 is a schematic depiction of the physical map and the His6-Trx expression cassette (FIG. 24A) (SEQ ID NO:229 and SEQ ID NO:230) showing the promoter sequences at -35 and at -10 from the initiation codon and a TEV protease cleavage site, and the nucleotide sequence (FIGS. 24B-D) (SEQ ID NO:132), of Destination Vector pDEST4. This vector may also be referred to as pTrx-DEST4.

FIG. 27 is a schematic depiction of the attR1 site, CMV promoter, and the physical map (FIG. 27A) (SEQ ID NO:235), and the nucleotide sequence (FIGS. 27B-C) (SEQ ID NO:135), of Destination Vector pDEST7. This vector may also be referred to as pCMV-DEST7.

FIG. 28 is a schematic depiction of the attR1 site, baculovirus polyhedrin promoter, and the physical map (SEQ ID NO:236), and the nucleotide sequence (FIGS. 28B-D) (SEQ ID NO:136), of Destination Vector pDEST8. This vector may also be referred to as pFastBac-DEST8.

FIG. 29 is a schematic depiction of the attR1 site, Semliki Forest Virus promoter, and the physical map (FIG. 29A) (SEQ ID NO:237), and the nucleotide sequence (FIGS. 29B-E) (SEQ ID NO:137), of Destination Vector pDEST9. This vector may also be referred to as pSFV-DEST9.

FIG. 30 is a schematic depiction of the attR1 site, baculovirus polyhedrin promoter, His6 fusion domain, and the physical map (FIG. 30A) (SEQ ID NO:238 and SEQ ID NO:239), and the nucleotide sequence (FIGS. 30B-D) (SEQ ID NO:138), of Destination Vector pDEST10. This vector may also be referred to as pFastBacHT-DEST10.

FIG. 31 is a schematic depiction of the attR1 cassette containing a tetracycline-regulated CMV promoter and the physical map (FIG. 31A) (SEQ ID NO:240), and the nucleotide sequence (FIGS. 31B-D) (SEQ ID NO:139), of Destination Vector pDEST11. This vector may also be referred to as pTet-DEST11.

FIG. 32 is a schematic depiction of the attR1 site, the start of the mRNA of the CMV promoter, and the physical map (FIG. 32A) (SEQ ID NO:241), and the nucleotide sequence (FIGS. 32B-D) (SEQ ID NO:140), of Destination Vector pDEST12.2. This vector may also be referred to as pCMV-neo-DEST12, as pCMV-DEST12, or as pDEST12.

FIG. 33 is a schematic depiction of the attR1 site, the $\lambda P_L$ promoter, and the physical map (FIG. 33A) (SEQ ID NO:242), and the nucleotide sequence (FIGS. 33B-C) (SEQ ID NO:141), of Destination Vector pDEST13. This vector may also be referred to as p$\lambda P_L$-DEST13.

FIG. 34 is a schematic depiction of the attR1 site, the T7 promoter, and the physical map (FIG. 34A) (SEQ ID NO:243), and the nucleotide sequence (FIGS. 34B-D) (SEQ ID NO:142), of Destination Vector pDEST14. This vector may also be referred to as pPT7-DEST14.

FIG. 35 is a schematic depiction of the attR1 site, the T7 promoter, and the N-terminal GST fusion sequence, and the physical map (FIG. 35A) (SEQ ID NO:244, SEQ ID NO:245, SEQ ID NO:246, and SEQ ID NO:247), and the nucleotide sequence (FIG. 35B-D) (SEQ ID NO:143), of Destination Vector pDEST15. This vector may also be referred to as pT7 GST-DEST15.

FIG. 37 is a schematic depiction of the attR1 site, the T7 promoter, and the N-terminal His6 fusion sequence, and the physical map (FIG. 37A) (SEQ ID NO:252 and SEQ ID NO:253), and the nucleotide sequence (FIGS. 37B-D) (SEQ ID NO:145), of Destination Vector pDEST17. This vector may also be referred to as pT7 His-DEST17.

FIG. 38 is a schematic depiction of the attR1 site and the p10 baculovirus promoter, and the physical map (FIG. 38A) (SEQ ID NO:254), and the nucleotide sequence (FIGS. 38B-D) (SEQ ID NO:146), of Destination Vector pDEST18. This vector may also be referred to as pFBp10-DEST18.

FIG. 39 is a schematic depiction of the attR1 site, and the 39k baculovirus promoter, and the physical map (FIG. 39A) (SEQ ID NO:255), and the nucleotide sequence (FIGS. 39B-D) (SEQ ID NO:147), of Destination Vector pDEST19. This vector may also be referred to as pFB39k-DEST19.

FIG. 40 is a schematic depiction of the attR1 site, the polh baculovirus promoter, and the N-terminal GST fusion sequence, and the physical map (FIG. 40A) (SEQ ID NO:256, SEQ ID NO:257, SEQ ID NO:258, and SEQ ID NO:259), and the nucleotide sequence (FIGS. 40B-D) (SEQ ID NO:148), of Destination Vector pDEST20. This vector may also be referred to as pFB GST-DEST20.

FIG. 41 is a schematic depiction of a 2-hybrid vector with a DNA-binding domain, the attR1 site, and the ADH promoter, and the physical map (FIG. 41A) (SEQ ID NO:260, SEQ ID NO:261, SEQ ID NO:262, and SEQ ID NO:263), and the nucleotide sequence (FIGS. 41B-E) (SEQ ID NO:149), of Destination Vector pDEST21. This vector may also be referred to as pDB Leu-DEST21.

FIG. 42 is a schematic depiction of a 2-hybrid vector with an activation domain, the attR1 site, and the ADH promoter, and the physical map (FIG. 42A) (SEQ ID NO:264, SEQ ID NO:265, SEQ ID NO:266, and SEQ ID NO:267), and the nucleotide sequence (FIG. 42B-D) (SEQ ID NO:150), of Destination Vector pDEST22. This vector may also be referred to as pPC86-DEST22.

FIG. 43 is a schematic depiction of the attR1 and attR2 sites, the T7 promoter, and the C-terminal His6 fusion sequence, and the physical map (FIG. 43A) (SEQ ID NO:268, SEQ ID NO:269, and SEQ ID NO:270), and the nucleotide sequence (FIGS. 43B-D) (SEQ ID NO:151), of Destination Vector pDEST23. This vector may also be referred to as pC-term-His6-DEST23.

FIG. 44 is a schematic depiction of the attR1 and attR2 sites, the T7 promoter, and the C-terminal GST fusion sequence, and the physical map (FIG. 44A) (SEQ ID NO:271, SEQ ID NO:272, and SEQ ID NO:273), and the nucleotide sequence (FIGS. 44B-D) (SEQ ID NO:152), of Destination Vector pDEST24. This vector may also be referred to as pC-term-GST-DEST24.

FIG. 45 is a schematic depiction of the attR1 and attR2 sites, the T7 promoter, and the C-terminal thioredoxin fusion sequence, and the physical map (FIG. 45A) (SEQ ID NO:274, SEQ ID NO:275, and SEQ ID NO:276), and the nucleotide sequence (FIG. 45B-D) (SEQ ID NO:153), of Destination Vector pDEST25. This vector may also be referred to as pC-term-Trx-DEST25.

FIG. 46 is a schematic depiction of the attR1 site, the CMV promoter, and an N-terminal His6 fusion sequence, and the physical map (FIG. 46A) (SEQ ID NO:277 and SEQ ID NO:278), and the nucleotide sequence (FIGS. 46B-D) (SEQ ID NO:154), of Destination Vector pDEST26. This vector may also be referred to as pCMV-SPneo-His-DEST26.

FIG. 47 is a schematic depiction of the attR1 site, the CMV promoter, and an N-terminal GST fusion sequence, and the physical map (FIG. 47A) (SEQ ID NO:279, SEQ ID NO:280, SEQ ID NO:281, and SEQ ID NO:282), and the nucleotide sequence (FIG. 47B-D) (SEQ ID NO:155), of Destination Vector pDEST27. This vector may also be referred to as pCMV-Spneo-GST-DEST27.

FIG. 55 depicts the attB1 site (SEQ ID NO:284 and SEQ ID NO:285), and the physical map, of an Entry Clone (pENTR7) of CAT subcloned into the Destination Vector pDEST2 (FIG. 22).

FIG. 64 shows the physical maps of plasmids containing three attR reading frame cassettes, pEZC15101 (reading frame A.

FIG. 65 depicts the attB primers used for amplifying the tetr and amp$^r$ genes from pBR322 by the cloning methods of the invention.

FIG. 66 is a table listing the results of recombinational cloning of the tetr and amp$^r$ PCR products made using the primers shown in FIG. 65.

FIG. 77 is a table summarizing the results of the PCR product cloning efficiency experiments depicted in FIGS. 69-74, for PCR fragments ranging in size from 0.256 kb to 6.9 kb.

FIG. 78 is a depiction of the sequences at the ends of attR Cassettes (SEQ ID NOs:163-170). Sequences contributed by the Cm$^r$-ccdB cassette are shown, including the outer ends of the flanking attR sites (boxed). The staggered cleavage sites for Int are indicated in the boxed regions. Following recombination with an Entry Clone, only the outer sequences in attR sites contribute to the resulting attB sites in the Expression Clone. The underlined sequences at both ends dictate the different reading frames (reading frames A, B, or C, with two alternative reading frame C cassettes depicted) for fusion proteins.

DETAILED DESCRIPTION OF THE INVENTION

Definitions

In the description that follows, a number of terms used in recombinant DNA technology are utilized extensively. In order to provide a clear and consistent understanding of the specification and claims, including the scope to be given such terms, the following definitions are provided.

Byproduct: is a daughter molecule (a new clone produced after the second recombination event during the recombinational cloning process) lacking the segment which is desired to be cloned or subcloned.

Cointegrate: is at least one recombination intermediate nucleic acid molecule of the present invention that contains both parental (starting) molecules. It will usually be linear. In some embodiments it can be circular. RNA and polypeptides may be expressed from cointegrates using an appropriate host cell strain, for example *E. coli* DB3.1 (particularly *E. coli*

LIBRARY EFFICIENCY® DB3.1™ Competent Cells), and selecting for both selection markers found on the cointegrate molecule.

Host: is any prokaryotic or eukaryotic organism that can be a recipient of the recombinational cloning Product, vector, or nucleic acid molecule of the invention. A "host," as the term is used herein, includes prokaryotic or eukaryotic organisms that can be genetically engineered. For examples of such hosts, see Maniatis et al., *Molecular Cloning: A Laboratory Manual*, Cold Spring Harbor Laboratory, Cold Spring Harbor, N.Y. (1982).

Insert or Inserts: include the desired nucleic acid segment or a population of nucleic acid segments (segment A of FIG. 1) which may be manipulated by the methods of the present invention. Thus, the terms Insert(s) are meant to include a particular nucleic acid (preferably DNA) segment or a population of segments. Such Insert(s) can comprise one or more nucleic acid molecules.

Insert Donor: is one of the two parental nucleic acid molecules (e.g. RNA or DNA) of the present invention which carries the Insert. The Insert Donor molecule comprises the Insert flanked on both sides with recombination sites. The Insert Donor can be linear or circular. In one embodiment of the invention, the Insert Donor is a circular DNA molecule and further comprises a cloning vector sequence outside of the recombination signals (see FIG. 1). When a population of Inserts or population of nucleic acid segments are used to make the Insert Donor, a population of Insert Donors results and may be used in accordance with the invention. Examples of such Insert Donor molecules are GATEWAY™ Entry Vectors, which include but are not limited to those Entry Vectors depicted in FIGS. 10-20, as well as other vectors comprising a gene of interest flanked by one or more attL sites (e.g., attL1, attL2, etc.), or by one or more attB sites (e.g., attB1, attB2, etc.) for the production of library clones.

Figure 1:
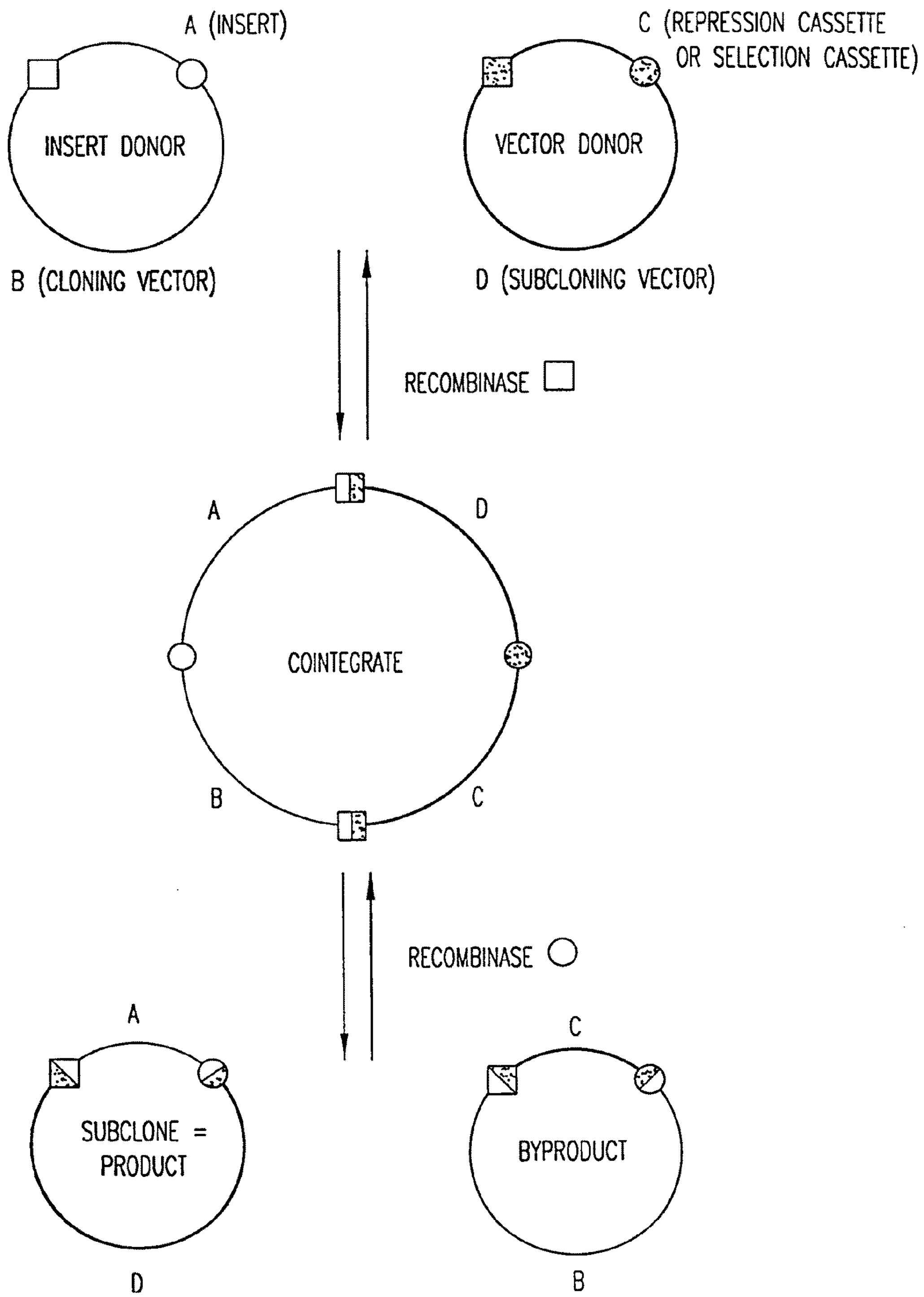
FIG. 1 depicts one general method of the present invention, wherein the starting (parent) DNA molecules can be circular or linear. The goal is to exchange the new subcloning vector D for the original cloning vector B. It is desirable in one embodiment to select for AD and against all the other molecules, including the Cointegrate. The square and circle are sites of recombination: e.g., lox (such as loxP) sites, att sites, etc. For example, segment D can contain expression signals, protein fusion domains, new drug markers, new origins of replication, or specialized functions for mapping or sequencing DNA. It should be noted that the cointegrate molecule contains Segment D (Destination vector) adjacent to segment A (Insert), thereby juxtaposing functional elements in D with the insert in A. Such molecules can be used directly in vitro (e.g., if a promoter is positioned adjacent to a gene—for in vitro transcription/translation) or in vivo (following isolation in a cell capable of propagating ccdB-containing vectors) by selecting for the selection markers in Segments B+D. As one skilled in the art will recognize, this single step method has utility in certain envisioned applications of the invention.

Product: is one of the desired daughter molecules comprising the A and D sequences which is produced after the second recombination event during the recombinational cloning process (see FIG. 1). The Product contains the nucleic acid which was to be cloned or subcloned. In accordance with the invention, when a population of Insert Donors are used, the resulting population of Product molecules will contain all or a portion of the population of Inserts of the Insert Donors and preferably will contain a representative population of the original molecules of the Insert Donors.

Promoter: is a DNA sequence generally described as the 5'-region of a gene, located proximal to the start codon. The transcription of an adjacent DNA segment is initiated at the promoter region. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

Recognition sequence: Recognition sequences are particular sequences which a protein, chemical compound, DNA, or RNA molecule (e.g., restriction endonuclease, a modification methylase, or a recombinase) recognizes and binds. In the present invention, a recognition sequence will usually refer to a recombination site. For example, the recognition sequence for Cre recombinase is loxP which is a 34 base pair sequence comprised of two 13 base pair inverted repeats (serving as the recombinase binding sites) flanking an 8 base pair core sequence. See FIG. 1 of Sauer, B., *Current Opinion in Biotechnology* 5:521-527 (1994). Other examples of recognition sequences are the attB, attP, attL, and attR sequences which are recognized by the recombinase enzyme λ Integrase. attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins integration host factor (IHF), FIS and excisionase (Xis). See Landy, *Current Opinion in Biotechnology* 3:699-707 (1993). Such sites may also be engineered according to the present invention to enhance production of products in the methods of the invention. When such engineered sites lack the P1 or H1 domains to make the recombination reactions irreversible (e.g., attR or attP), such sites may be designated attR' or attP' to show that the domains of these sites have been modified in some way.

Recombination proteins: include excisive or integrative proteins, enzymes, co-factors or associated proteins that are involved in recombination reactions involving one or more recombination sites, which may be wild-type proteins (See Landy, *Current Opinion in Biotechnology* 3:699-707 (1993)), or mutants, derivatives (e.g., fusion proteins containing the recombination protein sequences or fragments thereof), fragments, and variants thereof.

Recombination site: is a recognition sequence on a DNA molecule participating in an integration/recombination reaction by the recombinational cloning methods of the invention. Recombination sites are discrete sections or segments of DNA on the participating nucleic acid molecules that are recognized and bound by a site-specific recombination protein during the initial stages of integration or recombination. For example, the recombination site for Cre recombinase is loxP which is a 34 base pair sequence comprised of two 13 base pair inverted repeats (serving as the recombinase binding sites) flanking an 8 base pair core sequence. See FIG. 1 of Sauer, B., *Curr. Opin. Biotech.* 5:521-527 (1994). Other examples of recognition sequences include the attB, attP, attL, and attR sequences described herein, and mutants, fragments, variants and derivatives thereof, which are recognized by the recombination protein λ Int and by the auxiliary proteins integration host factor (IHF), FIS and excisionase (Xis). See Landy, *Curr. Opin. Biotech.* 3:699-707 (1993).

Recombinational Cloning: is a method described herein, whereby segments of nucleic acid molecules or populations of such molecules are exchanged, inserted, replaced, substituted or modified, in vitro or in vivo. By "in vitro" and "in vivo" herein is meant recombinational cloning that is carried out outside of host cells (e.g., in cell-free systems) or inside of host cells (e.g., using recombination proteins expressed by host cells), respectively.

Repression cassette: is a nucleic acid segment that contains a repressor or a Selectable marker present in the subcloning vector.

Selectable marker: is a DNA segment that allows one to select for or against a molecule (e.g., a replicon) or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of Selectable markers include but are not limited to: (1) DNA segments that encode products which provide resistance against otherwise toxic compounds (e.g., antibiotics); (2) DNA segments that encode products which are otherwise lacking in the recipient cell (e.g., tRNA genes, auxotrophic markers); (3) DNA segments that encode products which suppress the activity of a gene product; (4) DNA segments that encode products which can be readily identified (e.g., phenotypic markers such as β-galactosidase, green fluorescent protein (GFP), and cell surface proteins); (5) DNA segments that bind products which are otherwise detrimental to cell survival and/or function; (6) DNA segments that otherwise inhibit the activity of any of the DNA segments described in Nos. 1-5 above (e.g., antisense oligonucleotides); (7) DNA segments that bind products that modify a substrate (e.g. restriction endonucleases); (8) DNA segments that can be used to isolate or identify a desired molecule (e.g. specific protein binding sites); (9) DNA segments that encode a specific nucleotide sequence which can be otherwise non-functional (e.g., for PCR amplification of subpopulations of molecules); (10) DNA segments, which when absent, directly or indirectly confer resistance or sensitivity to particular compounds; (11) DNA segments that encode products which are toxic in recipient cells; (12) DNA segments that inhibit replication, partition or heritability of nucleic acid molecules that contain them; and/or (13) DNA segments that encode conditional replication functions, e.g., replication in certain hosts or host cell strains or under certain environmental conditions (e.g., temperature, nutritional conditions, etc.).

Selection scheme: is any method which allows selection, enrichment, or identification of a desired Product or Product(s) from a mixture containing an Entry Clone or Vector, a Destination Vector, a Donor Vector, an Expression Clone or Vector, any intermediates (e.g. a Cointegrate or a replicon), and/or Byproducts. The selection schemes of one preferred embodiment have at least two components that are either linked or unlinked during recombinational cloning. One component is a Selectable marker. The other component controls the expression in vitro or in vivo of the Selectable marker, or survival of the cell (or the nucleic acid molecule, e.g., a replicon) harboring the plasmid carrying the Selectable marker. Generally, this controlling element will be a repressor or inducer of the Selectable marker, but other means for controlling expression or activity of the Selectable marker can be used. Whether a repressor or activator is used will depend on whether the marker is for a positive or negative selection, and the exact arrangement of the various DNA segments, as will be readily apparent to those skilled in the art. A preferred requirement is that the selection scheme results in selection of or enrichment for only one or more desired Products. As defined herein, selecting for a DNA molecule includes (a) selecting or enriching for the presence of the desired DNA molecule, and (b) selecting or enriching against the presence of DNA molecules that are not the desired DNA molecule.

In one embodiment, the selection schemes (which can be carried out in reverse) will take one of three forms, which will be discussed in terms of FIG. 1. The first, exemplified herein with a Selectable marker and a repressor therefore, selects for molecules having segment D and lacking segment C. The second selects against molecules having segment C and for molecules having segment D. Possible embodiments of the second form would have a DNA segment carrying a gene toxic to cells into which the in vitro reaction products are to be introduced. A toxic gene can be a DNA that is expressed as a toxic gene product (a toxic protein or RNA), or can be toxic in and of itself. (In the latter case, the toxic gene is understood to carry its classical definition of "heritable trait".)

Examples of such toxic gene products are well known in the art, and include, but are not limited to, restriction endonucleases (e.g., DpnI), apoptosis-related genes (e.g. ASK1 or members of the bcl-2/ced-9 family), retroviral genes including those of the human immunodeficiency virus (HIV), defensins such as NP-1, inverted repeats or paired palindromic DNA sequences, bacteriophage lytic genes such as those from ΦX174 or bacteriophage T4; antibiotic sensitivity genes such as rpsL, antimicrobial sensitivity genes such as pheS, plasmid killer genes, eukaryotic transcriptional vector genes that produce a gene product toxic to bacteria, such as GATA-1, and genes that kill hosts in the absence of a suppressing function, e.g., kicB, ccdB, ΦX174 E (Liu, Q. et al., *Curr. Biol.* 8:1300-1309 (1998)), and other genes that negatively affect replicon stability and/or replication. A toxic gene can alternatively be selectable in vitro, e.g., a restriction site.

Many genes coding for restriction endonucleases operably linked to inducible promoters are known, and may be used in the present invention. See, e.g. U.S. Pat. Nos. 4,960,707 (DpnI and DpnII); 5,000,333, 5,082,784 and 5,192,675 (KpnI); 5,147,800 (NgoAIII and NgoAI); 5,179,015 (FspI and HaeIII): 5,200,333 (HaeII and TaqI); 5,248,605 (HpaII); 5,312,746 (ClaI); 5,231,021 and 5,304,480 (XhoI and XhoII); 5,334,526 (AluI); 5,470,740 (NsiI); 5,534,428 (SstI/SacI); 5,202,248 (NcoI); 5,139,942 (NdeI); and 5,098,839 (PacI). See also Wilson, G. G., *Nucl. Acids Res.* 19:2539-2566 (1991); and Lunnen, K. D., et al., *Gene* 74:25-32 (1988).

In the second form, segment D carries a Selectable marker. The toxic gene would eliminate transformants harboring the Vector Donor, Cointegrate, and Byproduct molecules, while the Selectable marker can be used to select for cells containing the Product and against cells harboring only the Insert Donor.

The third form selects for cells that have both segments A and D in cis on the same molecule, but not for cells that have both segments in trans on different molecules. This could be embodied by a Selectable marker that is split into two inactive fragments, one each on segments A and D.

The fragments are so arranged relative to the recombination sites that when the segments are brought together by the recombination event, they reconstitute a functional Selectable marker. For example, the recombinational event can link a promoter with a structural nucleic acid molecule (e.g., a gene), can link two fragments of a structural nucleic acid molecule, or can link nucleic acid molecules that encode a heterodimeric gene product needed for survival, or can link portions of a replicon.

Site-specific recombinase: is a type of recombinase which typically has at least the following four activities (or combinations thereof): (1) recognition of one or two specific nucleic acid sequences; (2) cleavage of said sequence or sequences; (3) topoisomerase activity involved in strand exchange; and (4) ligase activity to reseal the cleaved strands of nucleic acid. See Sauer, B., *Current Opinions in Biotechnology* 5:521-527 (1994). Conservative site-specific recombination is distinguished from homologous recombination and transposition by a high degree of sequence specificity for both partners. The strand exchange mechanism involves the cleavage and rejoining of specific DNA sequences in the absence of DNA synthesis (Landy, A. (1989) *Ann. Rev. Biochem.* 58:913-949).

Subcloning vector: is a cloning vector comprising a circular or linear nucleic acid molecule which includes preferably an appropriate replicon. In the present invention, the subcloning vector (segment D in FIG. 1) can also contain functional and/or regulatory elements that are desired to be incorporated into the final product to act upon or with the cloned DNA Insert (segment A in FIG. 1). The subcloning vector can also contain a Selectable marker (preferably DNA).

Vector: is a nucleic acid molecule (preferably DNA) that provides a useful biological or biochemical property to an Insert. Examples include plasmids, phages, autonomously replicating sequences (ARS), centromeres, and other sequences which are able to replicate or be replicated in vitro or in a host cell, or to convey a desired nucleic acid segment to a desired location within a host cell. A Vector can have one or more restriction endonuclease recognition sites at which the sequences can be cut in a determinable fashion without loss of an essential biological function of the vector, and into which a nucleic acid fragment can be spliced in order to bring about its replication and cloning. Vectors can further provide primer sites, e.g., for PCR, transcriptional and/or translational initiation and/or regulation sites, recombinational signals, replicons, Selectable markers, etc. Clearly, methods of inserting a desired nucleic acid fragment which do not require the use of homologous recombination, transpositions or restriction enzymes (such as, but not limited to, UDG cloning of PCR fragments (U.S. Pat. No. 5,334,575, entirely incorporated herein by reference), T:A cloning, and the like) can also be applied to clone a fragment into a cloning vector to be used according to the present invention. The cloning vector can further contain one or more selectable markers suitable for use in the identification of cells transformed with the cloning vector.

Vector Donor: is one of the two parental nucleic acid molecules (e.g. RNA or DNA) of the present invention which carries the DNA segments comprising the DNA vector which is to become part of the desired Product. The Vector Donor comprises a subcloning vector D (or it can be called the cloning vector if the Insert Donor does not already contain a cloning vector (e.g., for PCR fragments containing attB sites; see below)) and a segment C flanked by recombination sites (see FIG. 1). Segments C and/or D can contain elements that contribute to selection for the desired Product daughter molecule, as described above for selection schemes. The recombination signals can be the same or different, and can be acted upon by the same or different recombinases. In addition, the Vector Donor can be linear or circular. Examples of such Vector Donor molecules include GATEWAY™ Destination Vectors, which include but are not limited to those Destination Vectors depicted in FIGS. 21-47 and 90-96.

Primer: refers to a single stranded or double stranded oligonucleotide that is extended by covalent bonding of nucleotide monomers during amplification or polymerization of a nucleic acid molecule (e.g. a DNA molecule). In a preferred aspect, a primer comprises one or more recombination sites or portions of such recombination sites. Portions of recombination sites comprise at least 2 bases (or basepairs, abbreviated herein as "bp"), at least 5-200 bases, at least 10-100 bases, at least 15-75 bases, at least 15-50 bases, at least 15-25 bases, or at least 16-25 bases, of the recombination sites of interest, as described in further detail below and in the Examples. When using portions of recombination sites, the missing portion of the recombination site may be provided as a template by the newly synthesized nucleic acid molecule. Such recombination sites may be located within and/or at one or both termini of the primer. Preferably, additional sequences are added to the primer adjacent to the recombination site(s) to enhance or improve recombination and/or to stabilize the recombination site during recombination. Such stabilization sequences may be any sequences (preferably G/C rich sequences) of any length. Preferably, such sequences range in size from 1 to about 1000 bases, 1 to about 500 bases, and 1 to about 100 bases, 1 to about 60 bases, 1 to about 25, 1 to about 10, 2 to about 10 and preferably about 4 bases. Preferably, such sequences are greater than 1 base in length and preferably greater than 2 bases in length.

Template: refers to double stranded or single stranded nucleic acid molecules which are to be amplified, synthesized or sequenced. In the case of double stranded molecules, denaturation of its strands to form a first and a second strand is preferably performed before these molecules will be amplified, synthesized or sequenced, or the double stranded molecule may be used directly as a template. For single stranded templates, a primer complementary to a portion of the template is hybridized under appropriate conditions and one or more polypeptides having polymerase activity (e.g. DNA polymerases and/or reverse transcriptases) may then synthesize a nucleic acid molecule complementary to all or a portion of said template. Alternatively, for double stranded templates, one or more promoters may be used in combination with one or more polymerases to make nucleic acid molecules complementary to all or a portion of the template. The newly synthesized molecules, according to the invention, may be equal or shorter in length than the original template. Additionally, a population of nucleic acid templates may be used during synthesis or amplification to produce a population of nucleic acid molecules typically representative of the original template population.

Adapter: is an oligonucleotide or nucleic acid fragment or segment (preferably DNA) which comprises one or more recombination sites (or portions of such recombination sites) which in accordance with the invention can be added to a circular or linear Insert Donor molecule as well as other nucleic acid molecules described herein. When using portions of recombination sites, the missing portion may be provided by the Insert Donor molecule. Such adapters may be added at any location within a circular or linear molecule, although the adapters are preferably added at or near one or both termini of a linear molecule. Preferably, adapters are positioned to be located on both sides (flanking) a particular nucleic acid molecule of interest. In accordance with the invention, adapters may be added to nucleic acid molecules of interest by standard recombinant techniques (e.g. restriction digest and ligation). For example, adapters may be added to a circular molecule by first digesting the molecule with an appropriate restriction enzyme, adding the adapter at the cleavage site and reforming the circular molecule which contains the adapter(s) at the site of cleavage. In other aspects, adapters may be added by homologous recombination, by integration of RNA molecules, and the like. Alternatively, adapters may be ligated directly to one or more and preferably both termini of a linear molecule thereby resulting in linear molecule(s) having adapters at one or both termini. In one aspect of the invention, adapters may be added to a population of linear molecules, (e.g. a cDNA library or genomic DNA which has been cleaved or digested) to form a population of linear molecules containing adapters at one and preferably both termini of all or substantial portion of said population.

Adapter-Primer: is primer molecule which comprises one or more recombination sites (or portions of such recombination sites) which in accordance with the invention can be added to a circular or linear nucleic acid molecule described herein. When using portions of recombination sites, the missing portion may be provided by a nucleic acid molecule (e.g., an adapter) of the invention. Such adapter-primers may be added at any location within a circular or linear molecule, although the adapter-primers are preferably added at or near one or both termini of a linear molecule. Examples of such adapter-primers and the use thereof in accordance with the methods of the invention are shown in Example 25 herein. Such adapter-primers may be used to add one or more recombination sites or portions thereof to circular or linear nucleic acid molecules in a variety of contexts and by a variety of techniques, including but not limited to amplification (e.g., PCR), ligation (e.g., enzymatic or chemical/synthetic ligation), recombination (e.g., homologous or non-homologous (illegitimate) recombination) and the like.

Library: refers to a collection of nucleic acid molecules (circular or linear). In one embodiment, a library may comprise a plurality (i.e., two or more) of DNA molecules, which may or may not be from a common source organism, organ, tissue, or cell. In another embodiment, a library is representative of all or a portion or a significant portion of the DNA content of an organism (a “genomic” library), or a set of nucleic acid molecules representative of all or a portion or a significant portion of the expressed nucleic acid molecules (a cDNA library) in a cell, tissue, organ or organism. A library may also comprise random sequences made by de novo synthesis, mutagenesis of one or more sequences and the like. Such libraries may or may not be contained in one or more vectors.

Amplification: refers to any in vitro method for increasing a number of copies of a nucleotide sequence with the use of a polymerase. Nucleic acid amplification results in the incorporation of nucleotides into a DNA and/or RNA molecule or primer thereby forming a new molecule complementary to a template. The formed nucleic acid molecule and its template can be used as templates to synthesize additional nucleic acid molecules. As used herein, one amplification reaction may consist of many rounds of replication. DNA amplification reactions include, for example, polymerase chain reaction (PCR). One PCR reaction may consist of 5-100 “cycles” of denaturation and synthesis of a DNA molecule.

Oligonucleotide: refers to a synthetic or natural molecule comprising a covalently linked sequence of nucleotides which are joined by a phosphodiester bond between the 3' position of the deoxyribose or ribose of one nucleotide and the 5' position of the deoxyribose or ribose of the adjacent nucleotide. This term may be used interchangeably herein with the terms “nucleic acid molecule” and “polynucleotide,” without any of these terms necessarily indicating any particular length of the nucleic acid molecule to which the term specifically refers.

Nucleotide: refers to a base-sugar-phosphate combination. Nucleotides are monomeric units of a nucleic acid molecule (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a “nucleotide” may be unlabeled or detectably labeled by well known techniques. Detectable labels include, for example, radioactive isotopes, fluorescent labels, chemiluminescent labels, bioluminescent labels and enzyme labels.

Hybridization: The terms “hybridization” and “hybridizing” refers to base pairing of two complementary single-stranded nucleic acid molecules (RNA and/or DNA) to give a double stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used. In some aspects, hybridization is said to be under “stringent conditions.” By “stringent conditions” as used herein is meant overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1×SSC at about 65° C.

Other terms used in the fields of recombinant DNA technology and molecular and cell biology as used herein will be generally understood by one of ordinary skill in the applicable arts.

OVERVIEW

Two reactions constitute the recombinational cloning system of the present invention, referred to herein as the “GATEWAY™ Cloning System,” as depicted generally in FIG. 1. The first of these reactions, the LR Reaction (FIG. 2), which may also be referred to interchangeably herein as the Destination Reaction, is the main pathway of this system. The LR Reaction is a recombination reaction between an Entry vector or clone and a Destination Vector, mediated by a cocktail of recombination proteins such as the GATEWAY™ LR Clonase™ Enzyme Mix described herein. This reaction transfers nucleic acid molecules of interest (which may be genes, cDNAs, cDNA libraries, or fragments thereof) from the Entry Clone to an Expression Vector, to create an Expression Clone.

The sites labeled L, R, B, and P are respectively the attL, attR, attB, and attP recombination sites for the bacteriophage A recombination proteins that constitute the Clonase cocktail (referred to herein variously as “Clonase” or “GATEWAY™ LR Clonase™ Enzyme Mix” (for recombination protein mixtures mediating attB x attP recombination reactions, as described herein) or “GATEWAY™ BP Clonase™ Enzyme Mix” (for recombination protein mixtures mediating attB x attP recombination reactions, as described herein)). The Recombinational Cloning reactions are equivalent to concerted, highly specific, cutting and ligation reactions. Viewed in this way, the recombination proteins cut to the left and right of the nucleic acid molecule of interest in the Entry Clone and ligate it into the Destination vector, creating a new Expression Clone.

The nucleic acid molecule of interest in an Expression Clone is flanked by the small attB1 and attB2 sites. The orientation and reading frame of the nucleic acid molecule of interest are maintained throughout the subcloning, because attL1 reacts only with attR1, and attL2 reacts only with attR2. Likewise, attB1 reacts only with attP1, and attB2 reacts only with attP2. Thus, the invention also relates to methods of controlled or directional cloning using the recombination sites of the invention (or portions thereof), including variants, fragments, mutants and derivatives thereof which may have altered or enhanced specificity. The invention also relates more generally to any number of recombination site partners or pairs (where each recombination site is specific for and interacts with its corresponding recombination site). Such recombination sites are preferably made by mutating or modifying the recombination site to provide any number of necessary specificities (e.g., attB1-10, attP1-10, attL1-10, attR1-10, etc.), non-limiting examples of which are described in detail in the Examples herein.

When an aliquot from the recombination reaction is transformed into host cells (e.g., *E. coli*) and spread on plates containing an appropriate selection agent, e.g., an antibiotic such as ampicillin with or without methicillin, cells that take up the desired clone form colonies. The unreacted Destination Vector does not give ampicillin-resistant colonies, even though it carries the ampicillin-resistance gene, because it contains a toxic gene, e.g., ccdB. Thus selection for ampicillin resistance selects for *E. coli* cells that carry the desired product, which usually comprise >90% of the colonies on the ampicillin plate.

To participate in the Recombinational (or “GATEWAY™”) Cloning Reaction, a nucleic acid molecule of interest first may be cloned into an Entry Vector, creating an Entry Clone. Multiple options are available for creating Entry Clones, including: cloning of PCR sequences with terminal attB recombination sites into Entry Vectors; using the GATEWAY™ Cloning System recombination reaction; transfer of genes from libraries prepared in GATEWAY™ Cloning System vectors by recombination into Entry Vectors; and cloning of restriction enzyme-generated fragments and PCR fragments into Entry Vectors by standard recombinant DNA methods. These approaches are discussed in further detail herein.

Figure 3:
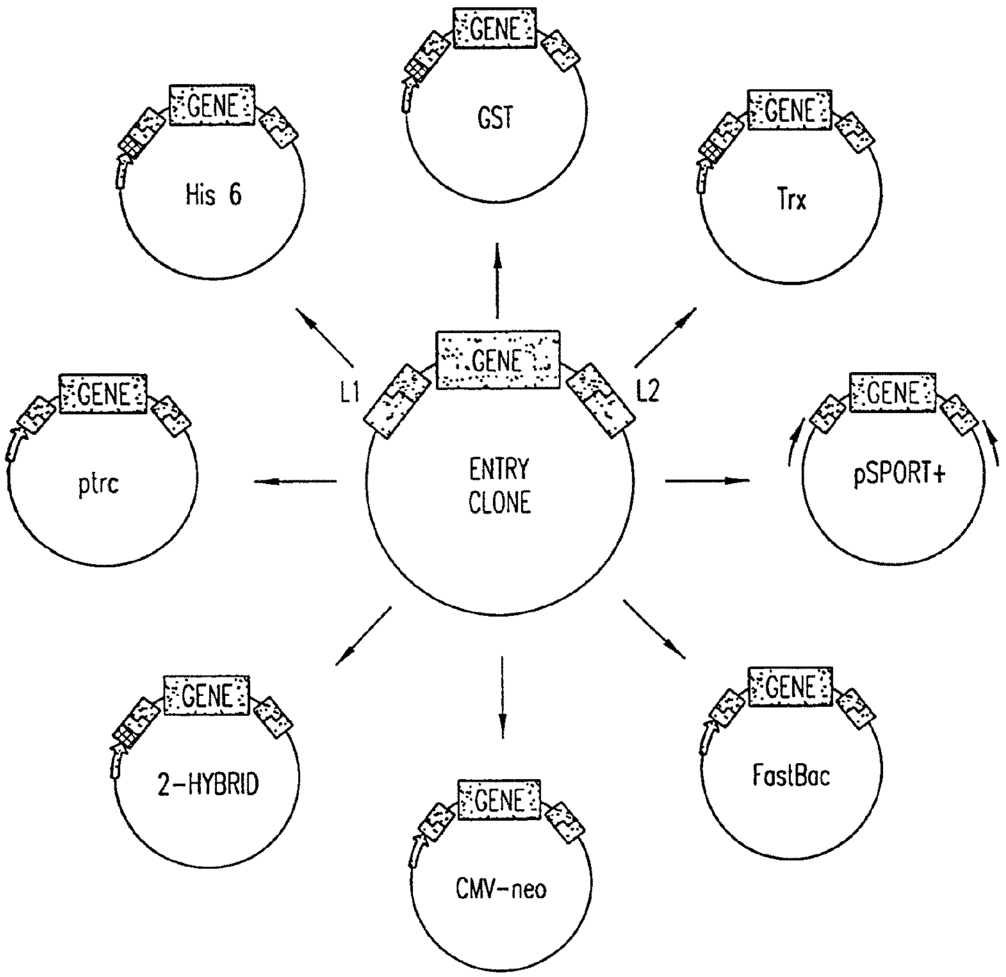
FIG. 3 is a schematic depiction of the cloning of a nucleic acid molecule from an Entry clone into multiple types of Destination vectors, to produce a variety of Expression Clones. Recombination between a given Entry clone and different types of Destination vectors (not shown), via the LR Reaction depicted in FIG. 2, produces multiple different Expression Clones for use in a variety of applications and host cell types.

A key advantage of the GATEWAY™ Cloning System is that a nucleic acid molecule of interest (or even a population of nucleic acid molecules of interest) present as an Entry Clone can be subcloned in parallel into one or more Destination Vectors in a simple reactions for anywhere from about 30 seconds to about 60 minutes (preferably about 1-60 minutes, about 1-45 minutes, about 1-30 minutes, about 2-60 minutes, about 2-45 minutes, about 2-30 minutes, about 1-2 minutes, about 30-60 minutes, about 45-60 minutes, or about 30-45 minutes). Longer reaction times (e.g., 2-24 hours, or overnight) may increase recombination efficiency, particularly where larger nucleic acid molecules are used, as described in the Examples herein. Moreover, a high percentage of the colonies obtained carry the desired Expression Clone. This process is illustrated schematically in FIG. 3, which shows an advantage of the invention in which the molecule of interest can be moved simultaneously or separately info multiple Destination Vectors. In the LR Reaction, one or both of the nucleic acid molecules to be recombined may have any topology (e.g., linear, relaxed circular, nicked circular, supercoiled, etc.), although one or both are preferably linear.

The second major pathway of the GATEWAY™ Cloning System is the BP Reaction (FIG. 4), which may also be referred to interchangeably herein as the Entry Reaction or the Gateward Reaction. The BP Reaction may recombine an Expression Clone with a Donor Plasmid (the counterpart of the byproduct in FIG. 2). This reaction transfers the nucleic acid molecule of interest (which may have any of a variety of topologies, including linear, coiled, supercoiled, etc.) in the Expression Clone into an Entry Vector, to produce a new Entry Clone. Once this nucleic acid molecule of interest is cloned into an Entry Vector, it can be transferred into new Expression Vectors, through the LR Reaction as described above. In the BP Reaction, one or both of the nucleic acid molecules to be recombined may have any topology (e.g., linear, relaxed circular, nicked circular, supercoiled, etc.), although one or both are preferably linear.

A useful variation of the BP Reaction permits rapid cloning and expression of products of amplification (e.g., PCR) or nucleic acid synthesis. Amplification (e.g., PCR) products synthesized with primers containing terminal 25 bp attB sites serve as efficient substrates for the Gateward Cloning reaction. Such amplification products may be recombined with a Donor Vector to produce an Entry Clone (see FIG. 7). The result is an Entry Clone containing the amplification fragment. Such Entry Clones can then be recombined with Destination Vectors—through the LR Reaction—to yield Expression Clones of the PCR product.

Figure 5A:
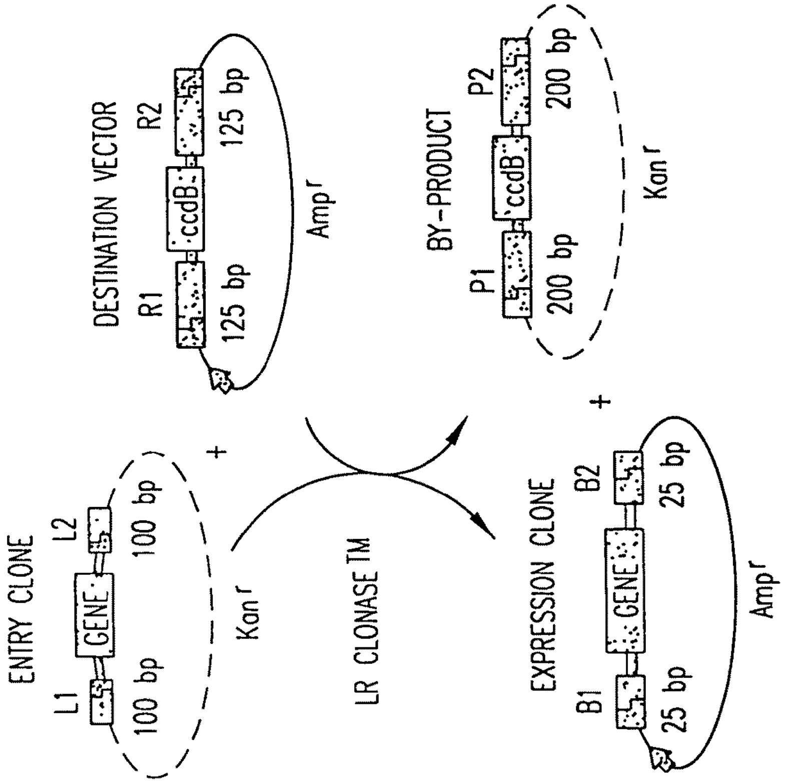
FIG. 5 is a more detailed schematic depiction of the LR ("Destination") reaction (FIG. 5A) and the BP ("Entry" or "Gateward") reaction (FIG. 5B) of the GATEWAY™ Cloning System, showing the reactants, products and byproducts of each reaction.

Additional details of the LR Reaction are shown in FIG. 5A. The GATEWAY™ LR Clonase™ Enzyme Mix that mediates this reaction contains lambda recombination proteins Int (Integrase), Xis (Excisionase), and IHF (Integration Host Factor). In contrast, the GATEWAY™ BP Clonase™ Enzyme Mix, which mediates the BP Reaction (FIG. 5B), comprises Int and IHF alone.

Figure 5B:
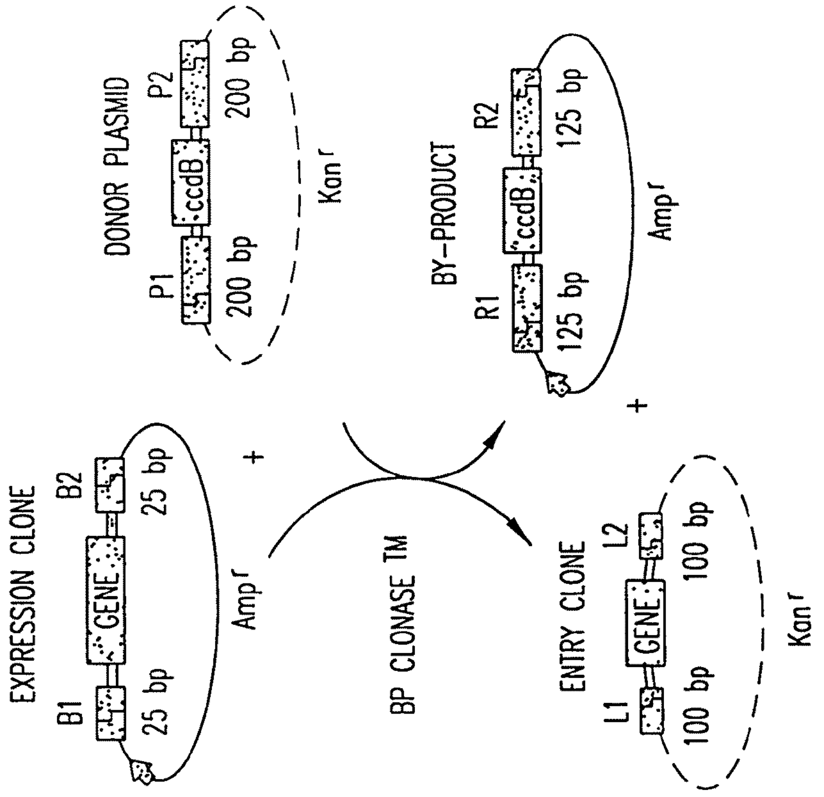

The recombination (att) sites of each vector comprise two distinct segments, donated by the parental vectors. The staggered lines dividing the two portions of each att site, depicted in FIGS. 5A and 5B, represent the seven-base staggered cut produced by Int during the recombination reactions. This structure is seen in greater detail in FIG. 6, which displays the attB recombination sequences of an Expression Clone, generated by recombination between the attL1 and attL2 sites of an Entry Clone and the attR1 and attR2 sites of a Destination Vector.

The nucleic acid molecule of interest in the Expression Clone is flanked by attB sites: attB1 to the left (amino terminus) and attB2 to the right (carboxy terminus). The bases in attB1 to the left of the seven-base staggered cut produced by Int are derived from the Destination vector, and the bases to the right of the staggered cut are derived from the Entry Vector (see FIG. 6). Note that the sequence is displayed in triplets corresponding to an open reading frame. If the reading frame of the nucleic acid molecule of interest cloned in the Entry Vector is in phase with the reading frame shown for attB1, amino-terminal protein fusions can be made between the nucleic acid molecule of interest and any GATEWAY™ Cloning System Destination Vector encoding an amino-terminal fusion domain. Entry Vectors and Destination Vectors that enable cloning in all three reading frames are described in more detail herein, particularly in the Examples.

Figure 7:
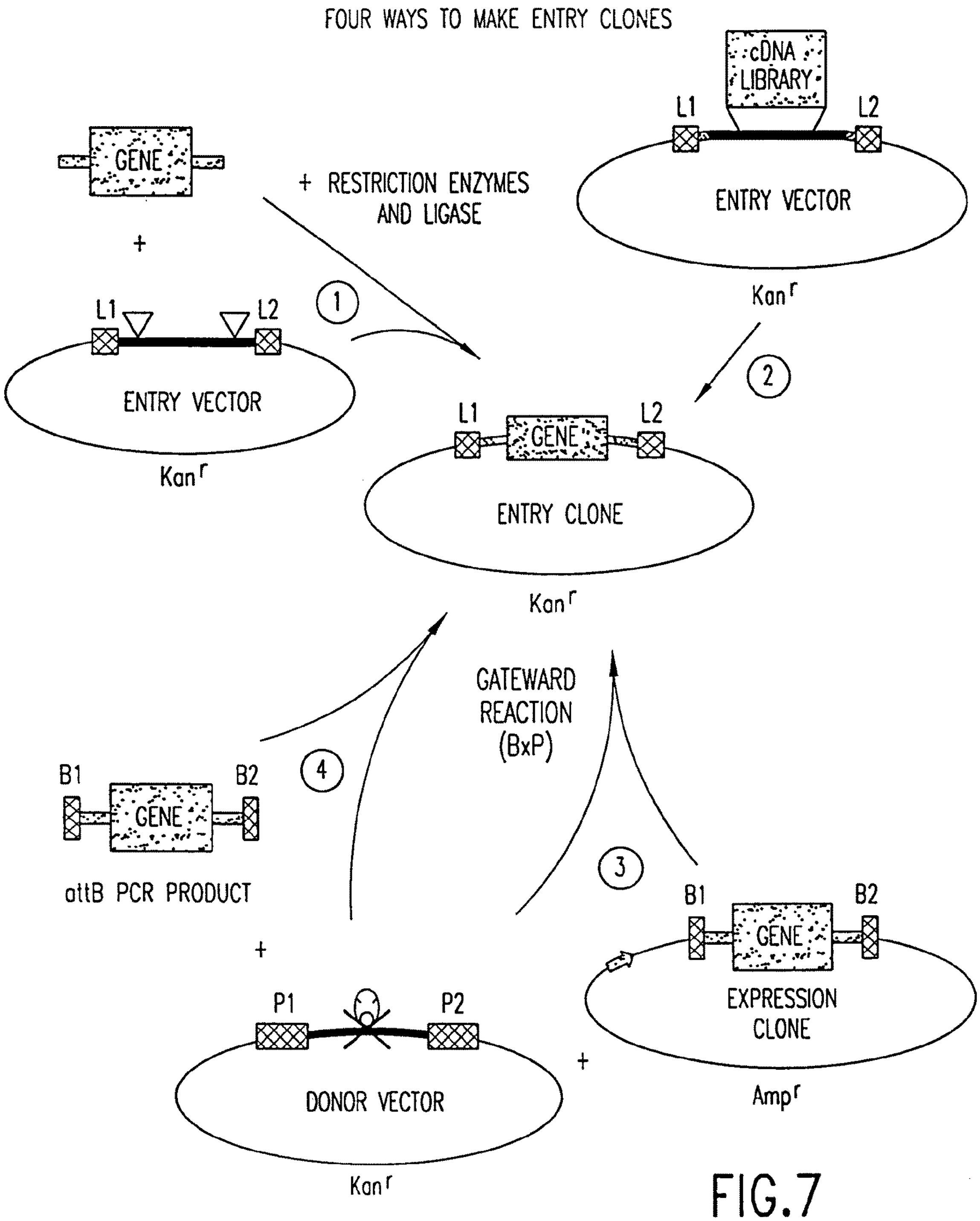

The LR Reaction allows the transfer of a desired nucleic acid molecule of interest into new Expression Vectors by recombining a Entry Clone with various Destination Vectors. To participate in the LR or Destination Reaction, however, a nucleic acid molecule of interest preferably is first converted to a Entry Clone. Entry Clones can be made in a number of ways, as shown in FIG. 7.

One approach is to clone the nucleic acid molecule of interest into one or more of the Entry Vectors, using standard recombinant DNA methods, with restriction enzymes and ligase. The starting DNA fragment can be generated by restriction enzyme digestion or as a PCR product. The fragment is cloned between the attL1 and attL2 recombination sites in the Entry Vector. Note that a toxic or "death" gene (e.g., ccdB), provided to minimize background colonies from incompletely digested Entry Vector, must be excised and replaced by the nucleic acid molecule of interest.

A second approach to making an Entry Clone (FIG. 7) is to make a library (genomic or cDNA) in an Entry Vector, as described in detail herein. Such libraries may then be transferred into Destination Vectors for expression screening, for example in appropriate host cells such as yeast cells or mammalian cells.

Figure 48A:
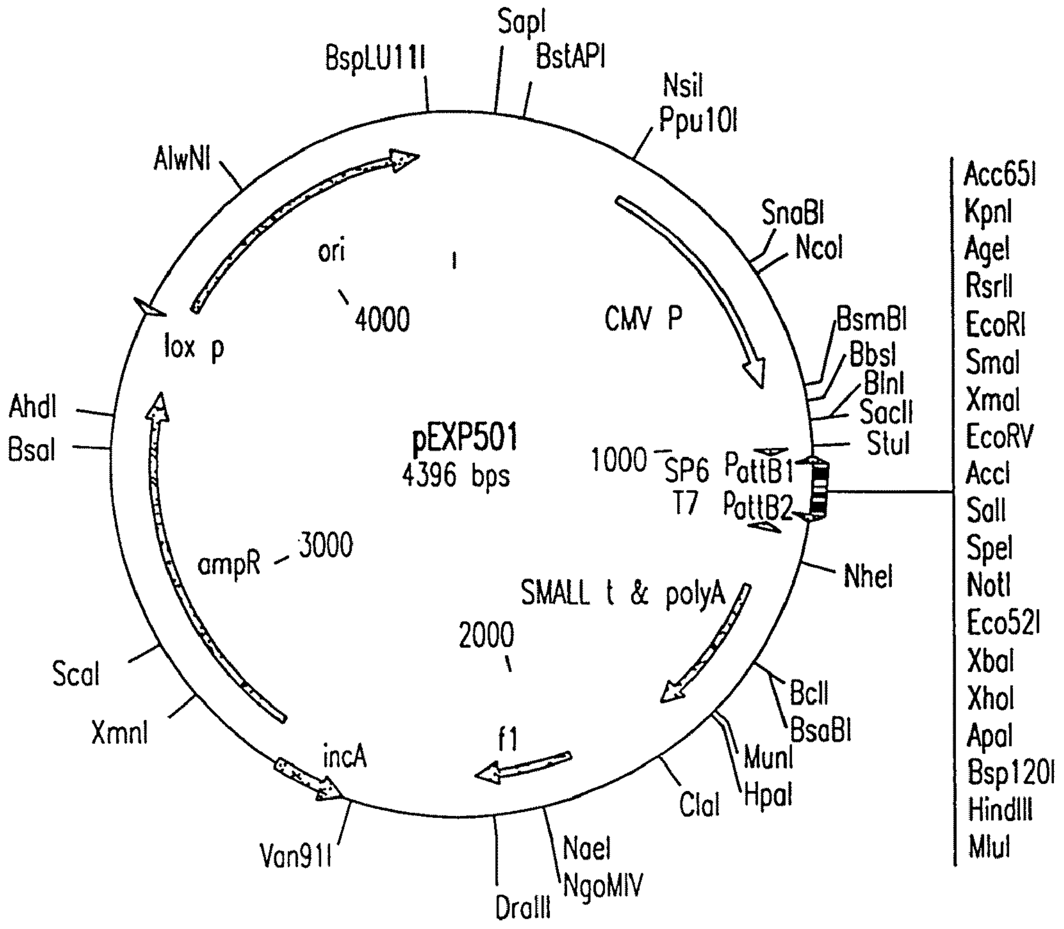
FIG. 48 is a depiction of the physical map (FIG. 48A) (SEQ ID NO:283), the cloning sites (FIG. 48B), and the nucleotide sequence (FIGS. 48C-D) (SEQ ID NO:156), for the attB cloning vector plasmid pEXP501. This vector may also be referred to equivalently herein as pCMV.SPORT6, pCMVSPORT6, and pCMVSport6.

A third approach to making Entry Clones (FIG. 7) is to use Expression Clones obtained from cDNA molecules or libraries prepared in Expression Vectors. Such cDNAs or libraries, flanked by attB sites, can be introduced into a Entry Vector by recombination with a Donor Vector via the BP Reaction. If desired, an entire Expression Clone library can be transferred into the Entry Vector through the BP Reaction. Expression Clone cDNA libraries may also be constructed in a variety of prokaryotic and eukaryotic GATEWAY™-modified vectors (e.g., the pEXP501 Expression Vector (see FIG. 48), and 2-hybrid and attB library vectors), as described in detail herein, particularly in the Examples below.

Figure 8:
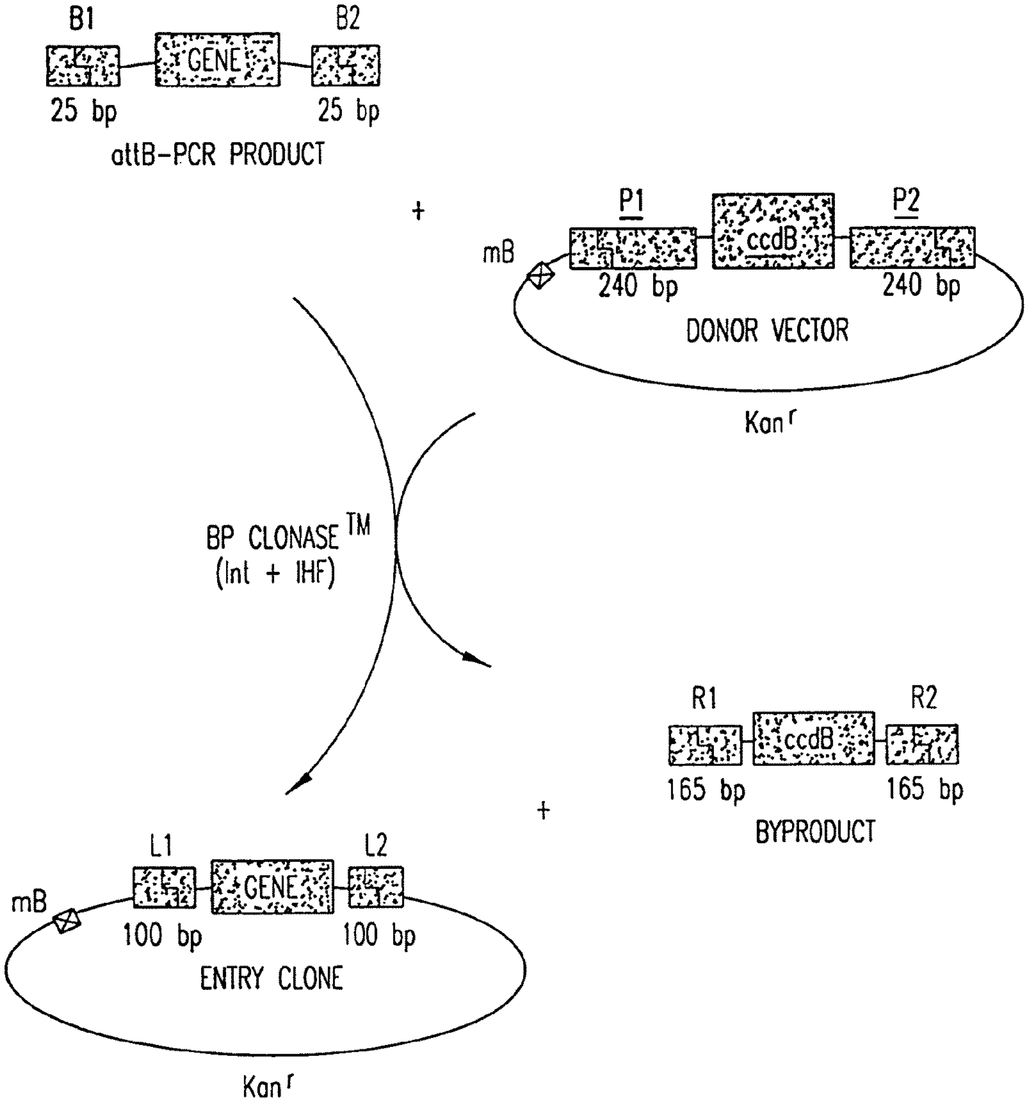
FIG. 8 is a schematic depiction of cloning of a PCR product by a BxP (Entry or Gateward) reaction. A PCR product with 25 bp terminal attB sites (plus four Gs) is shown as a substrate for the BxP reaction. Recombination between the attB-PCR product of a gene and a Donor vector (which donates an Entry Vector that carries $kan^r$) results in an Entry Clone of the PCR product.
Figure 10A:
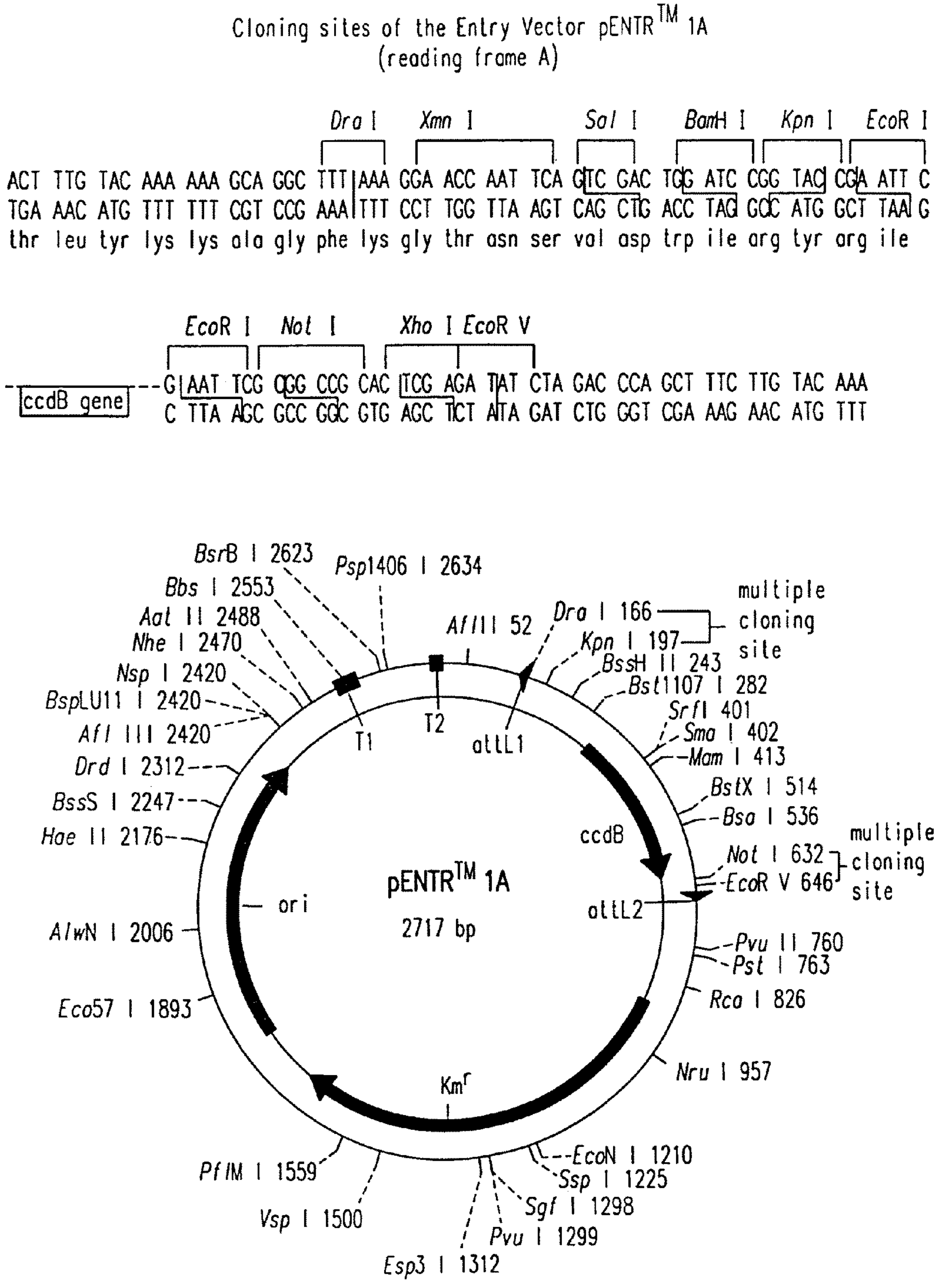
FIG. 10 is a schematic depiction of the physical map and cloning sites (FIG. 10A) (SEQ ID NO:185, SEQ ID NO:186, and SEQ ID NO:187), and the nucleotide sequence (FIG. 10B) (SEQ ID NO:118), of the Entry Vector pENTR1A.
Figure 25A:
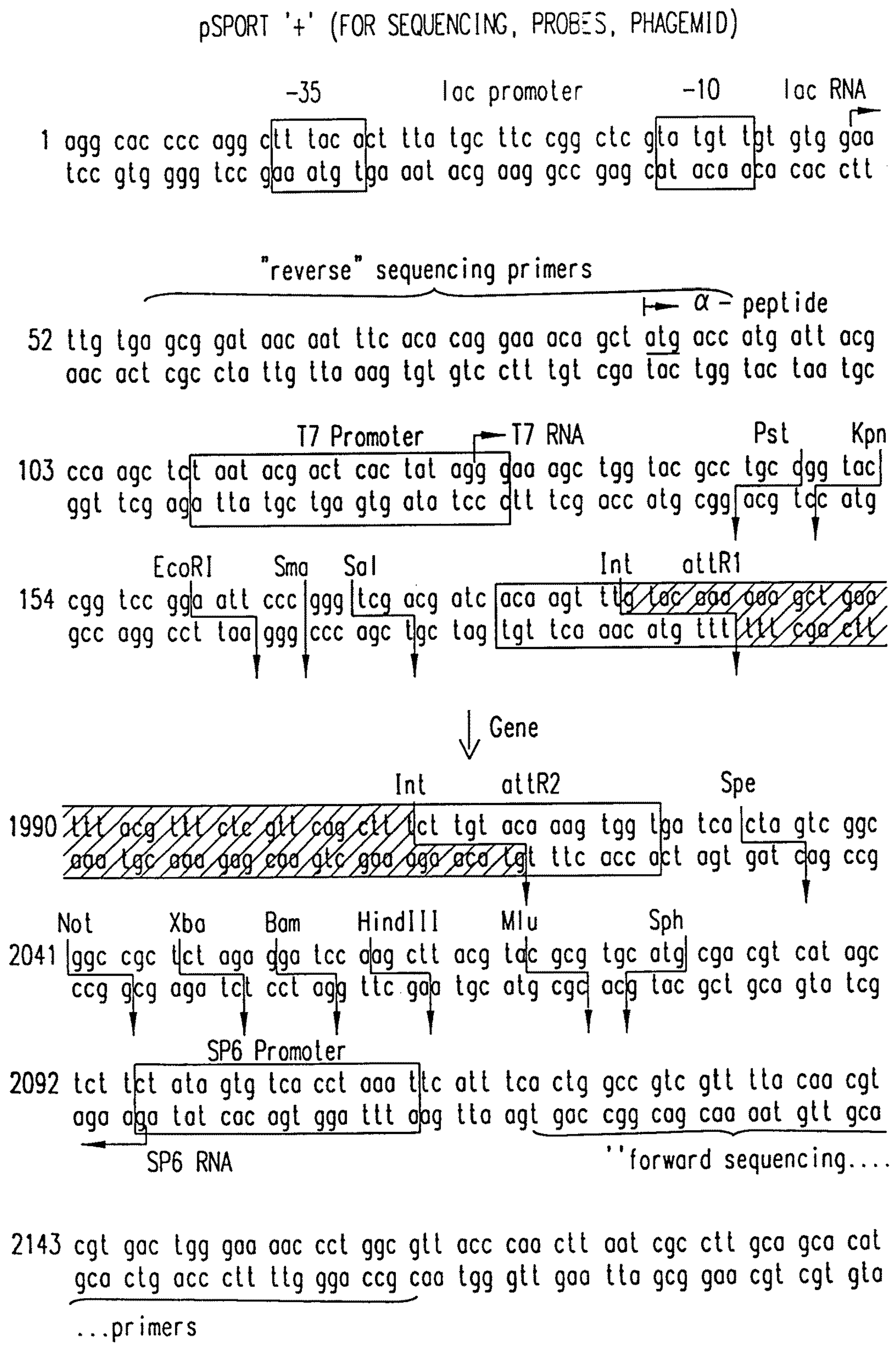
FIG. 25 is a schematic depiction of the attR1 and attR2 sites (FIG. 25A) (SEQ ID NO:231 and SEQ ID NO:232), the physical map (FIG. 25B), and the nucleotide sequence (FIGS. 25C-D) (SEQ ID NO:133), of Destination Vector pDEST5. This vector may also be referred to as pSPORT(+)-DEST5.
Figure 25B:
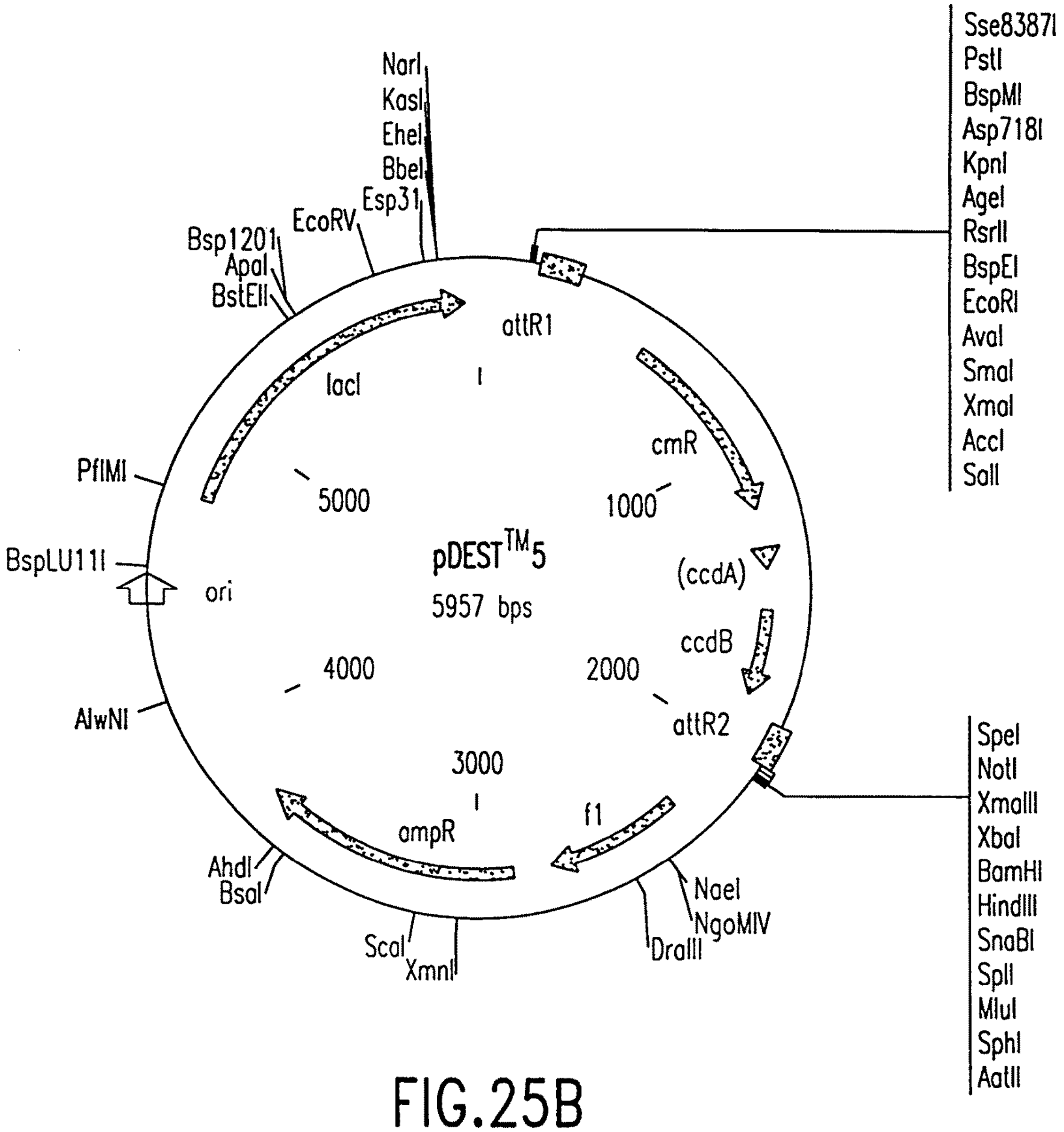

A fourth, and potentially most versatile, approach to making an Entry Clone (FIG. 7) is to introduce a sequence for a nucleic acid molecule of interest into an Entry Vector by amplification (e.g., PCR) fragment cloning. This method is diagramed in FIG. 8. The DNA sequence first is amplified (for example, with PCR) as outlined in detail below and in the Examples herein, using primers containing one or more bp, two or more bp, three or more bp, four or more bp, five or more bp, preferably six or more bp, more preferably 6-25 bp (particularly 12, 13, 14, 15, 16, 17, 18, 19, 20, 21, 22, 23, 24 or 25) bp of the attB nucleotide sequences (such as, but not limited to, those depicted in FIG. 9), and optionally one or more, two or more, three or more, four or more, and most preferably four or five or more additional terminal nucleotide bases which preferably are guanines. The PCR product then may be converted to a Entry Clone by performing a BP Reaction, in which the attB-PCR product recombines with a Donor Vector containing one or more attP sites. Details of this approach and protocols for PCR fragment subcloning are provided in Examples 8 and 21-25.

A variety of Entry Clones may be produced by these methods, providing a wide array of cloning options; a number of specific Entry Vectors are also available commercially from Life Technologies, Inc. (Rockville, Md.). The Examples herein provide a more in-depth description of selected Entry Vectors and details of their cloning sites. Choosing the optimal Entry Vector for a particular application is discussed in Example 4.

Entry Vectors and Destination Vectors should be constructed so that the amino-terminal region of a nucleic acid molecule of interest (e.g., a gene, cDNA library or insert, or fragment thereof) will be positioned next to the attL1 site. Entry Vectors preferably contain the rrnB transcriptional terminator upstream of the attL1 site. This sequence ensures that expression of cloned nucleic acid molecules of interest is reliably "off" in *E. coli*, so that even toxic genes can be successfully cloned. Thus, Entry Clones may be designed to be transcriptionally silent. Note also that Entry Vectors, and hence Entry Clones, may contain the kanamycin antibiotic resistance ($kan^r$) gene to facilitate selection of host cells containing Entry Clones after transformation. In certain applications, however, Entry Clones may contain other selection markers, including but not limited to a gentamycin resistance ($gen^r$) or tetracycline resistance ($tet^r$) gene, to facilitate selection of host cells containing Entry Clones after transformation.

Once a nucleic acid molecule of interest has been cloned into an Entry Vector, it may be moved into a Destination Vector. The upper right portion of FIG. 5A shows a schematic of a Destination Vector. The thick arrow represents some function (often transcription or translation) that will act on the nucleic acid molecule of interest in the clone. During the recombination reaction, the region between the attR1 and attR2 sites, including a toxic or "death" gene (e.g., ccdB), is replaced by the DNA segment from the Entry Clone. Selection for recombinants that have acquired the ampicillin resistance ($amp^r$) gene (carried on the Destination Vector) and that have also lost the death gene ensures that a high percentage (usually >90%) of the resulting colonies will contain the correct insert.

To move a nucleic acid molecule of interest into a Destination Vector, the Destination Vector is mixed with the Entry Clone comprising the desired nucleic acid molecule of interest, a cocktail of recombination proteins (e.g., GATEWAY™ LR Clonase™ Enzyme Mix) is added, the mixture is incubated (preferably at about 25° C. for about 60 minutes, or longer under certain circumstances, e.g. for transfer of large nucleic acid molecules, as described below) and any standard host cell (including bacterial cells such as *E. coli*; animal cells such as insect cells, mammalian cells, nematode cells and the like; plant cells; and yeast cells) strain is transformed with the reaction mixture. The host cell used will be determined by the desired selection (e.g., *E. coli* DB3.1, available commercially from Life Technologies, Inc., allows survival of clones containing the ccdB death gene, and thus can be used to select for cointegrate molecules—i.e., molecules that are hybrids between the Entry Clone and Destination Vector). The Examples below provide further details and protocols for use of Entry and Destination Vectors in transferring nucleic acid molecules of interest and expressing RNAs or polypeptides encoded by these nucleic acid molecules in a variety of host cells.

The cloning system of the invention therefore offers multiple advantages:

Once a nucleic acid molecule of interest is cloned into the GATEWAY™ Cloning System, it can be moved into and out of other vectors with complete fidelity of reading frame and orientation. That is, since the reactions proceed whereby attL1 on the Entry Clone recombines with attR1 on the Destination Vector, the directionality of the nucleic acid molecule of interest is maintained or may be controlled upon transfer from the Entry Clone into the Destination Vector. Hence, the GATEWAY™ Cloning System provides a powerful and easy method of directional cloning of nucleic acid molecule of interest.

One-step cloning or subcloning: Mix the Entry Clone and the Destination Vector with Clonase, incubate, and transform.

Clone PCR products readily by in vitro recombination, by adding attB sites to PCR primers. Then directly transfer these Entry Clones into Destination Vectors. This process may also be carried out in one step (see Examples below).

Powerful selections give high reliability: >90% (and often >99%) of the colonies contain the desired DNA in its new vector.

One-step conversion of existing standard vectors into GATEWAY™ Cloning System vectors.

Ideal for large vectors or those with few cloning sites.

Recombination sites are short (25 bp), and may be engineered to contain no stop codons or secondary structures.

Reactions may be automated, for high-throughput applications (e.g., for diagnostic purposes or for therapeutic candidate screening).

The reactions are economical: 0.3 μg of each DNA; no restriction enzymes, phosphatase, ligase, or gel purification. Reactions work well with miniprep DNA.

Transfer multiple clones, and even libraries, into one or more Destination Vectors, in a single experiment.

A variety of Destination Vectors may be produced, for applications including, but not limited to:

Protein expression in *E. coli*: native proteins; fusion proteins with GST, His6, thioredoxin, etc., for purification, or one or more epitope tags; any promoter useful in expressing proteins in *E. coli* may be used, such as ptrc, $\lambda P_L$, and T7 promoters.

Protein expression in eukaryotic cells: CMV promoter, baculovirus (with or without His6 tag), Semliki Forest virus, Tet regulation.

DNA sequencing (all lac primers), RNA probes, phagemids (both strands)

A variety of Entry Vectors (for recombinational cloning entry by standard recombinant DNA methods) may be produced:

Strong transcription stop just upstream, for genes toxic to *E. coli.*

Three reading frames.

With or without TEV protease cleavage site.

Motifs for prokaryotic and/or eukaryotic translation.

Compatible with commercial cDNA libraries.

Expression Clone cDNA (attB) libraries, for expression screening, including 2-hybrid libraries and phage display libraries, may also be constructed.

Recombination Site Sequences

In one aspect, the invention relates to nucleic acid molecules, which may or may not be isolated nucleic acid molecules, comprising one or more nucleotide sequences encoding one or more recombination sites or portions thereof. In particular, this aspect of the invention relates to such nucleic acid molecules comprising one or more nucleotide sequences encoding attB, attP, attL, or attR, or portions of these recombination site sequences. The invention also relates to mutants, derivatives, and fragments of such nucleic acid molecules. Unless otherwise indicated, all nucleotide sequences that may have been determined by sequencing a DNA molecule herein were determined using manual or automated DNA sequencing, such as dideoxy sequencing, according to methods that are routine to one of ordinary skill in the art (Sanger, F., and Coulson, A. R., *J. Mol. Biol.* 94:444-448 (1975); Sanger, F., et al., *Proc. Natl. Acad. Sci. USA* 74:5463-5467 (1977)). All amino acid sequences of polypeptides encoded by DNA molecules determined herein were predicted by conceptual translation of a DNA sequence determined as above. Therefore, as is known in the art for any DNA sequence determined by these approaches, any nucleotide sequence determined herein may contain some errors. Nucleotide sequences determined by such methods are typically at least about 90% identical, more typically at least about 95% to at least about 99.9% identical to the actual nucleotide sequence of the sequenced DNA molecule. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). Thus, the invention relates to sequences of the invention in the form of DNA or RNA molecules, or hybrid DNA/RNA molecules, and their corresponding complementary DNA, RNA, or DNA/RNA strands.

In a first such aspect, the invention provides nucleic acid molecules comprising one or more nucleotide sequences encoding attB1, or mutants, fragments, variants or derivatives thereof. Such nucleic acid molecules may comprise an attB1 nucleotide sequence having the sequence set forth in FIG. 9, such as: ACAAGTTTGTACAAAAAAGCAGGCT (SEQ ID NO:1), or a nucleotide sequence complementary to the nucleotide sequence set forth in FIG. 9 for attB1, or mutants, fragments, variants or derivatives thereof. As one of ordinary skill will appreciate, however, certain mutations, insertions, or deletions of one or more bases in the attB1 sequence contained in the nucleic acid molecules of the invention may be made without compromising the structural and functional integrity of these molecules; hence, nucleic acid molecules comprising such mutations, insertions, or deletions in the attB1 sequence are encompassed within the scope of the invention.

In a related aspect, the invention provides nucleic acid molecules comprising one or more nucleotide sequences encoding attB2, or mutants, fragments, variants or derivatives thereof. Such nucleic acid molecules may comprise an attB2 nucleotide sequence having the sequence set forth in FIG. 9, such as: ACCCAGCTTTCTTGTACAAAGTGGT (SEQ ID NO:2), or a nucleotide sequence complementary to the nucleotide sequence set forth in FIG. 9 for attB2, or mutants, fragments, variants or derivatives thereof. As noted above for attB1, certain mutations, insertions, or deletions of one or more bases in the attB2 sequence contained in the nucleic acid molecules of the invention may be made without compromising the structural and functional integrity of these molecules; hence, nucleic acid molecules comprising such mutations, insertions, or deletions in the attB2 sequence are encompassed within the scope of the invention.

A recombinant host cell comprising a nucleic acid molecule containing attB1 and attB2 sites (the vector pEXP501, also known as pCMVSport6; see FIG. 48), *E. coli* DB3.1 (pCMVSport6), was deposited on Feb. 27, 1999, with the Collection, Agricultural Research Culture Collection (NRRL), 1815 North University Street, Peoria, Ill. 61604 USA, as Deposit No. NRRL B-30108. The attB1 and attB2 sites within the deposited nucleic acid molecule are contained in nucleic acid cassettes in association with one or more additional functional sequences as described in more detail below.

In another related aspect, the invention provides nucleic acid molecules comprising one or more nucleotide sequences encoding attP1, or mutants, fragments, variants or derivatives thereof. Such nucleic acid molecules may comprise an attP1 nucleotide sequence having the sequence set forth in FIG. 9, such as: TACAGGTCACTAATACCATCTAAGTAGTTGATTCATAGTGA-CTGGATATGTTGTGTTTTACAGTATTATGTAGTCTGTTTTTTAT-GCAAAATCTAATTTAATATATTGATATTTATATCATTTTACGTT-TCTCGTTCAGCTTTTTTGTACAAAGTTGGCATTATAAAAAAGCATTG-CTCATCAATTTGTTGCAACGAACAGGTCACTATCAGTCAAAATAA-AATCATTATTTG (SEQ ID NO:3), or a nucleotide sequence complementary to the nucleotide sequence set forth in FIG. 9 for attP1, or mutants, fragments, variants or derivatives thereof. As noted above for attB1, certain mutations, insertions, or deletions of one or more bases in the attP1 sequence contained in the nucleic acid molecules of the invention may be made without compromising the structural and functional integrity of these molecules; hence, nucleic acid molecules comprising such mutations, insertions, or deletions in the attP1 sequence are encompassed within the scope of the invention.

In another related aspect, the invention provides nucleic acid molecules comprising one or more nucleotide sequences encoding attP2, or mutants, fragments, variants or derivatives thereof. Such nucleic acid molecules may comprise an attP2 nucleotide sequence having the sequence set forth in FIG. 9, such as: CAAATAATGATTTTATTTTGACTGATAGTGACCTGTTCGTTG-CAACAAATTGATAAGCAATGCTTTCTTATAATGCCAACTTT-GTACAAGAAAGCTGAACGAGAAACGTAAAATGATA-TAAATATCAATATATTAAATTAGATTTTGCATAAAAAACAG-ACTACATAATACTGTAAAACACAACATATCCAGTCACTATGAATCAA-CTACTTAGATGGTATTAGTGACCTGTA (SEQ ID NO:4), or a nucleotide sequence complementary to the nucleotide sequence set forth in FIG. 9 for attP2, or mutants, fragments, variants or derivatives thereof. As noted above for attB1, certain mutations, insertions, or deletions of one or more bases in the attP2 sequence contained in the nucleic acid molecules of the invention may be made without compromising the structural and functional integrity of these molecules; hence, nucleic acid molecules comprising such mutations, insertions, or deletions in the attP2 sequence are encompassed within the scope of the invention.

Figure 49A:
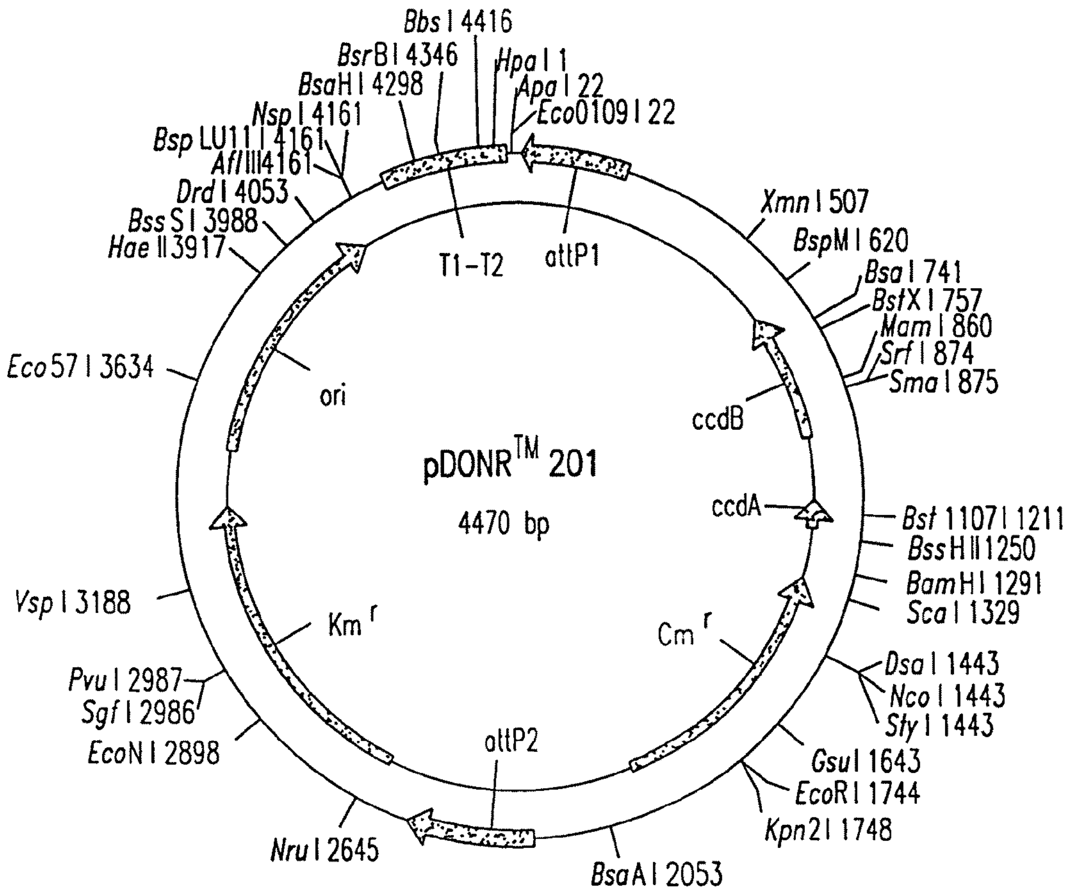
FIG. 49 is a depiction of the physical map (FIG. 49A), and the nucleotide sequence (FIGS. 49B-C) (SEQ ID NO:157), for the Donor plasmid pDONR201 which donates a kanamycin-resistant vector in the BP Reaction. This vector may also be referred to as pAttPkanr Donor Plasmid, or as pAttPkan Donor Plasmid

A recombinant host cell comprising a nucleic acid molecule (the attP vector pDONR201, also known as pENTR21-attPkan or pAttPkan; see FIG. 49) containing attP1 and attP2 sites, *E. coli* DB3.1 (pAttPkan) (also called *E. coli* DB3.1 (pAHKan)), was deposited on Feb. 27, 1999, with the Collection, Agricultural Research Culture Collection (NRRL), 1815 North University Street, Peoria, Ill. 61604 USA, as Deposit No. NRRL B-30099. The attP1 and attP2 sites within the deposited nucleic acid molecule are contained in nucleic acid cassettes in association with one or more additional functional sequences as described in more detail below.

In another related aspect, the invention provides nucleic acid molecules comprising one or more nucleotide sequences encoding attR1, or mutants, fragments, variants or derivatives thereof. Such nucleic acid molecules may comprise an attR1 nucleotide sequence having the sequence set forth in FIG. 9, such as: ACAAGTTTGTACAAAAAAGCTGAACGAG-AAACGTAAAATGATATAAATATCAATATATTAAATT-AGATTTTGCAT-AAAAAACAGACTACATAATACTG-TAAAACACAACATATCCAGTCA-CTATG (SEQ ID NO:5), or a nucleotide sequence complementary to the nucleotide sequence set forth in FIG. 9 for attR1, or mutants, fragments, variants or derivatives thereof. As noted above for attB1, certain mutations, insertions, or deletions of one or more bases in the attR1 sequence contained in the nucleic acid molecules of the invention may be made without compromising the structural and functional integrity of these molecules; hence, nucleic acid molecules comprising such mutations, insertions, or deletions in the attR1 sequence are encompassed within the scope of the invention.

In another related aspect, the invention provides nucleic acid molecules comprising one or more nucleotide sequences encoding attR2, or mutants, fragments, variants or derivatives thereof. Such nucleic acid molecules may comprise an attR2 nucleotide sequence having the sequence set forth in FIG. 9, such as: GCAGGTCGACCATAGTGACTGGATAT-GT-TGTGTTTTACAGTATTATGTAGTCTGTTTTTTATG-CAAAATCTA-ATTTAATATATTGATATTTATATCATTT-TACGTTTCTCGTTCAGCTT-TCTTGTACAAAGTGGT (SEQ ID NO:6), or a nucleotide sequence complementary to the nucleotide sequence set forth in FIG. 9 for attR2, or mutants, fragments, variants or derivatives thereof. As noted above for attB1, certain mutations, insertions, or deletions of one or more bases in the attR2 sequence contained in the nucleic acid molecules of the invention may be made without compromising the structural and functional integrity of these molecules; hence, nucleic acid molecules comprising such mutations, insertions, or deletions in the attR2 sequence are encompassed within the scope of the invention.

Recombinant host cell strains containing attR1 sites apposed to cloning sites in reading frame A, reading frame B, and reading frame C, *E. coli* DB3.1 (pEZC15101) (reading frame A; see FIG. 64A), *E. coli* DB3.1 (pEZC15102) (reading frame B; see FIG. 64B), and *E. coli* DB3.1 (pEZC15103) (reading frame C; see FIG. 64C), and containing corresponding attR2 sites, were deposited on Feb. 27, 1999, with the Collection, Agricultural Research Culture Collection (NRRL), 1815 North University Street, Peoria, Ill. 61604 USA, as Deposit Nos. NRRL B-30103, NRRL B-30104, and NRRL B-30105, respectively. The attR1 and attR2 sites within the deposited nucleic acid molecules are contained in nucleic acid cassettes in association with one or more additional functional sequences as described in more detail below.

In another related aspect, the invention provides nucleic acid molecules comprising one or more nucleotide sequences encoding attL1, or mutants, fragments, variants and derivatives thereof. Such nucleic acid molecules may comprise an attL1 nucleotide sequence having the sequence set forth in FIG. 9, such as: CAA ATA ATG ATT TTA TTT TGA CTG ATA GTG ACC TGT TCG TTG CAA CAA ATT GAT AAG CAA TGC TTT TTT ATA ATG CCA ACT TTG TAC AAA AAA GCA GGC T (SEQ ID NO:7), or a nucleotide sequence complementary to the nucleotide sequence set forth in FIG. 9 for attL1, or mutants, fragments, variants or derivatives thereof. As noted above for attB1, certain mutations, insertions, or deletions of one or more bases in the attL1 sequence contained in the nucleic acid molecules of the invention may be made without compromising the structural and functional integrity of these molecules; hence, nucleic acid molecules comprising such mutations, insertions, or deletions in the attL1 sequence are encompassed within the scope of the invention.

In another related aspect, the invention provides nucleic acid molecules comprising one or more nucleotide sequences encoding attL2, or mutants, fragments, variants and derivatives thereof. Such nucleic acid molecules may comprise an attL2 nucleotide sequence having the sequence set forth in FIG. 9, such as: C AAA TAA TGA TTT TAT TTT GAC TGA TAG TGA CCT GTT CGT TGC AAC AAA TTG ATA AGC AAT GCT TTC TTA TAA TGC CAA CTT TGT ACA AGA AAG CTG GGT (SEQ ID NO:8), or a nucleotide sequence complementary to the nucleotide sequence set forth in FIG. 9 for attL2, or mutants, fragments, variants or derivatives thereof. As noted above for attB1, certain mutations, insertions, or deletions of one or more bases in the attL2 sequence contained in the nucleic acid molecules of the invention may be made without compromising the structural and functional integrity of these molecules; hence, nucleic acid molecules comprising such mutations, insertions, or deletions in the attL2 sequence are encompassed within the scope of the invention.

Recombinant host cell strains containing attL1 sites apposed to cloning sites in reading frame A, reading frame B, and reading frame C, *E. coli* DB3.1 (pENTR1A) (reading frame A; see FIG. 10), *E. coli* DB3.1 (pENTR2B) (reading frame B; see FIG. 11), and *E. coli* DB3.1 (pENTR3C) (reading frame C; see FIG. 12), and containing corresponding attL2 sites, were deposited on Feb. 27, 1999, with the Collection, Agricultural Research Culture Collection (NRRL), 1815 North University Street, Peoria, Ill. 61604 USA, as Deposit Nos. NRRL B-30100, NRRL B-30101, and NRRL B-30102, respectively. The attL1 and attL2 sites within the deposited nucleic acid molecules are contained in nucleic acid cassettes in association with one or more additional functional sequences as described in more detail below.

Each of the recombination site sequences described herein or portions thereof, or the nucleotide sequence cassettes contained in the deposited clones, may be cloned or inserted into a vector of interest (for example, using the recombinational cloning methods described herein and/or standard restriction cloning techniques that are routine in the art) to generate, for example, Entry Vectors or Destination Vectors which may be used to transfer a desired segment of a nucleic acid molecule of interest (e.g., a gene, cDNA molecule, or cDNA library) into a desired vector or into a host cell.

Using the information provided herein, such as the nucleotide sequences for the recombination site sequences described herein, an isolated nucleic acid molecule of the present invention encoding one or more recombination sites or portions thereof may be obtained using standard cloning and screening procedures, such as those for cloning cDNAs using mRNA as starting material. Preferred such methods include PCR-based cloning methods, such as reverse transcriptase-PCR(RT-PCR) using primers such as those described herein and in the Examples below. Alternatively, vectors comprising the cassettes containing the recombination site sequences described herein are available commercially from Life Technologies, Inc. (Rockville, Md.).

The invention is also directed to nucleic acid molecules comprising one or more of the recombination site sequences or portions thereof and one or more additional nucleotide sequences, which may encode functional or structural sites such as one or more multiple cloning sites, one or more transcription termination sites, one or more transcriptional regulatory sequences (which may be promoters, enhancers, repressors, and the like), one or more translational signals (e.g., secretion signal sequences), one or more origins of replication, one or more fusion partner peptides (particularly glutathione S-transferase (GST), hexahistidine ($His_6$), and thioredoxin (Trx)), one or more selection markers or modules, one or more nucleotide sequences encoding localization signals such as nuclear localization signals or secretion signals, one or more origins of replication, one or more protease cleavage sites, one or more genes or portions of genes encoding a protein or polypeptide of interest, and one or more 5' polynucleotide extensions (particularly an extension of guanine residues ranging in length from about 1 to about 20, from about 2 to about 15, from about 3 to about 10, from about 4 to about 10, and most preferably an extension of 4 or 5 guanine residues at the 5' end of the recombination site nucleotide sequence. The one or more additional functional or structural sequences may or may not flank one or more of the recombination site sequences contained on the nucleic acid molecules of the invention.

In some nucleic acid molecules of the invention, the one or more nucleotide sequences encoding one or more additional functional or structural sites may be operably linked to the nucleotide sequence encoding the recombination site. For example, certain nucleic acid molecules of the invention may have a promoter sequence operably linked to a nucleotide sequence encoding a recombination site or portion thereof of the invention, such as a T7 promoter, a phage lambda PL promoter, an *E. coli* lac, trp or tac promoter, and other suitable promoters which will be familiar to the skilled artisan.

Nucleic acid molecules of the present invention, which may be isolated nucleic acid molecules, may be in the form of RNA, such as mRNA, or in the form of DNA, including, for instance, cDNA and genomic DNA obtained by cloning or produced synthetically, or in the form of DNA-RNA hybrids. The nucleic acid molecules of the invention may be double-stranded or single-stranded. Single-stranded DNA or RNA may be the coding strand, also known as the sense strand, or it may be the non-coding strand, also referred to as the anti-sense strand. The nucleic acid molecules of the invention may also have a number of topologies, including linear, circular, coiled, or supercoiled.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells, and those DNA molecules purified (partially or substantially) from a solution whether produced by recombinant DNA or synthetic chemistry techniques. Isolated RNA molecules include in vivo or in vitro RNA transcripts of the DNA molecules of the present invention.

The present invention further relates to mutants, fragments, variants and derivatives of the nucleic acid molecules of the present invention, which encode portions, analogs or derivatives of one or more recombination sites. Variants may occur naturally, such as a natural allelic variant. By an "allelic variant" is intended one of several alternate forms of a gene occupying a given locus on a chromosome of an organism (see Lewin, B., ed., *Genes II*, John Wiley & Sons, New York (1985)). Non-naturally occurring variants may be produced using art-known mutagenesis techniques, such as those described hereinbelow.

Such variants include those produced by nucleotide substitutions, deletions or additions or portions thereof, or combinations thereof. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the encoded polypeptide(s) or portions thereof, and which also do not substantially alter the reactivities of the recombination site nucleic acid sequences in recombination reactions. Also especially preferred in this regard are conservative substitutions.

Particularly preferred mutants, fragments, variants, and derivatives of the nucleic acid molecules of the invention include, but are not limited to, insertions, deletions or substitutions of one or more nucleotide bases within the 15 bp core region (GCTTTTTTATACTAA) (SEQ ID NO:9) which is identical in all four wildtype lambda att sites, attB, attP, attL and attR (see U.S. application Ser. Nos. 08/663,002, filed Jun. 7, 1996 (now U.S. Pat. No. 5,888,732), 09/005,476, filed Jan. 12, 1998, and 09/177,387, filed Oct. 23, 1998, which describes the core region in further detail, and the disclosures of which are incorporated herein by reference in their entireties). Analogously, the core regions in attB1, attP1, attL1 and attR1 are identical to one another, as are the core regions in attB2, attP2, attL2 and attR2. Particularly preferred in this regard are nucleic acid molecules comprising insertions, deletions or substitutions of one or more nucleotides within the seven bp overlap region (TTTATAC, which is defined by the cut sites for the integrase protein and is the region where strand exchange takes place) that occurs within this 15 bp core region (GCTTTTTTATACTAA) (SEQ ID NO:9). Examples of such preferred mutants, fragments, variants and derivatives according to this aspect of the invention include, but are not limited to, nucleic acid molecules in which the thymine at position 1 of the seven bp overlap region has been deleted or substituted with a guanine, cytosine, or adenine; in which the thymine at position 2 of the seven bp overlap region has been deleted or substituted with a guanine, cytosine, or adenine; in which the thymine at position 3 of the seven bp overlap region has been deleted or substituted with a guanine, cytosine, or adenine; in which the adenine at position 4 of the seven bp overlap region has been deleted or substituted with a guanine, cytosine, or thymine; in which the thymine at position 5 of the seven bp overlap region has been deleted or substituted with a guanine, cytosine, or adenine; in which the adenine at position 6 of the seven bp overlap region has been deleted or substituted with a guanine, cytosine, or thymine; and in which the cytosine at position 7 of the seven bp overlap region has been deleted or substituted with a guanine, thymine, or adenine; or any combination of one or more such deletions and/or substitutions within this seven bp overlap region. As described in detail in Example 21 herein, mutants of the nucleic acid molecules of the invention in which substitutions have been made within the first three positions of the seven bp overlap (TTTATAC) have been found in the present invention to strongly affect the specificity of recombination, mutant nucleic acid molecules in which substitutions have been made in the last four positions (TTTATAC) only partially alter recombination specificity, and mutant nucleic acid molecules comprising nucleotide substitutions outside of the seven bp overlap, but elsewhere within the 15 bp core region, do not affect specificity of recombination but do influence the efficiency of recombination. Hence, in an additional aspect, the present invention is also directed to nucleic acid molecules comprising one or more recombination site nucleotide sequences that affect recombination specificity, particularly one or more nucleotide sequences that may correspond substantially to the seven base pair overlap within the 15 bp core region, having one or more mutations that affect recombination specificity. Particularly preferred such molecules may comprise a consensus sequence (described in detail in Example 21 herein) such as NNNATAC, wherein "N" refers to any nucleotide (i.e., may be A, G, T/U or C), with the proviso that if one of the first three nucleotides in the consensus sequence is a T/U, then at least one of the other two of the first three nucleotides is not a T/U.

In a related aspect, the present invention is also directed to nucleic acid molecules comprising one or more recombination site nucleotide sequences that enhance recombination efficiency, particularly one or more nucleotide sequences that may correspond substantially to the core region and having one or more mutations that enhance recombination efficiency. By sequences or mutations that "enhance recombination efficiency" is meant a sequence or mutation in a recombination site, preferably in the core region (e.g., the 15 bp core region of att recombination sites), that results in an increase in cloning efficiency (typically measured by determining successful cloning of a test sequence, e.g., by determining CFU/ml for a given cloning mixture) when recombining molecules comprising the mutated sequence or core region as compared to molecules that do not comprise the mutated sequence or core region (e.g., those comprising a wildtype recombination site core region sequence). More specifically, whether or not a given sequence or mutation enhances recombination efficiency may be determined using the sequence or mutation in recombinational cloning as described herein, and determining whether the sequence or mutation provides enhanced recombinational cloning efficiency when compared to a non-mutated (e.g., wildtype) sequence. Methods of determining preferred cloning efficiency-enhancing mutations for a number of recombination sites, particularly for att recombination sites, are described herein, for example in Examples 22-25. Examples of preferred such mutant recombination sites include but are not limited to the attL consensus core sequence of caacttnntnnnannaagttg (SEQ ID NO:92) (wherein "n" represents any nucleotide), for example the attL5 sequence agcctgctttattatactaagttggcatta (SEQ ID NO:10) and the attL6 sequence agcctgctttttatattaagttggcatta (SEQ ID NO:11); the attB1.6 sequence ggggacaactttgtacaaaaaagttggct (SEQ ID NO:12); the attB2.2 sequence ggggacaactttgtacaagaaagctgggt (SEQ ID NO:13); and the attB2.10 sequence ggggacaactttgtacaagaaagttgggt (SEQ ID NO:14). Those of skill in the art will appreciate that, in addition to the core region, other portions of the att site may affect the efficiency of recombination. There are five so-called arm binding sites for the integrase protein in the bacteriophage lambda attP site, two in attR (P1 and P2), and three in attL (P'1, P'2 and P'3). Compared to the core binding sites, the integrase protein binds to arm sites with high affinity and interacts with core and arm sites through two different domains of the protein. As with the core binding site a consensus sequence for the arm binding site consisting of C/AAGTCACTAT has been inferred from sequence comparison of the five arm binding sites and seven non-att sites (Ross and Landy, *Proc. Natl. Acad. Sci. USA* 79:7724-7728 (1982)). Each arm site has been mutated and tested for its effect in the excision and integration reactions (Numrych et al., *Nucl. Acids Res.* 18:3953 (1990)). Hence, specific sites are utilized in each reaction in different ways, namely, the P1 and P'3 sites are essential for the integration reaction whereas the other three sites are dispensable to the integration reaction to varying degrees. Similarly, the P2, P'1 and P'2 sites are most important for the excision reaction, whereas P1 and P'3 are completely dispensable. Interestingly, when P2 is mutated the integration reaction occurs more efficiently than with the wild type attP site. Similarly, when P1 and P'3 are mutated the excision reaction occurs more efficiently. The stimulatory effect of mutating integrase arm binding sites can be explained by removing sites that compete or inhibit a specific recombination pathway or that function in a reaction that converts products back to starting substrates. In fact there is evidence for an XIS-independent LR reaction (Abremski and Gottesman, *J. Mol. Biol.* 153:67-78 (1981)). Thus, in addition to modifications in the core region of the att site, the present invention contemplates the use of att sites containing one or more modifications in the integrase arm-type binding sites. In some preferred embodiments, one or more mutations may be introduced into one or more of the P1, P'1, P2, P'2 and P'3 sites. In some preferred embodiments, multiple mutations may be introduced into one or more of these sites. Preferred such mutations include those which increase the recombination in vitro. For example, in some embodiments mutations may be introduced into the arm-type binding sites such that integrative recombination, corresponding to the BP reaction, is enhanced. In other embodiments, mutations may be introduced into the arm-type binding sites such that excisive recombination, corresponding to the LR reaction, is enhanced. Of course, based on the guidance contained herein, particularly in the construction and evaluation of effects of mutated recombination sites upon recombinational specificity and efficiency, analogous mutated or engineered sequences may be produced for other recombination sites described herein (including but not limited to lox, FRT, and the like) and used in accordance with the invention. For example, much like the mutagenesis strategy used to select core binding sites that enhance recombination efficiency, similar strategies can be employed to select changes in the arms of attP, attL and attR, and in analogous sequences in other recombination sites such as lox, FRT and the like, that enhance recombination efficiency. Hence, the construction and evaluation of such mutants is well within the abilities of those of ordinary skill in the art without undue experimentation. One suitable methodology for preparing and evaluating such mutations is found in Numrych, et al., (1990) *Nucleic Acids Research* 18(13): 3953-3959.

Other mutant sequences and nucleic acid molecules that may be suitable to enhance recombination efficiency will be apparent from the description herein, or may be easily determined by one of ordinary skill using only routine experimentation in molecular biology in view of the description herein and information that is readily available in the art Since the genetic code is well known in the art, it is also routine for one of ordinary skill in the art to produce degenerate variants of the nucleic acid molecules described herein without undue experimentation. Hence, nucleic acid molecules comprising degenerate variants of nucleic acid sequences encoding the recombination sites described herein are also encompassed within the scope of the invention.

Further embodiments of the invention include isolated nucleic acid molecules comprising a polynucleotide having a nucleotide sequence at least 50% identical, at least 60% identical, at least 70% identical, at least 75% identical, at least 80% identical, at least 85% identical, at least 90% identical, and more preferably at least 95%, 96%, 97%, 98% or 99% identical to the nucleotide sequences of the seven bp overlap region within the 15 bp core region of the recombination sites described herein, or the nucleotide sequences of attB1, attB2, attP1, attP2, attL1, attL2, attR1 or attR2 as set forth in FIG. 9 (or portions thereof), or a nucleotide sequence complementary to any of these nucleotide sequences, or fragments, variants, mutants, and derivatives thereof.

By a polynucleotide having a nucleotide sequence at least, for example, 95% "identical" to a reference nucleotide sequence encoding a particular recombination site or portion thereof is intended that the nucleotide sequence of the polynucleotide is identical to the reference sequence except that the polynucleotide sequence may include up to five point mutations (e.g., insertions, substitutions, or deletions) per each 100 nucleotides of the reference nucleotide sequence encoding the recombination site. For example, to obtain a polynucleotide having a nucleotide sequence at least 95% identical to a reference attB1 nucleotide sequence, up to 5% of the nucleotides in the attB1 reference sequence may be deleted or substituted with another nucleotide, or a number of nucleotides up to 5% of the total nucleotides in the attB1 reference sequence may be inserted into the attB1 reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 50%, 60%, 70%, 75%, 80%, 85%, 90%, 95%, 96%, 97%, 98% or 99% identical to, for instance, a given recombination site nucleotide sequence or portion thereof can be determined conventionally using known computer programs such as DNAsis software (Hitachi Software, San Bruno, Calif.) for initial sequence alignment followed by ESEE version 3.0 DNA/protein sequence software (cabot@trog.mbb.sfu.ca) for multiple sequence alignments. Alternatively, such determinations may be accomplished using the BESTFIT program (Wisconsin Sequence Analysis Package, Genetics Computer Group, University Research Park, 575 Science Drive, Madison, Wis. 53711), which employs a local homology algorithm (Smith and Waterman, *Advances in Applied Mathematics* 2: 482-489 (1981)) to find the best segment of homology between two sequences. When using DNAsis, ESEE, BESTFIT or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The present invention is directed to nucleic acid molecules at least 50%, 60%, 70%, 75%, 80%, 85%, 90%, 95%, 96%, 97%, 98% or 99% identical to the attB1, attB2, attP1, attP2, attL1, attL2, attR1 or attR2 nucleotide sequences as set forth in FIG. 9, or to the nucleotide sequence of the deposited clones, irrespective of whether they encode particular functional polypeptides. This is because even where a particular nucleic acid molecule does not encode a particular functional polypeptide, one of skill in the art would still know how to use the nucleic acid molecule, for instance, as a hybridization probe or a polymerase chain reaction (PCR) primer.

Mutations can also be introduced into the recombination site nucleotide sequences for enhancing site specific recombination or altering the specificities of the reactants, etc. Such mutations include, but are not limited to: recombination sites without translation stop codons that allow fusion proteins to be encoded; recombination sites recognized by the same proteins but differing in base sequence such that they react largely or exclusively with their homologous partners allowing multiple reactions to be contemplated; and mutations that prevent hairpin formation of recombination sites. Which particular reactions take place can be specified by which particular partners are present in the reaction mixture.

There are well known procedures for introducing specific mutations into nucleic acid sequences. A number of these are described in Ausubel, F. M. et al., *Current Protocols in Molecular Biology*, Wiley Interscience, New York (1989-1996). Mutations can be designed into oligonucleotides, which can be used to modify existing cloned sequences, or in amplification reactions. Random mutagenesis can also be employed if appropriate selection methods are available to isolate the desired mutant DNA or RNA. The presence of the desired mutations can be confirmed by sequencing the nucleic acid by well known methods.

The following non-limiting methods can be used to modify or mutate a given nucleic acid molecule encoding a particular recombination site to provide mutated sites that can be used in the present invention:

1. By recombination of two parental DNA sequences by site-specific (e.g. attL and attR to give attP) or other (e.g. homologous) recombination mechanisms where the parental DNA segments contain one or more base alterations resulting in the final mutated nucleic acid molecule;
2. By mutation or mutagenesis (site-specific, PCR, random, spontaneous, etc) directly of the desired nucleic acid molecule;
3. By mutagenesis (site-specific, PCR, random, spontaneous, etc) of parental DNA sequences, which are recombined to generate a desired nucleic acid molecule;
4. By reverse transcription of an RNA encoding the desired core sequence; and
5. By de novo synthesis (chemical synthesis) of a sequence having the desired base changes, or random base changes followed by sequencing or functional analysis according to methods that are routine in the art.

The functionality of the mutant recombination sites can be demonstrated in ways that depend on the particular characteristic that is desired. For example, the lack of translation stop codons in a recombination site can be demonstrated by expressing the appropriate fusion proteins. Specificity of recombination between homologous partners can be demonstrated by introducing the appropriate molecules into in vitro reactions, and assaying for recombination products as described herein or known in the art. Other desired mutations in recombination sites might include the presence or absence of restriction sites, translation or transcription start signals, protein binding sites, particular coding sequences, and other known functionalities of nucleic acid base sequences. Genetic selection schemes for particular functional attributes in the recombination sites can be used according to known method steps. For example, the modification of sites to provide (from a pair of sites that do not interact) partners that do interact could be achieved by requiring deletion, via recombination between the sites, of a DNA sequence encoding a toxic substance. Similarly, selection for sites that remove translation stop sequences, the presence or absence of protein binding sites, etc., can be easily devised by those skilled in the art.

Accordingly, the present invention also provides a nucleic acid molecule, comprising at least one DNA segment having at least one, and preferably at least two, engineered recombination site nucleotide sequences of the invention flanking a selectable marker and/or a desired DNA segment, wherein at least one of said recombination site nucleotide sequences has at least one engineered mutation that enhances recombination in vitro in the formation of a Cointegrate DNA or a Product DNA. Such engineered mutations may be in the core sequence of the recombination site nucleotide sequence of the invention; see U.S. application Ser. Nos. 08/486,139, filed Jun. 7, 1995, 08/663,002, filed Jun. 7, 1996 (now U.S. Pat. No. 5,888,732), 09/005,476, filed Jan. 12, 1998, and 09/177,387, filed Oct. 23, 1998, the disclosures of which are all incorporated herein by reference in their entireties.

While in the preferred embodiment the recombination sites differ in sequence and do not interact with each other, it is recognized that sites comprising the same sequence, which may interact with each other, can be manipulated or engineered to inhibit recombination with each other. Such conceptions are considered and incorporated herein. For example, a protein binding site (e.g., an antibody-binding site, a histone-binding site, an enzyme-binding site, or a binding site for any nucleic acid molecule-binding protein) can be engineered adjacent to one of the sites. In the presence of the protein that recognizes the engineered site, the recombinase fails to access the site and another recombination site in the nucleic acid molecule is therefore used preferentially. In the cointegrate this site can no longer react since it has been changed, e.g., from attB to attL. During or upon resolution of the cointegrate, the protein can be inactivated (e.g., by antibody, heat or a change of buffer) and the second site can undergo recombination.

The nucleic acid molecules of the invention can have at least one mutation that confers at least one enhancement of said recombination, said enhancement selected from the group consisting of substantially (i) favoring integration; (ii) favoring recombination; (ii) relieving the requirement for host factors; (iii) increasing the efficiency of said Cointegrate DNA or Product DNA formation; (iv) increasing the specificity of said Cointegrate DNA or Product DNA formation; and (v) adding or deleting protein binding sites.

In other embodiments, the nucleic acid molecules of the invention may be PCR primer molecules, which comprise one or more of the recombination site sequences described herein or portions thereof, particularly those shown in FIG. 9 (or sequences complementary to those shown in FIG. 9), or mutants, fragments, variants or derivatives thereof, attached at the 3' end to a target-specific template sequence which specifically interacts with a target nucleic acid molecule which is to be amplified. Primer molecules according to this aspect of the invention may further comprise one or more, (e.g., 1, 2, 3, 4, 5, 10, 20, 25, 50, 100, 500, 1000, or more) additional bases at their 5' ends, and preferably comprise one or more (particularly four or five) additional bases, which are preferably guanines, at their 5' ends, to increase the efficiency of the amplification products incorporating the primer molecules in the recombinational cloning system of the invention. Such nucleic acid molecules and primers are described in detail in the examples herein, particularly in Examples 22-25.

Certain primers of the invention may comprise one or more nucleotide deletions in the attB1, attB2, attP1, attP2, attL1, attL2, attR1 or attR2 sequences as set forth in FIG. 9. In one such aspect, for example, attB2 primers may be constructed in which one or more of the first four nucleotides at the 5' end of the attB2 sequence shown in FIG. 9 have been deleted. Primers according to this aspect of the invention may therefore have the sequence:

(attB2(-1)): CCCAGCTTTCTTGTACAAAGTGGT-nnnnnnnnnnnnn . . . n (SEQ ID NO:15)

(attB2(-2)): CCAGCTTTCTTGTACAAAGTGGT-nnnnnnnnnnnnnn . . . n (SEQ ID NO:16)

(attB2(-3)): CAGCTTTCTTGTACAAAGTGGT-nnnnnnnnnnnnnnn . . . n (SEQ ID NO:17)

(attB2(-4)): AGCTTTCTTGTACAAAGTGGT-nnnnnnnnnnnnnnnn . . . n (SEQ ID NO:18),

Wherein "nnnnnnnnnnnn . . . n" at the 3' end of the primer represents a target-specific sequence of any length, for example from one base up to all of the bases of a target nucleic acid molecule (e.g., a gene) or a portion thereof, the sequence and length which will depend upon the identity of the target nucleic acid molecule which is to be amplified.

The primer nucleic acid molecules according to this aspect of the invention may be produced synthetically by attaching the recombination site sequences depicted in FIG. 9, or portions thereof, to the 5' end of a standard PCR target-specific primer according to methods that are well-known in the art. Alternatively, additional primer nucleic acid molecules of the invention may be produced synthetically by adding one or more nucleotide bases, which preferably correspond to one or more, preferably five or more, and more preferably six or more, contiguous nucleotides of the att nucleotide sequences described herein (see, e.g., Example 20 herein; see also U.S. application Ser. Nos. 08/663,002, filed Jun. 7, 1996 (now U.S. Pat. No. 5,888,732), 09/005,476, filed Jan. 12, 1998, and 09/177,387, filed Oct. 23, 1998, the disclosures of which are all incorporated herein by reference in their entireties), to the 5' end of a standard PCR target-specific primer according to methods that are well-known in the art, to provide primers having the specific nucleotide sequences described herein. As noted above, primer nucleic acid molecules according to this aspect of the invention may also optionally comprise one, two, three, four, five, or more additional nucleotide bases at their 5' ends, and preferably will comprise four or five guanines at their 5' ends. In one particularly preferred such aspect, the primer nucleic acid molecules of the invention may comprise one or more, preferably five or more, more preferably six or more, still more preferably 6-18 or 6-25, and most preferably 6, 7, 8, 9, 10, 11, 12, 13, 14, 15, 16, 17, 18, 19, 20, 21, 22, 23, 24 or 25, contiguous nucleotides or bp of the attB1 or attB2 nucleotide sequences depicted in FIG. 9 (or nucleotides complementary thereto), linked to the 5' end of a target-specific (e.g., a gene-specific) primer molecule. Primer nucleic acid molecules according to this aspect of the invention include, but are not limited to, attB1- and attB2-derived primer nucleic acid molecules having the following nucleotide sequences:

ACAAGTTTGTACAAAAAAGCAGGCT-nnnnnnnnnnnn . . . n (SEQ ID NO:19)

ACCACTTTGTACAAGAAAGCTGGGT-nnnnnnnnnnn nn . . . n (SEQ ID NO:20)

TGTACAAAAAAGCAGGCT-nnnnnnnnnnnnn . . . n (SEQ ID NO:21)

TGTACAAGAAAGCTGGGT-nnnnnnnnnnnnn . . . n (SEQ ID NO:22)

ACAAAAAAGCAGGCT-nnnnnnnnnnnnn . . . n (SEQ ID NO:23)

ACAAGAAAGCTGGGT-nnnnnnnnnnnnn . . . n (SEQ ID NO:24)

AAAAAGCAGGCT-nnnnnnnnnnnnn . . . n (SEQ ID NO:25)

AGAAAGCTGGGT-nnnnnnnnnnnnn . . . n (SEQ ID NO:26)

AAAAGCAGGCT-nnnnnnnnnnnnn . . . n (SEQ ID NO:27)

GAAAGCTGGGT-nnnnnnnnnnnnn . . . n (SEQ ID NO:28)

AAAGCAGGCT-nnnnnnnnnnnnn . . . n (SEQ ID NO:29)

AAAGCTGGGT-nnnnnnnnnnnnn . . . n (SEQ ID NO:30)

AAGCAGGCT-nnnnnnnnnnnnn . . . n

AAGCTGGGT-nnnnnnnnnnnnn . . . n

AGCAGGCT-nnnnnnnnnnnnn . . . n

AGCTGGGT-nnnnnnnnnnnnn . . . n

GCAGGCT-nnnnnnnnnnnnn . . . n

GCTGGGT-nnnnnnnnnnnnn . . . n

CAGGCT-nnnnnnnnnnnnn . . . n

CTGGGT-nnnnnnnnnnnnn . . . n, wherein "nnnnnnnnnnnnn . . . n" at the 3' end of the primer represents a target-specific sequence of any length, for example from one base up to all of the bases of a target nucleic acid molecule (e.g., a gene) or a portion thereof, the sequence and length which will depend upon the identity of the target nucleic acid molecule which is to be amplified.

Of course, it will be apparent to one of ordinary skill from the teachings contained herein that additional primer nucleic acid molecules analogous to those specifically described herein may be produced using one or more, preferably five or more, more preferably six or more, still more preferably ten or more, 15 or more, 20 or more, 25 or more, 30 or more, etc. (through to and including all) of the contiguous nucleotides or bp of the attP1, attP2, attL1, attL2, attR1 or attR2 nucleotide sequences depicted in FIG. 9 (or nucleotides complementary thereto), linked to the 5' end of a target-specific (e.g., a gene-specific) primer molecule. As noted above, such primer nucleic acid molecules may optionally further comprise one, two, three, four, five, or more additional nucleotide bases at their 5' ends, and preferably will comprise four guanines at their 5' ends. Other primer molecules comprising the attB1, attB2, attP1, attP2, attL1, attL2, attR1 and attR2 sequences depicted in FIG. 9, or portions thereof, may be made by one of ordinary skill without resorting to undue experimentation in accordance with the guidance provided herein.

The primers of the invention described herein are useful in producing PCR fragments having a nucleic acid molecule of interest flanked at each end by a recombination site sequence (as described in detail below in Example 9), for use in cloning of PCR-amplified DNA fragments using the recombination system of the invention (as described in detail below in Examples 8, 19 and 21-25).

Vectors

The invention also relates to vectors comprising one or more of the nucleic acid molecules of the invention, as described herein. In accordance with the invention, any vector may be used to construct the vectors of the invention. In particular, vectors known in the art and those commercially available (and variants or derivatives thereof) may in accordance with the invention be engineered to include one or more nucleic acid molecules encoding one or more recombination sites (or portions thereof), or mutants, fragments, or derivatives thereof, for use in the methods of the invention. Such vectors may be obtained from, for example, Vector Laboratories Inc., InVitrogen, Promega, Novagen, New England Biolabs, Clontech, Roche, Pharmacia, EpiCenter, OriGenes Technologies Inc., Stratagene, Perkin Elmer, Pharmingen, Life Technologies, Inc., and Research Genetics. Such vectors may then for example be used for cloning or subcloning nucleic acid molecules of interest. General classes of vectors of particular interest include prokaryotic and/or eukaryotic cloning vectors, Expression Vectors, fusion vectors, two-hybrid or reverse two-hybrid vectors, shuttle vectors for use in different hosts, mutagenesis vectors, transcription vectors, vectors for receiving large inserts and the like.

Other vectors of interest include viral origin vectors (M13 vectors, bacterial phage λ vectors, bacteriophage P1 vectors, adenovirus vectors, herpesvirus vectors, retrovirus vectors, phage display vectors, combinatorial library vectors), high, low, and adjustable copy number vectors, vectors which have compatible replicons for use in combination in a single host (pACYC184 and pBR322) and eukaryotic episomal replication vectors (pCDM8).

Particular vectors of interest include prokaryotic Expression Vectors such as pcDNA II, pSL301, pSE280, pSE380, pSE420, pTrcHisA, B, and C, pRSET A, B, and C (Invitrogen, Inc.), pGEMEX-1, and pGEMEX-2 (Promega, Inc.), the pET vectors (Novagen, Inc.), pTrc99A, pKK223-3, the pGEX vectors, pEZZ18, pRIT2T, and pMC 1871 (Pharmacia, Inc.), pKK233-2 and pKK388-1 (Clontech, Inc.), and pProEx-HT (Life Technologies, Inc.) and variants and derivatives thereof. Destination Vectors can also be made from eukaryotic Expression Vectors such as pFastBac, pFastBac HT, pFastBac DUAL, pSFV, and pTet-Splice (Life Technologies, Inc.), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMC1neo, and pOG44 (Stratagene, Inc.), and pYES2, pAC360, pBlueBacHisA, B, and C, pVL1392, pBsueBacIII, pCDM8, pcDNA1, pZeoSV, pcDNA3 pREP4, pCEP4, and pEBVHis (Invitrogen, Inc.) and variants or derivatives thereof.

Other vectors of particular interest include pUC18, pUC19, pBlueScript, pSPORT, cosmids, phagemids, YACs (yeast artificial chromosomes), BACs (bacterial artificial chromosomes), MACs (mammalian artificial chromosomes), pQE70, pQE60, pQE9 (Quiagen), pBS vectors, PhageScript vectors, BlueScript vectors, pNH8A, pNH16A, pNH18A, pNH46A (Stratagene), pcDNA3 (InVitrogen), pGEX, pTrsfus, pTrc99A, pET-5, pET-9, pKK223-3, pKK233-3, pDR540, pRIT5 (Pharmacia), pSPORT1, pSPORT2, pCMVSPORT2.0 and pSV-SPORT1 (Life Technologies, Inc.) and variants or derivatives thereof.

Additional vectors of interest include pTrxFus, pThioHis, pLEX, pTrcHis, pTrcHis2, pRSET, pBlueBacHis2, pcDNA3.1/His, pcDNA3.1 (–)/Myc-His, pSecTag, pEBVHis, pPIC9K, pPIC3.5K, pAO815, pPICZ, pPICZα, pGAPZ, pGAPZα, pBlueBac4.5, pBlueBacHis2, pMelBac, pSinRep5, pSinHis, pIND, pIND(SP1), pVgRXR, pcDNA2.1. pYES2, pZErO1.1, pZErO-2.1, pCR-Blunt, pSE280, pSE380, pSE420, pVL1392, pVL1393, pCDM8, pcDNA1.1, pcDNA 1.1/Amp, pcDNA3.1, pcDNA3.1/Zeo, pSe, SV2, pRc/CMV2, pRc/RSV, pREP4, pREP7, pREP8, pREP9, pREP10, pCEP4, pEBVHis, pCR3.1, pCR2.1, pCR3.1—Uni, and pCRBac from Invitrogen; λExCell, λgt11, pTrc99A, pKK223-3, pGEX-1λT, pGEX-2T, pGEX-2TK, pGEX-4T-1, pGEX4T-2, pGEX-4T-3, pGEX-3X, pGEX-5X-1, pGEX-5X-2, pGEX-5X-3, pEZZ18, pRIT2T, pMC1871, pSVK3, pSVL, pMSG, pCH110, pKK232-8, pSL1180, pNEO, and pUC4K from Pharmacia; pSCREEN-1b(+), pT7Blue(R), pT7Blue-2, pCITE4abc(+), pOCUS-2, pTAg, pET-32 LIC, pET-30 LIC, pBAC-2 cp LIC, pBAC-gus-2 cp LIC, pT7Blue-2 LIC, pT7Blue-2, λSCREEN-1, λBlueSTAR, pET-3abcd, pET-7abc, pET9abcd, pET11abcd, pET12abc, pET-14b, pET-15b, pET-16b, pET-17b-pET-17xb, pET-19b, pET-20b(+), pET-21abcd(+), pET-22b(+), pET-23abcd(+), pET-24abcd(+), pET-25b(+), pET-26b(+), pET-27b(+), pET-28abc(+), pET-29abc(+), pET-30abc(+), pET-31b(+), pET-32abc(+), pET-33b(+), pBAC-1, pBAC-gus-1, pBAC4x-1, pBACgus4x-1, pBAC-3 cp, pBACgus-2 cp, pBACsurf-1, plg, Signal plg, pYX, Selecta Vecta-Neo, Selecta Vecta-Hyg, and Selecta Vecta-Gpt from Novagen; pLexA, pB42AD, pGBT9, pAS2-1, pGAD424, pACT2, pGAD GL, pGAD GH, pGAD10, pGilda, pEZM3, pEGFP, pEGFP-1, pEGFP-N, pEGFP-C, pEBFP, pGFPuv, pGFP, p6xHis-GFP, pSEAP2-Basic, pSEAP2-Contral, pSEAP2-Promoter, pSEAP2-Enhancer, pβgal-Basic, pβgal-Control, pβgal-Promoter, pβgal-Enhancer, pCMVβ, pTet-Off, pTet-On, pTK-Hyg, pRetro-Off, pRetro-On, pIRES1neo, pIRES1hyg, pLXSN, pLNCX, pLAPSN, pMAMneo, pMAMneo-CAT, pMAMneo-LUC, pPUR, pSV2neo, pYEX 4T-1/2/3, pYEX-S1, pBacPAK-His, pBacPAK8/9, pAcUW31, BacPAK6, pTriplEx, λgt10, λgt11, pWE15, and λTrip1Ex from Clontech; Lambda ZAP II, pBK-CMV, pBK-RSV, pBluescript II KS +/−, pBluescript II SK +/−, pAD-GAL4, pBD-GAL4 Cam, pSurfscript, Lambda FIX II, Lambda DASH, Lambda EMBL3, Lambda EMBL4, SuperCos, pCR-Scrigt Amp, pCR-Script Cam, pCR-Script Direct, pBS +/−, pBC KS +/−, pBC SK +/−, Phagescript, pCAL-n-EK, pCAL-n, pCAL-c, pCAL-kc, pET-3abcd, pET-11abcd, pSPUTK, pESP-1, pCMVLacI, pOPRSVI/MCS, pOPI3 CAT, pXT1, pSG5, pPbac, pMbac, pMC1neo, pMC1neo Poly A, pOG44, pOG45, pFRTβGAL, pNEOβGAL, pRS403, pRS404, pRS405, pRS406, pRS413, pRS414, pRS415, and pRS416 from Stratagene.

Two-hybrid and reverse two-hybrid vectors of particular interest include pPC86, pDBLeu, pDBTrp, pPC97, p2.5, pGAD1-3, pGAD10, pACt, pACT2, pGADGL, pGADGH, pAS2-1, pGAD424, pGBT8, pGBT9, pGAD-GAL4, pLexA, pBD-GAL4, pHISi, pHISi-1, placZi, pB42AD, pDG202, pJK202, pJG4-5, pNLexA, pYESTrp and variants or derivatives thereof.

Yeast Expression Vectors of particular interest include pESP-1, pESP-2, pESC-His, pESC-Trp, pESC-URA, pESC-Leu (Stratagene), pRS401, pRS402, pRS411, pRS412, pRS421, pRS422, and variants or derivatives thereof.

According to the invention, the vectors comprising one or more nucleic acid molecules encoding one or more recombination sites, or mutants, variants, fragments, or derivatives thereof, may be produced by one of ordinary skill in the art without resorting to undue experimentation using standard molecular biology methods. For example, the vectors of the invention may be produced by introducing one or more of the nucleic acid molecules encoding one or more recombination sites (or mutants, fragments, variants or derivatives thereof) into one or more of the vectors described herein, according to the methods described, for example, in Maniatis et al., *Molecular Cloning: A Laboratory Manual*, Cold Spring Harbor Laboratory, Cold Spring Harbor, N.Y. (1982). In a related aspect of the invention, the vectors may be engineered to contain, in addition to one or more nucleic acid molecules encoding one or more recombination sites (or portions thereof), one or more additional physical or functional nucleotide sequences, such as those encoding one or more multiple cloning sites, one or more transcription termination sites, one or more transcriptional regulatory sequences (e.g., one or more promoters, enhancers, or repressors), one or more selection markers or modules, one or more genes or portions of genes encoding a protein or polypeptide of interest, one or more translational signal sequences, one or more nucleotide sequences encoding a fusion partner protein or peptide (e.g., GST, $His_6$ or thioredoxin), one or more origins of replication, and one or more 5' or 3' polynucleotide tails (particularly a poly-G tail). According to this aspect of the invention, the one or more recombination site nucleotide sequences (or portions thereof) may optionally be operably linked to the one or more additional physical or functional nucleotide sequences described herein.

Figure 50A:
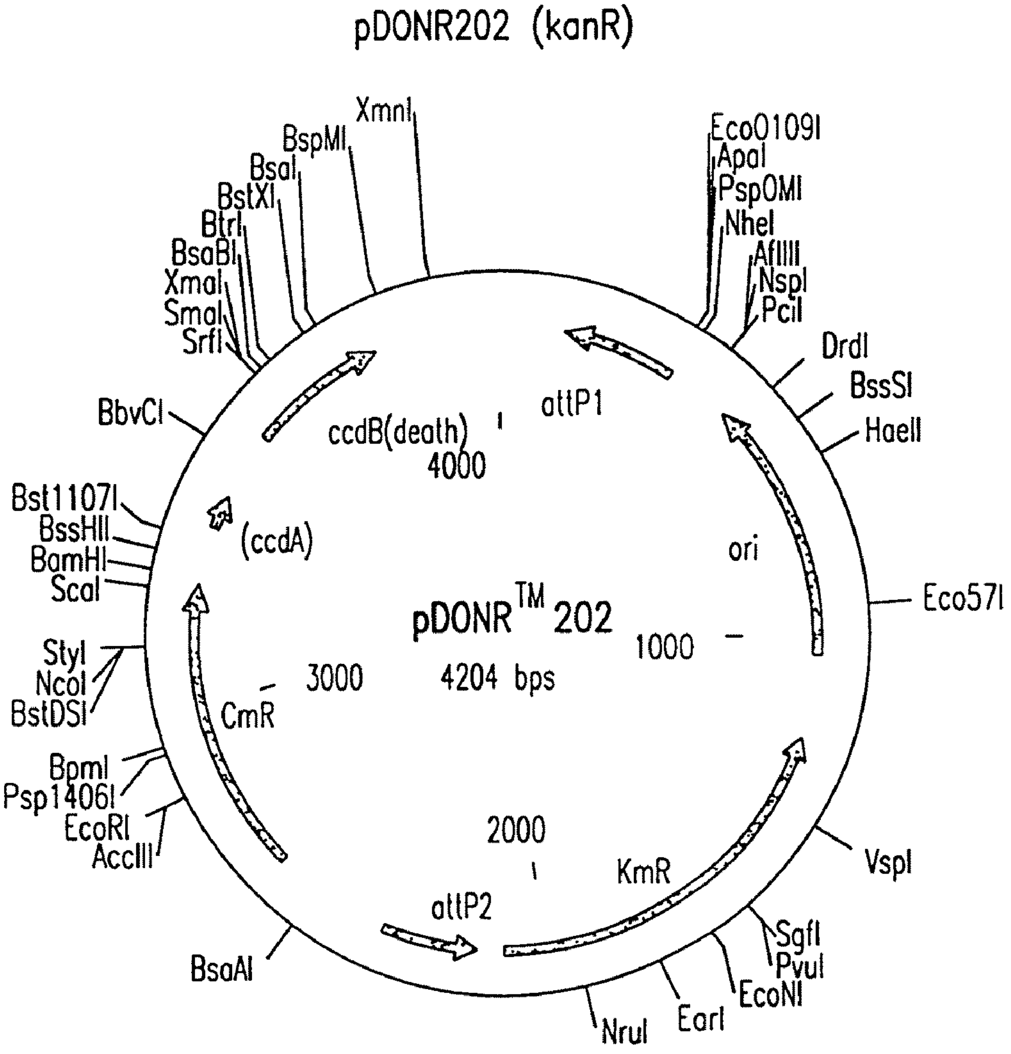
FIG. 50 is a depiction of the physical map (FIG. 50A), and the nucleotide sequence (FIG. 50B-C) (SEQ ID NO:158), for the Donor plasmid pDONR202 which donates a kanamycin-resistant vector in the BP Reaction.
Figure 51A:
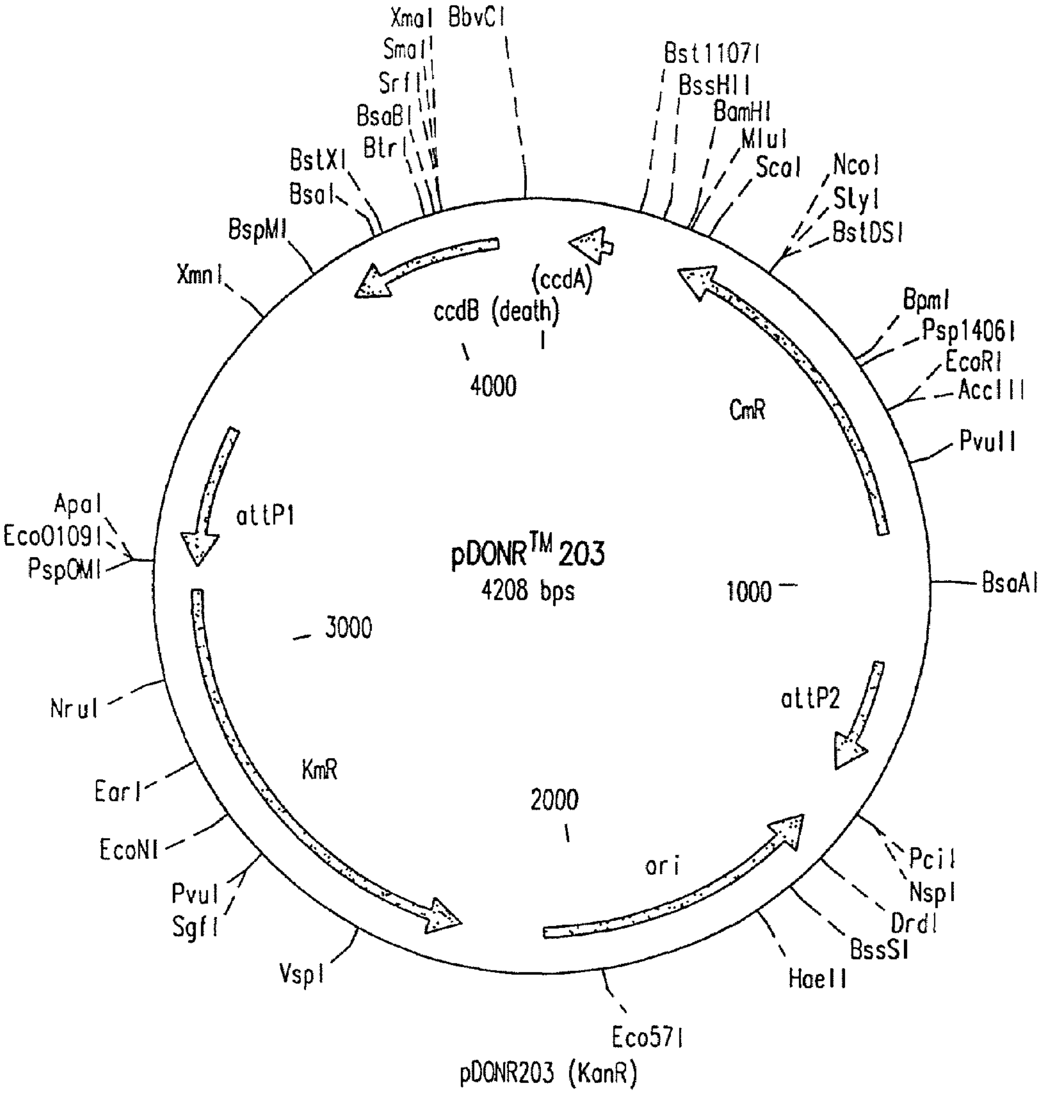
FIG. 51 is a depiction of the physical map (FIG. 51A), and the nucleotide sequence (FIG. 51B-C) (SEQ ID NO:159), for the Donor plasmid pDONR203 which donates a kanamycin-resistant vector in the BP Reaction.
Figure 52A:
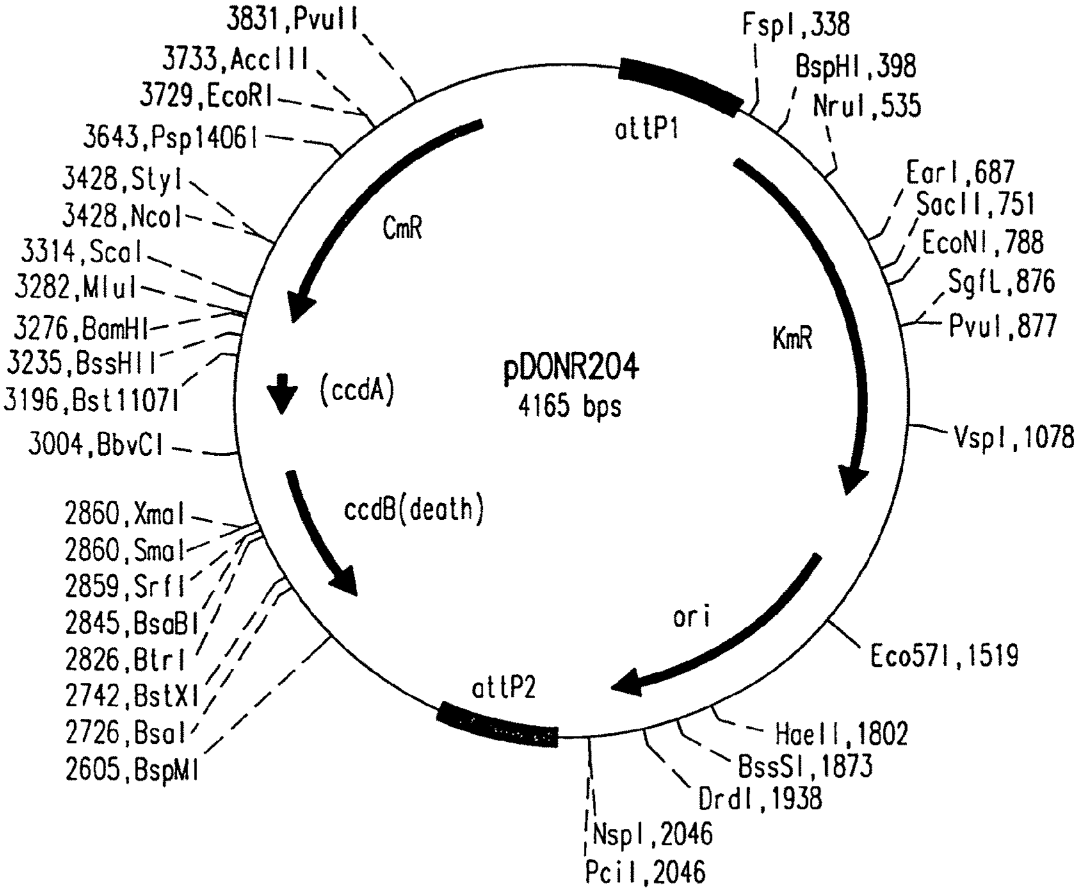
FIG. 52 is a depiction of the physical map (FIG. 52A), and the nucleotide sequence (FIGS. 52B-C) (SEQ ID NO:160), for the Donor plasmid pDONR204 which donates a kanamycin-resistant vector in the BP Reaction.
Figure 53A:
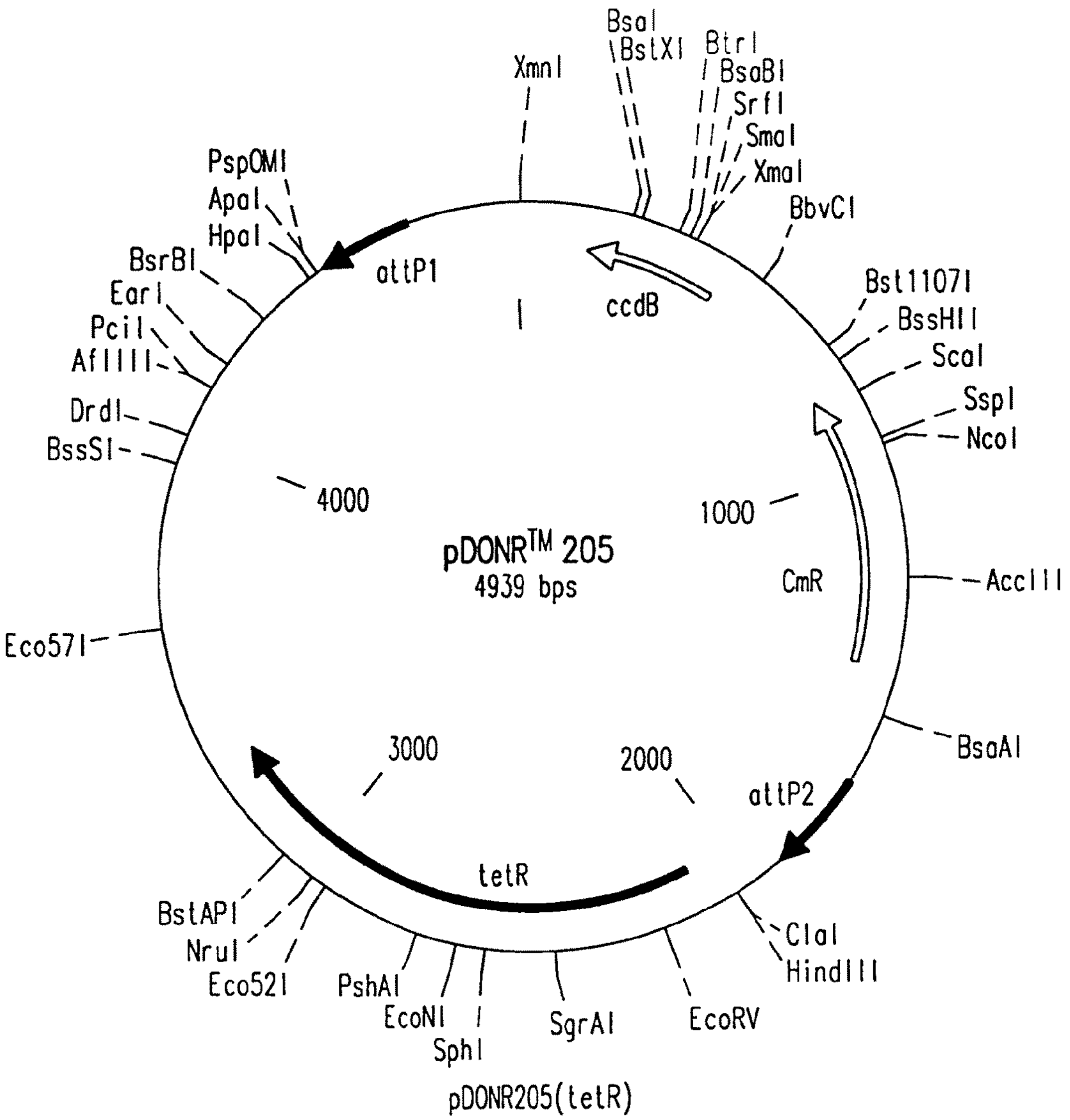
FIG. 53 is a depiction of the physical map (FIG. 53A), and the nucleotide sequence (FIGS. 53B-C) (SEQ ID NO:161), for the Donor plasmid pDONR205 which donates a tetracycline-resistant vector in the BP Reaction.
Figure 54A:
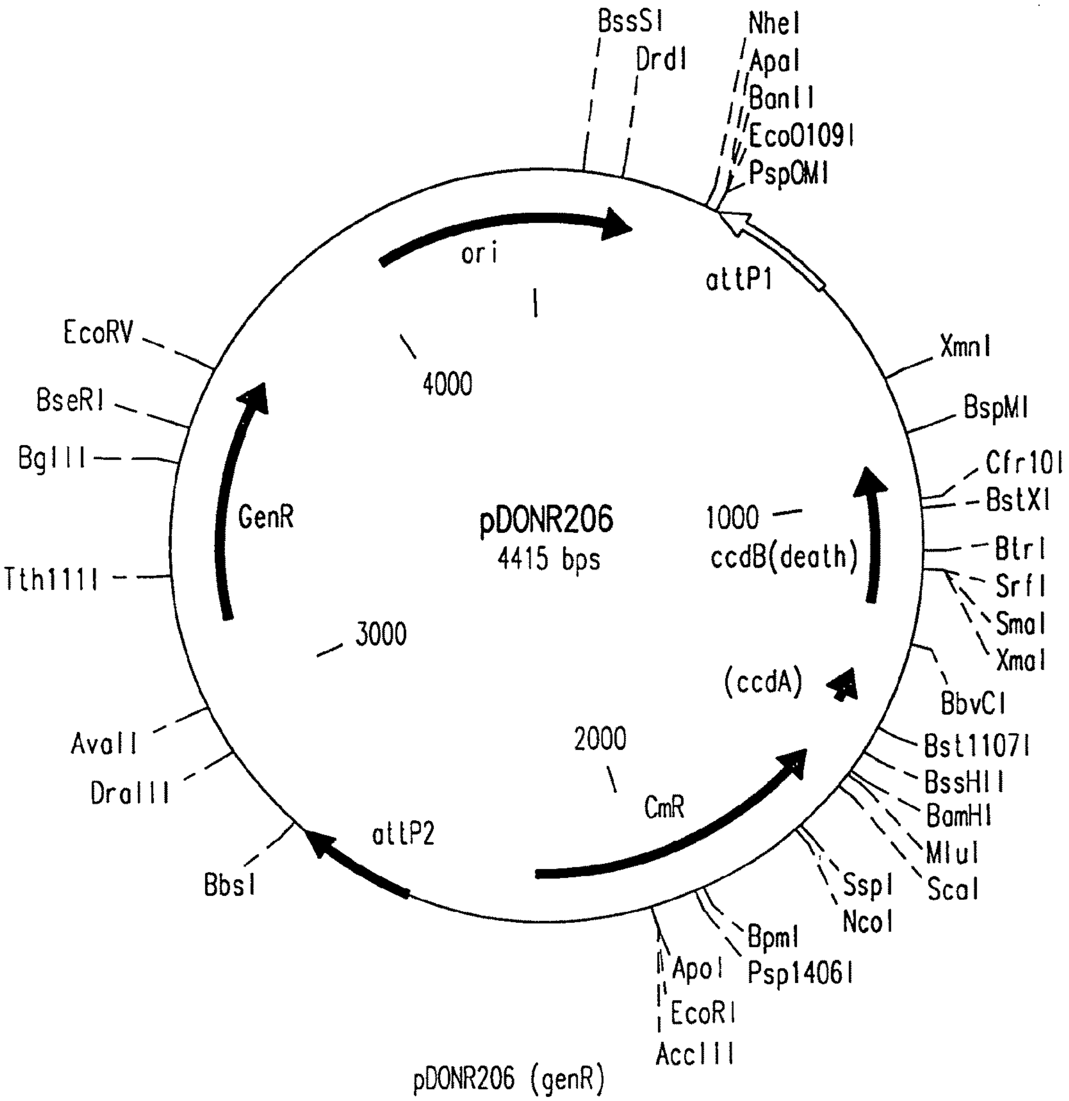
FIG. 54 is a depiction of the physical map (FIG. 54A), and the nucleotide sequence (FIGS. 54B-C) (SEQ ID NO:162), for the Donor plasmid pDONR206 which donates a gentamycin-resistant vector in the BP Reaction. This vector may also be referred to as pENTR22 attP Donor Plasmid, pAttP-Genr Donor Plasmid, or pAttPgent Donor Plasmid.
Figure 87:
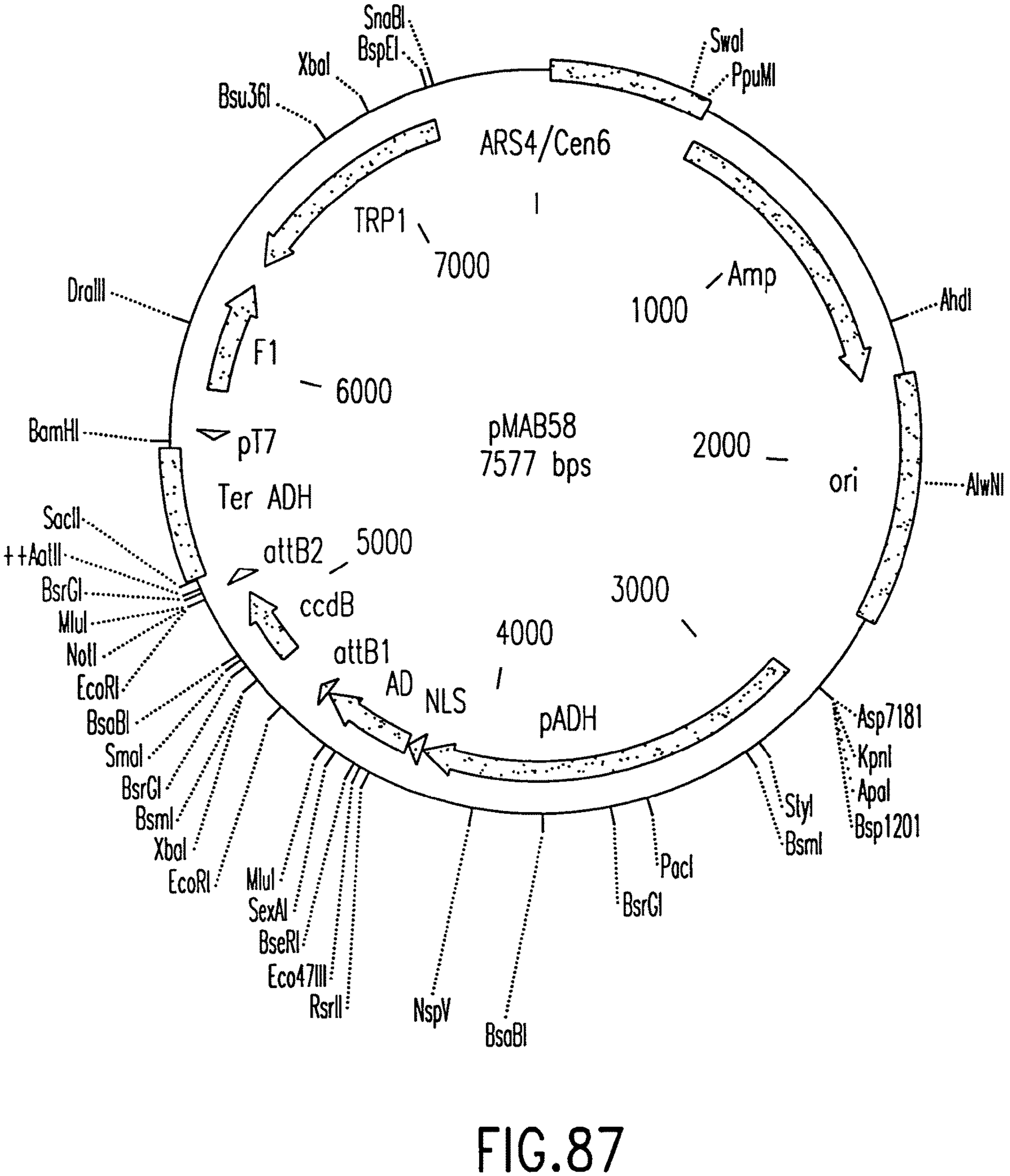
FIG. 87 is a physical map of plasmid pMAB58.
Figure 88:
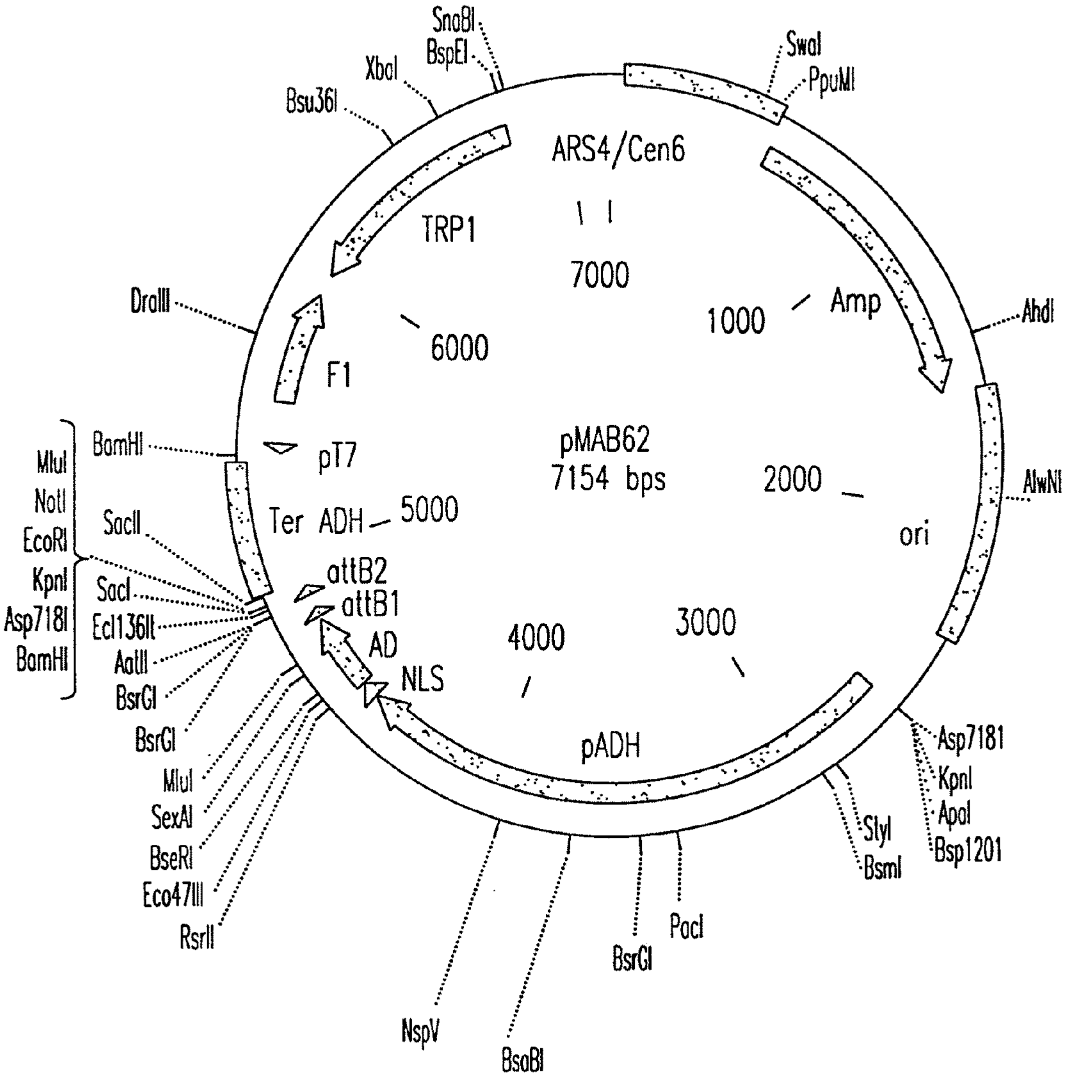
FIG. 88 is a physical map of plasmid pMAB62.
Figure 89:
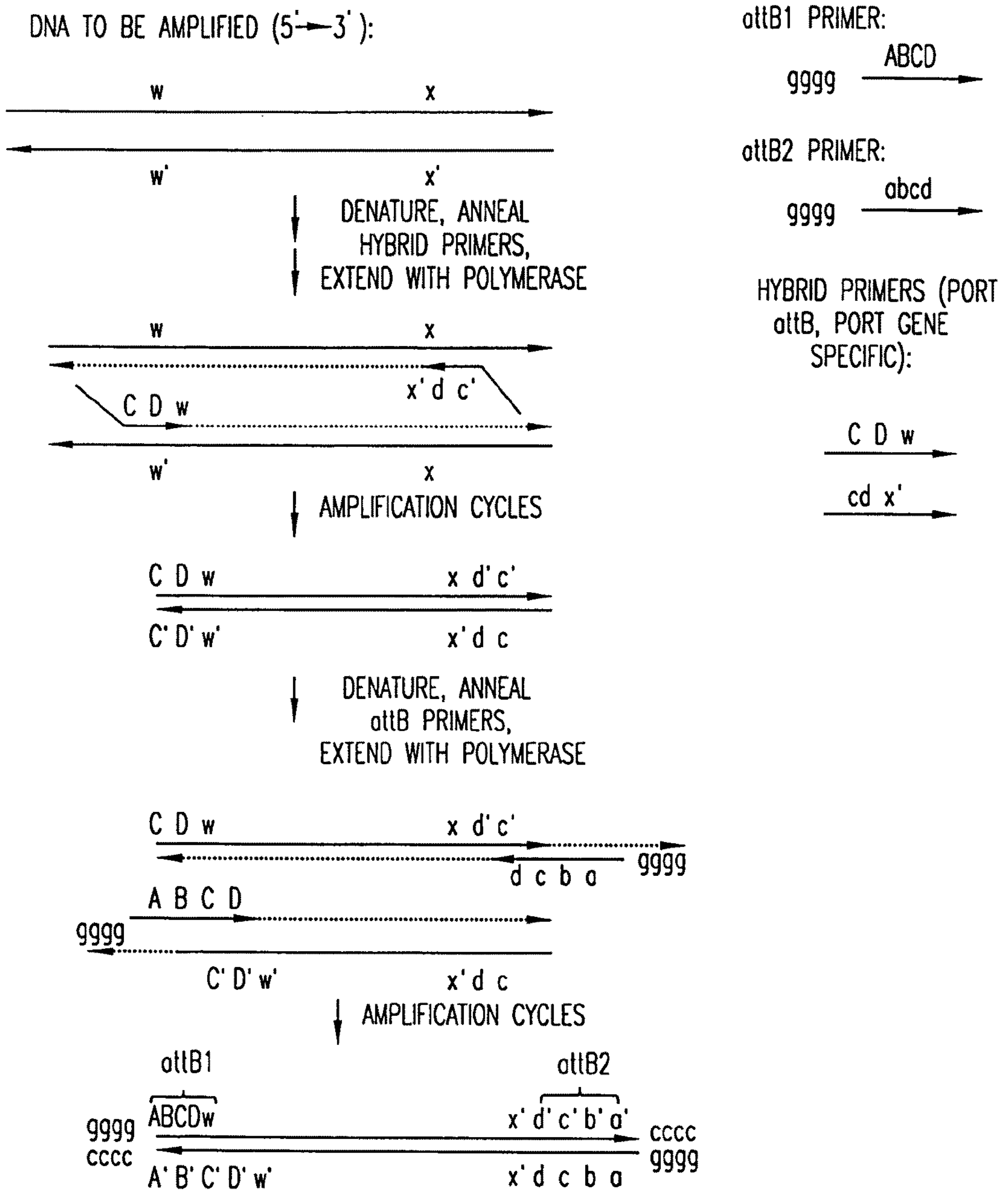
FIG. 89 is a depiction of a synthesis reaction using two pairs of homologous primers of the invention.
Figure 90A:
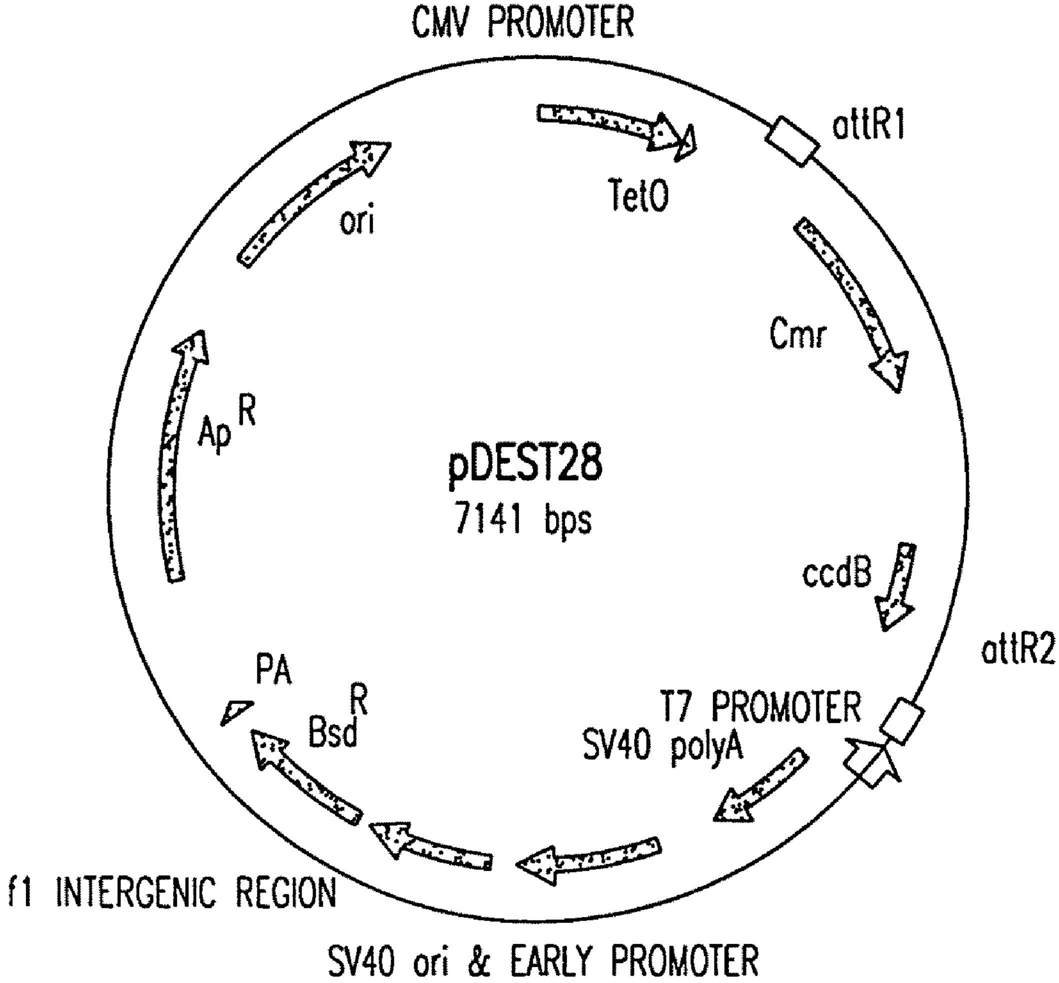
FIG. 90 is a schematic depiction of the physical map (FIG. 90A), and the nucleotide sequence (FIGS. 90B-D) (SEQ ID NO:175), of Destination Vector pDEST28.
Figure 91A:
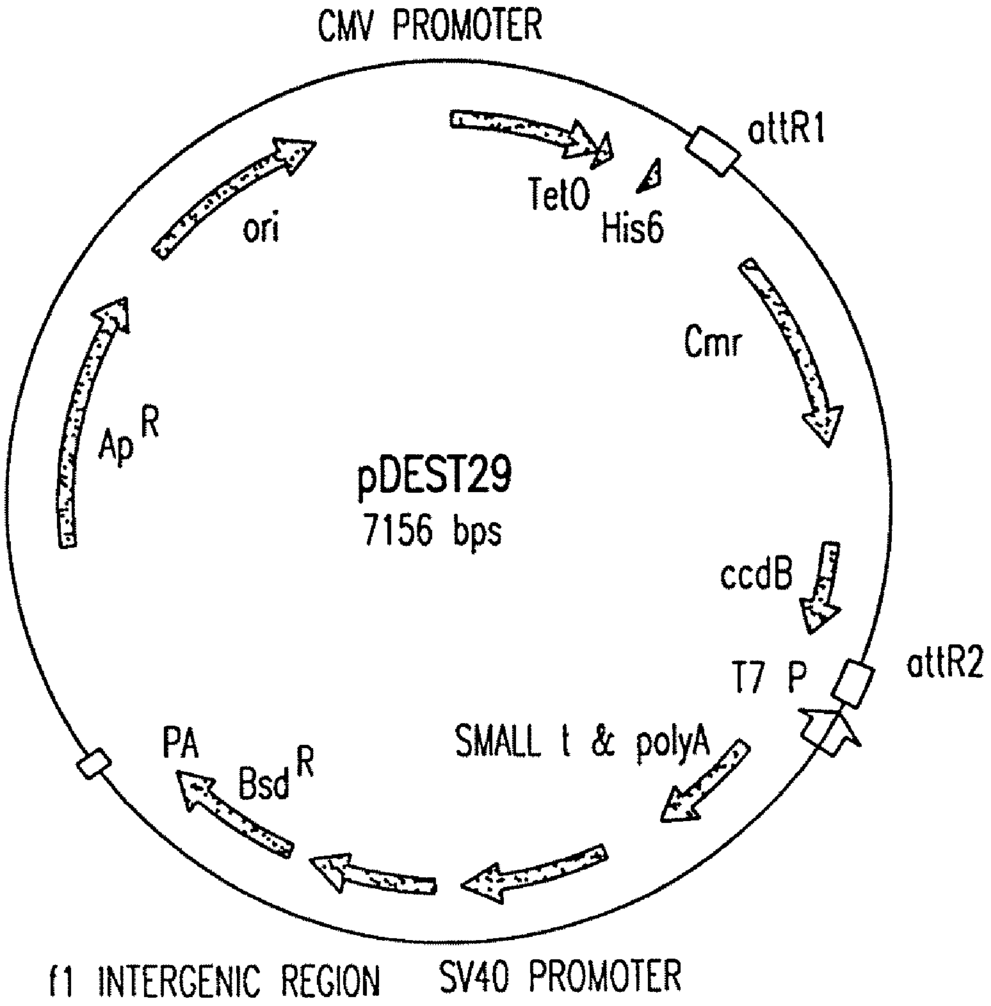
FIG. 91 is a schematic depiction of the physical map (FIG. 91A), and the nucleotide sequence (FIGS. 91B-D) (SEQ ID NO:176), of Destination Vector pDEST29.
Figure 92A:
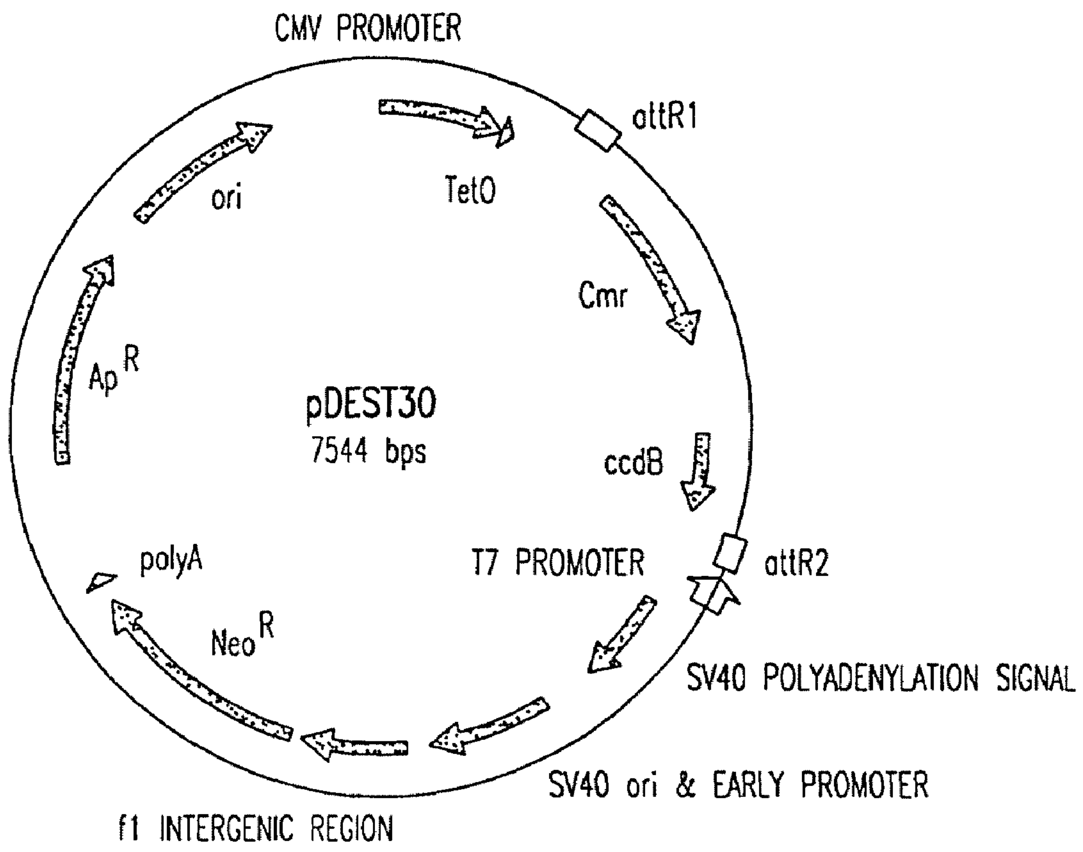
FIG. 92 is a schematic depiction of the physical map (FIG. 92A), and the nucleotide sequence (FIGS. 92B-D) (SEQ ID NO:177), of Destination Vector pDEST30.
Figure 93A:
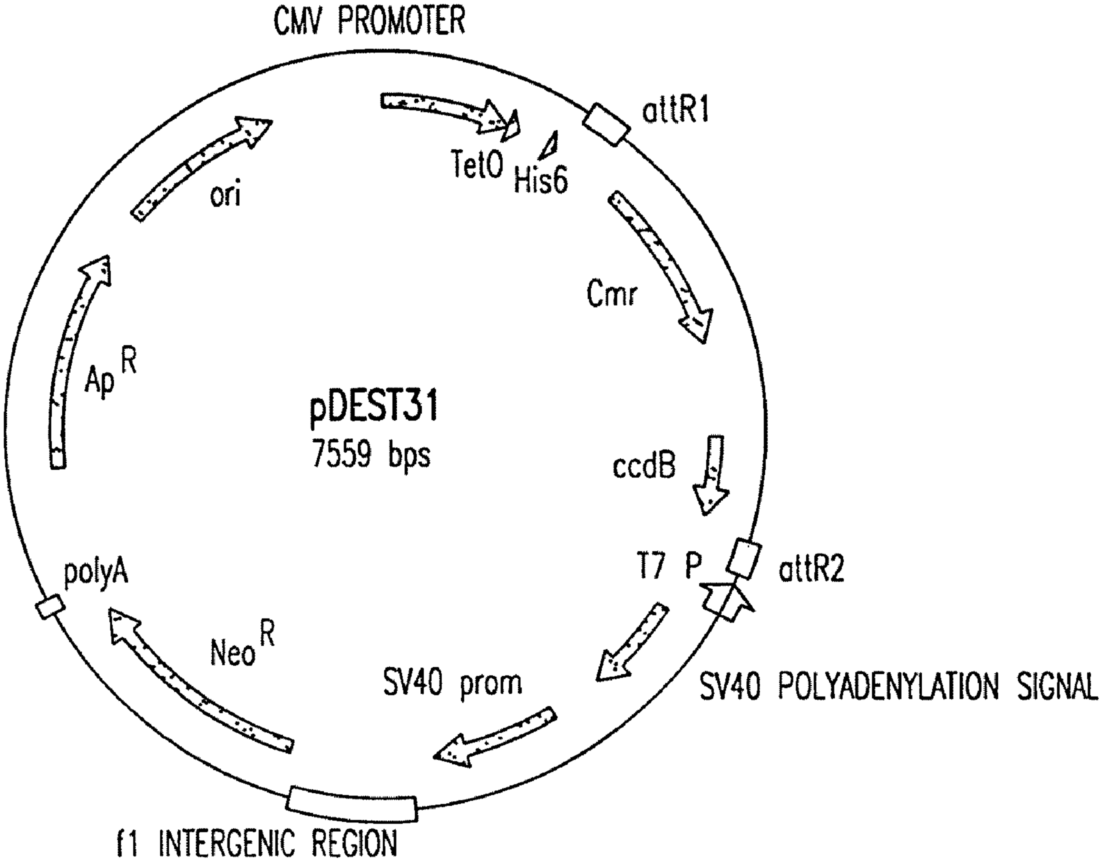
FIG. 93 is a schematic depiction of the physical map (FIG. 93A), and the nucleotide sequence (FIGS. 93B-D) (SEQ ID NO:178), of Destination Vector pDEST31.
Figure 94A:
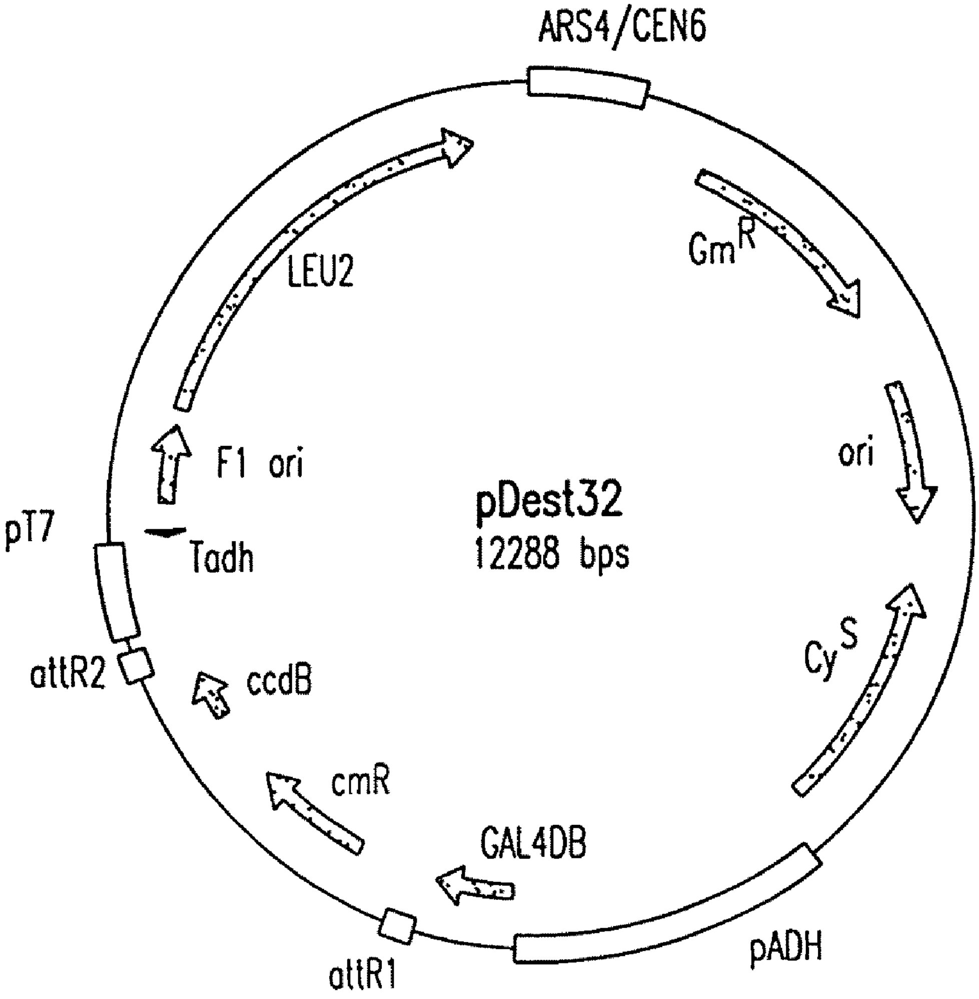
FIG. 94 is a schematic depiction of the physical map (FIG. 94A), and the nucleotide sequence (FIGS. 94B-E) (SEQ ID NO:179), of Destination Vector pDEST32.
Figure 95A:
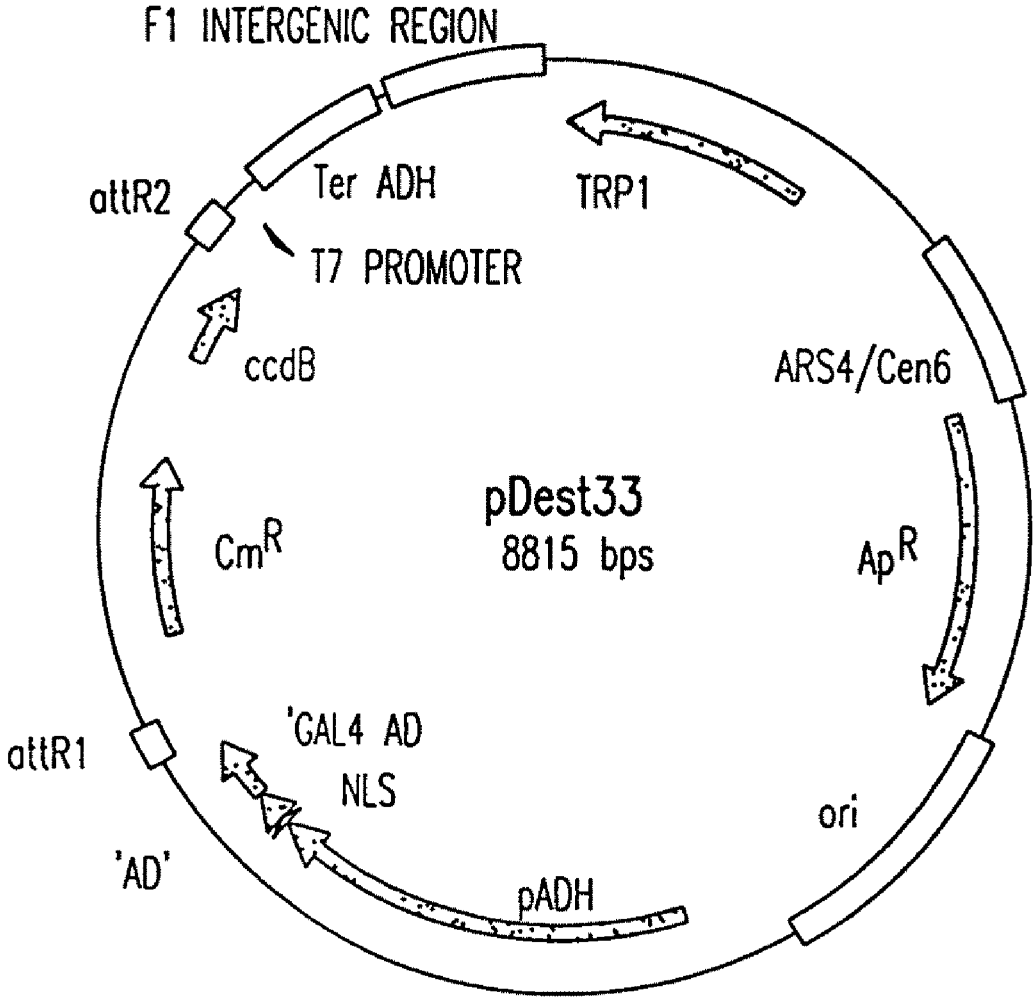
FIG. 95 is a schematic depiction of the physical map (FIG. 95A), and the nucleotide sequence (FIGS. 95B-D) (SEQ ID NO:180), of Destination Vector pDEST33.
Figure 96A:
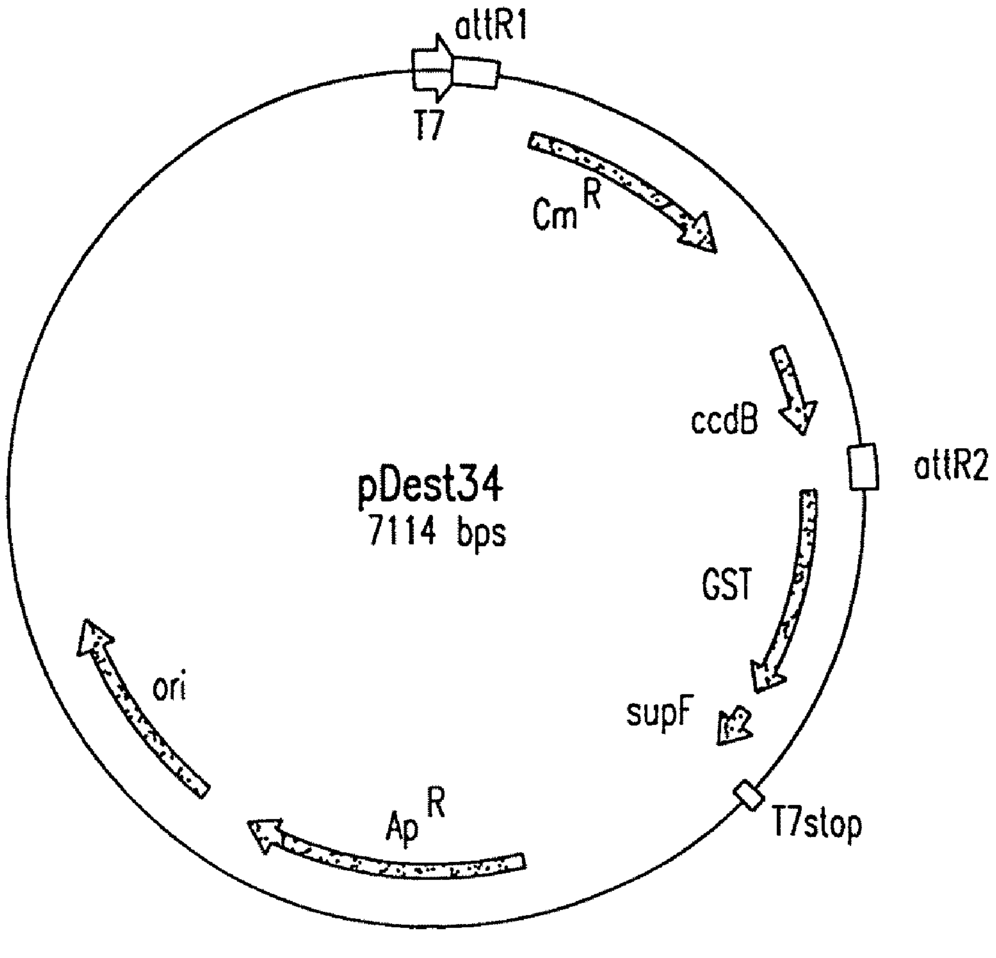
FIG. 96 is a schematic depiction of the physical map (FIG. 96A), and the nucleotide sequence (FIGS. 96B-D) (SEQ ID NO:181), of Destination Vector pDEST34.
Figure 97A:
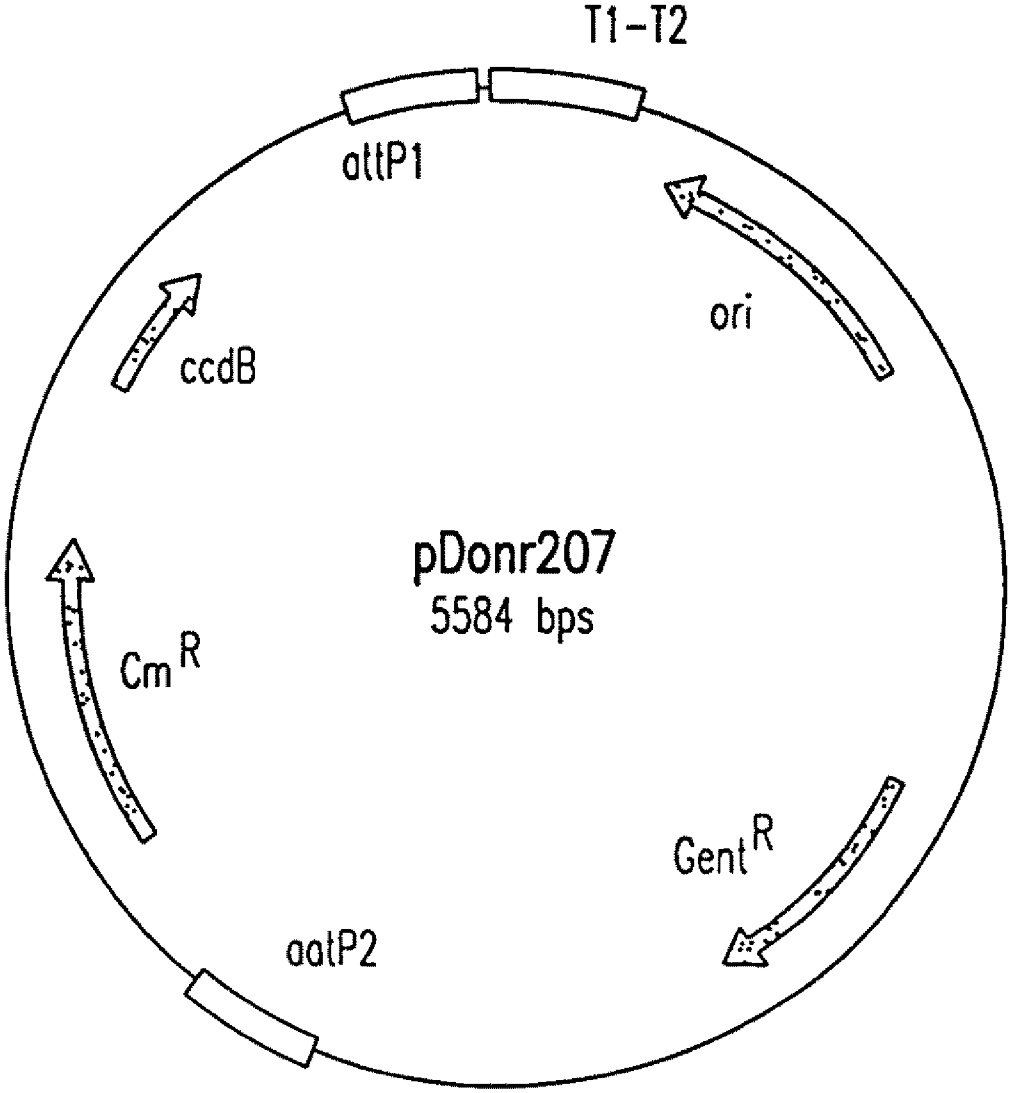
FIG. 97 is a depiction of the physical map (FIG. 97A), and the nucleotide sequence (FIGS. 97B-C) (SEQ ID NO:182), for the Donor plasmid pDONR207 which donates a gentamycin-resistant vector in the BP Reaction.
Figure 98A:
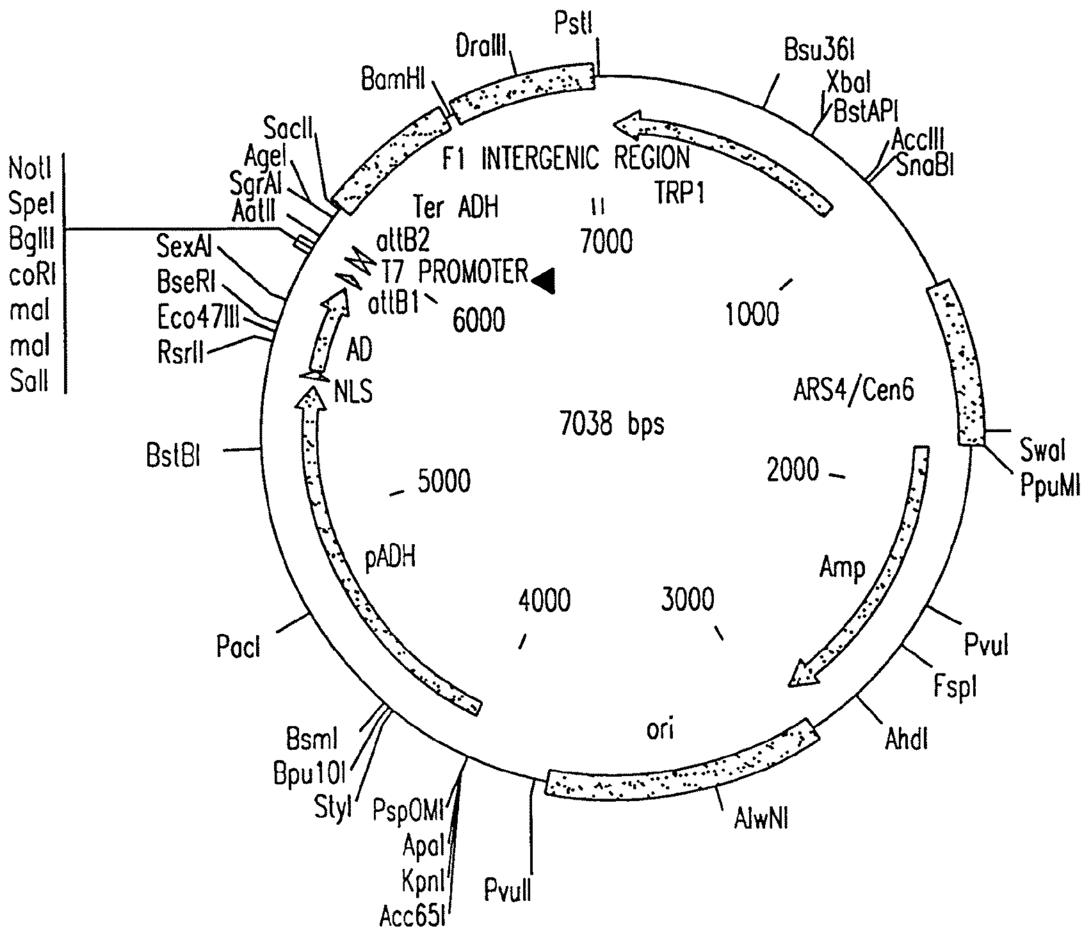
FIG. 98 is a schematic depiction of the physical map (FIG. 98A), and the nucleotide sequence (FIGS. 98B-D) (SEQ ID NO:183), of the 2-hybrid vector pMAB85.
Figure 99A:
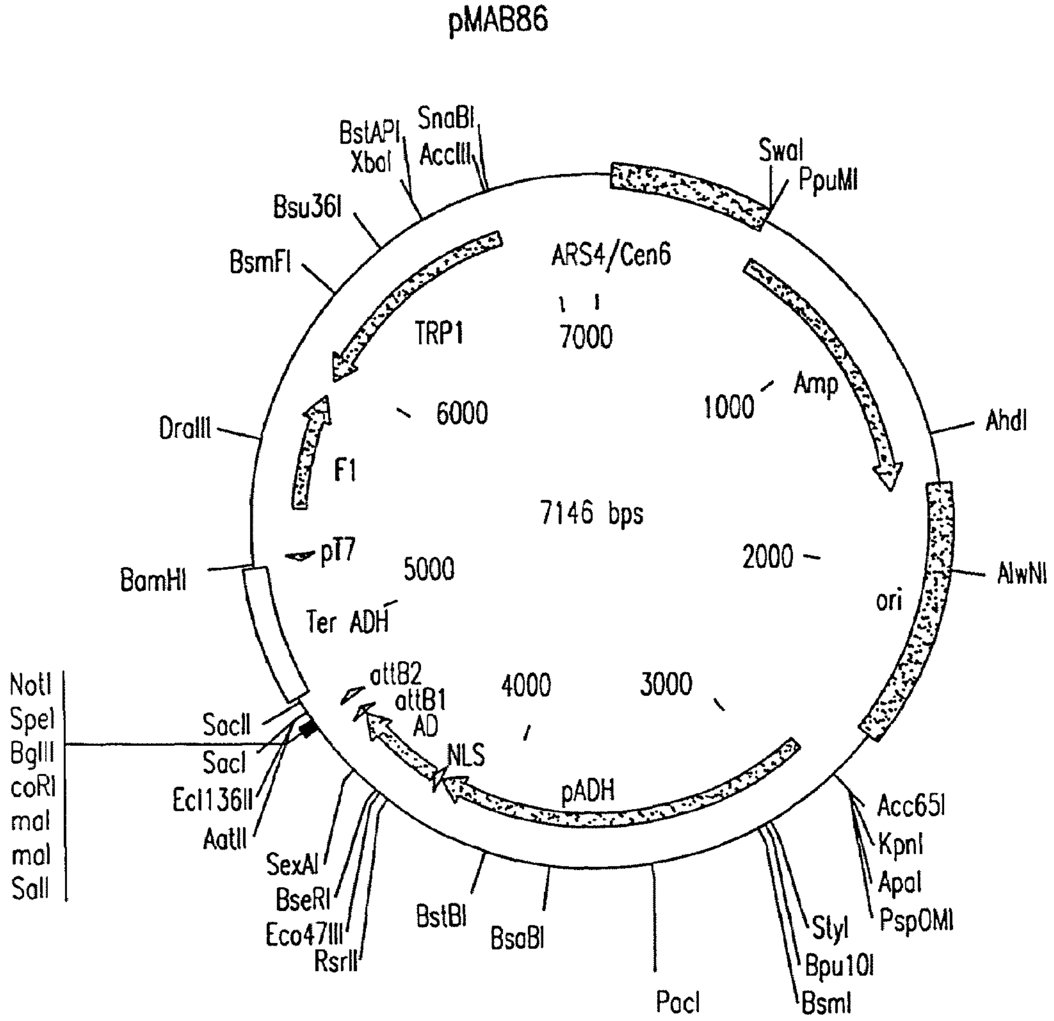
FIG. 99 is a schematic depiction of the physical map (FIG. 99A), and the nucleotide sequence (FIGS. 99B-D) (SEQ ID NO:184), of the 2-hybrid vector pMAB86.

Preferred vectors according to this aspect of the invention include, but are not limited to: pENTR1A (FIGS. 10A and 10B), pENTR2B (FIGS. 11A and 11B), pENTR3C (FIGS. 12A and 12B), pENTR4 (FIGS. 13A and 13B), pENTR5 (FIGS. 14A and 14B), pENTR6 (FIGS. 15A and 15B), pENTR7 (FIGS. 16A and 16B), pENTR8 (FIGS. 17A and 17B), pENTR9 (FIGS. 18A and 18B), pENTR10 (FIGS. 19A and 19B), pENTR11 (FIGS. 20A and 20B), pDEST1 (FIGS. 21A-D), pDEST2 (FIGS. 22A-D), pDEST3 (FIGS. 23A-D), pDEST4 (FIGS. 24A-D), pDEST5 (FIGS. 25A-D), pDEST6 (FIGS. 26A-D), pDEST7 (FIGS. 27A-C), pDEST8 (FIGS. 28A-D), pDEST9 (FIGS. 29A-E), pDEST10 (FIGS. 30A-D), pDEST11 (FIGS. 31A-D), pDEST12.2 (also known as pDEST12) (FIGS. 32A-D), pDEST13 (FIGS. 33A-C), pDEST14 (FIG. 34A-D), pDEST15 (FIGS. 35A-D), pDEST16 (FIGS. 36A-D), pDEST17 (FIGS. 37A-D), pDEST18 (FIGS. 38A-D), pDEST19 (FIGS. 39A-D), pDEST20 (FIGS. 40A-D), pDEST21 (FIG. 41A-E), pDEST22 (FIGS. 42A-D), pDEST23 (FIGS. 43A-D), pDEST24 (FIGS. 44A-D), pDEST25 (FIGS. 45A-D), pDEST26 (FIGS. 46A-D), pDEST27 (FIGS. 47A-D), pEXP501 (also known as pCMVSPORT6) (FIGS. 48A-B), pDONR201 (also known as pENTR21 attP vector or pAttP-kan Donor Vector) (FIG. 49), pDONR202 (FIG. 50), pDONR203 (also known as pEZ15812) (FIG. 51), pDONR204 (FIG. 52), pDONR205 (FIG. 53), pDONR206 (also known as pENTR22 attP vector or pAttPgen Donor Vector) (FIG. 54), pMAB58 (FIG. 87), pMAB62 (FIG. 88), pDEST28 (FIG. 90), pDEST29 (FIG. 91), pDEST30 (FIG. 92), pDEST31 (FIG. 93), pDEST32 (FIG. 94), pDEST33 (FIG. 95), pDEST34 (FIG. 96), pDONR207 (FIG. 97), pMAB85 (FIG. 98), pMAB86 (FIG. 99), and fragments, mutants, variants, and derivatives thereof. However, it will be understood by one of ordinary skill that the present invention also encompasses other vectors not specifically designated herein, which comprise one or more of the isolated nucleic acid molecules of the invention encoding one or more recombination sites or portions thereof (or mutants, fragments, variants or derivatives thereof), and which may further comprise one or more additional physical or functional nucleotide sequences described herein which may optionally be operably linked to the one or more nucleic acid molecules encoding one or more recombination sites or portions thereof. Such additional vectors may be produced by one of ordinary skill according to the guidance provided in the present specification.

Polymerases

Preferred polypeptides having reverse transcriptase activity (i.e., those polypeptides able to catalyze the synthesis of a DNA molecule from an RNA template) for use in accordance with the present invention include, but are not limited to Moloney Murine Leukemia Virus (M-MLV) reverse transcriptase, Rous Sarcoma Virus (RSV) reverse transcriptase, Avian Myeloblastosis Virus (AMV) reverse transcriptase, Rous Associated Virus (RAV) reverse transcriptase, Myeloblastosis Associated Virus (MAV) reverse transcriptase, Human Immunodeficiency Virus (HIV) reverse transcriptase, retroviral reverse transcriptase, retrotransposon reverse transcriptase, hepatitis B reverse transcriptase, cauliflower mosaic virus reverse transcriptase and bacterial reverse transcriptase. Particularly preferred are those polypeptides having reverse transcriptase activity that are also substantially reduced in RNAse H activity (i.e., "RNAse H-" polypeptides). By a polypeptide that is "substantially reduced in RNase H activity" is meant that the polypeptide has less than about 20%, more preferably less than about 15%, 10% or 5%, and most preferably less than about 2%, of the RNase H activity of a wildtype or RNase $H^+$ enzyme such as wildtype M-MLV reverse transcriptase. The RNase H activity may be determined by a variety of assays, such as those described, for example, in U.S. Pat. No. 5,244,797, in Kotewicz, M. L. et al., *Nucl. Acids Res.* 16:265 (1988) and in Gerard, G. F., et al., *FOCUS* 14(5):91 (1992), the disclosures of all of which are fully incorporated herein by reference. Suitable RNAse $H^-$ polypeptides for use in the present invention include, but are not limited to, M-MLV H— reverse transcriptase, RSV $H^-$ reverse transcriptase, AMV $H^-$ reverse transcriptase, RAV $H^-$ reverse transcriptase, MAV $H^-$ reverse transcriptase, HIV $H^-$ reverse transcriptase, THERMOSCRIPT™ reverse transcriptase and THERMOSCRIPT™ II reverse transcriptase, and SUPERSCRIPT™ I reverse transcriptase and SUPERSCRIPT™ II reverse transcriptase, which are obtainable, for example, from Life Technologies, Inc. (Rockville, Md.). See generally published PCT application WO 98/47912.

Other polypeptides having nucleic acid polymerase activity suitable for use in the present methods include thermophilic DNA polymerases such as DNA polymerase I, DNA polymerase III, Klenow fragment, T7 polymerase, and T5 polymerase, and thermostable DNA polymerases including, but not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT®) DNA polymerase, *Pyrococcus furiosus* (Pfu) DNA polymerase, *Pyrococcus* species GB-D (or DEEPVENT®) DNA polymerase, *Pyrococcus woosii* (Pwo) DNA polymerase, *Bacillus sterothermophilus* (Bst) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME®) DNA polymerase, *Methanobacterium thermoautotrophicum* (Mth) DNA polymerase, and mutants, variants and derivatives thereof. Such polypeptides are available commercially, for example from Life Technologies, Inc. (Rockville, Md.), New Englan BioLabs (Beverly, Mass.), and Sigma/Aldrich (St. Louis, Mo.).

Host Cells

The invention also relates to host cells comprising one or more of the nucleic acid molecules or vectors of the invention, particularly those nucleic acid molecules and vectors described in detail herein. Representative host cells that may be used according to this aspect of the invention include, but are not limited to, bacterial cells, yeast cells, plant cells and animal cells. Preferred bacterial host cells include *Escherichia* spp. cells (particularly *E. coli* cells and most particularly *E. coli* strains DH10B, Stb12, DH5α, DB3, DB3.1 (preferably *E. coli* LIBRARY EFFICIENCY® DB3.1™ Competent Cells; Life Technologies, Inc., Rockville, Md.), DB4 and DB5; see U.S. Provisional Application No. 60/122,392, filed on Mar. 2, 1999, the disclosure of which is incorporated by reference herein in its entirety), *Bacillus* spp. cells (particularly *B. subtilis* and *B. megaterium* cells), *Streptomyces* spp. cells, *Erwinia* spp. cells, *Klebsiella* spp. cells, *Serratia* spp. cells (particularly *S. marcessans* cells), *Pseudomonas* spp. cells (particularly *P. aeruginosa* cells), and *Salmonella* spp. cells (particularly *S. typhimurium* and *S. typhi* cells). Preferred animal host cells include insect cells (most particularly *Drosophila melanogaster* cells, *Spodoptera frugiperda* Sf9 and Sf21 cells and *Trichoplusa* High-Five cells), nematode cells (particularly *C. elegans* cells), avian cells, amphibian cells (particularly *Xenopus laevis* cells), reptilian cells, and mammalian cells (most particularly CHO, COS, VERO, BHK and human cells). Preferred yeast host cells include *Saccharomyces cerevisiae* cells and *Pichia pastoris* cells. These and other suitable host cells are available commercially, for example from Life Technologies, Inc. (Rockville, Md.), American Type Culture Collection (Manassas, Va.), and Agricultural Research Culture Collection (NRRL; Peoria, Ill.).

Methods for introducing the nucleic acid molecules and/or vectors of the invention into the host cells described herein, to produce host cells comprising one or more of the nucleic acid molecules and/or vectors of the invention, will be familiar to those of ordinary skill in the art. For instance, the nucleic acid molecules and/or vectors of the invention may be introduced into host cells using well known techniques of infection, transduction, transfection, and transformation. The nucleic acid molecules and/or vectors of the invention may be introduced alone or in conjunction with other the nucleic acid molecules and/or vectors. Alternatively, the nucleic acid molecules and/or vectors of the invention may be introduced into host cells as a precipitate, such as a calcium phosphate precipitate, or in a complex with a lipid. Electroporation also may be used to introduce the nucleic acid molecules and/or vectors of the invention into a host. Likewise, such molecules may be introduced into chemically competent cells such as *E. coli*. If the vector is a virus, it may be packaged in vitro or introduced into a packaging cell and the packaged virus may be transduced into cells. Hence, a wide variety of techniques suitable for introducing the nucleic acid molecules and/or vectors of the invention into cells in accordance with this aspect of the invention are well known and routine to those of skill in the art. Such techniques are reviewed at length, for example, in Sambrook, J., et al., *Molecular Cloning, a Laboratory Manual,* 2nd Ed., Cold Spring Harbor, N.Y.: Cold Spring Harbor Laboratory Press, pp. 16.30-16.55 (1989), Watson, J. D., et al., *Recombinant DNA,* 2nd Ed., New York: W. H. Freeman and Co., pp. 213-234 (1992), and Winnacker, E.-L., *From Genes to Clones*, New York: VCH Publishers (1987), which are illustrative of the many laboratory manuals that detail these techniques and which are incorporated by reference herein in their entireties for their relevant disclosures.

Polypeptides

In another aspect, the invention relates to polypeptides encoded by the nucleic acid molecules of the invention (including polypeptides and amino acid sequences encoded by all possible reading frames of the nucleic acid molecules of the invention), and to methods of producing such polypeptides. Polypeptides of the present invention include purified or isolated natural products, products of chemical synthetic procedures, and products produced by recombinant techniques from a prokaryotic or eukaryotic host, including, for example, bacterial, yeast, insect, mammalian, avian and higher plant cells.

The polypeptides of the invention may be produced by synthetic organic chemistry, and are preferably produced by standard recombinant methods, employing one or more of the host cells of the invention comprising the vectors or isolated nucleic acid molecules of the invention. According to the invention, polypeptides are produced by cultivating the host cells of the invention (which comprise one or more of the nucleic acid molecules of the invention, preferably contained within an Expression Vector) under conditions favoring the expression of the nucleotide sequence contained on the nucleic acid molecule of the invention, such that the polypeptide encoded by the nucleic acid molecule of the invention is produced by the host cell. As used herein, "conditions favoring the expression of the nucleotide sequence" or "conditions favoring the production of a polypeptide" include optimal physical (e.g., temperature, humidity, etc.) and nutritional (e.g., culture medium, ionic) conditions required for production of a recombinant polypeptide by a given host cell. Such optimal conditions for a variety of host cells, including prokaryotic (bacterial), mammalian, insect, yeast, and plant cells will be familiar to one of ordinary skill in the art, and may be found, for example, in Sambrook, J., et al., *Molecular Cloning, A Laboratory Manual,* 2nd Ed., Cold Spring Harbor, N.Y.: Cold Spring Harbor Laboratory Press, (1989), Watson, J. D., et al., *Recombinant DNA,* 2nd Ed., New York: W.H. Freeman and Co., and Winnacker, E.-L., *From Genes to Clones*, New York: VCH Publishers (1987).

In some aspects, it may be desirable to isolate or purify the polypeptides of the invention (e.g., for production of antibodies as described below), resulting in the production of the polypeptides of the invention in isolated form. The polypeptides of the invention can be recovered and purified from recombinant cell cultures by well-known methods of protein purification that are routine in the art, including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. For example, His6 or GST fusion tags on polypeptides made by the methods of the invention may be isolated using appropriate affinity chromatography matrices which bind polypeptides bearing His6 or GST tags, as will be familiar to one of ordinary skill in the art. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Isolated polypeptides of the invention include those comprising the amino acid sequences encoded by one or more of the reading frames of the polynucleotides comprising one or more of the recombination site-encoding nucleic acid molecules of the invention, including those encoding attB1, attB2, attP1, attP2, attL1, attL2, attR1 and attR2 having the nucleotide sequences set forth in FIG. 9 (or nucleotide sequences complementary thereto), or fragments, variants, mutants and derivatives thereof; the complete amino acid sequences encoded by the polynucleotides contained in the deposited clones described herein; the amino acid sequences encoded by polynucleotides which hybridize under stringent hybridization conditions to polynucleotides having the nucleotide sequences encoding the recombination site sequences of the invention as set forth in FIG. 9 (or a nucleotide sequence complementary thereto); or a peptide or polypeptide comprising a portion or a fragment of the above polypeptides. The invention also relates to additional polypeptides having one or more additional amino acids linked (typically by peptidyl bonds to form a nascent polypeptide) to the polypeptides encoded by the recombination site nucleotide sequences or the deposited clones. Such additional amino acid residues may comprise one or more functional peptide sequences, for example one or more fusion partner peptides (e.g., GST, $His_6$, Trx, etc.) and the like.

As used herein, the terms "protein," "peptide," "oligopeptide" and "polypeptide" are considered synonymous (as is commonly recognized) and each term can be used interchangeably as the context requires to indicate a chain of two or more amino acids, preferably five or more amino acids, or more preferably ten or more amino acids, coupled by (a) peptidyl linkage(s), unless otherwise defined in the specific contexts below. As is commonly recognized in the art, all polypeptide formulas or sequences herein are written from left to right and in the direction from amino terminus to carboxy terminus.

It will be recognized by those of ordinary skill in the art that some amino acid sequences of the polypeptides of the invention can be varied without significant effect on the structure or function of the polypeptides. If such differences in sequence are contemplated, it should be remembered that there will be critical areas on the protein which determine structure and activity. In general, it is possible to replace residues which form the tertiary structure, provided that residues performing a similar function are used. In other instances, the type of residue may be completely unimportant if the alteration occurs at a non-critical region of the polypeptide.

Thus, the invention further includes variants of the polypeptides of the invention, including allelic variants, which show substantial structural homology to the polypeptides described herein, or which include specific regions of these polypeptides such as the portions discussed below. Such mutants may include deletions, insertions, inversions, repeats, and type substitutions (for example, substituting one hydrophilic residue for another, but not strongly hydrophilic for strongly hydrophobic as a rule). Small changes or such "neutral" or "conservative" amino acid substitutions will generally have little effect on activity.

Typical conservative substitutions are the replacements, one for another, among the aliphatic amino acids Ala, Val, Leu and Ile; interchange of the hydroxylated residues Ser and Thr; exchange of the acidic residues Asp and Glu; substitution between the amidated residues Asn and Gln; exchange of the basic residues Lys and Arg; and replacements among the aromatic residues Phe and Tyr.

Thus, the fragment, derivative or analog of the polypeptides of the invention, such as those comprising peptides encoded by the recombination site nucleotide sequences described herein, may be (i) one in which one or more of the amino acid residues are substituted with a conservative or non-conservative amino acid residue (preferably a conservative amino acid residue), and such substituted amino acid residue may be encoded by the genetic code or may be an amino acid (e.g., desmosine, citrulline, ornithine, etc.) that is not encoded by the genetic code; (ii) one in which one or more of the amino acid residues includes a substituent group (e.g., a phosphate, hydroxyl, sulfate or other group) in addition to the normal “R” group of the amino acid; (iii) one in which the mature polypeptide is fused with another compound, such as a compound to increase the half-life of the polypeptide (for example, polyethylene glycol), or (iv) one in which additional amino acids are fused to the mature polypeptide, such as an immunoglobulin Fc region peptide, a leader or secretory sequence, a sequence which is employed for purification of the mature polypeptide (such as GST) or a proprotein sequence. Such fragments, derivatives and analogs are intended to be encompassed by the present invention, and are within the scope of those skilled in the art from the teachings herein and the state of the art at the time of invention.

The polypeptides of the present invention are preferably provided in an isolated form, and preferably are substantially purified. Recombinantly produced versions of the polypeptides of the invention can be substantially purified by the one-step method described in Smith and Johnson, *Gene* 67:31-40 (1988). As used herein, the term “substantially purified” means a preparation of an individual polypeptide of the invention wherein at least 50%, preferably at least 60%, 70%, or 75% and more preferably at least 80%, 85%, 90%, 91%, 92%, 93%, 94%, 95%, 96%, 97%, 98% or 99% (by mass) of contaminating proteins (i.e., those that are not the individual polypeptides described herein or fragments, variants, mutants or derivatives thereof) have been removed from the preparation.

The polypeptides of the present invention include those which are at least about 50% identical, at least 60% identical, at least 65% identical, more preferably at least about 70%, at least about 75%, at least about 80%, at least about 85%, at least about 90%, at least about 95%, at least about 96%, at least about 97%, at least about 98% or at least about 99% identical, to the polypeptides described herein. For example, preferred attB1-containing polypeptides of the invention include those that are at least about 50% identical, at least 60% identical, at least 65% identical, more preferably at least about 70%, at least about 75%, at least about 80%, at least about 85%, at least about 90%, at least about 95%, at least about 96%, at least about 97%, at least about 98% or at least about 99% identical, to the polypeptide(s) encoded by the three reading frames of a polynucleotide comprising a nucleotide sequence of attB1 having a nucleic acid sequence as set forth in FIG. 9 (or a nucleic acid sequence complementary thereto), to a polypeptide encoded by a polynucleotide contained in the deposited cDNA clones described herein, or to a polypeptide encoded by a polynucleotide hybridizing under stringent conditions to a polynucleotide comprising a nucleotide sequence of attB1 having a nucleic acid sequence as set forth in FIG. 9 (or a nucleic acid sequence complementary thereto). Analogous polypeptides may be prepared that are at least about 65% identical, more preferably at least about 70%, at least about 75%, at least about 80%, at least about 85%, at least about 90%, at least about 95%, at least about 96%, at least about 97%, at least about 98% or at least about 99% identical, to the attB2, attP1, attP2, attL1, attL2, attR1 and attR2 polypeptides of the invention as depicted in FIG. 9. The present polypeptides also include portions or fragments of the above-described polypeptides with at least 5, 10, 15, 20, or 25 amino acids.

By a polypeptide having an amino acid sequence at least, for example, 65% “identical” to a reference amino acid sequence of a given polypeptide of the invention is intended that the amino acid sequence of the polypeptide is identical to the reference sequence except that the polypeptide sequence may include up to 35 amino acid alterations per each 100 amino acids of the reference amino acid sequence of a given polypeptide of the invention. In other words, to obtain a polypeptide having an amino acid sequence at least 65% identical to a reference amino acid sequence, up to 35% of the amino acid residues in the reference sequence may be deleted or substituted with another amino acid, or a number of amino acids up to 35% of the total amino acid residues in the reference sequence may be inserted into the reference sequence. These alterations of the reference sequence may occur at the amino (N-) or carboxy (C-) terminal positions of the reference amino acid sequence or anywhere between those terminal positions, interspersed either individually among residues in the reference sequence or in one or more contiguous groups within the reference sequence. As a practical matter, whether a given amino acid sequence is, for example, at least 65% identical to the amino acid sequence of a given polypeptide of the invention can be determined conventionally using known computer programs such as those described above for nucleic acid sequence identity determinations, or more preferably using the CLUSTAL W program (Thompson, J. D., et al., *Nucleic Acids Res.* 22:4673-4680 (1994)).

The polypeptides of the present invention can be used as molecular weight markers on SDS-PAGE gels or on molecular sieve gel filtration columns using methods well known to those of skill in the art. In addition, as described in detail below, the polypeptides of the present invention can be used to raise polyclonal and monoclonal antibodies which are useful in a variety of assays for detecting protein expression, localization, detection of interactions with other molecules, or for the isolation of a polypeptide (including a fusion polypeptide) of the invention.

In another aspect, the present invention provides a peptide or polypeptide comprising an epitope-bearing portion of a polypeptide of the invention, which may be used to raise antibodies, particularly monoclonal antibodies, that bind specifically to a one or more of the polypeptides of the invention. The epitope of this polypeptide portion is an immunogenic or antigenic epitope of a polypeptide of the invention. An “immunogenic epitope” is defined as a part of a protein that elicits an antibody response when the whole protein is the immunogen. These immunogenic epitopes are believed to be confined to a few loci on the molecule. On the other hand, a region of a protein molecule to which an antibody can bind is defined as an “antigenic epitope.” The number of immunogenic epitopes of a protein generally is less than the number of antigenic epitopes (see, e.g., Geysen et al., *Proc. Natl. Acad. Sci. USA* 81:3998-4002 (1983)).

As to the selection of peptides or polypeptides bearing an antigenic epitope (i.e., that contain a region of a protein molecule to which an antibody can bind), it is well-known in the art that relatively short synthetic peptides that mimic part of a protein sequence are routinely capable of eliciting an antiserum that reacts with the partially mimicked protein (see, e.g., Sutcliffe, J. G., et al., *Science* 219:660-666 (1983)). Peptides capable of eliciting protein-reactive sera are frequently represented in the primary sequence of a protein, can be characterized by a set of simple chemical rules, and are not confined to the immunodominant regions of intact proteins (i.e., immunogenic epitopes) or to the amino or carboxy termini. Peptides that are extremely hydrophobic and those of six or fewer residues generally are ineffective at inducing antibodies that bind to the mimicked protein; longer peptides, especially those containing proline residues, usually are effective (Sutcliffe, J. G., et al., *Science* 219:660-666 (1983)).

Epitope-bearing peptides and polypeptides of the invention designed according to the above guidelines preferably contain a sequence of at least five, more preferably at least seven or more amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a given polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); sequences containing proline residues are particularly preferred.

Non-limiting examples of epitope-bearing polypeptides or peptides that can be used to generate antibodies specific for the polypeptides of the invention include certain epitope-bearing regions of the polypeptides comprising amino acid sequences encoded by polynucleotides comprising one or more of the recombination site-encoding nucleic acid molecules of the invention, including those encoding attB1, attB2, attP1, attP2, attL1, attL2, attR1 and attR2 having the nucleotide sequences set forth in FIG. 9 (or a nucleotide sequence complementary thereto); the complete amino acid sequences encoded by the three reading frames of the polynucleotides contained in the deposited clones described herein; and the amino acid sequences encoded by all reading frames of polynucleotides which hybridize under stringent hybridization conditions to polynucleotides having the nucleotide sequences encoding the recombination site sequences (or portions thereof) of the invention as set forth in FIG. 9 (or a nucleic acid sequence complementary thereto). Other epitope-bearing polypeptides or peptides that may be used to generate antibodies specific for the polypeptides of the invention will be apparent to one of ordinary skill in the art based on the primary amino acid sequences of the polypeptides of the invention described herein, via the construction of Kyte-Doolittle hydrophilicity and Jameson-Wolf antigenic index plots of the polypeptides of the invention using, for example, PROTEAN computer software (DNASTAR, Inc.; Madison, Wis.).

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis (see, e.g., U.S. Pat. No. 4,631,211 and Houghten, R. A., *Proc. Natl. Acad. Sci. USA* 82:5131-5135 (1985), both of which are incorporated by reference herein in their entireties).

As one of skill in the art will appreciate, the polypeptides of the present invention and epitope-bearing fragments thereof may be immobilized onto a solid support, by techniques that are well-known and routine in the art. By "solid support" is intended any solid support to which a peptide can be immobilized. Such solid supports include, but are not limited to nitrocellulose, diazocellulose, glass, polystyrene, polyvinylchloride, polypropylene, polyethylene, dextran, Sepharose, agar, starch, nylon, beads and microtitre plates. Linkage of the peptide of the invention to a solid support can be accomplished by attaching one or both ends of the peptide to the support. Attachment may also be made at one or more internal sites in the peptide. Multiple attachments (both internal and at the ends of the peptide) may also be used according to the invention. Attachment can be via an amino acid linkage group such as a primary amino group, a carboxyl group, or a sulfhydryl (SH) group or by chemical linkage groups such as with cyanogen bromide (CNBr) linkage through a spacer. For non-covalent attachments to the support, addition of an affinity tag sequence to the peptide can be used such as GST (Smith, D. B., and Johnson, K. S., *Gene* 67:31 (1988)), polyhistidines (Hochuli, E., et al., *J. Chromatog.* 411:77 (1987)), or biotin. Such affinity tags may be used for the reversible attachment of the peptide to the support. Such immobilized polypeptides or fragments may be useful, for example, in isolating antibodies directed against one or more of the polypeptides of the invention, or other proteins or peptides that recognize other proteins or peptides that bind to one or more of the polypeptides of the invention, as described below.

As one of skill in the art will also appreciate, the polypeptides of the present invention and the epitope-bearing fragments thereof described herein can be combined with one or more fusion partner proteins or peptides, or portions thereof, including but not limited to GST, $HiS_6$, Trx, and portions of the constant domain of immunoglobulins (Ig), resulting in chimeric or fusion polypeptides. These fusion polypeptides facilitate purification of the polypeptides of the invention (EP 0 394 827; Traunecker et al., *Nature* 331:84-86 (1988)) for use in analytical or diagnostic (including high-throughput) format.

Antibodies

In another aspect, the invention relates to antibodies that recognize and bind to the polypeptides (or epitope-bearing fragments thereof) or nucleic acid molecules (or portions thereof) of the invention. In a related aspect, the invention relates to antibodies that recognize and bind to one or more polypeptides encoded by all reading frames of one or more recombination site nucleic acid sequences or portions thereof, or to one or more nucleic acid molecules comprising one or more recombination site nucleic acid sequences or portions thereof, including but not limited to att sites (including attB1, attB2, attP1, attP2, attL1, attL2, attR1, attR2 and the like), lox sites (e.g., loxP, loxP511, and the like), FRT, and the like, or mutants, fragments, variants and derivatives thereof. See generally U.S. Pat. No. 5,888,732, which is incorporated herein by reference in its entirety. The antibodies of the present invention may be polyclonal or monoclonal, and may be prepared by any of a variety of methods and in a variety of species according to methods that are well-known in the art. See, for instance, U.S. Pat. No. 5,587,287; Sutcliffe, J. G., et al., *Science* 219:660-666 (1983); Wilson et al., *Cell* 37: 767 (1984); and Bittle, F. J., et al., *J. Gen. Virol.* 66:2347-2354 (1985). Antibodies specific for any of the polypeptides or nucleic acid molecules described herein, such as antibodies specifically binding to one or more of the polypeptides encoded by the recombination site nucleotide sequences, or one or more nucleic acid molecules, described herein or contained in the deposited clones, antibodies against fusion polypeptides (e.g., binding to fusion polypeptides between one or more of the fusion partner proteins and one or more of the recombination site polypeptides of the invention, as described herein), and the like, can be raised against the intact polypeptides or polynucleotides of the invention or one or more antigenic polypeptide fragments thereof.

As used herein, the term "antibody" (Ab) may be used interchangeably with the terms "polyclonal antibody" or "monoclonal antibody" (mAb), except in specific contexts as described below. These terms, as used herein, are meant to include intact molecules as well as antibody fragments (such as, for example, Fab and $F(ab')_2$ fragments) which are capable of specifically binding to a polypeptide or nucleic acid molecule of the invention or a portion thereof. It will therefore be appreciated that, in addition to the intact antibodies of the invention, Fab, $F(ab')_2$ and other fragments of the antibodies described herein, and other peptides and peptide fragments that bind one or more polypeptides or polynucleotides of the invention, are also encompassed within the scope of the invention. Such antibody fragments are typically produced by proteolytic cleavage of intact antibodies, using enzymes such as papain (to produce Fab fragments) or pepsin (to produce $F(ab')_2$ fragments). Antibody fragments, and peptides or peptide fragments, may also be produced through the application of recombinant DNA technology or through synthetic chemistry.

Epitope-bearing peptides and polypeptides, and nucleic acid molecules or portions thereof, of the invention may be used to induce antibodies according to methods well known in the art, as generally described herein (see, e.g., Sutcliffe, et al., supra; Wilson, et al., supra; and Bittle, F. J., et al., *J. Gen. Virol.* 66:2347-2354 (1985)).

Polyclonal antibodies according to this aspect of the invention may be made by immunizing an animal with one or more of the polypeptides or nucleic acid molecules of the invention described herein or portions thereof according to standard techniques (see, e.g., Harlow, E., and Lane, D., *Antibodies: A Laboratory Manual*, Cold Spring Harbor, N.Y.: Cold Spring Harbor Laboratory Press (1988); Kaufman, P. B., et al., In: *Handbook of Molecular and Cellular Methods in Biology and Medicine*, Boca Raton, Fla.: CRC Press, pp. 468-469 (1995)). For producing antibodies that recognize and bind to the polypeptides or nucleic acid molecules of the invention or portions thereof, animals may be immunized with free peptide or free nucleic acid molecules; however, antibody titer may be boosted by coupling of the peptide to a macromolecular carrier, such as albumin, KLH, or tetanus toxoid (particularly for producing antibodies against the nucleic acid molecules of the invention or portions thereof; see Harlow and Lane, supra, at page 154), or to a solid phase carrier such as a latex or glass microbead. For instance, peptides containing cysteine may be coupled to carrier using a linker such as m-maleimidobenzoyl-N— hydroxysuccinimide ester (MBS), while other peptides may be coupled to carrier using a more general linking agent such as glutaraldehyde. Animals such as rabbits, rats and mice may be immunized with either free (if the polypeptide immunogen is larger than about 25 amino acids in length) or carrier-coupled peptides or nucleic acid molecules, for instance, by intraperitoneal and/or intradermal injection of emulsions containing about 100 μg peptide, polynucleotide, or carrier protein, and Freund's adjuvant. Several booster injections may be needed, for instance, at intervals of about two weeks, to provide a useful titer of antibody which can be detected, for example, by ELISA assay using free peptide or nucleic acid molecule adsorbed to a solid surface. In another approach, cells expressing one or more of the polypeptides or polynucleotides of the invention or an antigenic fragment thereof can be administered to an animal in order to induce the production of sera containing polyclonal antibodies, according to routine immunological methods. In yet another method, a preparation of one or more of the polypeptides or polynucleotides of the invention is prepared and purified as described herein, to render it substantially free of natural contaminants. Such a preparation may then be introduced into an animal in order to produce polyclonal antisera of greater specific activity. The titer of antibodies in serum from an immunized animal, regardless of the method of immunization used, may be increased by selection of anti-peptide or anti-polynucleotide antibodies, for instance, by adsorption to the peptide or polynucleotide on a solid support and elution of the selected antibodies according to methods well known in the art.

In an alternative method, the antibodies of the present invention are monoclonal antibodies (or fragments thereof which bind to one or more of the polypeptides of the invention). Such monoclonal antibodies can be prepared using hybridoma technology (Kohler et al., *Nature* 256:495 (1975); Köhler et al., *Eur. J. Immunol.* 6:511 (1976); Köhler et al., *Eur. J. Immunol.* 6:292 (1976); Hammerling et al., In: *Monoclonal Antibodies and T-Cell Hybridomas*, Elsevier, N.Y., pp. 563-681 (1981)). In general, such procedures involve immunizing an animal (preferably a mouse) with a polypeptide or polynucleotide of the invention (or a fragment thereof), or with a cell expressing a polypeptide or polynucleotide of the invention (or a fragment thereof). The splenocytes of such mice are extracted and fused with a suitable myeloma cell line. Any suitable myeloma cell line may be employed in accordance with the present invention; however, it is preferable to employ the parent myeloma cell line ($SP_2O$), available from the American Type Culture Collection, Rockville, Md. After fusion, the resulting hybridoma cells are selectively maintained in HAT medium, and then cloned by limiting dilution as described by Wands et al. (*Gastroenterol.* 80:225-232 (1981)). The hybridoma cells obtained through such a selection are then assayed to identify clones which secrete antibodies capable of binding one or more of the polypeptides or nucleic acid molecules of the invention, or fragments thereof. Hence, the present invention also provides hybridoma cells and cell lines producing monoclonal antibodies of the invention, particularly that recognize and bind to one or more of the polypeptides or nucleic acid molecules of the invention.

Alternatively, additional antibodies capable of binding to one or more of the polypeptides of the invention, or fragments thereof, may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, antibodies specific for one or more of the polypeptides or polynucleotides of the invention, prepared as described above, are used to immunize an animal, preferably a mouse. The splenocytes of such an animal are then used to produce hybridoma cells, and the hybridoma cells are screened to identify clones which produce an antibody whose ability to bind to an antibody specific for one or more of the polypeptides or polynucleotides of the invention can be blocked by polypeptides of the invention themselves. Such antibodies comprise anti-idiotypic antibodies to the antibodies recognizing one or more of the polypeptides or polynucleotides of the invention, and can be used to immunize an animal to induce formation of further antibodies specific for one or more of the polypeptides or polynucleotides of the invention.

For use, the antibodies of the invention may optionally be detectably labeled by covalent or non-covalent attachment of one or more labels, including but not limited to chromogenic, enzymatic, radioisotopic, isotopic, fluorescent, toxic, chemiluminescent, or nuclear magnetic resonance contrast agents or other labels.

Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc. $^{111}In$ is a preferred isotope where in vivo imaging is used since its avoids the problem of dehalogenation of the $^{125}I$ or $^{131}I$-labeled monoclonal antibody by the liver. In addition, this radionucleotide has a more favorable gamma emission energy for imaging (Perkins et al., *Eur. J. Nucl. Med.* 10:296-301 (1985); Carasquillo et al., *J. Nucl. Med.* 28:281-287 (1987)). For example, $^{111}In$ coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861-870 (1987)).

Examples of suitable non-radioactive isotopic labels include $^{157}Gd$, $^{55}Mn$, $^{162}Dy$, $^{52}Tr$, and $^{56}Fe$.

Examples of suitable fluorescent labels include an $^{152}Eu$ label, a fluorescein label, an isothiocyanate label, a rhodamine label, a phycoerythrin label, a phycocyanin label, an allophycocyanin label, an o-phthaldehyde label, a green fluorescent protein (GFP) label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to the antibodies of the invention are provided by Kennedy et al., *Clin. Chim. Acta* 70:1-31 (1976), and Schurs et al., *Clin. Chim. Acta* 81:1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

It will be appreciated by one of ordinary skill that the antibodies of the present invention may alternatively be coupled to a solid support, to facilitate, for example, chromatographic and other immunological procedures using such solid phase-immobilized antibodies. Included among such procedures are the use of the antibodies of the invention to isolate or purify polypeptides comprising one or more epitopes encoded by the nucleic acid molecules of the invention (which may be fusion polypeptides or other polypeptides of the invention described herein), or to isolate or purify polynucleotides comprising one or more recombination site sequences of the invention or portions thereof. Methods for isolation and purification of polypeptides (and, by analogy, polynucleotides) by affinity chromatography, for example using the antibodies of the invention coupled to a solid phase support, are well-known in the art and will be familiar to one of ordinary skill. The antibodies of the invention may also be used in other applications, for example to cross-link or couple two or more proteins, polypeptides, polynucleotides, or portions thereof into a structural and/or functional complex. In one such use, an antibody of the invention may have two or more distinct epitope-binding regions that may bind, for example, a first polypeptide (which may be a polypeptide of the invention) at one epitope-binding region on the antibody and a second polypeptide (which may be a polypeptide of the invention) at a second epitope-binding region on the antibody, thereby bringing the first and second polypeptides into close proximity to each other such that the first and second polypeptides are able to interact structurally and/or functionally (as, for example, linking an enzyme and its substrate to carry out enzymatic catalysis, or linking an effector molecule and its receptor to carry out or induce a specific binding of the effector molecule to the receptor or a response to the effector molecule mediated by the receptor). Additional applications for the antibodies of the invention include, for example, the preparation of large-scale arrays of the antibodies, polypeptides, or nucleic acid molecules of the invention, or portions thereof, on a solid support, for example to facilitate high-throughput screening of protein or RNA expression by host cells containing nucleic acid molecules of the invention (known in the art as "chip array" protocols; see, e.g., U.S. Pat. Nos. 5,856,101, 5,837,832, 5,770,456, 5,744,305, 5,631,734, and 5,593,839, which are directed to production and use of chip arrays of polypeptides (including antibodies) and polynucleotides, and the disclosures of which are incorporated herein by reference in their entireties). By "solid support" is intended any solid support to which an antibody can be immobilized. Such solid supports include, but are not limited to nitrocellulose, diazocellulose, glass, polystyrene, polyvinylchloride, polycarbonate, polypropylene, polyethylene, dextran, Sepharose, agar, starch, nylon, beads and microtitre plates. Preferred are beads made of glass, latex or a magnetic material. Linkage of an antibody of the invention to a solid support can be accomplished by attaching one or both ends of the antibody to the support. Attachment may also be made at one or more internal sites in the antibody. Multiple attachments (both internal and at the ends of the antibody) may also be used according to the invention. Attachment can be via an amino acid linkage group such as a primary amino group, a carboxyl group, or a sulfhydryl (SH) group or by chemical linkage groups such as with cyanogen bromide (CNBr) linkage through a spacer. For non-covalent attachments, addition of an affinity tag sequence to the peptide can be used such as GST (Smith, D. B., and Johnson, K. S., *Gene* 67:31 (1988)), polyhistidines (Hochuli, E., et al., *J. Chromatog.* 411:77 (1987)), or biotin. Alternatively, attachment can be accomplished using a ligand which binds the Fc region of the antibodies of the invention, e.g., protein A or protein G. Such affinity tags may be used for the reversible attachment of the antibodies to the support. Peptides may also be recognized via specific ligand-receptor interactions or using phage display methodologies that will be familiar to the skilled artisan, for their ability to bind polypeptides of the invention or fragments thereof.

Kits

In another aspect, the invention provides kits which may be used in producing the nucleic acid molecules, polypeptides, vectors, host cells, and antibodies, and in the recombinational cloning methods, of the invention. Kits according to this aspect of the invention may comprise one or more containers, which may contain one or more of the nucleic acid molecules, primers, polypeptides, vectors, host cells, or antibodies of the invention. In particular, a kit of the invention may comprise one or more components (or combinations thereof) selected from the group consisting of one or more recombination proteins (e.g., Int) or auxiliary factors (e.g. IHF and/or Xis) or combinations thereof, one or more compositions comprising one or more recombination proteins or auxiliary factors or combinations thereof (for example, GATEWAY™ LR Clonase™ Enzyme Mix or GATEWAY™ BP Clonase™ Enzyme Mix) one or more Destination Vector molecules (including those described herein), one or more Entry Clone or Entry Vector molecules (including those described herein), one or more primer nucleic acid molecules (particularly those described herein), one or more host cells (e.g. competent cells, such as *E. coli* cells, yeast cells, animal cells (including mammalian cells, insect cells, nematode cells, avian cells, fish cells, etc.), plant cells, and most particularly *E. coli* DB3, DB3.1 (preferably *E. coli* LIBRARY EFFICIENCY® DB3.1™ Competent Cells; Life Technologies, Inc., Rockville, Md.), DB4 and DB5; see U.S. Provisional Application No. 60/122,392, filed on Mar. 2, 1999, and the corresponding U.S. Utility Application Ser. No. 09/518,188 of Hartley et al., entitled "Cells Resistant to Toxic Genes and Uses Thereof," filed on even day herewith, the disclosures of which are incorporated by reference herein in its entirety), and the like. In related aspects, the kits of the invention may comprise one or more nucleic acid molecules encoding one or more recombination sites or portions thereof, such as one or more nucleic acid molecules comprising a nucleotide sequence encoding the one or more recombination sites (or portions thereof) of the invention, and particularly one or more of the nucleic acid molecules contained in the deposited clones described herein. Kits according to this aspect of the invention may also comprise one or more isolated nucleic acid molecules of the invention, one or more vectors of the invention, one or more primer nucleic acid molecules of the invention, and/or one or more antibodies of the invention. The kits of the invention may further comprise one or more additional containers containing one or more additional components useful in combination with the nucleic acid molecules, polypeptides, vectors, host cells, or antibodies of the invention, such as one or more buffers, one or more detergents, one or more polypeptides having nucleic acid polymerase activity, one or more polypeptides having reverse transcriptase activity, one or more transfection reagents, one or more nucleotides, and the like. Such kits may be used in any process advantageously using the nucleic acid molecules, primers, vectors, host cells, polypeptides, antibodies and other compositions of the invention, for example in methods of synthesizing nucleic acid molecules (e.g., via amplification such as via PCR), in methods of cloning nucleic acid molecules (preferably via recombinational cloning as described herein), and the like.

Optimization of Recombinational Cloning System

The usefulness of a particular nucleic acid molecule, or vector comprising a nucleic acid molecule, of the invention in methods of recombinational cloning may be determined by any one of a number of assay methods. For example, Entry and Destination vectors of the present invention may be assessed for their ability to function (i.e., to mediate the transfer of a nucleic acid molecule, DNA segment, gene, cDNA molecule or library from a cloning vector to an Expression Vector) by carrying out a recombinational cloning reaction as described in more detail in the Examples below and as described in U.S. application Ser. Nos. 08/663,002, filed Jun. 7, 1996 (now U.S. Pat. No. 5,888,732), 09/005,476, filed Jan. 12, 1998,09/177,387, filed Oct. 23, 1998, and 60/108,324, filed Nov. 13, 1998, the disclosures of which are incorporated by reference herein in their entireties. Alternatively, the functionality of Entry and Destination Vectors prepared according to the invention may be assessed by examining the ability of these vectors to recombine and create cointegrate molecules, or to transfer a nucleic acid molecule of interest, using an assay such as that described in detail below in Example 19. Analogously, the formulation of compositions comprising one or more recombination proteins or combinations thereof, for example GATEWAY™ LR Clonase™ Enzyme Mix and GATEWAY™ BP Clonase™ Enzyme Mix, may be optimized using assays such as those described below in Example 18.

Uses

There are a number of applications for the compositions, methods and kits of the present invention. These uses include, but are not limited to, changing vectors, targeting gene products to intracellular locations, cleaving fusion tags from desired proteins, operably linking nucleic acid molecules of interest to regulatory genetic sequences (e.g., promoters, enhancers, and the like), constructing genes for fusion proteins, changing copy number, changing replicons, cloning into phages, and cloning, e.g., PCR products, genomic DNAs, and cDNAs. In addition, the nucleic acid molecules, vectors, and host cells of the invention may be used in the production of polypeptides encoded by the nucleic acid molecules, in the production of antibodies directed against such polypeptides, in recombinational cloning of desired nucleic acid sequences, and in other applications that may be enhanced or facilitated by the use of the nucleic acid molecules, vectors, and host cells of the invention.

In particular, the nucleic acid molecules, vectors, host cells, polypeptides, antibodies, and kits of the invention may be used in methods of transferring one or more desired nucleic acid molecules or DNA segments, for example one or more genes, cDNA molecules or cDNA libraries, into a cloning or Expression Vector for use in transforming additional host cells for use in cloning or amplification of, or expression of the polypeptide encoded by, the desired nucleic acid molecule or DNA segment. Such recombinational cloning methods which may advantageously use the nucleic acid molecules, vectors, and host cells of the invention, are described in detail in the Examples below, and in commonly owned U.S. application Ser. Nos. 08/486,139, filed Jun. 7, 1995, 08/663,002, filed Jun. 7, 1996 (now U.S. Pat. No. 5,888,732), 09/005,476, filed Jan. 12, 1998, 09/177,387, filed Oct. 23, 1998, and 60/108,324, filed Nov. 13, 1998, the disclosures of all of which are incorporated by reference herein in their entireties.

It will be understood by one of ordinary skill in the relevant arts that other suitable modifications and adaptations to the methods and applications described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Recombination Reactions of Bacteriophage λ

Figure 60:
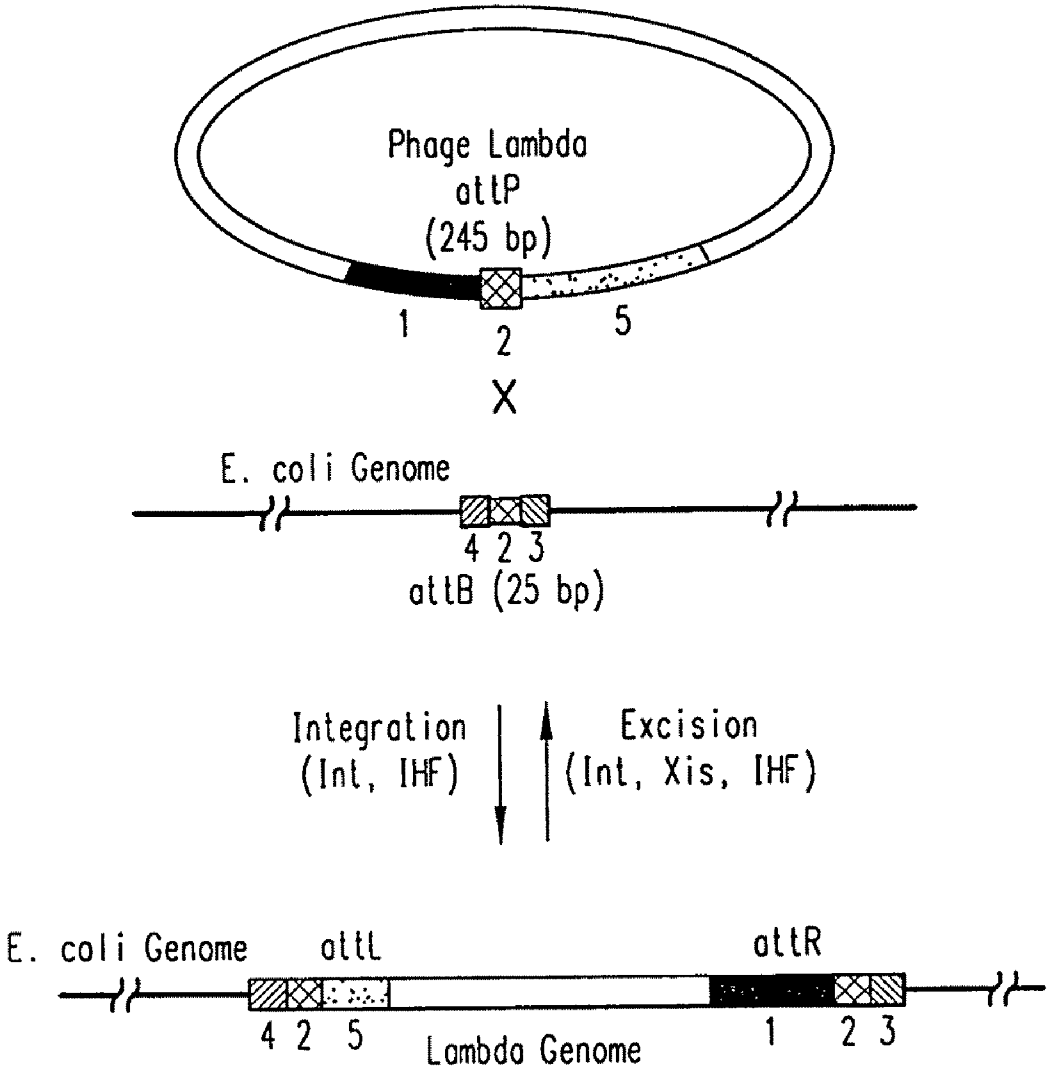
FIG. 60 is a schematic depiction of the bacteriophage lambda recombination pathways in *E. coli.*

The *E. coli* bacteriophage λ can grow as a lytic phage, in which case the host cell is lysed, with the release of progeny virus. Alternatively, lambda can integrate into the genome of its host by a process called lysogenization (see FIG. 60). In this lysogenic state, the phage genome can be transmitted to daughter cells for many generations, until conditions arise that trigger its excision from the genome. At this point, the virus enters the lytic part of its life cycle. The control of the switch between the lytic and lysogenic pathways is one of the best understood processes in molecular biology (M. Ptashne, *A Genetic Switch*, Cell Press, 1992).

The integrative and excisive recombination reactions of λ, performed in vitro, are the basis of Recombinational Cloning System of the present invention. They can be represented schematically as follows:

attB x attP↔attL x attR (where "x" signifies recombination)

The four att sites contain binding sites for the proteins that mediate the reactions. The wild type attP, attB, attL, and attR sites contain about 243, 25, 100, and 168 base pairs, respectively. The attBxattP reaction (hereinafter referred to as a "BP Reaction," or alternatively and equivalently as an "Entry Reaction" or a "Gateward Reaction") is mediated by the proteins Int and IHF. The attLxattR reaction (hereinafter referred to as an "LR Reaction," or alternatively and equivalently as a "Destination Reaction") is mediated by the proteins Int, IHF, and Xis. Int (integrase) and Xis (excisionase) are encoded by the λ genome, while IHF (integration host factor) is an *E. coli* protein. For a general review of lambda recombination, see: A. Landy, *Ann. Rev. Biochem.* 58: 913-949 (1989).

Example 2

Recombination Reactions of the Recombinational Cloning System

The LR Reaction—the exchange of a DNA segment from an Entry Clone to a Destination Vector—is the in vitro version of the λ excision reaction:

attL x attR⇒attB+attP.

There is a practical imperative for this configuration: after an LR Reaction in one configuration of the present method, an att site usually separates a functional motif (such as a promoter or a fusion tag) from a nucleic acid molecule of interest in an Expression Clone, and the 25 bp attB site is much smaller than the attP, attL, and attR sites.

Note that the recombination reaction is conservative, i.e., there is no net synthesis or loss of base pairs. The DNA segments that flank the recombination sites are merely switched. The wild type λ recombination sites are modified for purposes of the GATEWAY™ Cloning System, as follows:

To create certain preferred Destination Vectors, a part (43 bp) of attR was removed, to make the excisive reaction irreversible and more efficient (W. Bushman et al., *Science* 230: 906, 1985). The attR sites in preferred Destination Vectors of the invention are 125 bp in length. Mutations were made to the core regions of the att sites, for two reasons: (1) to eliminate stop codons, and (2) to ensure specificity of the recombination reactions (i.e., attR1 reacts only with attL1, attR2 reacts only with attL2, etc.).

Other mutations were introduced into the short (5 bp) regions flanking the 15 bp core regions of the attB sites to minimize secondary structure formation in single-stranded forms of attB plasmids, e.g., in phagemid ssDNA or in mRNA. Sequences of attB1 and attB2 to the left and right of a nucleic acid molecule of interest after it has been cloned into a Destination Vector are given in FIG. 6.

Figure 61:
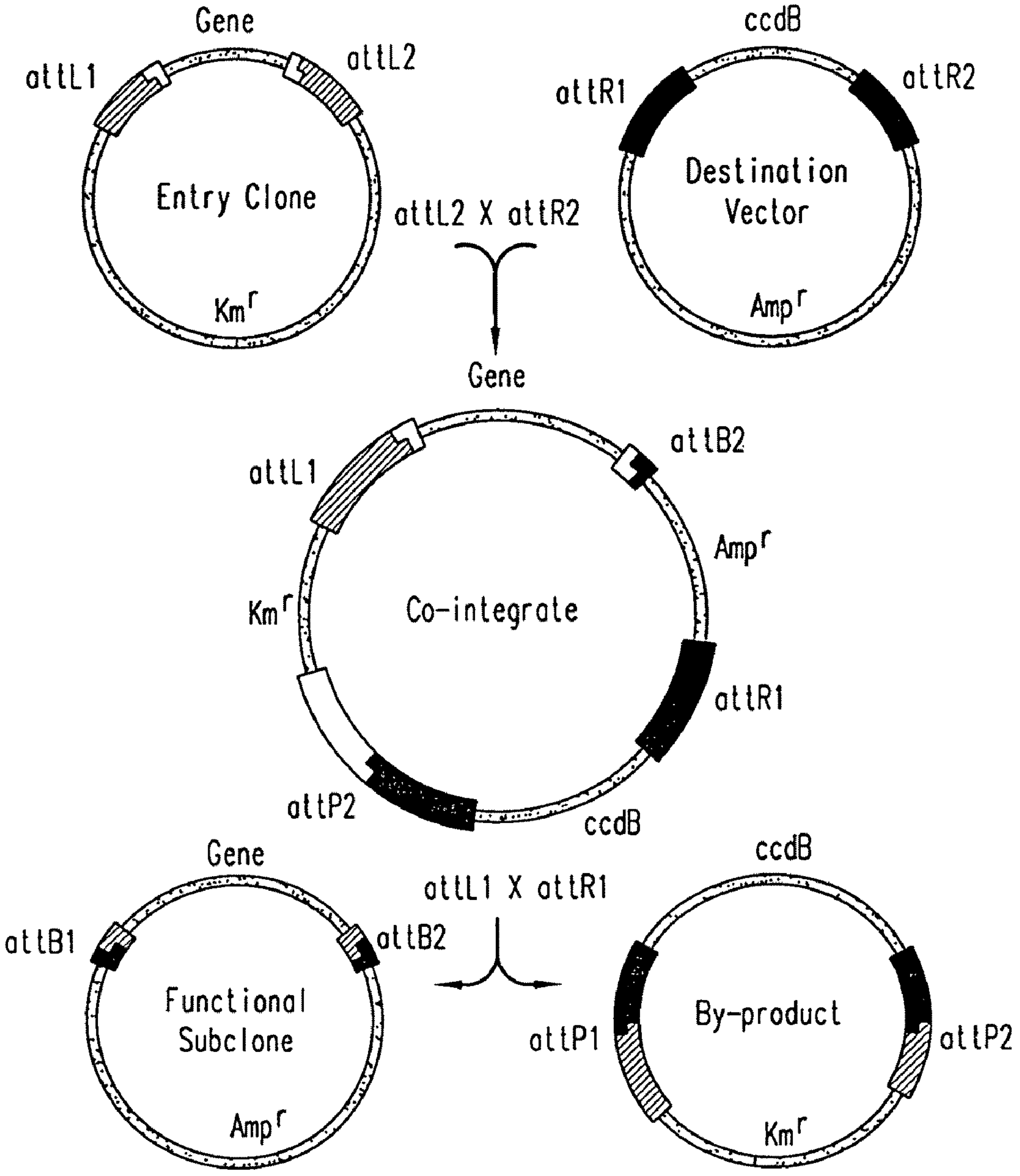
FIG. 61 is a schematic depiction of the DNA molecules participating in the LR Reaction. Two different co-integrates form during the LR Reaction (only one of which is shown here), depending on whether attL1 and attR1 or attL2 and attR2 are first to recombine. In one aspect, the invention provides directional cloning of a nucleic acid molecule of interest, since the recombination sites react with specificity (attL1 reacts with attR1; attL2 with attR2; attB1 with attP1; and attB2 with attP2). Thus, positioning of the sites allows construction of desired vectors having recombined fragments in the desired orientation.

FIG. 61 illustrates how an Entry Clone and a Destination Vector recombine in the LR Reaction to form a co-integrate, which resolves through a second reaction into two daughter molecules. The two daughter molecules have the same general structure regardless of which pair of sites, attL1 and attR1 or attL2 and attR2, react first to form the co-integrate. The segments change partners by these reactions, regardless of whether the parental molecules are both circular, one is circular and one is linear, or both are linear. In this example, selection for ampicillin resistance carried on the Destination Vector, which also carries the death gene ccdB, provides the means for selecting only for the desired attB product plasmid.

Example 3

Protein Expression in the Recombinational Cloning System

Proteins are expressed in vivo as a result of two processes, transcription (DNA into RNA), and translation (RNA into protein). For a review of protein expression in prokaryotes and eukaryotes, see Example 13 below. Many vectors (pUC, BlueScript, pGem) use interruption of a transcribed lacZ gene for blue-white screening. These plasmids, and many Expression Vectors, use the lac promoter to control expression of cloned genes. Transcription from the lac promoter is turned on by adding the inducer IPTG. However, a low level of RNA is made in the absence of inducer, i.e., the lac promoter is never completely off. The result of this "leakiness" is that genes whose expression is harmful to *E. coli* may prove difficult or impossible to clone in vectors that contain the lac promoter, or they may be cloned only as inactive mutants.

In contrast to other gene expression systems, nucleic acid molecules cloned into an Entry Vector may be designed not to be expressed. The presence of the strong transcriptional terminator rrnB (Orosz, et al., *Eur. J. Biochem.* 201: 653, 1991) just upstream of the attL1 site keeps transcription from the vector promoters (drug resistance and replication origin) from reaching the cloned gene. However, if a toxic gene is cloned into a Destination Vector, the host may be sick, just as in other expression systems. But the reliability of subcloning by in vitro recombination makes it easier to recognize that this has happened—and easier to try another expression option in accordance with the methods of the invention, if necessary.

Example 4

Choosing the Right Entry Vector

There are two kinds of choices that must be made in choosing the best Entry Vector, dictated by (1) the particular DNA segment that is to be cloned, and (2) what is to be accomplished with the cloned DNA segment. These factors are critical in the choice of Entry Vector used, because when the desired nucleic acid molecule of interest is moved from the Entry Vector to a Destination Vector, all the base pairs between the nucleic acid molecule of interest and the Int cutting sites in attL1 and attL2 (such as in FIG. 6) move into the Destination Vector as well. For genomic DNAs that are not expressed as a result of moving into a Destination Vector, these decisions are not as critical.

Figure 62:
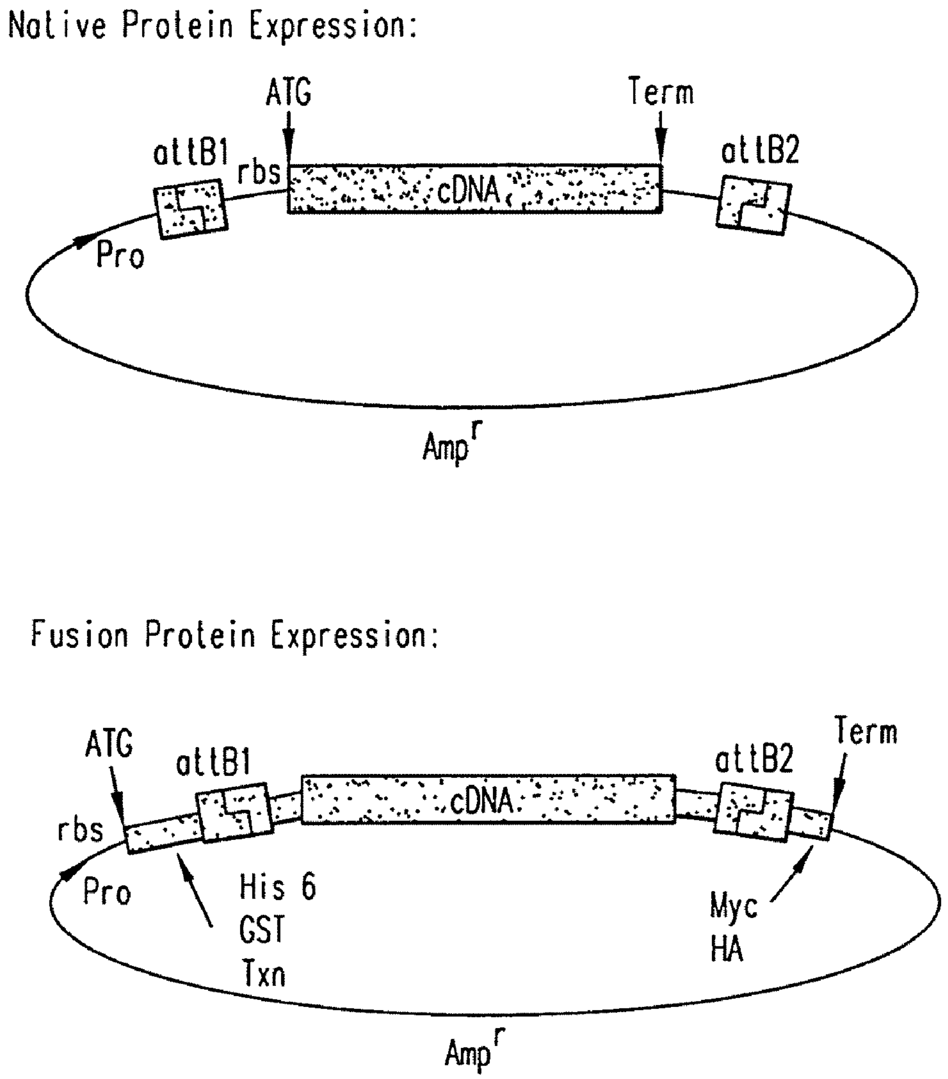
FIG. 62 is a depiction of native and fusion protein expression using the recombinational cloning methods and compositions of the invention. In the upper figure depicting native protein expression, all of the translational start signals are included between the attB1 and attB2 sites; therefore, these signals must be present in the starting Entry Clone. The lower figure depicts fusion protein expression (here showing expression with both N-terminal and C-terminal fusion tags so that ribosomes read through attB1 and attB2 to create the fusion protein). Unlike native protein expression vectors, N-terminal fusion vectors have their translational start signals upstream of the attB1 site.

For example, if an Entry Vector with certain translation start signals is used, those sequences will be translated into amino acids if an amino-terminal fusion to the desired nucleic acid molecule of interest is made. Whether the desired nucleic acid molecule of interest is to be expressed as fusion protein, native protein, or both, dictates whether translational start sequences must be included between the attB sites of the clone (native protein) or, alternatively, supplied by the Destination Vector (fusion protein). In particular, Entry Clones that include translational start sequences may prove less suitable for making fusion proteins, as internal initiation of translation at these sites can decrease the yield of N-terminal fusion protein. These two types of expression afforded by the compositions and methods of the invention are illustrated in FIG. 62.

No Entry Vector is likely to be optimal for all applications. The nucleic acid molecule of interest may be cloned into any of several optimal Entry Vectors.

As an example, consider pENTR7 (FIG. 16) and pENTR11 (FIG. 20), which are useful in a variety of applications, including (but not limited to):

- Cloning cDNAs from most of the commercially available libraries. The sites to the left and right of the ccdB death gene have been chosen so that directional cloning is possible if the DNA to be cloned does not have two or more of these restriction sites.
- Cloning of genes directionally: SalI, BamHI, XmnI (blunt), or KpnI on the left of ccdB; NotI, XhoI, XbaI, or EcoRV (blunt), on the right.
- Cloning of genes or gene fragments with a blunt amino end at the XmnI site. The XmnI site has four of the six most favored bases for eukaryotic expression (see Example 13, below), so that if the first three bases of the DNA to be cloned are ATG, the open reading frame (ORF) will be expressed in eukaryotic cells (e.g., mammalian cells, insect cells, yeast cells) when it is transcribed in the appropriate Destination Vector. In addition, in pENTR11, a Shine-Dalgarno sequence is situated 8 bp upstream, for initiating protein synthesis in a prokaryotic host cell (particularly a bacterial cell, such as *E. coli*) at an ATG.
- Cleaving off amino terminal fusions (e.g., $His_6$, GST, or thioredoxin) using the highly specific TEV (Tobacco Etch Virus) protease (available from Life Technologies, Inc.). If the nucleic acid molecule of interest is cloned at the blunt XmnI site, TEV cleavage will leave two amino acids on the amino end of the expressed protein.
- Selecting against uncut or singly cut Entry Vector molecules during cloning with restriction enzymes and ligase. If the ccdB gene is not removed with a double digest, it will kill any recipient *E. coli* cell that does not contain a mutation that makes the cell resistant to ccdB (see U.S. Provisional Application No. 60/122,392, filed on Mar. 2, 1999, the disclosure of which is incorporated by reference herein in its entirety).
- Allowing production of amino fusions with ORFs in all cloning sites. There are no stop codons (in the attL1 reading frame) upstream of the ccdB gene.

In addition, pENTR11 is also useful in the following applications:

- Cloning cDNAs that have an NcoI site at the initiating ATG into the NcoI site. Similar to the XmnI site, this site has four of the six most favored bases for eukaryotic expression. Also, a Shine-Dalgarno sequence is situated 8 bp upstream, for initiating protein synthesis in a prokaryotic host cell (particularly a bacterial cell, such as *E. coli*) at an ATG.
- Producing carboxy fusion proteins with ORFs positioned in phase with the reading frame convention for carboxy-terminal fusions (see FIG. 20A).

Table 1 lists some non-limiting examples of Entry Vectors and their characteristics, and FIGS. 10-20 show their cloning sites. All of the Entry Vectors listed in Table 1 are available commercially from Life Technologies, Inc., Rockville, Md. Other Entry Vectors not specifically listed here, which comprise alternative or additional features may be made by one of ordinary skill using routine methods of molecular and cellular biology, in view of the disclosure contained herein.

TABLE 1

Examples of Entry Vectors

| Designation | Mnemonic Name | Class of Entry Vector | Distinctive Cloning Sites | Amino Fusions | Native Protein in *E. coli* | Native Protein in Eukaryotic Cells | Protein Synthesis Features |
|---|---|---|---|---|---|---|---|
| pENTR-1A, 2B, 3C | Minimal blunt RF A, B, C | Alternative Reading Frame Vectors | Reading frame A, B, or C; blunt cut closest to attL1 | Good | Poor | Good | Minimal amino acids between tag and protein; no SD |
| pENTR4 | Minimal Nco | Restr. Enz. Cleavage Vectors | Nco I site (common in euk. cDNAs) closest to attL1 | Good | Poor | Good | Good Kozac; no SD |
| pENTR5 | Minimal Nde | Restr. Enz. Cleavage Vectors | NdeI site closest to attL1 | Good | Poor | Poor at Nde I, Good at Xmn I | No SD; poor Kozac at Nde, good atXmn |
| pENTR6 | Minimal Sph | Restr. Enz. Cleavage Vectors | Sph I site closest to attL1 | Good | Poor | Poor at Sph I, Good at Xmn I | No SD; poor Kozac at Sph, good at Xmn |
| pENTR7 | TEV Blunt | TEV Cleavage Site Present | Xmn I (blunt) is first cloning site after TEV site | Good | Poor | Good at Xmn I site | TEV protease leaves Gly-Thr on amino end of protein; no SD |
| pENTR8 | TEV Nco | TEV Cleavage Site Present | Nco I is first cloning site after TEV site | Good | Poor | Good | TEV protease leaves Gly-Thr on amino end of protein: no SD |
| pENTR9 | TEV Nde | TEV Cleavage Site Present | Nde I is first cloning site after TEV site | Good | Poor | Poor | TEV protease leaves Gly-Thr on amino end of protein; no SD, poor Kozac |

TABLE 1-continued

Examples of Entry Vectors

| Designation | Mnemonic Name | Class of Entry Vector | Distinctive Cloning Sites | Amino Fusions | Native Protein in *E. coli* | Native Protein in Eukaryotic Cells | Protein Synthesis Features |
|---|---|---|---|---|---|---|---|
| pENTR10 | Nde with SD | Good SD for *E. coli* Expression | Strong SD; Nde I site, no TEV | Poor | Good | Poor | Strong SD, internal starts in amino fusions. Poor Kz. No TEV |
| pENTR11 | 2 X SD + Kozac | Good SD for *E. coli* Expression | Xmn I (blunt) and Nco I sites each preceded by SD and Kozac | Good | Good | Good | Strong SD/Koz Internal starts in amino fusions. No TEV |

Entry vectors pENTR1A (FIGS. 10A and 10B), pENTR2B (FIGS. 11A and 11B), and pENTR3C (FIGS. 12A and 12B) are almost identical, except that the restriction sites are in different reading frames. Entry vectors pENTR4 (FIGS. 13A and 13B), pENTR5 (FIGS. 14A and 14B), and pENTR6 (FIGS. 15A and 15B) are essentially identical to pENTR1A, except that the blunt DraI site has been replaced with sites containing the ATG methionine codon: NcoI in pENTR4, NdeI in pENTR5, and SphI in pENTR6. Nucleic acid molecules that contain one of these sites at the initiating ATG can be conveniently cloned in these Entry vectors. The NcoI site in pENTR4 is especially useful for expression of nucleic acid molecules in eukaryotic cells, since it contains many of the bases that give efficient translation (see Example 13, below). (Nucleic acid molecules of interest cloned into the NdeI site of pENTR5 are not expected to be highly expressed in eukaryotic cells, because the cytosine at position-3 from the initiating ATG is rare in eukaryotic genes.)

Entry vectors pENTR7 (FIGS. 16A and 16B), pENTR8 (FIGS. 17A and 17B), and pENTR9 (FIGS. 18A and 18B) contain the recognition site for the TEV protease between the attL1 site and the cloning sites. Cleavage sites for XmnI (blunt), NcoI, and NdeI, respectively, are the most 5' sites in these Entry vectors. Amino fusions can be removed efficiently if nucleic acid molecules are cloned into these Entry vectors. TEV protease is highly active and highly specific.

Example 5

Controlling Reading Frame

One of the trickiest tasks in expression of cloned nucleic acid molecules is making sure the reading frame is correct. (Reading frame is important if fusions are being made between two ORFs, for example between a nucleic acid molecule of interest and a His6 or GST domain.) For purposes of the present invention, the following convention has been adopted: The reading frame of the DNA cloned into any Entry Vector must be in phase with that of the attB1 site shown in FIG. 16A, pENTR7. Notice that the six As of the attL1 site are split into two lysine codons (aaa aaa). The Destination Vectors that make amino fusions were constructed such that they enter the attR1 site in this reading frame. Destination Vectors for carboxy terminal fusions were also constructed, including those containing $HiS_6$ (pDEST23; FIG. 43), GST (pDEST24; FIG. 44), or thioredoxin (pDEST25; FIG. 45) C-terminal fusion sequences.

Therefore, if a nucleic acid molecule of interest is cloned into an Entry Vector so that the aaa aaa reading frame within the attL1 site is in phase with the nucleic acid molecule's ORF, amino terminal fusions will automatically be correctly phased, for all the fusion tags. This is a significant improvement over the usual case, where each different vector can have different restriction sites and different reading frames.

See Example 15 for a practical example of how to choose the most appropriate combinations of Entry Vector and Destination Vector.

Materials

Unless otherwise indicated, the following materials were used in the remaining Examples included herein:

5×LR Reaction Buffer:

200-250 mM (preferably 250 mM) Tris-HCl, pH 7.5

250-350 mM (preferably 320 mM) NaCl 1.25-5 mM (preferably 4.75 mM) EDTA 12.5-35 mM (preferably 22-35 mM, and most preferably 35 mM)

Spermidine-HCl 1 mg/ml bovine serum albumin

GATEWAY™ LR Clonase™ Enzyme Mix:

per 4 μl of 1×LR Reaction Buffer:

150 ng carboxy-His6-tagged Int (see U.S. Appl. Nos. 60/108,324, filed Nov. 13, 1998, and 09/438,358, filed Nov. 12, 1999, both entirely incorporated by reference herein)

25 ng carboxy-His6-tagged Xis (see U.S. Appl. Nos. 60/108,324, filed Nov. 13, 1998, and 09/438,358, filed Nov. 12, 1999, both entirely incorporated by reference herein)

30 ng IHF

50% glycerol

5×BP Reaction Buffer:

125 mM Tris-HCl, pH 7.5

110 mM NaCl 25 mM EDTA 25 mM Spermidine-HCl 5 mg/ml bovine serum albumin

GATEWAY™ BP Clonase™ Enzyme Mix:

per 4 μl of 1×BP Reaction Buffer:

200 ng carboxy-His6-tagged Int (see U.S. Appl. Nos. 60/108,324, filed Nov. 13, 1998, and 09/438,358, filed Nov. 12, 1999, both entirely incorporated by reference herein)

80 ng IHF

50% glycerol

10× Clonase Stop Solution:
 50 mM Tris-HCl, pH 8.0
 1 mM EDTA
 2 mg/ml Proteinase K Example 6

LR ("Destination") Reaction

To create a new Expression Clone containing the nucleic acid molecule of interest (and which may be introduced into a host cell, ultimately for production of the polypeptide encoded by the nucleic acid molecule), an Entry Clone or Vector containing the nucleic acid molecule of interest, prepared as described herein, is reacted with a Destination Vector. In the present example, a β-Gal gene flanked by attL sites is transferred from an Entry Clone to a Destination Vector.

Materials needed:
- 5×LR Reaction buffer
- Destination Vector (preferably linearized), 75-150 ng/μl
- Entry Clone containing nucleic acid molecule of interest, 100-300 ng in ≦8 μl TE buffer
- Positive control Entry Clone (pENTR-β-Gal) DNA (See note, below)
- Positive control Destination Vector, pDEST1(pTrc), 75 ng/μl
- GATEWAY™ LR Clonase™ Enzyme Mix (stored at −80° C.)
- 10× Clonase Stop solution
- pUC19 DNA, 10 pg/μl
- Chemically competent *E. coli* cells (competence: ≧$1\times10^7$ CFU/μg), 400 μl.
- LB Plates containing ampicillin (100 μg/ml) and methicillin (200 μg/ml)±X-gal and IPTG (See below)

Notes:

Preparation of the Entry Clone DNA: Miniprep DNA that has been Treated with RNase works well. A reasonably accurate quantitation (±50%) of the DNA to be cloned is advised, as the GATEWAY™ reaction appears to have an optimum of about 100-300 ng of Entry Clone per 20 μl of reaction nix. The positive control Entry Clone, pENTR-β-Gal, permits functional analysis of clones based on the numbers of expected blue vs. white colonies on LB plates containing IPTG+Bluo-gal (or X-gal), in addition to ampicillin (100 μg/ml) and methicillin (200 μg/ml). Because β-Galactosidase is a large protein, it often yields a less prominent band than many smaller proteins do on SDS protein gels.

In the Positive Control Entry Vector pENTR-β-Gal, the coding sequence of β-Gal has been cloned into pENTR11 (FIGS. 20A and 20B), with translational start signals permitting expression in *E. coli*, as well as in eukaryotic cells. The positive control Destination Vector, for example pDEST1 (FIG. 21), is preferably linearized.

To prepare X-gal+IPTG plates, either of the following protocols may be used:

A. With a glass rod, spread over the surface of an LB agar plate: 40 μl of 20 mg/ml X-gal (or Bluo-gal) in DMF plus 4 μl 200 mg/ml IPTG. Allow liquid to adsorb into agar for 3-4 hours at 37° C. before plating cells.

B. To liquid LB agar at ~45° C., add: X-gal (or Bluo-Gal) (20 mg/ml in DMF) to make 50 μg/ml and IPTG (200 mM in water) to make 0.5-1 mM, just prior to pouring plates. Store X-gal and Bluo-Gal in a light-shielded container.

Colony color may be enhanced by placing the plates at 5° C. for a few hours after the overnight incubation at 37° C. Protocol B can give more consistent colony color than A, but A is more convenient when selection plates are needed on short notice.

Recombination in Clonase reactions continues for many hours. While incubations of 45-60 minutes are usually sufficient, reactions with large DNAs, or in which both parental DNAs are supercoiled, or which will be transformed into cells of low competence, can be improved with longer incubation times, such as 2-24 hours at 25° C.

Procedure:

1. Assemble reactions as follows (combine all components at room temperature, except GATEWAY™ LR Clonase™ Enzyme Mix ("Clonase LR"), before removing Clonase LR from frozen storage):

| Component | Tube 1 Neg. | Tube 2 Pos. | Tube 3 Neg. | Tube 4 Test |
|---|---|---|---|---|
| p-Gate-βGal, (Positive control Entry Clone) 75 ng/μl | 4 μl | 4 μl | | |
| pDEST1 (Positive control Destination Vector), 75 ng/μl | 4 μl | 4 μl | | |
| Your Entry Clone (100-300 ng) | | | 1-8 μl | 1-8 μl |
| Destination Vector for your nucleic acid molecule, 75 ng/μl | | | 4 μl | 4 μl |
| 5 X LR Reaction Buffer | 4 μl | 4 μl | 4 μl | 4 μl |
| TE | 8 μl | 4 μl | To 20 μl | To 16 μl |
| GATEWAY ™ LR | — | 4 μl | — | 4 μl |
| Clonase ™ Enzyme Mix (store at −80° C., add last) | | | | |
| Total Volume | 20 μl | 20 μl | 20 μl | 20 μl |

2. Remove the GATEWAY™ LR Clonase™ Enzyme Mix from the −80° C. freezer, place immediately on ice. The Clonase takes only a few minutes to thaw.

3. Add 4 μl of GATEWAY™ LR Clonase™ Enzyme Mix to reactions #2 and #4; 4. Return GATEWAY™ LR Clonase™ Enzyme Mix to −80° C. freezer.

5. Incubate tubes at 25° for at least 60 minutes.

6. Add 2 μl Clonase Stop solution to all reactions. Incubate for 20 min at 37° C. (This step usually increases the total number of colonies obtained by 10-20 fold.)

7. Transform 2 μl into 100 μl competent *E. coli*. Select on plates containing ampicillin at 100 μg/ml.

Example 7

Transformation of *E. coli*

To introduce cloning or Expression Vectors prepared using the recombinational cloning system of the invention, any standard *E. coli* transformation protocol should be satisfactory. The following steps are recommended for best results:

1. Let the mixture of competent cells and Recombinational Cloning System reaction product stand on ice at least 15 minutes prior to the heat-shock step. This gives time for the recombination proteins to dissociate from the DNA, and improves the transformation efficiency.
2. Expect the reaction to be about 1%-5% efficient, i.e., 2 μl of the reaction should contain at least 100 pg of the Expression Clone plasmid (taking into account the amounts of each parental plasmid in the reaction, and the subsequent dilution). If the *E. coli* cells have a competence of $10^7$ CFU/μg, 100 pg of the desired clone plasmid will give about 1000 colonies, or more, if the entire transformation is spread on one ampicillin plate.

3. Always do a control pUC DNA transformation. If the number of colonies is not what you expect, the pUC DNA transformation gives you an indication of where the problem was.

Example 8

Preparation of attB-PCR Product

For preparation of attB-PCR products in the PCR cloning methods described in Example 9 below, PCR primers containing attB1 and attB2 sequences are used. The attB1 and attB2 primer sequences are as follows:

attB1: 5'-GGGGACAAGTTTGTACAAAAAAGCAGGCT-(template-specific sequence)-3' (SEQ ID NO:31)

attB2: 5'-GGGGACCACTTTGTACAAGAAAGCTGGGT-(template-specific sequence)-3' (SEQ ID NO:32)

The attB1 sequence should be added to the amino primer, and the attB2 sequence to the carboxy primer. The 4 guanines at the 5' ends of each of these primers enhance the efficiency of the minimal 25 bp attB sequences as substrates for use in the cloning methods of the invention.

Standard PCR conditions may be used to prepare the PCR product. The following suggested protocol employs Platinum Taq DNA Polymerase High Fidelity®, available commercially from Life Technologies, Inc. (Rockville, Md.). This enzyme mix eliminates the need for hot starts, has improved fidelity over Taq, and permits synthesis of a wide range of amplicon sizes, from 200 bp to 10 kb, or more, even on genomic templates.

Materials needed:

Platinum Taq DNA Polymerase High Fidelity® (Life Technologies, Inc.)

attB1- and attB2-containing primer pair (see above) specific for your template

DNA template (linearized plasmid or genomic DNA)

10× High Fidelity PCR Buffer 10 mM dNTP mix $PEG/MgCl_2$ Mix (30% PEG 8000, 30 mM $MgCl_2$)

Procedure:

1.) Assemble the reaction as follows:

| Component | Reaction with Plasmid Target | Reaction with Genomic Target |
|---|---|---|
| 10X High Fidelity PCR Buffer | 5 μl | 5 μl |
| dNTP Mix 10 mM | 1 μl | 1 μl |
| $MgSO_4$, 50 mM | 2 μl | 2 μl |
| attB1 Primer, 10 μM | 2 μl | 1 μl |
| attB2 Primer, 10 μM | 2 μl | 1 μl |
| Template DNA | 1-5 ng* | ≧100 ng |
| PLATINUM Taq High Fidelity | 2 μl | 1 μl |
| Water | to 50 μl | to 50 μl |

*Use of higher amounts of plasmid template may permit fewer cycles (10-15) of PCR 2.) Add 2 drops mineral oil, as appropriate.

3.) Denature for 30 sec. at 94° C.

4.) Perform 25 cycles:

94° C. for 15 sec-30 sec

55° C. for 15 sec-30 sec

68° C. for 1 nm per kb of template.

5.) Following the PCR reaction, apply 1-2 μl of the reaction mixture to an agarose gel, together with size standards (e.g., 1 Kb Plus Ladder, Life Technologies, Inc.) and quantitation standards (e.g., Low Mass Ladder, Life Technologies, Inc.), to assess the yield and uniformity of the product.

Purification of the PCR product is recommended, to remove attB primer dimers which can clone efficiently into the Entry Vector. The following protocol is fast and will remove DNA <300 bp in size:

6.) Dilute the 50 μl PCR reaction to 200 μl with TE.

7.) Add 100 μl $PEG/MgCl_2$ Solution. Mix and centrifuge immediately at 13,000 RPM for 10 min at room temperature. Remove the supernatant (pellet is clear and hard to see).

8.) Dissolve the pellet in 50 μl TE and check recovery on a gel.

If the starting PCR template is a plasmid that contains the gene for $Kan^r$, it is advisable to treat the completed PCR reaction with the restriction enzyme DpnI, to degrade the plasmid since unreacted residual starting plasmid is a potential source of false-positive colonies from the transformation of the GATEWAY™ Cloning System reaction. Adding ~5 units of DpnI to the completed PCR reaction and incubating for 15 min at 37° C. will eliminate this potential problem. Heat inactivate the DpnI at 65° C. for 15 min, prior to using the PCR product in the GATEWAY™ Cloning System reaction.

Example 9

Cloning attB-PCR Products into Entry Vectors via the BP ("Gateward") Reaction

The addition of 5'-terminal attB sequences to PCR primers allows synthesis of a PCR product that is an efficient substrate for recombination with a Donor (attP) Plasmid in the presence of GATEWAY™ BP Clonase™ Enzyme Mix. This reaction produces an Entry Clone of the PCR product (See FIG. 8).

The conditions of the Gateward Cloning reaction with an attB PCR substrate are similar to those of the BP Reaction (see Example 10 below), except that the attB-PCR product (see Example 8) substitutes for the Expression Clone, and the attB-PCR positive control (attB-$tet^r$) substitutes for the Expression Clone Positive Control (GFP).

Materials needed:

5×BP Reaction Buffer

Desired attB-PCR product DNA, 50-100 ng in ≦8 μl TE.

Donor (attP) Plasmid (FIGS. 49-54), 75 ng/μl, supercoiled DNA attB-$tet^r$ PCR product positive control, 25 ng/μl GATEWAY™ BP Clonase™ Enzyme Mix (stored at −80° C.)

10× Clonase Stop Solution pUC19 DNA, 10 pg/μl.

Chemically competent *E. coli* cells (competence: ≧$1\times10^7$ CFU/μg), 400 μl Notes:

Preparation of attB-PCR DNA: see Example 8.

The Positive Control attB-$tet^r$ PCR product contains a functional copy of the $tet^r$ gene of pBR322, with its own promoter. By plating the transformation of the control BP Reaction on kanamycin (50 μg/ml) plates (if $kan^r$ Donor Plasmids are used; see FIGS. 49-52) or an alternative selection agent (e.g., gentamycin, if $gen^r$ Donor Plasmids are used; see FIG. 54), and then picking about 50 of these colonies onto plates with tetracycline (20 μg/ml), the percentage of Entry Clones containing functional $tet^r$ among the colonies from the positive control reaction can be determined (% Expression Clones=(number of $tet^r$+$kan^r$ (or $gen^r$) colonies/$kan^r$ (or $gen^r$) colonies).

Procedure:

1. Assemble reactions as follows. Combine all components except GATEWAY™ BP Clonase™ Enzyme Mix, before removing GATEWAY™ BP Clonase™ Enzyme Mix from frozen storage.

| Component | Neg. Tube 1 | Pos. Tube 2 | Test Tube 3 |
|---|---|---|---|
| attB-PCR product, 50-100 ng | | | 1-8 μl |
| Donor (attP) Plasmid 75 ng/μl | 2 μl | 2 μl | 2 μl |
| attB-PCR $tet^r$ control DNA (75 ng/μl) | | 4 μl | |
| 5 × BP Reaction Buffer | 4 μl | 4 μl | 4 μl |
| TE | 10 μl | 6 μl | To 16 μl |
| GATEWAY ™ BP Clonase ™ | 4 μl | 4 μl | 4 μl |
| Enzyme Mix (store at −80° C., add last) | | | |
| Total Volume | 20 μl | 20 μl | 20 μl |

2. Remove the GATEWAY™ BP Clonase™ Enzyme Mix from the −80° C. freezer, place immediately on ice. The Clonase takes only a few minutes to thaw.

3. Add 4 μl of GATEWAY™ BP Clonase™ Enzyme Mix to the subcloning reaction, mix.

4. Return GATEWAY™ BP Clonase™ Enzyme Mix to −80° C. freezer.

5. Incubate tubes at 25° for at least 60 minutes.

6. Add 2 μl Proteinase K (2 μg/μl) to all reactions. Incubate for 20 min at 37° C.

7. Transform 2 μl into 100 μl competent *E. coli*, as per 3.2, above. Select on LB plates containing kanamycin, 50 μg/ml.

Figure 67:
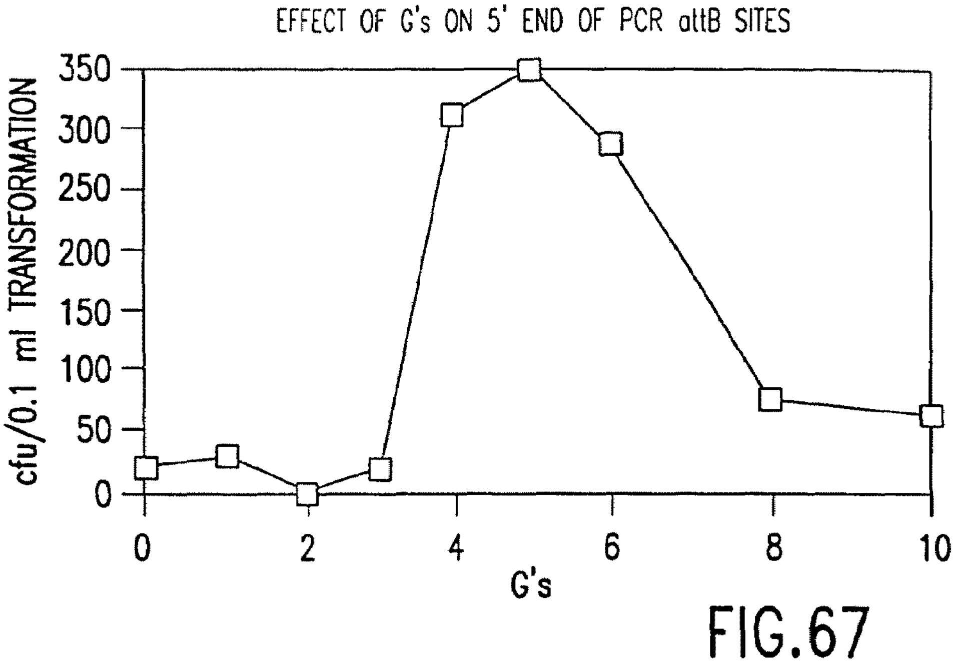
FIG. 67 is a graph showing the effect of the number of guanines (G's) contained on the 5' end of the PCR primers on the cloning efficiency of PCR products. It is noted, however, that other nucleotides besides guanine (including A, T, C, U or combinations thereof) may be used as 5' extensions on the PCR primers to enhance cloning efficiency of PCR products.

Results:

In initial experiments, primers for amplifying tetR and ampR from pBR322 were constructed containing only the tetR- or ampR-specific targeting sequences, the targeting sequences plus attB1 (for forward primers) or attB2 (for reverse primers) sequences shown in FIG. 9, or the attB1 or attB2 sequences with a 5' tail of four guanines. The construction of these primers is depicted in FIG. 65. After PCR amplification of tetR and ampR from pBR322 using these primers and cloning the PCR products into host cells using the recombinational cloning system of the invention, the results shown in FIG. 66 were obtained. These results demonstrated that primers containing attB sequences provided for a somewhat higher number of colonies on the tetracycline and ampicillin plates. However, inclusion of the 5' extensions of four or five guanines on the primers in addition to the attB sequences provided significantly better cloning results, as shown in FIGS. 66 and 67. These results indicate that the optimal primers for cloning of PCR products using recombinational cloning will contain the recombination site sequences with a 5' extension of four or five guanine bases.

Figure 68:
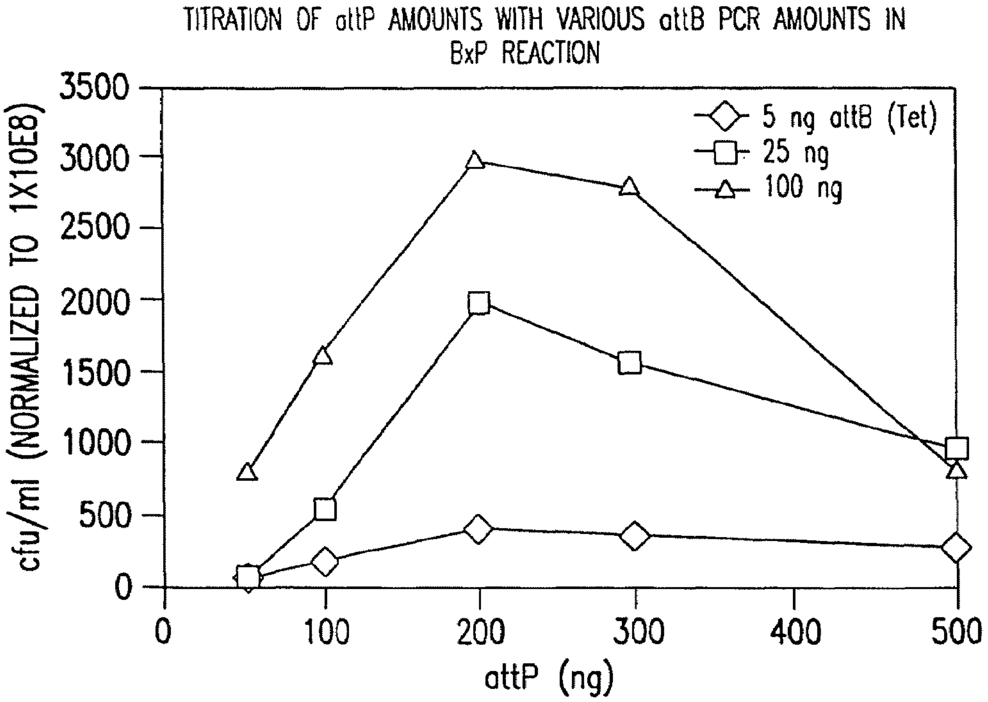
FIG. 68 is a graph showing a titration of various amounts of attP and attB reactants in the BxP reaction, and the effects on cloning efficiency of PCR products.

To determine the optimal stoichiometry between attB-containing PCR products and attP-containing Donor plasmid, experiments were conducted where the amount of PCR product and Donor plasmid were varied during the BP Reaction. Reaction mixtures were then transformed into host cells and plated on tetracycline plates as above. Results are shown in FIG. 68. These results indicate that, for optimal recombinational cloning results with a PCR product in the size range of the tet gene, the amounts of attP-containing Donor plasmids are between about 100-500 ng (most preferably about 200-300 ng), while the optimal concentrations of attB-containing PCR products is about 25-100 ng (most preferably about 100 ng), per 20 μl reaction.

Experiments were then conducted to examine the effect of PCR product size on efficiency of cloning via the recombinational cloning approach of the invention. PCR products containing attB1 and attB2 sites, at sizes 256 bp, 1 kb, 1.4 kb, 3.4 kb, 4.6 kb, 6.9 kb and 10.1 kb were prepared and cloned into Entry vectors as described above, and host cells were transformed with the Entry vectors containing the cloned PCR products. For each PCR product, cloning efficiency was calculated relative to cloning of pUC19 positive control plasmids as follows:

$$\text{Cloning Efficiency} = \frac{\text{CFU/ng } attB\,PCR \text{ product}}{\text{CFU/ng } pUC19 \text{ control}} \times \frac{\text{Size (kb) } PCR \text{ product}}{\text{Size (kb) } pUC19 \text{ control}}$$

Figure 69A:
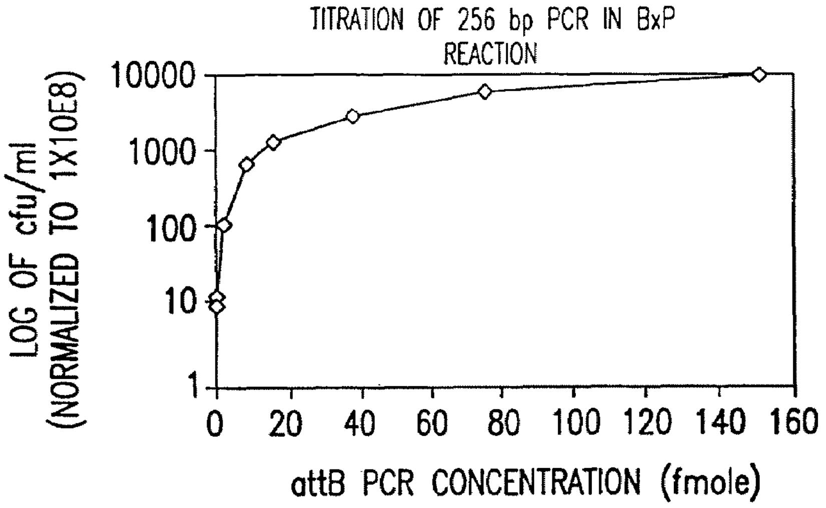
FIG. 69 is a series of graphs showing the effects of various weights (FIG. 69A) or moles (FIG. 69B) of a 256 bp PCR product on formation of colonies, and on efficiency of cloning of the 256 bp PCR product into a Donor Vector (FIG. 69C).
Figure 69B:
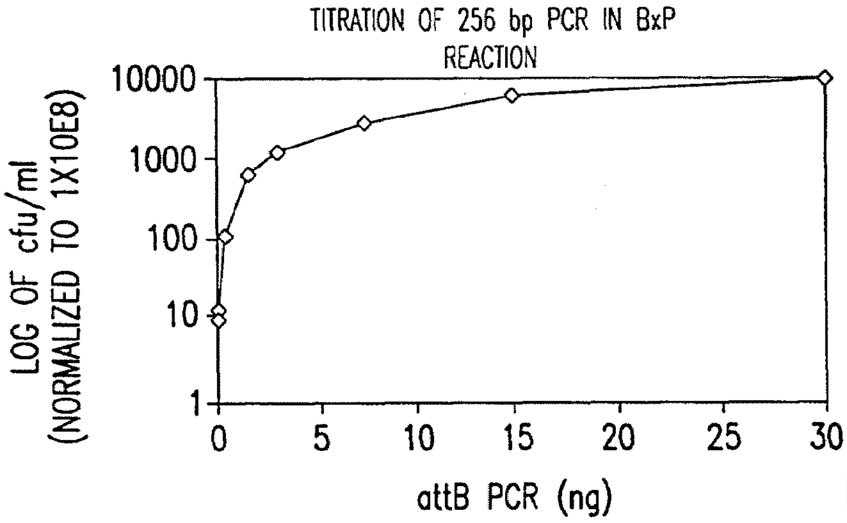
Figure 69C:
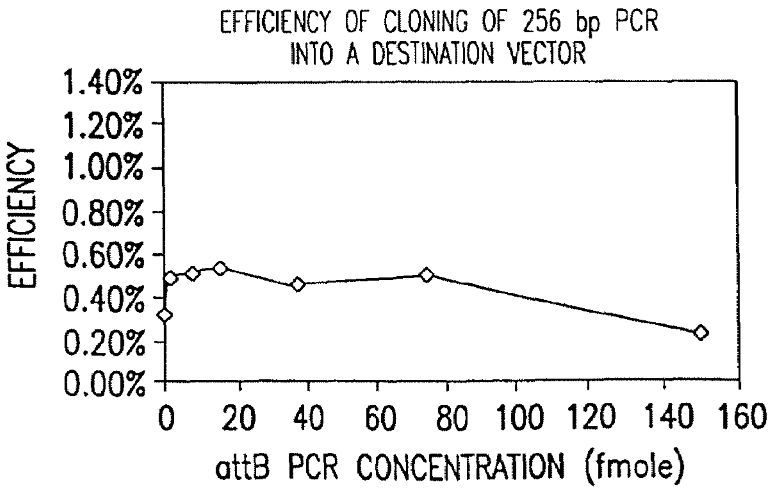
Figure 70A:
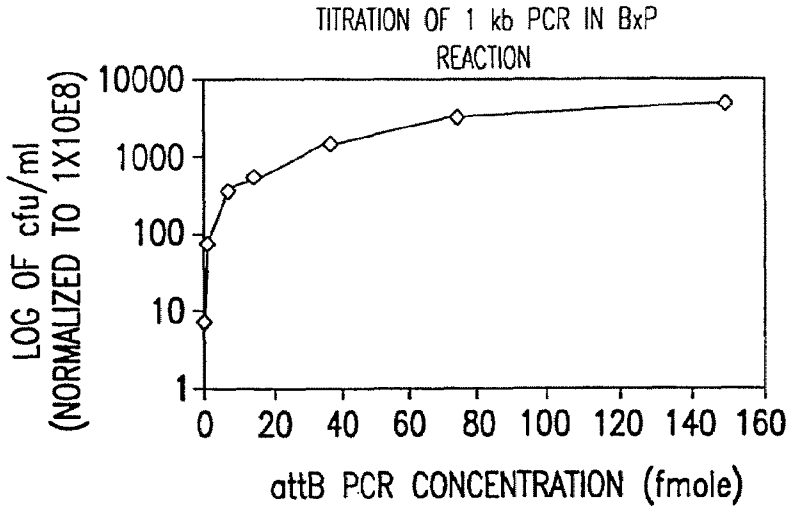
FIG. 70 is a series of graphs showing the effects of various weights (FIG. 70A) or moles (FIG. 70B) of a 1 kb PCR product on formation of colonies, and on efficiency of cloning of the 1 kb PCR product into a Donor Vector (FIG. 70C).
Figure 70B:
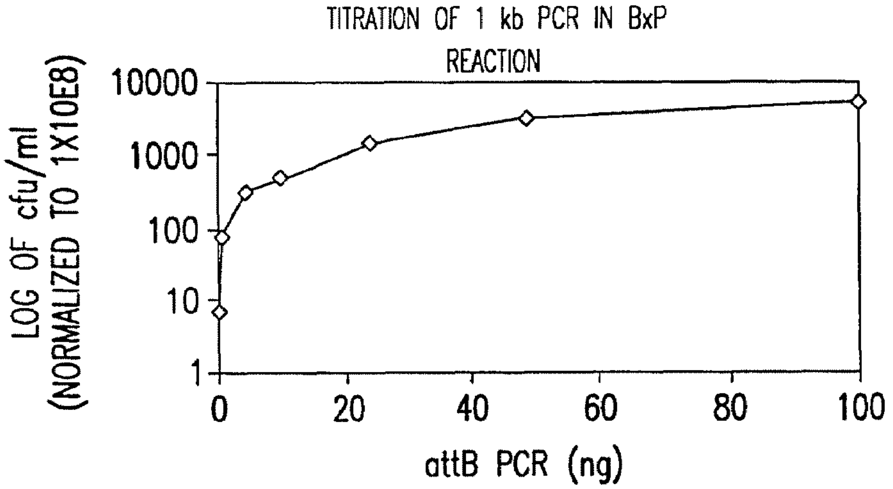
Figure 70C:
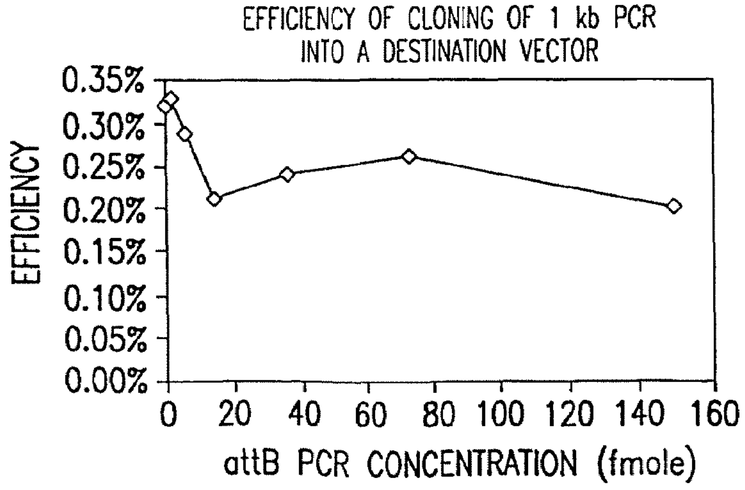
Figure 71A:
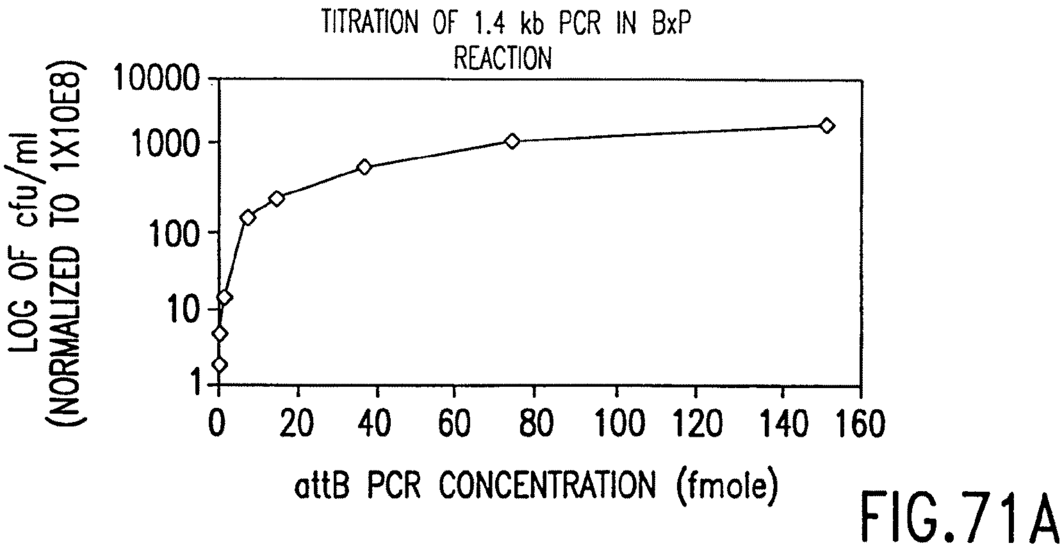
FIG. 71 is a series of graphs showing the effects of various weights (FIG. 71A) or moles (FIG. 71B) of a 1.4 kb PCR product on formation of colonies, and on efficiency of cloning of the 1.4 kb PCR product into a Donor Vector (FIG. 71C).
Figure 71B:
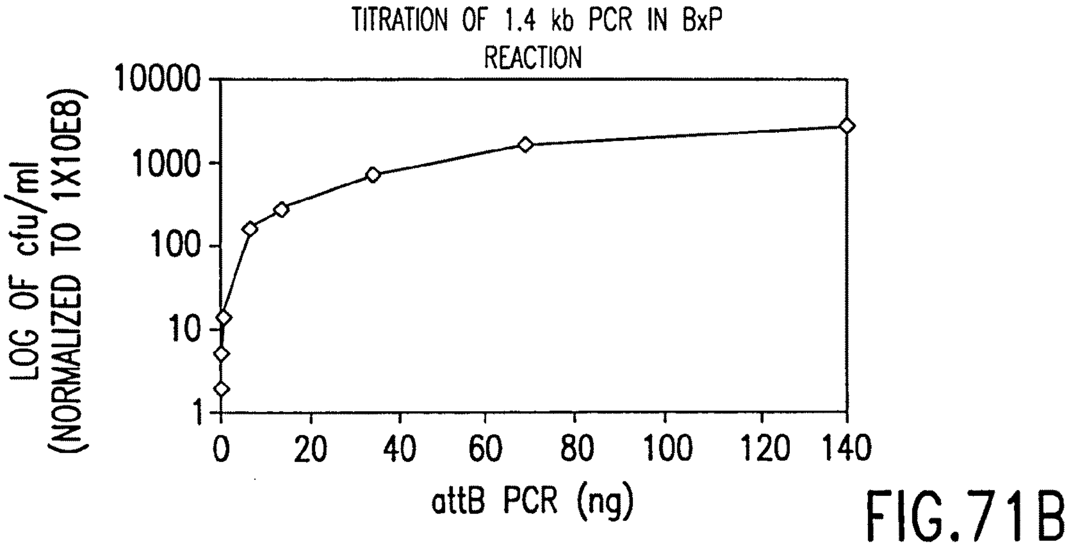
Figure 71C:
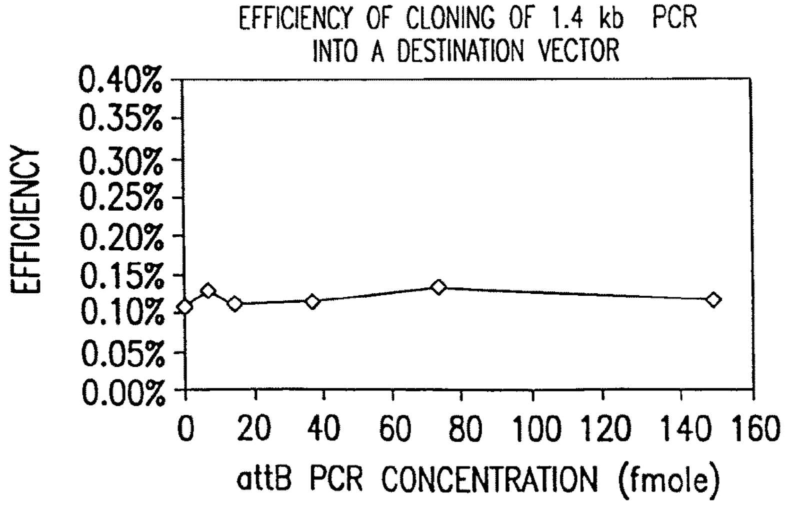
Figure 72A:
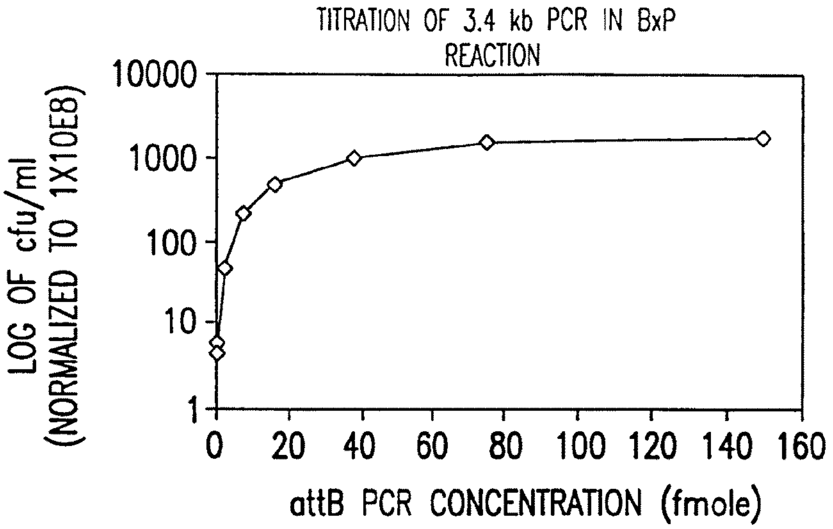
FIG. 72 is a series of graphs showing the effects of various weights (FIG. 72A) or moles (FIG. 72B) of a 3.4 kb PCR product on formation of colonies, and on efficiency of cloning of the 3.4 kb PCR product into a Donor Vector (FIG. 72C).
Figure 72B:
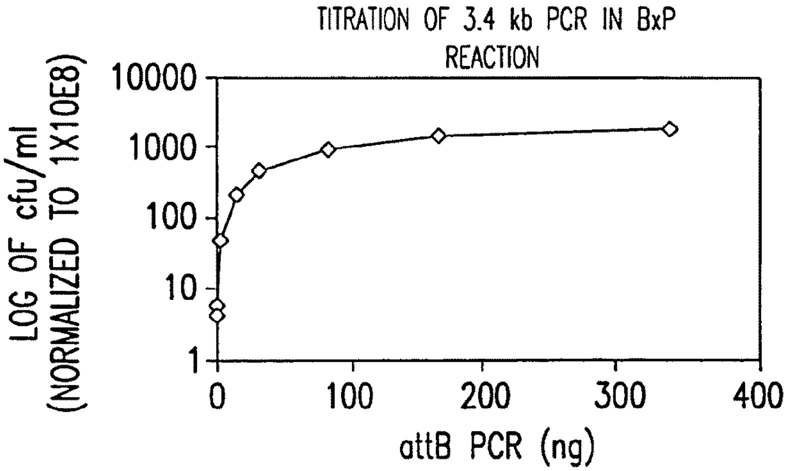
Figure 72C:
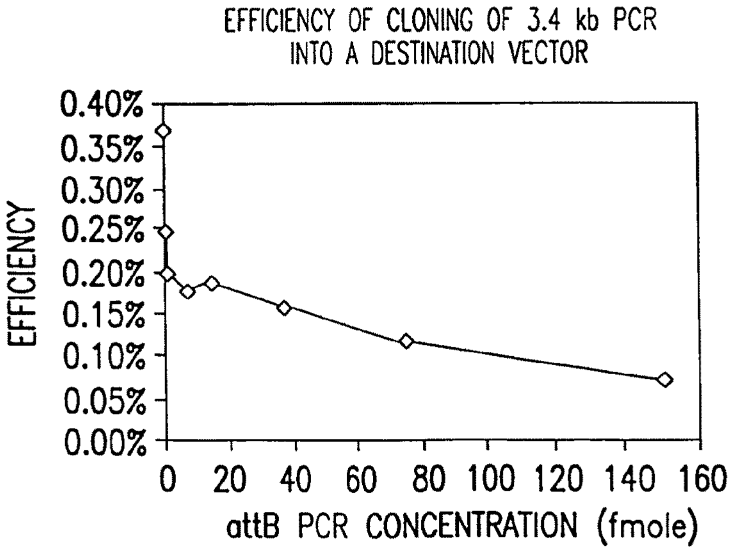
Figure 73A:
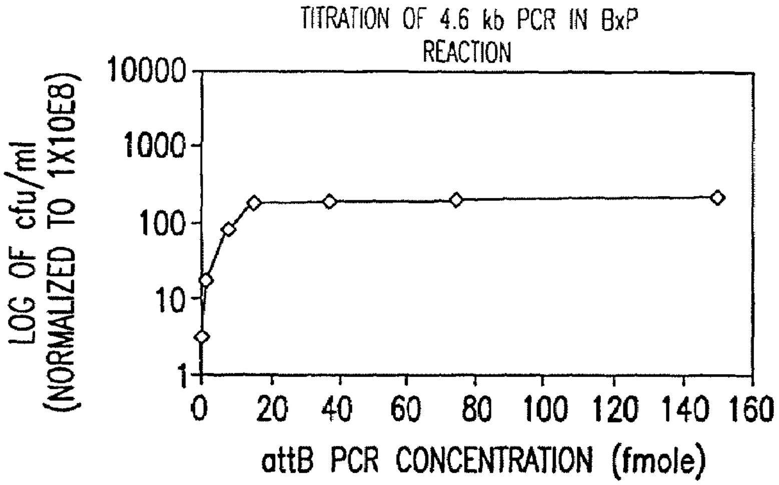
FIG. 73 is a series of graphs showing the effects of various weights (FIG. 73A) or moles (FIG. 73B) of a 4.6 kb PCR product on formation of colonies, and on efficiency of cloning of the 4.6 kb PCR product into a Donor Vector (FIG. 73C).
Figure 73B:
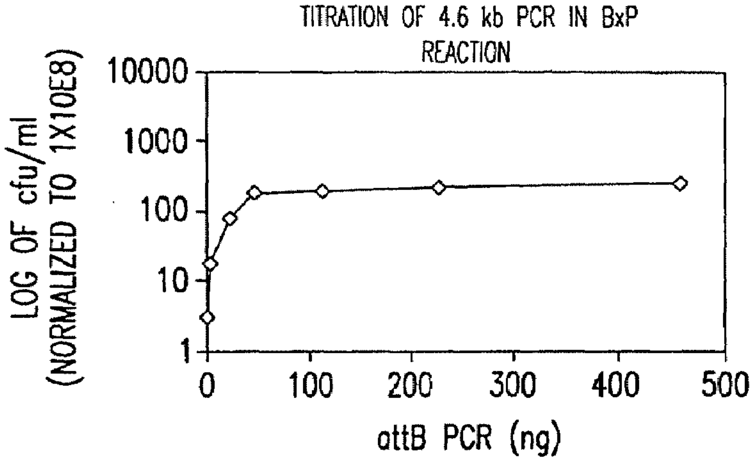
Figure 73C:
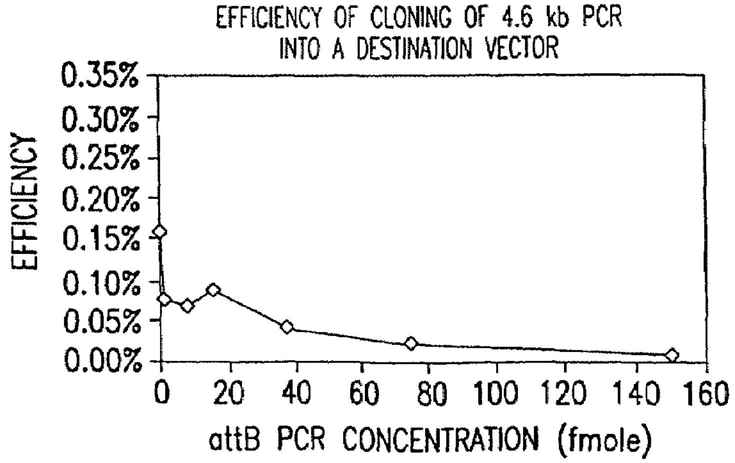
Figure 74:
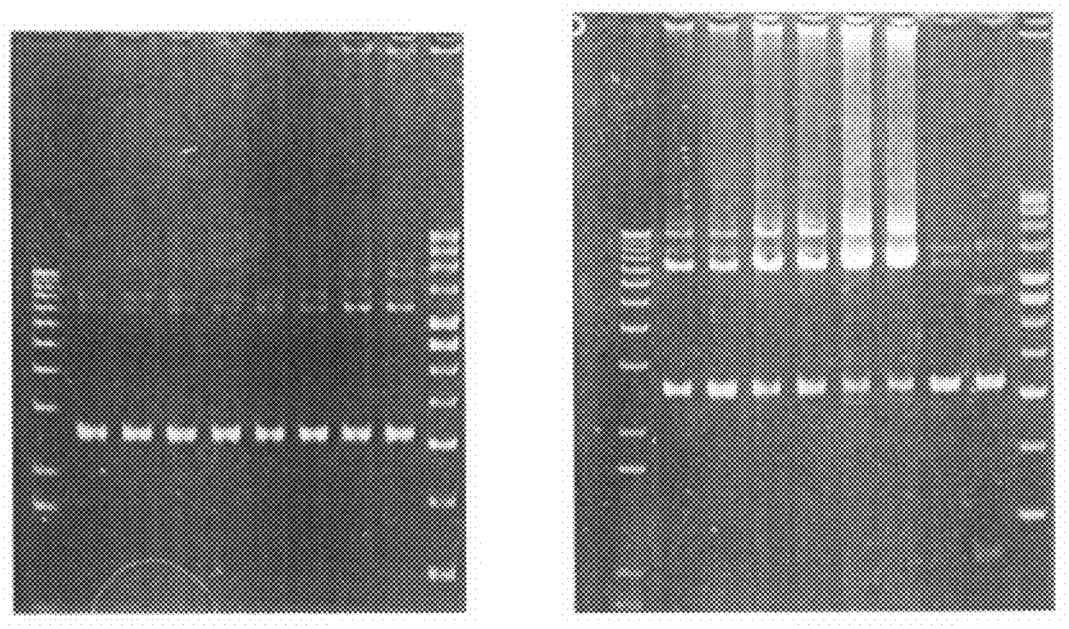
FIG. 74 is photograph of an ethidium bromide-stained gel of a titration of a 6.9 kb PCR product in a BxP reaction.
Figure 75:
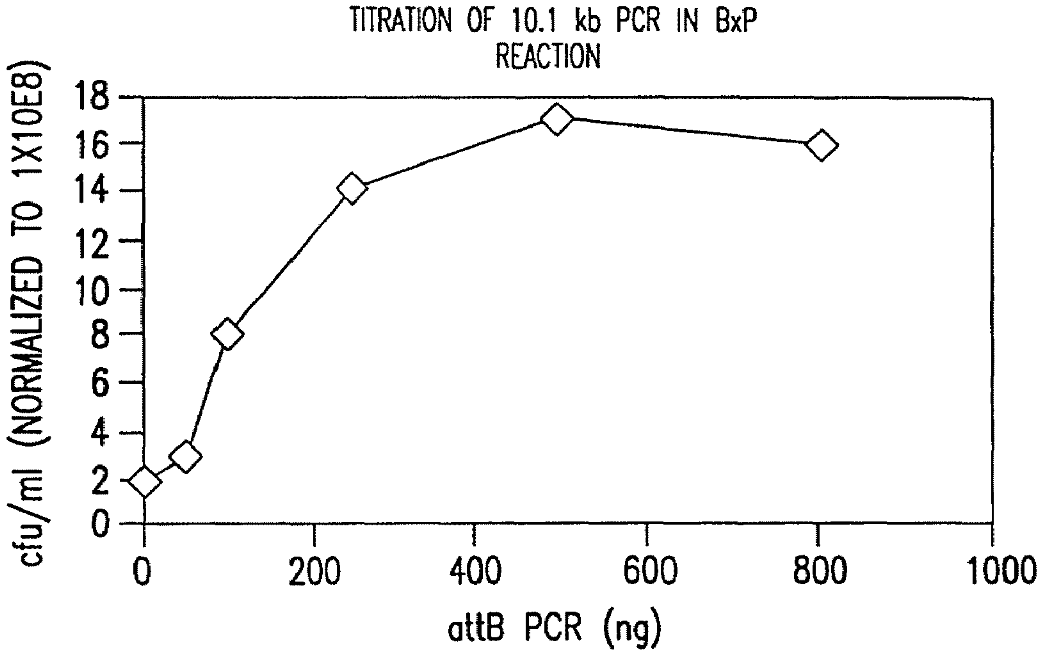
FIG. 75 is a graph showing the effects of various amounts of a 10.1 kb PCR product on formation of colonies upon cloning of the 10.1 kb PCR product into a Donor Vector.
Figure 76:
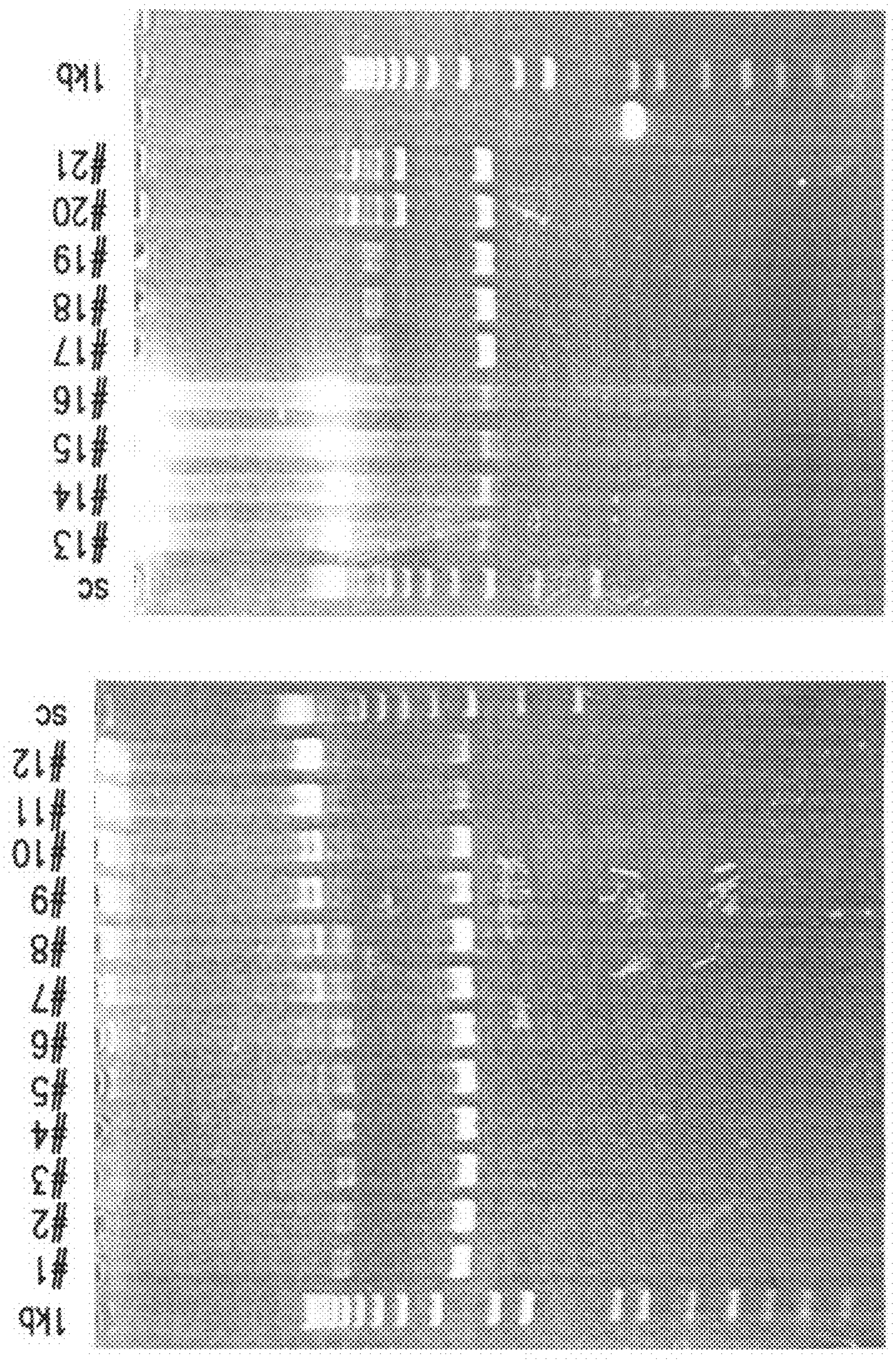
FIG. 76 is photograph of an ethidium bromide-stained gel of a titration of a 10.1 kb PCR product in a BxP reaction.

The results of these experiments are depicted in FIGS. 69A-69C (for 256 bp PCR fragments), 70A-70C (for 1 kb PCR fragments), 71A-71C (for 1.4 kb PCR fragments), 72A-72C (for 3.4 kb PCR fragments), 73A-73C (for 4.6 kb PCR fragments), 74 (for 6.9 kb PCR fragments), and 75-76 (for 10.1 kb PCR fragments). The results shown in these figures are summarized in FIG. 77, for different weights and moles of input PCR DNA.

Together, these results demonstrate that attB-containing PCR products ranging in size from about 0.25 kb to about 5 kb clone relatively efficiently in the recombinational cloning system of the invention. While PCR products larger than about 5 kb clone less efficiently (apparently due to slow resolution of cointegrates), longer incubation times during the recombination reaction appears to improve the efficiency of cloning of these larger PCR fragments. Alternatively, it may also be possible to improve efficiency of cloning of large (>about 5 kb) PCR fragments by using lower levels of input attP Donor plasmid and perhaps attB-containing PCR product, and/or by adjusting reaction conditions (e.g., buffer conditions) to favor more rapid resolution of the cointegrates.

Example 10

The BP Reaction

One purpose of the Gateward ("Entry") reaction is to convert an Expression Clone into an Entry Clone. This is useful when you have isolated an individual Expression Clone from an Expression Clone cDNA library, and you wish to transfer the nucleic acid molecule of interest into another Expression Vector, or to move a population of molecules from an attB or attL library. Alternatively, you may have mutated an Expression Clone and now wish to transfer the mutated nucleic acid molecule of interest into one or more new Expression Vectors. In both cases, it is necessary first to convert the nucleic acid molecule of interest to an Entry Clone.

Materials needed: 5×BP Reaction Buffer

Expression Clone DNA, 100-300 ng in ≦8 μl TE.

Donor (attP) Vector, 75 ng/μl, supercoiled DNA

Positive control attB-tet-PCR DNA, 25 ng/μl

GATEWAY™ BP Clonase™ Enzyme Mix (stored at −80° C.)

Clonase Stop Solution (Proteinase K, 2 μl/μl).

Notes:

Preparation of the Expression Clone DNA: Miniprep DNA Treated with Rnase works well.

1. As with the LR Reaction (see Example 14), the BP Reaction is strongly influenced by the topology of the reacting DNAs. In general, the reaction is most efficient when one of the DNAs is linear and the other is supercoiled, compared to reactions where the DNAs are both linear or both supercoiled. Further, linearizing the attB Expression Clone (anywhere within the vector) will usually give more colonies than linearizing the Donor (attP) Plasmid. If finding a suitable cleavage site within your Expression Clone vector proves difficult, you may linearize the Donor (attP) Plasmid between the attP1 and attP2 sites (for example, at the NcoI site), avoiding the ccdB gene. Maps of Donor (attP) Plasmids are given in FIGS. 49-54.

Procedure:

1. Assemble reactions as follows. Combine all components at room temperature, except GATEWAY™ BP Clonase™ Enzyme Mix, before removing GATEWAY™ BP Clonase™ Enzyme Mix from freezer.

| Component | Neg. Tube 1 | Pos. Tube 2 | Test Tube 3 |
|---|---|---|---|
| Positive Control, attB-tet-PCR DNA, 25 ng/μl | 4 μl | 4 μl | |
| Desired attB Expression Clone DNA (100 ng) linearized | | | 1-8 μl |
| Donor (attP) Plasmid, 75 ng/μl | 2 μl | 2 μl | 2 μl |
| 5 × BP Reaction Buffer | 4 μl | 4 μl | 4 μl |
| TE | 10 μl | 6 μl | To 16 μl |
| GATEWAY ™ BP Clonase ™ Enzyme | — | 4 μl | 4 μl |
| Mix (store at −80° C., add last) | | | |
| Total Volume | 20 μl | 20 μl | 20 μl |

2. Remove the GATEWAY™ BP Clonase™ Enzyme Mix from the −80° C. freezer, place immediately on ice. The mixture takes only a few minutes to thaw.

3. Add 4 μl of GATEWAY™ BP Clonase™ Enzyme Mix to the subcloning reaction, mix.

4. Return GATEWAY™ BP Clonase™ Enzyme Mix to −80° C. freezer.

5. Incubate tubes at 25° for at least 60 minutes. If both the attB and attP DNAs are supercoiled, incubation for 2-24 hours at 25° C. is recommended.

6. Add 2 μl Clonase Stop Solution. Incubate for 10 min at 37° C.

7. Transform 2 μl into 100 μl competent *E. coli*, as above. Select on LB plates containing 50 μg/ml kanamycin.

Example 11

Cloning PCR Products into Entry Vectors using Standard Cloning Methods

Preparation of Entry Vectors for Cloning of PCR Products

All of the Entry Vectors of the invention contain the death gene ccdB as a stuffer between the "left" and "right" restriction sites. The advantage of this arrangement is that there is virtually no background from vector that has not been cut with both restriction enzymes, because the presence of the ccdB gene will kill all standard *E. coli* strains. Thus it is necessary to cut each Entry Vector twice, to remove the ccdB fragment.

We strongly recommend that, after digestion of the Entry Vector with the second restriction enzyme, you treat the reaction with phosphatase (calf intestine alkaline phosphatase, CIAP or thermosensitive alkaline phosphatase, TSAP). The phosphatase can be added directly to the reaction mixture, incubated for an additional time, and inactivated. This step dephosphorylates both the vector and ccdB fragments, so that during subsequent ligation there is less competition between the ccdB fragment and the DNA of interest for the termini of the Entry Vector.

Blunt Cloning of PCR Products

Generally PCR products do not have 5' phosphates (because the primers are usually 5' OH), and they are not necessarily blunt. (On this latter point, see Brownstein, et al., *BioTechniques* 20: 1006, 1996 for a discussion of how the sequence of the primers affects the addition of single 3' bases.) The following protocol repairs these two defects.

In a 0.5 ml tube, ethanol precipitate about 40 ng of PCR product (as judged from an agarose gel).

1. Dissolve the precipitated DNA in 10 μl comprising 1 μl 10 mM rATP, 1 μl mixed 2 mM dNTPs (i.e., 2 mM each dATP, dCTP, dTTP, and dGTP), 2 μl 5× T4 polynucleotide kinase buffer (350 mM Tris HCl (pH7.6), 50 mM $MgCl_2$, 500 mM KCl, 5 mM 2-mercaptoethanol) 10 units T4 polynucleotide kinase, 1 μl T4 DNA polymerase, and water to 10 μl.
2. Incubate the tube at 37° for 10 minutes, then at 65° for 15 minutes, cool, centrifuge briefly to bring any condensate to the tip of the tube.
3. Add 5 μl of the PEG/$MgCl_2$ solution, mix and centrifuge at room temperature for 10 minutes. Discard supernatant.
4. Dissolve the invisible precipitate in 10 μl containing 2 μl 5×T4 DNA ligase buffer (Life Technologies, Inc.), 0.5 units T4 DNA ligase, and about 50 ng of blunt, phosphatase-treated Entry Vector.
5. Incubate at 25° for 1 hour, then 65° for 10 minutes. Add 90 μl TE, transform 10 μl into 50-100 μl competent *E. coli* cells.
6. Plate on kanamycin.

Note: In the above protocol, steps b-c simultaneously polish the ends of the PCR product (through the exonuclease and polymerase activities of T4 DNA polymerase) and phosphorylate the 5' ends (using T4 polynucleotide kinase). It is necessary to inactivate the kinase, so that the blunt, dephosphorylated vector in step e cannot self ligate. Step d (the PEG precipitation) removes all small molecules (primers, nucleotides), and has also been found to improve the yield of cloned PCR product by 50 fold.

Cloning PCR Products after Digestion with Restriction Enzymes

Efficient cloning of PCR products that have been digested with restriction enzymes includes three steps: inactivation of Taq DNA polymerase, efficient restriction enzyme cutting, and removal of small DNA fragments.

Inactivation of Tag DNA Polymerase: Carryover of Taq DNA polymerase and dNTPs into a RE digestion significantly reduces the success in cloning a PCR product (D. Fox et al., *FOCUS* 20(1):15, 1998), because Taq DNA polymerase can fill in sticky ends and add bases to blunt ends. Either TaqQuench™ (obtainable from Life Technologies, Inc.; Rockville, Md.) or extraction with phenol can be used to inactivate the Taq.

Efficient Restriction Enzyme Cutting: Extra bases on the 5' end of each PCR primer help the RE cut near ends of PCR products. With the availability of cheap primers, adding 6 to 9 bases on the 5' sides of the restriction sites is a good investment to ensure that most of the ends are digested. Incubation of the DNA with a 5-fold excess of restriction enzyme for an hour or more helps ensure success.

Removal of Small Molecules before Ligation: Primers, nucleotides, primer dimers, and small fragments produced by the restriction enzyme digestion, can all inhibit or compete with the desired ligation of the PCR product to the cloning vector. This protocol uses PEG precipitation to remove small molecules.

Protocol for Cutting the Ends of PCR Products with Restriction Enzyme(s):

1. Inactivation of Taq DNA polymerase in the PCR product:

Option A: Extraction with Phenol

A1. Dilute the PCR reaction to 200 μl with TE. Add an equal volume of phenol:chloroform:isoamyl alcohol, vortex vigorously for 20 seconds, and centrifuge for 1 minute at room temperature. Discard the lower phase.

A2. Extract the phenol from the DNA and concentrate as follows. Add an equal volume of 2-butanol (colored red with "Oil Red O" from Aldrich, if desired), vortex briefly, centrifuge briefly at room temperature. Discard the upper butanol phase. Repeat the extraction with 2-butanol. This time the volume of the lower aqueous phase should decrease significantly. Discard the upper 2-butanol phase.

A3. Ethanol precipitate the DNA from the aqueous phase of the above extractions. Dissolve in a 200 μl of a suitable restriction enzyme (RE) buffer.

Option B: Inactivation with TaqQuench

B1. Ethanol precipitate an appropriate amount of PCR product (100 ng to 1 μg), dissolve in 200 μl of a suitable RE buffer.

B2. Add 2 μl TaqQuench.

2. Add 10 to 50 units of restriction enzyme and incubate for at least 1 hour. Ethanol precipitate if necessary to change buffers for digestion at the other end of the PCR product.

3. Add ½ volume of the PEG/$MgCl_2$ mix to the RE digestion. Mix well and immediately centrifuge at room temperature for 10 minutes. Discard the supernatant (pellet is usually invisible), centrifuge again for a few seconds, discard any remaining supernatant.

4. Dissolve the DNA in a suitable volume of TE (depending on the amount of PCR product in the original amplification reaction) and apply an aliquot to an agarose gel to confirm recovery. Apply to the same gel 20-100 ng of the appropriate Entry Vector that will be used for the cloning.

Example 12

Determining the Expected Size of the GATEWAY™ Cloning Reaction Products

If you have access to a software program that will electronically cut and splice sequences, you can create electronic clones to aid you in predicting the sizes and restriction patterns of GATEWAY™ Cloning System recombination products.

The cleavage and ligation steps performed by the enzyme Int in the GATEWAY™ Cloning System recombination reactions mimic a restriction enzyme cleavage that creates a 7-bp 5'-end overhang followed by a ligation step that reseals the ends of the daughter molecules. The recombination proteins present in the Clonase cocktails (see Example 19 below) recognize the 15 bp core sequence present within all four types of att sites (in addition to other flanking sequences characteristic of each of the different types of att sites).

By treating these sites in your software program as if they were restriction sites, you can cut and splice your Entry Clones with various Destination Vectors and obtain accurate maps and sequences of the expected results from your GATEWAY™ Cloning System reactions.

Example 13

Protein Expression

Brief Review of Protein Expression

Transcription: The most commonly used promoters in *E. coli* Expression Vectors are variants of the lac promoter, and these can be turned on by adding IPTG to the growth medium. It is usually good to keep promoters off until expression is desired, so that the host cells are not made sick by the overabundance of some heterologous protein. This is reasonably easy in the case of the lac promoters used in *E. coli*. One needs to supply the lac I gene (or its more productive relative, the lac $I^q$ gene) to make lac repressor protein, which binds near the promoter and keeps transcription levels low. Some Destination Vectors for *E. coli* expression carry their own $lacI^q$ gene for this purpose. (However, lac promoters are always a little "on," even in the absence of IPTG.)

Controlling transcription in eukaryotic cells is not nearly so straightforward or efficient. The tetracycline system of Bujard and colleagues is the most successful approach, and one of the Destination Vectors (pDEST11; FIG. 31) has been constructed to supply this function.

Translation: Ribosomes convert the information present in mRNA into protein. Ribosomes scan RNA molecules looking for methionine (AUG) codons, which begin nearly all nascent proteins. Ribosomes must, however, be able to distinguish between AUG codons that code for methionine in the middle of proteins from those at the start. Most often ribosomes choose AUGs that are 1) first in the RNA (toward the 5' end), and 2) have the proper sequence context. In *E. coli* the favored context (first recognized by Shine and Dalgarno, *Eur. J. Biochem.* 57: 221 (1975)) is a run of purines (As and Gs) from five to 12 bases upstream of the initiating AUG, especially <u>AGGAGG</u> or some variant.

In eukaryotes, a survey of translated mRNAs by Kozak (*J. Biol. Chem.* 266: 19867 (1991)) has revealed a preferred sequence context, gcc <u>A</u>cc ATGG, around the initiating methionine, with the A at −3 being most important, and a purine at +4 (where the A of the ATG is +1), preferably a G, being next most influential. Having an A at −3 is enough to make most ribosomes choose the first AUG of an mRNA, in plants, insects, yeast, and mammals. (For a review of initiation of protein synthesis in eukaryotic cells, see: Pain, V. M. Eur. J. Biochem. 236:747-771, 1996.)

Consequences of Translation Signals for GATEWAY™ Cloning System: First, translation signals (Shine-Dalgarno in *E. coli*, Kozak in eukaryotes) have to be close to the initiating ATG. The attB site is 25 base pairs long. Thus if translation signals are desired near the natural ATG of the nucleic acid molecule of interest, they must be present in the Entry Clone of that nucleic acid molecule of interest. Also, when a nucleic acid molecule of interest is moved from an Entry Clone to a Destination vector, any translation signals will move along. The result is that the presence or absence of Shine-Dalgarno and/or Kozak sequences in the Entry Clone must be considered, with the eventual Destination Vectors to be used in mind.

Second, although ribosomes choose the 5' ATG most often, internal ATGs are also used to begin protein synthesis. The better the translation context around this internal ATG, the more internal translation initiation will be seen. This is important in the GATEWAY™ Cloning System, because you can make an Entry Clone of your nucleic acid molecule of interest, and arrange to have Shine-Dalgarno and/or Kozak sequences near the ATG. When this cassette is recombined into a Destination Vector that transcribes your nucleic acid molecule of interest, you get native protein. If you want, you can make a fusion protein in a different Destination Vector, since the Shine-Dalgarno and/or Kozak sequences do not contain any stop signals in the same reading frame. However, the presence of these internal translation signals may result in a significant amount of native protein being made, contaminating, and lowering the yield of, your fusion protein. This is especially likely with short fusion tags, like His6.

A good compromise can be recommended. If an Entry Vector like pENTR7 (FIG. 16) or pENTR8 (FIG. 17) is chosen, the Kozak bases are present for native eukaryotic expression. The context for *E. coli* translation is poor, so the yield of an amino-terminal fusion should be good, and the fusion protein can be digested with the TEV protease to make near-native protein following purification.

Recommended Conditions for Synthesis of Proteins in *E. coli*: When making proteins in *E. coli* it is advisable, at least initially, to incubate your cultures at 30° C., instead of at 37° C. Our experience indicates that proteins are less likely to form aggregates at 30° C. In addition, the yields of proteins from cells grown at 30° C. frequently are improved.

The yields of proteins that are difficult to express may also be improved by inducing the cultures in mid-log phase of growth, using cultures begun in the morning from overnight growths, as opposed to harvesting directly from an overnight culture. In the latter case, the cells are preferably in late log or stationary growth, which can favor the formation of insoluble aggregates.

Example 14

Constructing Destination Vectors from Existing Vectors

Figure 63:
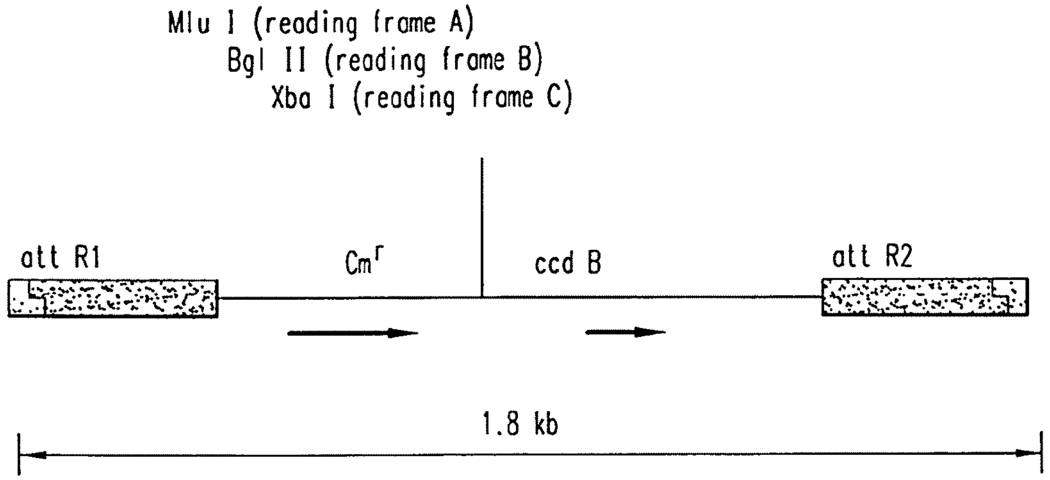
FIG. 63 is a schematic depiction of three GATEWAY™ Cloning System cassettes. Three blunt-ended cassettes are depicted which convert standard expression vectors to Destination Vectors. Each of the depicted cassettes provides amino-terminal fusions in one of three possible reading frames, and each has a distinctive restriction cleavage site as shown.
Figure 64A:
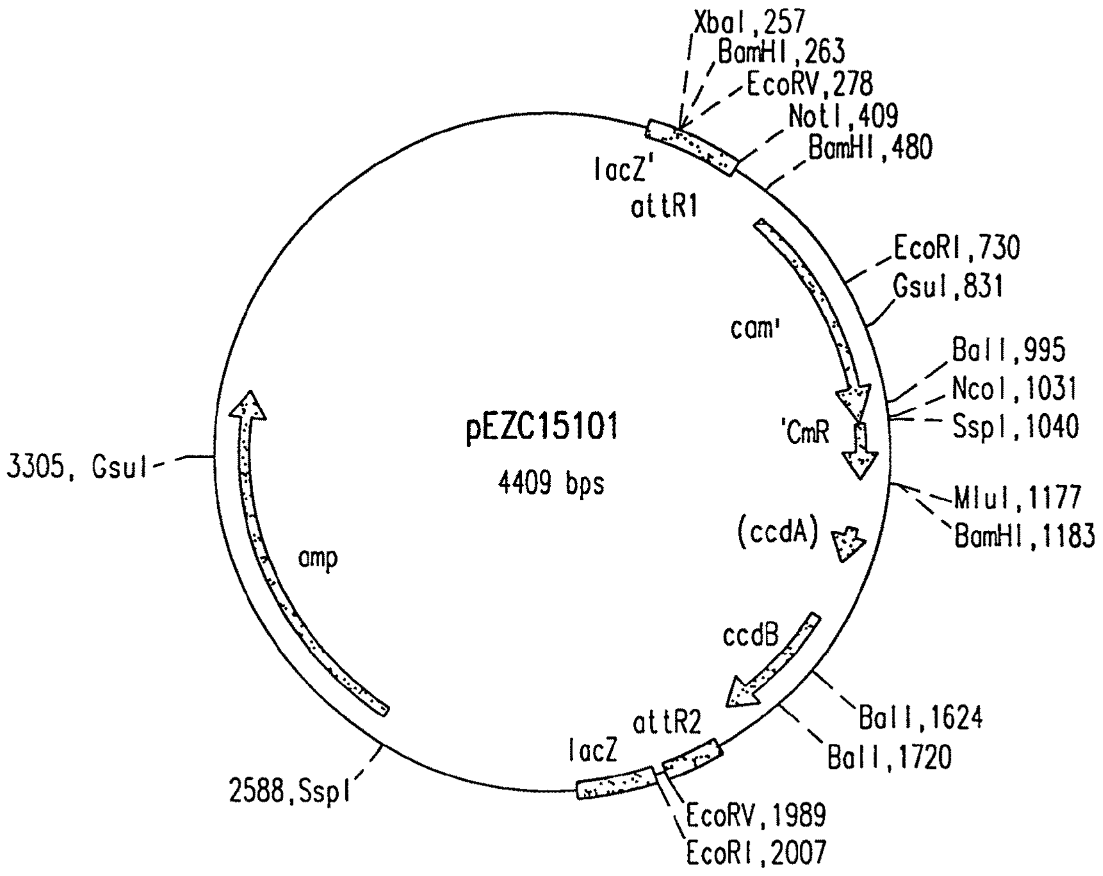
FIG. 64A), pEZC15102 (reading frame B.
Figure 64B:
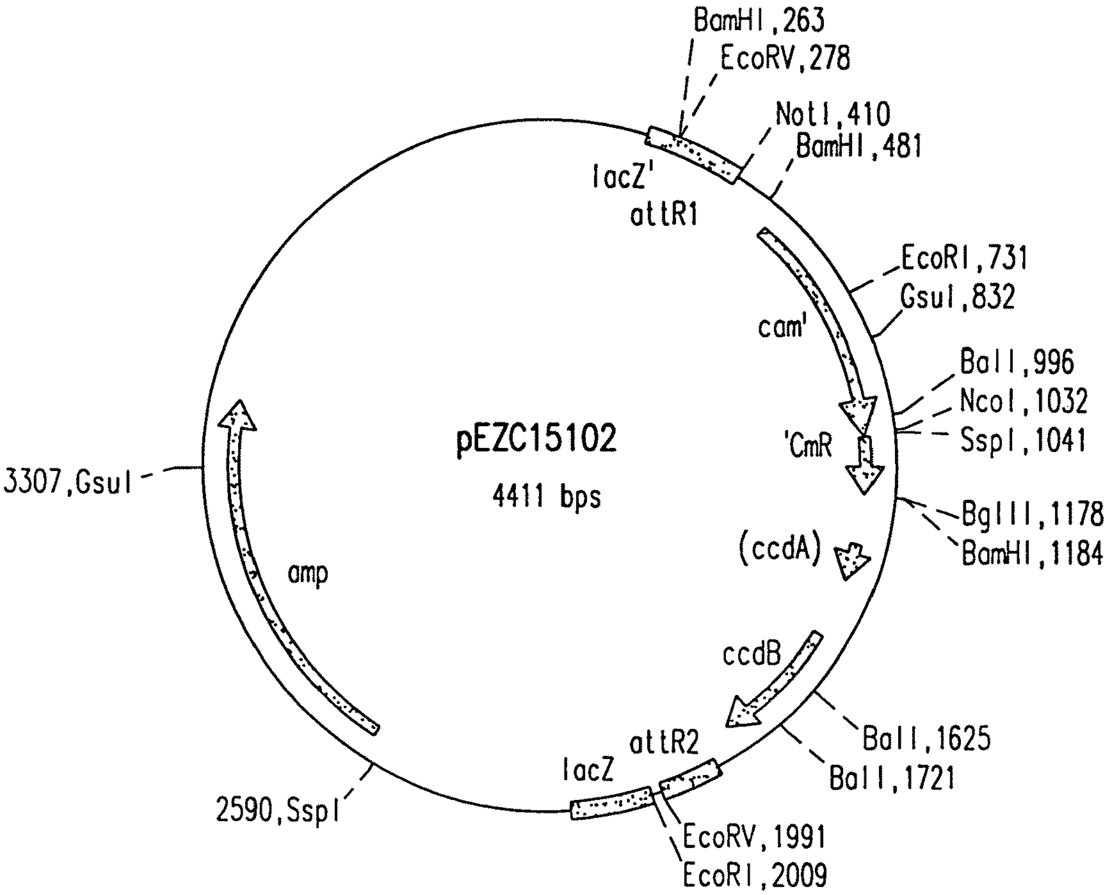
FIG. 64B), and pEZC15103 (reading frame C.
Figure 64C:
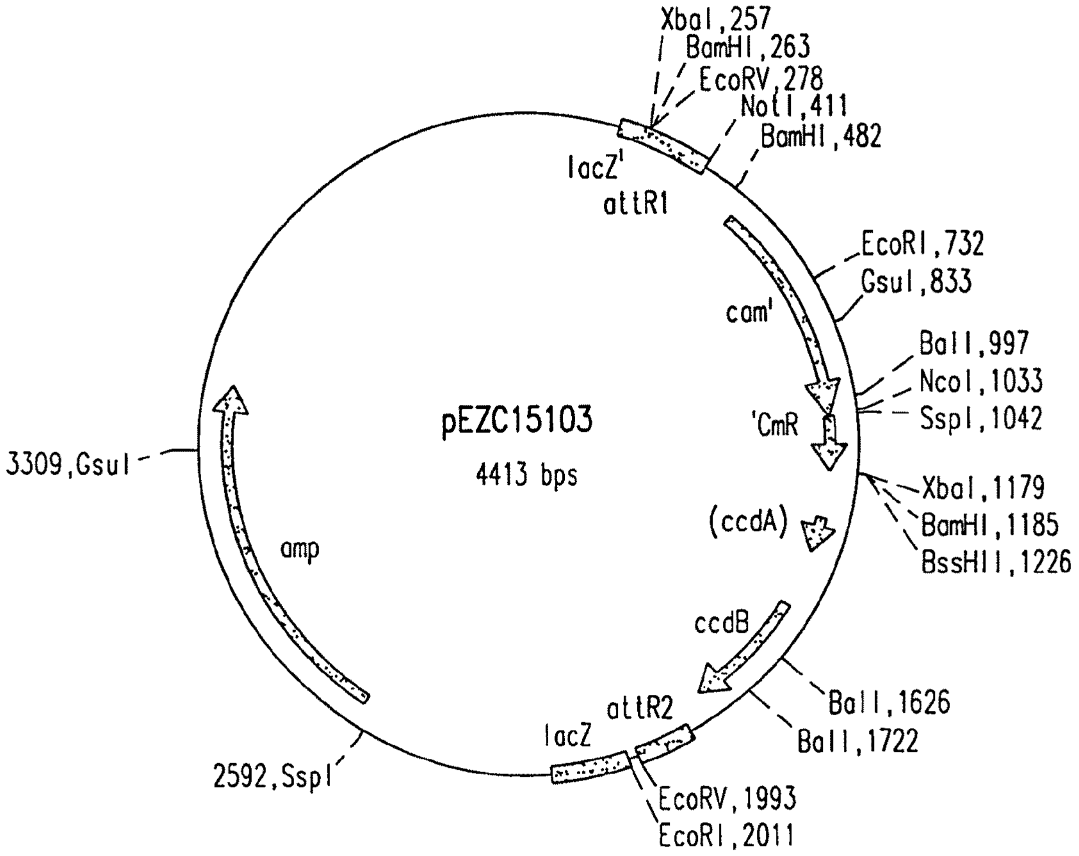
FIG. 64C).

Destination Vectors function because they have two recombination sites, attR1 and attR2, flanking a chloramphenicol resistance (CmR) gene and a death gene, ccdB. The GATEWAY™ Cloning System recombination reactions exchange the entire Cassette (except for a few bases comprising part of the attB sites) for the DNA segment of interest from the Entry Vector. Because attR1, CmR, ccdB gene, and attR2 are contiguous, they can be moved on a single DNA segment. If this Cassette is cloned into a plasmid, the plasmid becomes a Destination Vector. FIG. 63 shows a schematic of the GATEWAY™ Cloning System Cassette; attR cassettes in all three reading frames contained in vectors pEZC15101, pEZC15102 and pEZC15103 are shown in FIGS. 64A, 64B, and 64C, respectively.

The protocol for constructing a Destination Vector is presented below. Keep in mind the following points:

- Destination Vectors must be constructed and propagated in one of the DB strains of *E. coli* (e.g., DB3.1, and particularly *E. coli* LIBRARY EFFICIENCY® DB3.1™ Competent Cells) available from Life Technologies, Inc. (and described in detail in U.S. Provisional Application No. 60/122,392, filed on Mar. 2, 1999, which is incorporated herein by reference), because the ccdB death gene will kill any *E. coli* strain that has not been mutated such that it will survive the presence of the ccdB gene.
- If your Destination Vector will be used to make a fusion protein, a GATEWAY™ Cloning System cassette with the correct reading frame must be used. The nucleotide sequences of the ends of the cassettes are shown in FIG. 78. The reading frame of the fusion protein domain must be in frame with the core region of the attR1 site (for an amino terminal fusion) so that the six As are translated into two lysine codons. For a C-terminal fusion protein, translation through the core region of the attR2 site should be in frame with -TAC-AAA-, to yield -Tyr-Lys-.
- Note that each reading frame Cassette has a different unique restriction site between the chloramphenicol resistance and ccdB genes (MluI for reading frame A, BglII for reading frame B, and XbaI for reading frame C; see FIG. 63).
- Most standard vectors can be converted to Destination Vectors, by inserting the Entry Cassette into the MCS of that vector.

Protocol for Making a Destination Vector

Figure 79:
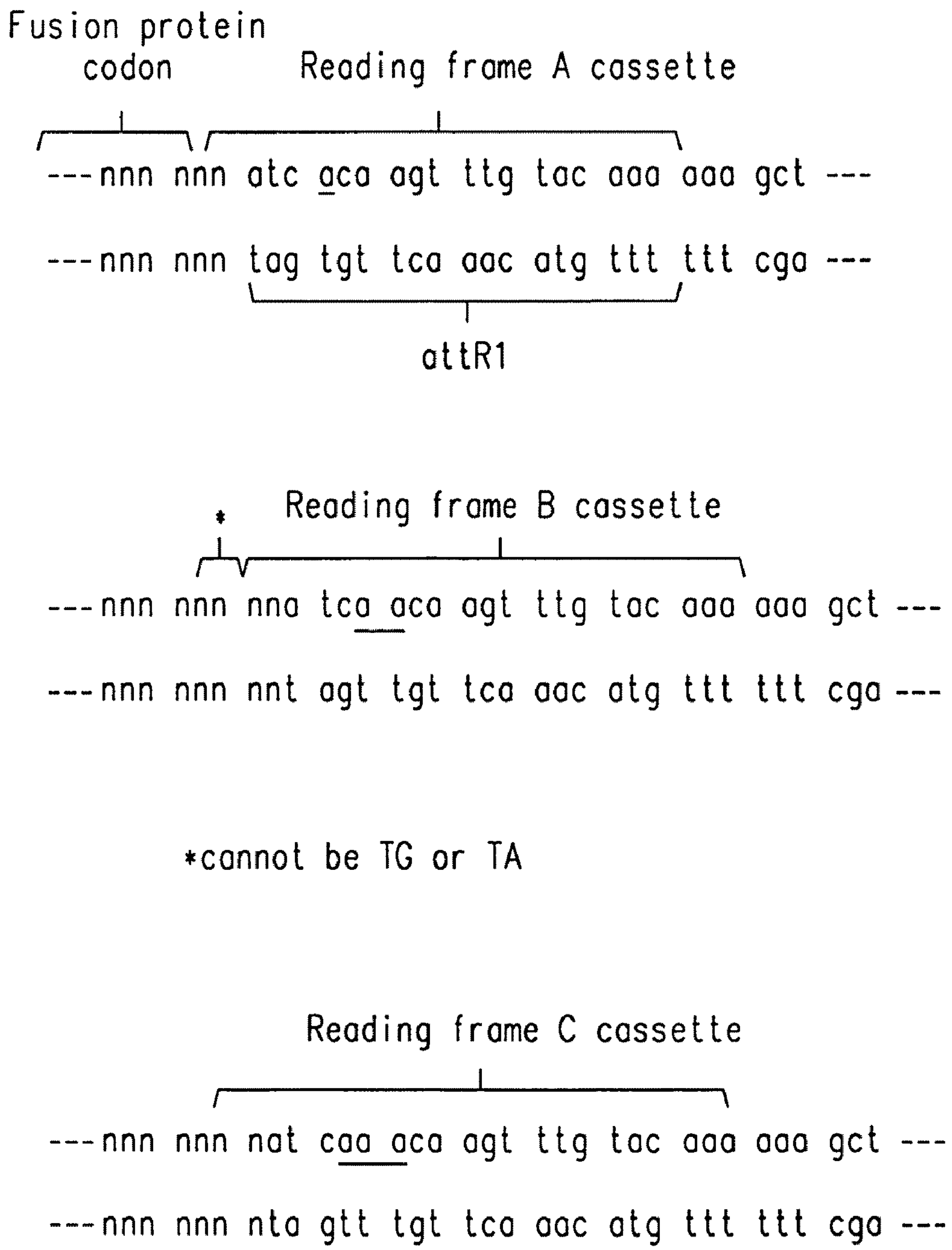
FIG. 79 is a depiction of several different attR cassettes (SEQ ID NOs: 171-173) (in reading frames A, B, or C) which may provide fusion codons at the amino-terminus of the encoded protein.

1. If the vector will make an amino fusion protein, it is necessary to keep the "aaa aaa" triplets in attR1 in phase with the triplets of the fusion protein. Determine which Entry cassette to use as follows:
   - a.) Write out the nucleotide sequence of the existing vector near the restriction site into which the Entry cassette will be cloned. These must be written in triplets corresponding to the amino acid sequence of the fusion domain.
   - b.) Draw a vertical line through the sequence that corresponds to the restriction site end, after it has been cut and made blunt, i.e., after filling in a protruding 5' end or polishing a protruding 3' end.
   - c.) Choose the appropriate reading frame cassette:
     - If the coding sequence of the blunt end ends after a complete codon triplet, use the reading frame A cassette. See FIGS. 78, 79 and 80.
     - If the coding sequence of the blunt end ends in a single base, use the reading frame B cassette. See FIGS. 78, 79 and 81.
     - If the coding sequence of the blunt end ends in two bases, use the reading frame C cassette. See FIGS. 78, 79, 82A-B, and 83A-C.
2. Cut one to five micrograms of the existing plasmid at the position where you wish your nucleic acid molecule of interest (flanked by att sites) to be after the recombination reactions. Note: it is better to remove as many of the MCS restriction sites as possible at this step. This makes it more likely that restriction enzyme sites within the GATEWAY™ Cloning System Cassette will be unique in the new plasmid, which is important for linearizing the Destination Vector (Example 14, below).

3. Remove the 5' phosphates with alkaline phosphatase. While this is not mandatory, it increases the probability of success.

4. Make the end(s) blunt with fill-in or polishing reactions. For example, to 1 μg of restriction enzyme-cut, ethanol-precipitated vector DNA, add:

i. 20 μl 5×T4 DNA Polymerase Buffer (165 mM Tris-acetate (pH 7.9), 330 mM Na acetate, 50 mM Mg acetate, 500 μg/ml BSA, 2.5 mM DTT)

ii. 5 μl 10 mM dNTP mix iii. 1 Unit of T4 DNA Polymerase iv. Water to a final volume of 100 μl v. Incubate for 15 min at 37° C.

5. Remove dNTPs and small DNA fragments: Ethanol precipitate (add three volumes of room temperature ethanol containing 0.1 M sodium acetate, mix well, immediately centrifuge at room temperature 5-10 minutes), dissolve wet precipitate in 200 μl TE, add 100 μl 30% PEG 8000, 30 mM $MgCl_2$, mix well, immediately centrifuge for 10 minutes at room temperature, discard supernatant, centrifuge again a few seconds, discard any residual liquid.

6. Dissolve the DNA to a final concentration of 10-50 ng per microliter. Apply 20-100 ng to a gel next to supercoiled plasmid and linear size standards to confirm cutting and recovery. The cutting does not have to be 100% complete, since you will be selecting for the chloramphenicol marker on the Entry cassette.

7. In a 10 μl ligation reaction combine 10-50 ng vector, 10-20 ng of Entry Cassette (FIG. 79), and 0.5 units T4 DNA ligase in ligase buffer. After one hour (or overnight, whichever is most convenient), transform 1 μl into one of the DB strains of competent *E. coli* cells with a gyrA462 mutation (See U.S. Provisional Application No. 60/122,392, filed on Mar. 2, 1999, which is incorporated herein by reference), preferably DB3.1, and most preferably *E. coli* LIBRARY EFFICIENCY® DB3.1™ Competent Cells. The ccdB gene on the Entry Cassette will kill other strains of *E. coli* that have not been mutated so as to survive the presence of the ccdB gene.

8. After expression in SOC medium, plate 10 μl and 100 μl on chloramphenicol-containing (30 μg/ml) plates, incubate at 37° C.

9. Pick colonies, make miniprep DNA. Treat the miniprep with RNase A and store in TE. Cut with the appropriate restriction enzyme to determine the orientation of the Cassette. Choose clones with the attR1 site next to the amino end of the protein expression function of the plasmid.

Notes on Using Destination Vectors

We have found that about ten-fold more colonies result from a GATEWAY™ Cloning System reaction if the Destination Vector is linear or relaxed. If the competent cells you use are highly competent (>$10^8$ per microgram), linearizing the Destination Vector is less essential.

Figure 80:
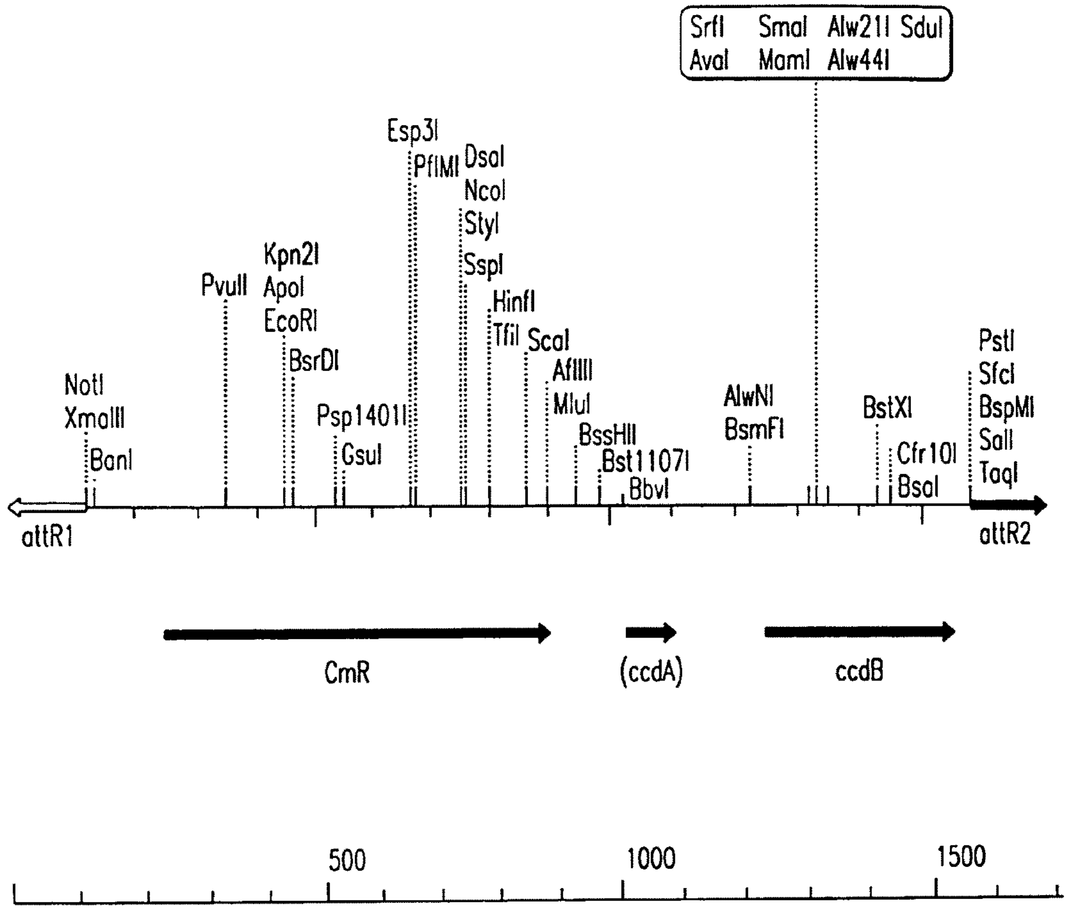
FIG. 80 illustrates the single-cutting restriction sites in an attR reading frame A cassette of the invention.
Figure 81:
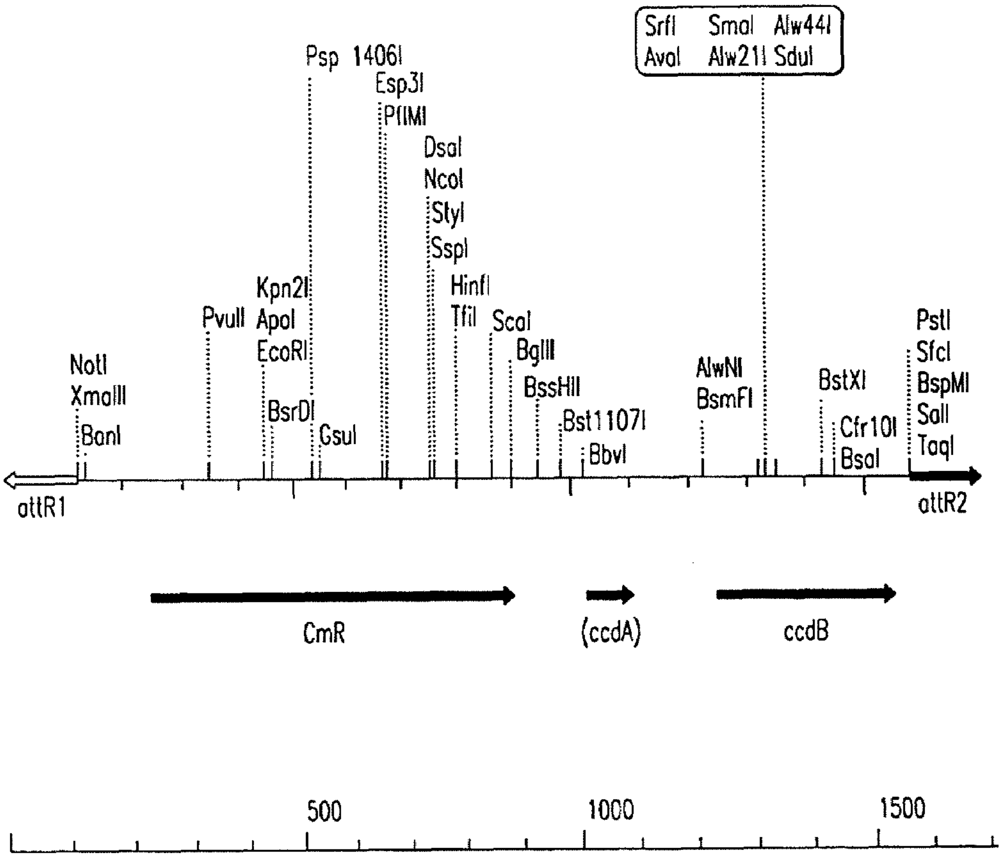
FIG. 81 illustrates the single-cutting restriction sites in an attR reading frame B cassette of the invention.
Figure 82A:
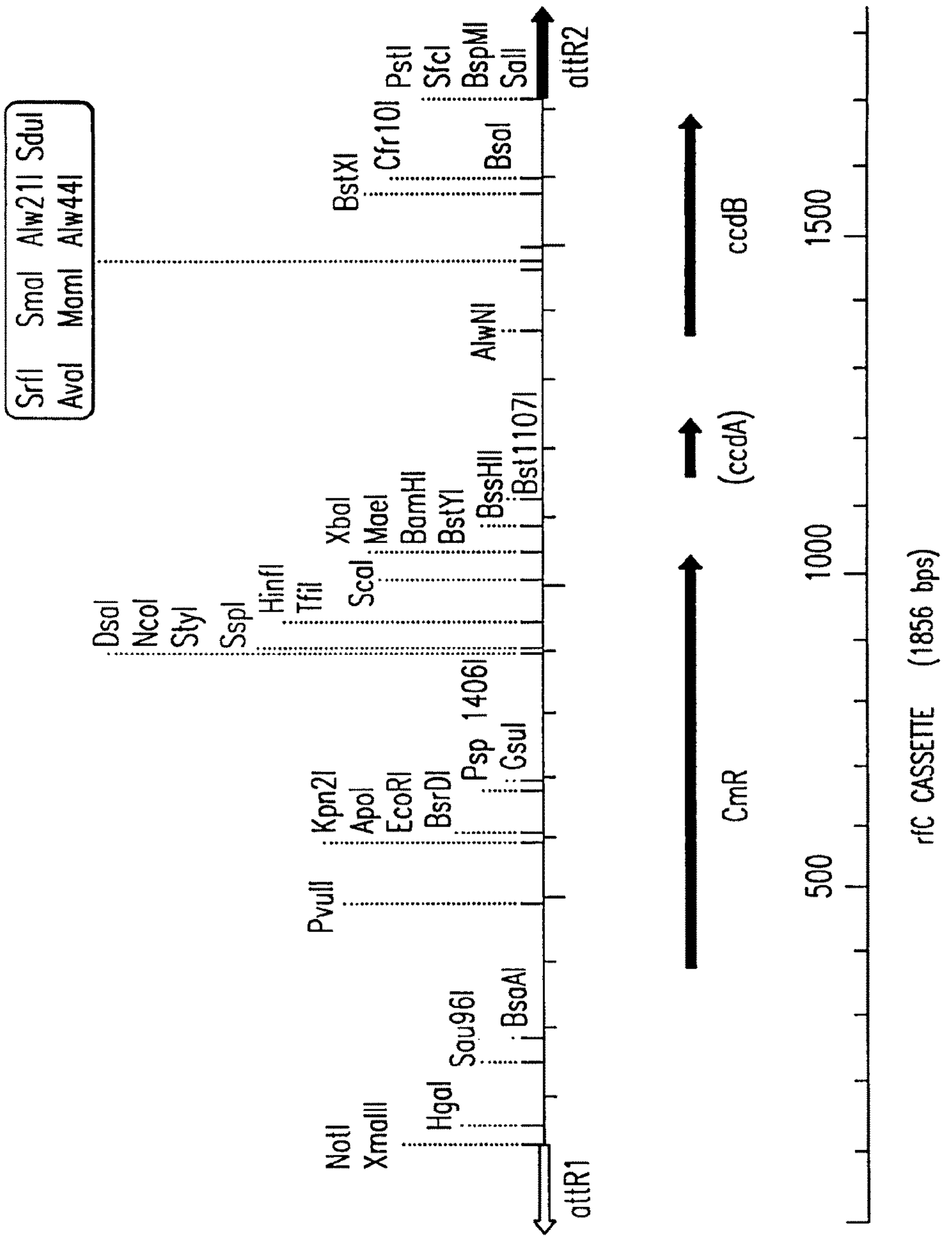
FIG. 82 illustrates the single-cutting restriction sites in two alternative attR reading frame C cassettes of the invention (FIGS. 82A and 82B) depicted in FIG. 78.
Figure 82B:
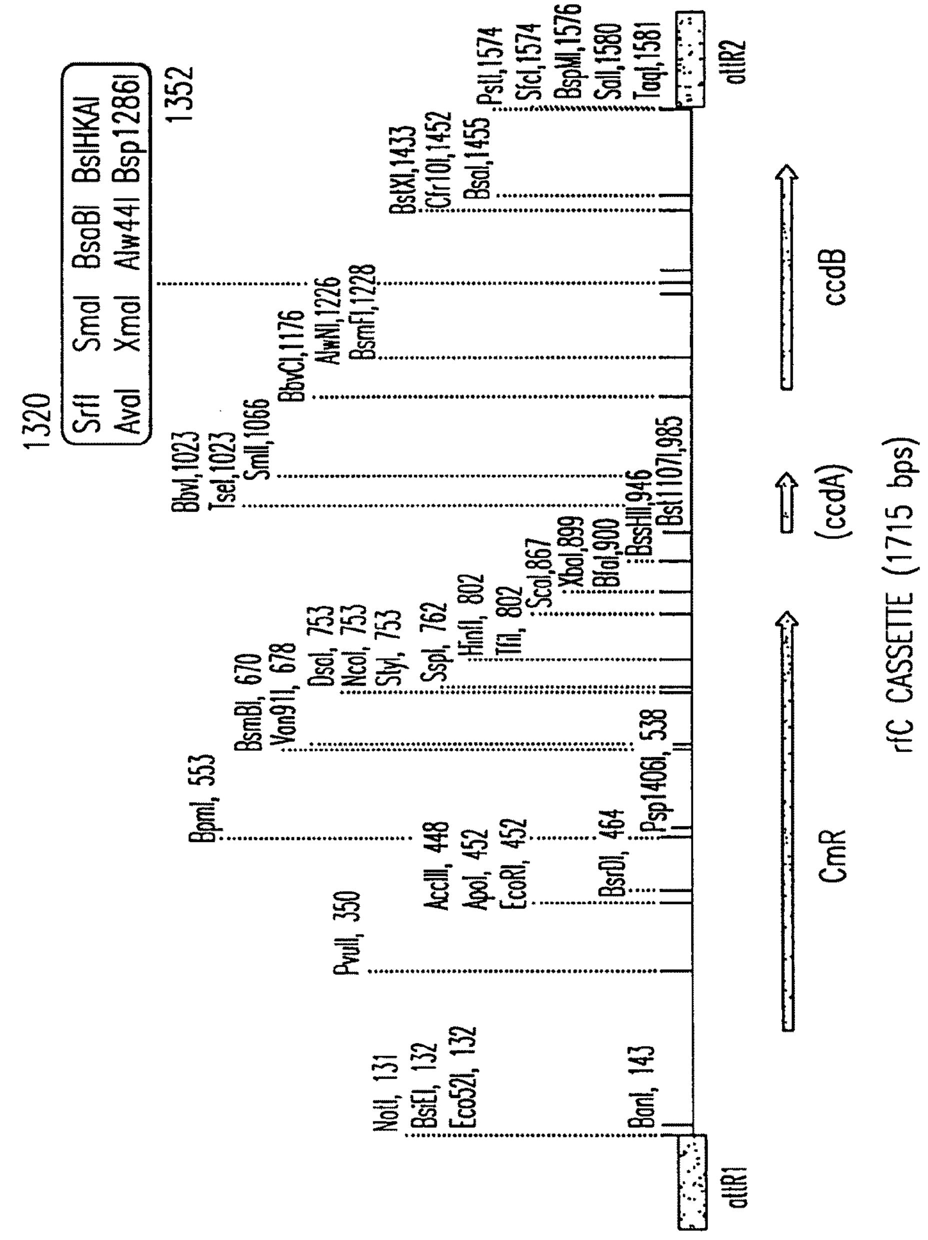
Figure 83A:
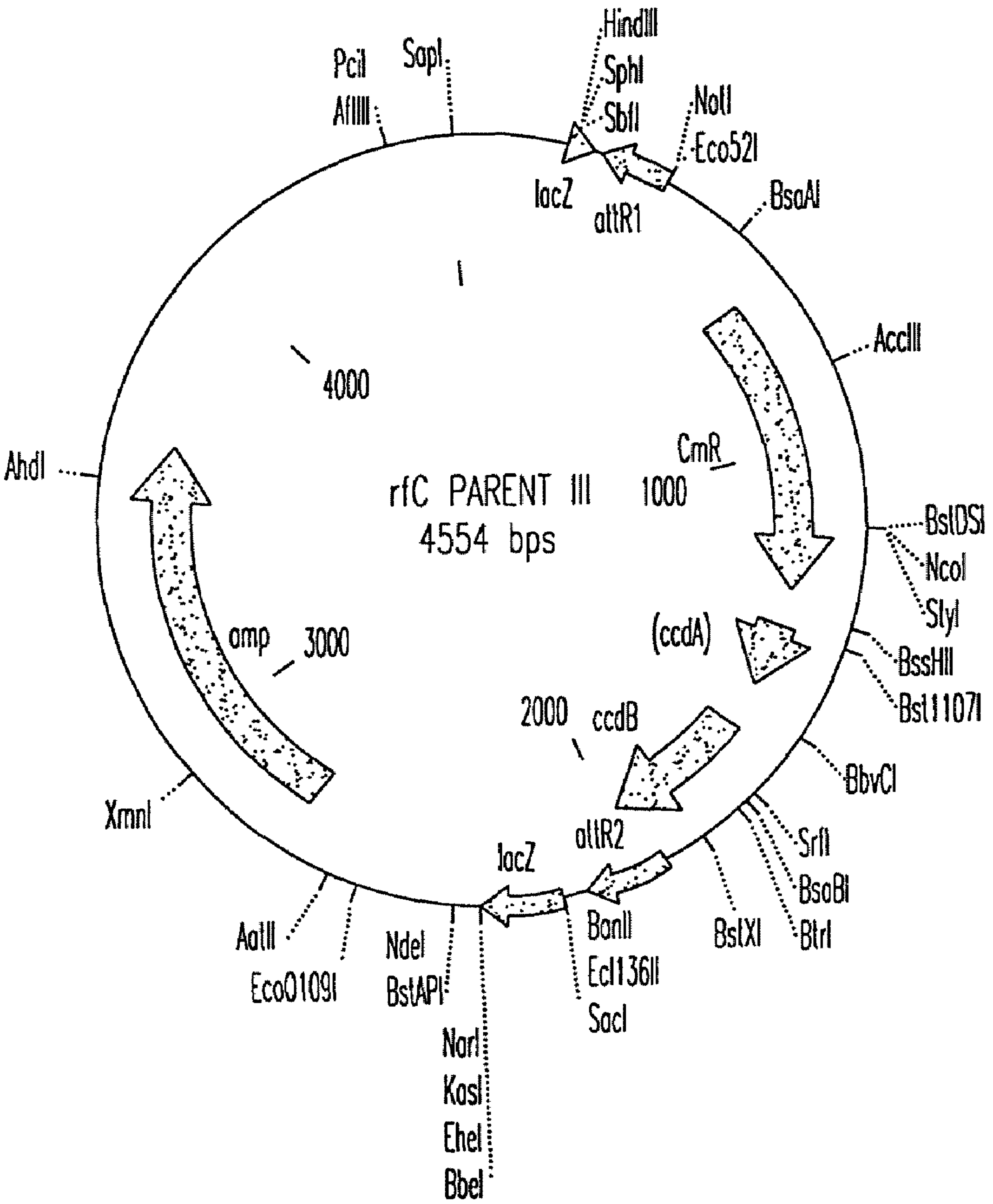
FIG. 83 shows the physical map (FIG. 83A), and the nucleotide sequence (FIGS. 83B-C) (SEQ ID NO:174), for an attR reading frame C parent plasmid prfC Parent III, which contains an attR reading frame C cassette of the invention (alternative A in FIGS. 78 and 82).

The site or sites used for the linearization must be within the Entry Cassette. Sites that cut once or twice within each cassette are shown in FIGS. 80-82.

Minipreps of Destination Vectors will work fine, so long as they have been treated with RNase. Since most DB strains are endA- (See U.S. Provisional Application No. 60/122,392, filed on Mar. 2, 1999, which is incorporated herein by reference), minipreps can be digested with restriction enzymes without a prior phenol extraction.

Reading the $OD_{260}$ of miniprep DNA is inaccurate unless the RNA and ribonucleotides have been removed, for example, by a PEG precipitation.

Example 15

Some Options in Choosing Appropriate Entry Vectors and Destination Vectors an Example In some applications, it may be desirable to express a nucleic acid molecule of interest in two forms: as an amino-terminal fusion in *E. coli*, and as a native protein in eukaryotic cells. This may be accomplished in any of several ways:

Option 1: Your choices depend on your nucleic acid molecule of interest and the fragment that contains it, as well as the available Entry Vectors. For eukaryotic translation, you need consensus bases according to Kozak (*J. Biol. Chem.* 266:19867, 1991) near the initiating methionine (ATG) codon. All of the Entry Vectors offer this motif upstream of the XmnI site (blunt cutter). One option is to amplify your nucleic acid molecule of interest, with its ATG, by PCR, making the amino end blunt and the carboxy end containing the natural stop codon followed by one of the "right side" restriction sites (EcoRI, NotI, XhoI, EcoRV, or XbaI of the pENTR vectors).

If you know your nucleic acid molecule of interest does not have, for example, an XhoI site, you can make a PCR product that has this structure (SEQ ID NO:33):

```
                                Xho I
5' ATG nnn nnn --- nnn TAA ctc gag nnn nnn 3'
3' tac nnn nnn --- nnn att gag ctc nnn nnn 5'
```

After cutting with XhoI, the fragment is ready to clone:

```
5' ATG nnn nnn --- nnn TAA c      3'
3' tac nnn nnn --- nnn att gag ct 5'
```

(If You Follow this Example, Don't Forget to Put a Phosphate on the Amino Oligo.)

Option 2: This PCR product could be cloned into two Entry Vectors to give the desired products, between the XmnI and XhoI sites: pENTR1A (FIGS. 10A, 10B) or pENTR7 (FIGS. 16A, 16B). If you clone into pENTR1 A, amino fusions will have the minimal number of amino acids between the fusion domain and your nucleic acid molecule of interest, but the fusion cannot be removed with TEV protease. The converse is true of clones in pENTR7, i.e., an amino fusion can be cleaved with TEV protease, at the cost of more amino acids between the fusion and your nucleic acid molecule of interest.

Figure 26B:
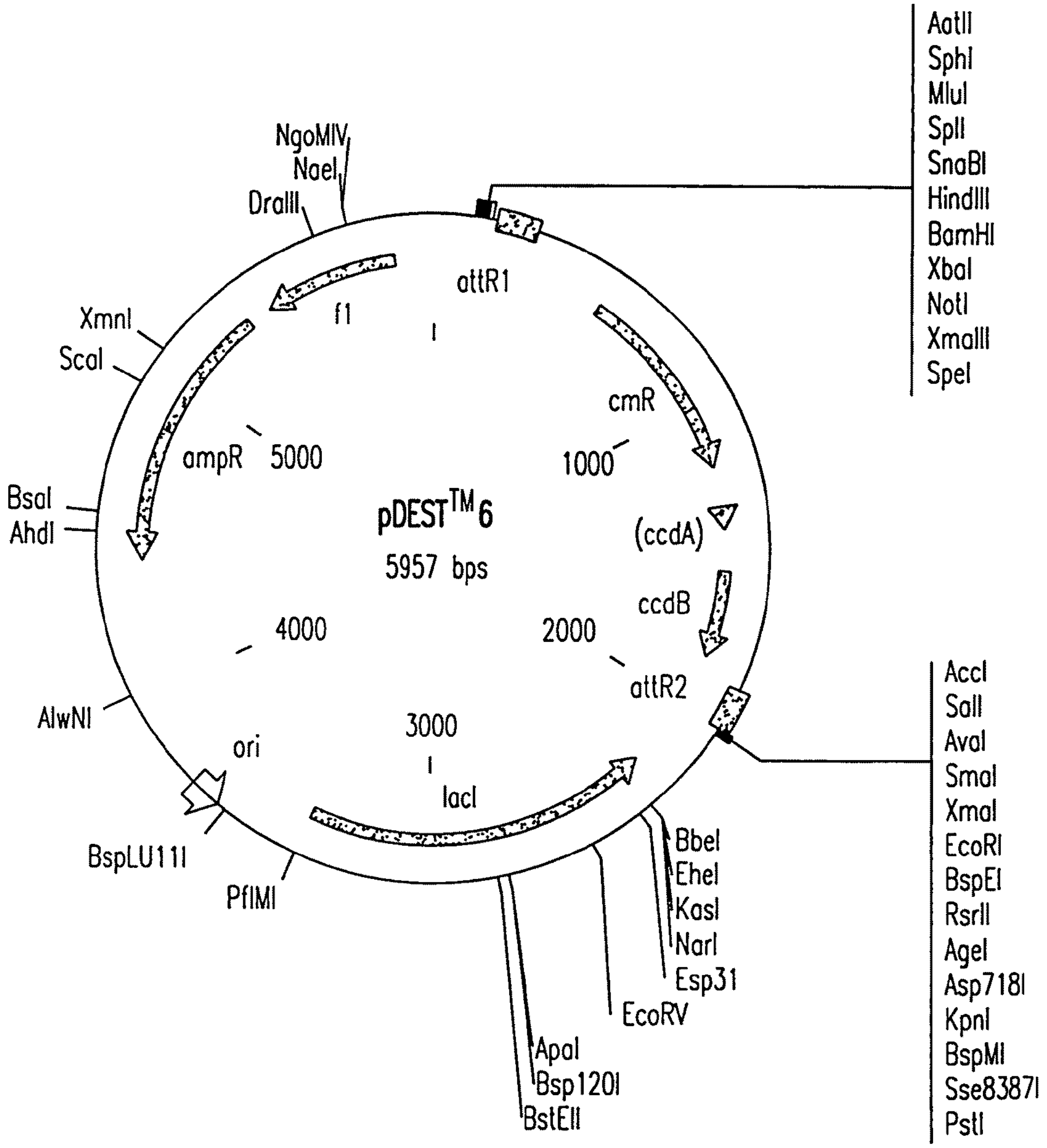
FIG. 26 is a schematic depiction of the attR1 and attR2 sites (FIG. 26A) (SEQ ID NO:233 and SEQ ID NO:234), the physical map (FIG. 26B), and the nucleotide sequence (FIGS. 26C-D) (SEQ ID NO:134), of Destination Vector pDEST6. This vector may also be referred to as pSPORT(−)-DEST6.
Figure 36A:
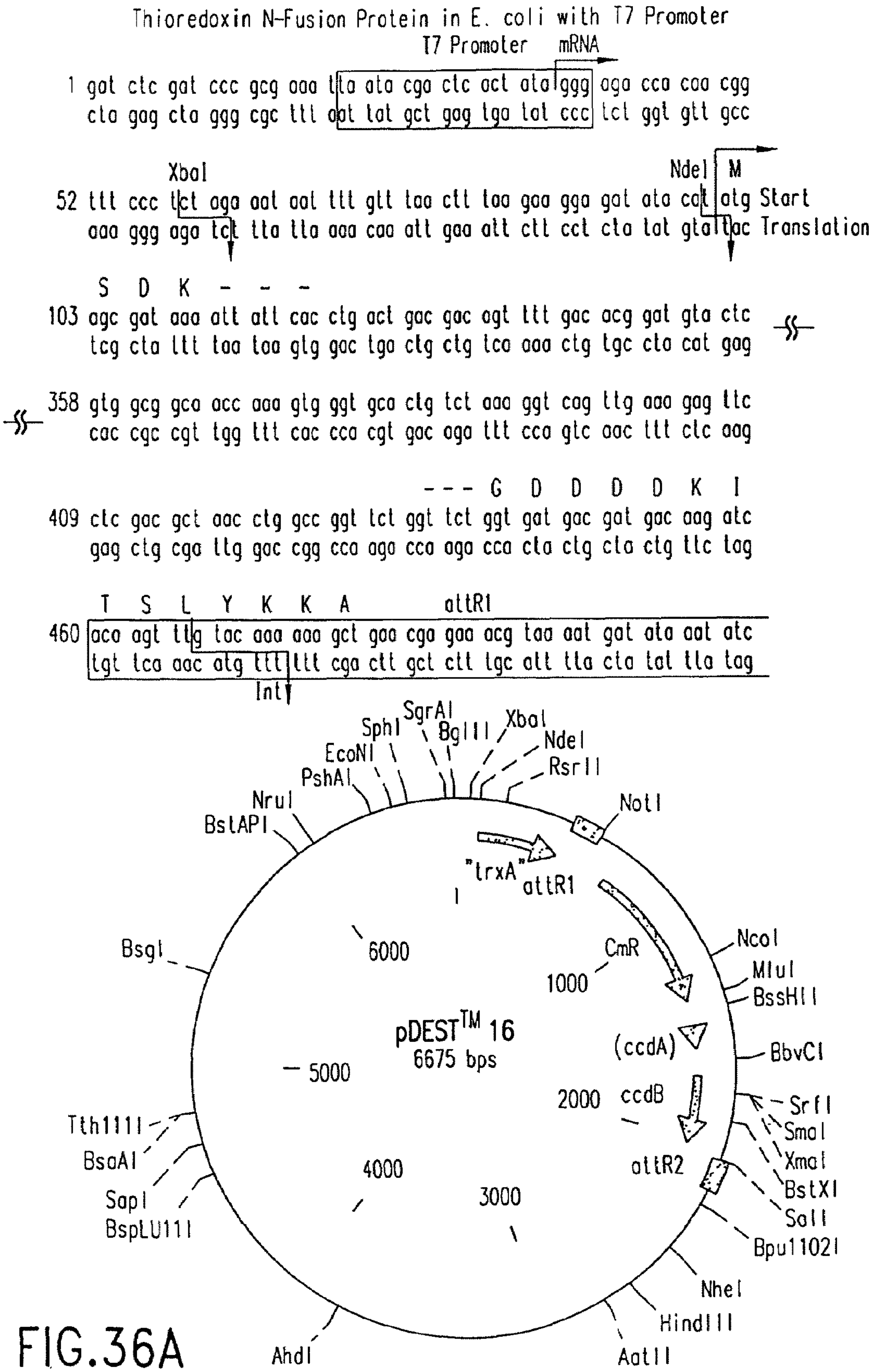
FIG. 36 is a schematic depiction of the attR1 site, the T7 promoter, and the N-terminal thioredoxin fusion sequence, and the physical map (FIG. 36A) (SEQ ID NO:248, SEQ ID NO:249, SEQ ID:250, and SEQ ID NO:251), and the nucleotide sequence (FIGS. 36B-D) (SEQ ID NO:144), of Destination Vector pDEST16. This vector may also be referred to as pT7 Trx-DEST16.

In this example, let us choose to clone our hypothetical nucleic acid molecule of interest into pENTR7, between the XmnI and XhoI sites. Once this is accomplished, several optional protocols using the Entry Clone pENTR7 may be followed:

Option 3: Since the nucleic acid molecule of interest has been amplified with PCR, it may be desirable to sequence it. To do this, transfer the nucleic acid molecule of interest from the Entry Vector into a vector that has priming sites for the standard sequencing primers. Such a vector is pDEST6 (FIGS. 26A, 26B). This Destination Vector places the nucleic acid molecule of interest in the opposite orientation to the lac promoter (which is leaky—see Example 3 above). If the gene product is toxic to *E. coli*, this Destination Vector will minimize its toxicity.

Option 4: While the sequencing is going on, you might wish to check the expression of the nucleic acid molecule of interest in, for example, CHO cells, by recombining the nucleic acid molecule of interest into a CMV promoter vector (pDEST7, FIG. 27; or pDEST12, FIG. 32), or into a baculovirus vector (pDEST8, FIG. 28; or pDEST10, FIG. 30) for expression in insect cells. Both of these vectors will transcribe the coding sequence of your nucleic acid molecule of interest, and translate it from the ATG of the PCR product using the Kozak bases upstream of the XmnI site.

Option 5: If you wish to purify protein, for example to make antibodies, you can clone the nucleic acid molecule of interest into a His6 fusion vector, pDEST2 (FIG. 22). Since the nucleic acid molecule of interest is cloned downstream of the TEV protease cleavage domain of pENTR7 (FIG. 16), the amino acid sequence of the protein produced will be:

```
                                            (SEQ ID NO:34)
                    [-- attB1 -]     TEV protease
NH2- MSYYHHHHHHGITSLYKKAGFENLYFQ↓GTM----COOH
```

The attB site and the restriction sites used to make the Destination and Entry Vectors are translated into the underlined 11 amino acids (GITSLYKKAGF) (SEQ ID NO:35). Cleavage with TEV protease (arrow) leaves two amino acids, GT, on the amino end of the gene product.

See FIG. 55 for an example of a nucleic acid molecule of interest, the chloramphenicol acetyl transferase (CAT) gene, cloned into pENTR7 (FIG. 16) as a blunt (amino)-XhoI (carboxy) fragment, then cloned by recombination into the His6 fusion vector pDEST2 (FIG. 22).

Option 6: If the His6 fusion protein is insoluble, you may go on and try a GST fusion. The appropriate Destination vector is pDEST3 (FIG. 23).

Option 7: If you need to make RNA probes and prefer SP6 RNA polymerase, you can make the top strand RNA with your nucleic acid molecule of interest cloned into pSPORT+ (pDEST5 (FIGS. 25A, 25B)), and the bottom strand RNA with the nucleic acid molecule of interest cloned into pSPORT(−) (pDEST6 (FIGS. 26A, 26B)). Opposing promoters for T7 RNA polymerase and SP6 RNA polymerase are also present in these clones.

Option 8: It is often worthwhile to clone your nucleic acid molecule of interest into a variety of Destination Vectors in the same experiment. For example, if the number of colonies varies widely when the various recombination reactions are transformed into *E. coli*, this may be an indication that the nucleic acid molecule of interest is toxic in some contexts. (This problem is more clearly evident when a positive control gene is used for each Destination Vector.) Specifically, if many more colonies are obtained when the nucleic acid molecule of interest is recombined into pDEST6 than in pDEST5, there is a good chance that leakiness of the lac promoter is causing some expression of the nucleic acid molecule of interest in pSPORT "+" (which is not harmful in pDEST6 because the nucleic acid molecule of interest is in the opposite orientation).

Example 16

Demonstration of a One-Tube Transfer of a PCR Product (or Expression Clone) to Expression Clone Via a Recombinational Cloning Reaction In the BxP recombination (Entry or Gateward) reaction described herein, a DNA segment flanked by attB1 and attB2 sites in a plasmid conferring ampicillin resistance was transferred by recombination into an attP plasmid conferring kanamycin resistance, which resulted in a product molecule wherein the DNA segment was flanked by attL sites (attL1 and attL2). This product plasmid comprises an "attL Entry Clone" molecule, because it can react with a "attR Destination Vector" molecule via the LxR (Destination) reaction, resulting in the transfer of the DNA segment to a new (ampicillin resistant) vector. In the previously described examples, it was necessary to transform the BxP reaction products into *E. coli*, select kanamycin resistant colonies, grow those colonies in liquid culture, and prepare miniprep DNA, before reacting this DNA with a Destination Vector in an LxR reaction.

The goal of the following experiment was to eliminate the transformation and miniprep DNA steps, by adding the BxP Reaction products directly to an LxR Reaction. This is especially appropriate when the DNA segment flanked by attB sites is a PCR product instead of a plasmid, because the PCR product cannot give ampicillin-resistant colonies upon transformation, whereas attB plasmids (in general) carry an ampicillin resistance gene. Thus use of a PCR product flanked by attB sites in a BxP Reaction allows one to select for the ampicillin resistance encoded by the desired attB product of a subsequent LxR Reaction.

Two reactions were prepared: Reaction A, negative control, no attB PCR product, (8 μl) contained 50 ng pEZC7102 (attP Donor plasmid, confers kanamycin resistance) and 2 μl BxP Clonase (22 ng/μl Int protein and 8 ng/μl IHF protein) in BxP buffer (25 mM Tris HCl, pH 7.8, 70 mM KCl, 5 mM spermidine, 0.5 mM EDTA, 250 μg/ml BSA). Reaction B (24 μl) contained 150 ng pEZC7102, 6 μl BxP Clonase, and 120 ng of the attB-tet-PCR product in the same buffer as reaction A. The attB-tet-PCR product comprised the tetracycline resistance gene of plasmid pBR322, amplified with two primers containing either attB1 or attB2 sites, and having 4 Gs at their 5' ends, as described earlier.

The two reactions were incubated at 25° C. for 30 minutes. Then aliquots of these reactions were added to new components that comprised LxR Reactions or appropriate controls for the LxR Reaction. Five new reactions were thus produced:

Reaction 1: 5 μl of reaction A was added to a 5 μl LxR Reaction containing 25 ng NcoI-cut pEZC8402 (the attR Destination Vector plasmid) in LxR buffer (37.5 mM Tris HCl, pH 7.7, 16.5 mM NaCl, 35 mM KCl, 5 mM spermidine, 375 μg/ml BSA), and 1 μl of GATEWAY™ LR Clonase™ Enzyme Mix (total volume of 10 μl).

Reaction 2: Same as reaction 1, except 5 μl of reaction B (positive) were added instead of reaction A (negative).

Reaction 3: Same as reaction 2, except that the amounts of Nco-cut pEZC8402 and GATEWAY™ LR Clonase™ Enzyme Mix were doubled, to 50 ng and 2 μl, respectively.

Reaction 4: Same as reaction 2, except that 25 ng of pEZ1104 (a positive control attL Entry Clone plasmid) were added in addition to the aliquot of reaction B.

Reaction 5: Positive control LxR Reaction, containing 25 ng NcoI-cut pEZC8402, 25 ng pEZ111104, 37.5 mM Tris HCl pH 7.7, 16.5 mM NaCl, 35 mM KCl, 5 mM spermidine, 375 µg/ml BSA and 1 µl GATEWAY™ LR Clonase™ Enzyme Mix in a total volume of 5 µl.

All five reactions were incubated at 25° C. for 30 minutes. Then, 1 µl aliquots of each of the above five reactions, plus 1 µl from the remaining volume of Reaction B, the standard BxP Reaction, were used to transform 50 µl competent DH5α E. coli. DNA and cells were incubated on ice for 15 min., heat shocked at 42° C. for 45 sec., and 450 µl SOC were added. Each tube was incubated with shaking at 37° C. for 60 min. Aliquots of 100 µl and 400 µl of each transformation were plated on LB plates containing either 50 µg/ml kanamycin or 100 µg/ml ampicillin (see Table 2). A transformation with 10 pg of pUC19 DNA (plated on LB-amp$_{100}$) served as a control on the transformation efficiency of the DH5α cells. Following incubation overnight at 37° C., the number of colonies on each plate was determined.

Results of these reactions are shown in Table 2.

TABLE 2*

| | Reaction No.: | | | | | |
|---|---|---|---|---|---|---|
| | 1 | 2 | 3 | 4 | 5 | 6 |
| | | | Number of Colonies | | | |
| Vol. plated: | Neg. Control B × P Reaction | 1X pEZC8402 and LR Clonase ™ | 2X pEZC8402 and LR Clonase ™ | L × R Reaction with Pos. Control DNA | L × R Reaction alone | B × P Reaction alone |
| 100 µl | 2 | 1 | 8 | 9 | ~1000 | ~1000 |
| 400 µl | 5 | 10 | 35 | 62 | >2000 | >2000 |
| Selection: | Kan | Amp | Amp | Amp | Amp | Kan |

*(Transformation with pUC 19 DNA yielded 1.4 × 10$^9$ CFU/µg DNA.)

34 of the 43 colonies obtained from Reaction 3 were picked into 2 ml Terrific Broth with 100 µg/ml ampicillin and these cultures were grown overnight, with shaking, at 37° C. 27 of the 34 cultures gave at least moderate growth, and of these 24 were used to prepare miniprep DNA, using the standard protocol. These 24 DNAs were initially analyzed as supercoiled (SC) DNA on a 1% agarose gel to identify those with inserts and to estimate the sizes of the inserts. Fifteen of the 24 samples displayed SC DNA of the size predicted (5553 bp) if tetx7102 had correctly recombined with pEZC8402 to yield tetx8402. One of these samples contained two plasmids, one of ~5500 bp and a one of ~3500 bp. The majority of the remaining clones were approximately 4100 bp in size.

Figure 57:
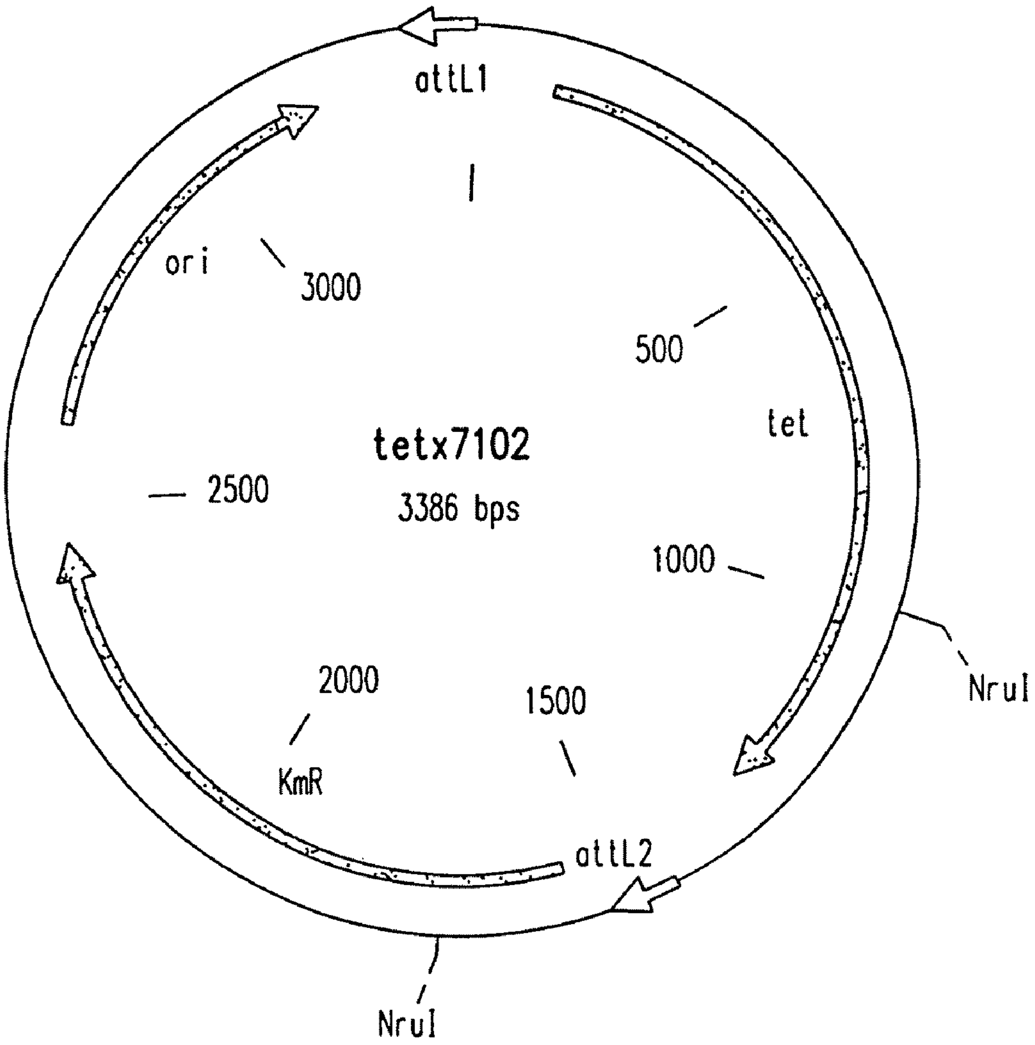
FIG. 57 is a physical map of the desired product of Reaction B of the one-tube BxP reaction described in Example 16, tetx7102.
Figure 58:
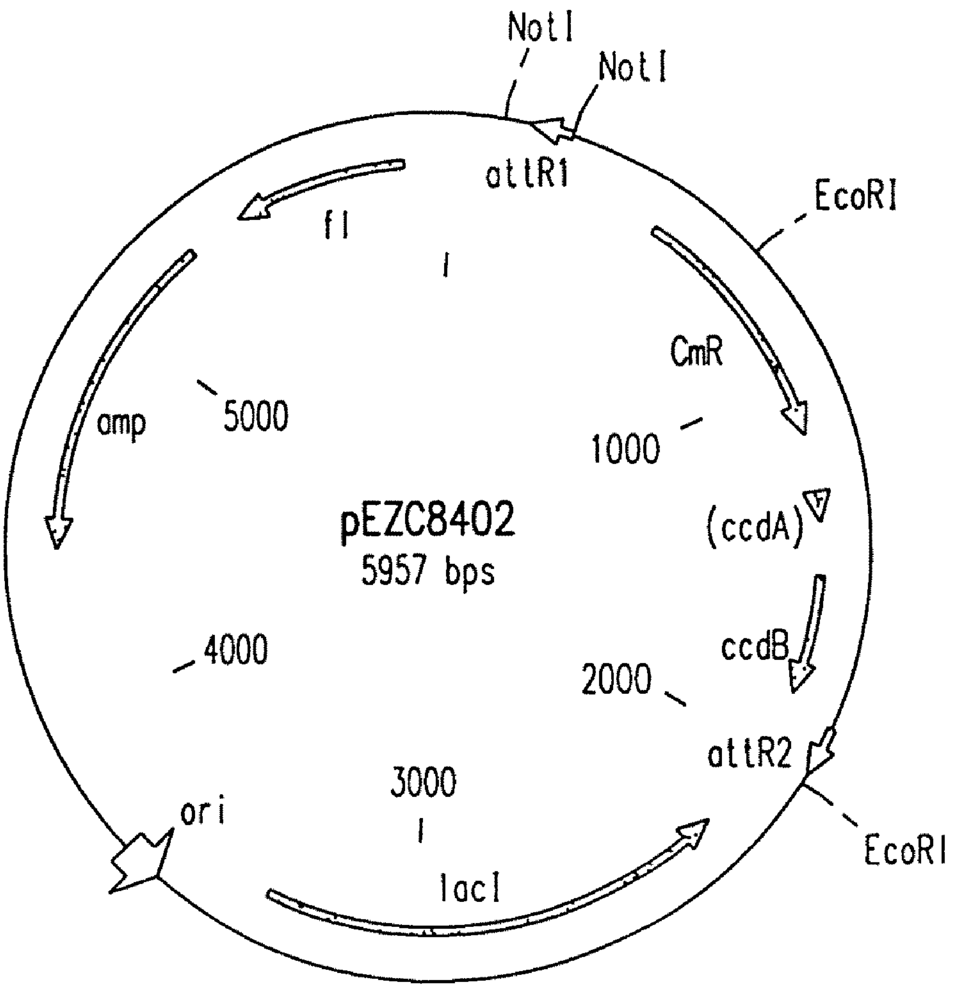
FIG. 58 is a physical map of the Destination Vector pEZC8402.

All 15 of the clones displaying SC DNA of predicted size (~5500 bp) were analyzed by two different double digests with restriction endonucleases to confirm the structure of the expected product: tetx8402. (See plasmid maps, FIGS. 57-59) In one set of digests, the DNAs were treated with Not I and Eco RI, which should cut the predicted product just outside both attB sites, releasing the tetr insert on a fragment of 1475 bp. In the second set of digests, the DNAs were digested with NotI and with NruI. NruI cleaves asymmetrically within the subcloned tet$^r$ insert, and together with NotI will release a fragment of 1019 bp.

Of the 15 clones analyzed by double restriction digestion, 14 revealed the predicted sizes of fragments for the expected product.

Figure 56:
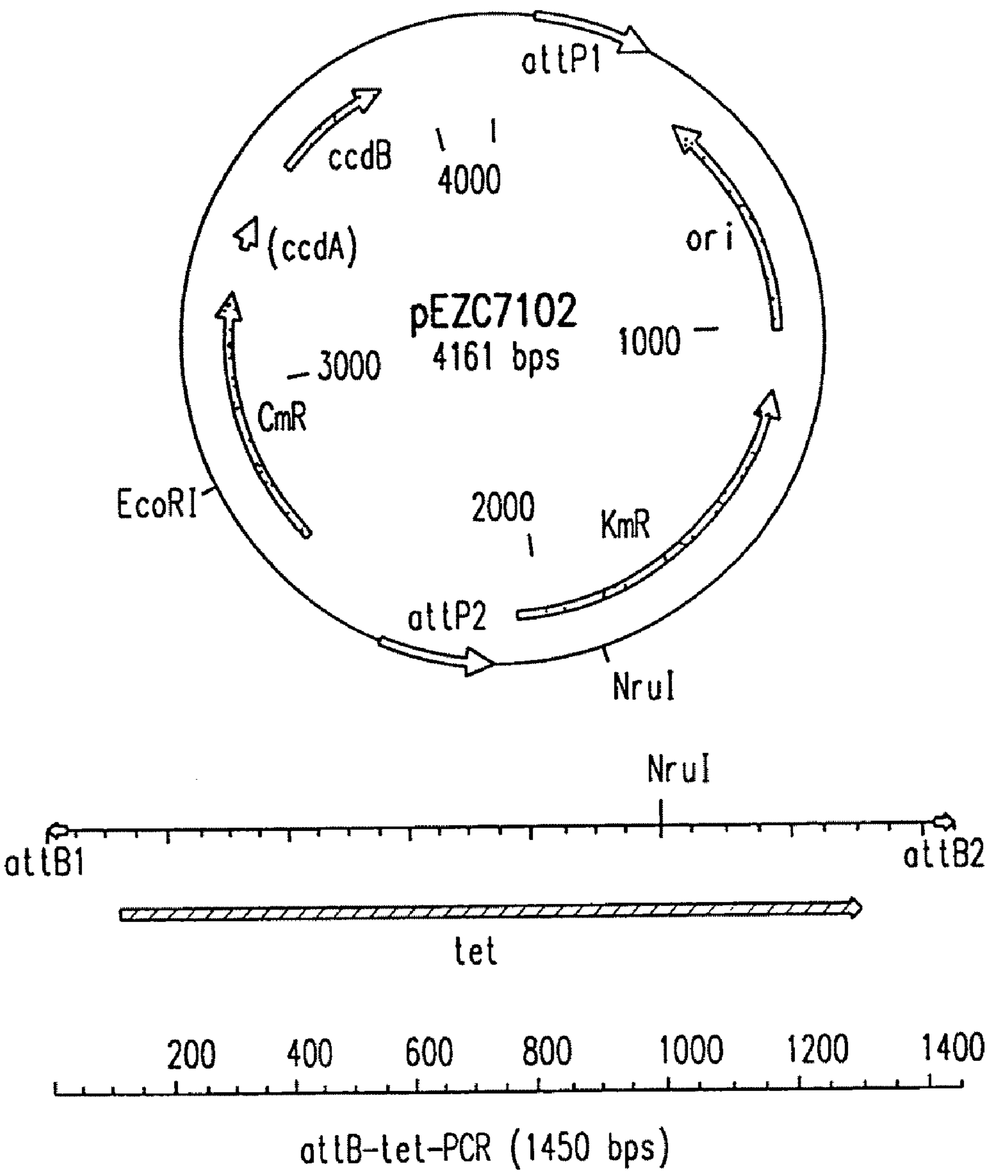
FIG. 56 depicts the DNA components of Reaction B of the one-tube BxP reaction described in Example 16, pEZC7102 and attB-tet-PCR.

Interpretation:

The DNA components of Reaction B, pEZC7102 and attB-tet-PCR, are shown in FIG. 56. The desired product of BxP Reaction B is tetx7102, depicted in FIG. 57. The LxR Reaction recombines the product of the BxP Reaction, tetx7102 (FIG. 57), with the Destination Vector, pEZC8402, shown in FIG. 58. The LxR Reaction with tetx7102 plus pEZC8402 is predicted to yield the desired product tetx8402, shown in FIG. 59.

Reaction 2, which combined the BxP Reaction and LxR Reaction, gave few colonies beyond those of the negative control Reaction. In contrast, Reaction 3, with twice the amount of pEZC8402 (FIG. 58) and LxR Clonase, yielded a larger number of colonies. These colonies were analyzed further, by restriction digestion, to confirm the presence of expected product. Reaction 4 included a known amount of attL Entry Clone plasmid in the combined BxP-plus-LxR reaction. But reaction 4 yielded only about 1% of the colonies obtained when the same DNA was used in a LxR reaction alone, Reaction 6. This result suggests that the LxR reaction may be inhibited by components of the BxP reaction.

Figure 59:
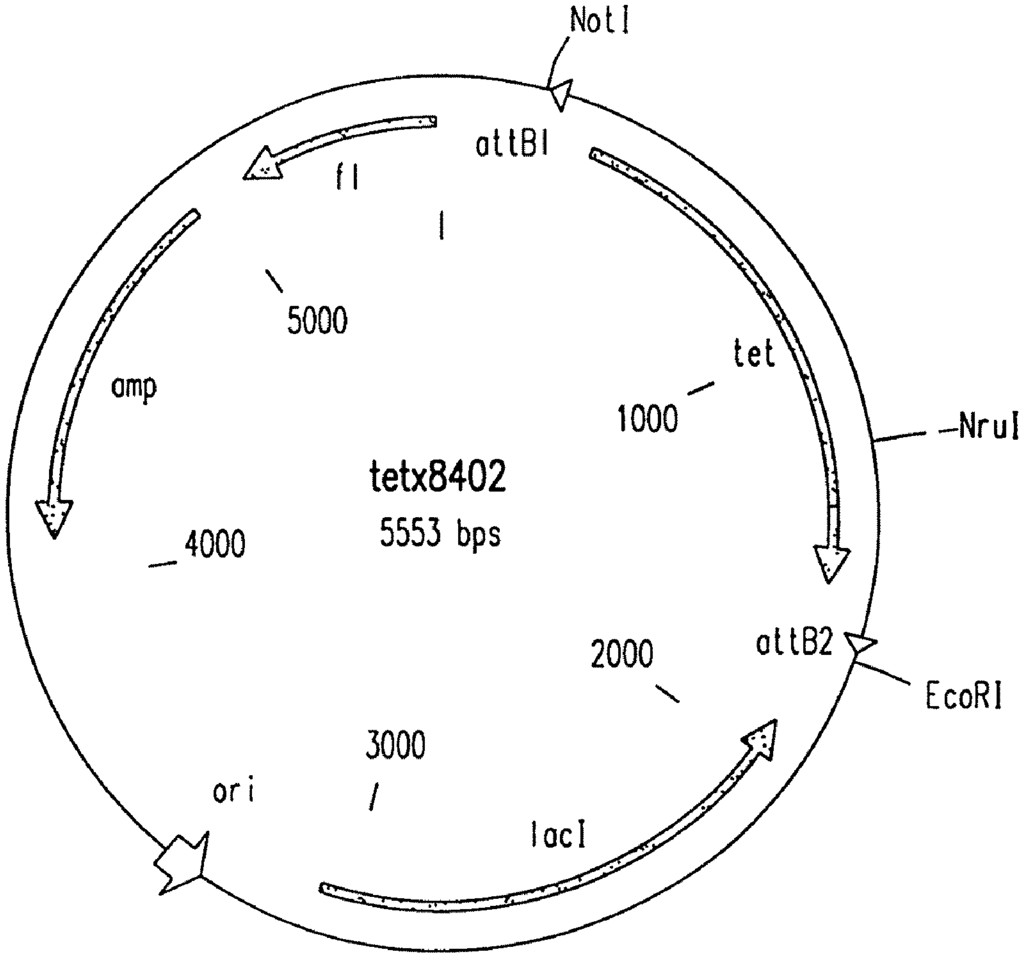
FIG. 59 is a physical map of the expected tetr subclone product, tetx8402, resulting from the LxR Reaction with tetx7102 (FIG. 57) plus pEZC8402 (FIG. 58).

Restriction endonuclease analysis of the products of Reaction 3 revealed that a sizeable proportion of the colonies (14 of the 34 analyzed) contained the desired tet$^r$ subclone, tetx8402 (FIG. 59).

The above results establish the feasibility of performing first a BxP recombination reaction followed by a LxR recombination reaction—in the same tube—simply by adding the appropriate buffer mix, recombination proteins, and DNAs to a completed BxP reaction. This method should prove useful as a faster method to convert attB-containing PCR products into different Expression Clones, eliminating the need to isolate first the intermediate attL-PCR insert subclones, before recombining these with Destination Vectors. This may prove especially valuable for automated applications of these reactions.

This same one-tube approach allows for the rapid transfer of nucleic acid molecules contained in attB plasmid clones into new functional vectors as well. As in the above examples, attL subclones generated in a BxP Reaction can be recombined directly with various Destination Vectors in a LxR reaction. The only additional requirement for using attB plasmids, instead of attB-containing PCR products, is that the Destination Vector(s) employed must contain a different selection marker from the one present on the attB plasmid itself and the attP vector.

Two alternative protocols for a one-tube reaction have also proven useful and somewhat more optimal than the conditions described above.

Alternative 1

Reaction buffer contained 50 mM Tris-HCl (pH 7.5), 50 mM NaCl, 0.25 mM EDTA, 2.5-mM spermidine, and 200 μg/ml BSA. After a 16 (or 3) hour incubation of the PCR product (100 ng)+attP Donor plasmid (100 ng)+GATEWAY™ BP Clonase™ Enzyme Mix+Destination Vector (100 ng), 2 μl of GATEWAY™ LR Clonase™ Enzyme Mix (per 10 μl reaction mix) was added and the mixture was incubated an additional 6 (or 2) hours at 25° C. Stop solution was then added as above and the mixture was incubated at 37° C. as above and transformed by electroporation with 1 μl directly into electrocompetent host cells. Results of this series of experiments demonstrated that longer incubation times (16 hours vs. 3 hours for the BP Reaction, 6 hours vs. 2 hours for the LR Reaction) resulted in about twice as many colonies being obtained as for the shorter incubation times. With two independent genes, 10/10 colonies having the correct cloning patterns were obtained.

Alternative 2

A standard BP Reaction under the reaction conditions described above for Alternative 1 was performed for 2 hours at 25° C. Following the BP Reaction, the following components were added to the reaction mixture in a total volume of 7 μl:

20 mM Tris-HCl, pH 7.5

100 mM NaCl

5 μg/ml Xis-His6

15% glycerol

~1000 ng of Destination Vector

The reaction mixture was then incubated for 2 hours at 25° C., and 2.5 μl of stop solution (containing 2 μg/ml proteinase K) was added and the mixture was incubated at 37° C. for an additional 10 minutes. Chemically competent host cells were then transformed with 2 μl of the reaction mixture, or electrocompetent host cells (e.g., EMax DH10B cells; Life Technologies, Inc.) were electroporated with 2 μl of the reaction mixture per 25-40 μl of cells. Following transformation, mixtures were diluted with SOC, incubated at 37° C., and plated as described above on media selecting for the selection markers on the Destination Vector and the Entry clone (B x P reaction product). Analogous results to those described for Alternative 1 were obtained with these reaction conditions—a higher level of colonies containing correctly recombined reaction products were observed.

Example 17

Demonstration of a One-Tube Transfer of a PCR Product (or Expression Clone) to Expression Clone Via a Recombinational Cloning Reaction Single-tube transfer of PCR product DNA or Expression Clones into Expression Clones by recombinational cloning has also been accomplished using a procedure modified from that described in Example 16. This procedure is as follows:

Perform a standard BP (Gateward) Reaction (see Examples 9 and 10) in 20 μl volume at 25° C. for 1 hour.

After the incubation is over, take a 10 μl aliquot from the 20 μl total volume and add 1 μl of Proteinase K (2 mg/ml) and incubate at 37° C. for 10 minutes. This first aliquot can be used for transformation and gel assay of BP reaction analysis. Plate BP reaction transformation on LB plates with Kanamycin (50 ug/ml).

Add the following reagents to the remaining 10 μl aliquot of the BP reaction:

1 μl of 0.75 M NaCl

2 μl of destination vector (150 ng/μl)

4 μl of LR Clonase™ (after thawing and brief mixing)

Mix all reagents well and incubate at 25° C. for 3 hours. Stop the reaction at the end of incubation with 1.7 μl of Proteinase K (2 mg/ml) and incubate at 37° C. for 10 minutes.

Transform 2 μl of the completed reaction into 100 μl of competent cells. Plate 100 μl and 400 μl on LB plates with Ampicilin (100 μg/ml).

Notes:

If your competent cells are less than $10^8$ CFU/μg, and you are concerned about getting enough colonies, you can improve the yield several fold by incubating the BP reaction for 6-20 hours. Electroporation also can yield better colony output than chemical transformation.

PCR products greater than about 5-6 kb show significantly lower cloning efficiency in the BP reaction. In this case, we recommend using longer incubation times for both BP and LR steps.

If you want to move your insert gene into several destination vectors simultaneously, then scale up the initial BP reaction volume so that you have a 10 μl aliquot for adding each destination vector.

Example 18

Optimization of GATEWAY™ Clonase™ Enzyme Compositions

The enzyme compositions containing Int and IHF (for BP Reactions) were optimized using a standard functional recombinational cloning reaction (a BP reaction) between attB-containing plasmids and attP-containing plasmids, according to the following protocol:

Materials and Methods:

Substrates:

AttP—supercoiled pDONR201

AttB—linear ~1 Kb [$^3$H]PCR product amplified from pEZC7501

Proteins:

IntH6—$His_6$-carboxy-tagged λ Integrase

IHF—Integration Host Factor

Clonase:

50 ng/μl IntH6 and 20 ng/μl IHF, admixed in 25 mM Tris-HCl (pH 7.5), 22 mM NaCl, 5 mM EDTA, 1 mg/ml BSA, 5 mM Spermidine, and 50% glycerol.

Reaction Mixture (total volume of 40 μl):

1000 ng AttP plasmid 600 ng AttB [$^3$H] PCR product

8 μl Clonase (400 ng IntH6, 160 ng IHF) in 25 mM Tris-HCl (pH 7.5), 22 mM NaCl, 5 mM EDTA, 1 mg/ml BSA, 5 mM Spermidine, 5 mM DTT.

Reaction mixture was incubated for 1 hour at 25° C., 4 µl of 2 µg/µl proteinase K was added and mixture was incubated for an additional 20 minutes at 37° C. Mixture was then extracted with an equal volume of Phenol/Chloroform/Isoamyl alcohol. The aqueous layer was then collected, and 0.1 volumes of 3 M sodium acetate and 2 volumes of cold 100% ethanol were added. Tubes were then spun in a microcentrifuge at maximum RPM for 10 minutes at room temperature. Ethanol was decanted, and pellets were rinsed with 70% ethanol and re-centrifuged as above. Ethanol was decanted, and pellets were allowed to air dry for 5-10 minutes and then dissolved in 20 µl of 33 mM Tris-Acetate (pH 7.8), 66 mM potassium acetate, 10 mM magnesium acetate, 1 mM DTT, and 1 mM ATP. 2 units of exonuclease V (e.g., Plasmid Safe; EpiCentre, Inc., Madison, Wis.) was then added, and the mixture was incubated at 37° C. for 30 minutes.

Samples were then TCA-washed by spotting 30 µl of reaction mixture onto a Whatman GF/C filter, washing filters once with 10% TCA+1% NaPPi for 10 minutes, three times with 5% TCA for 5 minutes each, and twice with ethanol for 5 minutes each. Filters were then dried under a heat lamp, placed into a scintillation vial, and counted on a β liquid scintillation counter (LSC).

The principle behind this assay is that, after exonuclease V digestion, only double-stranded circular DNA survives in an acid-insoluble form. All DNA substrates and products that have free ends are digested to an acid-soluble form and are not retained on the filters. Therefore, only the $^3$H-labeled attB linear DNA which ends up in circular form after both inter- and intramolecular integration is complete is resistant to digestion and is recovered as acid-insoluble product. Optimal enzyme and buffer formulations in the Clonase compositions therefore are those that give the highest levels of circularized $^3$H-labeled attB-containing sequences, as determined by highest cpm in the LSC. Although this assay was designed for optimization of GATEWAY™ BP Clonase™ Enzyme Mix compositions (Int+IHF), the same type of assay may be performed to optimize GATEWAY™ LR Clonase™ Enzyme Mix compositions (Int+IHF+Xis), except that the reaction mixtures would comprise 1000 ng of AttR (instead of AttP) and 600 ng of AttL (instead of AttB), and 40 ng of $His_6$-carboxy-tagged Xis (Xis H6) in addition to the IntH6 and IHF.

Example 19

Testing Functionality of Entry and Destination Vectors

As part of assessment of the functionality of particular vectors of the invention, it is important to functionally test the ability of the vectors to recombine. This assessment can be carried out by performing a recombinational cloning reaction (as schematized in FIGS. 2, 4, and 5A and 5B, and as described herein and in commonly owned U.S. application Ser. Nos. 08/486,139, filed Jun. 7, 1995, 08/663,002, filed Jun. 7, 1996 (now U.S. Pat. No. 5,888,732), 09/005,476, filed Jan. 12, 1998, and 09/177,387, filed Oct. 23, 1998, the disclosures of all of which are incorporated by reference herein in their entireties), by transforming *E. coli* and scoring colony forming units. However, an alternative assay may also be performed to allow faster, more simple assessment of the functionality of a given Entry or Destination Vector by agarose gel electrophoresis. The following is a description of such an in vitro assay.

Figure 84:
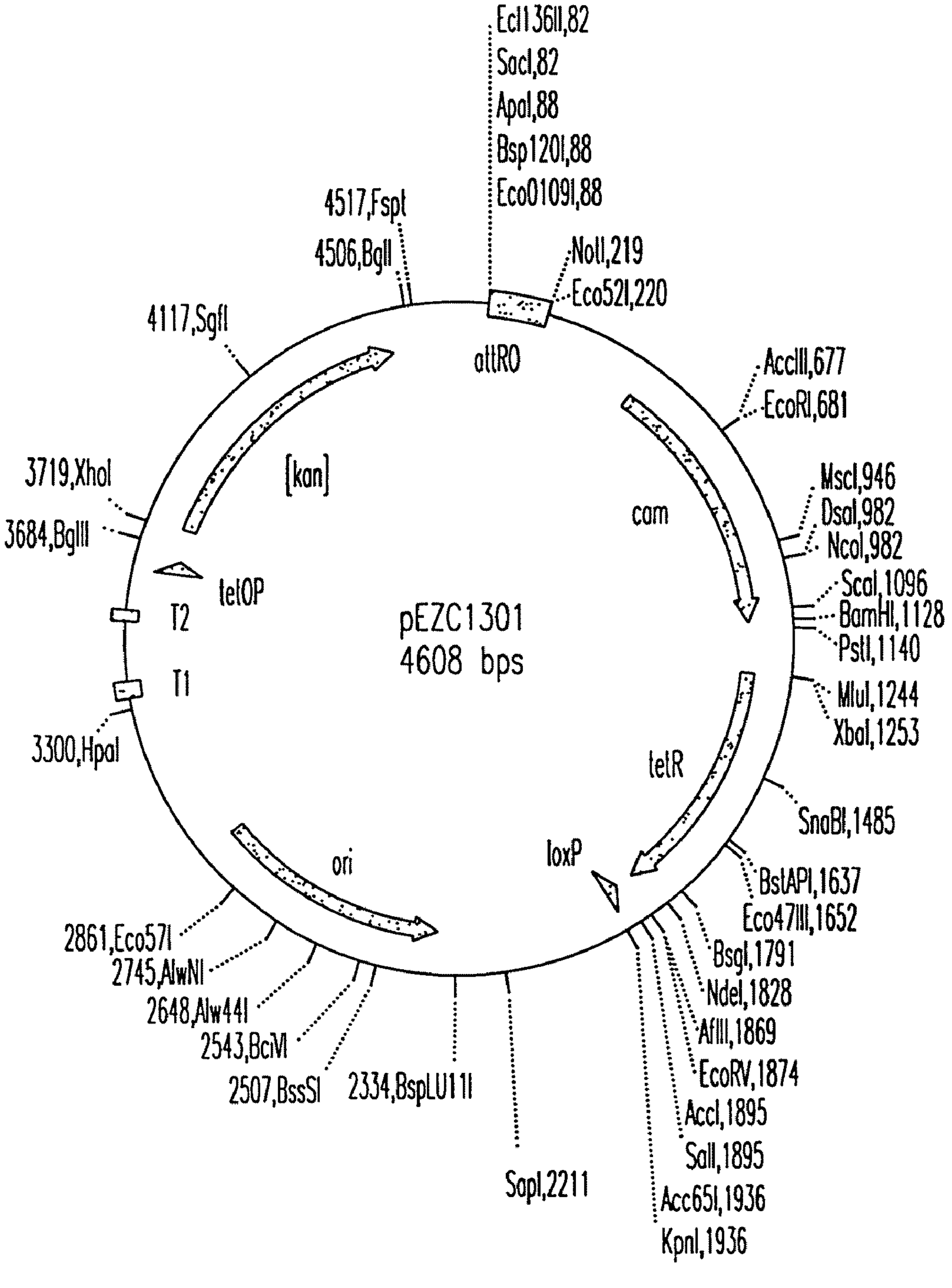
FIG. 84 is a physical map of plasmid pEZC1301.
Figure 85:
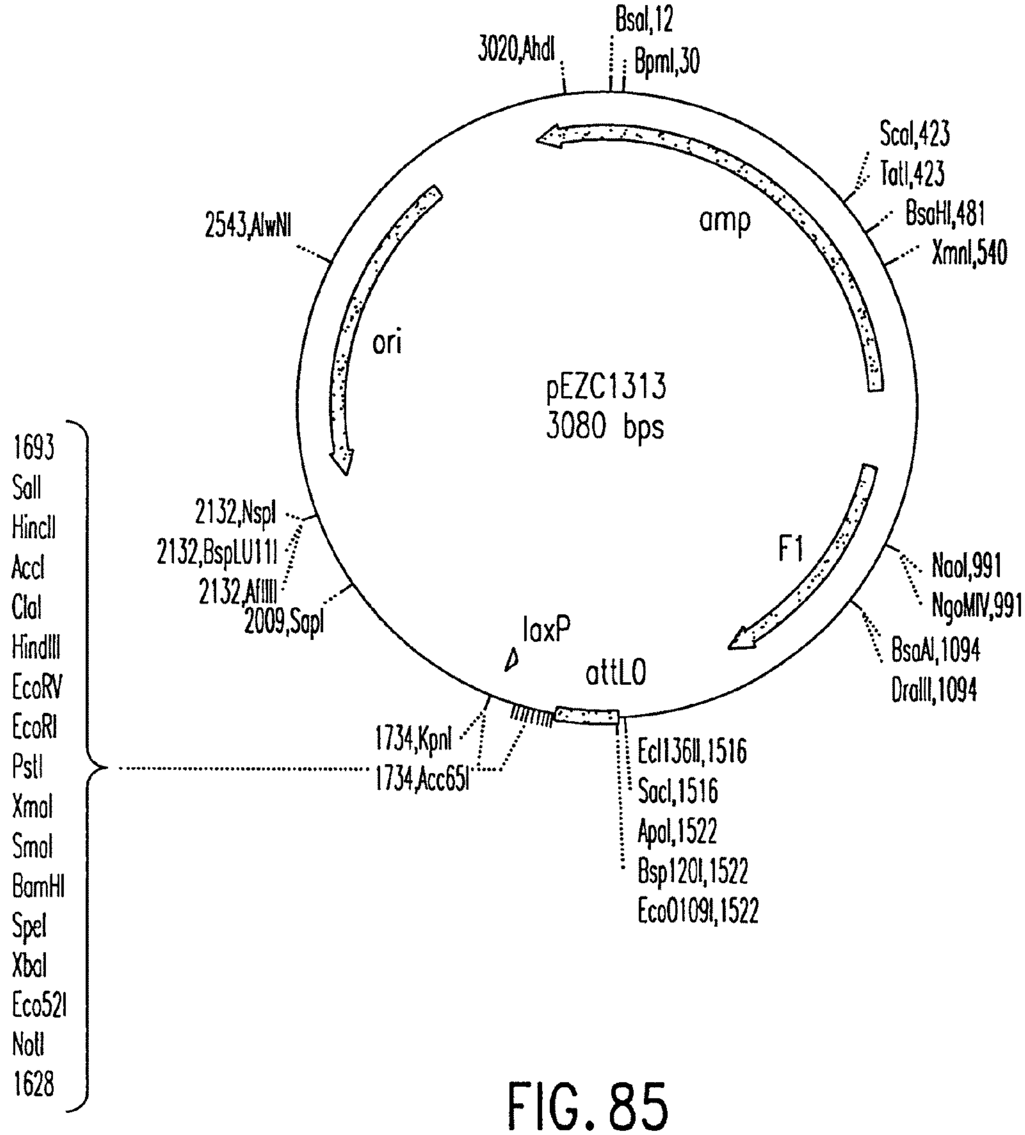
FIG. 85 is a physical map of plasmid pEZC1313.
Figure 86:
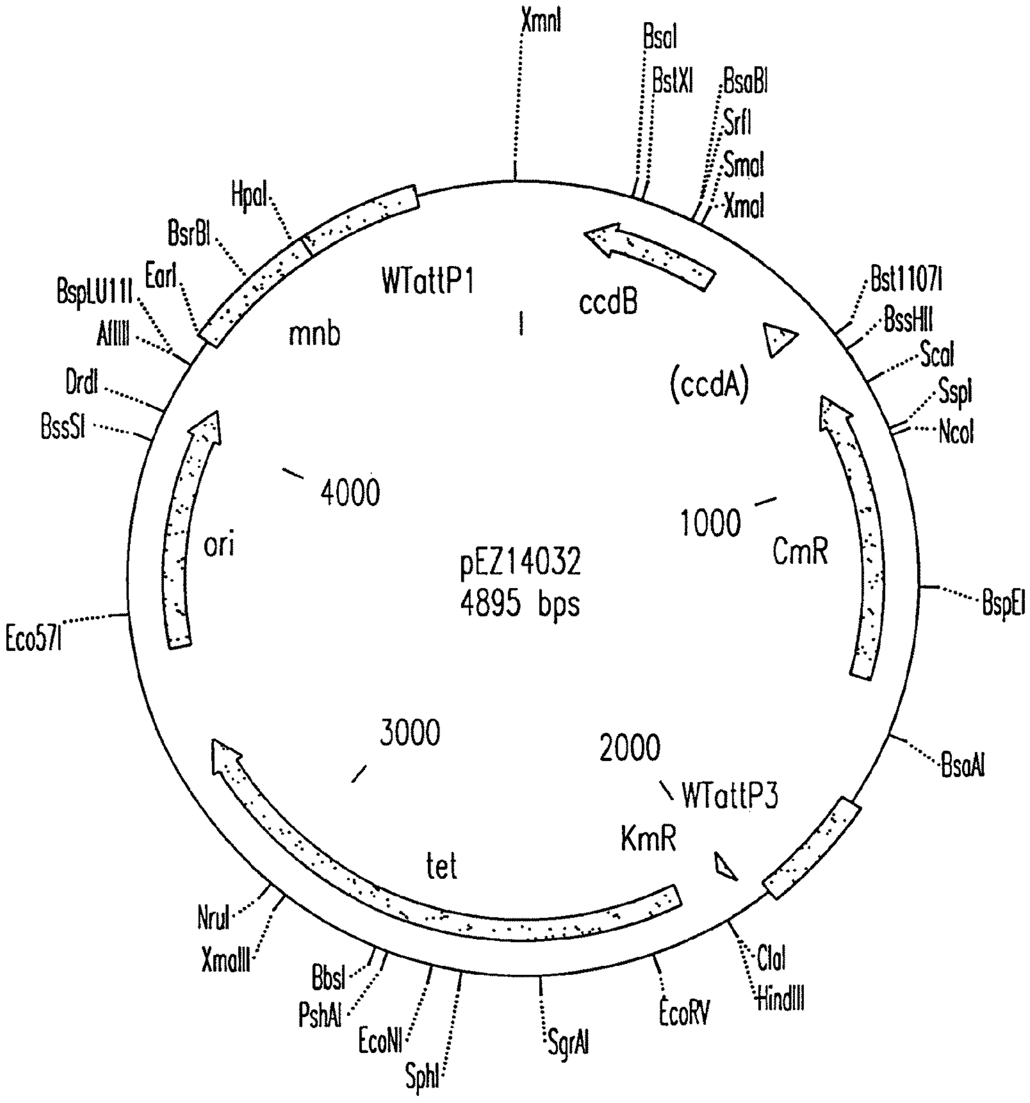
FIG. 86 is a physical map of plasmid pEZ14032.

Materials and Methods:

Plasmid templates pEZC1301 (FIG. 84) and pEZC1313 (FIG. 85), each containing a single wild type att site, were used for the generation of PCR products containing attL or attR sites, respectively. Plasmid templates were linearized with AlwNI, phenol extracted, ethanol precipitated and dissolved in TE to a concentration of 1 ng/µl.

PCR primers (capital letters represent base changes from wildtype):

attL1 gggg agcct gcttttttGtacAaa gttggcatta taaaaaagca ttgc (SEQ ID NO:36):

attL2 gggg agcct gctttCttGtacAaa gttggcatta taaaaaagca ttgc (SEQ ID NO:37);

attL right tgttgccggg aagctagagt aa (SEQ ID NO:38):

attR1 gggg Acaag ttTgtaCaaaaaagc tgaacgaga aacgtaaaat (SEQ ID NO:39);

attR2 gggg Acaag ttTgtaCaaGaaagc tgaacgaga aacgtaaaat (SEQ ID NO:40):

attR right ca gacggcatga tgaacctgaa (SEQ ID NO:41)

PCR primers were dissolved in TE to a concentration of 500 pmol/µl. Primer mixes were prepared, consisting of attL1+attLright primers, attL2+attLright primers, attR1+attRright primers, and attR2+attRright primers, each mix containing 20 pmol/µl of each primer.

PCR reactions:

1 µl plasmid template (1 ng)

1 µl primer pairs (20 pmoles of each)

3 µl of $H_20$

45 µl of Platinum PCR SuperMix® (Life Technologies, Inc.)

Cycling conditions (performed in MJ thermocycler):

95° C./2 minutes

94° C./30 seconds 25 cycles of 58° C./30 seconds and 72° C./1.5 minutes

72° C./5 minutes

5° C./hold

The resulting attL PCR product was 1.5 kb, and the resulting attR PCR product was 1.0 kb.

PCR reactions were PEG/$MgCl_2$ precipitated by adding 150 µl $H_2O$ and 100 µl of 3×PEG/$MgCl_2$ solution followed by centrifugation. The PCR products were dissolved in 50 µl of TE. Quantification of the PCR product was performed by gel electrophoresis of 1 µl and was estimated to be 50-100 ng/µl.

Recombination reactions of PCR products containing attL or attR sites with GATEWAY™ plasmids was performed as follows:

8 µl of $H_2O$

2 µl of attL or attR PCR product (100-200 ng)

2 µl of GATEWAY™ plasmid (100 ng)

4 µl of 5× Destination buffer

4 µl of GATEWAY™ LR Clonase™ Enzyme Mix

20 µl total volume (the reactions can be scaled down to a 5 µl total volume by adjusting the volumes of the components to about ¼ of those shown above, while keeping the stoichiometries the same).

Clonase reactions were incubated at 25° C. for 2 hours. 2 µl of proteinase K (2 mg/ml) was added to stop the reaction. 10 µl was then run on a 1% agarose gel. Positive control reactions were performed by reacting attL1 PCR product (1.0 kb) with attR1 PCR product (1.5 kb) and by similarly reacting attL2 PCR product with attR2PCR product to observe the formation of a larger (2.5 kb) recombination product. Negative controls were similarly performed by reacting attL1 PCR product with attR2PCR product and vice versa or reactions of attL PCR product with an attL plasmid, etc.

In alternative assays, to test attB Entry vectors, plasmids containing single attP sites were used. Plasmids containing single att sites could also be used as recombination substrates in general to test all Entry and Destination vectors (i.e., those containing attL, attR, attB and attP sites). This would eliminate the need to do PCR reactions.

Figure 2:
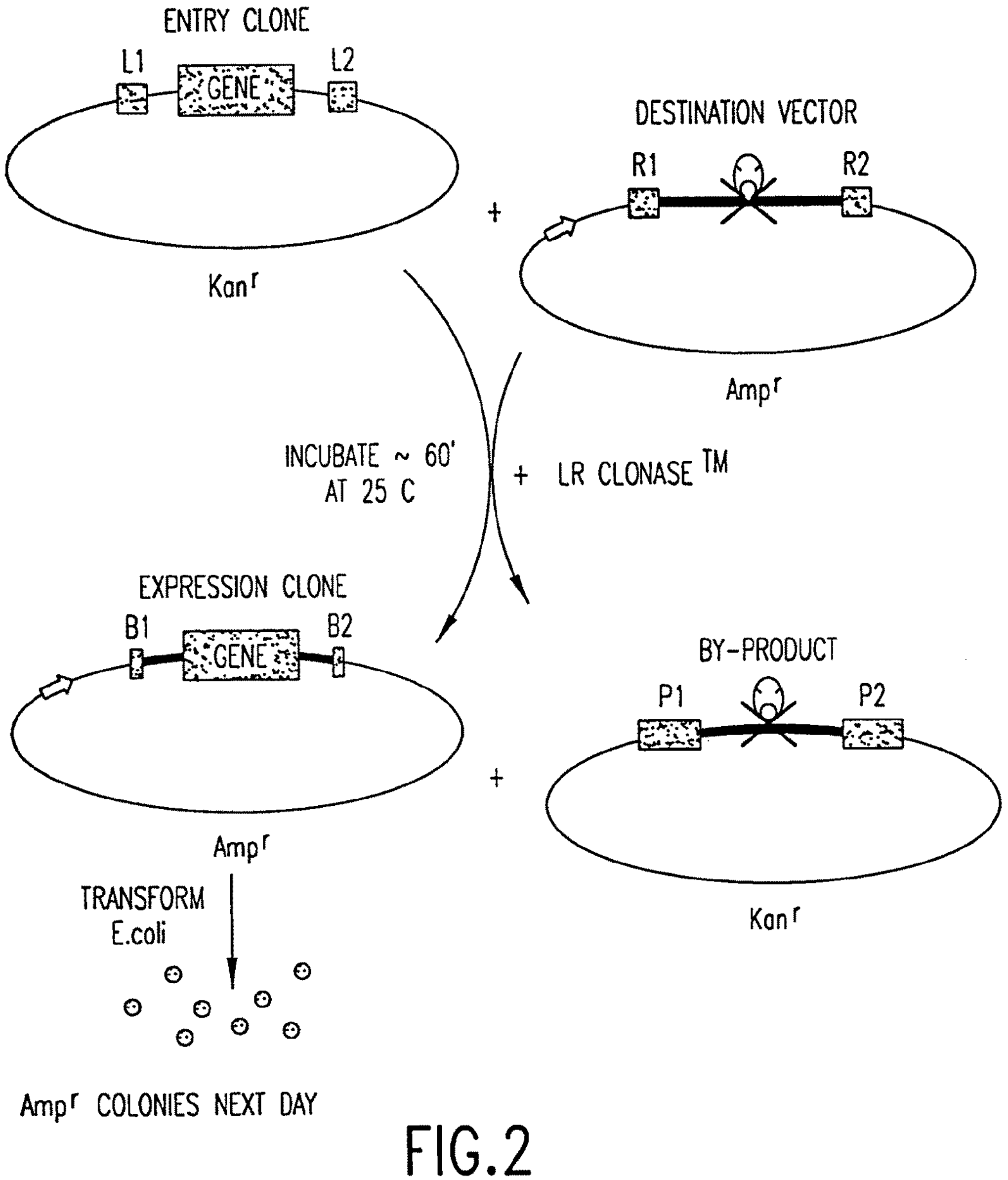
FIG. 2 is a more detailed depiction of the recombinational cloning system of the invention, referred to herein as the "GATEWAY™ Cloning System." This figure depicts the production of Expression Clones via a "Destination Reaction," which may also be referred to herein as an "LR Reaction." A $kan^r$ vector (referred to herein as an "Entry clone") containing a DNA molecule of interest (e.g., a gene) localized between an attL1 site and an attL2 site is reacted with an amp' vector (referred to herein as a "Destination Vector") containing a toxic or "death" gene localized between an attR1 site and an attR2 site, in the presence of GATEWAY™ LR Clonase™ Enzyme Mix (a mixture of Int, IHF and Xis). After incubation at 25° C. for about 60 minutes, the reaction yields an $amp^r$ Expression Clone containing the DNA molecule of interest localized between an attB1 site and an attB2 site, and a $kan^r$ byproduct molecule, as well as intermediates. The reaction mixture may then be transformed into host cells (e.g., *E. coli*) and clones containing the nucleic acid molecule of interest may be selected by plating the cells onto ampicillin-containing media and picking $amp^r$ colonies.
Figure 4:
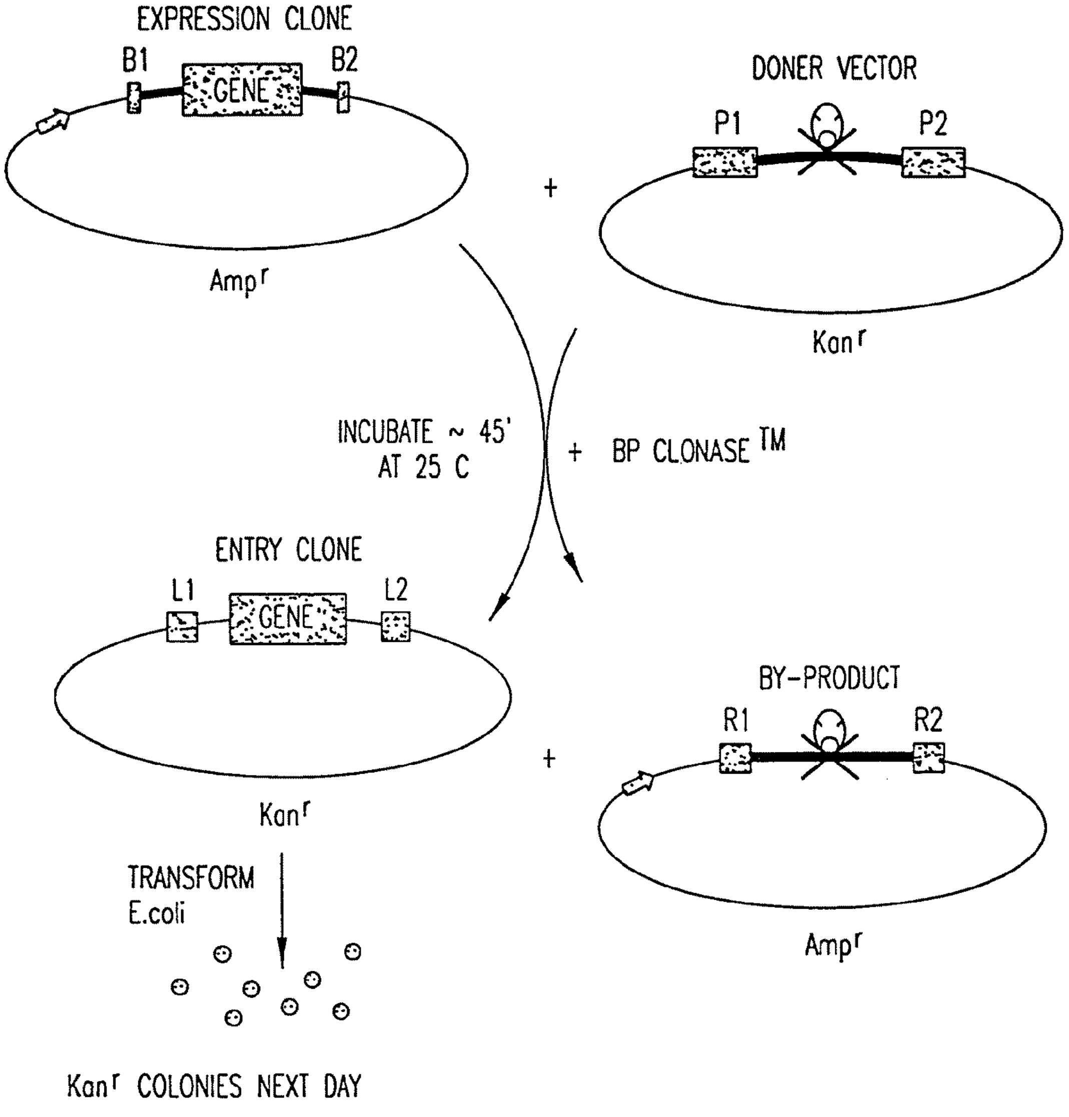
FIG. 4 is a detailed depiction of the production of Entry Clones via a "BP reaction," also referred to herein as an "Entry Reaction" or a "Gateward Reaction." In the example shown in this figure, an $amp^r$ expression vector containing a DNA molecule of interest (e.g., a gene) localized between an attB1 site and an attB2 site is reacted with a $kan^r$ Donor vector (e.g., an attP vector; here, GATEWAY™ pDONR201 (see FIGS. 49A-C)) containing a toxic or "death" gene localized between an attP1 site and an attP2 site, in the presence of GATEWAY™ BP Clonase™ Enzyme Mix (a mixture of Int and IHF). After incubation at 25° C. for about 60 minutes, the reaction yields a $kan^r$ Entry clone containing the DNA molecule of interest localized between an attL1 site and an attL2 site, and an $amp^r$ by-product molecule. The Entry clone may then be transformed into host cells (e.g., *E. coli*) and clones containing the Entry clone (and therefore the nucleic acid molecule of interest) may be selected by plating the cells onto kanamycin-containing media and picking $kan^r$ colonies. Although this figure shows an example of use of a $kan^r$ Donor vector, it is also possible to use Donor vectors containing other selection markers, such as the gentamycin resistance or tetracycline resistance markers, as discussed herein.

Results:

Destination and Entry plasmids when reacted with appropriate att-containing PCR products formed linear recombinant molecules that could be easily visualized on an agarose gel when compared to control reactions containing no attL or attR PCR product. Thus, the functionality of Destination and Entry vectors constructed according to the invention may be determined either by carrying out the Destination or Entry recombination reactions as depicted in FIGS. 2, 4, and 5A and SB, or more rapidly by carrying out the linearization assay described in this Example.

Example 20

PCR Cloning Using Universal Adapter-Primers

As described herein, the cloning of PCR products using the GATEWAY™ PCR Cloning System (Life Technologies, Inc.; Rockville, Md.) requires the addition of attB sites (attB1 and attB2) to the ends of gene-specific primers used in the PCR reaction. The protocols described in the preceding Examples suggest that the user add 29 bp (25 bp containing the attB site plus four G residues) to the gene-specific primer. It would be advantageous to high volume users of the GATEWAY™ PCR Cloning System to generate attB-containing PCR product using universal attB adapter-primers in combination with shorter gene-specific primers containing a specified overlap to the adapters. The following experiments demonstrate the utility of this strategy using universal attB adapter-primers and gene-specific primers containing overlaps of various lengths from 6 bp to 18 bp. The results demonstrate that gene-specific primers with overlaps of 10 bp to 18 bp can be used successfully in PCR amplifications with universal attB adapter-primers to generate full-length PCR products. These PCR products can then be successfully cloned with high fidelity in a specified orientation using the GATEWAY™ PCR Cloning System.

Methods and Results:

To demonstrate that universal attB adapter-primers can be used with gene-specific primers containing partial attB sites in PCR reactions to generate full-length PCR product, a small 256 bp region of the human hemoglobin cDNA was chosen as a target so that intermediate sized products could be distinguished from full-length products by agarose gel electrophoresis.

The following oligonucleotides were used:

```
B1-Hgb:        GGGG ACA AGT TTG TAC AAA AAA GCA GGC T-5'-Hgb*   (SEQ ID NO:42);
B2-Hgb:        GGGG ACC ACT TTG TAC AAG AAA GCT GGG T-3'-Hgb**  (SEQ ID NO:43);
18B1-Hgb:                     TG TAC AAA AAA GCA GGC T-5'-Hgb   (SEQ ID NO:44);
18B2-Hgb:                     TG TAC AAG AAA GCT GGG T-3'-Hgb   (SEQ ID NO:45);
15B1-Hgb:                        AC AAA AAA GCA GGC T-5'-Hgb    (SEQ ID NO:46);
15B2-Hgb:                        AC AAG AAA GCT GGG T-3'-Hgb    (SEQ ID NO:47);
12B1-Hgb:                           AA AAA GCA GGC T-5'-Hgb     (SEQ ID NO:48);
12B2-Hgb:                           AG AAA GCT GGG T-3'-Hgb     (SEQ ID NO:49);
11B1-Hgb:                            A AAA GCA GGC T-5'-Hgb     (SEQ ID NO:50);
11B2-Hgb:                            G AAA GCT GGG T-3'-Hgb     (SEQ ID NO:51);
10B1-Hgb:                              AAA GCA GGC T-5'-Hgb     (SEQ ID NO:52);
10B2-Hgb:                              AAA GCT GGG T-3'-Hgb     (SEQ ID NO:53);
9B1-Hgb:                                AA GCA GGC T-5'-Hgb
9B2-Hgb:                                AA GCT GGG T-3'-Hgb
8B1-Hgb:                                 A GCA GGC T-5'-Hgb
8B2-Hgb:                                 A GCT GGG T-3'-Hgb
7B1-Hgb:                                   GCA GGC T-5'-Hgb
7B2-Hgb:                                   GCT GGG T-3'-Hgb
6B1-Hgb:                                    CA GGC T-5'-Hgb
6B2-Hgb:                                    CT GGG T-3'-Hgb
attB1 adapter: GGGG ACA AGT TTG TAC AAA AAA GCA GGC T           (SEQ ID NO:54);
attB2 adapter: GGGG ACC ACT TTG TAC AAG AAA GCT GGG T           (SEQ ID NO:55);
```

-continued

```
*-5'-Hgb = GTC ACT AGC CTG TGG AGC AAG A (SEQ ID NO:56);
**-3'-Hgb = AGG ATG GCA GAG GGA GAC GAC A (SEQ ID NO:57)
```

The aim of these experiments was to develop a simple and efficient universal adapter PCR method to generate attB containing PCR products suitable for use in the GATEWAY™ PCR Cloning System. The reaction mixtures and thermocycling conditions should be simple and efficient so that the universal adapter PCR method could be routinely applicable to any PCR product cloning application.

PCR reaction conditions were initially found that could successfully amplify predominately full-length PCR product using gene-specific primers containing 18 bp and 15 bp overlap with universal attB primers. These conditions are outlined below:

10 pmoles of gene-specific primers
10 pmoles of universal attB adapter-primers
1 ng of plasmid containing the human hemoglobin cDNA.
100 ng of human leukocyte cDNA library DNA.
5 μl of 10× PLATINUM Taq HiFi® reaction buffer (Life Technologies, Inc.)
2 μl of 50 mM $MgSO_4$
1 μl of 10 mM dNTPs
0.2 μl of PLATINUM Taq HiFi® (1.0 unit)
$H_2O$ to 50 μl total reaction volume Cycling Conditions:

95° C./5 min
25× | 94° C./15 sec
    | 50° C./30 sec
    | 68° C./1 min
68° C./5 min
5° C./hold To assess the efficiency of the method, 2 μl (1/25) of the 50 μl PCR reaction was electrophoresed in a 3% Agarose-1000 gel. With overlaps of 12 bp or less, smaller intermediate products containing one or no universal attB adapter predominated the reactions. Further optimization of PCR reaction conditions was obtained by titrating the amounts of gene-specific primers and universal attB adapter-primers. The PCR reactions were set up as outlined above except that the amounts of primers added were:

0, 1, 3 or 10 pmoles of gene-specific primers 0, 10, 30 or 100 pmoles of adapter-primers Cycling Conditions:

95° C./3 min
25× | 94° C./15 sec
    | 50° C./45 sec
    | 68° C./1 min
68° C./5 min
5° C./hold The use of limiting amounts of gene-specific primers (3 pmoles) and excess adapter-primers (30 pmoles) reduced the amounts of smaller intermediate products. Using these reaction conditions the overlap necessary to obtain predominately full-length PCR product was reduced to 12 bp. The amounts of gene-specific and adapter-primers was further optimized in the following PCR reactions:

0, 1, 2 or 3 pmoles of gene-specific primers 0, 30, 40 or 50 pmoles of adapter-primers Cycling Conditions:

95° C./3 min
25× | 94° C./15 sec
    | 48° C./1 min
    | 68° C./1 min
68° C./5 min
5° C./hold The use of 2 pmoles of gene-specific primers and 40 pmoles of adapter-primers further reduced the amounts of intermediate products and generated predominately full-length PCR products with gene-specific primers containing an 11 bp overlap. The success of the PCR reactions can be assessed in any PCR application by performing a no adapter control. The use of limiting amounts of gene-specific primers should give faint or barely visible bands when 1/25 to 1/10 of the PCR reaction is electrophoresed on a standard agarose gel. Addition of the universal attB adapter-primers should generate a robust PCR reaction with a much higher overall yield of product.

PCR products from reactions using the 18 bp, 15 bp, 12 bp, 11 bp and 10 bp overlap gene-specific primers were purified using the CONCERT® Rapid PCR Purification System (PCR products greater than 500 bp can be PEG precipitated). The purified PCR products were subsequently cloned into an attP containing plasmid vector using the GATEWAY™ PCR Cloning System (Life Technologies, Inc.; Rockville, Md.) and transformed into *E. coli*. Colonies were selected and counted on the appropriate antibiotic media and screened by PCR for correct inserts and orientation.

Raw PCR products (unpurified) from the attB adapter PCR of a plasmid clone of part of the human beta-globin (Hgb) gene were also used in GATEWAY™ PCR Cloning System reactions. PCR products generated with the full attB B1/B2-Hgb, the 12B1/B2, 11B1/B2 and 10B1/B2 attB overlap Hgb primers were successfully cloned into the GATEWAY™ pENTR21 attP vector (FIG. 49). 24 colonies from each (24×4=96 total) were tested and each was verified by PCR to contain correct inserts. The cloning efficiency expressed as cfu/ml is shown below:

| Primer Used | cfu/ml |
|---|---|
| Hgb full attB | 8,700 |
| Hgb 12 bp overlap | 21,000 |
| Hgb 11 bp overlap | 20,500 |

-continued

| Primer Used | cfu/ml |
|---|---|
| Hgb 10 bp overlap | 13,500 |
| GFP control | 1,300 |

Interestingly, the overlap PCR products cloned with higher efficiency than did the full attB PCR product. Presumably, and as verified by visualization on agarose gel, the adapter PCR products were slightly cleaner than was the full attB PCR product. The differences in colony output may also reflect the proportion of PCR product molecules with intact attB sites.

Using the attB adapter PCR method, PCR primers with 12 bp attB overlaps were used to amplify cDNAs of different sizes (ranging from 1 to 4 kb) from a leukocyte cDNA library and from first strand cDNA prepared from HeLa total RNA. While three of the four cDNAs were able to be amplified by this method, a non-specific amplification product was also observed that under some conditions would interfere with the gene-specific amplification. This non-specific product was amplified in reactions containing the attB adapter-primers alone without any gene-specific overlap primers present. The non-specific amplification product was reduced by increasing the stringency of the PCR reaction and lowering the attB adapter PCR primer concentration.

These results indicate that the adapter-primer PCR approach described in this Example will work well for cloned genes. These results also demonstrate the development of a simple and efficient method to amplify PCR products that are compatible with the GATEWAY™ PCR Cloning System that allows the use of shorter gene-specific primers that partially overlap universal attB adapter-primers. In routine PCR cloning applications, the use of 12 bp overlaps is recommended. The methods described in this Example can thus reduce the length of gene-specific primers by up to 17 residues or more, resulting in a significant savings in oligonucleotide costs for high volume users of the GATEWAY™ PCR Cloning System. In addition, using the methods and assays described in this Example, one of ordinary skill can, using only routine experimentation, design and use analogous primer-adapters based on or containing other recombination sites or fragments thereof, such as attL, attR, attP, lox, FRT, etc.

Example 21

Mutational Analysis of the Bacteriophage Lambda attL and attR Sites

Determinants of att Site Specificity in Site-specific Recombination

To investigate the determinants of att site specificity, the bacteriophage lambda attL and attR sites were systematically mutagenized. As noted herein, the determinants of specificity have previously been localized to the 7 bp overlap region (TTTATAC, which is defined by the cut sites for the integrase protein and is the region where strand exchange takes place) within the 15 bp core region (GCTTTTTTATACTAA) (SEQ ID NO:58) which is identical in all four lambda att sites, attB, attP, attL and attR. This core region, however, has not heretofore been systematically mutagenized and examined to define precisely which mutations produce unique changes in att site specificity.

Therefore, to examine the effect of att sequence on site specificity, mutant attL and attR sites were generated by PCR and tested in an in vitro site-specific recombination assay. In this way all possible single base pair changes within the 7 bp overlap region of the core att site were generated as well as five additional changes outside the 7 bp overlap but within the 15 bp core att site. Each attL PCR substrate was tested in the in vitro recombination assay with each of the attR PCR substrates.

Methods

To examine both the efficiency and specificity of recombination of mutant attL and attR sites, a simple in vitro site-specific recombination assay was developed. Since the core regions of attL and attR lie near the ends of these sites, it was possible to incorporate the desired nucleotide base changes within PCR primers and generate a series of PCR products containing mutant attL and attR sites. PCR products containing attL and attR sites were used as substrates in an in vitro reaction with GATEWAY™ LR Clonase™ Enzyme Mix (Life Technologies, Inc.; Rockville, Md.). Recombination between a 1.5 kb attL PCR product and a 1.0 kb attR PCR product resulted in a 2.5 kb recombinant molecule that was monitored using agarose gel electrophoresis and ethidium bromide staining.

Plasmid templates pEZC1301 (FIG. 84) and pEZC1313 (FIG. 85), each containing a single wild type attL or attR site, respectively, were used for the generation of recombination substrates. The following list shows primers that were used in PCR reactions to generate the attL PCR products that were used as substrates in L x R Clonase reactions (capital letters represent changes from the wild-type sequence, and the underline represents the 7 bp overlap region within the 15 bp core att site; a similar set of PCR primers was used to prepare the attR PCR products containing matching mutations):

GATEWAY™ sites (note: attL2 sequence in GATEWAY™ plasmids begins "accca" while the attL2 site in this example begins "agcct" to reflect wild-type attL outside the core region.):

attL1: gggg agcct gcttttttGtacAaa gttggcatta taaaaa-agca ttgc (SEQ ID NO:36)

attL2: gggg agcct gctttCttGtacAaa gttggcatta taaaaa-agca ttgc (SEQ ID NO:37)

Wild-type:

attL0: gggg agcct gcttttttatactaa gttggcatta taaaaa-agca ttgc (SEQ ID NO:59)

Single base changes from wild-type:

attLT1A: gggg agcct gctttAttatactaa gttggcatta taaaaa-agca ttgc (SEQ ID NO:60)

attLT1C: gggg agcct gctttcttatactaa gttggcatta taaaaa-agca ttgc (SEQ ID NO:61)

attLT1G: gggg agcct gctttGttatac taa gttggcatta taaaaa-agca ttgc (SEQ ID NO:62)

attLT2A: gggg agcct gcttttAtatac taa gttggcatta taaaaa-agca ttgc (SEQ ID NO:63)

attLT2C: gggg agcct gcttttCtatactaa gttggcatta taaaaa-agca ttgc (SEQ ID NO:64)

attLT2G: gggg agcct gcttttGtatactaa gttggcatta taaaa-aagca ttgc (SEQ D NO:65)

attLT3A: gggg agcct gctttttAatactaa gttggcatta taaaa-aagca ttgc (SEQ ID NO:66 attLT3C: gggg agcct gctttttCatactaa gttggcatta taaaa-aagca ttgc (SEQ ID NO:67)

attLT3G: gggg agcct gctttttGatactaa gttggcatta taaaa-aagca ttgc (SEQ ID NO:68)

attLA4C: gggg agcct gcttttttCtactaa gttggcatta taaaa-aagca ttgc (SEQ ID NO:69)

attLA4G: gggg agcct gcttttttGtactaa gttggcatta taaaa-aagca ttgc (SEQ ID NO:70)

attLA4T: gggg agcct gcttttttTtactaa gttggcatta taaaa-aagca ttgc (SEQ ID NO:71)

attLT5A: gggg agcct gcttttttaAactaa gttggcatta taaaa-aagca ttgc (SEQ ID NO:72)

attLT5C: gggg agcct gcttttttaCactaa gttggcatta taaaa-aagca ttgc (SEQ ID NO:73)

attLT5G: gggg agcct gcttttttaGactaa gttggcatta taaaa-aagca ttgc (SEQ ID NO:74)

attLA6C: gggg agcct gcttttttatCctaa gttggcatta taaaa-aagca ttgc (SEQ ID NO:75)

attLA6G: gggg agcct gcttttttatGctaa gttggcatta taaaa-aagca ttgc (SEQ ID NO:76)

attLA6T: gggg agcct gcttttttatTctaa gttggcatta taaaa-aagca ttgc (SEQ ID NO:77)

attLC7A: gggg agcct gcttttttataAtaa gttggcatta taaaa-aagca ttgc (SEQ ID NO:78)

attLC7G: gggg agcct gcttttttataGtaa gttggcatta taaaa-aagca ttgc (SEQ ID NO:79 attLC7T: gggg agcct gcttttttataTtaa gttggcatta taaaa-aagca ttgc (SEQ ID NO:80)

Single base changes outside of the 7 bp overlap:

attL8: gggg agcct Actttttttatactaa gttggcatta taaaa-aagca ttgc (SEQ ID NO:81)

attL9: gggg agcct gcCtttttatactaa gttggcatta taaaaa-agca ttgc (SEQ ID NO:82)

attL10: gggg agcct gcttCtttatactaa gttggcatta taaaaa-agca ttgc (SEQ ID NO:83)

attL14: gggg agcct gcttttttatacCaa gttggcatta taaaaa-agca ttgc (SEQ ID NO:84)

attL15: gggg agcct gcttttttatactaG gttggcatta taaaaa-agca ttgc (SEQ ID NO:85)

Note: additional vectors wherein the first nine bases are gggg agcca (i.e., substituting an adenine for the thymine in the position immediately preceding the 15-bp core region), which may or may not contain the single base pair substitutions (or deletions) outlined above, can also be used in these experiments.

Recombination reactions of attL- and attR-containing PCR products was performed as follows:

8 μL of $H_20$
2 μl of attL PCR product (100 ng)
2 μl of attR PCR product (100 ng)
4 μl of 5× buffer
4 μl of GATEWAY™ LR Clonase™ Enzyme Mix
20 μl total volume Clonase reactions were incubated at 25° C. for 2 hours.

2 μl of 10× Clonase stop solution (proteinase K, 2 mg/ml) were added to stop the reaction.

10 μl were run on a 1% agarose gel.

Results

Each attL PCR substrate was tested in the in vitro recombination assay with each of the attR PCR substrates. Changes within the first three positions of the 7 bp overlap (TTTATAC) strongly altered the specificity of recombination. These mutant att sites each recombined as well as the wild-type, but only with their cognate partner mutant; they did not recombine detectably with any other att site mutant. In contrast, changes in the last four positions (TTTATAC) only partially altered specificity; these mutants recombined with their cognate mutant as well as wild-type att sites and recombined partially with all other mutant att sites except for those having mutations in the first three positions of the 7 bp overlap. Changes outside of the 7 bp overlap were found not to affect specificity of recombination, but some did influence the efficiency of recombination.

Based on these results, the following rules for att site specificity were determined:

Only changes within the 7 bp overlap affect specificity.

Changes within the first 3 positions strongly affect specificity.

Changes within the last 4 positions weakly affect specificity.

Mutations that affected the overall efficiency of the recombination reaction were also assessed by this method. In these experiments, a slightly increased (less than 2-fold) recombination efficiency with attLT1A and attLC7T substrates was observed when these substrates were reacted with their cognate attR partners. Also observed were mutations that decreased recombination efficiency (approximately 2-3 fold), including attLA6G, attL14 and attL15. These mutations presumably reflect changes that affect Int protein binding at the core att site.

The results of these experiments demonstrate that changes within the first three positions of the 7 bp overlap (TTTATAC) strongly altered the specificity of recombination (i.e., att sequences with one or more mutations in the first three thymidines would only recombine with their cognate partners and would not cross-react with any other att site mutation). In contrast, mutations in the last four positions (TTTATAC) only partially altered specificity (i.e., att sequences with one or more mutations in the last four base positions would cross-react partially with the wild-type att site and all other mutant att sites, except for those having mutations in one or more of the first three positions of the 7 bp overlap). Mutations outside of the 7 bp overlap were not found to affect specificity of recombination, but some were found to influence (i.e., to cause a decrease in) the efficiency of recombination.

Example 22

Discovery of Att Site Mutations that Increase the Cloning Efficiency of GATEWAY™ Cloning Reactions In experiments designed to understand the determinants of att site specificity, point mutations in the core region of attL were made. Nucleic acid molecules containing these mutated attL sequences were then reacted in an LR reaction with nucleic acid molecules containing the cognate attR site (i.e., an attR site containing a mutation corresponding to that in the attL site), and recombinational efficiency was determined as described above. Several mutations located in the core region of the att site were noted that either slightly increased (less than 2-fold) or decreased (between 2-4-fold) the efficiency of the recombination reaction (Table 3).

TABLE 3

Effects of attL mutations on Recombination Reactions.

| Site | SEQ ID NO: | Sequence | Effect on Recombination |
|---|---|---|---|
| attL0 | 86 | agcctgctttttatactaagttggcatta | |
| attL5 | 87 | agcctgctttAttatactaagttggcatta | slightly increased |
| attL6 | 88 | agcctgcttttttataTtaagttggcatta | slightly increased |
| attL13 | 89 | agcctgctttttatGctaagttggcatta | decreased |
| attL14 | 90 | agcctgctttttatacCaagttggcatta | decreased |

TABLE 3-continued

| Effects of attL mutations on Recombination Reactions. | | | |
|---|---|---|---|
| Site | SEQ ID NO: | Sequence | Effect on Recombination |
| attL15 | 91 | agcctgcttttttatactaGgttggcatta | decreased |
| consensus | 92 | CAACTTnnTnnnAnnAAGTTG | |

It was also noted that these mutations presumably reflected changes that either increased or decreased, respectively, the relative affinity of the integrase protein for binding the core att site. A consensus sequence for an integrase core-binding site (CAACTTNNT) has been inferred in the literature but not directly tested (see, e.g., Ross and Landy, *Cell* 33:261-272 (1983)). This consensus core integrase-binding sequence was established by comparing the sequences of each of the four core att sites found in attP and attB as well as the sequences of five non-att sites that resemble the core sequence and to which integrase has been shown to bind in vitro. These experiments suggest that many more att site mutations might be identified which increase the binding of integrase to the core att site and thus increase the efficiency of GATEWAY™ cloning reactions.

Example 23

Effects of Core Region Mutations on Recombination Efficiency

To directly compare the cloning efficiency of mutations in the att site core region, single base changes were made in the attB2 site of an attB1-TET-attB2 PCR product. Nucleic acid molecules containing these mutated attB2 sequences were then reacted in a BP reaction with nucleic acid molecules containing non-cognate attP sites (i.e., wildtype attP2), and recombinational efficiency was determined as described above The cloning efficiency of these mutant attB2 containing PCR products compared to standard attB1-TET-attB2 PCR product are shown in Table 4.

TABLE 4

| Efficiency of Recombination With Mutated attB2 Sites. | | | | |
|---|---|---|---|---|
| Site | SEQ ID NO: | Sequence | Mutation | Cloning Efficiency |
| attB0 | 93 | tcaagttagtataaaaaagcaggct | | |
| attB1 | 94 | ggggacaagtttgtacaaaaaagcaggct | | |
| attB2 | 95 | ggggaccactttgtacaagaaagctgggt | 100% | |
| attB2.1 | 96 | ggggaAcactttgtacaagaaagctgggt | C→A | 40% |
| attB2.2 | 97 | ggggacAactttgtacaagaaagctgggt | C→A | 131% |
| attB2.3 | 98 | ggggaccCctttgtacaagaaagctgggt | A→C | 4% |
| attB2.4 | 99 | ggggaccaAtttgtacaagaaagctgggt | C→A | 11% |
| attB2.5 | 100 | ggggaccacGttgtacaagaaagctgggt | T→G | 4% |
| attB2.6 | 101 | ggggaccactGtgtacaagaaagctgggt | T→G | 6% |
| attB2.7 | 102 | ggggaccacttGgtacaagaaagctgggt | T→G | 1% |
| attB2.8 | 103 | ggggaccactttTtacaagaaagctgggt | G→T | 0.5% |

As noted above, a single base change in the attB2.2 site increased the cloning efficiency of the attB1-TET-attB2.2 PCR product to 131% compared to the attB1-TET-attB2 PCR product. Interestingly, this mutation changes the integrase core binding site of attB2 to a sequence that matches more closely the proposed consensus sequence.

Additional experiments were performed to directly compare the cloning efficiency of an attB1-TET-attB2 PCR product with a PCR product that contained attB sites containing the proposed consensus sequence (see Example 22) of an integrase core binding site. The following attB sites were used to amplify attB-TET PCR products:

attB1 (SEQ ID NO:104) ggggacaagtttgtacaaaaaagcaggct attB1.6 SEQ ID NO:105) ggggacaaCtttgtacaaaaaagTTggct attB2 (SEQ ID NO:106) ggggaccactttgtacaagaaagctgggt attB2.10 (SEQ ID NO:107) ggggacAactttgtacaagaaagTtgggt BP reactions were carried out between 300 ng (100 fmoles) of pDONR201 (FIG. 49A) with 80 ng (80 fmoles) of attB-TET PCR product in a 20 μl volume with incubation for 1.5 hrs at 25° C., creating pENTR201-TET Entry clones. A comparison of the cloning efficiencies of the above-noted attB sites in BP reactions is shown in Table 5.

TABLE 5

| Cloning efficiency of BP Reactions. | | |
|---|---|---|
| PCR product | CFU/ml | Fold Increase |
| B1-tet-B2 | 7,500 | |
| B1.6-tet-B2 | 12,000 | 1.6× |
| B1-tet-B2.10 | 20,900 | 2.8× |
| B1.6-tet-B2.10 | 30,100 | 4.0× |

These results demonstrate that attB PCR products containing sequences that perfectly match the proposed consensus sequence for integrase core binding sites can produce Entry clones with four-fold higher efficiency than standard Gateway attB1 and attB2 PCR products.

The entry clones produced above were then transferred to pDEST20 (FIG. 40A) via LR reactions (300 ng (64 fmoles) pDEST20 mixed with 50 ng (77 fmoles) of the respective pENTR201-TET Entry clone in 20 μl volume; incubated for 1 hr incubation at 25° C.). The efficiencies of cloning for these reactions are compared in Table 6.

TABLE 6

| Cloning Efficiency of LR Reactions. | | |
|---|---|---|
| pENTR201-TET × pDEST20 | CFU/ml | Fold Increase |
| L1-tet-L2 | 5,800 | |
| L1.6-tet-L2 | 8,000 | 1.4 |
| L1-tet-L2.10 | 10,000 | 1.7 |
| L1.6-tet-L2.10 | 9.300 | 1.6 |

These results demonstrate that the mutations introduced into attB1.6 and attB2.10 that transfer with the gene into entry clones slightly increase the efficiency of LR reactions. Thus, the present invention encompasses not only mutations in attB sites that increase recombination efficiency, but also to the corresponding mutations that result in the attL sites created by the BP reaction.

To examine the increased cloning efficiency of the attB1.6-TET-attB2.10 PCR product over a range of PCR product amounts, experiments analogous to those described above were performed in which the amount of attB PCR product was titrated into the reaction mixture. The results are shown in Table 7.

TABLE 7

| Titration of attB PCR products. | | | |
|---|---|---|---|
| Amount of attB PCR product (ng) | PCR product | CFU/ml | Fold Increase |
| 20 | attB1-TET-attB2 | 3,500 | 6.1 |
| | attB1.6-TET-attB2.10 | 21,500 | |
| 50 | attB1-TET-attB2 | 9,800 | 5.0 |
| | attB1.6-TET-attB2.10 | 49,000 | |
| 100 | attB1-TET-attB2 | 18,800 | 2.8 |
| | attB1.6-TET-attB2.10 | 53,000 | |
| 200 | attB1-TET-attB2 | 19,000 | 2.5 |
| | attB1.6-TET-attB2.10 | 48,000 | |

These results demonstrate that as much as a six-fold increase in cloning efficiency is achieved with the attB1.6-TET-attB2.10 PCR product as compared to the standard attB1-TET-attB2 PCR product at the 20 ng amount.

Example 24

Determination of attB Sequence Requirements for Optimum Recombination Efficiency To examine the sequence requirements for attB and to determine which attB sites would clone with the highest efficiency from populations of degenerate attB sites, a series of experiments was performed. Degenerate PCR primers were designed which contained five bases of degeneracy in the B-arm of the attB site. These degenerate sequences would thus transfer with the gene into Entry clone in BP reactions and subsequently be transferred with the gene into expression clones in LR reactions. The populations of degenerate attB and attL sites could thus be cycled from attB to attL back and forth for any number of cycles. By altering the reaction conditions at each transfer step (for example by decreasing the reaction time and/or decreasing the concentration of DNA) the reaction can be made increasingly more stringent at each cycle and thus enrich for populations of attB and attL sites that react more efficiently.

The following degenerate PCR primers were used to amplify a 500 bp fragment from pUC18 which contained the lacZ alpha fragment (only the attB portion of each primer is shown):

attB1 (SEQ ID NO:108) GGGGACAAGTTTGTACAAA AAAGCAGGCT attB1n16-20 (SEQ ID NO:109) GGGG ACAAGTTTGTACAAA nnnnn-AGGCT attB1n21-25 (SEQ ID NO:110) GGGG ACAAGTTT GTACAAA AAAGC-nnnnn attB2 (SEQ ID NO:111) GGGG ACCACTTTGTACAAG AAAGC TGGGT attB2n16-20 (SEQ ID NO:112) GGGG ACCACTTT GTACAAG nnnnn-TGGGT attB2n21-25 (SEQ D NO:113) GGGG ACCACTTT GTACAAG AAAGC-nnnnn The starting population size of degenerate att sites is $4^5$ or 1024 molecules. Four different populations were transferred through two BP reactions and two LR reactions. Following transformation of each reaction, the population of transformants was amplified by growth in liquid media containing the appropriate selection antibiotic. DNA was prepared from the population of clones by alkaline lysis miniprep and used in the next reaction. The results of the BP and LR cloning reactions are shown below.

| BP-1, overnight reactions | | |
|---|---|---|
| | cfu/ml | percent of control |
| attB1-LacZa-attB2 | 78,500 | 100% |
| attB1n16-20-LacZa-attB2 | 1,140 | 1.5% |
| attB1n21-25-LacZa-attB2 | 11,100 | 14% |
| attB1-LacZa-attB2n16-20 | 710 | 0.9% |
| attB1-LacZa-attB2n21-25 | 16,600 | 21% |

| LR-1, pENTR201-LacZa × pDEST20/EcoRI, 1 hr reactions | | |
|---|---|---|
| | cfu/ml | percent of control |
| attL1-LacZa-attL2 | 20,000 | 100% |
| attL1n16-20-LacZa-attL2 | 2,125 | 11% |
| attL1n21-25-LacZa-attL2 | 2,920 | 15% |
| attL1-LacZa-attL2n16-20 | 3,190 | 16% |
| attL1-LacZa-attL2n21-25 | 1,405 | 7% |

| BP-2, pEXP20-LacZa/ScaI × pDONR 201, 1 hr reactions | | |
|---|---|---|
| | cfu/ml | percent of control |
| attB1-LacZa-attB2 | 48,600 | 100% |
| attB1n16-20-LacZa-attB2 | 22,800 | 47% |
| attB1n21-25-LacZa-attB2 | 31,500 | 65% |
| attB1-LacZa-attB2n16-20 | 42,400 | 87% |
| attB1-LacZa-attB2n21-25 | 34,500 | 71% |

| LR-2, pENTR201-LacZa × pDEST6/NcoI, 1 hr reactions | | |
|---|---|---|
| | cfu/ml | percent of control |
| attL1-LacZa-attL2 | 23,000 | 100% |
| attL1n16-20-LacZa-attL2 | 49,000 | 213% |
| attL1n21-25-LacZa-attL2 | 18,000 | 80% |
| attL1-LacZa-attL2n16-20 | 37,000 | 160% |
| attL1-LacZa-attL2n21-25 | 57,000 | 250% |

These results demonstrate that at each successive transfer, the cloning efficiency of the entire population of att sites increases, and that there is a great deal of flexibility in the definition of an attB site. Specific clones may be isolated from the above reactions, tested individually for recombination efficiency, and sequenced. Such new specificities may then be compared to known examples to guide the design of new sequences with new recombination specificities. In addition, based on the enrichment and screening protocols described herein, one of ordinary skill can easily identify and use sequences in other recombination sites, e.g., other att sites, lox, FRT, etc., that result in increased specificity in the recombination reactions using nucleic acid molecules containing such sequences.

Example 25

Design of att Site PCR Adapter-Primers

Additional studies were performed to design gene-specific primers with 12 bp of attB1 and attB2 at their 5'-ends. The optimal primer design for att-containing primers is the same as for any PCR primers: the gene-specific portion of the primers should ideally have a Tm of >50° C. at 50 mM salt (calculation of Tm is based on the formula 59.9+41(% GC)−675/n).

Primers:

12bp attB1 (SEQ ID NO:114): AA AAA GCA GGC TNN-forward gene-specific primer

12bp attB2 (SEQ ID NO:115): A GAA AGC TGG GTN-reverse gene-specific primer attB1 adapter primer (SEQ ID NO:116): GGGGA-CAAGTTTGTACAAAAAA-GCAGGCT attB2 adapter primer (SEQ ID NO:117): GGGGACCACTIT-GTACAAGAAA-GCTGGGT Protocol:

(1) Mix 200 ng of cDNA library or 1 ng of plasmid clone DNA (alternatively, genomic DNA or RNA could be used) with 10 pmoles of gene specific primers in a 50 μl PCR reaction, using one or more polypeptides having DNA polymerase activity such as those described herein. (The addition of greater than 10 pmoles of gene-specific primers can decrease the yield of attB PCR product. In addition, if RNA is used, a standard reverse transcriptase-PCR(RT-PCR) protocol should be followed; see, e.g., Gerard, G. F., et al., *FOCUS* 11:60 (1989); Myers, T. W., and Gelfand, D. H., *Biochem.* 30:7661 (1991); Freeman, W. N., et al., *BioTechniques* 20:782 (1996); and U.S. application Ser. No. 09/064,057, filed Apr. 22, 1998, the disclosures of all of which are incorporated herein by reference.)

1st PCR profile:

(a) 95° C. for 3 minutes (b) 10 cycles of:
  (i) 94° C. for 15 seconds
  (ii) 50° C.* for 30 seconds
  (iii) 68° C. for 1 minute/kb of target amplicon (c) 68° C. for 5 minutes (d) 10° C. hold

*The optimal annealing temperature is determined by the calculated Tm of the gene-specific part of the primer.

(2) Transfer 10 μl to a 40 μl PCR reaction mix containing 35 pmoles each of the attB1 and attB2 adapter primers.

2nd PCR profile:

(a) 95° C. for 1 minute (b) 5 cycles of:
  (i) 94° C. for 15 seconds
  (ii) 45° C.* for 30 seconds
  (iii) 68° C. for 1 minute/kb of target amplicon (c) 15-20 cycles** of:
  (i) 94° C. for 15 seconds
  (ii) 55° C.* for 30 seconds
  (iii) 68° C. for 1 minute/kb of target amplicon (d) 68° C. for 5 minutes (e) 10° C. hold

*The optimal annealing temperature is determined by the calculated Tm of the gene-specific part of the primer.

**15 cycles is sufficient for low complexity targets.

Notes:

1. It is useful to perform a no-adapter primer control to assess the yield of attB PCR product produced.
2. Linearized template usually results in slightly greater yield of PCR product.

Example 26

One-Tube Recombinational Cloning Using the GATEWAY™ Cloning System

To provide for easier and more rapid cloning using the GATEWAY™ cloning system, we have designed a protocol whereby the BP and LR reactions may be performed in a single tube (a "one-tube" protocol). The following is an example of such a one-tube protocol; in this example, an aliquot of the BP reaction is taken before adding the LR components, but the BP and LR reactions may be performed in a one-tube protocol without first taking the BP aliquot:

| Reaction Component | Volume |
|---|---|
| attB DNA (100-200 ng/25 μl reaction) | 1-12.5 μl |
| attP DNA (pDONR201) 150 ng/μl | 2.5 μl |
| 5X BP Reaction Buffer | 5.0 μl |
| Tris-EDTA | (to 20 μl) |
| BP Clonase | 5.0 μl |
| Total vol. | 25 μl |

After the above components were mixed in a single tube, the reaction mixtures were incubated for 4 hours at 25° C. A 5 μl aliquot of reaction mixture was removed, and 0.5 μl of 10× stop solution was added to this reaction mixture and incubated for 10 minutes at 37° C. Competent cells were then transformed with 1-21 μl of the BP reaction per 1001 μl of cells; this transformation yielded colonies of Entry Clones for isolation of individual Entry Clones and for quantitation of the BP Reaction efficiency.

To the remaining 20 μl of BP reaction mixture, the following components of the LR reaction were added:

| Reaction Component | Final Concentration | Volume Added |
|---|---|---|
| NaCl | 0.75 M | 1 μl |
| Destination Vector | 150 ng/ul | 3 μl |
| LR Clonase | | 6 μl |
| Total vol. | | 30 μl |

After the above components were mixed in a single tube, the reaction mixtures were incubated for 2 hours at 25° C. 3 μl of 10× stop solution was added, and the mixture was incubated for 10 minutes at 37° C. Competent cells were then transformed with 1-2 μl of the reaction mixture per 100 μL of cells Notes:

1. If desired, the Destination Vector can be added to the initial BP reaction.
2. The reactions can be scaled down by 2×, if desired.
3. Shorter incubation times for the BP and/or LR reactions can be used (scaled to the desired cloning efficiencies of the reaction), but a lower number of colonies will typically result.

4. To increase the number of colonies obtained by several fold, incubate the BP reaction for 6-20 hours and increase the LR reaction to 3 hours. Electroporation also works well with 1-2 ul of the PK-treated reaction mixture.
5. PCR products greater than about 5 kb may show significantly lower cloning efficiency in the BP reaction. In this case, we recommend using a one-tube reaction with longer incubation times (e.g., 6-18 hours) for both the BP and LR steps.

Example 27

Relaxation of Destination Vectors During the LR Reaction

To further optimize the LR Reaction, the composition of the LR Reaction buffer was modified from that described above and this modified buffer was used in a protocol to examine the impact of enzymatic relaxation of Destination Vectors during the LR Reaction.

LR Reactions were set up as usual (see, e.g., Example 6), except that 5× BP Reaction Buffer (see Example 5) was used for the LR Reaction. To accomplish Destination Vector relaxation during the LR Reaction, Topoisomerase I (Life Technologies, Inc., Rockville, Md.; Catalogue No. 38042-016) was added to the reaction mixture at a final concentration of ~15 U per µg of total DNA in the reaction (for example, for reaction mixtures with a total of 400 ng DNA in the 20 µl LR Reaction, ~6 units of Topoisomerase I was added). Reaction mixtures were set up as follows:

| Reaction Component | Volume |
|---|---|
| $ddH_2O$ | 6.5 µl |
| 4X BP Reaction Buffer | 5 µl |
| 100 ng single chain/linear pENTR CAT, 50 ng/µl | 2 µl |
| 300 ng single chain/linear pDEST6, 150 ng/µl | 2 µl |
| Topoisomerase I, 15 U/ml | 0.5 µl |
| LR Clonase | 4 µl |

Reaction mixtures were incubated at 25° C. for 1 hour, and 2 µl of 2 µg/µl Proteinase K was then added and mixtures incubated for 10 minutes at 37° C. to stop the LR Reaction. Competent cells were then transformed as described in the preceding examples. The results of these studies demonstrated that relaxation of substrates in the LR reaction using Topoisomerase I resulted in a 2- to 10-fold increase in colony output compared to those LR reactions performed without including Topoisomerase I.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An isolated nucleic acid molecule comprising a lambda att recombination site wherein a sequence of the seven base pair overlap region within the fifteen base pair core region is ATTATAC.

2. The isolated nucleic acid molecule of claim 1, which comprises two or more lambda att recombination sites.

3. The isolated nucleic acid molecule of claim 1, wherein the lambda att-recombination site is located between a transcriptional regulatory sequence and an open reading frame, wherein the transcriptional regulatory sequence and open reading frame are operably linked.

4. The isolated nucleic acid molecule of claim 3, wherein the transcriptional regulatory sequence is a promoter.

5. The isolated nucleic acid molecule of claim 1, which is a vector.

6. The isolated nucleic acid molecule of claim 5, wherein the vector is a plasmid.

7. The isolated nucleic acid molecule of claim 1, which further comprises at least one origin of replication.

8. The isolated nucleic acid molecule of claim 7, which comprises at least two origins of replication.

9. The isolated nucleic acid molecule of claim 7, which comprises at least one origin of replication that allows for replication of the nucleic acid molecule in a prokaryotic cell.

10. The isolated nucleic acid molecule of claim 9, wherein the prokaryotic cell is an *Escherichia coli* cell.

11. An isolated host cell comprising one or more isolated nucleic acid molecules of claim 1.

* * * * *

SEQUENCE LISTING

```
<160> NUMBER OF SEQ ID NOS: 285

<210> SEQ ID NO 1
<211> LENGTH: 25
<212> TYPE: DNA
<213> ORGANISM: Artificial Sequence
<220> FEATURE:
<223> OTHER INFORMATION: attB1 site

<400> SEQUENCE: 1

acaagtttgt acaaaaaagc aggct                                           25


<210> SEQ ID NO 2
<211> LENGTH: 25
<212> TYPE: DNA
<213> ORGANISM: Artificial Sequence
<220> FEATURE:
<223> OTHER INFORMATION: attB2 site

<400> SEQUENCE: 2

acccagcttt cttgtacaaa gtggt                                           25


<210> SEQ ID NO 3
<211> LENGTH: 233
<212> TYPE: DNA
<213> ORGANISM: Artificial Sequence
<220> FEATURE:
<223> OTHER INFORMATION: attP1 site
```

-continued

<400> SEQUENCE: 3
tacaggtcac taataccatc taagtagttg attcatagtg actggatatg ttgtgtttta 60
cagtattatg tagtctgttt tttatgcaaa atctaattta atatattgat atttatatca 120
ttttacgttt ctcgttcagc ttttttgtac aaagttggca ttataaaaaa gcattgctca 180
tcaatttgtt gcaacgaaca ggtcactatc agtcaaaata aaatcattat ttg 233

<210> SEQ ID NO 4
<211> LENGTH: 233
<212> TYPE: DNA
<213> ORGANISM: Artificial Sequence
<220> FEATURE:
<223> OTHER INFORMATION: attP2

<400> SEQUENCE: 4
caaataatga ttttattttg actgatagtg acctgttcgt tgcaacaaat tgataagcaa 60
tgctttctta taatgccaac tttgtacaag aaagctgaac gagaaacgta aaatgatata 120
aatatcaata tattaaatta gattttgcat aaaaaacaga ctacataata ctgtaaaaca 180
caacatatcc agtcactatg aatcaactac ttagatggta ttagtgacct gta 233

<210> SEQ ID NO 5
<211> LENGTH: 125
<212> TYPE: DNA
<213> ORGANISM: Artificial Sequence
<220> FEATURE:
<223> OTHER INFORMATION: attL1

<400> SEQUENCE: 5
acaagtttgt acaaaaaagc tgaacgagaa acgtaaaatg atataaatat caatatatta 60
aattagattt tgcataaaaa acagactaca taatactgta aaacacaaca tatccagtca 120
ctatg 125

<210> SEQ ID NO 6
<211> LENGTH: 135
<212> TYPE: DNA
<213> ORGANISM: Artificial Sequence
<220> FEATURE:
<223> OTHER INFORMATION: attL2

<400> SEQUENCE: 6
gcaggtcgac catagtgact ggatatgttg tgttttacag tattatgtag tctgtttttt 60
atgcaaaatc taatttaata tattgatatt tatatcattt tacgtttctc gttcagcttt 120
cttgtacaaa gtggt 135

<210> SEQ ID NO 7
<211> LENGTH: 100
<212> TYPE: DNA
<213> ORGANISM: Artificial Sequence
<220> FEATURE:
<223> OTHER INFORMATION: attR1

<400> SEQUENCE: 7
caaataatga ttttattttg actgatagtg acctgttcgt tgcaacaaat tgataagcaa 60
tgctttttta taatgccaac tttgtacaaa aaagcaggct 100

<210> SEQ ID NO 8
<211> LENGTH: 100
<212> TYPE: DNA
<213> ORGANISM: Artificial Sequence

```
<220> FEATURE:
<223> OTHER INFORMATION: attR2

<400> SEQUENCE: 8

caaataatga ttttattttg actgatagtg acctgttcgt tgcaacaaat tgataagcaa        60

tgctttctta taatgccaac tttgtacaag aaagctgggt                             100

<210> SEQ ID NO 9
<211> LENGTH: 15
<212> TYPE: DNA
<213> ORGANISM: Artificial Sequence
<220> FEATURE:
<223> OTHER INFORMATION: 15 bp core region of attB, attP, attL and attR

<400> SEQUENCE: 9

gcttttttat actaa                                                         15

<210> SEQ ID NO 10
<211> LENGTH: 30
<212> TYPE: DNA
<213> ORGANISM: Artificial Sequence
<220> FEATURE:
<223> OTHER INFORMATION: attL5

<400> SEQUENCE: 10

agcctgcttt attatactaa gttggcatta                                         30

<210> SEQ ID NO 11
<211> LENGTH: 30
<212> TYPE: DNA
<213> ORGANISM: Artificial Sequence
<220> FEATURE:
<223> OTHER INFORMATION: attL6

<400> SEQUENCE: 11

agcctgcttt tttatattaa gttggcatta                                         30

<210> SEQ ID NO 12
<211> LENGTH: 28
<212> TYPE: DNA
<213> ORGANISM: Artificial Sequence
<220> FEATURE:
<223> OTHER INFORMATION: attB1.6

<400> SEQUENCE: 12

ggggacaact ttgtacaaaa aagttggc                                           28

<210> SEQ ID NO 13
<211> LENGTH: 29
<212> TYPE: DNA
<213> ORGANISM: Artificial Sequence
<220> FEATURE:
<223> OTHER INFORMATION: attB2.2

<400> SEQUENCE: 13

ggggacaact ttgtacaaga aagctgggt                                          29

<210> SEQ ID NO 14
<211> LENGTH: 29
<212> TYPE: DNA
<213> ORGANISM: Artificial Sequence
<220> FEATURE:
<223> OTHER INFORMATION: attB2.10

<400> SEQUENCE: 14
```

-continued

```
ggggacaact ttgtacaaga aagttgggt                                     29


<210> SEQ ID NO 15
<211> LENGTH: 25
<212> TYPE: DNA
<213> ORGANISM: Artificial Sequence
<220> FEATURE:
<223> OTHER INFORMATION: attB2(-1) Oligonucleotide Primer
<220> FEATURE:
<221> NAME/KEY: misc_feature
<222> LOCATION: (25)..(25)
<223> OTHER INFORMATION: 'n' can be any nucleotide (A, T, C, G or U),
      and primer can have variable length up to maximum of
      about 100 kbp; some residues may be missing

<400> SEQUENCE: 15

cccagctttc ttgtacaaag tggtn                                         25


<210> SEQ ID NO 16
<211> LENGTH: 24
<212> TYPE: DNA
<213> ORGANISM: Artificial Sequence
<220> FEATURE:
<223> OTHER INFORMATION: attB2(-2) Oligonucleotide Primer
<220> FEATURE:
<221> NAME/KEY: misc_feature
<222> LOCATION: (24)..(24)
<223> OTHER INFORMATION: 'n' can be any nucleotide (A, T, C, G or U),
      and primer can have variable length up to maximum of
      about 100 kbp; some residues may be missing

<400> SEQUENCE: 16

ccagctttct tgtacaaagt ggtn                                          24


<210> SEQ ID NO 17
<211> LENGTH: 23
<212> TYPE: DNA
<213> ORGANISM: Artificial Sequence
<220> FEATURE:
<223> OTHER INFORMATION: attB2(-3) Oligonucleotide Primer
<220> FEATURE:
<221> NAME/KEY: misc_feature
<222> LOCATION: (23)..(23)
<223> OTHER INFORMATION: 'n' can be any nucleotide (A, T, C, G or U),
      and primer can have variable length up to maximum of
      about 100 kbp; some residues may be missing

<400> SEQUENCE: 17

cagctttctt gtacaaagtg gtn                                           23


<210> SEQ ID NO 18
<211> LENGTH: 22
<212> TYPE: DNA
<213> ORGANISM: Artificial Sequence
<220> FEATURE:
<223> OTHER INFORMATION: attB2(-4) Oligonucleotide Primer
<220> FEATURE:
<221> NAME/KEY: misc_feature
<222> LOCATION: (22)..(22)
<223> OTHER INFORMATION: 'n' can be any nucleotide (A, T, C, G or U),
      and primer can have variable length up to maximum of
      about 100 kbp; some residues may be missing

<400> SEQUENCE: 18

agctttcttg tacaaagtgg tn                                            22


<210> SEQ ID NO 19
<211> LENGTH: 26
<212> TYPE: DNA
<213> ORGANISM: Artificial Sequence
```

-continued

```
<220> FEATURE:
<223> OTHER INFORMATION: attB1- and attB2-derived Oligonucleotide Primer
<220> FEATURE:
<221> NAME/KEY: misc_feature
<222> LOCATION: (26)..(26)
<223> OTHER INFORMATION: 'n' can be any nucleotide (A, T, C, G or U),
      and primer can have variable length up to maximum of
      about 100 kbp; some residues may be missing

<400> SEQUENCE: 19

acaagtttgt acaaaaaagc aggctn                                          26


<210> SEQ ID NO 20
<211> LENGTH: 26
<212> TYPE: DNA
<213> ORGANISM: Artificial Sequence
<220> FEATURE:
<223> OTHER INFORMATION: attB1- and attB2-derived Oligonucleotide Primer
<220> FEATURE:
<221> NAME/KEY: misc_feature
<222> LOCATION: (26)..(26)
<223> OTHER INFORMATION: 'n' can be any nucleotide (A, T, C, G or U),
      and primer can have variable length up to maximum of
      about 100 kbp; some residues may be missing

<400> SEQUENCE: 20

accactttgt acaagaaagc tgggtn                                          26


<210> SEQ ID NO 21
<211> LENGTH: 19
<212> TYPE: DNA
<213> ORGANISM: Artificial Sequence
<220> FEATURE:
<223> OTHER INFORMATION: attB1- and attB2-derived Oligonucleotide Primer
<220> FEATURE:
<221> NAME/KEY: misc_feature
<222> LOCATION: (19)..(19)
<223> OTHER INFORMATION: 'n' can be any nucleotide (A, T, C, G or U),
      and primer can have variable length up to maximum of
      about 100 kbp; some residues may be missing

<400> SEQUENCE: 21

tgtacaaaaa agcaggctn                                                  19


<210> SEQ ID NO 22
<211> LENGTH: 19
<212> TYPE: DNA
<213> ORGANISM: Artificial Sequence
<220> FEATURE:
<223> OTHER INFORMATION: attB1- and attB2-derived Oligonucleotide Primer
<220> FEATURE:
<221> NAME/KEY: misc_feature
<222> LOCATION: (19)..(19)
<223> OTHER INFORMATION: 'n' can be any nucleotide (A, T, C, G or U),
      and primer can have variable length up to maximum of
      about 100 kbp; some residues may be missing

<400> SEQUENCE: 22

tgtacaagaa agctgggtn                                                  19


<210> SEQ ID NO 23
<211> LENGTH: 16
<212> TYPE: DNA
<213> ORGANISM: Artificial Sequence
<220> FEATURE:
<223> OTHER INFORMATION: attB1- and attB2-derived Oligonucleotide Primer
<220> FEATURE:
<221> NAME/KEY: misc_feature
<222> LOCATION: (16)..(16)
<223> OTHER INFORMATION: 'n' can be any nucleotide (A, T, C, G or U),
      and primer can have variable length up to maximum of
```

-continued about 100 kbp; some residues may be missing

<400> SEQUENCE: 23
acaaaaaagc aggctn 16

<210> SEQ ID NO 24
<211> LENGTH: 16
<212> TYPE: DNA
<213> ORGANISM: Artificial Sequence
<220> FEATURE:
<223> OTHER INFORMATION: attB1- and attB2-derived Oligonucleotide Primer
<220> FEATURE:
<221> NAME/KEY: misc_feature
<222> LOCATION: (16)..(16)
<223> OTHER INFORMATION: 'n' can be any nucleotide (A, T, C, G or U), and primer can have variable length up to maximum of about 100 kbp; some residues may be missing

<400> SEQUENCE: 24
acaagaaagc tgggtn 16

<210> SEQ ID NO 25
<211> LENGTH: 13
<212> TYPE: DNA
<213> ORGANISM: Artificial Sequence
<220> FEATURE:
<223> OTHER INFORMATION: attB1- and attB2-derived Oligonucleotide Primer
<220> FEATURE:
<221> NAME/KEY: misc_feature
<222> LOCATION: (13)..(13)
<223> OTHER INFORMATION: 'n' can be any nucleotide (A, T, C, G or U), and primer can have variable length up to maximum of about 100 kbp; some residues may be missing

<400> SEQUENCE: 25
aaaaagcagg ctn 13

<210> SEQ ID NO 26
<211> LENGTH: 13
<212> TYPE: DNA
<213> ORGANISM: Artificial Sequence
<220> FEATURE:
<223> OTHER INFORMATION: attB1- and attB2-derived Oligonucleotide Primer
<220> FEATURE:
<221> NAME/KEY: misc_feature
<222> LOCATION: (13)..(13)
<223> OTHER INFORMATION: 'n' can be any nucleotide (A, T, C, G or U), and primer can have variable length up to maximum of about 100 kbp; some residues may be missing

<400> SEQUENCE: 26
agaaagctgg gtn 13

<210> SEQ ID NO 27
<211> LENGTH: 12
<212> TYPE: DNA
<213> ORGANISM: Artificial Sequence
<220> FEATURE:
<223> OTHER INFORMATION: attB1- and attB2-derived Oligonucleotide Primer
<220> FEATURE:
<221> NAME/KEY: misc_feature
<222> LOCATION: (12)..(12)
<223> OTHER INFORMATION: 'n' can be any nucleotide (A, T, C, G or U), and primer can have variable length up to maximum of about 100 kbp; some residues may be missing

<400> SEQUENCE: 27
aaaagcaggc tn 12

-continued

<210> SEQ ID NO 28
<211> LENGTH: 12
<212> TYPE: DNA
<213> ORGANISM: Artificial Sequence
<220> FEATURE:
<223> OTHER INFORMATION: attB1- and attB2-derived Oligonucleotide Primer
<220> FEATURE:
<221> NAME/KEY: misc_feature
<222> LOCATION: (12)..(12)
<223> OTHER INFORMATION: 'n' can be any nucleotide (A, T, C, G or U), and primer can have variable length up to maximum of about 100 kbp; some residues may be missing

<400> SEQUENCE: 28
gaaagctggg tn 12

<210> SEQ ID NO 29
<211> LENGTH: 11
<212> TYPE: DNA
<213> ORGANISM: Artificial Sequence
<220> FEATURE:
<223> OTHER INFORMATION: attB1- and attB2-derived Oligonucleotide Primer
<220> FEATURE:
<221> NAME/KEY: misc_feature
<222> LOCATION: (11)..(11)
<223> OTHER INFORMATION: 'n' can be any nucleotide (A, T, C, G or U), and primer can have variable length up to maximum of about 100 kbp; some residues may be missing

<400> SEQUENCE: 29
aaagcaggct n 11

<210> SEQ ID NO 30
<211> LENGTH: 11
<212> TYPE: DNA
<213> ORGANISM: Artificial Sequence
<220> FEATURE:
<223> OTHER INFORMATION: attB1- and attB2-derived Oligonucleotide Primer
<220> FEATURE:
<221> NAME/KEY: misc_feature
<222> LOCATION: (11)..(11)
<223> OTHER INFORMATION: 'n' can be any nucleotide (A, T, C, G or U), and primer can have variable length up to maximum of about 100 kbp; some residues may be missing

<400> SEQUENCE: 30
aaagctgggt n 11

<210> SEQ ID NO 31
<211> LENGTH: 29
<212> TYPE: DNA
<213> ORGANISM: Artificial Sequence
<220> FEATURE:
<223> OTHER INFORMATION: attB1 Oligonucleotide Primer

<400> SEQUENCE: 31
ggggacaagt ttgtacaaaa aagcaggct 29

<210> SEQ ID NO 32
<211> LENGTH: 29
<212> TYPE: DNA
<213> ORGANISM: Artificial Sequence
<220> FEATURE:
<223> OTHER INFORMATION: attB2 Oligonucleotide Primer

<400> SEQUENCE: 32
ggggaccact ttgtacaaga aagctgggt 29

<210> SEQ ID NO 33

-continued

<211> LENGTH: 27
<212> TYPE: DNA
<213> ORGANISM: Artificial Sequence
<220> FEATURE:
<223> OTHER INFORMATION: XhoI Insertion Primer
<220> FEATURE:
<221> NAME/KEY: misc_feature
<222> LOCATION: (4)..(12)
<223> OTHER INFORMATION: 'n' can be any nucleotide (A, T, C, G or U), and primer can have variable length up to maximum of about 100 kbp; some residues may be missing
<220> FEATURE:
<221> NAME/KEY: misc_feature
<222> LOCATION: (22)..(27)
<223> OTHER INFORMATION: 'n' can be any nucleotide (A, T, C, G or U), and primer can have variable length up to maximum of about 100 kbp; some residues may be missing

<400> SEQUENCE: 33
atgnnnnnnn nntaactcga gnnnnnn 27

<210> SEQ ID NO 34
<211> LENGTH: 30
<212> TYPE: PRT
<213> ORGANISM: Artificial Sequence
<220> FEATURE:
<223> OTHER INFORMATION: attB1 fused into a His6 fusion vector

<400> SEQUENCE: 34

Met Ser Tyr Tyr His His His His His His Gly Ile Thr Ser Leu Tyr
1 5 10 15

Lys Lys Ala Gly Phe Glu Asn Leu Tyr Phe Gln Gly Thr Met
20 25 30

<210> SEQ ID NO 35
<211> LENGTH: 11
<212> TYPE: PRT
<213> ORGANISM: Artificial Sequence
<220> FEATURE:
<223> OTHER INFORMATION: attB Amino Acid Sequence

<400> SEQUENCE: 35

Gly Ile Thr Ser Leu Tyr Lys Lys Ala Gly Phe
1 5 10

<210> SEQ ID NO 36
<211> LENGTH: 48
<212> TYPE: DNA
<213> ORGANISM: Artificial Sequence
<220> FEATURE:
<223> OTHER INFORMATION: attL1 PCR Primer

<400> SEQUENCE: 36
ggggagcctg cttttttgta caaagttggc attataaaaa agcattgc 48

<210> SEQ ID NO 37
<211> LENGTH: 48
<212> TYPE: DNA
<213> ORGANISM: Artificial Sequence
<220> FEATURE:
<223> OTHER INFORMATION: attL2 PCR Primer

<400> SEQUENCE: 37
ggggagcctg ctttcttgta caaagttggc attataaaaa agcattgc 48

<210> SEQ ID NO 38
<211> LENGTH: 22
<212> TYPE: DNA

-continued

<213> ORGANISM: Artificial Sequence
<220> FEATURE:
<223> OTHER INFORMATION: attL Right PCR Primer

<400> SEQUENCE: 38
tgttgccggg aagctagagt aa 22

<210> SEQ ID NO 39
<211> LENGTH: 43
<212> TYPE: DNA
<213> ORGANISM: Artificial Sequence
<220> FEATURE:
<223> OTHER INFORMATION: attR1 PCR Primer

<400> SEQUENCE: 39
ggggacaagt ttgtacaaaa aagctgaacg agaaacgtaa aat 43

<210> SEQ ID NO 40
<211> LENGTH: 43
<212> TYPE: DNA
<213> ORGANISM: Artificial Sequence
<220> FEATURE:
<223> OTHER INFORMATION: attR2

<400> SEQUENCE: 40
ggggacaagt ttgtacaaga aagctgaacg agaaacgtaa aat 43

<210> SEQ ID NO 41
<211> LENGTH: 22
<212> TYPE: DNA
<213> ORGANISM: Artificial Sequence
<220> FEATURE:
<223> OTHER INFORMATION: attR Right

<400> SEQUENCE: 41
cagacggcat gatgaacctg aa 22

<210> SEQ ID NO 42
<211> LENGTH: 29
<212> TYPE: DNA
<213> ORGANISM: Artificial Sequence
<220> FEATURE:
<223> OTHER INFORMATION: B1-Hgb oligonucleotide

<400> SEQUENCE: 42
ggggacaagt ttgtacaaaa aagcaggct 29

<210> SEQ ID NO 43
<211> LENGTH: 28
<212> TYPE: DNA
<213> ORGANISM: Artificial Sequence
<220> FEATURE:
<223> OTHER INFORMATION: B2-Hgb oligonucleotide

<400> SEQUENCE: 43
ggggaccact ttgtacaaga aagctggg 28

<210> SEQ ID NO 44
<211> LENGTH: 18
<212> TYPE: DNA
<213> ORGANISM: Artificial Sequence
<220> FEATURE:
<223> OTHER INFORMATION: 18B1-Hgb oligonucleotide

<400> SEQUENCE: 44
tgtacaaaaa agcaggct 18

-continued

<210> SEQ ID NO 45
<211> LENGTH: 18
<212> TYPE: DNA
<213> ORGANISM: Artificial Sequence
<220> FEATURE:
<223> OTHER INFORMATION: 18B2-Hgb oligonucleotide

<400> SEQUENCE: 45
tgtacaagaa agctgggt 18

<210> SEQ ID NO 46
<211> LENGTH: 15
<212> TYPE: DNA
<213> ORGANISM: Artificial Sequence
<220> FEATURE:
<223> OTHER INFORMATION: 15B1-Hgb oligonucleotide

<400> SEQUENCE: 46
acaaaaaagc aggct 15

<210> SEQ ID NO 47
<211> LENGTH: 15
<212> TYPE: DNA
<213> ORGANISM: Artificial Sequence
<220> FEATURE:
<223> OTHER INFORMATION: 15B2-Hgb oligonucleotide

<400> SEQUENCE: 47
acaagaaagc tgggt 15

<210> SEQ ID NO 48
<211> LENGTH: 12
<212> TYPE: DNA
<213> ORGANISM: Artificial Sequence
<220> FEATURE:
<223> OTHER INFORMATION: 12B1-Hgb oligonucleotide

<400> SEQUENCE: 48
aaaaagcagg ct 12

<210> SEQ ID NO 49
<211> LENGTH: 12
<212> TYPE: DNA
<213> ORGANISM: Artificial Sequence
<220> FEATURE:
<223> OTHER INFORMATION: 12B2-Hgb oligonucleotide

<400> SEQUENCE: 49
agaaagctgg gt 12

<210> SEQ ID NO 50
<211> LENGTH: 11
<212> TYPE: DNA
<213> ORGANISM: Artificial Sequence
<220> FEATURE:
<223> OTHER INFORMATION: 11B1-Hgb oligonucleotide

<400> SEQUENCE: 50
aaaagcaggc t 11

<210> SEQ ID NO 51
<211> LENGTH: 11
<212> TYPE: DNA
<213> ORGANISM: Artificial Sequence
<220> FEATURE:

-continued

<223> OTHER INFORMATION: 11B2-Hgb oligonucleotide

<400> SEQUENCE: 51
gaaagctggg t 11

<210> SEQ ID NO 52
<211> LENGTH: 10
<212> TYPE: DNA
<213> ORGANISM: Artificial Sequence
<220> FEATURE:
<223> OTHER INFORMATION: 10B1-Hgb oligonucleotide

<400> SEQUENCE: 52
aaagcaggct 10

<210> SEQ ID NO 53
<211> LENGTH: 10
<212> TYPE: DNA
<213> ORGANISM: Artificial Sequence
<220> FEATURE:
<223> OTHER INFORMATION: 10B2-Hgb oligonucleotide

<400> SEQUENCE: 53
aaagctgggt 10

<210> SEQ ID NO 54
<211> LENGTH: 29
<212> TYPE: DNA
<213> ORGANISM: Artificial Sequence
<220> FEATURE:
<223> OTHER INFORMATION: attB1 adapter

<400> SEQUENCE: 54
ggggacaagt ttgtacaaaa aagcaggct 29

<210> SEQ ID NO 55
<211> LENGTH: 29
<212> TYPE: DNA
<213> ORGANISM: Artificial Sequence
<220> FEATURE:
<223> OTHER INFORMATION: attB2 adapter

<400> SEQUENCE: 55
ggggaccact ttgtacaaga aagctgggt 29

<210> SEQ ID NO 56
<211> LENGTH: 22
<212> TYPE: DNA
<213> ORGANISM: Artificial Sequence
<220> FEATURE:
<223> OTHER INFORMATION: -5' -Hgb oligonucleotide

<400> SEQUENCE: 56
gtcactagcc tgtggagcaa ga 22

<210> SEQ ID NO 57
<211> LENGTH: 22
<212> TYPE: DNA
<213> ORGANISM: Artificial Sequence
<220> FEATURE:
<223> OTHER INFORMATION: -3' -Hgb oligonucleotide

<400> SEQUENCE: 57
aggatggcag agggagacga ca 22

<210> SEQ ID NO 58
<211> LENGTH: 15
<212> TYPE: DNA
<213> ORGANISM: Artificial Sequence
<220> FEATURE:
<223> OTHER INFORMATION: 15 bp Core Region of attB, attP, attL and attR

<400> SEQUENCE: 58
gcttttttat actaa                                                    15

<210> SEQ ID NO 59
<211> LENGTH: 48
<212> TYPE: DNA
<213> ORGANISM: Artificial Sequence
<220> FEATURE:
<223> OTHER INFORMATION: attL0 PCR Primer

<400> SEQUENCE: 59
ggggagcctg cttttttata ctaagttggc attataaaaa agcattgc                48

<210> SEQ ID NO 60
<211> LENGTH: 48
<212> TYPE: DNA
<213> ORGANISM: Artificial Sequence
<220> FEATURE:
<223> OTHER INFORMATION: attLT1A PCR Primer

<400> SEQUENCE: 60
ggggagcctg ctttattata ctaagttggc attataaaaa agcattgc                48

<210> SEQ ID NO 61
<211> LENGTH: 48
<212> TYPE: DNA
<213> ORGANISM: Artificial Sequence
<220> FEATURE:
<223> OTHER INFORMATION: attLT1C PCR Primer

<400> SEQUENCE: 61
ggggagcctg ctttcttata ctaagttggc attataaaaa agcattgc                48

<210> SEQ ID NO 62
<211> LENGTH: 48
<212> TYPE: DNA
<213> ORGANISM: Artificial Sequence
<220> FEATURE:
<223> OTHER INFORMATION: attLT1G PCR Primer

<400> SEQUENCE: 62
ggggagcctg ctttgttata ctaagttggc attataaaaa agcattgc                48

<210> SEQ ID NO 63
<211> LENGTH: 48
<212> TYPE: DNA
<213> ORGANISM: Artificial Sequence
<220> FEATURE:
<223> OTHER INFORMATION: attLT2A PCR Primer

<400> SEQUENCE: 63
ggggagcctg cttttatata ctaagttggc attataaaaa agcattgc                48

<210> SEQ ID NO 64
<211> LENGTH: 48
<212> TYPE: DNA
<213> ORGANISM: Artificial Sequence
<220> FEATURE:
<223> OTHER INFORMATION: attLT2C PCR Primer -continued

<400> SEQUENCE: 64
ggggagcctg cttttctata ctaagttggc attataaaaa agcattgc 48

<210> SEQ ID NO 65
<211> LENGTH: 48
<212> TYPE: DNA
<213> ORGANISM: Artificial Sequence
<220> FEATURE:
<223> OTHER INFORMATION: attLT2G PCR Primer

<400> SEQUENCE: 65
ggggagcctg cttttgtata ctaagttggc attataaaaa agcattgc 48

<210> SEQ ID NO 66
<211> LENGTH: 48
<212> TYPE: DNA
<213> ORGANISM: Artificial Sequence
<220> FEATURE:
<223> OTHER INFORMATION: attLT3A PCR Primer

<400> SEQUENCE: 66
ggggagcctg ctttttaata ctaagttggc attataaaaa agcattgc 48

<210> SEQ ID NO 67
<211> LENGTH: 48
<212> TYPE: DNA
<213> ORGANISM: Artificial Sequence
<220> FEATURE:
<223> OTHER INFORMATION: attLT3C PCR Primer

<400> SEQUENCE: 67
ggggagcctg ctttttcata ctaagttggc attataaaaa agcattgc 48

<210> SEQ ID NO 68
<211> LENGTH: 48
<212> TYPE: DNA
<213> ORGANISM: Artificial Sequence
<220> FEATURE:
<223> OTHER INFORMATION: attLT3G PCR Primer

<400> SEQUENCE: 68
ggggagcctg ctttttgata ctaagttggc attataaaaa agcattgc 48

<210> SEQ ID NO 69
<211> LENGTH: 48
<212> TYPE: DNA
<213> ORGANISM: Artificial Sequence
<220> FEATURE:
<223> OTHER INFORMATION: attLA4C PCR Primer

<400> SEQUENCE: 69
ggggagcctg cttttttcta ctaagttggc attataaaaa agcattgc 48

<210> SEQ ID NO 70
<211> LENGTH: 48
<212> TYPE: DNA
<213> ORGANISM: Artificial Sequence
<220> FEATURE:
<223> OTHER INFORMATION: attLA4G PCR Primer

<400> SEQUENCE: 70
ggggagcctg cttttttgta ctaagttggc attataaaaa agcattgc 48

<210> SEQ ID NO 71
<211> LENGTH: 48

-continued

<212> TYPE: DNA
<213> ORGANISM: Artificial Sequence
<220> FEATURE:
<223> OTHER INFORMATION: attLA4T PCR Primer

<400> SEQUENCE: 71
ggggagcctg cttttttta ctaagttggc attataaaaa agcattgc 48

<210> SEQ ID NO 72
<211> LENGTH: 48
<212> TYPE: DNA
<213> ORGANISM: Artificial Sequence
<220> FEATURE:
<223> OTHER INFORMATION: attLT5A PCR Primer

<400> SEQUENCE: 72
ggggagcctg ctttttaaa ctaagttggc attataaaaa agcattgc 48

<210> SEQ ID NO 73
<211> LENGTH: 48
<212> TYPE: DNA
<213> ORGANISM: Artificial Sequence
<220> FEATURE:
<223> OTHER INFORMATION: attLT5C PCR Primer

<400> SEQUENCE: 73
ggggagcctg cttttttaca ctaagttggc attataaaaa agcattgc 48

<210> SEQ ID NO 74
<211> LENGTH: 48
<212> TYPE: DNA
<213> ORGANISM: Artificial Sequence
<220> FEATURE:
<223> OTHER INFORMATION: attLT5G PCR Primer

<400> SEQUENCE: 74
ggggagcctg cttttttaga ctaagttggc attataaaaa agcattgc 48

<210> SEQ ID NO 75
<211> LENGTH: 48
<212> TYPE: DNA
<213> ORGANISM: Artificial Sequence
<220> FEATURE:
<223> OTHER INFORMATION: attLA6C PCR Primer

<400> SEQUENCE: 75
ggggagcctg cttttttatc ctaagttggc attataaaaa agcattgc 48

<210> SEQ ID NO 76
<211> LENGTH: 48
<212> TYPE: DNA
<213> ORGANISM: Artificial Sequence
<220> FEATURE:
<223> OTHER INFORMATION: attLA6G PCR Primer

<400> SEQUENCE: 76
ggggagcctg cttttttatg ctaagttggc attataaaaa agcattgc 48

<210> SEQ ID NO 77
<211> LENGTH: 48
<212> TYPE: DNA
<213> ORGANISM: Artificial Sequence
<220> FEATURE:
<223> OTHER INFORMATION: attLA6T PCR Primer

<400> SEQUENCE: 77
ggggagcctg cttttttatt ctaagttggc attataaaaa agcattgc                48

<210> SEQ ID NO 78
<211> LENGTH: 48
<212> TYPE: DNA
<213> ORGANISM: Artificial Sequence
<220> FEATURE:
<223> OTHER INFORMATION: attLC7A PCR Primer

<400> SEQUENCE: 78
ggggagcctg cttttttata ataagttggc attataaaaa agcattgc                48

<210> SEQ ID NO 79
<211> LENGTH: 48
<212> TYPE: DNA
<213> ORGANISM: Artificial Sequence
<220> FEATURE:
<223> OTHER INFORMATION: attLC7G PCR Primer

<400> SEQUENCE: 79
ggggagcctg cttttttata gtaagttggc attataaaaa agcattgc                48

<210> SEQ ID NO 80
<211> LENGTH: 48
<212> TYPE: DNA
<213> ORGANISM: Artificial Sequence
<220> FEATURE:
<223> OTHER INFORMATION: attLC7T PCR Primer

<400> SEQUENCE: 80
ggggagcctg cttttttata ttaagttggc attataaaaa agcattgc                48

<210> SEQ ID NO 81
<211> LENGTH: 48
<212> TYPE: DNA
<213> ORGANISM: Artificial Sequence
<220> FEATURE:
<223> OTHER INFORMATION: attL8

<400> SEQUENCE: 81
ggggagccta cttttttata ctaagttggc attataaaaa agcattgc                48

<210> SEQ ID NO 82
<211> LENGTH: 48
<212> TYPE: DNA
<213> ORGANISM: Artificial Sequence
<220> FEATURE:
<223> OTHER INFORMATION: attL9

<400> SEQUENCE: 82
ggggagcctg cctttttata ctaagttggc attataaaaa agcattgc                48

<210> SEQ ID NO 83
<211> LENGTH: 48
<212> TYPE: DNA
<213> ORGANISM: Artificial Sequence
<220> FEATURE:
<223> OTHER INFORMATION: attL10

<400> SEQUENCE: 83
ggggagcctg cttctttata ctaagttggc attataaaaa agcattgc                48

<210> SEQ ID NO 84
<211> LENGTH: 48
<212> TYPE: DNA
<213> ORGANISM: Artificial Sequence -continued
<220> FEATURE:
<223> OTHER INFORMATION: attL14

<400> SEQUENCE: 84
ggggagcctg ctttttata ccaagttggc attataaaaa agcattgc 48

<210> SEQ ID NO 85
<211> LENGTH: 48
<212> TYPE: DNA
<213> ORGANISM: Artificial Sequence
<220> FEATURE:
<223> OTHER INFORMATION: attL15

<400> SEQUENCE: 85
ggggagcctg ctttttata ctaggttggc attataaaaa agcattgc 48

<210> SEQ ID NO 86
<211> LENGTH: 30
<212> TYPE: DNA
<213> ORGANISM: Artificial Sequence
<220> FEATURE:
<223> OTHER INFORMATION: attL0

<400> SEQUENCE: 86
agcctgcttt tttatactaa gttggcatta 30

<210> SEQ ID NO 87
<211> LENGTH: 30
<212> TYPE: DNA
<213> ORGANISM: Artificial Sequence
<220> FEATURE:
<223> OTHER INFORMATION: attL5

<400> SEQUENCE: 87
agcctgcttt attatactaa gttggcatta 30

<210> SEQ ID NO 88
<211> LENGTH: 30
<212> TYPE: DNA
<213> ORGANISM: Artificial Sequence
<220> FEATURE:
<223> OTHER INFORMATION: attL6

<400> SEQUENCE: 88
agcctgcttt tttatattaa gttggcatta 30

<210> SEQ ID NO 89
<211> LENGTH: 30
<212> TYPE: DNA
<213> ORGANISM: Artificial Sequence
<220> FEATURE:
<223> OTHER INFORMATION: attL13

<400> SEQUENCE: 89
agcctgcttt tttatgctaa gttggcatta 30

<210> SEQ ID NO 90
<211> LENGTH: 30
<212> TYPE: DNA
<213> ORGANISM: Artificial Sequence
<220> FEATURE:
<223> OTHER INFORMATION: attL14

<400> SEQUENCE: 90
agcctgcttt tttataccaa gttggcatta 30

-continued

<210> SEQ ID NO 91
<211> LENGTH: 30
<212> TYPE: DNA
<213> ORGANISM: Artificial Sequence
<220> FEATURE:
<223> OTHER INFORMATION: attL15

<400> SEQUENCE: 91
agcctgcttt tttatactag gttggcatta 30

<210> SEQ ID NO 92
<211> LENGTH: 21
<212> TYPE: DNA
<213> ORGANISM: Artificial Sequence
<220> FEATURE:
<223> OTHER INFORMATION: Consensus sequence for integrase core-binding
<220> FEATURE:
<221> NAME/KEY: misc_feature
<222> LOCATION: (7)..(8)
<223> OTHER INFORMATION: 'n' can be any nucleotide (A, T, C, G or U)
<220> FEATURE:
<221> NAME/KEY: misc_feature
<222> LOCATION: (10)..(12)
<223> OTHER INFORMATION: 'n' can be any nucleotide (A, T, C, G or U)
<220> FEATURE:
<221> NAME/KEY: misc_feature
<222> LOCATION: (14)..(15)
<223> OTHER INFORMATION: 'n' can be any nucleotide (A, T, C, G or U)

<400> SEQUENCE: 92
caacttnntn nnannaagtt g 21

<210> SEQ ID NO 93
<211> LENGTH: 25
<212> TYPE: DNA
<213> ORGANISM: Artificial Sequence
<220> FEATURE:
<223> OTHER INFORMATION: attB0

<400> SEQUENCE: 93
tcaagttagt ataaaaaagc aggct 25

<210> SEQ ID NO 94
<211> LENGTH: 29
<212> TYPE: DNA
<213> ORGANISM: Artificial Sequence
<220> FEATURE:
<223> OTHER INFORMATION: attB1

<400> SEQUENCE: 94
ggggacaagt ttgtacaaaa aagcaggct 29

<210> SEQ ID NO 95
<211> LENGTH: 29
<212> TYPE: DNA
<213> ORGANISM: Artificial Sequence
<220> FEATURE:
<223> OTHER INFORMATION: attB2

<400> SEQUENCE: 95
ggggaccact ttgtacaaga aagctgggt 29

<210> SEQ ID NO 96
<211> LENGTH: 29
<212> TYPE: DNA
<213> ORGANISM: Artificial Sequence
<220> FEATURE:
<223> OTHER INFORMATION: attB2.1

-continued

<400> SEQUENCE: 96
ggggaacact ttgtacaaga aagctgggt 29

<210> SEQ ID NO 97
<211> LENGTH: 29
<212> TYPE: DNA
<213> ORGANISM: Artificial Sequence
<220> FEATURE:
<223> OTHER INFORMATION: attB2.2

<400> SEQUENCE: 97
ggggacaact ttgtacaaga aagctgggt 29

<210> SEQ ID NO 98
<211> LENGTH: 29
<212> TYPE: DNA
<213> ORGANISM: Artificial Sequence
<220> FEATURE:
<223> OTHER INFORMATION: attB2.3

<400> SEQUENCE: 98
ggggacccct ttgtacaaga aagctgggt 29

<210> SEQ ID NO 99
<211> LENGTH: 29
<212> TYPE: DNA
<213> ORGANISM: Artificial Sequence
<220> FEATURE:
<223> OTHER INFORMATION: attB2.4

<400> SEQUENCE: 99
ggggaccaat ttgtacaaga aagctgggt 29

<210> SEQ ID NO 100
<211> LENGTH: 29
<212> TYPE: DNA
<213> ORGANISM: Artificial Sequence
<220> FEATURE:
<223> OTHER INFORMATION: attB2.5

<400> SEQUENCE: 100
ggggaccacg ttgtacaaga aagctgggt 29

<210> SEQ ID NO 101
<211> LENGTH: 29
<212> TYPE: DNA
<213> ORGANISM: Artificial Sequence
<220> FEATURE:
<223> OTHER INFORMATION: attB2.6

<400> SEQUENCE: 101
ggggaccact gtgtacaaga aagctgggt 29

<210> SEQ ID NO 102
<211> LENGTH: 29
<212> TYPE: DNA
<213> ORGANISM: Artificial Sequence
<220> FEATURE:
<223> OTHER INFORMATION: attB2.7

<400> SEQUENCE: 102
ggggaccact tggtacaaga aagctgggt 29

<210> SEQ ID NO 103

-continued

<211> LENGTH: 29
<212> TYPE: DNA
<213> ORGANISM: Artificial Sequence
<220> FEATURE:
<223> OTHER INFORMATION: attB2.8

<400> SEQUENCE: 103
ggggaccact ttttacaaga aagctgggt 29

<210> SEQ ID NO 104
<211> LENGTH: 29
<212> TYPE: DNA
<213> ORGANISM: Artificial Sequence
<220> FEATURE:
<223> OTHER INFORMATION: attB1 Amplification Site

<400> SEQUENCE: 104
ggggacaagt ttgtacaaaa aagcaggct 29

<210> SEQ ID NO 105
<211> LENGTH: 29
<212> TYPE: DNA
<213> ORGANISM: Artificial Sequence
<220> FEATURE:
<223> OTHER INFORMATION: attB1.6 Amplification Site

<400> SEQUENCE: 105
ggggacaact ttgtacaaaa aagttggct 29

<210> SEQ ID NO 106
<211> LENGTH: 29
<212> TYPE: DNA
<213> ORGANISM: Artificial Sequence
<220> FEATURE:
<223> OTHER INFORMATION: attB2 Amplification Site

<400> SEQUENCE: 106
ggggaccact ttgtacaaga aagctgggt 29

<210> SEQ ID NO 107
<211> LENGTH: 29
<212> TYPE: DNA
<213> ORGANISM: Artificial Sequence
<220> FEATURE:
<223> OTHER INFORMATION: attB2.10 Amplification Site

<400> SEQUENCE: 107
ggggacaact ttgtacaaga aagttgggt 29

<210> SEQ ID NO 108
<211> LENGTH: 29
<212> TYPE: DNA
<213> ORGANISM: Artificial Sequence
<220> FEATURE:
<223> OTHER INFORMATION: attB1 PCR Primer

<400> SEQUENCE: 108
ggggacaagt ttgtacaaaa aagcaggct 29

<210> SEQ ID NO 109
<211> LENGTH: 29
<212> TYPE: DNA
<213> ORGANISM: Artificial Sequence
<220> FEATURE:
<223> OTHER INFORMATION: attB1n16-20 PCR Primer
<220> FEATURE:
<221> NAME/KEY: misc_feature
<222> LOCATION: (20)..(24)
<223> OTHER INFORMATION: 'n' can be any nucleotide (A, T, C, G or U)

<400> SEQUENCE: 109
ggggacaagt ttgtacaaan nnnnaggct 29

<210> SEQ ID NO 110
<211> LENGTH: 29
<212> TYPE: DNA
<213> ORGANISM: Artificial Sequence
<220> FEATURE:
<223> OTHER INFORMATION: attB1n21-25 PCR Primer
<220> FEATURE:
<221> NAME/KEY: misc_feature
<222> LOCATION: (25)..(29)
<223> OTHER INFORMATION: 'n' can be any nucleotide (A, T, C, G or U)

<400> SEQUENCE: 110
ggggacaagt ttgtacaaaa aagcnnnnn 29

<210> SEQ ID NO 111
<211> LENGTH: 29
<212> TYPE: DNA
<213> ORGANISM: Artificial Sequence
<220> FEATURE:
<223> OTHER INFORMATION: attB2 PCR Primer

<400> SEQUENCE: 111
ggggaccact ttgtacaaga aagctgggt 29

<210> SEQ ID NO 112
<211> LENGTH: 29
<212> TYPE: DNA
<213> ORGANISM: Artificial Sequence
<220> FEATURE:
<223> OTHER INFORMATION: attB2n16-20 PCR Primer
<220> FEATURE:
<221> NAME/KEY: misc_feature
<222> LOCATION: (20)..(24)
<223> OTHER INFORMATION: 'n' can be any nucleotide (A, T, C, G or U)

<400> SEQUENCE: 112
ggggaccact ttgtacaagn nnnntgggt 29

<210> SEQ ID NO 113
<211> LENGTH: 29
<212> TYPE: DNA
<213> ORGANISM: Artificial Sequence
<220> FEATURE:
<223> OTHER INFORMATION: attB2n21-25 PCR Primer
<220> FEATURE:
<221> NAME/KEY: misc_feature
<222> LOCATION: (25)..(29)
<223> OTHER INFORMATION: 'n' can be any nucleotide (A, T, C, G or U)

<400> SEQUENCE: 113
ggggaccact ttgtacaaga aagcnnnnn 29

<210> SEQ ID NO 114
<211> LENGTH: 14
<212> TYPE: DNA
<213> ORGANISM: Artificial Sequence
<220> FEATURE:
<223> OTHER INFORMATION: 12bp attB1 forward gene-specific primer
<220> FEATURE:
<221> NAME/KEY: misc_feature
<222> LOCATION: (13)..(14)
<223> OTHER INFORMATION: 'n' can be any nucleotide (A, T, C, G or U)

-continued

<400> SEQUENCE: 114
aaaaagcagg ctnn 14

<210> SEQ ID NO 115
<211> LENGTH: 13
<212> TYPE: DNA
<213> ORGANISM: Artificial Sequence
<220> FEATURE:
<223> OTHER INFORMATION: 12bp attB2 reverse gene-specific primer
<220> FEATURE:
<221> NAME/KEY: misc_feature
<222> LOCATION: (13)..(13)
<223> OTHER INFORMATION: 'n' can be any nucleotide (A, T, C, G or U)

<400> SEQUENCE: 115
agaaagctgg gtn 13

<210> SEQ ID NO 116
<211> LENGTH: 29
<212> TYPE: DNA
<213> ORGANISM: Artificial Sequence
<220> FEATURE:
<223> OTHER INFORMATION: attB1 adapter primer

<400> SEQUENCE: 116
ggggacaagt ttgtacaaaa aagcaggct 29

<210> SEQ ID NO 117
<211> LENGTH: 29
<212> TYPE: DNA
<213> ORGANISM: Artificial Sequence
<220> FEATURE:
<223> OTHER INFORMATION: attB2 adapter primer

<400> SEQUENCE: 117
ggggaccact ttgtacaaga aagctgggt 29

<210> SEQ ID NO 118
<211> LENGTH: 2717
<212> TYPE: DNA
<213> ORGANISM: Artificial Sequence
<220> FEATURE:
<223> OTHER INFORMATION: Entry Vector pENTR1A
<220> FEATURE:
<221> NAME/KEY: gene
<222> LOCATION: (67)..(166)
<223> OTHER INFORMATION: attL1
<220> FEATURE:
<221> NAME/KEY: gene
<222> LOCATION: (321)..(626)
<223> OTHER INFORMATION: ccdB
<220> FEATURE:
<221> NAME/KEY: gene
<222> LOCATION: (655)..(754)
<223> OTHER INFORMATION: attL2
<220> FEATURE:
<221> NAME/KEY: gene
<222> LOCATION: (877)..(1686)
<223> OTHER INFORMATION: KmR
<220> FEATURE:
<221> NAME/KEY: gene
<222> LOCATION: (1791)..(2364)
<223> OTHER INFORMATION: ori

<400> SEQUENCE: 118
ctgacggatg gcctttttgc gtttctacaa actcttcctg ttagttagtt acttaagctc 60
gggccccaaa taatgatttt attttgactg atagtgacct gttcgttgca acaaattgat 120
aagcaatgct tttttataat gccaactttg tacaaaaaag caggctttaa aggaaccaat 180

-continued

```
tcagtcgact ggatccggta ccgaattcgc ttactaaaag ccagataaca gtatgcgtat    240
ttgcgcgctg atttttgcgg tataagaata tatactgata tgtatacccg aagtatgtca    300
aaaagaggtg tgcttctaga atgcagttta aggtttacac ctataaaaga gagagccgtt    360
atcgtctgtt tgtggatgta cagagtgata ttattgacac gcccgggcga cggatagtga    420
tccccctggc cagtgcacgt ctgctgtcag ataaagtctc ccgtgaactt tacccggtgg    480
tgcatatcgg ggatgaaagc tggcgcatga tgaccaccga tatggccagt gtgccggtct    540
ccgttatcgg ggaagaagtg gctgatctca gccaccgcga aatgacatc aaaaacgcca    600
ttaacctgat gttctgggga atatagaatt cgcggccgca ctcgagatat ctagacccag    660
ctttcttgta caaagttggc attataagaa agcattgctt atcaatttgt tgcaacgaac    720
aggtcactat cagtcaaaat aaaatcatta tttgccatcc agctgcagct ctggcccgtg    780
tctcaaaatc tctgatgtta cattgcacaa gataaaaata tatcatcatg aacaataaaa    840
ctgtctgctt acataaacag taatacaagg ggtgttatga gccatattca acgggaaacg    900
tcgaggccgc gattaaattc caacatggat gctgatttat atgggtataa atgggctcgc    960
gataatgtcg ggcaatcagg tgcgacaatc tatcgcttgt atgggaagcc cgatgcgcca   1020
gagttgtttc tgaaacatgg caaaggtagc gttgccaatg atgttacaga tgagatggtc   1080
agactaaact ggctgacgga atttatgcct cttccgacca tcaagcattt tatccgtact   1140
cctgatgatg catggttact caccactgcg atccccggaa aaacagcatt ccaggtatta   1200
gaagaatatc ctgattcagg tgaaaatatt gttgatgcgc tggcagtgtc cctgcgccgg   1260
ttgcattcga ttcctgtttg taattgtcct tttaacagcg atcgcgtatt tcgtctcgct   1320
caggcgcaat cacgaatgaa taacggtttg gttgatgcga gtgattttga tgacgagcgt   1380
aatggctggc ctgttgaaca agtctggaaa gaaatgcata aacttttgcc attctcaccg   1440
gattcagtcg tcactcatgg tgatttctca cttgataacc ttatttttga cgaggggaaa   1500
ttaataggtt gtattgatgt tggacgagtc ggaatcgcag accgatacca ggatcttgcc   1560
atcctatgga actgcctcgg tgagttttct ccttcattac agaaacggct ttttcaaaaa   1620
tatggtattg ataatcctga tatgaataaa ttgcagtttc atttgatgct cgatgagttt   1680
ttctaatcag aattggttaa ttggttgtaa cattattcag attgggcccc gttccactga   1740
gcgtcagacc ccgtagaaaa gatcaaagga tcttcttgag atcctttttt tctgcgcgta   1800
atctgctgct tgcaaacaaa aaaaccaccg ctaccagcgg tggtttgttt gccggatcaa   1860
gagctaccaa ctctttttcc gaaggtaact ggcttcagca gagcgcagat accaaatact   1920
gttcttctag tgtagccgta gttaggccac cacttcaaga actctgtagc accgcctaca   1980
tacctcgctc tgctaatcct gttaccagtg gctgctgcca gtggcgataa gtcgtgtctt   2040
accgggttgg actcaagacg atagttaccg gataaggcgc agcggtcggg ctgaacgggg   2100
ggttcgtgca cacagcccag cttggagcga acgacctaca ccgaactgag atacctacag   2160
cgtgagctat gagaaagcgc cacgcttccc gaagggagaa aggcggacag gtatccggta   2220
agcggcaggg tcggaacagg agagcgcacg agggagcttc caggggaaa cgcctggtat    2280
ctttatagtc ctgtcgggtt tcgccacctc tgacttgagc gtcgattttt gtgatgctcg   2340
tcaggggggc ggagcctatg gaaaaacgcc agcaacgcgg cctttttacg gttcctggcc   2400
ttttgctggc cttttgctca catgttcttt cctgcgttat cccctgattc tgtggataac   2460
cgtattaccg ctagcatgga tctcggggac gtctaactac taagcgagag tagggaactg   2520
```

-continued

```
ccaggcatca aataaaacga aaggctcagt cggaagactg ggcctttcgt tttatctgtt   2580

gtttgtcggt gaacgctctc ctgagtagga caaatccgcc gggagcggat ttgaacgttg   2640

tgaagcaacg gcccggaggg tggcgggcag gacgcccgcc ataaactgcc aggcatcaaa   2700

ctaagcagaa ggccatc                                                 2717
```

<210> SEQ ID NO 119
<211> LENGTH: 2718
<212> TYPE: DNA
<213> ORGANISM: Artificial Sequence
<220> FEATURE:
<223> OTHER INFORMATION: Entry Vector pENTR2B
<220> FEATURE:
<221> NAME/KEY: gene
<222> LOCATION: (67)..(166)
<223> OTHER INFORMATION: attL1
<220> FEATURE:
<221> NAME/KEY: gene
<222> LOCATION: (322)..(627)
<223> OTHER INFORMATION: ccdB
<220> FEATURE:
<221> NAME/KEY: gene
<222> LOCATION: (656)..(755)
<223> OTHER INFORMATION: attL2
<220> FEATURE:
<221> NAME/KEY: gene
<222> LOCATION: (878)..(1687)
<223> OTHER INFORMATION: KmR
<220> FEATURE:
<221> NAME/KEY: gene
<222> LOCATION: (1792)..(2365)
<223> OTHER INFORMATION: ori

<400> SEQUENCE: 119

```
ctgacggatg gcctttttgc gtttctacaa actcttcctg ttagttagtt acttaagctc     60

gggccccaaa taatgatttt attttgactg atagtgacct gttcgttgca acaaattgat    120

aagcaatgct tttttataat gccaactttg tacaaaaaag caggctggcg ccggaaccaa    180

ttcagtcgac tggatccggt accgaattcg cttactaaaa gccagataac agtatgcgta    240

tttgcgcgct gatttttgcg gtataagaat atatactgat atgtataccc gaagtatgtc    300

aaaaagaggt gtgcttctag aatgcagttt aaggtttaca cctataaaag agagagccgt    360

tatcgtctgt ttgtggatgt acagagtgat attattgaca cgcccgggcg acggatggtg    420

atccccctgg ccagtgcacg tctgctgtca gataaagtct cccgtgaact ttacccggtg    480

gtgcatatcg gggatgaaag ctggcgcatg atgaccaccg atatggccag tgtgccggtc    540

tccgttatcg gggaagaagt ggctgatctc agccaccgcg aaaatgacat caaaaacgcc    600

attaacctga tgttctgggg aatatagaat tcgcggccgc actcgagata tctagaccca    660

gctttcttgt acaaagttgg cattataaga aagcattgct tatcaatttg ttgcaacgaa    720

caggtcacta tcagtcaaaa taaaatcatt atttgccatc cagctgcagc tctggcccgt    780

gtctcaaaat ctctgatgtt acattgcaca agataaaaat atatcatcat gaacaataaa    840

actgtctgct tacataaaca gtaatacaag gggtgttatg agccatattc aacgggaaac    900

gtcgaggccg cgattaaatt ccaacatgga tgctgattta tatgggtata aatgggctcg    960

cgataatgtc gggcaatcag gtgcgacaat ctatcgcttg tatgggaagc ccgatgcgcc   1020

agagttgttt ctgaaacatg gcaaaggtag cgttgccaat gatgttacag atgagatggt   1080

cagactaaac tggctgacgg aatttatgcc tcttccgacc atcaagcatt ttatccgtac   1140

tcctgatgat gcatggttac tcaccactgc gatccccgga aaaacagcat tccaggtatt   1200

agaagaatat cctgattcag gtgaaaatat tgttgatgcg ctggcagtgt tcctgcgccg   1260
```

```
gttgcattcg attcctgttt gtaattgtcc ttttaacagc gatcgcgtat ttcgtctcgc   1320

tcaggcgcaa tcacgaatga ataacggttt ggttgatgcg agtgattttg atgacgagcg   1380

taatggctgg cctgttgaac aagtctggaa agaaatgcat aaacttttgc cattctcacc   1440

ggattcagtc gtcactcatg gtgatttctc acttgataac cttatttttg acgaggggaa   1500

attaataggt tgtattgatg ttggacgagt cggaatcgca gaccgatacc aggatcttgc   1560

catcctatgg aactgcctcg gtgagttttc tccttcatta cagaaacggc tttttcaaaa   1620

atatggtatt gataatcctg atatgaataa attgcagttt catttgatgc tcgatgagtt   1680

tttctaatca gaattggtta attggttgta acattattca gattgggccc cgttccactg   1740

agcgtcagac cccgtagaaa agatcaaagg atcttcttga gatccttttt ttctgcgcgt   1800

aatctgctgc ttgcaaacaa aaaaaccacc gctaccagcg gtggtttgtt tgccggatca   1860

agagctacca actctttttc cgaaggtaac tggcttcagc agagcgcaga taccaaatac   1920

tgttcttcta gtgtagccgt agttaggcca ccacttcaag aactctgtag caccgcctac   1980

atacctcgct ctgctaatcc tgttaccagt ggctgctgcc agtggcgata agtcgtgtct   2040

taccgggttg gactcaagac gatagttacc ggataaggcg cagcggtcgg gctgaacggg   2100

gggttcgtgc acacagccca gcttggagcg aacgacctac accgaactga gatacctaca   2160

gcgtgagcta tgagaaagcg ccacgcttcc cgaagggaga aaggcggaca ggtatccggt   2220

aagcggcagg gtcggaacag gagagcgcac gagggagctt ccagggggaa acgcctggta   2280

tctttatagt cctgtcgggt ttcgccacct ctgacttgag cgtcgatttt tgtgatgctc   2340

gtcagggggg cggagcctat ggaaaaacgc cagcaacgcg gcctttttac ggttcctggc   2400

cttttgctgg ccttttgctc acatgttctt tcctgcgtta tcccctgatt ctgtggataa   2460

ccgtattacc gctagcatgg atctcgggga cgtctaacta ctaagcgaga gtagggaact   2520

gccaggcatc aaataaaacg aaaggctcag tcggaagact gggcctttcg ttttatctgt   2580

tgtttgtcgg tgaacgctct cctgagtagg acaaatccgc cgggagcgga tttgaacgtt   2640

gtgaagcaac ggcccggagg gtggcgggca ggacgcccgc cataaactgc caggcatcaa   2700

actaagcaga aggccatc                                                 2718
```

```
<210> SEQ ID NO 120
<211> LENGTH: 2723
<212> TYPE: DNA
<213> ORGANISM: Artificial Sequence
<220> FEATURE:
<223> OTHER INFORMATION: Entry Vector pENTR3C
<220> FEATURE:
<221> NAME/KEY: gene
<222> LOCATION: (67)..(166)
<223> OTHER INFORMATION: attL1
<220> FEATURE:
<221> NAME/KEY: gene
<222> LOCATION: (327)..(632)
<223> OTHER INFORMATION: ccdB
<220> FEATURE:
<221> NAME/KEY: gene
<222> LOCATION: (661)..(760)
<223> OTHER INFORMATION: attL2
<220> FEATURE:
<221> NAME/KEY: gene
<222> LOCATION: (883)..(1692)
<223> OTHER INFORMATION: KmR
<220> FEATURE:
<221> NAME/KEY: gene
<222> LOCATION: (1797)..(2370)
<223> OTHER INFORMATION: ori
```

-continued

<400> SEQUENCE: 120
ctgacggatg gccttttgc gtttctacaa actcttcctg ttagttagtt acttaagctc 60
gggccccaaa taatgatttt attttgactg atagtgacct gttcgttgca acaaattgat 120
aagcaatgct tttttataat gccaactttg tacaaaaaag caggctcttt aaaggaacca 180
attcagtcga ctggatccgg taccgaattc gatcgcttac taaaagccag ataacagtat 240
gcgtatttgc gcgctgattt ttgcggtata agaatatata ctgatatgta tacccgaagt 300
atgtcaaaaa gaggtgtgct tctagaatgc agtttaaggt ttacacctat aaaagagaga 360
gccgttatcg tctgtttgtg gatgtacaga gtgatattat tgacacgccc gggcgacgga 420
tggtgatccc cctggccagt gcacgtctgc tgtcagataa agtctcccgt gaactttacc 480
cggtggtgca tatcggggat gaaagctggc gcatgatgac caccgatatg gccagtgtgc 540
cggtctccgt tatcggggaa gaagtggctg atctcagcca ccgcgaaaat gacatcaaaa 600
acgccattaa cctgatgttc tggggaatat agaattcgcg gccgcactcg agatatctag 660
acccagcttt cttgtacaaa gttggcatta taagaaagca ttgcttatca atttgttgca 720
acgaacaggt cactatcagt caaaataaaa tcattatttg ccatccagct gcagctctgg 780
cccgtgtctc aaaatctctg atgttacatt gcacaagata aaaatatatc atcatgaaca 840
ataaaactgt ctgcttacat aaacagtaat acaaggggtg ttatgagcca tattcaacgg 900
gaaacgtcga ggccgcgatt aaattccaac atggatgctg atttatatgg gtataaatgg 960
gctcgcgata atgtcgggca atcaggtgcg acaatctatc gcttgtatgg gaagcccgat 1020
gcgccagagt tgtttctgaa acatggcaaa ggtagcgttg ccaatgatgt tacagatgag 1080
atggtcagac taaactggct gacggaattt atgcctcttc cgaccatcaa gcattttatc 1140
cgtactcctg atgatgcatg gttactcacc actgcgatcc ccggaaaaac agcattccag 1200
gtattagaag aatatcctga ttcaggtgaa aatattgttg atgcgctggc agtgttcctg 1260
cgccggttgc attcgattcc tgtttgtaat tgtcctttta acagcgatcg cgtatttcgt 1320
ctcgctcagg cgcaatcacg aatgaataac ggtttggttg atgcgagtga ttttgatgac 1380
gagcgtaatg gctggcctgt tgaacaagtc tggaaagaaa tgcataaact tttgccattc 1440
tcaccggatt cagtcgtcac tcatggtgat ttctcacttg ataaccttat ttttgacgag 1500
gggaaattaa taggttgtat tgatgttgga cgagtcggaa tcgcagaccg ataccaggat 1560
cttgccatcc tatggaactg cctcggtgag ttttctcctt cattacagaa acggcttttt 1620
caaaaatatg gtattgataa tcctgatatg aataaattgc agtttcattt gatgctcgat 1680
gagtttttct aatcagaatt ggttaattgg ttgtaacatt attcagattg ggccccgttc 1740
cactgagcgt cagaccccgt agaaaagatc aaaggatctt cttgagatcc tttttttctg 1800
cgcgtaatct gctgcttgca aacaaaaaaa ccaccgctac cagcggtggt ttgtttgccg 1860
gatcaagagc taccaactct ttttccgaag gtaactggct tcagcagagc gcagatacca 1920
aatactgttc ttctagtgta gccgtagtta ggccaccact tcaagaactc tgtagcaccg 1980
cctacatacc tcgctctgct aatcctgtta ccagtggctg ctgccagtgg cgataagtcg 2040
tgtcttaccg ggttggactc aagacgatag ttaccggata aggcgcagcg gtcgggctga 2100
acggggggtt cgtgcacaca gcccagcttg gagcgaacga cctacaccga actgagatac 2160
ctacagcgtg agctatgaga aagcgccacg cttcccgaag ggagaaaggc ggacaggtat 2220
ccggtaagcg gcagggtcgg aacaggagag cgcacgaggg agcttccagg gggaaacgcc 2280
tggtatcttt atagtcctgt cgggtttcgc cacctctgac ttgagcgtcg atttttgtga 2340

-continued tgctcgtcag gggggcggag cctatggaaa aacgccagca acgcggcctt tttacggttc 2400
ctggcctttt gctggccttt tgctcacatg ttctttcctg cgttatcccc tgattctgtg 2460
gataaccgta ttaccgctag catggatctc ggggacgtct aactactaag cgagagtagg 2520
gaactgccag gcatcaaata aaacgaaagg ctcagtcgga agactgggcc tttcgtttta 2580
tctgttgttt gtcggtgaac gctctcctga gtaggacaaa tccgccggga gcggatttga 2640
acgttgtgaa gcaacggccc ggagggtggc gggcaggacg cccgccataa actgccaggc 2700
atcaaactaa gcagaaggcc atc 2723

<210> SEQ ID NO 121
<211> LENGTH: 2720
<212> TYPE: DNA
<213> ORGANISM: Artificial Sequence
<220> FEATURE:
<223> OTHER INFORMATION: Entry Vector pENTR4
<220> FEATURE:
<221> NAME/KEY: gene
<222> LOCATION: (67)..(166)
<223> OTHER INFORMATION: attL1
<220> FEATURE:
<221> NAME/KEY: gene
<222> LOCATION: (324)..(629)
<223> OTHER INFORMATION: ccdB
<220> FEATURE:
<221> NAME/KEY: gene
<222> LOCATION: (658)..(757)
<223> OTHER INFORMATION: attL2
<220> FEATURE:
<221> NAME/KEY: gene
<222> LOCATION: (880)..(1689)
<223> OTHER INFORMATION: KmR
<220> FEATURE:
<221> NAME/KEY: gene
<222> LOCATION: (1794)..(2367)
<223> OTHER INFORMATION: ori

<400> SEQUENCE: 121
ctgacggatg gcctttttgc gtttctacaa actcttcctg ttagttagtt acttaagctc 60
gggccccaaa taatgatttt attttgactg atagtgacct gttcgttgca acaaattgat 120
aagcaatgct tttttataat gccaactttg tacaaaaaag caggctccac catgggaacc 180
aattcagtcg actggatccg gtaccgaatt cgcttactaa aagccagata acagtatgcg 240
tatttgcgcg ctgatttttg cggtataaga atatatactg atatgtatac ccgaagtatg 300
tcaaaaagag gtgtgcttct agaatgcagt ttaaggttta cacctataaa agagagagcc 360
gttatcgtct gtttgtggat gtacagagtg atattattga cacgcccggg cgacggatgg 420
tgatccccct ggccagtgca cgtctgctgt cagataaagt ctcccgtgaa ctttacccgg 480
tggtgcatat cggggatgaa agctggcgca tgatgaccac cgatatggcc agtgtgccgg 540
tctccgttat cggggaagaa gtggctgatc tcagccaccg cgaaaatgac atcaaaaacg 600
ccattaacct gatgttctgg ggaatataga attcgcggcc gcactcgaga tatctagacc 660
cagctttctt gtacaaagtt ggcattataa gaaagcattg cttatcaatt tgttgcaacg 720
aacaggtcac tatcagtcaa aataaaatca ttatttgcca tccagctgca gctctggccc 780
gtgtctcaaa atctctgatg ttacattgca caagataaaa atatatcatc atgaacaata 840
aaactgtctg cttacataaa cagtaataca aggggtgtta tgagccatat tcaacgggaa 900
acgtcgaggc cgcgattaaa ttccaacatg gatgctgatt tatatgggta taaatgggct 960
cgcgataatg tcgggcaatc aggtgcgaca atctatcgct tgtatgggaa gcccgatgcg 1020

-continued

```
ccagagttgt ttctgaaaca tggcaaaggt agcgttgcca atgatgttac agatgagatg   1080

gtcagactaa actggctgac ggaatttatg cctcttccga ccatcaagca ttttatccgt   1140

actcctggtg atgcatggtt actcaccact gcgatccccg gaaaaacagc attccaggta   1200

ttagaagaat atcctgattc aggtgaaaat attgttgatg cgctggcagt gttcctgcgc   1260

cggttgcatt cgattcctgt ttgtaattgt ccttttaaca gcgatcgcgt atttcgtctc   1320

gctcaggcgc aatcacgaat gaataacggt ttggttgatg cgagtgattt tgatgacgag   1380

cgtaatggct ggcctgttga acaagtctgg aaagaaatgc ataaactttt gccattctca   1440

ccggattcag tcgtcactca tggtgatttc tcacttgata accttatttt tgacgagggg   1500

aaattaatag gttgtattga tgttggacga gtcggaatcg cagaccgata ccaggatctt   1560

gccatcctat ggaactgcct cggtgagttt tctccttcat tacagaaacg gctttttcaa   1620

aaatatggta ttgataatcc tgatatgaat aaattgcagt ttcatttgat gctcgatgag   1680

tttttctaat cagaattggt taattggttg taacattatt cagattgggc cccgttccac   1740

tgagcgtcag accccgtaga aaagatcaaa ggatcttctt gagatccttt ttttctgcgc   1800

gtaatctgct gcttgcaaac aaaaaaacca ccgctaccag cggtggtttg tttgccggat   1860

caagagctac caactctttt tccgaaggta actggcttca gcagagcgca gataccaaat   1920

actgttcttc tagtgtagcc gtagttaggc caccacttca agaactctgt agcaccgcct   1980

acatacctcg ctctgctaat cctgttacca gtggctgctg ccagtggcga taagtcgtgt   2040

cttaccgggt tggactcaag acgatagtta ccggataagg cgcagcggtc gggctgaacg   2100

gggggttcgt gcacacagcc cagcttggag cgaacgacct acaccgaact gagataccta   2160

cagcgtgagc tatgagaaag cgccacgctt cccgaaggga gaaaggcgga caggtatccg   2220

gtaagcggca gggtcggaac aggagagcgc acgagggagc ttccaggggg aaacgcctgg   2280

tatctttata gtcctgtcgg gtttcgccac ctctgacttg agcgtcgatt tttgtgatgc   2340

tcgtcagggg ggcggagcct atggaaaaac gccagcaacg cggccttttt acggttcctg   2400

gccttttgct ggccttttgc tcacatgttc tttcctgcgt tatcccctga ttctgtggat   2460

aaccgtatta ccgctagcat ggatctcggg gacgtctaac tactaagcga gagtagggaa   2520

ctgccaggca tcaaataaaa cgaaaggctc agtcggaaga ctgggccttt cgttttatct   2580

gttgtttgtc ggtgaacgct ctcctgagta ggacaaatcc gccgggagcg gatttgaacg   2640

ttgtgaagca acggcccgga gggtggcggg caggacgccc gccataaact gccaggcatc   2700

aaactaagca gaaggccatc                                                2720
```

```
<210> SEQ ID NO 122
<211> LENGTH: 2720
<212> TYPE: DNA
<213> ORGANISM: Artificial Sequence
<220> FEATURE:
<223> OTHER INFORMATION: Entry Vector pENTR5
<220> FEATURE:
<221> NAME/KEY: gene
<222> LOCATION: (67)..(166)
<223> OTHER INFORMATION: attL1
<220> FEATURE:
<221> NAME/KEY: gene
<222> LOCATION: (324)..(629)
<223> OTHER INFORMATION: ccdB
<220> FEATURE:
<221> NAME/KEY: gene
<222> LOCATION: (658)..(757)
<223> OTHER INFORMATION: attL2
<220> FEATURE:
<221> NAME/KEY: gene
```

-continued

<222> LOCATION: (880)..(1689)
<223> OTHER INFORMATION: KmR
<220> FEATURE:
<221> NAME/KEY: gene
<222> LOCATION: (1794)..(2367)
<223> OTHER INFORMATION: ori

<400> SEQUENCE: 122
ctgacggatg gccttttttgc gtttctacaa actcttcctg ttagttagtt acttaagctc 60
gggccccaaa taatgatttt attttgactg atagtgacct gttcgttgca acaaattgat 120
aagcaatgct tttttataat gccaactttg tacaaaaaag caggctttca tatgggaacc 180
aattcagtcg actggatccg gtaccgaatt cgcttactaa aagccagata acagtatgcg 240
tatttgcgcg ctgatttttg cggtataaga atatatactg atatgtatac ccgaagtatg 300
tcaaaaagag gtgtgcttct agaatgcagt ttaaggttta cacctataaa agagagagcc 360
gttatcgtct gtttgtggat gtacagagtg atattattga cacgcccggg cgacggatgg 420 tgatcccccct ggccagtgca cgtctgctgt cagataaagt ctcccgtgaa ctttacccgg 480
tggtgcatat cggggatgaa agctggcgca tgatgaccac cgatatggcc agtgtgccgg 540
tctccgttat cggggaagaa gtggctgatc tcagccaccg cgaaaatgac atcaaaaacg 600
ccattaacct gatgttctgg ggaatataga attcgcggcc gcactcgaga tatctagacc 660
cagctttctt gtacaaagtt ggcattataa gaaagcattg cttatcaatt tgttgcaacg 720
aacaggtcac tatcagtcaa aataaaatca ttatttgcca tccagctgca gctctggccc 780
gtgtctcaaa atctctgatg ttacattgca caagataaaa atatatcatc atgaacaata 840
aaactgtctg cttacataaa cagtaataca aggggtgtta tgagccatat tcaacgggaa 900
acgtcgaggc cgcgattaaa ttccaacatg gatgctgatt tatatgggta taaatgggct 960
cgcgataatg tcgggcaatc aggtgcgaca atctatcgct tgtatgggaa gcccgatgcg 1020
ccagagttgt ttctgaaaca tggcaaaggt agcgttgcca atgatgttac agatgagatg 1080
gtcagactaa actggctgac ggaatttatg cctcttccga ccatcaagca ttttatccgt 1140
actcctgatg atgcatggtt actcaccact gcgatccccg gaaaaacagc attccaggta 1200
ttagaagaat atcctgattc aggtgaaaat attgttgatg cgctggcagt gttcctgcgc 1260
cggttgcatt cgattcctgt ttgtaattgt ccttttaaca gcgatcgcgt atttcgtctc 1320
gctcaggcgc aatcacgaat gaataacggt ttggttgatg cgagtgattt tgatgacgag 1380
cgtaatggct ggcctgttga acaagtctgg aaagaaatgc ataaactttt gccattctca 1440
ccggattcag tcgtcactca tggtgatttc tcacttgata accttatttt tgacgagggg 1500
aaattaatag gttgtattga tgttggacga gtcggaatcg cagaccgata ccaggatctt 1560
gccatcctat ggaactgcct cggtgagttt tctccttcat tacagaaacg gctttttcaa 1620
aaatatggta ttgataatcc tgatatgaat aaattgcagt ttcatttgat gctcgatgag 1680
tttttctaat cagaattggt taattggttg taacattatt cagattgggc cccgttccac 1740
tgagcgtcag accccgtaga aaagatcaaa ggatcttctt gagatccttt ttttctgcgc 1800
gtaatctgct gcttgcaaac aaaaaaacca ccgctaccag cggtggtttg tttgccggat 1860
caagagctac caactctttt tccgaaggta actggcttca gcagagcgca gataccaaat 1920
actgttcttc tagtgtagcc gtagttaggc caccacttca agaactctgt agcaccgcct 1980
acatacctcg ctctgctaat cctgttacca gtggctgctg ccagtggcga taagtcgtgt 2040
cttaccgggt tggactcaag acgatagtta ccggataagg cgcagcggtc gggctgaacg 2100

-continued

```
gggggttcgt gcacacagcc cagcttggag cgaacgacct acaccgaact gagataccta   2160

cagcgtgagc tatgagaaag cgccacgctt cccgaaggga gaaaggcgga caggtatccg   2220

gtaagcggca gggtcggaac aggagagcgc acgagggagc ttccaggggg aaacgcctgg   2280

tatctttata gtcctgtcgg gtttcgccac ctctgacttg agcgtcgatt tttgtgatgc   2340

tcgtcagggg ggcggagcct atggaaaaac gccagcaacg cggccttttt acggttcctg   2400

gccttttgct ggccttttgc tcacatgttc tttcctgcgt tatcccctga ttctgtggat   2460

aaccgtatta ccgctagcat ggatctcggg gacgtctaac tactaagcga gagtagggaa   2520

ctgccaggca tcgaataaaa cgaaaggctc agtcggaaga ctgggccttt cgttttatct   2580

gttgtttgtc ggtgaacgct ctcctgagta ggacaaatcc gccgggagcg gatttgaacg   2640

ttgtgaagca acggcccgga gggtggcggg caggacgccc gccataaact gccaggcatc   2700

aaactaagca gaaggccatc                                                2720
```

<210> SEQ ID NO 123
<211> LENGTH: 2717
<212> TYPE: DNA
<213> ORGANISM: Artificial Sequence
<220> FEATURE:
<223> OTHER INFORMATION: Entry Vector pENTR6
<220> FEATURE:
<221> NAME/KEY: gene
<222> LOCATION: (67)..(166)
<223> OTHER INFORMATION: attL1
<220> FEATURE:
<221> NAME/KEY: gene
<222> LOCATION: (321)..(626)
<223> OTHER INFORMATION: ccdB
<220> FEATURE:
<221> NAME/KEY: gene
<222> LOCATION: (655)..(754)
<223> OTHER INFORMATION: attL2
<220> FEATURE:
<221> NAME/KEY: gene
<222> LOCATION: (877)..(1686)
<223> OTHER INFORMATION: KmR
<220> FEATURE:
<221> NAME/KEY: gene
<222> LOCATION: (1791)..(2364)
<223> OTHER INFORMATION: ori

<400> SEQUENCE: 123

```
ctgacggatg gcctttttgc gtttctacaa actcttcctg ttagttagtt acttaagctc     60

gggccccaaa taatgatttt attttgactg atagtgacct gttcgttgca acaaattgat    120

aagcaatgct tttttataat gccaactttg tacaaaaaag caggctgcat gcgaaccaat    180

tcagtcgact ggatccggta ccgaattcgc ttactaaaag ccagataaca gtatgcgtat    240

ttgcgcgctg atttttgcgg tataagaata tatactgata tgtatacccg aagtatgtca    300

aaaagaggtg tgcttctaga atgcagttta aggtttacac ctataaaaga gagagccgtt    360

atcgtctgtt tgtggatgta cagagtgata ttattgacac gcccgggcga cggatggtga    420

tccccctggc cagtgcacgt ctgctgtcag ataaagtctc ccgtgaactt tacccggtgg    480

tgcatatcgg ggatgaaagc tggcgcatga tgaccaccga tatggccagt gtgccggtct    540

ccgttatcgg ggaagaagtg gctgatctca gccaccgcga aaatgacatc aaaaacgcca    600

ttaacctgat gttctgggga atatagaatt cgcggccgca ctcgagatat ctagacccag    660

ctttcttgta caaagttggc attataagaa agcattgctt atcaatttgt tgcaacgaac    720

aggtcactat cagtcaaaat aaaatcatta tttgccatcc agctgcagct ctggcccgtg    780

tctcaaaatc tctgatgtta cattgcacaa gataaaaata tatcatcatg aacaataaaa    840
```

-continued

```
ctgtctgctt acataaacag taatacaagg ggtgttatga gccatattca acgggaaacg     900

tcgaggccgc gattaaattc caacatggat gctgatttat atgggtataa atgggctcgc     960

gataatgtcg ggcaatcagg tgcgacaatc tatcgcttgt atgggaagcc cgatgcgcca    1020

gagttgtttc tgaaacatgg caaaggtagc gttgccaatg atgttacaga tgagatggtc    1080

agactaaact ggctgacgga atttatgcct cttccgacca tcaagcattt tatccgtact    1140

cctgatgatg catggttact caccactgcg atccccggaa aaacagcatt ccaggtatta    1200

gaagaatatc ctgattcagg tgaaaatatt gttgatgcgc tggcagtgtt cctgcgccgg    1260

ttgcattcga ttcctgtttg taattgtcct tttaacagcg atcgcgtatt tcgtctcgct    1320

caggcgcaat cacgaatgaa taacggtttg gttgatgcga gtgattttga tgacgagcgt    1380

aatggctggc ctgttgaaca agtctggaaa gaaatgcata aacttttgcc attctcaccg    1440

gattcagtcg tcactcatgg tgatttctca cttgataacc ttatttttga cgaggggaaa    1500

ttaataggtt gtattgatgt tggacgagtc ggaatcgcag accgatacca ggatcttgcc    1560

atcctatgga actgcctcgg tgagttttct ccttcattac agaaacggct ttttcaaaaa    1620

tatggtattg ataatcctga tatgaataaa ttgcagtttc atttgatgct cgatgagttt    1680

ttctaatcag aattggttaa ttggttgtaa cattattcag attgggcccc gttccactga    1740

gcgtcagacc ccgtagaaaa gatcaaagga tcttcttgag atcctttttt tctgcgcgta    1800

atctgctgct tgcaaacaaa aaaaccaccg ctaccagcgg tggtttgttt gccggatcaa    1860

gagctaccaa ctctttttcc gaaggtaact ggcttcagca gagcgcagat accaaatact    1920

gttcttctag tgtagccgta gttaggccac cacttcaaga actctgtagc accgcctaca    1980

tacctcgctc tgctaatcct gttaccagtg gctgctgcca gtggcgataa gtcgtgtctt    2040

accgggttgg actcaagacg atagttaccg gataaggcgc agcggtcggg ctgaacgggg    2100

ggttcgtgca cacagcccag cttggagcga acgacctaca ccgaactgag atacctacag    2160

cgtgagctat gagaaagcgc cacgcttccc gaagggagaa aggcggacag gtatccggta    2220

agcggcaggg tcggaacagg agagcgcacg agggagcttc cagggggaaa cgcctggtat    2280

ctttatagtc ctgtcgggtt tcgccacctc tgacttgagc gtcgattttt gtgatgctcg    2340

tcaggggggc ggagcctatg gaaaaacgcc agcaacgcgg cctttttacg gttcctggcc    2400

ttttgctggc cttttgctca catgttcttt cctgcgttat cccctgattc tgtggataac    2460

cgtattaccg ctagcatgga tctcggggac gtctaactac taagcgagag tagggaactg    2520

ccaggcatca aataaaacga aaggctcagt cggaagactg ggcctttcgt tttatctgtt    2580

gtttgtcggt gaacgctctc ctgagtagga caaatccgcc gggagcggat ttgaacgttg    2640

tgaagcaacg gcccggaggg tggcgggcag gacgcccgcc ataaactgcc aggcatcaaa    2700

ctaagcagaa ggccatc                                                   2717
```

<210> SEQ ID NO 124
<211> LENGTH: 2738
<212> TYPE: DNA
<213> ORGANISM: Artificial Sequence
<220> FEATURE:
<223> OTHER INFORMATION: Entry Vector pENTR7
<220> FEATURE:
<221> NAME/KEY: gene
<222> LOCATION: (67)..(166)
<223> OTHER INFORMATION: attL1
<220> FEATURE:
<221> NAME/KEY: gene
<222> LOCATION: (342)..(647)

-continued

<223> OTHER INFORMATION: ccdB
<220> FEATURE:
<221> NAME/KEY: gene
<222> LOCATION: (676)..(775)
<223> OTHER INFORMATION: attL2
<220> FEATURE:
<221> NAME/KEY: gene
<222> LOCATION: (898)..(1707)
<223> OTHER INFORMATION: KmR
<220> FEATURE:
<221> NAME/KEY: gene
<222> LOCATION: (1812)..(2385)
<223> OTHER INFORMATION: ori

<400> SEQUENCE: 124

```
ctgacggatg gcctttttgc gtttctacaa actcttcctg ttagttagtt acttaagctc     60

gggccccaaa taatgatttt attttgactg atagtgacct gttcgttgca acaaattgat    120

aagcaatgct tttttataat gccaactttg tacaaaaaag caggctttga aaacctgtat    180

tttcaaggaa ccgtttcatg catcgtcgac tggatccggt accgaattcg cttactaaaa    240

gccagataac agtatgcgta tttgcgcgct gatttttgcg gtataagaat atatactgat    300

atgtataccc gaagtatgtc aaaaagaggt gtgcttctag aatgcagttt aaggtttaca    360

cctataaaag agagagccgt tatcgtctgt ttgtggatgt acagagtgat attattgaca    420

cgcccgggcg acggatagtg atccccctgg ccagtgcacg tctgctgtca gataaagtct    480

cccgtgaact ttacccggtg gtgcatatcg gggatgaaag ctggcgcatg atgaccaccg    540

atatggccag tgtgccggtc tccgttatcg gggaagaagt ggctgatctc agccaccgcg    600

aaaatgacat caaaaacgcc attaacctga tgttctgggg aatatagaat tcgcggccgc    660

actcgagata tctagaccca gctttcttgt acaaagttgg cattataaga aagcattgct    720

tatcaatttg ttgcaacgaa caggtcacta tcagtcaaaa taaaatcatt atttgccatc    780

cagctgcagc tctggcccgt gtctcaaaat ctctgatgtt acattgcaca agataaaaat    840

atatcatcat gaacaataaa actgtctgct tacataaaca gtaatacaag gggtgttatg    900

agccatattc aacgggaaac gtcgaggccg cgattaaatt ccaacatgga tgctgattta    960

tatgggtata aatgggctcg cgataatgtc gggcaatcag gtgcgacaat ctatcgcttg   1020

tatgggaagc ccgatgcgcc agagttgttt ctgaaacatg gcaaaggtag cgttgccaat   1080

gatgttacag atgagatggt cagactaaac tggctgacgg aatttatgcc tcttccgacc   1140

atcaagcatt ttatccgtac tcctgatgat gcatggttac tcaccactgc gatccccgga   1200

aaaacagcat tccaggtatt agaagaatat cctgattcag gtgaaaatat tgttgatgcg   1260

ctggcagtgt tcctgcgccg gttgcattcg attcctgttt gtaattgtcc ttttaacagc   1320

gatcgcgtat ttcgtctcgc tcaggcgcaa tcacgaatga ataacggttt ggttgatgcg   1380

agtgattttg atgacgagcg taatggctgg cctgttgaac aagtctggaa agaaatgcat   1440

aaacttttgc cattctcacc ggattcagtc gtcactcatg gtgatttctc acttgataac   1500

cttatttttg acgaggggaa attaataggt tgtattgatg ttggacgagt cggaatcgca   1560

gaccgatacc aggatcttgc catcctatgg aactgcctcg gtgagttttc tccttcatta   1620

cagaaacggc tttttcaaaa atatggtatt gataatcctg atatgaataa attgcagttt   1680

catttgatgc tcgatgagtt tttctaatca gaattggtta attggttgta acattattca   1740

gattgggccc cgttccactg agcgtcagac cccgtagaaa agatcaaagg atcttcttga   1800

gatccttttt ttctgcgcgt aatctgctgc ttgcaaacaa aaaaaccacc gctaccagcg   1860

gtggtttgtt tgccggatca agagctacca actctttttc cgaaggtaac tggcttcagc   1920
```

```
agagcgcaga taccaaatac tgttcttcta gtgtagccgt agttaggcca ccacttcaag   1980

aactctgtag caccgcctac atacctcgct ctgctaatcc tgttaccagt ggctgctgcc   2040

agtggcgata agtcgtgtct taccgggttg gactcaagac gatagttacc ggataaggcg   2100

cagcggtcgg gctgaacggg gggttcgtgc acacagccca gcttggagcg aacgacctac   2160

accgaactga gatacctaca gcgtgagcta tgagaaagcg ccacgcttcc cgaagggaga   2220

aaggcggaca ggtatccggt aagcggcagg gtcggaacag gagagcgcac gagggagctt   2280

ccagggggaa acgcctggta tctttatagt cctgtcgggt ttcgccacct ctgacttgag   2340

cgtcgatttt tgtgatgctc gtcagggggg cggagcctat ggaaaaacgc cagcaacgcg   2400

gcctttttac ggttcctggc cttttgctgg ccttttgctc acatgttctt tcctgcgtta   2460

tcccctgatt ctgtggataa ccgtattacc gctagcatgg atctcgggga cgtctaacta   2520

ctaagcgaga gtagggaact gccaggcatc aaataaaacg aaaggctcag tcggaagact   2580

gggcctttcg ttttatctgt tgtttgtcgg tgaacgctct cctgagtagg acaaatccgc   2640

cgggagcgga tttgaacgtt gtgaagcaac ggcccggagg gtggcgggca ggacgcccgc   2700

cataaactgc caggcatcaa actaagcaga aggccatc                           2738


<210> SEQ ID NO 125
<211> LENGTH: 2735
<212> TYPE: DNA
<213> ORGANISM: Artificial Sequence
<220> FEATURE:
<223> OTHER INFORMATION: Entry Vector pENTR8
<220> FEATURE:
<221> NAME/KEY: gene
<222> LOCATION: (67)..(166)
<223> OTHER INFORMATION: attL1
<220> FEATURE:
<221> NAME/KEY: gene
<222> LOCATION: (339)..(644)
<223> OTHER INFORMATION: ccdB
<220> FEATURE:
<221> NAME/KEY: gene
<222> LOCATION: (673)..(772)
<223> OTHER INFORMATION: attL2
<220> FEATURE:
<221> NAME/KEY: gene
<222> LOCATION: (895)..(1704)
<223> OTHER INFORMATION: KmR
<220> FEATURE:
<221> NAME/KEY: gene
<222> LOCATION: (1809)..(2382)
<223> OTHER INFORMATION: ori

<400> SEQUENCE: 125

ctgacggatg gcctttttgc gtttctacaa actcttcctg ttagttagtt acttaagctc     60

gggccccaaa taatgatttt attttgactg atagtgacct gttcgttgca acaaattgat    120

aagcaatgct tttttataat gccaactttg tacaaaaaag caggctttga aaacctgtat    180

tttcaaggaa ccatggacct agtcgactgg atccggtacc gaattcgctt actaaaagcc    240

agataacagt atgcgtattt gcgcgctgat ttttgcggta taagaatata tactgatatg    300

tatacccgaa gtatgtcaaa aagaggtgtg cttctagaat gcagtttaag gtttacacct    360

ataaaagaga gagccgttat cgtctgtttg tggatgtaca gagtgatatt attgacacgc    420

ccgggcgacg gatagtgatc cccctggcca gtgcacgtct gctgtcagat aaagtctccc    480

gtgaacttta cccggtggtg catatcgggg atgaaagctg gcgcatgatg accaccgata    540

tggccagtgt gccggtctcc gttatcgggg aagaagtggc tgatctcagc caccgcgaaa    600
```

-continued

```
atgacatcaa aaacgccatt aacctgatgt tctggggaat atagaattcg cggccgcact    660

cgagatatct agacccagct ttcttgtaca aagttggcat tataagaaag cattgcttat    720

caatttgttg caacgaacag gtcactatca gtcaaaataa aatcattatt tgccatccag    780

ctgcagctct ggcccgtgtc tcaaaatctc tgatgttaca ttgcacaaga taaaaatata    840

tcatcatgaa caataaaact gtctgcttac ataaacagta atacaagggg tgttatgagc    900

catattcaac gggaaacgtc gaggccgcga ttaaattcca acatggatgc tgatttatat    960

gggtataaat gggctcgcga taatgtcggg caatcaggtg cgacaatcta tcgcttgtat   1020

gggaagcccg atgcgccaga gttgtttctg aaacatggca aaggtagcgt tgccaatgat   1080

gttacagatg agatggtcag actaaactgg ctgacggaat ttatgcctct tccgaccatc   1140

aagcatttta tccgtactcc tgatgatgca tggttactca ccactgcgat ccccggaaaa   1200

acagcattcc aggtattaga agaatatcct gattcaggtg aaaatattgt tgatgcgctg   1260

gcagtgtccc tgcgccggtt gcattcgatt cctgtttgta attgtccttt taacagcgat   1320

cgcgtatttc gtctcgctca ggcgcaatca cgaatgaata acggtttggt tgatgcgagt   1380

gattttgatg acgagcgtaa tggctggcct gttgaacaag tctggaaaga aatgcataaa   1440

cttttgccat tctcaccgga ttcagtcgtc actcatggtg atttctcact tgataacctt   1500

atttttgacg aggggaaatt aataggttgt attgatgttg gacgagtcgg aatcgcagac   1560

cgataccagg atcttgccat cctatggaac tgcctcggtg agttttctcc ttcattacag   1620

aaacggcttt ttcaaaaata tggtattgat aatcctgata tgaataaatt gcagtttcat   1680

ttgatgctcg atgagttttt ctaatcagaa ttggttaatt ggttgtaaca ttattcagat   1740

tgggccccgt tccactgagc gtcagacccc gtagaaaaga tcaaaggatc ttcttgagat   1800

cctttttttc tgcgcgtaat ctgctgcttg caaacaaaaa aaccaccgct accagcggtg   1860

gtttgtttgc cggatcaaga gctaccaact ctttttccga aggtaactgg cttcagcaga   1920

gcgcagatac caaatactgt tcttctagtg tagccgtagt taggccacca cttcaagaac   1980

tctgtagcac cgcctacata cctcgctctg ctaatcctgt taccagtggc tgctgccagt   2040

ggcgataagt cgtgtcttac cgggttggac tcaagacgat agttaccgga taaggcgcag   2100

cggtcgggct gaacgggggg ttcgtgcaca cagcccagct tggagcgaac gacctacacc   2160

gaactgagat acctacagcg tgagctatga gaaagcgcca cgcttcccga agggagaaag   2220

gcggacaggt atccggtaag cggcagggtc ggaacaggag agcgcacgag ggagcttcca   2280

gggggaaacg cctggtatct ttatagtcct gtcgggtttc gccacctctg acttgagcgt   2340

cgatttttgt gatgctcgtc aggggggcgg agcctatgga aaaacgccag caacgcggcc   2400

tttttacggt tcctggcctt ttgctggcct tttgctcaca tgttctttcc tgcgttatcc   2460

cctgattctg tggataaccg tattaccgct agcatggatc tcggggacgt ctaactacta   2520

agcgagagta gggaactgcc aggcatcaaa taaaacgaaa ggctcagtcg gaagactggg   2580

cctttcgttt tatctgttgt ttgtcggtga acgctctcct gagtaggaca aatccgccgg   2640

gagcggattt gaacgttgtg aagcaacggc ccggagggtg gcgggcagga cgcccgccat   2700

aaactgccag gcatcaaact aagcagaagg ccatc                              2735
```

<210> SEQ ID NO 126
<211> LENGTH: 2735
<212> TYPE: DNA
<213> ORGANISM: Artificial Sequence
<220> FEATURE:
<223> OTHER INFORMATION: Entry Vector pENTR9

-continued

<220> FEATURE:
<221> NAME/KEY: gene
<222> LOCATION: (67)..(166)
<223> OTHER INFORMATION: attL1
<220> FEATURE:
<221> NAME/KEY: gene
<222> LOCATION: (339)..(644)
<223> OTHER INFORMATION: ccdB
<220> FEATURE:
<221> NAME/KEY: gene
<222> LOCATION: (673)..(772)
<223> OTHER INFORMATION: attL2
<220> FEATURE:
<221> NAME/KEY: gene
<222> LOCATION: (895)..(1704)
<223> OTHER INFORMATION: KmR
<220> FEATURE:
<221> NAME/KEY: gene
<222> LOCATION: (1809)..(2382)
<223> OTHER INFORMATION: ori

<400> SEQUENCE: 126
ctgacggatg gcctttttgc gtttctacaa actcttcctg ttagttagtt acttaagctc 60
gggccccaaa taatgatttt attttgactg atagtgacct gttcgttgca acaaattgat 120
aagcaatgct tttttataat gccaactttg tacaaaaaag caggctttga aaacctgtat 180
tttcaaggac atatgagatc tgtcgactgg atccggtacc gaattcgctt actaaaagcc 240
agataacagt atgcgtattt gcgcgctgat ttttgcggta taagaatata tactgatatg 300
tatacccgaa gtatgtcaaa aagaggtgtg cttctagaat gcagtttaag gtttacacct 360
ataaaagaga gagccgttat cgtctgtttg tggatgtaca gagtgatatt attgacacgc 420
ccgggcgacg gatagtgatc cccctggcca gtgcacgtct gctgtcagat aaagtctccc 480
gtgaacttta cccggtggtg catatcgggg atgaaagctg gcgcatgatg accaccgata 540
tggccagtgt gccggtctcc gttatcgggg aagaagtggc tgatctcagc caccgcgaaa 600
atgacatcaa aaacgccatt aacctgatgt tctggggaat atagaattcg cggccgcact 660
cgagatatct agacccagct ttcttgtaca aagttggcat tataagaaag cattgcttat 720
caatttgttg caacgaacag gtcactatca gtcaaaataa aatcattatt tgccatccag 780
ctgcagctct ggcccgtgtc tcaaaatctc tgatgttaca ttgcacaaga taaaaatata 840
tcatcatgaa caataaaact gtctgcttac ataaacagta atacaagggg tgttatgagc 900
catattcaac gggaaacgtc gaggccgcga ttaaattcca acatggatgc tgatttatat 960
gggtataaat gggctcgcga taatgtcggg caatcaggtg cgacaatcta tcgcttgtat 1020
gggaagcccg atgcgccaga gttgtttctg aaacatggca aaggtagcgt tgccaatgat 1080
gttacagatg agatggtcag actaaactgg ctgacggaat ttatgcctct tccgaccatc 1140
aagcatttta tccgtactcc tgatgatgca tggttactca ccactgcgat ccccggaaaa 1200
acagcattcc aggtattaga agaatatcct gattcaggtg aaaatattgt tgatgcgctg 1260
gcagtgtccc tgcgccggtt gcattcgatt cctgtttgta attgtccttt taacagcgat 1320
cgcgtatttc gtctcgctca ggcgcaatca cgaatgaata acggtttggt tgatgcgagt 1380
gattttgatg acgagcgtaa tggctggcct gttgaacaag tctggaaaga aatgcataaa 1440
cttttgccat tctcaccgga ttcagtcgtc actcatggtg atttctcact tgataacctt 1500
atttttgacg aggggaaatt aataggttgt attgatgttg gacgagtcgg aatcgcagac 1560
cgataccagg atcttgccat cctatggaac tgcctcggtg agttttctcc ttcattacag 1620
aaacggcttt ttcaaaaata tggtattgat aatcctgata tgaataaatt gcagtttcat 1680

-continued

```
ttgatgctcg atgagttttt ctaatcagaa ttggttaatt ggttgtaaca ttattcagat   1740

tgggccccgt tccactgagc gtcagacccc gtagaaaaga tcaaaggatc ttcttgagat   1800

cctttttttc tgcgcgtaat ctgctgcttg caaacaaaaa aaccaccgct accagcggtg   1860

gtttgtttgc cggatcaaga gctaccaact ctttttccga aggtaactgg cttcagcaga   1920

gcgcagatac caaatactgt tcttctagtg tagccgtagt taggccacca cttcaagaac   1980

tctgtagcac cgcctacata cctcgctctg ctaatcctgt taccagtggc tgctgccagt   2040

ggcgataagt cgtgtcttac cgggttggac tcaagacgat agttaccgga taaggcgcag   2100

cggtcgggct gaacgggggg ttcgtgcaca cagcccagct tggagcgaac gacctacacc   2160

gaactgagat acctacagcg tgagctatga gaaagcgcca cgcttcccga agggagaaag   2220

gcggacaggt atccggtaag cggcagggtc ggaacaggag agcgcacgag ggagcttcca   2280

gggggaaacg cctggtatct ttatagtcct gtcgggtttc gccacctctg acttgagcgt   2340

cgatttttgt gatgctcgtc aggggggcgg agcctatgga aaaacgccag caacgcggcc   2400

tttttacggt tcctggcctt ttgctggcct tttgctcaca tgttctttcc tgcgttatcc   2460

cctgattctg tggataaccg tattaccgct agcatggatc tcggggacgt ctaactacta   2520

agcgagagta gggaactgcc aggcatcaaa taaaacgaaa ggctcagtcg gaagactggg   2580

cctttcgttt tatctgttgt ttgtcggtga acgctctcct gagtaggaca aatccgccgg   2640

gagcggattt gaacgttgtg aagcaacggc ccggagggtg gcgggcagga cgcccgccat   2700

aaactgccag gcatcaaact aagcagaagg ccatc                               2735
```

<210> SEQ ID NO 127
<211> LENGTH: 2738
<212> TYPE: DNA
<213> ORGANISM: Artificial Sequence
<220> FEATURE:
<223> OTHER INFORMATION: Entry Vector pENTR10
<220> FEATURE:
<221> NAME/KEY: gene
<222> LOCATION: (67)..(166)
<223> OTHER INFORMATION: attL1
<220> FEATURE:
<221> NAME/KEY: gene
<222> LOCATION: (342)..(647)
<223> OTHER INFORMATION: ccdB
<220> FEATURE:
<221> NAME/KEY: gene
<222> LOCATION: (676)..(775)
<223> OTHER INFORMATION: attL2
<220> FEATURE:
<221> NAME/KEY: gene
<222> LOCATION: (898)..(1707)
<223> OTHER INFORMATION: KmR
<220> FEATURE:
<221> NAME/KEY: gene
<222> LOCATION: (1812)..(2385)
<223> OTHER INFORMATION: ori

<400> SEQUENCE: 127

```
ctgacggatg gcctttttgc gtttctacaa actcttcctg ttagttagtt acttaagctc     60

gggccccaaa taatgatttt attttgactg atagtgacct gttcgttgca acaaattgat    120

aagcaatgct ttttataat gccaactttg tacaaaaaag caggcttcga actaaggaaa    180

tacttacata tgggaaccaa ttcagtcgac tggatccggt accgaattcg cttactaaaa    240

gccagataac agtatgcgta tttgcgcgct gatttttgcg gtataagaat atatactgat    300

atgtataccc gaagtatgtc aaaaagaggt gtgcttctag aatgcagttt aaggtttaca    360

cctataaaag agagagccgt tatcgtctgt ttgtggatgt acagagtgat attattgaca    420
```

-continued

```
cgcccgggcg acggatggtg atccccctgg ccagtgcacg tctgctgtca gataaagtct    480
cccgtgaact ttacccggtg gtgcatatcg gggatgaaag ctggcgcatg atgaccaccg    540
atatggccag tgtgccggtc tccgttatcg gggaagaagt ggctgatctc agccaccgcg    600
aaaatgacat caaaaacgcc attaacctga tgttctgggg aatatagaat tcgcggccgc    660
actcgagata tctagaccca gctttcttgt acaaagttgg cattataaga aagcattgct    720
tatcaatttg ttgcaacgaa caggtcacta tcagtcaaaa taaaatcatt atttgccatc    780
cagctgcagc tctggcccgt gtctcaaaat ctctgatgtt acattgcaca agataaaaat    840
atatcatcat gaacaataaa actgtctgct tacataaaca gtaatacaag gggtgttatg    900
agccatattc aacgggaaac gtcgaggccg cgattaaatt ccaacatgga tgctgattta    960
tatgggtata aatgggctcg cgataatgtc gggcaatcag gtgcgacaat ctatcgcttg   1020
tatgggaagc ccgatgcgcc agagttgttt ctgaaacatg gcaaaggtag cgttgccaat   1080
gatgttacag atgagatggt cagactaaac tggctgacgg aatttatgcc tcttccgacc   1140
atcaagcatt ttatccgtac tcctgatgat gcatggttac tcaccactgc gatccccgga   1200
aaaacagcat tccaggtatt agaagaatat cctgattcag gtgaaaatat tgttgatgcg   1260
ctggcagtgt tcctgcgccg gttgcattcg attcctgttt gtaattgtcc ttttaacagc   1320
gatcgcgtat ttcgtctcgc tcaggcgcaa tcacgaatga ataacggttt ggttgatgcg   1380
agtgattttg atgacgagcg taatggctgg cctgttgaac aagtctggaa agaaatgcat   1440
aaacttttgc cattctcacc ggattcagtc gtcactcatg gtgatttctc acttgataac   1500
cttatttttg acgaggggaa attaataggt tgtattgatg ttggacgagt cggaatcgca   1560
gaccgatacc aggatcttgc catcctatgg aactgcctcg gtgagttttc tccttcatta   1620
cagaaacggc tttttcaaaa atatggtatt gataatcctg atatgaataa attgcagttt   1680
catttgatgc tcgatgagtt tttctaatca gaattggtta attggttgta acattattca   1740
gattgggccc cgttccactg agcgtcagac cccgtagaaa agatcaaagg atcttcttga   1800
gatccttttt ttctgcgcgt aatctgctgc ttgcaaacaa aaaaaccacc gctaccagcg   1860
gtggtttgtt tgccggatca agagctacca actctttttc cgaaggtaac tggcttcagc   1920
agagcgcaga taccaaatac tgttcttcta gtgtagccgt agttaggcca ccacttcaag   1980
aactctgtag caccgcctac atacctcgct ctgctaatcc tgttaccagt ggctgctgcc   2040
agtggcgata agtcgtgtct taccgggttg gactcaagac gatagttacc ggataaggcg   2100
cagcggtcgg gctgaacggg gggttcgtgc acacagccca gcttggagcg aacgacctac   2160
accgaactga gatacctaca gcgtgagcta tgagaaagcg ccacgcttcc cgaagggaga   2220
aaggcggaca ggtatccggt aagcggcagg gtcggaacag gagagcgcac gagggagctt   2280
ccagggggaa acgcctggta tctttatagt cctgtcgggt ttcgccacct ctgacttgag   2340
cgtcgatttt tgtgatgctc gtcagggggg cggagcctat ggaaaaacgc cagcaacgcg   2400
gcctttttac ggttcctggc cttttgctgg ccttttgctc acatgttctt tcctgcgtta   2460
tcccctgatt ctgtggataa ccgtattacc gctagcatgg atctcgggga cgtctaacta   2520
ctaagcgaga gtagggaact gccaggcatc gaataaaacg aaaggctcag tcggaagact   2580
gggcctttcg ttttatctgt tgtttgtcgg tgaacgctct cctgagtagg acaaatccgc   2640
cgggagcgga tttgaacgtt gtgaagcaac ggcccggagg gtggcgggca ggacgcccgc   2700
cataaactgc caggcatcaa actaagcaga aggccatc                            2738
```

-continued

<210> SEQ ID NO 128
<211> LENGTH: 2744
<212> TYPE: DNA
<213> ORGANISM: Artificial Sequence
<220> FEATURE:
<223> OTHER INFORMATION: Entry Vector pENTR11
<220> FEATURE:
<221> NAME/KEY: gene
<222> LOCATION: (67)..(166)
<223> OTHER INFORMATION: attL1
<220> FEATURE:
<221> NAME/KEY: gene
<222> LOCATION: (348)..(653)
<223> OTHER INFORMATION: ccdB
<220> FEATURE:
<221> NAME/KEY: gene
<222> LOCATION: (683)..(781)
<223> OTHER INFORMATION: attL2
<220> FEATURE:
<221> NAME/KEY: gene
<222> LOCATION: (904)..(1713)
<223> OTHER INFORMATION: KmR
<220> FEATURE:
<221> NAME/KEY: gene
<222> LOCATION: (1818)..(2391)
<223> OTHER INFORMATION: ori

<400> SEQUENCE: 128
ctgacggatg gcctttttgc gtttctacaa actcttcctg ttagttagtt acttaagctc 60
gggccccaaa taatgatttt attttgactg atagtgacct gttcgttgca acaaattgat 120
aagcaatgct tttttataat gccaactttg tacaaaaaag caggcttcga aggagataga 180
accaattctc taaggaaata cttaaccatg gtcgactgga tccggtaccg aattcgctta 240
ctaaaagcca gataacagta tgcgtatttg cgcgctgatt tttgcggtat aagaatatat 300
actgatatgt atacccgaag tatgtcaaaa agaggtgtgc ttctagaatg cagtttaagg 360
tttacaccta taaaagagag agccgttatc gtctgtttgt ggatgtacag agtgatatta 420
ttgacacgcc cgggcgacgg atagtgatcc ccctggccag tgcacgtctg ctgtcagata 480
aagtctcccg tgaactttac ccggtggtgc atatcgggga tgaaagctgg cgcatgatga 540
ccaccgatat ggccagtgtg ccggtctccg ttatcgggga agaagtggct gatctcagcc 600
accgcgaaaa tgacatcaaa aacgccatta acctgatgtt ctggggaata tagaattcgc 660
ggccgcactc gagatatcta gacccagctt tcttgtacaa agttggcatt ataagaaagc 720
attgcttatc aatttgttgc aacgaacagg tcactatcag tcaaaataaa atcattattt 780
gccatccagc tgcagctctg gcccgtgtct caaaatctct gatgttacat tgcacaagat 840
aaaaatatat catcatgaac aataaaactg tctgcttaca taaacagtaa tacaaggggt 900
gttatgagcc atattcaacg ggaaacgtcg aggccgcgat taaattccaa catggatgct 960
gatttatatg ggtataaatg ggctcgcgat aatgtcgggc aatcaggtgc gacaatctat 1020
cgcttgtatg ggaagcccga tgcgccagag ttgtttctga aacatggcaa aggtagcgtt 1080
gccaatgatg ttacagatga gatggtcaga ctaaactggc tgacggaatt tatgcctctt 1140
ccgaccatca agcattttat ccgtactcct gatgatgcat ggttactcac cactgcgatc 1200
cccggaaaaa cagcattcca ggtattagaa gaatatcctg attcaggtga aaatattgtt 1260
gatgcgctgg cagtgttcct gcgccggttg cattcgattc ctgtttgtaa ttgtcctttt 1320
aacagcgatc gcgtatttcg tctcgctcag gcgcaatcac gaatgaataa cggtttggtt 1380
gatgcgagtg attttgatga cgagcgtaat ggctggcctg ttgaacaagt ctggaaagaa 1440
atgcataaac ttttgccatt ctcaccggat tcagtcgtca ctcatggtga tttctcactt 1500

-continued

```
gataacctta tttttgacga ggggaaatta ataggttgta ttgatgttgg acgagtcgga   1560
atcgcagacc gataccagga tcttgccatc ctatggaact gcctcggtga gttttctcct   1620
tcattacaga aacggctttt tcaaaaatat ggtattgata atcctgatat gaataaattg   1680
cagtttcatt tgatgctcga tgagtttttc taatcagaat tggttaattg gttgtaacat   1740
tattcagatt gggccccgtt ccactgagcg tcagaccccg tagaaaagat caaaggatct   1800
tcttgagatc ctttttttct gcgcgtaatc tgctgcttgc aaacaaaaaa accaccgcta   1860
ccagcggtgg tttgtttgcc ggatcaagag ctaccaactc tttttccgaa ggtaactggc   1920
ttcagcagag cgcagatacc aaatactgtt cttctagtgt agccgtagtt aggccaccac   1980
ttcaagaact ctgtagcacc gcctacatac ctcgctctgc taatcctgtt accagtggct   2040
gctgccagtg gcgataagtc gtgtcttacc gggttggact caagacgata gttaccggat   2100
aaggcgcagc ggtcgggctg aacggggggt tcgtgcacac agcccagctt ggagcgaacg   2160
acctacaccg aactgagata cctacagcgt gagctatgag aaagcgccac gcttcccgaa   2220
gggagaaagg cggacaggta tccggtaagc ggcagggtcg gaacaggaga gcgcacgagg   2280
gagcttccag ggggaaacgc ctggtatctt tatagtcctg tcgggtttcg ccacctctga   2340
cttgagcgtc gatttttgtg atgctcgtca ggggggcgga gcctatggaa aaacgccagc   2400
aacgcggcct ttttacggtt cctggccttt tgctggcctt ttgctcacat gttctttcct   2460
gcgttatccc ctgattctgt ggataaccgt attaccgcta gcatggatct cggggacgtc   2520
taactactaa gcgagagtag ggaactgcca ggcatcaaat aaaacgaaag gctcagtcgg   2580
aagactgggc ctttcgtttt atctgttgtt tgtcggtgaa cgctctcctg agtaggacaa   2640
atccgccggg agcggatttg aacgttgtga agcaacggcc cggagggtgg cgggcaggac   2700
gcccgccata aactgccagg catcaaacta agcagaaggc catc                     2744
```

```
<210> SEQ ID NO 129
<211> LENGTH: 6464
<212> TYPE: DNA
<213> ORGANISM: Artificial Sequence
<220> FEATURE:
<223> OTHER INFORMATION: pDEST1
<220> FEATURE:
<221> NAME/KEY: gene
<222> LOCATION: (216)..(257)
<223> OTHER INFORMATION: Trc promoter
<220> FEATURE:
<221> NAME/KEY: gene
<222> LOCATION: (273)..(393)
<223> OTHER INFORMATION: attR1
<220> FEATURE:
<221> NAME/KEY: gene
<222> LOCATION: (647)..(1306)
<223> OTHER INFORMATION: CmR
<220> FEATURE:
<221> NAME/KEY: gene
<222> LOCATION: (1426)..(1510)
<223> OTHER INFORMATION: inactivated ccdA
<220> FEATURE:
<221> NAME/KEY: gene
<222> LOCATION: (1648)..(1953)
<223> OTHER INFORMATION: ccdB
<220> FEATURE:
<221> NAME/KEY: gene
<222> LOCATION: (1994)..(2118)
<223> OTHER INFORMATION: attR2
<220> FEATURE:
<221> NAME/KEY: gene
<222> LOCATION: (2598)..(3503)
<223> OTHER INFORMATION: ampR
<220> FEATURE:
```

-continued

<221> NAME/KEY: gene
<222> LOCATION: (4104)..(4264)
<223> OTHER INFORMATION: ori
<220> FEATURE:
<221> NAME/KEY: gene
<222> LOCATION: (4504)..(4941)
<223> OTHER INFORMATION: f1ori (f1 intergenic region)
<220> FEATURE:
<221> NAME/KEY: gene
<222> LOCATION: (5340)..(6420)
<223> OTHER INFORMATION: lacIq

<400> SEQUENCE: 129
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gtttttttgcg ccgacatcat aacggttctg gcaaatattc 180
tgaaatgagc tgttgacaat taatcatccg gtccgtataa tctgtggaat tgtgagcggg 240
ataacaattt catcgcgagg taccaagcta tcacaagttt gtacaaaaaa gctgaacgag 300
aaacgtaaaa tgatataaat atcaatatat taaattagat tttgcataaa aaacagacta 360
cataatactg taaaacacaa catatccagt cactatggcg gccgctaagt tggcagcatc 420
acccgacgca ctttgcgccg aataaatacc tgtgacggaa gatcacttcg cagaataaat 480
aaatcctggt gtccctgttg ataccgggaa gccctgggcc aacttttggc gaaaatgaga 540
cgttgatcgg cacgtaagag gttccaactt tcaccataat gaaataagat cactaccggg 600
cgtatttttt gagttatcga gattttcagg agctaaggaa gctaaaatgg agaaaaaaat 660
cactggatat accaccgttg atatatccca atggcatcgt aaagaacatt ttgaggcatt 720
tcagtcagtt gctcaatgta cctataacca gaccgttcag ctggatatta cggccttttt 780
aaagaccgta aagaaaaata agcacaagtt ttatccggcc tttattcaca ttcttgcccg 840
cctgatgaat gctcatccgg aattccgtat ggcaatgaaa gacggtgagc tggtgatatg 900
ggatagtgtt cacccttgtt acaccgtttt ccatgagcaa actgaaacgt tttcatcgct 960
ctggagtgaa taccacgacg atttccggca gtttctacac atatattcgc aagatgtggc 1020
gtgttacggt gaaaacctgg cctatttccc taaagggttt attgagaata tgtttttcgt 1080
ctcagccaat ccctgggtga gtttcaccag ttttgattta aacgtggcca atatggacaa 1140
cttcttcgcc cccgttttca ccatgggcaa atattatacg caaggcgaca aggtgctgat 1200
gccgctggcg attcaggttc atcatgccgt ctgtgatggc ttccatgtcg gcagaatgct 1260
taatgaatta caacagtact gcgatgagtg gcagggcggg gcgtaaacgc gtggatccgg 1320
cttactaaaa gccagataac agtatgcgta tttgcgcgct gatttttgcg gtataagaat 1380
atatactgat atgtataccc gaagtatgtc aaaaagaggt gtgctatgaa gcagcgtatt 1440
acagtgacag ttgacagcga cagctatcag ttgctcaagg catatatgat gtcaatatct 1500
ccggtctggt aagcacaacc atgcagaatg aagcccgtcg tctgcgtgcc gaacgctgga 1560
aagcggaaaa tcaggaaggg atggctgagg tcgcccggtt tattgaaatg aacggctctt 1620
ttgctgacga gaacagggac tggtgaaatg cagtttaagg tttacaccta taaaagagag 1680
agccgttatc gtctgtttgt ggatgtacag agtgatatta ttgacacgcc cgggcgacgg 1740
atggtgatcc ccctggccag tgcacgtctg ctgtcagata aagtctcccg tgaactttac 1800
ccggtggtgc atatcgggga tgaaagctgg cgcatgatga ccaccgatat ggccagtgtg 1860
ccggtctccg ttatcgggga agaagtggct gatctcagcc accgcgaaaa tgacatcaaa 1920
aacgccatta acctgatgtt ctggggaata taaatgtcag gctcccttat acacagccag 1980

-continued

```
tctgcaggtc gaccatagtg actggatatg ttgtgtttta cagtattatg tagtctgttt   2040
tttatgcaaa atctaattta atatattgat atttatatca ttttacgttt ctcgttcagc   2100
tttcttgtac aaagtggtga tagcttggct gttttggcgg atgagagaag attttcagcc   2160
tgatacagat taaatcagaa cgcagaagcg gtctgataaa acagaatttg cctggcggca   2220
gtagcgcggt ggtcccacct gaccccatgc cgaactcaga agtgaaacgc cgtagcgccg   2280
atggtagtgt ggggtctccc catgcgagag tagggaactg ccaggcatca aataaaacga   2340
aaggctcagt cgaaagactg ggcctttcgt tttatctgtt gtttgtcggt gaacgctctc   2400
ctgagtagga caaatccgcc gggagcggat ttgaacgttg cgaagcaacg gcccggaggg   2460
tggcgggcag gacgcccgcc ataaactgcc aggcatcaaa ttaagcagaa ggccatcctg   2520
acggatggcc tttttgcgtt tctacaaact ctttttgttt atttttctaa atacattcaa   2580
atatgtatcc gctcatgaga caataaccct gataaatgct tcaataatat tgaaaaagga   2640
agagtatgag tattcaacat ttccgtgtcg cccttattcc cttttttgcg gcattttgcc   2700
ttcctgtttt tgctcaccca gaaacgctgg tgaaagtaaa agatgctgaa gatcagttgg   2760
gtgcacgagt gggttacatc gaactggatc tcaacagcgg taagatcctt gagagttttc   2820
gccccgaaga acgttttcca atgatgagca cttttaaagt tctgctatgt ggcgcggtat   2880
tatcccgtgt tgacgccggg caagagcaac tcggtcgccg catacactat tctcagaatg   2940
acttggttga gtactcacca gtcacagaaa agcatcttac ggatggcatg acagtaagag   3000
aattatgcag tgctgccata accatgagtg ataacactgc ggccaactta cttctgacaa   3060
cgatcggagg accgaaggag ctaaccgctt ttttgcacaa catgggggat catgtaactc   3120
gccttgatcg ttgggaaccg gagctgaatg aagccatacc aaacgacgag cgtgacacca   3180
cgatgcctac agcaatggca acaacgttgc gcaaactatt aactggcgaa ctacttactc   3240
tagcttcccg gcaacaatta atagactgga tggaggcgga taaagttgca ggaccacttc   3300
tgcgctcggc ccttccggct ggctggttta ttgctgataa atctggagcc ggtgagcgtg   3360
ggtctcgcgg tatcattgca gcactggggc cagatggtaa gccctcccgt atcgtagtta   3420
tctacacgac ggggagtcag gcaactatgg atgaacgaaa tagacagatc gctgagatag   3480
gtgcctcact gattaagcat tggtaactgt cagaccaagt ttactcatat atactttaga   3540
ttgatttaaa acttcatttt taatttaaaa ggatctaggt gaagatcctt tttgataatc   3600
tcatgaccaa aatcccttaa cgtgagtttt cgttccactg agcgtcagac cccgtagaaa   3660
agatcaaagg atcttcttga gatccttttt ttctgcgcgt aatctgctgc ttgcaaacaa   3720
aaaaaccacc gctaccagcg gtggtttgtt tgccggatca agagctacca actctttttc   3780
cgaaggtaac tggcttcagc agagcgcaga taccaaatac tgtccttcta gtgtagccgt   3840
agttaggcca ccacttcaag aactctgtag caccgcctac atacctcgct ctgctaatcc   3900
tgttaccagt ggctgctgcc agtggcgata agtcgtgtct taccgggttg gactcaagac   3960
gatagttacc ggataaggcg cagcggtcgg gctgaacggg gggttcgtgc acacagccca   4020
gcttggagcg aacgacctac accgaactga gatacctaca gcgtgagcta tgagaaagcg   4080
ccacgcttcc cgaagggaga aaggcggaca ggtatccggt aagcggcagg gtcggaacag   4140
gagagcgcac gagggagctt ccagggggaa acgcctggta tctttatagt cctgtcgggt   4200
ttcgccacct ctgacttgag cgtcgatttt tgtgatgctc gtcagggggg cggagcctat   4260
ggaaaaacgc cagcaacgcg gcctttttac ggttcctggc cttttgctgg ccttttgctc   4320
```

-continued

```
acatgttctt tcctgcgtta tcccctgatt ctgtggataa ccgtattacc gcctttgagt   4380

gagctgatac cgctcgccgc agccgaacga ccgagcgcag cgagtcagtg agcgaggaag   4440

cggaagagcg cctgatgcgg tattttctcc ttacgcatct gtgcggtatt tcacaccgca   4500

taattttgtt aaaattcgcg ttaaattttt gttaaatcag ctcatttttt aaccaatagg   4560

ccgaaatcgg caaaatccct tataaatcaa aagaatagac cgagataggg ttgagtgttg   4620

ttccagtttg gaacaagagt ccactattaa agaacgtgga ctccaacgtc aaagggcgaa   4680

aaaccgtcta tcagggcgat ggcccactac gtgaaccatc accctaatca agttttttgg   4740

ggtcgaggtg ccgtaaagca ctaaatcgga accctaaagg gagcccccga tttagagctt   4800

gacggggaaa gccggcgaac gtggcgagaa aggaagggaa gaaagcgaaa ggagcgggcg   4860

ctagggcgct ggcaagtgta gcggtcacgc tgcgcgtaac caccacaccc gccgcgctta   4920

atgcgccgct acagggcgcg tccattcgcc attcaggctg ctatggtgca ctctcagtac   4980

aatctgctct gatgccgcat agttaagcca gtaccagtca cgtagcgata tcggagtgta   5040

tacactccgc tatcgctacg tgactgggtc atggctgcgc cccgacaccc gccaacaccc   5100

gctgacgcgc cctgacgggc ttgtctgctc ccggcatccg cttacagaca agctgtgacc   5160

gtctccggga gctgcatgtg tcagaggttt tcaccgtcat caccgaaacg cgcgaggcag   5220

cagatcaatt cgcgcgcgaa ggcgaagcgg catgcattta cgttgacacc atcgaatggt   5280

gcaaaacctt tcgcggtatg gcatgatagc gcccggaaga gagtcaattc agggtggtga   5340

atgtgaaacc agtaacgtta tacgatgtcg cagagtatgc cggtgtctct tatcagaccg   5400

tttcccgcgt ggtgaaccag gccagccacg tttctgcgaa aacgcgggaa aaagtggaag   5460

cggcgatggc ggagctgaat tacattccca accgcgtggc acaacaactg gcgggcaaac   5520

agtcgttgct gattggcgtt gccacctcca gtctggccct gcacgcgccg tcgcaaattg   5580

tcgcggcgat taaatctcgc gccgatcaac tgggtgccag cgtggtggtg tcgatggtag   5640

aacgaagcgg cgtcgaagcc tgtaaagcgg cggtgcacaa tcttctcgcg caacgcgtca   5700

gtgggctgat cattaactat ccgctggatg accaggatgc cattgctgtg gaagctgcct   5760

gcactaatgt tccggcgtta tttcttgatg tctctgacca gacacccatc aacagtatta   5820

ttttctccca tgaagacggt acgcgactgg gcgtggagca tctggtcgca ttgggtcacc   5880

agcaaatcgc gctgttagcg ggcccattaa gttctgtctc ggcgcgtctg cgtctggctg   5940

gctggcataa atatctcact cgcaatcaaa ttcagccgat agcggaacgg gaaggcgact   6000

ggagtgccat gtccggtttt caacaaacca tgcaaatgct gaatgagggc atcgttccca   6060

ctgcgatgct ggttgccaac gatcagatgg cgctgggcgc aatgcgcgcc attaccgagt   6120

ccgggctgcg cgttggtgcg gatatctcgg tagtgggata cgacgatacc gaagacagct   6180

catgttatat cccgccgtta accaccatca aacaggattt tcgcctgctg gggcaaacca   6240

gcgtggaccg cttgctgcaa ctctctcagg gccaggcggt gaagggcaat cagctgttgc   6300

ccgtctcact ggtgaaaaga aaaaccaccc tggcacccaa tacgcaaacc gcctctcccc   6360

gcgcgttggc cgattcatta atgcagctgg cacgacaggt ttcccgactg gaaagcgggc   6420

agtgagcgca acgcaattaa tgtgagttag cgcgaattga tctg                    6464
```

<210> SEQ ID NO 130
<211> LENGTH: 6553
<212> TYPE: DNA
<213> ORGANISM: Artificial Sequence
<220> FEATURE:
<223> OTHER INFORMATION: pDEST2

-continued

<220> FEATURE:
<221> NAME/KEY: gene
<222> LOCATION: (912)..(962)
<223> OTHER INFORMATION: Trc
<220> FEATURE:
<221> NAME/KEY: gene
<222> LOCATION: (1009)..(1223)
<223> OTHER INFORMATION: attR1
<220> FEATURE:
<221> NAME/KEY: gene
<222> LOCATION: (1473)..(2132)
<223> OTHER INFORMATION: CmR
<220> FEATURE:
<221> NAME/KEY: gene
<222> LOCATION: (2252)..(2336)
<223> OTHER INFORMATION: inactivated ccdA
<220> FEATURE:
<221> NAME/KEY: gene
<222> LOCATION: (2474)..(2779)
<223> OTHER INFORMATION: ccdB
<220> FEATURE:
<221> NAME/KEY: gene
<222> LOCATION: (2820)..(2944)
<223> OTHER INFORMATION: attR2
<220> FEATURE:
<221> NAME/KEY: gene
<222> LOCATION: (3509)..(4414)
<223> OTHER INFORMATION: ampR
<220> FEATURE:
<221> NAME/KEY: gene
<222> LOCATION: (5015)..(5175)
<223> OTHER INFORMATION: ori
<220> FEATURE:
<221> NAME/KEY: gene
<222> LOCATION: (5415)..(5825)
<223> OTHER INFORMATION: f1ori (f1 intergenic region)
<220> FEATURE:
<221> NAME/KEY: gene
<222> LOCATION: (752)..(6225)
<223> OTHER INFORMATION: lacIq

<400> SEQUENCE: 130
ggcggtgcac aatcttctcg cgcaacgcgt cagtgggctg atcattaact atccgctgga 60
tgaccaggat gccattgctg tggaagctgc ctgcactaat gttccggcgt tatttcttga 120
tgtctctgac cagacaccca tcaacagtat tattttctcc catgaagacg gtacgcgact 180
gggcgtggag catctggtcg cattgggtca ccagcaaatc gcgctgttag cgggcccatt 240
aagttctgtc tcggcgcgtc tgcgtctggc tggctggcat aaatatctca ctcgcaatca 300
aattcagccg atagcggaac gggaaggcga ctggagtgcc atgtccggtt ttcaacaaac 360
catgcaaatg ctgaatgagg gcatcgttcc cactgcgatg ctggttgcca acgatcagat 420
ggcgctgggc gcaatgcgcg ccattaccga gtccgggctg cgcgttggtg cggatatctc 480
ggtagtggga tacgacgata ccgaagacag ctcatgttat atcccgccgt caaccaccat 540
caaacaggat tttcgcctgc tggggcaaac cagcgtggac cgcttgctgc aactctctca 600
gggccaggcg gtgaagggca atcagctgtt gcccgtctca ctggtgaaaa gaaaaaccac 660
cctggcaccc aatacgcaaa ccgcctctcc ccgcgcgttg gccgattcat taatgcagct 720
ggcacgacag gtttcccgac tggaaagcgg gcagtgagcg caacgcaatt aatgtgagtt 780
agcgcgaatt gatctggttt gacagcttat catcgactgc acggtgcacc aatgcttctg 840
gcgtcaggca gccatcggaa gctgtggtat ggctgtgcag gtcgtaaatc actgcataat 900
tcgtgtcgct caaggcgcac tcccgttctg gataatgttt tttgcgccga catcataacg 960
gttctggcaa atattctgaa atgagctgtt gacaattaat catccggtcc gtataatctg 1020
tggaattgtg agcggataac aatttcacac aggaaacaga ccatgtcgta ctaccatcac 1080

-continued

```
catcaccatc acggcatcac aagtttgtac aaaaaagctg aacgagaaac gtaaaatgat   1140
ataaatatca atatattaaa ttagattttg cataaaaaac agactacata atactgtaaa   1200
acacaacata tccagtcact atggcggccg ctaagttggc agcatcaccc gacgcacttt   1260
gcgccgaata aatacctgtg acggaagatc acttcgcaga ataaataaat cctggtgtcc   1320
ctgttgatac cgggaagccc tgggccaact tttggcgaaa atgagacgtt gatcggcacg   1380
taagaggttc caactttcac cataatgaaa taagatcact accgggcgta tttttgagt   1440
tatcgagatt ttcaggagct aaggaagcta aaatggagaa aaaaatcact ggatatacca   1500
ccgttgatat atcccaatgg catcgtaaag aacattttga ggcatttcag tcagttgctc   1560
aatgtaccta taaccagacc gttcagctgg atattacggc ctttttaaag accgtaaaga   1620
aaaataagca caagttttat ccggccttta ttcacattct tgcccgcctg atgaatgctc   1680
atccggaatt ccgtatggca atgaaagacg gtgagctggt gatatgggat agtgttcacc   1740
cttgttacac cgttttccat gagcaaactg aaacgttttc atcgctctgg agtgaatacc   1800
acgacgattt ccggcagttt ctacacatat attcgcaaga tgtggcgtgt tacggtgaaa   1860
acctggccta tttccctaaa gggtttattg agaatatgtt tttcgtctca gccaatccct   1920
gggtgagttt caccagtttt gatttaaacg tggccaatat ggacaacttc ttcgcccccg   1980
ttttcaccat gggcaaatat tatacgcaag gcgacaaggt gctgatgccg ctggcgattc   2040
aggttcatca tgccgtctgt gatggcttcc atgtcggcag aatgcttaat gaattacaac   2100
agtactgcga tgagtggcag ggcggggcgt aaacgcgtgg atccggctta ctaaaagcca   2160
gataacagta tgcgtatttg cgcgctgatt tttgcggtat aagaatatat actgatatgt   2220
atacccgaag tatgtcaaaa agaggtgtgc tatgaagcag cgtattacag tgacagttga   2280
cagcgacagc tatcagttgc tcaaggcata tatgatgtca atatctccgg tctggtaagc   2340
acaaccatgc agaatgaagc ccgtcgtctg cgtgccgaac gctggaaagc ggaaaatcag   2400
gaagggatgg ctgaggtcgc ccggtttatt gaaatgaacg gctcttttgc tgacgagaac   2460
agggactggt gaaatgcagt ttaaggttta cacctataaa agagagagcc gttatcgtct   2520
gtttgtggat gtacagagtg atattattga cacgcccggg cgacggatgg tgatccccct   2580
ggccagtgca cgtctgctgt cagataaagt ctcccgtgaa ctttacccgg tggtgcatat   2640
cggggatgaa agctggcgca tgatgaccac cgatatggcc agtgtgccgg tctccgttat   2700
cggggaagaa gtggctgatc tcagccaccg cgaaaatgac atcaaaaacg ccattaacct   2760
gatgttctgg ggaatataaa tgtcaggctc ccttatacac agccagtctg caggtcgacc   2820
atagtgactg gatatgttgt gttttacagt attatgtagt ctgtttttta tgcaaaatct   2880
aatttaatat attgatattt atatcatttt acgtttctcg ttcagctttc ttgtacaaag   2940
tggtgatgcc catatgggaa ttcaaaggcc tacgtcgacg agctcactag tcgcggccgc   3000
ttctagagga tccctcgagg catgcggtac caagcttggc tgttttggcg gatgagagaa   3060
gattttcagc ctgatacaga ttaaatcaga acgcagaagc ggtctgataa aacagaattt   3120
gcctggcggc agtagcgcgg tggtcccacc tgaccccatg ccgaactcag aagtgaaacg   3180
ccgtagcgcc gatggtagtg tggggtctcc ccatgcgaga gtagggaact gccaggcatc   3240
aaataaaacg aaaggctcag tcgaaagact gggcctttcg ttttatctgt tgtttgtcgg   3300
tgaacgctct cctgagtagg acaaatccgc cgggagcgga tttgaacgtt gcgaagcaac   3360
ggcccggagg gtggcgggca ggacgcccgc cataaactgc caggcatcaa attaagcaga   3420
aggccatcct gacggatggc ctttttgcgt ttctacaaac tctttttgtt tatttttcta   3480
```

-continued aatacattca aatatgtatc cgctcatgag acaataaccc tgataaatgc ttcaataata 3540
ttgaaaaagg aagagtatga gtattcaaca tttccgtgtc gcccttattc cctttttgc 3600
ggcattttgc cttcctgttt ttgctcaccc agaaacgctg gtgaaagtaa aagatgctga 3660
agatcagttg ggtgcacgag tgggttacat cgaactggat ctcaacagcg gtaagatcct 3720
tgagagtttt cgccccgaag aacgttttcc aatgatgagc acttttaaag ttctgctatg 3780
tggcgcggta ttatcccgtg ttgacgccgg gcaagagcaa ctcggtcgcc gcatacacta 3840
ttctcagaat gacttggttg agtactcacc agtcacagaa aagcatctta cggatggcat 3900
gacagtaaga gaattatgca gtgctgccat aaccatgagt gataacactg cggccaactt 3960
acttctgaca acgatcggag gaccgaagga gctaaccgct tttttgcaca acatggggga 4020
tcatgtaact cgccttgatc gttgggaacc ggagctgaat gaagccatac caaacgacga 4080
gcgtgacacc acgatgccta cagcaatggc aacaacgttg cgcaaactat taactggcga 4140
actacttact ctagcttccc ggcaacaatt aatagactgg atggaggcgg ataaagttgc 4200
aggaccactt ctgcgctcgg cccttccggc tggctggttt attgctgata aatctggagc 4260
cggtgagcgt gggtctcgcg gtatcattgc agcactgggg ccagatggta agccctcccg 4320
tatcgtagtt atctacacga cggggagtca ggcaactatg gatgaacgaa atagacagat 4380
cgctgagata ggtgcctcac tgattaagca ttggtaactg tcagaccaag tttactcata 4440
tatactttag attgatttaa aacttcattt ttaatttaaa aggatctagg tgaagatcct 4500
ttttgataat ctcatgacca aaatccctta acgtgagttt tcgttccact gagcgtcaga 4560
ccccgtagaa aagatcaaag gatcttcttg agatcctttt tttctgcgcg taatctgctg 4620
cttgcaaaca aaaaaaccac cgctaccagc ggtggtttgt ttgccggatc aagagctacc 4680
aactcttttt ccgaaggtaa ctggcttcag cagagcgcag ataccaaata ctgtccttct 4740
agtgtagccg tagttaggcc accacttcaa gaactctgta gcaccgccta catacctcgc 4800
tctgctaatc ctgttaccag tggctgctgc cagtggcgat aagtcgtgtc ttaccgggtt 4860
ggactcaaga cgatagttac cggataaggc gcagcggtcg ggctgaacgg ggggttcgtg 4920
cacacagccc agcttggagc gaacgaccta caccgaactg agatacctac agcgtgagct 4980
atgagaaagc gccacgcttc ccgaagggag aaaggcggac aggtatccgg taagcggcag 5040
ggtcggaaca ggagagcgca cgagggagct tccaggggga aacgcctggt atctttatag 5100
tcctgtcggg tttcgccacc tctgacttga gcgtcgattt ttgtgatgct cgtcaggggg 5160
gcggagccta tggaaaaacg ccagcaacgc ggccttttta cggttcctgg ccttttgctg 5220
gccttttgct cacatgttct ttcctgcgtt atcccctgat tctgtggata accgtattac 5280
cgcctttgag tgagctgata ccgctcgccg cagccgaacg accgagcgca gcgagtcagt 5340
gagcgaggaa gcggaagagc gcctgatgcg gtattttctc cttacgcatc tgtgcggtat 5400
ttcacaccgc ataattttgt taaaattcgc gttaaatttt tgttaaatca gctcattttt 5460
taaccaatag gccgaaatcg gcaaaatccc ttataaatca aaagaataga ccgagatagg 5520
gttgagtgtt gttccagttt ggaacaagag tccactatta aagaacgtgg actccaacgt 5580
caaagggcga aaaaccgtct atcagggcga tggcccacta cgtgaaccat caccctaatc 5640
aagttttttg gggtcgaggt gccgtaaagc actaaatcgg aaccctaaag ggagcccccg 5700
atttagagct tgacggggaa agccggcgaa cgtggcgaga aaggaaggga agaaagcgaa 5760
aggagcgggc gctagggcgc tggcaagtgt agcggtcacg ctgcgcgtaa ccaccacacc 5820

-continued

```
cgccgcgctt aatgcgccgc tacagggcgc gtcccattcg ccattcaggc tgctatggtg   5880

cactctcagt acaatctgct ctgatgccgc atagttaagc cagtatacac tccgctatcg   5940

ctacgtgact gggtcatggc tgcgccccga cacccgccaa cacccgctga cgcgccctga   6000

cgggcttgtc tgctcccggc atccgcttac agacaagctg tgaccgtctc cgggagctgc   6060

atgtgtcaga ggttttcacc gtcatcaccg aaacgcgcga ggcagcagat caattcgcgc   6120

gcgaaggcga agcggcatgc atttacgttg acaccatcga atggtgcaaa acctttcgcg   6180

gtatggcatg atagcgcccg gaagagagtc aattcagggt ggtgaatgtg aaaccagtaa   6240

cgttatacga tgtcgcagag tatgccggtg tctcttatca gaccgtttcc cgcgtggtga   6300

accaggccag ccacgtttct gcgaaaacgc gggaaaaagt ggaagcggcg atggcggagc   6360

tgaattacat tcccaaccgc gtggcacaac aactggcggg caaacagtcg ttgctgattg   6420

gcgttgccac ctccagtctg gccctgcacg cgccgtcgca aattgtcgcg gcgattaaat   6480

ctcgcgccga tcaactgggt gccagcgtgg tggtgtcgat ggtagaacga agcggcgtcg   6540

aagcctgtaa agc                                                      6553
```

<210> SEQ ID NO 131
<211> LENGTH: 6823
<212> TYPE: DNA
<213> ORGANISM: Artificial Sequence
<220> FEATURE:
<223> OTHER INFORMATION: pDEST3
<220> FEATURE:
<221> NAME/KEY: gene
<222> LOCATION: (150)..(200)
<223> OTHER INFORMATION: Trc
<220> FEATURE:
<221> NAME/KEY: gene
<222> LOCATION: (963)..(1087)
<223> OTHER INFORMATION: attR1
<220> FEATURE:
<221> NAME/KEY: gene
<222> LOCATION: (1337)..(1996)
<223> OTHER INFORMATION: CmR
<220> FEATURE:
<221> NAME/KEY: gene
<222> LOCATION: (2116)..(2200)
<223> OTHER INFORMATION: inactivated ccdA
<220> FEATURE:
<221> NAME/KEY: gene
<222> LOCATION: (2338)..(2643)
<223> OTHER INFORMATION: ccdB
<220> FEATURE:
<221> NAME/KEY: gene
<222> LOCATION: (2684)..(2808)
<223> OTHER INFORMATION: attR2
<220> FEATURE:
<221> NAME/KEY: gene
<222> LOCATION: (3231)..(4091)
<223> OTHER INFORMATION: ampR
<220> FEATURE:
<221> NAME/KEY: gene
<222> LOCATION: (5295)..(6254)
<223> OTHER INFORMATION: lacIq

<400> SEQUENCE: 131

```
acgttatcga ctgcacggtg caccaatgct tctggcgtca ggcagccatc ggaagctgtg     60

gtatggctgt gcaggtcgta aatcactgca taattcgtgt cgctcaaggc gcactcccgt    120

tctggataat gtttttgcg ccgacatcat aacggttctg gcaaatattc tgaaatgagc    180

tgttgacaat taatcatcgg ctcgtataat gtgtggaatt gtgagcggat aacaatttca    240

cacaggaaac agtattcatg tcccctatac taggttattg gaaaattaag ggccttgtgc    300

aacccactcg acttcttttg gaatatcttg aagaaaaata tgaagagcat ttgtatgagc    360
```

-continued

```
gcgatgaagg tgataaatgg cgaaacaaaa agtttgaatt gggtttggag tttcccaatc    420
ttccttatta tattgatggt gatgttaaat taacacagtc tatggccatc atacgttata    480
tagctgacaa gcacaacatg ttgggtggtt gtccaaaaga gcgtgcagag atttcaatgc    540
ttgaaggagc ggttttggat attagatacg gtgtttcgag aattgcatat agtaaagact    600
ttgaaactct caaagttgat ttccttagca agctacctga aatgctgaaa atgttcgaag    660
atcgtttatg tcataaaaca tatttaaatg gtgatcatgt aacccatcct gacttcatgt    720
tgtatgacgc tcttgatgtt gttttataca tggacccaat gtgcctggat gcgttcccaa    780
aattagtttg ttttaaaaaa cgtattgaag ctatcccaca aattgataag tacttgaaat    840
ccagcaagta tatagcatgg cctttgcagg gctggcaagc cacgtttggt ggtggcgacc    900
atcctccaaa atcggatctg gttccgcgtg gatctcgtcg tgcatctgtt ggatccccat    960
caacaagttt gtacaaaaaa gctgaacgag aaacgtaaaa tgatataaat atcaatatat   1020
taaattagat tttgcataaa aaacagacta cataatactg taaaacacaa catatccagt   1080
cactatggcg gccgctaagt tggcagcatc acccgacgca ctttgcgccg aataaatacc   1140
tgtgacggaa gatcacttcg cagaataaat aaatcctggt gtccctgttg ataccgggaa   1200
gccctgggcc aacttttggc gaaaatgaga cgttgatcgg cacgtaagag gttccaactt   1260
tcaccataat gaaataagat cactaccggg cgtatttttt gagttatcga gattttcagg   1320
agctaaggaa gctaaaatgg agaaaaaaat cactggatat accaccgttg atatatccca   1380
atggcatcgt aaagaacatt ttgaggcatt tcagtcagtt gctcaatgta cctataacca   1440
gaccgttcag ctggatatta cggccttttt aaagaccgta aagaaaaata agcacaagtt   1500
ttatccggcc tttattcaca ttcttgcccg cctgatgaat gctcatccgg aattccgtat   1560
ggcaatgaaa gacggtgagc tggtgatatg ggatagtgtt cacccttgtt acaccgtttt   1620
ccatgagcaa actgaaacgt tttcatcgct ctggagtgaa taccacgacg atttccggca   1680
gtttctacac atatattcgc aagatgtggc gtgttacggt gaaaacctgg cctatttccc   1740
taaagggttt attgagaata tgtttttcgt ctcagccaat ccctgggtga gtttcaccag   1800
ttttgattta aacgtggcca atatggacaa cttcttcgcc cccgttttca ccatgggcaa   1860
atattatacg caaggcgaca aggtgctgat gccgctggcg attcaggttc atcatgccgt   1920
ctgtgatggc ttccatgtcg gcagaatgct taatgaatta caacagtact gcgatgagtg   1980
gcagggcggg gcgtaaagat ctggatccgg cttactaaaa gccagataac agtatgcgta   2040
tttgcgcgct gatttttgcg gtataagaat atatactgat atgtataccc gaagtatgtc   2100
aaaaagaggt gtgctatgaa gcagcgtatt acagtgacag ttgacagcga cagctatcag   2160
ttgctcaagg catatatgat gtcaatatct ccggtctggt aagcacaacc atgcagaatg   2220
aagcccgtcg tctgcgtgcc gaacgctgga aagcggaaaa tcaggaaggg atggctgagg   2280
tcgcccggtt tattgaaatg aacggctctt ttgctgacga gaacagggac tggtgaaatg   2340
cagtttaagg tttacaccta taaaagagag agccgttatc gtctgtttgt ggatgtacag   2400
agtgatatta ttgacacgcc cgggcgacgg atggtgatcc ccctggccag tgcacgtctg   2460
ctgtcagata aagtctcccg tgaactttac ccggtggtgc atatcgggga tgaaagctgg   2520
cgcatgatga ccaccgatat ggccagtgtg ccggtctccg ttatcgggga agaagtggct   2580
gatctcagcc accgcgaaaa tgacatcaaa aacgccatta acctgatgtt ctggggaata   2640
taaatgtcag gctcccttat acacagccag tctgcaggtc gaccatagtg actggatatg   2700
```

-continued

```
ttgtgtttta cagtattatg tagtctgttt tttatgcaaa atctaattta atatattgat   2760

atttatatca ttttacgttt ctcgttcagc tttcttgtac aaagtggttg atgggaattc   2820

atcgtgactg actgacgatc tgcctcgcgc gtttcggtga tgacggtgaa aacctctgac   2880

acatgcagct cccggagacg gtcacagctt gtctgtaagc ggatgccggg agcagacaag   2940

cccgtcaggg cgcgtcagcg ggtgttggcg ggtgtcgggg cgcagccatg acccagtcac   3000

gtagcgatag cggagtgtat aattcttgaa gacgaaaggg cctcgtgata cgcctatttt   3060

tataggttaa tgtcatgata ataatggttt cttagacgtc aggtggcact tttcggggaa   3120

atgtgcgcgg aacccctatt tgtttatttt tctaaataca ttcaaatatg tatccgctca   3180

tgagacaata accctgataa atgcttcaat aatattgaaa aaggaagagt atgagtattc   3240

aacatttccg tgtcgccctt attccctttt ttgcggcatt ttgccttcct gtttttgctc   3300

acccagaaac gctggtgaaa gtaaaagatg ctgaagatca gttgggtgca cgagtgggtt   3360

acatcgaact ggatctcaac agcggtaaga tccttgagag ttttcgcccc gaagaacgtt   3420

ttccaatgat gagcactttt aaagttctgc tatgtggcgc ggtattatcc cgtgttgacg   3480

ccgggcaaga gcaactcggt cgccgcatac actattctca gaatgacttg gttgagtact   3540

caccagtcac agaaaagcat cttacggatg gcatgacagt aagagaatta tgcagtgctg   3600

ccataaccat gagtgataac actgcggcca acttacttct gacaacgatc ggaggaccga   3660

aggagctaac cgcttttttg cacaacatgg gggatcatgt aactcgcctt gatcgttggg   3720

aaccggagct gaatgaagcc ataccaaacg acgagcgtga caccacgatg cctgcagcaa   3780

tggcaacaac gttgcgcaaa ctattaactg gcgaactact tactctagct tcccggcaac   3840

aattaataga ctggatggag gcggataaag ttgcaggacc acttctgcgc tcggcccttc   3900

cggctggctg gtttattgct gataaatctg gagccggtga gcgtgggtct cgcggtatca   3960

ttgcagcact ggggccagat ggtaagccct cccgtatcgt agttatctac acgacgggga   4020

gtcaggcaac tatggatgaa cgaaatagac agatcgctga gataggtgcc tcactgatta   4080

agcattggta actgtcagac caagtttact catatatact ttagattgat ttaaaacttc   4140

atttttaatt taaaaggatc taggtgaaga tcctttttga taatctcatg accaaaatcc   4200

cttaacgtga gttttcgttc cactgagcgt cagaccccgt agaaaagatc aaaggatctt   4260

cttgagatcc tttttttctg cgcgtaatct gctgcttgca aacaaaaaaa ccaccgctac   4320

cagcggtggt ttgtttgccg gatcaagagc taccaactct ttttccgaag gtaactggct   4380

tcagcagagc gcagatacca aatactgtcc ttctagtgta gccgtagtta ggccaccact   4440

tcaagaactc tgtagcaccg cctacatacc tcgctctgct aatcctgtta ccagtggctg   4500

ctgccagtgg cgataagtcg tgtcttaccg ggttggactc aagacgatag ttaccggata   4560

aggcgcagcg gtcgggctga acggggggtt cgtgcacaca gcccagcttg gagcgaacga   4620

cctacaccga actgagatac ctacagcgtg agctatgaga aagcgccacg cttcccgaag   4680

ggagaaaggc ggacaggtat ccggtaagcg gcagggtcgg aacaggagag cgcacgaggg   4740

agcttccagg gggaaacgcc tggtatcttt atagtcctgt cgggtttcgc cacctctgac   4800

ttgagcgtcg atttttgtga tgctcgtcag gggggcggag cctatggaaa aacgccagca   4860

acgcggcctt tttacggttc ctggcctttt gctggccttt tgctcacatg ttctttcctg   4920

cgttatcccc tgattctgtg gataaccgta ttaccgcctt tgagtgagct gataccgctc   4980

gccgcagccg aacgaccgag cgcagcgagt cagtgagcga ggaagcggaa gagcgcctga   5040

tgcggtattt tctccttacg catctgtgcg gtatttcaca ccgcataaat tccgacacca   5100
```

-continued

```
tcgaatggtg caaaaccttt cgcggtatgg catgatagcg cccggaagag agtcaattca   5160

gggtggtgaa tgtgaaacca gtaacgttat acgatgtcgc agagtatgcc ggtgtctctt   5220

atcagaccgt ttcccgcgtg gtgaaccagg ccagccacgt ttctgcgaaa acgcgggaaa   5280

aagtggaagc ggcgatggcg gagctgaatt acattcccaa ccgcgtggca caacaactgg   5340

cgggcaaaca gtcgttgctg attggcgttg ccacctccag tctggccctg cacgcgccgt   5400

cgcaaattgt cgcggcgatt aaatctcgcg ccgatcaact gggtgccagc gtggtggtgt   5460

cgatggtaga acgaagcggc gtcgaagcct gtaaagcggc ggtgcacaat cttctcgcgc   5520

aacgcgtcag tgggctgatc attaactatc cgctggatga ccaggatgcc attgctgtgg   5580

aagctgcctg cactaatgtt ccggcgttat ttcttgatgt ctctgaccag acacccatca   5640

acagtattat tttctcccat gaagacggta cgcgactggg cgtggagcat ctggtcgcat   5700

tgggtcacca gcaaatcgcg ctgttagcgg gcccattaag ttctgtctcg gcgcgtctgc   5760

gtctggctgg ctggcataaa tatctcactc gcaatcaaat tcagccgata gcggaacggg   5820

aaggcgactg gagtgccatg tccggttttc aacaaaccat gcaaatgctg aatgagggca   5880

tcgttcccac tgcgatgctg gttgccaacg atcagatggc gctgggcgca atgcgcgcca   5940

ttaccgagtc cgggctgcgc gttggtgcgg atatctcggt agtgggatac gacgataccg   6000

aagacagctc atgttatatc ccgccgttaa ccaccatcaa acaggatttt cgcctgctgg   6060

ggcaaaccag cgtggaccgc ttgctgcaac tctctcaggg ccaggcggtg aagggcaatc   6120

agctgttgcc cgtctcactg gtgaaaagaa aaaccaccct ggcgcccaat acgcaaaccg   6180

cctctccccg cgcgttggcc gattcattaa tgcagctggc acgacaggtt tcccgactgg   6240

aaagcgggca gtgagcgcaa cgcaattaat gtgagttagc tcactcatta ggcaccccag   6300

gctttacact ttatgcttcc ggctcgtatg ttgtgtggaa ttgtgagcgg ataacaattt   6360

cacacaggaa acagctatga ccatgattac ggattcactg gccgtcgttt tacaacgtcg   6420

tgactgggaa aaccctggcg ttacccaact taatcgcctt gcagcacatc ccccctttcgc  6480

cagctggcgt aatagcgaag aggcccgcac cgatcgccct tcccaacagt tgcgcagcct   6540

gaatggcgaa tggcgctttg cctggtttcc ggcaccagaa gcggtgccgg aaagctggct   6600

ggagtgcgat cttcctgagg ccgatactgt cgtcgtcccc tcaaactggc agatgcacgg   6660

ttacgatgcg cccatctaca ccaacgtaac ctatcccatt acggtcaatc cgccgtttgt   6720

tcccacggag aatccgacgg gttgttactc gctcacattt aatgttgatg aaagctggct   6780

acaggaaggc cagacgcgaa ttatttttga tggcgttgga att                     6823
```

<210> SEQ ID NO 132
<211> LENGTH: 6964
<212> TYPE: DNA
<213> ORGANISM: Artificial Sequence
<220> FEATURE:
<223> OTHER INFORMATION: pDEST4
<220> FEATURE:
<221> NAME/KEY: misc_feature
<222> LOCATION: (6950)..(6950)
<223> OTHER INFORMATION: 'n' can be any nucleotide (A, T, C, G or U)
<220> FEATURE:
<221> NAME/KEY: gene
<222> LOCATION: (964)..(1003)
<223> OTHER INFORMATION: Trc
<220> FEATURE:
<221> NAME/KEY: gene
<222> LOCATION: (1453)..(1577)
<223> OTHER INFORMATION: attR1
<220> FEATURE:

-continued

<221> NAME/KEY: gene
<222> LOCATION: (1827)..(2486)
<223> OTHER INFORMATION: CmR
<220> FEATURE:
<221> NAME/KEY: gene
<222> LOCATION: (2606)..(2690)
<223> OTHER INFORMATION: inactivated ccdA
<220> FEATURE:
<221> NAME/KEY: gene
<222> LOCATION: (2828)..(3133)
<223> OTHER INFORMATION: ccdB
<220> FEATURE:
<221> NAME/KEY: gene
<222> LOCATION: (3174)..(3298)
<223> OTHER INFORMATION: attR2
<220> FEATURE:
<221> NAME/KEY: gene
<222> LOCATION: (3872)..(4777)
<223> OTHER INFORMATION: ampR
<220> FEATURE:
<221> NAME/KEY: gene
<222> LOCATION: (5378)..(5538)
<223> OTHER INFORMATION: ori
<220> FEATURE:
<221> NAME/KEY: gene
<222> LOCATION: (5778)..(6215)
<223> OTHER INFORMATION: f1ori (f1 intergenic region)
<220> FEATURE:
<221> NAME/KEY: gene
<222> LOCATION: (704)..(6587)
<223> OTHER INFORMATION: lacIq

<400> SEQUENCE: 132
ctatccgctg gatgaccagg atgccattgc tgtggaagct gcctgcacta atgttccggc 60
gttatttctt gatgtctctg accagacacc catcaacagt attattttct cccatgaaga 120
cggtacgcga ctgggcgtgg agcatctggt cgcattgggt caccagcaaa tcgcgctgtt 180
agcgggccca ttaagttctg tctcggcgcg tctgcgtctg gctggctggc ataaatatct 240
cactcgcaat caaattcagc cgatagcgga acgggaaggc gactggagtg ccatgtccgg 300
ttttcaacaa accatgcaaa tgctgaatga gggcatcgtt cccactgcga tgctggttgc 360
caacgatcag atggcgctgg gcgcaatgcg cgccattacc gagtccgggc tgcgcgttgg 420
tgcggatatc tcggtagtgg gatacgacga taccgaagac agctcatgtt atatcccgcc 480
gtcaaccacc atcaaacagg attttcgcct gctggggcaa accagcgtgg accgcttgct 540
gcaactctct cagggccagg cggtgaaggg caatcagctg ttgcccgtct cactggtgaa 600
aagaaaaacc accctggcac ccaatacgca aaccgcctct ccccgcgcgt tggccgattc 660
attaatgcag ctggcacgac aggtttcccg actggaaagc gggcagtgag cgcaacgcaa 720
ttaatgtgag ttagcgcgaa ttgatctggt ttgacagctt atcatcgact gcacggtgca 780
ccaatgcttc tggcgtcagg cagccatcgg aagctgtggt atggctgtgc aggtcgtaaa 840
tcactgcata attcgtgtcg ctcaaggcgc actcccgttc tggataatgt tttttgcgcc 900
gacatcataa cggttctggc aaatattctg aaatgagctg ttgacaatta atcatccggt 960
ccgtataatc tgtggaattg tgagcggata acaatttcac acaggaaaca gaccatgggt 1020
catcatcatc atcatcacga ttacgatatc ccaacgaccg aaaacctgta ttttcagggc 1080
gcccatatga gcgataaaat tattcacctg actgacgaca gttttgacac ggatgtactc 1140
aaagcggacg gggcgatcct cgtcgatttc tgggcagagt ggtgcggtcc gtgcaaaatg 1200
atcgccccga ttctggatga aatcgctgac gaatatcagg gcaaactgac cgttgcaaaa 1260
ctgaacatcg atcaaaaccc tggcactgcg ccgaaatatg gcatccgtgg tatcccgact 1320
ctgctgctgt tcaaaaacgg tgaagtggcg gcaaccaaag tgggtgcact gtctaaaggt 1380

-continued

```
cagttgaaag agttcctcga cgctaacctg gccggttctg gttctggtga tgacgatgac   1440
aaggtaccca tcacaagttt gtacaaaaaa gctgaacgag aaacgtaaaa tgatataaat   1500
atcaatatat taaattagat tttgcataaa aaacagacta cataatactg taaaacacaa   1560
catatccagt cactatggcg gccgctaagt tggcagcatc acccgacgca ctttgcgccg   1620
aataaatacc tgtgacggaa gatcacttcg cagaataaat aaatcctggt gtccctgttg   1680
ataccgggaa gccctgggcc aacttttggc gaaaatgaga cgttgatcgg cacgtaagag   1740
gttccaactt tcaccataat gaaataagat cactaccggg cgtatttttt gagttatcga   1800
gattttcagg agctaaggaa gctaaaatgg agaaaaaaat cactggatat accaccgttg   1860
atatatccca atggcatcgt aaagaacatt ttgaggcatt tcagtcagtt gctcaatgta   1920
cctataacca gaccgttcag ctggatatta cggccttttt aaagaccgta aagaaaaata   1980
agcacaagtt ttatccggcc tttattcaca ttcttgcccg cctgatgaat gctcatccgg   2040
aattccgtat ggcaatgaaa gacggtgagc tggtgatatg ggatagtgtt cacccttgtt   2100
acaccgtttt ccatgagcaa actgaaacgt tttcatcgct ctggagtgaa taccacgacg   2160
atttccggca gtttctacac atatattcgc aagatgtggc gtgttacggt gaaaacctgg   2220
cctatttccc taaagggttt attgagaata tgtttttcgt ctcagccaat ccctgggtga   2280
gtttcaccag ttttgattta aacgtggcca atatggacaa cttcttcgcc cccgttttca   2340
ccatgggcaa atattatacg caaggcgaca aggtgctgat gccgctggcg attcaggttc   2400
atcatgccgt ctgtgatggc ttccatgtcg gcagaatgct taatgaatta caacagtact   2460
gcgatgagtg gcagggcggg gcgtaaacgc gtggatccgg cttactaaaa gccagataac   2520
agtatgcgta tttgcgcgct gatttttgcg gtataagaat atatactgat atgtataccc   2580
gaagtatgtc aaaaagaggt gtgctatgaa gcagcgtatt acagtgacag ttgacagcga   2640
cagctatcag ttgctcaagg catatatgat gtcaatatct ccggtctggt aagcacaacc   2700
atgcagaatg aagcccgtcg tctgcgtgcc gaacgctgga aagcggaaaa tcaggaaggg   2760
atggctgagg tcgcccggtt tattgaaatg aacggctctt ttgctgacga gaacagggac   2820
tggtgaaatg cagtttaagg tttacaccta taaaagagag agccgttatc gtctgtttgt   2880
ggatgtacag agtgatatta ttgacacgcc cgggcgacgg atggtgatcc ccctggccag   2940
tgcacgtctg ctgtcagata aagtctcccg tgaactttac ccggtggtgc atatcgggga   3000
tgaaagctgg cgcatgatga ccaccgatat ggccagtgtg ccggtctccg ttatcgggga   3060
agaagtggct gatctcagcc accgcgaaaa tgacatcaaa aacgccatta acctgatgtt   3120
ctggggaata taaatgtcag gctcccttat acacagccag tctgcaggtc gaccatagtg   3180
actggatatg ttgtgtttta cagtattatg tagtctgttt tttatgcaaa atctaattta   3240
atatattgat atttatatca ttttacgttt ctcgttcagc tttcttgtac aaagtggtga   3300
tggggatcct ctagagtcga cctgcagtaa tcgtacaggg tagtacaaat aaaaaaggca   3360
cgtcagatga cgtgcctttt ttcttgtgag cagtaagctt ggctgttttg gcggatgaga   3420
gaagattttc agcctgatac agattaaatc agaacgcaga agcggtctga taaaacagaa   3480
tttgcctggc ggcagtagcg cggtggtccc acctgacccc atgccgaact cagaagtgaa   3540
acgccgtagc gccgatggta gtgtggggtc tccccatgcg agagtaggga actgccaggc   3600
atcaaataaa acgaaaggct cagtcgaaag actgggcctt tcgttttatc tgttgtttgt   3660
cggtgaacgc tctcctgagt aggacaaatc cgccgggagc ggatttgaac gttgcgaagc   3720
```

-continued

```
aacggcccgg agggtggcgg gcaggacgcc cgccataaac tgccaggcat caaattaagc   3780
agaaggccat cctgacggat ggcctttttg cgtttctaca aactcttttt gtttattttt   3840
ctaaatacat tcaaatatgt atccgctcat gagacaataa ccctgataaa tgcttcaata   3900
atattgaaaa aggaagagta tgagtattca acatttccgt gtcgccctta ttcccttttt   3960
tgcggcattt tgccttcctg tttttgctca cccagaaacg ctggtgaaag taaaagatgc   4020
tgaagatcag ttgggtgcac gagtgggtta catcgaactg gatctcaaca gcggtaagat   4080
ccttgagagt tttcgccccg aagaacgttt tccaatgatg agcactttta aagttctgct   4140
atgtggcgcg gtattatccc gtgttgacgc cgggcaagag caactcggtc gccgcataca   4200
ctattctcag aatgacttgg ttgagtactc accagtcaca gaaaagcatc ttacggatgg   4260
catgacagta agagaattat gcagtgctgc cataaccatg agtgataaca ctgcggccaa   4320
cttacttctg acaacgatcg gaggaccgaa ggagctaacc gcttttttgc acaacatggg   4380
ggatcatgta actcgccttg atcgttggga accggagctg aatgaagcca taccaaacga   4440
cgagcgtgac accacgatgc ctacagcaat ggcaacaacg ttgcgcaaac tattaactgg   4500
cgaactactt actctagctt cccggcaaca attaatagac tggatggagg cggataaagt   4560
tgcaggacca cttctgcgct cggcccttcc ggctggctgg tttattgctg ataaatctgg   4620
agccggtgag cgtgggtctc gcggtatcat tgcagcactg gggccagatg gtaagccctc   4680
ccgtatcgta gttatctaca cgacggggag tcaggcaact atggatgaac gaaatagaca   4740
gatcgctgag ataggtgcct cactgattaa gcattggtaa ctgtcagacc aagtttactc   4800
atatatactt tagattgatt taaaacttca tttttaattt aaaaggatct aggtgaagat   4860
cctttttgat aatctcatga ccaaaatccc ttaacgtgag ttttcgttcc actgagcgtc   4920
agaccccgta gaaaagatca aaggatcttc ttgagatcct ttttttctgc gcgtaatctg   4980
ctgcttgcaa acaaaaaaac caccgctacc agcggtggtt tgtttgccgg atcaagagct   5040
accaactctt tttccgaagg taactggctt cagcagagcg cagataccaa atactgtcct   5100
tctagtgtag ccgtagttag gccaccactt caagaactct gtagcaccgc ctacatacct   5160
cgctctgcta atcctgttac cagtggctgc tgccagtggc gataagtcgt gtcttaccgg   5220
gttggactca agacgatagt taccggataa ggcgcagcgg tcgggctgaa cggggggttc   5280
gtgcacacag cccagcttgg agcgaacgac ctacaccgaa ctgagatacc tacagcgtga   5340
gctatgagaa agcgccacgc ttcccgaagg gagaaaggcg gacaggtatc cggtaagcgg   5400
cagggtcgga acaggagagc gcacgaggga gcttccaggg ggaaacgcct ggtatcttta   5460
tagtcctgtc gggtttcgcc acctctgact tgagcgtcga tttttgtgat gctcgtcagg   5520
ggggcggagc ctatggaaaa acgccagcaa cgcggccttt ttacggttcc tggccttttg   5580
ctggcctttt gctcacatgt tctttcctgc gttatcccct gattctgtgg ataaccgtat   5640
taccgccttt gagtgagctg ataccgctcg ccgcagccga acgaccgagc gcagcgagtc   5700
agtgagcgag gaagcggaag agcgcctgat gcggtatttt ctccttacgc atctgtgcgg   5760
tatttcacac cgcataattt tgttaaaatt cgcgttaaat ttttgttaaa tcagctcatt   5820
ttttaaccaa taggccgaaa tcggcaaaat cccttataaa tcaaaagaat agaccgagat   5880
agggttgagt gttgttccag tttggaacaa gagtccacta ttaaagaacg tggactccaa   5940
cgtcaaaggg cgaaaaaccg tctatcaggg cgatggccca ctacgtgaac catcacccta   6000
atcaagtttt ttggggtcga ggtgccgtaa agcactaaat cggaacccta aagggagccc   6060
ccgatttaga gcttgacggg gaaagccggc gaacgtggcg agaaaggaag ggaagaaagc   6120
```

-continued

```
gaaaggagcg ggcgctaggg cgctggcaag tgtagcggtc acgctgcgcg taaccaccac   6180
acccgccgcg cttaatgcgc cgctacaggg cgcgtccatt cgccattcag gctgctatgg   6240
tgcactctca gtacaatctg ctctgatgcc gcatagttaa gccagtatac actccgctat   6300
cgctacgtga ctgggtcatg gctgcgcccc gacacccgcc aacacccgct gacgcgccct   6360
gacgggcttg tctgctcccg gcatccgctt acagacaagc tgtgaccgtc tccgggagct   6420
gcatgtgtca gaggttttca ccgtcatcac cgaaacgcgc gaggcagcag atcaattcgc   6480
gcgcgaaggc gaagcggcat gcatttacgt tgacaccatc gaatggtgca aaacctttcg   6540
cggtatggca tgatagcgcc cggaagagag tcaattcagg gtggtgaatg tgaaaccagt   6600
aacgttatac gatgtcgcag agtatgccgg tgtctcttat cagaccgttt cccgcgtggt   6660
gaaccaggcc agccacgttt ctgcgaaaac gcgggaaaaa gtggaagcgg cgatggcgga   6720
gctgaattac attcccaacc gcgtggcaca acaactggcg ggcaaacagt cgttgctgat   6780
tggcgttgcc acctccagtc tggccctgca cgcgccgtcg caaattgtcg cggcgattaa   6840
atctcgcgcc gatcaactgg gtgccagcgt ggtggtgtcg atggtagaac gaagcggcgt   6900
cgaagcctgt aaagcggcgg tgcacaatct tctcgcgcaa cgcgtcagtn gggctgatca   6960
ttaa                                                                6964
```

```
<210> SEQ ID NO 133
<211> LENGTH: 5957
<212> TYPE: DNA
<213> ORGANISM: Artificial Sequence
<220> FEATURE:
<223> OTHER INFORMATION: pDEST5
<220> FEATURE:
<221> NAME/KEY: gene
<222> LOCATION: (181)..(305)
<223> OTHER INFORMATION: attR1
<220> FEATURE:
<221> NAME/KEY: gene
<222> LOCATION: (555)..(1214)
<223> OTHER INFORMATION: CmR
<220> FEATURE:
<221> NAME/KEY: gene
<222> LOCATION: (1334)..(1418)
<223> OTHER INFORMATION: inactivated ccdA
<220> FEATURE:
<221> NAME/KEY: gene
<222> LOCATION: (1556)..(1861)
<223> OTHER INFORMATION: ccdB
<220> FEATURE:
<221> NAME/KEY: gene
<222> LOCATION: (1902)..(2026)
<223> OTHER INFORMATION: attR2
<220> FEATURE:
<221> NAME/KEY: gene
<222> LOCATION: (2278)..(2733)
<223> OTHER INFORMATION: f1 (f1 intergenic region)
<220> FEATURE:
<221> NAME/KEY: gene
<222> LOCATION: (2865)..(3722)
<223> OTHER INFORMATION: ampR
<220> FEATURE:
<221> NAME/KEY: gene
<222> LOCATION: (5378)..(5538)
<223> OTHER INFORMATION: ori
<220> FEATURE:
<221> NAME/KEY: gene
<222> LOCATION: (4756)..(5922)
<223> OTHER INFORMATION: lacI

<400> SEQUENCE: 133

aggcacccca ggctttacac tttatgcttc cggctcgtat gttgtgtgga attgtgagcg     60
```

-continued

```
gataacaatt tcacacagga aacagctatg accatgatta cgccaagctc taatacgact    120
cactataggg aaagctggta cgcctgcagg taccggtccg gaattcccgg gtcgacgatc    180
acaagtttgt acaaaaaagc tgaacgagaa acgtaaaatg atataaatat caatatatta    240
aattagattt tgcataaaaa acagactaca taatactgta aaacacaaca tatccagtca    300
ctatggcggc cgctaagttg gcagcatcac ccgacgcact ttgcgccgaa taaatacctg    360
tgacggaaga tcacttcgca gaataaataa atcctggtgt ccctgttgat accgggaagc    420
cctgggccaa cttttggcga aaatgagacg ttgatcggca cgtaagaggt tccaactttc    480
accataatga aataagatca ctaccgggcg tatttttga gttatcgaga ttttcaggag    540
ctaaggaagc taaaatggag aaaaaaatca ctggatatac caccgttgat atatcccaat    600
ggcatcgtaa agaacatttt gaggcatttc agtcagttgc tcaatgtacc tataaccaga    660
ccgttcagct ggatattacg gcctttttaa agaccgtaaa gaaaaataag cacaagtttt    720
atccggcctt tattcacatt cttgcccgcc tgatgaatgc tcatccggaa ttccgtatgg    780
caatgaaaga cggtgagctg gtgatatggg atagtgttca cccttgttac accgttttcc    840
atgagcaaac tgaaacgttt tcatcgctct ggagtgaata ccacgacgat ttccggcagt    900
ttctacacat atattcgcaa gatgtggcgt gttacggtga aaacctggcc tatttcccta    960
aagggtttat tgagaatatg tttttcgtct cagccaatcc ctgggtgagt ttcaccagtt   1020
ttgatttaaa cgtggccaat atggacaact tcttcgcccc cgttttcacc atgggcaaat   1080
attatacgca aggcgacaag gtgctgatgc cgctggcgat tcaggttcat catgccgtct   1140
gtgatggctt ccatgtcggc agaatgctta atgaattaca acagtactgc gatgagtggc   1200
agggcggggc gtaaacgcgt ggatccggct tactaaaagc cagataacag tatgcgtatt   1260
tgcgcgctga tttttgcggt ataagaatat atactgatat gtatacccga agtatgtcaa   1320
aaagaggtgt gctatgaagc agcgtattac agtgacagtt gacagcgaca gctatcagtt   1380
gctcaaggca tatatgatgt caatatctcc ggtctggtaa gcacaaccat gcagaatgaa   1440
gcccgtcgtc tgcgtgccga acgctggaaa gcggaaaatc aggaagggat ggctgaggtc   1500
gcccggttta ttgaaatgaa cggctctttt gctgacgaga acagggactg gtgaaatgca   1560
gtttaaggtt tacacctata aaagagagag ccgttatcgt ctgtttgtgg atgtacagag   1620
tgatattatt gacacgcccg ggcgacggat ggtgatcccc ctggccagtg cacgtctgct   1680
gtcagataaa gtctcccgtg aactttaccc ggtggtgcat atcggggatg aaagctggcg   1740
catgatgacc accgatatgg ccagtgtgcc ggtctccgtt atcggggaag aagtggctga   1800
tctcagccac cgcgaaaatg acatcaaaaa cgccattaac ctgatgttct ggggaatata   1860
aatgtcaggc tcccttatac acagccagtc tgcaggtcga ccatagtgac tggatatgtt   1920
gtgttttaca gtattatgta gtctgttttt tatgcaaaat ctaatttaat atattgatat   1980
ttatatcatt ttacgtttct cgttcagctt tcttgtacaa agtggtgatc actagtcggc   2040
ggccgctcta gaggatccaa gcttacgtac gcgtgcatgc gacgtcatag ctcttctata   2100
gtgtcaccta aattcaattc actggccgtc gttttacaac gtcgtgactg ggaaaaccct   2160
ggcgttaccc aacttaatcg ccttgcagca catccccctt tcgccagctg gcgtaatagc   2220
gaagaggccc gcaccgatcg cccttcccaa cagttgcgca gcctgaatgg cgaatggacg   2280
cgccctgtag cggcgcatta agcgcggcgg gtgtggtggt tacgcgcagc gtgaccgcta   2340
cacttgccag cgccctagcg cccgctcctt tcgctttctt cccttccttt ctcgccacgt   2400
tcgccggctt tccccgtcaa gctctaaatc gggggctccc tttagggttc cgatttagtg   2460
```

-continued

```
ctttacggca cctcgacccc aaaaaacttg attagggtga tggttcacgt agtgggccat   2520
cgccctgata gacggttttt cgccctttga cgttggagtc cacgttcttt aatagtggac   2580
tcttgttcca aactggaaca acactcaacc ctatctcggt ctattctttt gatttataag   2640
ggattttgcc gatttcggcc tattggttaa aaaatgagct gatttaacaa aaatttaacg   2700
cgaattttaa caaaatatta acgtttacaa tttcaggtgg cacttttcgg ggaaatgtgc   2760
gcggaacccc tatttgttta tttttctaaa tacattcaaa tatgtatccg ctcatgagac   2820
aataaccctg ataaatgctt caataatatt gaaaaaggaa gagtatgagt attcaacatt   2880
tccgtgtcgc ccttattccc ttttttgcgg cattttgcct tcctgttttt gctcacccag   2940
aaacgctggt gaaagtaaaa gatgctgaag atcagttggg tgcacgagtg ggttacatcg   3000
aactggatct caacagcggt aagatccttg agagttttcg ccccgaagaa cgttttccaa   3060
tgatgagcac ttttaaagtt ctgctatgtg gcgcggtatt atcccgtatt gacgccgggc   3120
aagagcaact cggtcgccgc atacactatt ctcagaatga cttggttgag tactcaccag   3180
tcacagaaaa gcatcttacg gatggcatga cagtaagaga attatgcagt gctgccataa   3240
ccatgagtga taacactgcg gccaacttac ttctgacaac gatcggagga ccgaaggagc   3300
taaccgcttt tttgcacaac atgggggatc atgtaactcg ccttgatcgt tgggaaccgg   3360
agctgaatga agccatacca aacgacgagc gtgacaccac gatgcctgta gcaatggcaa   3420
caacgttgcg caaactatta actggcgaac tacttactct agcttcccgg caacaattaa   3480
tagactggat ggaggcggat aaagttgcag gaccacttct gcgctcggcc cttccggctg   3540
gctggtttat tgctgataaa tctggagccg gtgagcgtgg gtctcgcggt atcattgcag   3600
cactggggcc agatggtaag ccctcccgta tcgtagttat ctacacgacg gggagtcagg   3660
caactatgga tgaacgaaat agacagatcg ctgagatagg tgcctcactg attaagcatt   3720
ggtaactgtc agaccaagtt tactcatata tactttagat tgatttaaaa cttcattttt   3780
aatttaaaag gatctaggtg aagatccttt ttgataatct catgaccaaa atcccttaac   3840
gtgagttttc gttccactga gcgtcagacc ccgtagaaaa gatcaaagga tcttcttgag   3900
atcctttttt tctgcgcgta atctgctgct tgcaaacaaa aaaaccaccg ctaccagcgg   3960
tggtttgttt gccggatcaa gagctaccaa ctctttttcc gaaggtaact ggcttcagca   4020
gagcgcagat accaaatact gtccttctag tgtagccgta gttaggccac cacttcaaga   4080
actctgtagc accgcctaca tacctcgctc tgctaatcct gttaccagtg gctgctgcca   4140
gtggcgataa gtcgtgtctt accgggttgg actcaagacg atagttaccg gataaggcgc   4200
agcggtcggg ctgaacgggg ggttcgtgca cacagcccag cttggagcga acgacctaca   4260
ccgaactgag atacctacag cgtgagcatt gagaaagcgc cacgcttccc gaagggagaa   4320
aggcggacag gtatccggta agcggcaggg tcggaacagg agagcgcacg agggagcttc   4380
caggggggaaa cgcctggtat ctttatagtc ctgtcgggtt tcgccacctc tgacttgagc   4440
gtcgattttt gtgatgctcg tcaggggggc ggagcctatg gaaaaacgcc agcaacgcgg   4500
cctttttacg gttcctggcc ttttgctggc cttttgctca catgttcttt cctgcgttat   4560
cccctgattc tgtggataac cgtattaccg cctttgagtg agctgatacc gctcgccgca   4620
gccgaacgac cgagcgcagc gagtcagtga gcgaggaagc ggaagagcgc ccaatacgca   4680
aaccgcctct ccccgcgcgt tggccgattc attaatgcag agcttgcaat tcgcgcgcga   4740
aggcgaagcg gcatttacgt tgacaccatc gaatggcgca aaacctttcg cggtatggca   4800
```

-continued

```
tgatagcgcc cggaagagag tcaattcagg gtggtgaatg tgaaaccagt aacgttatac   4860

gatgtcgcag agtatgccgg tgtctcttat cagaccgttt cccgcgtggt gaaccaggcc   4920

agccacgttt ctgcgaaaac gcgggaaaaa gtggaagcgg cgatggcgga gctgaattac   4980

attcccaacc gcgtggcaca acaactggcg ggcaaacagt cgttgctgat tggcgttgcc   5040

acctccagtc tggccctgca cgcgccgtcg caaattgtcg cggcgattaa atctcgcgcc   5100

gatcaactgg gtgccagcgt ggtggtgtcg atggtagaac gaagcggcgt cgaagcctgt   5160

aaagcggcgg tgcacaatct tctcgcgcaa cgggtcagtg ggctgatcat taactatccg   5220

ctggatgacc aggatgccat tgctgtggaa gctgcctgca ctaatgttcc ggcgttattt   5280

cttgatgtct ctgaccagac acccatcaac agtattattt tctcccatga agacggtacg   5340

cgactgggcg tggagcatct ggtcgcattg ggtcaccagc aaatcgcgct gttagcgggc   5400

ccattaagtt ctgtctcggc gcgtctgcgt ctggctggct ggcataaata tctcactcgc   5460

aatcaaattc agccgatagc ggaacgggaa ggcgactgga gtgccatgtc cggttttcaa   5520

caaaccatgc aaatgctgaa tgagggcatc gttcccactg cgatgctggt tgccaacgat   5580

cagatggcgc tgggcgcaat gcgcgccatt accgagtccg ggctgcgcgt tggtgcggat   5640

atctcggtag tgggatacga cgataccgaa gacagctcat gttatatccc gccgtcaacc   5700

accatcaaac aggattttcg cctgctgggg caaaccagcg tggaccgctt gctgcaactc   5760

tctcagggcc aggcggtgaa gggcaatcag ctgttgcccg tctcactggt gaaaagaaaa   5820

accaccctgg cgcccaatac gcaaaccgcc tctccccgcg cgttggccga ttcattaatg   5880

cagctggcac gacaggtttc ccgactggaa agcgggcagt gagcgcaacg caattaatgt   5940

gagttagctc actcatt                                                  5957
```

<210> SEQ ID NO 134
<211> LENGTH: 5957
<212> TYPE: DNA
<213> ORGANISM: Artificial Sequence
<220> FEATURE:
<223> OTHER INFORMATION: pDEST6
<220> FEATURE:
<221> NAME/KEY: gene
<222> LOCATION: (142)..(266)
<223> OTHER INFORMATION: attR1
<220> FEATURE:
<221> NAME/KEY: gene
<222> LOCATION: (516)..(1175)
<223> OTHER INFORMATION: CmR
<220> FEATURE:
<221> NAME/KEY: gene
<222> LOCATION: (1295)..(1379)
<223> OTHER INFORMATION: inactivated ccdA
<220> FEATURE:
<221> NAME/KEY: gene
<222> LOCATION: (1517)..(1822)
<223> OTHER INFORMATION: ccdB
<220> FEATURE:
<221> NAME/KEY: gene
<222> LOCATION: (1863)..(1987)
<223> OTHER INFORMATION: attR2
<220> FEATURE:
<221> NAME/KEY: gene
<222> LOCATION: (2203)..(3369)
<223> OTHER INFORMATION: lacI
<220> FEATURE:
<221> NAME/KEY: gene
<222> LOCATION: (4403)..(5260)
<223> OTHER INFORMATION: ampR
<220> FEATURE:
<221> NAME/KEY: gene
<222> LOCATION: (5392)..(5847)
<223> OTHER INFORMATION: f1 (f1 intergenic region)

-continued

<400> SEQUENCE: 134

```
taacgccagg gttttcccag tcacgacgtt gtaaaacgac ggccagtgaa ttgaatttag      60
gtgacactat agaagagcta tgacgtcgca tgcacgcgta cgtaagcttg gatcctctag     120
agcggccgcc gactagtgat cacaagtttg tacaaaaaag ctgaacgaga aacgtaaaat     180
gatataaata tcaatatatt aaattagatt ttgcataaaa aacagactac ataatactgt     240
aaaacacaac atatccagtc actatggcgg ccgctaagtt ggcagcatca cccgacgcac     300
tttgcgccga ataaatacct gtgacggaag atcacttcgc agaataaata aatcctggtg     360
tccctgttga taccgggaag ccctgggcca acttttggcg aaaatgagac gttgatcggc     420
acgtaagagg ttccaacttt caccataatg aaataagatc actaccgggc gtattttttg     480
agttatcgag attttcagga gctaaggaag ctaaaatgga gaaaaaaatc actggatata     540
ccaccgttga tatatcccaa tggcatcgta aagaacattt tgaggcattt cagtcagttg     600
ctcaatgtac ctataaccag accgttcagc tggatattac ggccttttta aagaccgtaa     660
agaaaaataa gcacaagttt tatccggcct ttattcacat tcttgcccgc ctgatgaatg     720
ctcatccgga attccgtatg gcaatgaaag acggtgagct ggtgatatgg gatagtgttc     780
acccttgtta caccgttttc catgagcaaa ctgaaacgtt ttcatcgctc tggagtgaat     840
accacgacga tttccggcag tttctacaca tatattcgca agatgtggcg tgttacggtg     900
aaaacctggc ctatttccct aaagggttta ttgagaatat gtttttcgtc tcagccaatc     960
cctgggtgag tttcaccagt tttgatttaa acgtggccaa tatggacaac ttcttcgccc    1020
ccgttttcac catgggcaaa tattatacgc aaggcgacaa ggtgctgatg ccgctggcga    1080
ttcaggttca tcatgccgtc tgtgatggct tccatgtcgg cagaatgctt aatgaattac    1140
aacagtactg cgatgagtgg cagggcgggg cgtaaacgcg tggatccggc ttactaaaag    1200
ccagataaca gtatgcgtat ttgcgcgctg atttttgcgg tataagaata tatactgata    1260
tgtatacccg aagtatgtca aaaagaggtg tgctatgaag cagcgtatta cagtgacagt    1320
tgacagcgac agctatcagt tgctcaaggc atatatgatg tcaatatctc cggtctggta    1380
agcacaacca tgcagaatga agcccgtcgt ctgcgtgccg aacgctggaa agcggaaaat    1440
caggaaggga tggctgaggt cgcccggttt attgaaatga acggctcttt tgctgacgag    1500
aacagggact ggtgaaatgc agtttaaggt ttacacctat aaaagagaga gccgttatcg    1560
tctgtttgtg gatgtacaga gtgatattat tgacacgccc gggcgacgga tggtgatccc    1620
cctggccagt gcacgtctgc tgtcagataa agtctcccgt gaactttacc cggtggtgca    1680
tatcggggat gaaagctggc gcatgatgac caccgatatg gccagtgtgc cggtctccgt    1740
tatcggggaa gaagtggctg atctcagcca ccgcgaaaat gacatcaaaa acgccattaa    1800
cctgatgttc tggggaatat aaatgtcagg ctcccttata cacagccagt ctgcaggtcg    1860
accatagtga ctggatatgt tgtgttttac agtattatgt agtctgtttt ttatgcaaaa    1920
tctaatttaa tatattgata tttatatcat tttacgtttc tcgttcagct ttcttgtaca    1980
aagtggtgat cgtcgacccg ggaattccgg accggtacct gcaggcgtac cagctttccc    2040
tatagtgagt cgtattagag cttggcgtaa tcatggtcat agctgtttcc tgtgtgaaat    2100
tgttatccgc tcacaattcc acacaacata cgagccggaa gcataaagtg taaagcctgg    2160
ggtgcctaat gagtgagcta actcacatta attgcgttgc gctcactgcc cgctttccag    2220
tcgggaaacc tgtcgtgcca gctgcattaa tgaatcggcc aacgcgcggg gagaggcggt    2280
```

-continued

```
ttgcgtattg ggcgccaggg tggtttttct tttcaccagt gagacgggca acagctgatt   2340
gcccttcacc gcctggccct gagagagttg cagcaagcgg tccacgctgg tttgccccag   2400
caggcgaaaa tcctgtttga tggtggttga cggcgggata taacatgagc tgtcttcggt   2460
atcgtcgtat cccactaccg agatatccgc accaacgcgc agcccggact cggtaatggc   2520
gcgcattgcg cccagcgcca tctgatcgtt ggcaaccagc atcgcagtgg gaacgatgcc   2580
ctcattcagc atttgcatgg tttgttgaaa accggacatg gcactccagt cgccttcccg   2640
ttccgctatc ggctgaattt gattgcgagt gagatattta tgccagccag ccagacgcag   2700
acgcgccgag acagaactta atgggcccgc taacagcgcg atttgctggt gacccaatgc   2760
gaccagatgc tccacgccca gtcgcgtacc gtcttcatgg gagaaaataa tactgttgat   2820
gggtgtctgg tcagagacat caagaaataa cgccggaaca ttagtgcagg cagcttccac   2880
agcaatggca tcctggtcat ccagcggata gttaatgatc agcccactga cccgttgcgc   2940
gagaagattg tgcaccgccg ctttacaggc ttcgacgccg cttcgttcta ccatcgacac   3000
caccacgctg gcacccagtt gatcggcgcg agatttaatc gccgcgacaa tttgcgacgg   3060
cgcgtgcagg gccagactgg aggtggcaac gccaatcagc aacgactgtt tgcccgccag   3120
ttgttgtgcc acgcggttgg gaatgtaatt cagctccgcc atcgccgctt ccactttttc   3180
ccgcgttttc gcagaaacgt ggctggcctg gttcaccacg cgggaaacgg tctgataaga   3240
gacaccggca tactctgcga catcgtataa cgttactggt ttcacattca ccaccctgaa   3300
ttgactctct tccgggcgct atcatgccat accgcgaaag gttttgcgcc attcgatggt   3360
gtcaacgtaa atgccgcttc gccttcgcgc gcgaattgca agctctgcat taatgaatcg   3420
gccaacgcgc ggggagaggc ggtttgcgta ttgggcgctc ttccgcttcc tcgctcactg   3480
actcgctgcg ctcggtcgtt cggctgcggc gagcggtatc agctcactca aaggcggtaa   3540
tacggttatc cacagaatca ggggataacg caggaaagaa catgtgagca aaaggccagc   3600
aaaaggccag gaaccgtaaa aaggccgcgt tgctggcgtt tttccatagg ctccgccccc   3660
ctgacgagca tcacaaaaat cgacgctcaa gtcagaggtg gcgaaacccg acaggactat   3720
aaagatacca ggcgtttccc cctggaagct ccctcgtgcg ctctcctgtt ccgaccctgc   3780
cgcttaccgg atacctgtcc gcctttctcc cttcgggaag cgtggcgctt tctcaatgct   3840
cacgctgtag gtatctcagt tcggtgtagg tcgttcgctc caagctgggc tgtgtgcacg   3900
aaccccccgt tcagcccgac cgctgcgcct tatccggtaa ctatcgtctt gagtccaacc   3960
cggtaagaca cgacttatcg ccactggcag cagccactgg taacaggatt agcagagcga   4020
ggtatgtagg cggtgctaca gagttcttga agtggtggcc taactacggc tacactagaa   4080
ggacagtatt tggtatctgc gctctgctga agccagttac cttcggaaaa agagttggta   4140
gctcttgatc cggcaaacaa accaccgctg gtagcggtgg tttttttgtt tgcaagcagc   4200
agattacgcg cagaaaaaaa ggatctcaag aagatccttt gatcttttct acggggtctg   4260
acgctcagtg gaacgaaaac tcacgttaag ggattttggt catgagatta tcaaaaagga   4320
tcttcaccta gatcctttta aattaaaaat gaagttttaa atcaatctaa agtatatatg   4380
agtaaacttg gtctgacagt taccaatgct taatcagtga ggcacctatc tcagcgatct   4440
gtctatttcg ttcatccata gttgcctgac tccccgtcgt gtagataact acgatacggg   4500
agggcttacc atctggcccc agtgctgcaa tgataccgcg agacccacgc tcaccggctc   4560
cagatttatc agcaataaac cagccagccg gaagggccga gcgcagaagt ggtcctgcaa   4620
ctttatccgc ctccatccag tctattaatt gttgccggga agctagagta agtagttcgc   4680
```

-continued

```
cagttaatag tttgcgcaac gttgttgcca ttgctacagg catcgtggtg tcacgctcgt   4740

cgtttggtat ggcttcattc agctccggtt cccaacgatc aaggcgagtt acatgatccc   4800

ccatgttgtg caaaaaagcg gttagctcct tcggtcctcc gatcgttgtc agaagtaagt   4860

tggccgcagt gttatcactc atggttatgg cagcactgca taattctctt actgtcatgc   4920

catccgtaag atgcttttct gtgactggtg agtactcaac caagtcattc tgagaatagt   4980

gtatgcggcg accgagttgc tcttgcccgg cgtcaatacg ggataatacc gcgccacata   5040

gcagaacttt aaaagtgctc atcattggaa aacgttcttc ggggcgaaaa ctctcaagga   5100

tcttaccgct gttgagatcc agttcgatgt aacccactcg tgcacccaac tgatcttcag   5160

catcttttac tttcaccagc gtttctgggt gagcaaaaac aggaaggcaa aatgccgcaa   5220

aaaagggaat aagggcgaca cggaaatgtt gaatactcat actcttcctt tttcaatatt   5280

attgaagcat ttatcagggt tattgtctca tgagcggata catatttgaa tgtatttaga   5340

aaaataaaca aataggggtt ccgcgcacat ttccccgaaa agtgccacct gaaattgtaa   5400

acgttaatat tttgttaaaa ttcgcgttaa atttttgtta aatcagctca ttttttaacc   5460

aataggccga aatcggcaaa atcccttata aatcaaaaga atagaccgag atagggttga   5520

gtgttgttcc agtttggaac aagagtccac tattaaagaa cgtggactcc aacgtcaaag   5580

ggcgaaaaac cgtctatcag ggcgatggcc cactacgtga accatcaccc taatcaagtt   5640

ttttggggtc gaggtgccgt aaagcactaa atcggaaccc taaagggagc ccccgattta   5700

gagcttgacg gggaaagccg gcgaacgtgg cgagaaagga agggaagaaa gcgaaaggag   5760

cgggcgctag ggcgctggca agtgtagcgg tcacgctgcg cgtaaccacc acacccgccg   5820

cgcttaatgc gccgctacag ggcgcgtcca ttcgccattc aggctgcgca actgttggga   5880

agggcgatcg gtgcgggcct cttcgctatt acgccagctg gcgaaagggg gatgtgctgc   5940

aaggcgatta agttggg                                                  5957
```

```
<210> SEQ ID NO 135
<211> LENGTH: 6025
<212> TYPE: DNA
<213> ORGANISM: Artificial Sequence
<220> FEATURE:
<223> OTHER INFORMATION: pDEST7
<220> FEATURE:
<221> NAME/KEY: gene
<222> LOCATION: (67)..(589)
<223> OTHER INFORMATION: CMV promoter
<220> FEATURE:
<221> NAME/KEY: gene
<222> LOCATION: (782)..(906)
<223> OTHER INFORMATION: attR1
<220> FEATURE:
<221> NAME/KEY: gene
<222> LOCATION: (1015)..(1674)
<223> OTHER INFORMATION: CmR
<220> FEATURE:
<221> NAME/KEY: gene
<222> LOCATION: (1794)..(1878)
<223> OTHER INFORMATION: inactivated ccdA
<220> FEATURE:
<221> NAME/KEY: gene
<222> LOCATION: (2016)..(2321)
<223> OTHER INFORMATION: ccdB
<220> FEATURE:
<221> NAME/KEY: gene
<222> LOCATION: (2362)..(2486)
<223> OTHER INFORMATION: attR2
<220> FEATURE:
<221> NAME/KEY: gene
<222> LOCATION: (2671)..(3033)
```

-continued

<223> OTHER INFORMATION: small t & polyA
<220> FEATURE:
<221> NAME/KEY: gene
<222> LOCATION: (3227)..(3502)
<223> OTHER INFORMATION: f1
<220> FEATURE:
<221> NAME/KEY: gene
<222> LOCATION: (3962)..(4822)
<223> OTHER INFORMATION: ampR
<220> FEATURE:
<221> NAME/KEY: gene
<222> LOCATION: (5022)..(5661)
<223> OTHER INFORMATION: ori

<400> SEQUENCE: 135
attatcatga cattaaccta taaaaatagg cgtagtacga ggccctttca ctcattagat 60
gcatgtcgtt acataactta cggtaaatgg cccgcctggc tgaccgccca acgacccccg 120
cccattgacg tcaataatga cgtatgttcc catagtaacg ccaataggga ctttccattg 180
acgtcaatgg gtggagtatt tacggtaaac tgcccacttg gcagtacatc aagtgtatca 240
tatgccaagt acgcccccta ttgacgtcaa tgacggtaaa tggcccgcct ggcattatgc 300
ccagtacatg accttatggg actttcctac ttggcagtac atctacgtat tagtcatcgc 360
tattaccatg gtgatgcggt tttggcagta catcaatggg cgtggatagc ggtttgactc 420
acggggattt ccaagtctcc accccattga cgtcaatggg agtttgtttt ggcaccaaaa 480
tcaacgggac tttccaaaat gtcgtaacaa ctccgcccca ttgacgcaaa tgggcggtag 540
gcgtgtacgg tgggaggtct atataagcag agctcgttta gtgaaccgtc agatcgcctg 600
gagacgccat ccacgctgtt ttgacctcca tagaagacac cgggaccgat ccagcctccg 660
gactctagcc taggccgcgg agcggataac aatttcacac aggaaacagc tatgaccatt 720
aggcctttgc aaaaagctat ttaggtgaca ctatagaagg tacgcctgca ggtaccggat 780
cacaagtttg tacaaaaaag ctgaacgaga aacgtaaaat gatataaata tcaatatatt 840
aaattagatt ttgcataaaa aacagactac ataatactgt aaaacacaac atatccagtc 900
actatggcgg ccgcattagg caccccaggc tttacacttt atgcttccgg ctcgtataat 960
gtgtggattt tgagttagga tccgtcgaga ttttcaggag ctaaggaagc taaaatggag 1020
aaaaaaatca ctggatatac caccgttgat atatcccaat ggcatcgtaa agaacatttt 1080
gaggcatttc agtcagttgc tcaatgtacc tataaccaga ccgttcagct ggatattacg 1140
gcctttttaa agaccgtaaa gaaaaataag cacaagtttt atccggcctt tattcacatt 1200
cttgcccgcc tgatgaatgc tcatccggaa ttccgtatgg caatgaaaga cggtgagctg 1260
gtgatatggg atagtgttca cccttgttac accgttttcc atgagcaaac tgaaacgttt 1320
tcatcgctct ggagtgaata ccacgacgat ttccggcagt ttctacacat atattcgcaa 1380
gatgtggcgt gttacggtga aaacctggcc tatttcccta aagggtttat tgagaatatg 1440
tttttcgtct cagccaatcc ctgggtgagt ttcaccagtt ttgatttaaa cgtggccaat 1500
atggacaact tcttcgcccc cgttttcacc atgggcaaat attatacgca aggcgacaag 1560
gtgctgatgc cgctggcgat tcaggttcat catgccgtct gtgatggctt ccatgtcggc 1620
agaatgctta atgaattaca acagtactgc gatgagtggc agggcggggc gtaaacgcgt 1680
ggatccggct tactaaaagc cagataacag tatgcgtatt tgcgcgctga tttttgcggt 1740
ataagaatat atactgatat gtatacccga agtatgtcaa aaagaggtgt gctatgaagc 1800
agcgtattac agtgacagtt gacagcgaca gctatcagtt gctcaaggca tatatgatgt 1860
caatatctcc ggtctggtaa gcacaaccat gcagaatgaa gcccgtcgtc tgcgtgccga 1920

-continued acgctggaaa gcggaaaatc aggaagggat ggctgaggtc gcccggttta ttgaaatgaa 1980
cggctctttt gctgacgaga acagggactg gtgaaatgca gtttaaggtt tacacctata 2040
aaagagagag ccgttatcgt ctgtttgtgg atgtacagag tgatattatt gacacgcccg 2100
ggcgacggat ggtgatcccc ctggccagtg cacgtctgct gtcagataaa gtctcccgtg 2160
aactttaccc ggtggtgcat atcggggatg aaagctggcg catgatgacc accgatatgg 2220
ccagtgtgcc ggtctccgtt atcggggaag aagtggctga tctcagccac cgcgaaaatg 2280
acatcaaaaa cgccattaac ctgatgttct ggggaatata aatgtcaggc tcccttatac 2340
acagccagtc tgcaggtcga ccatagtgac tggatatgtt gtgttttaca gtattatgta 2400
gtctgttttt tatgcaaaat ctaatttaat atattgatat ttatatcatt ttacgtttct 2460
cgttcagctt tcttgtacaa agtggtgatc gcgtgcatgc gacgtcatag ctctctccct 2520
atagtgagtc gtattataag ctaggcactg gccgtcgttt tacaacgtcg tgactgggaa 2580
aactgctagc ttgggatctt tgtgaaggaa ccttacttct gtggtgtgac ataattggac 2640
aaactaccta cagagattta aagctctaag gtaaatataa aatttttaag tgtataatgt 2700
gttaaactag ctgcatatgc ttgctgcttg agagttttgc ttactgagta tgatttatga 2760
aaatattata cacaggagct agtgattcta attgtttgtg tattttagat tcacagtccc 2820
aaggctcatt tcaggcccct cagtcctcac agtctgttca tgatcataat cagccatacc 2880
acatttgtag aggttttact tgctttaaaa aacctcccac acctccccct gaacctgaaa 2940
cataaaatga atgcaattgt tgttgttaac ttgtttattg cagcttataa tggttacaaa 3000
taaagcaata gcatcacaaa tttcacaaat aaagcatttt tttcactgca ttctagttgt 3060
ggtttgtcca aactcatcaa tgtatcttat catgtctgga tcgatcctgc attaatgaat 3120
cggccaacgc gcggggagag gcggtttgcg tattggctgg cgtaatagcg aagaggcccg 3180
caccgatcgc ccttcccaac agttgcgcag cctgaatggc gaatgggacg cgccctgtag 3240
cggcgcatta agcgcggcgg gtgtggtggt tacgcgcagc gtgaccgcta cacttgccag 3300
cgccctagcg cccgctcctt tcgctttctt cccttccttt ctcgccacgt tcgccggctt 3360
tccccgtcaa gctctaaatc gggggctccc tttagggttc cgatttagtg ctttacggca 3420
cctcgacccc aaaaaacttg attagggtga tggttcacgt agtgggccat cgccctgata 3480
gacggttttt cgccctttga cgttggagtc cacgttcttt aatagtggac tcttgttcca 3540
aactggaaca acactcaacc ctatctcggt ctattctttt gatttataag ggattttgcc 3600
gatttcggcc tattggttaa aaaatgagct gatttaacaa aaatttaacg cgaattttaa 3660
caaaatatta acgtttacaa tttcaggtgg cacttttcgg ggaaatgtgc gcggaacccc 3720
tatttgttta tttttctaaa tacattcaaa tatgtatccg ctcatgccag gtcttggact 3780
ggtgagaacg gcttgctcgg cagcttcgat gtgtgctgga gggagaataa aggtctaaga 3840
tgtgcgatag agggaagtcg cattgaatta tgtgctgtgt agggatcgct ggtatcaaat 3900
atgtgtgccc acccctggca tgagacaata accctgataa atgcttcaat aatattgaaa 3960
aaggaagagt atgagtattc aacatttccg tgtcgccctt attccctttt ttgcggcatt 4020
ttgccttcct gtttttgctc acccagaaac gctggtgaaa gtaaaagatg ctgaagatca 4080
gttgggtgca cgagtgggtt acatcgaact ggatctcaac agcggtaaga tccttgagag 4140
ttttcgcccc gaagaacgtt ttccaatgat gagcactttt aaagttctgc tatgtggcgc 4200
ggtattatcc cgtattgacg ccgggcaaga gcaactcggt cgccgcatac actattctca 4260

-continued

```
gaatgacttg gttgagtact caccagtcac agaaaagcat cttacggatg gcatgacagt   4320

aagagaatta tgcagtgctg ccataaccat gagtgataac actgcggcca acttacttct   4380

gacaacgatc ggaggaccga aggagctaac cgcttttttg cacaacatgg gggatcatgt   4440

aactcgcctt gatcgttggg aaccggagct gaatgaagcc ataccaaacg acgagcgtga   4500

caccacgatg cctgtagcaa tggcaacaac gttgcgcaaa ctattaactg gcgaactact   4560

tactctagct tcccggcaac aattaataga ctggatggag gcggataaag ttgcaggacc   4620

acttctgcgc tcggcccttc cggctggctg gtttattgct gataaatctg gagccggtga   4680

gcgtgggtct cgcggtatca ttgcagcact ggggccagat ggtaagccct cccgtatcgt   4740

agttatctac acgacgggga gtcaggcaac tatggatgaa cgaaatagac agatcgctga   4800

gataggtgcc tcactgatta agcattggta actgtcagac caagtttact catatatact   4860

ttagattgat ttaaaacttc atttttaatt taaaaggatc taggtgaaga tcctttttga   4920

taatctcatg ccataacttc gtataatgta tgctatacga agttatggca tgaccaaaat   4980

cccttaacgt gagttttcgt tccactgagc gtcagacccc gtagaaaaga tcaaaggatc   5040

ttcttgagat cctttttttc tgcgcgtaat ctgctgcttg caaacaaaaa aaccaccgct   5100

accagcggtg gtttgtttgc cggatcaaga gctaccaact ctttttccga aggtaactgg   5160

cttcagcaga gcgcagatac caaatactgt ccttctagtg tagccgtagt taggccacca   5220

cttcaagaac tctgtagcac cgcctacata cctcgctctg ctaatcctgt taccagtggc   5280

tgctgccagt ggcgataagt cgtgtcttac cgggttggac tcaagacgat agttaccgga   5340

taaggcgcag cggtcgggct gaacgggggg ttcgtgcaca cagcccagct tggagcgaac   5400

gacctacacc gaactgagat acctacagcg tgagcattga gaaagcgcca cgcttcccga   5460

agggagaaag gcggacaggt atccggtaag cggcagggtc ggaacaggag agcgcacgag   5520

ggagcttcca gggggaaacg cctggtatct ttatagtcct gtcgggtttc gccacctctg   5580

acttgagcgt cgatttttgt gatgctcgtc aggggggcgg agcctatgga aaaacgccag   5640

caacgcggcc tttttacggt tcctggcctt ttgctggcct tttgctcaca tgttctttcc   5700

tgcgttatcc cctgattctg tggataaccg tattaccgcc tttgagtgag ctgataccgc   5760

tcgccgcagc cgaacgaccg agcgcagcga gtcagtgagc gaggaagcgg aagagcgccc   5820

aatacgcaaa ccgcctctcc ccgcgcgttg gccgattcat taatgcagag cttgcaattc   5880

gcgcgttttt caatattatt gaagcattta tcagggttat tgtctcatga gcggatacat   5940

atttgaatgt atttagaaaa ataaacaaat aggggttccg cgcacatttc cccgaaaagt   6000

gccacctgac gtctaagaaa ccatt                                         6025
```

<210> SEQ ID NO 136
<211> LENGTH: 6526
<212> TYPE: DNA
<213> ORGANISM: Artificial Sequence
<220> FEATURE:
<223> OTHER INFORMATION: pDEST8
<220> FEATURE:
<221> NAME/KEY: gene
<222> LOCATION: (23)..(152)
<223> OTHER INFORMATION: Ppolh
<220> FEATURE:
<221> NAME/KEY: gene
<222> LOCATION: (160)..(284)
<223> OTHER INFORMATION: attR1
<220> FEATURE:
<221> NAME/KEY: gene
<222> LOCATION: (534)..(1193)
<223> OTHER INFORMATION: CmR -continued
<220> FEATURE:
<221> NAME/KEY: gene
<222> LOCATION: (1313)..(1397)
<223> OTHER INFORMATION: inactivated ccdA
<220> FEATURE:
<221> NAME/KEY: gene
<222> LOCATION: (1535)..(1840)
<223> OTHER INFORMATION: ccdB
<220> FEATURE:
<221> NAME/KEY: gene
<222> LOCATION: (1881)..(2005)
<223> OTHER INFORMATION: attR2
<220> FEATURE:
<221> NAME/KEY: gene
<222> LOCATION: (2766)..(3146)
<223> OTHER INFORMATION: f1
<220> FEATURE:
<221> NAME/KEY: gene
<222> LOCATION: (3240)..(4090)
<223> OTHER INFORMATION: ampR
<220> FEATURE:
<221> NAME/KEY: gene
<222> LOCATION: (4289)..(4869)
<223> OTHER INFORMATION: ori
<220> FEATURE:
<221> NAME/KEY: gene
<222> LOCATION: (5564)..(6496)
<223> OTHER INFORMATION: genR

<400> SEQUENCE: 136
cgtatactcc ggaatattaa tagatcatgg agataattaa aatgataacc atctcgcaaa 60
taaataagta ttttactgtt ttcgtaacag ttttgtaata aaaaaaccta taaatattcc 120
ggattattca taccgtccca ccatcgggcg cggatcatca caagtttgta caaaaaagct 180
gaacgagaaa cgtaaaatga tataaatatc aatatattaa attagatttt gcataaaaaa 240
cagactacat aatactgtaa aacacaacat atccagtcac tatggcggcc gctaagttgg 300
cagcatcacc cgacgcactt tgcgccgaat aaatacctgt gacggaagat cacttcgcag 360
aataaataaa tcctggtgtc cctgttgata ccgggaagcc ctgggccaac ttttggcgaa 420
aatgagacgt tgatcggcac gtaagaggtt ccaactttca ccataatgaa ataagatcac 480
taccgggcgt atttttgag ttatcgagat tttcaggagc taaggaagct aaaatggaga 540
aaaaaatcac tggatatacc accgttgata tatcccaatg gcatcgtaaa gaacattttg 600
aggcatttca gtcagttgct caatgtacct ataaccagac cgttcagctg gatattacgg 660
cctttttaaa gaccgtaaag aaaaataagc acaagtttta tccggccttt attcacattc 720
ttgcccgcct gatgaatgct catccggaat tccgtatggc aatgaaagac ggtgagctgg 780
tgatatggga tagtgttcac ccttgttaca ccgttttcca tgagcaaact gaaacgtttt 840
catcgctctg gagtgaatac cacgacgatt tccggcagtt tctacacata tattcgcaag 900
atgtggcgtg ttacggtgaa aacctggcct atttccctaa agggtttatt gagaatatgt 960
ttttcgtctc agccaatccc tgggtgagtt tcaccagttt tgatttaaac gtggccaata 1020
tggacaactt cttcgccccc gttttcacca tgggcaaata ttatacgcaa ggcgacaagg 1080
tgctgatgcc gctggcgatt caggttcatc atgccgtctg tgatggcttc catgtcggca 1140
gaatgcttaa tgaattacaa cagtactgcg atgagtggca gggcggggcg taaacgcgtg 1200
gatccggctt actaaaagcc agataacagt atgcgtattt gcgcgctgat ttttgcggta 1260
taagaatata tactgatatg tatacccgaa gtatgtcaaa aagaggtgtg ctatgaagca 1320
gcgtattaca gtgacagttg acagcgacag ctatcagttg ctcaaggcat atatgatgtc 1380
aatatctccg gtctggtaag cacaaccatg cagaatgaag cccgtcgtct gcgtgccgaa 1440

-continued

```
cgctggaaag cggaaaatca ggaagggatg gctgaggtcg cccggtttat tgaaatgaac   1500
ggctcttttg ctgacgagaa cagggactgg tgaaatgcag tttaaggttt acacctataa   1560
aagagagagc cgttatcgtc tgtttgtgga tgtacagagt gatattattg acacgcccgg   1620
gcgacggatg gtgatccccc tggccagtgc acgtctgctg tcagataaag tctcccgtga   1680
actttacccg gtggtgcata tcggggatga aagctggcgc atgatgacca ccgatatggc   1740
cagtgtgccg gtctccgtta tcggggaaga agtggctgat ctcagccacc gcgaaaatga   1800
catcaaaaac gccattaacc tgatgttctg ggaatataa atgtcaggct ccccttataca   1860
cagccagtct gcaggtcgac catagtgact ggatatgttg tgttttacag tattatgtag   1920
tctgtttttt atgcaaaatc taatttaata tattgatatt tatatcattt tacgtttctc   1980
gttcagcttt cttgtacaaa gtggtgatag cttgtcgaga agtactagag gatcataatc   2040
agccatacca catttgtaga ggttttactt gctttaaaaa acctcccaca cctccccctg   2100
aacctgaaac ataaaatgaa tgcaattgtt gttgttaact tgtttattgc agcttataat   2160
ggttacaaat aaagcaatag catcacaaat ttcacaaata aagcattttt ttcactgcat   2220
tctagttgtg gtttgtccaa actcatcaat gtatcttatc atgtctggat ctgatcactg   2280
cttgagccta ggagatccga accagataag tgaaatctag ttccaaacta ttttgtcatt   2340
tttaattttc gtattagctt acgacgctac acccagttcc catctatttt gtcactcttc   2400
cctaaataat ccttaaaaac tccatttcca cccctcccag ttcccaacta ttttgtccgc   2460
ccacagcggg gcattttct tcctgttatg tttttaatca aacatcctgc caactccatg   2520
tgacaaaccg tcatcttcgg ctactttttc tctgtcacag aatgaaaatt tttctgtcat   2580
ctcttcgtta ttaatgtttg taattgactg aatatcaacg cttatttgca gcctgaatgg   2640
cgaatggacg cgccctgtag cggcgcatta agcgcggcgg gtgtggtggt tacgcgcagc   2700
gtgaccgcta cacttgccag cgccctagcg cccgctcctt tcgctttctt cccttccttt   2760
ctcgccacgt tcgccggctt tccccgtcaa gctctaaatc gggggctccc tttagggttc   2820
cgatttagtg ctttacggca cctcgacccc aaaaaacttg attagggtga tggttcacgt   2880
agtgggccat cgccctgata gacggttttt cgccctttga cgttggagtc cacgttcttt   2940
aatagtggac tcttgttcca aactggaaca acactcaacc ctatctcggt ctattctttt   3000
gatttataag ggattttgcc gatttcggcc tattggttaa aaaatgagct gatttaacaa   3060
aaatttaacg cgaattttaa caaaatatta acgtttacaa tttcaggtgg cacttttcgg   3120
ggaaatgtgc gcggaacccc tatttgttta tttttctaaa tacattcaaa tatgtatccg   3180
ctcatgagac aataaccctg ataaatgctt caataatatt gaaaaaggaa gagtatgagt   3240
attcaacatt tccgtgtcgc ccttattccc ttttttgcgg cattttgcct tcctgttttt   3300
gctcacccag aaacgctggt gaaagtaaaa gatgctgaag atcagttggg tgcacgagtg   3360
ggttacatcg aactggatct caacagcggt aagatccttg agagttttcg ccccgaagaa   3420
cgttttccaa tgatgagcac ttttaaagtt ctgctatgtg gcgcggtatt atcccgtatt   3480
gacgccgggc aagagcaact cggtcgccgc atacactatt ctcagaatga cttggttgag   3540
tactcaccag tcacagaaaa gcatcttacg gatggcatga cagtaagaga attatgcagt   3600
gctgccataa ccatgagtga taacactgcg gccaacttac ttctgacaac gatcggagga   3660
ccgaaggagc taaccgcttt tttgcacaac atgggggatc atgtaactcg ccttgatcgt   3720
tgggaaccgg agctgaatga agccatacca aacgacgagc gtgacaccac gatgcctgta   3780
gcaatggcaa caacgttgcg caaactatta actggcgaac tacttactct agcttcccgg   3840
```

-continued

```
caacaattaa tagactggat ggaggcggat aaagttgcag gaccacttct gcgctcggcc   3900
cttccggctg gctggtttat tgctgataaa tctggagccg gtgagcgtgg gtctcgcggt   3960
atcattgcag cactggggcc agatggtaag ccctcccgta tcgtagttat ctacacgacg   4020
gggagtcagg caactatgga tgaacgaaat agacagatcg ctgagatagg tgcctcactg   4080
attaagcatt ggtaactgtc agaccaagtt tactcatata tactttagat tgatttaaaa   4140
cttcattttt aatttaaaag gatctaggtg aagatccttt ttgataatct catgaccaaa   4200
atcccttaac gtgagttttc gttccactga gcgtcagacc ccgtagaaaa gatcaaagga   4260
tcttcttgag atcctttttt tctgcgcgta atctgctgct tgcaaacaaa aaaaccaccg   4320
ctaccagcgg tggtttgttt gccggatcaa gagctaccaa ctctttttcc gaaggtaact   4380
ggcttcagca gagcgcagat accaaatact gtccttctag tgtagccgta gttaggccac   4440
cacttcaaga actctgtagc accgcctaca tacctcgctc tgctaatcct gttaccagtg   4500
gctgctgcca gtggcgataa gtcgtgtctt accgggttgg actcaagacg atagttaccg   4560
gataaggcgc agcggtcggg ctgaacgggg ggttcgtgca cacagcccag cttggagcga   4620
acgacctaca ccgaactgag atacctacag cgtgagcatt gagaaagcgc cacgcttccc   4680
gaagggagaa aggcggacag gtatccggta agcggcaggg tcggaacagg agagcgcacg   4740
agggagcttc caggggggaaa cgcctggtat ctttatagtc ctgtcgggtt tcgccacctc   4800
tgacttgagc gtcgattttt gtgatgctcg tcaggggggc ggagcctatg gaaaaacgcc   4860
agcaacgcgg cctttttacg gttcctggcc ttttgctggc cttttgctca catgttcttt   4920
cctgcgttat cccctgattc tgtggataac cgtattaccg cctttgagtg agctgatacc   4980
gctcgccgca gccgaacgac cgagcgcagc gagtcagtga gcgaggaagc ggaagagcgc   5040
ctgatgcggt attttctcct tacgcatctg tgcggtattt cacaccgcag accagccgcg   5100
taacctggca aaatcggtta cggttgagta ataaatggat gccctgcgta agcgggtgtg   5160
ggcggacaat aaagtcttaa actgaacaaa atagatctaa actatgacaa taaagtctta   5220
aactagacag aatagttgta aactgaaatc agtccagtta tgctgtgaaa aagcatactg   5280
gacttttgtt atggctaaag caaactcttc attttctgaa gtgcaaattg cccgtcgtat   5340
taaagagggg cgtggccaag ggcatggtaa agactatatt cgcggcgttg tgacaattta   5400
ccgaacaact ccgcggccgg gaagccgatc tcggcttgaa cgaattgtta ggtggcggta   5460
cttgggtcga tatcaaagtg catcacttct tcccgtatgc ccaactttgt atagagagcc   5520
actgcgggat cgtcaccgta atctgcttgc acgtagatca cataagcacc aagcgcgttg   5580
gcctcatgct tgaggagatt gatgagcgcg gtggcaatgc cctgcctccg gtgctcgccg   5640
gagactgcga gatcatagat atagatctca ctacgcggct gctcaaacct gggcagaacg   5700
taagccgcga gagcgccaac aaccgcttct tggtcgaagg cagcaagcgc gatgaatgtc   5760
ttactacgga gcaagttccc gaggtaatcg gagtccggct gatgttggga gtaggtggct   5820
acgtctccga actcacgacc gaaaagatca agagcagccc gcatggattt gacttggtca   5880
gggccgagcc tacatgtgcg aatgatgccc atacttgagc cacctaactt tgttttaggg   5940
cgactgccct gctgcgtaac atcgttgctg ctgcgtaaca tcgttgctgc tccataacat   6000
caaacatcga cccacggcgt aacgcgcttg ctgcttggat gcccgaggca tagactgtac   6060
aaaaaaacag tcataacaag ccatgaaaac cgccactgcg ccgttaccac cgctgcgttc   6120
ggtcaaggtt ctggaccagt tgcgtgagcg catacgctac ttgcattaca gtttacgaac   6180
```

-continued

```
cgaacaggct tatgtcaact gggttcgtgc cttcatccgt ttccacggtg tgcgtcaccc   6240

ggcaaccttg ggcagcagcg aagtcgaggc atttctgtcc tggctggcga acgagcgcaa   6300

ggtttcggtc tccacgcatc gtcaggcatt ggcggccttg ctgttcttct acggcaaggt   6360

gctgtgcacg gatctgccct ggcttcagga gatcggaaga cctcggccgt cgcggcgctt   6420

gccggtggtg ctgaccccgg atgaagtggt tcgcatcctc ggttttctgg aaggcgagca   6480

tcgtttgttc gcccaggact ctagctatag ttctagtggt tggcta                  6526
```

<210> SEQ ID NO 137
<211> LENGTH: 12464
<212> TYPE: DNA
<213> ORGANISM: Artificial Sequence
<220> FEATURE:
<223> OTHER INFORMATION: pDEST9
<220> FEATURE:
<221> NAME/KEY: gene
<222> LOCATION: (232)..(355)
<223> OTHER INFORMATION: attR1
<220> FEATURE:
<221> NAME/KEY: gene
<222> LOCATION: (605)..(1264)
<223> OTHER INFORMATION: CmR
<220> FEATURE:
<221> NAME/KEY: gene
<222> LOCATION: (1384)..(1468)
<223> OTHER INFORMATION: inactivated ccdA
<220> FEATURE:
<221> NAME/KEY: gene
<222> LOCATION: (1606)..(1911)
<223> OTHER INFORMATION: ccdB
<220> FEATURE:
<221> NAME/KEY: gene
<222> LOCATION: (1952)..(2078)
<223> OTHER INFORMATION: attR2
<220> FEATURE:
<221> NAME/KEY: gene
<222> LOCATION: (2532)..(2782)
<223> OTHER INFORMATION: ori
<220> FEATURE:
<221> NAME/KEY: gene
<222> LOCATION: (3482)..(4282)
<223> OTHER INFORMATION: ampR
<220> FEATURE:
<221> NAME/KEY: gene
<222> LOCATION: (5232)..(5365)
<223> OTHER INFORMATION: SP6 promoter
<220> FEATURE:
<221> NAME/KEY: gene
<222> LOCATION: (5365)..(6965)
<223> OTHER INFORMATION: nsP1:non-structural protein 1
<220> FEATURE:
<221> NAME/KEY: gene
<222> LOCATION: (6965)..(9265)
<223> OTHER INFORMATION: nsP2:non-structural protein 2
<220> FEATURE:
<221> NAME/KEY: gene
<222> LOCATION: (9265)..(10865)
<223> OTHER INFORMATION: nsP3:non-structural protein 3
<220> FEATURE:
<221> NAME/KEY: gene
<222> LOCATION: (161)..(10865)
<223> OTHER INFORMATION: nsP4:non-structural protein 4

<400> SEQUENCE: 137

```
agcaagtggt tccggacagg cttgggggcc gaactggagg tggcactaac atctaggtat     60

gaggtagagg gctgcaaaag tatcctcata gccatggcca ccttggcgag ggacattaag    120

gcgtttaaga aattgagagg acctgttata cacctctacg gcggtcctag attggtgcgt    180

taatacacag aattctgatt ggatcccggt ccgaagcgcg ctttcccatc acaagtttgt    240

acaaaaaagc tgaacgagaa acgtaaaatg atataaatat caatatatta aattagattt    300
```

-continued

```
tgcataaaaa acagactaca taatactgta aaacacaaca tatccagtca ctatggcggc    360
cgctaagttg gcagcatcac ccgacgcact ttgcgccgaa taaataccctg tgacggaaga    420
tcacttcgca gaataaataa atcctggtgt ccctgttgat accgggaagc cctgggccaa    480
cttttggcga aaatgagacg ttgatcggca cgtaagaggt tccaactttc accataatga    540
aataagatca ctaccgggcg tattttttga gttatcgaga ttttcaggag ctaaggaagc    600
taaaatggag aaaaaaatca ctggatatac caccgttgat atatcccaat ggcatcgtaa    660
agaacatttt gaggcatttc agtcagttgc tcaatgtacc tataaccaga ccgttcagct    720
ggatattacg gcctttttaa agaccgtaaa gaaaaataag cacaagtttt atccggcctt    780
tattcacatt cttgcccgcc tgatgaatgc tcatccggaa ttccgtatgg caatgaaaga    840
cggtgagctg gtgatatggg atagtgttca cccttgttac accgttttcc atgagcaaac    900
tgaaacgttt tcatcgctct ggagtgaata ccacgacgat ttccggcagt ttctacacat    960
atattcgcaa gatgtggcgt gttacggtga aaacctggcc tatttcccta aagggtttat   1020
tgagaatatg tttttcgtct cagccaatcc ctgggtgagt ttcaccagtt ttgatttaaa   1080
cgtggccaat atggacaact tcttcgcccc cgttttcacc atgggcaaat attatacgca   1140
aggcgacaag gtgctgatgc cgctggcgat tcaggttcat catgccgtct gtgatggctt   1200
ccatgtcggc agaatgctta atgaattaca acagtactgc gatgagtggc agggcggggc   1260
gtaaagatct ggatccggct tactaaaagc cagataacag tatgcgtatt tgcgcgctga   1320
tttttgcggt ataagaatat atactgatat gtatacccga agtatgtcaa aaagaggtgt   1380
gctatgaagc agcgtattac agtgacagtt gacagcgaca gctatcagtt gctcaaggca   1440
tatatgatgt caatatctcc ggtctggtaa gcacaaccat gcagaatgaa gcccgtcgtc   1500
tgcgtgccga acgctggaaa gcggaaaatc aggaagggat ggctgaggtc gcccggttta   1560
ttgaaatgaa cggctctttt gctgacgaga acagggactg gtgaaatgca gtttaaggtt   1620
tacacctata aaagagagag ccgttatcgt ctgtttgtgg atgtacagag tgatattatt   1680
gacacgcccg ggcgacggat ggtgatcccc ctggccagtg cacgtctgct gtcagataaa   1740
gtctcccgtg aactttaccc ggtggtgcat atcggggatg aaagctggcg catgatgacc   1800
accgatatgg ccagtgtgcc ggtctccgtt atcggggaag aagtggctga tctcagccac   1860
cgcgaaaatg acatcaaaaa cgccattaac ctgatgttct ggggaatata aatgtcaggc   1920
tcccttatac acagccagtc tgcaggtcga ccatagtgac tggatatgtt gtgttttaca   1980
gtattatgta gtctgttttt tatgcaaaag tgctaattta atatattgat atttatatca   2040
ttttacgttt ctcgttcagc tttcttgtac aaagtggtga tgggaactcg agttcactag   2100
tcgatcccgc ggccgctttc gaacctaggc aagcatgcgg gcccagtggg taattaattg   2160
aattacatcc ctacgcaaac gttttacggc cgccggtggc gcccgcgccc ggcggcccgt   2220
ccttggccgt tgcaggccac tccggtggct cccgtcgtcc ccgacttcca ggcccagcag   2280
atgcagcaac tcatcagcgc cgtaaatgcg ctgacaatga gacagaacgc aattgctcct   2340
gctaggagct taattcgacg aataattgga tttttatttt attttgcaat tggtttttaa   2400
tatttccaaa aaaaaaaaaa aaaaaaaaaa aaaaaaaaaa aaaaaaaaaa aaaaaaaaaa   2460
aaaaaaaaaa aaaaaaacta gaaatcgcga tttctagtct gcattaatga atcggccaac   2520
gcgcggggag aggcggtttg cgtattgggc gctcttccgc ttcctcgctc actgactcgc   2580
tgcgctcggt cgttcggctg cggcgagcgg tatcagctca ctcaaaggcg gtaatacggt   2640
```

-continued

```
tatccacaga atcaggggat aacgcaggaa agaacatgtg agcaaaaggc cagcaaaagg   2700
ccaggaaccg taaaaaggcc gcgttgctgg cgtttttcca taggctccgc ccccctgacg   2760
agcatcacaa aaatcgacgc tcaagtcaga ggtggcgaaa cccgacagga ctataaagat   2820
accaggcgtt tccccctgga agctccctcg tgcgctctcc tgttccgacc ctgccgctta   2880
ccggatacct gtccgccttt ctcccttcgg gaagcgtggc gctttctcaa tgctcgcgct   2940
gtaggtatct cagttcggtg taggtcgttc gctccaagct gggctgtgtg cacgaacccc   3000
ccgttcagcc cgaccgctgc gccttatccg gtaactatcg tcttgagtcc aacccggtaa   3060
gacacgactt atcgccactg gcagcagcca ctggtaacag gattagcaga gcgaggtatg   3120
taggcggtgc tacagagttc ttgaagtggt ggcctaacta cggctacact agaaggacag   3180
tatttggtat ctgcgctctg ctgaagccag ttaccttcgg aaaaagagtt ggtagctctt   3240
gatccggcaa acaaaccacc gctggtagcg gtggtttttt tgtttgcaag cagcagatta   3300
cgcgcagaaa aaaaggatct caagaagatc ctttgatctt ttctacgggg tctgacgctc   3360
agtggaacga aaactcacgt taagggattt tggtcatgag attatcaaaa aggatcttca   3420
cctagatcct tttaaattaa aaatgaagtt ttaaatcaat ctaaagtata tatgagtaaa   3480
cttggtctga cagttaccaa tgcttaatca gtgaggcacc tatctcagcg atctgtctat   3540
ttcgttcatc catagttgcc tgactccccg tcgtgtagat aactacgata cgggagggct   3600
taccatctgg ccccagtgct gcaatgatac cgcgagaccc acgctcaccg gctccagatt   3660
tatcagcaat aaaccagcca gccggaaggg ccgagcgcag aagtggtcct gcaactttat   3720
ccgcctccat ccagtctatt aattgttgcc gggaagctag agtaagtagt tcgccagtta   3780
atagtttgcg caacgttgtt gccattgcta caggcatcgt ggtgtcacgc tcgtcgtttg   3840
gtatggcttc attcagctcc ggttcccaac gatcaaggcg agttacatga tcccccatgt   3900
tgtgcaaaaa agcggttagc tccttcggtc ctccgatcgt tgtcagaagt aagttggccg   3960
cagtgttatc actcatggtt atggcagcac tgcataattc tcttactgtc atgccatccg   4020
taagatgctt ttctgtgact ggtgagtact caaccaagtc attctgagaa tagtgtatgc   4080
ggcgaccgag ttgctcttgc ccggcgtcaa tacgggataa taccgcgcca catagcagaa   4140
ctttaaaagt gctcatcatt ggaaaacgtt cttcggggcg aaaactctca aggatcttac   4200
cgctgttgag atccagttcg atgtaaccca ctcgtgcacc caactgatct tcagcatctt   4260
ttactttcac cagcgtttct gggtgagcaa aaacaggaag gcaaaatgcc gcaaaaaagg   4320
gaataagggc gacacggaaa tgttgaatac tcatactctt cctttttcaa tattattgaa   4380
gcatttatca gggttattgt ctcatgagcg gatacatatt tgaatgtatt tagaaaaata   4440
aacaaatagg ggttccgcgc acatttcccc gaaaagtgcc acctgacgtc taagaaacca   4500
ttattatcat gacattaacc tataaaaata ggcgtatcac gaggcccttt cgtctcgcgc   4560
gtttcggtga tgacggtgaa aacctctgac acatgcagct cccggagacg gtcacagctt   4620
ctgtctaagc ggatgccggg agcagacaag cccgtcaggg cgcgtcagcg ggtgttggcg   4680
ggtgtcgggg ctggcttaac tatgcggcat cagagcagat tgtactgaga gtgcaccata   4740
tcgacgctct cccttatgcg actcctgcat taggaagcag cccagtacta ggttgaggcc   4800
gttgagcacc gccgccgcaa ggaatggtgc atgcaaggag atggcgccca acagtccccc   4860
ggccacgggg cctgccacca tacccacgcc gaaacaagcg ctcatgagcc cgaagtggcg   4920
agcccgatct tccccatcgg tgatgtcggc gatataggcg ccagcaaccg cacctgtggc   4980
gccggtgatg ccggccacga tgcgtccggc gtagaggatc tggctagcga tgaccctgct   5040
```

-continued

```
gattggttcg ctgaccattt ccggggtgcg gaacggcgtt accagaaact cagaaggttc   5100
gtccaaccaa accgactctg acggcagttt acgagagaga tgatagggtc tgcttcagta   5160
agccagatgc tacacaatta ggcttgtaca tattgtcgtt agaacgcggc tacaattaat   5220
acataacctt atgtatcata cacatacgat ttaggtgaca ctatagatgg cggatgtgtg   5280
acatacacga cgccaaaaga ttttgttcca gctcctgcca cctccgctac gcgagagatt   5340
aaccacccac gatggccgcc aaagtgcatg ttgatattga ggctgacagc ccattcatca   5400
agtctttgca gaaggcattt ccgtcgttcg aggtggagtc attgcaggtc acaccaaatg   5460
accatgcaaa tgccagagca ttttcgcacc tggctaccaa attgatcgag caggagactg   5520
acaaagacac actcatcttg gatatcggca gtgcgccttc caggagaatg atgtctacgc   5580
acaaatacca ctgcgtatgc cctatgcgca gcgcagaaga ccccgaaagg ctcgatagct   5640
acgcaaagaa actggcagcg gcctccggga aggtgctgga tagagagatc gcaggaaaaa   5700
tcaccgacct gcagaccgtc atggctacgc cagacgctga atctcctacc ttttgcctgc   5760
atacagacgt cacgtgtcgt acggcagccg aagtggccgt ataccaggac gtgtatgctg   5820
tacatgcacc aacatcgctg taccatcagg cgatgaaagg tgtcagaacg gcgtattgga   5880
ttgggtttga caccaccccg tttatgtttg acgcgctagc aggcgcgtat ccaacctacg   5940
ccacaaactg ggccgacgag caggtgttac aggccaggaa cataggactg tgtgcagcat   6000
ccttgactga gggaagactc ggcaaactgt ccattctccg caagaagcaa ttgaaacctt   6060
gcgacacagt catgttctcg gtaggatcta cattgtacac tgagagcaga aagctactga   6120
ggagctggca cttaccctcc gtattccacc tgaaaggtaa acaatccttt acctgtaggt   6180
gcgataccat cgtatcatgt gaagggtacg tagttaagaa aatcactatg tgccccggcc   6240
tgtacggtaa aacggtaggg tacgccgtga cgtatcacgc ggagggattc ctagtgtgca   6300
agaccacaga cactgtcaaa ggagaaagag tctcattccc tgtatgcacc tacgtcccct   6360
caaccatctg tgatcaaatg actggcatac tagcgaccga cgtcacaccg gaggacgcac   6420
agaagttgtt agtgggattg aatcagagga tagttgtgaa cggaagaaca cagcgaaaca   6480
ctaacacgat gaagaactat ctgcttccga ttgtggccgt cgcatttagc aagtgggcga   6540
gggaatacaa ggcagacctt gatgatgaaa aacctctggg tgtccgagag aggtcactta   6600
cttgctgctg cttgtgggca tttaaaacga ggaagatgca caccatgtac aagaaaccag   6660
acacccagac aatagtgaag gtgccttcag agtttaactc gttcgtcatc ccgagcctat   6720
ggtctacagg cctcgcaatc ccagtcagat cacgcattaa gatgcttttg gccaagaaga   6780
ccaagcgaga gttaatacct gttctcgacg cgtcgtcagc cagggatgct gaacaagagg   6840
agaaggagag gttggaggcc gagctgacta gagaagcctt accacccctc gtccccatcg   6900
cgccggcgga gacgggagtc gtcgacgtcg acgttgaaga actagagtat cacgcaggtg   6960
caggggtcgt ggaaacacct cgcagcgcgt tgaaagtcac cgcacagccg aacgacgtac   7020
tactaggaaa ttacgtagtt ctgtccccgc agaccgtgct caagagctcc aagttggccc   7080
ccgtgcaccc tctagcagag caggtgaaaa taataacaca taacgggagg gccggcggtt   7140
accaggtcga cggatatgac ggcagggtcc tactaccatg tggatcggcc attccggtcc   7200
ctgagtttca ggctttgagc gagagcgcca ctatggtgta caacgaaagg gagttcgtca   7260
acaggaaact ataccatatt gccgttcacg gaccctcgct gaacaccgac gaggagaact   7320
acgagaaagt cagagctgaa agaactgacg ccgagtacgt gttcgacgta gataaaaaat   7380
```

-continued gctgcgtcaa gagagaggaa gcgtcgggtt tggtgttggt gggagagcta accaaccccc 7440
cgttccatga attcgcctac gaagggctga agatcaggcc gtcggcacca tataagacta 7500
cagtagtagg agtctttggg gttccgggat caggcaagtc tgctattatt aagagcctcg 7560
tgaccaaaca cgatctggtc accagcggca agaaggagaa ctgccaggaa atagttaacg 7620
acgtgaagaa gcaccgcggg aaggggacaa gtagggaaaa cagtgactcc atcctgctaa 7680
acgggtgtcg tcgtgccgtg gacatcctat atgtggacga ggctttcgct tgccattccg 7740
gtactctgct ggccctaatt gctcttgtta aacctcggag caaagtggtg ttatgcggag 7800
accccaagca atgcggattc ttcaatatga tgcagcttaa ggtgaacttc aaccacaaca 7860
tctgcactga agtatgtcat aaaagtatat ccagacgttg cacgcgtcca gtcacggcca 7920
tcgtgtctac gttgcactac ggaggcaaga tgcgcacgac caacccgtgc aacaaaccca 7980
taatcataga caccacagga cagaccaagc ccaagccagg agacatcgtg ttaacatgct 8040
tccgaggctg ggcaaagcag ctgcagttgg actaccgtgg acacgaagtc atgacagcag 8100
cagcatctca gggcctcacc cgcaaagggg tatacgccgt aaggcagaag gtgaatgaaa 8160
atcccttgta tgcccctgcg tcggagcacg tgaatgtact gctgacgcgc actgaggata 8220
ggctggtgtg gaaaacgctg gccggcgatc cctggattaa ggtcctatca aacattccac 8280
agggtaactt tacggccaca ttggaagaat ggcaagaaga acacgacaaa ataatgaagg 8340
tgattgaagg accggctgcg cctgtggacg cgttccagaa caaagcgaac gtgtgttggg 8400
cgaaaagcct ggtgcctgtc ctggacactg ccggaatcag attgacagca gaggagtgga 8460
gcaccataat tacagcattt aaggaggaca gagcttactc tccagtggtg gccttgaatg 8520
aaatttgcac caagtactat ggagttgacc tggacagtgg cctgttttct gccccgaagg 8580
tgtccctgta ttacgagaac aaccactggg ataacagacc tggtggaagg atgtatggat 8640
tcaatgccgc aacagctgcc aggctggaag ctagacatac cttcctgaag gggcagtggc 8700
atacgggcaa gcaggcagtt atcgcagaaa gaaaaatcca accgctttct gtgctggaca 8760
atgtaattcc tatcaaccgc aggctgccgc acgccctggt ggctgagtac aagacggtta 8820
aaggcagtag ggttgagtgg ctggtcaata aagtaagagg gtaccacgtc ctgctggtga 8880
gtgagtacaa cctggctttg cctcgacgca gggtcacttg gttgtcaccg ctgaatgtca 8940
caggcgccga taggtgctac gacctaagtt taggactgcc ggctgacgcc ggcaggttcg 9000
acttggtctt tgtgaacatt cacacggaat tcagaatcca ccactaccag cagtgtgtcg 9060
accacgccat gaagctgcag atgcttgggg gagatgcgct acgactgcta aaacccggcg 9120
gcatcttgat gagagcttac ggatacgccg ataaaatcag cgaagccgtt gtttcctcct 9180
taagcagaaa gttctcgtct gcaagagtgt tgcgcccgga ttgtgtcacc agcaatacag 9240
aagtgttctt gctgttctcc aactttgaca acggaaagag accctctacg ctacaccaga 9300
tgaataccaa gctgagtgcc gtgtatgccg gagaagccat gcacacggcc gggtgtgcac 9360
catcctacag agttaagaga gcagacatag ccacgtgcac agaagcggct gtggttaacg 9420
cagctaacgc ccgtggaact gtaggggatg gcgtatgcag ggccgtggcg aagaaatggc 9480
cgtcagcctt taagggagca gcaacaccag tgggcacaat taaaacagtc atgtgcggct 9540
cgtaccccgt catccacgct gtagcgccta atttctctgc cacgactgaa gcggaagggg 9600
accgcgaatt ggccgctgtc taccgggcag tggccgccga agtaaacaga ctgtcactga 9660
gcagcgtagc catcccgctg ctgtccacag gagtgttcag cggcggaaga gataggctgc 9720
agcaatccct caaccatcta ttcacagcaa tggacgccac ggacgctgac gtgaccatct 9780

-continued

```
actgcagaga caaaagttgg gagaagaaaa tccaggaagc cattgacatg aggacggctg   9840
tggagttgct caatgatgac gtggagctga ccacagactt ggtgagagtg cacccggaca   9900
gcagcctggt gggtcgtaag ggctacagta ccactgacgg gtcgctgtac tcgtactttg   9960
aaggtacgaa attcaaccag gctgctattg atatggcaga gatactgacg ttgtggccca  10020
gactgcaaga ggcaaacgaa cagatatgcc tatacgcgct gggcgaaaca atggacaaca  10080
tcagatccaa atgtccggtg aacgattccg attcatcaac acctcccagg acagtgccct  10140
gcctgtgccg ctacgcaatg acagcagaac ggatcgcccg ccttaggtca caccaagtta  10200
aaagcatggt ggtttgctca tcttttcccc tcccgaaata ccatgtagat ggggtgcaga  10260
aggtaaagtg cgagaaggtt ctcctgttcg acccgacggt accttcagtg gttagtccgc  10320
ggaagtatgc cgcatctacg acggaccact cagatcggtc gttacgaggg tttgacttgg  10380
actggaccac cgactcgtct tccactgcca gcgataccat gtcgctaccc agtttgcagt  10440
cgtgtgacat cgactcgatc tacgagccaa tggctcccat agtagtgacg gctgacgtac  10500
accctgaacc cgcaggcatc gcggacctgg cggcagatgt gcaccctgaa cccgcagacc  10560
atgtggacct ggagaacccg attcctccac cgcgcccgaa gagagctgca taccttgcct  10620
cccgcgcggc ggagcgaccg gtgccggcgc cgagaaagcc gacgcctgcc ccaaggactg  10680
cgtttaggaa caagctgcct ttgacgttcg gcgactttga cgagcacgag gtcgatgcgt  10740
tggcctccgg gattactttc ggagacttcg acgacgtcct gcgactaggc cgcgcgggtg  10800
catatatttt ctcctcggac actggcagcg gacatttaca acaaaaatcc gttaggcagc  10860
acaatctcca gtgcgcacaa ctggatgcgg tccaggagga gaaaatgtac ccgccaaaat  10920
tggatactga gagggagaag ctgttgctgc tgaaaatgca gatgcaccca tcggaggcta  10980
ataagagtcg ataccagtct cgcaaagtgg agaacatgaa agccacggtg gtggacaggc  11040
tcacatcggg ggccagattg tacacgggag cggacgtagg ccgcatacca acatacgcgg  11100
ttcggtaccc ccgccccgtg tactccccta ccgtgatcga aagattctca agccccgatg  11160
tagcaatcgc agcgtgcaac gaatacctat ccagaaatta cccaacagtg gcgtcgtacc  11220
agataacaga tgaatacgac gcatacttgg acatggttga cgggtcggat agttgcttgg  11280
acagagcgac attctgcccg gcgaagctcc ggtgctaccc gaaacatcat gcgtaccacc  11340
agccgactgt acgcagtgcc gtcccgtcac cctttcagaa cacactacag aacgtgctag  11400
cggctgccac caagagaaac tgcaacgtca cgcaaatgcg agaactaccc accatggact  11460
cggcagtgtt caacgtggag tgcttcaagc gctatgcctg ctccggagaa tattgggaag  11520
aatatgctaa acaacctatc cggataacca ctgagaacat cactacctat gtgaccaaat  11580
tgaaaggccc gaaagctgct gccttgttcg ctaagaccca caacttggtt ccgctgcagg  11640
aggttcccat ggacagattc acggtcgaca tgaaacgaga tgtcaaagtc actccaggga  11700
cgaaacacac agaggaaaga cccaaagtcc aggtaattca agcagcggag ccattggcga  11760
ccgcttacct gtgcggcatc cacagggaat tagtaaggag actaaatgct gtgttacgcc  11820
ctaacgtgca cacattgttt gatatgtcgg ccgaagactt tgacgcgatc atcgcctctc  11880
acttccaccc aggagacccg gttctagaga cggacattgc atcattcgac aaaagccagg  11940
acgactcctt ggctcttaca ggtttaatga tcctcgaaga tctaggggtg gatcagtacc  12000
tgctggactt gatcgaggca gcctttgggg aaatatccag ctgtcaccta ccaactggca  12060
cgcgcttcaa gttcggagct atgatgaaat cgggcatgtt tctgactttg tttattaaca  12120
```

-continued

```
ctgttttgaa catcaccata gcaagcaggg tactggagca gagactcact gactccgcct  12180

gtgcggcctt catcggcgac gacaacatcg ttcacggagt gatctccgac aagctgatgg  12240

cggagaggtg cgcgtcgtgg gtcaacatgg aggtgaagat cattgacgct gtcatgggcg  12300

aaaaaccccc atatttttgt gggggattca tagtttttga cagcgtcaca cagaccgcct  12360

gccgtgtttc agacccactt aagcgcctgt tcaagttggg taagccgcta acagctgaag  12420

acaagcagga cgaagacagg cgacgagcac tgagtgacga ggtt                  12464
```

```
<210> SEQ ID NO 138
<211> LENGTH: 6708
<212> TYPE: DNA
<213> ORGANISM: Artificial Sequence
<220> FEATURE:
<223> OTHER INFORMATION: pDEST10
<220> FEATURE:
<221> NAME/KEY: gene
<222> LOCATION: (23)..(152)
<223> OTHER INFORMATION: Ppolh
<220> FEATURE:
<221> NAME/KEY: gene
<222> LOCATION: (337)..(461)
<223> OTHER INFORMATION: attR1
<220> FEATURE:
<221> NAME/KEY: gene
<222> LOCATION: (711)..(1370)
<223> OTHER INFORMATION: CmR
<220> FEATURE:
<221> NAME/KEY: gene
<222> LOCATION: (1490)..(1574)
<223> OTHER INFORMATION: inactivated ccdA
<220> FEATURE:
<221> NAME/KEY: gene
<222> LOCATION: (1712)..(2017)
<223> OTHER INFORMATION: ccdB
<220> FEATURE:
<221> NAME/KEY: gene
<222> LOCATION: (2058)..(2182)
<223> OTHER INFORMATION: attR2
<220> FEATURE:
<221> NAME/KEY: gene
<222> LOCATION: (3394)..(4369)
<223> OTHER INFORMATION: ampR
<220> FEATURE:
<221> NAME/KEY: gene
<222> LOCATION: (4510)..(5164)
<223> OTHER INFORMATION: ori
<220> FEATURE:
<221> NAME/KEY: gene
<222> LOCATION: (62)..(5658)
<223> OTHER INFORMATION: genR

<400> SEQUENCE: 138

ccccggatga agtggttcgc atcctcggtt ttctggaagg cgagcatcgt ttgttcgccc     60

aggactctag ctatagttct agtggttggc tacgtatact ccggaatatt aatagatcat    120

ggagataatt aaaatgataa ccatctcgca aataaataag tattttactg ttttcgtaac    180

agttttgtaa taaaaaaacc tataaatatt ccggattatt cataccgtcc caccatcggg    240

cgcggatctc ggtccgaaac catgtcgtac taccatcacc atcaccatca cgattacgat    300

atcccaacga ccgaaaacct gtattttcag ggcatcacaa gtttgtacaa aaaagctgaa    360

cgagaaacgt aaaatgatat aaatatcaat atattaaatt agattttgca taaaaaacag    420

actacataat actgtaaaac acaacatatc cagtcactat ggcggccgct aagttggcag    480

catcacccga cgcactttgc gccgaataaa tacctgtgac ggaagatcac ttcgcagaat    540

aaataaatcc tggtgtccct gttgataccg ggaagccctg ggccaacttt tggcgaaaat    600

gagacgttga tcggcacgta agaggttcca actttcacca taatgaaata agatcactac    660
```

-continued cgggcgtatt ttttgagtta tcgagatttt caggagctaa ggaagctaaa atggagaaaa 720
aaatcactgg atataccacc gttgatatat cccaatggca tcgtaaagaa cattttgagg 780
catttcagtc agttgctcaa tgtacctata accagaccgt tcagctggat attacggcct 840
ttttaaagac cgtaaagaaa aataagcaca agttttatcc ggcctttatt cacattcttg 900
cccgcctgat gaatgctcat ccggaattcc gtatggcaat gaaagacggt gagctggtga 960
tatgggatag tgttcaccct tgttacaccg ttttccatga gcaaactgaa acgttttcat 1020
cgctctggag tgaataccac gacgatttcc ggcagtttct acacatatat tcgcaagatg 1080
tggcgtgtta cggtgaaaac ctggcctatt tccctaaagg gtttattgag aatatgtttt 1140
tcgtctcagc caatccctgg gtgagtttca ccagttttga tttaaacgtg gccaatatgg 1200
acaacttctt cgcccccgtt ttcaccatgg gcaaatatta tacgcaaggc gacaaggtgc 1260
tgatgccgct ggcgattcag gttcatcatg ccgtctgtga tggcttccat gtcggcagaa 1320
tgcttaatga attacaacag tactgcgatg agtggcaggg cggggcgtaa acgcgtggat 1380
ccggcttact aaaagccaga taacagtatg cgtatttgcg cgctgatttt tgcggtataa 1440
gaatatatac tgatatgtat acccgaagta tgtcaaaaag aggtgtgcta tgaagcagcg 1500
tattacagtg acagttgaca gcgacagcta tcagttgctc aaggcatata tgatgtcaat 1560
atctccggtc tggtaagcac aaccatgcag aatgaagccc gtcgtctgcg tgccgaacgc 1620
tggaaagcgg aaaatcagga agggatggct gaggtcgccc ggtttattga aatgaacggc 1680
tcttttgctg acgagaacag ggactggtga aatgcagttt aaggtttaca cctataaaag 1740
agagagccgt tatcgtctgt ttgtggatgt acagagtgat attattgaca cgcccgggcg 1800
acggatggtg atccccctgg ccagtgcacg tctgctgtca gataaagtct cccgtgaact 1860
ttacccggtg gtgcatatcg gggatgaaag ctggcgcatg atgaccaccg atatggccag 1920
tgtgccggtc tccgttatcg gggaagaagt ggctgatctc agccaccgcg aaaatgacat 1980
caaaaacgcc attaacctga tgttctgggg aatataaatg tcaggctccc ttatacacag 2040
ccagtctgca ggtcgaccat agtgactgga tatgttgtgt tttacagtat tatgtagtct 2100
gtttttttatg caaaatctaa tttaatatat tgatatttat atcattttac gtttctcgtt 2160
cagctttctt gtacaaagtg gtgatgccat ggatccggaa ttcaaaggcc tacgtcgacg 2220
agctcaacta gtgcggccgc tttcgaatct agagcctgca gtctcgaggc atgcggtacc 2280
aagcttgtcg agaagtacta gaggatcata atcagccata ccacatttgt agaggtttta 2340
cttgctttaa aaaacctccc acacctcccc ctgaacctga aacataaaat gaatgcaatt 2400
gttgttgtta acttgtttat tgcagcttat aatggttaca aataaagcaa tagcatcaca 2460
aatttcacaa ataaagcatt tttttcactg cattctagtt gtggtttgtc caaactcatc 2520
aatgtatctt atcatgtctg gatctgatca ctgcttgagc ctaggagatc cgaaccagat 2580
aagtgaaatc tagttccaaa ctattttgtc atttttaatt ttcgtattag cttacgacgc 2640
tacacccagt tcccatctat tttgtcactc ttccctaaat aatccttaaa aactccattt 2700
ccacccctcc cagttcccaa ctattttgtc cgcccacagc ggggcatttt tcttcctgtt 2760
atgtttttaa tcaaacatcc tgccaactcc atgtgacaaa ccgtcatctt cggctacttt 2820
ttctctgtca cagaatgaaa atttttctgt catctcttcg ttattaatgt ttgtaattga 2880
ctgaatatca acgcttattt gcagcctgaa tggcgaatgg gacgcgccct gtagcggcgc 2940
attaagcgcg gcgggtgtgg tggttacgcg cagcgtgacc gctacacttg ccagcgccct 3000

-continued agcgcccgct cctttcgctt tcttcccttc ctttctcgcc acgttcgccg gctttccccg 3060
tcaagctcta aatcgggggc tccctttagg gttccgattt agtgctttac ggcacctcga 3120
ccccaaaaaa cttgattagg gtgatggttc acgtagtggg ccatcgccct gatagacggt 3180
ttttcgccct ttgacgttgg agtccacgtt ctttaatagt ggactcttgt tccaaactgg 3240
aacaacactc aaccctatct cggtctattc ttttgattta taagggattt tgccgatttc 3300
ggcctattgg ttaaaaaatg agctgattta acaaaaattt aacgcgaatt ttaacaaaat 3360
attaacgttt acaatttcag gtggcacttt tcggggaaat gtgcgcggaa cccctatttg 3420
tttatttttc taaatacatt caaatatgta tccgctcatg agacaataac cctgataaat 3480
gcttcaataa tattgaaaaa ggaagagtat gagtattcaa catttccgtg tcgcccttat 3540
tccctttttt gcggcatttt gccttcctgt ttttgctcac ccagaaacgc tggtgaaagt 3600
aaaagatgct gaagatcagt tgggtgcacg agtgggttac atcgaactgg atctcaacag 3660
cggtaagatc cttgagagtt ttcgccccga agaacgtttt ccaatgatga gcacttttaa 3720
agttctgcta tgtggcgcgg tattatcccg tattgacgcc gggcaagagc aactcggtcg 3780
ccgcatacac tattctcaga atgacttggt tgagtactca ccagtcacag aaaagcatct 3840
tacggatggc atgacagtaa gagaattatg cagtgctgcc ataaccatga gtgataacac 3900
tgcggccaac ttacttctga caacgatcgg aggaccgaag gagctaaccg cttttttgca 3960
caacatgggg gatcatgtaa ctcgccttga tcgttgggaa ccggagctga atgaagccat 4020
accaaacgac gagcgtgaca ccacgatgcc tgtagcaatg gcaacaacgt tgcgcaaact 4080
attaactggc gaactactta ctctagcttc ccggcaacaa ttaatagact ggatggaggc 4140
ggataaagtt gcaggaccac ttctgcgctc ggcccttccg gctggctggt ttattgctga 4200
taaatctgga gccggtgagc gtgggtctcg cggtatcatt gcagcactgg ggccagatgg 4260
taagccctcc cgtatcgtag ttatctacac gacggggagt caggcaacta tggatgaacg 4320
aaatagacag atcgctgaga taggtgcctc actgattaag cattggtaac tgtcagacca 4380
agtttactca tatatacttt agattgattt aaaacttcat ttttaattta aaaggatcta 4440
ggtgaagatc ctttttgata atctcatgac caaaatccct taacgtgagt tttcgttcca 4500
ctgagcgtca gaccccgtag aaaagatcaa aggatcttct tgagatcctt tttttctgcg 4560
cgtaatctgc tgcttgcaaa caaaaaaacc accgctacca gcggtggttt gtttgccgga 4620
tcaagagcta ccaactcttt ttccgaaggt aactggcttc agcagagcgc agataccaaa 4680
tactgtcctt ctagtgtagc cgtagttagg ccaccacttc aagaactctg tagcaccgcc 4740
tacatacctc gctctgctaa tcctgttacc agtggctgct gccagtggcg ataagtcgtg 4800
tcttaccggg ttggactcaa gacgatagtt accggataag gcgcagcggt cgggctgaac 4860
ggggggttcg tgcacacagc ccagcttgga gcgaacgacc tacaccgaac tgagatacct 4920
acagcgtgag cattgagaaa gcgccacgct tcccgaaggg agaaaggcgg acaggtatcc 4980
ggtaagcggc agggtcggaa caggagagcg cacgagggag cttccagggg gaaacgcctg 5040
gtatctttat agtcctgtcg ggtttcgcca cctctgactt gagcgtcgat ttttgtgatg 5100
ctcgtcaggg gggcggagcc tatggaaaaa cgccagcaac gcggcctttt tacggttcct 5160
ggccttttgc tggccttttg ctcacatgtt ctttcctgcg ttatcccctg attctgtgga 5220
taaccgtatt accgcctttg agtgagctga taccgctcgc cgcagccgaa cgaccgagcg 5280
cagcgagtca gtgagcgagg aagcggaaga gcgcctgatg cggtattttc tccttacgca 5340
tctgtgcggt atttcacacc gcagaccagc cgcgtaacct ggcaaaatcg gttacggttg 5400

-continued

```
agtaataaat ggatgccctg cgtaagcggg tgtgggcgga caataaagtc ttaaactgaa   5460

caaaatagat ctaaactatg acaataaagt cttaaactag acagaatagt tgtaaactga   5520

aatcagtcca gttatgctgt gaaaaagcat actggacttt tgttatggct aaagcaaact   5580

cttcattttc tgaagtgcaa attgcccgtc gtattaaaga ggggcgtggc caagggcatg   5640

gtaaagacta tattcgcggc gttgtgacaa tttaccgaac aactccgcgg ccgggaagcc   5700

gatctcggct tgaacgaatt gttaggtggc ggtacttggg tcgatatcaa agtgcatcac   5760

ttcttcccgt atgcccaact ttgtatagag agccactgcg ggatcgtcac cgtaatctgc   5820

ttgcacgtag atcacataag caccaagcgc gttggcctca tgcttgagga gattgatgag   5880

cgcggtggca atgccctgcc tccggtgctc gccggagact gcgagatcat agatatagat   5940

ctcactacgc ggctgctcaa acctgggcag aacgtaagcc gcgagagcgc caacaaccgc   6000

ttcttggtcg aaggcagcaa gcgcgatgaa tgtcttacta cggagcaagt tcccgaggta   6060

atcggagtcc ggctgatgtt gggagtaggt ggctacgtct ccgaactcac gaccgaaaag   6120

atcaagagca gcccgcatgg atttgacttg gtcagggccg agcctacatg tgcgaatgat   6180

gcccatactt gagccaccta actttgtttt agggcgactg ccctgctgcg taacatcgtt   6240

gctgctgcgt aacatcgttg ctgctccata acatcaaaca tcgacccacg gcgtaacgcg   6300

cttgctgctt ggatgcccga ggcatagact gtacaaaaaa acagtcataa caagccatga   6360

aaaccgccac tgcgccgtta ccaccgctgc gttcggtcaa ggttctggac cagttgcgtg   6420

agcgcatacg ctacttgcat tacagtttac gaaccgaaca ggcttatgtc aactgggttc   6480

gtgccttcat ccgtttccac ggtgtgcgtc acccggcaac cttgggcagc agcgaagtcg   6540

aggcatttct gtcctggctg gcgaacgagc gcaaggtttc ggtctccacg catcgtcagg   6600

cattggcggc cttgctgttc ttctacggca aggtgctgtg cacggatctg ccctggcttc   6660

aggagatcgg aagacctcgg ccgtcgcggc gcttgccggt ggtgctga                6708
```

<210> SEQ ID NO 139
<211> LENGTH: 7026
<212> TYPE: DNA
<213> ORGANISM: Artificial Sequence
<220> FEATURE:
<223> OTHER INFORMATION: pDEST11
<220> FEATURE:
<221> NAME/KEY: gene
<222> LOCATION: (4)..(479)
<223> OTHER INFORMATION: Tetp ((tet operator) 7 and min hCMV promoter)
<220> FEATURE:
<221> NAME/KEY: gene
<222> LOCATION: (514)..(638)
<223> OTHER INFORMATION: attR1
<220> FEATURE:
<221> NAME/KEY: gene
<222> LOCATION: (888)..(1547)
<223> OTHER INFORMATION: CmR
<220> FEATURE:
<221> NAME/KEY: gene
<222> LOCATION: (1667)..(1751)
<223> OTHER INFORMATION: inactivated ccdA
<220> FEATURE:
<221> NAME/KEY: gene
<222> LOCATION: (1889)..(2194)
<223> OTHER INFORMATION: ccdB
<220> FEATURE:
<221> NAME/KEY: gene
<222> LOCATION: (2235)..(2359)
<223> OTHER INFORMATION: attR2
<220> FEATURE:
<221> NAME/KEY: gene
<222> LOCATION: (2402)..(4132)

-continued

<223> OTHER INFORMATION: polyA
<220> FEATURE:
<221> NAME/KEY: gene
<222> LOCATION: (4347)..(4803)
<223> OTHER INFORMATION: f1 ori
<220> FEATURE:
<221> NAME/KEY: gene
<222> LOCATION: (4940)..(5797)
<223> OTHER INFORMATION: ampR

<400> SEQUENCE: 139
cgagtttacc actccctatc agtgatagag aaaagtgaaa gtcgagttta ccactcccta 60
tcagtgatag agaaaagtga aagtcgagtt taccactccc tatcagtgat agagaaaagt 120
gaaagtcgag tttaccactc cctatcagtg atagagaaaa gtgaaagtcg agtttaccac 180
tccctatcag tgatagagaa aagtgaaagt cgagtttacc actccctatc agtgatagag 240
aaaagtgaaa gtcgagttta ccactcccta tcagtgatag agaaaagtga aagtcgagct 300
cggtacccgg gtcgagtagg cgtgtacggt gggaggccta tataagcaga gctcgtttag 360
tgaaccgtca gatcgcctgg agacgccatc cacgctgttt tgacctccat agaagacacc 420
gggaccgatc cagcctccgc ggccccgaat tcgagctcgg tacccgggga tcctctagag 480
tcgaggtcga cggtatcgat aagcttgata tcaacaagtt tgtacaaaaa agctgaacga 540
gaaacgtaaa atgatataaa tatcaatata ttaaattaga ttttgcataa aaaacagact 600
acataatact gtaaaacaca acatatccag tcactatggc ggccgctaag ttggcagcat 660
cacccgacgc actttgcgcc gaataaatac ctgtgacgga agatcacttc gcagaataaa 720
taaatcctgg tgtccctgtt gataccggga agccctgggc caacttttgg cgaaaatgag 780
acgttgatcg gcacgtaaga ggttccaact ttcaccataa tgaaataaga tcactaccgg 840
gcgtattttt tgagttatcg agattttcag gagctaagga agctaaaatg gagaaaaaaa 900
tcactggata taccaccgtt gatatatccc aatggcatcg taaagaacat tttgaggcat 960
ttcagtcagt tgctcaatgt acctataacc agaccgttca gctggatatt acggcctttt 1020
taaagaccgt aaagaaaaat aagcacaagt tttatccggc ctttattcac attcttgccc 1080
gcctgatgaa tgctcatccg gaattccgta tggcaatgaa agacggtgag ctggtgatat 1140
gggatagtgt tcacccttgt tacaccgttt tccatgagca aactgaaacg ttttcatcgc 1200
tctggagtga ataccacgac gatttccggc agtttctaca catatattcg caagatgtgg 1260
cgtgttacgg tgaaaacctg gcctatttcc ctaaagggtt tattgagaat atgtttttcg 1320
tctcagccaa tccctgggtg agtttcacca gttttgattt aaacgtggcc aatatggaca 1380
acttcttcgc ccccgttttc accatgggca aatattatac gcaaggcgac aaggtgctga 1440
tgccgctggc gattcaggtt catcatgccg tctgtgatgg cttccatgtc ggcagaatgc 1500
ttaatgaatt acaacagtac tgcgatgagt ggcagggcgg ggcgtaaaga tctggatccg 1560
gcttactaaa agccagataa cagtatgcgt atttgcgcgc tgatttttgc ggtataagaa 1620
tatatactga tatgtatacc cgaagtatgt caaaaagagg tgtgctatga agcagcgtat 1680
tacagtgaca gttgacagcg acagctatca gttgctcaag gcatatatga tgtcaatatc 1740
tccggtctgg taagcacaac catgcagaat gaagcccgtc gtctgcgtgc cgaacgctgg 1800
aaagcggaaa atcaggaagg gatggctgag gtcgcccggt ttattgaaat gaacggctct 1860
tttgctgacg agaacaggga ctggtgaaat gcagtttaag gtttacacct ataaaagaga 1920
gagccgttat cgtctgtttg tggatgtaca gagtgatatt attgacacgc ccgggcgacg 1980
gatggtgatc cccctggcca gtgcacgtct gctgtcagat aaagtctccc gtgaacttta 2040

-continued

```
cccggtggtg catatcgggg atgaaagctg gcgcatgatg accaccgata tggccagtgt   2100
gccggtctcc gttatcgggg aagaagtggc tgatctcagc caccgcgaaa atgacatcaa   2160
aaacgccatt aacctgatgt tctggggaat ataaatgtca ggctccctta tacacagcca   2220
gtctgcaggt cgaccatagt gactggatat gttgtgtttt acagtattat gtagtctgtt   2280
ttttatgcaa aatctaattt aatatattga tatttatatc attttacgtt tctcgttcag   2340
ctttcttgta caaagtggtt gatatcgaat tcctgcagcc cgggggatcc actagttcta   2400
gagcactgcg atgagtggca gggcggggcg taattttttt aaggcagtta ttggtgccct   2460
taaacgcctg gtgctacgcc tgaataagtg ataataagcg gatgaatggc agaaattcgc   2520
cggatctttg tgaaggaacc ttacttctgt ggtgtgacat aattggacaa actacctaca   2580
gagatttaaa gctctaaggt aaatataaaa tttttaagtg tataatgtgt taaactactg   2640
attctaattg tttgtgtatt ttagattcca acctatggaa ctgatgaatg ggagcagtgg   2700
tggaatgcct ttaatgagga aaacctgttt tgctcagaag aaatgccatc tagtgatgat   2760
gaggctactg ctgactctca acattctact cctccaaaaa agaagagaaa ggtagaagac   2820
cccaaggact ttccttcaga attgctaagt tttttgagtc atgctgtgtt tagtaataga   2880
actcttgctt gctttgctat ttacaccaca aaggaaaaag ctgcactgct atacaagaaa   2940
attatggaaa aatattctgt aacctttata agtaggcata acagttataa tcataacata   3000
ctgttttttc ttactccaca caggcataga gtgtctgcta ttaataacta tgctcaaaaa   3060
ttgtgtacct ttagcttttt aatttgtaaa ggggttaata aggaatattt gatgtatagt   3120
gccttgacta gagatcataa tcagccatac cacatttgta gaggttttac ttgctttaaa   3180
aaacctccca cacctccccc tgaacctgaa acataaaatg aatgcaattg ttgttgttaa   3240
cttgtttatt gcagcttata atggttacaa ataaagcaat agcatcacaa atttcacaaa   3300
taaagcattt ttttcactgc attctagttg tggtttgtcc aaactcatca atgtatctta   3360
tcatgtctgg atccccagga agctcctctg tgtcctcata aaccctaacc tcctctactt   3420
gagaggacat tccaatcata ggctgcccat ccaccctctg tgtcctcctg ttaattaggt   3480
cacttaacaa aaaggaaatt gggtaggggt ttttcacaga ccgctttcta agggtaattt   3540
taaaatatct gggaagtccc ttccactgct gtgttccaga agtgttggta aacagcccac   3600
aaatgtcaac agcagaaaca tacaagctgt cagctttgca caagggccca acaccctgct   3660
catcaagaag cactgtggtt gctgtgttag taatgtgcaa aacaggaggc acattttccc   3720
cacctgtgta ggttccaaaa tatctagtgt tttcattttt acttggatca ggaacccagc   3780
actccactgg ataagcatta tccttatcca aaacagcctt gtggtcagtg ttcatctgct   3840
gactgtcaac tgtagcattt tttggggtta cagtttgagc aggatatttg gtcctgtagt   3900
ttgctaacac accctgcagc tccaaaggtt ccccaccaac agcaaaaaaa tgaaaatttg   3960
acccttgaat gggttttcca gcaccatttt catgagtttt ttgtgtccct gaatgcaagt   4020
ttaacatagc agttacccca ataacctcag ttttaacagt aacagcttcc cacatcaaaa   4080
tatttccaca ggttaagtcc tcatttaaat taggcaaagg aattgctcta gagcggccgc   4140
caccgcggtg gagctccaat tcgccctata gtgagtcgta ttacgcgcgc tcactggccg   4200
tcgttttaca acgtcgtgac tgggaaaacc ctggcgttac ccaacttaat cgccttgcag   4260
cacatccccc tttcgccagc tggcgtaata gcgaagaggc ccgcaccgat cgcccttccc   4320
aacagttgcg cagcctgaat ggcgaatggg acgcgccctg tagcggcgca ttaagcgcgg   4380
```

-continued

```
cgggtgtggt ggttacgcgc agcgtgaccg ctacacttgc cagcgcccta gcgcccgctc   4440
ctttcgcttt cttcccttcc tttctcgcca cgttcgccgg ctttccccgt caagctctaa   4500
atcgggggct ccctttaggg ttccgattta gtgctttacg gcacctcgac cccaaaaaac   4560
ttgattaggg tgatggttca cgtagtgggc catcgccctg atagacggtt tttcgccctt   4620
tgacgttgga gtccacgttc tttaatagtg gactcttgtt ccaaactgga acaacactca   4680
accctatctc ggtctattct tttgatttat aagggatttt gccgatttcg gcctattggt   4740
taaaaaatga gctgatttaa caaaaattta acgcgaattt taacaaaata ttaacgctta   4800
caatttaggt ggcacttttc ggggaaatgt gcgcggaacc cctatttgtt tatttttcta   4860
aatacattca aatatgtatc cgctcatgag acaataaccc tgataaatgc ttcaataata   4920
ttgaaaaagg aagagtatga gtattcaaca tttccgtgtc gcccttattc cctttttgc   4980
ggcattttgc cttcctgttt ttgctcaccc agaaacgctg gtgaaagtaa aagatgctga   5040
agatcagttg ggtgcacgag tgggttacat cgaactggat ctcaacagcg gtaagatcct   5100
tgagagtttt cgccccgaag aacgttttcc aatgatgagc acttttaaag ttctgctatg   5160
tggcgcggta ttatcccgta ttgacgccgg gcaagagcaa ctcggtcgcc gcatacacta   5220
ttctcagaat gacttggttg agtactcacc agtcacagaa aagcatctta cggatggcat   5280
gacagtaaga gaattatgca gtgctgccat aaccatgagt gataacactg cggccaactt   5340
acttctgaca acgatcggag gaccgaagga gctaaccgct tttttgcaca acatggggga   5400
tcatgtaact cgccttgatc gttgggaacc ggagctgaat gaagccatac caaacgacga   5460
gcgtgacacc acgatgcctg tagcaatggc aacaacgttg cgcaaactat taactggcga   5520
actacttact ctagcttccc ggcaacaatt aatagactgg atggaggcgg ataaagttgc   5580
aggaccactt ctgcgctcgg cccttccggc tggctggttt attgctgata aatctggagc   5640
cggtgagcgt gggtctcgcg gtatcattgc agcactgggg ccagatggta agccctcccg   5700
tatcgtagtt atctacacga cggggagtca ggcaactatg gatgaacgaa atagacagat   5760
cgctgagata ggtgcctcac tgattaagca ttggtaactg tcagaccaag tttactcata   5820
tatactttag attgatttaa aacttcattt ttaatttaaa aggatctagg tgaagatcct   5880
ttttgataat ctcatgacca aaatccctta acgtgagttt tcgttccact gagcgtcaga   5940
ccccgtagaa aagatcaaag gatcttcttg agatcctttt tttctgcgcg taatctgctg   6000
cttgcaaaca aaaaaaccac cgctaccagc ggtggtttgt ttgccggatc aagagctacc   6060
aactcttttt ccgaaggtaa ctggcttcag cagagcgcag ataccaaata ctgtccttct   6120
agtgtagccg tagttaggcc accacttcaa gaactctgta gcaccgccta catacctcgc   6180
tctgctaatc ctgttaccag tggctgctgc cagtggcgat aagtcgtgtc ttaccgggtt   6240
ggactcaaga cgatagttac cggataaggc gcagcggtcg ggctgaacgg ggggttcgtg   6300
cacacagccc agcttggagc gaacgaccta caccgaactg agatacctac agcgtgagct   6360
atgagaaagc gccacgcttc ccgaagggag aaaggcggac aggtatccgg taagcggcag   6420
ggtcggaaca ggagagcgca cgagggagct tccaggggga aacgcctggt atctttatag   6480
tcctgtcggg tttcgccacc tctgacttga gcgtcgattt ttgtgatgct cgtcaggggg   6540
gcggagccta tggaaaaacg ccagcaacgc ggccttttta cggttcctgg ccttttgctg   6600
gccttttgct cacatgttct ttcctgcgtt atcccctgat tctgtggata accgtattac   6660
cgcctttgag tgagctgata ccgctcgccg cagccgaacg accgagcgca gcgagtcagt   6720
gagcgaggaa gcggaagagc gcccaatacg caaaccgcct ctccccgcgc gttggccgat   6780
```

tcattaatgc agctggcacg acaggtttcc cgactggaaa gcgggcagtg agcgcaacgc 6840
aattaatgtg agttagctca ctcattaggc accccaggct ttacacttta tgcttccggc 6900
tcgtatgttg tgtggaattg tgagcggata acaatttcac acaggaaaca gctatgacca 6960
tgattacgcc aagcgcgcaa ttaaccctca ctaaagggaa caaaagctgg gtaccgggcc 7020
cccccct 7026

<210> SEQ ID NO 140
<211> LENGTH: 7278
<212> TYPE: DNA
<213> ORGANISM: Artificial Sequence
<220> FEATURE:
<223> OTHER INFORMATION: pDEST12.2
<220> FEATURE:
<221> NAME/KEY: gene
<222> LOCATION: (86)..(136)
<223> OTHER INFORMATION: ori
<220> FEATURE:
<221> NAME/KEY: gene
<222> LOCATION: (220)..(742)
<223> OTHER INFORMATION: CMV promoter
<220> FEATURE:
<221> NAME/KEY: gene
<222> LOCATION: (935)..(1059)
<223> OTHER INFORMATION: attR1
<220> FEATURE:
<221> NAME/KEY: gene
<222> LOCATION: (1168)..(1827)
<223> OTHER INFORMATION: CmR
<220> FEATURE:
<221> NAME/KEY: gene
<222> LOCATION: (1947)..(2031)
<223> OTHER INFORMATION: inactivated ccdA
<220> FEATURE:
<221> NAME/KEY: gene
<222> LOCATION: (2169)..(2474)
<223> OTHER INFORMATION: ccdB
<220> FEATURE:
<221> NAME/KEY: gene
<222> LOCATION: (2515)..(2639)
<223> OTHER INFORMATION: attR2
<220> FEATURE:
<221> NAME/KEY: gene
<222> LOCATION: (2824)..(3186)
<223> OTHER INFORMATION: small t & polyA
<220> FEATURE:
<221> NAME/KEY: gene
<222> LOCATION: (3310)..(3378)
<223> OTHER INFORMATION: lac
<220> FEATURE:
<221> NAME/KEY: gene
<222> LOCATION: (4363)..(5157)
<223> OTHER INFORMATION: neo
<220> FEATURE:
<221> NAME/KEY: gene
<222> LOCATION: (5680)..(6540)
<223> OTHER INFORMATION: neo

<400> SEQUENCE: 140 gggggcgga gcctatggaa aaacgccagc aacgcggcct ttttacggtt cctggccttt 60
tgctggcctt ttgctcacat gttctttcct gcgttatccc ctgattctgt ggataaccgt 120
attaccgcct ttgagtgagc tgataccgct cgccgcagcc gaacgaccga gcgcagcgag 180
tcagtgagcg aggaagcgga agagctcgcg aatgcatgtc gttacataac ttacggtaaa 240
tggcccgcct ggctgaccgc ccaacgaccc ccgcccattg acgtcaataa tgacgtatgt 300
tcccatagta acgccaatag ggactttcca ttgacgtcaa tgggtggagt atttacggta 360
aactgcccac ttggcagtac atcaagtgta tcatatgcca agtacgcccc ctattgacgt 420

-continued

```
caatgacggt aaatggcccg cctggcatta tgcccagtac atgaccttat gggactttcc     480
tacttggcag tacatctacg tattagtcat cgctattacc atggtgatgc ggttttggca     540
gtacatcaat gggcgtggat agcggtttga ctcacgggga tttccaagtc tccaccccat     600
tgacgtcaat gggagtttgt tttggcacca aaatcaacgg gactttccaa aatgtcgtaa     660
caactccgcc ccattgacgc aaatgggcgg taggcgtgta cggtgggagg tctatataag     720
cagagctcgt ttagtgaacc gtcagatcgc ctggagacgc catccacgct gttttgacct     780
ccatagaaga caccgggacc gatccagcct ccggactcta gcctaggccg cgggacggat     840
aacaatttca cacaggaaac agctatgacc attaggcctt tgcaaaaagc tatttaggtg     900
acactataga aggtacgcct gcaggtaccg gatcacaagt ttgtacaaaa aagctgaacg     960
agaaacgtaa aatgatataa atatcaatat attaaattag attttgcata aaaaacagac    1020
tacataatac tgtaaaacac aacatatcca gtcactatgg cggccgcatt aggcacccca    1080
ggctttacac tttatgcttc cggctcgtat aatgtgtgga ttttgagtta ggatccgtcg    1140
agattttcag gagctaagga agctaaaatg gagaaaaaaa tcactggata taccaccgtt    1200
gatatatccc aatggcatcg taaagaacat tttgaggcat ttcagtcagt tgctcaatgt    1260
acctataacc agaccgttca gctggatatt acggcctttt taaagaccgt aaagaaaaat    1320
aagcacaagt tttatccggc ctttattcac attcttgccc gcctgatgaa tgctcatccg    1380
gaattccgta tggcaatgaa agacggtgag ctggtgatat gggatagtgt tcacccttgt    1440
tacaccgttt tccatgagca aactgaaacg ttttcatcgc tctggagtga ataccacgac    1500
gatttccggc agtttctaca catatattcg caagatgtgg cgtgttacgg tgaaaacctg    1560
gcctatttcc ctaaagggtt tattgagaat atgtttttcg tctcagccaa tccctgggtg    1620
agtttcacca gttttgattt aaacgtggcc aatatggaca acttcttcgc ccccgttttc    1680
accatgggca aatattatac gcaaggcgac aaggtgctga tgccgctggc gattcaggtt    1740
catcatgccg tctgtgatgg cttccatgtc ggcagaatgc ttaatgaatt acaacagtac    1800
tgcgatgagt ggcagggcgg ggcgtaaacg cgtggatccg gcttactaaa agccagataa    1860
cagtatgcgt atttgcgcgc tgatttttgc ggtataagaa tatatactga tatgtatacc    1920
cgaagtatgt caaaaagagg tgtgctatga agcagcgtat tacagtgaca gttgacagcg    1980
acagctatca gttgctcaag gcatatatga tgtcaatatc tccggtctgg taagcacaac    2040
catgcagaat gaagcccgtc gtctgcgtgc cgaacgctgg aaagcggaaa atcaggaagg    2100
gatggctgag gtcgcccggt ttattgaaat gaacggctct tttgctgacg agaacaggga    2160
ctggtgaaat gcagtttaag gtttacacct ataaaagaga gagccgttat cgtctgtttg    2220
tggatgtaca gagtgatatt attgacacgc ccgggcgacg gatggtgatc cccctggcca    2280
gtgcacgtct gctgtcagat aaagtctccc gtgaacttta cccggtggtg catatcgggg    2340
atgaaagctg gcgcatgatg accaccgata tggccagtgt gccggtctcc gttatcgggg    2400
aagaagtggc tgatctcagc caccgcgaaa atgacatcaa aaacgccatt aacctgatgt    2460
tctggggaat ataaatgtca ggctccctta tacacagcca gtctgcaggt cgaccatagt    2520
gactggatat gttgtgtttt acagtattat gtagtctgtt ttttatgcaa aatctaattt    2580
aatatattga tatttatatc attttacgtt tctcgttcag ctttcttgta caaagtggtg    2640
atcgcgtgca tgcgacgtca tagctctctc cctatagtga gtcgtattat aagctaggca    2700
ctggccgtcg ttttacaacg tcgtgactgg gaaaactgct agcttgggat ctttgtgaag    2760
gaaccttact tctgtggtgt gacataattg gacaaactac ctacagagat ttaaagctct    2820
```

-continued

```
aaggtaaata taaaattttt aagtgtataa tgtgttaaac tagctgcata tgcttgctgc   2880
ttgagagttt tgcttactga gtatgattta tgaaaatatt atacacagga gctagtgatt   2940
ctaattgttt gtgtatttta gattcacagt cccaaggctc atttcaggcc cctcagtcct   3000
cacagtctgt tcatgatcat aatcagccat accacatttg tagaggtttt acttgcttta   3060
aaaaacctcc cacacctccc cctgaacctg aaacataaaa tgaatgcaat tgttgttgtt   3120
aacttgttta ttgcagctta taatggttac aaataaagca atagcatcac aaatttcaca   3180
aataaagcat ttttttcact gcattctagt tgtggtttgt ccaaactcat caatgtatct   3240
tatcatgtct ggatcgatcc tgcattaatg aatcggccaa cgcgcgggga gaggcggttt   3300
gcgtattggc tggcgtaata gcgaagaggc ccgcaccgat cgcccttccc aacagttgcg   3360
cagcctgaat ggcgaatggg acgcgccctg tagcggcgca ttaagcgcgg cgggtgtggt   3420
ggttacgcgc agcgtgaccg ctacacttgc cagcgcccta gcgcccgctc ctttcgcttt   3480
cttcccttcc tttctcgcca cgttcgccgg ctttccccgt caagctctaa atcgggggct   3540
ccctttaggg ttccgattta gtgctttacg gcacctcgac cccaaaaaac ttgattaggg   3600
tgatggttca cgtagtgggc catcgccctg atagacggtt tttcgccctt tgacgttgga   3660
gtccacgttc tttaatagtg gactcttgtt ccaaactgga acaacactca accctatctc   3720
ggtctattct tttgatttat aagggatttt gccgatttcg gcctattggt taaaaaatga   3780
gctgatttaa caaatattta acgcgaattt taacaaaata ttaacgttta caatttcgcc   3840
tgatgcggta ttttctcctt acgcatctgt gcggtatttc acaccgcata cgcggatctg   3900
cgcagcacca tggcctgaaa taacctctga aagaggaact tggttaggta ccttctgagg   3960
cggaaagaac cagctgtgga atgtgtgtca gttagggtgt ggaaagtccc caggctcccc   4020
agcaggcaga agtatgcaaa gcatgcatct caattagtca gcaaccaggt gtggaaagtc   4080
cccaggctcc ccagcaggca gaagtatgca aagcatgcat ctcaattagt cagcaaccat   4140
agtcccgccc ctaactccgc ccatcccgcc cctaactccg cccagttccg cccattctcc   4200
gccccatggc tgactaattt tttttattta tgcagaggcc gaggccgcct cggcctctga   4260
gctattccag aagtagtgag gaggcttttt tggaggccta ggcttttgca aaaagcttga   4320
ttcttctgac acaacagtct cgaacttaag gctagagcca ccatgattga acaagatgga   4380
ttgcacgcag gttctccggc cgcttgggtg gagaggctat tcggctatga ctgggcacaa   4440
cagacaatcg gctgctctga tgccgccgtg ttccggctgt cagcgcaggg gcgcccggtt   4500
ctttttgtca agaccgacct gtccggtgcc ctgaatgaac tgcaggacga ggcagcgcgg   4560
ctatcgtggc tggccacgac gggcgttcct tgcgcagctg tgctcgacgt tgtcactgaa   4620
gcgggaaggg actggctgct attgggcgaa gtgccggggc aggatctcct gtcatctcac   4680
cttgctcctg ccgagaaagt atccatcatg gctgatgcaa tgcggcggct gcatacgctt   4740
gatccggcta cctgcccatt cgaccaccaa gcgaaacatc gcatcgagcg agcacgtact   4800
cggatggaag ccggtcttgt cgatcaggat gatctggacg aagagcatca ggggctcgcg   4860
ccagccgaac tgttcgccag gctcaaggcg cgcatgcccg acggcgagga tctcgtcgtg   4920
acccatggcg atgcctgctt gccgaatatc atggtggaaa atggccgctt ttctggattc   4980
atcgactgtg gccggctggg tgtggcggac cgctatcagg acatagcgtt ggctacccgt   5040
gatattgctg aagagcttgg cggcgaatgg gctgaccgct tcctcgtgct ttacggtatc   5100
gccgctcccg attcgcagcg catcgccttc tatcgccttc ttgacgagtt cttctgagcg   5160
```

-continued

```
ggactctggg gttcgaaatg accgaccaag cgacgcccaa cctgccatca cgatggccgc   5220

aataaaatat ctttattttc attacatctg tgtgttggtt ttttgtgtga atcgatagcg   5280

ataaggatcc gcgtatggtg cactctcagt acaatctgct ctgatgccgc atagttaagc   5340

cagccccgac acccgccaac acccgctgac gcgccctgac gggcttgtct gctcccggca   5400

tccgcttaca gacaagctgt gaccgtctcc gggagctgca tgtgtcagag gttttcaccg   5460

tcatcaccga aacgcgcgag acgaaagggc ctcgtgatac gcctattttt ataggttaat   5520

gtcatgataa taatggtttc ttagacgtca ggtggcactt ttcggggaaa tgtgcgcgga   5580

acccctattt gtttattttt ctaaatacat tcaaatatgt atccgctcat gagacaataa   5640

ccctgataaa tgcttcaata atattgaaaa aggaagagta tgagtattca acatttccgt   5700

gtcgccctta ttcccttttt tgcggcattt tgccttcctg tttttgctca cccagaaacg   5760

ctggtgaaag taaaagatgc tgaagatcag ttgggtgcac gagtgggtta catcgaactg   5820

gatctcaaca gcggtaagat ccttgagagt tttcgccccg aagaacgttt tccaatgatg   5880

agcactttta aagttctgct atgtggcgcg gtattatccc gtattgacgc cgggcaagag   5940

caactcggtc gccgcataca ctattctcag aatgacttgg ttgagtactc accagtcaca   6000

gaaaagcatc ttacggatgg catgacagta agagaattat gcagtgctgc cataaccatg   6060

agtgataaca ctgcggccaa cttacttctg acaacgatcg gaggaccgaa ggagctaacc   6120

gcttttttgc acaacatggg ggatcatgta actcgccttg atcgttggga accggagctg   6180

aatgaagcca taccaaacga cgagcgtgac accacgatgc ctgtagcaat ggcaacaacg   6240

ttgcgcaaac tattaactgg cgaactactt actctagctt cccggcaaca attaatagac   6300

tggatggagg cggataaagt tgcaggacca cttctgcgct cggcccttcc ggctggctgg   6360

tttattgctg ataaatctgg agccggtgag cgtgggtctc gcggtatcat tgcagcactg   6420

gggccagatg gtaagccctc ccgtatcgta gttatctaca cgacggggag tcaggcaact   6480

atggatgaac gaaatagaca gatcgctgag ataggtgcct cactgattaa gcattggtaa   6540

ctgtcagacc aagtttactc atatatactt tagattgatt taaaacttca tttttaattt   6600

aaaaggatct aggtgaagat cctttttgat aatctcatga ccaaaatccc ttaacgtgag   6660

ttttcgttcc actgagcgtc agaccccgta gaaaagatca aaggatcttc ttgagatcct   6720

tttttctgc gcgtaatctg ctgcttgcaa acaaaaaaac caccgctacc agcggtggtt   6780

tgtttgccgg atcaagagct accaactctt tttccgaagg taactggctt cagcagagcg   6840

cagataccaa atactgtcct tctagtgtag ccgtagttag gccaccactt caagaactct   6900

gtagcaccgc ctacatacct cgctctgcta atcctgttac cagtggctgc tgccagtggc   6960

gataagtcgt gtcttaccgg gttggactca agacgatagt taccggataa ggcgcagcgg   7020

tcgggctgaa cggggggttc gtgcacacag cccagcttgg agcgaacgac ctacaccgaa   7080

ctgagatacc tacagcgtga gcattgagaa agcgccacgc ttcccgaagg gagaaaggcg   7140

gacaggtatc cggtaagcgg cagggtcgga acaggagagc gcacgaggga gcttccaggg   7200

ggaaacgcct ggtatcttta tagtcctgtc gggtttcgcc acctctgact tgagcgtcga   7260

tttttgtgat gctcgtca                                                 7278
```

<210> SEQ ID NO 141
<211> LENGTH: 5848
<212> TYPE: DNA
<213> ORGANISM: Artificial Sequence
<220> FEATURE:
<223> OTHER INFORMATION: pDEST13

-continued

<220> FEATURE:
<221> NAME/KEY: gene
<222> LOCATION: (599)..(1458)
<223> OTHER INFORMATION: ampR
<220> FEATURE:
<221> NAME/KEY: gene
<222> LOCATION: (3998)..(4123)
<223> OTHER INFORMATION: attR1
<220> FEATURE:
<221> NAME/KEY: gene
<222> LOCATION: (4372)..(5031)
<223> OTHER INFORMATION: CmR
<220> FEATURE:
<221> NAME/KEY: gene
<222> LOCATION: (5151)..(5235)
<223> OTHER INFORMATION: inactivated ccdA
<220> FEATURE:
<221> NAME/KEY: gene
<222> LOCATION: (5373)..(5678)
<223> OTHER INFORMATION: ccdB
<220> FEATURE:
<221> NAME/KEY: gene
<222> LOCATION: (5719)..(5843)
<223> OTHER INFORMATION: attR2

<400> SEQUENCE: 141
ttcactggcc gtcgttttac aacgtcgtga ctgggaaaac cctggcgtta cccaacttaa 60
tcgccttgca gcacatcccc ctttcgccag ctggcgtaat agcgaagagg cccgcaccga 120
tcgcccttcc caacagttgc gcagcctgaa tggcgaatgg cgcctgatgc ggtattttct 180
ccttacgcat ctgtgcggta tttcacaccg catatggtgc actctcagta caatctgctc 240
tgatgccgca tagttaagcc agccccgaca cccgccaaca cccgctgacg cgccctgacg 300
ggcttgtctg ctcccggcat ccgcttacag acaagctgtg accgtctccg ggagctgcat 360
gtgtcagagg ttttcaccgt catcaccgaa acgcgcgaga cgaaagggcc tcgtgatacg 420
cctattttta taggttaatg tcatgataat aatggtttct tagacgtcag gtggcacttt 480
tcggggaaat gtgcgcggaa cccctatttg tttatttttc taaatacatt caaatatgta 540
tccgctcatg agacaataac cctgataaat gcttcaataa tattgaaaaa ggaagagtat 600
gagtattcaa catttccgtg tcgcccttat tccctttttt gcggcatttt gccttcctgt 660
ttttgctcac ccagaaacgc tggtgaaagt aaaagatgct gaagatcagt tgggtgcacg 720
agtgggttac atcgaactgg atctcaacag cggtaagatc cttgagagtt ttcgccccga 780
agaacgtttt ccaatgatga gcacttttaa agttctgcta tgtggcgcgg tattatcccg 840
tattgacgcc gggcaagagc aactcggtcg ccgcatacac tattctcaga atgacttggt 900
tgagtactca ccagtcacag aaaagcatct tacggatggc atgacagtaa gagaattatg 960
cagtgctgcc ataaccatga gtgataacac tgcggccaac ttacttctga caacgatcgg 1020
aggaccgaag gagctaaccg cttttttgca caacatgggg gatcatgtaa ctcgccttga 1080
tcgttgggaa ccggagctga atgaagccat accaaacgac gagcgtgaca ccacgatgcc 1140
tgtagcaatg gcaacaacgt tgcgcaaact attaactggc gaactactta ctctagcttc 1200
ccggcaacaa ttaatagact ggatggaggc ggataaagtt gcaggaccac ttctgcgctc 1260
ggcccttccg gctggctggt ttattgctga taaatctgga gccggtgagc gtgggtctcg 1320
cggtatcatt gcagcactgg ggccagatgg taagccctcc cgtatcgtag ttatctacac 1380
gacggggagt caggcaacta tggatgaacg aaatagacag atcgctgaga taggtgcctc 1440
actgattaag cattggtaac tgtcagacca agtttactca tatatacttt agattgattt 1500
aaaacttcat ttttaattta aaaggatcta ggtgaagatc ctttttgata atctcatgac 1560

-continued

```
caaaatccct taacgtgagt tttcgttcca ctgagcgtca gaccccgtag aaaagatcaa   1620
aggatcttct tgagatcctt tttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgttctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag gcgcagcggt cgggctgaac ggggggttcg tgcacacagc ccagcttgga   1980
gcgaacgacc tacaccgaac tgagatacct acagcgtgag cattgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggcctttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcccaata cgcaaaccgc ctctccccgc gcgttggccg attcattaat gcagctggca   2460
cgacaggttt cccgactgga aagcgggcag tgagcgcaac gcaattaatg tgagttagct   2520
cactcattag gcaccccagg ctttacactt tatgcttccg gctcgtatgt tgtgtggaat   2580
tgtgagcgga taacaatttc acacaggaaa cagctatgac catgattacg ccaagcttgg   2640
ctgcaggtga tgattatcag ccagcagaga ttaaggaaaa cagacaggtt tattgagcgc   2700
ttatctttcc ctttattttt gctgcggtaa gtcgcataaa aaccattctt cataattcaa   2760
tccatttact atgttatgtt ctgaggggag tgaaaattcc cctaattcga tgaagattct   2820
tgctcaattg ttatcagcta tgcgccgacc agaacacctt gccgatcagc caaacgtctc   2880
ttcaggccac tgactagcga taactttccc cacaacggaa caactctcat tgcatgggat   2940
cattgggtac tgtgggttta gtggttgtaa aaacacctga ccgctatccc tgatcagttt   3000
cttgaaggta aactcatcac ccccaagtct ggctatgcag aaatcacctg gctcaacagc   3060
ctgctcaggg tcaacgagaa ttaacattcc gtcaggaaag cttggcttgg agcctgttgg   3120
tgcggtcatg gaattacctt caacctcaag ccagaatgca gaatcactgg ctttttttggt   3180
tgtgcttacc catctctccg catcaccttt ggtaaaggtt ctaagcttag gtgagaacat   3240
ccctgcctga acatgagaaa aaacagggta ctcatactca cttctaagtg acggctgcat   3300
actaaccgct tcatacatct cgtagatttc tctggcgatt gaagggctaa attcttcaac   3360
gctaactttg agaatttttg caagcaatgc ggcgttataa gcatttaatg cattgatgcc   3420
attaaataaa gcaccaacgc ctgactgccc catccccatc ttgtctgcga cagattcctg   3480
ggataagcca agttcatttt tctttttttc ataaattgct ttaaggcgac gtgcgtcctc   3540
aagctgctct tgtgttaatg gtttcttttt tgtgctcata cgttaaatct atcaccgcaa   3600
gggataaata tctaacaccg tgcgtgttga ctattttacc tctggcggtg ataatggttg   3660
catgtactaa ggaggttgta tggaacaacg cataaccctg aaagattatg caatgcgctt   3720
tgggcaaacc aagacagcta aagatctctc acctaccaaa caatgccccc ctgcaaaaaa   3780
taaattcata taaaaaacat acagataacc atctgcggtg ataaattatc tctggcggtg   3840
ttgacataaa taccactggc ggtgatactg agcacatcag caggacgcac tgaccaccat   3900
gaaggtgacg ctcttaaaaa ttaagccctg aagaagggca gcattcaaag cagaaggctt   3960
```

-continued

```
tggggtgtgt gatacgaaac gaagcattgg gatcatcaca agtttgtaca aaaaagctga   4020

acgagaaacg taaaatgata taaatatcaa tatattaaat tagattttgc ataaaaaaca   4080

gactacataa tactgtaaaa cacaacatat ccagtcacta tggcggccgc taagttggca   4140

gcatcacccg acgcactttg cgccgaataa atacctgtga cggaagatca cttcgcagaa   4200

taaataaatc ctggtgtccc tgttgatacc gggaagccct gggccaactt ttggcgaaaa   4260

tgagacgttg atcggcacgt aagaggttcc aactttcacc ataatgaaat aagatcacta   4320

ccgggcgtat tttttgagtt atcgagattt tcaggagcta aggaagctaa aatggagaaa   4380

aaaatcactg gatataccac cgttgatata tcccaatggc atcgtaaaga acattttgag   4440

gcatttcagt cagttgctca atgtacctat aaccagaccg ttcagctgga tattacggcc   4500

tttttaaaga ccgtaaagaa aaataagcac aagttttatc cggcctttat tcacattctt   4560

gcccgcctga tgaatgctca tccggaattc cgtatggcaa tgaaagacgg tgagctggtg   4620

atatgggata gtgttcaccc ttgttacacc gttttccatg agcaaactga aacgttttca   4680

tcgctctgga gtgaatacca cgacgatttc cggcagtttc tacacatata ttcgcaagat   4740

gtggcgtgtt acggtgaaaa cctggcctat ttccctaaag ggtttattga gaatatgttt   4800

ttcgtctcag ccaatccctg ggtgagtttc accagttttg atttaaacgt ggccaatatg   4860

gacaacttct tcgcccccgt tttcaccatg ggcaaatatt atacgcaagg cgacaaggtg   4920

ctgatgccgc tggcgattca ggttcatcat gccgtctgtg atggcttcca tgtcggcaga   4980

atgcttaatg aattacaaca gtactgcgat gagtggcagg gcggggcgta aacgcgtgga   5040

tccggcttac taaaagccag ataacagtat gcgtatttgc gcgctgattt ttgcggtata   5100

agaatatata ctgatatgta tacccgaagt atgtcaaaaa gaggtgtgct atgaagcagc   5160

gtattacagt gacagttgac agcgacagct atcagttgct caaggcatat atgatgtcaa   5220

tatctccggt ctggtaagca caaccatgca gaatgaagcc cgtcgtctgc gtgccgaacg   5280

ctggaaagcg gaaaatcagg aagggatggc tgaggtcgcc cggtttattg aaatgaacgg   5340

ctcttttgct gacgagaaca gggactggtg aaatgcagtt taaggtttac acctataaaa   5400

gagagagccg ttatcgtctg tttgtggatg tacagagtga tattattgac acgcccgggc   5460

gacggatggt gatccccctg gccagtgcac gtctgctgtc agataaagtc tcccgtgaac   5520

tttacccggt ggtgcatatc ggggatgaaa gctggcgcat gatgaccacc gatatggcca   5580

gtgtgccggt ctccgttatc ggggaagaag tggctgatct cagccaccgc gaaaatgaca   5640

tcaaaaacgc cattaacctg atgttctggg gaatataaat gtcaggctcc gttatacaca   5700

gccagtctgc aggtcgacca tagtgactgg atatgttgtg ttttacagta ttatgtagtc   5760

tgttttttat gcaaaatcta atttaatata ttgatattta tatcatttta cgtttctcgt   5820

tcagctttct tgtacaaagt ggtgataa                                      5848
```

<210> SEQ ID NO 142
<211> LENGTH: 6422
<212> TYPE: DNA
<213> ORGANISM: Artificial Sequence
<220> FEATURE:
<223> OTHER INFORMATION: pDEST14
<220> FEATURE:
<221> NAME/KEY: gene
<222> LOCATION: (61)..(185)
<223> OTHER INFORMATION: attR1
<220> FEATURE:
<221> NAME/KEY: gene
<222> LOCATION: (435)..(1094)

-continued

<223> OTHER INFORMATION: CmR
<220> FEATURE:
<221> NAME/KEY: gene
<222> LOCATION: (1214)..(1298)
<223> OTHER INFORMATION: inactivated ccdA
<220> FEATURE:
<221> NAME/KEY: gene
<222> LOCATION: (1436)..(1741)
<223> OTHER INFORMATION: ccdB
<220> FEATURE:
<221> NAME/KEY: gene
<222> LOCATION: (1782)..(1906)
<223> OTHER INFORMATION: attR2
<220> FEATURE:
<221> NAME/KEY: gene
<222> LOCATION: (2632)..(3489)
<223> OTHER INFORMATION: ampR

<400> SEQUENCE: 142
cgatcccgcg aaattaatac gactcactat agggagacca caacggtttc cctctagatc 60
acaagtttgt acaaaaaagc tgaacgagaa acgtaaaatg atataaatat caatatatta 120
aattagattt tgcataaaaa acagactaca taatactgta aaacacaaca tatccagtca 180
ctatggcggc cgctaagttg gcagcatcac ccgacgcact ttgcgccgaa taaatacctg 240
tgacggaaga tcacttcgca gaataaataa atcctggtgt ccctgttgat accgggaagc 300
cctgggccaa cttttggcga aaatgagacg ttgatcggca cgtaagaggt tccaactttc 360
accataatga aataagatca ctaccgggcg tatttttga gttatcgaga ttttcaggag 420
ctaaggaagc taaaatggag aaaaaaatca ctggatatac caccgttgat atatcccaat 480
ggcatcgtaa agaacatttt gaggcatttc agtcagttgc tcaatgtacc tataaccaga 540
ccgttcagct ggatattacg gcctttttaa agaccgtaaa gaaaaataag cacaagtttt 600
atccggcctt tattcacatt cttgcccgcc tgatgaatgc tcatccggaa ttccgtatgg 660
caatgaaaga cggtgagctg gtgatatggg atagtgttca cccttgttac accgttttcc 720
atgagcaaac tgaaacgttt tcatcgctct ggagtgaata ccacgacgat ttccggcagt 780
ttctacacat atattcgcaa gatgtggcgt gttacggtga aaacctggcc tatttcccta 840
aagggtttat tgagaatatg tttttcgtct cagccaatcc ctgggtgagt ttcaccagtt 900
ttgatttaaa cgtggccaat atggacaact tcttcgcccc cgttttcacc atgggcaaat 960
attatacgca aggcgacaag gtgctgatgc cgctggcgat tcaggttcat catgccgtct 1020
gtgatggctt ccatgtcggc agaatgctta atgaattaca acagtactgc gatgagtggc 1080
agggcggggc gtaaacgcgt ggatccggct tactaaaagc cagataacag tatgcgtatt 1140
tgcgcgctga tttttgcggt ataagaatat atactgatat gtatacccga agtatgtcaa 1200
aaagaggtgt gctatgaagc agcgtattac agtgacagtt gacagcgaca gctatcagtt 1260
gctcaaggca tatatgatgt caatatctcc ggtctggtaa gcacaaccat gcagaatgaa 1320
gcccgtcgtc tgcgtgccga acgctggaaa gcggaaaatc aggaagggat ggctgaggtc 1380
gcccggttta ttgaaatgaa cggctctttt gctgacgaga acagggactg gtgaaatgca 1440
gtttaaggtt tacacctata aaagagagag ccgttatcgt ctgtttgtgg atgtacagag 1500
tgatattatt gacacgcccg ggcgacggat ggtgatcccc ctggccagtg cacgtctgct 1560
gtcagataaa gtctcccgtg aactttaccc ggtggtgcat atcggggatg aaagctggcg 1620
catgatgacc accgatatgg ccagtgtgcc ggtctccgtt atcggggaag aagtggctga 1680
tctcagccac cgcgaaaatg acatcaaaaa cgccattaac ctgatgttct ggggaatata 1740
aatgtcaggc tcccttatac acagccagtc tgcaggtcga ccatagtgac tggatatgtt 1800

-continued

```
gtgttttaca gtattatgta gtctgttttt tatgcaaaat ctaatttaat atattgatat   1860
ttatatcatt ttacgtttct cgttcagctt tcttgtacaa agtggtgatg atccggctgc   1920
taacaaagcc cgaaaggaag ctgagttggc tgctgccacc gctgagcaat aactagcata   1980
accccttggg gcctctaaac gggtcttgag gggttttttg ctgaaaggag gaactatatc   2040
cggatatcca caggacgggt gtggtcgcca tgatcgcgta gtcgatagtg gctccaagta   2100
gcgaagcgag caggactggg cggcggccaa agcggtcgga cagtgctccg agaacgggtg   2160
cgcatagaaa ttgcatcaac gcatatagcg ctagcagcac gccatagtga ctggcgatgc   2220
tgtcggaatg gacgatatcc cgcaagaggc ccggcagtac cggcataacc aagcctatgc   2280
ctacagcatc cagggtgacg gtgccgagga tgacgatgag cgcattgtta gatttcatac   2340
acggtgcctg actgcgttag caatttaact gtgataaact accgcattaa agcttatcga   2400
tgataagctg tcaaacatga gaattcttga agacgaaagg gcctcgtgat acgcctattt   2460
ttataggtta atgtcatgat aataatggtt tcttagacgt caggtggcac ttttcgggga   2520
aatgtgcgcg gaacccctat ttgtttattt ttctaaatac attcaaatat gtatccgctc   2580
atgagacaat aaccctgata aatgcttcaa taatattgaa aaaggaagag tatgagtatt   2640
caacatttcc gtgtcgccct tattcccttt tttgcggcat tttgccttcc tgtttttgct   2700
cacccagaaa cgctggtgaa agtaaaagat gctgaagatc agttgggtgc acgagtgggt   2760
tacatcgaac tggatctcaa cagcggtaag atccttgaga gttttcgccc cgaagaacgt   2820
tttccaatga tgagcacttt taaagttctg ctatgtggcg cggtattatc ccgtgttgac   2880
gccgggcaag agcaactcgg tcgccgcata cactattctc agaatgactt ggttgagtac   2940
tcaccagtca cagaaaagca tcttacggat ggcatgacag taagagaatt atgcagtgct   3000
gccataacca tgagtgataa cactgcggcc aacttacttc tgacaacgat cggaggaccg   3060
aaggagctaa ccgctttttt gcacaacatg ggggatcatg taactcgcct tgatcgttgg   3120
gaaccggagc tgaatgaagc cataccaaac gacgagcgtg acaccacgat gcctgcagca   3180
atggcaacaa cgttgcgcaa actattaact ggcgaactac ttactctagc ttcccggcaa   3240
caattaatag actggatgga ggcggataaa gttgcaggac cacttctgcg ctcggccctt   3300
ccggctggct ggtttattgc tgataaatct ggagccggtg agcgtgggtc tcgcggtatc   3360
attgcagcac tggggccaga tggtaagccc tcccgtatcg tagttatcta cacgacgggg   3420
agtcaggcaa ctatggatga acgaaataga cagatcgctg agataggtgc ctcactgatt   3480
aagcattggt aactgtcaga ccaagtttac tcatatatac tttagattga tttaaaactt   3540
catttttaat ttaaaaggat ctaggtgaag atcctttttg ataatctcat gaccaaaatc   3600
ccttaacgtg agttttcgtt ccactgagcg tcagaccccg tagaaaagat caaaggatct   3660
tcttgagatc cttttttct gcgcgtaatc tgctgcttgc aaacaaaaaa accaccgcta   3720
ccagcggtgg tttgtttgcc ggatcaagag ctaccaactc tttttccgaa ggtaactggc   3780
ttcagcagag cgcagatacc aaatactgtc cttctagtgt agccgtagtt aggccaccac   3840
ttcaagaact ctgtagcacc gcctacatac ctcgctctgc taatcctgtt accagtggct   3900
gctgccagtg gcgataagtc gtgtcttacc gggttggact caagacgata gttaccggat   3960
aaggcgcagc ggtcgggctg aacggggggt tcgtgcacac agcccagctt ggagcgaacg   4020
acctacaccg aactgagata cctacagcgt gagctatgag aaagcgccac gcttcccgaa   4080
gggagaaagg cggacaggta tccggtaagc ggcagggtcg gaacaggaga gcgcacgagg   4140
```

-continued

```
gagcttccag ggggaaacgc ctggtatctt tatagtcctg tcgggtttcg ccacctctga   4200
cttgagcgtc gatttttgtg atgctcgtca ggggggcgga gcctatggaa aaacgccagc   4260
aacgcggcct ttttacggtt cctggccttt tgctggcctt ttgctcacat gttctttcct   4320
gcgttatccc ctgattctgt ggataaccgt attaccgcct ttgagtgagc tgataccgct   4380
cgccgcagcc gaacgaccga gcgcagcgag tcagtgagcg aggaagcgga agagcgcctg   4440
atgcggtatt ttctccttac gcatctgtgc ggtatttcac accgcatata tggtgcactc   4500
tcagtacaat ctgctctgat gccgcatagt taagccagta tacactccgc tatcgctacg   4560
tgactgggtc atggctgcgc cccgacaccc gccaacaccc gctgacgcgc cctgacgggc   4620
ttgtctgctc ccggcatccg cttacagaca agctgtgacc gtctccggga gctgcatgtg   4680
tcagaggttt tcaccgtcat caccgaaacg cgcgaggcag ctgcggtaaa gctcatcagc   4740
gtggtcgtga agcgattcac agatgtctgc ctgttcatcc gcgtccagct cgttgagttt   4800
ctccagaagc gttaatgtct ggcttctgat aaagcgggcc atgttaaggg cggttttttc   4860
ctgtttggtc actgatgcct ccgtgtaagg gggatttctg ttcatggggg taatgatacc   4920
gatgaaacga gagaggatgc tcacgatacg ggttactgat gatgaacatg cccggttact   4980
ggaacgttgt gagggtaaac aactggcggt atggatgcgg cgggaccaga gaaaaatcac   5040
tcagggtcaa tgccagcgct tcgttaatac agatgtaggt gttccacagg gtagccagca   5100
gcatcctgcg atgcagatcc ggaacataat ggtgcagggc gctgacttcc gcgtttccag   5160
actttacgaa acacggaaac cgaagaccat tcatgttgtt gctcaggtcg cagacgtttt   5220
gcagcagcag tcgcttcacg ttcgctcgcg tatcggtgat tcattctgct aaccagtaag   5280
gcaaccccgc cagcctagcc gggtcctcaa cgacaggagc acgatcatgc gcacccgtgg   5340
ccaggaccca acgctgcccg agatgcgccg cgtgcggctg ctggagatgg cggacgcgat   5400
ggatatgttc tgccaagggt tggtttgcgc attcacagtt ctccgcaaga attgattggc   5460
tccaattctt ggagtggtga atccgttagc gaggtgccgc cggcttccat tcaggtcgag   5520
gtggcccggc tccatgcacc gcgacgcaac gcggggaggc agacaaggta tagggcggcg   5580
cctacaatcc atgccaaccc gttccatgtg ctcgccgagg cggcataaat cgccgtgacg   5640
atcagcggtc cagtgatcga agttaggctg gtaagagccg cgagcgatcc ttgaagctgt   5700
ccctgatggt cgtcatctac ctgcctggac agcatggcct gcaacgcggg catcccgatg   5760
ccgccggaag cgagaagaat cataatgggg aaggccatcc agcctcgcgt cgcgaacgcc   5820
agcaagacgt agcccagcgc gtcggccgcc atgccggcga taatggcctg cttctcgccg   5880
aaacgtttgg tggcgggacc agtgacgaag gcttgagcga gggcgtgcaa gattccgaat   5940
accgcaagcg acaggccgat catcgtcgcg ctccagcgaa agcggtcctc gccgaaaatg   6000
acccagagcg ctgccggcac ctgtcctacg agttgcatga taaagaagac agtcataagt   6060
gcggcgacga tagtcatgcc ccgcgcccac cggaaggagc tgactgggtt gaaggctctc   6120
aagggcatcg gtcgatcgac gctctccctt atgcgactcc tgcattagga agcagcccag   6180
tagtaggttg aggccgttga gcaccgccgc cgcaaggaat ggtgcatgca aggagatggc   6240
gcccaacagt cccccggcca cggggcctgc caccataccc acgccgaaac aagcgctcat   6300
gagcccgaag tggcgagccc gatcttcccc atcggtgatg tcggcgatat aggcgccagc   6360
aaccgcacct gtggcgccgg tgatgccggc cacgatgcgt ccggcgtaga ggatcgagat   6420
ct                                                                  6422
```

-continued

<210> SEQ ID NO 143
<211> LENGTH: 7013
<212> TYPE: DNA
<213> ORGANISM: Artificial Sequence
<220> FEATURE:
<223> OTHER INFORMATION: pDEST15
<220> FEATURE:
<221> NAME/KEY: gene
<222> LOCATION: (108)..(776)
<223> OTHER INFORMATION: GST
<220> FEATURE:
<221> NAME/KEY: gene
<222> LOCATION: (792)..(916)
<223> OTHER INFORMATION: attR1
<220> FEATURE:
<221> NAME/KEY: gene
<222> LOCATION: (1025)..(1537)
<223> OTHER INFORMATION: CmR
<220> FEATURE:
<221> NAME/KEY: gene
<222> LOCATION: (1804)..(1888)
<223> OTHER INFORMATION: inactivated ccdA
<220> FEATURE:
<221> NAME/KEY: gene
<222> LOCATION: (2026)..(2331)
<223> OTHER INFORMATION: ccdB
<220> FEATURE:
<221> NAME/KEY: gene
<222> LOCATION: (2372)..(2496)
<223> OTHER INFORMATION: attR2
<220> FEATURE:
<221> NAME/KEY: gene
<222> LOCATION: (3233)..(4093)
<223> OTHER INFORMATION: ampR

<400> SEQUENCE: 143
atcgagatct cgatcccgcg aaattaatac gactcactat agggagacca caacggtttc 60
cctctagaaa taattttgtt taactttaag aaggagatat acatatgtcc cctatactag 120
gttattggaa aattaagggc cttgtgcaac ccactcgact tcttttggaa tatcttgaag 180
aaaaatatga agagcatttg tatgagcgcg atgaaggtga taaatggcga aacaaaaagt 240
ttgaattggg tttggagttt cccaatcttc cttattatat tgatggtgat gttaaattaa 300
cacagtctat ggccatcata cgttatatag ctgacaagca caacatgttg ggtggttgtc 360
caaaagagcg tgcagagatt tcaatgcttg aaggagcggt tttggatatt agatacggtg 420
tttcgagaat tgcatatagt aaagactttg aaactctcaa agttgatttt cttagcaagc 480
tacctgaaat gctgaaaatg ttcgaagatc gtttatgtca taaaacatat ttaaatggtg 540
atcatgtaac ccatcctgac ttcatgttgt atgacgctct tgatgttgtt ttatacatgg 600
acccaatgtg cctggatgcg ttcccaaaat tagtttgttt taaaaaacgt attgaagcta 660
tcccacaaat tgataagtac ttgaaatcca gcaagtatat agcatggcct ttgcagggct 720
ggcaagccac gtttggtggt ggcgaccatc ctccaaaatc ggatctggtt ccgcgtccat 780
ggtcgaatca aacaagtttg tacaaaaaag ctgaacgaga aacgtaaaat gatataaata 840
tcaatatatt aaattagatt ttgcataaaa aacagactac ataatactgt aaaacacaac 900
atatccagtc actatggcgg ccgcattagg caccccaggc tttacacttt atgcttccgg 960
ctcgtataat gtgtggattt tgagttagga tccgtcgaga ttttcaggag ctaaggaagc 1020
taaaatggag aaaaaaatca ctggatatac caccgttgat atatcccaat ggcatcgtaa 1080
agaacatttt gaggcatttc agtcagttgc tcaatgtacc tataaccaga ccgttcagct 1140
ggatattacg gcctttttaa agaccgtaaa gaaaaataag cacaagtttt atccggcctt 1200
tattcacatt cttgcccgcc tgatgaatgc tcatccggaa ttccgtatgg caatgaaaga 1260

-continued

```
cggtgagctg gtgatatggg atagtgttca cccttgttac accgttttcc atgagcaaac   1320
tgaaacgttt tcatcgctct ggagtgaata ccacgacgat ttccggcagt ttctacacat   1380
atattcgcaa gatgtggcgt gttacggtga aaacctggcc tatttcccta aagggtttat   1440
tgagaatatg tttttcgtct cagccaatcc ctgggtgagt ttcaccagtt ttgatttaaa   1500
cgtggccaat atggacaact tcttcgcccc cgttttcacc atgggcaaat attatacgca   1560
aggcgacaag gtgctgatgc cgctggcgat tcaggttcat catgccgtct gtgatggctt   1620
ccatgtcggc agaatgctta atgaattaca acagtactgc gatgagtggc agggcggggc   1680
gtaatctaga ggatccggct tactaaaagc cagataacag tatgcgtatt tgcgcgctga   1740
tttttgcggt ataagaatat atactgatat gtatacccga agtatgtcaa aaagaggtgt   1800
gctatgaagc agcgtattac agtgacagtt gacagcgaca gctatcagtt gctcaaggca   1860
tatatgatgt caatatctcc ggtctggtaa gcacaaccat gcagaatgaa gcccgtcgtc   1920
tgcgtgccga acgctggaaa gcggaaaatc aggaagggat ggctgaggtc gcccggttta   1980
ttgaaatgaa cggctctttt gctgacgaga acagggactg gtgaaatgca gtttaaggtt   2040
tacacctata aaagagagag ccgttatcgt ctgtttgtgg atgtacagag tgatattatt   2100
gacacgcccg ggcgacggat ggtgatcccc ctggccagtg cacgtctgct gtcagataaa   2160
gtctcccgtg aactttaccc ggtggtgcat atcggggatg aaagctggcg catgatgacc   2220
accgatatgg ccagtgtgcc ggtctccgtt atcggggaag aagtggctga tctcagccac   2280
cgcgaaaatg acatcaaaaa cgccattaac ctgatgttct ggggaatata aatgtcaggc   2340
tcccttatac acagccagtc tgcaggtcga ccatagtgac tggatatgtt gtgttttaca   2400
gtattatgta gtctgttttt tatgcaaaat ctaatttaat atattgatat ttatatcatt   2460
ttacgtttct cgttcagctt tcttgtacaa agtggtttga ttcgacccgg gatccggctg   2520
ctaacaaagc ccgaaaggaa gctgagttgg ctgctgccac cgctgagcaa taactagcat   2580
aaccccttgg ggcctctaaa cgggtcttga ggggtttttt gctgaaagga ggaactatat   2640
ccggatatcc acaggacggg tgtggtcgcc atgatcgcgt agtcgatagt ggctccaagt   2700
agcgaagcga gcaggactgg gcggcggcca aagcggtcgg acagtgctcc gagaacgggt   2760
gcgcatagaa attgcatcaa cgcatatagc gctagcagca cgccatagtg actggcgatg   2820
ctgtcggaat ggacgatatc ccgcaagagg cccggcagta ccggcataac caagcctatg   2880
cctacagcat ccagggtgac ggtgccgagg atgacgatga gcgcattgtt agatttcata   2940
cacggtgcct gactgcgtta gcaatttaac tgtgataaac taccgcatta aagcttatcg   3000
atgataagct gtcaaacatg agaattcttg aagacgaaag ggcctcgtga tacgcctatt   3060
tttataggtt aatgtcatga taataatggt ttcttagacg tcaggtggca cttttcgggg   3120
aaatgtgcgc ggaaccccta tttgtttatt tttctaaata cattcaaata tgtatccgct   3180
catgagacaa taaccctgat aaatgcttca ataatattga aaaaggaaga gtatgagtat   3240
tcaacatttc cgtgtcgccc ttattccctt ttttgcggca ttttgccttc ctgtttttgc   3300
tcacccagaa acgctggtga aagtaaaaga tgctgaagat cagttgggtg cacgagtggg   3360
ttacatcgaa ctggatctca acagcggtaa gatccttgag agttttcgcc ccgaagaacg   3420
ttttccaatg atgagcactt ttaaagttct gctatgtggc gcggtattat cccgtgttga   3480
cgccgggcaa gagcaactcg gtcgccgcat acactattct cagaatgact tggttgagta   3540
ctcaccagtc acagaaaagc atcttacgga tggcatgaca gtaagagaat tatgcagtgc   3600
tgccataacc atgagtgata acactgcggc caacttactt ctgacaacga tcggaggacc   3660
```

-continued

```
gaaggagcta accgcttttt tgcacaacat gggggatcat gtaactcgcc ttgatcgttg   3720
ggaaccggag ctgaatgaag ccataccaaa cgacgagcgt gacaccacga tgcctgcagc   3780
aatggcaaca acgttgcgca aactattaac tggcgaacta cttactctag cttcccggca   3840
acaattaata gactggatgg aggcggataa agttgcagga ccacttctgc gctcggccct   3900
tccggctggc tggtttattg ctgataaatc tggagccggt gagcgtgggt ctcgcggtat   3960
cattgcagca ctggggccag atggtaagcc ctcccgtatc gtagttatct acacgacggg   4020
gagtcaggca actatggatg aacgaaatag acagatcgct gagataggtg cctcactgat   4080
taagcattgg taactgtcag accaagttta ctcatatata ctttagattg atttaaaact   4140
tcatttttaa tttaaaagga tctaggtgaa gatccttttt gataatctca tgaccaaaat   4200
cccttaacgt gagttttcgt tccactgagc gtcagacccc gtagaaaaga tcaaaggatc   4260
ttcttgagat cctttttttc tgcgcgtaat ctgctgcttg caaacaaaaa aaccaccgct   4320
accagcggtg gtttgtttgc cggatcaaga gctaccaact ctttttccga aggtaactgg   4380
cttcagcaga gcgcagatac caaatactgt ccttctagtg tagccgtagt taggccacca   4440
cttcaagaac tctgtagcac cgcctacata cctcgctctg ctaatcctgt taccagtggc   4500
tgctgccagt ggcgataagt cgtgtcttac cgggttggac tcaagacgat agttaccgga   4560
taaggcgcag cggtcgggct gaacgggggg ttcgtgcaca cagcccagct tggagcgaac   4620
gacctacacc gaactgagat acctacagcg tgagctatga gaaagcgcca cgcttcccga   4680
agggagaaag gcggacaggt atccggtaag cggcagggtc ggaacaggag agcgcacgag   4740
ggagcttcca gggggaaacg cctggtatct ttatagtcct gtcgggtttc gccacctctg   4800
acttgagcgt cgatttttgt gatgctcgtc aggggggcgg agcctatgga aaaacgccag   4860
caacgcggcc tttttacggt tcctggcctt ttgctggcct tttgctcaca tgttctttcc   4920
tgcgttatcc cctgattctg tggataaccg tattaccgcc tttgagtgag ctgataccgc   4980
tcgccgcagc cgaacgaccg agcgcagcga gtcagtgagc gaggaagcgg aagagcgcct   5040
gatgcggtat tttctcctta cgcatctgtg cggtatttca caccgcatat atggtgcact   5100
ctcagtacaa tctgctctga tgccgcatag ttaagccagt atacactccg ctatcgctac   5160
gtgactgggt catggctgcg ccccgacacc cgccaacacc cgctgacgcg ccctgacggg   5220
cttgtctgct cccggcatcc gcttacagac aagctgtgac cgtctccggg agctgcatgt   5280
gtcagaggtt ttcaccgtca tcaccgaaac gcgcgaggca gctgcggtaa agctcatcag   5340
cgtggtcgtg aagcgattca cagatgtctg cctgttcatc cgcgtccagc tcgttgagtt   5400
tctccagaag cgttaatgtc tggcttctga taaagcgggc catgttaagg gcggtttttt   5460
cctgtttggt cactgatgcc tccgtgtaag ggggatttct gttcatgggg gtaatgatac   5520
cgatgaaacg agagaggatg ctcacgatac gggttactga tgatgaacat gcccggttac   5580
tggaacgttg tgagggtaaa caactggcgg tatggatgcg gcgggaccag agaaaaatca   5640
ctcagggtca atgccagcgc ttcgttaata cagatgtagg tgttccacag ggtagccagc   5700
agcatcctgc gatgcagatc cggaacataa tggtgcaggg cgctgacttc cgcgtttcca   5760
gactttacga aacacggaaa ccgaagacca ttcatgttgt tgctcaggtc gcagacgttt   5820
tgcagcagca gtcgcttcac gttcgctcgc gtatcggtga ttcattctgc taaccagtaa   5880
ggcaaccccg ccagcctagc cgggtcctca acgacaggag cacgatcatg cgcacccgtg   5940
gccaggaccc aacgctgccc gagatgcgcc gcgtgcggct gctggagatg gcggacgcga   6000
```

-continued

```
tggatatgtt ctgccaaggg ttggtttgcg cattcacagt tctccgcaag aattgattgg   6060

ctccaattct tggagtggtg aatccgttag cgaggtgccg ccggcttcca ttcaggtcga   6120

ggtggcccgg ctccatgcac cgcgacgcaa cgcggggagg cagacaaggt atagggcggc   6180

gcctacaatc catgccaacc cgttccatgt gctcgccgag gcggcataaa tcgccgtgac   6240

gatcagcggt ccagtgatcg aagttaggct ggtaagagcc gcgagcgatc cttgaagctg   6300

tccctgatgg tcgtcatcta cctgcctgga cagcatggcc tgcaacgcgg gcatcccgat   6360

gccgccggaa gcgagaagaa tcataatggg gaaggccatc cagcctcgcg tcgcgaacgc   6420

cagcaagacg tagcccagcg cgtcggccgc catgccggcg ataatggcct gcttctcgcc   6480

gaaacgtttg gtggcgggac cagtgacgaa ggcttgagcg agggcgtgca agattccgaa   6540

taccgcaagc gacaggccga tcatcgtcgc gctccagcga aagcggtcct cgccgaaaat   6600

gacccagagc gctgccggca cctgtcctac gagttgcatg ataaagaaga cagtcataag   6660

tgcggcgacg atagtcatgc cccgcgccca ccggaaggag ctgactgggt tgaaggctct   6720

caagggcatc ggtcgatcga cgctctccct tatgcgactc ctgcattagg aagcagccca   6780

gtagtaggtt gaggccgttg agcaccgccg ccgcaaggaa tggtgcatgc aaggagatgg   6840

cgcccaacag tcccccggcc acggggcctg ccaccatacc cacgccgaaa caagcgctca   6900

tgagcccgaa gtggcgagcc cgatcttccc catcggtgat gtcggcgata taggcgccag   6960

caaccgcacc tgtggcgccg gtgatgccgg ccacgatgcg tccggcgtag agg          7013
```

<210> SEQ ID NO 144
<211> LENGTH: 6675
<212> TYPE: DNA
<213> ORGANISM: Artificial Sequence
<220> FEATURE:
<223> OTHER INFORMATION: pDEST16
<220> FEATURE:
<221> NAME/KEY: gene
<222> LOCATION: (104)..(457)
<223> OTHER INFORMATION: trxA
<220> FEATURE:
<221> NAME/KEY: gene
<222> LOCATION: (461)..(585)
<223> OTHER INFORMATION: attR1
<220> FEATURE:
<221> NAME/KEY: gene
<222> LOCATION: (694)..(1353)
<223> OTHER INFORMATION: CmR
<220> FEATURE:
<221> NAME/KEY: gene
<222> LOCATION: (1473)..(1557)
<223> OTHER INFORMATION: inactivated ccdA
<220> FEATURE:
<221> NAME/KEY: gene
<222> LOCATION: (1695)..(2000)
<223> OTHER INFORMATION: ccdB
<220> FEATURE:
<221> NAME/KEY: gene
<222> LOCATION: (2041)..(2165)
<223> OTHER INFORMATION: attR2

<400> SEQUENCE: 144

```
agatctcgat cccgcgaaat taatacgact cactataggg agaccacaac ggtttccctc     60

tagaaataat tttgtttaac tttaagaagg agatatacat atgagcgata aaattattca    120

cctgactgac gacagttttg acacggatgt actcaaagcg gacggggcga tcctcgtcga    180

tttctgggca gagtggtgcg gtccgtgcaa aatgatcgcc ccgattctgg atgaaatcgc    240

tgacgaatat cagggcaaac tgaccgttgc aaaactgaac atcgatcaaa accctggcac    300

tgcgccgaaa tatggcatcc gtggtatccc gactctgctg ctgttcaaaa acggtgaagt    360
```

-continued

```
ggcggcaacc aaagtgggtg cactgtctaa aggtcagttg aaagagttcc tcgacgctaa    420
cctggccggt tctggttctg gtgatgacga tgacaagatc acaagtttgt acaaaaaagc    480
tgaacgagaa acgtaaaatg atataaatat caatatatta aattagattt tgcataaaaa    540
acagactaca taatactgta aaacacaaca tatccagtca ctatggcggc cgcattaggc    600
accccaggct ttacacttta tgcttccggc tcgtataatg tgtggatttt gagttaggat    660
ccggcgagat tttcaggagc taaggaagct aaaatggaga aaaaaatcac tggatatacc    720
accgttgata tatcccaatg gcatcgtaaa gaacattttg aggcatttca gtcagttgct    780
caatgtacct ataaccagac cgttcagctg gatattacgg cctttttaaa gaccgtaaag    840
aaaaataagc acaagtttta tccggccttt attcacattc ttgcccgcct gatgaatgct    900
catccggaat tccgtatggc aatgaaagac ggtgagctgg tgatatggga tagtgttcac    960
ccttgttaca ccgttttcca tgagcaaact gaaacgtttt catcgctctg gagtgaatac   1020
cacgacgatt tccggcagtt tctacacata tattcgcaag atgtggcgtg ttacggtgaa   1080
aacctggcct atttccctaa agggtttatt gagaatatgt ttttcgtctc agccaatccc   1140
tgggtgagtt tcaccagttt tgatttaaac gtggccaata tggacaactt cttcgccccc   1200
gttttcacca tgggcaaata ttatacgcaa ggcgacaagg tgctgatgcc gctggcgatt   1260
caggttcatc atgccgtctg tgatggcttc catgtcggca gaatgcttaa tgaattacaa   1320
cagtactgcg atgagtggca gggcggggcg taaacgcgtg gatccggctt actaaaagcc   1380
agataacagt atgcgtattt gcgcgctgat ttttgcggta taagaatata tactgatatg   1440
tatacccgaa gtatgtcaaa aagaggtgtg ctatgaagca gcgtattaca gtgacagttg   1500
acagcgacag ctatcagttg ctcaaggcat atatgatgtc aatatctccg gtctggtaag   1560
cacaaccatg cagaatgaag cccgtcgtct gcgtgccgaa cgctggaaag cggaaaatca   1620
ggaagggatg gctgaggtcg cccggtttat tgaaatgaac ggctcttttg ctgacgagaa   1680
cagggactgg tgaaatgcag tttaaggttt acacctataa aagagagagc cgttatcgtc   1740
tgtttgtgga tgtacagagt gatattattg acacgcccgg gcgacggatg gtgatccccc   1800
tggccagtgc acgtctgctg tcagataaag tctcccgtga actttacccg gtggtgcata   1860
tcggggatga aagctggcgc atgatgacca ccgatatggc cagtgtgccg gtctccgtta   1920
tcggggaaga agtggctgat ctcagccacc gcgaaaatga catcaaaaac gccattaacc   1980
tgatgttctg gggaatataa atgtcaggct cccttataca cagccagtct gcaggtcgac   2040
catagtgact ggatatgttg tgttttacag tattatgtag tctgtttttt atgcaaaatc   2100
taatttaata tattgatatt tatatcattt tacgtttctc gttcagcttt cttgtacaaa   2160
gtggtgatga tccggctgct aacaaagccc gaaaggaagc tgagttggct gctgccaccg   2220
ctgagcaata actagcataa ccccttgggg cctctaaacg ggtcttgagg ggttttttgc   2280
tgaaaggagg aactatatcc ggatatccac aggacgggtg tggtcgccat gatcgcgtag   2340
tcgatagtgg ctccaagtag cgaagcgagc aggactgggc ggcggccaaa gcggtcggac   2400
agtgctccga gaacgggtgc gcatagaaat tgcatcaacg catatagcgc tagcagcacg   2460
ccatagtgac tggcgatgct gtcggaatgg acgatatccc gcaagaggcc cggcagtacc   2520
ggcataacca agcctatgcc tacagcatcc agggtgacgg tgccgaggat gacgatgagc   2580
gcattgttag atttcataca cggtgcctga ctgcgttagc aatttaactg tgataaacta   2640
ccgcattaaa gcttatcgat gataagctgt caaacatgag aattcttgaa gacgaaaggg   2700
```

-continued

```
cctcgtgata cgcctatttt tataggttaa tgtcatgata ataatggttt cttagacgtc   2760
aggtggcact tttcggggaa atgtgcgcgg aacccctatt tgtttatttt tctaaataca   2820
ttcaaatatg tatccgctca tgagacaata accctgataa atgcttcaat aatattgaaa   2880
aaggaagagt atgagtattc aacatttccg tgtcgccctt attccctttt ttgcggcatt   2940
ttgccttcct gtttttgctc acccagaaac gctggtgaaa gtaaaagatg ctgaagatca   3000
gttgggtgca cgagtgggtt acatcgaact ggatctcaac agcggtaaga tccttgagag   3060
ttttcgcccc gaagaacgtt ttccaatgat gagcactttt aaagttctgc tatgtggcgc   3120
ggtattatcc cgtgttgacg ccgggcaaga gcaactcggt cgccgcatac actattctca   3180
gaatgacttg gttgagtact caccagtcac agaaaagcat cttacggatg gcatgacagt   3240
aagagaatta tgcagtgctg ccataaccat gagtgataac actgcggcca acttacttct   3300
gacaacgatc ggaggaccga aggagctaac cgcttttttg cacaacatgg gggatcatgt   3360
aactcgcctt gatcgttggg aaccggagct gaatgaagcc ataccaaacg acgagcgtga   3420
caccacgatg cctgcagcaa tggcaacaac gttgcgcaaa ctattaactg gcgaactact   3480
tactctagct tcccggcaac aattaataga ctggatggag gcggataaag ttgcaggacc   3540
acttctgcgc tcggcccttc cggctggctg gtttattgct gataaatctg gagccggtga   3600
gcgtgggtct cgcggtatca ttgcagcact ggggccagat ggtaagccct cccgtatcgt   3660
agttatctac acgacgggga gtcaggcaac tatggatgaa cgaaatagac agatcgctga   3720
gataggtgcc tcactgatta agcattggta actgtcagac caagtttact catatatact   3780
ttagattgat ttaaaacttc atttttaatt taaaaggatc taggtgaaga tcctttttga   3840
taatctcatg accaaaatcc cttaacgtga gttttcgttc cactgagcgt cagaccccgt   3900
agaaaagatc aaaggatctt cttgagatcc tttttttctg cgcgtaatct gctgcttgca   3960
aacaaaaaaa ccaccgctac cagcggtggt ttgtttgccg gatcaagagc taccaactct   4020
ttttccgaag gtaactggct tcagcagagc gcagatacca aatactgtcc ttctagtgta   4080
gccgtagtta ggccaccact tcaagaactc tgtagcaccg cctacatacc tcgctctgct   4140
aatcctgtta ccagtggctg ctgccagtgg cgataagtcg tgtcttaccg ggttggactc   4200
aagacgatag ttaccggata aggcgcagcg gtcgggctga acggggggtt cgtgcacaca   4260
gcccagcttg gagcgaacga cctacaccga actgagatac ctacagcgtg agctatgaga   4320
aagcgccacg cttcccgaag ggagaaaggc ggacaggtat ccggtaagcg gcagggtcgg   4380
aacaggagag cgcacgaggg agcttccagg gggaaacgcc tggtatcttt atagtcctgt   4440
cgggtttcgc cacctctgac ttgagcgtcg atttttgtga tgctcgtcag gggggcggag   4500
cctatggaaa aacgccagca acgcggcctt tttacggttc ctggcctttt gctggccttt   4560
tgctcacatg ttctttcctg cgttatcccc tgattctgtg gataaccgta ttaccgcctt   4620
tgagtgagct gataccgctc gccgcagccg aacgaccgag cgcagcgagt cagtgagcga   4680
ggaagcggaa gagcgcctga tgcggtattt tctccttacg catctgtgcg gtatttcaca   4740
ccgcatatat ggtgcactct cagtacaatc tgctctgatg ccgcatagtt aagccagtat   4800
acactccgct atcgctacgt gactgggtca tggctgcgcc ccgacacccg ccaacacccg   4860
ctgacgcgcc ctgacgggct tgtctgctcc cggcatccgc ttacagacaa gctgtgaccg   4920
tctccgggag ctgcatgtgt cagaggtttt caccgtcatc accgaaacgc gcgaggcagc   4980
tgcggtaaag ctcatcagcg tggtcgtgaa gcgattcaca gatgtctgcc tgttcatccg   5040
cgtccagctc gttgagtttc tccagaagcg ttaatgtctg gcttctgata aagcgggcca   5100
```

-continued

```
tgttaagggc ggtttttcc tgtttggtca ctgatgcctc cgtgtaaggg ggatttctgt   5160

tcatgggggt aatgataccg atgaaacgag agaggatgct cacgatacgg gttactgatg   5220

atgaacatgc ccggttactg gaacgttgtg agggtaaaca actggcggta tggatgcggc   5280

gggaccagag aaaaatcact cagggtcaat gccagcgctt cgttaataca gatgtaggtg   5340

ttccacaggg tagccagcag catcctgcga tgcagatccg gaacataatg gtgcagggcg   5400

ctgacttccg cgtttccaga ctttacgaaa cacggaaacc gaagaccatt catgttgttg   5460

ctcaggtcgc agacgttttg cagcagcagt cgcttcacgt tcgctcgcgt atcggtgatt   5520

cattctgcta accagtaagg caaccccgcc agcctagccg ggtcctcaac gacaggagca   5580

cgatcatgcg cacccgtggc caggacccaa cgctgcccga gatgcgccgc gtgcggctgc   5640

tggagatggc ggacgcgatg gatatgttct gccaagggtt ggtttgcgca ttcacagttc   5700

tccgcaagaa ttgattggct ccaattcttg gagtggtgaa tccgttagcg aggtgccgcc   5760

ggcttccatt caggtcgagg tggcccggct ccatgcaccg cgacgcaacg cggggaggca   5820

gacaaggtat agggcggcgc ctacaatcca tgccaacccg ttccatgtgc tcgccgaggc   5880

ggcataaatc gccgtgacga tcagcggtcc agtgatcgaa gttaggctgg taagagccgc   5940

gagcgatcct tgaagctgtc cctgatggtc gtcatctacc tgcctggaca gcatggcctg   6000

caacgcgggc atcccgatgc cgccggaagc gagaagaatc ataatgggga aggccatcca   6060

gcctcgcgtc gcgaacgcca gcaagacgta gcccagcgcg tcggccgcca tgccggcgat   6120

aatggcctgc ttctcgccga aacgtttggt ggcgggacca gtgacgaagg cttgagcgag   6180

ggcgtgcaag attccgaata ccgcaagcga caggccgatc atcgtcgcgc tccagcgaaa   6240

gcggtcctcg ccgaaaatga cccagagcgc tgccggcacc tgtcctacga gttgcatgat   6300

aaagaagaca gtcataagtg cggcgacgat agtcatgccc cgcgcccacc ggaaggagct   6360

gactgggttg aaggctctca agggcatcgg tcgatcgacg ctctccctta tgcgactcct   6420

gcattaggaa gcagcccagt agtaggttga ggccgttgag caccgccgcc gcaaggaatg   6480

gtgcatgcaa ggagatggcg cccaacagtc ccccggccac ggggcctgcc accataccca   6540

cgccgaaaca agcgctcatg agcccgaagt ggcgagcccg atcttcccca tcggtgatgt   6600

cggcgatata ggcgccagca accgcacctg tggcgccggt gatgccggcc acgatgcgtc   6660

cggcgtagag gatcg                                                    6675
```

<210> SEQ ID NO 145
<211> LENGTH: 6354
<212> TYPE: DNA
<213> ORGANISM: Artificial Sequence
<220> FEATURE:
<223> OTHER INFORMATION: pDEST17
<220> FEATURE:
<221> NAME/KEY: gene
<222> LOCATION: (134)..(258)
<223> OTHER INFORMATION: attR1
<220> FEATURE:
<221> NAME/KEY: gene
<222> LOCATION: (367)..(1026)
<223> OTHER INFORMATION: CmR
<220> FEATURE:
<221> NAME/KEY: gene
<222> LOCATION: (1146)..(1230)
<223> OTHER INFORMATION: inactivated ccdA
<220> FEATURE:
<221> NAME/KEY: gene
<222> LOCATION: (1368)..(1673)
<223> OTHER INFORMATION: ccdB
<220> FEATURE:

-continued

<221> NAME/KEY: gene
<222> LOCATION: (1714)..(1838)
<223> OTHER INFORMATION: attR2
<220> FEATURE:
<221> NAME/KEY: gene
<222> LOCATION: (2564)..(3421)
<223> OTHER INFORMATION: ampR

<400> SEQUENCE: 145
cgatcccgcg aaattaatac gactcactat agggagacca caacggtttc cctctagaaa 60
taattttgtt taactttaag aaggagatat acatatgtcg tactaccatc accatcacca 120
tcacctcgaa tcaacaagtt tgtacaaaaa agctgaacga gaaacgtaaa atgatataaa 180
tatcaatata ttaaattaga ttttgcataa aaaacagact acataatact gtaaaacaca 240
acatatccag tcactatggc ggccgcatta ggcaccccag gctttacact ttatgcttcc 300
ggctcgtata atgtgtggat tttgagttag gatccgtcga gattttcagg agctaaggaa 360
gctaaaatgg agaaaaaaat cactggatat accaccgttg atatatccca atggcatcgt 420
aaagaacatt ttgaggcatt tcagtcagtt gctcaatgta cctataacca gaccgttcag 480
ctggatatta cggccttttt aaagaccgta aagaaaaata agcacaagtt ttatccggcc 540
tttattcaca ttcttgcccg cctgatgaat gctcatccgg aattccgtat ggcaatgaaa 600
gacggtgagc tggtgatatg ggatagtgtt cacccttgtt acaccgtttt ccatgagcaa 660
actgaaacgt tttcatcgct ctggagtgaa taccacgacg atttccggca gtttctacac 720
atatattcgc aagatgtggc gtgttacggt gaaaacctgg cctatttccc taaagggttt 780
attgagaata tgtttttcgt ctcagccaat ccctgggtga gtttcaccag ttttgattta 840
aacgtggcca atatggacaa cttcttcgcc cccgttttca ccatgggcaa atattatacg 900
caaggcgaca aggtgctgat gccgctggcg attcaggttc atcatgccgt ctgtgatggc 960
ttccatgtcg gcagaatgct taatgaatta caacagtact gcgatgagtg gcagggcggg 1020
gcgtaaagat ctggatccgg cttactaaaa gccagataac agtatgcgta tttgcgcgct 1080
gatttttgcg gtataagaat atatactgat atgtataccc gaagtatgtc aaaaagaggt 1140
gtgctatgaa gcagcgtatt acagtgacag ttgacagcga cagctatcag ttgctcaagg 1200
catatatgat gtcaatatct ccggtctggt aagcacaacc atgcagaatg aagcccgtcg 1260
tctgcgtgcc gaacgctgga aagcggaaaa tcaggaaggg atggctgagg tcgcccggtt 1320
tattgaaatg aacggctctt ttgctgacga gaacagggac tggtgaaatg cagtttaagg 1380
tttacaccta taaaagagag agccgttatc gtctgtttgt ggatgtacag agtgatatta 1440
ttgacacgcc cgggcgacgg atggtgatcc ccctggccag tgcacgtctg ctgtcagata 1500
aagtctcccg tgaactttac ccggtggtgc atatcgggga tgaaagctgg cgcatgatga 1560
ccaccgatat ggccagtgtg ccggtctccg ttatcgggga agaagtggct gatctcagcc 1620
accgcgaaaa tgacatcaaa aacgccatta acctgatgtt ctggggaata taaatgtcag 1680
gctcccttat acacagccag tctgcaggtc gaccatagtg actggatatg ttgtgtttta 1740
cagtattatg tagtctgttt tttatgcaaa atctaattta atatattgat atttatatca 1800
ttttacgttt ctcgttcagc tttcttgtac aaagtggttg attcgaggct gctaacaaag 1860
cccgaaagga agctgagttg gctgctgcca ccgctgagca ataactagca taaccccttg 1920
gggcctctaa acgggtcttg aggggttttt tgctgaaagg aggaactata tccggatatc 1980
cacaggacgg gtgtggtcgc catgatcgcg tagtcgatag tggctccaag tagcgaagcg 2040
agcaggactg ggcggcggcc aaagcggtcg gacagtgctc cgagaacggg tgcgcataga 2100

-continued

```
aattgcatca acgcatatag cgctagcagc acgccatagt gactggcgat gctgtcggaa   2160
tggacgatat cccgcaagag gcccggcagt accggcataa ccaagcctat gcctacagca   2220
tccagggtga cggtgccgag gatgacgatg agcgcattgt tagatttcat acacggtgcc   2280
tgactgcgtt agcaatttaa ctgtgataaa ctaccgcatt aaagcttatc gatgataagc   2340
tgtcaaacat gagaattctt gaagacgaaa gggcctcgtg atacgcctat ttttataggt   2400
taatgtcatg ataataatgg tttcttagac gtcaggtggc acttttcggg gaaatgtgcg   2460
cggaacccct atttgtttat ttttctaaat acattcaaat atgtatccgc tcatgagaca   2520
ataaccctga taaatgcttc aataatattg aaaaaggaag agtatgagta ttcaacattt   2580
ccgtgtcgcc cttattccct tttttgcggc attttgcctt cctgtttttg ctcacccaga   2640
aacgctggtg aaagtaaaag atgctgaaga tcagttgggt gcacgagtgg gttacatcga   2700
actggatctc aacagcggta agatccttga gagttttcgc cccgaagaac gttttccaat   2760
gatgagcact tttaaagttc tgctatgtgg cgcggtatta tcccgtgttg acgccgggca   2820
agagcaactc ggtcgccgca tacactattc tcagaatgac ttggttgagt actcaccagt   2880
cacagaaaag catcttacgg atggcatgac agtaagagaa ttatgcagtg ctgccataac   2940
catgagtgat aacactgcgg ccaacttact tctgacaacg atcggaggac cgaaggagct   3000
aaccgctttt ttgcacaaca tgggggatca tgtaactcgc cttgatcgtt gggaaccgga   3060
gctgaatgaa gccataccaa acgacgagcg tgacaccacg atgcctgcag caatggcaac   3120
aacgttgcgc aaactattaa ctggcgaact acttactcta gcttcccggc aacaattaat   3180
agactggatg gaggcggata aagttgcagg accacttctg cgctcggccc ttccggctgg   3240
ctggtttatt gctgataaat ctggagccgg tgagcgtggg tctcgcggta tcattgcagc   3300
actggggcca gatggtaagc cctcccgtat cgtagttatc tacacgacgg ggagtcaggc   3360
aactatggat gaacgaaata gacagatcgc tgagataggt gcctcactga ttaagcattg   3420
gtaactgtca gaccaagttt actcatatat actttagatt gatttaaaac ttcattttta   3480
atttaaaagg atctaggtga agatcctttt tgataatctc atgaccaaaa tcccttaacg   3540
tgagttttcg ttccactgag cgtcagaccc cgtagaaaag atcaaaggat cttcttgaga   3600
tccttttttt ctgcgcgtaa tctgctgctt gcaaacaaaa aaaccaccgc taccagcggt   3660
ggtttgtttg ccggatcaag agctaccaac tctttttccg aaggtaactg gcttcagcag   3720
agcgcagata ccaaatactg tccttctagt gtagccgtag ttaggccacc acttcaagaa   3780
ctctgtagca ccgcctacat acctcgctct gctaatcctg ttaccagtgg ctgctgccag   3840
tggcgataag tcgtgtctta ccgggttgga ctcaagacga tagttaccgg ataaggcgca   3900
gcggtcgggc tgaacggggg gttcgtgcac acagcccagc ttggagcgaa cgacctacac   3960
cgaactgaga tacctacagc gtgagctatg agaaagcgcc acgcttcccg aagggagaaa   4020
ggcggacagg tatccggtaa gcggcagggt cggaacagga gagcgcacga gggagcttcc   4080
agggggaaac gcctggtatc tttatagtcc tgtcgggttt cgccacctct gacttgagcg   4140
tcgatttttg tgatgctcgt caggggggcg gagcctatgg aaaaacgcca gcaacgcggc   4200
ctttttacgg ttcctggcct tttgctggcc ttttgctcac atgttctttc ctgcgttatc   4260
ccctgattct gtggataacc gtattaccgc ctttgagtga gctgataccg ctcgccgcag   4320
ccgaacgacc gagcgcagcg agtcagtgag cgaggaagcg gaagagcgcc tgatgcggta   4380
ttttctcctt acgcatctgt gcggtatttc acaccgcata tatggtgcac tctcagtaca   4440
```

-continued

```
atctgctctg atgccgcata gttaagccag tatacactcc gctatcgcta cgtgactggg   4500

tcatggctgc gccccgacac ccgccaacac ccgctgacgc gccctgacgg gcttgtctgc   4560

tcccggcatc cgcttacaga caagctgtga ccgtctccgg gagctgcatg tgtcagaggt   4620

tttcaccgtc atcaccgaaa cgcgcgaggc agctgcggta aagctcatca gcgtggtcgt   4680

gaagcgattc acagatgtct gcctgttcat ccgcgtccag ctcgttgagt ttctccagaa   4740

gcgttaatgt ctggcttctg ataaagcggg ccatgttaag ggcggttttt tcctgtttgg   4800

tcactgatgc ctccgtgtaa gggggatttc tgttcatggg ggtaatgata ccgatgaaac   4860

gagagaggat gctcacgata cgggttactg atgatgaaca tgcccggtta ctggaacgtt   4920

gtgagggtaa acaactggcg gtatggatgc ggcgggacca gagaaaaatc actcagggtc   4980

aatgccagcg cttcgttaat acagatgtag gtgttccaca gggtagccag cagcatcctg   5040

cgatgcagat ccggaacata atggtgcagg gcgctgactt ccgcgtttcc agactttacg   5100

aaacacggaa accgaagacc attcatgttg ttgctcaggt cgcagacgtt ttgcagcagc   5160

agtcgcttca cgttcgctcg cgtatcggtg attcattctg ctaaccagta aggcaacccc   5220

gccagcctag ccgggtcctc aacgacagga gcacgatcat gcgcacccgt ggccaggacc   5280

caacgctgcc cgagatgcgc cgcgtgcggc tgctggagat ggcggacgcg atggatatgt   5340

tctgccaagg gttggtttgc gcattcacag ttctccgcaa gaattgattg gctccaattc   5400

ttggagtggt gaatccgtta gcgaggtgcc gccggcttcc attcaggtcg aggtggcccg   5460

gctccatgca ccgcgacgca acgcggggag gcagacaagg tatagggcgg cgcctacaat   5520

ccatgccaac ccgttccatg tgctcgccga ggcggcataa atcgccgtga cgatcagcgg   5580

tccagtgatc gaagttaggc tggtaagagc cgcgagcgat ccttgaagct gtccctgatg   5640

gtcgtcatct acctgcctgg acagcatggc ctgcaacgcg ggcatcccga tgccgccgga   5700

agcgagaaga atcataatgg ggaaggccat ccagcctcgc gtcgcgaacg ccagcaagac   5760

gtagcccagc gcgtcggccg ccatgccggc gataatggcc tgcttctcgc cgaaacgttt   5820

ggtggcggga ccagtgacga aggcttgagc gagggcgtgc aagattccga ataccgcaag   5880

cgacaggccg atcatcgtcg cgctccagcg aaagcggtcc tcgccgaaaa tgacccagag   5940

cgctgccggc acctgtccta cgagttgcat gataaagaag acagtcataa gtgcggcgac   6000

gatagtcatg ccccgcgccc accggaagga gctgactggg ttgaaggctc tcaagggcat   6060

cggtcgatcg acgctctccc ttatgcgact cctgcattag gaagcagccc agtagtaggt   6120

tgaggccgtt gagcaccgcc gccgcaagga atggtgcatg caaggagatg gcgcccaaca   6180

gtcccccggc cacggggcct gccaccatac ccacgccgaa acaagcgctc atgagcccga   6240

agtggcgagc ccgatcttcc ccatcggtga tgtcggcgat ataggcgcca gcaaccgcac   6300

ctgtggcgcc ggtgatgccg gccacgatgc gtccggcgta gaggatcgag atct         6354
```

<210> SEQ ID NO 146
<211> LENGTH: 6613
<212> TYPE: DNA
<213> ORGANISM: Artificial Sequence
<220> FEATURE:
<223> OTHER INFORMATION: pDEST18
<220> FEATURE:
<221> NAME/KEY: gene
<222> LOCATION: (474)..(1449)
<223> OTHER INFORMATION: ampR
<220> FEATURE:
<221> NAME/KEY: gene
<222> LOCATION: (1590)..(2244)
<223> OTHER INFORMATION: ori
<220> FEATURE:
<221> NAME/KEY: gene
<222> LOCATION: (2738)..(3850)
<223> OTHER INFORMATION: genR
<220> FEATURE:
<221> NAME/KEY: gene
<222> LOCATION: (4127)..(4251)
<223> OTHER INFORMATION: attR1
<220> FEATURE:
<221> NAME/KEY: gene
<222> LOCATION: (4501)..(5160)
<223> OTHER INFORMATION: CmR
<220> FEATURE:
<221> NAME/KEY: gene
<222> LOCATION: (5280)..(5364)
<223> OTHER INFORMATION: inactivated ccdA
<220> FEATURE:
<221> NAME/KEY: gene
<222> LOCATION: (5502)..(5807)
<223> OTHER INFORMATION: ccdB
<220> FEATURE:
<221> NAME/KEY: gene
<222> LOCATION: (5848)..(5972)
<223> OTHER INFORMATION: attR2
<220> FEATURE:
<221> NAME/KEY: gene
<222> LOCATION: (25)..(6595)
<223> OTHER INFORMATION: lacZ

<400> SEQUENCE: 146
gacgcgccct gtagcggcgc attaagcgcg gcgggtgtgg tggttacgcg cagcgtgacc 60
gctacacttg ccagcgccct agcgcccgct cctttcgctt tcttcccttc ctttctcgcc 120
acgttcgccg gctttccccg tcaagctcta aatcgggggc tccctttagg gttccgattt 180
agtgctttac ggcacctcga ccccaaaaaa cttgattagg gtgatggttc acgtagtggg 240
ccatcgccct gatagacggt ttttcgccct ttgacgttgg agtccacgtt ctttaatagt 300
ggactcttgt tccaaactgg aacaacactc aaccctatct cggtctattc ttttgattta 360
taagggattt tgccgatttc ggcctattgg ttaaaaaatg agctgattta acaaaaattt 420
aacgcgaatt ttaacaaaat attaacgttt acaatttcag gtggcacttt tcggggaaat 480
gtgcgcggaa cccctatttg tttatttttc taaatacatt caaatatgta tccgctcatg 540
agacaataac cctgataaat gcttcaataa tattgaaaaa ggaagagtat gagtattcaa 600
catttccgtg tcgcccttat tccctttttt gcggcatttt gccttcctgt ttttgctcac 660
ccagaaacgc tggtgaaagt aaaagatgct gaagatcagt tgggtgcacg agtgggttac 720
atcgaactgg atctcaacag cggtaagatc cttgagagtt ttcgccccga agaacgtttt 780
ccaatgatga gcacttttaa agttctgcta tgtggcgcgg tattatcccg tattgacgcc 840
gggcaagagc aactcggtcg ccgcatacac tattctcaga atgacttggt tgagtactca 900
ccagtcacag aaaagcatct tacggatggc atgacagtaa gagaattatg cagtgctgcc 960
ataaccatga gtgataacac tgcggccaac ttacttctga caacgatcgg aggaccgaag 1020
gagctaaccg cttttttgca caacatgggg gatcatgtaa ctcgccttga tcgttgggaa 1080
ccggagctga atgaagccat accaaacgac gagcgtgaca ccacgatgcc tgtagcaatg 1140
gcaacaacgt tgcgcaaact attaactggc gaactactta ctctagcttc ccggcaacaa 1200
ttaatagact ggatggaggc ggataaagtt gcaggaccac ttctgcgctc ggcccttccg 1260
gctggctggt ttattgctga taaatctgga gccggtgagc gtgggtctcg cggtatcatt 1320
gcagcactgg ggccagatgg taagccctcc cgtatcgtag ttatctacac gacggggagt 1380
caggcaacta tggatgaacg aaatagacag atcgctgaga taggtgcctc actgattaag 1440

-continued

```
cattggtaac tgtcagacca agtttactca tatatacttt agattgattt aaaacttcat   1500
ttttaattta aaaggatcta ggtgaagatc ctttttgata atctcatgac caaaatccct   1560
taacgtgagt tttcgttcca ctgagcgtca gaccccgtag aaaagatcaa aggatcttct   1620
tgagatcctt tttttctgcg cgtaatctgc tgcttgcaaa caaaaaaacc accgctacca   1680
gcggtggttt gtttgccgga tcaagagcta ccaactcttt ttccgaaggt aactggcttc   1740
agcagagcgc agataccaaa tactgtcctt ctagtgtagc cgtagttagg ccaccacttc   1800
aagaactctg tagcaccgcc tacatacctc gctctgctaa tcctgttacc agtggctgct   1860
gccagtggcg ataagtcgtg tcttaccggg ttggactcaa gacgatagtt accggataag   1920
gcgcagcggt cgggctgaac ggggggttcg tgcacacagc ccagcttgga gcgaacgacc   1980
tacaccgaac tgagatacct acagcgtgag cattgagaaa gcgccacgct tcccgaaggg   2040
agaaaggcgg acaggtatcc ggtaagcggc agggtcggaa caggagagcg cacgagggag   2100
cttccagggg gaaacgcctg gtatctttat agtcctgtcg ggtttcgcca cctctgactt   2160
gagcgtcgat ttttgtgatg ctcgtcaggg gggcggagcc tatggaaaaa cgccagcaac   2220
gcggcctttt tacggttcct ggccttttgc tggccttttg ctcacatgtt ctttcctgcg   2280
ttatcccctg attctgtgga taaccgtatt accgcctttg agtgagctga taccgctcgc   2340
cgcagccgaa cgaccgagcg cagcgagtca gtgagcgagg aagcggaaga gcgcctgatg   2400
cggtattttc tccttacgca tctgtgcggt atttcacacc gcagaccagc cgcgtaacct   2460
ggcaaaatcg gttacggttg agtaataaat ggatgccctg cgtaagcggg tgtgggcgga   2520
caataaagtc ttaaactgaa caaaatagat ctaaactatg acaataaagt cttaaactag   2580
acagaatagt tgtaaactga aatcagtcca gttatgctgt gaaaaagcat actggacttt   2640
tgttatggct aaagcaaact cttcattttc tgaagtgcaa attgcccgtc gtattaaaga   2700
ggggcgtggc caagggcatg gtaaagacta tattcgcggc gttgtgacaa tttaccgaac   2760
aactccgcgg ccgggaagcc gatctcggct tgaacgaatt gttaggtggc ggtacttggg   2820
tcgatatcaa agtgcatcac ttcttcccgt atgcccaact ttgtatagag agccactgcg   2880
ggatcgtcac cgtaatctgc ttgcacgtag atcacataag caccaagcgc gttggcctca   2940
tgcttgagga gattgatgag cgcggtggca atgccctgcc tccggtgctc gccggagact   3000
gcgagatcat agatatagat ctcactacgc ggctgctcaa acctgggcag aacgtaagcc   3060
gcgagagcgc caacaaccgc ttcttggtcg aaggcagcaa gcgcgatgaa tgtcttacta   3120
cggagcaagt tcccgaggta atcggagtcc ggctgatgtt gggagtaggt ggctacgtct   3180
ccgaactcac gaccgaaaag atcaagagca gcccgcatgg atttgacttg gtcagggccg   3240
agcctacatg tgcgaatgat gcccatactt gagccaccta actttgtttt agggcgactg   3300
ccctgctgcg taacatcgtt gctgctgcgt aacatcgttg ctgctccata acatcaaaca   3360
tcgacccacg gcgtaacgcg cttgctgctt ggatgcccga ggcatagact gtacaaaaaa   3420
acagtcataa caagccatga aaaccgccac tgcgccgtta ccaccgctgc gttcggtcaa   3480
ggttctggac cagttgcgtg agcgcatacg ctacttgcat tacagtttac gaaccgaaca   3540
ggcttatgtc aactgggttc gtgccttcat ccgtttccac ggtgtgcgtc acccggcaac   3600
cttgggcagc agcgaagtcg aggcatttct gtcctggctg gcgaacgagc gcaaggtttc   3660
ggtctccacg catcgtcagg cattggcggc cttgctgttc ttctacggca aggtgctgtg   3720
cacggatctg ccctggcttc aggagatcgg aagacctcgg ccgtcgcggc gcttgccggt   3780
ggtgctgacc ccggatgaag tggttcgcat cctcggtttt ctggaaggcg agcatcgttt   3840
```

-continued

```
gttcgcccag gactctagct atagttctag tggttggcta cgtatcgagc aagaaaataa   3900
aacgccaaac gcgttggagt cttgtgtgct atttttacaa agattcagaa atacgcatca   3960
cttacaacaa gggggactat gaaattatgc attttgagga tgccgggacc tttaattcaa   4020
cccaacacaa tatattatag ttaaataaga attatttatc aaatcatttg tatattaatt   4080
aaaatactat actgtaaatt acattttatt tacaatgagg atcatcacaa gtttgtacaa   4140
aaaagctgaa cgagaaacgt aaaatgatat aaatatcaat atattaaatt agattttgca   4200
taaaaaacag actacataat actgtaaaac acaacatatc cagtcactat ggcggccgct   4260
aagttggcag catcacccga cgcactttgc gccgaataaa tacctgtgac ggaagatcac   4320
ttcgcagaat aaataaatcc tggtgtccct gttgataccg ggaagccctg ggccaacttt   4380
tggcgaaaat gagacgttga tcggcacgta agaggttcca actttcacca taatgaaata   4440
agatcactac cgggcgtatt ttttgagtta tcgagatttt caggagctaa ggaagctaaa   4500
atggagaaaa aaatcactgg atataccacc gttgatatat cccaatggca tcgtaaagaa   4560
cattttgagg catttcagtc agttgctcaa tgtacctata accagaccgt tcagctggat   4620
attacggcct ttttaaagac cgtaaagaaa aataagcaca agttttatcc ggcctttatt   4680
cacattcttg cccgcctgat gaatgctcat ccggaattcc gtatggcaat gaaagacggt   4740
gagctggtga tatgggatag tgttcaccct tgttacaccg ttttccatga gcaaactgaa   4800
acgttttcat cgctctggag tgaataccac gacgatttcc ggcagtttct acacatatat   4860
tcgcaagatg tggcgtgtta cggtgaaaac ctggcctatt tccctaaagg gtttattgag   4920
aatatgtttt tcgtctcagc caatccctgg gtgagtttca ccagttttga tttaaacgtg   4980
gccaatatgg acaacttctt cgcccccgtt ttcaccatgg gcaaatatta tacgcaaggc   5040
gacaaggtgc tgatgccgct ggcgattcag gttcatcatg ccgtctgtga tggcttccat   5100
gtcggcagaa tgcttaatga attacaacag tactgcgatg agtggcaggg cggggcgtaa   5160
acgcgtggat ccggcttact aaaagccaga taacagtatg cgtatttgcg cgctgatttt   5220
tgcggtataa gaatatatac tgatatgtat acccgaagta tgtcaaaaag aggtgtgcta   5280
tgaagcagcg tattacagtg acagttgaca gcgacagcta tcagttgctc aaggcatata   5340
tgatgtcaat atctccggtc tggtaagcac aaccatgcag aatgaagccc gtcgtctgcg   5400
tgccgaacgc tggaaagcgg aaaatcagga agggatggct gaggtcgccc ggtttattga   5460
aatgaacggc tcttttgctg acgagaacag ggactggtga aatgcagttt aaggtttaca   5520
cctataaaag agagagccgt tatcgtctgt ttgtggatgt acagagtgat attattgaca   5580
cgcccgggcg acggatggtg atccccctgg ccagtgcacg tctgctgtca gataaagtct   5640
cccgtgaact ttacccggtg gtgcatatcg gggatgaaag ctggcgcatg atgaccaccg   5700
atatggccag tgtgccggtc tccgttatcg gggaagaagt ggctgatctc agccaccgcg   5760
aaaatgacat caaaaacgcc attaacctga tgttctgggg aatataaatg tcaggctccc   5820
ttatacacag ccagtctgca ggtcgaccat agtgactgga tatgttgtgt tttacagtat   5880
tatgtagtct gtttttatg caaaatctaa tttaatatat tgatatttat atcattttac   5940
gtttctcgtt cagctttctt gtacaaagtg gtgatagctt gtcgagaagt actagaggat   6000
cataatcagc cataccacat ttgtagaggt tttacttgct ttaaaaaacc tcccacacct   6060
ccccctgaac ctgaaacata aaatgaatgc aattgttgtt gttaacttgt ttattgcagc   6120
ttataatggt tacaaataaa gcaatagcat cacaaatttc acaaataaag cattttttc   6180
```

-continued

```
actgcattct agttgtggtt tgtccaaact catcaatgta tcttatcatg tctggatctg   6240

atcactgctt gagcctagga gatccgaacc agataagtga aatctagttc caaactattt   6300

tgtcattttt aatttttcgta ttagcttacg acgctacacc cagttcccat ctattttgtc   6360

actcttccct aaataatcct taaaaactcc atttccaccc ctcccagttc ccaactattt   6420

tgtccgccca cagcggggca tttttcttcc tgttatgttt ttaatcaaac atcctgccaa   6480

ctccatgtga caaaccgtca tcttcggcta ctttttctct gtcacagaat gaaaattttt   6540

ctgtcatctc ttcgttatta atgtttgtaa ttgactgaat atcaacgctt atttgcagcc   6600

tgaatggcga atg                                                      6613
```

```
<210> SEQ ID NO 147
<211> LENGTH: 6668
<212> TYPE: DNA
<213> ORGANISM: Artificial Sequence
<220> FEATURE:
<223> OTHER INFORMATION: pDEST19
<220> FEATURE:
<221> NAME/KEY: gene
<222> LOCATION: (391)..(515)
<223> OTHER INFORMATION: attR1
<220> FEATURE:
<221> NAME/KEY: gene
<222> LOCATION: (765)..(1424)
<223> OTHER INFORMATION: CmR
<220> FEATURE:
<221> NAME/KEY: gene
<222> LOCATION: (1544)..(1628)
<223> OTHER INFORMATION: inactivated ccdA
<220> FEATURE:
<221> NAME/KEY: gene
<222> LOCATION: (1766)..(2071)
<223> OTHER INFORMATION: ccdB
<220> FEATURE:
<221> NAME/KEY: gene
<222> LOCATION: (2112)..(2236)
<223> OTHER INFORMATION: attR2
<220> FEATURE:
<221> NAME/KEY: gene
<222> LOCATION: (2852)..(2895)
<223> OTHER INFORMATION: lacZ
<220> FEATURE:
<221> NAME/KEY: gene
<222> LOCATION: (3344)..(4319)
<223> OTHER INFORMATION: ampR
<220> FEATURE:
<221> NAME/KEY: gene
<222> LOCATION: (4460)..(5114)
<223> OTHER INFORMATION: ori
<220> FEATURE:
<221> NAME/KEY: gene
<222> LOCATION: (52)..(5608)
<223> OTHER INFORMATION: genR

<400> SEQUENCE: 147
```

```
agtggttcgc atcctcggtt ttctggaagg cgagcatcgt ttgttcgccc aggactctag     60

ctatagttct agtggttggc tacgtatatc aaatacttgt aggtgacgcc gtcatctttc    120

cattgtaacg taaatggcaa cttgtagatg aacgcgctgt caaaaaaccg gccagtttct    180

tccacaaact cgcgcacggc tgtctcgtaa acttttgcgt cgcaacaatc gcgatgacct    240

cgtggtatgg aaattttttc taaaaaagtg tcgttcatgt cggcggcggg cgcgttcgcg    300

ctccggtacg cgcgacgggc acacagcagg acagccttgt ccggctcgat tatcataaac    360

aatcctgcag gcatgcaagc tcggatcatc acaagtttgt acaaaaaagc tgaacgagaa    420

acgtaaaatg atataaatat caatatatta aattagattt tgcataaaaa acagactaca    480

taatactgta aaacacaaca tatccagtca ctatggcggc cgctaagttg gcagcatcac    540
```

-continued

```
ccgacgcact ttgcgccgaa taaatacctg tgacggaaga tcacttcgca gaataaataa    600
atcctggtgt ccctgttgat accgggaagc cctgggccaa cttttggcga aaatgagacg    660
ttgatcggca cgtaagaggt tccaactttc accataatga aataagatca ctaccgggcg    720
tattttttga gttatcgaga ttttcaggag ctaaggaagc taaaatggag aaaaaaatca    780
ctggatatac caccgttgat atatcccaat ggcatcgtaa agaacatttt gaggcatttc    840
agtcagttgc tcaatgtacc tataaccaga ccgttcagct ggatattacg gcctttttaa    900
agaccgtaaa gaaaaataag cacaagtttt atccggcctt tattcacatt cttgcccgcc    960
tgatgaatgc tcatccggaa ttccgtatgg caatgaaaga cggtgagctg gtgatatggg   1020
atagtgttca cccttgttac accgttttcc atgagcaaac tgaaacgttt tcatcgctct   1080
ggagtgaata ccacgacgat ttccggcagt ttctacacat atattcgcaa gatgtggcgt   1140
gttacggtga aaacctggcc tatttcccta aagggtttat tgagaatatg tttttcgtct   1200
cagccaatcc ctgggtgagt ttcaccagtt ttgatttaaa cgtggccaat atggacaact   1260
tcttcgcccc cgttttcacc atgggcaaat attatacgca aggcgacaag gtgctgatgc   1320
cgctggcgat tcaggttcat catgccgtct gtgatggctt ccatgtcggc agaatgctta   1380
atgaattaca acagtactgc gatgagtggc agggcggggc gtaaacgcgt ggatccggct   1440
tactaaaagc cagataacag tatgcgtatt tgcgcgctga tttttgcggt ataagaatat   1500
atactgatat gtatacccga agtatgtcaa aaagaggtgt gctatgaagc agcgtattac   1560
agtgacagtt gacagcgaca gctatcagtt gctcaaggca tatatgatgt caatatctcc   1620
ggtctggtaa gcacaaccat gcagaatgaa gcccgtcgtc tgcgtgccga acgctggaaa   1680
gcggaaaatc aggaagggat ggctgaggtc gcccggttta ttgaaatgaa cggctctttt   1740
gctgacgaga acagggactg gtgaaatgca gtttaaggtt tacacctata aaagagagag   1800
ccgttatcgt ctgtttgtgg atgtacagag tgatattatt gacacgcccg ggcgacggat   1860
ggtgatcccc ctggccagtg cacgtctgct gtcagataaa gtctcccgtg aactttaccc   1920
ggtggtgcat atcggggatg aaagctggcg catgatgacc accgatatgg ccagtgtgcc   1980
ggtctccgtt atcggggaag aagtggctga tctcagccac cgcgaaaatg acatcaaaaa   2040
cgccattaac ctgatgttct ggggaatata aatgtcaggc tcccttatac acagccagtc   2100
tgcaggtcga ccatagtgac tggatatgtt gtgttttaca gtattatgta gtctgttttt   2160
tatgcaaaat ctaatttaat atattgatat ttatatcatt ttacgtttct cgttcagctt   2220
tcttgtacaa agtggtgatc gagaagtact agaggatcat aatcagccat accacatttg   2280
tagaggtttt acttgcttta aaaaacctcc cacacctccc cctgaacctg aaacataaaa   2340
tgaatgcaat tgttgttgtt aacttgttta ttgcagctta taatggttac aaataaagca   2400
atagcatcac aaatttcaca aataaagcat ttttttcact gcattctagt tgtggtttgt   2460
ccaaactcat caatgtatct tatcatgtct ggatctgatc actgcttgag cctaggagat   2520
ccgaaccaga taagtgaaat ctagttccaa actattttgt catttttaat tttcgtatta   2580
gcttacgacg ctacacccag ttcccatcta ttttgtcact cttccctaaa taatccttaa   2640
aaactccatt tccacccctc ccagttccca actattttgt ccgcccacag cggggcattt   2700
ttcttcctgt tatgttttta atcaaacatc ctgccaactc catgtgacaa accgtcatct   2760
tcggctactt tttctctgtc acagaatgaa aatttttctg tcatctcttc gttattaatg   2820
tttgtaattg actgaatatc aacgcttatt tgcagcctga atggcgaatg gacgcgccct   2880
```

-continued

```
gtagcggcgc attaagcgcg gcgggtgtgg tggttacgcg cagcgtgacc gctacacttg   2940
ccagcgccct agcgcccgct cctttcgctt tcttcccttc ctttctcgcc acgttcgccg   3000
gctttccccg tcaagctcta aatcgggggc tccctttagg gttccgattt agtgctttac   3060
ggcacctcga ccccaaaaaa cttgattagg gtgatggttc acgtagtggg ccatcgccct   3120
gatagacggt ttttcgccct ttgacgttgg agtccacgtt ctttaatagt ggactcttgt   3180
tccaaactgg aacaacactc aaccctatct cggtctattc ttttgattta taagggattt   3240
tgccgatttc ggcctattgg ttaaaaaatg agctgattta acaaaaattt aacgcgaatt   3300
ttaacaaaat attaacgttt acaatttcag gtggcacttt tcggggaaat gtgcgcggaa   3360
cccctatttg tttatttttc taaatacatt caaatatgta tccgctcatg agacaataac   3420
cctgataaat gcttcaataa tattgaaaaa ggaagagtat gagtattcaa catttccgtg   3480
tcgcccttat tccctttttt gcggcatttt gccttcctgt ttttgctcac ccagaaacgc   3540
tggtgaaagt aaaagatgct gaagatcagt tgggtgcacg agtgggttac atcgaactgg   3600
atctcaacag cggtaagatc cttgagagtt ttcgccccga agaacgtttt ccaatgatga   3660
gcacttttaa agttctgcta tgtggcgcgg tattatcccg tattgacgcc gggcaagagc   3720
aactcggtcg ccgcatacac tattctcaga atgacttggt tgagtactca ccagtcacag   3780
aaaagcatct tacggatggc atgacagtaa gagaattatg cagtgctgcc ataaccatga   3840
gtgataacac tgcggccaac ttacttctga caacgatcgg aggaccgaag gagctaaccg   3900
cttttttgca caacatgggg gatcatgtaa ctcgccttga tcgttgggaa ccggagctga   3960
atgaagccat accaaacgac gagcgtgaca ccacgatgcc tgtagcaatg gcaacaacgt   4020
tgcgcaaact attaactggc gaactactta ctctagcttc ccggcaacaa ttaatagact   4080
ggatggaggc ggataaagtt gcaggaccac ttctgcgctc ggcccttccg gctggctggt   4140
ttattgctga taaatctgga gccggtgagc gtgggtctcg cggtatcatt gcagcactgg   4200
ggccagatgg taagccctcc cgtatcgtag ttatctacac gacggggagt caggcaacta   4260
tggatgaacg aaatagacag atcgctgaga taggtgcctc actgattaag cattggtaac   4320
tgtcagacca agtttactca tatatacttt agattgattt aaaacttcat ttttaattta   4380
aaaggatcta ggtgaagatc ctttttgata atctcatgac caaaatccct taacgtgagt   4440
tttcgttcca ctgagcgtca gaccccgtag aaaagatcaa aggatcttct tgagatcctt   4500
tttttctgcg cgtaatctgc tgcttgcaaa caaaaaaacc accgctacca gcggtggttt   4560
gtttgccgga tcaagagcta ccaactcttt ttccgaaggt aactggcttc agcagagcgc   4620
agataccaaa tactgtcctt ctagtgtagc cgtagttagg ccaccacttc aagaactctg   4680
tagcaccgcc tacatacctc gctctgctaa tcctgttacc agtggctgct gccagtggcg   4740
ataagtcgtg tcttaccggg ttggactcaa gacgatagtt accggataag gcgcagcggt   4800
cgggctgaac ggggggttcg tgcacacagc ccagcttgga gcgaacgacc tacaccgaac   4860
tgagatacct acagcgtgag cattgagaaa gcgccacgct tcccgaaggg agaaaggcgg   4920
acaggtatcc ggtaagcggc agggtcggaa caggagagcg cacgagggag cttccagggg   4980
gaaacgcctg gtatctttat agtcctgtcg ggtttcgcca cctctgactt gagcgtcgat   5040
ttttgtgatg ctcgtcaggg gggcggagcc tatggaaaaa cgccagcaac gcggcctttt   5100
tacggttcct ggccttttgc tggccttttg ctcacatgtt ctttcctgcg ttatcccctg   5160
attctgtgga taaccgtatt accgcctttg agtgagctga taccgctcgc cgcagccgaa   5220
cgaccgagcg cagcgagtca gtgagcgagg aagcggaaga gcgcctgatg cggtattttc   5280
```

```
tccttacgca tctgtgcggt atttcacacc gcagaccagc cgcgtaacct ggcaaaatcg   5340
gttacggttg agtaataaat ggatgccctg cgtaagcggg tgtgggcgga caataaagtc   5400
ttaaactgaa caaaatagat ctaaactatg acaataaagt cttaaactag acagaatagt   5460
tgtaaactga aatcagtcca gttatgctgt gaaaaagcat actggacttt tgttatggct   5520
aaagcaaact cttcattttc tgaagtgcaa attgcccgtc gtattaaaga ggggcgtggc   5580
caagggcatg gtaaagacta tattcgcggc gttgtgacaa tttaccgaac aactccgcgg   5640
ccgggaagcc gatctcggct tgaacgaatt gttaggtggc ggtacttggg tcgatatcaa   5700
agtgcatcac ttcttcccgt atgcccaact ttgtatagag agccactgcg ggatcgtcac   5760
cgtaatctgc ttgcacgtag atcacataag caccaagcgc gttggcctca tgcttgagga   5820
gattgatgag cgcggtggca atgccctgcc tccggtgctc gccggagact gcgagatcat   5880
agatatagat ctcactacgc ggctgctcaa acctgggcag aacgtaagcc gcgagagcgc   5940
caacaaccgc ttcttggtcg aaggcagcaa gcgcgatgaa tgtcttacta cggagcaagt   6000
tcccgaggta atcggagtcc ggctgatgtt gggagtaggt ggctacgtct ccgaactcac   6060
gaccgaaaag atcaagagca gcccgcatgg atttgacttg gtcagggccg agcctacatg   6120
tgcgaatgat gcccatactt gagccaccta actttgtttt agggcgactg ccctgctgcg   6180
taacatcgtt gctgctgcgt aacatcgttg ctgctccata acatcaaaca tcgacccacg   6240
gcgtaacgcg cttgctgctt ggatgcccga ggcatagact gtacaaaaaa acagtcataa   6300
caagccatga aaaccgccac tgcgccgtta ccaccgctgc gttcggtcaa ggttctggac   6360
cagttgcgtg agcgcatacg ctacttgcat tacagtttac gaaccgaaca ggcttatgtc   6420
aactgggttc gtgccttcat ccgtttccac ggtgtgcgtc acccggcaac cttgggcagc   6480
agcgaagtcg aggcatttct gtcctggctg gcgaacgagc gcaaggtttc ggtctccacg   6540
catcgtcagg cattggcggc cttgctgttc ttctacggca aggtgctgtg cacggatctg   6600
ccctggcttc aggagatcgg aagacctcgg ccgtcgcggc gcttgccggt ggtgctgacc   6660
ccggatga                                                            6668
```

<210> SEQ ID NO 148
<211> LENGTH: 7066
<212> TYPE: DNA
<213> ORGANISM: Artificial Sequence
<220> FEATURE:
<223> OTHER INFORMATION: pDEST20
<220> FEATURE:
<221> NAME/KEY: gene
<222> LOCATION: (592)..(1263)
<223> OTHER INFORMATION: GST
<220> FEATURE:
<221> NAME/KEY: gene
<222> LOCATION: (1273)..(1397)
<223> OTHER INFORMATION: attR1
<220> FEATURE:
<221> NAME/KEY: gene
<222> LOCATION: (1506)..(2165)
<223> OTHER INFORMATION: CmR
<220> FEATURE:
<221> NAME/KEY: gene
<222> LOCATION: (2285)..(2369)
<223> OTHER INFORMATION: inactivated ccdA
<220> FEATURE:
<221> NAME/KEY: gene
<222> LOCATION: (2507)..(2812)
<223> OTHER INFORMATION: ccdB
<220> FEATURE:
<221> NAME/KEY: gene
<222> LOCATION: (2853)..(2977)

-continued

<223> OTHER INFORMATION: attR2
<220> FEATURE:
<221> NAME/KEY: gene
<222> LOCATION: (4214)..(5064)
<223> OTHER INFORMATION: ampR
<220> FEATURE:
<221> NAME/KEY: gene
<222> LOCATION: (5263)..(5843)
<223> OTHER INFORMATION: ori

<400> SEQUENCE: 148

```
ccactgcgcc gttaccaccg ctgcgttcgg tcaaggttct ggaccagttg cgtgagcgca     60
tacgctactt gcattacagt ttacgaaccg aacaggctta tgtcaactgg gttcgtgcct    120
tcatccgttt ccacggtgtg cgtcacccgg caaccttggg cagcagcgaa gtcgaggcat    180
ttctgtcctg gctggcgaac gagcgcaagg tttcggtctc cacgcatcgt caggcattgg    240
cggccttgct gttcttctac ggcaaggtgc tgtgcacgga tctgccctgg cttcaggaga    300
tcggaagacc tcggccgtcg cggcgcttgc cggtggtgct gaccccggat gaagtggttc    360
gcatcctcgg ttttctggaa ggcgagcatc gtttgttcgc ccaggactct agctatagtt    420
ctagtggttg gctacgtata ctccggaata ttaatagatc atggagataa ttaaaatgat    480
aaccatctcg caaataaata agtattttac tgttttcgta acagttttgt aataaaaaaa    540
cctataaata ttccggatta ttcataccgt cccaccatcg ggcgcggatc catggcccct    600
atactaggtt attggaaaat taagggcctt gtgcaaccca ctcgacttct tttggaatat    660
cttgaagaaa aatatgaaga gcatttgtat gagcgcgatg aaggtgataa atggcgaaac    720
aaaaagtttg aattgggttt ggagtttccc aatcttcctt attatattga tggtgatgtt    780
aaattaacac agtctatggc catcatacgt tatatagctg acaagcacaa catgttgggt    840
ggttgtccaa aagagcgtgc agagatttca atgcttgaag gagcggtttt ggatattaga    900
tacggtgttt cgagaattgc atatagtaaa gactttgaaa ctctcaaagt tgattttctt    960
agcaagctac ctgaaatgct gaaaatgttc gaagatcgtt tatgtcataa aacatattta   1020
aatggtgatc atgtaaccca tcctgacttc atgttgtatg acgctcttga tgttgtttta   1080
tacatggacc caatgtgcct ggatgcgttc ccaaaattag tttgttttaa aaaacgtatt   1140
gaagctatcc cacaaattga taagtacttg aaatccagca agtatatagc atggcctttg   1200
cagggctggc aagccacgtt tggtggtggc gaccatcctc caaaatcgga tctggttccg   1260
cgtcataatc aaacaagttt gtacaaaaaa gctgaacgag aaacgtaaaa tgatataaat   1320
atcaatatat taaattagat tttgcataaa aaacagacta cataatactg taaaacacaa   1380
catatccagt cactatggcg gccgcattag gcaccccagg ctttacactt tatgcttccg   1440
gctcgtatgt tgtgtggatt ttgagttagg atccggcgag attttcagga gctaaggaag   1500
ctaaaatgga gaaaaaaatc actggatata ccaccgttga tatatcccaa tggcatcgta   1560
aagaacattt tgaggcattt cagtcagttg ctcaatgtac ctataaccag accgttcagc   1620
tggatattac ggccttttta aagaccgtaa agaaaaataa gcacaagttt tatccggcct   1680
ttattcacat tcttgcccgc ctgatgaatg ctcatccgga attccgtatg gcaatgaaag   1740
acggtgagct ggtgatatgg gatagtgttc acccttgtta caccgttttc catgagcaaa   1800
ctgaaacgtt ttcatcgctc tggagtgaat accacgacga tttccggcag tttctacaca   1860
tatattcgca agatgtggcg tgttacggtg aaaacctggc ctatttccct aaagggttta   1920
ttgagaatat gtttttcgtc tcagccaatc cctgggtgag tttcaccagt tttgatttaa   1980
acgtggccaa tatggacaac ttcttcgccc ccgttttcac catgggcaaa tattatacgc   2040
```

-continued

```
aaggcgacaa ggtgctgatg ccgctggcga ttcaggttca tcatgccgtc tgtgatggct   2100
tccatgtcgg cagaatgctt aatgaattac aacagtactg cgatgagtgg cagggcgggg   2160
cgtaatctag aggatccggc ttactaaaag ccagataaca gtatgcgtat ttgcgcgctg   2220
atttttgcgg tataagaata tatactgata tgtatacccg aagtatgtca aaaagaggtg   2280
tgctatgaag cagcgtatta cagtgacagt tgacagcgac agctatcagt tgctcaaggc   2340
atatatgatg tcaatatctc cggtctggta agcacaacca tgcagaatga agcccgtcgt   2400
ctgcgtgccg aacgctggaa agcggaaaat caggaaggga tggctgaggt cgcccggttt   2460
attgaaatga acggctcttt tgctgacgag aacagggact ggtgaaatgc agtttaaggt   2520
ttacacctat aaaagagaga gccgttatcg tctgtttgtg gatgtacaga gtgatattat   2580
tgacacgccc gggcgacgga tggtgatccc cctggccagt gcacgtctgc tgtcagataa   2640
agtctcccgt gaactttacc cggtggtgca tatcggggat gaaagctggc gcatgatgac   2700
caccgatatg gccagtgtgc cggtctccgt tatcggggaa gaagtggctg atctcagcca   2760
ccgcgaaaat gacatcaaaa acgccattaa cctgatgttc tggggaatat aaatgtcagg   2820
ctcccttata cacagccagt ctgcaggtcg accatagtga ctggatatgt tgtgttttac   2880
agtattatgt agtctgtttt ttatgcaaaa tctaatttaa tatattgata tttatatcat   2940
tttacgtttc tcgttcagct ttcttgtaca aagtggtttg atagcttgtc gagaagtact   3000
agaggatcat aatcagccat accacatttg tagaggtttt acttgcttta aaaaacctcc   3060
cacacctccc cctgaacctg aaacataaaa tgaatgcaat tgttgttgtt aacttgttta   3120
ttgcagctta taatggttac aaataaagca atagcatcac aaatttcaca aataaagcat   3180
tttttcact gcattctagt tgtggtttgt ccaaactcat caatgtatct tatcatgtct   3240
ggatctgatc actgcttgag cctaggagat ccgaaccaga taagtgaaat ctagttccaa   3300
actattttgt catttttaat tttcgtatta gcttacgacg ctacacccag ttcccatcta   3360
ttttgtcact cttccctaaa taatccttaa aaactccatt tccacccctc ccagttccca   3420
actattttgt ccgcccacag cggggcattt ttcttcctgt tatgttttta atcaaacatc   3480
ctgccaactc catgtgacaa accgtcatct tcggctactt tttctctgtc acagaatgaa   3540
aatttttctg tcatctcttc gttattaatg tttgtaattg actgaatatc aacgcttatt   3600
tgcagcctga atggcgaatg gacgcgccct gtagcggcgc attaagcgcg gcgggtgtgg   3660
tggttacgcg cagcgtgacc gctacacttg ccagcgccct agcgcccgct cctttcgctt   3720
tcttcccttc ctttctcgcc acgttcgccg gctttccccg tcaagctcta aatcgggggc   3780
tccctttagg gttccgattt agtgctttac ggcacctcga ccccaaaaaa cttgattagg   3840
gtgatggttc acgtagtggg ccatcgccct gatagacggt ttttcgccct ttgacgttgg   3900
agtccacgtt ctttaatagt ggactcttgt tccaaactgg aacaacactc aaccctatct   3960
cggtctattc ttttgattta taagggattt tgccgatttc ggcctattgg ttaaaaaatg   4020
agctgattta acaaaaattt aacgcgaatt ttaacaaaat attaacgttt acaatttcag   4080
gtggcacttt tcggggaaat gtgcgcggaa cccctatttg tttatttttc taaatacatt   4140
caaatatgta tccgctcatg agacaataac cctgataaat gcttcaataa tattgaaaaa   4200
ggaagagtat gagtattcaa catttccgtg tcgcccttat tccctttttt gcggcatttt   4260
gccttcctgt ttttgctcac ccagaaacgc tggtgaaagt aaaagatgct gaagatcagt   4320
tgggtgcacg agtgggttac atcgaactgg atctcaacag cggtaagatc cttgagagtt   4380
```

-continued

```
ttcgccccga agaacgtttt ccaatgatga gcacttttaa agttctgcta tgtggcgcgg   4440
tattatcccg tattgacgcc gggcaagagc aactcggtcg ccgcatacac tattctcaga   4500
atgacttggt tgagtactca ccagtcacag aaaagcatct tacggatggc atgacagtaa   4560
gagaattatg cagtgctgcc ataaccatga gtgataacac tgcggccaac ttacttctga   4620
caacgatcgg aggaccgaag gagctaaccg cttttttgca caacatgggg gatcatgtaa   4680
ctcgccttga tcgttgggaa ccggagctga atgaagccat accaaacgac gagcgtgaca   4740
ccacgatgcc tgtagcaatg gcaacaacgt tgcgcaaact attaactggc gaactactta   4800
ctctagcttc ccggcaacaa ttaatagact ggatggaggc ggataaagtt gcaggaccac   4860
ttctgcgctc ggcccttccg gctggctggt ttattgctga taaatctgga gccggtgagc   4920
gtgggtctcg cggtatcatt gcagcactgg ggccagatgg taagccctcc cgtatcgtag   4980
ttatctacac gacggggagt caggcaacta tggatgaacg aaatagacag atcgctgaga   5040
taggtgcctc actgattaag cattggtaac tgtcagacca agtttactca tatatacttt   5100
agattgattt aaaacttcat ttttaattta aaaggatcta ggtgaagatc ctttttgata   5160
atctcatgac caaaatccct taacgtgagt tttcgttcca ctgagcgtca gaccccgtag   5220
aaaagatcaa aggatcttct tgagatcctt tttttctgcg cgtaatctgc tgcttgcaaa   5280
caaaaaaacc accgctacca gcggtggttt gtttgccgga tcaagagcta ccaactcttt   5340
ttccgaaggt aactggcttc agcagagcgc agataccaaa tactgtcctt ctagtgtagc   5400
cgtagttagg ccaccacttc aagaactctg tagcaccgcc tacatacctc gctctgctaa   5460
tcctgttacc agtggctgct gccagtggcg ataagtcgtg tcttaccggg ttggactcaa   5520
gacgatagtt accggataag gcgcagcggt cgggctgaac ggggggttcg tgcacacagc   5580
ccagcttgga gcgaacgacc tacaccgaac tgagatacct acagcgtgag cattgagaaa   5640
gcgccacgct tcccgaaggg agaaaggcgg acaggtatcc ggtaagcggc agggtcggaa   5700
caggagagcg cacgagggag cttccagggg gaaacgcctg gtatctttat agtcctgtcg   5760
ggtttcgcca cctctgactt gagcgtcgat ttttgtgatg ctcgtcaggg gggcggagcc   5820
tatggaaaaa cgccagcaac gcggcctttt tacggttcct ggccttttgc tggccttttg   5880
ctcacatgtt ctttcctgcg ttatcccctg attctgtgga taaccgtatt accgcctttg   5940
agtgagctga taccgctcgc cgcagccgaa cgaccgagcg cagcgagtca gtgagcgagg   6000
aagcggaaga gcgcctgatg cggtattttc tccttacgca tctgtgcggt atttcacacc   6060
gcagaccagc cgcgtaacct ggcaaaatcg gttacggttg agtaataaat ggatgccctg   6120
cgtaagcggg tgtgggcgga caataaagtc ttaaactgaa caaaatagat ctaaactatg   6180
acaataaagt cttaaactag acagaatagt tgtaaactga aatcagtcca gttatgctgt   6240
gaaaaagcat actggacttt tgttatggct aaagcaaact cttcattttc tgaagtgcaa   6300
attgcccgtc gtattaaaga ggggcgtggc caagggcatg gtaaagacta tattcgcggc   6360
gttgtgacaa tttaccgaac aactccgcgg ccgggaagcc gatctcggct tgaacgaatt   6420
gttaggtggc ggtacttggg tcgatatcaa agtgcatcac ttcttcccgt atgcccaact   6480
ttgtatagag agccactgcg ggatcgtcac cgtaatctgc ttgcacgtag atcacataag   6540
caccaagcgc gttggcctca tgcttgagga gattgatgag cgcggtggca atgccctgcc   6600
tccggtgctc gccggagact gcgagatcat agatatagat ctcactacgc ggctgctcaa   6660
acctgggcag aacgtaagcc gcgagagcgc caacaaccgc ttcttggtcg aaggcagcaa   6720
gcgcgatgaa tgtcttacta cggagcaagt tcccgaggta atcggagtcc ggctgatgtt   6780
```

-continued

```
gggagtaggt ggctacgtct ccgaactcac gaccgaaaag atcaagagca gcccgcatgg   6840

atttgacttg gtcagggccg agcctacatg tgcgaatgat gcccatactt gagccaccta   6900

actttgtttt agggcgactg ccctgctgcg taacatcgtt gctgctgcgt aacatcgttg   6960

ctgctccata acatcaaaca tcgacccacg gcgtaacgcg cttgctgctt ggatgcccga   7020

ggcatagact gtacaaaaaa acagtcataa caagccatga aaaccg                  7066
```

<210> SEQ ID NO 149
<211> LENGTH: 11713
<212> TYPE: DNA
<213> ORGANISM: Artificial Sequence
<220> FEATURE:
<223> OTHER INFORMATION: pDEST21
<220> FEATURE:
<221> NAME/KEY: gene
<222> LOCATION: (857)..(1322)
<223> OTHER INFORMATION: GAL4DB
<220> FEATURE:
<221> NAME/KEY: gene
<222> LOCATION: (1332)..(1456)
<223> OTHER INFORMATION: attR1
<220> FEATURE:
<221> NAME/KEY: gene
<222> LOCATION: (1706)..(2365)
<223> OTHER INFORMATION: CmR
<220> FEATURE:
<221> NAME/KEY: gene
<222> LOCATION: (2485)..(2569)
<223> OTHER INFORMATION: inactivated ccdA
<220> FEATURE:
<221> NAME/KEY: gene
<222> LOCATION: (2707)..(3012)
<223> OTHER INFORMATION: ccdB
<220> FEATURE:
<221> NAME/KEY: gene
<222> LOCATION: (3053)..(3177)
<223> OTHER INFORMATION: attR2
<220> FEATURE:
<221> NAME/KEY: gene
<222> LOCATION: (3716)..(3735)
<223> OTHER INFORMATION: pT7 (T7 promoter)
<220> FEATURE:
<221> NAME/KEY: gene
<222> LOCATION: (3899)..(4354)
<223> OTHER INFORMATION: f1 (f1 intergenic region)
<220> FEATURE:
<221> NAME/KEY: gene
<222> LOCATION: (4414)..(6642)
<223> OTHER INFORMATION: Leu2
<220> FEATURE:
<221> NAME/KEY: gene
<222> LOCATION: (7541)..(8515)
<223> OTHER INFORMATION: kanR
<220> FEATURE:
<221> NAME/KEY: gene
<222> LOCATION: (9668)..(10958)
<223> OTHER INFORMATION: CYH2
<220> FEATURE:
<221> NAME/KEY: gene
<222> LOCATION: (848)..(11118)
<223> OTHER INFORMATION: pADH (ADH promoter)

<400> SEQUENCE: 149

```
tttattatgt tacaatatgg aagggaactt tacacttctc ctatgcacat atattaatta     60

aagtccaatg ctagtagaga aggggggtaa cacccctccg cgctcttttc cgattttttt    120

ctaaaccgtg gaatatttcg gatatccttt tgttgtttcc gggtgtacaa tatggacttc    180

ctcttttctg gcaaccaaac ccatacatcg ggattcctat aataccttcg ttggtctccc    240

taacatgtag gtggcggagg ggagatatac aatagaacag ataccagaca agacataatg    300
```

-continued

```
ggctaaacaa gactacacca attacactgc ctcattgatg gtggtacata acgaactaat    360
actgtagccc tagacttgat agccatcatc atatcgaagt ttcactaccc tttttccatt    420
tgccatctat tgaagtaata ataggcgcat gcaacttctt ttcttttttt ttcttttctc    480
tctcccccgt tgttgtctca ccatatccgc aatgacaaaa aaaatgatgg aagacactaa    540
aggaaaaaat taacgacaaa gacagcacca acagatgtcg ttgttccaga gctgatgagg    600
ggtatcttcg aacacacgaa actttttcct tccttcattc acgcacacta ctctctaatg    660
agcaacggta tacggccttc cttccagtta cttgaatttg aaataaaaaa agtttgccgc    720
tttgctatca agtataaata gacctgcaat tattaatctt ttgtttcctc gtcattgttc    780
tcgttccctt tcttccttgt ttctttttct gcacaatatt tcaagctata ccaagcatac    840
aatcaactcc aagcttgaag caagcctcct gaaagatgaa gctactgtct tctatcgaac    900
aagcatgcga tatttgccga cttaaaaagc tcaagtgctc caaagaaaaa ccgaagtgcg    960
ccaagtgtct gaagaacaac tgggagtgtc gctactctcc caaaaccaaa aggtctccgc   1020
tgactagggc acatctgaca gaagtggaat caaggctaga aagactggaa cagctatttc   1080
tactgatttt tcctcgagaa gaccttgaca tgattttgaa aatggattct ttacaggata   1140
taaaagcatt gttaacagga ttatttgtac aagataatgt gaataaagat gccgtcacag   1200
atagattggc ttcagtggag actgatatgc ctctaacatt gagacagcat agaataagtg   1260
cgacatcatc atcggaagag agtagtaaca aaggtcaaag acagttgact gtatcgtcga   1320
ggtcgaatca aacaagtttg tacaaaaaag ctgaacgaga aacgtaaaat gatataaata   1380
tcaatatatt aaattagatt ttgcataaaa aacagactac ataatactgt aaaacacaac   1440
atatccagtc actatggcgg ccgctaagtt ggcagcatca cccgacgcac tttgcgccga   1500
ataaatacct gtgacggaag atcacttcgc agaataaata aatcctggtg tccctgttga   1560
taccgggaag ccctgggcca acttttggcg aaaatgagac gttgatcggc acgtaagagg   1620
ttccaacttt caccataatg aaataagatc actaccgggc gtattttttg agttatcgag   1680
attttcagga gctaaggaag ctaaaatgga gaaaaaaatc actggatata ccaccgttga   1740
tatatcccaa tggcatcgta aagaacattt tgaggcattt cagtcagttg ctcaatgtac   1800
ctataaccag accgttcagc tggatattac ggccttttta aagaccgtaa agaaaaataa   1860
gcacaagttt tatccggcct ttattcacat tcttgcccgc ctgatgaatg ctcatccgga   1920
attccgtatg gcaatgaaag acggtgagct ggtgatatgg gatagtgttc acccttgtta   1980
caccgttttc catgagcaaa ctgaaacgtt ttcatcgctc tggagtgaat accacgacga   2040
tttccggcag tttctacaca tatattcgca agatgtggcg tgttacggtg aaaacctggc   2100
ctatttccct aaagggttta ttgagaatat gtttttcgtc tcagccaatc cctgggtgag   2160
tttcaccagt tttgatttaa acgtggccaa tatggacaac ttcttcgccc ccgttttcac   2220
catgggcaaa tattatacgc aaggcgacaa ggtgctgatg ccgctggcga ttcaggttca   2280
tcatgccgtc tgtgatggct tccatgtcgg cagaatgctt aatgaattac aacagtactg   2340
cgatgagtgg cagggcgggg cgtaatctag aggatccggc ttactaaaag ccagataaca   2400
gtatgcgtat ttgcgcgctg atttttgcgg tataagaata tatactgata tgtatacccg   2460
aagtatgtca aaaagaggtg tgctatgaag cagcgtatta cagtgacagt tgacagcgac   2520
agctatcagt tgctcaaggc atatatgatg tcaatatctc cggtctggta agcacaacca   2580
tgcagaatga agcccgtcgt ctgcgtgccg aacgctggaa agcggaaaat caggaaggga   2640
tggctgaggt cgcccggttt attgaaatga acggctcttt tgctgacgag aacagggact   2700
```

-continued

```
ggtgaaatgc agtttaaggt ttacacctat aaaagagaga gccgttatcg tctgtttgtg   2760
gatgtacaga gtgatattat tgacacgccc gggcgacgga tggtgatccc cctggccagt   2820
gcacgtctgc tgtcagataa agtctcccgt gaactttacc cggtggtgca tatcggggat   2880
gaaagctggc gcatgatgac caccgatatg gccagtgtgc cggtctccgt tatcggggaa   2940
gaagtggctg atctcagcca ccgcgaaaat gacatcaaaa acgccattaa cctgatgttc   3000
tggggaatat aaatgtcagg ctcccttata cacagccagt ctgcaggtcg accatagtga   3060
ctggatatgt tgtgttttac agtattatgt agtctgtttt ttatgcaaaa tctaatttaa   3120
tatattgata tttatatcat tttacgtttc tcgttcagct ttcttgtaca aagtggtttg   3180
atggccgcta agtaagtaag acgtcgagct ctaagtaagt aacggccgcc accgcggtgg   3240
agctttggac ttcttcgcca gaggtttggt caagtctcca atcaaggttg tcggcttgtc   3300
taccttgcca gaaatttacg aaaagatgga aaagggtcaa atcgttggta gatacgttgt   3360
tgacacttct aaataagcga atttcttatg atttatgatt tttattatta aataagttat   3420
aaaaaaaata agtgtataca aattttaaag tgactcttag gttttaaaac gaaaattctt   3480
attcttgagt aactctttcc tgtaggtcag gttgctttct caggtatagc atgaggtcgc   3540
tcttattgac cacacctcta ccggcatgcc gagcaaatgc ctgcaaatcg ctccccattt   3600
cacccaattg tagatatgct aactccagca atgagttgat gaatctcggt gtgtatttta   3660
tgtcctcaga ggacaatacc tgttgtaatc gttcttccac acggatccca attcgcccta   3720
tagtgagtcg tattacaatt cactggccgt cgttttacaa cgtcgtgact gggaaaaccc   3780
tggcgttacc caacttaatc gccttgcagc acatccccct ttcgccagct ggcgtaatag   3840
cgaagaggcc cgcaccgatc gcccttccca acagttgcgc agcctgaatg gcgaatggac   3900
gcgccctgta gcggcgcatt aagcgcggcg ggtgtggtgg ttacgcgcag cgtgaccgct   3960
acacttgcca gcgccctagc gcccgctcct ttcgctttct tcccttcctt tctcgccacg   4020
ttcgccggct ttccccgtca agctctaaat cgggggctcc ctttagggtt ccgatttagt   4080
gctttacggc acctcgaccc caaaaaactt gattagggtg atggttcacg tagtgggcca   4140
tcgccctgat agacggtttt tcgccctttg acgttggagt ccacgttctt taatagtgga   4200
ctcttgttcc aaactggaac aacactcaac cctatctcgg tctattcttt tgatttataa   4260
gggattttgc cgatttcggc ctattggtta aaaaatgagc tgatttaaca aaaatttaac   4320
gcgaatttta acaaaatatt aacgtttaca atttcctgat gcggtatttt ctccttacgc   4380
atctgtgcgg tatttcacac cgcatatcga ccggtcgagg agaacttcta gtatatccac   4440
atacctaata ttattgcctt attaaaaatg gaatcggaac aattacatca aaatccacat   4500
tctcttcaaa atcaattgtc ctgtacttcc ttgttcatgt gtgttcaaaa acgttatatt   4560
tataggataa ttatactcta tttctcaaca agtaattggt tgtttggccg agcggtctaa   4620
ggcgcctgat tcaagaaata tcttgaccgc agttaactgt gggaatactc aggtatcgta   4680
agatgcaaga gttcgaatct cttagcaacc attatttttt tcctcaacat aacgagaaca   4740
cacaggggcg ctatcgcaca gaatcaaatt cgatgactgg aaattttttg ttaatttcag   4800
aggtcgcctg acgcatatac ctttttcaac tgaaaaattg ggagaaaaag gaaaggtgag   4860
aggccggaac cggcttttca tatagaatag agaagcgttc atgactaaat gcttgcatca   4920
caatacttga agttgacaat attatttaag gacctattgt tttttccaat aggtggttag   4980
caatcgtctt actttctaac ttttcttacc ttttacattt cagcaatata tatatatatt   5040
```

-continued

```
tcaaggatat accattctaa tgtctgcccc tatgtctgcc cctaagaaga tcgtcgtttt   5100

gccaggtgac cacgttggtc aagaaatcac agccgaagcc attaaggttc ttaaagctat   5160

ttctgatgtt cgttccaatg tcaagttcga tttcgaaaat catttaattg gtggtgctgc   5220

tatcgatgct acaggtgtcc cacttccaga tgaggcgctg gaagcctcca agaaggttga   5280

tgccgttttg ttaggtgctg tgggtggtcc taaatggggt accggtagtg ttagacctga   5340

acaaggttta ctaaaaatcc gtaaagaact tcaattgtac gccaacttaa gaccatgtaa   5400

ctttgcatcc gactctcttt tagacttatc tccaatcaag ccacaatttg ctaaaggtac   5460

tgacttcgtt gttgtcagag aattagtggg aggtatttac tttggtaaga gaaaggaaga   5520

cgatggtgat ggtgtcgctt gggatagtga acaatacacc gttccagaag tgcaaagaat   5580

cacaagaatg gccgctttca tggccctaca acatgagcca ccattgccta tttggtcctt   5640

ggataaagct aatgttttgg cctcttcaag attatggaga aaaactgtgg aggaaaccat   5700

caagaacgaa ttccctacat tgaaggttca acatcaattg attgattctg ccgccatgat   5760

cctagttaag aacccaaccc acctaaatgg tattataatc accagcaaca tgtttggtga   5820

tatcatctcc gatgaagcct ccgttatccc aggttccttg ggtttgttgc catctgcgtc   5880

cttggcctct ttgccagaca agaacaccgc atttggtttg tacgaaccat gccacggttc   5940

tgctccagat ttgccaaaga ataaggttga ccctatcgcc actatcttgt ctgctgcaat   6000

gatgttgaaa ttgtcattga acttgcctga agaaggtaag gccattgaag atgcagttaa   6060

aaaggttttg gatgcaggta tcagaactgg tgatttaggt ggttccaaca gtaccaccga   6120

agtcggtgat gctgtcgccg aagaagttaa gaaaatcctt gcttaaaaag attctctttt   6180

tttatgatat ttgtacataa actttataaa tgaaattcat aatagaaacg acacgaaatt   6240

acaaaatgga atatgttcat agggtagacg aaactatata cgcaatctac atacatttat   6300

caagaaggag aaaaaggagg atagtaaagg aatacaggta agcaaattga tactaatggc   6360

tcaacgtgat aaggaaaaag aattgcactt taacattaat attgacaagg aggagggcac   6420

cacacaaaaa gttaggtgta acagaaaatc atgaaactac gattcctaat ttgatattgg   6480

aggattttct ctaaaaaaaa aaaaatacaa caaataaaaa acactcaatg acctgaccat   6540

ttgatggagt ttaagtcaat accttcttga accatttccc ataatggtga aagttccctc   6600

aagaatttta ctctgtcaga aacggcctta cgacgtagtc gatatggtgc actctcagta   6660

caatctgctc tgatgccgca tagttaagcc agccccgaca cccgccaaca cccgctgacg   6720

cgccctgacg ggcttgtctg ctcccggcat ccgcttacag acaagctgtg accgtctccg   6780

ggagctgcat gtgtcagagg ttttcaccgt catcaccgaa acgcgcgaga cgaaagggcc   6840

tcgtgatacg cctattttta taggttaatg tcatgataat aatggtttct taggacggat   6900

cgcttgcctg taacttacac gcgcctcgta tcttttaatg atggaataat ttgggaattt   6960

actctgtgtt tatttatttt tatgttttgt atttggattt tagaaagtaa ataaagaagg   7020

tagaagagtt acggaatgaa gaaaaaaaaa taaacaaagg tttaaaaaat ttcaacaaaa   7080

agcgtacttt acatatatat ttattagaca agaaaagcag attaaataga tatacattcg   7140

attaacgata agtaaaatgt aaaatcacag gattttcgtg tgtggtcttc tacacagaca   7200

agatgaaaca attcggcatt aatacctgag agcaggaaga gcaagataaa aggtagtatt   7260

tgttggcgat ccccctagag tcttttacat cttcggaaaa caaaaactat tttttcttta   7320

atttcttttt ttactttcta tttttaattt atatatttat attaaaaaat ttaaattata   7380

attattttta tagcacgtga tgaaaaggac ccaggtggca cttttcgggg aaatgtgcgc   7440
```

-continued

```
ggaaccccta tttgtttatt tttctaaata cattcaaata tgtatccgct catgagacaa   7500
taaccctgat aaatgcttca ataatctgca gctctggccc gtgtctcaaa atctctgatg   7560
ttacattgca caagataaaa atatatcatc atgaacaata aaactgtctg cttacataaa   7620
cagtaataca aggggtgtta tgagccatat tcaacgggaa acgtcttgct ggaggccgcg   7680
attaaattcc aacatggatg ctgatttata tgggtataaa tgggctcgcg ataatgtcgg   7740
gcaatcaggt gcgacaatct ttcgattgta tgggaagccc gatgcgccag agttgtttct   7800
gaaacatggc aaaggtagcg ttgccaatga tgttacagat gagatggtca gactaaactg   7860
gctgacggaa tttatgcctc ttccgaccat caagcatttt atccgtactc ctgatgatgc   7920
atggttactc accactgcga tccgcgggaa aacagcattc caggtattag aagaatatcc   7980
tgattcaggt gaaaatattg ttgatgcgct ggcagtgttc ctgcgccggt tgcattcgat   8040
tcctgtttgt aattgtcctt ttaacagcga tcgcgtattt cgtctcgctc aggcgcaatc   8100
acgaatgaat aacggtttgg ttgatgcgag tgattttgat gacgagcgta atggctggcc   8160
tgttgaacaa gtctggaaag aaatgcatac gcttttgcca ttctcaccgg attcagtcgt   8220
cactcatggt gatttctcac ttgataacct tatttttgac gaggggaaat taataggttg   8280
tattgatgtt ggacgagtcg gaatcgcaga ccgataccag gatcttgcca tcctatggaa   8340
ctgcctcggt gagttttctc cttcattaca gaaacggctt tttcaaaaat atggtattga   8400
taatcctgat atgaataaat tgcagtttca tttgatgctc gatgagtttt tctaatcaga   8460
attggttaat tggttgtaac actggcagag cattacgctg acttgacggg acggcgcatg   8520
accaaaatcc cttaacgtga gttttcgttc cactgagcgt cagaccccgt agaaaagatc   8580
aaaggatctt cttgagatcc tttttttctg cgcgtaatct gctgcttgca aacaaaaaaa   8640
ccaccgctac cagcggtggt ttgtttgccg gatcaagagc taccaactct ttttccgaag   8700
gtaactggct tcagcagagc gcagatacca aatactgtcc ttctagtgta gccgtagtta   8760
ggccaccact tcaagaactc tgtagcaccg cctacatacc tcgctctgct aatcctgtta   8820
ccagtggctg ctgccagtgg cgataagtcg tgtcttaccg ggttggactc aagacgatag   8880
ttaccggata aggcgcagcg gtcgggctga acggggggtt cgtgcacaca gcccagcttg   8940
gagcgaacga cctacaccga actgagatac ctacagcgtg agcattgaga aagcgccacg   9000
cttcccgaag ggagaaaggc ggacaggtat ccggtaagcg gcagggtcgg aacaggagag   9060
cgcacgaggg agcttccagg gggaaacgcc tggtatcttt atagtcctgt cgggtttcgc   9120
cacctctgac ttgagcgtcg atttttgtga tgctcgtcag gggggcgag cctatggaaa    9180
aacgccagca acgcggcctt tttacggttc ctggcctttt gctggccttt tgctcacatg   9240
ttctttcctg cgttatcccc tgattctgtg gataaccgta ttaccgcctt tgagtgagct   9300
gataccgctc gccgcagccg aacgaccgag cgcagcgagt cagtgagcga ggaagcggaa   9360
gagcgcccaa tacgcaaacc gcctctcccc gcgcgttggc cgattcatta atgcagctgg   9420
cacgacaggt ttcccgactg gaaagcgggc agtgagcgca acgcaattaa tgtgagttac   9480
ctcactcatt aggcacccca ggctttacac tttatgcttc cggctcctat gttgtgtgga   9540
attgtgagcg gataacaatt tcacacagga aacagctatg accatgatta cgccaagctc   9600
ggaattaacc ctcactaaag ggaacaaaag ctggtaccga tcccgagctt tgcaaattaa   9660
agccttcgag cgtcccaaaa ccttctcaag caaggttttc agtataatgt tacatgcgta   9720
cacgcgtctg tacagaaaaa aaagaaaaat ttgaaatata aataacgttc ttaatactaa   9780
```

-continued

```
cataactata aaaaaataaa tagggaccta gacttcaggt tgtctaactc cttccttttc   9840

ggttagagcg gatgtggggg gagggcgtga atgtaagcgt gacataacta attacatgat   9900

atcgacaaag gaaaaggggc ctgtttactc acaggctttt ttcaagtagg taattaagtc   9960

gtttctgtct ttttccttct tcaacccacc aaaggccatc ttggtacttt ttttttttt  10020

ttttttttt ttttttttt ttttttttt ttttttttt ttttttttt ttttttttt  10080

ttttttttt ttttttttt tcatagaaat aatacagaag tagatgttga attagattaa  10140

actgaagata tataatttat tggaaaatac atagagcttt ttgttgatgc gcttaagcga  10200

tcaattcaac aacaccacca gcagctctga tttttttcttc agccaacttg gagacgaatc  10260

tagctttgac gataactgga acatttggaa ttctaccctt acccaagatc ttaccgtaac  10320

cggctgccaa agtgtcaata actggagcag tttccttaga agcagatttc aagtattggt  10380

ctctcttgtc ttctgggatc aatgtccaca atttgtccaa gttcaagact ggcttccaga  10440

aatgagcttg ttgcttgtgg aagtatctca taccaacctt accgaaataa cctggatggt  10500

atttatccat gttaattctg tggtgatgtt gaccaccggc catacctcta ccaccggggt  10560

gctttctgtg cttaccgata cgacctttac cggctgagac gtgacctctg tgctttctag  10620

tcttagtgaa tctggaaggc attcttgatt agttggatga ttgttctggg atttaatgca  10680

aaaatcactt aagaaggaaa atcaacggag aaagcaaacg ccatcttaaa tatacgggat  10740

acagatgaaa gggtttgaac ctatctggaa aatagcatta aacaagcgaa aaactgcgag  10800

gaaaattgtt tgcgtctctg cgggctattc acgcgccaga ggaaaatagg aaaaataaca  10860

gggcattaga aaaataattt tgattttggt aatgtgtggg tcctggtgta cagatgttac  10920

attggttaca gtactcttgt tttgctgtg tttttcgatg aatctccaaa atggttgtta  10980

gcacatggaa gagtcaccga tgctaagtta tctctatgta agctacgtgg cgtgactttt  11040

gatgaagccg cacaagagat acaggattgg caactgcaaa tagaatctgg ggatcccccc  11100

tcgagatccg ggatcgaaga aatgatggta aatgaaatag gaaatcaagg agcatgaagg  11160

caaaagacaa atataagggt cgaacgaaaa ataaagtgaa aagtgttgat atgatgtatt  11220

tggctttgcg gcgccgaaaa aacgagttta cgcaattgca caatcatgct gactctgtgg  11280

cggacccgcg ctcttgccgg cccggcgata acgctgggcg tgaggctgtg cccggcggag  11340

ttttttgcgc ctgcattttc caaggtttac cctgcgctaa ggggcgagat tggagaagca  11400

ataagaatgc cggttggggt tgcgatgatg acgaccacga caactggtgt cattatttaa  11460

gttgccgaaa gaacctgagt gcatttgcaa catgagtata ctagaagaat gagccaagac  11520

ttgcgagacg cgagtttgcc ggtggtgcga acaatagagc gaccatgacc ttgaaggtga  11580

gacgcgcata accgctagag tactttgaag aggaaacagc aatagggttg ctaccagtat  11640

aaatagacag gtacatacaa cactggaaat ggttgtctgt ttgagtacgc tttcaattca  11700

tttgggtgtg cac                                                     11713
```

<210> SEQ ID NO 150
<211> LENGTH: 8923
<212> TYPE: DNA
<213> ORGANISM: Artificial Sequence
<220> FEATURE:
<223> OTHER INFORMATION: pDEST22
<220> FEATURE:
<221> NAME/KEY: gene
<222> LOCATION: (904)..(1248)
<223> OTHER INFORMATION: GAL4 AD
<220> FEATURE:
<221> NAME/KEY: gene -continued
<222> LOCATION: (1264)..(1388)
<223> OTHER INFORMATION: attR1
<220> FEATURE:
<221> NAME/KEY: gene
<222> LOCATION: (1638)..(2297)
<223> OTHER INFORMATION: CmR
<220> FEATURE:
<221> NAME/KEY: gene
<222> LOCATION: (2417)..(2501)
<223> OTHER INFORMATION: inactivated ccdA
<220> FEATURE:
<221> NAME/KEY: gene
<222> LOCATION: (2639)..(2944)
<223> OTHER INFORMATION: ccdB
<220> FEATURE:
<221> NAME/KEY: gene
<222> LOCATION: (2985)..(3109)
<223> OTHER INFORMATION: attR2
<220> FEATURE:
<221> NAME/KEY: gene
<222> LOCATION: (3831)..(4318)
<223> OTHER INFORMATION: f1 (f1 intergenic region)
<220> FEATURE:
<221> NAME/KEY: gene
<222> LOCATION: (4334)..(5176)
<223> OTHER INFORMATION: TRP1
<220> FEATURE:
<221> NAME/KEY: gene
<222> LOCATION: (6110)..(7194)
<223> OTHER INFORMATION: ampR
<220> FEATURE:
<221> NAME/KEY: gene
<222> LOCATION: (866)..(8344)
<223> OTHER INFORMATION: pADH (yeast ADH promoter)

<400> SEQUENCE: 150
ttcatttggg tgtgcacttt attatgttac aatatggaag ggaactttac acttctccta 60
tgcacatata ttaattaaag tccaatgcta gtagagaagg ggggtaacac ccctccgcgc 120
tcttttccga tttttttcta aaccgtggaa tatttcggat atccttttgt tgtttccggg 180
tgtacaatat ggacttcctc ttttctggca accaaaccca tacatcggga ttcctataat 240
accttcgttg gtctccctaa catgtaggtg gcggagggga gatatacaat agaacagata 300
ccagacaaga cataatgggc taaacaagac tacaccaatt acactgcctc attgatggtg 360
gtacataacg aactaatact gtagccctag acttgatagc catcatcata tcgaagtttc 420
actacccttt ttccatttgc catctattga agtaataata ggcgcatgca acttcttttc 480
tttttttttc ttttctctct cccccgttgt tgtctcacca tatccgcaat gacaaaaaaa 540
atgatggaag acactaaagg aaaaaattaa cgacaaagac agcaccaaca gatgtcgttg 600
ttccagagct gatgaggggt atcttcgaac acacgaaact tttccttcc ttcattcacg 660 cacactactc tctaatgagc aacggtatac ggccttcctt ccagttactt gaatttgaaa 720
taaaaaaagt ttgccgcttt gctatcaagt ataaatagac ctgcaattat taatcttttg 780
tttcctcgtc attgttctcg ttccctttct tccttgtttc tttttctgca caatatttca 840
agctatacca agcatacaat caactccaag cttatgccca agaagaagcg gaaggtctcg 900
agcggcgcca attttaatca aagtgggaat attgctgata gctcattgtc cttcactttc 960
actaacagta gcaacggtcc gaacctcata acaactcaaa caaattctca agcgctttca 1020
caaccaattg cctcctctaa cgttcatgat aacttcatga ataatgaaat cacggctagt 1080
aaaattgatg atggtaataa ttcaaaacca ctgtcacctg gttggacgga ccaaactgcg 1140
tataacgcgt ttggaatcac tacagggatg tttaatacca ctacaatgga tgatgtatat 1200
aactatctat tcgatgatga agataccccca ccaaacccaa aaaaagaggg tgggtcgaat 1260

-continued

```
caaacaagtt tgtacaaaaa agctgaacga gaaacgtaaa atgatataaa tatcaatata   1320
ttaaattaga ttttgcataa aaaacagact acataatact gtaaaacaca acatatccag   1380
tcactatggc ggccgctaag ttggcagcat cacccgacgc actttgcgcc gaataaatac   1440
ctgtgacgga agatcacttc gcagaataaa taaatcctgg tgtccctgtt gataccggga   1500
agccctgggc caacttttgg cgaaaatgag acgttgatcg gcacgtaaga ggttccaact   1560
ttcaccataa tgaaataaga tcactaccgg gcgtattttt tgagttatcg agattttcag   1620
gagctaagga agctaaaatg gagaaaaaaa tcactggata taccaccgtt gatatatccc   1680
aatggcatcg taaagaacat tttgaggcat ttcagtcagt tgctcaatgt acctataacc   1740
agaccgttca gctggatatt acggcctttt taaagaccgt aaagaaaaat aagcacaagt   1800
tttatccggc ctttattcac attcttgccc gcctgatgaa tgctcatccg gaattccgta   1860
tggcaatgaa agacggtgag ctggtgatat gggatagtgt tcacccttgt tacaccgttt   1920
tccatgagca aactgaaacg ttttcatcgc tctggagtga ataccacgac gatttccggc   1980
agtttctaca catatattcg caagatgtgg cgtgttacgg tgaaaacctg gcctatttcc   2040
ctaaagggtt tattgagaat atgtttttcg tctcagccaa tccctgggtg agtttcacca   2100
gttttgattt aaacgtggcc aatatggaca acttcttcgc ccccgttttc accatgggca   2160
aatattatac gcaaggcgac aaggtgctga tgccgctggc gattcaggtt catcatgccg   2220
tctgtgatgg cttccatgtc ggcagaatgc ttaatgaatt acaacagtac tgcgatgagt   2280
ggcagggcgg ggcgtaatct agaggatccg gcttactaaa agccagataa cagtatgcgt   2340
atttgcgcgc tgatttttgc ggtataagaa tatatactga tatgtatacc cgaagtatgt   2400
caaaaagagg tgtgctatga agcagcgtat tacagtgaca gttgacagcg acagctatca   2460
gttgctcaag gcatatatga tgtcaatatc tccggtctgg taagcacaac catgcagaat   2520
gaagcccgtc gtctgcgtgc cgaacgctgg aaagcggaaa atcaggaagg gatggctgag   2580
gtcgcccggt ttattgaaat gaacggctct tttgctgacg agaacaggga ctggtgaaat   2640
gcagtttaag gtttacacct ataaaagaga gagccgttat cgtctgtttg tggatgtaca   2700
gagtgatatt attgacacgc ccgggcgacg gatggtgatc cccctggcca gtgcacgtct   2760
gctgtcagat aaagtctccc gtgaacttta cccggtggtg catatcgggg atgaaagctg   2820
gcgcatgatg accaccgata tggccagtgt gccggtctcc gttatcgggg aagaagtggc   2880
tgatctcagc caccgcgaaa atgacatcaa aaacgccatt aacctgatgt tctggggaat   2940
ataaatgtca ggctccctta tacacagcca gtctgcaggt cgaccatagt gactggatat   3000
gttgtgtttt acagtattat gtagtctgtt ttttatgcaa aatctaattt aatatattga   3060
tatttatatc attttacgtt tctcgttcag ctttcttgta caaagtggtt tgatggccgc   3120
taagtaagta agacgtcgag ctctaagtaa gtaacggccg ccaccgcggt ggagctttgg   3180
acttcttcgc cagaggtttg gtcaagtctc caatcaaggt tgtcggcttg tctaccttgc   3240
cagaaattta cgaaaagatg gaaaagggtc aaatcgttgg tagatacgtt gttgacactt   3300
ctaaataagc gaatttctta tgatttatga tttttattat taaataagtt ataaaaaaaa   3360
taagtgtata caaattttaa agtgactctt aggttttaaa acgaaaattc ttattcttga   3420
gtaactcttt cctgtaggtc aggttgcttt ctcaggtata gcatgaggtc gctcttattg   3480
accacacctc taccggcatg ccgagcaaat gcctgcaaat cgctccccat ttcacccaat   3540
tgtagatatg ctaactccag caatgagttg atgaatctcg gtgtgtattt tatgtcctca   3600
gaggacaata cctgttgtaa tcgttcttcc acacggatcc caattcgccc tatagtgagt   3660
```

-continued

```
cgtattacaa ttcactggcc gtcgttttac aacgtcgtga ctgggaaaac cctggcgtta   3720
cccaacttaa tcgccttgca gcacatcccc ctttcgccag ctggcgtaat agcgaagagg   3780
cccgcaccga tcgcccttcc caacagttgc gcagcctgaa tggcgaatgg acgcgccctg   3840
tagcggcgca ttaagcgcgg cgggtgtggt ggttacgcgc agcgtgaccg ctacacttgc   3900
cagcgcccta gcgcccgctc ctttcgcttt cttcccttcc tttctcgcca cgttcgccgg   3960
ctttccccgt caagctctaa atcgggggct ccctttaggg ttccgattta gtgctttacg   4020
gcacctcgac cccaaaaaac ttgattaggg tgatggttca cgtagtgggc catcgccctg   4080
atagacggtt tttcgccctt tgacgttgga gtccacgttc tttaatagtg gactcttgtt   4140
ccaaactgga acaacactca accctatctc ggtctattct tttgatttat aagggatttt   4200
gccgatttcg gcctattggt taaaaaatga gctgatttaa caaaaattta acgcgaattt   4260
taacaaaata ttaacgttta caatttcctg atgcggtatt ttctccttac gcatctgtgc   4320
ggtatttcac accgcaggca agtgcacaaa caatacttaa ataaatacta ctcagtaata   4380
acctatttct tagcattttt gacgaaattt gctattttgt tagagtcttt tacaccattt   4440
gtctccacac ctccgcttac atcaacacca ataacgccat ttaatctaag cgcatcacca   4500
acattttctg gcgtcagtcc accagctaac ataaaatgta agctttcggg gctctcttgc   4560
cttccaaccc agtcagaaat cgagttccaa tccaaaagtt cacctgtccc acctgcttct   4620
gaatcaaaca agggaataaa cgaatgaggt ttctgtgaag ctgcactgag tagtatgttg   4680
cagtcttttg gaaatacgag tcttttaata actggcaaac cgaggaactc ttggtattct   4740
tgccacgact catctccatg cagttggacg atatcaatgc cgtaatcatt gaccagagcc   4800
aaaacatcct ccttaggttg attacgaaac acgccaacca agtatttcgg agtgcctgaa   4860
ctatttttat atgcttttac aagacttgaa attttccttg caataaccgg gtcaattgtt   4920
ctctttctat tgggcacaca tataataccc agcaagtcag catcggaatc tagagcacat   4980
tctgcggcct ctgtgctctg caagccgcaa actttcacca atggaccaga actacctgtg   5040
aaattaataa cagacatact ccaagctgcc tttgtgtgct taatcacgta tactcacgtg   5100
ctcaatagtc accaatgccc tccctcttgg ccctctcctt ttcttttttc gaccgaatta   5160
attcttaatc ggcaaaaaaa gaaaagctcc ggatcaagat tgtacgtaag gtgacaagct   5220
atttttcaat aaagaatatc ttccactact gccatctggc gtcataactg caaagtacac   5280
atatattacg atgctgtcta ttaaatgctt cctatattat atatatagta atgtcgttta   5340
tggtgcactc tcagtacaat ctgctctgat gccgcatagt taagccagcc ccgacacccg   5400
ccaacacccg ctgacgcgcc ctgacgggct tgtctgctcc cggcatccgc ttacagacaa   5460
gctgtgaccg tctccgggag ctgcatgtgt cagaggtttt caccgtcatc accgaaacgc   5520
gcgagacgaa agggcctcgt gatacgccta tttttatagg ttaatgtcat gataataatg   5580
gtttcttagg acggatcgct tgcctgtaac ttacacgcgc ctcgtatctt ttaatgatgg   5640
aataatttgg gaatttactc tgtgtttatt tatttttatg ttttgtattt ggattttaga   5700
aagtaaataa agaaggtaga agagttacgg aatgaagaaa aaaaaataaa caaaggttta   5760
aaaaatttca acaaaaagcg tactttacat atatatttat tagacaagaa aagcagatta   5820
aatagatata cattcgatta acgataagta aaatgtaaaa tcacaggatt ttcgtgtgtg   5880
gtcttctaca cagacaagat gaaacaattc ggcattaata cctgagagca ggaagagcaa   5940
gataaaaggt agtatttgtt ggcgatcccc ctagagtctt ttacatcttc ggaaaacaaa   6000
```

-continued

```
aactattttt tctttaattt cttttttttac tttctatttt taatttatat atttatatta   6060
aaaaatttaa attataatta tttttatagc acgtgatgaa aaggacccag gtggcacttt   6120
tcggggaaat gtgcgcggaa cccctatttg tttatttttc taaatacatt caaatatgta   6180
tccgctcatg agacaataac cctgataaat gcttcaataa tattgaaaaa ggaagagtat   6240
gagtattcaa catttccgtg tcgcccttat tccctttttt gcggcatttt gccttcctgt   6300
ttttgctcac ccagaaacgc tggtgaaagt aaaagatgct gaagatcagt tgggtgcacg   6360
agtgggttac atcgaactgg atctcaacag cggtaagatc cttgagagtt ttcgccccga   6420
agaacgtttt ccaatgatga gcacttttaa agttctgcta tgtggcgcgg tattatcccg   6480
tattgacgcc gggcaagagc aactcggtcg ccgcatacac tattctcaga atgacttggt   6540
tgagtactca ccagtcacag aaaagcatct tacggatggc atgacagtaa gagaattatg   6600
cagtgctgcc ataaccatga gtgataacac tgcggccaac ttacttctga caacgatcgg   6660
aggaccgaag gagctaaccg cttttttgca caacatgggg gatcatgtaa ctcgccttga   6720
tcgttgggaa ccggagctga atgaagccat accaaacgac gagcgtgaca ccacgatgcc   6780
tgtagcaatg gcaacaacgt tgcgcaaact attaactggc gaactactta ctctagcttc   6840
ccggcaacaa ttaatagact ggatggaggc ggataaagtt gcaggaccac ttctgcgctc   6900
ggcccttccg gctggctggt ttattgctga taaatctgga gccggtgagc gtgggtctcg   6960
cggtatcatt gcagcactgg ggccagatgg taagccctcc cgtatcgtag ttatctacac   7020
gacgggcagt caggcaacta tggatgaacg aaatagacag atcgctgaga taggtgcctc   7080
actgattaag cattggtaac tgtcagacca agtttactca tatatacttt agattgattt   7140
aaaacttcat ttttaattta aaaggatcta ggtgaagatc ctttttgata atctcatgac   7200
caaaatccct taacgtgagt tttcgttcca ctgagcgtca gaccccgtag aaaagatcaa   7260
aggatcttct tgagatcctt tttttctgcg cgtaatctgc tgcttgcaaa caaaaaaacc   7320
accgctacca gcggtggttt gtttgccgga tcaagagcta ccaactcttt ttccgaaggt   7380
aactggcttc agcagagcgc agataccaaa tactgtcctt ctagtgtagc cgtagttagg   7440
ccaccacttc aagaactctg tagcaccgcc tacatacctc gctctgctaa tcctgttacc   7500
agtggctgct gccagtggcg ataagtcgtg tcttaccggg ttggactcaa gacgatagtt   7560
accggataag gcgcagcggt cgggctgaac ggggggttcg tgcacacagc ccagcttgga   7620
gcgaacgacc tacaccgaac tgagatacct acagcgtgag cattgagaaa gcgccacgct   7680
tcccgaaggg agaaaggcgg acaggtatcc ggtaagcggc agggtcggaa caggagagcg   7740
cacgagggag cttccagggg ggaacgcctg gtatctttat agtcctgtcg ggtttcgcca   7800
cctctgactt gagcgtcgat ttttgtgatg ctcgtcaggg gggccgagcc tatggaaaaa   7860
cgccagcaac gcggcctttt tacggttcct ggccttttgc tggccttttg ctcacatgtt   7920
ctttcctgcg ttatcccctg attctgtgga taaccgtatt accgcctttg agtgagctga   7980
taccgctcgc cgcagccgaa cgaccgagcg cagcgagtca gtgagcgagg aagcggaaga   8040
gcgcccaata cgcaaaccgc ctctccccgc gcgttggccg attcattaat gcagctggca   8100
cgacaggttt cccgactgga aagcgggcag tgagcgcaac gcaattaatg tgagttacct   8160
cactcattag gcaccccagg ctttacactt tatgcttccg gctcctatgt tgtgtggaat   8220
tgtgagcgga taacaatttc acacaggaaa cagctatgac catgattacg ccaagctcgg   8280
aattaaccct cactaaaggg aacaaaagct gggtaccggg ccccccctcg agatccggga   8340
tcgaagaaat gatggtaaat gaaataggaa atcaaggagc atgaaggcaa aagacaaata   8400
```

-continued

```
taagggtcga acgaaaaata aagtgaaaag tgttgatatg atgtatttgg ctttgcggcg   8460

ccgaaaaaac gagtttacgc aattgcacaa tcatgctgac tctgtggcgg acccgcgctc   8520

ttgccggccc ggcgataacg ctgggcgtga ggctgtgccc ggcggagttt tttgcgcctg   8580

cattttccaa ggtttaccct gcgctaaggg gcgagattgg agaagcaata agaatgccgg   8640

ttggggttgc gatgatgacg accacgacaa ctggtgtcat tatttaagtt gccgaaagaa   8700

cctgagtgca tttgcaacat gagtatacta gaagaatgag ccaagacttg cgagacgcga   8760

gtttgccggt ggtgcgaaca atagagcgac catgaccttg aaggtgagac gcgcataacc   8820

gctagagtac tttgaagagg aaacagcaat agggttgcta ccagtataaa tagacaggta   8880

catacaacac tggaaatggt tgtctgtttg agtacgcttt caa                     8923
```

```
<210> SEQ ID NO 151
<211> LENGTH: 6264
<212> TYPE: DNA
<213> ORGANISM: Artificial Sequence
<220> FEATURE:
<223> OTHER INFORMATION: pDEST23
<220> FEATURE:
<221> NAME/KEY: gene
<222> LOCATION: (161)..(285)
<223> OTHER INFORMATION: attR1
<220> FEATURE:
<221> NAME/KEY: gene
<222> LOCATION: (394)..(1053)
<223> OTHER INFORMATION: CmR
<220> FEATURE:
<221> NAME/KEY: gene
<222> LOCATION: (1173)..(1257)
<223> OTHER INFORMATION: inactivated ccdA
<220> FEATURE:
<221> NAME/KEY: gene
<222> LOCATION: (1395)..(1700)
<223> OTHER INFORMATION: ccdB
<220> FEATURE:
<221> NAME/KEY: gene
<222> LOCATION: (1741)..(1865)
<223> OTHER INFORMATION: attR2
<220> FEATURE:
<221> NAME/KEY: gene
<222> LOCATION: (1883)..(1911)
<223> OTHER INFORMATION: his6
<220> FEATURE:
<221> NAME/KEY: gene
<222> LOCATION: (2574)..(3434)
<223> OTHER INFORMATION: ampR
<220> FEATURE:
<221> NAME/KEY: gene
<222> LOCATION: (3583)..(4222)
<223> OTHER INFORMATION: ori

<400> SEQUENCE: 151
```

```
tcttccccat cggtgatgtc ggcgatatag gcgccagcaa ccgcacctgt ggcgccggtg     60

atgccggcca cgatgcgtcc ggcgtagagg atcgagatct cgatcccgcg aaattaatac    120

gactcactat agggagacca caacggtttc cctctagatc acaagtttgt acaaaaaagc    180

tgaacgagaa acgtaaaatg atataaatat caatatatta aattagattt tgcataaaaa    240

acagactaca taatactgta aaacacaaca tatccagtca ctatggcggc cgcattaggc    300

accccaggct ttacacttta tgcttccggc tcgtataatg tgtggatttt gagttaggat    360

ccggcgagat tttcaggagc taaggaagct aaaatggaga aaaaaatcac tggatatacc    420

accgttgata tatcccaatg gcatcgtaaa gaacattttg aggcatttca gtcagttgct    480

caatgtacct ataaccagac cgttcagctg gatattacgg cctttttaaa gaccgtaaag    540
```

-continued

```
aaaaataagc acaagtttta tccggccttt attcacattc ttgcccgcct gatgaatgct    600
catccggaat tccgtatggc aatgaaagac ggtgagctgg tgatatggga tagtgttcac    660
ccttgttaca ccgttttcca tgagcaaact gaaacgtttt catcgctctg gagtgaatac    720
cacgacgatt tccggcagtt tctacacata tattcgcaag atgtggcgtg ttacggtgaa    780
aacctggcct atttccctaa agggtttatt gagaatatgt ttttcgtctc agccaatccc    840
tgggtgagtt tcaccagttt tgatttaaac gtggccaata tggacaactt cttcgccccc    900
gttttcacca tgggcaaata ttatacgcaa ggcgacaagg tgctgatgcc gctggcgatt    960
caggttcatc atgccgtctg tgatggcttc catgtcggca gaatgcttaa tgaattacaa   1020
cagtactgcg atgagtggca gggcggggcg taaacgcgtg gatccggctt actaaaagcc   1080
agataacagt atgcgtattt gcgcgctgat ttttgcggta taagaatata tactgatatg   1140
tatacccgaa gtatgtcaaa aagaggtgtg ctatgaagca gcgtattaca gtgacagttg   1200
acagcgacag ctatcagttg ctcaaggcat atatgatgtc aatatctccg gtctggtaag   1260
cacaaccatg cagaatgaag cccgtcgtct gcgtgccgaa cgctggaaag cggaaaatca   1320
ggaagggatg gctgaggtcg cccggtttat tgaaatgaac ggctcttttg ctgacgagaa   1380
cagggactgg tgaaatgcag tttaaggttt acacctataa aagagagagc cgttatcgtc   1440
tgtttgtgga tgtacagagt gatattattg acacgcccgg gcgacggatg gtgatccccc   1500
tggccagtgc acgtctgctg tcagataaag tctcccgtga actttacccg gtggtgcata   1560
tcggggatga aagctggcgc atgatgacca ccgatatggc cagtgtgccg gtctccgtta   1620
tcggggaaga agtggctgat ctcagccacc gcgaaaatga catcaaaaac gccattaacc   1680
tgatgttctg gggaatataa atgtcaggct cccttataca cagccagtct gcaggtcgac   1740
catagtgact ggatatgttg tgttttacag tattatgtag tctgtttttt atgcaaaatc   1800
taatttaata tattgatatt tatatcattt tacgtttctc gttcagcttt cttgtacaaa   1860
gtggtgatta tgtcgtacta ccatcaccat caccatcacc tcgatgagca ataactagca   1920
taaccccttg gggcctctaa acgggtcttg aggggttttt tgctgaaagg aggaactata   1980
tccggatatc cacaggacgg gtgtggtcgc catgatcgcg tagtcgatag tggctccaag   2040
tagcgaagcg agcaggactg ggcggcggcc aaagcggtcg gacagtgctc cgagaacggg   2100
tgcgcataga aattgcatca acgcatatag cgctagcagc acgccatagt gactggcgat   2160
gctgtcggaa tggacgatat cccgcaagag gcccggcagt accggcataa ccaagcctat   2220
gcctacagca tccagggtga cggtgccgag gatgacgatg agcgcattgt tagatttcat   2280
acacggtgcc tgactgcgtt agcaatttaa ctgtgataaa ctaccgcatt aaagcttatc   2340
gatgataagc tgtcaaacat gagaattctt gaagacgaaa gggcctcgtg atacgcctat   2400
ttttataggt taatgtcatg ataataatgg tttcttagac gtcaggtggc acttttcggg   2460
gaaatgtgcg cggaacccct atttgtttat ttttctaaat acattcaaat atgtatccgc   2520
tcatgagaca ataaccctga taaatgcttc aataatattg aaaaaggaag agtatgagta   2580
ttcaacattt ccgtgtcgcc cttattccct tttttgcggc attttgcctt cctgtttttg   2640
ctcacccaga aacgctggtg aaagtaaaag atgctgaaga tcagttgggt gcacgagtgg   2700
gttacatcga actggatctc aacagcggta agatccttga gagttttcgc cccgaagaac   2760
gttttccaat gatgagcact tttaaagttc tgctatgtgg cgcggtatta tcccgtgttg   2820
acgccgggca agagcaactc ggtcgccgca tacactattc tcagaatgac ttggttgagt   2880
actcaccagt cacagaaaag catcttacgg atggcatgac agtaagagaa ttatgcagtg   2940
```

-continued ctgccataac catgagtgat aacactgcgg ccaacttact tctgacaacg atcggaggac 3000
cgaaggagct aaccgctttt ttgcacaaca tgggggatca tgtaactcgc cttgatcgtt 3060
gggaaccgga gctgaatgaa gccataccaa acgacgagcg tgacaccacg atgcctgcag 3120
caatggcaac aacgttgcgc aaactattaa ctggcgaact acttactcta gcttcccggc 3180
aacaattaat agactggatg gaggcggata aagttgcagg accacttctg cgctcggccc 3240
ttccggctgg ctggtttatt gctgataaat ctggagccgg tgagcgtggg tctcgcggta 3300
tcattgcagc actggggcca gatggtaagc cctcccgtat cgtagttatc tacacgacgg 3360
ggagtcaggc aactatggat gaacgaaata gacagatcgc tgagataggt gcctcactga 3420
ttaagcattg gtaactgtca gaccaagttt actcatatat actttagatt gatttaaaac 3480
ttcattttta atttaaaagg atctaggtga agatcctttt tgataatctc atgaccaaaa 3540
tcccttaacg tgagttttcg ttccactgag cgtcagaccc cgtagaaaag atcaaaggat 3600
cttcttgaga tccttttttt ctgcgcgtaa tctgctgctt gcaaacaaaa aaaccaccgc 3660
taccagcggt ggtttgtttg ccggatcaag agctaccaac tctttttccg aaggtaactg 3720
gcttcagcag agcgcagata ccaaatactg tccttctagt gtagccgtag ttaggccacc 3780
acttcaagaa ctctgtagca ccgcctacat acctcgctct gctaatcctg ttaccagtgg 3840
ctgctgccag tggcgataag tcgtgtctta ccgggttgga ctcaagacga tagttaccgg 3900
ataaggcgca gcggtcgggc tgaacggggg gttcgtgcac acagcccagc ttggagcgaa 3960
cgacctacac cgaactgaga tacctacagc gtgagctatg agaaagcgcc acgcttcccg 4020
aagggagaaa ggcggacagg tatccggtaa gcggcagggt cggaacagga gagcgcacga 4080
gggagcttcc agggggaaac gcctggtatc tttatagtcc tgtcgggttt cgccacctct 4140
gacttgagcg tcgatttttg tgatgctcgt caggggggcg gagcctatgg aaaaacgcca 4200
gcaacgcggc ctttttacgg ttcctggcct tttgctggcc ttttgctcac atgttctttc 4260
ctgcgttatc ccctgattct gtggataacc gtattaccgc ctttgagtga gctgataccg 4320
ctcgccgcag ccgaacgacc gagcgcagcg agtcagtgag cgaggaagcg gaagagcgcc 4380
tgatgcggta ttttctcctt acgcatctgt gcggtatttc acaccgcata tatggtgcac 4440
tctcagtaca atctgctctg atgccgcata gttaagccag tatacactcc gctatcgcta 4500
cgtgactggg tcatggctgc gccccgacac ccgccaacac ccgctgacgc gccctgacgg 4560
gcttgtctgc tcccggcatc cgcttacaga caagctgtga ccgtctccgg gagctgcatg 4620
tgtcagaggt tttcaccgtc atcaccgaaa cgcgcgaggc agctgcggta aagctcatca 4680
gcgtggtcgt gaagcgattc acagatgtct gcctgttcat ccgcgtccag ctcgttgagt 4740
ttctccagaa gcgttaatgt ctggcttctg ataaagcggg ccatgttaag ggcggttttt 4800
tcctgtttgg tcactgatgc ctccgtgtaa gggggatttc tgttcatggg ggtaatgata 4860
ccgatgaaac gagagaggat gctcacgata cgggttactg atgatgaaca tgcccggtta 4920
ctggaacgtt gtgagggtaa acaactggcg gtatggatgc ggcgggacca gagaaaaatc 4980
actcagggtc aatgccagcg cttcgttaat acagatgtag gtgttccaca gggtagccag 5040
cagcatcctg cgatgcagat ccggaacata atggtgcagg gcgctgactt ccgcgtttcc 5100
agactttacg aaacacggaa accgaagacc attcatgttg ttgctcaggt cgcagacgtt 5160
ttgcagcagc agtcgcttca cgttcgctcg cgtatcggtg attcattctg ctaaccagta 5220
aggcaacccc gccagcctag ccgggtcctc aacgacagga gcacgatcat gcgcacccgt 5280

-continued

```
ggccaggacc caacgctgcc cgagatgcgc cgcgtgcggc tgctggagat ggcggacgcg   5340

atggatatgt tctgccaagg gttggtttgc gcattcacag ttctccgcaa gaattgattg   5400

gctccaattc ttggagtggt gaatccgtta gcgaggtgcc gccggcttcc attcaggtcg   5460

aggtggcccg gctccatgca ccgcgacgca acgcggggag gcagacaagg tatagggcgg   5520

cgcctacaat ccatgccaac ccgttccatg tgctcgccga ggcggcataa atcgccgtga   5580

cgatcagcgg tccagtgatc gaagttaggc tggtaagagc cgcgagcgat ccttgaagct   5640

gtccctgatg gtcgtcatct acctgcctgg acagcatggc ctgcaacgcg ggcatcccga   5700

tgccgccgga agcgagaaga atcataatgg ggaaggccat ccagcctcgc gtcgcgaacg   5760

ccagcaagac gtagcccagc gcgtcggccg ccatgccggc gataatggcc tgcttctcgc   5820

cgaaacgttt ggtggcggga ccagtgacga aggcttgagc gagggcgtgc aagattccga   5880

ataccgcaag cgacaggccg atcatcgtcg cgctccagcg aaagcggtcc tcgccgaaaa   5940

tgacccagag cgctgccggc acctgtccta cgagttgcat gataaagaag acagtcataa   6000

gtgcggcgac gatagtcatg ccccgcgccc accggaagga gctgactggg ttgaaggctc   6060

tcaagggcat cggtcgatcg acgctctccc ttatgcgact cctgcattag gaagcagccc   6120

agtagtaggt tgaggccgtt gagcaccgcc gccgcaagga atggtgcatg caaggagatg   6180

gcgcccaaca gtcccccggc cacggggcct gccaccatac ccacgccgaa acaagcgctc   6240

atgagcccga agtggcgagc ccga                                          6264
```

<210> SEQ ID NO 152
<211> LENGTH: 6961
<212> TYPE: DNA
<213> ORGANISM: Artificial Sequence
<220> FEATURE:
<223> OTHER INFORMATION: pDEST24
<220> FEATURE:
<221> NAME/KEY: gene
<222> LOCATION: (71)..(195)
<223> OTHER INFORMATION: attR1
<220> FEATURE:
<221> NAME/KEY: gene
<222> LOCATION: (304)..(963)
<223> OTHER INFORMATION: CmR
<220> FEATURE:
<221> NAME/KEY: gene
<222> LOCATION: (1083)..(1167)
<223> OTHER INFORMATION: inactivated ccdA
<220> FEATURE:
<221> NAME/KEY: gene
<222> LOCATION: (1305)..(1610)
<223> OTHER INFORMATION: ccdB
<220> FEATURE:
<221> NAME/KEY: gene
<222> LOCATION: (1651)..(1775)
<223> OTHER INFORMATION: attR2
<220> FEATURE:
<221> NAME/KEY: gene
<222> LOCATION: (1783)..(2451)
<223> OTHER INFORMATION: GST
<220> FEATURE:
<221> NAME/KEY: gene
<222> LOCATION: (3181)..(4041)
<223> OTHER INFORMATION: ampR
<220> FEATURE:
<221> NAME/KEY: gene
<222> LOCATION: (4190)..(4829)
<223> OTHER INFORMATION: ori

<400> SEQUENCE: 152

```
atcgagatct cgatcccgcg aaattaatac gactcactat agggagacca caacggtttc     60

cctctagatc acaagtttgt acaaaaaagc tgaacgagaa acgtaaaatg atataaatat    120
```

-continued

```
caatatatta aattagattt tgcataaaaa acagactaca taatactgta aaacacaaca    180
tatccagtca ctatggcggc cgcattaggc accccaggct ttacacttta tgcttccggc    240
tcgtataatg tgtggatttt gagttaggat ccggcgagat tttcaggagc taaggaagct    300
aaaatggaga aaaaaatcac tggatatacc accgttgata tatcccaatg gcatcgtaaa    360
gaacattttg aggcatttca gtcagttgct caatgtacct ataaccagac cgttcagctg    420
gatattacgg cctttttaaa gaccgtaaag aaaaataagc acaagtttta tccggccttt    480
attcacattc ttgcccgcct gatgaatgct catccggaat tccgtatggc aatgaaagac    540
ggtgagctgg tgatatggga tagtgttcac ccttgttaca ccgttttcca tgagcaaact    600
gaaacgtttt catcgctctg gagtgaatac cacgacgatt tccggcagtt tctacacata    660
tattcgcaag atgtggcgtg ttacggtgaa aacctggcct atttccctaa agggtttatt    720
gagaatatgt ttttcgtctc agccaatccc tgggtgagtt tcaccagttt tgatttaaac    780
gtggccaata tggacaactt cttcgccccc gttttcacca tgggcaaata ttatacgcaa    840
ggcgacaagg tgctgatgcc gctggcgatt caggttcatc atgccgtctg tgatggcttc    900
catgtcggca gaatgcttaa tgaattacaa cagtactgcg atgagtggca gggcggggcg    960
taaacgcgtg gatccggctt actaaaagcc agataacagt atgcgtattt gcgcgctgat   1020
ttttgcggta taagaatata tactgatatg tatacccgaa gtatgtcaaa aagaggtgtg   1080
ctatgaagca gcgtattaca gtgacagttg acagcgacag ctatcagttg ctcaaggcat   1140
atatgatgtc aatatctccg gtctggtaag cacaaccatg cagaatgaag cccgtcgtct   1200
gcgtgccgaa cgctggaaag cggaaaatca ggaagggatg gctgaggtcg cccggtttat   1260
tgaaatgaac ggctcttttg ctgacgagaa cagggactgg tgaaatgcag tttaaggttt   1320
acacctataa aagagagagc cgttatcgtc tgtttgtgga tgtacagagt gatattattg   1380
acacgcccgg gcgacggatg gtgatccccc tggccagtgc acgtctgctg tcagataaag   1440
tctcccgtga actttacccg gtggtgcata tcggggatga aagctggcgc atgatgacca   1500
ccgatatggc cagtgtgccg gtctccgtta tcggggaaga agtggctgat ctcagccacc   1560
gcgaaaatga catcaaaaac gccattaacc tgatgttctg gggaatataa atgtcaggct   1620
cccttataca cagccagtct gcaggtcgac catagtgact ggatatgttg tgttttacag   1680
tattatgtag tctgtttttt atgcaaaatc taatttaata tattgatatt tatatcattt   1740
tacgtttctc gttcagcttt cttgtacaaa gtggtgatta tgtcccctat actaggttat   1800
tggaaaatta agggccttgt gcaacccact cgacttcttt tggaatatct tgaagaaaaa   1860
tatgaagagc atttgtatga gcgcgatgaa ggtgataaat ggcgaaacaa aaagtttgaa   1920
ttgggtttgg agtttcccaa tcttccttat tatattgatg gtgatgttaa attaacacag   1980
tctatggcca tcatacgtta tatagctgac aagcacaaca tgttgggtgg ttgtccaaaa   2040
gagcgtgcag agatttcaat gcttgaagga gcggttttgg atattagata cggtgtttcg   2100
agaattgcat atagtaaaga ctttgaaact ctcaaagttg attttcttag caagctacct   2160
gaaatgctga aaatgttcga agatcgttta tgtcataaaa catatttaaa tggtgatcat   2220
gtaacccatc ctgacttcat gttgtatgac gctcttgatg ttgttttata catggaccca   2280
atgtgcctgg atgcgttccc aaaattagtt tgttttaaaa aacgtattga agctatccca   2340
caaattgata agtacttgaa atccagcaag tatatagcat ggcctttgca gggctggcaa   2400
gccacgtttg gtggtggcga ccatcctcca aaatcggatc tggttccgcg tccatgggga   2460
```

-continued

```
tccggctgct aacaaagccc gaaaggaagc tgagttggct gctgccaccg ctgagcaata   2520
actagcataa ccccttgggg cctctaaacg ggtcttgagg ggttttttgc tgaaaggagg   2580
aactatatcc ggatatccac aggacgggtg tggtcgccat gatcgcgtag tcgatagtgg   2640
ctccaagtag cgaagcgagc aggactgggc ggcggccaaa gcggtcggac agtgctccga   2700
gaacgggtgc gcatagaaat tgcatcaacg catatagcgc tagcagcacg ccatagtgac   2760
tggcgatgct gtcggaatgg acgatatccc gcaagaggcc cggcagtacc ggcataacca   2820
agcctatgcc tacagcatcc agggtgacgg tgccgaggat gacgatgagc gcattgttag   2880
atttcataca cggtgcctga ctgcgttagc aatttaactg tgataaacta ccgcattaaa   2940
gcttatcgat gataagctgt caaacatgag aattcttgaa gacgaaaggg cctcgtgata   3000
cgcctatttt tataggttaa tgtcatgata ataatggttt cttagacgtc aggtggcact   3060
tttcggggaa atgtgcgcgg aacccctatt tgtttatttt tctaaataca ttcaaatatg   3120
tatccgctca tgagacaata accctgataa atgcttcaat aatattgaaa aaggaagagt   3180
atgagtattc aacatttccg tgtcgccctt attccctttt ttgcggcatt ttgccttcct   3240
gtttttgctc acccagaaac gctggtgaaa gtaaaagatg ctgaagatca gttgggtgca   3300
cgagtgggtt acatcgaact ggatctcaac agcggtaaga tccttgagag ttttcgcccc   3360
gaagaacgtt ttccaatgat gagcactttt aaagttctgc tatgtggcgc ggtattatcc   3420
cgtgttgacg ccgggcaaga gcaactcggt cgccgcatac actattctca gaatgacttg   3480
gttgagtact caccagtcac agaaaagcat cttacggatg gcatgacagt aagagaatta   3540
tgcagtgctg ccataaccat gagtgataac actgcggcca acttacttct gacaacgatc   3600
ggaggaccga aggagctaac cgcttttttg cacaacatgg gggatcatgt aactcgcctt   3660
gatcgttggg aaccggagct gaatgaagcc ataccaaacg acgagcgtga caccacgatg   3720
cctgcagcaa tggcaacaac gttgcgcaaa ctattaactg gcgaactact tactctagct   3780
tcccggcaac aattaataga ctggatggag gcggataaag ttgcaggacc acttctgcgc   3840
tcggcccttc cggctggctg gtttattgct gataaatctg gagccggtga gcgtgggtct   3900
cgcggtatca ttgcagcact ggggccagat ggtaagccct cccgtatcgt agttatctac   3960
acgacgggga gtcaggcaac tatggatgaa cgaaatagac agatcgctga gataggtgcc   4020
tcactgatta agcattggta actgtcagac caagtttact catatatact ttagattgat   4080
ttaaaacttc atttttaatt taaaaggatc taggtgaaga tcctttttga taatctcatg   4140
accaaaatcc cttaacgtga gttttcgttc cactgagcgt cagaccccgt agaaaagatc   4200
aaaggatctt cttgagatcc tttttttctg cgcgtaatct gctgcttgca aacaaaaaaa   4260
ccaccgctac cagcggtggt ttgtttgccg gatcaagagc taccaactct ttttccgaag   4320
gtaactggct tcagcagagc gcagatacca aatactgtcc ttctagtgta gccgtagtta   4380
ggccaccact tcaagaactc tgtagcaccg cctacatacc tcgctctgct aatcctgtta   4440
ccagtggctg ctgccagtgg cgataagtcg tgtcttaccg ggttggactc aagacgatag   4500
ttaccggata aggcgcagcg gtcgggctga acggggggtt cgtgcacaca gcccagcttg   4560
gagcgaacga cctacaccga actgagatac ctacagcgtg agctatgaga aagcgccacg   4620
cttcccgaag ggagaaaggc ggacaggtat ccggtaagcg gcagggtcgg aacaggagag   4680
cgcacgaggg agcttccagg gggaaacgcc tggtatcttt atagtcctgt cgggtttcgc   4740
cacctctgac ttgagcgtcg atttttgtga tgctcgtcag gggggcggag cctatggaaa   4800
aacgccagca acgcggcctt tttacggttc ctggcctttt gctggccttt tgctcacatg   4860
```

-continued

```
ttctttcctg cgttatcccc tgattctgtg gataaccgta ttaccgcctt tgagtgagct   4920
gataccgctc gccgcagccg aacgaccgag cgcagcgagt cagtgagcga ggaagcggaa   4980
gagcgcctga tgcggtattt tctccttacg catctgtgcg gtatttcaca ccgcatatat   5040
ggtgcactct cagtacaatc tgctctgatg ccgcatagtt aagccagtat acactccgct   5100
atcgctacgt gactgggtca tggctgcgcc ccgacacccg ccaacacccg ctgacgcgcc   5160
ctgacgggct tgtctgctcc cggcatccgc ttacagacaa gctgtgaccg tctccgggag   5220
ctgcatgtgt cagaggtttt caccgtcatc accgaaacgc gcgaggcagc tgcggtaaag   5280
ctcatcagcg tggtcgtgaa gcgattcaca gatgtctgcc tgttcatccg cgtccagctc   5340
gttgagtttc tccagaagcg ttaatgtctg gcttctgata aagcgggcca tgttaagggc   5400
ggtttttttcc tgtttggtca ctgatgcctc cgtgtaaggg ggatttctgt tcatgggggt   5460
aatgataccg atgaaacgag agaggatgct cacgatacgg gttactgatg atgaacatgc   5520
ccggttactg gaacgttgtg agggtaaaca actggcggta tggatgcggc gggaccagag   5580
aaaaatcact cagggtcaat gccagcgctt cgttaataca gatgtaggtg ttccacaggg   5640
tagccagcag catcctgcga tgcagatccg gaacataatg gtgcagggcg ctgacttccg   5700
cgtttccaga ctttacgaaa cacggaaacc gaagaccatt catgttgttg ctcaggtcgc   5760
agacgttttg cagcagcagt cgcttcacgt tcgctcgcgt atcggtgatt cattctgcta   5820
accagtaagg caaccccgcc agcctagccg ggtcctcaac gacaggagca cgatcatgcg   5880
cacccgtggc caggacccaa cgctgcccga gatgcgccgc gtgcggctgc tggagatggc   5940
ggacgcgatg gatatgttct gccaagggtt ggtttgcgca ttcacagttc tccgcaagaa   6000
ttgattggct ccaattcttg gagtggtgaa tccgttagcg aggtgccgcc ggcttccatt   6060
caggtcgagg tggcccggct ccatgcaccg cgacgcaacg cggggaggca gacaaggtat   6120
agggcggcgc ctacaatcca tgccaacccg ttccatgtgc tcgccgaggc ggcataaatc   6180
gccgtgacga tcagcggtcc agtgatcgaa gttaggctgg taagagccgc gagcgatcct   6240
tgaagctgtc cctgatggtc gtcatctacc tgcctggaca gcatggcctg caacgcgggc   6300
atcccgatgc cgccggaagc gagaagaatc ataatgggga aggccatcca gcctcgcgtc   6360
gcgaacgcca gcaagacgta gcccagcgcg tcggccgcca tgccggcgat aatggcctgc   6420
ttctcgccga aacgtttggt ggcgggacca gtgacgaagg cttgagcgag ggcgtgcaag   6480
attccgaata ccgcaagcga caggccgatc atcgtcgcgc tccagcgaaa gcggtcctcg   6540
ccgaaaatga cccagagcgc tgccggcacc tgtcctacga gttgcatgat aaagaagaca   6600
gtcataagtg cggcgacgat agtcatgccc cgcgcccacc ggaaggagct gactgggttg   6660
aaggctctca agggcatcgg tcgatcgacg ctctccctta tgcgactcct gcattaggaa   6720
gcagcccagt agtaggttga ggccgttgag caccgccgcc gcaaggaatg gtgcatgcaa   6780
ggagatggcg cccaacagtc ccccggccac ggggcctgcc accataccca cgccgaaaca   6840
agcgctcatg agcccgaagt ggcgagcccg atcttcccca tcggtgatgt cggcgatata   6900
ggcgccagca accgcacctg tggcgccggt gatgccggcc acgatgcgtc cggcgtagag   6960
g                                                                   6961
```

<210> SEQ ID NO 153
<211> LENGTH: 6652
<212> TYPE: DNA
<213> ORGANISM: Artificial Sequence
<220> FEATURE:

-continued

```
<223> OTHER INFORMATION: pDEST25
<220> FEATURE:
<221> NAME/KEY: gene
<222> LOCATION: (720)..(844)
<223> OTHER INFORMATION: attR1
<220> FEATURE:
<221> NAME/KEY: gene
<222> LOCATION: (953)..(1612)
<223> OTHER INFORMATION: CmR
<220> FEATURE:
<221> NAME/KEY: gene
<222> LOCATION: (1732)..(1816)
<223> OTHER INFORMATION: inactivated ccdA
<220> FEATURE:
<221> NAME/KEY: gene
<222> LOCATION: (1954)..(2259)
<223> OTHER INFORMATION: ccdB
<220> FEATURE:
<221> NAME/KEY: gene
<222> LOCATION: (2300)..(2424)
<223> OTHER INFORMATION: attR2
<220> FEATURE:
<221> NAME/KEY: gene
<222> LOCATION: (2432)..(2794)
<223> OTHER INFORMATION: trx

<400> SEQUENCE: 153

ccggaagcga gaagaatcat aatggggaag gccatccagc ctcgcgtcgc gaacgccagc     60

aagacgtagc ccagcgcgtc ggccgccatg ccggcgataa tggcctgctt ctcgccgaaa    120

cgtttggtgg cgggaccagt gacgaaggct tgagcgaggg cgtgcaagat tccgaatacc    180

gcaagcgaca ggccgatcat cgtcgcgctc cagcgaaagc ggtcctcgcc gaaaatgacc    240

cagagcgctg ccggcacctg tcctacgagt tgcatgataa agaagacagt cataagtgcg    300

gcgacgatag tcatgccccg cgcccaccgg aaggagctga ctgggttgaa ggctctcaag    360

ggcatcggtc gatcgacgct ctcccttatg cgactcctgc attaggaagc agcccagtag    420

taggttgagg ccgttgagca ccgccgccgc aaggaatggt gcatgcaagg agatggcgcc    480

caacagtccc ccggccacgg ggcctgccac catacccacg ccgaaacaag cgctcatgag    540

cccgaagtgg cgagcccgat cttccccatc ggtgatgtcg gcgatatagg cgccagcaac    600

cgcacctgtg gcgccggtga tgccggccac gatgcgtccg gcgtagagga tcgagatctc    660

gatcccgcga aattaatacg actcactata gggagaccac aacggtttcc ctctagatca    720

caagtttgta caaaaaagct gaacgagaaa cgtaaaatga tataaatatc aatatattaa    780

attagatttt gcataaaaaa cagactacat aatactgtaa aacacaacat atccagtcac    840

tatggcggcc gcattaggca ccccaggctt tacactttat gcttccggct cgtataatgt    900

gtggattttg agttaggatc cggcgagatt ttcaggagct aaggaagcta aaatggagaa    960

aaaaatcact ggatatacca ccgttgatat atcccaatgg catcgtaaag aacattttga   1020

ggcatttcag tcagttgctc aatgtaccta taaccagacc gttcagctgg atattacggc   1080

ctttttaaag accgtaaaga aaaataagca caagttttat ccggccttta ttcacattct   1140

tgcccgcctg atgaatgctc atccggaatt ccgtatggca atgaaagacg gtgagctggt   1200

gatatgggat agtgttcacc cttgttacac cgttttccat gagcaaactg aaacgttttc   1260

atcgctctgg agtgaatacc acgacgattt ccggcagttt ctacacatat attcgcaaga   1320

tgtggcgtgt tacggtgaaa acctggccta tttccctaaa gggtttattg agaatatgtt   1380

tttcgtctca gccaatccct gggtgagttt caccagtttt gatttaaacg tggccaatat   1440

ggacaacttc ttcgcccccg ttttcaccat gggcaaatat tatacgcaag gcgacaaggt   1500

gctgatgccg ctggcgattc aggttcatca tgccgtctgt gatggcttcc atgtcggcag   1560
```

-continued

```
aatgcttaat gaattacaac agtactgcga tgagtggcag ggcggggcgt aaacgcgtgg   1620
atccggctta ctaaaagcca gataacagta tgcgtatttg cgcgctgatt tttgcggtat   1680
aagaatatat actgatatgt atacccgaag tatgtcaaaa agaggtgtgc tatgaagcag   1740
cgtattacag tgacagttga cagcgacagc tatcagttgc tcaaggcata tatgatgtca   1800
atatctccgg tctggtaagc acaaccatgc agaatgaagc ccgtcgtctg cgtgccgaac   1860
gctggaaagc ggaaaatcag gaagggatgg ctgaggtcgc ccggtttatt gaaatgaacg   1920
gctcttttgc tgacgagaac agggactggt gaaatgcagt ttaaggttta cacctataaa   1980
agagagagcc gttatcgtct gtttgtggat gtacagagtg atattattga cacgcccggg   2040
cgacggatgg tgatccccct ggccagtgca cgtctgctgt cagataaagt ctcccgtgaa   2100
ctttacccgg tggtgcatat cggggatgaa agctggcgca tgatgaccac cgatatggcc   2160
agtgtgccgg tctccgttat cggggaagaa gtggctgatc tcagccaccg cgaaaatgac   2220
atcaaaaacg ccattaacct gatgttctgg ggaatataaa tgtcaggctc ccttatacac   2280
agccagtctg caggtcgacc atagtgactg gatatgttgt gttttacagt attatgtagt   2340
ctgtttttta tgcaaaatct aatttaatat attgatattt atatcatttt acgtttctcg   2400
ttcagctttc ttgtacaaag tggtgattat gagcgataaa attattcacc tgactgacga   2460
cagttttgac acggatgtac tcaaagcgga cggggcgatc ctcgtcgatt tctgggcaga   2520
gtggtgcggt ccgtgcaaaa tgatcgcccc gattctggat gaaatcgctg acgaatatca   2580
gggcaaactg accgttgcaa aactgaacat cgatcaaaac cctggcactg cgccgaaata   2640
tggcatccgt ggtatcccga ctctgctgct gttcaaaaac ggtgaagtgg cggcaaccaa   2700
agtgggtgca ctgtctaaag gtcagttgaa agagttcctc gacgctaacc tggccggttc   2760
tggttctggt gatgacgatg acaaggtacc cggggatcga tccggctgct aacaaagccc   2820
gaaaggaagc tgagttggct gctgccaccg ctgagcaata actagcataa ccccttgggg   2880
cctctaaacg ggtcttgagg ggttttttgc tgaaaggagg aactatatcc ggatatccac   2940
aggacgggtg tggtcgccat gatcgcgtag tcgatagtgg ctccaagtag cgaagcgagc   3000
aggactgggc ggcggccaaa gcggtcggac agtgctccga gaacgggtgc gcatagaaat   3060
tgcatcaacg catatagcgc tagcagcacg ccatagtgac tggcgatgct gtcggaatgg   3120
acgatatccc gcaagaggcc cggcagtacc ggcataacca agcctatgcc tacagcatcc   3180
agggtgacgg tgccgaggat gacgatgagc gcattgttag atttcataca cggtgcctga   3240
ctgcgttagc aatttaactg tgataaacta ccgcattaaa gcttatcgat gataagctgt   3300
caaacatgag aattcttgaa gacgaaaggg cctcgtgata cgcctatttt tataggttaa   3360
tgtcatgata ataatggttt cttagacgtc aggtggcact tttcggggaa atgtgcgcgg   3420
aacccctatt tgtttatttt tctaaataca ttcaaatatg tatccgctca tgagacaata   3480
accctgataa atgcttcaat aatattgaaa aaggaagagt atgagtattc aacatttccg   3540
tgtcgccctt attccctttt ttgcggcatt ttgccttcct gtttttgctc acccagaaac   3600
gctggtgaaa gtaaaagatg ctgaagatca gttgggtgca cgagtgggtt acatcgaact   3660
ggatctcaac agcggtaaga tccttgagag ttttcgcccc gaagaacgtt ttccaatgat   3720
gagcactttt aaagttctgc tatgtggcgc ggtattatcc cgtgttgacg ccgggcaaga   3780
gcaactcggt cgccgcatac actattctca gaatgacttg gttgagtact caccagtcac   3840
agaaaagcat cttacggatg gcatgacagt aagagaatta tgcagtgctg ccataaccat   3900
```

-continued

```
gagtgataac actgcggcca acttacttct gacaacgatc ggaggaccga aggagctaac   3960
cgcttttttg cacaacatgg gggatcatgt aactcgcctt gatcgttggg aaccggagct   4020
gaatgaagcc ataccaaacg acgagcgtga caccacgatg cctgcagcaa tggcaacaac   4080
gttgcgcaaa ctattaactg gcgaactact tactctagct tcccggcaac aattaataga   4140
ctggatggag gcggataaag ttgcaggacc acttctgcgc tcggcccttc cggctggctg   4200
gtttattgct gataaatctg gagccggtga gcgtgggtct cgcggtatca ttgcagcact   4260
ggggccagat ggtaagccct cccgtatcgt agttatctac acgacgggga gtcaggcaac   4320
tatggatgaa cgaaatagac agatcgctga gataggtgcc tcactgatta agcattggta   4380
actgtcagac caagtttact catatatact ttagattgat ttaaaacttc atttttaatt   4440
taaaaggatc taggtgaaga tcctttttga taatctcatg accaaaatcc cttaacgtga   4500
gttttcgttc cactgagcgt cagaccccgt agaaaagatc aaaggatctt cttgagatcc   4560
tttttttctg cgcgtaatct gctgcttgca aacaaaaaaa ccaccgctac cagcggtggt   4620
ttgtttgccg gatcaagagc taccaactct ttttccgaag gtaactggct tcagcagagc   4680
gcagatacca aatactgtcc ttctagtgta gccgtagtta ggccaccact tcaagaactc   4740
tgtagcaccg cctacatacc tcgctctgct aatcctgtta ccagtggctg ctgccagtgg   4800
cgataagtcg tgtcttaccg ggttggactc aagacgatag ttaccggata aggcgcagcg   4860
gtcgggctga acggggggtt cgtgcacaca gcccagcttg gagcgaacga cctacaccga   4920
actgagatac ctacagcgtg agctatgaga aagcgccacg cttcccgaag ggagaaaggc   4980
ggacaggtat ccggtaagcg gcagggtcgg aacaggagag cgcacgaggg agcttccagg   5040
gggaaacgcc tggtatcttt atagtcctgt cgggtttcgc cacctctgac ttgagcgtcg   5100
atttttgtga tgctcgtcag gggggcggag cctatggaaa aacgccagca acgcggcctt   5160
tttacggttc ctggcctttt gctggccttt tgctcacatg ttctttcctg cgttatcccc   5220
tgattctgtg gataaccgta ttaccgcctt tgagtgagct gataccgctc gccgcagccg   5280
aacgaccgag cgcagcgagt cagtgagcga ggaagcggaa gagcgcctga tgcggtattt   5340
tctccttacg catctgtgcg gtatttcaca ccgcatatat ggtgcactct cagtacaatc   5400
tgctctgatg ccgcatagtt aagccagtat acactccgct atcgctacgt gactgggtca   5460
tggctgcgcc ccgacacccg ccaacacccg ctgacgcgcc ctgacgggct tgtctgctcc   5520
cggcatccgc ttacagacaa gctgtgaccg tctccgggag ctgcatgtgt cagaggtttt   5580
caccgtcatc accgaaacgc gcgaggcagc tgcggtaaag ctcatcagcg tggtcgtgaa   5640
gcgattcaca gatgtctgcc tgttcatccg cgtccagctc gttgagtttc tccagaagcg   5700
ttaatgtctg gcttctgata aagcgggcca tgttaagggc ggtttttcc tgtttggtca   5760
ctgatgcctc cgtgtaaggg ggatttctgt tcatgggggt aatgataccg atgaaacgag   5820
agaggatgct cacgatacgg gttactgatg atgaacatgc ccggttactg gaacgttgtg   5880
agggtaaaca actggcggta tggatgcggc gggaccagag aaaaatcact cagggtcaat   5940
gccagcgctt cgttaataca gatgtaggtg ttccacaggg tagccagcag catcctgcga   6000
tgcagatccg gaacataatg gtgcagggcg ctgacttccg cgtttccaga ctttacgaaa   6060
cacggaaacc gaagaccatt catgttgttg ctcaggtcgc agacgttttg cagcagcagt   6120
cgcttcacgt tcgctcgcgt atcggtgatt cattctgcta accagtaagg caaccccgcc   6180
agcctagccg ggtcctcaac gacaggagca cgatcatgcg cacccgtggc caggacccaa   6240
cgctgcccga gatgcgccgc gtgcggctgc tggagatggc ggacgcgatg gatatgttct   6300
```

-continued

```
gccaagggtt ggtttgcgca ttcacagttc tccgcaagaa ttgattggct ccaattcttg   6360

gagtggtgaa tccgttagcg aggtgccgcc ggcttccatt caggtcgagg tggcccggct   6420

ccatgcaccg cgacgcaacg cggggaggca gacaaggtat agggcggcgc ctacaatcca   6480

tgccaacccg ttccatgtgc tcgccgaggc ggcataaatc gccgtgacga tcagcggtcc   6540

agtgatcgaa gttaggctgg taagagccgc gagcgatcct tgaagctgtc cctgatggtc   6600

gtcatctacc tgcctggaca gcatggcctg caacgcgggc atcccgatgc cg           6652
```

<210> SEQ ID NO 154
<211> LENGTH: 7481
<212> TYPE: DNA
<213> ORGANISM: Artificial Sequence
<220> FEATURE:
<223> OTHER INFORMATION: pDEST26
<220> FEATURE:
<221> NAME/KEY: gene
<222> LOCATION: (492)..(509)
<223> OTHER INFORMATION: his6
<220> FEATURE:
<221> NAME/KEY: gene
<222> LOCATION: (519)..(619)
<223> OTHER INFORMATION: attR1
<220> FEATURE:
<221> NAME/KEY: gene
<222> LOCATION: (752)..(1411)
<223> OTHER INFORMATION: CmR
<220> FEATURE:
<221> NAME/KEY: gene
<222> LOCATION: (1531)..(1615)
<223> OTHER INFORMATION: inactivated ccdA
<220> FEATURE:
<221> NAME/KEY: gene
<222> LOCATION: (1753)..(2058)
<223> OTHER INFORMATION: ccdB
<220> FEATURE:
<221> NAME/KEY: gene
<222> LOCATION: (2099)..(2223)
<223> OTHER INFORMATION: attR2
<220> FEATURE:
<221> NAME/KEY: gene
<222> LOCATION: (2409)..(2771)
<223> OTHER INFORMATION: SV40 polyA
<220> FEATURE:
<221> NAME/KEY: gene
<222> LOCATION: (2966)..(3421)
<223> OTHER INFORMATION: f1 intergenic region
<220> FEATURE:
<221> NAME/KEY: gene
<222> LOCATION: (3485)..(3903)
<223> OTHER INFORMATION: SV40 promoter
<220> FEATURE:
<221> NAME/KEY: gene
<222> LOCATION: (3948)..(4742)
<223> OTHER INFORMATION: neo
<220> FEATURE:
<221> NAME/KEY: gene
<222> LOCATION: (4806)..(4854)
<223> OTHER INFORMATION: polyA
<220> FEATURE:
<221> NAME/KEY: gene
<222> LOCATION: (5265)..(6125)
<223> OTHER INFORMATION: Apr
<220> FEATURE:
<221> NAME/KEY: gene
<222> LOCATION: (5274)..(6913)
<223> OTHER INFORMATION: ori
<220> FEATURE:
<221> NAME/KEY: gene
<222> LOCATION: (385)..(7344)
<223> OTHER INFORMATION: CMV promoter

<400> SEQUENCE: 154

-continued

```
gtaaactgcc cacttggcag tacatcaagt gtatcatatg ccaagtacgc cccctattga     60
cgtcaatgac ggtaaatggc ccgcctggca ttatgcccag tacatgacct tatgggactt    120
tcctacttgg cagtacatct acgtattagt catcgctatt accatggtga tgcggttttg    180
gcagtacatc aatgggcgtg gatagcggtt tgactcacgg ggatttccaa gtctccaccc    240
cattgacgtc aatgggagtt tgttttggca ccaaaatcaa cgggactttc caaaatgtcg    300
taacaactcc gccccattga cgcaaatggg cggtaggcgt gtacggtggg aggtctatat    360
aagcagagct cgtttagtga accgtcagat cgcctggaga cgccatccac gctgttttga    420
cctccataga agacaccggg accgatccag cctccggact ctagcctagg ccgcggacca    480
tggcgtacta ccatcaccat caccatcact ctagatcaac aagtttgtac aaaaaagctg    540
aacgagaaac gtaaaatgat ataaatatca atatattaaa ttagattttg cataaaaaac    600
agactacata atactgtaaa acacaacata tccagtcact atggcggccg cattaggcac    660
cccaggcttt acactttatg cttccggctc gtataatgtg tggattttga gttaggatcc    720
ggcgagattt tcaggagcta aggaagctaa aatggagaaa aaaatcactg gatataccac    780
cgttgatata tcccaatggc atcgtaaaga acattttgag gcatttcagt cagttgctca    840
atgtacctat aaccagaccg ttcagctgga tattacggcc tttttaaaga ccgtaaagaa    900
aaataagcac aagttttatc cggcctttat tcacattctt gcccgcctga tgaatgctca    960
tccggaattc cgtatggcaa tgaaagacgg tgagctggtg atatgggata gtgttcaccc   1020
ttgttacacc gttttccatg agcaaactga aacgttttca tcgctctgga gtgaatacca   1080
cgacgatttc cggcagtttc tacacatata ttcgcaagat gtggcgtgtt acggtgaaaa   1140
cctggcctat ttccctaaag ggtttattga gaatatgttt ttcgtctcag ccaatccctg   1200
ggtgagtttc accagttttg atttaaacgt ggccaatatg gacaacttct tcgcccccgt   1260
tttcaccatg ggcaaatatt atacgcaagg cgacaaggtg ctgatgccgc tggcgattca   1320
ggttcatcat gccgtctgtg atggcttcca tgtcggcaga atgcttaatg aattacaaca   1380
gtactgcgat gagtggcagg gcggggcgta aagatctgga tccggcttac taaaagccag   1440
ataacagtat gcgtatttgc gcgctgattt ttgcggtata agaatatata ctgatatgta   1500
tacccgaagt atgtcaaaaa gaggtgtgct atgaagcagc gtattacagt gacagttgac   1560
agcgacagct atcagttgct caaggcatat atgatgtcaa tatctccggt ctggtaagca   1620
caaccatgca gaatgaagcc cgtcgtctgc gtgccgaacg ctggaaagcg gaaaatcagg   1680
aagggatggc tgaggtcgcc cggtttattg aaatgaacgg ctcttttgct gacgagaaca   1740
gggactggtg aaatgcagtt taaggtttac acctataaaa gagagagccg ttatcgtctg   1800
tttgtggatg tacagagtga tattattgac acgcccgggc gacggatggt gatccccctg   1860
gccagtgcac gtctgctgtc agataaagtc tcccgtgaac tttacccggt ggtgcatatc   1920
ggggatgaaa gctggcgcat gatgaccacc gatatggcca gtgtgccggt ctccgttatc   1980
ggggaagaag tggctgatct cagccaccgc gaaaatgaca tcaaaaacgc cattaacctg   2040
atgttctggg gaatataaat gtcaggctcc cttatacaca gccagtctgc aggtcgacca   2100
tagtgactgg atatgttgtg ttttacagta ttatgtagtc tgttttttat gcaaaatcta   2160
atttaatata ttgatattta tatcatttta cgtttctcgt tcagctttct tgtacaaagt   2220
ggttgatcgc gtgcatgcga cgtcatagct ctctccctat agtgagtcgt attataagct   2280
aggcactggc cgtcgtttta caacgtcgtg actgggaaaa ctgctagctt gggatctttg   2340
tgaaggaacc ttacttctgt ggtgtgacat aattggacaa actacctaca gagatttaaa   2400
```

-continued

```
gctctaaggt aaatataaaa tttttaagtg tataatgtgt taaactagct gcatatgctt   2460
gctgcttgag agttttgctt actgagtatg atttatgaaa atattataca caggagctag   2520
tgattctaat tgtttgtgta ttttagattc acagtcccaa ggctcatttc aggcccctca   2580
gtcctcacag tctgttcatg atcataatca gccataccac atttgtagag gttttacttg   2640
ctttaaaaaa cctcccacac ctccccctga acctgaaaca taaaatgaat gcaattgttg   2700
ttgttaactt gtttattgca gcttataatg gttacaaata aagcaatagc atcacaaatt   2760
tcacaaataa agcatttttt tcactgcatt ctagttgtgg tttgtccaaa ctcatcaatg   2820
tatcttatca tgtctggatc gatcctgcat taatgaatcg gccaacgcgc ggggagaggc   2880
ggtttgcgta ttggctggcg taatagcgaa gaggcccgca ccgatcgccc ttcccaacag   2940
ttgcgcagcc tgaatggcga atgggacgcg ccctgtagcg gcgcattaag cgcggcgggt   3000
gtggtggtta cgcgcagcgt gaccgctaca cttgccagcg ccctagcgcc cgctcctttc   3060
gctttcttcc cttcctttct cgccacgttc gccggctttc cccgtcaagc tctaaatcgg   3120
gggctccctt tagggttccg atttagtgct ttacggcacc tcgaccccaa aaaacttgat   3180
tagggtgatg gttcacgtag tgggccatcg ccctgataga cggtttttcg ccctttgacg   3240
ttggagtcca cgttctttaa tagtggactc ttgttccaaa ctggaacaac actcaaccct   3300
atctcggtct attcttttga tttataaggg attttgccga tttcggccta ttggttaaaa   3360
aatgagctga tttaacaaat atttaacgcg aattttaaca aaatattaac gtttacaatt   3420
tcgcctgatg cggtattttc tccttacgca tctgtgcggt atttcacacc gcatacgcgg   3480
atctgcgcag caccatggcc tgaaataacc tctgaaagag gaacttggtt aggtaccttc   3540
tgaggcggaa agaaccagct gtggaatgtg tgtcagttag ggtgtggaaa gtccccaggc   3600
tccccagcag gcagaagtat gcaaagcatg catctcaatt agtcagcaac caggtgtgga   3660
aagtccccag gctccccagc aggcagaagt atgcaaagca tgcatctcaa ttagtcagca   3720
accatagtcc cgcccctaac tccgcccatc ccgcccctaa ctccgcccag ttccgcccat   3780
tctccgcccc atggctgact aatttttttt atttatgcag aggccgaggc cgcctcggcc   3840
tctgagctat tccagaagta gtgaggaggc ttttttggag gcctaggctt ttgcaaaaag   3900
cttgattctt ctgacacaac agtctcgaac ttaaggctag agccaccatg attgaacaag   3960
atggattgca cgcaggttct ccggccgctt gggtggagag gctattcggc tatgactggg   4020
cacaacagac aatcggctgc tctgatgccg ccgtgttccg gctgtcagcg caggggcgcc   4080
cggttctttt tgtcaagacc gacctgtccg gtgccctgaa tgaactgcag gacgaggcag   4140
cgcggctatc gtggctggcc acgacgggcg ttccttgcgc agctgtgctc gacgttgtca   4200
ctgaagcggg aagggactgg ctgctattgg gcgaagtgcc ggggcaggat ctcctgtcat   4260
ctcaccttgc tcctgccgag aaagtatcca tcatggctga tgcaatgcgg cggctgcata   4320
cgcttgatcc ggctacctgc ccattcgacc accaagcgaa acatcgcatc gagcgagcac   4380
gtactcggat ggaagccggt cttgtcgatc aggatgatct ggacgaagag catcaggggc   4440
tcgcgccagc cgaactgttc gccaggctca aggcgcgcat gcccgacggc gaggatctcg   4500
tcgtgaccca tggcgatgcc tgcttgccga atatcatggt ggaaaatggc cgcttttctg   4560
gattcatcga ctgtggccgg ctgggtgtgg cggaccgcta tcaggacata gcgttggcta   4620
cccgtgatat tgctgaagag cttggcggcg aatgggctga ccgcttcctc gtgctttacg   4680
gtatcgccgc tcccgattcg cagcgcatcg ccttctatcg ccttcttgac gagttcttct   4740
```

-continued

```
gagcgggact ctggggttcg aaatgaccga ccaagcgacg cccaacctgc catcacgatg   4800
gccgcaataa aatatcttta ttttcattac atctgtgtgt tggtttttg tgtgaatcga   4860
tagcgataag gatccgcgta tggtgcactc tcagtacaat ctgctctgat gccgcatagt   4920
taagccagcc ccgacacccg ccaacacccg ctgacgcgcc ctgacgggct tgtctgctcc   4980
cggcatccgc ttacagacaa gctgtgaccg tctccgggag ctgcatgtgt cagaggtttt   5040
caccgtcatc accgaaacgc gcgagacgaa agggcctcgt gatacgccta tttttatagg   5100
ttaatgtcat gataataatg gtttcttaga cgtcaggtgg cacttttcgg ggaaatgtgc   5160
gcggaacccc tatttgttta tttttctaaa tacattcaaa tatgtatccg ctcatgagac   5220
aataaccctg ataaatgctt caataatatt gaaaaaggaa gagtatgagt attcaacatt   5280
tccgtgtcgc ccttattccc ttttttgcgg cattttgcct tcctgttttt gctcacccag   5340
aaacgctggt gaaagtaaaa gatgctgaag atcagttggg tgcacgagtg ggttacatcg   5400
aactggatct caacagcggt aagatccttg agagttttcg ccccgaagaa cgttttccaa   5460
tgatgagcac ttttaaagtt ctgctatgtg gcgcggtatt atcccgtatt gacgccgggc   5520
aagagcaact cggtcgccgc atacactatt ctcagaatga cttggttgag tactcaccag   5580
tcacagaaaa gcatcttacg gatggcatga cagtaagaga attatgcagt gctgccataa   5640
ccatgagtga taacactgcg gccaacttac ttctgacaac gatcggagga ccgaaggagc   5700
taaccgcttt tttgcacaac atgggggatc atgtaactcg ccttgatcgt tgggaaccgg   5760
agctgaatga agccatacca aacgacgagc gtgacaccac gatgcctgta gcaatggcaa   5820
caacgttgcg caaactatta actggcgaac tacttactct agcttcccgg caacaattaa   5880
tagactggat ggaggcggat aaagttgcag gaccacttct gcgctcggcc cttccggctg   5940
gctggtttat tgctgataaa tctggagccg gtgagcgtgg gtctcgcggt atcattgcag   6000
cactggggcc agatggtaag ccctcccgta tcgtagttat ctacacgacg gggagtcagg   6060
caactatgga tgaacgaaat agacagatcg ctgagatagg tgcctcactg attaagcatt   6120
ggtaactgtc agaccaagtt tactcatata tactttagat tgatttaaaa cttcattttt   6180
aatttaaaag gatctaggtg aagatccttt ttgataatct catgaccaaa atcccttaac   6240
gtgagttttc gttccactga gcgtcagacc ccgtagaaaa gatcaaagga tcttcttgag   6300
atcctttttt tctgcgcgta atctgctgct tgcaaacaaa aaaaccaccg ctaccagcgg   6360
tggtttgttt gccggatcaa gagctaccaa ctctttttcc gaaggtaact ggcttcagca   6420
gagcgcagat accaaatact gtccttctag tgtagccgta gttaggccac cacttcaaga   6480
actctgtagc accgcctaca tacctcgctc tgctaatcct gttaccagtg gctgctgcca   6540
gtggcgataa gtcgtgtctt accgggttgg actcaagacg atagttaccg gataaggcgc   6600
agcggtcggg ctgaacgggg ggttcgtgca cacagcccag cttggagcga acgacctaca   6660
ccgaactgag atacctacag cgtgagcatt gagaaagcgc cacgcttccc gaagggagaa   6720
aggcggacag gtatccggta agcggcaggg tcggaacagg agagcgcacg agggagcttc   6780
cagggggaaa cgcctggtat ctttatagtc ctgtcgggtt tcgccacctc tgacttgagc   6840
gtcgattttt gtgatgctcg tcaggggggc ggagcctatg gaaaaacgcc agcaacgcgg   6900
cctttttacg gttcctggcc ttttgctggc cttttgctca catgttcttt cctgcgttat   6960
cccctgattc tgtggataac cgtattaccg cctttgagtg agctgatacc gctcgccgca   7020
gccgaacgac cgagcgcagc gagtcagtga gcgaggaagc ggaagagcgc ccaatacgca   7080
aaccgcctct ccccgcgcgt tggccgattc attaatgcag agcttgcaat tcgcgcgttt   7140
```

-continued

```
ttcaatatta ttgaagcatt tatcagggtt attgtctcat gagcggatac atatttgaat   7200

gtatttagaa aaataaacaa ataggggttc cgcgcacatt tccccgaaaa gtgccacctg   7260

acgtctaaga aaccattatt atcatgacat taacctataa aaataggcgt agtacgaggc   7320

cctttcactc attagatgca tgtcgttaca taacttacgg taaatggccc gcctggctga   7380

ccgcccaacg acccccgccc attgacgtca ataatgacgt atgttcccat agtaacgcca   7440

atagggactt tccattgacg tcaatgggtg gagtatttac g                       7481
```

<210> SEQ ID NO 155
<211> LENGTH: 8123
<212> TYPE: DNA
<213> ORGANISM: Artificial Sequence
<220> FEATURE:
<223> OTHER INFORMATION: pDEST27
<220> FEATURE:
<221> NAME/KEY: gene
<222> LOCATION: (130)..(793)
<223> OTHER INFORMATION: GST
<220> FEATURE:
<221> NAME/KEY: gene
<222> LOCATION: (803)..(927)
<223> OTHER INFORMATION: attR1
<220> FEATURE:
<221> NAME/KEY: gene
<222> LOCATION: (1036)..(1695)
<223> OTHER INFORMATION: CmR
<220> FEATURE:
<221> NAME/KEY: gene
<222> LOCATION: (1815)..(1899)
<223> OTHER INFORMATION: inactivated ccdA
<220> FEATURE:
<221> NAME/KEY: gene
<222> LOCATION: (2037)..(2342)
<223> OTHER INFORMATION: ccdB
<220> FEATURE:
<221> NAME/KEY: gene
<222> LOCATION: (2383)..(2507)
<223> OTHER INFORMATION: attR2
<220> FEATURE:
<221> NAME/KEY: gene
<222> LOCATION: (2693)..(3055)
<223> OTHER INFORMATION: SV40 polyA
<220> FEATURE:
<221> NAME/KEY: gene
<222> LOCATION: (3250)..(3705)
<223> OTHER INFORMATION: f1 intergenic region
<220> FEATURE:
<221> NAME/KEY: gene
<222> LOCATION: (3769)..(4187)
<223> OTHER INFORMATION: SV40 promoter
<220> FEATURE:
<221> NAME/KEY: gene
<222> LOCATION: (4232)..(5026)
<223> OTHER INFORMATION: neo
<220> FEATURE:
<221> NAME/KEY: gene
<222> LOCATION: (5090)..(5138)
<223> OTHER INFORMATION: polyA
<220> FEATURE:
<221> NAME/KEY: gene
<222> LOCATION: (5549)..(6409)
<223> OTHER INFORMATION: Apr
<220> FEATURE:
<221> NAME/KEY: gene
<222> LOCATION: (6558)..(7197)
<223> OTHER INFORMATION: ori
<220> FEATURE:
<221> NAME/KEY: gene
<222> LOCATION: (27)..(7628)
<223> OTHER INFORMATION: CMV promoter

<400> SEQUENCE: 155

-continued

```
ataagcagag ctcgtttagt gaaccgtcag atcgcctgga gacgccatcc acgctgtttt     60
gacctccata gaagacaccg ggaccgatcc agcctccgga ctctagccta ggccgcggac    120
catggcccct atactaggtt attggaaaat taagggcctt gtgcaaccca ctcgacttct    180
tttggaatat cttgaagaaa aatatgaaga gcatttgtat gagcgcgatg aaggtgataa    240
atggcgaaac aaaaagtttg aattgggttt ggagtttccc aatcttcctt attatattga    300
tggtgatgtt aaattaacac agtctatggc catcatacgt tatatagctg acaagcacaa    360
catgttgggt ggttgtccaa aagagcgtgc agagatttca atgcttgaag gagcggtttt    420
ggatattaga tacggtgttt cgagaattgc atatagtaaa gactttgaaa ctctcaaagt    480
tgattttctt agcaagctac ctgaaatgct gaaaatgttc gaagatcgtt tatgtcataa    540
aacatattta aatggtgatc atgtaaccca tcctgacttc atgttgtatg acgctcttga    600
tgttgtttta tacatggacc caatgtgcct ggatgcgttc ccaaaattag tttgttttaa    660
aaaacgtatt gaagctatcc cacaaattga taagtacttg aaatccagca agtatatagc    720
atggcctttg cagggctggc aagccacgtt tggtggtggc gaccatcctc caaaatcgga    780
tctggttccg cgttctagat caacaagttt gtacaaaaaa gctgaacgag aaacgtaaaa    840
tgatataaat atcaatatat taaattagat tttgcataaa aaacagacta cataatactg    900
taaaacacaa catatccagt cactatggcg gccgcattag gcaccccagg ctttacactt    960
tatgcttccg gctcgtataa tgtgtggatt ttgagttagg atccggcgag attttcagga   1020
gctaaggaag ctaaaatgga gaaaaaaatc actggatata ccaccgttga tatatcccaa   1080
tggcatcgta aagaacattt tgaggcattt cagtcagttg ctcaatgtac ctataaccag   1140
accgttcagc tggatattac ggccttttta aagaccgtaa agaaaaataa gcacaagttt   1200
tatccggcct ttattcacat tcttgcccgc ctgatgaatg ctcatccgga attccgtatg   1260
gcaatgaaag acggtgagct ggtgatatgg gatagtgttc acccttgtta caccgttttc   1320
catgagcaaa ctgaaacgtt ttcatcgctc tggagtgaat accacgacga tttccggcag   1380
tttctacaca tatattcgca agatgtggcg tgttacggtg aaaacctggc ctatttccct   1440
aaagggttta ttgagaatat gtttttcgtc tcagccaatc cctgggtgag tttcaccagt   1500
tttgatttaa acgtggccaa tatggacaac ttcttcgccc ccgttttcac catgggcaaa   1560
tattatacgc aaggcgacaa ggtgctgatg ccgctggcga ttcaggttca tcatgccgtc   1620
tgtgatggct tccatgtcgg cagaatgctt aatgaattac aacagtactg cgatgagtgg   1680
cagggcgggg cgtaaagatc tggatccggc ttactaaaag ccagataaca gtatgcgtat   1740
ttgcgcgctg atttttgcgg tataagaata tatactgata tgtatacccg aagtatgtca   1800
aaaagaggtg tgctatgaag cagcgtatta cagtgacagt tgacagcgac agctatcagt   1860
tgctcaaggc atatatgatg tcaatatctc cggtctggta agcacaacca tgcagaatga   1920
agcccgtcgt ctgcgtgccg aacgctggaa agcggaaaat caggaaggga tggctgaggt   1980
cgcccggttt attgaaatga acggctcttt tgctgacgag aacagggact ggtgaaatgc   2040
agtttaaggt ttacacctat aaaagagaga gccgttatcg tctgtttgtg gatgtacaga   2100
gtgatattat tgacacgccc gggcgacgga tggtgatccc cctggccagt gcacgtctgc   2160
tgtcagataa agtctcccgt gaactttacc cggtggtgca tatcggggat gaaagctggc   2220
gcatgatgac caccgatatg gccagtgtgc cggtctccgt tatcggggaa gaagtggctg   2280
atctcagcca ccgcgaaaat gacatcaaaa acgccattaa cctgatgttc tggggaatat   2340
aaatgtcagg ctcccttata cacagccagt ctgcaggtcg accatagtga ctggatatgt   2400
```

-continued

```
tgtgttttac agtattatgt agtctgtttt ttatgcaaaa tctaatttaa tatattgata   2460
tttatatcat tttacgtttc tcgttcagct ttcttgtaca aagtggttga tcgcgtgcat   2520
gcgacgtcat agctctctcc ctatagtgag tcgtattata agctaggcac tggccgtcgt   2580
tttacaacgt cgtgactggg aaaactgcta gcttgggatc tttgtgaagg aaccttactt   2640
ctgtggtgtg acataattgg acaaactacc tacagagatt taaagctcta aggtaaatat   2700
aaaattttta agtgtataat gtgttaaact agctgcatat gcttgctgct tgagagtttt   2760
gcttactgag tatgatttat gaaaatatta tacacaggag ctagtgattc taattgtttg   2820
tgtattttag attcacagtc ccaaggctca tttcaggccc ctcagtcctc acagtctgtt   2880
catgatcata atcagccata ccacatttgt agaggtttta cttgctttaa aaaacctccc   2940
acacctcccc ctgaacctga aacataaaat gaatgcaatt gttgttgtta acttgtttat   3000
tgcagcttat aatggttaca aataaagcaa tagcatcaca aatttcacaa ataaagcatt   3060
tttttcactg cattctagtt gtggtttgtc caaactcatc aatgtatctt atcatgtctg   3120
gatcgatcct gcattaatga atcggccaac gcgcggggag aggcggtttg cgtattggct   3180
ggcgtaatag cgaagaggcc cgcaccgatc gcccttccca acagttgcgc agcctgaatg   3240
gcgaatggga cgcgccctgt agcggcgcat taagcgcggc gggtgtggtg gttacgcgca   3300
gcgtgaccgc tacacttgcc agcgccctag cgcccgctcc tttcgctttc ttcccttcct   3360
ttctcgccac gttcgccggc tttccccgtc aagctctaaa tcgggggctc cctttagggt   3420
tccgatttag tgctttacgg cacctcgacc ccaaaaaact tgattagggt gatggttcac   3480
gtagtgggcc atcgccctga tagacggttt ttcgcccttt gacgttggag tccacgttct   3540
ttaatagtgg actcttgttc caaactggaa caacactcaa ccctatctcg gtctattctt   3600
ttgatttata agggattttg ccgatttcgg cctattggtt aaaaaatgag ctgatttaac   3660
aaatatttaa cgcgaatttt aacaaaatat taacgtttac aatttcgcct gatgcggtat   3720
tttctcctta cgcatctgtg cggtatttca caccgcatac gcggatctgc gcagcaccat   3780
ggcctgaaat aacctctgaa agaggaactt ggttaggtac cttctgaggc ggaaagaacc   3840
agctgtggaa tgtgtgtcag ttagggtgtg gaaagtcccc aggctcccca gcaggcagaa   3900
gtatgcaaag catgcatctc aattagtcag caaccaggtg tggaaagtcc ccaggctccc   3960
cagcaggcag aagtatgcaa agcatgcatc tcaattagtc agcaaccata gtcccgcccc   4020
taactccgcc catcccgccc ctaactccgc ccagttccgc ccattctccg ccccatggct   4080
gactaatttt ttttatttat gcagaggccg aggccgcctc ggcctctgag ctattccaga   4140
agtagtgagg aggctttttt ggaggcctag gcttttgcaa aaagcttgat tcttctgaca   4200
caacagtctc gaacttaagg ctagagccac catgattgaa caagatggat tgcacgcagg   4260
ttctccggcc gcttgggtgg agaggctatt cggctatgac tgggcacaac agacaatcgg   4320
ctgctctgat gccgccgtgt tccggctgtc agcgcagggg cgcccggttc tttttgtcaa   4380
gaccgacctg tccggtgccc tgaatgaact gcaggacgag gcagcgcggc tatcgtggct   4440
ggccacgacg ggcgttcctt gcgcagctgt gctcgacgtt gtcactgaag cgggaaggga   4500
ctggctgcta ttgggcgaag tgccggggca ggatctcctg tcatctcacc ttgctcctgc   4560
cgagaaagta tccatcatgg ctgatgcaat gcggcggctg catacgcttg atccggctac   4620
ctgcccattc gaccaccaag cgaaacatcg catcgagcga gcacgtactc ggatggaagc   4680
cggtcttgtc gatcaggatg atctggacga agagcatcag gggctcgcgc cagccgaact   4740
```

-continued

```
gttcgccagg ctcaaggcgc gcatgcccga cggcgaggat ctcgtcgtga cccatggcga   4800
tgcctgcttg ccgaatatca tggtggaaaa tggccgcttt tctggattca tcgactgtgg   4860
ccggctgggt gtggcggacc gctatcagga catagcgttg gctacccgtg atattgctga   4920
agagcttggc ggcgaatggg ctgaccgctt cctcgtgctt tacggtatcg ccgctcccga   4980
ttcgcagcgc atcgccttct atcgccttct tgacgagttc ttctgagcgg gactctgggg   5040
ttcgaaatga ccgaccaagc gacgcccaac ctgccatcac gatggccgca ataaaatatc   5100
tttattttca ttacatctgt gtgttggttt tttgtgtgaa tcgatagcga taaggatccg   5160
cgtatggtgc actctcagta caatctgctc tgatgccgca tagttaagcc agccccgaca   5220
cccgccaaca cccgctgacg cgccctgacg ggcttgtctg ctcccggcat ccgcttacag   5280
acaagctgtg accgtctccg ggagctgcat gtgtcagagg ttttcaccgt catcaccgaa   5340
acgcgcgaga cgaaagggcc tcgtgatacg cctattttta taggttaatg tcatgataat   5400
aatggtttct tagacgtcag gtggcacttt tcggggaaat gtgcgcggaa cccctatttg   5460
tttatttttc taaatacatt caaatatgta tccgctcatg agacaataac cctgataaat   5520
gcttcaataa tattgaaaaa ggaagagtat gagtattcaa catttccgtg tcgcccttat   5580
tccctttttt gcggcatttt gccttcctgt ttttgctcac ccagaaacgc tggtgaaagt   5640
aaaagatgct gaagatcagt tgggtgcacg agtgggttac atcgaactgg atctcaacag   5700
cggtaagatc cttgagagtt ttcgccccga agaacgtttt ccaatgatga gcacttttaa   5760
agttctgcta tgtggcgcgg tattatcccg tattgacgcc gggcaagagc aactcggtcg   5820
ccgcatacac tattctcaga atgacttggt tgagtactca ccagtcacag aaaagcatct   5880
tacggatggc atgacagtaa gagaattatg cagtgctgcc ataaccatga gtgataacac   5940
tgcggccaac ttacttctga caacgatcgg aggaccgaag gagctaaccg cttttttgca   6000
caacatgggg gatcatgtaa ctcgccttga tcgttgggaa ccggagctga atgaagccat   6060
accaaacgac gagcgtgaca ccacgatgcc tgtagcaatg gcaacaacgt tgcgcaaact   6120
attaactggc gaactactta ctctagcttc ccggcaacaa ttaatagact ggatggaggc   6180
ggataaagtt gcaggaccac ttctgcgctc ggcccttccg gctggctggt ttattgctga   6240
taaatctgga gccggtgagc gtgggtctcg cggtatcatt gcagcactgg ggccagatgg   6300
taagccctcc cgtatcgtag ttatctacac gacggggagt caggcaacta tggatgaacg   6360
aaatagacag atcgctgaga taggtgcctc actgattaag cattggtaac tgtcagacca   6420
agtttactca tatatacttt agattgattt aaaacttcat ttttaattta aaaggatcta   6480
ggtgaagatc ctttttgata atctcatgac caaaatccct taacgtgagt tttcgttcca   6540
ctgagcgtca gaccccgtag aaaagatcaa aggatcttct tgagatcctt tttttctgcg   6600
cgtaatctgc tgcttgcaaa caaaaaaacc accgctacca gcggtggttt gtttgccgga   6660
tcaagagcta ccaactcttt ttccgaaggt aactggcttc agcagagcgc agataccaaa   6720
tactgtcctt ctagtgtagc cgtagttagg ccaccacttc aagaactctg tagcaccgcc   6780
tacatacctc gctctgctaa tcctgttacc agtggctgct gccagtggcg ataagtcgtg   6840
tcttaccggg ttggactcaa gacgatagtt accggataag gcgcagcggt cgggctgaac   6900
ggggggttcg tgcacacagc ccagcttgga gcgaacgacc tacaccgaac tgagatacct   6960
acagcgtgag cattgagaaa gcgccacgct tcccgaaggg agaaaggcgg acaggtatcc   7020
ggtaagcggc agggtcggaa caggagagcg cacgagggag cttccagggg gaaacgcctg   7080
gtatctttat agtcctgtcg ggtttcgcca cctctgactt gagcgtcgat ttttgtgatg   7140
```

-continued

```
ctcgtcaggg gggcggagcc tatggaaaaa cgccagcaac gcggcctttt tacggttcct   7200

ggccttttgc tggccttttg ctcacatgtt ctttcctgcg ttatcccctg attctgtgga   7260

taaccgtatt accgcctttg agtgagctga taccgctcgc cgcagccgaa cgaccgagcg   7320

cagcgagtca gtgagcgagg aagcggaaga gcgcccaata cgcaaaccgc ctctccccgc   7380

gcgttggccg attcattaat gcagagcttg caattcgcgc gtttttcaat attattgaag   7440

catttatcag ggttattgtc tcatgagcgg atacatattt gaatgtattt agaaaaataa   7500

acaaataggg gttccgcgca catttccccg aaaagtgcca cctgacgtct aagaaaccat   7560

tattatcatg acattaacct ataaaaatag gcgtagtacg aggccctttc actcattaga   7620

tgcatgtcgt tacataactt acggtaaatg gcccgcctgg ctgaccgccc aacgaccccc   7680

gcccattgac gtcaataatg acgtatgttc ccatagtaac gccaataggg actttccatt   7740

gacgtcaatg ggtggagtat ttacggtaaa ctgcccactt ggcagtacat caagtgtatc   7800

atatgccaag tacgccccct attgacgtca atgacggtaa atggcccgcc tggcattatg   7860

cccagtacat gaccttatgg gactttccta cttggcagta catctacgta ttagtcatcg   7920

ctattaccat ggtgatgcgg ttttggcagt acatcaatgg gcgtggatag cggtttgact   7980

cacggggatt tccaagtctc caccccattg acgtcaatgg gagtttgttt tggcaccaaa   8040

atcaacggga ctttccaaaa tgtcgtaaca actccgcccc attgacgcaa atgggcggta   8100

ggcgtgtacg gtgggaggtc tat                                           8123
```

<210> SEQ ID NO 156
<211> LENGTH: 4396
<212> TYPE: DNA
<213> ORGANISM: Artificial Sequence
<220> FEATURE:
<223> OTHER INFORMATION: pEXP501

<400> SEQUENCE: 156

```
ccattcgcca ttcaggctgc gcaactgttg ggaagggcga tcggtgcggg cctcttcgct     60

attacgccag ccaatacgca aaccgcctct ccccgcgcgt tggccgattc attaatgcag    120

gatcgatcca gacatgataa gatacattga tgagtttgga caaaccacaa ctagaatgca    180

gtgaaaaaaa tgctttattt gtgaaatttg tgatgctatt gctttatttg taaccattat    240

aagctgcaat aaacaagtta acaacaacaa ttgcattcat tttatgtttc aggttcaggg    300

ggaggtgtgg gaggtttttt aaagcaagta aaacctctac aaatgtggta tggctgatta    360

tgatcatgaa cagactgtga ggactgaggg gcctgaaatg agccttggga ctgtgaatct    420

aaaatacaca aacaattaga atcactagct cctgtgtata atattttcat aaatcatact    480

cagtaagcaa aactctcaag cagcaagcat atgcagctag tttaacacat tatacactta    540

aaaattttat atttacctta gagctttaaa tctctgtagg tagtttgtcc aattatgtca    600

caccacagaa gtaaggttcc ttcacaaaga tcccaagcta gcagttttcc cagtcacgac    660

gttgtaaaac gacggccagt gcctagctta taatacgact cactataggg accactttgt    720

acaagaaagc tgggtacgcg taagcttggg cccctcgagg gatcctctag agcggccgcc    780

gactagtgag ctcgtcgacg atatcccggg aattccggac cggtaccagc ctgctttttt    840

gtacaaactt gttctatagt gtcacctaaa taggcctaat ggtcatagct gtttcctgtg    900

tgaaattgtt atccgctccg cggcctaggc tagagtccgg aggctggatc ggtcccggtg    960

tcttctatgg aggtcaaaac agcgtggatg gcgtctccag gcgatctgac ggttcactaa   1020
```

-continued

```
acgagctctg cttatataga cctcccaccg tacacgccta ccgcccattt gcgtcaatgg   1080
ggcggagttg ttacgacatt ttggaaagtc ccgttgattt tggtgccaaa acaaactccc   1140
attgacgtca atggggtgga gacttggaaa tccccgtgag tcaaaccgct atccacgccc   1200
attgatgtac tgccaaaacc gcatcaccat ggtaatagcg atgactaata cgtagatgta   1260
ctgccaagta ggaaagtccc ataaggtcat gtactgggca taatgccagg cgggccattt   1320
accgtcattg acgtcaatag ggggcgtact tggcatatga tacacttgat gtactgccaa   1380
gtgggcagtt taccgtaaat actccaccca ttgacgtcaa tggaaagtcc ctattggcgt   1440
tactatggga acatacgtca ttattgacgt caatgggcgg gggtcgttgg gcggtcagcc   1500
aggcgggcca tttaccgtaa gttatgtaac gacatgcatc taatgagtga aagggcctcg   1560
tactacgcct atttttatag gttaatgtca tgataataat ggtttcttag acgtcaggtg   1620
gcacttttcg gggaaatgtg cgcggaaccc ctatttgttt atttttctaa atacattcaa   1680
atatgtatcc gctcatgaga caataaccct gataaatgct tcaataatat tgaaaaacgc   1740
gcgaattgca agctctgcat taatgaatcg gccaacgcgc ggggagaggc ggtttgcgta   1800
ttgggcgctc ttccgcttcc tcgctcactg actcgctgcg ctcggtcgtt cggctgcggc   1860
gagcggtatc agctcactca aaggcggtaa tacggttatc cacagaatca ggggataacg   1920
caggaaagaa catgtgagca aaaggccagc aaaaggccag gaaccgtaaa aaggccgcgt   1980
tgctggcgtt tttccatagg ctccgccccc ctgacgagca tcacaaaaat cgacgctcaa   2040
gtcagaggtg gcgaaacccg acaggactat aaagatacca ggcgtttccc cctggaagct   2100
ccctcgtgcg ctctcctgtt ccgaccctgc cgcttaccgg atacctgtcc gcctttctcc   2160
cttcgggaag cgtggcgctt tctcaatgct cacgctgtag gtatctcagt tcggtgtagg   2220
tcgttcgctc caagctgggc tgtgtgcacg aaccccccgt tcagcccgac cgctgcgcct   2280
tatccggtaa ctatcgtctt gagtccaacc cggtaagaca cgacttatcg ccactggcag   2340
cagccactgg taacaggatt agcagagcga ggtatgtagg cggtgctaca gagttcttga   2400
agtggtggcc taactacggc tacactagaa ggacagtatt tggtatctgc gctctgctga   2460
agccagttac cttcggaaaa agagttggta gctcttgatc cggcaaacaa accaccgctg   2520
gtagcggtgg tttttttgtt tgcaagcagc agattacgcg cagaaaaaaa ggatctcaag   2580
aagatccttt gatcttttct acggggtctg acgctcagtg gaacgaaaac tcacgttaag   2640
ggattttggt catgccataa cttcgtatag catacattat acgaagttat ggcatgagat   2700
tatcaaaaag gatcttcacc tagatccttt taaattaaaa atgaagtttt aaatcaatct   2760
aaagtatata tgagtaaact tggtctgaca gttaccaatg cttaatcagt gaggcaccta   2820
tctcagcgat ctgtctattt cgttcatcca tagttgcctg actccccgtc gtgtagataa   2880
ctacgatacg ggagggctta ccatctggcc ccagtgctgc aatgataccg cgagacccac   2940
gctcaccggc tccagattta tcagcaataa accagccagc cggaagggcc gagcgcagaa   3000
gtggtcctgc aactttatcc gcctccatcc agtctattaa ttgttgccgg gaagctagag   3060
taagtagttc gccagttaat agtttgcgca acgttgttgc cattgctaca ggcatcgtgg   3120
tgtcacgctc gtcgtttggt atggcttcat tcagctccgg ttcccaacga tcaaggcgag   3180
ttacatgatc ccccatgttg tgcaaaaaag cggttagctc cttcggtcct ccgatcgttg   3240
tcagaagtaa gttggccgca gtgttatcac tcatggttat ggcagcactg cataattctc   3300
ttactgtcat gccatccgta agatgctttt ctgtgactgg tgagtactca accaagtcat   3360
tctgagaata gtgtatgcgg cgaccgagtt gctcttgccc ggcgtcaata cgggataata   3420
```

ccgcgccaca tagcagaact ttaaaagtgc tcatcattgg aaaacgttct tcggggcgaa 3480
aactctcaag gatcttaccg ctgttgagat ccagttcgat gtaacccact cgtgcaccca 3540
actgatcttc agcatctttt actttcacca gcgtttctgg gtgagcaaaa acaggaaggc 3600
aaaatgccgc aaaaaaggga ataagggcga cacggaaatg ttgaatactc atactcttcc 3660
tttttcaata ttattgaagc atttatcagg gttattgtct catgccaggg gtgggcacac 3720
atatttgata ccagcgatcc ctacacagca cataattcaa tgcgacttcc ctctatcgca 3780
catcttagac ctttattctc cctccagcac acatcgaagc tgccgagcaa gccgttctca 3840
ccagtccaag acctggcatg agcggataca tatttgaatg tatttagaaa aataaacaaa 3900
taggggttcc gcgcacattt ccccgaaaag tgccacctga aattgtaaac gttaatattt 3960
tgttaaaatt cgcgttaaat ttttgttaaa tcagctcatt ttttaaccaa taggccgaaa 4020
tcggcaaaat cccttataaa tcaaaagaat agaccgagat agggttgagt gttgttccag 4080
tttggaacaa gagtccacta ttaaagaacg tggactccaa cgtcaaaggg cgaaaaaccg 4140
tctatcaggg cgatggccca ctacgtgaac catcacccta atcaagtttt ttggggtcga 4200
ggtgccgtaa agcactaaat cggaacccta aagggagccc ccgatttaga gcttgacggg 4260
gaaagccggc gaacgtggcg agaaaggaag ggaagaaagc gaaaggagcg ggcgctaggg 4320
cgctggcaag tgtagcggtc acgctgcgcg taaccaccac acccgccgcg cttaatgcgc 4380
cgctacaggg cgcgtc 4396

<210> SEQ ID NO 157
<211> LENGTH: 4470
<212> TYPE: DNA
<213> ORGANISM: Artificial Sequence
<220> FEATURE:
<223> OTHER INFORMATION: pDONR201
<220> FEATURE:
<221> NAME/KEY: gene
<222> LOCATION: (29)..(260)
<223> OTHER INFORMATION: attP1
<220> FEATURE:
<221> NAME/KEY: gene
<222> LOCATION: (656)..(961)
<223> OTHER INFORMATION: ccdB
<220> FEATURE:
<221> NAME/KEY: gene
<222> LOCATION: (1099)..(1184)
<223> OTHER INFORMATION: ccdA
<220> FEATURE:
<221> NAME/KEY: gene
<222> LOCATION: (1303)..(1962)
<223> OTHER INFORMATION: CmR
<220> FEATURE:
<221> NAME/KEY: gene
<222> LOCATION: (2210)..(2442)
<223> OTHER INFORMATION: attP2
<220> FEATURE:
<221> NAME/KEY: gene
<222> LOCATION: (2565)..(3374)
<223> OTHER INFORMATION: Kmr
<220> FEATURE:
<221> NAME/KEY: gene
<222> LOCATION: (3495)..(4134)
<223> OTHER INFORMATION: ori

<400> SEQUENCE: 157
gttaacgcta gcatggatct cgggccccaa ataatgattt tattttgact gatagtgacc 60
tgttcgttgc aacaaattga tgagcaatgc ttttttataa tgccaacttt gtacaaaaaa 120
gctgaacgag aaacgtaaaa tgatataaat atcaatatat taaattagat tttgcataaa 180

-continued

```
aaacagacta cataatactg taaaacacaa catatccagt cactatgaat caactactta    240
gatggtatta gtgacctgta gtcgaccgac agccttccaa atgttcttcg ggtgatgctg    300
ccaacttagt cgaccgacag ccttccaaat gttcttctca aacggaatcg tcgtatccag    360
cctactcgct attgtcctca atgccgtatt aaatcataaa aagaaataag aaaaagaggt    420
gcgagcctct tttttgtgtg acaaaataaa aacatctacc tattcatata cgctagtgtc    480
atagtcctga aaatcatctg catcaagaac aatttcacaa ctcttatact tttctcttac    540
aagtcgttcg gcttcatctg gattttcagc ctctatactt actaaacgtg ataaagtttc    600
tgtaatttct actgtatcga cctgcagact ggctgtgtat aagggagcct gacatttata    660
ttccccagaa catcaggtta atggcgtttt tgatgtcatt ttcgcggtgg ctgagatcag    720
ccacttcttc cccgataacg gagaccggca cactggccat atcggtggtc atcatgcgcc    780
agctttcatc cccgatatgc accaccgggt aaagttcacg ggagacttta tctgacagca    840
gacgtgcact ggccaggggg atcaccatcc gtcgcccggg cgtgtcaata atatcactct    900
gtacatccac aaacagacga taacggctct ctcttttata ggtgtaaacc ttaaactgca    960
tttcaccagt ccctgttctc gtcagcaaaa gagccgttca tttcaataaa ccgggcgacc   1020
tcagccatcc cttcctgatt ttccgctttc cagcgttcgg cacgcagacg acgggcttca   1080
ttctgcatgg ttgtgcttac cagaccggag atattgacat catatatgcc ttgagcaact   1140
gatagctgtc gctgtcaact gtcactgtaa tacgctgctt catagcacac ctctttttga   1200
catacttcgg gtatacatat cagtatatat tcttataccg caaaaatcag cgcgcaaata   1260
cgcatactgt tatctggctt ttagtaagcc ggatccacgc gattacgccc cgccctgcca   1320
ctcatcgcag tactgttgta attcattaag cattctgccg acatggaagc catcacagac   1380
ggcatgatga acctgaatcg ccagcggcat cagcaccttg tcgccttgcg tataatattt   1440
gcccatggtg aaaacggggg cgaagaagtt gtccatattg gccacgttta aatcaaaact   1500
ggtgaaactc acccagggat tggctgagac gaaaaacata ttctcaataa accctttagg   1560
gaaataggcc aggttttcac cgtaacacgc cacatcttgc gaatatatgt gtagaaactg   1620
ccggaaatcg tcgtggtatt cactccagag cgatgaaaac gtttcagttt gctcatggaa   1680
aacggtgtaa caagggtgaa cactatccca tatcaccagc tcaccgtctt tcattgccat   1740
acggaattcc ggatgagcat tcatcaggcg ggcaagaatg tgaataaagg ccggataaaa   1800
cttgtgctta tttttcttta cggtctttaa aaaggccgta atatccagct gaacggtctg   1860
gttataggta cattgagcaa ctgactgaaa tgcctcaaaa tgttctttac gatgccattg   1920
ggatatatca acggtggtat atccagtgat ttttttctcc attttagctt ccttagctcc   1980
tgaaaatctc gataactcaa aaaatacgcc cggtagtgat cttatttcat tatggtgaaa   2040
gttggaacct cttacgtgcc gatcaacgtc tcattttcgc caaaagttgg cccagggctt   2100
cccggtatca acagggacac caggatttat ttattctgcg aagtgatctt ccgtcacagg   2160
tatttattcg gcgcaaagtg cgtcgggtga tgctgccaac ttagtcgact acaggtcact   2220
aataccatct aagtagttga ttcatagtga ctggatatgt tgtgttttac agtattatgt   2280
agtctgtttt ttatgcaaaa tctaatttaa tatattgata tttatatcat tttacgtttc   2340
tcgttcagct ttcttgtaca aagttggcat tataagaaag cattgcttat caatttgttg   2400
caacgaacag gtcactatca gtcaaaataa aatcattatt tgccatccag ctgcagctct   2460
ggcccgtgtc tcaaaatctc tgatgttaca ttgcacaaga taaaaatata tcatcatgaa   2520
caataaaact gtctgcttac ataaacagta atacaagggg tgttatgagc catattcaac   2580
```

-continued

```
gggaaacgtc gaggccgcga ttaaattcca acatggatgc tgatttatat gggtataaat   2640

gggctcgcga taatgtcggg caatcaggtg cgacaatcta tcgcttgtat gggaagcccg   2700

atgcgccaga gttgtttctg aaacatggca aaggtagcgt tgccaatgat gttacagatg   2760

agatggtcag actaaactgg ctgacggaat ttatgcctct tccgaccatc aagcatttta   2820

tccgtactcc tgatgatgca tggttactca ccactgcgat ccccggaaaa acagcattcc   2880

aggtattaga agaatatcct gattcaggtg aaaatattgt tgatgcgctg gcagtgttcc   2940

tgcgccggtt gcattcgatt cctgtttgta attgtccttt taacagcgat cgcgtatttc   3000

gtctcgctca ggcgcaatca cgaatgaata acggtttggt tgatgcgagt gattttgatg   3060

acgagcgtaa tggctggcct gttgaacaag tctggaaaga aatgcataaa cttttgccat   3120

tctcaccgga ttcagtcgtc actcatggtg atttctcact tgataacctt atttttgacg   3180

aggggaaatt aataggttgt attgatgttg gacgagtcgg aatcgcagac cgataccagg   3240

atcttgccat cctatggaac tgcctcggtg agttttctcc ttcattacag aaacggcttt   3300

ttcaaaaata tggtattgat aatcctgata tgaataaatt gcagtttcat ttgatgctcg   3360

atgagttttt ctaatcagaa ttggttaatt ggttgtaaca ctggcagagc attacgctga   3420

cttgacggga cggcgcaagc tcatgaccaa aatcccttaa cgtgagtttt cgttccactg   3480

agcgtcagac cccgtagaaa agatcaaagg atcttcttga gatccttttt ttctgcgcgt   3540

aatctgctgc ttgcaaacaa aaaaaccacc gctaccagcg gtggtttgtt tgccggatca   3600

agagctacca actctttttc cgaaggtaac tggcttcagc agagcgcaga taccaaatac   3660

tgtccttcta gtgtagccgt agttaggcca ccacttcaag aactctgtag caccgcctac   3720

atacctcgct ctgctaatcc tgttaccagt ggctgctgcc agtggcgata agtcgtgtct   3780

taccgggttg gactcaagac gatagttacc ggataaggcg cagcggtcgg gctgaacggg   3840

gggttcgtgc acacagccca gcttggagcg aacgacctac accgaactga gatacctaca   3900

gcgtgagcta tgagaaagcg ccacgcttcc cgaagggaga aaggcggaca ggtatccggt   3960

aagcggcagg gtcggaacag gagagcgcac gagggagctt ccagggggaa acgcctggta   4020

tctttatagt cctgtcgggt ttcgccacct ctgacttgag cgtcgatttt tgtgatgctc   4080

gtcagggggg cggagcctat ggaaaaacgc cagcaacgcg gcctttttac ggttcctggc   4140

cttttgctgg ccttttgctc acatgttctt tcctgcgtta tcccctgatt ctgtggataa   4200

ccgtattacc gctagccagg aagagtttgt agaaacgcaa aaaggccatc cgtcaggatg   4260

gccttctgct tagtttgatg cctggcagtt tatggcgggc gtcctgcccg ccaccctccg   4320

ggccgttgct tcacaacgtt caaatccgct cccggcggat ttgtcctact caggagagcg   4380

ttcaccgaca aacaacagat aaaacgaaag gcccagtctt ccgactgagc ctttcgtttt   4440

atttgatgcc tggcagttcc ctactctcgc                                    4470
```

<210> SEQ ID NO 158
<211> LENGTH: 4204
<212> TYPE: DNA
<213> ORGANISM: Artificial Sequence
<220> FEATURE:
<223> OTHER INFORMATION: pDONR202
<220> FEATURE:
<221> NAME/KEY: gene
<222> LOCATION: (127)..(269)
<223> OTHER INFORMATION: attP1
<220> FEATURE:
<221> NAME/KEY: gene
<222> LOCATION: (486)..(1059)

-continued

<223> OTHER INFORMATION: ori
<220> FEATURE:
<221> NAME/KEY: gene
<222> LOCATION: (1228)..(2107)
<223> OTHER INFORMATION: KmR
<220> FEATURE:
<221> NAME/KEY: gene
<222> LOCATION: (2140)..(2381)
<223> OTHER INFORMATION: attP2
<220> FEATURE:
<221> NAME/KEY: gene
<222> LOCATION: (2629)..(3288)
<223> OTHER INFORMATION: CmR
<220> FEATURE:
<221> NAME/KEY: gene
<222> LOCATION: (3408)..(3492)
<223> OTHER INFORMATION: inactivated ccdA
<220> FEATURE:
<221> NAME/KEY: gene
<222> LOCATION: (3630)..(3935)
<223> OTHER INFORMATION: ccdB

<400> SEQUENCE: 158
cggcattgag gacaatagcg agtaggctgg atacgacgat tccgtttgag aagaacattt 60
ggaaggctgt cggtcgacta agttggcagc atcacccgaa gaacatttgg aaggctgtcg 120
gtcgactaca ggtcactaat accatctaag tagttgattc atagtgactg gatatgttgt 180
gttttacagt attatgtagt ctgtttttta tgcaaaatct aatttaatat attgatattt 240
atatcatttt acgtttctcg ttcagctttt ttgtacaaag ttggcattat aaaaaagcat 300
tgctcatcaa tttgttgcaa cgaacaggtc actatcagtc aaaataaaat cattatttgg 360
ggcccgagat ccatgctagc ggtaatacgg ttatccacag aatcagggga taacgcagga 420
aagaacatgt gagcaaaagg ccagcaaaag gccaggaacc gtaaaaaggc cgcgttgctg 480
gcgtttttcc ataggctccg cccccctgac gagcatcaca aaaatcgacg ctcaagtcag 540
aggtggcgaa acccgacagg actataaaga taccaggcgt ttccccctgg aagctccctc 600
gtgcgctctc ctgttccgac cctgccgctt accggatacc tgtccgcctt tctcccttcg 660
ggaagcgtgg cgctttctca tagctcacgc tgtaggtatc tcagttcggt gtaggtcgtt 720
cgctccaagc tgggctgtgt gcacgaaccc cccgttcagc ccgaccgctg cgccttatcc 780
ggtaactatc gtcttgagtc caacccggta agacacgact tatcgccact ggcagcagcc 840
actggtaaca ggattagcag agcgaggtat gtaggcggtg ctacagagtt cttgaagtgg 900
tggcctaact acggctacac tagaaggaca gtatttggta tctgcgctct gctgaagcca 960
gttaccttcg gaaaaagagt tggtagctct tgatccggca aacaaaccac cgctggtagc 1020
ggtggttttt ttgtttgcaa gcagcagatt acgcgcagaa aaaaaggatc tcaagaagat 1080
cctttgatct tttctacggg gtctgacgct cagtggaacg aaaactcacg ttaagggatt 1140
ttggtcatga gcttgcgccg tcccgtcaag tcagcgtaat gctctgccag tgttacaacc 1200
aattaaccaa ttctgattag aaaaactcat cgagcatcaa atgaaactgc aatttattca 1260
tatcaggatt atcaatacca tatttttgaa aaagccgttt ctgtaatgaa ggagaaaact 1320
caccgaggca gttccatagg atggcaagat cctggtatcg gtctgcgatt ccgactcgtc 1380
caacatcaat acaacctatt aatttcccct cgtcaaaaat aaggttatca agtgagaaat 1440
caccatgagt gacgactgaa tccggtgaga atggcaaaag tttatgcatt tctttccaga 1500
cttgttcaac aggccagcca ttacgctcgt catcaaaatc actcgcatca accaaaccgt 1560
tattcattcg tgattgcgcc tgagcgagac gaaatacgcg atcgctgtta aaaggacaat 1620
tacaaacagg aatcgaatgc aaccggcgca ggaacactgc cagcgcatca acaatatttt 1680

-continued

```
cacctgaatc aggatattct tctaatacct ggaatgctgt ttttccgggg atcgcagtgg   1740
tgagtaacca tgcatcatca ggagtacgga taaaatgctt gatggtcgga agaggcataa   1800
attccgtcag ccagtttagt ctgaccatct catctgtaac atcattggca acgctacctt   1860
tgccatgttt cagaaacaac tctggcgcat cgggcttccc atacaagcga tagattgtcg   1920
cacctgattg cccgacatta tcgcgagccc atttataccc atataaatca gcatccatgt   1980
tggaatttaa tcgcggcctc gacgtttccc gttgaatatg gctcataaca ccccttgtat   2040
tactgtttat gtaagcagac agttttattg ttcatgatga tatattttta tcttgtgcaa   2100
tgtaacatca gagattttga gacacgggcc agagctgcag ctggatggca aataatgatt   2160
ttattttgac tgatagtgac ctgttcgttg caacaaattg ataagcaatg ctttcttata   2220
atgccaactt tgtacaagaa agctgaacga gaaacgtaaa atgatataaa tatcaatata   2280
ttaaattaga ttttgcataa aaaacagact acataatact gtaaaacaca acatatccag   2340
tcactatgaa tcaactactt agatggtatt agtgacctgt agtcgactaa gttggcagca   2400
tcacccgacg cactttgcgc cgaataaata cctgtgacgg aagatcactt cgcagaataa   2460
ataaatcctg gtgtccctgt tgataccggg aagccctggg ccaacttttg gcgaaaatga   2520
gacgttgatc ggcacgtaag aggttccaac tttcaccata atgaaataag atcactaccg   2580
ggcgtatttt ttgagttatc gagattttca ggagctaagg aagctaaaat ggagaaaaaa   2640
atcactggat ataccaccgt tgatatatcc caatggcatc gtaaagaaca ttttgaggca   2700
tttcagtcag ttgctcaatg tacctataac cagaccgttc agctggatat tacggccttt   2760
ttaaagaccg taaagaaaaa taagcacaag ttttatccgg cctttattca cattcttgcc   2820
cgcctgatga atgctcatcc ggaattccgt atggcaatga aagacggtga gctggtgata   2880
tgggatagtg ttcacccttg ttacaccgtt ttccatgagc aaactgaaac gttttcatcg   2940
ctctggagtg aataccacga cgatttccgg cagtttctac acatatattc gcaagatgtg   3000
gcgtgttacg gtgaaaacct ggcctatttc cctaaagggt ttattgagaa tatgtttttc   3060
gtctcagcca atccctgggt gagtttcacc agttttgatt taaacgtggc caatatggac   3120
aacttcttcg cccccgtttt caccatgggc aaatattata cgcaaggcga caaggtgctg   3180
atgccgctgg cgattcaggt tcatcatgcc gtctgtgatg gcttccatgt cggcagaatg   3240
cttaatgaat tacaacagta ctgcgatgag tggcagggcg gggcgtaatc gcgtggatcc   3300
ggcttactaa aagccagata acagtatgcg tatttgcgcg ctgatttttg cggtataaga   3360
atatatactg atatgtatac ccgaagtatg tcaaaaagag gtgtgctatg aagcagcgta   3420
ttacagtgac agttgacagc gacagctatc agttgctcaa ggcatatatg atgtcaatat   3480
ctccggtctg gtaagcacaa ccatgcagaa tgaagcccgt cgtctgcgtg ccgaacgctg   3540
gaaagcggaa aatcaggaag ggatggctga ggtcgcccgg tttattgaaa tgaacggctc   3600
ttttgctgac gagaacaggg actggtgaaa tgcagtttaa ggtttacacc tataaaagag   3660
agagccgtta tcgtctgttt gtggatgtac agagtgatat tattgacacg cccgggcgac   3720
ggatggtgat ccccctggcc agtgcacgtc tgctgtcaga taaagtctcc cgtgaacttt   3780
acccggtggt gcatatcggg gatgaaagct ggcgcatgat gaccaccgat atggccagtg   3840
tgccggtctc cgttatcggg gaagaagtgg ctgatctcag ccaccgcgaa aatgacatca   3900
aaaacgccat taacctgatg ttctggggaa tataaatgtc aggctccctt atacacagcc   3960
agtctgcagg tcgatacagt agaaattaca gaaactttat cacgtttagt aagtatagag   4020
```

-continued

```
gctgaaaatc cagatgaagc cgaacgactt gtaagagaaa agtataagag ttgtgaaatt   4080

gttcttgatg cagatgattt tcaggactat gacactagcg tatatgaata ggtagatgtt   4140

tttattttgt cacacaaaaa agaggctcgc acctcttttt cttatttctt tttatgattt   4200

aata                                                                4204
```

<210> SEQ ID NO 159
<211> LENGTH: 4208
<212> TYPE: DNA
<213> ORGANISM: Artificial Sequence
<220> FEATURE:
<223> OTHER INFORMATION: pDONR203
<220> FEATURE:
<221> NAME/KEY: gene
<222> LOCATION: (47)..(131)
<223> OTHER INFORMATION: inactivated ccdA
<220> FEATURE:
<221> NAME/KEY: gene
<222> LOCATION: (251)..(910)
<223> OTHER INFORMATION: CmR
<220> FEATURE:
<221> NAME/KEY: gene
<222> LOCATION: (1158)..(1398)
<223> OTHER INFORMATION: attP2
<220> FEATURE:
<221> NAME/KEY: gene
<222> LOCATION: (1509)..(2082)
<223> OTHER INFORMATION: ori
<220> FEATURE:
<221> NAME/KEY: gene
<222> LOCATION: (2251)..(3130)
<223> OTHER INFORMATION: KmR
<220> FEATURE:
<221> NAME/KEY: gene
<222> LOCATION: (3174)..(3464)
<223> OTHER INFORMATION: attP1
<220> FEATURE:
<221> NAME/KEY: gene
<222> LOCATION: (3812)..(4117)
<223> OTHER INFORMATION: ccdB

<400> SEQUENCE: 159

```
gcgttcggca cgcagacgac gggcttcatt ctgcatggtt gtgcttacca gaccggagat     60

attgacatca tatatgcctt gagcaactga tagctgtcgc tgtcaactgt cactgtaata    120

cgctgcttca tagcacacct ctttttgaca tacttcgggt atacatatca gtatatattc    180

ttataccgca aaaatcagcg cgcaaatacg catactgtta tctggctttt agtaagccgg    240

atccacgcgt ttacgccccg ccctgccact catcgcagta ctgttgtaat tcattaagca    300

ttctgccgac atggaagcca tcacagacgg catgatgaac ctgaatcgcc agcggcatca    360

gcaccttgtc gccttgcgta taatatttgc ccatggtgaa aacgggggcg aagaagttgt    420

ccatattggc cacgtttaaa tcaaaactgg tgaaactcac ccagggattg gctgagacga    480

aaaacatatt ctcaataaac cctttaggga aataggccag gttttcaccg taacacgcca    540

catcttgcga atatatgtgt agaaactgcc ggaaatcgtc gtggtattca ctccagagcg    600

atgaaaacgt ttcagtttgc tcatggaaaa cggtgtaaca agggtgaaca ctatcccata    660

tcaccagctc accgtctttc attgccatac ggaattccgg atgagcattc atcaggcggg    720

caagaatgtg aataaaggcc ggataaaact tgtgcttatt tttctttacg gtctttaaaa    780

aggccgtaat atccagctga acggtctggt tataggtaca ttgagcaact gactgaaatg    840

cctcaaaatg ttctttacga tgccattggg atatatcaac ggtggtatat ccagtgattt    900

ttttctccat tttagcttcc ttagctcctg aaaatctcga taactcaaaa aatacgcccg    960

gtagtgatct tatttcatta tggtgaaagt tggaacctct tacgtgccga tcaacgtctc   1020
```

-continued

```
attttcgcca aaagttggcc cagggcttcc cggtatcaac agggacacca ggatttattt   1080
attctgcgaa gtgatcttcc gtcacaggta tttattcggc gcaaagtgcg tcgggtgatg   1140
ctgccaactt agtcgactac aggtcactaa taccatctaa gtagttgatt catagtgact   1200
ggatatgttg tgttttacag tattatgtag tctgtttttt atgcaaaatc taatttaata   1260
tattgatatt tatatcattt tacgtttctc gttcagcttt cttgtacaaa gttggcatta   1320
taagaaagca ttgcttatca atttgttgca acgaacaggt cactatcagt caaaataaaa   1380
tcattatttg ccatccagct agcggtaata cggttatcca cagaatcagg ggataacgca   1440
ggaaagaaca tgtgagcaaa aggccagcaa aaggccagga accgtaaaaa ggccgcgttg   1500
ctggcgtttt tccataggct ccgcccccct gacgagcatc acaaaaatcg acgctcaagt   1560
cagaggtggc gaaacccgac aggactataa agataccagg cgtttccccc tggaagctcc   1620
ctcgtgcgct ctcctgttcc gaccctgccg cttaccggat acctgtccgc ctttctccct   1680
tcgggaagcg tggcgctttc tcatagctca cgctgtaggt atctcagttc ggtgtaggtc   1740
gttcgctcca agctgggctg tgtgcacgaa ccccccgttc agcccgaccg ctgcgcctta   1800
tccggtaact atcgtcttga gtccaacccg gtaagacacg acttatcgcc actggcagca   1860
gccactggta acaggattag cagagcgagg tatgtaggcg gtgctacaga gttcttgaag   1920
tggtggccta actacggcta cactagaaga acagtatttg gtatctgcgc tctgctgaag   1980
ccagttacct tcggaaaaag agttggtagc tcttgatccg gcaaacaaac caccgctggt   2040
agcggtggtt tttttgtttg caagcagcag attacgcgca gaaaaaaagg atctcaagaa   2100
gatcctttga tcttttctac ggggtctgac gctcagtgga acgaaaactc acgttaaggg   2160
attttggtca tgagcttgcg ccgtcccgtc aagtcagcgt aatgctctgc cagtgttaca   2220
accaattaac caattctgat tagaaaaact catcgagcat caaatgaaac tgcaatttat   2280
tcatatcagg attatcaata ccatattttt gaaaaagccg tttctgtaat gaaggagaaa   2340
actcaccgag gcagttccat aggatggcaa gatcctggta tcggtctgcg attccgactc   2400
gtccaacatc aatacaacct attaatttcc cctcgtcaaa aataaggtta tcaagtgaga   2460
aatcaccatg agtgacgact gaatccggtg agaatggcaa aagtttatgc atttctttcc   2520
agacttgttc aacaggccag ccattacgct cgtcatcaaa atcactcgca tcaaccaaac   2580
cgttattcat tcgtgattgc gcctgagcga gacgaaatac gcgatcgctg ttaaaaggac   2640
aattacaaac aggaatcgaa tgcaaccggc gcaggaacac tgccagcgca tcaacaatat   2700
tttcacctga atcaggatat tcttctaata cctggaatgc tgtttttccg gggatcgcag   2760
tggtgagtaa ccatgcatca tcaggagtac ggataaaatg cttgatggtc ggaagaggca   2820
taaattccgt cagccagttt agtctgacca tctcatctgt aacatcattg gcaacgctac   2880
ctttgccatg tttcagaaac aactctggcg catcgggctt cccatacaag cgatagattg   2940
tcgcacctga ttgcccgaca ttatcgcgag cccatttata cccatataaa tcagcatcca   3000
tgttggaatt taatcgcggc ctcgacgttt cccgttgaat atggctcata acaccccttg   3060
tattactgtt tatgtaagca gacagtttta ttgttcatga tgatatattt ttatcttgtg   3120
caatgtaaca tcagagattt tgagacacgg gccagagctg cagctagcat ggatctcggg   3180
ccccaaataa tgattttatt ttgactgata gtgacctgtt cgttgcaaca aattgatgag   3240
caatgctttt ttataatgcc aactttgtac aaaaaagctg aacgagaaac gtaaaatgat   3300
ataaatatca atatattaaa ttagattttg cataaaaaac agactacata atactgtaaa   3360
```

-continued

```
acacaacata tccagtcact atgaatcaac tacttagatg gtattagtga cctgtagtcg   3420

accgacagcc ttccaaatgt tcttcgggtg atgctgccaa cttagtcgac cgacagcctt   3480

ccaaatgttc ttctcaaacg gaatcgtcgt atccagccta ctcgctattg tcctcaatgc   3540

cgtattaaat cataaaaaga aataagaaaa agaggtgcga gcctcttttt tgtgtgacaa   3600

aataaaaaca tctacctatt catatacgct agtgtcatag tcctgaaaat catctgcatc   3660

aagaacaatt tcacaactct tatacttttc tcttacaagt cgttcggctt catctggatt   3720

ttcagcctct atacttacta aacgtgataa agtttctgta atttctactg tatcgacctg   3780

cagactggct gtgtataagg gagcctgaca tttatattcc ccagaacatc aggttaatgg   3840

cgtttttgat gtcattttcg cggtggctga gatcagccac ttcttccccg ataacggaga   3900

ccggcacact ggccatatcg gtggtcatca tgcgccagct ttcatccccg atatgcacca   3960

ccgggtaaag ttcacgggag actttatctg acagcagacg tgcactggcc agggggatca   4020

ccatccgtcg cccgggcgtg tcaataatat cactctgtac atccacaaac agacgataac   4080

ggctctctct tttataggtg taaaccttaa actgcatttc accagtccct gttctcgtca   4140

gcaaaagagc cgttcatttc aataaaccgg gcgacctcag ccatcccttc ctgattttcc   4200

gctttcca                                                            4208
```

<210> SEQ ID NO 160
<211> LENGTH: 4165
<212> TYPE: DNA
<213> ORGANISM: Artificial Sequence
<220> FEATURE:
<223> OTHER INFORMATION: pDONR204
<220> FEATURE:
<221> NAME/KEY: misc_feature
<222> LOCATION: (1326)..(1326)
<223> OTHER INFORMATION: 'n' can be any nucleotide (A, T, C, G or U)

<400> SEQUENCE: 160

```
cggcattgag gacaatagcg agtaggctgg atacgacgat tccgtttgag aagaacattt     60

ggaaggctgt cggtcgacta caggtcacta ataccatcta agtagttgaa tcatagtgac    120

tggatatgtt gtgttttaca gtattatgta gtctgttttt tatgcaaaat ctaatttaat    180

atattgatat ttatatcatt ttacgtttct cgttcagctt ttttgtacaa agttggcatt    240

ataaaaaagc attgcttatc aatttgttgc aacgaacagg tcactatcag tcaaaataaa    300

atcattattt ggggcccgag atccatgcta gctgcagtgc gcagggcccg tgtctcaaaa    360

tctctgatgt tacattgcac aagataaaaa tatatcatca tgaacaataa aactgtctgc    420

ttacataaac agtaatacaa ggggtgttat gagccatatt caacgggaaa cgtcttgctg    480

gaggccgcga ttaaattcca acatggatgc tgatttatat gggtataaat gggctcgcga    540

taatgtcggg caatcaggtg cgacaatctt tcgattgtat gggaagcccg atgcgccaga    600

gttgtttctg aaacatggca aaggtagcgt tgccaatgat gttacagatg agatggtcag    660

actaaactgg ctgacggaat ttatgcctct tccgaccatc aagcatttta tccgtactcc    720

tgatgatgca tggttactca ccactgcgat ccgcgggaaa acagcattcc aggtattaga    780

agaatatcct gattcaggtg aaaatattgt tgatgcgctg gcagtgttcc tgcgccggtt    840

gcattcgatt cctgtttgta attgtccttt taacagcgat cgcgtatttc gtctcgctca    900

ggcgcaatca cgaatgaata acggtttggt tgatgcgagt gattttgatg acgagcgtaa    960

tggctggcct gttgaacaag tctggaaaga aatgcatacg cttttgccat tctcaccgga   1020

ttcagtcgtc actcatggtg atttctcact tgataacctt atttttgacg aggggaaatt   1080
```

-continued

```
aataggttgt attgatgttg gacgagtcgg aatcgcagac cgataccagg atcttgccat   1140
cctatggaac tgcctcggtg agttttctcc ttcattacag aaacggcttt ttcaaaaata   1200
tggtattgat aatcctgata tgaataaatt gcagtttcat ttgatgctcg atgagttttt   1260
ctaatcagaa ttggttaatt ggttgtaaca ctggcagagc attacgctga cttgacggga   1320
cggcgncatg accaaaatcc cttaacgtga gttttcgttc cactgagcgt cagaccccgt   1380
agaaaagatc aaaggatctt cttgagatcc tttttttctg cgcgtaatct gctgcttgca   1440
aacaaaaaaa ccaccgctac cagcggtggt ttgtttgccg gatcaagagc taccaactct   1500
ttttccgaag gtaactggct tcagcagagc gcagatacca aatactgtcc ttctagtgta   1560
gccgtagtta ggccaccact tcaagaactc tgtagcaccg cctacatacc tcgctctgct   1620
aatcctgtta ccagtggctg ctgccagtgg cgataagtcg tgtcttaccg ggttggactc   1680
aagacgatag ttaccggata aggcgcagcg gtcgggctga acggggggtt cgtgcacaca   1740
gcccagcttg gagcgaacga cctacaccga actgagatac ctacagcgtg agctatgaga   1800
aagcgccacg cttcccgaag ggagaaaggc ggacaggtat ccggtaagcg gcagggtcgg   1860
aacaggagag cgcacgaggg agcttccagg gggaaacgcc tggtatcttt atagtcctgt   1920
cgggtttcgc cacctctgac ttgagcgtcg atttttgtga tgctcgtcag gggggcggag   1980
cctatggaaa aacgccagca acgcggcctt tttacggttc ctggcctttt gctggccttt   2040
tgctcacatg ttctttcctg cgttatcccc tgattctgtg gataaccgta ttaccgctag   2100
ctggatcggc aaataatgat tttattttga ctgatagtga cctgttcgtt gcaacaaatt   2160
gataagcaat gctttttat aatgccaact ttgtacaaga aagctgaacg agaaacgtaa    2220
aatgatataa atatcaatat attaaattag attttgcata aaaaacagac tacataatac   2280
tgtaaaacac aacatatcca gtcactatga ttcaactact tagatggtat tagtgacctg   2340
tagtcgacta agttggcagc atcacccgac gcactttgcg ccgaataaat acctgtgacg   2400
gaagatcact tcgcagaata aataaatcct ggtgtccctg ttgataccgg gaagccctgg   2460
gccaactttt ggcgaaaatg agacgttgat cggcacattt cacaactctt atacttttct   2520
cttacaagtc gttcggcttc atctggattt tcagcctcta tacttactaa acgtgataaa   2580
gtttctgtaa tttctactgt atcgacctgc agactggctg tgtataacgg agcctgacat   2640
ttatattccc cagaacatca ggttaatggc gtttttgatg tcattttcgc ggtggctgag   2700
atcagccact tcttccccga taacggagac cggcacactg gccatatcgg tggtcatcat   2760
gcgccagctt tcatccccga tatgcaccac cgggtaaagt tcacgggaga ctttatctga   2820
cagcagacgt gcactggcca gggggatcac catccgtcgc ccgggcgtgt caataatatc   2880
actctgtaca tccacaaaca gacgataacg gctctctctt ttataggtgt aaaccttaaa   2940
ctgcatttca ccagtccctg ttctcgtcag caaaagagcc gttcatttca ataaaccggg   3000
cgacctcagc catcccttcc tgattttccg ctttccagcg ttcggcacgc agacgacggg   3060
cttcattctg catggttgtg cttaccagac cggagatatt gacatcatat atgccttgag   3120
caactgatag ctgtcgctgt caactgtcac tgtaatacgc tgcttcatag cacacctctt   3180
tttgacatac ttcgggtata catatcagta tatattctta taccgcaaaa atcagcgcgc   3240
aaatacgcat actgttatct ggcttttagt aagccggatc cacgcgttta cgccccgccc   3300
tgccactcat cgcagtactg ttgtaattca ttaagcattc tgccgacatg gaagccatca   3360
cagacggcat gatgaacctg aatcgccagc ggcatcagca ccttgtcgcc ttgcgtataa   3420
```

-continued

```
tatttgccca tggtgaaaac gggggcgaag aagttgtcca tattggccac gtttaaatca   3480

aaactggtga aactcaccca gggattggct gagacgaaaa acatattctc aataaaccct   3540

ttagggaaat aggccaggtt ttcaccgtaa cacgccacat cttgcgaata tatgtgtaga   3600

aactgccgga aatcgtcgtg gtattcactc cagagcgatg aaaacgtttc agtttgctca   3660

tggaaaacgg tgtaacaagg gtgaacacta tcccatatca ccagctcacc gtctttcatt   3720

gccatacgga attccggatg agcattcatc aggcgggcaa gaatgtgaat aaaggccgga   3780

taaaacttgt gcttattttt ctttacggtc tttaaaaagg ccgtaatatc cagctgaacg   3840

gtctggttat aggtacattg agcaactgac tgaaatgcct caaaatgttc tttacgatgc   3900

cattgggata tatcaacggt ggtatatcca gtgatttttt tctccatttt agcttcctta   3960

gctcctgaaa atctcgataa ctcaaaaaat acgcccggta gtgatcttat ttcattatgg   4020

tgaaagttgg aacctcttac tgttcttgat gcagatgatt ttcaggacta tgacactagc   4080

atatatgaat aggtagatgt ttttattttg tcacacaaaa aagaggctcg cacctctttt   4140

tcttatttct ttttatgatt taata                                         4165
```

```
<210> SEQ ID NO 161
<211> LENGTH: 4939
<212> TYPE: DNA
<213> ORGANISM: Artificial Sequence
<220> FEATURE:
<223> OTHER INFORMATION: pDONR205

<400> SEQUENCE: 161
```

```
ggcatcagca ccttgtcgcc ttgcgtataa tatttgccca tggtgaaaac gggggcgaag     60

aagttgtcca tattggccac gtttaaatca aaactggtga aactcaccca gggattggct    120

gagacgaaaa acatattctc aataaaccct ttagggaaat aggccaggtt ttcaccgtaa    180

cacgccacat cttgcgaata tatgtgtaga aactgccgga aatcgtcgtg gtattcactc    240

cagagcgatg aaaacgtttc agtttgctca tggaaaacgg tgtaacaagg gtgaacacta    300

tcccatatca ccagctcacc gtctttcatt gccatacgga attccggatg agcattcatc    360

aggcgggcaa gaatgtgaat aaaggccgga taaaacttgt gcttattttt ctttacggtc    420

tttaaaaagg ccgtaatatc cagctgaacg gtctggttat aggtacattg agcaactgac    480

tgaaatgcct caaaatgttc tttacgatgc cattgggata tatcaacggt ggtatatcca    540

gtgatttttt tctccatttt agcttcctta gctcctgaaa atctcgataa ctcaaaaaat    600

acgcccggta gtgatcttat ttcattatgg tgaaagttgg aacctcttac gtgccgatca    660

acgtctcatt ttcgccaaaa gttggcccag ggcttcccgg tatcaacagg gacaccagga    720

tttatttatt ctgcgaagtg atcttccgtc acaggtattt attcggcgca aagtgcgtcg    780

ggtgatgctg ccaacttagt cgactacagg tcactaatac catctaagta gttgattcat    840

agtgactgga tatgttgtgt tttacagtat tatgtagtct gtttttttatg caaaatctaa   900

tttaatatat tgatatttat atcattttac gtttctcgtt cagctttctt gtacaaagtt    960

ggcattataa gaaagcattg cttatcaatt tgttgcaacg aacaggtcac tatcagtcaa   1020

aataaaatca ttatttgcca tccagctgca gctctggccc gtgtctcaaa atctctgatg   1080

ttacattgca caagataaaa atatatcatc atgaattctc atgtttgaca gcttatcatc   1140

gataagcttt aatgcggtag tttatcacag ttaaattgct aacgcagtca ggcaccgtgt   1200

atgaaatcta acaatgcgct catcgtcatc ctcggcaccg tcaccctgga tgctgtaggc   1260

ataggcttgg ttatgccggt actgccgggc ctcttgcggg atatcgtcca ttccgacagc   1320
```

-continued

```
atcgccagtc actatggcgt gctgctagcg ctatatgcgt tgatgcaatt tctatgcgca   1380
cccgttctcg gagcactgtc cgaccgcttt ggccgccgcc cagtcctgct cgcttcgcta   1440
cttggagcca ctatcgacta cgcgatcatg gcgaccacac ccgtcctgtg gatcctctac   1500
gccggacgca tcgtggccgg catcaccggc gccacaggtg cggttgctgg cgcctatatc   1560
gccgacatca ccgatgggga agatcgggct cgccacttcg ggctcatgag cgcttgtttc   1620
ggcgtgggta tggtggcagg ccccgtggcc gggggactgt tgggcgccat ctccttgcat   1680
gcaccattcc ttgcggcggc ggtgctcaac ggcctcaacc tactactggg ctgcttccta   1740
atgcaggagt cgcataaggg agagcgtcga ccgatgccct tgagagcctt caacccagtc   1800
agctccttcc ggtgggcgcg gggcatgact atcgtcgccg cacttatgac tgtcttcttt   1860
atcatgcaac tcgtaggaca ggtgccggca gcgctctggg tcattttcgg cgaggaccgc   1920
tttcgctgga gcgcgacgat gatcggcctg tcgcttgcgg tattcggaat cttgcacgcc   1980
ctcgctcaag ccttcgtcac tggtcccgcc accaaacgtt tcggcgagaa gcaggccatt   2040
atcgccggca tggcggccga cgcgctgggc tacgtcttgc tggcgttcgc gacgcgaggc   2100
tggatggcct tccccattat gattcttctc gcttccggcg gcatcgggat gcccgcgttg   2160
caggccatgc tgtccaggca ggtagatgac gaccatcagg gacagcttca aggatcgctc   2220
gcggctctta ccagcctaac ttcgatcatt ggaccgctga tcgtcacggc gatttatgcc   2280
gcctcggcga gcacatggaa cgggttggca tggattgtag gcgccgccct ataccttgtc   2340
tgcctccccg cgttgcgtcg cggtgcatgg agccgggcca cctcgacctg aatggaagcc   2400
ggcggcacct cgctaacgga ttcaccactc caagaattgg agccaatcaa ttcttgcgga   2460
gaactgtgaa tgcgcaaacc aacccttggc agaacatatc catcgcatga ccaaaatccc   2520
ttaacgtgag ttttcgttcc actgagcgtc agaccccgta gaaaagatca aaggatcttc   2580
ttgagatcct ttttttctgc gcgtaatctg ctgcttgcaa acaaaaaaac caccgctacc   2640
agcggtggtt tgtttgccgg atcaagagct accaactctt tttccgaagg taactggctt   2700
cagcagagcg cagataccaa atactgtcct tctagtgtag ccgtagttag gccaccactt   2760
caagaactct gtagcaccgc ctacatacct cgctctgcta atcctgttac cagtggctgc   2820
tgccagtggc gataagtcgt gtcttaccgg gttggactca agacgatagt taccggataa   2880
ggcgcagcgg tcgggctgaa cggggggttc gtgcacacag cccagcttgg agcgaacgac   2940
ctacaccgaa ctgagatacc tacagcgtga gctatgagaa agcgccacgc ttcccgaagg   3000
gagaaaggcg gacaggtatc cggtaagcgg cagggtcgga acaggagagc gcacgaggga   3060
gcttccaggg ggaaacgcct ggtatcttta tagtcctgtc gggtttcgcc acctctgact   3120
tgagcgtcga tttttgtgat gctcgtcagg ggggcggagc ctatggaaaa acgccagcaa   3180
cgcggccttt ttacggttcc tggccttttg ctggcctttt gctcacatgt tctttcctgc   3240
gttatcccct gattctgtgg ataaccgtat taccgctagc caggaagagt ttgtagaaac   3300
gcaaaaaggc catccgtcag gatggccttc tgcttagttt gatgcctggc agtttatggc   3360
gggcgtcctg cccgccaccc tccgggccgt tgcttcacaa cgttcaaatc cgctcccggc   3420
ggatttgtcc tactcaggag agcgttcacc gacaaacaac agataaaacg aaaggcccag   3480
tcttccgact gagcctttcg ttttatttga tgcctggcag ttccctactc tcgcgttaac   3540
gctagcatgg atctcgggcc ccaaataatg attttatttt gactgatagt gacctgttcg   3600
ttgcaacaaa ttgatgagca atgctttttt ataatgccaa ctttgtacaa aaaagctgaa   3660
```

-continued

```
cgagaaacgt aaaatgatat aaatatcaat atattaaatt agattttgca taaaaaacag   3720

actacataat actgtaaaac acaacatatc cagtcactat gaatcaacta cttagatggt   3780

attagtgacc tgtagtcgac cgacagcctt ccaaatgttc ttcgggtgat gctgccaact   3840

tagtcgaccg acagccttcc aaatgttctt ctcaaacgga atcgtcgtat ccagcctact   3900

cgctattgtc ctcaatgccg tattaaatca taaaaagaaa taagaaaaag aggtgcgagc   3960

ctcttttttg tgtgacaaaa taaaaacatc tacctattca tatacgctag tgtcatagtc   4020

ctgaaaatca tctgcatcaa gaacaatttc acaactctta tacttttctc ttacaagtcg   4080

ttcggcttca tctggatttt cagcctctat acttactaaa cgtgataaag tttctgtaat   4140

ttctactgta tcgacctgca gactggctgt gtataaggga gcctgacatt tatattcccc   4200

agaacatcag gttaatggcg tttttgatgt cattttcgcg gtggctgaga tcagccactt   4260

cttccccgat aacggagacc ggcacactgg ccatatcggt ggtcatcatg cgccagcttt   4320

catccccgat atgcaccacc gggtaaagtt cacgggagac tttatctgac agcagacgtg   4380

cactggccag ggggatcacc atccgtcgcc cgggcgtgtc aataatatca ctctgtacat   4440

ccacaaacag acgataacgg ctctctcttt tataggtgta aaccttaaac tgcatttcac   4500

cagtccctgt tctcgtcagc aaaagagccg ttcatttcaa taaaccgggc gacctcagcc   4560

atcccttcct gattttccgc tttccagcgt tcggcacgca gacgacgggc ttcattctgc   4620

atggttgtgc ttaccagacc ggagatattg acatcatata tgccttgagc aactgatagc   4680

tgtcgctgtc aactgtcact gtaatacgct gcttcatagc acacctcttt ttgacatact   4740

tcgggtatac atatcagtat atattcttat accgcaaaaa tcagcgcgca aatacgcata   4800

ctgttatctg gcttttagta agccggatcc acgcgattac gccccgccct gccactcatc   4860

gcagtactgt tgtaattcat taagcattct gccgacatgg aagccatcac agacggcatg   4920

atgaacctga atcgccagc                                                4939
```

<210> SEQ ID NO 162
<211> LENGTH: 5156
<212> TYPE: DNA
<213> ORGANISM: Artificial Sequence
<220> FEATURE:
<223> OTHER INFORMATION: pDONR206
<220> FEATURE:
<221> NAME/KEY: misc_feature
<222> LOCATION: (1102)..(1102)
<223> OTHER INFORMATION: 'n' can be any nucleotide (A, T, C, G or U)
<220> FEATURE:
<221> NAME/KEY: misc_feature
<222> LOCATION: (3080)..(3080)
<223> OTHER INFORMATION: 'n' can be any nucleotide (A, T, C, G or U)

<400> SEQUENCE: 162

```
cggcattgag gacaatagcg agtaggctgg atacgacgat tccgtttgag aagaacattt     60

ggaaggctgt cggtcgacta caggtcacta ataccatcta agtagttgaa tcatagtgac    120

tggatatgtt gtgttttaca gtattatgta gtctgttttt tatgcaaaat ctaatttaat    180

atattgatat ttatatcatt ttacgtttct cgttcagctt ttttgtacaa agttggcatt    240

ataaaaaagc attgcttatc aatttgttgc aacgaacagg tcactatcag tcaaaataaa    300

atcattattt ggggcccgag atccatgcta gcggtaatac ggttatccac agaatcaggg    360

gataacgcag gaaagaacat gtgagcaaaa ggccagcaaa aggccaggaa ccgtaaaaag    420

gccgcgttgc tggcgttttt ccataggctc cgcccccctg acgagcatca caaaaatcga    480

cgctcaagtc agaggtggcg aaacccgaca ggactataaa gataccaggc gtttccccct    540
```

-continued

```
ggaagctccc tcgtgcgctc tcctgttccg accctgccgc ttaccggata cctgtccgcc    600
tttctccctt cgggaagcgt ggcgctttct catagctcac gctgtaggta tctcagttcg    660
gtgtaggtcg ttcgctccaa gctgggctgt gtgcacgaac cccccgttca gcccgaccgc    720
tgcgccttat ccggtaacta tcgtcttgag tccaacccgg taagacacga cttatcgcca    780
ctggcagcag ccactggtaa caggattagc agagcgaggt atgtaggcgg tgctacagag    840
ttcttgaagt ggtggcctaa ctacggctac actagaagga cagtatttgg tatctgcgct    900
ctgctgaagc cagttacctt cggaaaaaga gttggtagct cttgatccgg caaacaaacc    960
accgctggta gcggtggttt ttttgtttgc aagcagcaga ttacgcgcag aaaaaaagga   1020
tctcaagaag atcctttgat cttttctacg gggtctgacg ctcagtggaa cgaaaactca   1080
cgttaaggga ttttggtcat gncgccgtcc cgtcaagtca gcgtaatgct ctgccagtgt   1140
tacaaccaat taaccaattc tgattagaaa aactcatcga gcatcaaatg aaactgcaat   1200
ttattcatat caggattatc aataccatat ttttgaaaaa gccgtttctg taatgaagga   1260
gaaaactcac cgaggcagtt ccataggatg gcaagatcct ggtatcggtc tgcgattccg   1320
actcgtccaa catcaataca acctattagc cgaggtcttc cgatctcctg aagccagggc   1380
agatccgtgc acagcacctt gccgtagaag aacagcaagg ccgccaatgc ctgacgatgc   1440
gtggagaccg aaaccttgcg ctcgttcgcc agccaggaca gaaatgcctc gacttcgctg   1500
ctgcccaagg ttgccgggtg acgcacaccg tggaaacgga tgaaggcacg aacccagttg   1560
acataagcct gttcggttcg taaactgtaa tgcaagtagc gtatgcgctc acgcaactgg   1620
tccagaacct tgaccgaacg cagcggtggt aacggcgcag tggcggtttt catggcttgt   1680
tatgactgtt tttttgtaca gtctatgcct cgggcatcca agcagcaagc gcgttacgcc   1740
gtgggtcgat gtttgatgtt atggagcagc aacgatgtta cgcagcagca acgatgttac   1800
gcagcagggc agtcgcccta aaacaaagtt aggtggctca agtatgggca tcattcgcac   1860
atgtaggctc ggccctgacc aagtcaaatc catgcgggct gctcttgatc ttttcggtcg   1920
tgagttcgga gacgtagcca cctactccca acatcagccg gactccgatt acctcgggaa   1980
cttgctccgt agtaagacat tcatcgcgct tgctgccttc gaccaagaag cggttgttgg   2040
cgctctcgcg gcttacgttc tgcccaggtt tgagcagccg cgtagtgaga tctatatcta   2100
tgatctcgca gtctccggcg agcaccggag gcagggcatt gccaccgcgc tcatcaatct   2160
cctcaagcat gaggccaacg cgcttggtgc ttatgtgatc tacgtgcaag cagattacgg   2220
tgacgatccc gcagtggctc tctatacaaa gttgggcata cgggaagaag tgatgcactt   2280
tgatatcgac ccaagtaccg ccacctaaca attcgttcaa gccgagatcg gcttcccggc   2340
ctaatttccc ctcgtcaaaa ataaggttat caagtgagaa atcaccatga gtgacgactg   2400
aatccggtga gaatggcaaa agcgtatgca tttctttcca gacttgttca acaggccagc   2460
cattacgctc gtcatcaaaa tcactcgcat caaccaaacc gttattcatt cgtgattgcg   2520
cctgagcgag acgaaatacg cgatcgctgt taaaaggaca attacaaaca ggaatcgaat   2580
gcaaccggcg caggaacact gccagcgcat caacaatatt ttcacctgaa tcaggatatt   2640
cttctaatac ctggaatgct gttttcccgc ggatcgcagt ggtgagtaac catgcatcat   2700
caggagtacg gataaaatgc ttgatggtcg gaagaggcat aaattccgtc agccagttta   2760
gtctgaccat ctcatctgta acatcattgg caacgctacc tttgccatgt ttcagaaaca   2820
actctggcgc atcgggcttc ccatacaatc gaaagattgt cgcacctgat tgcccgacat   2880
```

-continued

```
tatcgcgagc ccatttatac ccatataaat cagcatccat gttggaattt aatcgcggcc   2940

tccagcaaga cgtttcccgt tgaatatggc tcataacacc ccttgtatta ctgtttatgt   3000

aagcagacag ttttattgtt catgatgata tatttttatc ttgtgcaatg taacatcaga   3060

gattttgaga cacgggcccn gcgcactgca gctggatcgg caaataatga ttttattttg   3120

actgatagtg acctgttcgt tgcaacaaat tgataagcaa tgctttttta taatgccaac   3180

tttgtacaag aaagctgaac gagaaacgta aaatgatata aatatcaata tattaaatta   3240

gattttgcat aaaaaacaga ctacataata ctgtaaaaca caacatatcc agtcactatg   3300

attcaactac ttagatggta ttagtgacct gtagtcgact aagttggcag catcacccga   3360

cgcactttgc gccgaataaa tacctgtgac ggaagatcac ttcgcagaat aaataaatcc   3420

tggtgtccct gttgataccg ggaagccctg ggccaacttt tggcgaaaat gagacgttga   3480

tcggcacgta agaggttcca actttcacca taatgaaata agatcactac cgggcgtatt   3540

ttttgagtta tcgagatttt caggagctaa ggaagctaaa atggagaaaa aaatcactgg   3600

atataccacc gttgatatat cccaatggca tcgtaaagaa cattttgagg catttcagtc   3660

agttgctcaa tgtacctata accagaccgt tcagctggat attacggcct ttttaaagac   3720

cgtaaagaaa aataagcaca agttttatcc ggcctttatt cacattcttg cccgcctgat   3780

gaatgctcat ccggaattcc gtatggcaat gaaagacggt gagctggtga tatgggatag   3840

tgttcaccct tgttacaccg ttttccatga gcaaactgaa acgttttcat cgctctggag   3900

tgaataccac gacgatttcc ggcagtttct acacatatat tcgcaagatg tggcgtgtta   3960

cggtgaaaac ctggcctatt tccctaaagg gtttattgag aatatgtttt tcgtctcagc   4020

caatccctgg gtgagtttca ccagttttga tttaaacgtg gccaatatgg acaacttctt   4080

cgcccccgtt ttcaccatgg gcaaatatta tacgcaaggc gacaaggtgc tgatgccgct   4140

ggcgattcag gttcatcatg ccgtctgtga tggcttccat gtcggcagaa tgcttaatga   4200

attacaacag tactgcgatg agtggcaggg cggggcgtaa acgcgtggat ccggcttact   4260

aaaagccaga taacagtatg cgtatttgcg cgctgatttt tgcggtataa gaatatatac   4320

tgatatgtat acccgaagta tgtcaaaaag aggtgtgcta tgaagcagcg tattacagtg   4380

acagttgaca gcgacagcta tcagttgctc aaggcatata tgatgtcaat atctccggtc   4440

tggtaagcac aaccatgcag aatgaagccc gtcgtctgcg tgccgaacgc tggaaagcgg   4500

aaaatcagga agggatggct gaggtcgccc ggtttattga aatgaacggc tcttttgctg   4560

acgagaacag ggactggtga aatgcagttt aaggtttaca cctataaaag agagagccgt   4620

tatcgtctgt ttgtggatgt acagagtgat attattgaca cgcccgggcg acggatggtg   4680

atccccctgg ccagtgcacg tctgctgtca gataaagtct cccgtgaact ttacccggtg   4740

gtgcatatcg gggatgaaag ctggcgcatg atgaccaccg atatggccag tgtgccggtc   4800

tccgttatcg gggaagaagt ggctgatctc agccaccgcg aaaatgacat caaaaacgcc   4860

attaacctga tgttctgggg aatataaatg tcaggctccg ttatacacag ccagtctgca   4920

ggtcgataca gtagaaatta cagaaacttt atcacgttta gtaagtatag aggctgaaaa   4980

tccagatgaa gccgaacgac ttgtaagaga aaagtataag agttgtgaaa ttgttcttga   5040

tgcagatgat tttcaggact atgacactag catatatgaa taggtagatg tttttatttt   5100

gtcacacaaa aaagaggctc gcacctcttt ttcttatttc tttttatgat ttaata       5156
```

<210> SEQ ID NO 163
<211> LENGTH: 21

-continued

<212> TYPE: DNA
<213> ORGANISM: Artificial Sequence
<220> FEATURE:
<223> OTHER INFORMATION: attR1 Reading Frame A

<400> SEQUENCE: 163
atcacaagtt tgtacaaaaa a 21

<210> SEQ ID NO 164
<211> LENGTH: 22
<212> TYPE: DNA
<213> ORGANISM: Artificial Sequence
<220> FEATURE:
<223> OTHER INFORMATION: attR1 Reading Frame B

<400> SEQUENCE: 164
atcaacaagt ttgtacaaaa aa 22

<210> SEQ ID NO 165
<211> LENGTH: 23
<212> TYPE: DNA
<213> ORGANISM: Artificial Sequence
<220> FEATURE:
<223> OTHER INFORMATION: attR1 Reading Frame C

<400> SEQUENCE: 165
atcaaacaag tttgtacaaa aaa 23

<210> SEQ ID NO 166
<211> LENGTH: 21
<212> TYPE: DNA
<213> ORGANISM: Artificial Sequence
<220> FEATURE:
<223> OTHER INFORMATION: attR2 Reading Frame A

<400> SEQUENCE: 166
tttcttgtac aaagtggtga t 21

<210> SEQ ID NO 167
<211> LENGTH: 22
<212> TYPE: DNA
<213> ORGANISM: Artificial Sequence
<220> FEATURE:
<223> OTHER INFORMATION: attR2 Reading Frame B

<400> SEQUENCE: 167
tttcttgtac aaagtggttg at 22

<210> SEQ ID NO 168
<211> LENGTH: 23
<212> TYPE: DNA
<213> ORGANISM: Artificial Sequence
<220> FEATURE:
<223> OTHER INFORMATION: attR2 Reading Frame C

<400> SEQUENCE: 168
tttcttgtac aaagtggttc gat 23

<210> SEQ ID NO 169
<211> LENGTH: 23
<212> TYPE: DNA
<213> ORGANISM: Artificial Sequence
<220> FEATURE:
<223> OTHER INFORMATION: attR1 Reading Frame C (Alternative B)

<400> SEQUENCE: 169

-continued atcaaacaag tttgtacaaa aaa 23

<210> SEQ ID NO 170
<211> LENGTH: 23
<212> TYPE: DNA
<213> ORGANISM: Artificial Sequence
<220> FEATURE:
<223> OTHER INFORMATION: attR2 Reading Frame C (Alternative B)

<400> SEQUENCE: 170
tttcttgtac aaagtggttt gat 23

<210> SEQ ID NO 171
<211> LENGTH: 30
<212> TYPE: DNA
<213> ORGANISM: Artificial Sequence
<220> FEATURE:
<223> OTHER INFORMATION: attR1 Reading Frame A Cassette
<220> FEATURE:
<221> NAME/KEY: misc_feature
<222> LOCATION: (1)..(6)
<223> OTHER INFORMATION: 'n' can be any nucleotide (A, T, C, G or U)

<400> SEQUENCE: 171
nnnnnnatca caagtttgta caaaaaagct 30

<210> SEQ ID NO 172
<211> LENGTH: 33
<212> TYPE: DNA
<213> ORGANISM: Artificial Sequence
<220> FEATURE:
<223> OTHER INFORMATION: attR1 Reading Frame B Cassette
<220> FEATURE:
<221> NAME/KEY: misc_feature
<222> LOCATION: (1)..(8)
<223> OTHER INFORMATION: 'n' can be any nucleotide (A, T, C, G or U)

<400> SEQUENCE: 172
nnnnnnnnat caacaagttt gtacaaaaaa gct 33

<210> SEQ ID NO 173
<211> LENGTH: 33
<212> TYPE: DNA
<213> ORGANISM: Artificial Sequence
<220> FEATURE:
<223> OTHER INFORMATION: attR1 Reading Frame C Cassette
<220> FEATURE:
<221> NAME/KEY: misc_feature
<222> LOCATION: (1)..(7)
<223> OTHER INFORMATION: 'n' can be any nucleotide (A, T, C, G or U)

<400> SEQUENCE: 173
nnnnnnnatc aaacaagttt gtacaaaaaa gct 33

<210> SEQ ID NO 174
<211> LENGTH: 4554
<212> TYPE: DNA
<213> ORGANISM: Artificial Sequence
<220> FEATURE:
<223> OTHER INFORMATION: prfC Parent III
<220> FEATURE:
<221> NAME/KEY: gene
<222> LOCATION: (286)..(410)
<223> OTHER INFORMATION: attR1
<220> FEATURE:
<221> NAME/KEY: gene
<222> LOCATION: (660)..(1319)
<223> OTHER INFORMATION: CmR
<220> FEATURE:
<221> NAME/KEY: gene -continued
<222> LOCATION: (1439)..(1523)
<223> OTHER INFORMATION: inactivated ccdA
<220> FEATURE:
<221> NAME/KEY: gene
<222> LOCATION: (1661)..(1966)
<223> OTHER INFORMATION: ccdB
<220> FEATURE:
<221> NAME/KEY: gene
<222> LOCATION: (2007)..(2131)
<223> OTHER INFORMATION: attR2
<220> FEATURE:
<221> NAME/KEY: gene
<222> LOCATION: (2753)..(3613)
<223> OTHER INFORMATION: amp

<400> SEQUENCE: 174
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg ccaagcttgc 240
atgcctgcag gtcgactcta gaggatcccc gggtaccgat atcaaacaag tttgtacaaa 300
aaagctgaac gagaaacgta aaatgatata aatatcaata tattaaatta gattttgcat 360
aaaaaacaga ctacataata ctgtaaaaca caacatatcc agtcactatg gcggccgcta 420
agttggcagc atcacccgac gcactttgcg ccgaataaat acctgtgacg gaagatcact 480
tcgcagaata aataaatcct ggtgtccctg ttgataccgg gaagccctgg gccaactttt 540
ggcgaaaatg agacgttgat cggcacgtaa gaggttccaa ctttcaccat aatgaaataa 600
gatcactacc gggcgtattt tttgagttat cgagattttc aggagctaag gaagctaaaa 660
tggagaaaaa aatcactgga tataccaccg ttgatatatc ccaatggcat cgtaaagaac 720
attttgaggc atttcagtca gttgctcaat gtacctataa ccagaccgtt cagctggata 780
ttacggcctt tttaaagacc gtaaagaaaa ataagcacaa gttttatccg gcctttattc 840
acattcttgc ccgcctgatg aatgctcatc cggaattccg tatggcaatg aaagacggtg 900
agctggtgat atgggatagt gttcaccctt gttacaccgt tttccatgag caaactgaaa 960
cgttttcatc gctctggagt gaataccacg acgatttccg gcagtttcta cacatatatt 1020
cgcaagatgt ggcgtgttac ggtgaaaacc tggcctattt ccctaaaggg tttattgaga 1080
atatgttttt cgtctcagcc aatccctggg tgagtttcac cagttttgat ttaaacgtgg 1140
ccaatatgga caacttcttc gcccccgttt tcaccatggg caaatattat acgcaaggcg 1200
acaaggtgct gatgccgctg gcgattcagg ttcatcatgc cgtctgtgat ggcttccatg 1260
tcggcagaat gcttaatgaa ttacaacagt actgcgatga gtggcagggc ggggcgtaat 1320
ctagaggatc cggcttacta aaagccagat aacagtatgc gtatttgcgc gctgattttt 1380
gcggtataag aatatatact gatatgtata cccgaagtat gtcaaaaaga ggtgtgctat 1440
gaagcagcgt attacagtga cagttgacag cgacagctat cagttgctca aggcatatat 1500
gatgtcaata tctccggtct ggtaagcaca accatgcaga atgaagcccg tcgtctgcgt 1560
gccgaacgct ggaaagcgga aaatcaggaa gggatggctg aggtcgcccg gtttattgaa 1620
atgaacggct cttttgctga cgagaacagg gactggtgaa atgcagttta aggtttacac 1680
ctataaaaga gagagccgtt atcgtctgtt tgtggatgta cagagtgata ttattgacac 1740
gcccgggcga cggatggtga tccccctggc cagtgcacgt ctgctgtcag ataaagtctc 1800
ccgtgaactt tacccggtgg tgcatatcgg ggatgaaagc tggcgcatga tgaccaccga 1860

-continued

```
tatggccagt gtgccggtct ccgttatcgg ggaagaagtg gctgatctca gccaccgcga   1920
aaatgacatc aaaaacgcca ttaacctgat gttctgggga atataaatgt caggctccgt   1980
tatacacagc cagtctgcag gtcgaccata gtgactggat atgttgtgtt ttacagtatt   2040
atgtagtctg tttttatgc aaaatctaat ttaatatatt gatatttata tcattttacg   2100
tttctcgttc agctttcttg tacaaagtgg ttcgatatcg gtaccgagct cgaattcact   2160
ggccgtcgtt ttacaacgtc gtgactggga aaaccctggc gttacccaac ttaatcgcct   2220
tgcagcacat ccccctttcg ccagctggcg taatagcgaa gaggcccgca ccgatcgccc   2280
ttcccaacag ttgcgcagcc tgaatggcga atggcgcctg atgcggtatt ttctccttac   2340
gcatctgtgc ggtatttcac accgcatatg gtgcactctc agtacaatct gctctgatgc   2400
cgcatagtta agccagcccc gacacccgcc aacacccgct gacgcgccct gacgggcttg   2460
tctgctcccg gcatccgctt acagacaagc tgtgaccgtc tccgggagct gcatgtgtca   2520
gaggttttca ccgtcatcac cgaaacgcgc gagacgaaag ggcctcgtga tacgcctatt   2580
tttataggtt aatgtcatga taataatggt ttcttagacg tcaggtggca cttttcgggg   2640
aaatgtgcgc ggaaccccta tttgtttatt tttctaaata cattcaaata tgtatccgct   2700
catgagacaa taaccctgat aaatgcttca ataatattga aaaaggaaga gtatgagtat   2760
tcaacatttc cgtgtcgccc ttattccctt ttttgcggca ttttgccttc ctgtttttgc   2820
tcacccagaa acgctggtga aagtaaaaga tgctgaagat cagttgggtg cacgagtggg   2880
ttacatcgaa ctggatctca acagcggtaa gatccttgag agttttcgcc ccgaagaacg   2940
ttttccaatg atgagcactt ttaaagttct gctatgtggc gcggtattat cccgtattga   3000
cgccgggcaa gagcaactcg gtcgccgcat acactattct cagaatgact tggttgagta   3060
ctcaccagtc acagaaaagc atcttacgga tggcatgaca gtaagagaat tatgcagtgc   3120
tgccataacc atgagtgata acactgcggc caacttactt ctgacaacga tcggaggacc   3180
gaaggagcta accgcttttt tgcacaacat gggggatcat gtaactcgcc ttgatcgttg   3240
ggaaccggag ctgaatgaag ccataccaaa cgacgagcgt gacaccacga tgcctgtagc   3300
aatggcaaca acgttgcgca aactattaac tggcgaacta cttactctag cttcccggca   3360
acaattaata gactggatgg aggcggataa agttgcagga ccacttctgc gctcggccct   3420
tccggctggc tggtttattg ctgataaatc tggagccggt gagcgtgggt ctcgcggtat   3480
cattgcagca ctggggccag atggtaagcc ctcccgtatc gtagttatct acacgacggg   3540
gagtcaggca actatggatg aacgaaatag acagatcgct gagataggtg cctcactgat   3600
taagcattgg taactgtcag accaagttta ctcatatata ctttagattg atttaaaact   3660
tcatttttaa tttaaaagga tctaggtgaa gatccttttt gataatctca tgaccaaaat   3720
cccttaacgt gagttttcgt tccactgagc gtcagacccc gtagaaaaga tcaaaggatc   3780
ttcttgagat cctttttttc tgcgcgtaat ctgctgcttg caaacaaaaa aaccaccgct   3840
accagcggtg gtttgtttgc cggatcaaga gctaccaact ctttttccga aggtaactgg   3900
cttcagcaga gcgcagatac caaatactgt ccttctagtg tagccgtagt taggccacca   3960
cttcaagaac tctgtagcac cgcctacata cctcgctctg ctaatcctgt taccagtggc   4020
tgctgccagt ggcgataagt cgtgtcttac cgggttggac tcaagacgat agttaccgga   4080
taaggcgcag cggtcgggct gaacgggggg ttcgtgcaca cagcccagct tggagcgaac   4140
gacctacacc gaactgagat acctacagcg tgagctatga gaaagcgcca cgcttcccga   4200
agggagaaag gcggacaggt atccggtaag cggcagggtc ggaacaggag agcgcacgag   4260
```

-continued

```
ggagcttcca gggggaaacg cctggtatct ttatagtcct gtcgggtttc gccacctctg   4320

acttgagcgt cgatttttgt gatgctcgtc aggggggcgg agcctatgga aaaacgccag   4380

caacgcggcc tttttacggt tcctggcctt ttgctggcct tttgctcaca tgttctttcc   4440

tgcgttatcc cctgattctg tggataaccg tattaccgcc tttgagtgag ctgataccgc   4500

tcgccgcagc cgaacgaccg agcgcagcga gtcagtgagc gaggaagcgg aaga         4554
```

```
<210> SEQ ID NO 175
<211> LENGTH: 7141
<212> TYPE: DNA
<213> ORGANISM: Artificial Sequence
<220> FEATURE:
<223> OTHER INFORMATION: pDEST28

<400> SEQUENCE: 175
```

```
atgcatgtcg ttacataact tacggtaaat ggcccgcctg gctgaccgcc caacgacccc     60

cgcccattga cgtcaataat gacgtatgtt cccatagtaa cgccaatagg gactttccat    120

tgacgtcaat gggtggagta tttacggtaa actgcccact tggcagtaca tcaagtgtat    180

catatgccaa gtacgccccc tattgacgtc aatgacggta aatggcccgc ctggcattat    240

gcccagtaca tgaccttatg ggactttcct acttggcagt acatctacgt attagtcatc    300

gctattacca tggtgatgcg gttttggcag tacatcaatg ggcgtggata gcggtttgac    360

tcacggggat ttccaagtct ccaccccatt gacgtcaatg ggagtttgtt ttggcaccaa    420

aatcaacggg actttccaaa atgtcgtaac aactccgccc cattgacgca aatgggcggt    480

aggcgtgtac ggtgggaggt ctatataagc agagctctcc ctatcagtga tagagatctc    540

cctatcagtg atagagatcg tcgacgagct cgtttagtga accgtcagat cgcctggaga    600

cgccatccac gctgttttga cctccataga agacaccggg accgatccag cctccggact    660

ctagaggatc cctaccggtg atatcctcga gcccatcaac aagtttgtac aaaaaagctg    720

aacgagaaac gtaaaatgat ataaatatca atatattaaa ttagattttg cataaaaaac    780

agactacata atactgtaaa acacaacata tccagtcact atggcggccg cattaggcac    840

cccaggcttt acactttatg cttccggctc gtataatgtg tggattttga gttaggatcc    900

ggcgagattt tcaggagcta aggaagctaa aatggagaaa aaaatcactg gatataccac    960

cgttgatata tcccaatggc atcgtaaaga acattttgag gcatttcagt cagttgctca   1020

atgtacctat aaccagaccg ttcagctgga tattacggcc tttttaaaga ccgtaaagaa   1080

aaataagcac aagttttatc cggcctttat tcacattctt gcccgcctga tgaatgctca   1140

tccggaattc cgtatggcaa tgaaagacgg tgagctggtg atatgggata gtgttcaccc   1200

ttgttacacc gttttccatg agcaaactga aacgttttca tcgctctgga gtgaatacca   1260

cgacgatttc cggcagtttc tacacatata ttcgcaagat gtggcgtgtt acggtgaaaa   1320

cctggcctat ttccctaaag ggtttattga gaatatgttt ttcgtctcag ccaatccctg   1380

ggtgagtttc accagttttg atttaaacgt ggccaatatg gacaacttct tcgcccccgt   1440

tttcaccatg ggcaaatatt atacgcaagg cgacaaggtg ctgatgccgc tggcgattca   1500

ggttcatcat gccgtctgtg atggcttcca tgtcggcaga atgcttaatg aattacaaca   1560

gtactgcgat gagtggcagg gcggggcgta aagatctgga tccggcttac taaaagccag   1620

ataacagtat gcgtatttgc gcgctgattt ttgcggtata agaatatata ctgatatgta   1680

tacccgaagt atgtcaaaaa gaggtgtgct atgaagcagc gtattacagt gacagttgac   1740
```

-continued

```
agcgacagct atcagttgct caaggcatat atgatgtcaa tatctccggt ctggtaagca   1800
caaccatgca gaatgaagcc cgtcgtctgc gtgccgaacg ctggaaagcg gaaaatcagg   1860
aagggatggc tgaggtcgcc cggtttattg aaatgaacgg ctcttttgct gacgagaaca   1920
gggactggtg aaatgcagtt taaggtttac acctataaaa gagagagccg ttatcgtctg   1980
tttgtggatg tacagagtga tattattgac acgcccgggc gacggatggt gatcccccctg   2040
gccagtgcac gtctgctgtc agataaagtc tcccgtgaac tttacccggt ggtgcatatc   2100
ggggatgaaa gctggcgcat gatgaccacc gatatggcca gtgtgccggt ctccgttatc   2160
ggggaagaag tggctgatct cagccaccgc gaaaatgaca tcaaaaacgc cattaacctg   2220
atgttctggg gaatataaat gtcaggctcc cttatacaca gccagtctgc aggtcgacca   2280
tagtgactgg atatgttgtg ttttacagta ttatgtagtc tgttttttat gcaaaatcta   2340
atttaatata ttgatattta tatcatttta cgtttctcgt tcagctttct tgtacaaagt   2400
ggttgatggg cggccgctct agagggccca agcttacgcg tgcatgcgac gtcatagctc   2460
tctccctata gtgagtcgta ttataagcta ggcactggcc gtcgttttac aacgtcgtga   2520
ctgggaaaac tgctagcttg ggatctttgt gaaggaacct tacttctgtg gtgtgacata   2580
attggacaaa ctacctacag agatttaaag ctctaaggta aatataaaat ttttaagtgt   2640
ataatgtgtt aaactagctg catatgcttg ctgcttgaga gttttgctta ctgagtatga   2700
tttatgaaaa tattatacac aggagctagt gattctaatt gtttgtgtat tttagattca   2760
cagtcccaag gctcatttca ggcccctcag tcctcacagt ctgttcatga tcataatcag   2820
ccataccaca tttgtagagg ttttacttgc tttaaaaaac ctcccacacc tccccctgaa   2880
cctgaaacat aaaatgaatg caattgttgt tgttaacttg tttattgcag cttataatgg   2940
ttacaaataa agcaatagca tcacaaattt cacaaataaa gcattttttt cactgcattc   3000
tagttgtggt ttgtccaaac tcatcaatgt atcttatcat gtctggatcg atcctgcatt   3060
aatgaatcgg ccaacgcgcg gggagaggcg gtttgcgtat tggctggcgt aatagcgaag   3120
aggcccgcac cgatcgccct tcccaacagt tgcgcagcct gaatggcgaa tgggacgcgc   3180
cctgtagcgg cgcattaagc gcggcgggtg tggtggttac gcgcagcgtg accgctacac   3240
ttgccagcgc cctagcgccc gctcctttcg ctttcttccc ttcctttctc gccacgttcg   3300
ccggctttcc ccgtcaagct ctaaatcggg ggctcccttt agggttccga tttagtgctt   3360
tacggcacct cgaccccaaa aaacttgatt agggtgatgg ttcacgtagt gggccatcgc   3420
cctgatagac ggtttttcgc cctttgacgt tggagtccac gttctttaat agtggactct   3480
tgttccaaac tggaacaaca ctcaacccta tctcggtcta ttcttttgat ttataaggga   3540
ttttgccgat ttcggcctat tggttaaaaa atgagctgat ttaacaaata tttaacgcga   3600
attttaacaa aatattaacg tttacaattt cgcctgatgc ggtattttct ccttacgcat   3660
ctgtgcggta tttcacaccg catacgcgga tctgcgcagc accatggcct gaaataacct   3720
ctgaaagagg aacttggtta ggtaccttct gaggcggaaa gaaccagctg tggaatgtgt   3780
gtcagttagg gtgtggaaag tccccaggct ccccagcagg cagaagtatg caaagcatgc   3840
atctcaatta gtcagcaacc aggtgtggaa agtccccagg ctccccagca ggcagaagta   3900
tgcaaagcat gcatctcaat tagtcagcaa ccatagtccc gcccctaact ccgcccatcc   3960
cgcccctaac tccgcccagt tccgcccatt ctccgcccca tggctgacta attttttta    4020
tttatgcaga ggccgaggcc gcctcggcct ctgagctatt ccagaagtag tgaggaggct   4080
tttttggagg cctaggcttt tgcaaaaagc ttgattcttc tgacacaaca gtctcgaact   4140
```

-continued

```
taagaccatg gccaagcctt tgtctcaaga agaatccacc ctcattgaaa gagcaacggc   4200
tacaatcaac agcatcccca tctctgaaga ctacagcgtc gccagcgcag ctctctctag   4260
cgacggccgc atcttcactg gtgtcaatgt atatcatttt actgggggac cttgtgcaga   4320
actcgtggtg ctgggcactg ctgctgctgc ggcagctggc aacctgactt gtatcgtcgc   4380
gatcggaaat gagaacaggg gcatcttgag cccctgcgga cggtgccgac aggtgcttct   4440
cgatctgcat cctgggatca aagccatagt gaaggacagt gatggacagc cgacggcagt   4500
tgggattcgt gaattgctgc cctctggtta tgtgtgggag ggctaagcac ttcgtggccg   4560
agttcgaaat gaccgaccaa gcgacgccca acctgccatc acgatggccg caataaaata   4620
tctttatttt cattacatct gtgtgttggt tttttgtgtg aatcgatagc gataaggatc   4680
cgcgtatggt gcactctcag tacaatctgc tctgatgccg catagttaag ccagccccga   4740
cacccgccaa cacccgctga cgcgccctga cgggcttgtc tgctcccggc atccgcttac   4800
agacaagctg tgaccgtctc cgggagctgc atgtgtcaga ggttttcacc gtcatcaccg   4860
aaacgcgcga gacgaaaggg cctcgtgata cgcctatttt tataggttaa tgtcatgata   4920
ataatggttt cttagacgtc aggtggcact tttcggggaa atgtgcgcgg aacccctatt   4980
tgtttatttt tctaaataca ttcaaatatg tatccgctca tgagacaata accctgataa   5040
atgcttcaat aatattgaaa aaggaagagt atgagtattc aacatttccg tgtcgccctt   5100
attccctttt ttgcggcatt ttgccttcct gtttttgctc acccagaaac gctggtgaaa   5160
gtaaaagatg ctgaagatca gttgggtgca cgagtgggtt acatcgaact ggatctcaac   5220
agcggtaaga tccttgagag ttttcgcccc gaagaacgtt ttccaatgat gagcactttt   5280
aaagttctgc tatgtggcgc ggtattatcc cgtattgacg ccgggcaaga gcaactcggt   5340
cgccgcatac actattctca gaatgacttg gttgagtact caccagtcac agaaaagcat   5400
cttacggatg gcatgacagt aagagaatta tgcagtgctg ccataaccat gagtgataac   5460
actgcggcca acttacttct gacaacgatc ggaggaccga aggagctaac cgcttttttg   5520
cacaacatgg gggatcatgt aactcgcctt gatcgttggg aaccggagct gaatgaagcc   5580
ataccaaacg acgagcgtga caccacgatg cctgtagcaa tggcaacaac gttgcgcaaa   5640
ctattaactg gcgaactact tactctagct tcccggcaac aattaataga ctggatggag   5700
gcggataaag ttgcaggacc acttctgcgc tcggcccttc cggctggctg gtttattgct   5760
gataaatctg gagccggtga gcgtgggtct cgcggtatca ttgcagcact ggggccagat   5820
ggtaagccct cccgtatcgt agttatctac acgacgggga gtcaggcaac tatggatgaa   5880
cgaaatagac agatcgctga gataggtgcc tcactgatta agcattggta actgtcagac   5940
caagtttact catatatact ttagattgat ttaaaacttc atttttaatt taaaaggatc   6000
taggtgaaga tcctttttga taatctcatg accaaaatcc cttaacgtga gttttcgttc   6060
cactgagcgt cagaccccgt agaaaagatc aaaggatctt cttgagatcc tttttttctg   6120
cgcgtaatct gctgcttgca aacaaaaaaa ccaccgctac cagcggtggt ttgtttgccg   6180
gatcaagagc taccaactct ttttccgaag gtaactggct tcagcagagc gcagatacca   6240
aatactgtcc ttctagtgta gccgtagtta ggccaccact tcaagaactc tgtagcaccg   6300
cctacatacc tcgctctgct aatcctgtta ccagtggctg ctgccagtgg cgataagtcg   6360
tgtcttaccg ggttggactc aagacgatag ttaccggata aggcgcagcg gtcgggctga   6420
acgggggggtt cgtgcacaca gcccagcttg gagcgaacga cctacaccga actgagatac   6480
```

-continued

```
ctacagcgtg agcattgaga aagcgccacg cttcccgaag ggagaaaggc ggacaggtat   6540
ccggtaagcg gcagggtcgg aacaggagag cgcacgaggg agcttccagg gggaaacgcc   6600
tggtatcttt atagtcctgt cgggtttcgc cacctctgac ttgagcgtcg atttttgtga   6660
tgctcgtcag gggggcggag cctatggaaa aacgccagca acgcggcctt tttacggttc   6720
ctggcctttt gctggccttt tgctcacatg ttctttcctg cgttatcccc tgattctgtg   6780
gataaccgta ttaccgcctt tgagtgagct gataccgctc gccgcagccg aacgaccgag   6840
cgcagcgagt cagtgagcga ggaagcggaa gagcgcccaa tacgcaaacc gcctctcccc   6900
gcgcgttggc cgattcatta atgcagagct tgcaattcgc gcgtttttca atattattga   6960
agcatttatc agggttattg tctcatgagc ggatacatat ttgaatgtat ttagaaaaat   7020
aaacaaatag gggttccgcg cacatttccc cgaaaagtgc cacctgacgt ctaagaaacc   7080
attattatca tgacattaac ctataaaaat aggcgtagta cgaggccctt tcactcatta   7140
g                                                                   7141
```

<210> SEQ ID NO 176
<211> LENGTH: 7156
<212> TYPE: DNA
<213> ORGANISM: Artificial Sequence
<220> FEATURE:
<223> OTHER INFORMATION: pDEST29

<400> SEQUENCE: 176

```
atgcatgtcg ttacataact tacggtaaat ggcccgcctg gctgaccgcc caacgacccc     60
cgcccattga cgtcaataat gacgtatgtt cccatagtaa cgccaatagg gactttccat    120
tgacgtcaat gggtggagta tttacggtaa actgcccact tggcagtaca tcaagtgtat    180
catatgccaa gtacgccccc tattgacgtc aatgacggta aatggcccgc ctggcattat    240
gcccagtaca tgaccttatg ggactttcct acttggcagt acatctacgt attagtcatc    300
gctattacca tggtgatgcg gttttggcag tacatcaatg ggcgtggata gcggtttgac    360
tcacggggat ttccaagtct ccaccccatt gacgtcaatg ggagtttgtt ttggcaccaa    420
aatcaacggg actttccaaa atgtcgtaac aactccgccc cattgacgca aatgggcggt    480
aggcgtgtac ggtgggaggt ctatataagc agagctctcc ctatcagtga tagagatctc    540
cctatcagtg atagagatcg tcgacgagct cgtttagtga accgtcagat cgcctggaga    600
cgccatccac gctgttttga cctccataga agacaccggg accgatccag cctccggacc    660
atggcgtact accatcacca tcaccatcac accggtgata tcctcgagcc catcacaagt    720
ttgtacaaaa aagctgaacg agaaacgtaa aatgatataa atatcaatat attaaattag    780
attttgcata aaaaacagac tacataatac tgtaaaacac aacatatcca gtcactatgg    840
cggccgcatt aggcacccca ggctttacac tttatgcttc cggctcgtat aatgtgtgga    900
ttttgagtta ggatccggcg agattttcag gagctaagga agctaaaatg gagaaaaaaa    960
tcactggata taccaccgtt gatatatccc aatggcatcg taaagaacat tttgaggcat   1020
ttcagtcagt tgctcaatgt acctataacc agaccgttca gctggatatt acggcctttt   1080
taaagaccgt aaagaaaaat aagcacaagt tttatccggc ctttattcac attcttgccc   1140
gcctgatgaa tgctcatccg gaattccgta tggcaatgaa agacggtgag ctggtgatat   1200
gggatagtgt tcacccttgt tacaccgttt tccatgagca aactgaaacg ttttcatcgc   1260
tctggagtga ataccacgac gatttccggc agtttctaca catatattcg caagatgtgg   1320
cgtgttacgg tgaaaacctg gcctatttcc ctaaagggtt tattgagaat atgtttttcg   1380
```

-continued

```
tctcagccaa tccctgggtg agtttcacca gttttgattt aaacgtggcc aatatggaca   1440
acttcttcgc ccccgttttc accatgggca aatattatac gcaaggcgac aaggtgctga   1500
tgccgctggc gattcaggtt catcatgccg tctgtgatgg cttccatgtc ggcagaatgc   1560
ttaatgaatt acaacagtac tgcgatgagt ggcagggcgg ggcgtaaacg cgtggatccg   1620
gcttactaaa agccagataa cagtatgcgt atttgcgcgc tgatttttgc ggtataagaa   1680
tatatactga tatgtatacc cgaagtatgt caaaaagagg tgtgctatga agcagcgtat   1740
tacagtgaca gttgacagcg acagctatca gttgctcaag gcatatatga tgtcaatatc   1800
tccggtctgg taagcacaac catgcagaat gaagcccgtc gtctgcgtgc cgaacgctgg   1860
aaagcggaaa atcaggaagg gatggctgag gtcgcccggt ttattgaaat gaacggctct   1920
tttgctgacg agaacaggga ctggtgaaat gcagtttaag gtttacacct ataaaagaga   1980
gagccgttat cgtctgtttg tggatgtaca gagtgatatt attgacacgc ccgggcgacg   2040
gatggtgatc cccctggcca gtgcacgtct gctgtcagat aaagtctccc gtgaacttta   2100
cccggtggtg catatcgggg atgaaagctg gcgcatgatg accaccgata tggccagtgt   2160
gccggtctcc gttatcgggg aagaagtggc tgatctcagc caccgcgaaa atgacatcaa   2220
aaacgccatt aacctgatgt tctggggaat ataaatgtca ggctccgtta tacacagcca   2280
gtctgcaggt cgaccatagt gactggatat gttgtgtttt acagtattat gtagtctgtt   2340
ttttatgcaa aatctaattt aatatattga tatttatatc attttacgtt tctcgttcag   2400
ctttcttgta caaagtggtg atgggcggcc gctctagagg gcccaagctt acgcgtgcat   2460
gcgacgtcat agctctctcc ctatagtgag tcgtattata agctaggcac tggccgtcgt   2520
tttacaacgt cgtgactggg aaaactgcta gcttgggatc tttgtgaagg aaccttactt   2580
ctgtggtgtg acataattgg acaaactacc tacagagatt taaagctcta aggtaaatat   2640
aaaattttta agtgtataat gtgttaaact agctgcatat gcttgctgct tgagagtttt   2700
gcttactgag tatgatttat gaaaatatta tacacaggag ctagtgattc taattgtttg   2760
tgtattttag attcacagtc ccaaggctca tttcaggccc ctcagtcctc acagtctgtt   2820
catgatcata atcagccata ccacatttgt agaggtttta cttgctttaa aaaacctccc   2880
acacctcccc ctgaacctga aacataaaat gaatgcaatt gttgttgtta acttgtttat   2940
tgcagcttat aatggttaca aataaagcaa tagcatcaca aatttcacaa ataaagcatt   3000
tttttcactg cattctagtt gtggtttgtc caaactcatc aatgtatctt atcatgtctg   3060
gatcgatcct gcattaatga atcggccaac gcgcggggag aggcggtttg cgtattggct   3120
ggcgtaatag cgaagaggcc cgcaccgatc gcccttccca acagttgcgc agcctgaatg   3180
gcgaatggga cgcgccctgt agcggcgcat taagcgcggc gggtgtggtg gttacgcgca   3240
gcgtgaccgc tacacttgcc agcgccctag cgcccgctcc tttcgctttc ttcccttcct   3300
ttctcgccac gttcgccggc tttccccgtc aagctctaaa tcgggggctc cctttagggt   3360
tccgatttag tgctttacgg cacctcgacc ccaaaaaact tgattagggt gatggttcac   3420
gtagtgggcc atcgccctga tagacggttt ttcgcccttt gacgttggag tccacgttct   3480
ttaatagtgg actcttgttc caaactggaa caacactcaa ccctatctcg gtctattctt   3540
ttgatttata agggattttg ccgatttcgg cctattggtt aaaaaatgag ctgatttaac   3600
aaatatttaa cgcgaatttt aacaaaatat taacgtttac aatttcgcct gatgcggtat   3660
tttctcctta cgcatctgtg cggtatttca caccgcatac gcggatctgc gcagcaccat   3720
```

-continued

```
ggcctgaaat aacctctgaa agaggaactt ggttaggtac cttctgaggc ggaaagaacc   3780
agctgtggaa tgtgtgtcag ttagggtgtg gaaagtcccc aggctcccca gcaggcagaa   3840
gtatgcaaag catgcatctc aattagtcag caaccaggtg tggaaagtcc ccaggctccc   3900
cagcaggcag aagtatgcaa agcatgcatc tcaattagtc agcaaccata gtcccgcccc   3960
taactccgcc catcccgccc ctaactccgc ccagttccgc ccattctccg ccccatggct   4020
gactaatttt ttttatttat gcagaggccg aggccgcctc ggcctctgag ctattccaga   4080
agtagtgagg aggctttttt ggaggcctag gcttttgcaa aaagcttgat tcttctgaca   4140
caacagtctc gaacttaaga ccatggccaa gcctttgtct caagaagaat ccaccctcat   4200
tgaaagagca acggctacaa tcaacagcat ccccatctct gaagactaca gcgtcgccag   4260
cgcagctctc tctagcgacg gccgcatctt cactggtgtc aatgtatatc attttactgg   4320
gggaccttgt gcagaactcg tggtgctggg cactgctgct gctgcggcag ctggcaacct   4380
gacttgtatc gtcgcgatcg gaaatgagaa caggggcatc ttgagcccct gcggacggtg   4440
ccgacaggtg cttctcgatc tgcatcctgg gatcaaagcc atagtgaagg acagtgatgg   4500
acagccgacg gcagttggga ttcgtgaatt gctgccctct ggttatgtgt gggagggcta   4560
agcacttcgt ggccgagttc gaaatgaccg accaagcgac gcccaacctg ccatcacgat   4620
ggccgcaata aaatatcttt attttcatta catctgtgtg ttggtttttt gtgtgaatcg   4680
atagcgataa ggatccgcgt atggtgcact ctcagtacaa tctgctctga tgccgcatag   4740
ttaagccagc cccgacaccc gccaacaccc gctgacgcgc cctgacgggc ttgtctgctc   4800
ccggcatccg cttacagaca agctgtgacc gtctccggga gctgcatgtg tcagaggttt   4860
tcaccgtcat caccgaaacg cgcgagacga aagggcctcg tgatacgcct atttttatag   4920
gttaatgtca tgataataat ggtttcttag acgtcaggtg gcacttttcg gggaaatgtg   4980
cgcggaaccc ctatttgttt atttttctaa atacattcaa atatgtatcc gctcatgaga   5040
caataaccct gataaatgct tcaataatat tgaaaaagga agagtatgag tattcaacat   5100
ttccgtgtcg cccttattcc cttttttgcg gcattttgcc ttcctgtttt tgctcaccca   5160
gaaacgctgg tgaaagtaaa agatgctgaa gatcagttgg gtgcacgagt gggttacatc   5220
gaactggatc tcaacagcgg taagatcctt gagagttttc gccccgaaga acgttttcca   5280
atgatgagca cttttaaagt tctgctatgt ggcgcggtat tatcccgtat tgacgccggg   5340
caagagcaac tcggtcgccg catacactat tctcagaatg acttggttga gtactcacca   5400
gtcacagaaa agcatcttac ggatggcatg acagtaagag aattatgcag tgctgccata   5460
accatgagtg ataacactgc ggccaactta cttctgacaa cgatcggagg accgaaggag   5520
ctaaccgctt ttttgcacaa catgggggat catgtaactc gccttgatcg ttgggaaccg   5580
gagctgaatg aagccatacc aaacgacgag cgtgacacca cgatgcctgt agcaatggca   5640
acaacgttgc gcaaactatt aactggcgaa ctacttactc tagcttcccg gcaacaatta   5700
atagactgga tggaggcgga taaagttgca ggaccacttc tgcgctcggc ccttccggct   5760
ggctggttta ttgctgataa atctggagcc ggtgagcgtg ggtctcgcgg tatcattgca   5820
gcactggggc cagatggtaa gccctcccgt atcgtagtta tctacacgac ggggagtcag   5880
gcaactatgg atgaacgaaa tagacagatc gctgagatag gtgcctcact gattaagcat   5940
tggtaactgt cagaccaagt ttactcatat atactttaga ttgatttaaa acttcatttt   6000
taatttaaaa ggatctaggt gaagatcctt tttgataatc tcatgaccaa aatcccttaa   6060
cgtgagtttt cgttccactg agcgtcagac cccgtagaaa agatcaaagg atcttcttga   6120
```

-continued

```
gatcctttttt ttctgcgcgt aatctgctgc ttgcaaacaa aaaaaccacc gctaccagcg   6180

gtggtttgtt tgccggatca agagctacca actctttttc cgaaggtaac tggcttcagc   6240

agagcgcaga taccaaatac tgtccttcta gtgtagccgt agttaggcca ccacttcaag   6300

aactctgtag caccgcctac atacctcgct ctgctaatcc tgttaccagt ggctgctgcc   6360

agtggcgata agtcgtgtct taccgggttg gactcaagac gatagttacc ggataaggcg   6420

cagcggtcgg gctgaacggg gggttcgtgc acacagccca gcttggagcg aacgacctac   6480

accgaactga gatacctaca gcgtgagcat tgagaaagcg ccacgcttcc cgaagggaga   6540

aaggcggaca ggtatccggt aagcggcagg gtcggaacag gagagcgcac gagggagctt   6600

ccagggggaa acgcctggta tctttatagt cctgtcgggt ttcgccacct ctgacttgag   6660

cgtcgatttt tgtgatgctc gtcagggggg cggagcctat ggaaaaacgc cagcaacgcg   6720

gcctttttac ggttcctggc cttttgctgg ccttttgctc acatgttctt tcctgcgtta   6780

tcccctgatt ctgtggataa ccgtattacc gcctttgagt gagctgatac cgctcgccgc   6840

agccgaacga ccgagcgcag cgagtcagtg agcgaggaag cggaagagcg cccaatacgc   6900

aaaccgcctc tccccgcgcg ttggccgatt cattaatgca gagcttgcaa ttcgcgcgtt   6960

tttcaatatt attgaagcat ttatcagggt tattgtctca tgagcggata catatttgaa   7020

tgtatttaga aaaataaaca aataggggtt ccgcgcacat ttccccgaaa agtgccacct   7080

gacgtctaag aaaccattat tatcatgaca ttaacctata aaaataggcg tagtacgagg   7140

ccctttcact cattag                                                    7156
```

<210> SEQ ID NO 177
<211> LENGTH: 7544
<212> TYPE: DNA
<213> ORGANISM: Artificial Sequence
<220> FEATURE:
<223> OTHER INFORMATION: pDEST30

<400> SEQUENCE: 177

```
atgcatgtcg ttacataact tacggtaaat ggcccgcctg gctgaccgcc caacgacccc     60

cgcccattga cgtcaataat gacgtatgtt cccatagtaa cgccaatagg gactttccat    120

tgacgtcaat gggtggagta tttacggtaa actgcccact tggcagtaca tcaagtgtat    180

catatgccaa gtacgccccc tattgacgtc aatgacggta aatggcccgc ctggcattat    240

gcccagtaca tgaccttatg ggactttcct acttggcagt acatctacgt attagtcatc    300

gctattacca tggtgatgcg gttttggcag tacatcaatg ggcgtggata gcggtttgac    360

tcacggggat ttccaagtct ccaccccatt gacgtcaatg ggagtttgtt ttggcaccaa    420

aatcaacggg actttccaaa atgtcgtaac aactccgccc cattgacgca aatgggcggt    480

aggcgtgtac ggtgggaggt ctatataagc agagctctcc ctatcagtga tagagatctc    540

cctatcagtg atagagatcg tcgacgagct cgtttagtga accgtcagat cgcctggaga    600

cgccatccac gctgttttga cctccataga agacaccggg accgatccag cctccggact    660

ctagaggatc cctaccggtg atatcctcga gcccatcaac aagtttgtac aaaaaagctg    720

aacgagaaac gtaaaatgat ataaatatca atatattaaa ttagattttg cataaaaaac    780

agactacata atactgtaaa acacaacata tccagtcact atggcggccg cattaggcac    840

cccaggcttt acactttatg cttccggctc gtataatgtg tggattttga gttaggatcc    900

ggcgagattt tcaggagcta aggaagctaa aatggagaaa aaaatcactg gatataccac    960
```

-continued

```
cgttgatata tcccaatggc atcgtaaaga acattttgag gcatttcagt cagttgctca   1020
atgtacctat aaccagaccg ttcagctgga tattacggcc tttttaaaga ccgtaaagaa   1080
aaataagcac aagttttatc cggcctttat tcacattctt gcccgcctga tgaatgctca   1140
tccggaattc cgtatggcaa tgaaagacgg tgagctggtg atatgggata gtgttcaccc   1200
ttgttacacc gttttccatg agcaaactga aacgttttca tcgctctgga gtgaatacca   1260
cgacgatttc cggcagtttc tacacatata ttcgcaagat gtggcgtgtt acggtgaaaa   1320
cctggcctat ttccctaaag ggtttattga gaatatgttt ttcgtctcag ccaatccctg   1380
ggtgagtttc accagttttg atttaaacgt ggccaatatg gacaacttct tcgcccccgt   1440
tttcaccatg ggcaaatatt atacgcaagg cgacaaggtg ctgatgccgc tggcgattca   1500
ggttcatcat gccgtctgtg atggcttcca tgtcggcaga atgcttaatg aattacaaca   1560
gtactgcgat gagtggcagg gcggggcgta aagatctgga tccggcttac taaaagccag   1620
ataacagtat gcgtatttgc gcgctgattt ttgcggtata agaatatata ctgatatgta   1680
tacccgaagt atgtcaaaaa gaggtgtgct atgaagcagc gtattacagt gacagttgac   1740
agcgacagct atcagttgct caaggcatat atgatgtcaa tatctccggt ctggtaagca   1800
caaccatgca gaatgaagcc cgtcgtctgc gtgccgaacg ctggaaagcg gaaaatcagg   1860
aagggatggc tgaggtcgcc cggtttattg aaatgaacgg ctcttttgct gacgagaaca   1920
gggactggtg aaatgcagtt taaggtttac acctataaaa gagagagccg ttatcgtctg   1980
tttgtggatg tacagagtga tattattgac acgcccgggc gacggatggt gatccccctg   2040
gccagtgcac gtctgctgtc agataaagtc tcccgtgaac tttacccggt ggtgcatatc   2100
ggggatgaaa gctggcgcat gatgaccacc gatatggcca gtgtgccggt ctccgttatc   2160
ggggaagaag tggctgatct cagccaccgc gaaaatgaca tcaaaaacgc cattaacctg   2220
atgttctggg gaatataaat gtcaggctcc cttatacaca gccagtctgc aggtcgacca   2280
tagtgactgg atatgttgtg ttttacagta ttatgtagtc tgttttttat gcaaaatcta   2340
atttaatata ttgatattta tatcatttta cgtttctcgt tcagctttct tgtacaaagt   2400
ggttgatggg cggccgctct agagggccca agcttacgcg tgcatgcgac gtcatagctc   2460
tctccctata gtgagtcgta ttataagcta ggcactggcc gtcgttttac aacgtcgtga   2520
ctgggaaaac tgctagcttg ggatctttgt gaaggaacct tacttctgtg gtgtgacata   2580
attggacaaa ctacctacag agatttaaag ctctaaggta aatataaaat ttttaagtgt   2640
ataatgtgtt aaactagctg catatgcttg ctgcttgaga gttttgctta ctgagtatga   2700
tttatgaaaa tattatacac aggagctagt gattctaatt gtttgtgtat tttagattca   2760
cagtcccaag gctcatttca ggcccctcag tcctcacagt ctgttcatga tcataatcag   2820
ccataccaca tttgtagagg ttttacttgc tttaaaaaac ctcccacacc tccccctgaa   2880
cctgaaacat aaaatgaatg caattgttgt tgttaacttg tttattgcag cttataatgg   2940
ttacaaataa agcaatagca tcacaaattt cacaaataaa gcattttttt cactgcattc   3000
tagttgtggt ttgtccaaac tcatcaatgt atcttatcat gtctggatcg atcctgcatt   3060
aatgaatcgg ccaacgcgcg gggagaggcg gtttgcgtat tggctggcgt aatagcgaag   3120
aggcccgcac cgatcgccct tcccaacagt tgcgcagcct gaatggcgaa tgggacgcgc   3180
cctgtagcgg cgcattaagc gcggcgggtg tggtggttac gcgcagcgtg accgctacac   3240
ttgccagcgc cctagcgccc gctcctttcg ctttcttccc ttcctttctc gccacgttcg   3300
ccggctttcc ccgtcaagct ctaaatcggg ggctcccttt agggttccga tttagtgctt   3360
```

-continued

```
tacggcacct cgaccccaaa aaacttgatt agggtgatgg ttcacgtagt gggccatcgc   3420
cctgatagac ggtttttcgc cctttgacgt tggagtccac gttctttaat agtggactct   3480
tgttccaaac tggaacaaca ctcaacccta tctcggtcta ttcttttgat ttataaggga   3540
ttttgccgat ttcggcctat tggttaaaaa atgagctgat ttaacaaata tttaacgcga   3600
attttaacaa aatattaacg tttacaattt cgcctgatgc ggtattttct ccttacgcat   3660
ctgtgcggta tttcacaccg catacgcgga tctgcgcagc accatggcct gaaataacct   3720
ctgaaagagg aacttggtta ggtaccttct gaggcggaaa gaaccagctg tggaatgtgt   3780
gtcagttagg gtgtggaaag tccccaggct ccccagcagg cagaagtatg caaagcatgc   3840
atctcaatta gtcagcaacc aggtgtggaa agtccccagg ctccccagca ggcagaagta   3900
tgcaaagcat gcatctcaat tagtcagcaa ccatagtccc gcccctaact ccgcccatcc   3960
cgcccctaac tccgcccagt tccgcccatt ctccgcccca tggctgacta attttttta   4020
tttatgcaga ggccgaggcc gcctcggcct ctgagctatt ccagaagtag tgaggaggct   4080
tttttggagg cctaggcttt tgcaaaaagc ttgattcttc tgacacaaca gtctcgaact   4140
taaggctaga gccaccatga ttgaacaaga tggattgcac gcaggttctc cggccgcttg   4200
ggtggagagg ctattcggct atgactgggc acaacagaca atcggctgct ctgatgccgc   4260
cgtgttccgg ctgtcagcgc aggggcgccc ggttcttttt gtcaagaccg acctgtccgg   4320
tgccctgaat gaactgcagg acgaggcagc gcggctatcg tggctggcca cgacgggcgt   4380
tccttgcgca gctgtgctcg acgttgtcac tgaagcggga agggactggc tgctattggg   4440
cgaagtgccg gggcaggatc tcctgtcatc tcaccttgct cctgccgaga aagtatccat   4500
catggctgat gcaatgcggc ggctgcatac gcttgatccg gctacctgcc cattcgacca   4560
ccaagcgaaa catcgcatcg agcgagcacg tactcggatg gaagccggtc ttgtcgatca   4620
ggatgatctg gacgaagagc atcaggggct cgcgccagcc gaactgttcg ccaggctcaa   4680
ggcgcgcatg cccgacggcg aggatctcgt cgtgacccat ggcgatgcct gcttgccgaa   4740
tatcatggtg gaaaatggcc gcttttctgg attcatcgac tgtggccggc tgggtgtggc   4800
ggaccgctat caggacatag cgttggctac ccgtgatatt gctgaagagc ttggcggcga   4860
atgggctgac cgcttcctcg tgctttacgg tatcgccgct cccgattcgc agcgcatcgc   4920
cttctatcgc cttcttgacg agttcttctg agcgggactc tggggttcga aatgaccgac   4980
caagcgacgc ccaacctgcc atcacgatgg ccgcaataaa atatctttat tttcattaca   5040
tctgtgtgtt ggttttttgt gtgaatcgat agcgataagg atccgcgtat ggtgcactct   5100
cagtacaatc tgctctgatg ccgcatagtt aagccagccc cgacacccgc caacacccgc   5160
tgacgcgccc tgacgggctt gtctgctccc ggcatccgct tacagacaag ctgtgaccgt   5220
ctccgggagc tgcatgtgtc agaggttttc accgtcatca ccgaaacgcg cgagacgaaa   5280
gggcctcgtg atacgcctat ttttataggt taatgtcatg ataataatgg tttcttagac   5340
gtcaggtggc acttttcggg gaaatgtgcg cggaacccct atttgtttat ttttctaaat   5400
acattcaaat atgtatccgc tcatgagaca ataaccctga taaatgcttc aataatattg   5460
aaaaaggaag agtatgagta ttcaacattt ccgtgtcgcc cttattccct tttttgcggc   5520
attttgcctt cctgtttttg ctcacccaga aacgctggtg aaagtaaaag atgctgaaga   5580
tcagttgggt gcacgagtgg gttacatcga actggatctc aacagcggta agatccttga   5640
gagttttcgc cccgaagaac gttttccaat gatgagcact tttaaagttc tgctatgtgg   5700
```

-continued

```
cgcggtatta tcccgtattg acgccgggca agagcaactc ggtcgccgca tacactattc   5760
tcagaatgac ttggttgagt actcaccagt cacagaaaag catcttacgg atggcatgac   5820
agtaagagaa ttatgcagtg ctgccataac catgagtgat aacactgcgg ccaacttact   5880
tctgacaacg atcggaggac cgaaggagct aaccgctttt ttgcacaaca tgggggatca   5940
tgtaactcgc cttgatcgtt gggaaccgga gctgaatgaa gccataccaa acgacgagcg   6000
tgacaccacg atgcctgtag caatggcaac aacgttgcgc aaactattaa ctggcgaact   6060
acttactcta gcttcccggc aacaattaat agactggatg gaggcggata aagttgcagg   6120
accacttctg cgctcggccc ttccggctgg ctggtttatt gctgataaat ctggagccgg   6180
tgagcgtggg tctcgcggta tcattgcagc actggggcca gatggtaagc cctcccgtat   6240
cgtagttatc tacacgacgg ggagtcaggc aactatggat gaacgaaata gacagatcgc   6300
tgagataggt gcctcactga ttaagcattg gtaactgtca gaccaagttt actcatatat   6360
actttagatt gatttaaaac ttcattttta atttaaaagg atctaggtga agatcctttt   6420
tgataatctc atgaccaaaa tcccttaacg tgagttttcg ttccactgag cgtcagaccc   6480
cgtagaaaag atcaaaggat cttcttgaga tccttttttt ctgcgcgtaa tctgctgctt   6540
gcaaacaaaa aaaccaccgc taccagcggt ggtttgtttg ccggatcaag agctaccaac   6600
tctttttccg aaggtaactg gcttcagcag agcgcagata ccaaatactg tccttctagt   6660
gtagccgtag ttaggccacc acttcaagaa ctctgtagca ccgcctacat acctcgctct   6720
gctaatcctg ttaccagtgg ctgctgccag tggcgataag tcgtgtctta ccgggttgga   6780
ctcaagacga tagttaccgg ataaggcgca gcggtcgggc tgaacggggg gttcgtgcac   6840
acagcccagc ttggagcgaa cgacctacac cgaactgaga tacctacagc gtgagcattg   6900
agaaagcgcc acgcttcccg aagggagaaa ggcggacagg tatccggtaa gcggcagggt   6960
cggaacagga gagcgcacga gggagcttcc agggggaaac gcctggtatc tttatagtcc   7020
tgtcgggttt cgccacctct gacttgagcg tcgatttttg tgatgctcgt caggggggcg   7080
gagcctatgg aaaaacgcca gcaacgcggc ctttttacgg ttcctggcct tttgctggcc   7140
ttttgctcac atgttctttc ctgcgttatc ccctgattct gtggataacc gtattaccgc   7200
ctttgagtga gctgataccg ctcgccgcag ccgaacgacc gagcgcagcg agtcagtgag   7260
cgaggaagcg gaagagcgcc caatacgcaa accgcctctc cccgcgcgtt ggccgattca   7320
ttaatgcaga gcttgcaatt cgcgcgtttt tcaatattat tgaagcattt atcagggtta   7380
ttgtctcatg agcggataca tatttgaatg tatttagaaa aataaacaaa taggggttcc   7440
gcgcacattt ccccgaaaag tgccacctga cgtctaagaa accattatta tcatgacatt   7500
aacctataaa aataggcgta gtacgaggcc ctttcactca ttag                    7544
```

<210> SEQ ID NO 178
<211> LENGTH: 7559
<212> TYPE: DNA
<213> ORGANISM: Artificial Sequence
<220> FEATURE:
<223> OTHER INFORMATION: pDEST31

<400> SEQUENCE: 178

```
atgcatgtcg ttacataact tacggtaaat ggcccgcctg gctgaccgcc caacgacccc     60
cgcccattga cgtcaataat gacgtatgtt cccatagtaa cgccaatagg gactttccat    120
tgacgtcaat gggtggagta tttacggtaa actgcccact tggcagtaca tcaagtgtat    180
catatgccaa gtacgccccc tattgacgtc aatgacggta aatggcccgc ctggcattat    240
```

-continued

```
gcccagtaca tgaccttatg ggactttcct acttggcagt acatctacgt attagtcatc    300
gctattacca tggtgatgcg gttttggcag tacatcaatg ggcgtggata gcggtttgac    360
tcacggggat ttccaagtct ccaccccatt gacgtcaatg ggagtttgtt ttggcaccaa    420
aatcaacggg actttccaaa atgtcgtaac aactccgccc cattgacgca aatgggcggt    480
aggcgtgtac ggtgggaggt ctatataagc agagctctcc ctatcagtga tagagatctc    540
cctatcagtg atagagatcg tcgacgagct cgtttagtga accgtcagat cgcctggaga    600
cgccatccac gctgttttga cctccataga agacaccggg accgatccag cctccggacc    660
atggcgtact accatcacca tcaccatcac accggtgata tcctcgagcc catcacaagt    720
ttgtacaaaa aagctgaacg agaaacgtaa aatgatataa atatcaatat attaaattag    780
attttgcata aaaaacagac tacataatac tgtaaaacac aacatatcca gtcactatgg    840
cggccgcatt aggcacccca ggctttacac tttatgcttc cggctcgtat aatgtgtgga    900
ttttgagtta ggatccggcg agattttcag gagctaagga agctaaaatg gagaaaaaaa    960
tcactggata taccaccgtt gatatatccc aatggcatcg taaagaacat tttgaggcat   1020
ttcagtcagt tgctcaatgt acctataacc agaccgttca gctggatatt acggcctttt   1080
taaagaccgt aaagaaaaat aagcacaagt tttatccggc ctttattcac attcttgccc   1140
gcctgatgaa tgctcatccg gaattccgta tggcaatgaa agacggtgag ctggtgatat   1200
gggatagtgt tcacccttgt tacaccgttt tccatgagca aactgaaacg ttttcatcgc   1260
tctggagtga ataccacgac gatttccggc agtttctaca catatattcg caagatgtgg   1320
cgtgttacgg tgaaaacctg gcctatttcc ctaaagggtt tattgagaat atgtttttcg   1380
tctcagccaa tccctgggtg agtttcacca gttttgattt aaacgtggcc aatatggaca   1440
acttcttcgc ccccgttttc accatgggca aatattatac gcaaggcgac aaggtgctga   1500
tgccgctggc gattcaggtt catcatgccg tctgtgatgg cttccatgtc ggcagaatgc   1560
ttaatgaatt acaacagtac tgcgatgagt ggcagggcgg ggcgtaaacg cgtggatccg   1620
gcttactaaa agccagataa cagtatgcgt atttgcgcgc tgatttttgc ggtataagaa   1680
tatatactga tatgtatacc cgaagtatgt caaaaagagg tgtgctatga agcagcgtat   1740
tacagtgaca gttgacagcg acagctatca gttgctcaag gcatatatga tgtcaatatc   1800
tccggtctgg taagcacaac catgcagaat gaagcccgtc gtctgcgtgc cgaacgctgg   1860
aaagcggaaa atcaggaagg gatggctgag gtcgcccggt ttattgaaat gaacggctct   1920
tttgctgacg agaacaggga ctggtgaaat gcagtttaag gtttacacct ataaaagaga   1980
gagccgttat cgtctgtttg tggatgtaca gagtgatatt attgacacgc ccgggcgacg   2040
gatggtgatc cccctggcca gtgcacgtct gctgtcagat aaagtctccc gtgaacttta   2100
cccggtggtg catatcgggg atgaaagctg gcgcatgatg accaccgata tggccagtgt   2160
gccggtctcc gttatcgggg aagaagtggc tgatctcagc caccgcgaaa atgacatcaa   2220
aaacgccatt aacctgatgt tctggggaat ataaatgtca ggctccgtta tacacagcca   2280
gtctgcaggt cgaccatagt gactggatat gttgtgtttt acagtattat gtagtctgtt   2340
ttttatgcaa aatctaattt aatatattga tatttatatc attttacgtt tctcgttcag   2400
ctttcttgta caaagtggtg atgggcggcc gctctagagg gcccaagctt acgcgtgcat   2460
gcgacgtcat agctctctcc ctatagtgag tcgtattata agctaggcac tggccgtcgt   2520
tttacaacgt cgtgactggg aaaactgcta gcttgggatc tttgtgaagg aaccttactt   2580
```

-continued

```
ctgtggtgtg acataattgg acaaactacc tacagagatt taaagctcta aggtaaatat   2640
aaaattttta agtgtataat gtgttaaact agctgcatat gcttgctgct tgagagtttt   2700
gcttactgag tatgatttat gaaaatatta tacacaggag ctagtgattc taattgtttg   2760
tgtattttag attcacagtc ccaaggctca tttcaggccc ctcagtcctc acagtctgtt   2820
catgatcata atcagccata ccacatttgt agaggtttta cttgctttaa aaaacctccc   2880
acacctcccc ctgaacctga aacataaaat gaatgcaatt gttgttgtta acttgtttat   2940
tgcagcttat aatggttaca aataaagcaa tagcatcaca aatttcacaa ataaagcatt   3000
tttttcactg cattctagtt gtggtttgtc caaactcatc aatgtatctt atcatgtctg   3060
gatcgatcct gcattaatga atcggccaac gcgcggggag aggcggtttg cgtattggct   3120
ggcgtaatag cgaagaggcc cgcaccgatc gcccttccca acagttgcgc agcctgaatg   3180
gcgaatggga cgcgccctgt agcggcgcat taagcgcggc gggtgtggtg gttacgcgca   3240
gcgtgaccgc tacacttgcc agcgccctag cgcccgctcc tttcgctttc ttcccttcct   3300
ttctcgccac gttcgccggc tttccccgtc aagctctaaa tcgggggctc cctttagggt   3360
tccgatttag tgctttacgg cacctcgacc ccaaaaaact tgattagggt gatggttcac   3420
gtagtgggcc atcgccctga tagacggttt ttcgcccttt gacgttggag tccacgttct   3480
ttaatagtgg actcttgttc caaactggaa caacactcaa ccctatctcg gtctattctt   3540
ttgatttata agggattttg ccgatttcgg cctattggtt aaaaaatgag ctgatttaac   3600
aaatatttaa cgcgaatttt aacaaaatat taacgtttac aatttcgcct gatgcggtat   3660
tttctcctta cgcatctgtg cggtatttca caccgcatac gcggatctgc gcagcaccat   3720
ggcctgaaat aacctctgaa agaggaactt ggttaggtac cttctgaggc ggaaagaacc   3780
agctgtggaa tgtgtgtcag ttagggtgtg gaaagtcccc aggctcccca gcaggcagaa   3840
gtatgcaaag catgcatctc aattagtcag caaccaggtg tggaaagtcc ccaggctccc   3900
cagcaggcag aagtatgcaa agcatgcatc tcaattagtc agcaaccata gtcccgcccc   3960
taactccgcc catcccgccc ctaactccgc ccagttccgc ccattctccg ccccatggct   4020
gactaatttt ttttatttat gcagaggccg aggccgcctc ggcctctgag ctattccaga   4080
agtagtgagg aggctttttt ggaggcctag gcttttgcaa aaagcttgat tcttctgaca   4140
caacagtctc gaacttaagg ctagagccac catgattgaa caagatggat tgcacgcagg   4200
ttctccggcc gcttgggtgg agaggctatt cggctatgac tgggcacaac agacaatcgg   4260
ctgctctgat gccgccgtgt tccggctgtc agcgcagggg cgcccggttc tttttgtcaa   4320
gaccgacctg tccggtgccc tgaatgaact gcaggacgag gcagcgcggc tatcgtggct   4380
ggccacgacg ggcgttcctt gcgcagctgt gctcgacgtt gtcactgaag cgggaaggga   4440
ctggctgcta ttgggcgaag tgccggggca ggatctcctg tcatctcacc ttgctcctgc   4500
cgagaaagta tccatcatgg ctgatgcaat gcggcggctg catacgcttg atccggctac   4560
ctgcccattc gaccaccaag cgaaacatcg catcgagcga gcacgtactc ggatggaagc   4620
cggtcttgtc gatcaggatg atctggacga agagcatcag gggctcgcgc cagccgaact   4680
gttcgccagg ctcaaggcgc gcatgcccga cggcgaggat ctcgtcgtga cccatggcga   4740
tgcctgcttg ccgaatatca tggtggaaaa tggccgcttt tctggattca tcgactgtgg   4800
ccggctgggt gtggcggacc gctatcagga catagcgttg gctacccgtg atattgctga   4860
agagcttggc ggcgaatggg ctgaccgctt cctcgtgctt tacggtatcg ccgctcccga   4920
ttcgcagcgc atcgccttct atcgccttct tgacgagttc ttctgagcgg gactctgggg   4980
```

-continued

```
ttcgaaatga ccgaccaagc gacgcccaac ctgccatcac gatggccgca ataaaatatc   5040
tttattttca ttacatctgt gtgttggttt tttgtgtgaa tcgatagcga taaggatccg   5100
cgtatggtgc actctcagta caatctgctc tgatgccgca tagttaagcc agccccgaca   5160
cccgccaaca cccgctgacg cgccctgacg ggcttgtctg ctcccggcat ccgcttacag   5220
acaagctgtg accgtctccg ggagctgcat gtgtcagagg ttttcaccgt catcaccgaa   5280
acgcgcgaga cgaaagggcc tcgtgatacg cctattttta taggttaatg tcatgataat   5340
aatggtttct tagacgtcag gtggcacttt tcggggaaat gtgcgcggaa cccctatttg   5400
tttatttttc taaatacatt caaatatgta tccgctcatg agacaataac cctgataaat   5460
gcttcaataa tattgaaaaa ggaagagtat gagtattcaa catttccgtg tcgcccttat   5520
tccctttttt gcggcatttt gccttcctgt ttttgctcac ccagaaacgc tggtgaaagt   5580
aaaagatgct gaagatcagt tgggtgcacg agtgggttac atcgaactgg atctcaacag   5640
cggtaagatc cttgagagtt ttcgccccga agaacgtttt ccaatgatga gcacttttaa   5700
agttctgcta tgtggcgcgg tattatcccg tattgacgcc gggcaagagc aactcggtcg   5760
ccgcatacac tattctcaga atgacttggt tgagtactca ccagtcacag aaaagcatct   5820
tacggatggc atgacagtaa gagaattatg cagtgctgcc ataaccatga gtgataacac   5880
tgcggccaac ttacttctga caacgatcgg aggaccgaag gagctaaccg cttttttgca   5940
caacatgggg gatcatgtaa ctcgccttga tcgttgggaa ccggagctga atgaagccat   6000
accaaacgac gagcgtgaca ccacgatgcc tgtagcaatg gcaacaacgt tgcgcaaact   6060
attaactggc gaactactta ctctagcttc ccggcaacaa ttaatagact ggatggaggc   6120
ggataaagtt gcaggaccac ttctgcgctc ggcccttccg gctggctggt ttattgctga   6180
taaatctgga gccggtgagc gtgggtctcg cggtatcatt gcagcactgg ggccagatgg   6240
taagccctcc cgtatcgtag ttatctacac gacggggagt caggcaacta tggatgaacg   6300
aaatagacag atcgctgaga taggtgcctc actgattaag cattggtaac tgtcagacca   6360
agtttactca tatatacttt agattgattt aaaacttcat ttttaattta aaaggatcta   6420
ggtgaagatc ctttttgata atctcatgac caaaatccct taacgtgagt tttcgttcca   6480
ctgagcgtca gaccccgtag aaaagatcaa aggatcttct tgagatcctt tttttctgcg   6540
cgtaatctgc tgcttgcaaa caaaaaaacc accgctacca gcggtggttt gtttgccgga   6600
tcaagagcta ccaactcttt ttccgaaggt aactggcttc agcagagcgc agataccaaa   6660
tactgtcctt ctagtgtagc cgtagttagg ccaccacttc aagaactctg tagcaccgcc   6720
tacatacctc gctctgctaa tcctgttacc agtggctgct gccagtggcg ataagtcgtg   6780
tcttaccggg ttggactcaa gacgatagtt accggataag gcgcagcggt cgggctgaac   6840
ggggggttcg tgcacacagc ccagcttgga gcgaacgacc tacaccgaac tgagatacct   6900
acagcgtgag cattgagaaa gcgccacgct tcccgaaggg agaaaggcgg acaggtatcc   6960
ggtaagcggc agggtcggaa caggagagcg cacgagggag cttccagggg gaaacgcctg   7020
gtatctttat agtcctgtcg ggtttcgcca cctctgactt gagcgtcgat ttttgtgatg   7080
ctcgtcaggg gggcggagcc tatggaaaaa cgccagcaac gcggcctttt tacggttcct   7140
ggccttttgc tggccttttg ctcacatgtt ctttcctgcg ttatcccctg attctgtgga   7200
taaccgtatt accgcctttg agtgagctga taccgctcgc cgcagccgaa cgaccgagcg   7260
cagcgagtca gtgagcgagg aagcggaaga gcgcccaata cgcaaaccgc ctctccccgc   7320
```

-continued

```
gcgttggccg attcattaat gcagagcttg caattcgcgc gtttttcaat attattgaag   7380

catttatcag ggttattgtc tcatgagcgg atacatattt gaatgtattt agaaaaataa   7440

acaaataggg gttccgcgca catttccccg aaaagtgcca cctgacgtct aagaaaccat   7500

tattatcatg acattaacct ataaaaatag gcgtagtacg aggccctttc actcattag    7559


<210> SEQ ID NO 179
<211> LENGTH: 12288
<212> TYPE: DNA
<213> ORGANISM: Artificial Sequence
<220> FEATURE:
<223> OTHER INFORMATION: pDEST32
<220> FEATURE:
<221> NAME/KEY: misc_feature
<222> LOCATION: (2263)..(2263)
<223> OTHER INFORMATION: 'n' can be any nucleotide (A, T, C, G or U)

<400> SEQUENCE: 179

gacgaaaggg cctcgtgata cgcctatttt tataggttaa tgtcatgata ataatggttt     60

cttaggacgg atcgcttgcc tgtaacttac acgcgcctcg tatcttttaa tgatggaata    120

atttgggaat ttactctgtg tttatttatt tttatgtttt gtatttggat tttagaaagt    180

aaataaagaa ggtagaagag ttacggaatg aagaaaaaaa aataaacaaa ggtttaaaaa    240

atttcaacaa aaagcgtact ttacatatat atttattaga caagaaaagc agattaaata    300

gatatacatt cgattaacga taagtaaaat gtaaaatcac aggattttcg tgtgtggtct    360

tctacacaga caagatgaaa caattcggca ttaatacctg agagcaggaa gagcaagata    420

aaaggtagta tttgttggcg atccccctag agtcttttac atcttcggaa aacaaaaact    480

atttttttctt taatttcttt ttttactttc tatttttaat ttatatattt atattaaaaa    540

atttaaatta taattatttt tatagcacgt gatgaaaagg acccaggtgg cacttttcgg    600

ggaaatgtgc gcggaacccc tatttgttta tttttctaaa tacattcaaa tatgtatccg    660

ctcatgagac aataaccctg ataaatgctt caataatctg cagtgcgcag ggcccgtgtc    720

tcaaaatctc tgatgttaca ttgcacaaga taaaaatata tcatcatgaa caataaaact    780

gtctgcttac ataaacagta atacaagggg tgttatgagc catattcaac gggaaacgtc    840

ttgctggagg ccgcgattaa attccaacat ggatgctgat ttatatgggt ataaatgggc    900

tcggtagcca accactagaa ctatagctag agtcctgggc gaacaaacga tgctcgcctt    960

ccagaaaacc gaggatgcga accacttcat ccggggtcag caccaccggc aagcgccgcg   1020

acggccgagg tcttccgatc tcctgaagcc agggcagatc cgtgcacagc accttgccgt   1080

agaagaacag caaggccgcc aatgcctgac gatgcgtgga gaccgaaacc ttgcgctcgt   1140

tcgccagcca ggacagaaat gcctcgactt cgctgctgcc caaggttgcc gggtgacgca   1200

caccgtggaa acggatgaag gcacgaaccc agttgacata agcctgttcg gttcgtaaac   1260

tgtaatgcaa gtagcgtatg cgctcacgca actggtccag aaccttgacc gaacgcagcg   1320

gtggtaacgg cgcagtggcg gttttcatgg cttgttatga ctgttttttt gtacagtcta   1380

tgcctcgggc atccaagcag caagcgcgtt acgccgtggg tcgatgtttg atgttatgga   1440

gcagcaacga tgttacgcag cagcaacgat gttacgcagc agggcagtcg ccctaaaaca   1500

aagttaggtg gctcaagtat gggcatcatt cgcacatgta ggctcggccc tgaccaagtc   1560

aaatccatgc gggctgctct tgatcttttc ggtcgtgagt tcggagacgt agccacctac   1620

tcccaacatc agccggactc cgattacctc gggaacttgc tccgtagtaa gacattcatc   1680

gcgcttgctg ccttcgacca agaagcggtt gttggcgctc tcgcggctta cgttctgccc   1740
```

-continued

```
aggtttgagc agccgcgtag tgagatctat atctatgatc tcgcagtctc cggcgagcac   1800
cggaggcagg gcattgccac cgcgctcatc aatctcctca agcatgaggc caacgcgctt   1860
ggtgcttatg tgatctacgt gcaagcagat tacggtgacg atcccgcagt ggctctctat   1920
acaaagttgg gcatacggga agaagtgatg cactttgata tcgacccaag taccgccacc   1980
taacaattcg ttcaagccga gatcggcttc ccggcctaat aggttgtatt gatgttggac   2040
gagtcggaat cgcagaccga taccaggatc ttgccatcct atggaactgc ctcggtgagt   2100
tttctccttc attacagaaa cggctttttc aaaaatatgg tattgataat cctgatatga   2160
ataaattgca gtttcatttg atgctcgatg agtttttcta atcagaattg gttaattggt   2220
tgtaacactg gcagagcatt acgctgactt gacgggacgg cgncatgacc aaaatccctt   2280
aacgtgagtt ttcgttccac tgagcgtcag accccgtaga aaagatcaaa ggatcttctt   2340
gagatccttt ttttctgcgc gtaatctgct gcttgcaaac aaaaaaacca ccgctaccag   2400
cggtggtttg tttgccggat caagagctac caactctttt tccgaaggta actggcttca   2460
gcagagcgca gataccaaat actgtccttc tagtgtagcc gtagttaggc caccacttca   2520
agaactctgt agcaccgcct acatacctcg ctctgctaat cctgttacca gtggctgctg   2580
ccagtggcga taagtcgtgt cttaccgggt tggactcaag acgatagtta ccggataagg   2640
cgcagcggtc gggctgaacg gggggttcgt gcacacagcc cagcttggag cgaacgacct   2700
acaccgaact gagataccta cagcgtgagc attgagaaag cgccacgctt cccgaaggga   2760
gaaaggcgga caggtatccg gtaagcggca gggtcggaac aggagagcgc acgagggagc   2820
ttccaggggg gaacgcctgg tatctttata gtcctgtcgg gtttcgccac ctctgacttg   2880
agcgtcgatt tttgtgatgc tcgtcagggg ggccgagcct atggaaaaac gccagcaacg   2940
cggccttttt acggttcctg gccttttgct ggccttttgc tcacatgttc tttcctgcgt   3000
tatcccctga ttctgtggat aaccgtatta ccgcctttga gtgagctgat accgctcgcc   3060
gcagccgaac gaccgagcgc agcgagtcag tgagcgagga agcggaagag cgcccaatac   3120
gcaaaccgcc tctccccgcg cgttggccga ttcattaatg cagctggcac gacaggtttc   3180
ccgactggaa agcgggcagt gagcgcaacg caattaatgt gagttacctc actcattagg   3240
caccccaggc tttacacttt atgcttccgg ctcctatgtt gtgtggaatt gtgagcggat   3300
aacaatttca cacaggaaac agctatgacc atgattacgc caagctcgga attaaccctc   3360
actaaaggga acaaaagctg gtaccgatcc cgagctttgc aaattaaagc cttcgagcgt   3420
cccaaaacct tctcaagcaa ggttttcagt ataatgttac atgcgtacac gcgtctgtac   3480
agaaaaaaaa gaaaaatttg aaatataaat aacgttctta atactaacat aactataaaa   3540
aaataaatag ggacctagac ttcaggttgt ctaactcctt ccttttcggt tagagcggat   3600
gtgggggggag ggcgtgaatg taagcgtgac ataactaatt acatgatatc gacaaaggaa   3660
aaggggcctg tttactcaca ggctttttttc aagtaggtaa ttaagtcgtt tctgtctttt   3720
tccttcttca acccaccaaa ggccatcttg gtactttttt tttttttttt tttttttttt   3780
tttttttttt tttttttttt tttttttttt tttttttttt tttttttttt tttttttttt   3840
ttttttttca tagaaataat acagaagtag atgttgaatt agattaaact gaagatatat   3900
aatttattgg aaaatacata gagctttttg ttgatgcgct taagcgatca attcaacaac   3960
accaccagca gctctgattt tttcttcagc caacttggag acgaatctag ctttgacgat   4020
aactggaaca tttggaattc tacccttacc caagatctta ccgtaaccgg ctgccaaagt   4080
```

-continued

```
gtcaataact ggagcagttt ccttagaagc agatttcaag tattggtctc tcttgtcttc   4140
tgggatcaat gtccacaatt tgtccaagtt caagactggc ttccagaaat gagcttgttg   4200
cttgtggaag tatctcatac caaccttacc gaaataacct ggatggtatt tatccatgtt   4260
aattctgtgg tgatgttgac caccggccat acctctacca ccggggtgct ttctgtgctt   4320
accgatacga cctttaccgg ctgagacgtg acctctgtgc tttctagtct tagtgaatct   4380
ggaaggcatt cttgattagt tggatgattg ttctgggatt taatgcaaaa atcacttaag   4440
aaggaaaatc aacggagaaa gcaaacgcca tcttaaatat acgggataca gatgaaaggg   4500
tttgaaccta tctggaaaat agcattaaac aagcgaaaaa ctgcgaggaa aattgtttgc   4560
gtctctgcgg gctattcacg cgccagagga aaataggaaa aataacaggg cattagaaaa   4620
ataattttga ttttggtaat gtgtgggtcc tggtgtacag atgttacatt ggttacagta   4680
ctcttgtttt tgctgtgttt ttcgatgaat ctccaaaatg gttgttagca catggaagag   4740
tcaccgatgc taagttatct ctatgtaagc tacgtggcgt gacttttgat gaagccgcac   4800
aagagataca ggattggcaa ctgcaaatag aatctgggga tccccccctcg agatccggga   4860
tcgaagaaat gatggtaaat gaaataggaa atcaaggagc atgaaggcaa aagacaaata   4920
taagggtcga acgaaaaata aagtgaaaag tgttgatatg atgtatttgg ctttgcggcg   4980
ccgaaaaaac gagtttacgc aattgcacaa tcatgctgac tctgtggcgg acccgcgctc   5040
ttgccggccc ggcgataacg ctgggcgtga ggctgtgccc ggcggagttt tttgcgcctg   5100
cattttccaa ggtttaccct gcgctaaggg gcgagattgg agaagcaata agaatgccgg   5160
ttggggttgc gatgatgacg accacgacaa ctggtgtcat tatttaagtt gccgaaagaa   5220
cctgagtgca tttgcaacat gagtatacta gaagaatgag ccaagacttg cgagacgcga   5280
gtttgccggt ggtgcgaaca atagagcgac catgaccttg aaggtgagac gcgcataacc   5340
gctagagtac tttgaagagg aaacagcaat agggttgcta ccagtataaa tagacaggta   5400
catacaacac tggaaatggt tgtctgtttg agtacgcttt caattcattt gggtgtgcac   5460
tttattatgt tacaatatgg aagggaactt tacacttctc ctatgcacat atattaatta   5520
aagtccaatg ctagtagaga aggggggtaa cacccctccg cgctcttttc cgattttttt   5580
ctaaaccgtg gaatatttcg gatatccttt tgttgtttcc gggtgtacaa tatggacttc   5640
ctcttttctg gcaaccaaac ccatacatcg ggattcctat aataccttcg ttggtctccc   5700
taacatgtag gtggcggagg ggagatatac aatagaacag ataccagaca agacataatg   5760
ggctaaacaa gactacacca attacactgc ctcattgatg gtggtacata acgaactaat   5820
actgtagccc tagacttgat agccatcatc atatcgaagt ttcactaccc tttttccatt   5880
tgccatctat tgaagtaata ataggcgcat gcaacttctt ttcttttttt ttcttttctc   5940
tctcccccgt tgttgtctca ccatatccgc aatgacaaaa aaaatgatgg aagacactaa   6000
aggaaaaaat taacgacaaa gacagcacca acagatgtcg ttgttccaga gctgatgagg   6060
ggtatcttcg aacacacgaa actttttcct tccttcattc acgcacacta ctctctaatg   6120
agcaacggta tacggccttc cttccagtta cttgaatttg aaataaaaaa agtttgccgc   6180
tttgctatca agtataaata gacctgcaat tattaatctt ttgtttcctc gtcattgttc   6240
tcgttccctt tcttccttgt ttctttttct gcacaatatt tcaagctata ccaagcatac   6300
aatcaactcc aagcttgaag caagcctcct gaaagatgaa gctactgtct tctatcgaac   6360
aagcatgcga tatttgccga cttaaaaagc tcaagtgctc caaagaaaaa ccgaagtgcg   6420
ccaagtgtct gaagaacaac tgggagtgtc gctactctcc caaaaccaaa aggtctccgc   6480
```

-continued

```
tgactagggc acatctgaca gaagtggaat caaggctaga aagactggaa cagctatttc   6540
tactgatttt tcctcgagaa gaccttgaca tgattttgaa aatggattct ttacaggata   6600
taaaagcatt gttaacagga ttatttgtac aagataatgt gaataaagat gccgtcacag   6660
atagattggc ttcagtggag actgatatgc ctctaacatt gagacagcat agaataagtg   6720
cgacatcatc atcggaagag agtagtaaca aaggtcaaag acagttgact gtatcgtcga   6780
ggtcgaatca aacaagtttg tacaaaaaag ctgaacgaga aacgtaaaat gatataaata   6840
tcaatatatt aaattagatt ttgcataaaa aacagactac ataatactgt aaaacacaac   6900
atatccagtc actatggcgg ccgctaagtt ggcagcatca cccgacgcac tttgcgccga   6960
ataaatacct gtgacggaag atcacttcgc agaataaata aatcctggtg tccctgttga   7020
taccgggaag ccctgggcca acttttggcg aaaatgagac gttgatcggc acgtaagagg   7080
ttccaacttt caccataatg aaataagatc actaccgggc gtattttttg agttatcgag   7140
attttcagga gctaaggaag ctaaaatgga gaaaaaaatc actggatata ccaccgttga   7200
tatatcccaa tggcatcgta aagaacattt tgaggcattt cagtcagttg ctcaatgtac   7260
ctataaccag accgttcagc tggatattac ggccttttta aagaccgtaa agaaaaataa   7320
gcacaagttt tatccggcct ttattcacat tcttgcccgc ctgatgaatg ctcatccgga   7380
attccgtatg gcaatgaaag acggtgagct ggtgatatgg gatagtgttc acccttgtta   7440
caccgttttc catgagcaaa ctgaaacgtt ttcatcgctc tggagtgaat accacgacga   7500
tttccggcag tttctacaca tatattcgca agatgtggcg tgttacggtg aaaacctggc   7560
ctatttccct aaagggttta ttgagaatat gtttttcgtc tcagccaatc cctgggtgag   7620
tttcaccagt tttgatttaa acgtggccaa tatggacaac ttcttcgccc ccgttttcac   7680
catgggcaaa tattatacgc aaggcgacaa ggtgctgatg ccgctggcga ttcaggttca   7740
tcatgccgtc tgtgatggct tccatgtcgg cagaatgctt aatgaattac aacagtactg   7800
cgatgagtgg cagggcgggg cgtaatctag aggatccggc ttactaaaag ccagataaca   7860
gtatgcgtat ttgcgcgctg atttttgcgg tataagaata tatactgata tgtatacccg   7920
aagtatgtca aaaagaggtg tgctatgaag cagcgtatta cagtgacagt tgacagcgac   7980
agctatcagt tgctcaaggc atatatgatg tcaatatctc cggtctggta agcacaacca   8040
tgcagaatga agcccgtcgt ctgcgtgccg aacgctggaa agcggaaaat caggaaggga   8100
tggctgaggt cgcccggttt attgaaatga acggctcttt tgctgacgag aacagggact   8160
ggtgaaatgc agtttaaggt ttacacctat aaaagagaga gccgttatcg tctgtttgtg   8220
gatgtacaga gtgatattat tgacacgccc gggcgacgga tggtgatccc cctggccagt   8280
gcacgtctgc tgtcagataa agtctcccgt gaactttacc cggtggtgca tatcggggat   8340
gaaagctggc gcatgatgac caccgatatg gccagtgtgc cggtctccgt tatcggggaa   8400
gaagtggctg atctcagcca ccgcgaaaat gacatcaaaa acgccattaa cctgatgttc   8460
tggggaatat aaatgtcagg ctcccttata cacagccagt ctgcaggtcg accatagtga   8520
ctggatatgt tgtgttttac agtattatgt agtctgtttt ttatgcaaaa tctaatttaa   8580
tatattgata tttatatcat tttacgtttc tcgttcagct ttcttgtaca aagtggtttg   8640
atggccgcta agtaagtaag acgtcgagct ctaagtaagt aacggccgcc accgcggtgg   8700
agctttggac ttcttcgcca gaggtttggt caagtctcca atcaaggttg tcggcttgtc   8760
taccttgcca gaaatttacg aaaagatgga aaagggtcaa atcgttggta gatacgttgt   8820
```

-continued tgacacttct aaataagcga atttcttatg atttatgatt tttattatta aataagttat 8880
aaaaaaaata agtgtataca aattttaaag tgactcttag gttttaaaac gaaaattctt 8940
gttcttgagt aactctttcc tgtaggtcag gttgctttct caggtatagc atgaggtcgc 9000
tcttattgac cacacctcta ccggcatgcc gagcaaatgc ctgcaaatcg ctccccattt 9060
cacccaattg tagatatgct aactccagca atgagttgat gaatctcggt gtgtatttta 9120
tgtcctcaga ggacaatacc tgttgtaatc gttcttccac acggatccca attcgcccta 9180
tagtgagtcg tattacaatt cactggccgt cgttttacaa cgtcgtgact gggaaaaccc 9240
tggcgttacc caacttaatc gccttgcagc acatccccct ttcgccagct ggcgtaatag 9300
cgaagaggcc cgcaccgatc gcccttccca acagttgcgc agcctgaatg gcgaatggac 9360
gcgccctgta gcggcgcatt aagcgcggcg ggtgtggtgg ttacgcgcag cgtgaccgct 9420
acacttgcca gcgccctagc gcccgctcct ttcgctttct tcccttcctt tctcgccacg 9480
ttcgccggct ttccccgtca agctctaaat cgggggctcc ctttagggtt ccgatttagt 9540
gctttacggc acctcgaccc caaaaaactt gattagggtg atggttcacg tagtgggcca 9600
tcgccctgat agacggtttt tcgccctttg acgttggagt ccacgttctt taatagtgga 9660
ctcttgttcc aaactggaac aacactcaac cctatctcgg tctattcttt tgatttataa 9720
gggattttgc cgatttcggc ctattggtta aaaaatgagc tgatttaaca aaaatttaac 9780
gcgaatttta acaaaatatt aacgtttaca atttcctgat gcggtatttt ctccttacgc 9840
atctgtgcgg tatttcacac cgcatatcga ccggtcgagg agaacttcta gtatatccac 9900
atacctaata ttattgcctt attaaaaatg gaatcggaac aattacatca aaatccacat 9960
tctcttcaaa atcaattgtc ctgtacttcc ttgttcatgt gtgttcaaaa acgttatatt 10020
tataggataa ttatactcta tttctcaaca agtaattggt tgtttggccg agcggtctaa 10080
ggcgcctgat tcaagaaata tcttgaccgc agttaactgt gggaatactc aggtatcgta 10140
agatgcaaga gttcgaatct cttagcaacc attatttttt tcctcaacat aacgagaaca 10200
cacaggggcg ctatcgcaca gaatcaaatt cgatgactgg aaattttttg ttaatttcag 10260
aggtcgcctg acgcatatac ctttttcaac tgaaaaattg ggagaaaaag gaaaggtgag 10320
aggccggaac cggcttttca tatagaatag agaagcgttc atgactaaat gcttgcatca 10380
caatacttga agttgacaat attatttaag gacctattgt tttttccaat aggtggttag 10440
caatcgtctt actttctaac ttttcttacc ttttacattt cagcaatata tatatatatt 10500
tcaaggatat accattctaa tgtctgcccc tatgtctgcc cctaagaaga tcgtcgtttt 10560
gccaggtgac cacgttggtc aagaaatcac agccgaagcc attaaggttc ttaaagctat 10620
ttctgatgtt cgttccaatg tcaagttcga tttcgaaaat catttaattg gtggtgctgc 10680
tatcgatgct acaggtgtcc cacttccaga tgaggcgctg gaagcctcca agaaggttga 10740
tgccgttttg ttaggtgctg tgggtggtcc taaatggggt accggtagtg ttagacctga 10800
acaaggttta ctaaaaatcc gtaaagaact tcaattgtac gccaacttaa gaccatgtaa 10860
ctttgcatcc gactctcttt tagacttatc tccaatcaag ccacaatttg ctaaaggtac 10920
tgacttcgtt gttgtcagag aattagtggg aggtatttac tttggtaaga gaaaggaaga 10980
cgatggtgat ggtgtcgctt gggatagtga acaatacacc gttccagaag tgcaaagaat 11040
cacaagaatg gccgctttca tggccctaca acatgagcca ccattgccta tttggtcctt 11100
ggataaagct aatgttttgg cctcttcaag attatggaga aaaactgtgg aggaaaccat 11160
caagaacgaa ttccctacat tgaaggttca acatcaattg attgattctg ccgccatgat 11220
cctagttaag aacccaaccc acctaaatgg tattataatc accagcaaca tgtttggtga 11280
tatcatctcc gatgaagcct ccgttatccc aggttccttg ggtttgttgc catctgcgtc 11340
cttggcctct ttgccagaca agaacaccgc atttggtttg tacgaaccat gccacggttc 11400
tgctccagat ttgccaaaga ataaggttga ccctatcgcc actatcttgt ctgctgcaat 11460
gatgttgaaa ttgtcattga acttgcctga agaaggtaag gccattgaag atgcagttaa 11520
aaaggttttg gatgcaggta tcagaactgg tgatttaggt ggttccaaca gtaccaccga 11580
agtcggtgat gctgtcgccg aagaagttaa gaaaatcctt gcttaaaaag attctctttt 11640
tttatgatat ttgtacataa actttataaa tgaaattcat aatagaaacg acacgaaatt 11700
acaaaatgga atatgttcat agggtagacg aaactatata cgcaatctac atacatttat 11760
caagaaggag aaaaaggagg atagtaaagg aatacaggta agcaaattga tactaatggc 11820
tcaacgtgat aaggaaaaag aattgcactt taacattaat attgacaagg aggagggcac 11880
cacacaaaaa gttaggtgta acagaaaatc atgaaactac gattcctaat ttgatattgg 11940
aggattttct ctaaaaaaaa aaaaatacaa caaataaaaa acactcaatg acctgaccat 12000
ttgatggagt ttaagtcaat accttcttga accatttccc ataatggtga aagttccctc 12060
aagaatttta ctctgtcaga aacggcctta cgacgtagtc gatatggtgc actctcagta 12120
caatctgctc tgatgccgca tagttaagcc agccccgaca cccgccaaca cccgctgacg 12180
cgccctgacg ggcttgtctg ctcccggcat ccgcttacag acaagctgtg accgtctccg 12240
ggagctgcat gtgtcagagg ttttcaccgt catcaccgaa acgcgcga 12288

<210> SEQ ID NO 180
<211> LENGTH: 8815
<212> TYPE: DNA
<213> ORGANISM: Artificial Sequence
<220> FEATURE:
<223> OTHER INFORMATION: pDEST33

<400> SEQUENCE: 180
gccttacgca tctgtgcggt atttcacacc gcaggcaagt gcacaaacaa tacttaaata 60
aatactactc agtaataacc tatttcttag catttttgac gaaatttgct attttgttag 120
agtcttttac accatttgtc tccacacctc cgcttacatc aacaccaata acgccattta 180
atctaagcgc atcaccaaca ttttctggcg tcagtccacc agctaacata aaatgtaagc 240
tttcggggct ctcttgcctt ccaacccagt cagaaatcga gttccaatcc aaaagttcac 300
ctgtcccacc tgcttctgaa tcaaacaagg gaataaacga atgaggtttc tgtgaagctg 360
cactgagtag tatgttgcag tcttttggaa atacgagtct tttaataact ggcaaaccga 420
ggaactcttg gtattcttgc cacgactcat ctccatgcag ttggacgata tcaatgccgt 480
aatcattgac cagagccaaa acatcctcct taggttgatt acgaaacacg ccaaccaagt 540
atttcggagt gcctgaacta tttttatatg cttttacaag acttgaaatt ttccttgcaa 600
taaccgggtc aattgttctc tttctattgg gcacacatat aatacccagc aagtcagcat 660
cggaatctag agcacattct gcggcctctg tgctctgcaa gccgcaaact ttcaccaatg 720
gaccagaact acctgtgaaa ttaataacag acatactcca agctgccttt gtgtgcttaa 780
tcacgtatac tcacgtgctc aatagtcacc aatgccctcc ctcttggccc tctcctttc 840 ttttttcgac cgaattaatt cttaatcggc aaaaaaagaa aagctccgga tcaagattgt 900
acgtaaggtg acaagctatt tttcaataaa gaatatcttc cactactgcc atctggcgtc 960

-continued

```
ataactgcaa agtacacata tattacgatg ctgtctatta aatgcttcct atattatata   1020
tatagtaatg tcgtttatgg tgcactctca gtacaatctg ctctgatgcc gcatagttaa   1080
gccagccccg acacccgcca acacccgctg acgcgccctg acgggcttgt ctgctcccgg   1140
catccgctta cagacaagct gtgaccgtct ccgggagctg catgtgtcag aggttttcac   1200
cgtcatcacc gaaacgcgcg agacgaaagg gcctcgtgat acgcctattt ttataggtta   1260
atgtcatgat aataatggtt tcttaggacg gatcgcttgc ctgtaactta cacgcgcctc   1320
gtatctttta atgatggaat aatttgggaa tttactctgt gtttatttat ttttatgttt   1380
tgtatttgga ttttagaaag taaataaaga aggtagaaga gttacggaat gaagaaaaaa   1440
aaataaacaa aggtttaaaa aatttcaaca aaaagcgtac tttacatata tatttattag   1500
acaagaaaag cagattaaat agatatacat tcgattaacg ataagtaaaa tgtaaaatca   1560
caggattttc gtgtgtggtc ttctacacag acaagatgaa acaattcggc attaatacct   1620
gagagcagga agagcaagat aaaaggtagt atttgttggc gatcccccta gagtctttta   1680
catcttcgga aaacaaaaac tatttttttct ttaatttctt tttttacttt ctatttttaa   1740
tttatatatt tatattaaaa aatttaaatt ataattattt ttatagcacg tgatgaaaag   1800
gacccaggtg gcacttttcg gggaaatgtg cgcggaaccc ctatttgttt atttttctaa   1860
atacattcaa atatgtatcc gctcatgaga caataaccct gataaatgct tcaataatat   1920
tgaaaaagga agagtatgag tattcaacat ttccgtgtcg cccttattcc cttttttgcg   1980
gcattttgcc ttcctgtttt tgctcaccca gaaacgctgg tgaaagtaaa agatgctgaa   2040
gatcagttgg gtgcacgagt gggttacatc gaactggatc tcaacagcgg taagatcctt   2100
gagagttttc gccccgaaga acgttttcca atgatgagca cttttaaagt tctgctatgt   2160
ggcgcggtat tatcccgtat tgacgccggg caagagcaac tcggtcgccg catacactat   2220
tctcagaatg acttggttga gtactcacca gtcacagaaa agcatcttac ggatggcatg   2280
acagtaagag aattatgcag tgctgccata accatgagtg ataacactgc ggccaactta   2340
cttctgacaa cgatcggagg accgaaggag ctaaccgctt ttttcacaa catgggggat   2400
catgtaactc gccttgatcg ttgggaaccg gagctgaatg aagccatacc aaacgacgag   2460
cgtgacacca cgatgcctgt agcaatggca acaacgttgc gcaaactatt aactggcgaa   2520
ctacttactc tagcttcccg gcaacaatta atagactgga tggaggcgga taaagttgca   2580
ggaccacttc tgcgctcggc ccttccggct ggctggttta ttgctgataa atctggagcc   2640
ggtgagcgtg ggtctcgcgg tatcattgca gcactggggc cagatggtaa gccctcccgt   2700
atcgtagtta tctacacgac gggcagtcag gcaactatgg atgaacgaaa tagacagatc   2760
gctgagatag gtgcctcact gattaagcat tggtaactgt cagaccaagt ttactcatat   2820
atactttaga ttgatttaaa acttcatttt taatttaaaa ggatctaggt gaagatcctt   2880
tttgataatc tcatgaccaa aatcccttaa cgtgagtttt cgttccactg agcgtcagac   2940
cccgtagaaa agatcaaagg atcttcttga gatccttttt ttctgcgcgt aatctgctgc   3000
ttgcaaacaa aaaaaccacc gctaccagcg gtggtttgtt tgccggatca agagctacca   3060
actctttttc cgaaggtaac tggcttcagc agagcgcaga taccaaatac tgtccttcta   3120
gtgtagccgt agttaggcca ccacttcaag aactctgtag caccgcctac atacctcgct   3180
ctgctaatcc tgttaccagt ggctgctgcc agtggcgata agtcgtgtct taccgggttg   3240
gactcaagac gatagttacc ggataaggcg cagcggtcgg gctgaacggg gggttcgtgc   3300
acacagccca gcttggagcg aacgacctac accgaactga gatacctaca gcgtgagcat   3360
```

-continued

```
tgagaaagcg ccacgcttcc cgaagggaga aaggcggaca ggtatccggt aagcggcagg   3420
gtcggaacag gagagcgcac gagggagctt ccagggggga acgcctggta tctttatagt   3480
cctgtcgggt ttcgccacct ctgacttgag cgtcgatttt tgtgatgctc gtcagggggg   3540
ccgagcctat ggaaaaacgc cagcaacgcg gcctttttac ggttcctggc cttttgctgg   3600
ccttttgctc acatgttctt tcctgcgtta tcccctgatt ctgtggataa ccgtattacc   3660
gcctttgagt gagctgatac cgctcgccgc agccgaacga ccgagcgcag cgagtcagtg   3720
agcgaggaag cggaagagcg cccaatacgc aaaccgcctc tccccgcgcg ttggccgatt   3780
cattaatgca gctggcacga caggtttccc gactggaaag cgggcagtga gcgcaacgca   3840
attaatgtga gttacctcac tcattaggca ccccaggctt tacactttat gcttccggct   3900
cctatgttgt gtggaattgt gagcggataa caatttcaca caggaaacag ctatgaccat   3960
gattacgcca agctcggaat taaccctcac taaagggaac aaaagctggg taccgggccc   4020
cccctcgaga tccgggatcg aagaaatgat ggtaaatgaa ataggaaatc aaggagcatg   4080
aaggcaaaag acaaatataa gggtcgaacg aaaaataaag tgaaaagtgt tgatatgatg   4140
tatttggctt tgcggcgccg aaaaaacgag tttacgcaat tgcacaatca tgctgactct   4200
gtggcggacc cgcgctcttg ccggcccggc gataacgctg ggcgtgaggc tgtgcccggc   4260
ggagtttttt gcgcctgcat ttccaaggt ttaccctgcg ctaaggggcg agattggaga   4320
agcaataaga atgccggttg gggttgcgat gatgacgacc acgacaactg gtgtcattat   4380
ttaagttgcc gaaagaacct gagtgcattt gcaacatgag tatactagaa gaatgagcca   4440
agacttgcga gacgcgagtt tgccggtggt gcgaacaata gagcgaccat gaccttgaag   4500
gtgagacgcg cataaccgct agagtacttt gaagaggaaa cagcaatagg gttgctacca   4560
gtataaatag acaggtacat acaacactgg aaatggttgt ctgtttgagt acgctttcaa   4620
ttcatttggg tgtgcacttt attatgttac aatatggaag ggaactttac acttctccta   4680
tgcacatata ttaattaaag tccaatgcta gtagagaagg ggggtaacac ccctccgcgc   4740
tcttttccga tttttttcta aaccgtggaa tatttcggat atccttttgt tgtttccggg   4800
tgtacaatat ggacttcctc ttttctggca accaaaccca tacatcggga ttcctataat   4860
accttcgttg gtctccctaa catgtaggtg gcggaggga gatatacaat agaacagata   4920
ccagacaaga cataatgggc taaacaagac tacaccaatt acactgcctc attgatggtg   4980
gtacataacg aactaatact gtagccctag acttgatagc catcatcata tcgaagtttc   5040
actacccttt ttccatttgc catctattga agtaataata ggcgcatgca acttcttttc   5100
tttttttttc ttttctctct cccccgttgt tgtctcacca tatccgcaat gacaaaaaaa   5160
atgatggaag acactaaagg aaaaaattaa cgacaaagac agcaccaaca gatgtcgttg   5220
ttccagagct gatgaggggt atcttcgaac acacgaaact ttttccttcc ttcattcacg   5280
cacactactc tctaatgagc aacggtatac ggccttcctt ccagttactt gaatttgaaa   5340
taaaaaaagt ttgccgcttt gctatcaagt ataaatagac ctgcaattat taatcttttg   5400
tttcctcgtc attgttctcg ttccctttct tccttgtttc tttttctgca caatatttca   5460
agctatacca agcatacaat caactccaag cttatgccca agaagaagcg gaaggtctcg   5520
agcggcgcca attttaatca aagtgggaat attgctgata gctcattgtc cttcactttc   5580
actaacagta gcaacggtcc gaacctcata acaactcaaa caaattctca agcgctttca   5640
caaccaattg cctcctctaa cgttcatgat aacttcatga ataatgaaat cacggctagt   5700
```

-continued

```
aaaattgatg atggtaataa ttcaaaacca ctgtcacctg gttggacgga ccaaactgcg   5760
tataacgcgt ttggaatcac tacagggatg tttaatacca ctacaatgga tgatgtatat   5820
aactatctat tcgatgatga agatacccca ccaaacccaa aaaaagaggg tgggtcgaat   5880
caaacaagtt tgtacaaaaa agctgaacga gaaacgtaaa atgatataaa tatcaatata   5940
ttaaattaga ttttgcataa aaaacagact acataatact gtaaaacaca acatatccag   6000
tcactatggc ggccgctaag ttggcagcat cacccgacgc actttgcgcc gaataaatac   6060
ctgtgacgga agatcacttc gcagaataaa taaatcctgg tgtccctgtt gataccggga   6120
agccctgggc caacttttgg cgaaaatgag acgttgatcg gcacgtaaga ggttccaact   6180
ttcaccataa tgaaataaga tcactaccgg gcgtattttt tgagttatcg agattttcag   6240
gagctaagga agctaaaatg gagaaaaaaa tcactggata taccaccgtt gatatatccc   6300
aatggcatcg taaagaacat tttgaggcat ttcagtcagt tgctcaatgt acctataacc   6360
agaccgttca gctggatatt acggcctttt taaagaccgt aaagaaaaat aagcacaagt   6420
tttatccggc ctttattcac attcttgccc gcctgatgaa tgctcatccg gaattccgta   6480
tggcaatgaa agacggtgag ctggtgatat gggatagtgt tcacccttgt tacaccgttt   6540
tccatgagca aactgaaacg ttttcatcgc tctggagtga ataccacgac gatttccggc   6600
agtttctaca catatattcg caagatgtgg cgtgttacgg tgaaaacctg gcctatttcc   6660
ctaaagggtt tattgagaat atgtttttcg tctcagccaa tccctgggtg agtttcacca   6720
gttttgattt aaacgtggcc aatatggaca acttcttcgc ccccgttttc accatgggca   6780
aatattatac gcaaggcgac aaggtgctga tgccgctggc gattcaggtt catcatgccg   6840
tctgtgatgg cttccatgtc ggcagaatgc ttaatgaatt acaacagtac tgcgatgagt   6900
ggcagggcgg ggcgtaatct agaggatccg gcttactaaa agccagataa cagtatgcgt   6960
atttgcgcgc tgatttttgc ggtataagaa tatatactga tatgtatacc cgaagtatgt   7020
caaaaagagg tgtgctatga agcagcgtat tacagtgaca gttgacagcg acagctatca   7080
gttgctcaag gcatatatga tgtcaatatc tccggtctgg taagcacaac catgcagaat   7140
gaagcccgtc gtctgcgtgc cgaacgctgg aaagcggaaa atcaggaagg gatggctgag   7200
gtcgcccggt ttattgaaat gaacggctct tttgctgacg agaacaggga ctggtgaaat   7260
gcagtttaag gtttacacct ataaaagaga gagccgttat cgtctgtttg tggatgtaca   7320
gagtgatatt attgacacgc ccgggcgacg gatggtgatc cccctggcca gtgcacgtct   7380
gctgtcagat aaagtctccc gtgaacttta cccggtggtg catatcgggg atgaaagctg   7440
gcgcatgatg accaccgata tggccagtgt gccggtctcc gttatcgggg aagaagtggc   7500
tgatctcagc caccgcgaaa atgacatcaa aaacgccatt aacctgatgt tctggggaat   7560
ataaatgtca ggctccgtta tacacagcca gtctgcaggt cgaccatagt gactggatat   7620
gttgtgtttt acagtattat gtagtctgtt ttttatgcaa aatctaattt aatatattga   7680
tatttatatc attttacgtt tctcgttcag ctttcttgta caaagtggtt tgatggccgc   7740
taagtaagta agacgtcgag ctccctatag tgagtcgtat tacactggcc gtcgttttac   7800
aacgtcgtga ctgggaaaac accggtgagc tctaagtaag taacggccgc caccgcggtg   7860
gagctttgga cttcttcgcc agaggtttgg tcaagtctcc aatcaaggtt gtcggcttgt   7920
ctaccttgcc agaaatttac gaaaagatgg aaaagggtca aatcgttggt agatacgttg   7980
ttgacacttc taaataagcg aatttcttat gatttatgat ttttattatt aaataagtta   8040
taaaaaaaat aagtgtatac aaattttaaa gtgactctta ggttttaaaa cgaaaattct   8100
```

tgttcttgag taactctttc ctgtaggtca ggttgctttc tcaggtatag catgaggtcg 8160
ctcttattga ccacacctct accggcatgc cgagcaaatg cctgcaaatc gctccccatt 8220
tcacccaatt gtagatatgc taactccagc aatgagttga tgaatctcgg tgtgtatttt 8280
atgtcctcag aggacaatac ctgttgtaat cgttcttcca cacggatccg catcaggcga 8340
aattgtaaac gttaatattt tgttaaaatt cgcgttaaat atttgttaaa tcagctcatt 8400
ttttaaccaa taggccgaaa tcggcaaaat cccttataaa tcaaaagaat agaccgagat 8460
agggttgagt gttgttccag tttggaacaa gagtccacta ttaaagaacg tggactccaa 8520
cgtcaaaggg cgaaaaaccg tctatcaggg cgatggccca ctacgtgaac catcacccta 8580
atcaagtttt ttggggtcga ggtgccgtaa agcactaaat cggaacccta aagggagccc 8640
ccgatttaga gcttgacggg gaaagccggc gaacgtggcg agaaaggaag ggaagaaagc 8700
gaaaggagcg ggcgctaggg cgctggcaag tgtagcggtc acgctgcgcg taaccaccac 8760
acccgccgcg cttaatgcgc cgctacaggg cgcgtcccat tcgccattca ctgca 8815

<210> SEQ ID NO 181
<211> LENGTH: 7114
<212> TYPE: DNA
<213> ORGANISM: Artificial Sequence
<220> FEATURE:
<223> OTHER INFORMATION: pDEST34

<400> SEQUENCE: 181
atcgagatct cgatcccgcg aaattaatac gactcactat agggagacca caacggtttc 60
cctctagatc acaagtttgt acaaaaaagc tgaacgagaa acgtaaaatg atataaatat 120
caatatatta aattagattt tgcataaaaa acagactaca taatactgta aaacacaaca 180
tatccagtca ctatggcggc cgcattaggc accccaggct ttacacttta tgcttccggc 240
tcgtataatg tgtggatttt gagttaggat ccggcgagat tttcaggagc taaggaagct 300
aaaatggaga aaaaaatcac tggatatacc accgttgata tatcccaatg gcatcgtaaa 360
gaacattttg aggcatttca gtcagttgct caatgtacct ataaccagac cgttcagctg 420
gatattacgg cctttttaaa gaccgtaaag aaaaataagc acaagtttta tccggccttt 480
attcacattc ttgcccgcct gatgaatgct catccggaat tccgtatggc aatgaaagac 540
ggtgagctgg tgatatggga tagtgttcac ccttgttaca ccgttttcca tgagcaaact 600
gaaacgtttt catcgctctg gagtgaatac cacgacgatt tccggcagtt tctacacata 660
tattcgcaag atgtggcgtg ttacggtgaa aacctggcct atttccctaa agggtttatt 720
gagaatatgt ttttcgtctc agccaatccc tgggtgagtt tcaccagttt tgatttaaac 780
gtggccaata tggacaactt cttcgccccc gttttcacca tgggcaaata ttatacgcaa 840
ggcgacaagg tgctgatgcc gctggcgatt caggttcatc atgccgtctg tgatggcttc 900
catgtcggca gaatgcttaa tgaattacaa cagtactgcg atgagtggca gggcggggcg 960
taaacgcgtg gatccggctt actaaaagcc agataacagt atgcgtattt gcgcgctgat 1020
ttttgcggta taagaatata tactgatatg tatacccgaa gtatgtcaaa aagaggtgtg 1080
ctatgaagca gcgtattaca gtgacagttg acagcgacag ctatcagttg ctcaaggcat 1140
atatgatgtc aatatctccg gtctggtaag cacaaccatg cagaatgaag cccgtcgtct 1200
gcgtgccgaa cgctggaaag cggaaaatca ggaagggatg gctgaggtcg cccggtttat 1260
tgaaatgaac ggctcttttg ctgacgagaa cagggactgg tgaaatgcag tttaaggttt 1320

-continued

```
acacctataa aagagagagc cgttatcgtc tgtttgtgga tgtacagagt gatattattg   1380
acacgcccgg gcgacggatg gtgatccccc tggccagtgc acgtctgctg tcagataaag   1440
tctcccgtga actttacccg gtggtgcata tcggggatga aagctggcgc atgatgacca   1500
ccgatatggc cagtgtgccg gtctccgtta tcggggaaga agtggctgat ctcagccacc   1560
gcgaaaatga catcaaaaac gccattaacc tgatgttctg ggaatataa atgtcaggct   1620
cccttataca cagccagtct gcaggtcgac catagtgact ggatatgttg tgttttacag   1680
tattatgtag tctgtttttt atgcaaaatc taatttaata tattgatatt tatatcattt   1740
tacgtttctc gttcagcttt cttgtacaaa gtggtgatta tgtcccctat actaggttat   1800
tggaaaatta agggccttgt gcaacccact cgacttcttt tggaatatct tgaagaaaaa   1860
tatgaagagc atttgtatga gcgcgatgaa ggtgataaat ggcgaaacaa aaagtttgaa   1920
ttgggtttgg agtttcccaa tcttccttat tatattgatg gtgatgttaa attaacacag   1980
tctatggcca tcatacgtta tatagctgac aagcacaaca tgttgggtgg ttgtccaaaa   2040
gagcgtgcag agatttcaat gcttgaagga gcggttttgg atattagata cggtgtttcg   2100
agaattgcat atagtaaaga ctttgaaact ctcaaagttg attttcttag caagctacct   2160
gaaatgctga aaatgttcga agatcgttta tgtcataaaa catatttaaa tggtgatcat   2220
gtaacccatc ctgacttcat gttgtatgac gctcttgatg ttgttttata catggaccca   2280
atgtgcctgg atgcgttccc aaaattagtt tgttttaaaa aacgtattga agctatccca   2340
caaattgata agtacttgaa atccagcaag tatatagcat ggcctttgca gggctggcaa   2400
gccacgtttg gtggtggcga ccatcctcca aaatcggatc tggttccgcg tccatgggga   2460
tccggctgct aacaaagccc gaaaggaagc tgagttggct gctgccaccg ctgagcgctt   2520
cccgataagg gagcaggcca gtaaaagcat tacccgtggt ggggttcccg agcggccaaa   2580
gggagcagac tctaaatctg ccgtcatcga cttcgaaggt tcgaatcctt cccccaccac   2640
catcactttc aaaagtgaat tcgctgagca ataactagca taaccccttg gggcctctaa   2700
acgggtcttg aggggttttt tgctgaaagg aggaactata tccggatatc cacaggacgg   2760
gtgtggtcgc catgatcgcg tagtcgatag tggctccaag tagcgaagcg agcaggactg   2820
ggcggcggcc aaagcggtcg gacagtgctc cgagaacggg tgcgcataga aattgcatca   2880
acgcatatag cgctagcagc acgccatagt gactggcgat gctgtcggaa tggacgatat   2940
cccgcaagag gcccggcagt accggcataa ccaagcctat gcctacagca tccagggtga   3000
cggtgccgag gatgacgatg agcgcattgt tagatttcat acacggtgcc tgactgcgtt   3060
agcaatttaa ctgtgataaa ctaccgcatt aaagcttatc gatgataagc tgtcaaacat   3120
gagaattctt gaagacgaaa gggcctcgtg atacgcctat ttttataggt taatgtcatg   3180
ataataatgg tttcttagac gtcaggtggc acttttcggg gaaatgtgcg cggaacccct   3240
atttgtttat ttttctaaat acattcaaat atgtatccgc tcatgagaca ataaccctga   3300
taaatgcttc aataatattg aaaaaggaag agtatgagta ttcaacattt ccgtgtcgcc   3360
cttattccct tttttgcggc attttgcctt cctgtttttg ctcacccaga aacgctggtg   3420
aaagtaaaag atgctgaaga tcagttgggt gcacgagtgg gttacatcga actggatctc   3480
aacagcggta agatccttga gagttttcgc cccgaagaac gttttccaat gatgagcact   3540
tttaaagttc tgctatgtgg cgcggtatta tcccgtgttg acgccgggca agagcaactc   3600
ggtcgccgca tacactattc tcagaatgac ttggttgagt actcaccagt cacagaaaag   3660
catcttacgg atggcatgac agtaagagaa ttatgcagtg ctgccataac catgagtgat   3720
```

-continued aacactgcgg ccaacttact tctgacaacg atcggaggac cgaaggagct aaccgctttt 3780
ttgcacaaca tgggggatca tgtaactcgc cttgatcgtt gggaaccgga gctgaatgaa 3840
gccataccaa acgacgagcg tgacaccacg atgcctgcag caatggcaac aacgttgcgc 3900
aaactattaa ctggcgaact acttactcta gcttcccggc aacaattaat agactggatg 3960
gaggcggata aagttgcagg accacttctg cgctcggccc ttccggctgg ctggtttatt 4020
gctgataaat ctggagccgg tgagcgtggg tctcgcggta tcattgcagc actggggcca 4080
gatggtaagc cctcccgtat cgtagttatc tacacgacgg ggagtcaggc aactatggat 4140
gaacgaaata gacagatcgc tgagataggt gcctcactga ttaagcattg gtaactgtca 4200
gaccaagttt actcatatat actttagatt gatttaaaac ttcattttta atttaaaagg 4260
atctaggtga agatcctttt tgataatctc atgaccaaaa tcccttaacg tgagttttcg 4320
ttccactgag cgtcagaccc cgtagaaaag atcaaaggat cttcttgaga tccttttttt 4380
ctgcgcgtaa tctgctgctt gcaaacaaaa aaaccaccgc taccagcggt ggtttgtttg 4440
ccggatcaag agctaccaac tctttttccg aaggtaactg gcttcagcag agcgcagata 4500
ccaaatactg tccttctagt gtagccgtag ttaggccacc acttcaagaa ctctgtagca 4560
ccgcctacat acctcgctct gctaatcctg ttaccagtgg ctgctgccag tggcgataag 4620
tcgtgtctta ccgggttgga ctcaagacga tagttaccgg ataaggcgca gcggtcgggc 4680
tgaacggggg gttcgtgcac acagcccagc ttggagcgaa cgacctacac cgaactgaga 4740
tacctacagc gtgagctatg agaaagcgcc acgcttcccg aagggagaaa ggcggacagg 4800
tatccggtaa gcggcagggt cggaacagga gagcgcacga gggagcttcc agggggaaac 4860
gcctggtatc tttatagtcc tgtcgggttt cgccacctct gacttgagcg tcgatttttg 4920
tgatgctcgt caggggggcg gagcctatgg aaaaacgcca gcaacgcggc ctttttacgg 4980
ttcctggcct tttgctggcc ttttgctcac atgttctttc ctgcgttatc ccctgattct 5040
gtggataacc gtattaccgc ctttgagtga gctgataccg ctcgccgcag ccgaacgacc 5100
gagcgcagcg agtcagtgag cgaggaagcg gaagagcgcc tgatgcggta ttttctcctt 5160
acgcatctgt gcggtatttc acaccgcata tatggtgcac tctcagtaca atctgctctg 5220
atgccgcata gttaagccag tatacactcc gctatcgcta cgtgactggg tcatggctgc 5280
gccccgacac ccgccaacac ccgctgacgc gccctgacgg gcttgtctgc tcccggcatc 5340
cgcttacaga caagctgtga ccgtctccgg gagctgcatg tgtcagaggt tttcaccgtc 5400
atcaccgaaa cgcgcgaggc agctgcggta aagctcatca gcgtggtcgt gaagcgattc 5460
acagatgtct gcctgttcat ccgcgtccag ctcgttgagt ttctccagaa gcgttaatgt 5520
ctggcttctg ataaagcggg ccatgttaag ggcggttttt tcctgtttgg tcactgatgc 5580
ctccgtgtaa gggggatttc tgttcatggg ggtaatgata ccgatgaaac gagagaggat 5640
gctcacgata cgggttactg atgatgaaca tgcccggtta ctggaacgtt gtgagggtaa 5700
acaactggcg gtatggatgc ggcgggacca gagaaaaatc actcagggtc aatgccagcg 5760
cttcgttaat acagatgtag gtgttccaca gggtagccag cagcatcctg cgatgcagat 5820
ccggaacata atggtgcagg gcgctgactt ccgcgtttcc agactttacg aaacacggaa 5880
accgaagacc attcatgttg ttgctcaggt cgcagacgtt ttgcagcagc agtcgcttca 5940
cgttcgctcg cgtatcggtg attcattctg ctaaccagta aggcaacccc gccagcctag 6000
ccgggtcctc aacgacagga gcacgatcat gcgcacccgt ggccaggacc caacgctgcc 6060

-continued

```
cgagatgcgc cgcgtgcggc tgctggagat ggcggacgcg atggatatgt tctgccaagg   6120

gttggtttgc gcattcacag ttctccgcaa gaattgattg gctccaattc ttggagtggt   6180

gaatccgtta gcgaggtgcc gccggcttcc attcaggtcg aggtggcccg gctccatgca   6240

ccgcgacgca acgcggggag gcagacaagg tatagggcgg cgcctacaat ccatgccaac   6300

ccgttccatg tgctcgccga ggcggcataa atcgccgtga cgatcagcgg tccagtgatc   6360

gaagttaggc tggtaagagc cgcgagcgat ccttgaagct gtccctgatg gtcgtcatct   6420

acctgcctgg acagcatggc ctgcaacgcg ggcatcccga tgccgccgga agcgagaaga   6480

atcataatgg ggaaggccat ccagcctcgc gtcgcgaacg ccagcaagac gtagcccagc   6540

gcgtcggccg ccatgccggc gataatggcc tgcttctcgc cgaaacgttt ggtggcggga   6600

ccagtgacga aggcttgagc gagggcgtgc aagattccga ataccgcaag cgacaggccg   6660

atcatcgtcg cgctccagcg aaagcggtcc tcgccgaaaa tgacccagag cgctgccggc   6720

acctgtccta cgagttgcat gataaagaag acagtcataa gtgcggcgac gatagtcatg   6780

ccccgcgccc accggaagga gctgactggg ttgaaggctc tcaagggcat cggtcgatcg   6840

acgctctccc ttatgcgact cctgcattag gaagcagccc agtagtaggt tgaggccgtt   6900

gagcaccgcc gccgcaagga atggtgcatg caaggagatg gcgcccaaca gtcccccggc   6960

cacggggcct gccaccatac ccacgccgaa acaagcgctc atgagcccga agtggcgagc   7020

ccgatcttcc ccatcggtga tgtcggcgat ataggcgcca gcaaccgcac ctgtggcgcc   7080

ggtgatgccg gccacgatgc gtccggcgta gagg                               7114
```

<210> SEQ ID NO 182
<211> LENGTH: 5584
<212> TYPE: DNA
<213> ORGANISM: Artificial Sequence
<220> FEATURE:
<223> OTHER INFORMATION: pDONR207

<400> SEQUENCE: 182

```
gcgagagtag ggaactgcca ggcatcaaat aaaacgaaag gctcagtcgg aagactgggc     60

ctttcgtttt atctgttgtt tgtcggtgaa cgctctcctg agtaggacaa atccgccggg    120

agcggatttg aacgttgtga agcaacggcc cggagggtgg cgggcaggac gcccgccata    180

aactgccagg catcaaacta agcagaaggc catcctgacg gatggccttt ttgcgtttct    240

acaaactctt cctggctagc ggtaatacgg ttatccacag aatcagggga taacgcagga    300

aagaacatgt gagcaaaagg ccagcaaaag gccaggaacc gtaaaaaggc cgcgttgctg    360

gcgtttttcc ataggctccg cccccctgac gagcatcaca aaaatcgacg ctcaagtcag    420

aggtggcgaa acccgacagg actataaaga taccaggcgt ttccccctgg aagctccctc    480

gtgcgctctc ctgttccgac cctgccgctt accggatacc tgtccgcctt tctcccttcg    540

ggaagcgtgg cgctttctca tagctcacgc tgtaggtatc tcagttcggt gtaggtcgtt    600

cgctccaagc tgggctgtgt gcacgaaccc cccgttcagc ccgaccgctg cgccttatcc    660

ggtaactatc gtcttgagtc caacccggta agacacgact tatcgccact ggcagcagcc    720

actggtaaca ggattagcag agcgaggtat gtaggcggtg ctacagagtt cttgaagtgg    780

tggcctaact acggctacac tagaaggaca gtatttggta tctgcgctct gctgaagcca    840

gttaccttcg gaaaaagagt tggtagctct tgatccggca aacaaaccac cgctggtagc    900

ggtggttttt ttgtttgcaa gcagcagatt acgcgcagaa aaaaaggatc tcaagaagat    960

cctttgatct tttctacggg gtctgacgct cagtggaacg aaaactcacg ttaagggatt   1020
```

-continued ttggtcatga gcttgcgccg tcccgtcaag tcagcgtaat gctctgccag tgttacaacc 1080
aattaaccaa ttctgattag aaaaactcat cgagcatcaa atgaaactgc aatttattca 1140
tatcaggatt atcaatacca tatttttgaa aaagccgttt ctgtaatgaa ggagaaaact 1200
caccgaggca gttccatagg atggcaagat cctggtatcg gtctgcgatt ccgactcgtc 1260
caacatcaat acaacctatt agtagccaac cactagaact atagctagag tcctgggcga 1320
acaaacgatg ctcgccttcc agaaaaccga ggatgcgaac cacttcatcc ggggtcagca 1380
ccaccggcaa gcgccgcgac ggccgaggtc ttccgatctc ctgaagccag ggcagatccg 1440
tgcacagcac cttgccgtag aagaacagca aggccgccaa tgcctgacga tgcgtggaga 1500
ccgaaacctt gcgctcgttc gccagccagg acagaaatgc ctcgacttcg ctgctgccca 1560
aggttgccgg gtgacgcaca ccgtggaaac ggatgaaggc acgaacccag ttgacataag 1620
cctgttcggt tcgtaaactg taatgcaagt agcgtatgcg ctcacgcaac tggtccagaa 1680
ccttgaccga acgcagcggt ggtaacggcg cagtggcggt tttcatggct tgttatgact 1740
gtttttttgt acagtctatg cctcgggcat ccaagcagca agcgcgttac gccgtgggtc 1800
gatgtttgat gttatggagc agcaacgatg ttacgcagca gcaacgatgt tacgcagcag 1860
ggcagtcgcc ctaaaacaaa gttaggtggc tcaagtatgg gcatcattcg cacatgtagg 1920
ctcggccctg accaagtcaa atccatgcgg gctgctcttg atcttttcgg tcgtgagttc 1980
ggagacgtag ccacctactc ccaacatcag ccggactccg attacctcgg gaacttgctc 2040
cgtagtaaga cattcatcgc gcttgctgcc ttcgaccaag aagcggttgt tggcgctctc 2100
gcggcttacg ttctgcccag gtttgagcag ccgcgtagtg agatctatat ctatgatctc 2160
gcagtctccg gcgagcaccg gaggcagggc attgccaccg cgctcatcaa tctcctcaag 2220
catgaggcca acgcgcttgg tgcttatgtg atctacgtgc aagcagatta cggtgacgat 2280
cccgcagtgg ctctctatac aaagttgggc atacgggaag aagtgatgca ctttgatatc 2340
gacccaagta ccgccaccta acaattcgtt caagccgaga tcggcttccc ggcctaattt 2400
cccctcgtca aaaataaggt tatcaagtga gaaatcacca tgagtgacga ctgaatccgg 2460
tgagaatggc aaaagtttat gcatttcttt ccagacttgt tcaacaggcc agccattacg 2520
ctcgtcatca aaatcactcg catcaaccaa accgttattc attcgtgatt gcgcctgagc 2580
gagacgaaat acgcgatcgc tgttaaaagg acaattacaa acaggaatcg aatgcaaccg 2640
gcgcaggaac actgccagcg catcaacaat attttcacct gaatcaggat attcttctaa 2700
tacctggaat gctgttttc cggggatcgc agtggtgagt aaccatgcat catcaggagt 2760
acggataaaa tgcttgatgg tcggaagagg cataaattcc gtcagccagt ttagtctgac 2820
catctcatct gtaacatcat tggcaacgct acctttgcca tgtttcagaa acaactctgg 2880
cgcatcgggc ttcccataca agcgatagat tgtcgcacct gattgcccga cattatcgcg 2940
agcccattta tacccatata aatcagcatc catgttggaa tttaatcgcg gcctcgacgt 3000
ttcccgttga atatggctca taacaccccc tgtattactg tttatgtaag cagacagttt 3060
tattgttcat gatgatatat ttttatcttg tgcaatgtaa catcagagat tttgagacac 3120
gggccagagc tgcagctgga tggcaaataa tgattttatt ttgactgata gtgacctgtt 3180
cgttgcaaca aattgataag caatgctttc ttataatgcc aactttgtac aagaaagctg 3240
aacgagaaac gtaaaatgat ataaatatca atatattaaa ttagattttg cataaaaaac 3300
agactacata atactgtaaa acacaacata tccagtcact atgaatcaac tacttagatg 3360

-continued

```
gtattagtga cctgtagtcg actaagttgg cagcatcacc cgacgcactt tgcgccgaat   3420
aaatacctgt gacggaagat cacttcgcag aataaataaa tcctggtgtc cctgttgata   3480
ccgggaagcc ctgggccaac tttggcgaaa atgagacgtt gatcggcacg taagaggttc   3540
caactttcac cataatgaaa taagatcact accgggcgta tttttgagt tatcgagatt   3600
ttcaggagct aaggaagcta aaatggagaa aaaaatcact ggatatacca ccgttgatat   3660
atcccaatgg catcgtaaag aacattttga ggcatttcag tcagttgctc aatgtaccta   3720
taaccagacc gttcagctgg atattacggc ctttttaaag accgtaaaga aaaataagca   3780
caagttttat ccggccttta ttcacattct tgcccgcctg atgaatgctc atccggaatt   3840
ccgtatggca atgaaagacg gtgagctggt gatatgggat agtgttcacc cttgttacac   3900
cgttttccat gagcaaactg aaacgttttc atcgctctgg agtgaatacc acgacgattt   3960
ccggcagttt ctacacatat attcgcaaga tgtggcgtgt tacggtgaaa acctggccta   4020
tttccctaaa gggtttattg agaatatgtt tttcgtctca gccaatccct gggtgagttt   4080
caccagtttt gatttaaacg tggccaatat ggacaacttc ttcgcccccg ttttcaccat   4140
gggcaaatat tatacgcaag gcgacaaggt gctgatgccg ctggcgattc aggttcatca   4200
tgccgtctgt gatggcttcc atgtcggcag aatgcttaat gaattacaac agtactgcga   4260
tgagtggcag ggcggggcgt aatcgcgtgg atccggctta ctaaaagcca gataacagta   4320
tgcgtatttg cgcgctgatt tttgcggtat aagaatatat actgatatgt atacccgaag   4380
tatgtcaaaa agaggtgtgc tatgaagcag cgtattacag tgacagttga cagcgacagc   4440
tatcagttgc tcaaggcata tatgatgtca atatctccgg tctggtaagc acaaccatgc   4500
agaatgaagc ccgtcgtctg cgtgccgaac gctggaaagc ggaaaatcag gaagggatgg   4560
ctgaggtcgc ccggtttatt gaaatgaacg gctcttttgc tgacgagaac agggactggt   4620
gaaatgcagt ttaaggttta cacctataaa agagagagcc gttatcgtct gtttgtggat   4680
gtacagagtg atattattga cacgcccggg cgacggatgg tgatcccccct ggccagtgca   4740
cgtctgctgt cagataaagt ctcccgtgaa ctttacccgg tggtgcatat cggggatgaa   4800
agctggcgca tgatgaccac cgatatggcc agtgtgccgg tctccgttat cggggaagaa   4860
gtggctgatc tcagccaccg cgaaaatgac atcaaaaacg ccattaacct gatgttctgg   4920
ggaatataaa tgtcaggctc ccttatacac agccagtctg caggtcgata cagtagaaat   4980
tacagaaact ttatcacgtt tagtaagtat agaggctgaa aatccagatg aagccgaacg   5040
acttgtaaga gaaaagtata agagttgtga aattgttctt gatgcagatg attttcagga   5100
ctatgacact agcgtatatg aataggtaga tgtttttatt ttgtcacaca aaaaagaggc   5160
tcgcacctct ttttcttatt tctttttatg atttaatacg gcattgagga caatagcgag   5220
taggctggat acgacgattc cgtttgagaa gaacatttgg aaggctgtcg gtcgactaag   5280
ttggcagcat cacccgaaga acatttggaa ggctgtcggt cgactacagg tcactaatac   5340
catctaagta gttgattcat agtgactgga tatgttgtgt tttacagtat tatgtagtct   5400
gttttttatg caaaatctaa tttaatatat tgatatttat atcattttac gtttctcgtt   5460
cagctttttt gtacaaagtt ggcattataa aaaagcattg ctcatcaatt tgttgcaacg   5520
aacaggtcac tatcagtcaa aataaaatca ttatttgggg cccgagatcc atgctagcgt   5580
taac                                                                5584
```

<210> SEQ ID NO 183
<211> LENGTH: 7038

-continued

<212> TYPE: DNA
<213> ORGANISM: Artificial Sequence
<220> FEATURE:
<223> OTHER INFORMATION: pMAB85

<400> SEQUENCE: 183
gccttacgca tctgtgcggt atttcacacc gcaggcaagt gcacaaacaa tacttaaata 60
aatactactc agtaataacc tatttcttag catttttgac gaaatttgct attttgttag 120
agtcttttac accatttgtc tccacacctc cgcttacatc aacaccaata acgccattta 180
atctaagcgc atcaccaaca ttttctggcg tcagtccacc agctaacata aaatgtaagc 240
tttcggggct ctcttgcctt ccaacccagt cagaaatcga gttccaatcc aaaagttcac 300
ctgtcccacc tgcttctgaa tcaaacaagg gaataaacga atgaggtttc tgtgaagctg 360
cactgagtag tatgttgcag tcttttggaa atacgagtct tttaataact ggcaaaccga 420
ggaactcttg gtattcttgc cacgactcat ctccatgcag ttggacgata tcaatgccgt 480
aatcattgac cagagccaaa acatcctcct taggttgatt acgaaacacg ccaaccaagt 540
atttcggagt gcctgaacta tttttatatg cttttacaag acttgaaatt ttccttgcaa 600
taaccgggtc aattgttctc tttctattgg gcacacatat aatacccagc aagtcagcat 660
cggaatctag agcacattct gcggcctctg tgctctgcaa gccgcaaact ttcaccaatg 720
gaccagaact acctgtgaaa ttaataacag acatactcca agctgccttt gtgtgcttaa 780
tcacgtatac tcacgtgctc aatagtcacc aatgccctcc ctcttggccc tctccttttc 840 tttttcgac cgaattaatt cttaatcggc aaaaaaagaa aagctccgga tcaagattgt 900
acgtaaggtg acaagctatt tttcaataaa gaatatcttc cactactgcc atctggcgtc 960
ataactgcaa agtacacata tattacgatg ctgtctatta aatgcttcct atattatata 1020
tatagtaatg tcgtttatgg tgcactctca gtacaatctg ctctgatgcc gcatagttaa 1080
gccagccccg acacccgcca acacccgctg acgcgccctg acgggcttgt ctgctcccgg 1140
catccgctta cagacaagct gtgaccgtct ccgggagctg catgtgtcag aggttttcac 1200
cgtcatcacc gaaacgcgcg agacgaaagg gcctcgtgat acgcctattt ttataggtta 1260
atgtcatgat aataatggtt tcttaggacg gatcgcttgc ctgtaactta cacgcgcctc 1320
gtatctttta atgatggaat aatttgggaa tttactctgt gtttatttat ttttatgttt 1380
tgtatttgga ttttagaaag taaataaaga aggtagaaga gttacggaat gaagaaaaaa 1440
aaataaacaa aggtttaaaa aatttcaaca aaaagcgtac tttacatata tatttattag 1500
acaagaaaag cagattaaat agatatacat tcgattaacg ataagtaaaa tgtaaaatca 1560
caggattttc gtgtgtggtc ttctacacag acaagatgaa acaattcggc attaatacct 1620
gagagcagga agagcaagat aaaaggtagt atttgttggc gatcccccta gagtctttta 1680
catcttcgga aaacaaaaac tatttttct ttaatttctt tttttacttt ctatttttaa 1740
tttatatatt tatattaaaa aatttaaatt ataattattt ttatagcacg tgatgaaaag 1800
gacccaggtg gcacttttcg gggaaatgtg cgcggaaccc ctatttgttt atttttctaa 1860
atacattcaa atatgtatcc gctcatgaga caataaccct gataaatgct tcaataatat 1920
tgaaaaagga agagtatgag tattcaacat ttccgtgtcg cccttattcc cttttttgcg 1980
gcattttgcc ttcctgtttt tgctcaccca gaaacgctgg tgaaagtaaa agatgctgaa 2040
gatcagttgg gtgcacgagt gggttacatc gaactggatc tcaacagcgg taagatcctt 2100
gagagttttc gccccgaaga acgttttcca atgatgagca cttttaaagt tctgctatgt 2160

-continued

```
ggcgcggtat tatcccgtat tgacgccggg caagagcaac tcggtcgccg catacactat   2220
tctcagaatg acttggttga gtactcacca gtcacagaaa agcatcttac ggatggcatg   2280
acagtaagag aattatgcag tgctgccata accatgagtg ataacactgc ggccaactta   2340
cttctgacaa cgatcggagg accgaaggag ctaaccgctt ttttcacaa catgggggat    2400
catgtaactc gccttgatcg ttgggaaccg gagctgaatg aagccatacc aaacgacgag   2460
cgtgacacca cgatgcctgt agcaatggca acaacgttgc gcaaactatt aactggcgaa   2520
ctacttactc tagcttcccg gcaacaatta atagactgga tggaggcgga taaagttgca   2580
ggaccacttc tgcgctcggc ccttccggct ggctggttta ttgctgataa atctggagcc   2640
ggtgagcgtg ggtctcgcgg tatcattgca gcactggggc cagatggtaa gccctcccgt   2700
atcgtagtta tctacacgac gggcagtcag gcaactatgg atgaacgaaa tagacagatc   2760
gctgagatag gtgcctcact gattaagcat tggtaactgt cagaccaagt ttactcatat   2820
atactttaga ttgatttaaa acttcatttt taatttaaaa ggatctaggt gaagatcctt   2880
tttgataatc tcatgaccaa aatcccttaa cgtgagtttt cgttccactg agcgtcagac   2940
cccgtagaaa agatcaaagg atcttcttga gatccttttt ttctgcgcgt aatctgctgc   3000
ttgcaaacaa aaaaaccacc gctaccagcg gtggtttgtt tgccggatca agagctacca   3060
actctttttc cgaaggtaac tggcttcagc agagcgcaga taccaaatac tgtccttcta   3120
gtgtagccgt agttaggcca ccacttcaag aactctgtag caccgcctac atacctcgct   3180
ctgctaatcc tgttaccagt ggctgctgcc agtggcgata agtcgtgtct taccgggttg   3240
gactcaagac gatagttacc ggataaggcg cagcggtcgg gctgaacggg gggttcgtgc   3300
acacagccca gcttggagcg aacgacctac accgaactga gatacctaca gcgtgagcat   3360
tgagaaagcg ccacgcttcc cgaagggaga aaggcggaca ggtatccggt aagcggcagg   3420
gtcggaacag gagagcgcac gagggagctt ccagggggga acgcctggta tctttatagt   3480
cctgtcgggt ttcgccacct ctgacttgag cgtcgatttt tgtgatgctc gtcagggggg   3540
ccgagcctat ggaaaaacgc cagcaacgcg gcctttttac ggttcctggc cttttgctgg   3600
ccttttgctc acatgttctt tcctgcgtta tcccctgatt ctgtggataa ccgtattacc   3660
gcctttgagt gagctgatac cgctcgccgc agccgaacga ccgagcgcag cgagtcagtg   3720
agcgaggaag cggaagagcg cccaatacgc aaaccgcctc tccccgcgcg ttggccgatt   3780
cattaatgca gctggcacga caggtttccc gactggaaag cgggcagtga gcgcaacgca   3840
attaatgtga gttacctcac tcattaggca ccccaggctt tacactttat gcttccggct   3900
cctatgttgt gtggaattgt gagcggataa caatttcaca caggaaacag ctatgaccat   3960
gattacgcca agctcggaat taaccctcac taaagggaac aaaagctggg taccgggccc   4020
cccctcgaga tccgggatcg aagaaatgat ggtaaatgaa ataggaaatc aaggagcatg   4080
aaggcaaaag acaaatataa gggtcgaacg aaaaataaag tgaaaagtgt tgatatgatg   4140
tatttggctt tgcggcgccg aaaaaacgag tttacgcaat tgcacaatca tgctgactct   4200
gtggcggacc cgcgctcttg ccggcccggc gataacgctg ggcgtgaggc tgtgcccggc   4260
ggagtttttt gcgcctgcat tttccaaggt ttaccctgcg ctaaggggcg agattggaga   4320
agcaataaga atgccggttg gggttgcgat gatgacgacc acgacaactg gtgtcattat   4380
ttaagttgcc gaaagaacct gagtgcattt gcaacatgag tatactagaa gaatgagcca   4440
agacttgcga gacgcgagtt tgccggtggt gcgaacaata gagcgaccat gaccttgaag   4500
gtgagacgcg cataaccgct agagtacttt gaagaggaaa cagcaatagg gttgctacca   4560
```

-continued

```
gtataaatag acaggtacat acaacactgg aaatggttgt ctgtttgagt acgctttcaa   4620
ttcatttggg tgtgcacttt attatgttac aatatggaag ggaactttac acttctccta   4680
tgcacatata ttaattaaag tccaatgcta gtagagaagg ggggtaacac ccctccgcgc   4740
tcttttccga tttttttcta aaccgtggaa tatttcggat atccttttgt tgtttccggg   4800
tgtacaatat ggacttcctc ttttctggca accaaaccca tacatcggga ttcctataat   4860
accttcgttg gtctccctaa catgtaggtg gcggagggga gatatacaat agaacagata   4920
ccagacaaga cataatgggc taaacaagac tacaccaatt acactgcctc attgatggtg   4980
gtacataacg aactaatact gtagccctag acttgatagc catcatcata tcgaagtttc   5040
actacccttt ttccatttgc catctattga agtaataata ggcgcatgca acttcttttc   5100
tttttttttc ttttctctct cccccgttgt tgtctcacca tatccgcaat gacaaaaaaa   5160
atgatggaag acactaaagg aaaaaattaa cgacaaagac agcaccaaca gatgtcgttg   5220
ttccagagct gatgaggggt atcttcgaac acacgaaact ttttccttcc ttcattcacg   5280
cacactactc tctaatgagc aacggtatac ggccttcctt ccagttactt gaatttgaaa   5340
taaaaaaagt ttgccgcttt gctatcaagt ataaatagac ctgcaattat taatcttttg   5400
tttcctcgtc attgttctcg ttccctttct tccttgtttc tttttctgca caatatttca   5460
agctatacca agcatacaat caactccaag cttatgccca agaagaagcg gaaggtctcg   5520
agcggcgcca attttaatca aagtgggaat attgctgata gctcattgtc cttcactttc   5580
actaacagta gcaacggtcc gaacctcata acaactcaaa caaattctca agcgctttca   5640
caaccaattg cctcctctaa cgttcatgat aacttcatga ataatgaaat cacggctagt   5700
aaaattgatg atggtaataa ttcaaaacca ctgtcacctg gttggacgga ccaaactgcg   5760
tataacgcgt ttggaatcac tacagggatg tttaatacca ctacaatgga tgatgtatat   5820
aactatctat tcgatgatga agatacccca ccaaacccaa aaaaagaggg tgggtcgatc   5880
acaagtttgt acaaaaaagc aggcttgtcg accccgggaa ttcagatcta ctagtgcggc   5940
cgcacgcgta cccagctttc ttgtacaaag tggtgacgtc gagctcccta tagtgagtcg   6000
tattacactg gccgtcgttt tacaacgtcg tgactgggaa aacaccggtg agctctaagt   6060
aagtaacggc cgccaccgcg gtggagcttt ggacttcttc gccagaggtt tggtcaagtc   6120
tccaatcaag gttgtcggct tgtctacctt gccagaaatt tacgaaaaga tggaaaaggg   6180
tcaaatcgtt ggtagatacg ttgttgacac ttctaaataa gcgaatttct tatgatttat   6240
gatttttatt attaaataag ttataaaaaa aataagtgta tacaaatttt aaagtgactc   6300
ttaggtttta aaacgaaaat tcttgttctt gagtaactct ttcctgtagg tcaggttgct   6360
ttctcaggta tagcatgagg tcgctcttat tgaccacacc tctaccggca tgccgagcaa   6420
atgcctgcaa atcgctcccc atttcaccca attgtagata tgctaactcc agcaatgagt   6480
tgatgaatct cggtgtgtat tttatgtcct cagaggacaa tacctgttgt aatcgttctt   6540
ccacacggat ccgcatcagg cgaaattgta aacgttaata ttttgttaaa attcgcgtta   6600
aatatttgtt aaatcagctc atttttttaac caataggccg aaatcggcaa aatcccttat   6660
aaatcaaaag aatagaccga gatagggttg agtgttgttc cagtttggaa caagagtcca   6720
ctattaaaga acgtggactc caacgtcaaa gggcgaaaaa ccgtctatca gggcgatggc   6780
ccactacgtg aaccatcacc ctaatcaagt tttttggggt cgaggtgccg taaagcacta   6840
aatcggaacc ctaaagggag cccccgattt agagcttgac ggggaaagcc ggcgaacgtg   6900
```

-continued

```
gcgagaaagg aagggaagaa agcgaaagga gcgggcgcta gggcgctggc aagtgtagcg   6960

gtcacgctgc gcgtaaccac cacacccgcc gcgcttaatg cgccgctaca gggcgcgtcc   7020

cattcgccat tcactgca                                                 7038
```

<210> SEQ ID NO 184
<211> LENGTH: 7146
<212> TYPE: DNA
<213> ORGANISM: Artificial Sequence
<220> FEATURE:
<223> OTHER INFORMATION: pMAB86

<400> SEQUENCE: 184

```
gacgaaaggg cctcgtgata cgcctatttt tataggttaa tgtcatgata ataatggttt     60

cttaggacgg atcgcttgcc tgtaacttac acgcgcctcg tatcttttaa tgatggaata    120

atttgggaat ttactctgtg tttatttatt tttatgtttt gtatttggat tttagaaagt    180

aaataaagaa ggtagaagag ttacggaatg aagaaaaaaa aataaacaaa ggtttaaaaa    240

atttcaacaa aaagcgtact ttacatatat atttattaga caagaaaagc agattaaata    300

gatatacatt cgattaacga taagtaaaat gtaaaatcac aggattttcg tgtgtggtct    360

tctacacaga caagatgaaa caattcggca ttaatacctg agagcaggaa gagcaagata    420

aaaggtagta tttgttggcg atcccccctag agtcttttac atcttcggaa aacaaaaact    480

attttttctt taatttcttt ttttacttc tatttttaat ttatatattt atattaaaaa    540

atttaaatta taattatttt tatagcacgt gatgaaaagg acccaggtgg cacttttcgg    600

ggaaatgtgc gcggaacccc tatttgttta tttttctaaa tacattcaaa tatgtatccg    660

ctcatgagac aataaccctg ataaatgctt caataatatt gaaaaaggaa gagtatgagt    720

attcaacatt tccgtgtcgc ccttattccc ttttttgcgg cattttgcct tcctgttttt    780

gctcacccag aaacgctggt gaaagtaaaa gatgctgaag atcagttggg tgcacgagtg    840

ggttacatcg aactggatct caacagcggt aagatccttg agagttttcg ccccgaagaa    900

cgttttccaa tgatgagcac ttttaaagtt ctgctatgtg gcgcggtatt atcccgtatt    960

gacgccgggc aagagcaact cggtcgccgc atacactatt ctcagaatga cttggttgag   1020

tactcaccag tcacagaaaa gcatcttacg gatggcatga cagtaagaga attatgcagt   1080

gctgccataa ccatgagtga taacactgcg gccaacttac ttctgacaac gatcggagga   1140

ccgaaggagc taaccgcttt tttcacaac atgggggatc atgtaactcg ccttgatcgt   1200

tgggaaccgg agctgaatga agccatacca aacgacgagc gtgacaccac gatgcctgta   1260

gcaatggcaa caacgttgcg caaactatta actggcgaac tacttactct agcttcccgg   1320

caacaattaa tagactggat ggaggcggat aaagttgcag gaccacttct gcgctcggcc   1380

cttccggctg gctggtttat tgctgataaa tctggagccg gtgagcgtgg gtctcgcggt   1440

atcattgcag cactggggcc agatggtaag ccctcccgta tcgtagttat ctacacgacg   1500

ggcagtcagg caactatgga tgaacgaaat agacagatcg ctgagatagg tgcctcactg   1560

attaagcatt ggtaactgtc agaccaagtt tactcatata tactttagat tgatttaaaa   1620

cttcattttt aatttaaaag gatctaggtg aagatccttt ttgataatct catgaccaaa   1680

atcccttaac gtgagttttc gttccactga gcgtcagacc ccgtagaaaa gatcaaagga   1740

tcttcttgag atcctttttt tctgcgcgta atctgctgct tgcaaacaaa aaaaccaccg   1800

ctaccagcgg tggtttgttt gccggatcaa gagctaccaa ctctttttcc gaaggtaact   1860

ggcttcagca gagcgcagat accaaatact gtccttctag tgtagccgta gttaggccac   1920
```

-continued

```
cacttcaaga actctgtagc accgcctaca tacctcgctc tgctaatcct gttaccagtg   1980
gctgctgcca gtggcgataa gtcgtgtctt accgggttgg actcaagacg atagttaccg   2040
gataaggcgc agcggtcggg ctgaacgggg ggttcgtgca cacagcccag cttggagcga   2100
acgacctaca ccgaactgag atacctacag cgtgagcatt gagaaagcgc cacgcttccc   2160
gaagggagaa aggcggacag gtatccggta agcggcaggg tcggaacagg agagcgcacg   2220
agggagcttc caggggggaa cgcctggtat ctttatagtc ctgtcgggtt tcgccacctc   2280
tgacttgagc gtcgattttt gtgatgctcg tcaggggggc cgagcctatg gaaaaacgcc   2340
agcaacgcgg cctttttacg gttcctggcc ttttgctggc cttttgctca catgttcttt   2400
cctgcgttat cccctgattc tgtggataac cgtattaccg cctttgagtg agctgatacc   2460
gctcgccgca gccgaacgac cgagcgcagc gagtcagtga gcgaggaagc ggaagagcgc   2520
ccaatacgca aaccgcctct ccccgcgcgt tggccgattc attaatgcag ctggcacgac   2580
aggtttcccg actggaaagc gggcagtgag cgcaacgcaa ttaatgtgag ttacctcact   2640
cattaggcac cccaggcttt acactttatg cttccggctc ctatgttgtg tggaattgtg   2700
agcggataac aatttcacac aggaaacagc tatgaccatg attacgccaa gctcggaatt   2760
aaccctcact aaagggaaca aaagctgggt accgggcccc ccctcgagat ccgggatcga   2820
agaaatgatg gtaaatgaaa taggaaatca aggagcatga aggcaaaaga caaatataag   2880
ggtcgaacga aaaataaagt gaaaagtgtt gatatgatgt atttggcttt gcggcgccga   2940
aaaaacgagt ttacgcaatt gcacaatcat gctgactctg tggcggaccc gcgctcttgc   3000
cggcccggcg ataacgctgg gcgtgaggct gtgcccggcg gagttttttg cgcctgcatt   3060
ttccaaggtt taccctgcgc taaggggcga gattggagaa gcaataagaa tgccggttgg   3120
ggttgcgatg atgacgacca cgacaactgg tgtcattatt taagttgccg aaagaacctg   3180
agtgcatttg caacatgagt atactagaag aatgagccaa gacttgcgag acgcgagttt   3240
gccggtggtg cgaacaatag agcgaccatg accttgaagg tgagacgcgc ataaccgcta   3300
gagtactttg aagaggaaac agcaataggg ttgctaccag tataaataga caggtacata   3360
caacactgga aatggttgtc tgtttgagta cgctttcaat tcatttgggt gtgcacttta   3420
ttatgttaca atatggaagg gaactttaca cttctcctat gcacatatat taattaaagt   3480
ccaatgctag tagagaaggg gggtaacacc cctccgcgct cttttccgat ttttttctaa   3540
accgtggaat atttcggata tccttttgtt gtttccgggt gtacaatatg gacttcctct   3600
tttctggcaa ccaaacccat acatcgggat tcctataata ccttcgttgg tctccctaac   3660
atgtaggtgg cggaggggag atatacaata gaacagatac cagacaagac ataatgggct   3720
aaacaagact acaccaatta cactgcctca ttgatggtgg tacataacga actaatactg   3780
tagccctaga cttgatagcc atcatcatat cgaagtttca ctaccctttt tccatttgcc   3840
atctattgaa gtaataatag gcgcatgcaa cttcttttct tttttttttct tttctctctc   3900
ccccgttgtt gtctcaccat atccgcaatg acaaaaaaaa tgatggaaga cactaaagga   3960
aaaaattaac gacaaagaca gcaccaacag atgtcgttgt tccagagctg atgaggggta   4020
tcttcgaaca cacgaaactt tttccttcct tcattcacgc acactactct ctaatgagca   4080
acggtatacg gccttccttc cagttacttg aatttgaaat aaaaaaagtt tgccgctttg   4140
ctatcaagta taaatagacc tgcaattatt aatcttttgt ttcctcgtca ttgttctcgt   4200
tccctttctt ccttgtttct tttctgcac aatatttcaa gctataccaa gcatacaatc   4260
```

-continued

```
aactccaagc ttatgcccaa gaagaagcgg aaggtctcga gcggcgccaa ttttaatcaa   4320
agtgggaata ttgctgatag ctcattgtcc ttcactttca ctaacagtag caacggtccg   4380
aacctcataa caactcaaac aaattctcaa gcgctttcac aaccaattgc ctcctctaac   4440
gttcatgata acttcatgaa taatgaaatc acggctagta aaattgatga tggtaataat   4500
tcaaaaccac tgtcacctgg ttggacggac caaactgcgt ataacgcgtt tggaatcact   4560
acagggatgt ttaataccac tacaatggat gatgtatata actatctatt cgatgatgaa   4620
gataccccac caaacccaaa aaaagagggt gggtcgatca caagtttgta caaaaaagca   4680
ggcttgtcga ccccgggaat tcagatctac tagtgcggcc gcacgcgtac ccagctttct   4740
tgtacaaagt ggtgacgtcg agctctaagt aagtaacggc cgccaccgcg gtggagcttt   4800
ggacttcttc gccagaggtt tggtcaagtc tccaatcaag gttgtcggct tgtctacctt   4860
gccagaaatt tacgaaaaga tggaaaaggg tcaaatcgtt ggtagatacg ttgttgacac   4920
ttctaaataa gcgaatttct tatgatttat gatttttatt attaaataag ttataaaaaa   4980
aataagtgta tacaaatttt aaagtgactc ttaggtttta aaacgaaaat tcttgttctt   5040
gagtaactct ttcctgtagg tcaggttgct ttctcaggta tagcatgagg tcgctcttat   5100
tgaccacacc tctaccggca tgccgagcaa atgcctgcaa atcgctcccc atttcaccca   5160
attgtagata tgctaactcc agcaatgagt tgatgaatct cggtgtgtat tttatgtcct   5220
cagaggacaa tacctgttgt aatcgttctt ccacacggat cccaattcgc cctatagtga   5280
gtcgtattac aattcactgg ccgtcgtttt acaacgtcgt gactgggaaa accctggcgt   5340
tacccaactt aatcgccttg cagcacatcc ccctttcgcc agctggcgta atagcgaaga   5400
ggcccgcacc gatcgccctt cccaacagtt gcgcagcctg aatggcgaat ggacgcgccc   5460
tgtagcggcg cattaagcgc ggcgggtgtg gtggttacgc gcagcgtgac cgctacactt   5520
gccagcgccc tagcgcccgc tcctttcgct ttcttccctt cctttctcgc cacgttcgcc   5580
ggctttcccc gtcaagctct aaatcggggg ctccctttag ggttccgatt tagtgcttta   5640
cggcacctcg accccaaaaa acttgattag ggtgatggtt cacgtagtgg gccatcgccc   5700
tgatagacgg tttttcgccc tttgacgttg gagtccacgt tctttaatag tggactcttg   5760
ttccaaactg gaacaacact caaccctatc tcggtctatt cttttgattt ataagggatt   5820
ttgccgattt cggcctattg gttaaaaaat gagctgattt aacaaaaatt taacgcgaat   5880
tttaacaaaa tattaacgtt tacaatttcc tgatgcggta ttttctcctt acgcatctgt   5940
gcggtatttc acaccgcagg caagtgcaca aacaatactt aaataaatac tactcagtaa   6000
taacctattt cttagcattt ttgacgaaat ttgctatttt gttagagtct tttacaccat   6060
ttgtctccac acctccgctt acatcaacac caataacgcc atttaatcta agcgcatcac   6120
caacattttc tggcgtcagt ccaccagcta acataaaatg taagctttcg ggctctctt    6180
gccttccaac ccagtcagaa atcgagttcc aatccaaaag ttcacctgtc ccacctgctt   6240
ctgaatcaaa caagggaata aacgaatgag gtttctgtga agctgcactg agtagtatgt   6300
tgcagtcttt tggaaatacg agtcttttaa taactggcaa accgaggaac tcttggtatt   6360
cttgccacga ctcatctcca tgcagttgga cgatatcaat gccgtaatca ttgaccagag   6420
ccaaaacatc ctccttaggt tgattacgaa acacgccaac caagtatttc ggagtgcctg   6480
aactattttt atatgctttt acaagacttg aaattttcct tgcaataacc gggtcaattg   6540
ttctctttct attgggcaca catataatac ccagcaagtc agcatcggaa tctagagcac   6600
attctgcggc ctctgtgctc tgcaagccgc aaactttcac caatggacca gaactacctg   6660
```

```
tgaaattaat aacagacata ctccaagctg cctttgtgtg cttaatcacg tatactcacg   6720

tgctcaatag tcaccaatgc cctccctctt ggccctctcc ttttcttttt tcgaccgaat   6780

taattcttaa tcggcaaaaa aagaaaagct ccggatcaag attgtacgta aggtgacaag   6840

ctatttttca ataaagaata tcttccacta ctgccatctg gcgtcataac tgcaaagtac   6900

acatatatta cgatgctgtc tattaaatgc ttcctatatt atatatatag taatgtcgtt   6960

tatggtgcac tctcagtaca atctgctctg atgccgcata gttaagccag ccccgacacc   7020

cgccaacacc cgctgacgcg ccctgacggg cttgtctgct cccggcatcc gcttacagac   7080

aagctgtgac cgtctccggg agctgcatgt gtcagaggtt ttcaccgtca tcaccgaaac   7140

gcgcga                                                              7146


<210> SEQ ID NO 185
<211> LENGTH: 64
<212> TYPE: DNA
<213> ORGANISM: Artificial Sequence
<220> FEATURE:
<223> OTHER INFORMATION: pENTR1A multiple cloning site
<220> FEATURE:
<221> NAME/KEY: CDS
<222> LOCATION: (1)..(63)
<223> OTHER INFORMATION:

<400> SEQUENCE: 185

act ttg tac aaa aaa gca ggc ttt aaa gga acc aat tca gtc gac tgg       48
Thr Leu Tyr Lys Lys Ala Gly Phe Lys Gly Thr Asn Ser Val Asp Trp
1               5                   10                  15

atc cgg tac cga att c                                                 64
Ile Arg Tyr Arg Ile
            20


<210> SEQ ID NO 186
<211> LENGTH: 21
<212> TYPE: PRT
<213> ORGANISM: Artificial Sequence
<220> FEATURE:
<223> OTHER INFORMATION: pENTR1A multiple cloning site

<400> SEQUENCE: 186

Thr Leu Tyr Lys Lys Ala Gly Phe Lys Gly Thr Asn Ser Val Asp Trp
1               5                   10                  15

Ile Arg Tyr Arg Ile
            20


<210> SEQ ID NO 187
<211> LENGTH: 49
<212> TYPE: DNA
<213> ORGANISM: Artificial Sequence
<220> FEATURE:
<223> OTHER INFORMATION: pENTR1A multiple cloning site

<400> SEQUENCE: 187

gaattcgcgg ccgcactcga gatatctaga cccagctttc ttgtacaaa                 49


<210> SEQ ID NO 188
<211> LENGTH: 62
<212> TYPE: DNA
<213> ORGANISM: Artificial Sequence
<220> FEATURE:
<223> OTHER INFORMATION: pENTR2B multiple cloning site
<220> FEATURE:
<221> NAME/KEY: CDS
<222> LOCATION: (1)..(60)
```

```
<223> OTHER INFORMATION:

<400> SEQUENCE: 188

ttg tac aaa aaa gca ggc tgg cgc cgg aac caa ttc agt cga ctg gat       48
Leu Tyr Lys Lys Ala Gly Trp Arg Arg Asn Gln Phe Ser Arg Leu Asp
1               5                   10                  15

ccg gta ccg aat tc                                                    62
Pro Val Pro Asn
            20


<210> SEQ ID NO 189
<211> LENGTH: 20
<212> TYPE: PRT
<213> ORGANISM: Artificial Sequence
<220> FEATURE:
<223> OTHER INFORMATION: pENTR2B multiple cloning site

<400> SEQUENCE: 189

Leu Tyr Lys Lys Ala Gly Trp Arg Arg Asn Gln Phe Ser Arg Leu Asp
1               5                   10                  15

Pro Val Pro Asn
            20


<210> SEQ ID NO 190
<211> LENGTH: 50
<212> TYPE: DNA
<213> ORGANISM: Artificial Sequence
<220> FEATURE:
<223> OTHER INFORMATION: pENTR2B multiple cloning site
<220> FEATURE:
<221> NAME/KEY: CDS
<222> LOCATION: (2)..(49)
<223> OTHER INFORMATION:

<400> SEQUENCE: 190

g aat tcg cgg ccg cac tcg aga tat cta gac cca gct ttc ttg tac aaa     49
  Asn Ser Arg Pro His Ser Arg Tyr Leu Asp Pro Ala Phe Leu Tyr Lys
  1               5                   10                  15

g                                                                     50


<210> SEQ ID NO 191
<211> LENGTH: 16
<212> TYPE: PRT
<213> ORGANISM: Artificial Sequence
<220> FEATURE:
<223> OTHER INFORMATION: pENTR2B multiple cloning site

<400> SEQUENCE: 191

Asn Ser Arg Pro His Ser Arg Tyr Leu Asp Pro Ala Phe Leu Tyr Lys
1               5                   10                  15


<210> SEQ ID NO 192
<211> LENGTH: 69
<212> TYPE: DNA
<213> ORGANISM: Artificial Sequence
<220> FEATURE:
<223> OTHER INFORMATION: pENTR3C multiple cloning site
<220> FEATURE:
<221> NAME/KEY: CDS
<222> LOCATION: (1)..(63)
<223> OTHER INFORMATION:

<400> SEQUENCE: 192

ttg tac aaa aaa gca ggc tct tta aag gaa cca att cag tcg act gga       48
Leu Tyr Lys Lys Ala Gly Ser Leu Lys Glu Pro Ile Gln Ser Thr Gly
1               5                   10                  15
```

-continued

```
tcc ggt acc gaa ttc gatcgc                                        69
Ser Gly Thr Glu Phe
            20


<210> SEQ ID NO 193
<211> LENGTH: 21
<212> TYPE: PRT
<213> ORGANISM: Artificial Sequence
<220> FEATURE:
<223> OTHER INFORMATION: pENTR3C multiple cloning site

<400> SEQUENCE: 193

Leu Tyr Lys Lys Ala Gly Ser Leu Lys Glu Pro Ile Gln Ser Thr Gly
1               5                   10                  15

Ser Gly Thr Glu Phe
            20


<210> SEQ ID NO 194
<211> LENGTH: 50
<212> TYPE: DNA
<213> ORGANISM: Artificial Sequence
<220> FEATURE:
<223> OTHER INFORMATION: pENTR3C multiple cloning site
<220> FEATURE:
<221> NAME/KEY: CDS
<222> LOCATION: (2)..(49)
<223> OTHER INFORMATION:

<400> SEQUENCE: 194

g aat tcg cgg ccg cac tcg aga tat cta gac cca gct ttc ttg tac aaa     49
  Asn Ser Arg Pro His Ser Arg Tyr Leu Asp Pro Ala Phe Leu Tyr Lys
  1               5                   10                  15

g                                                                     50


<210> SEQ ID NO 195
<211> LENGTH: 16
<212> TYPE: PRT
<213> ORGANISM: Artificial Sequence
<220> FEATURE:
<223> OTHER INFORMATION: pENTR3C multiple cloning site

<400> SEQUENCE: 195

Asn Ser Arg Pro His Ser Arg Tyr Leu Asp Pro Ala Phe Leu Tyr Lys
1               5                   10                  15


<210> SEQ ID NO 196
<211> LENGTH: 64
<212> TYPE: DNA
<213> ORGANISM: Artificial Sequence
<220> FEATURE:
<223> OTHER INFORMATION: pENTR4 multiple cloning site
<220> FEATURE:
<221> NAME/KEY: CDS
<222> LOCATION: (1)..(63)
<223> OTHER INFORMATION:

<400> SEQUENCE: 196

ttg tac aaa aaa gca ggc tcc acc atg gga acc aat tca gtc gac tgg       48
Leu Tyr Lys Lys Ala Gly Ser Thr Met Gly Thr Asn Ser Val Asp Trp
1               5                   10                  15

atc cgg tac cga att c                                                 64
Ile Arg Tyr Arg Ile
            20


<210> SEQ ID NO 197
<211> LENGTH: 21
<212> TYPE: PRT
```

-continued

```
<213> ORGANISM: Artificial Sequence
<220> FEATURE:
<223> OTHER INFORMATION: pENTR4 multiple cloning site

<400> SEQUENCE: 197

Leu Tyr Lys Lys Ala Gly Ser Thr Met Gly Thr Asn Ser Val Asp Trp
1               5                   10                  15

Ile Arg Tyr Arg Ile
            20


<210> SEQ ID NO 198
<211> LENGTH: 50
<212> TYPE: DNA
<213> ORGANISM: Artificial Sequence
<220> FEATURE:
<223> OTHER INFORMATION: pENTR4 multiple cloning site
<220> FEATURE:
<221> NAME/KEY: CDS
<222> LOCATION: (2)..(49)
<223> OTHER INFORMATION:

<400> SEQUENCE: 198

g aat tcg cgg ccg cac tcg aga tat cta gac cca gct ttc ttg tac aaa     49
  Asn Ser Arg Pro His Ser Arg Tyr Leu Asp Pro Ala Phe Leu Tyr Lys
  1               5                   10                  15

g                                                                     50


<210> SEQ ID NO 199
<211> LENGTH: 16
<212> TYPE: PRT
<213> ORGANISM: Artificial Sequence
<220> FEATURE:
<223> OTHER INFORMATION: pENTR4 multiple cloning site

<400> SEQUENCE: 199

Asn Ser Arg Pro His Ser Arg Tyr Leu Asp Pro Ala Phe Leu Tyr Lys
1               5                   10                  15


<210> SEQ ID NO 200
<211> LENGTH: 66
<212> TYPE: DNA
<213> ORGANISM: Artificial Sequence
<220> FEATURE:
<223> OTHER INFORMATION: pENTR5 multiple cloning site
<220> FEATURE:
<221> NAME/KEY: CDS
<222> LOCATION: (1)..(63)
<223> OTHER INFORMATION:

<400> SEQUENCE: 200

ttg tac aaa aaa gca ggc ttt cat atg gga acc aat tca gtc gac tgg       48
Leu Tyr Lys Lys Ala Gly Phe His Met Gly Thr Asn Ser Val Asp Trp
1               5                   10                  15

atc cgg tac cga att cgc                                               66
Ile Arg Tyr Arg Ile
            20


<210> SEQ ID NO 201
<211> LENGTH: 21
<212> TYPE: PRT
<213> ORGANISM: Artificial Sequence
<220> FEATURE:
<223> OTHER INFORMATION: pENTR5 multiple cloning site

<400> SEQUENCE: 201

Leu Tyr Lys Lys Ala Gly Phe His Met Gly Thr Asn Ser Val Asp Trp
1               5                   10                  15
```

-continued

```
Ile Arg Tyr Arg Ile
            20


<210> SEQ ID NO 202
<211> LENGTH: 51
<212> TYPE: DNA
<213> ORGANISM: Artificial Sequence
<220> FEATURE:
<223> OTHER INFORMATION: pENTR5 multiple cloning site

<400> SEQUENCE: 202

agaattcgcg gccgcactcg agatatctag acccagcttt cttgtacaaa g              51


<210> SEQ ID NO 203
<211> LENGTH: 63
<212> TYPE: DNA
<213> ORGANISM: Artificial Sequence
<220> FEATURE:
<223> OTHER INFORMATION: pENTR6 multiple cloning site
<220> FEATURE:
<221> NAME/KEY: CDS
<222> LOCATION: (1)..(60)
<223> OTHER INFORMATION:

<400> SEQUENCE: 203

ttg tac aaa aaa gca ggc tgc atg cga acc aat tca gtc gac tgg atc       48
Leu Tyr Lys Lys Ala Gly Cys Met Arg Thr Asn Ser Val Asp Trp Ile
1               5                   10                  15

cgg tac cga att cgc                                                   63
Arg Tyr Arg Ile
            20


<210> SEQ ID NO 204
<211> LENGTH: 20
<212> TYPE: PRT
<213> ORGANISM: Artificial Sequence
<220> FEATURE:
<223> OTHER INFORMATION: pENTR6 multiple cloning site

<400> SEQUENCE: 204

Leu Tyr Lys Lys Ala Gly Cys Met Arg Thr Asn Ser Val Asp Trp Ile
1               5                   10                  15

Arg Tyr Arg Ile
            20


<210> SEQ ID NO 205
<211> LENGTH: 51
<212> TYPE: DNA
<213> ORGANISM: Artificial Sequence
<220> FEATURE:
<223> OTHER INFORMATION: pENTR6 multiple cloning site

<400> SEQUENCE: 205

agaattcgcg gccgcactcg agatatctag acccagcttt cttgtacaaa g              51


<210> SEQ ID NO 206
<211> LENGTH: 84
<212> TYPE: DNA
<213> ORGANISM: Artificial Sequence
<220> FEATURE:
<223> OTHER INFORMATION: pENTR7 multiple cloning site
<220> FEATURE:
<221> NAME/KEY: CDS
<222> LOCATION: (1)..(81)
<223> OTHER INFORMATION:

<400> SEQUENCE: 206
```

```
ttg tac aaa aaa gca ggc ttt gaa aac ctg tat ttt caa gga acc gtt       48
Leu Tyr Lys Lys Ala Gly Phe Glu Asn Leu Tyr Phe Gln Gly Thr Val
1               5                   10                  15

tca tgc atc gtc gac tgg atc cgg tac cga att cgc                       84
Ser Cys Ile Val Asp Trp Ile Arg Tyr Arg Ile
            20                  25
```

<210> SEQ ID NO 207
<211> LENGTH: 27
<212> TYPE: PRT
<213> ORGANISM: Artificial Sequence
<220> FEATURE:
<223> OTHER INFORMATION: pENTR7 multiple cloning site

<400> SEQUENCE: 207

```
Leu Tyr Lys Lys Ala Gly Phe Glu Asn Leu Tyr Phe Gln Gly Thr Val
1               5                   10                  15

Ser Cys Ile Val Asp Trp Ile Arg Tyr Arg Ile
            20                  25
```

<210> SEQ ID NO 208
<211> LENGTH: 51
<212> TYPE: DNA
<213> ORGANISM: Artificial Sequence
<220> FEATURE:
<223> OTHER INFORMATION: pENTR7 multiple cloning site

<400> SEQUENCE: 208

```
agaattcgcg gccgcactcg agatatctag acccagcttt cttgtacaaa g              51
```

<210> SEQ ID NO 209
<211> LENGTH: 81
<212> TYPE: DNA
<213> ORGANISM: Artificial Sequence
<220> FEATURE:
<223> OTHER INFORMATION: pENTR8 multiple cloning site
<220> FEATURE:
<221> NAME/KEY: CDS
<222> LOCATION: (1)..(78)
<223> OTHER INFORMATION:

<400> SEQUENCE: 209

```
ttg tac aaa aaa gca ggc ttt gaa aac ctg tat ttt caa gga acc atg       48
Leu Tyr Lys Lys Ala Gly Phe Glu Asn Leu Tyr Phe Gln Gly Thr Met
1               5                   10                  15

gac cta gtc gac tgg atc cgg tac cga att cgc                           81
Asp Leu Val Asp Trp Ile Arg Tyr Arg Ile
            20                  25
```

<210> SEQ ID NO 210
<211> LENGTH: 26
<212> TYPE: PRT
<213> ORGANISM: Artificial Sequence
<220> FEATURE:
<223> OTHER INFORMATION: pENTR8 multiple cloning site

<400> SEQUENCE: 210

```
Leu Tyr Lys Lys Ala Gly Phe Glu Asn Leu Tyr Phe Gln Gly Thr Met
1               5                   10                  15

Asp Leu Val Asp Trp Ile Arg Tyr Arg Ile
            20                  25
```

<210> SEQ ID NO 211
<211> LENGTH: 51
<212> TYPE: DNA

<213> ORGANISM: Artificial Sequence
<220> FEATURE:
<223> OTHER INFORMATION: pENTR8 multiple cloning site

<400> SEQUENCE: 211
agaattcgcg gccgcactcg agatatctag acccagcttt cttgtacaaa g 51

<210> SEQ ID NO 212
<211> LENGTH: 81
<212> TYPE: DNA
<213> ORGANISM: Artificial Sequence
<220> FEATURE:
<223> OTHER INFORMATION: pENTR9 multiple cloning site
<220> FEATURE:
<221> NAME/KEY: CDS
<222> LOCATION: (1)..(78)
<223> OTHER INFORMATION:

<400> SEQUENCE: 212

```
ttg tac aaa aaa gca ggc ttt gaa aac ctg tat ttt caa gga cat atg       48
Leu Tyr Lys Lys Ala Gly Phe Glu Asn Leu Tyr Phe Gln Gly His Met
1               5                   10                  15

aga tct gtc gac tgg atc cgg tac cga att cgc                           81
Arg Ser Val Asp Trp Ile Arg Tyr Arg Ile
            20                  25
```

<210> SEQ ID NO 213
<211> LENGTH: 26
<212> TYPE: PRT
<213> ORGANISM: Artificial Sequence
<220> FEATURE:
<223> OTHER INFORMATION: pENTR9 multiple cloning site

<400> SEQUENCE: 213

```
Leu Tyr Lys Lys Ala Gly Phe Glu Asn Leu Tyr Phe Gln Gly His Met
1               5                   10                  15

Arg Ser Val Asp Trp Ile Arg Tyr Arg Ile
            20                  25
```

<210> SEQ ID NO 214
<211> LENGTH: 51
<212> TYPE: DNA
<213> ORGANISM: Artificial Sequence
<220> FEATURE:
<223> OTHER INFORMATION: pENTR9 multiple cloning site

<400> SEQUENCE: 214
agaattcgcg gccgcactcg agatatctag acccagcttt cttgtacaaa g 51

<210> SEQ ID NO 215
<211> LENGTH: 84
<212> TYPE: DNA
<213> ORGANISM: Artificial Sequence
<220> FEATURE:
<223> OTHER INFORMATION: pENTR10 multiple cloning site
<220> FEATURE:
<221> NAME/KEY: CDS
<222> LOCATION: (1)..(81)
<223> OTHER INFORMATION:

<400> SEQUENCE: 215

```
ttg tac aaa aaa gca ggc ttc gaa cta agg aaa tac tta cat atg gga       48
Leu Tyr Lys Lys Ala Gly Phe Glu Leu Arg Lys Tyr Leu His Met Gly
1               5                   10                  15

acc aat tca gtc gac tgg atc cgg tac cga att cgc                       84
Thr Asn Ser Val Asp Trp Ile Arg Tyr Arg Ile
            20                  25
```

<210> SEQ ID NO 216
<211> LENGTH: 27
<212> TYPE: PRT
<213> ORGANISM: Artificial Sequence
<220> FEATURE:
<223> OTHER INFORMATION: pENTR10 multiple cloning site

<400> SEQUENCE: 216

```
Leu Tyr Lys Lys Ala Gly Phe Glu Leu Arg Lys Tyr Leu His Met Gly
1               5                   10                  15

Thr Asn Ser Val Asp Trp Ile Arg Tyr Arg Ile
            20                  25
```

<210> SEQ ID NO 217
<211> LENGTH: 51
<212> TYPE: DNA
<213> ORGANISM: Artificial Sequence
<220> FEATURE:
<223> OTHER INFORMATION: pENTR10 multiple cloning site

<400> SEQUENCE: 217

```
agaattcgcg gccgcactcg agatatctag acccagcttt cttgtacaaa g              51
```

<210> SEQ ID NO 218
<211> LENGTH: 88
<212> TYPE: DNA
<213> ORGANISM: Artificial Sequence
<220> FEATURE:
<223> OTHER INFORMATION: pENTR11 multiple cloning site
<220> FEATURE:
<221> NAME/KEY: CDS
<222> LOCATION: (1)..(87)
<223> OTHER INFORMATION:

<400> SEQUENCE: 218

```
ttg tac aaa aaa gca ggc ttc gaa gga gat aga acc aat tct cta agg       48
Leu Tyr Lys Lys Ala Gly Phe Glu Gly Asp Arg Thr Asn Ser Leu Arg
1               5                   10                  15

aaa tac tta acc atg gtc gac tgg atc cgg tac cga att c                 88
Lys Tyr Leu Thr Met Val Asp Trp Ile Arg Tyr Arg Ile
            20                  25
```

<210> SEQ ID NO 219
<211> LENGTH: 29
<212> TYPE: PRT
<213> ORGANISM: Artificial Sequence
<220> FEATURE:
<223> OTHER INFORMATION: pENTR11 multiple cloning site

<400> SEQUENCE: 219

```
Leu Tyr Lys Lys Ala Gly Phe Glu Gly Asp Arg Thr Asn Ser Leu Arg
1               5                   10                  15

Lys Tyr Leu Thr Met Val Asp Trp Ile Arg Tyr Arg Ile
            20                  25
```

<210> SEQ ID NO 220
<211> LENGTH: 50
<212> TYPE: DNA
<213> ORGANISM: Artificial Sequence
<220> FEATURE:
<223> OTHER INFORMATION: pENTR11 multiple cloning site
<220> FEATURE:
<221> NAME/KEY: CDS
<222> LOCATION: (2)..(49)
<223> OTHER INFORMATION:

-continued

<400> SEQUENCE: 220

```
g aat tcg cgg ccg cac tcg aga tat cta gac cca gct ttc ttg tac aaa      49
  Asn Ser Arg Pro His Ser Arg Tyr Leu Asp Pro Ala Phe Leu Tyr Lys
  1               5                   10                  15

g                                                                      50
```

<210> SEQ ID NO 221
<211> LENGTH: 16
<212> TYPE: PRT
<213> ORGANISM: Artificial Sequence
<220> FEATURE:
<223> OTHER INFORMATION: pENTR11 multiple cloning site

<400> SEQUENCE: 221

```
Asn Ser Arg Pro His Ser Arg Tyr Leu Asp Pro Ala Phe Leu Tyr Lys
1               5                   10                  15
```

<210> SEQ ID NO 222
<211> LENGTH: 120
<212> TYPE: DNA
<213> ORGANISM: Artificial Sequence
<220> FEATURE:
<223> OTHER INFORMATION: pDEST1

<400> SEQUENCE: 222

```
atgagctgtt gacaattaat catccggctc gtataatgtg tggaattgtg agcggataac      60

aatttcacac aggaaacaga caggtatagg atcacaagtt tgtacaaaaa agctgaacga     120
```

<210> SEQ ID NO 223
<211> LENGTH: 153
<212> TYPE: DNA
<213> ORGANISM: Artificial Sequence
<220> FEATURE:
<223> OTHER INFORMATION: pDEST2
<220> FEATURE:
<221> NAME/KEY: CDS
<222> LOCATION: (94)..(135)
<223> OTHER INFORMATION:

<400> SEQUENCE: 223

```
aatattctga aatgagctgt tgacaattaa tcatccggtc cgtataatct gtggaattgt      60

gagcggataa caatttcaca caggaaacag acc atg tcg tac tac cat cac cat     114
                                     Met Ser Tyr Tyr His His His
                                     1               5

cac cat cac ggc atc aca agt ttgtacaaaa aagctgaa                      153
His His His Gly Ile Thr Ser
        10
```

<210> SEQ ID NO 224
<211> LENGTH: 14
<212> TYPE: PRT
<213> ORGANISM: Artificial Sequence
<220> FEATURE:
<223> OTHER INFORMATION: pDEST2

<400> SEQUENCE: 224

```
Met Ser Tyr Tyr His His His His His His Gly Ile Thr Ser
1               5                   10
```

<210> SEQ ID NO 225
<211> LENGTH: 153
<212> TYPE: DNA
<213> ORGANISM: Artificial Sequence
<220> FEATURE:
<223> OTHER INFORMATION: pDEST3

-continued

<220> FEATURE:
<221> NAME/KEY: CDS
<222> LOCATION: (106)..(120)
<223> OTHER INFORMATION:

<400> SEQUENCE: 225

```
cggttctggc aaatattctg aaatgagctg ttgacaatta atcatcggct cgtataatgt      60

gtggaattgt gagcggataa caatttcaca caggaaacag tattc atg tcc cct ata     117
                                                  Met Ser Pro Ile
                                                  1

cta ggttattgga aaattaaggg ccttgtgcaa ccc                             153
Leu
5
```

<210> SEQ ID NO 226
<211> LENGTH: 5
<212> TYPE: PRT
<213> ORGANISM: Artificial Sequence
<220> FEATURE:
<223> OTHER INFORMATION: pDEST3

<400> SEQUENCE: 226

```
Met Ser Pro Ile Leu
1               5
```

<210> SEQ ID NO 227
<211> LENGTH: 102
<212> TYPE: DNA
<213> ORGANISM: Artificial Sequence
<220> FEATURE:
<223> OTHER INFORMATION: pDEST3
<220> FEATURE:
<221> NAME/KEY: CDS
<222> LOCATION: (10)..(63)
<223> OTHER INFORMATION:

<400> SEQUENCE: 227

```
ctggttccg cgt gga tct cgt cgt gca tct gtt gga tcc cca tca aca agt      51
          Arg Gly Ser Arg Arg Ala Ser Val Gly Ser Pro Ser Thr Ser
          1               5                   10

ttg tac aaa aaa gctgaacgag aaacgtaaaa tgatataaat atcaatata           102
Leu Tyr Lys Lys
15
```

<210> SEQ ID NO 228
<211> LENGTH: 18
<212> TYPE: PRT
<213> ORGANISM: Artificial Sequence
<220> FEATURE:
<223> OTHER INFORMATION: pDEST3

<400> SEQUENCE: 228

```
Arg Gly Ser Arg Arg Ala Ser Val Gly Ser Pro Ser Thr Ser Leu Tyr
1               5                   10                  15

Lys Lys
```

<210> SEQ ID NO 229
<211> LENGTH: 255
<212> TYPE: DNA
<213> ORGANISM: Artificial Sequence
<220> FEATURE:
<223> OTHER INFORMATION: pDEST4
<220> FEATURE:
<221> NAME/KEY: CDS
<222> LOCATION: (97)..(246)
<223> OTHER INFORMATION:

-continued

<400> SEQUENCE: 229

```
gcaaatattc tgaaatgagc tgttgacaat taatcatccg gtccgtataa tctgtggaat     60

tgtgagcgga taacaatttc acacaggaaa cagacc atg ggt cat cat cat cat      114
                                        Met Gly His His His His
                                        1               5

cat cac gat tac gat atc cca acg acc gaa aac ctg tat ttt cag ggc      162
His His Asp Tyr Asp Ile Pro Thr Thr Glu Asn Leu Tyr Phe Gln Gly
            10                  15                  20

gcc cat atg agc gat aaa att att cac ctg act gac gac agt gat gac      210
Ala His Met Ser Asp Lys Ile Ile His Leu Thr Asp Asp Ser Asp Asp
        25                  30                  35

gat gac aag gta ccc atc aca agt ttg tac aaa aaa gctgaacga            255
Asp Asp Lys Val Pro Ile Thr Ser Leu Tyr Lys Lys
    40                  45                  50
```

<210> SEQ ID NO 230
<211> LENGTH: 50
<212> TYPE: PRT
<213> ORGANISM: Artificial Sequence
<220> FEATURE:
<223> OTHER INFORMATION: pDEST4

<400> SEQUENCE: 230

```
Met Gly His His His His His His Asp Tyr Asp Ile Pro Thr Thr Glu
1               5                   10                  15

Asn Leu Tyr Phe Gln Gly Ala His Met Ser Asp Lys Ile Ile His Leu
            20                  25                  30

Thr Asp Asp Ser Asp Asp Asp Asp Lys Val Pro Ile Thr Ser Leu Tyr
        35                  40                  45

Lys Lys
    50
```

<210> SEQ ID NO 231
<211> LENGTH: 204
<212> TYPE: DNA
<213> ORGANISM: Artificial Sequence
<220> FEATURE:
<223> OTHER INFORMATION: pDEST5

<400> SEQUENCE: 231

```
aggcacccca ggctttacac tttatgcttc cggctcgtat gttgtgtgga attgtgagcg     60

gataacaatt tcacacagga aacagctatg accatgatta cgccaagctc taatacgact    120

cactataggg aaagctggta cgcctgcagg taccggtccg gaattcccgg gtcgacgatc    180

acaagtttgt acaaaaaagc tgaa                                           204
```

<210> SEQ ID NO 232
<211> LENGTH: 204
<212> TYPE: DNA
<213> ORGANISM: Artificial Sequence
<220> FEATURE:
<223> OTHER INFORMATION: pDEST5

<400> SEQUENCE: 232

```
tttacgtttc tcgttcagct ttcttgtaca aagtggtgat cactagtcgg cggccgctct     60

agaggatcca agcttacgta cgcgtgcatg cgacgtcata gctcttctat agtgtcacct    120

aaattcaatt cactggccgt cgttttacaa cgtcgtgact gggaaaaccc tggcgttacc    180

caacttaatc gccttgcagc acat                                           204
```

-continued

<210> SEQ ID NO 233
<211> LENGTH: 204
<212> TYPE: DNA
<213> ORGANISM: Artificial Sequence
<220> FEATURE:
<223> OTHER INFORMATION: pDEST6

<400> SEQUENCE: 233
taacgccagg gttttcccag tcacgacgtt gtaaaacgac ggccagtgaa ttgaatttag 60
gtgacactat agaagagcta tgacgtcgca tgcacgcgta cgtaagcttg gatcctctag 120
agcggccgcc gactagtgat cacaagtttg tacaaaaaag ctgaacgaga aacgtaaaat 180
gatataaata tcaatatatt aaat 204

<210> SEQ ID NO 234
<211> LENGTH: 255
<212> TYPE: DNA
<213> ORGANISM: Artificial Sequence
<220> FEATURE:
<223> OTHER INFORMATION: pDEST6

<400> SEQUENCE: 234
tatttatatc attttacgtt tctcgttcag ctttcttgta caaagtggtg atcgtcgacc 60
cgggaattcc ggaccggtac ctgcaggcgt accagctttc cctatagtga gtcgtattag 120
agcttggcgt aatcatggtc atagctgttt cctgtgtgaa attgttatcc gctcacaatt 180
ccacacaaca tacgagccgg aagcataaag tgtaaagcct ggggtgccta atgagtgagc 240
taactcacat taatt 255

<210> SEQ ID NO 235
<211> LENGTH: 306
<212> TYPE: DNA
<213> ORGANISM: Artificial Sequence
<220> FEATURE:
<223> OTHER INFORMATION: pDEST7

<400> SEQUENCE: 235
ccattgacgc aaatgggcgg taggcgtgta cggtgggagg tctatataag cagagctcgt 60
ttagtgaacc gtcagatcgc ctggagacgc catccacgct gttttgacct ccatagaaga 120
caccgggacc gatccagcct ccggactcta gcctaggccg cggagcggat aacaatttca 180
cacaggaaac agctatgacc actaggcttt tgcaaaaagc tatttaggtg acactataga 240
aggtacgcct gcaggtaccg gtccggaatt cccatcacaa gtttgtacaa aaaagctgaa 300
cgagaa 306

<210> SEQ ID NO 236
<211> LENGTH: 204
<212> TYPE: DNA
<213> ORGANISM: Artificial Sequence
<220> FEATURE:
<223> OTHER INFORMATION: pDEST8

<400> SEQUENCE: 236
cgtatactcc ggaatattaa tagatcatgg agataattaa aatgataacc atctcgcaaa 60
taaataagta ttttactgtt ttcgtaacag ttttgtaata aaaaaaccta taaatattcc 120
ggattattca taccgtccca ccatcgggcg cggatcatca caagtttgta caaaaaagct 180
gaacgagaaa cgtaaaatga tata 204

<210> SEQ ID NO 237

-continued

<211> LENGTH: 153
<212> TYPE: DNA
<213> ORGANISM: Artificial Sequence
<220> FEATURE:
<223> OTHER INFORMATION: pDEST9

<400> SEQUENCE: 237
ttggcgaggg acattaaggc gtttaagaaa ttgagaggac ctgttataca cctctacggc 60
ggtcctagat tggtgcgtta atacacagaa ttctgattgg atcccggtcc gaagcgcgct 120
ttcccatcaa caagtttgta caaaaaagct gaa 153

<210> SEQ ID NO 238
<211> LENGTH: 204
<212> TYPE: DNA
<213> ORGANISM: Artificial Sequence
<220> FEATURE:
<223> OTHER INFORMATION: pDEST10
<220> FEATURE:
<221> NAME/KEY: CDS
<222> LOCATION: (109)..(201)
<223> OTHER INFORMATION:

<400> SEQUENCE: 238
aaataagtat tttactgttt tcgtaacagt tttgtaataa aaaaacctat aaatattccg 60
gattattcat accgtcccac catcgggcgc ggatctcggt ccgaaacc atg tcg tac 117
Met Ser Tyr
1 tac cat cac cat cac cat cac gat tac gat atc cca acg acc gaa aac 165
Tyr His His His His His His Asp Tyr Asp Ile Pro Thr Thr Glu Asn
5 10 15 ctg tat ttt cag ggc atc aca agt ttg tac aaa aaa gct 204
Leu Tyr Phe Gln Gly Ile Thr Ser Leu Tyr Lys Lys
20 25 30

<210> SEQ ID NO 239
<211> LENGTH: 31
<212> TYPE: PRT
<213> ORGANISM: Artificial Sequence
<220> FEATURE:
<223> OTHER INFORMATION: pDEST10

<400> SEQUENCE: 239

Met Ser Tyr Tyr His His His His His His Asp Tyr Asp Ile Pro Thr
1 5 10 15

Thr Glu Asn Leu Tyr Phe Gln Gly Ile Thr Ser Leu Tyr Lys Lys
20 25 30

<210> SEQ ID NO 240
<211> LENGTH: 204
<212> TYPE: DNA
<213> ORGANISM: Artificial Sequence
<220> FEATURE:
<223> OTHER INFORMATION: pDEST11

<400> SEQUENCE: 240
tagtgaaccg tcagatcgcc tggagacgcc atccacgctg ttttgacctc catagaagac 60
accgggaccg atccagcctc cgcggccccg aattcgagct cggtacccgg ggatcctcta 120
gagtcgaggt cgacggtatc gataagcttg atatcaacaa gtttgtacaa aaaagctgaa 180
cgagaaacgt aaaatgatat aaat 204

<210> SEQ ID NO 241
<211> LENGTH: 255

-continued

```
<212> TYPE: DNA
<213> ORGANISM: Artificial Sequence
<220> FEATURE:
<223> OTHER INFORMATION: pDEST12.2

<400> SEQUENCE: 241

accgtcagat cgcctggaga cgccatccac gctgttttga cctccataga agacaccggg      60

accgatccag cctccggact ctagcctagg ccgcggagcg gataacaatt tcacacagga     120

aacagctatg accattaggc ctttgcaaaa agctatttag gtgacactat agaaggtacg     180

cctgcaggta ccggtccgga attcccatca acaagtttgt acaaaaaagc tgaacgagaa     240

acgtaaaatg atata                                                      255


<210> SEQ ID NO 242
<211> LENGTH: 300
<212> TYPE: DNA
<213> ORGANISM: Artificial Sequence
<220> FEATURE:
<223> OTHER INFORMATION: pDEST13

<400> SEQUENCE: 242

tgggcaaacc aagacagcta aagatctctc acctaccaaa caatgccccc ctgcaaaaaa      60

taaattcata taaaaaacat acagataacc atctgcggtg ataaattatc tctggcggtg     120

ttgacataaa taccactggc ggtgatactg agcacatcag caggacgcac tgaccaccat     180

gaaggtgacg ctcttaaaaa ttaagccctg aagaagggca gcattcaaag cagaaggctt     240

tggggtgtgt gatacgaaac gaagcattgg gatcatcaca agtttgtaca aaaaagctga     300


<210> SEQ ID NO 243
<211> LENGTH: 120
<212> TYPE: DNA
<213> ORGANISM: Artificial Sequence
<220> FEATURE:
<223> OTHER INFORMATION: pDEST14

<400> SEQUENCE: 243

tgccggccac gatgcgtccg gcgtagagga tcgagatctc gatcccgcga aattaatacg      60

actcactata gggagaccac aacggtttcc ctctagatca caagtttgta caaaaaagct     120


<210> SEQ ID NO 244
<211> LENGTH: 204
<212> TYPE: DNA
<213> ORGANISM: Artificial Sequence
<220> FEATURE:
<223> OTHER INFORMATION: pDEST15
<220> FEATURE:
<221> NAME/KEY: misc_feature
<222> LOCATION: (1)..(1)
<223> OTHER INFORMATION: 'n' can be any nucleotide (A, T, C, G or U)
<220> FEATURE:
<221> NAME/KEY: CDS
<222> LOCATION: (106)..(120)
<223> OTHER INFORMATION:

<400> SEQUENCE: 244

natcgagatc tcgatcccgc gaaattaata cgactcacta tagggagacc acaacggttt      60

ccctctagaa ataattttgt ttaactttaa gaaggagata tacat atg tcc cct ata     117
                                                  Met Ser Pro Ile
                                                  1

cta ggttattgga aaattaaggg ccttgtgcaa cccactcgac ttcttttgga            170
Leu
5
```

-continued

```
atatcttgaa gaaaaatatg aagagcattt gtat                           204


<210> SEQ ID NO 245
<211> LENGTH: 5
<212> TYPE: PRT
<213> ORGANISM: Artificial Sequence
<220> FEATURE:
<223> OTHER INFORMATION: pDEST15
<220> FEATURE:
<221> NAME/KEY: misc_feature
<222> LOCATION: (1)..(1)
<223> OTHER INFORMATION: may be any nucleotide

<400> SEQUENCE: 245

Met Ser Pro Ile Leu
1               5


<210> SEQ ID NO 246
<211> LENGTH: 153
<212> TYPE: DNA
<213> ORGANISM: Artificial Sequence
<220> FEATURE:
<223> OTHER INFORMATION: pDEST15
<220> FEATURE:
<221> NAME/KEY: CDS
<222> LOCATION: (70)..(99)
<223> OTHER INFORMATION:

<400> SEQUENCE: 246

cagggctggc aagccacgtt tggtggtggc gaccatcctc caaaatcgga tctggttccg     60

cgtccatgg tcg aat caa aca agt ttg tac aaa aaa gct gaacgagaaa         109
          Ser Asn Gln Thr Ser Leu Tyr Lys Lys Ala
          1               5                   10

cgtaaaatga tataaatatc aatatattaa attagatttt gcat                    153


<210> SEQ ID NO 247
<211> LENGTH: 10
<212> TYPE: PRT
<213> ORGANISM: Artificial Sequence
<220> FEATURE:
<223> OTHER INFORMATION: pDEST15

<400> SEQUENCE: 247

Ser Asn Gln Thr Ser Leu Tyr Lys Lys Ala
1               5                   10


<210> SEQ ID NO 248
<211> LENGTH: 153
<212> TYPE: DNA
<213> ORGANISM: Artificial Sequence
<220> FEATURE:
<223> OTHER INFORMATION: pDEST16 multiple cloning site
<220> FEATURE:
<221> NAME/KEY: CDS
<222> LOCATION: (100)..(111)
<223> OTHER INFORMATION:

<400> SEQUENCE: 248

gatctcgatc ccgcgaaatt aatacgactc actataggga gaccacaacg gtttccctct     60

agaaataatt ttgtttaact ttaagaagga gatatacat atg agc gat aaa           111
                                          Met Ser Asp Lys
                                          1

attattcacc tgactgacga cagttttgac acggatgtac tc                      153


<210> SEQ ID NO 249
<211> LENGTH: 4
```

-continued

```
<212> TYPE: PRT
<213> ORGANISM: Artificial Sequence
<220> FEATURE:
<223> OTHER INFORMATION: pDEST16 multiple cloning site

<400> SEQUENCE: 249

Met Ser Asp Lys
1


<210> SEQ ID NO 250
<211> LENGTH: 153
<212> TYPE: DNA
<213> ORGANISM: Artificial Sequence
<220> FEATURE:
<223> OTHER INFORMATION: pDEST16 multiple cloning site
<220> FEATURE:
<221> NAME/KEY: CDS
<222> LOCATION: (82)..(123)
<223> OTHER INFORMATION:

<400> SEQUENCE: 250

gtggcggcaa ccaaagtggg tgcactgtct aaaggtcagt tgaaagagtt cctcgacgct     60

aacctggccg gttctggttc t ggt gat gac gat gac aag atc aca agt ttg      111
                        Gly Asp Asp Asp Asp Lys Ile Thr Ser Leu
                        1               5                   10

tac aaa aaa gct gaacgagaaa cgtaaaatga tataaatatc                     153
Tyr Lys Lys Ala


<210> SEQ ID NO 251
<211> LENGTH: 14
<212> TYPE: PRT
<213> ORGANISM: Artificial Sequence
<220> FEATURE:
<223> OTHER INFORMATION: pDEST16 multiple cloning site

<400> SEQUENCE: 251

Gly Asp Asp Asp Asp Lys Ile Thr Ser Leu Tyr Lys Lys Ala
1               5                   10


<210> SEQ ID NO 252
<211> LENGTH: 153
<212> TYPE: DNA
<213> ORGANISM: Artificial Sequence
<220> FEATURE:
<223> OTHER INFORMATION: pDEST17 multiple cloning site
<220> FEATURE:
<221> NAME/KEY: CDS
<222> LOCATION: (94)..(153)
<223> OTHER INFORMATION:

<400> SEQUENCE: 252

gatcccgcga aattaatacg actcactata gggagaccac aacggtttcc ctctagaaat     60

aattttgttt aactttaaga aggagatata cat atg tcg tac tac cat cac cat     114
                                     Met Ser Tyr Tyr His His His
                                     1               5

cac cat cac ctc gaa tca aca agt ttg tac aaa aaa gct                  153
His His His Leu Glu Ser Thr Ser Leu Tyr Lys Lys Ala
        10                  15                  20


<210> SEQ ID NO 253
<211> LENGTH: 20
<212> TYPE: PRT
<213> ORGANISM: Artificial Sequence
<220> FEATURE:
<223> OTHER INFORMATION: pDEST17 multiple cloning site

<400> SEQUENCE: 253
```

-continued

```
Met Ser Tyr Tyr His His His His His His Leu Glu Ser Thr Ser Leu
1               5                   10                  15

Tyr Lys Lys Ala
            20
```

<210> SEQ ID NO 254
<211> LENGTH: 420
<212> TYPE: DNA
<213> ORGANISM: Artificial Sequence
<220> FEATURE:
<223> OTHER INFORMATION: pDEST18 p10 Promoter

<400> SEQUENCE: 254

```
gaagacctcg gccgtcgcgg cgcttgccgg tggtgctgac cccggatgaa gtggttcgca     60

tcctcggttt tctggaaggc gagcatcgtt tgttcgccca ggactctagc tatagttcta    120

gtggttggct acgtatcgag caagaaaata aaacgccaaa cgcgttggag tcttgtgtgc    180

tatttttaca aagattcaga aatacgcatc acttacaaca agggggacta tgaaattatg    240

cattttgagg atgccgggac ctttaattca acccaacaca atatattata gttaaataag    300

aattatttat caaatcattt gtatattaat taaaatacta tactgtaaat tacattttat    360

ttacaatgag gatcatcaca agtttgtaca aaaaagctga acgagaaacg taaaatgata    420
```

<210> SEQ ID NO 255
<211> LENGTH: 300
<212> TYPE: DNA
<213> ORGANISM: Artificial Sequence
<220> FEATURE:
<223> OTHER INFORMATION: pDEST19 39K Promoter

<400> SEQUENCE: 255

```
ggtgacgccg tcatctttcc attgtaacgt aaatggcaac ttgtagatga acgcgctgtc     60

aaaaaaccgg ccagtttctt ccacaaactc gcgcacggct gtctcgtaaa cttttgcgtc    120

gcaacaatcg cgatgacctc gtggtatgga aatttttttct aaaaaagtgt cgttcatgtc    180

ggcggcggcg ttcgcgctcc ggtacgcgcg acgggcacac agcaggacag ccttgtccgg    240

ctcgattatc ataaacaatc ctgcaggcat gcaagctgga tcatcacaag tttgtacaaa    300
```

<210> SEQ ID NO 256
<211> LENGTH: 204
<212> TYPE: DNA
<213> ORGANISM: Artificial Sequence
<220> FEATURE:
<223> OTHER INFORMATION: pDEST20 Polyhedron Promoter
<220> FEATURE:
<221> NAME/KEY: CDS
<222> LOCATION: (163)..(174)
<223> OTHER INFORMATION:

<400> SEQUENCE: 256

```
ggctacgtat actccggaat attaatagat catggagata attaaaatga taaccatctc     60

gcaaataaat aagtatttta ctgttttcgt aacagttttg taataaaaaa acctataaat    120

attccggatt attcataccg tcccaccatc gggcgcggat cc atg gcc cct ata       174
                                               Met Ala Pro Ile
                                               1

ctaggttatt ggaaaattaa gggccttgtg                                     204
```

<210> SEQ ID NO 257
<211> LENGTH: 4
<212> TYPE: PRT

-continued

<213> ORGANISM: Artificial Sequence
<220> FEATURE:
<223> OTHER INFORMATION: pDEST20 Polyhedron Promoter

<400> SEQUENCE: 257

Met Ala Pro Ile
1

<210> SEQ ID NO 258
<211> LENGTH: 95
<212> TYPE: DNA
<213> ORGANISM: Artificial Sequence
<220> FEATURE:
<223> OTHER INFORMATION: pDEST20 Polyhedron Promoter
<220> FEATURE:
<221> NAME/KEY: CDS
<222> LOCATION: (1)..(48)
<223> OTHER INFORMATION:

<400> SEQUENCE: 258

```
tcg gat ctg gtt ccg cgt cat aat caa aca agt ttg tac aaa aaa gct       48
Ser Asp Leu Val Pro Arg His Asn Gln Thr Ser Leu Tyr Lys Lys Ala
1               5                   10                  15

gaacgagaaa cgtaaaatga tataaatatc aatatattaa attagat                   95
```

<210> SEQ ID NO 259
<211> LENGTH: 16
<212> TYPE: PRT
<213> ORGANISM: Artificial Sequence
<220> FEATURE:
<223> OTHER INFORMATION: pDEST20 Polyhedron Promoter

<400> SEQUENCE: 259

```
Ser Asp Leu Val Pro Arg His Asn Gln Thr Ser Leu Tyr Lys Lys Ala
1               5                   10                  15
```

<210> SEQ ID NO 260
<211> LENGTH: 204
<212> TYPE: DNA
<213> ORGANISM: Artificial Sequence
<220> FEATURE:
<223> OTHER INFORMATION: pDEST21 Promoter region
<220> FEATURE:
<221> NAME/KEY: CDS
<222> LOCATION: (163)..(180)
<223> OTHER INFORMATION:

<400> SEQUENCE: 260

```
ttgccgcttt gctatcaagt ataaatagac ctgcaattat taatcttttg tttcctcgtc     60

attgttctcg ttccctttct tccttgtttc tttttctgca caatatttca agctatacca    120

agcatacaat caactccaag cttgaagcaa gcctcctgaa ag atg aag cta ctg       174
                                               Met Lys Leu Leu
                                               1

tct tct atcgaacaag catgcgatat ttgc                                   204
Ser Ser
5
```

<210> SEQ ID NO 261
<211> LENGTH: 6
<212> TYPE: PRT
<213> ORGANISM: Artificial Sequence
<220> FEATURE:
<223> OTHER INFORMATION: pDEST21 Promoter region

<400> SEQUENCE: 261

Met Lys Leu Leu Ser Ser

-continued

```
1               5


<210> SEQ ID NO 262
<211> LENGTH: 102
<212> TYPE: DNA
<213> ORGANISM: Artificial Sequence
<220> FEATURE:
<223> OTHER INFORMATION: pDEST21 Promoter region
<220> FEATURE:
<221> NAME/KEY: CDS
<222> LOCATION: (37)..(78)
<223> OTHER INFORMATION:

<400> SEQUENCE: 262

gaagagagta gtaacaaagg tcaaagacag ttgact gta tcg tcg agg tcg aat       54
                                        Val Ser Ser Arg Ser Asn
                                        1               5

caa aca agt ttg tac aaa aaa gct gaacgagaaa cgtaaaatga tata           102
Gln Thr Ser Leu Tyr Lys Lys Ala
            10


<210> SEQ ID NO 263
<211> LENGTH: 14
<212> TYPE: PRT
<213> ORGANISM: Artificial Sequence
<220> FEATURE:
<223> OTHER INFORMATION: pDEST21 Promoter region

<400> SEQUENCE: 263

Val Ser Ser Arg Ser Asn Gln Thr Ser Leu Tyr Lys Lys Ala
1               5                   10


<210> SEQ ID NO 264
<211> LENGTH: 255
<212> TYPE: DNA
<213> ORGANISM: Artificial Sequence
<220> FEATURE:
<223> OTHER INFORMATION: pDEST22 Promoter region
<220> FEATURE:
<221> NAME/KEY: CDS
<222> LOCATION: (217)..(228)
<223> OTHER INFORMATION:

<400> SEQUENCE: 264

acgcacacta ctctctaatg agcaacggta tacggccttc cttccagtta cttgaatttg     60

aaataaaaaa agtttgccgc tttgctatca agtataaata gacctgcaat tattaatctt    120

ttgtttcctc gtcattgttc tcgttccctt tcttccttgt ttcttttttct gcacaatatt   180

tcaagctata ccaagcatac aatcaactcc aagctt atg ccc aag aag              228
                                        Met Pro Lys Lys
                                        1

aagcggaagg tctcgagcgg cgccaat                                        255


<210> SEQ ID NO 265
<211> LENGTH: 4
<212> TYPE: PRT
<213> ORGANISM: Artificial Sequence
<220> FEATURE:
<223> OTHER INFORMATION: pDEST22 Promoter region

<400> SEQUENCE: 265

Met Pro Lys Lys
1


<210> SEQ ID NO 266
<211> LENGTH: 82
```

```
<212> TYPE: DNA
<213> ORGANISM: Artificial Sequence
<220> FEATURE:
<223> OTHER INFORMATION: pDEST22
<220> FEATURE:
<221> NAME/KEY: CDS
<222> LOCATION: (28)..(66)
<223> OTHER INFORMATION:

<400> SEQUENCE: 266

gaagataccc caccaaaccc aaaaaaa gag ggt ggg tcg aat caa aca agt ttg      54
                              Glu Gly Gly Ser Asn Gln Thr Ser Leu
                              1               5

tac aaa aaa gct gaacgagaaa cgtaaa                                      82
Tyr Lys Lys Ala
10


<210> SEQ ID NO 267
<211> LENGTH: 13
<212> TYPE: PRT
<213> ORGANISM: Artificial Sequence
<220> FEATURE:
<223> OTHER INFORMATION: pDEST22

<400> SEQUENCE: 267

Glu Gly Gly Ser Asn Gln Thr Ser Leu Tyr Lys Lys Ala
1               5                   10


<210> SEQ ID NO 268
<211> LENGTH: 102
<212> TYPE: DNA
<213> ORGANISM: Artificial Sequence
<220> FEATURE:
<223> OTHER INFORMATION: pDEST23 T7 promoter

<400> SEQUENCE: 268

atcccgcgaa attaatacga ctcactatag ggagaccaca acggtttccc tctagatcac      60

aagtttgtac aaaaaagctg aacgagaaac gtaaaatgat at                        102


<210> SEQ ID NO 269
<211> LENGTH: 153
<212> TYPE: DNA
<213> ORGANISM: Artificial Sequence
<220> FEATURE:
<223> OTHER INFORMATION: pDEST23 T7 promoter
<220> FEATURE:
<221> NAME/KEY: CDS
<222> LOCATION: (61)..(126)
<223> OTHER INFORMATION:

<400> SEQUENCE: 269

tttttatgca aaatctaatt taatatattg atatttatat cattttacgt ttctcgttca      60

gct ttc ttg tac aaa gtg gtg att atg tcg tac tac cat cac cat cac       108
Ala Phe Leu Tyr Lys Val Val Ile Met Ser Tyr Tyr His His His His
1               5                   10                  15

cat cac ctc gat gag caa taactagcat aaccccttgg ggcctct                 153
His His Leu Asp Glu Gln
            20


<210> SEQ ID NO 270
<211> LENGTH: 22
<212> TYPE: PRT
<213> ORGANISM: Artificial Sequence
<220> FEATURE:
<223> OTHER INFORMATION: pDEST23 T7 promoter

<400> SEQUENCE: 270
```

-continued

```
Ala Phe Leu Tyr Lys Val Val Ile Met Ser Tyr Tyr His His His His
1               5                   10                  15

His His Leu Asp Glu Gln
            20
```

<210> SEQ ID NO 271
<211> LENGTH: 102
<212> TYPE: DNA
<213> ORGANISM: Artificial Sequence
<220> FEATURE:
<223> OTHER INFORMATION: pDEST24 T7 promoter

<400> SEQUENCE: 271

```
atcgagatct cgatcccgcg aaattaatac gactcactat agggagacca caacggtttc     60

cctctagatc acaagtttgt acaaaaaagc tgaacgagaa ac                       102
```

<210> SEQ ID NO 272
<211> LENGTH: 102
<212> TYPE: DNA
<213> ORGANISM: Artificial Sequence
<220> FEATURE:
<223> OTHER INFORMATION: pDEST24 T7 promoter
<220> FEATURE:
<221> NAME/KEY: CDS
<222> LOCATION: (22)..(60)
<223> OTHER INFORMATION:

<400> SEQUENCE: 272

```
tcattttacg tttctcgttc a gct ttc ttg tac aaa gtg gtg att atg tcc       51
                        Ala Phe Leu Tyr Lys Val Val Ile Met Ser
                        1               5                   10

cct ata cta ggttattgga aaattaaggg ccttgtgcaa cccactcgac tt           102
Pro Ile Leu
```

<210> SEQ ID NO 273
<211> LENGTH: 13
<212> TYPE: PRT
<213> ORGANISM: Artificial Sequence
<220> FEATURE:
<223> OTHER INFORMATION: pDEST24 T7 promoter

<400> SEQUENCE: 273

```
Ala Phe Leu Tyr Lys Val Val Ile Met Ser Pro Ile Leu
1               5                   10
```

<210> SEQ ID NO 274
<211> LENGTH: 102
<212> TYPE: DNA
<213> ORGANISM: Artificial Sequence
<220> FEATURE:
<223> OTHER INFORMATION: pDEST25 T7 promoter
<220> FEATURE:
<221> NAME/KEY: misc_feature
<222> LOCATION: (1)..(1)
<223> OTHER INFORMATION: 'n' can be any nucleotide (A, T, C, G or U)

<400> SEQUENCE: 274

```
nagatctcga tcccgcgaaa ttaatacgac tcactatagg gagaccacaa cggtttccct     60

ctagatcaca agtttgtaca aaaaagctga acgagaaacg ta                       102
```

<210> SEQ ID NO 275
<211> LENGTH: 102
<212> TYPE: DNA

-continued

<213> ORGANISM: Artificial Sequence
<220> FEATURE:
<223> OTHER INFORMATION: pDEST25 T7 promoter
<220> FEATURE:
<221> NAME/KEY: CDS
<222> LOCATION: (19)..(60)
<223> OTHER INFORMATION:

<400> SEQUENCE: 275

```
ttttacgttt ctcgttca gct ttc ttg tac aaa gtg gtg att atg agc gat       51
                    Ala Phe Leu Tyr Lys Val Val Ile Met Ser Asp
                    1               5                   10

aaa att att cacctgactg acgacagttt tgacacggat gtactcaaag cg           102
Lys Ile Ile
```

<210> SEQ ID NO 276
<211> LENGTH: 14
<212> TYPE: PRT
<213> ORGANISM: Artificial Sequence
<220> FEATURE:
<223> OTHER INFORMATION: pDEST25 T7 promoter

<400> SEQUENCE: 276

```
Ala Phe Leu Tyr Lys Val Val Ile Met Ser Asp Lys Ile Ile
1               5                   10
```

<210> SEQ ID NO 277
<211> LENGTH: 306
<212> TYPE: DNA
<213> ORGANISM: Artificial Sequence
<220> FEATURE:
<223> OTHER INFORMATION: pDEST26 CMV promoter
<220> FEATURE:
<221> NAME/KEY: CDS
<222> LOCATION: (238)..(297)
<223> OTHER INFORMATION:

<400> SEQUENCE: 277

```
ttgacgtcaa tgggagtttg ttttggcacc aaaatcaacg ggactttcca aaatgtcgta     60

acaactccgc cccattgacg caaatgggcg gtaggcgtgt acggtgggag gtctatataa    120

gcagagctcg tttagtgaac cgtcagatcg cctggagacg ccatccacgc tgttttgacc    180

tccatagaag acaccgggac cgatccagcc tccggactct agcctaggcc gcggacc       237

atg gcg tac tac cat cac cat cac cat cac tct aga tca aca agt ttg      285
Met Ala Tyr Tyr His His His His His His Ser Arg Ser Thr Ser Leu
1               5                   10                  15

tac aaa aaa gct gaacgagaa                                            306
Tyr Lys Lys Ala
            20
```

<210> SEQ ID NO 278
<211> LENGTH: 20
<212> TYPE: PRT
<213> ORGANISM: Artificial Sequence
<220> FEATURE:
<223> OTHER INFORMATION: pDEST26 CMV promoter

<400> SEQUENCE: 278

```
Met Ala Tyr Tyr His His His His His His Ser Arg Ser Thr Ser Leu
1               5                   10                  15

Tyr Lys Lys Ala
            20
```

<210> SEQ ID NO 279
<211> LENGTH: 255

-continued

```
<212> TYPE: DNA
<213> ORGANISM: Artificial Sequence
<220> FEATURE:
<223> OTHER INFORMATION: pDEST27 promoter
<220> FEATURE:
<221> NAME/KEY: misc_feature
<222> LOCATION: (1)..(1)
<223> OTHER INFORMATION: 'n' can be any nucleotide (A, T, C, G or U)
<220> FEATURE:
<221> NAME/KEY: CDS
<222> LOCATION: (139)..(153)
<223> OTHER INFORMATION:

<400> SEQUENCE: 279

nacggtggga ggtctatata agcagagctc gtttagtgaa ccgtcagatc gcctggagac     60

gccatccacg ctgttttgac ctccatagaa gacaccggga ccgatccagc ctccggactc    120

tagcctaggc cgcggacc atg gcc cct ata cta ggttattgga aaattaaggg        173
                    Met Ala Pro Ile Leu
                    1               5

ccttgtgcaa cccactcgac ttcttttgga atatcttgaa gaaaaatatg aagagcattt    233

gtatgagcgc gatgaaggtg at                                              255


<210> SEQ ID NO 280
<211> LENGTH: 5
<212> TYPE: PRT
<213> ORGANISM: Artificial Sequence
<220> FEATURE:
<223> OTHER INFORMATION: pDEST27 promoter
<220> FEATURE:
<221> NAME/KEY: misc_feature
<222> LOCATION: (1)..(1)
<223> OTHER INFORMATION: 'n' can be any nucleotide (A, T, C, G or U)

<400> SEQUENCE: 280

Met Ala Pro Ile Leu
1               5


<210> SEQ ID NO 281
<211> LENGTH: 87
<212> TYPE: DNA
<213> ORGANISM: Artificial Sequence
<220> FEATURE:
<223> OTHER INFORMATION: pDEST27 promoter
<220> FEATURE:
<221> NAME/KEY: CDS
<222> LOCATION: (37)..(75)
<223> OTHER INFORMATION:

<400> SEQUENCE: 281

tttggtggtg gcgaccatcc tccaaaatcg gatctg gtt ccg cgt tct aga tca       54
                                        Val Pro Arg Ser Arg Ser
                                        1               5

aca agt ttg tac aaa aaa gct gaacgagaaa cg                              87
Thr Ser Leu Tyr Lys Lys Ala
            10


<210> SEQ ID NO 282
<211> LENGTH: 13
<212> TYPE: PRT
<213> ORGANISM: Artificial Sequence
<220> FEATURE:
<223> OTHER INFORMATION: pDEST27 promoter

<400> SEQUENCE: 282

Val Pro Arg Ser Arg Ser Thr Ser Leu Tyr Lys Lys Ala
1               5                   10
```

<210> SEQ ID NO 283
<211> LENGTH: 405
<212> TYPE: DNA
<213> ORGANISM: Artificial Sequence
<220> FEATURE:
<223> OTHER INFORMATION: pEXP501

<400> SEQUENCE: 283

```
agagctcgtt tagtgaaccg tcagatcgcc tggagacgcc atccacgctg ttttgacctc     60

catagaagac accgggaccg atccagcctc cggactctag cctaggccgc ggagcggata    120

acaatttcac acaggaaaca gctatgacca ttaggcctat ttaggtgaca ctatagaaca    180

agtttgtaca aaaaagcagg ctggtaccgg tccggaattc ccgggatatc gtcgacgagc    240

tcactagtcg gcggccgctc tagagtatcc ctcgaggggc ccaagcttac gcgtacccag    300

ctttcttgta caaagtggtc cctatagtga gtcgtattat aagctaggca ctggccgtcg    360

ttttacaacg tcgtgactgg gaaaactgct agcttgggat ctttg                    405
```

<210> SEQ ID NO 284
<211> LENGTH: 153
<212> TYPE: DNA
<213> ORGANISM: Artificial Sequence
<220> FEATURE:
<223> OTHER INFORMATION: His6-CAT
<220> FEATURE:
<221> NAME/KEY: CDS
<222> LOCATION: (31)..(153)
<223> OTHER INFORMATION:

<400> SEQUENCE: 284

```
cggataacaa tttcacacag gaaacagacc atg tcg tac tac cat cac cat cac      54
                                 Met Ser Tyr Tyr His His His His
                                 1               5

cat cac ggc atc aca agt ttg tac aaa aaa gca ggc ttt gaa aac ctg      102
His His Gly Ile Thr Ser Leu Tyr Lys Lys Ala Gly Phe Glu Asn Leu
    10                  15                  20

tat ttt caa gga acc atg gag aaa aaa atc act gga tat acc acc gtt      150
Tyr Phe Gln Gly Thr Met Glu Lys Lys Ile Thr Gly Tyr Thr Thr Val
25                  30                  35                  40

gat                                                                  153
Asp
```

<210> SEQ ID NO 285
<211> LENGTH: 41
<212> TYPE: PRT
<213> ORGANISM: Artificial Sequence
<220> FEATURE:
<223> OTHER INFORMATION: His6-CAT

<400> SEQUENCE: 285

```
Met Ser Tyr Tyr His His His His His His Gly Ile Thr Ser Leu Tyr
1               5                   10                  15

Lys Lys Ala Gly Phe Glu Asn Leu Tyr Phe Gln Gly Thr Met Glu Lys
            20                  25                  30

Lys Ile Thr Gly Tyr Thr Thr Val Asp
        35                  40
```